(12) United States Patent
Pavletich et al.

(10) Patent No.: US 7,124,068 B2
(45) Date of Patent: Oct. 17, 2006

(54) CRYSTAL STRUCTURE OF A DEACETYLASE AND INHIBITORS THEREOF

(75) Inventors: Nikola Pavletich, New York, NY (US); Michael Finnin, Alexandria, VA (US); Jill Donigian, North Arlington, NJ (US); Victoria M. Richon, Rye, NY (US); Richard A. Rifkind, New York, NY (US); Paul A. Marks, Washington, CT (US); Ronald Breslow, Englewood, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 470 days.

(21) Appl. No.: 10/095,109

(22) Filed: Mar. 8, 2002

(65) Prior Publication Data

US 2003/0013176 A1    Jan. 16, 2003

Related U.S. Application Data

(63) Continuation of application No. PCT/US00/24700, filed on Sep. 8, 2000.

(60) Provisional application No. 60/152,753, filed on Sep. 8, 1999.

(51) Int. Cl.
G06G 7/48 (2006.01)

(52) U.S. Cl. ...................................................... 703/11

(58) Field of Classification Search ................. 702/27, 702/19; 703/11
See application file for complete search history.

(56) References Cited

U.S. PATENT DOCUMENTS 5,550,316 A    8/1996 Mintz
5,608,108 A    3/1997 Marks et al.

(Continued)

OTHER PUBLICATIONS

Finnin et al., Nature, vol. 401, pp. 188-193, Sep. 9, 1999.*

(Continued)

*Primary Examiner*—Michael Borin
*Assistant Examiner*—Jerry Lin
(74) *Attorney, Agent, or Firm*—Mintz, Levin, Cohn, Ferris, Glovsky and Popeo, P.C.

(57) ABSTRACT

The present invention provides three-dimensional structural information from the hyperthermophilic bacterium *Aquifex aeolicus* which is a histone deacetylase-like protein (HDLP). HDLP shares 35.2% amino acid sequence identity with human histone deacetylase (HDAC1). The present invention further provides three-dimensional structural information of HDLP bound by inhibitor molecules. The three-dimensional structural information of the present invention is useful to design, isolate and screen deacetylase inhibitor compounds capable of inhibiting HDLP, HDAC family members and HDLP-related molecules. The invention also relates to nucleic acids encoding a mutant HDLP which facilitates the determination of the three-dimensional structure of HDLP in the presence of a zinc atom.

9 Claims, 263 Drawing Sheets

TABLE 1.    Statistics from the crystallographic analysis

| Data set | Native | thimerosal | Pb | AuCN | Zn | TSA |
|---|---|---|---|---|---|---|
| Space Group | C2 | C2 | C2 | C2 | C2 | P2₁2₁2₁ |
| Resolution (Å) | 1.8 | 2.3 | 3.5 | 2.8 | 2.0 | 2.1 |
| Observations | 134,952 | 79,023 | 11,454 | 27,722 | 125,769 | 180,427 |
| Unique reflections | 32,143 | 15,958 | 4,040 | 8,753 | 23,643 | 50,796 |
| Data coverage (%) | 92.3 | 95.7 | 86.4 | 94.3 | 90.6 | 93.8 |
| $R_{sym}$ (%) | 2.9 | 8.4 | 9.6 | 8.9 | 7.2 | 7.1 |
| MIR analysis (20.0-2.5 Å): | | | | | | |
| phasing power | - | 1.47 | 1.24 | 1.10 | - | - |
| $R_{cullis}$ | - | 0.72 | 0.78 | 0.85 | - | - |
| $R_{cullis}$ (ano) | | 0.92 | | | | |

Refinement statistics:

| Data Set | Resolution (Å) | Reflections (\|F\| > 1σ) | Total atoms | Water atoms | R-factor (%) | R-free (%) | RMSD bonds (Å) | RMSD angles (°) | B-factor (Å²) |
|---|---|---|---|---|---|---|---|---|---|
| HDLP | 1.8 | 31,550 | 3214 | 228 | 19.8 | 24.0 | 0.010 | 1.63 | 3.55 |
| HDLP-Zn | 2.0 | 23,582 | 3424 | 434 | 22.0 | 25.8 | 0.009 | 1.48 | 1.04 |
| HDLP-Zn-TSA | 2.1 | 44,122 | 6475 | 456 | 22.4 | 25.8 | 0.008 | 1.78 | 3.83 |

$R_{sym} = \Sigma_h\Sigma_i |I_{h,i} - \langle I_h \rangle| / \Sigma_h\Sigma_i I_{h,i}$ for the intensity (I) of i observations of reflection h. Phasing power = $\langle F_H \rangle / E$, where $\langle F_H \rangle$ is the root-mean-square heavy atom structure factor and E is the residual lack of closure error. Rcullis is the mean residual lack of closure error divided by the dispersive difference. R-factor = $\Sigma |F_{obs} - F_{calc}| / \Sigma |F_{obs}|$, where $F_{obs}$ and $F_{calc}$ are the observed and calculated structure factors, respectively. Figure of merit = $|F(hkl)_{best} / F(hkl)|$. R-free = R-factor calculated using 5% of the reflection data chosen randomly and omitted from the start of refinement. RMSD: root mean square deviations from ideal geometry and root mean square variation in the B-factor of bonded atoms.

U.S. PATENT DOCUMENTS

| | | | |
|---|---|---|---|
| 5,668,179 | A | 9/1997 | Breslow et al. |
| 5,698,764 | A | 12/1997 | Arbeit et al. |
| 5,700,811 | A | 12/1997 | Breslow et al. |
| 5,709,844 | A | 1/1998 | Arbeit et al. |
| 5,773,474 | A | 6/1998 | Breslow et al. |
| 5,777,193 | A | 7/1998 | Dunn et al. |
| 5,780,594 | A | 7/1998 | Carter |
| 5,811,634 | A | 9/1998 | O'Brien et al. |
| 5,840,960 | A | 11/1998 | Marks et al. |
| 5,917,090 | A | 6/1999 | Huxley et al. |
| 5,919,940 | A | 7/1999 | Martin |

OTHER PUBLICATIONS

Drenth, Jan., Principles of Protein X-ray Crystallography, Springer-Verlag:New York (1994) pp. 1-19.*

Service, Robert, "Tapping DNA for Strucutres Produces a Trickle," Science, vol. 298, (2002) pp. 948-950.*

Kakuta, et al., "Crystal Structure of the Sulfotransferase Domain of Human Heparan Sulfate N-Deacetylase/N-Sulfotransferase 1", The Journal of Biological Chemistry, 274 (16):10673-10676 (1999).

Sueyoshi, et al., "A role of Lys $^{614}$ in the sulfotransferase activity of human heparan sulfate N-deacetylase/N-sulfotransferase", FEBS Letters, 43:3211-214 (1998).

Ahmad, et al. "WD Repeats of the p48 Subunit of Chicken Chromatin Assembly Factor-1 Required for in Vitro Interaction with Chicken Histone Deacetylase-2". The Journal of Biological Chemistry, 274 (23):16646-16653 (1999).

John, et al., Rhizobium NodB protein involved in nodulation signal synthesis is a chitooligosaccharide deacetylase. PNAS, USA, 90:625-629, (1993).

Davie, J.R., and Chadee, D.N., "Regulation and Regulatory Parameters of Histone Modifications," J. Cell. Biochem. Supple., 30/31:203-213 (1998).

Erickson, J. W., "Design and structure of symmetry-based inhibitors of HIV-1 protease," Perspectives in Drug Discovery and Design, 1:109-128 (1993).

Kouzarides, T., "Histone acetylases and deacetylases in cell proliferation," Current Opinion in Genetics & Development, 9(1):40-48 (1999).

Hassig, C.A., et al., "Fiber-derived butyrate and the prevention of colon cancer," Chemistry & Biology, 4:783-789 (1997).

Fenrick, R. and Hiebert, S.W., "Role of Histone Deacetylases in Acute Leukemia," J. Cell. Bio. Supple., 30/31:194-202 (1998).

Richon, V. M., et al., "A class of hybrid polar inducers of transformed cell differentiation inhibits histone deacetylases," PNAS, USA, 95:3003-3007 (1998).

Yoshida, M., et al., "Potent and Specific Inhibition of Mammalian Histone Deacetylase Both in Vivo and in Vitro by Trichostatin A," J. of Bio. Chem., 265 (28):17174-17179 (1990).

Lea, M. A., et al., "Increased acetylation of histones induced by diallyl disulfide and structurally related molecules," Int'l. J. of Oncology, 15:347-352 (1999).

Kim, Y. B., et al., "Oxamflatin is a novel antitumor compound that inhibits mammalian histone deacetylase," Oncogene, 18:2461-2470 (1999).

Saito, A., et al., "A synthetic inhibitor of histone deacetylase, MS-27-275, with marked in vivo antitumor activity against human tumors," PNAS, USA, 96:4592-4597 (1999).

Lea, M.A. and Tulsyan, N., "Discordant Effects of Butyrate Analogues on Erythroleukemia Cell Proliferation, Differentiation and Histone Deacetylase," Anticancer Research, 15:879-884 (1995).

Nakajima, H., et al., "FR901228, a Potent Antitumor Antibiotic, Is a Novel Histone Deacetylase Inhibitor," Exper. Cell Research, 241 (1):126-133 (1998).

Kwon, H. J., et al., "Depudecin induces morphological reversion of transformed fibroblasts via the inhibition of histone deacetylase," PNAS, USA, 95:3356-3361 (1998).

Richon, V.M., et al., "Second generation hybrid polar compounds are potent inducers of transformed cell differentiation," PNAS USA 93:5705-5708 (1996).

Bugg, C.E.,eds "The CCP4 Suite: Programs for Protein Crystallography," Acta Cryst., D50:760-763 (1994).

Yoshida, M., et al., "Trichostatin A and trapoxin: novel chemical probes for the role of histone acetylation in chromatin structure and function," BioEssays, 17(5):423-430 (1995).

Yoshida, M. and Teruhiko, B., "Reversible Arrest of Proliferation of Rat 3Y1 Fibroblasts in Both the G1 and G2 Phases by Trichostatin A," Exp. Cell Research, 177:122-131 (1988).

Yoshida, M., et al., "Effects of Trichostatins on Differentiation of Murine Erythroleukemia Cells," Cancer Research 47:3688-3691 (1987).

Warrell, Jr., R. P., et al., "Therapeutic Targeting of Transcription in Acute Promyelocytic Leukemia by Use of an Inhibitor of Histone Deacetylase," J. of the National Cancer Institute, 90 (21):1621-1625 (1998).

Desai, D., et al., "Chemopreventive efficacy of suberanilohydroxamic acid (SAHA), a cytodifferentiating agent, against tobacco-specific nitrosamine 4-(methylnitros-amino)-1-(3-pyridyl)-1 butanone (NNK)—induced lung tumorigenesis in female A/J mice," Proceedings of the American Association for Cancer Research 40 Abstract:2396 (1999).

Struhl, K., "Histone acetylation and transcriptional regulatory mechanisms," J. of Cell. and Mol. Bio., 12 (5):599-606 (1998).

Kadosh, D. and K. Struhl., "Targeted Recruitment of the Sin3-Rpd3 Histone Deacetylase Complex Generates a Highly Localized Domain of Repressed Chromatin In Vivo," Mol. and Cell. Biology, 18(9) 5121-5127 (1998).

Rundlett, S. E., et al., "Transcriptional repression by UME6 involves deacetylation of lysine 5 of histone H4 by RPD3," Nature, 392:831-835 (1998).

Laherty, C. D., et al., "Histone Deacetylases Associated with the mSin3 Corepressor Mediate Mad Transcriptional Repression," Cell, 89:349-356 (1997).

Hassig, C. A., et al., "Histone Deacetylase Activity is Required for Full Transcriptional Repression by mSin3A," Cell, 89:341-347 (1997).

Kadosh, D. and Struhl, K., "Repressin by Ume6 Involves Recruitment of a Complex Containing Sin3 Corepressor and Rpd3 Histone Deacetylase to Target Promoters," Cell, 89:365-371 (1997).

Nagy, L., et al., "Nuclear Receptor Repression Mediated by a Complex Containing SMRT, mSin3A, and Histone Deacetylase," Cell, 89:373-380 (1997).

Alland, L., et al., "Role for N-CoR and histone deacetylase in Sin3-mediated transcriptional repression," Nature, 387:49-55 (1997).

Heinzel, T., et al., "A complex containing N-CoR, mSin3 and histone deacetylase mediates transcriptional repression," Nature, 387:43-48 (1997).

Grignani, F., et al., "Fusion proteins of the retinoic acid receptor-α recruit histone deacetylase in promyelocytic leukaemia," Nature, 391: 815-818 (1998).

Lin, R. J., et al., "Role of the histone deacetylase complex in acute promyelocytic leukaemia," Nature, 391:811-814 (1998).

Taunton, J., et al., "A Mammalian Histone Deacetylase Related to the Yeast Transcriptional Regulator Rpd3p," Science, 272:408-411 (1996).

Yang, W., et al., "Transcriptional repression by YY1 is mediated by interaction with a mammalian homolog of the yeast global regulator RPD3," PNAS, USA, 93:12845-12850 (1996).

Emiliani, S., et al., "Characterization of a human RPD3 ortholog, HDAC3," PNAS, USA, 95:2795-2800 (1998).

Vidal, M. and Gaber, R.F., "RPD3 Encodes a Second Factor Required to Achieve Maximum Positive and Negative Transcriptional States in Saccharomyces cerevisiae," Molecular and Cellular Biology 11(12):6317-6327 (1991).

Grozinger, C.M., et al., "Three proteins define a class of human histone deacetylases related to yeast Hdalp," PNAS USA 96: 4868-4873 (1999).

Fischle, W., et al., "A New Family of Human Histone Deacetylase Related to Saccharomyces cervisiae HDA1p," J. Biol. Chem. 274:11713-11720 (1999).

Rundlett, S. E., et al., "HDA1 and RPD3 are members of distinct yeast histone deacetylase complexes that regulate silencing and transcription," *PNAS, USA*, 93:14503-14508 (1996).

Leipe, D.D. and Landsman, D., "Histone deacetylases, acetoin utilization proteins and acetylpolyamine amidohydrolases are members of an ancient protein superfamily," *Nucleic Acids Research* 25 (18):3693-3697 (1997).

Grundy, F.J., et al., "Identification of genes involved in utilization of acetate and acetoin in *Bacillus subtilis*," *Molecular Microbiology*, 10(2):259-271 (1993).

Deckert, G., et al., "The complete genome of the hyperthermophilic bacterium Aquifex aeolicus," *Nature*, 392:353-358 (1998).

Cheng-Ming, C. and Roeder, R.G., "Expression and Purification of General Transcription Factors by FLAG Epitope-Tagging and Peptide Elution," *Peptide Research* 6(2):62-64 (1993).

Carmen, A.A., et al., "HDA1 and HDA3 Are Components of a Yeast Histone Deacetylase (HDA) Complex," *The Journal of Biological Chemistry*, 271(26):15837-15844 (1996).

Hendzel, M. J., et al., "Histone Deacetylase Is a Component of the Internal Nuclear Matrix," *The Journal of Biological Chemistry* 266(32): 21936-21942 (1991).

Otwinowski, Z. and Minor, W., "Processing of X-Ray Diffraction Data Collected in Oscillation Mode," *Methods in Enzymology*, 276:307-326 (1997).

Brünger, A.T., et al., "Crystallography & NMR System: A New Software Suite for Macromolecular Structure Determination," *Acta Crystallographica*, D54:905-921 (1998).

Chothia, C. and Lesk, A. M., "The relation between the divergence of sequence and structure in proteins," *The EMBO Journal*, 5(4):823-826 (1986).

Fersht, A. R. and Sperling, J., "The Charge Relay System in Chymotrypsin and Chymotrypsinogen," *J. Mol. Biol.*, 74:137-149 (1973).

Blow, D. M., et al., "Role of a Buried Acid Group in the Mechanism of Action of Chymotrypsin," *Nature*, 221:337-340 (1969).

Brändén, C-I., "Relation between structure and function of α/β-proteins," *Quarterly Reviews of Biophysics* 13(3):317-338 (1980).

Hassig, C. A., et al., "A role for histone deacetylase activity in HDAC1-mediated transcriptional repression," *PNAS, USA*, 95:3519-3524 (1998).

Kadosh, D., and Struhl, K., "Histone deacetylase activity of Rpd3 is important for transcriptional repression in vivo," *Journal of Cellular and Molecular Biology*, 12(6):797-805 (1998).

Tsuji, N., et al., "A New Antifungal Antibiotic , Trichostatin," *The Journal of Antibiotics*, 29:1-6 (1976).

Grams, F., et al., "Structure Determination and Analysis of Human Neutrophil Collagenase Complexed with a Hydroxamate Inhibitor," *Biochemistry*, 34:14012-14020 (1995).

Lovejoy, B., et al., "Crystal structures of MMP-1 and -13 reveal the structural basis for selectivity of collagenase inhibitors," *Nature Structural Biology*, 6(3):217-221 (1999).

Holmes, M.A., and Matthews, B.W., "Binding of Hydroxamic Acid Inhibitors to Crystalline Thermolysin Suggests Pentacoordinate Zinc Intermediate in Catalysis," *Biochemistry* 20(24):6912-6920 (1981).

Dunbrack, R. L., et al., "Meeting review: the Second Meeting on the Critical Assessment of Techniques for Protein Structure Prediction (CASP2), Asilomar, California, Dec. 13-16, 1996," *Folding & Design* 2(2):R27-R42 (1997).

Bugg, C. E., et al., "Drugs by Design," *Scientific American* 269(6):92-98 (1993).

West, M.L. and Fairlie, D. P., "Targeting HIV-1 protease: a test of drug-design methodologies," *Trends in Pharmacological Sciences* 16: 67-74 (1995).

Jones, T.A., et al., "Improved Methods for Building Protein Models in Electron Density Maps and the Location of Errors in these Models," *Acta Cryst.* A47:1-62 (1991).

Lam, P., et al., "Rational Design of Potent, Bioavailable, Nonpeptide Cyclic Ureas as HIV Protease Inhibitors," *Science*, 263:380-384 (1994).

Wlodawer, A. and Erickson, J. W., "Structure-Based Inhibitors of HIV-1 Protease," *Annu. Rev. Biochem.*, 62:543-585 (1993).

Appelt, K., "Crystal structures of HIV-1 protease-inhibitor complexes," *Perspectives in Drug Discovery and Design*, 1:23-48 (1993).

Deckert et al. (1998). *Nature* 392:353-358.

* cited by examiner

TABLE 1. Statistics from the crystallographic analysis

| Data set | Native | thimerosal | Pb | AuCN | Zn | TSA |
|---|---|---|---|---|---|---|
| Space Group | C2 | C2 | C2 | C2 | C2 | P2₁2₁2₁ |
| Resolution (Å) | 1.8 | 2.3 | 3.5 | 2.8 | 2.0 | 2.1 |
| Observations | 134,952 | 79,023 | 11,454 | 27,722 | 125,769 | 180,427 |
| Unique reflections | 32,143 | 15,958 | 4,040 | 8,753 | 23,643 | 50,796 |
| Data coverage (%) | 92.3 | 95.7 | 86.4 | 94.3 | 90.6 | 93.8 |
| $R_{sym}$ (%) | 2.9 | 8.4 | 9.6 | 8.9 | 7.2 | 7.1 |

MIR analysis (20.0–2.5 Å):

| | Native | thimerosal | Pb | AuCN | Zn | TSA |
|---|---|---|---|---|---|---|
| phasing power | - | 1.47 | 1.24 | 1.10 | - | - |
| $R_{cullis}$ | - | 0.72 | 0.78 | 0.85 | - | - |
| $R_{cullis}$ (ano) | | 0.92 | | | | |

Refinement statistics:

| Data Set | Resolution (Å) | Reflections (\|F\| > 1σ) | Total atoms | Water atoms | R-factor (%) | R-free (%) | RMSD bonds (Å) | RMSD angles (°) | B-factor (Å²) |
|---|---|---|---|---|---|---|---|---|---|
| HDLP | 1.8 | 31,550 | 3214 | 228 | 19.8 | 24.0 | 0.010 | 1.63 | 3.55 |
| HDLP-Zn | 2.0 | 23,582 | 3424 | 434 | 22.0 | 25.8 | 0.009 | 1.48 | 1.04 |
| HDLP-Zn-TSA | 2.1 | 44,122 | 6475 | 456 | 22.4 | 25.8 | 0.008 | 1.78 | 3.83 |

$R_{sym} = \Sigma_h \Sigma_i |I_{h,i} - \langle I_h \rangle| / \Sigma_h \Sigma_i I_{h,i}$ for the intensity (I) of i observations of reflection h. Phasing power = $\langle F_\lambda \rangle / E$, where $\langle F_\lambda \rangle$ is the root-mean-square heavy atom structure factor and E is the residual lack of closure error. $R_{cullis}$ is the mean residual lack of closure error divided by the dispersive difference. R-factor = $\Sigma |F_{obs} - F_{calc}| / \Sigma |F_{obs}|$, where $F_{obs}$ and $F_{calc}$ are the observed and calculated structure factors, respectively. Figure of merit = $|F(hkl)_{best}|/F(hkl)$. R-free = R-factor calculated using 5% of the reflection data chosen randomly and omitted from the start of refinement. RMSD: root mean square deviations from ideal geometry and root mean square variation in the B-factor of bonded atoms.

Fig. 1 a)
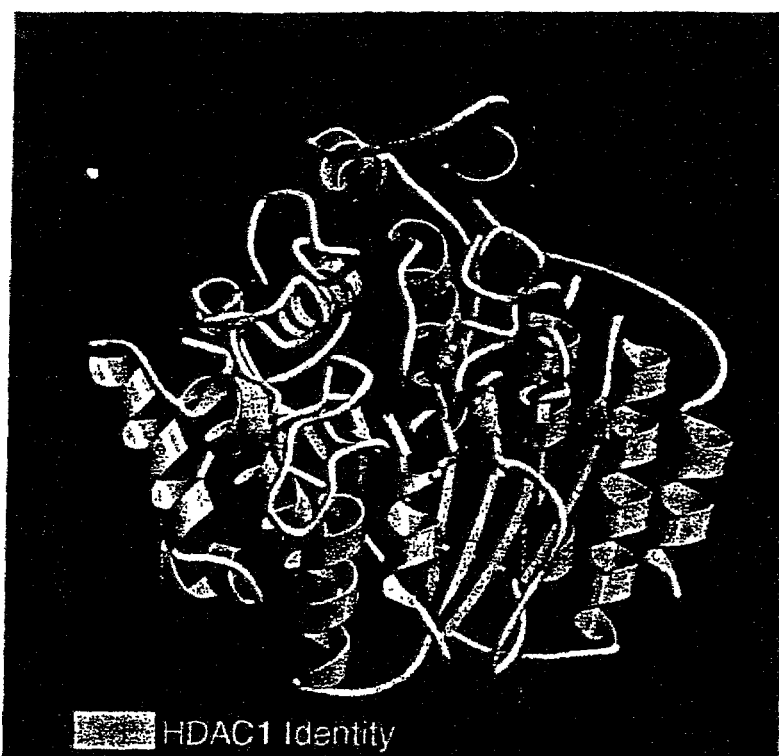
b)
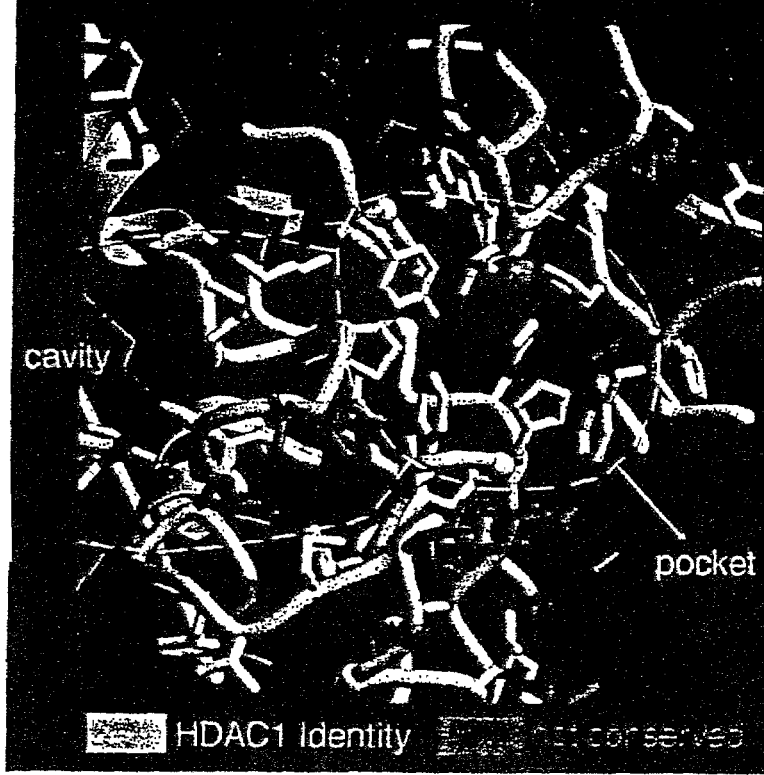
Fig. 7

```
          10        20        30        40
    |....|....|....|....|....|....|....|....|
    ATGAAGAAGGTTAAACTTATCGGAACTTTAGACTACGGAA   40
    AGTACAGATATCCCAAAAACCATCCTCTTAAAATACCAAG   80
    AGTTTCCCTACTCCTTAGGTTTTTAGATGCCATGAACCTT  120
    ATAGATGAGAAGGAATTAATCAAGAGCAGACCCGCAACTA  160
    AAGAAGAACTCCTTTTATTCCACACGGAAGACTACATAAA  200
         210       220       230       240
    |....|....|....|....|....|....|....|....|
    CACTTTAATGGAAGCGGAAAGGTGTCAGTGCGTTCCGAAG  240
    GGAGCTAGGGAAAAGTACAACATAGGCGGATACGAAAACC  280
    CCGTATCTTACGCGATGTTACAGGCTCTTCTCTCGCAAC   320
    GGGTTCAACAGTGCAGGCGATAGAGGAATTTTTAAAGGA   360
    AATGTAGCTTTCAATCCCGCGGGAGGTATGCACCACGCTT  400
         410       420       430       440
    |....|....|....|....|....|....|....|....|
    TTAAAAGCAGGGCAAACGGCTTTTGCTACATAAACGACCC  440
    CGCTGTGGGAATTGAGTACTTGAGAAAAAAAGGCTTTAAG  480
    AGAATACTCTACATAGACCTTGATGCCCACCACTGCGACG  520
    GTGTTCAGGAAGCCTTTTACGATACAGACCAGGTGTTCGT  560
    CCTGTCCCTTCACCAGTCGCCCGAGTACGCCTTTCCCTTT  600
         610       620       630       640
    |....|....|....|....|....|....|....|....|
    GAGAAGGGCTTCCTGGAGGAGATAGGAGAAGGAAAAGGAA  640
    AGGGCTACAACCTGAACATTCCCCTGCCAAAGGGCTTGAA  680
    CGACAACGAGTTCCTCTTTGCCCTAGAAAAATCTCTGGAA  720
    ATAGTCAAAGAAGTATTTGAGCCCGAGGTTTACCTTCTTC  760
    AACTCGGAACTGACCCACTCCTTGAAGATTACCTTTCCAA  800
         810       820       830       840
    |....|....|....|....|....|....|....|....|
    GTTCAACCTCTCAAACGTTGCCTTTTTAAAAGCTTTCAAC  840
    ATCGTTCGTGAGGTTTTCGGGGAGGGAGTATACCTCGGAG  880
    GAGGCGGATACCATCCTTACGCCCTCGCAAGGGCATGGAC  920
    CCTAATCTGGTGCCAGCTTTCGGAAGGGAAGTGCCGGAA   960
    AAGCTAAACAATAAAGCAAAGAGCTTTTAAAGAGTATAG  1000
         1010      1020      1030      1040
    |....|....|....|....|....|....|....|....|
    ACTTTGAAGAGTTTGACGACGAGGTGGACCGCTCGTACAT  1040
    GCTCGAAACCCTAAAGGACCCCTGGAGAGGAGGAGAGGTA  1080
    AGGAAAGAAGTAAAGGATACGCTTGAAAAGGCGAAAGCCT  1120
    CATCTTA  1127
```

Fig. 10

```
          10        20        30        40
 ....|....|....|....|....|....|....|....|
MKKVKLIGTLDYGKYRYPKNHPLKIPRVSLLLRFLDAMNL   40
IDEKELIKSRPATKEELLLFHIEDYINTLMEAERCQCVPK   80
GAREKYNIGGYENPVSYAMFTGSSLATGSIVQAIEEFLKG  120
NVAFNPAGGMHHAFKSRANGFCYINDPAVGIEYLRKKGFK  160
RILYIDLDAHHCDGVQEAFYDIDQVFVLSLHQSPEYAFPF  200
         210       220       230       240
 ....|....|....|....|....|....|....|....|
EKGFLEEIGEGKGKGYNLNIPLPKGLNDNEFLFALEKSLE  240
IVKEVFEPEVYLLQLGTDPLLEDYLSKFNLSNVAFLKAFN  280
IVREVFGEGVYLGGGGYHPYALARAWILIWCELSGREVPE  320
KLNNKAKELLKSIDFEEFDDEVDRSYMLETLKDPWRGGEV  360
RKEVKDILEKAKASS  375
```

Fig. 11

```
         10        20        30        40
 ....|....|....|....|....|....|....|....|
ATGAAGAAGGTTAAACTTATCGGAACTTTAGACTACGGAA   40
AGTACAGATATCCCAAAAACCATCCTCTTAAAATACCAAG   80
AGTTTCCCTACTCCTTAGGTTTTTAGATGCCATGAACCTT  120
ATAGATGAGAAGGAATTAATCAAGAGCAGACCCGCAACTA  160
AAGAAGAACTCCTTTTATTCCACACGGAAGACTACATAAA  200
        210       220       230       240
 ....|....|....|....|....|....|....|....|
CACTTTAATGGAAGCGGAAAGGTGTCAGTGCGTTCCGAAG  240
GGAGCTAGGGAAAAGTACAACATAGGCGGATACGAAAACC  280
CCGTATCTTACGCGATGTTTACAGGCTCTTCTCTCGCAAC  320
GGGTTCAACAGTGCAGGCGATAGAGGAATTTTTAAAGGGA  360
AATGTAGCTTTCAATCCCGCGGGAGGTATGCACCACGCTT  400
        410       420       430       440
 ....|....|....|....|....|....|....|....|
TTAAAAGCAGGGCAAACGGCTTTTGCTACATAAACGACCC  440
CGCTGTGGGAATTGAGTACTTGAGAAAAAAGGCTTTAAG   480
AGAATACTCTACATAGACCTTGATGCCCACCACTGCGACG  520
GTGTTCAGGAAGCCTTTTACGATACAGACCAGGTGTTCGT  560
CCTGTCCCTTCACCAGTCGCCCGAGTACGCCTTTCCCTTT  600
        610       620       630       640
 ....|....|....|....|....|....|....|....|
GAGAAGGGCTTCCTGGAGGAGATAGGAGAAGGAAAAGGAA  640
AGGGCTACAACCTGAACATTCCCCTGCCAAAGGGCTTGAA  680
CGACAACGAGTTCCTCTTTGCCCTAGAAAAATCTCTGGAA  720
ATAGTCAAAGAAGTATTTGAGCCCGAGGTTTACCTTCTTC  760
AACTCGGAACTGACCCACTCCTTGAAGATTACCTTTCCAA  800
        810       820       830       840
 ....|....|....|....|....|....|....|....|
GTTCAACCTCTCAAACGTTGCCTTTTTAAAAGCTTTCAAC  840
ATCGTTCGTGAGGTTTTCGGGGAGGGAGTATACCTCGGAG  880
GAGGCGGATTCCATCCTTACGCCCTCGCAAGGGCATGGAC  920
CCTAATCTGGTGCGAGCTTTCGGGAAGGGAAGTGCCGGAA  960
AAGCTAAACAATAAAGCAAAAGAGCTTTTAAAGAGTATAG 1000
       1010      1020      1030      1040
 ....|....|....|....|....|....|....|....|
ACTTTGAAGAGTTTGACGACGAGGTGGACCGCTCGTACAT 1040
GCTCGAAACCCTAAAGGACCCTGGAGAGGAGGAGAGGTA  1080
AGGAAAGAAGTAAAGGATACGCTTGAAAAGGCGAAAGCCT 1120
CATCTTA                                  1127
```

Fig. 12

```
         10          20          30          40
|....|....|....|....|....|....|....|....|....|
MKKVKLIGILDYGKYRYPKNHPLKIPRVSLLLRFLDAMNL  40
IDEKELIKSRPATKEELLLFHTEDYINILMEAERCQCVPK  80
GAREKYNIGGYENPVSYAMFTGSSLATGSTVQAIEEFLKG  120
NVAFNPAGGMHHAFKSRANGFCYINDPAVGIEYLRKKGFK  160
RILYIDLDAHHCDGVQEAFYDTDQVFVLSLHQSPEYAFPF  200
         210         220         230         240
|....|....|....|....|....|....|....|....|....|
EKGFLEEIGEGKGKGYNLNIPLPKGLNDNEFLFALEKSLE  240
IVKEVFEPEVYLLQLGTDPLLEDYLSKFNLSNVAFLKAFN  280
IVREVFGEGVYLGGGGFHPYALARAWTLIWCELSGREVPE  320
KLNNKAKELLKSIDFEEFDDEVDRSYMLETLKDPWRGGEV  360
RKEVKDTLEKAKASS  375
```

Fig. 13

```
         10        20        30        40
    ..|....|....|....|....|....|....|....|
    ATGAAGAAGGTTAAACTTATCGGAACTTTAGACTACGGAA  40
    AGTACAGATATCCCAAAAACCATCCTCTTAAAATACCAAG  80
    AGTTTCCCTACTCCTTAGGTTTTTAGATGCCATGAACCTT  120
    ATAGATGAGAAGGAATTAATCAAGAGCAGACCGCAACTA   160
    AAGAAGAACTCCTTTTATTCCACACGGAAGACTACATAAA  200
         210       220       230       240
    ..|....|....|....|....|....|....|....|
    CACTTTAATGGAAGCGGAAAGGAGTCAGAGCGTTCCGAAG  240
    GGAGCTAGGGAAAAGTACAACATAGGCGGATACGAAAACC  280
    CCGTATCTTACGCGATGTTTACAGGCTCTTCTCTCGCAAC  320
    GGGTTCAACAGTGCAGGCGATAGAGGAATTTTTAAAGGGA  360
    AATGTAGCTTTCAATCCGCGGGAGGTATGCACCACGCTT   400
         410       420       430       440
    ..|....|....|....|....|....|....|....|
    TTAAAAGCAGGGCAAACGGCTTTTGCTACATAAACGACCC  440
    CGCTGTGGGAATTGAGTACTTGAGAAAAAAGGCTTTAAG   480
    AGAATACTCTACATAGACCTTGATGCCCACCACTGCGACG  520
    GTGTTCAGGAAGCCTTTTACGATACAGACCAGGTGTTCGT  560
    CCTGTCCCTTCACCAGTCGCCCGAGTACGCCTTTCCCTTT  600
         610       620       630       640
    ..|....|....|....|....|....|....|....|
    GAGAAGGGCTTCCTGGAGGAGATAGGAGAAGGAAAAGGAA  640
    AGGGCTACAACCTGAACATTCCCCTGCCAAAGGGCTTGAA  680
    CGACAACGAGTTCCTCTTTGCCCTAGAAAAATCTCTGGAA  720
    ATAGTCAAAGAAGTATTTGAGCCGAGGTTTACCTTCTTC   760
    AACTCGGAACTGACCCACTCCTTGAAGATTACCTTTCCAA  800
         810       820       830       840
    ..|....|....|....|....|....|....|....|
    GTTCAACCTCTCAAACGTTGCCTTTTTAAAAGCTTTCAAC  840
    ATCGTTCGTGAGGTTTTCGGGGAGGGAGTATACCTCGGAG  880
    GAGGCGGATACCATCCTTACGCCCTCGCAAGGGCATGGAC  920
    CCTAATCTGGTGCGAGCTTTCGGGAAGGGAAGTGCCGGAA  960
    AAGCTAAACAATAAAGCAAAGAGCTTTTAAAGAGTATAG   1000
         1010      1020      1030      1040
    ..|....|....|....|....|....|....|....|
    ACTTTGAAGAGTTTGACGACGAGGTGGACCGCTCGTACAT  1040
    GCTCGAAACCCTAAAGGACCCCTGGAGAGGAGGAGAGGTA  1080
    AGGAAAGAAGTAAAGGATACGCTTGAAAAGGCGAAAGCCT  1120
    CATCTTA  1127
```

Fig. 14

```
         10        20        30        40
    ....|....|....|....|....|....|....|....|
    MKKVKLIGTLDYGKYRYPKNHPLKIPRVSLLLRFLDAMNL   40
    IDEKELIKSRPATKEELLLFHTEDYINTLMEAERSQSVPK   80
    GAREKYNIGGYENPVSYAMFTGSSLATGSTVQAIEEFLKG  120
    NVAFNPAGGMHHAFKSRANGFCYINDPAVGIEYLRKKGFK  160
    RILYIDLDAHHCDGVQEAFYDTDQVFVLSLHQSPEYAFPF  200
        210       220       230       240
    ....|....|....|....|....|....|....|....|
    EKGFLEEIGEGKGKGYNLNIPLPKGLNDNEFLFALEKSLE  240
    IVKEVFEPEVYLLQLGTDPLLEDYLSKFNLSNVAFLKAFN  280
    IVREVFGEGVYLGGGGYHPYALARAWTLIWCELSGREVPE  320
    KLNNKAKELLKSIDFEEFDDEVDRSYMLETLKDPWRGGEV  360
    RKEVKDILEKAKASS  375
```

Fig. 15

| | | | | Residue # | X | Y | Z | OCC. | B | Segment ID |
|---|---|---|---|---|---|---|---|---|---|---|
| ATOM | 1 | CB | ALA | 2 | 45.336 | 36.860 | 75.042 | 1.00 | 59.90 | AAAA |
| ATOM | 2 | C | ALA | 2 | 46.410 | 38.631 | 73.528 | 1.00 | 51.57 | AAAA |
| ATOM | 3 | O | ALA | 2 | 45.780 | 39.595 | 74.052 | 1.00 | 62.46 | AAAA |
| ATOM | 4 | N | ALA | 2 | 47.540 | 37.826 | 75.673 | 1.00 | 55.52 | AAAA |
| ATOM | 5 | CA | ALA | 2 | 46.668 | 37.432 | 74.527 | 1.00 | 57.32 | AAAA |
| ATOM | 6 | N | LYS | 3 | 46.890 | 38.570 | 72.389 | 1.00 | 59.61 | AAAA |
| ATOM | 7 | CA | LYS | 3 | 46.687 | 39.669 | 71.440 | 1.00 | 59.58 | AAAA |
| ATOM | 8 | CB | LYS | 3 | 47.855 | 39.763 | 70.459 | 1.00 | 56.03 | AAAA |
| ATOM | 9 | CG | LYS | 3 | 49.217 | 40.007 | 71.102 | 1.00 | 55.16 | AAAA |
| ATOM | 10 | CD | LYS | 3 | 50.315 | 40.000 | 70.039 | 1.00 | 66.28 | AAAA |
| ATOM | 11 | CE | LYS | 3 | 51.700 | 40.163 | 70.655 | 1.00 | 71.41 | AAAA |
| ATOM | 12 | NZ | LYS | 3 | 52.791 | 40.047 | 69.642 | 1.00 | 69.64 | AAAA |
| ATOM | 13 | C | LYS | 3 | 45.407 | 39.422 | 70.642 | 1.00 | 63.29 | AAAA |
| ATOM | 14 | O | LYS | 3 | 44.984 | 38.262 | 70.487 | 1.00 | 57.41 | AAAA |
| ATOM | 15 | N | VAL | 4 | 44.814 | 40.498 | 70.138 | 1.00 | 55.18 | AAAA |
| ATOM | 16 | CA | VAL | 4 | 43.535 | 40.418 | 69.349 | 1.00 | 52.20 | AAAA |
| ATOM | 17 | CB | VAL | 4 | 42.501 | 41.365 | 69.887 | 1.00 | 51.46 | AAAA |
| ATOM | 18 | CG1 | VAL | 4 | 41.214 | 41.202 | 69.066 | 1.00 | 56.35 | AAAA |
| ATOM | 19 | CG2 | VAL | 4 | 42.244 | 41.080 | 71.348 | 1.00 | 54.98 | AAAA |
| ATOM | 20 | C | VAL | 4 | 43.983 | 40.851 | 67.961 | 1.00 | 55.33 | AAAA |
| ATOM | 21 | O | VAL | 4 | 44.557 | 41.927 | 67.778 | 1.00 | 51.19 | AAAA |
| ATOM | 22 | N | LYS | 5 | 43.654 | 40.023 | 66.978 | 1.00 | 51.82 | AAAA |
| ATOM | 23 | CA | LYS | 5 | 44.052 | 40.291 | 65.607 | 1.00 | 50.10 | AAAA |
| ATOM | 24 | CB | LYS | 5 | 45.047 | 39.214 | 65.177 | 1.00 | 53.35 | AAAA |
| ATOM | 25 | CG | LYS | 5 | 46.331 | 39.092 | 66.049 | 1.00 | 53.75 | AAAA |
| ATOM | 26 | CD | LYS | 5 | 47.183 | 40.334 | 65.919 | 1.00 | 53.70 | AAAA |
| ATOM | 27 | CE | LYS | 5 | 48.510 | 40.151 | 66.669 | 1.00 | 54.34 | AAAA |
| ATOM | 28 | NZ | LYS | 5 | 49.351 | 41.387 | 66.585 | 1.00 | 58.04 | AAAA |
| ATOM | 29 | C | LYS | 5 | 42.914 | 40.294 | 64.596 | 1.00 | 50.27 | AAAA |
| ATOM | 30 | O | LYS | 5 | 41.949 | 39.535 | 64.728 | 1.00 | 48.48 | AAAA |
| ATOM | 31 | N | LEU | 6 | 43.071 | 41.111 | 63.564 | 1.00 | 49.28 | AAAA |
| ATOM | 32 | CA | LEU | 6 | 42.097 | 41.156 | 62.483 | 1.00 | 50.68 | AAAA |
| ATOM | 33 | CB | LEU | 6 | 41.571 | 42.574 | 62.291 | 1.00 | 53.51 | AAAA |
| ATOM | 34 | CG | LEU | 6 | 40.373 | 42.712 | 61.342 | 1.00 | 50.59 | AAAA |
| ATOM | 35 | CD1 | LEU | 6 | 40.079 | 44.192 | 61.153 | 1.00 | 49.90 | AAAA |
| ATOM | 36 | CD2 | LEU | 6 | 40.657 | 42.085 | 59.995 | 1.00 | 58.98 | AAAA |
| ATOM | 37 | C | LEU | 6 | 42.864 | 40.701 | 61.237 | 1.00 | 49.17 | AAAA |
| ATOM | 38 | O | LEU | 6 | 43.911 | 41.249 | 60.919 | 1.00 | 52.31 | AAAA |
| ATOM | 39 | N | ILE | 7 | 42.359 | 39.689 | 60.538 | 1.00 | 49.15 | AAAA |
| ATOM | 40 | CA | ILE | 7 | 43.045 | 39.199 | 59.338 | 1.00 | 48.36 | AAAA |
| ATOM | 41 | CB | ILE | 7 | 42.922 | 37.674 | 59.191 | 1.00 | 49.05 | AAAA |
| ATOM | 42 | CG2 | ILE | 7 | 43.930 | 37.162 | 58.144 | 1.00 | 56.45 | AAAA |
| ATOM | 43 | CG1 | ILE | 7 | 43.253 | 37.007 | 60.521 | 1.00 | 52.81 | AAAA |
| ATOM | 44 | CD1 | ILE | 7 | 43.086 | 35.543 | 60.450 | 1.00 | 54.99 | AAAA |
| ATOM | 45 | C | ILE | 7 | 42.396 | 39.850 | 58.125 | 1.00 | 57.95 | AAAA |
| ATOM | 46 | O | ILE | 7 | 41.188 | 39.729 | 57.928 | 1.00 | 49.07 | AAAA |
| ATOM | 47 | N | GLY | 8 | 43.183 | 40.562 | 57.330 | 1.00 | 57.70 | AAAA |
| ATOM | 48 | CA | GLY | 8 | 42.623 | 41.193 | 56.148 | 1.00 | 58.11 | AAAA |
| ATOM | 49 | C | GLY | 8 | 43.640 | 41.857 | 55.243 | 1.00 | 50.91 | AAAA |
| ATOM | 50 | O | GLY | 8 | 44.849 | 41.840 | 55.504 | 1.00 | 53.27 | AAAA |
| ATOM | 51 | N | THR | 9 | 43.134 | 42.428 | 54.155 | 1.00 | 53.99 | AAAA |
| ATOM | 52 | CA | THR | 9 | 43.950 | 43.141 | 53.183 | 1.00 | 55.95 | AAAA |
| ATOM | 53 | CB | THR | 9 | 44.739 | 42.295 | 52.263 | 1.00 | 55.80 | AAAA |
| ATOM | 54 | OG1 | THR | 9 | 45.321 | 42.962 | 51.199 | 1.00 | 56.56 | AAAA |
| ATOM | 55 | CG2 | THR | 9 | 43.823 | 41.144 | 51.657 | 1.00 | 55.04 | AAAA |
| ATOM | 56 | C | THR | 9 | 43.025 | 43.957 | 52.294 | 1.00 | 59.04 | AAAA |
| ATOM | 57 | O | THR | 9 | 41.872 | 43.582 | 52.082 | 1.00 | 53.05 | AAAA |
| ATOM | 58 | N | LEU | 10 | 43.517 | 45.079 | 51.781 | 1.00 | 59.19 | AAAA |
| ATOM | 59 | CA | LEU | 10 | 42.690 | 45.896 | 50.895 | 1.00 | 52.55 | AAAA |
| ATOM | 60 | CB | LEU | 10 | 43.256 | 47.319 | 50.761 | 1.00 | 58.09 | AAAA |
| ATOM | 61 | CG | LEU | 10 | 43.142 | 48.066 | 51.958 | 1.00 | 53.00 | AAAA |
| ATOM | 62 | CD1 | LEU | 10 | 41.680 | 48.403 | 52.347 | 1.00 | 56.65 | AAAA |
| ATOM | 63 | CD2 | LEU | 10 | 43.938 | 47.744 | 53.126 | 1.00 | 41.33 | AAAA |
| ATOM | 64 | C | LEU | 10 | 42.556 | 45.261 | 49.512 | 1.00 | 52.68 | AAAA |
| ATOM | 65 | O | LEU | 10 | 41.736 | 45.684 | 48.702 | 1.00 | 56.97 | AAAA |
| ATOM | 66 | N | ASP | 11 | 43.377 | 44.234 | 49.256 | 1.00 | 55.75 | AAAA |

Fig. 16-1

```
ATOM     67  CA  ASP    11      43.367  43.541  47.970  1.00 35.74      AAAA
ATOM     68  CB  ASP    11      44.477  42.485  47.922  1.00 37.61      AAAA
ATOM     69  CG  ASP    11      45.858  43.093  48.079  1.00 46.75      AAAA
ATOM     70  OD1 ASP    11      46.110  44.136  47.444  1.00 46.34      AAAA
ATOM     71  OD2 ASP    11      46.690  42.528  48.821  1.00 58.94      AAAA
ATOM     72  C   ASP    11      42.034  42.898  47.607  1.00 34.26      AAAA
ATOM     73  O   ASP    11      41.748  42.696  46.420  1.00 31.12      AAAA
ATOM     74  N   TYR    12      41.220  42.558  48.609  1.00 26.19      AAAA
ATOM     75  CA  TYR    12      39.923  41.963  48.314  1.00 28.45      AAAA
ATOM     76  CB  TYR    12      39.119  41.720  49.601  1.00 29.35      AAAA
ATOM     77  CG  TYR    12      39.648  40.595  50.470  1.00 28.47      AAAA
ATOM     78  CD1 TYR    12      40.137  40.846  51.755  1.00 32.17      AAAA
ATOM     79  CE1 TYR    12      40.592  39.808  52.572  1.00 30.35      AAAA
ATOM     80  CD2 TYR    12      39.629  39.276  50.017  1.00 22.97      AAAA
ATOM     81  CE2 TYR    12      40.077  38.228  50.822  1.00 19.60      AAAA
ATOM     82  CZ  TYR    12      40.554  38.499  52.096  1.00 21.42      AAAA
ATOM     83  OH  TYR    12      40.964  37.456  52.907  1.00 23.49      AAAA
ATOM     84  C   TYR    12      39.144  42.907  47.390  1.00 26.67      AAAA
ATOM     85  O   TYR    12      38.307  42.466  46.593  1.00 30.51      AAAA
ATOM     86  N   GLY    13      39.441  44.201  47.492  1.00 30.22      AAAA
ATOM     87  CA  GLY    13      38.767  45.203  46.675  1.00 25.13      AAAA
ATOM     88  C   GLY    13      38.911  45.009  45.177  1.00 27.31      AAAA
ATOM     89  O   GLY    13      38.096  45.522  44.415  1.00 29.38      AAAA
ATOM     90  N   LYS    14      39.937  44.269  44.755  1.00 33.56      AAAA
ATOM     91  CA  LYS    14      40.176  44.005  43.337  1.00 39.81      AAAA
ATOM     92  CB  LYS    14      41.680  44.026  43.031  1.00 51.10      AAAA
ATOM     93  CG  LYS    14      42.292  45.424  42.907  1.00 64.99      AAAA
ATOM     94  CD  LYS    14      41.757  46.218  41.692  1.00 72.74      AAAA
ATOM     95  CE  LYS    14      42.183  45.639  40.336  1.00 67.25      AAAA
ATOM     96  NZ  LYS    14      41.637  44.280  40.045  1.00 70.06      AAAA
ATOM     97  C   LYS    14      39.589  42.688  42.834  1.00 39.98      AAAA
ATOM     98  O   LYS    14      39.746  42.350  41.658  1.00 46.99      AAAA
ATOM     99  N   TYR    15      38.927  41.944  43.717  1.00 32.64      AAAA
ATOM    100  CA  TYR    15      38.318  40.655  43.355  1.00 41.01      AAAA
ATOM    101  CB  TYR    15      38.996  39.512  44.126  1.00 26.48      AAAA
ATOM    102  CG  TYR    15      40.496  39.571  44.033  1.00 34.97      AAAA
ATOM    103  CD1 TYR    15      41.289  39.401  45.167  1.00 43.28      AAAA
ATOM    104  CE1 TYR    15      42.677  39.548  45.106  1.00 36.05      AAAA
ATOM    105  CD2 TYR    15      41.127  39.879  42.827  1.00 40.78      AAAA
ATOM    106  CE2 TYR    15      42.508  40.027  42.755  1.00 37.13      AAAA
ATOM    107  CZ  TYR    15      43.275  39.865  43.899  1.00 36.87      AAAA
ATOM    108  OH  TYR    15      44.644  40.044  43.844  1.00 35.40      AAAA
ATOM    109  C   TYR    15      36.838  40.705  43.714  1.00 38.62      AAAA
ATOM    110  O   TYR    15      36.344  39.868  44.468  1.00 37.82      AAAA
ATOM    111  N   ARG    16      36.141  41.703  43.177  1.00 44.85      AAAA
ATOM    112  CA  ARG    16      34.716  41.890  43.431  1.00 45.75      AAAA
ATOM    113  CB  ARG    16      34.320  43.348  43.187  1.00 54.17      AAAA
ATOM    114  CG  ARG    16      35.170  44.399  43.875  1.00 66.77      AAAA
ATOM    115  CD  ARG    16      34.920  44.506  45.369  1.00 72.39      AAAA
ATOM    116  NE  ARG    16      35.649  45.646  45.923  1.00 85.39      AAAA
ATOM    117  CZ  ARG    16      35.489  46.906  45.518  1.00 81.94      AAAA
ATOM    118  NH1 ARG    16      34.624  47.197  44.554  1.00 80.19      AAAA
ATOM    119  NH2 ARG    16      36.205  47.878  46.069  1.00 85.46      AAAA
ATOM    120  C   ARG    16      33.915  41.029  42.460  1.00 43.50      AAAA
ATOM    121  O   ARG    16      34.400  40.667  41.385  1.00 38.62      AAAA
ATOM    122  N   TYR    17      32.689  40.692  42.833  1.00 32.68      AAAA
ATOM    123  CA  TYR    17      31.850  39.923  41.930  1.00 37.55      AAAA
ATOM    124  CB  TYR    17      30.662  39.306  42.672  1.00 41.05      AAAA
ATOM    125  CG  TYR    17      31.040  38.104  43.519  1.00 37.51      AAAA
ATOM    126  CD1 TYR    17      32.039  38.194  44.493  1.00 32.59      AAAA
ATOM    127  CE1 TYR    17      32.383  37.095  45.277  1.00 29.32      AAAA
ATOM    128  CD2 TYR    17      30.393  36.875  43.346  1.00 31.46      AAAA
ATOM    129  CE2 TYR    17      30.726  35.772  44.122  1.00 28.64      AAAA
ATOM    130  CZ  TYR    17      31.721  35.887  45.088  1.00 27.14      AAAA
ATOM    131  OH  TYR    17      32.044  34.807  45.881  1.00 21.73      AAAA
ATOM    132  C   TYR    17      31.380  40.871  40.836  1.00 40.97      AAAA
```

Fig. 16-2

| ATOM | 133 | O | TYR | 17 | 31.435 | 42.097 | 40.984 | 1.00 | 29.58 | AAAA |
|------|-----|-----|-----|----|--------|--------|--------|------|-------|------|
| ATOM | 134 | N | PRO | 18 | 30.904 | 40.321 | 39.722 | 1.00 | 41.02 | AAAA |
| ATOM | 135 | CD | PRO | 18 | 30.760 | 38.910 | 39.318 | 1.00 | 48.67 | AAAA |
| ATOM | 136 | CA | PRO | 18 | 30.459 | 41.197 | 38.649 | 1.00 | 49.35 | AAAA |
| ATOM | 137 | CB | PRO | 18 | 30.321 | 40.228 | 37.481 | 1.00 | 59.04 | AAAA |
| ATOM | 138 | CG | PRO | 18 | 29.756 | 39.017 | 38.179 | 1.00 | 54.15 | AAAA |
| ATOM | 139 | C | PRO | 18 | 29.178 | 41.982 | 38.864 | 1.00 | 54.97 | AAAA |
| ATOM | 140 | O | PRO | 18 | 28.457 | 41.823 | 39.850 | 1.00 | 46.85 | AAAA |
| ATOM | 141 | N | LYS | 19 | 28.961 | 42.868 | 37.904 | 1.00 | 60.87 | AAAA |
| ATOM | 142 | CA | LYS | 19 | 27.777 | 43.696 | 37.749 | 1.00 | 67.78 | AAAA |
| ATOM | 143 | CB | LYS | 19 | 27.155 | 43.278 | 36.425 | 1.00 | 73.26 | AAAA |
| ATOM | 144 | CG | LYS | 19 | 26.971 | 41.752 | 36.414 | 1.00 | 77.87 | AAAA |
| ATOM | 145 | CD | LYS | 19 | 26.276 | 41.166 | 35.209 | 1.00 | 81.01 | AAAA |
| ATOM | 146 | CE | LYS | 19 | 26.039 | 39.680 | 35.471 | 1.00 | 82.45 | AAAA |
| ATOM | 147 | NZ | LYS | 19 | 25.417 | 38.959 | 34.331 | 1.00 | 83.11 | AAAA |
| ATOM | 148 | C | LYS | 19 | 26.688 | 43.594 | 38.814 | 1.00 | 64.15 | AAAA |
| ATOM | 149 | O | LYS | 19 | 26.810 | 44.047 | 39.949 | 1.00 | 65.73 | AAAA |
| ATOM | 150 | N | ASN | 20 | 25.604 | 42.986 | 38.345 | 1.00 | 59.78 | AAAA |
| ATOM | 151 | CA | ASN | 20 | 24.353 | 42.703 | 39.025 | 1.00 | 59.91 | AAAA |
| ATOM | 152 | CB | ASN | 20 | 23.516 | 41.844 | 38.077 | 1.00 | 68.08 | AAAA |
| ATOM | 153 | CG | ASN | 20 | 22.108 | 42.355 | 37.907 | 1.00 | 78.73 | AAAA |
| ATOM | 154 | OD1 | ASN | 20 | 21.894 | 43.498 | 37.496 | 1.00 | 78.67 | AAAA |
| ATOM | 155 | ND2 | ASN | 20 | 21.132 | 41.505 | 38.211 | 1.00 | 83.22 | AAAA |
| ATOM | 156 | C | ASN | 20 | 24.474 | 41.977 | 40.361 | 1.00 | 53.35 | AAAA |
| ATOM | 157 | O | ASN | 20 | 23.611 | 42.112 | 41.234 | 1.00 | 59.92 | AAAA |
| ATOM | 158 | N | HIS | 21 | 25.543 | 41.206 | 40.511 | 1.00 | 44.23 | AAAA |
| ATOM | 159 | CA | HIS | 21 | 25.768 | 40.397 | 41.707 | 1.00 | 28.15 | AAAA |
| ATOM | 160 | CB | HIS | 21 | 27.088 | 39.639 | 41.570 | 1.00 | 31.84 | AAAA |
| ATOM | 161 | CG | HIS | 21 | 27.155 | 38.411 | 42.418 | 1.00 | 34.79 | AAAA |
| ATOM | 162 | CD2 | HIS | 21 | 27.344 | 38.259 | 43.752 | 1.00 | 25.03 | AAAA |
| ATOM | 163 | ND1 | HIS | 21 | 26.929 | 37.148 | 41.917 | 1.00 | 34.81 | AAAA |
| ATOM | 164 | CE1 | HIS | 21 | 26.979 | 36.269 | 42.900 | 1.00 | 17.01 | AAAA |
| ATOM | 165 | NE2 | HIS | 21 | 27.228 | 36.917 | 44.026 | 1.00 | 32.31 | AAAA |
| ATOM | 166 | C | HIS | 21 | 25.763 | 41.135 | 43.051 | 1.00 | 29.37 | AAAA |
| ATOM | 167 | O | HIS | 21 | 26.346 | 42.210 | 43.186 | 1.00 | 28.54 | AAAA |
| ATOM | 168 | N | PRO | 22 | 25.093 | 40.565 | 44.066 | 1.00 | 29.14 | AAAA |
| ATOM | 169 | CD | PRO | 22 | 24.301 | 39.322 | 44.061 | 1.00 | 31.20 | AAAA |
| ATOM | 170 | CA | PRO | 22 | 25.034 | 41.185 | 45.395 | 1.00 | 32.84 | AAAA |
| ATOM | 171 | CB | PRO | 22 | 24.174 | 40.192 | 46.187 | 1.00 | 34.98 | AAAA |
| ATOM | 172 | CG | PRO | 22 | 23.257 | 39.634 | 45.109 | 1.00 | 30.11 | AAAA |
| ATOM | 173 | C | PRO | 22 | 26.411 | 41.415 | 46.044 | 1.00 | 34.37 | AAAA |
| ATOM | 174 | O | PRO | 22 | 26.554 | 42.272 | 46.916 | 1.00 | 29.17 | AAAA |
| ATOM | 175 | N | LEU | 23 | 27.415 | 40.644 | 45.629 | 1.00 | 29.22 | AAAA |
| ATOM | 176 | CA | LEU | 23 | 28.765 | 40.781 | 46.181 | 1.00 | 26.49 | AAAA |
| ATOM | 177 | CB | LEU | 23 | 29.414 | 39.397 | 46.332 | 1.00 | 22.30 | AAAA |
| ATOM | 178 | CG | LEU | 23 | 28.703 | 38.527 | 47.380 | 1.00 | 21.04 | AAAA |
| ATOM | 179 | CD1 | LEU | 23 | 29.307 | 37.113 | 47.410 | 1.00 | 19.35 | AAAA |
| ATOM | 180 | CD2 | LEU | 23 | 28.850 | 39.197 | 48.746 | 1.00 | 26.51 | AAAA |
| ATOM | 181 | C | LEU | 23 | 29.661 | 41.718 | 45.361 | 1.00 | 25.81 | AAAA |
| ATOM | 182 | O | LEU | 23 | 30.893 | 41.693 | 45.477 | 1.00 | 28.45 | AAAA |
| ATOM | 183 | N | LYS | 24 | 29.018 | 42.539 | 44.532 | 1.00 | 24.86 | AAAA |
| ATOM | 184 | CA | LYS | 24 | 29.696 | 43.552 | 43.723 | 1.00 | 27.35 | AAAA |
| ATOM | 185 | CB | LYS | 24 | 28.662 | 44.244 | 42.830 | 1.00 | 28.57 | AAAA |
| ATOM | 186 | CG | LYS | 24 | 29.118 | 45.532 | 42.171 | 1.00 | 52.95 | AAAA |
| ATOM | 187 | CD | LYS | 24 | 28.025 | 46.603 | 42.283 | 1.00 | 63.74 | AAAA |
| ATOM | 188 | CE | LYS | 24 | 26.688 | 46.138 | 41.706 | 1.00 | 66.09 | AAAA |
| ATOM | 189 | NZ | LYS | 24 | 25.595 | 47.137 | 41.896 | 1.00 | 66.00 | AAAA |
| ATOM | 190 | C | LYS | 24 | 30.332 | 44.592 | 44.676 | 1.00 | 29.52 | AAAA |
| ATOM | 191 | O | LYS | 24 | 31.412 | 45.123 | 44.420 | 1.00 | 30.67 | AAAA |
| ATOM | 192 | N | ILE | 25 | 29.652 | 44.879 | 45.779 | 1.00 | 26.90 | AAAA |
| ATOM | 193 | CA | ILE | 25 | 30.151 | 45.865 | 46.738 | 1.00 | 25.02 | AAAA |
| ATOM | 194 | CB | ILE | 25 | 29.105 | 46.177 | 47.824 | 1.00 | 28.34 | AAAA |
| ATOM | 195 | CG2 | ILE | 25 | 27.961 | 46.951 | 47.237 | 1.00 | 23.84 | AAAA |
| ATOM | 196 | CG1 | ILE | 25 | 28.661 | 44.869 | 48.495 | 1.00 | 30.31 | AAAA |
| ATOM | 197 | CD1 | ILE | 25 | 27.718 | 45.051 | 49.660 | 1.00 | 44.90 | AAAA |
| ATOM | 198 | C | ILE | 25 | 31.424 | 45.463 | 47.483 | 1.00 | 32.19 | AAAA |

Fig. 16-3

| | | | | | | | | | | |
|---|---|---|---|---|---|---|---|---|---|---|
| ATOM | 199 | O | ILE | 25 | 31.736 | 44.271 | 47.623 | 1.00 | 26.54 | AAAA |
| ATOM | 200 | N | PRO | 26 | 32.191 | 46.463 | 47.956 | 1.00 | 30.14 | AAAA |
| ATOM | 201 | CD | PRO | 26 | 31.979 | 47.907 | 47.770 | 1.00 | 36.38 | AAAA |
| ATOM | 202 | CA | PRO | 26 | 33.431 | 46.241 | 48.707 | 1.00 | 30.63 | AAAA |
| ATOM | 203 | CB | PRO | 26 | 34.014 | 47.652 | 48.814 | 1.00 | 34.29 | AAAA |
| ATOM | 204 | CG | PRO | 26 | 33.397 | 48.373 | 47.617 | 1.00 | 43.39 | AAAA |
| ATOM | 205 | C | PRO | 26 | 32.943 | 45.727 | 50.061 | 1.00 | 25.99 | AAAA |
| ATOM | 206 | O | PRO | 26 | 31.854 | 46.110 | 50.484 | 1.00 | 25.51 | AAAA |
| ATOM | 207 | N | ARG | 27 | 33.719 | 44.860 | 50.743 | 1.00 | 21.98 | AAAA |
| ATOM | 208 | CA | ARG | 27 | 33.267 | 44.347 | 52.035 | 1.00 | 26.17 | AAAA |
| ATOM | 209 | CB | ARG | 27 | 32.641 | 42.969 | 51.834 | 1.00 | 22.70 | AAAA |
| ATOM | 210 | CG | ARG | 27 | 31.442 | 43.039 | 50.890 | 1.00 | 26.75 | AAAA |
| ATOM | 211 | CD | ARG | 27 | 30.832 | 41.672 | 50.581 | 1.00 | 33.22 | AAAA |
| ATOM | 212 | NE | ARG | 27 | 30.121 | 41.098 | 51.716 | 1.00 | 28.66 | AAAA |
| ATOM | 213 | CZ | ARG | 27 | 30.582 | 40.129 | 52.503 | 1.00 | 31.79 | AAAA |
| ATOM | 214 | NH1 | ARG | 27 | 31.778 | 39.598 | 52.290 | 1.00 | 34.08 | AAAA |
| ATOM | 215 | NH2 | ARG | 27 | 29.833 | 39.688 | 53.505 | 1.00 | 26.16 | AAAA |
| ATOM | 216 | C | ARG | 27 | 34.358 | 44.297 | 53.090 | 1.00 | 24.10 | AAAA |
| ATOM | 217 | O | ARG | 27 | 34.326 | 45.074 | 54.038 | 1.00 | 23.50 | AAAA |
| ATOM | 218 | N | VAL | 28 | 35.314 | 43.390 | 52.960 | 1.00 | 21.45 | AAAA |
| ATOM | 219 | CA | VAL | 28 | 36.385 | 43.385 | 53.953 | 1.00 | 21.75 | AAAA |
| ATOM | 220 | CB | VAL | 28 | 37.221 | 42.101 | 53.866 | 1.00 | 26.55 | AAAA |
| ATOM | 221 | CG1 | VAL | 28 | 38.407 | 42.177 | 54.830 | 1.00 | 23.84 | AAAA |
| ATOM | 222 | CG2 | VAL | 28 | 36.337 | 40.906 | 54.214 | 1.00 | 19.20 | AAAA |
| ATOM | 223 | C | VAL | 28 | 37.277 | 44.611 | 53.736 | 1.00 | 20.86 | AAAA |
| ATOM | 224 | O | VAL | 28 | 37.770 | 45.223 | 54.702 | 1.00 | 25.15 | AAAA |
| ATOM | 225 | N | SER | 29 | 37.480 | 44.996 | 52.475 | 1.00 | 19.22 | AAAA |
| ATOM | 226 | CA | SER | 29 | 38.320 | 46.169 | 52.209 | 1.00 | 19.63 | AAAA |
| ATOM | 227 | CB | SER | 29 | 38.591 | 46.352 | 50.702 | 1.00 | 24.45 | AAAA |
| ATOM | 228 | OG | SER | 29 | 37.411 | 46.697 | 49.984 | 1.00 | 28.74 | AAAA |
| ATOM | 229 | C | SER | 29 | 37.579 | 47.381 | 52.756 | 1.00 | 21.50 | AAAA |
| ATOM | 230 | O | SER | 29 | 38.184 | 48.320 | 53.271 | 1.00 | 18.95 | AAAA |
| ATOM | 231 | N | LEU | 30 | 36.256 | 47.353 | 52.673 | 1.00 | 19.56 | AAAA |
| ATOM | 232 | CA | LEU | 30 | 35.499 | 48.481 | 53.177 | 1.00 | 25.97 | AAAA |
| ATOM | 233 | CB | LEU | 30 | 34.032 | 48.396 | 52.744 | 1.00 | 22.90 | AAAA |
| ATOM | 234 | CG | LEU | 30 | 33.085 | 49.541 | 53.157 | 1.00 | 26.62 | AAAA |
| ATOM | 235 | CD1 | LEU | 30 | 32.885 | 49.539 | 54.648 | 1.00 | 38.27 | AAAA |
| ATOM | 236 | CD2 | LEU | 30 | 33.653 | 50.885 | 52.698 | 1.00 | 25.71 | AAAA |
| ATOM | 237 | C | LEU | 30 | 35.604 | 48.509 | 54.696 | 1.00 | 18.44 | AAAA |
| ATOM | 238 | O | LEU | 30 | 35.704 | 49.580 | 55.273 | 1.00 | 25.05 | AAAA |
| ATOM | 239 | N | LEU | 31 | 35.578 | 47.336 | 55.336 | 1.00 | 19.65 | AAAA |
| ATOM | 240 | CA | LEU | 31 | 35.672 | 47.270 | 56.797 | 1.00 | 20.47 | AAAA |
| ATOM | 241 | CB | LEU | 31 | 35.613 | 45.821 | 57.300 | 1.00 | 20.60 | AAAA |
| ATOM | 242 | CG | LEU | 31 | 34.988 | 45.456 | 58.665 | 1.00 | 39.80 | AAAA |
| ATOM | 243 | CD1 | LEU | 31 | 35.712 | 44.219 | 59.257 | 1.00 | 23.99 | AAAA |
| ATOM | 244 | CD2 | LEU | 31 | 35.085 | 46.591 | 59.637 | 1.00 | 28.48 | AAAA |
| ATOM | 245 | C | LEU | 31 | 37.009 | 47.870 | 57.229 | 1.00 | 23.85 | AAAA |
| ATOM | 246 | O | LEU | 31 | 37.070 | 48.673 | 58.154 | 1.00 | 21.24 | AAAA |
| ATOM | 247 | N | LEU | 32 | 38.079 | 47.462 | 56.562 | 1.00 | 23.91 | AAAA |
| ATOM | 248 | CA | LEU | 32 | 39.400 | 47.965 | 56.899 | 1.00 | 24.82 | AAAA |
| ATOM | 249 | CB | LEU | 32 | 40.479 | 47.320 | 56.018 | 1.00 | 24.81 | AAAA |
| ATOM | 250 | CG | LEU | 32 | 40.849 | 45.854 | 56.276 | 1.00 | 27.00 | AAAA |
| ATOM | 251 | CD1 | LEU | 32 | 41.995 | 45.435 | 55.354 | 1.00 | 27.13 | AAAA |
| ATOM | 252 | CD2 | LEU | 32 | 41.285 | 45.687 | 57.720 | 1.00 | 34.49 | AAAA |
| ATOM | 253 | C | LEU | 32 | 39.466 | 49.475 | 56.763 | 1.00 | 19.56 | AAAA |
| ATOM | 254 | O | LEU | 32 | 39.958 | 50.143 | 57.662 | 1.00 | 20.71 | AAAA |
| ATOM | 255 | N | ARG | 33 | 38.974 | 50.006 | 55.645 | 1.00 | 23.25 | AAAA |
| ATOM | 256 | CA | ARG | 33 | 39.007 | 51.449 | 55.441 | 1.00 | 24.33 | AAAA |
| ATOM | 257 | CB | ARG | 33 | 38.575 | 51.806 | 54.013 | 1.00 | 23.46 | AAAA |
| ATOM | 258 | CG | ARG | 33 | 39.571 | 51.327 | 52.945 | 1.00 | 26.94 | AAAA |
| ATOM | 259 | CD | ARG | 33 | 39.337 | 51.976 | 51.585 | 1.00 | 42.13 | AAAA |
| ATOM | 260 | NE | ARG | 33 | 38.023 | 51.661 | 51.037 | 1.00 | 59.06 | AAAA |
| ATOM | 261 | CZ | ARG | 33 | 37.583 | 52.088 | 49.857 | 1.00 | 60.87 | AAAA |
| ATOM | 262 | NH1 | ARG | 33 | 38.353 | 52.850 | 49.095 | 1.00 | 65.33 | AAAA |
| ATOM | 263 | NH2 | ARG | 33 | 36.373 | 51.743 | 49.433 | 1.00 | 56.24 | AAAA |
| ATOM | 264 | C | ARG | 33 | 38.124 | 52.156 | 56.455 | 1.00 | 30.33 | AAAA |

Fig. 16-4

```
ATOM  265  O    ARG  33   38.441  53.252  56.905  1.00  25.45      AAAA
ATOM  266  N    PHE  34   37.022  51.514  56.828  1.00  24.98      AAAA
ATOM  267  CA   PHE  34   36.099  52.085  57.789  1.00  27.09      AAAA
ATOM  268  CB   PHE  34   34.798  51.276  57.807  1.00  24.88      AAAA
ATOM  269  CG   PHE  34   33.719  51.898  58.631  1.00  20.46      AAAA
ATOM  270  CD1  PHE  34   33.043  53.018  58.171  1.00  18.74      AAAA
ATOM  271  CD2  PHE  34   33.396  51.383  59.889  1.00  20.19      AAAA
ATOM  272  CE1  PHE  34   32.043  53.627  58.956  1.00  23.04      AAAA
ATOM  273  CE2  PHE  34   32.406  51.974  60.681  1.00  25.08      AAAA
ATOM  274  CZ   PHE  34   31.726  53.104  60.209  1.00  23.31      AAAA
ATOM  275  C    PHE  34   36.709  52.115  59.194  1.00  23.93      AAAA
ATOM  276  O    PHE  34   36.668  53.138  59.883  1.00  21.71      AAAA
ATOM  277  N    LYS  35   37.298  51.013  59.645  1.00  21.33      AAAA
ATOM  278  CA   LYS  35   37.862  51.084  60.978  1.00  22.54      AAAA
ATOM  279  CB   LYS  35   38.276  49.716  61.476  1.00  29.70      AAAA
ATOM  280  CG   LYS  35   37.082  48.890  61.924  1.00  29.48      AAAA
ATOM  281  CD   LYS  35   37.517  47.535  62.398  1.00  42.17      AAAA
ATOM  282  CE   LYS  35   38.157  46.762  61.275  1.00  34.89      AAAA
ATOM  283  NZ   LYS  35   39.372  47.412  60.719  1.00  67.18      AAAA
ATOM  284  C    LYS  35   39.027  52.055  61.040  1.00  24.68      AAAA
ATOM  285  O    LYS  35   39.282  52.640  62.085  1.00  22.33      AAAA
ATOM  286  N    ASP  36   39.724  52.231  59.926  1.00  25.67      AAAA
ATOM  287  CA   ASP  36   40.842  53.163  59.898  1.00  25.57      AAAA
ATOM  288  CB   ASP  36   41.669  52.984  58.621  1.00  32.26      AAAA
ATOM  289  CG   ASP  36   42.881  53.914  58.572  1.00  33.92      AAAA
ATOM  290  OD1  ASP  36   43.641  53.969  59.563  1.00  40.22      AAAA
ATOM  291  OD2  ASP  36   43.078  54.575  57.538  1.00  40.06      AAAA
ATOM  292  C    ASP  36   40.285  54.578  59.973  1.00  28.04      AAAA
ATOM  293  O    ASP  36   40.761  55.397  60.765  1.00  29.52      AAAA
ATOM  294  N    ALA  37   39.272  54.864  59.159  1.00  23.32      AAAA
ATOM  295  CA   ALA  37   38.651  56.192  59.163  1.00  28.22      AAAA
ATOM  296  CB   ALA  37   37.506  56.251  58.119  1.00  25.93      AAAA
ATOM  297  C    ALA  37   38.127  56.549  60.565  1.00  28.41      AAAA
ATOM  298  O    ALA  37   38.186  57.708  60.972  1.00  29.27      AAAA
ATOM  299  N    MET  38   37.639  55.547  61.300  1.00  24.76      AAAA
ATOM  300  CA   MET  38   37.103  55.727  62.669  1.00  25.45      AAAA
ATOM  301  CB   MET  38   36.077  54.625  62.982  1.00  25.19      AAAA
ATOM  302  CG   MET  38   34.816  54.660  62.148  1.00  22.32      AAAA
ATOM  303  SD   MET  38   33.733  55.983  62.702  1.00  29.90      AAAA
ATOM  304  CE   MET  38   33.402  55.417  64.376  1.00  26.51      AAAA
ATOM  305  C    MET  38   38.203  55.667  63.744  1.00  26.42      AAAA
ATOM  306  O    MET  38   37.924  55.818  64.947  1.00  23.77      AAAA
ATOM  307  N    ASN  39   39.437  55.434  63.300  1.00  26.21      AAAA
ATOM  308  CA   ASN  39   40.607  55.308  64.170  1.00  28.53      AAAA
ATOM  309  CB   ASN  39   40.926  56.643  64.855  1.00  33.95      AAAA
ATOM  310  CG   ASN  39   41.153  57.751  63.858  1.00  29.46      AAAA
ATOM  311  OD1  ASN  39   41.930  57.596  62.925  1.00  36.28      AAAA
ATOM  312  ND2  ASN  39   40.472  58.880  64.046  1.00  40.03      AAAA
ATOM  313  C    ASN  39   40.374  54.223  65.205  1.00  30.07      AAAA
ATOM  314  O    ASN  39   40.682  54.390  66.395  1.00  25.47      AAAA
ATOM  315  N    LEU  40   39.814  53.105  64.744  1.00  28.19      AAAA
ATOM  316  CA   LEU  40   39.527  51.984  65.633  1.00  25.50      AAAA
ATOM  317  CB   LEU  40   38.060  51.562  65.514  1.00  32.14      AAAA
ATOM  318  CG   LEU  40   37.044  52.585  66.036  1.00  30.47      AAAA
ATOM  319  CD1  LEU  40   35.637  52.027  65.894  1.00  29.07      AAAA
ATOM  320  CD2  LEU  40   37.325  52.889  67.491  1.00  23.80      AAAA
ATOM  321  C    LEU  40   40.433  50.771  65.415  1.00  26.99      AAAA
ATOM  322  O    LEU  40   40.157  49.683  65.915  1.00  25.41      AAAA
ATOM  323  N    ILE  41   41.528  50.970  64.691  1.00  28.33      AAAA
ATOM  324  CA   ILE  41   42.459  49.882  64.459  1.00  25.08      AAAA
ATOM  325  CB   ILE  41   42.010  49.020  63.243  1.00  25.01      AAAA
ATOM  326  CG2  ILE  41   42.061  49.824  61.961  1.00  22.74      AAAA
ATOM  327  CG1  ILE  41   42.917  47.802  63.128  1.00  31.01      AAAA
ATOM  328  CD1  ILE  41   42.895  46.951  64.341  1.00  42.18      AAAA
ATOM  329  C    ILE  41   43.900  50.376  64.247  1.00  24.09      AAAA
ATOM  330  O    ILE  41   44.128  51.406  63.621  1.00  28.92      AAAA
```

Fig. 16-5

| | | | | | | | | | |
|---|---|---|---|---|---|---|---|---|---|
| ATOM | 331 | N | ASP | 42 | 44.866 | 49.634 | 64.787 | 1.00 28.95 | AAAA |
| ATOM | 332 | CA | ASP | 42 | 46.279 | 49.988 | 64.638 | 1.00 32.52 | AAAA |
| ATOM | 333 | CB | ASP | 42 | 46.951 | 50.094 | 66.007 | 1.00 34.24 | AAAA |
| ATOM | 334 | CG | ASP | 42 | 46.267 | 51.097 | 66.911 | 1.00 51.23 | AAAA |
| ATOM | 335 | OD1 | ASP | 42 | 46.079 | 52.250 | 66.467 | 1.00 50.19 | AAAA |
| ATOM | 336 | OD2 | ASP | 42 | 45.924 | 50.736 | 68.062 | 1.00 53.00 | AAAA |
| ATOM | 337 | C | ASP | 42 | 46.985 | 48.919 | 63.808 | 1.00 31.13 | AAAA |
| ATOM | 338 | O | ASP | 42 | 46.594 | 47.758 | 63.838 | 1.00 26.71 | AAAA |
| ATOM | 339 | N | GLU | 43 | 48.036 | 49.312 | 63.092 | 1.00 29.99 | AAAA |
| ATOM | 340 | CA | GLU | 43 | 48.793 | 48.392 | 62.240 | 1.00 31.34 | AAAA |
| ATOM | 341 | CB | GLU | 43 | 50.078 | 49.045 | 61.724 | 1.00 36.12 | AAAA |
| ATOM | 342 | CG | GLU | 43 | 49.886 | 50.118 | 60.676 | 1.00 52.72 | AAAA |
| ATOM | 343 | CD | GLU | 43 | 51.214 | 50.556 | 60.083 | 1.00 60.39 | AAAA |
| ATOM | 344 | OE1 | GLU | 43 | 51.928 | 49.688 | 59.536 | 1.00 70.32 | AAAA |
| ATOM | 345 | OE2 | GLU | 43 | 51.550 | 51.755 | 60.163 | 1.00 60.38 | AAAA |
| ATOM | 346 | C | GLU | 43 | 49.196 | 47.070 | 62.859 | 1.00 38.04 | AAAA |
| ATOM | 347 | O | GLU | 43 | 49.125 | 46.024 | 62.209 | 1.00 36.83 | AAAA |
| ATOM | 348 | N | LYS | 44 | 49.636 | 47.103 | 64.105 | 1.00 28.26 | AAAA |
| ATOM | 349 | CA | LYS | 44 | 50.084 | 45.879 | 64.740 | 1.00 32.71 | AAAA |
| ATOM | 350 | CB | LYS | 44 | 50.974 | 46.245 | 65.927 | 1.00 44.28 | AAAA |
| ATOM | 351 | CG | LYS | 44 | 52.211 | 47.007 | 65.418 | 1.00 59.37 | AAAA |
| ATOM | 352 | CD | LYS | 44 | 53.187 | 47.449 | 66.491 | 1.00 68.87 | AAAA |
| ATOM | 353 | CE | LYS | 44 | 54.373 | 48.167 | 65.849 | 1.00 67.21 | AAAA |
| ATOM | 354 | NZ | LYS | 44 | 55.361 | 48.648 | 66.850 | 1.00 74.00 | AAAA |
| ATOM | 355 | C | LYS | 44 | 48.982 | 44.889 | 65.115 | 1.00 26.75 | AAAA |
| ATOM | 356 | O | LYS | 44 | 49.265 | 43.792 | 65.586 | 1.00 27.37 | AAAA |
| ATOM | 357 | N | GLU | 45 | 47.731 | 45.278 | 64.881 | 1.00 29.20 | AAAA |
| ATOM | 358 | CA | GLU | 45 | 46.580 | 44.414 | 65.165 | 1.00 21.58 | AAAA |
| ATOM | 359 | CB | GLU | 45 | 45.387 | 45.243 | 65.676 | 1.00 18.24 | AAAA |
| ATOM | 360 | CG | GLU | 45 | 45.551 | 45.828 | 67.077 | 1.00 26.57 | AAAA |
| ATOM | 361 | CD | GLU | 45 | 44.418 | 46.772 | 67.453 | 1.00 23.12 | AAAA |
| ATOM | 362 | OE1 | GLU | 45 | 44.224 | 47.783 | 66.746 | 1.00 21.64 | AAAA |
| ATOM | 363 | OE2 | GLU | 45 | 43.725 | 46.509 | 68.454 | 1.00 26.48 | AAAA |
| ATOM | 364 | C | GLU | 45 | 46.163 | 43.710 | 63.870 | 1.00 26.31 | AAAA |
| ATOM | 365 | O | GLU | 45 | 45.400 | 42.739 | 63.889 | 1.00 22.32 | AAAA |
| ATOM | 366 | N | LEU | 46 | 46.674 | 44.204 | 62.748 | 1.00 20.15 | AAAA |
| ATOM | 367 | CA | LEU | 46 | 46.317 | 43.642 | 61.448 | 1.00 25.80 | AAAA |
| ATOM | 368 | CB | LEU | 46 | 46.137 | 44.774 | 60.433 | 1.00 27.25 | AAAA |
| ATOM | 369 | CG | LEU | 46 | 45.763 | 44.397 | 58.997 | 1.00 37.72 | AAAA |
| ATOM | 370 | CD1 | LEU | 46 | 44.356 | 43.810 | 58.984 | 1.00 39.46 | AAAA |
| ATOM | 371 | CD2 | LEU | 46 | 45.822 | 45.632 | 58.101 | 1.00 35.43 | AAAA |
| ATOM | 372 | C | LEU | 46 | 47.305 | 42.623 | 60.896 | 1.00 28.88 | AAAA |
| ATOM | 373 | O | LEU | 46 | 48.513 | 42.860 | 60.862 | 1.00 31.98 | AAAA |
| ATOM | 374 | N | ILE | 47 | 46.791 | 41.469 | 60.482 | 1.00 16.92 | AAAA |
| ATOM | 375 | CA | ILE | 47 | 47.638 | 40.448 | 59.872 | 1.00 20.98 | AAAA |
| ATOM | 376 | CB | ILE | 47 | 47.412 | 39.046 | 60.513 | 1.00 21.51 | AAAA |
| ATOM | 377 | CG2 | ILE | 47 | 48.115 | 37.958 | 59.696 | 1.00 20.32 | AAAA |
| ATOM | 378 | CG1 | ILE | 47 | 47.947 | 39.040 | 61.950 | 1.00 20.71 | AAAA |
| ATOM | 379 | CD1 | ILE | 47 | 49.450 | 39.207 | 62.052 | 1.00 38.87 | AAAA |
| ATOM | 380 | C | ILE | 47 | 47.227 | 40.417 | 58.406 | 1.00 24.50 | AAAA |
| ATOM | 381 | O | ILE | 47 | 46.036 | 40.279 | 58.101 | 1.00 20.74 | AAAA |
| ATOM | 382 | N | LYS | 48 | 48.195 | 40.550 | 57.500 | 1.00 18.73 | AAAA |
| ATOM | 383 | CA | LYS | 48 | 47.883 | 40.543 | 56.072 | 1.00 15.55 | AAAA |
| ATOM | 384 | CB | LYS | 48 | 49.095 | 40.991 | 55.239 | 1.00 16.52 | AAAA |
| ATOM | 385 | CG | LYS | 48 | 48.836 | 41.011 | 53.738 | 1.00 23.25 | AAAA |
| ATOM | 386 | CD | LYS | 48 | 50.072 | 41.451 | 52.957 | 1.00 32.69 | AAAA |
| ATOM | 387 | CE | LYS | 48 | 49.796 | 41.496 | 51.462 | 1.00 26.00 | AAAA |
| ATOM | 388 | NZ | LYS | 48 | 48.704 | 42.449 | 51.114 | 1.00 46.33 | AAAA |
| ATOM | 389 | C | LYS | 48 | 47.473 | 39.140 | 55.629 | 1.00 14.43 | AAAA |
| ATOM | 390 | O | LYS | 48 | 48.177 | 38.174 | 55.887 | 1.00 16.83 | AAAA |
| ATOM | 391 | N | SER | 49 | 46.343 | 39.049 | 54.945 | 1.00 16.61 | AAAA |
| ATOM | 392 | CA | SER | 49 | 45.838 | 37.780 | 54.439 | 1.00 14.33 | AAAA |
| ATOM | 393 | CB | SER | 49 | 44.517 | 37.984 | 53.694 | 1.00 13.21 | AAAA |
| ATOM | 394 | OG | SER | 49 | 43.509 | 38.613 | 54.492 | 1.00 16.86 | AAAA |
| ATOM | 395 | C | SER | 49 | 46.810 | 37.131 | 53.459 | 1.00 24.11 | AAAA |
| ATOM | 396 | O | SER | 49 | 47.463 | 37.815 | 52.663 | 1.00 19.59 | AAAA |

Fig. 16-6

| | | | | | | | | | | |
|---|---|---|---|---|---|---|---|---|---|---|
| ATOM | 397 | N | ARG | 50 | 46.890 | 35.805 | 53.519 | 1.00 | 16.83 | AAAA |
| ATOM | 398 | CA | ARG | 50 | 47.724 | 35.037 | 52.610 | 1.00 | 23.88 | AAAA |
| ATOM | 399 | CB | ARG | 50 | 48.805 | 34.247 | 53.366 | 1.00 | 27.48 | AAAA |
| ATOM | 400 | CG | ARG | 50 | 48.284 | 33.036 | 54.177 | 1.00 | 22.99 | AAAA |
| ATOM | 401 | CD | ARG | 50 | 49.453 | 32.263 | 54.759 | 1.00 | 25.20 | AAAA |
| ATOM | 402 | NE | ARG | 50 | 49.073 | 31.197 | 55.684 | 1.00 | 15.88 | AAAA |
| ATOM | 403 | CZ | ARG | 50 | 48.411 | 30.093 | 55.368 | 1.00 | 14.34 | AAAA |
| ATOM | 404 | NH1 | ARG | 50 | 48.023 | 29.863 | 54.117 | 1.00 | 15.78 | AAAA |
| ATOM | 405 | NH2 | ARG | 50 | 48.150 | 29.197 | 56.312 | 1.00 | 16.78 | AAAA |
| ATOM | 406 | C | ARG | 50 | 46.821 | 34.023 | 51.905 | 1.00 | 20.20 | AAAA |
| ATOM | 407 | O | ARG | 50 | 45.763 | 33.650 | 52.414 | 1.00 | 18.63 | AAAA |
| ATOM | 408 | N | PRO | 51 | 47.203 | 33.596 | 50.699 | 1.00 | 15.63 | AAAA |
| ATOM | 409 | CD | PRO | 51 | 48.322 | 34.028 | 49.850 | 1.00 | 19.45 | AAAA |
| ATOM | 410 | CA | PRO | 51 | 46.387 | 32.606 | 49.994 | 1.00 | 14.35 | AAAA |
| ATOM | 411 | CB | PRO | 51 | 47.076 | 32.514 | 48.629 | 1.00 | 17.73 | AAAA |
| ATOM | 412 | CG | PRO | 51 | 47.707 | 33.890 | 48.475 | 1.00 | 17.62 | AAAA |
| ATOM | 413 | C | PRO | 51 | 46.452 | 31.256 | 50.708 | 1.00 | 15.73 | AAAA |
| ATOM | 414 | O | PRO | 51 | 47.460 | 30.942 | 51.350 | 1.00 | 18.67 | AAAA |
| ATOM | 415 | N | ALA | 52 | 45.377 | 30.470 | 50.618 | 1.00 | 11.47 | AAAA |
| ATOM | 416 | CA | ALA | 52 | 45.375 | 29.117 | 51.161 | 1.00 | 9.78 | AAAA |
| ATOM | 417 | CB | ALA | 52 | 43.967 | 28.529 | 51.112 | 1.00 | 12.19 | AAAA |
| ATOM | 418 | C | ALA | 52 | 46.301 | 28.342 | 50.209 | 1.00 | 17.19 | AAAA |
| ATOM | 419 | O | ALA | 52 | 46.307 | 28.609 | 49.006 | 1.00 | 16.46 | AAAA |
| ATOM | 420 | N | THR | 53 | 47.081 | 27.392 | 50.723 | 1.00 | 16.40 | AAAA |
| ATOM | 421 | CA | THR | 53 | 47.952 | 26.615 | 49.843 | 1.00 | 16.32 | AAAA |
| ATOM | 422 | CB | THR | 53 | 49.109 | 25.959 | 50.612 | 1.00 | 15.82 | AAAA |
| ATOM | 423 | OG1 | THR | 53 | 48.582 | 25.016 | 51.559 | 1.00 | 16.25 | AAAA |
| ATOM | 424 | CG2 | THR | 53 | 49.923 | 27.030 | 51.336 | 1.00 | 14.34 | AAAA |
| ATOM | 425 | C | THR | 53 | 47.104 | 25.520 | 49.215 | 1.00 | 14.06 | AAAA |
| ATOM | 426 | O | THR | 53 | 46.012 | 25.241 | 49.690 | 1.00 | 17.87 | AAAA |
| ATOM | 427 | N | LYS | 54 | 47.599 | 24.903 | 48.145 | 1.00 | 16.10 | AAAA |
| ATOM | 428 | CA | LYS | 54 | 46.848 | 23.832 | 47.492 | 1.00 | 19.00 | AAAA |
| ATOM | 429 | CB | LYS | 54 | 47.671 | 23.245 | 46.339 | 1.00 | 22.92 | AAAA |
| ATOM | 430 | CG | LYS | 54 | 46.955 | 22.172 | 45.539 | 1.00 | 32.99 | AAAA |
| ATOM | 431 | CD | LYS | 54 | 45.787 | 22.733 | 44.757 | 1.00 | 51.34 | AAAA |
| ATOM | 432 | CE | LYS | 54 | 46.244 | 23.565 | 43.561 | 1.00 | 64.17 | AAAA |
| ATOM | 433 | NZ | LYS | 54 | 46.898 | 22.733 | 42.505 | 1.00 | 63.45 | AAAA |
| ATOM | 434 | C | LYS | 54 | 46.554 | 22.738 | 48.520 | 1.00 | 22.48 | AAAA |
| ATOM | 435 | O | LYS | 54 | 45.463 | 22.158 | 48.555 | 1.00 | 19.97 | AAAA |
| ATOM | 436 | N | GLU | 55 | 47.536 | 22.465 | 49.364 | 1.00 | 25.65 | AAAA |
| ATOM | 437 | CA | GLU | 55 | 47.389 | 21.432 | 50.383 | 1.00 | 25.08 | AAAA |
| ATOM | 438 | CB | GLU | 55 | 48.718 | 21.241 | 51.116 | 1.00 | 25.40 | AAAA |
| ATOM | 439 | CG | GLU | 55 | 48.703 | 20.185 | 52.199 | 1.00 | 48.95 | AAAA |
| ATOM | 440 | CD | GLU | 55 | 50.106 | 19.821 | 52.673 | 1.00 | 64.21 | AAAA |
| ATOM | 441 | OE1 | GLU | 55 | 50.220 | 19.033 | 53.640 | 1.00 | 62.38 | AAAA |
| ATOM | 442 | OE2 | GLU | 55 | 51.093 | 20.311 | 52.073 | 1.00 | 58.22 | AAAA |
| ATOM | 443 | C | GLU | 55 | 46.273 | 21.773 | 51.362 | 1.00 | 18.91 | AAAA |
| ATOM | 444 | O | GLU | 55 | 45.489 | 20.908 | 51.723 | 1.00 | 17.43 | AAAA |
| ATOM | 445 | N | GLU | 56 | 46.196 | 23.029 | 51.786 | 1.00 | 16.80 | AAAA |
| ATOM | 446 | CA | GLU | 56 | 45.137 | 23.432 | 52.698 | 1.00 | 17.24 | AAAA |
| ATOM | 447 | CB | GLU | 56 | 45.399 | 24.855 | 53.204 | 1.00 | 16.15 | AAAA |
| ATOM | 448 | CG | GLU | 56 | 46.709 | 24.941 | 54.009 | 1.00 | 14.41 | AAAA |
| ATOM | 449 | CD | GLU | 56 | 47.087 | 26.354 | 54.358 | 1.00 | 20.17 | AAAA |
| ATOM | 450 | OE1 | GLU | 56 | 46.713 | 27.252 | 53.567 | 1.00 | 17.12 | AAAA |
| ATOM | 451 | OE2 | GLU | 56 | 47.773 | 26.564 | 55.394 | 1.00 | 18.23 | AAAA |
| ATOM | 452 | C | GLU | 56 | 43.781 | 23.313 | 52.000 | 1.00 | 15.95 | AAAA |
| ATOM | 453 | O | GLU | 56 | 42.799 | 22.869 | 52.599 | 1.00 | 17.82 | AAAA |
| ATOM | 454 | N | LEU | 57 | 43.722 | 23.691 | 50.725 | 1.00 | 17.53 | AAAA |
| ATOM | 455 | CA | LEU | 57 | 42.466 | 23.579 | 49.989 | 1.00 | 16.34 | AAAA |
| ATOM | 456 | CB | LEU | 57 | 42.591 | 24.177 | 48.586 | 1.00 | 13.86 | AAAA |
| ATOM | 457 | CG | LEU | 57 | 42.773 | 25.707 | 48.552 | 1.00 | 15.24 | AAAA |
| ATOM | 458 | CD1 | LEU | 57 | 42.923 | 26.182 | 47.101 | 1.00 | 19.30 | AAAA |
| ATOM | 459 | CD2 | LEU | 57 | 41.546 | 26.380 | 49.207 | 1.00 | 15.14 | AAAA |
| ATOM | 460 | C | LEU | 57 | 42.016 | 22.126 | 49.868 | 1.00 | 18.46 | AAAA |
| ATOM | 461 | O | LEU | 57 | 40.824 | 21.823 | 49.972 | 1.00 | 17.27 | AAAA |
| ATOM | 462 | N | LEU | 58 | 42.975 | 21.234 | 49.636 | 1.00 | 16.43 | AAAA |

Fig. 16-7

| | | | | | | | | | |
|---|---|---|---|---|---|---|---|---|---|
| ATOM | 463 | CA | LEU | 58 | 42.662 | 19.822 | 49.475 | 1.00 15.18 | AAAA |
| ATOM | 464 | CB | LEU | 58 | 43.788 | 19.113 | 48.727 | 1.00 16.09 | AAAA |
| ATOM | 465 | CG | LEU | 58 | 44.029 | 19.682 | 47.321 | 1.00 21.72 | AAAA |
| ATOM | 466 | CD1 | LEU | 58 | 45.221 | 18.982 | 46.680 | 1.00 31.92 | AAAA |
| ATOM | 467 | CD2 | LEU | 58 | 42.786 | 19.549 | 46.469 | 1.00 34.38 | AAAA |
| ATOM | 468 | C | LEU | 58 | 42.339 | 19.116 | 50.787 | 1.00 21.19 | AAAA |
| ATOM | 469 | O | LEU | 58 | 42.067 | 17.914 | 50.795 | 1.00 20.40 | AAAA |
| ATOM | 470 | N | LEU | 59 | 42.377 | 19.849 | 51.896 | 1.00 13.50 | AAAA |
| ATOM | 471 | CA | LEU | 59 | 41.958 | 19.261 | 53.173 | 1.00 15.58 | AAAA |
| ATOM | 472 | CB | LEU | 59 | 42.182 | 20.236 | 54.339 | 1.00 18.98 | AAAA |
| ATOM | 473 | CG | LEU | 59 | 43.619 | 20.537 | 54.774 | 1.00 22.57 | AAAA |
| ATOM | 474 | CD1 | LEU | 59 | 43.640 | 21.654 | 55.808 | 1.00 19.88 | AAAA |
| ATOM | 475 | CD2 | LEU | 59 | 44.255 | 19.253 | 55.339 | 1.00 26.71 | AAAA |
| ATOM | 476 | C | LEU | 59 | 40.446 | 18.979 | 53.043 | 1.00 17.55 | AAAA |
| ATOM | 477 | O | LEU | 59 | 39.897 | 18.112 | 53.724 | 1.00 18.02 | AAAA |
| ATOM | 478 | N | PHE | 60 | 39.766 | 19.737 | 52.179 | 1.00 14.64 | AAAA |
| ATOM | 479 | CA | PHE | 60 | 38.338 | 19.536 | 51.970 | 1.00 18.17 | AAAA |
| ATOM | 480 | CB | PHE | 60 | 37.519 | 20.694 | 52.557 | 1.00 18.80 | AAAA |
| ATOM | 481 | CG | PHE | 60 | 36.028 | 20.564 | 52.316 | 1.00 15.94 | AAAA |
| ATOM | 482 | CD1 | PHE | 60 | 35.320 | 19.476 | 52.817 | 1.00 19.98 | AAAA |
| ATOM | 483 | CD2 | PHE | 60 | 35.339 | 21.524 | 51.576 | 1.00 18.09 | AAAA |
| ATOM | 484 | CE1 | PHE | 60 | 33.947 | 19.338 | 52.587 | 1.00 18.72 | AAAA |
| ATOM | 485 | CE2 | PHE | 60 | 33.964 | 21.399 | 51.338 | 1.00 19.19 | AAAA |
| ATOM | 486 | CZ | PHE | 60 | 33.268 | 20.295 | 51.850 | 1.00 18.43 | AAAA |
| ATOM | 487 | C | PHE | 60 | 37.916 | 19.337 | 50.510 | 1.00 16.45 | AAAA |
| ATOM | 488 | O | PHE | 60 | 37.227 | 18.371 | 50.179 | 1.00 19.18 | AAAA |
| ATOM | 489 | N | HIS | 61 | 38.308 | 20.257 | 49.638 | 1.00 18.26 | AAAA |
| ATOM | 490 | CA | HIS | 61 | 37.913 | 20.163 | 48.235 | 1.00 14.47 | AAAA |
| ATOM | 491 | CB | HIS | 61 | 38.004 | 21.545 | 47.582 | 1.00 17.15 | AAAA |
| ATOM | 492 | CG | HIS | 61 | 36.968 | 22.494 | 48.084 | 1.00 14.20 | AAAA |
| ATOM | 493 | CD2 | HIS | 61 | 35.645 | 22.580 | 47.816 | 1.00 11.05 | AAAA |
| ATOM | 494 | ND1 | HIS | 61 | 37.237 | 23.477 | 49.012 | 1.00 23.25 | AAAA |
| ATOM | 495 | CE1 | HIS | 61 | 36.121 | 24.131 | 49.291 | 1.00 13.35 | AAAA |
| ATOM | 496 | NE2 | HIS | 61 | 35.143 | 23.606 | 48.579 | 1.00 21.07 | AAAA |
| ATOM | 497 | C | HIS | 61 | 38.695 | 19.157 | 47.417 | 1.00 18.29 | AAAA |
| ATOM | 498 | O | HIS | 61 | 39.828 | 18.819 | 47.761 | 1.00 17.50 | AAAA |
| ATOM | 499 | N | THR | 62 | 38.071 | 18.658 | 46.346 | 1.00 15.39 | AAAA |
| ATOM | 500 | CA | THR | 62 | 38.741 | 17.686 | 45.473 | 1.00 19.02 | AAAA |
| ATOM | 501 | CB | THR | 62 | 37.734 | 16.767 | 44.756 | 1.00 19.61 | AAAA |
| ATOM | 502 | OG1 | THR | 62 | 36.795 | 17.548 | 44.006 | 1.00 22.05 | AAAA |
| ATOM | 503 | CG2 | THR | 62 | 36.995 | 15.925 | 45.767 | 1.00 28.99 | AAAA |
| ATOM | 504 | C | THR | 62 | 39.595 | 18.398 | 44.440 | 1.00 23.22 | AAAA |
| ATOM | 505 | O | THR | 62 | 39.311 | 19.532 | 44.044 | 1.00 17.47 | AAAA |
| ATOM | 506 | N | GLU | 63 | 40.657 | 17.732 | 44.009 | 1.00 18.94 | AAAA |
| ATOM | 507 | CA | GLU | 63 | 41.571 | 18.324 | 43.046 | 1.00 22.44 | AAAA |
| ATOM | 508 | CB | GLU | 63 | 42.736 | 17.384 | 42.750 | 1.00 28.31 | AAAA |
| ATOM | 509 | CG | GLU | 63 | 43.885 | 17.476 | 43.708 | 1.00 60.37 | AAAA |
| ATOM | 510 | CD | GLU | 63 | 45.154 | 16.893 | 43.115 | 1.00 65.08 | AAAA |
| ATOM | 511 | OE1 | GLU | 63 | 45.603 | 17.407 | 42.065 | 1.00 66.44 | AAAA |
| ATOM | 512 | OE2 | GLU | 63 | 45.697 | 15.927 | 43.694 | 1.00 71.72 | AAAA |
| ATOM | 513 | C | GLU | 63 | 40.983 | 18.764 | 41.730 | 1.00 18.63 | AAAA |
| ATOM | 514 | O | GLU | 63 | 41.340 | 19.827 | 41.228 | 1.00 18.37 | AAAA |
| ATOM | 515 | N | ASP | 64 | 40.108 | 17.943 | 41.153 | 1.00 19.77 | AAAA |
| ATOM | 516 | CA | ASP | 64 | 39.508 | 18.277 | 39.864 | 1.00 17.88 | AAAA |
| ATOM | 517 | CB | ASP | 64 | 38.584 | 17.159 | 39.372 | 1.00 20.43 | AAAA |
| ATOM | 518 | CG | ASP | 64 | 37.429 | 16.884 | 40.330 | 1.00 42.71 | AAAA |
| ATOM | 519 | OD1 | ASP | 64 | 36.415 | 16.291 | 39.899 | 1.00 45.01 | AAAA |
| ATOM | 520 | OD2 | ASP | 64 | 37.537 | 17.243 | 41.521 | 1.00 51.77 | AAAA |
| ATOM | 521 | C | ASP | 64 | 38.701 | 19.582 | 39.964 | 1.00 21.90 | AAAA |
| ATOM | 522 | O | ASP | 64 | 38.726 | 20.410 | 39.042 | 1.00 17.35 | AAAA |
| ATOM | 523 | N | TYR | 65 | 37.980 | 19.750 | 41.072 | 1.00 16.17 | AAAA |
| ATOM | 524 | CA | TYR | 65 | 37.178 | 20.957 | 41.292 | 1.00 15.62 | AAAA |
| ATOM | 525 | CB | TYR | 65 | 36.258 | 20.796 | 42.529 | 1.00 12.04 | AAAA |
| ATOM | 526 | CG | TYR | 65 | 35.501 | 22.065 | 42.886 | 1.00 12.23 | AAAA |
| ATOM | 527 | CD1 | TYR | 65 | 34.699 | 22.718 | 41.940 | 1.00 14.73 | AAAA |
| ATOM | 528 | CE1 | TYR | 65 | 34.028 | 23.910 | 42.253 | 1.00 18.23 | AAAA |

Fig. 16-8

| | | | | | | | | | |
|---|---|---|---|---|---|---|---|---|---|
| ATOM | 529 | CD2 | TYR | 65 | 35.609 | 22.631 | 44.163 | 1.00 13.67 | AAAA |
| ATOM | 530 | CE2 | TYR | 65 | 34.943 | 23.824 | 44.486 | 1.00 18.16 | AAAA |
| ATOM | 531 | CZ | TYR | 65 | 34.162 | 24.461 | 43.533 | 1.00 16.88 | AAAA |
| ATOM | 532 | OH | TYR | 65 | 33.555 | 25.665 | 43.837 | 1.00 14.59 | AAAA |
| ATOM | 533 | C | TYR | 65 | 38.090 | 22.177 | 41.459 | 1.00 15.27 | AAAA |
| ATOM | 534 | O | TYR | 65 | 37.882 | 23.189 | 40.798 | 1.00 15.96 | AAAA |
| ATOM | 535 | N | ILE | 66 | 39.098 | 22.073 | 42.321 | 1.00 14.29 | AAAA |
| ATOM | 536 | CA | ILE | 66 | 40.022 | 23.179 | 42.540 | 1.00 18.86 | AAAA |
| ATOM | 537 | CB | ILE | 66 | 41.090 | 22.836 | 43.617 | 1.00 15.56 | AAAA |
| ATOM | 538 | CG2 | ILE | 66 | 42.152 | 23.943 | 43.698 | 1.00 20.45 | AAAA |
| ATOM | 539 | CG1 | ILE | 66 | 40.405 | 22.659 | 44.967 | 1.00 19.68 | AAAA |
| ATOM | 540 | CD1 | ILE | 66 | 39.717 | 23.948 | 45.454 | 1.00 29.11 | AAAA |
| ATOM | 541 | C | ILE | 66 | 40.716 | 23.519 | 41.236 | 1.00 25.20 | AAAA |
| ATOM | 542 | O | ILE | 66 | 40.809 | 24.692 | 40.895 | 1.00 14.60 | AAAA |
| ATOM | 543 | N | ASN | 67 | 41.190 | 22.508 | 40.498 | 1.00 18.21 | AAAA |
| ATOM | 544 | CA | ASN | 67 | 41.879 | 22.789 | 39.236 | 1.00 20.03 | AAAA |
| ATOM | 545 | CB | ASN | 67 | 42.448 | 21.523 | 38.580 | 1.00 21.73 | AAAA |
| ATOM | 546 | CG | ASN | 67 | 43.645 | 20.954 | 39.333 | 1.00 21.69 | AAAA |
| ATOM | 547 | OD1 | ASN | 67 | 44.293 | 21.645 | 40.110 | 1.00 23.97 | AAAA |
| ATOM | 548 | ND2 | ASN | 67 | 43.947 | 19.692 | 39.086 | 1.00 23.23 | AAAA |
| ATOM | 549 | C | ASN | 67 | 40.970 | 23.500 | 38.250 | 1.00 15.87 | AAAA |
| ATOM | 550 | O | ASN | 67 | 41.431 | 24.347 | 37.473 | 1.00 18.64 | AAAA |
| ATOM | 551 | N | THR | 68 | 39.681 | 23.180 | 38.295 | 1.00 16.55 | AAAA |
| ATOM | 552 | CA | THR | 68 | 38.729 | 23.814 | 37.400 | 1.00 20.34 | AAAA |
| ATOM | 553 | CB | THR | 68 | 37.360 | 23.114 | 37.441 | 1.00 22.99 | AAAA |
| ATOM | 554 | OG1 | THR | 68 | 37.511 | 21.760 | 36.978 | 1.00 21.75 | AAAA |
| ATOM | 555 | CG2 | THR | 68 | 36.378 | 23.827 | 36.536 | 1.00 17.37 | AAAA |
| ATOM | 556 | C | THR | 68 | 38.561 | 25.291 | 37.755 | 1.00 16.66 | AAAA |
| ATOM | 557 | O | THR | 68 | 38.472 | 26.139 | 36.871 | 1.00 18.79 | AAAA |
| ATOM | 558 | N | LEU | 69 | 38.534 | 25.604 | 39.045 | 1.00 14.82 | AAAA |
| ATOM | 559 | CA | LEU | 69 | 38.405 | 27.000 | 39.447 | 1.00 15.20 | AAAA |
| ATOM | 560 | CB | LEU | 69 | 38.295 | 27.126 | 40.973 | 1.00 16.87 | AAAA |
| ATOM | 561 | CG | LEU | 69 | 37.057 | 26.551 | 41.666 | 1.00 14.76 | AAAA |
| ATOM | 562 | CD1 | LEU | 69 | 37.212 | 26.643 | 43.179 | 1.00 16.81 | AAAA |
| ATOM | 563 | CD2 | LEU | 69 | 35.832 | 27.312 | 41.217 | 1.00 17.26 | AAAA |
| ATOM | 564 | C | LEU | 69 | 39.623 | 27.796 | 38.969 | 1.00 15.11 | AAAA |
| ATOM | 565 | O | LEU | 69 | 39.500 | 28.934 | 38.504 | 1.00 13.30 | AAAA |
| ATOM | 566 | N | MET | 70 | 40.803 | 27.204 | 39.090 | 1.00 13.40 | AAAA |
| ATOM | 567 | CA | MET | 70 | 42.019 | 27.894 | 38.659 | 1.00 16.97 | AAAA |
| ATOM | 568 | CB | MET | 70 | 43.254 | 27.114 | 39.075 | 1.00 14.87 | AAAA |
| ATOM | 569 | CG | MET | 70 | 43.335 | 26.886 | 40.582 | 1.00 15.18 | AAAA |
| ATOM | 570 | SD | MET | 70 | 44.828 | 25.954 | 41.060 | 1.00 28.71 | AAAA |
| ATOM | 571 | CE | MET | 70 | 46.051 | 27.228 | 40.893 | 1.00 21.19 | AAAA |
| ATOM | 572 | C | MET | 70 | 42.064 | 28.119 | 37.155 | 1.00 19.11 | AAAA |
| ATOM | 573 | O | MET | 70 | 42.498 | 29.170 | 36.700 | 1.00 17.10 | AAAA |
| ATOM | 574 | N | GLU | 71 | 41.648 | 27.118 | 36.389 | 1.00 15.06 | AAAA |
| ATOM | 575 | CA | GLU | 71 | 41.651 | 27.226 | 34.934 | 1.00 16.12 | AAAA |
| ATOM | 576 | CB | GLU | 71 | 41.397 | 25.856 | 34.305 | 1.00 16.12 | AAAA |
| ATOM | 577 | CG | GLU | 71 | 41.387 | 25.882 | 32.800 | 1.00 20.26 | AAAA |
| ATOM | 578 | CD | GLU | 71 | 42.782 | 25.920 | 32.193 | 1.00 32.31 | AAAA |
| ATOM | 579 | OE1 | GLU | 71 | 42.893 | 25.741 | 30.958 | 1.00 27.07 | AAAA |
| ATOM | 580 | OE2 | GLU | 71 | 43.762 | 26.117 | 32.941 | 1.00 24.85 | AAAA |
| ATOM | 581 | C | GLU | 71 | 40.580 | 28.208 | 34.466 | 1.00 16.48 | AAAA |
| ATOM | 582 | O | GLU | 71 | 40.831 | 29.066 | 33.611 | 1.00 17.20 | AAAA |
| ATOM | 583 | N | ALA | 72 | 39.380 | 28.097 | 35.027 | 1.00 15.68 | AAAA |
| ATOM | 584 | CA | ALA | 72 | 38.300 | 28.998 | 34.644 | 1.00 16.07 | AAAA |
| ATOM | 585 | CB | ALA | 72 | 37.035 | 28.669 | 35.425 | 1.00 17.21 | AAAA |
| ATOM | 586 | C | ALA | 72 | 38.678 | 30.453 | 34.897 | 1.00 19.07 | AAAA |
| ATOM | 587 | O | ALA | 72 | 38.448 | 31.326 | 34.054 | 1.00 15.92 | AAAA |
| ATOM | 588 | N | GLU | 73 | 39.260 | 30.726 | 36.062 | 1.00 15.86 | AAAA |
| ATOM | 589 | CA | GLU | 73 | 39.616 | 32.097 | 36.372 | 1.00 15.50 | AAAA |
| ATOM | 590 | CB | GLU | 73 | 40.046 | 32.210 | 37.828 | 1.00 14.12 | AAAA |
| ATOM | 591 | CG | GLU | 73 | 40.430 | 33.615 | 38.214 | 1.00 14.24 | AAAA |
| ATOM | 592 | CD | GLU | 73 | 40.961 | 33.699 | 39.629 | 1.00 17.23 | AAAA |
| ATOM | 593 | OE1 | GLU | 73 | 40.147 | 33.696 | 40.573 | 1.00 18.51 | AAAA |
| ATOM | 594 | OE2 | GLU | 73 | 42.201 | 33.753 | 39.793 | 1.00 20.88 | AAAA |

Fig. 16-9

| | | | | | | | | | | |
|---|---|---|---|---|---|---|---|---|---|---|
| ATOM | 595 | C | GLU | 73 | 40.706 | 32.709 | 35.495 | 1.00 | 20.36 | AAAA |
| ATOM | 596 | O | GLU | 73 | 40.527 | 33.806 | 34.948 | 1.00 | 17.74 | AAAA |
| ATOM | 597 | N | ARG | 74 | 41.832 | 32.020 | 35.344 | 1.00 | 21.57 | AAAA |
| ATOM | 598 | CA | ARG | 74 | 42.911 | 32.623 | 34.574 | 1.00 | 19.48 | AAAA |
| ATOM | 599 | CB | ARG | 74 | 44.256 | 31.912 | 34.834 | 1.00 | 18.48 | AAAA |
| ATOM | 600 | CG | ARG | 74 | 44.365 | 30.489 | 34.351 | 1.00 | 14.96 | AAAA |
| ATOM | 601 | CD | ARG | 74 | 45.723 | 29.892 | 34.745 | 1.00 | 15.05 | AAAA |
| ATOM | 602 | NE | ARG | 74 | 45.918 | 28.696 | 33.950 | 1.00 | 18.16 | AAAA |
| ATOM | 603 | CZ | ARG | 74 | 46.439 | 28.682 | 32.727 | 1.00 | 16.31 | AAAA |
| ATOM | 604 | NH1 | ARG | 74 | 46.843 | 29.811 | 32.145 | 1.00 | 19.74 | AAAA |
| ATOM | 605 | NH2 | ARG | 74 | 46.466 | 27.536 | 32.047 | 1.00 | 14.73 | AAAA |
| ATOM | 606 | C | ARG | 74 | 42.643 | 32.718 | 33.084 | 1.00 | 16.86 | AAAA |
| ATOM | 607 | O | ARG | 74 | 43.148 | 33.621 | 32.426 | 1.00 | 15.41 | AAAA |
| ATOM | 608 | N | CYS | 75 | 41.859 | 31.794 | 32.547 | 1.00 | 17.56 | AAAA |
| ATOM | 609 | CA | CYS | 75 | 41.544 | 31.833 | 31.115 | 1.00 | 18.24 | AAAA |
| ATOM | 610 | CB | CYS | 75 | 41.474 | 30.414 | 30.545 | 1.00 | 20.94 | AAAA |
| ATOM | 611 | SG | CYS | 75 | 43.047 | 29.514 | 30.572 | 1.00 | 19.30 | AAAA |
| ATOM | 612 | C | CYS | 75 | 40.216 | 32.561 | 30.898 | 1.00 | 15.81 | AAAA |
| ATOM | 613 | O | CYS | 75 | 39.762 | 32.748 | 29.762 | 1.00 | 17.79 | AAAA |
| ATOM | 614 | N | GLN | 76 | 39.601 | 32.959 | 32.007 | 1.00 | 15.63 | AAAA |
| ATOM | 615 | CA | GLN | 76 | 38.339 | 33.686 | 32.010 | 1.00 | 23.22 | AAAA |
| ATOM | 616 | CB | GLN | 76 | 38.595 | 35.122 | 31.530 | 1.00 | 22.99 | AAAA |
| ATOM | 617 | CG | GLN | 76 | 37.564 | 36.107 | 32.027 | 1.00 | 44.69 | AAAA |
| ATOM | 618 | CD | GLN | 76 | 37.588 | 36.229 | 33.535 | 1.00 | 47.78 | AAAA |
| ATOM | 619 | OE1 | GLN | 76 | 37.563 | 35.228 | 34.243 | 1.00 | 62.95 | AAAA |
| ATOM | 620 | NE2 | GLN | 76 | 37.619 | 37.452 | 34.033 | 1.00 | 45.96 | AAAA |
| ATOM | 621 | C | GLN | 76 | 37.304 | 32.975 | 31.135 | 1.00 | 23.43 | AAAA |
| ATOM | 622 | O | GLN | 76 | 36.826 | 33.512 | 30.125 | 1.00 | 19.93 | AAAA |
| ATOM | 623 | N | CYS | 77 | 36.951 | 31.754 | 31.521 | 1.00 | 15.97 | AAAA |
| ATOM | 624 | CA | CYS | 77 | 36.004 | 30.979 | 30.741 | 1.00 | 18.91 | AAAA |
| ATOM | 625 | CB | CYS | 77 | 36.738 | 30.225 | 29.623 | 1.00 | 24.64 | AAAA |
| ATOM | 626 | SG | CYS | 77 | 37.848 | 28.887 | 30.269 | 1.00 | 25.26 | AAAA |
| ATOM | 627 | C | CYS | 77 | 35.302 | 29.951 | 31.594 | 1.00 | 19.68 | AAAA |
| ATOM | 628 | O | CYS | 77 | 35.685 | 29.702 | 32.732 | 1.00 | 20.02 | AAAA |
| ATOM | 629 | N | VAL | 78 | 34.254 | 29.366 | 31.022 | 1.00 | 16.00 | AAAA |
| ATOM | 630 | CA | VAL | 78 | 33.531 | 28.288 | 31.671 | 1.00 | 18.73 | AAAA |
| ATOM | 631 | CB | VAL | 78 | 32.016 | 28.455 | 31.557 | 1.00 | 15.57 | AAAA |
| ATOM | 632 | CG1 | VAL | 78 | 31.312 | 27.304 | 32.262 | 1.00 | 21.27 | AAAA |
| ATOM | 633 | CG2 | VAL | 78 | 31.603 | 29.792 | 32.151 | 1.00 | 19.47 | AAAA |
| ATOM | 634 | C | VAL | 78 | 33.950 | 27.077 | 30.859 | 1.00 | 24.02 | AAAA |
| ATOM | 635 | O | VAL | 78 | 33.499 | 26.894 | 29.718 | 1.00 | 24.08 | AAAA |
| ATOM | 636 | N | PRO | 79 | 34.848 | 26.249 | 31.420 | 1.00 | 18.91 | AAAA |
| ATOM | 637 | CD | PRO | 79 | 35.470 | 26.341 | 32.756 | 1.00 | 17.70 | AAAA |
| ATOM | 638 | CA | PRO | 79 | 35.320 | 25.056 | 30.720 | 1.00 | 23.37 | AAAA |
| ATOM | 639 | CB | PRO | 79 | 36.295 | 24.432 | 31.732 | 1.00 | 21.92 | AAAA |
| ATOM | 640 | CG | PRO | 79 | 36.802 | 25.677 | 32.498 | 1.00 | 20.90 | AAAA |
| ATOM | 641 | C | PRO | 79 | 34.152 | 24.144 | 30.376 | 1.00 | 27.44 | AAAA |
| ATOM | 642 | O | PRO | 79 | 33.177 | 24.064 | 31.119 | 1.00 | 22.20 | AAAA |
| ATOM | 643 | N | LYS | 80 | 34.245 | 23.488 | 29.224 | 1.00 | 23.35 | AAAA |
| ATOM | 644 | CA | LYS | 80 | 33.212 | 22.570 | 28.775 | 1.00 | 26.78 | AAAA |
| ATOM | 645 | CB | LYS | 80 | 33.708 | 21.853 | 27.518 | 1.00 | 32.33 | AAAA |
| ATOM | 646 | CG | LYS | 80 | 35.098 | 21.256 | 27.680 | 1.00 | 51.34 | AAAA |
| ATOM | 647 | CD | LYS | 80 | 35.669 | 20.817 | 26.336 | 1.00 | 68.70 | AAAA |
| ATOM | 648 | CE | LYS | 80 | 37.131 | 20.401 | 26.451 | 1.00 | 70.04 | AAAA |
| ATOM | 649 | NZ | LYS | 80 | 37.688 | 19.949 | 25.141 | 1.00 | 73.72 | AAAA |
| ATOM | 650 | C | LYS | 80 | 32.875 | 21.571 | 29.875 | 1.00 | 24.71 | AAAA |
| ATOM | 651 | O | LYS | 80 | 33.770 | 20.957 | 30.458 | 1.00 | 24.23 | AAAA |
| ATOM | 652 | N | GLY | 81 | 31.582 | 21.431 | 30.161 | 1.00 | 16.74 | AAAA |
| ATOM | 653 | CA | GLY | 81 | 31.126 | 20.509 | 31.194 | 1.00 | 18.96 | AAAA |
| ATOM | 654 | C | GLY | 81 | 31.151 | 21.039 | 32.630 | 1.00 | 22.38 | AAAA |
| ATOM | 655 | O | GLY | 81 | 30.604 | 20.396 | 33.527 | 1.00 | 19.29 | AAAA |
| ATOM | 656 | N | ALA | 82 | 31.754 | 22.202 | 32.863 | 1.00 | 22.57 | AAAA |
| ATOM | 657 | CA | ALA | 82 | 31.858 | 22.738 | 34.235 | 1.00 | 20.65 | AAAA |
| ATOM | 658 | CB | ALA | 82 | 33.065 | 23.704 | 34.333 | 1.00 | 20.41 | AAAA |
| ATOM | 659 | C | ALA | 82 | 30.610 | 23.425 | 34.781 | 1.00 | 21.81 | AAAA |
| ATOM | 660 | O | ALA | 82 | 30.425 | 23.529 | 35.994 | 1.00 | 16.95 | AAAA |

Fig. 16-10

| | | | | | | | | | |
|---|---|---|---|---|---|---|---|---|---|
| ATOM | 661 | N | ARG | 83 | 29.758 | 23.926 | 33.897 | 1.00 17.68 | AAAA |
| ATOM | 662 | CA | ARG | 83 | 28.549 | 24.596 | 34.360 | 1.00 15.04 | AAAA |
| ATOM | 663 | CB | ARG | 83 | 27.777 | 25.188 | 33.176 | 1.00 21.02 | AAAA |
| ATOM | 664 | CG | ARG | 83 | 26.938 | 26.395 | 33.528 | 1.00 36.77 | AAAA |
| ATOM | 665 | CD | ARG | 83 | 26.061 | 26.167 | 34.729 | 1.00 41.28 | AAAA |
| ATOM | 666 | NE | ARG | 83 | 25.366 | 27.393 | 35.105 | 1.00 40.05 | AAAA |
| ATOM | 667 | CZ | ARG | 83 | 24.530 | 27.492 | 36.134 | 1.00 51.15 | AAAA |
| ATOM | 668 | NH1 | ARG | 83 | 24.286 | 26.432 | 36.893 | 1.00 55.10 | AAAA |
| ATOM | 669 | NH2 | ARG | 83 | 23.931 | 28.646 | 36.399 | 1.00 54.26 | AAAA |
| ATOM | 670 | C | ARG | 83 | 27.701 | 23.530 | 35.030 | 1.00 21.33 | AAAA |
| ATOM | 671 | O | ARG | 83 | 27.193 | 23.708 | 36.130 | 1.00 24.88 | AAAA |
| ATOM | 672 | N | GLU | 84 | 27.565 | 22.406 | 34.352 | 1.00 18.76 | AAAA |
| ATOM | 673 | CA | GLU | 84 | 26.768 | 21.299 | 34.859 | 1.00 24.12 | AAAA |
| ATOM | 674 | CB | GLU | 84 | 26.527 | 20.290 | 33.744 | 1.00 32.64 | AAAA |
| ATOM | 675 | CG | GLU | 84 | 27.769 | 19.994 | 32.925 | 1.00 37.91 | AAAA |
| ATOM | 676 | CD | GLU | 84 | 27.832 | 20.784 | 31.612 | 1.00 51.24 | AAAA |
| ATOM | 677 | OE1 | GLU | 84 | 27.585 | 20.152 | 30.545 | 1.00 24.82 | AAAA |
| ATOM | 678 | OE2 | GLU | 84 | 28.114 | 22.018 | 31.650 | 1.00 22.57 | AAAA |
| ATOM | 679 | C | GLU | 84 | 27.394 | 20.570 | 36.043 | 1.00 25.36 | AAAA |
| ATOM | 680 | O | GLU | 84 | 26.739 | 20.321 | 37.057 | 1.00 26.17 | AAAA |
| ATOM | 681 | N | LYS | 85 | 28.665 | 20.232 | 35.897 | 1.00 18.78 | AAAA |
| ATOM | 682 | CA | LYS | 85 | 29.399 | 19.497 | 36.915 | 1.00 20.03 | AAAA |
| ATOM | 683 | CB | LYS | 85 | 30.658 | 18.900 | 36.280 | 1.00 18.59 | AAAA |
| ATOM | 684 | CG | LYS | 85 | 31.603 | 18.223 | 37.268 | 1.00 35.69 | AAAA |
| ATOM | 685 | CD | LYS | 85 | 31.151 | 16.832 | 37.644 | 1.00 51.51 | AAAA |
| ATOM | 686 | CE | LYS | 85 | 31.451 | 15.864 | 36.520 | 1.00 59.18 | AAAA |
| ATOM | 687 | NZ | LYS | 85 | 32.914 | 15.858 | 36.240 | 1.00 56.63 | AAAA |
| ATOM | 688 | C | LYS | 85 | 29.811 | 20.263 | 38.181 | 1.00 18.31 | AAAA |
| ATOM | 689 | O | LYS | 85 | 29.696 | 19.738 | 39.290 | 1.00 21.65 | AAAA |
| ATOM | 690 | N | TYR | 86 | 30.274 | 21.495 | 38.012 | 1.00 19.45 | AAAA |
| ATOM | 691 | CA | TYR | 86 | 30.776 | 22.272 | 39.145 | 1.00 14.26 | AAAA |
| ATOM | 692 | CB | TYR | 86 | 32.207 | 22.692 | 38.840 | 1.00 14.95 | AAAA |
| ATOM | 693 | CG | TYR | 86 | 33.107 | 21.508 | 38.585 | 1.00 19.76 | AAAA |
| ATOM | 694 | CD1 | TYR | 86 | 33.384 | 20.591 | 39.601 | 1.00 18.83 | AAAA |
| ATOM | 695 | CE1 | TYR | 86 | 34.247 | 19.519 | 39.388 | 1.00 20.29 | AAAA |
| ATOM | 696 | CD2 | TYR | 86 | 33.711 | 21.322 | 37.337 | 1.00 18.14 | AAAA |
| ATOM | 697 | CE2 | TYR | 86 | 34.567 | 20.261 | 37.112 | 1.00 22.66 | AAAA |
| ATOM | 698 | CZ | TYR | 86 | 34.832 | 19.364 | 38.145 | 1.00 22.61 | AAAA |
| ATOM | 699 | OH | TYR | 86 | 35.680 | 18.317 | 37.921 | 1.00 23.68 | AAAA |
| ATOM | 700 | C | TYR | 86 | 29.967 | 23.493 | 39.526 | 1.00 19.03 | AAAA |
| ATOM | 701 | O | TYR | 86 | 30.353 | 24.226 | 40.450 | 1.00 19.18 | AAAA |
| ATOM | 702 | N | ASN | 87 | 28.873 | 23.721 | 38.803 | 1.00 17.59 | AAAA |
| ATOM | 703 | CA | ASN | 87 | 27.953 | 24.843 | 39.071 | 1.00 18.07 | AAAA |
| ATOM | 704 | CB | ASN | 87 | 27.413 | 24.730 | 40.514 | 1.00 23.87 | AAAA |
| ATOM | 705 | CG | ASN | 87 | 26.020 | 25.349 | 40.688 | 1.00 30.67 | AAAA |
| ATOM | 706 | OD1 | ASN | 87 | 25.531 | 25.520 | 41.819 | 1.00 31.55 | AAAA |
| ATOM | 707 | ND2 | ASN | 87 | 25.370 | 25.661 | 39.580 | 1.00 20.18 | AAAA |
| ATOM | 708 | C | ASN | 87 | 28.641 | 26.197 | 38.875 | 1.00 24.24 | AAAA |
| ATOM | 709 | O | ASN | 87 | 28.283 | 27.190 | 39.519 | 1.00 18.57 | AAAA |
| ATOM | 710 | N | ILE | 88 | 29.617 | 26.237 | 37.970 | 1.00 18.80 | AAAA |
| ATOM | 711 | CA | ILE | 88 | 30.353 | 27.471 | 37.680 | 1.00 18.55 | AAAA |
| ATOM | 712 | CB | ILE | 88 | 31.865 | 27.166 | 37.508 | 1.00 26.44 | AAAA |
| ATOM | 713 | CG2 | ILE | 88 | 32.613 | 28.406 | 37.044 | 1.00 43.71 | AAAA |
| ATOM | 714 | CG1 | ILE | 88 | 32.439 | 26.703 | 38.835 | 1.00 36.30 | AAAA |
| ATOM | 715 | CD1 | ILE | 88 | 32.295 | 27.735 | 39.888 | 1.00 24.08 | AAAA |
| ATOM | 716 | C | ILE | 88 | 29.887 | 28.142 | 36.392 | 1.00 14.36 | AAAA |
| ATOM | 717 | O | ILE | 88 | 29.584 | 27.459 | 35.426 | 1.00 21.93 | AAAA |
| ATOM | 718 | N | GLY | 89 | 29.843 | 29.473 | 36.380 | 1.00 18.71 | AAAA |
| ATOM | 719 | CA | GLY | 89 | 29.479 | 30.162 | 35.154 | 1.00 20.23 | AAAA |
| ATOM | 720 | C | GLY | 89 | 28.147 | 30.873 | 35.106 | 1.00 20.85 | AAAA |
| ATOM | 721 | O | GLY | 89 | 28.006 | 31.817 | 34.330 | 1.00 25.47 | AAAA |
| ATOM | 722 | N | GLY | 90 | 27.172 | 30.414 | 35.889 | 1.00 21.17 | AAAA |
| ATOM | 723 | CA | GLY | 90 | 25.863 | 31.060 | 35.898 | 1.00 24.44 | AAAA |
| ATOM | 724 | C | GLY | 90 | 25.862 | 32.371 | 36.668 | 1.00 30.60 | AAAA |
| ATOM | 725 | O | GLY | 90 | 26.900 | 32.788 | 37.168 | 1.00 28.13 | AAAA |
| ATOM | 726 | N | TYR | 91 | 24.708 | 33.036 | 36.755 | 1.00 23.38 | AAAA |

Fig. 16-11

```
ATOM    727  CA  TYR    91      24.598  34.299  37.490  1.00  28.48      AAAA
ATOM    728  CB  TYR    91      23.144  34.753  37.545  1.00  29.88      AAAA
ATOM    729  CG  TYR    91      22.923  35.899  38.518  1.00  33.88      AAAA
ATOM    730  CD1 TYR    91      23.329  37.197  38.207  1.00  39.69      AAAA
ATOM    731  CE1 TYR    91      23.130  38.250  39.104  1.00  31.76      AAAA
ATOM    732  CD2 TYR    91      22.317  35.678  39.759  1.00  40.63      AAAA
ATOM    733  CE2 TYR    91      22.115  36.720  40.664  1.00  37.07      AAAA
ATOM    734  CZ  TYR    91      22.521  38.002  40.327  1.00  36.22      AAAA
ATOM    735  OH  TYR    91      22.306  39.035  41.210  1.00  44.71      AAAA
ATOM    736  C   TYR    91      25.075  34.157  38.937  1.00  23.59      AAAA
ATOM    737  O   TYR    91      25.713  35.041  39.502  1.00  22.64      AAAA
ATOM    738  N   GLU    92      24.724  33.032  39.531  1.00  23.09      AAAA
ATOM    739  CA  GLU    92      25.048  32.747  40.917  1.00  26.61      AAAA
ATOM    740  CB  GLU    92      24.289  31.476  41.306  1.00  32.57      AAAA
ATOM    741  CG  GLU    92      24.595  30.892  42.657  1.00  41.38      AAAA
ATOM    742  CD  GLU    92      23.604  29.800  43.023  1.00  49.02      AAAA
ATOM    743  OE1 GLU    92      24.008  28.829  43.715  1.00  45.51      AAAA
ATOM    744  OE2 GLU    92      22.418  29.931  42.628  1.00  38.16      AAAA
ATOM    745  C   GLU    92      26.541  32.636  41.251  1.00  25.78      AAAA
ATOM    746  O   GLU    92      27.045  33.358  42.125  1.00  24.95      AAAA
ATOM    747  N   ASN    93      27.243  31.742  40.556  1.00  21.41      AAAA
ATOM    748  CA  ASN    93      28.674  31.519  40.777  1.00  21.14      AAAA
ATOM    749  CB  ASN    93      28.876  30.075  41.226  1.00  17.27      AAAA
ATOM    750  CG  ASN    93      27.905  29.682  42.320  1.00  15.34      AAAA
ATOM    751  OD1 ASN    93      27.882  30.290  43.399  1.00  20.33      AAAA
ATOM    752  ND2 ASN    93      27.078  28.674  42.047  1.00  20.49      AAAA
ATOM    753  C   ASN    93      29.378  31.778  39.445  1.00  22.25      AAAA
ATOM    754  O   ASN    93      29.901  30.865  38.806  1.00  20.29      AAAA
ATOM    755  N   PRO    94      29.451  33.057  39.045  1.00  25.45      AAAA
ATOM    756  CD  PRO    94      29.027  34.221  39.839  1.00  23.03      AAAA
ATOM    757  CA  PRO    94      30.055  33.523  37.794  1.00  23.05      AAAA
ATOM    758  CB  PRO    94      29.669  35.004  37.759  1.00  28.71      AAAA
ATOM    759  CG  PRO    94      28.528  35.112  38.755  1.00  40.02      AAAA
ATOM    760  C   PRO    94      31.554  33.384  37.697  1.00  26.51      AAAA
ATOM    761  O   PRO    94      32.232  33.185  38.688  1.00  17.36      AAAA
ATOM    762  N   VAL    95      32.068  33.498  36.478  1.00  21.12      AAAA
ATOM    763  CA  VAL    95      33.506  33.493  36.281  1.00  17.00      AAAA
ATOM    764  CB  VAL    95      33.851  33.242  34.796  1.00  25.15      AAAA
ATOM    765  CG1 VAL    95      35.326  33.537  34.533  1.00  27.19      AAAA
ATOM    766  CG2 VAL    95      33.551  31.791  34.443  1.00  17.37      AAAA
ATOM    767  C   VAL    95      33.989  34.899  36.686  1.00  17.42      AAAA
ATOM    768  O   VAL    95      33.426  35.894  36.237  1.00  23.43      AAAA
ATOM    769  N   SER    96      34.986  34.982  37.563  1.00  18.84      AAAA
ATOM    770  CA  SER    96      35.564  36.270  37.982  1.00  21.77      AAAA
ATOM    771  CB  SER    96      34.608  37.070  38.867  1.00  23.11      AAAA
ATOM    772  OG  SER    96      34.723  36.679  40.223  1.00  24.43      AAAA
ATOM    773  C   SER    96      36.835  35.987  38.789  1.00  29.09      AAAA
ATOM    774  O   SER    96      37.117  34.828  39.115  1.00  27.12      AAAA
ATOM    775  N   TYR    97      37.610  37.020  39.124  1.00  17.51      AAAA
ATOM    776  CA  TYR    97      38.803  36.751  39.911  1.00  20.69      AAAA
ATOM    777  CB  TYR    97      39.865  37.835  39.712  1.00  21.82      AAAA
ATOM    778  CG  TYR    97      40.492  37.748  38.332  1.00  22.72      AAAA
ATOM    779  CD1 TYR    97      39.936  38.414  37.235  1.00  28.47      AAAA
ATOM    780  CE1 TYR    97      40.473  38.265  35.949  1.00  24.45      AAAA
ATOM    781  CD2 TYR    97      41.599  36.929  38.112  1.00  19.74      AAAA
ATOM    782  CE2 TYR    97      42.144  36.771  36.832  1.00  21.63      AAAA
ATOM    783  CZ  TYR    97      41.578  37.439  35.759  1.00  23.13      AAAA
ATOM    784  OH  TYR    97      42.122  37.273  34.501  1.00  28.54      AAAA
ATOM    785  C   TYR    97      38.510  36.515  41.393  1.00  20.12      AAAA
ATOM    786  O   TYR    97      39.413  36.285  42.194  1.00  19.76      AAAA
ATOM    787  N   ALA    98      37.243  36.558  41.764  1.00  18.56      AAAA
ATOM    788  CA  ALA    98      36.899  36.259  43.139  1.00  22.23      AAAA
ATOM    789  CB  ALA    98      35.561  36.888  43.515  1.00  27.92      AAAA
ATOM    790  C   ALA    98      36.776  34.743  43.224  1.00  23.56      AAAA
ATOM    791  O   ALA    98      36.931  34.166  44.289  1.00  20.14      AAAA
ATOM    792  N   MET    99      36.538  34.094  42.087  1.00  16.84      AAAA
```

Fig. 16-12

| | | | | | | | | | |
|---|---|---|---|---|---|---|---|---|---|
| ATOM | 793 | CA | MET | 99 | 36.295 | 32.643 | 42.117 | 1.00 17.60 | AAAA |
| ATOM | 794 | CB | MET | 99 | 35.864 | 32.137 | 40.736 | 1.00 17.05 | AAAA |
| ATOM | 795 | CG | MET | 99 | 36.999 | 31.824 | 39.793 | 1.00 11.16 | AAAA |
| ATOM | 796 | SD | MET | 99 | 36.314 | 31.698 | 38.113 | 1.00 16.54 | AAAA |
| ATOM | 797 | CE | MET | 99 | 35.165 | 30.295 | 38.312 | 1.00 17.83 | AAAA |
| ATOM | 798 | C | MET | 99 | 37.432 | 31.800 | 42.650 | 1.00 18.98 | AAAA |
| ATOM | 799 | O | MET | 99 | 37.197 | 30.753 | 43.251 | 1.00 18.21 | AAAA |
| ATOM | 800 | N | PHE | 100 | 38.670 | 32.216 | 42.420 | 1.00 12.87 | AAAA |
| ATOM | 801 | CA | PHE | 100 | 39.774 | 31.439 | 42.987 | 1.00 17.13 | AAAA |
| ATOM | 802 | CB | PHE | 100 | 40.559 | 30.681 | 41.917 | 1.00 15.23 | AAAA |
| ATOM | 803 | CG | PHE | 100 | 41.647 | 29.834 | 42.492 | 1.00 15.20 | AAAA |
| ATOM | 804 | CD1 | PHE | 100 | 41.342 | 28.638 | 43.140 | 1.00 22.96 | AAAA |
| ATOM | 805 | CD2 | PHE | 100 | 42.972 | 30.282 | 42.488 | 1.00 17.12 | AAAA |
| ATOM | 806 | CE1 | PHE | 100 | 42.341 | 27.901 | 43.782 | 1.00 19.23 | AAAA |
| ATOM | 807 | CE2 | PHE | 100 | 43.974 | 29.552 | 43.129 | 1.00 16.99 | AAAA |
| ATOM | 808 | CZ | PHE | 100 | 43.658 | 28.360 | 43.779 | 1.00 17.78 | AAAA |
| ATOM | 809 | C | PHE | 100 | 40.755 | 32.305 | 43.774 | 1.00 20.54 | AAAA |
| ATOM | 810 | O | PHE | 100 | 41.088 | 31.990 | 44.912 | 1.00 21.45 | AAAA |
| ATOM | 811 | N | THR | 101 | 41.219 | 33.401 | 43.187 | 1.00 18.02 | AAAA |
| ATOM | 812 | CA | THR | 101 | 42.177 | 34.245 | 43.902 | 1.00 15.25 | AAAA |
| ATOM | 813 | CB | THR | 101 | 42.715 | 35.341 | 42.976 | 1.00 16.33 | AAAA |
| ATOM | 814 | OG1 | THR | 101 | 43.386 | 34.720 | 41.870 | 1.00 16.01 | AAAA |
| ATOM | 815 | CG2 | THR | 101 | 43.706 | 36.226 | 43.697 | 1.00 16.31 | AAAA |
| ATOM | 816 | C | THR | 101 | 41.567 | 34.860 | 45.160 | 1.00 14.12 | AAAA |
| ATOM | 817 | O | THR | 101 | 42.110 | 34.707 | 46.244 | 1.00 16.86 | AAAA |
| ATOM | 818 | N | GLY | 102 | 40.435 | 35.541 | 45.008 | 1.00 13.77 | AAAA |
| ATOM | 819 | CA | GLY | 102 | 39.770 | 36.145 | 46.156 | 1.00 16.29 | AAAA |
| ATOM | 820 | C | GLY | 102 | 39.330 | 35.065 | 47.133 | 1.00 16.75 | AAAA |
| ATOM | 821 | O | GLY | 102 | 39.502 | 35.202 | 48.338 | 1.00 14.48 | AAAA |
| ATOM | 822 | N | SER | 103 | 38.752 | 33.986 | 46.615 | 1.00 16.24 | AAAA |
| ATOM | 823 | CA | SER | 103 | 38.315 | 32.890 | 47.488 | 1.00 16.72 | AAAA |
| ATOM | 824 | CB | SER | 103 | 37.567 | 31.821 | 46.684 | 1.00 15.97 | AAAA |
| ATOM | 825 | OG | SER | 103 | 36.339 | 32.349 | 46.197 | 1.00 26.86 | AAAA |
| ATOM | 826 | C | SER | 103 | 39.494 | 32.264 | 48.218 | 1.00 17.88 | AAAA |
| ATOM | 827 | O | SER | 103 | 39.405 | 31.974 | 49.419 | 1.00 14.17 | AAAA |
| ATOM | 828 | N | SER | 104 | 40.604 | 32.057 | 47.515 | 1.00 11.40 | AAAA |
| ATOM | 829 | CA | SER | 104 | 41.780 | 31.484 | 48.181 | 1.00 17.61 | AAAA |
| ATOM | 830 | CB | SER | 104 | 42.888 | 31.206 | 47.160 | 1.00 15.89 | AAAA |
| ATOM | 831 | OG | SER | 104 | 42.525 | 30.102 | 46.362 | 1.00 27.82 | AAAA |
| ATOM | 832 | C | SER | 104 | 42.332 | 32.404 | 49.271 | 1.00 17.02 | AAAA |
| ATOM | 833 | O | SER | 104 | 42.867 | 31.958 | 50.286 | 1.00 15.37 | AAAA |
| ATOM | 834 | N | LEU | 105 | 42.206 | 33.698 | 49.052 | 1.00 17.10 | AAAA |
| ATOM | 835 | CA | LEU | 105 | 42.709 | 34.652 | 50.016 | 1.00 16.95 | AAAA |
| ATOM | 836 | CB | LEU | 105 | 42.728 | 36.037 | 49.365 | 1.00 18.44 | AAAA |
| ATOM | 837 | CG | LEU | 105 | 43.613 | 37.108 | 49.981 | 1.00 29.88 | AAAA |
| ATOM | 838 | CD1 | LEU | 105 | 45.086 | 36.631 | 49.959 | 1.00 20.25 | AAAA |
| ATOM | 839 | CD2 | LEU | 105 | 43.438 | 38.418 | 49.175 | 1.00 29.39 | AAAA |
| ATOM | 840 | C | LEU | 105 | 41.837 | 34.637 | 51.282 | 1.00 14.81 | AAAA |
| ATOM | 841 | O | LEU | 105 | 42.334 | 34.703 | 52.404 | 1.00 17.74 | AAAA |
| ATOM | 842 | N | ALA | 106 | 40.532 | 34.531 | 51.095 | 1.00 19.28 | AAAA |
| ATOM | 843 | CA | ALA | 106 | 39.601 | 34.493 | 52.224 | 1.00 12.39 | AAAA |
| ATOM | 844 | CB | ALA | 106 | 38.140 | 34.574 | 51.704 | 1.00 11.58 | AAAA |
| ATOM | 845 | C | ALA | 106 | 39.807 | 33.210 | 53.023 | 1.00 14.79 | AAAA |
| ATOM | 846 | O | ALA | 106 | 39.704 | 33.203 | 54.250 | 1.00 13.58 | AAAA |
| ATOM | 847 | N | THR | 107 | 40.114 | 32.128 | 52.318 | 1.00 13.67 | AAAA |
| ATOM | 848 | CA | THR | 107 | 40.314 | 30.819 | 52.956 | 1.00 13.21 | AAAA |
| ATOM | 849 | CB | THR | 107 | 40.187 | 29.708 | 51.902 | 1.00 14.95 | AAAA |
| ATOM | 850 | OG1 | THR | 107 | 38.868 | 29.792 | 51.334 | 1.00 15.72 | AAAA |
| ATOM | 851 | CG2 | THR | 107 | 40.422 | 28.311 | 52.511 | 1.00 9.51 | AAAA |
| ATOM | 852 | C | THR | 107 | 41.649 | 30.751 | 53.687 | 1.00 15.80 | AAAA |
| ATOM | 853 | O | THR | 107 | 41.734 | 30.206 | 54.792 | 1.00 15.63 | AAAA |
| ATOM | 854 | N | GLY | 108 | 42.696 | 31.294 | 53.082 | 1.00 14.08 | AAAA |
| ATOM | 855 | CA | GLY | 108 | 43.368 | 31.298 | 53.765 | 1.00 14.62 | AAAA |
| ATOM | 856 | C | GLY | 108 | 43.801 | 32.119 | 55.041 | 1.00 20.05 | AAAA |
| ATOM | 857 | O | GLY | 108 | 44.417 | 31.813 | 56.063 | 1.00 17.53 | AAAA |
| ATOM | 858 | N | SER | 109 | 42.963 | 33.158 | 54.988 | 1.00 15.26 | AAAA |

Fig. 16-13

| | | | | | | | | | |
|---|---|---|---|---|---|---|---|---|---|
| ATOM | 859 | CA | SER | 109 | 42.727 | 34.020 | 56.153 | 1.00 14.54 | AAAA |
| ATOM | 860 | CB | SER | 109 | 41.906 | 35.248 | 55.737 | 1.00 15.58 | AAAA |
| ATOM | 861 | OG | SER | 109 | 42.627 | 36.045 | 54.809 | 1.00 16.97 | AAAA |
| ATOM | 862 | C | SER | 109 | 42.037 | 33.264 | 57.297 | 1.00 15.56 | AAAA |
| ATOM | 863 | O | SER | 109 | 42.189 | 33.600 | 58.487 | 1.00 17.00 | AAAA |
| ATOM | 864 | N | THR | 110 | 41.261 | 32.247 | 56.944 | 1.00 14.37 | AAAA |
| ATOM | 865 | CA | THR | 110 | 40.608 | 31.435 | 57.957 | 1.00 12.89 | AAAA |
| ATOM | 866 | CB | THR | 110 | 39.452 | 30.628 | 57.360 | 1.00 14.54 | AAAA |
| ATOM | 867 | OG1 | THR | 110 | 38.346 | 31.519 | 57.163 | 1.00 18.11 | AAAA |
| ATOM | 868 | CG2 | THR | 110 | 39.061 | 29.452 | 58.278 | 1.00 12.91 | AAAA |
| ATOM | 869 | C | THR | 110 | 41.633 | 30.524 | 58.601 | 1.00 18.44 | AAAA |
| ATOM | 870 | O | THR | 110 | 41.574 | 30.302 | 59.806 | 1.00 16.30 | AAAA |
| ATOM | 871 | N | VAL | 111 | 42.584 | 30.013 | 57.816 | 1.00 15.20 | AAAA |
| ATOM | 872 | CA | VAL | 111 | 43.614 | 29.180 | 58.403 | 1.00 20.45 | AAAA |
| ATOM | 873 | CB | VAL | 111 | 44.517 | 28.514 | 57.323 | 1.00 20.02 | AAAA |
| ATOM | 874 | CG1 | VAL | 111 | 45.652 | 27.765 | 58.005 | 1.00 21.79 | AAAA |
| ATOM | 875 | CG2 | VAL | 111 | 43.697 | 27.537 | 56.482 | 1.00 19.07 | AAAA |
| ATOM | 876 | C | VAL | 111 | 44.456 | 30.075 | 59.327 | 1.00 18.21 | AAAA |
| ATOM | 877 | O | VAL | 111 | 44.838 | 29.672 | 60.431 | 1.00 18.65 | AAAA |
| ATOM | 878 | N | GLN | 112 | 44.731 | 31.302 | 58.890 | 1.00 16.82 | AAAA |
| ATOM | 879 | CA | GLN | 112 | 45.493 | 32.232 | 59.719 | 1.00 20.13 | AAAA |
| ATOM | 880 | CB | GLN | 112 | 45.751 | 33.540 | 58.970 | 1.00 22.39 | AAAA |
| ATOM | 881 | CG | GLN | 112 | 46.593 | 33.360 | 57.723 | 1.00 21.17 | AAAA |
| ATOM | 882 | CD | GLN | 112 | 46.797 | 34.651 | 56.982 | 1.00 24.82 | AAAA |
| ATOM | 883 | OE1 | GLN | 112 | 47.772 | 35.381 | 57.219 | 1.00 25.62 | AAAA |
| ATOM | 884 | NE2 | GLN | 112 | 45.866 | 34.963 | 56.091 | 1.00 13.16 | AAAA |
| ATOM | 885 | C | GLN | 112 | 44.743 | 32.516 | 61.012 | 1.00 23.99 | AAAA |
| ATOM | 886 | O | GLN | 112 | 45.340 | 32.593 | 62.079 | 1.00 17.94 | AAAA |
| ATOM | 887 | N | ALA | 113 | 43.431 | 32.700 | 60.924 | 1.00 15.60 | AAAA |
| ATOM | 888 | CA | ALA | 113 | 42.653 | 32.941 | 62.138 | 1.00 15.04 | AAAA |
| ATOM | 889 | CB | ALA | 113 | 41.191 | 33.138 | 61.802 | 1.00 18.65 | AAAA |
| ATOM | 890 | C | ALA | 113 | 42.807 | 31.751 | 63.083 | 1.00 14.84 | AAAA |
| ATOM | 891 | O | ALA | 113 | 42.941 | 31.909 | 64.296 | 1.00 21.05 | AAAA |
| ATOM | 892 | N | ILE | 114 | 42.767 | 30.550 | 62.534 | 1.00 16.45 | AAAA |
| ATOM | 893 | CA | ILE | 114 | 42.919 | 29.383 | 63.389 | 1.00 15.38 | AAAA |
| ATOM | 894 | CB | ILE | 114 | 42.600 | 28.100 | 62.637 | 1.00 15.22 | AAAA |
| ATOM | 895 | CG2 | ILE | 114 | 42.888 | 26.893 | 63.537 | 1.00 15.72 | AAAA |
| ATOM | 896 | CG1 | ILE | 114 | 41.110 | 28.112 | 62.244 | 1.00 19.28 | AAAA |
| ATOM | 897 | CD1 | ILE | 114 | 40.744 | 27.038 | 61.191 | 1.00 13.43 | AAAA |
| ATOM | 898 | C | ILE | 114 | 44.329 | 29.318 | 63.968 | 1.00 18.02 | AAAA |
| ATOM | 899 | O | ILE | 114 | 44.508 | 28.998 | 65.156 | 1.00 20.38 | AAAA |
| ATOM | 900 | N | GLU | 115 | 45.328 | 29.629 | 63.144 | 1.00 15.27 | AAAA |
| ATOM | 901 | CA | GLU | 115 | 46.726 | 29.626 | 63.614 | 1.00 21.48 | AAAA |
| ATOM | 902 | CB | GLU | 115 | 47.690 | 30.080 | 62.506 | 1.00 21.76 | AAAA |
| ATOM | 903 | CG | GLU | 115 | 47.884 | 29.080 | 61.386 | 1.00 15.78 | AAAA |
| ATOM | 904 | CD | GLU | 115 | 48.670 | 29.648 | 60.211 | 1.00 20.04 | AAAA |
| ATOM | 905 | OE1 | GLU | 115 | 49.051 | 30.843 | 60.239 | 1.00 21.48 | AAAA |
| ATOM | 906 | OE2 | GLU | 115 | 48.901 | 28.902 | 59.241 | 1.00 26.59 | AAAA |
| ATOM | 907 | C | GLU | 115 | 46.877 | 30.559 | 64.814 | 1.00 23.55 | AAAA |
| ATOM | 908 | O | GLU | 115 | 47.509 | 30.212 | 65.815 | 1.00 23.03 | AAAA |
| ATOM | 909 | N | GLU | 116 | 46.295 | 31.748 | 64.703 | 1.00 22.73 | AAAA |
| ATOM | 910 | CA | GLU | 116 | 46.367 | 32.735 | 65.774 | 1.00 20.54 | AAAA |
| ATOM | 911 | CB | GLU | 116 | 45.744 | 34.044 | 65.320 | 1.00 18.40 | AAAA |
| ATOM | 912 | CG | GLU | 116 | 46.562 | 34.765 | 64.279 | 1.00 19.76 | AAAA |
| ATOM | 913 | CD | GLU | 116 | 47.985 | 34.998 | 64.756 | 1.00 27.24 | AAAA |
| ATOM | 914 | OE1 | GLU | 116 | 48.164 | 35.630 | 65.815 | 1.00 18.44 | AAAA |
| ATOM | 915 | OE2 | GLU | 116 | 48.919 | 34.543 | 64.078 | 1.00 23.17 | AAAA |
| ATOM | 916 | C | GLU | 116 | 45.682 | 32.253 | 67.034 | 1.00 25.39 | AAAA |
| ATOM | 917 | O | GLU | 116 | 46.207 | 32.427 | 68.137 | 1.00 22.87 | AAAA |
| ATOM | 918 | N | PHE | 117 | 44.510 | 31.647 | 66.872 | 1.00 18.78 | AAAA |
| ATOM | 919 | CA | PHE | 117 | 43.778 | 31.139 | 68.019 | 1.00 22.11 | AAAA |
| ATOM | 920 | CB | PHE | 117 | 42.451 | 30.530 | 67.581 | 1.00 23.14 | AAAA |
| ATOM | 921 | CG | PHE | 117 | 41.603 | 30.054 | 68.728 | 1.00 24.06 | AAAA |
| ATOM | 922 | CD1 | PHE | 117 | 40.880 | 30.961 | 69.493 | 1.00 19.67 | AAAA |
| ATOM | 923 | CD2 | PHE | 117 | 41.559 | 28.701 | 69.066 | 1.00 24.08 | AAAA |
| ATOM | 924 | CE1 | PHE | 117 | 40.115 | 30.531 | 70.586 | 1.00 23.68 | AAAA |

Fig. 16-14

| | | | | | | | | | |
|---|---|---|---|---|---|---|---|---|---|
| ATOM | 925 | CE2 | PHE | 117 | 40.799 | 28.262 | 70.156 | 1.00 24.04 | AAAA |
| ATOM | 926 | CZ | PHE | 117 | 40.078 | 29.179 | 70.915 | 1.00 19.62 | AAAA |
| ATOM | 927 | C | PHE | 117 | 44.587 | 30.068 | 68.747 | 1.00 23.87 | AAAA |
| ATOM | 928 | O | PHE | 117 | 44.613 | 30.031 | 69.979 | 1.00 24.40 | AAAA |
| ATOM | 929 | N | LEU | 118 | 45.238 | 29.194 | 67.981 | 1.00 21.09 | AAAA |
| ATOM | 930 | CA | LEU | 118 | 46.025 | 28.113 | 68.549 | 1.00 20.73 | AAAA |
| ATOM | 931 | CB | LEU | 118 | 46.358 | 27.075 | 67.480 | 1.00 17.90 | AAAA |
| ATOM | 932 | CG | LEU | 118 | 45.148 | 26.264 | 66.984 | 1.00 26.20 | AAAA |
| ATOM | 933 | CD1 | LEU | 118 | 45.591 | 25.288 | 65.924 | 1.00 34.23 | AAAA |
| ATOM | 934 | CD2 | LEU | 118 | 44.520 | 25.499 | 68.139 | 1.00 27.16 | AAAA |
| ATOM | 935 | C | LEU | 118 | 47.290 | 28.601 | 69.238 | 1.00 26.49 | AAAA |
| ATOM | 936 | O | LEU | 118 | 47.908 | 27.856 | 69.996 | 1.00 26.34 | AAAA |
| ATOM | 937 | N | LYS | 119 | 47.672 | 29.848 | 68.975 | 1.00 28.92 | AAAA |
| ATOM | 938 | CA | LYS | 119 | 48.835 | 30.459 | 69.624 | 1.00 28.53 | AAAA |
| ATOM | 939 | CB | LYS | 119 | 49.392 | 31.616 | 68.805 | 1.00 30.15 | AAAA |
| ATOM | 940 | CG | LYS | 119 | 49.915 | 31.267 | 67.437 | 1.00 35.14 | AAAA |
| ATOM | 941 | CD | LYS | 119 | 50.291 | 32.549 | 66.716 | 1.00 28.98 | AAAA |
| ATOM | 942 | CE | LYS | 119 | 50.905 | 32.262 | 65.380 | 1.00 31.07 | AAAA |
| ATOM | 943 | NZ | LYS | 119 | 51.195 | 33.551 | 64.745 | 1.00 22.46 | AAAA |
| ATOM | 944 | C | LYS | 119 | 48.335 | 31.053 | 70.932 | 1.00 35.74 | AAAA |
| ATOM | 945 | O | LYS | 119 | 49.117 | 31.541 | 71.750 | 1.00 27.10 | AAAA |
| ATOM | 946 | N | GLY | 120 | 47.018 | 31.050 | 71.103 | 1.00 25.20 | AAAA |
| ATOM | 947 | CA | GLY | 120 | 46.445 | 31.605 | 72.309 | 1.00 30.18 | AAAA |
| ATOM | 948 | C | GLY | 120 | 45.913 | 33.007 | 72.122 | 1.00 31.91 | AAAA |
| ATOM | 949 | O | GLY | 120 | 45.540 | 33.665 | 73.094 | 1.00 34.76 | AAAA |
| ATOM | 950 | N | ASN | 121 | 45.889 | 33.495 | 70.887 | 1.00 20.56 | AAAA |
| ATOM | 951 | CA | ASN | 121 | 45.353 | 34.825 | 70.681 | 1.00 25.58 | AAAA |
| ATOM | 952 | CB | ASN | 121 | 46.278 | 35.634 | 69.785 | 1.00 29.99 | AAAA |
| ATOM | 953 | CG | ASN | 121 | 47.641 | 35.827 | 70.427 | 1.00 24.43 | AAAA |
| ATOM | 954 | OD1 | ASN | 121 | 48.396 | 34.874 | 70.588 | 1.00 54.63 | AAAA |
| ATOM | 955 | ND2 | ASN | 121 | 47.944 | 37.045 | 70.817 | 1.00 41.69 | AAAA |
| ATOM | 956 | C | ASN | 121 | 43.941 | 34.759 | 70.135 | 1.00 18.85 | AAAA |
| ATOM | 957 | O | ASN | 121 | 43.421 | 33.675 | 69.899 | 1.00 24.77 | AAAA |
| ATOM | 958 | N | VAL | 122 | 43.310 | 35.918 | 69.991 | 1.00 19.55 | AAAA |
| ATOM | 959 | CA | VAL | 122 | 41.936 | 35.994 | 69.499 | 1.00 22.90 | AAAA |
| ATOM | 960 | CB | VAL | 122 | 41.053 | 36.832 | 70.449 | 1.00 31.47 | AAAA |
| ATOM | 961 | CG1 | VAL | 122 | 39.649 | 37.006 | 69.851 | 1.00 31.52 | AAAA |
| ATOM | 962 | CG2 | VAL | 122 | 40.986 | 36.154 | 71.810 | 1.00 32.50 | AAAA |
| ATOM | 963 | C | VAL | 122 | 41.953 | 36.632 | 68.130 | 1.00 16.87 | AAAA |
| ATOM | 964 | O | VAL | 122 | 42.518 | 37.710 | 67.938 | 1.00 24.08 | AAAA |
| ATOM | 965 | N | ALA | 123 | 41.321 | 35.983 | 67.159 | 1.00 18.67 | AAAA |
| ATOM | 966 | CA | ALA | 123 | 41.360 | 36.532 | 65.821 | 1.00 10.18 | AAAA |
| ATOM | 967 | CB | ALA | 123 | 42.346 | 35.743 | 64.990 | 1.00 19.04 | AAAA |
| ATOM | 968 | C | ALA | 123 | 40.000 | 36.551 | 65.131 | 1.00 13.72 | AAAA |
| ATOM | 969 | O | ALA | 123 | 39.108 | 35.761 | 65.439 | 1.00 20.78 | AAAA |
| ATOM | 970 | N | PHE | 124 | 39.871 | 37.457 | 64.180 | 1.00 12.92 | AAAA |
| ATOM | 971 | CA | PHE | 124 | 38.649 | 37.610 | 63.405 | 1.00 14.67 | AAAA |
| ATOM | 972 | CB | PHE | 124 | 37.904 | 38.878 | 63.856 | 1.00 14.67 | AAAA |
| ATOM | 973 | CG | PHE | 124 | 36.660 | 39.209 | 63.049 | 1.00 20.28 | AAAA |
| ATOM | 974 | CD1 | PHE | 124 | 35.811 | 38.209 | 62.587 | 1.00 18.56 | AAAA |
| ATOM | 975 | CD2 | PHE | 124 | 36.286 | 40.545 | 62.843 | 1.00 19.53 | AAAA |
| ATOM | 976 | CE1 | PHE | 124 | 34.609 | 38.532 | 61.937 | 1.00 18.75 | AAAA |
| ATOM | 977 | CE2 | PHE | 124 | 35.072 | 40.875 | 62.193 | 1.00 20.18 | AAAA |
| ATOM | 978 | CZ | PHE | 124 | 34.242 | 39.867 | 61.744 | 1.00 21.57 | AAAA |
| ATOM | 979 | C | PHE | 124 | 39.016 | 37.712 | 61.930 | 1.00 22.60 | AAAA |
| ATOM | 980 | O | PHE | 124 | 39.823 | 38.558 | 61.535 | 1.00 19.22 | AAAA |
| ATOM | 981 | N | ASN | 125 | 38.449 | 36.820 | 61.126 | 1.00 19.39 | AAAA |
| ATOM | 982 | CA | ASN | 125 | 38.651 | 36.858 | 59.691 | 1.00 16.80 | AAAA |
| ATOM | 983 | CB | ASN | 125 | 39.122 | 35.507 | 59.150 | 1.00 15.71 | AAAA |
| ATOM | 984 | CG | ASN | 125 | 39.063 | 35.469 | 57.649 | 1.00 12.84 | AAAA |
| ATOM | 985 | OD1 | ASN | 125 | 39.216 | 36.508 | 57.006 | 1.00 14.91 | AAAA |
| ATOM | 986 | ND2 | ASN | 125 | 38.853 | 34.272 | 57.065 | 1.00 16.21 | AAAA |
| ATOM | 987 | C | ASN | 125 | 37.315 | 37.210 | 59.038 | 1.00 16.22 | AAAA |
| ATOM | 988 | O | ASN | 125 | 36.502 | 36.330 | 58.755 | 1.00 15.28 | AAAA |
| ATOM | 989 | N | PRO | 126 | 37.071 | 38.502 | 58.775 | 1.00 14.84 | AAAA |
| ATOM | 990 | CD | PRO | 126 | 37.908 | 39.684 | 59.052 | 1.00 18.10 | AAAA |

Fig. 16-15

| ATOM | 991 | CA | PRO | 126 | 35.811 | 38.910 | 58.156 | 1.00 | 17.33 | AAAA |
|------|-----|-----|-----|-----|--------|--------|--------|------|-------|------|
| ATOM | 992 | CB | PRO | 126 | 35.912 | 40.434 | 58.177 | 1.00 | 16.32 | AAAA |
| ATOM | 993 | CG | PRO | 126 | 37.416 | 40.655 | 58.008 | 1.00 | 20.95 | AAAA |
| ATOM | 994 | C | PRO | 126 | 35.549 | 38.359 | 56.752 | 1.00 | 13.78 | AAAA |
| ATOM | 995 | O | PRO | 126 | 34.404 | 38.291 | 56.322 | 1.00 | 17.03 | AAAA |
| ATOM | 996 | N | ALA | 127 | 36.607 | 37.972 | 56.042 | 1.00 | 14.57 | AAAA |
| ATOM | 997 | CA | ALA | 127 | 36.463 | 37.443 | 54.691 | 1.00 | 17.37 | AAAA |
| ATOM | 998 | CB | ALA | 127 | 37.816 | 37.540 | 53.930 | 1.00 | 14.48 | AAAA |
| ATOM | 999 | C | ALA | 127 | 35.982 | 35.998 | 54.702 | 1.00 | 19.77 | AAAA |
| ATOM | 1000 | O | ALA | 127 | 35.490 | 35.500 | 53.688 | 1.00 | 15.62 | AAAA |
| ATOM | 1001 | N | GLY | 128 | 36.111 | 35.339 | 55.849 | 1.00 | 13.54 | AAAA |
| ATOM | 1002 | CA | GLY | 128 | 35.725 | 33.939 | 55.971 | 1.00 | 13.53 | AAAA |
| ATOM | 1003 | C | GLY | 128 | 34.234 | 33.679 | 56.101 | 1.00 | 14.49 | AAAA |
| ATOM | 1004 | O | GLY | 128 | 33.414 | 34.585 | 56.017 | 1.00 | 15.65 | AAAA |
| ATOM | 1005 | N | GLY | 129 | 33.883 | 32.420 | 56.314 | 1.00 | 13.35 | AAAA |
| ATOM | 1006 | CA | GLY | 129 | 32.487 | 32.058 | 56.446 | 1.00 | 16.28 | AAAA |
| ATOM | 1007 | C | GLY | 129 | 31.754 | 31.831 | 55.130 | 1.00 | 15.69 | AAAA |
| ATOM | 1008 | O | GLY | 129 | 30.543 | 32.021 | 55.072 | 1.00 | 16.10 | AAAA |
| ATOM | 1009 | N | MET | 130 | 32.479 | 31.448 | 54.079 | 1.00 | 15.00 | AAAA |
| ATOM | 1010 | CA | MET | 130 | 31.879 | 31.163 | 52.757 | 1.00 | 13.35 | AAAA |
| ATOM | 1011 | CB | MET | 130 | 32.969 | 31.215 | 51.689 | 1.00 | 12.20 | AAAA |
| ATOM | 1012 | CG | MET | 130 | 33.680 | 32.573 | 51.731 | 1.00 | 17.03 | AAAA |
| ATOM | 1013 | SD | MET | 130 | 34.863 | 32.877 | 50.425 | 1.00 | 15.41 | AAAA |
| ATOM | 1014 | CE | MET | 130 | 33.752 | 32.973 | 49.073 | 1.00 | 46.82 | AAAA |
| ATOM | 1015 | C | MET | 130 | 31.296 | 29.756 | 52.885 | 1.00 | 12.49 | AAAA |
| ATOM | 1016 | O | MET | 130 | 31.785 | 28.789 | 52.297 | 1.00 | 19.54 | AAAA |
| ATOM | 1017 | N | HIS | 131 | 30.188 | 29.695 | 53.617 | 1.00 | 16.24 | AAAA |
| ATOM | 1018 | CA | HIS | 131 | 29.556 | 28.448 | 54.014 | 1.00 | 13.80 | AAAA |
| ATOM | 1019 | CB | HIS | 131 | 28.772 | 28.694 | 55.316 | 1.00 | 15.91 | AAAA |
| ATOM | 1020 | CG | HIS | 131 | 27.606 | 29.625 | 55.175 | 1.00 | 13.08 | AAAA |
| ATOM | 1021 | CD2 | HIS | 131 | 26.712 | 30.063 | 56.096 | 1.00 | 12.46 | AAAA |
| ATOM | 1022 | ND1 | HIS | 131 | 27.225 | 30.190 | 53.976 | 1.00 | 22.48 | AAAA |
| ATOM | 1023 | CE1 | HIS | 131 | 26.148 | 30.936 | 54.166 | 1.00 | 16.56 | AAAA |
| ATOM | 1024 | NE2 | HIS | 131 | 25.817 | 30.875 | 55.442 | 1.00 | 23.56 | AAAA |
| ATOM | 1025 | C | HIS | 131 | 28.673 | 27.663 | 53.066 | 1.00 | 13.69 | AAAA |
| ATOM | 1026 | O | HIS | 131 | 28.125 | 26.658 | 53.470 | 1.00 | 17.21 | AAAA |
| ATOM | 1027 | N | HIS | 132 | 28.523 | 28.115 | 51.830 | 1.00 | 14.51 | AAAA |
| ATOM | 1028 | CA | HIS | 132 | 27.669 | 27.400 | 50.887 | 1.00 | 20.19 | AAAA |
| ATOM | 1029 | CB | HIS | 132 | 26.863 | 28.416 | 50.054 | 1.00 | 17.26 | AAAA |
| ATOM | 1030 | CG | HIS | 132 | 25.748 | 29.070 | 50.810 | 1.00 | 16.85 | AAAA |
| ATOM | 1031 | CD2 | HIS | 132 | 24.787 | 28.542 | 51.604 | 1.00 | 13.74 | AAAA |
| ATOM | 1032 | ND1 | HIS | 132 | 25.497 | 30.424 | 50.756 | 1.00 | 24.80 | AAAA |
| ATOM | 1033 | CE1 | HIS | 132 | 24.429 | 30.700 | 51.486 | 1.00 | 12.68 | AAAA |
| ATOM | 1034 | NE2 | HIS | 132 | 23.980 | 29.576 | 52.010 | 1.00 | 28.65 | AAAA |
| ATOM | 1035 | C | HIS | 132 | 28.372 | 26.412 | 49.946 | 1.00 | 16.89 | AAAA |
| ATOM | 1036 | O | HIS | 132 | 27.731 | 25.487 | 49.460 | 1.00 | 14.58 | AAAA |
| ATOM | 1037 | N | ALA | 133 | 29.669 | 26.580 | 49.689 | 1.00 | 16.79 | AAAA |
| ATOM | 1038 | CA | ALA | 133 | 30.338 | 25.680 | 48.740 | 1.00 | 13.76 | AAAA |
| ATOM | 1039 | CB | ALA | 133 | 31.738 | 26.194 | 48.412 | 1.00 | 14.95 | AAAA |
| ATOM | 1040 | C | ALA | 133 | 30.418 | 24.219 | 49.179 | 1.00 | 18.80 | AAAA |
| ATOM | 1041 | O | ALA | 133 | 30.557 | 23.939 | 50.355 | 1.00 | 16.86 | AAAA |
| ATOM | 1042 | N | PHE | 134 | 30.306 | 23.306 | 48.209 | 1.00 | 13.76 | AAAA |
| ATOM | 1043 | CA | PHE | 134 | 30.378 | 21.868 | 48.451 | 1.00 | 19.77 | AAAA |
| ATOM | 1044 | CB | PHE | 134 | 29.311 | 21.132 | 47.620 | 1.00 | 15.59 | AAAA |
| ATOM | 1045 | CG | PHE | 134 | 27.917 | 21.525 | 47.975 | 1.00 | 17.22 | AAAA |
| ATOM | 1046 | CD1 | PHE | 134 | 27.135 | 22.259 | 47.091 | 1.00 | 17.88 | AAAA |
| ATOM | 1047 | CD2 | PHE | 134 | 27.392 | 21.187 | 49.222 | 1.00 | 21.68 | AAAA |
| ATOM | 1048 | CE1 | PHE | 134 | 25.836 | 22.653 | 47.445 | 1.00 | 23.07 | AAAA |
| ATOM | 1049 | CE2 | PHE | 134 | 26.099 | 21.578 | 49.585 | 1.00 | 17.64 | AAAA |
| ATOM | 1050 | CZ | PHE | 134 | 25.323 | 22.308 | 48.696 | 1.00 | 19.71 | AAAA |
| ATOM | 1051 | C | PHE | 134 | 31.763 | 21.354 | 48.098 | 1.00 | 14.76 | AAAA |
| ATOM | 1052 | O | PHE | 134 | 32.547 | 22.049 | 47.442 | 1.00 | 18.05 | AAAA |
| ATOM | 1053 | N | LYS | 135 | 32.060 | 20.124 | 48.515 | 1.00 | 16.37 | AAAA |
| ATOM | 1054 | CA | LYS | 135 | 33.369 | 19.551 | 48.269 | 1.00 | 16.24 | AAAA |
| ATOM | 1055 | CB | LYS | 135 | 33.360 | 18.070 | 48.699 | 1.00 | 21.29 | AAAA |
| ATOM | 1056 | CG | LYS | 135 | 34.640 | 17.300 | 48.400 | 1.00 | 30.43 | AAAA |

Fig. 16-16

```
ATOM   1057  CD  LYS  135      34.597  15.867  48.977  1.00 30.26      AAAA
ATOM   1058  CE  LYS  135      34.862  15.805  50.486  1.00 35.01      AAAA
ATOM   1059  NZ  LYS  135      36.304  16.023  50.895  1.00 20.61      AAAA
ATOM   1060  C   LYS  135      33.854  19.687  46.836  1.00 16.60      AAAA
ATOM   1061  O   LYS  135      35.020  20.020  46.584  1.00 17.24      AAAA
ATOM   1062  N   SER  136      32.944  19.483  45.893  1.00 18.01      AAAA
ATOM   1063  CA  SER  136      33.301  19.528  44.490  1.00 15.26      AAAA
ATOM   1064  CB  SER  136      33.339  18.094  43.940  1.00 18.07      AAAA
ATOM   1065  OG  SER  136      34.135  17.261  44.762  1.00 22.22      AAAA
ATOM   1066  C   SER  136      32.345  20.355  43.658  1.00 15.40      AAAA
ATOM   1067  O   SER  136      32.162  20.071  42.475  1.00 18.77      AAAA
ATOM   1068  N   ARG  137      31.754  21.401  44.237  1.00 19.71      AAAA
ATOM   1069  CA  ARG  137      30.805  22.216  43.482  1.00 17.29      AAAA
ATOM   1070  CB  ARG  137      29.481  21.448  43.366  1.00 24.19      AAAA
ATOM   1071  CG  ARG  137      28.290  22.273  42.937  1.00 32.56      AAAA
ATOM   1072  CD  ARG  137      27.026  21.424  42.980  1.00 47.98      AAAA
ATOM   1073  NE  ARG  137      26.951  20.493  41.862  1.00 50.95      AAAA
ATOM   1074  CZ  ARG  137      26.392  20.781  40.691  1.00 50.38      AAAA
ATOM   1075  NH1 ARG  137      25.854  21.976  40.485  1.00 45.26      AAAA
ATOM   1076  NH2 ARG  137      26.375  19.876  39.722  1.00 55.31      AAAA
ATOM   1077  C   ARG  137      30.537  23.595  44.095  1.00 16.14      AAAA
ATOM   1078  O   ARG  137      30.439  23.711  45.308  1.00 16.88      AAAA
ATOM   1079  N   ALA  138      30.395  24.621  43.252  1.00 18.07      AAAA
ATOM   1080  CA  ALA  138      30.117  25.976  43.735  1.00 21.48      AAAA
ATOM   1081  CB  ALA  138      30.460  27.024  42.631  1.00 16.55      AAAA
ATOM   1082  C   ALA  138      28.642  26.090  44.135  1.00 21.04      AAAA
ATOM   1083  O   ALA  138      27.798  25.339  43.641  1.00 18.97      AAAA
ATOM   1084  N   ASN  139      28.321  27.019  45.029  1.00 13.83      AAAA
ATOM   1085  CA  ASN  139      26.952  27.158  45.468  1.00 12.92      AAAA
ATOM   1086  CB  ASN  139      26.566  25.899  46.274  1.00 13.14      AAAA
ATOM   1087  CG  ASN  139      25.162  25.961  46.832  1.00 20.34      AAAA
ATOM   1088  OD1 ASN  139      24.186  26.068  46.086  1.00 19.76      AAAA
ATOM   1089  ND2 ASN  139      25.048  25.881  48.157  1.00 16.36      AAAA
ATOM   1090  C   ASN  139      26.756  28.409  46.315  1.00 20.92      AAAA
ATOM   1091  O   ASN  139      27.603  28.738  47.148  1.00 16.81      AAAA
ATOM   1092  N   GLY  140      25.644  29.105  46.086  1.00 19.30      AAAA
ATOM   1093  CA  GLY  140      25.330  30.295  46.864  1.00 21.34      AAAA
ATOM   1094  C   GLY  140      26.393  31.378  46.888  1.00 20.19      AAAA
ATOM   1095  O   GLY  140      26.653  31.968  47.943  1.00 18.77      AAAA
ATOM   1096  N   PHE  141      26.996  31.649  45.733  1.00 15.52      AAAA
ATOM   1097  CA  PHE  141      28.034  32.675  45.600  1.00 20.71      AAAA
ATOM   1098  CB  PHE  141      27.711  33.952  46.388  1.00 20.03      AAAA
ATOM   1099  CG  PHE  141      26.355  34.544  46.127  1.00 28.32      AAAA
ATOM   1100  CD1 PHE  141      25.855  35.526  46.997  1.00 24.25      AAAA
ATOM   1101  CD2 PHE  141      25.589  34.170  45.029  1.00 30.11      AAAA
ATOM   1102  CE1 PHE  141      24.628  36.116  46.775  1.00 25.94      AAAA
ATOM   1103  CE2 PHE  141      24.346  34.766  44.801  1.00 21.6.      AAAA
ATOM   1104  CZ  PHE  141      23.870  35.741  45.677  1.00 24.4'      AAAA
ATOM   1105  C   PHE  141      29.357  32.188  46.158  1.00 14.45      AAAA
ATOM   1106  O   PHE  141      30.336  32.914  46.111  1.00 16.39      AAAA
ATOM   1107  N   CYS  142      29.389  30.982  46.716  1.00 16.77      AAAA
ATOM   1108  CA  CYS  142      30.629  30.466  47.285  1.00 17.71      AAAA
ATOM   1109  CB  CYS  142      30.347  29.845  48.659  1.00 13.95      AAAA
ATOM   1110  SG  CYS  142      29.606  30.985  49.846  1.00 16.63      AAAA
ATOM   1111  C   CYS  142      31.313  29.421  46.401  1.00 18.09      AAAA
ATOM   1112  O   CYS  142      30.647  28.527  45.856  1.00 16.60      AAAA
ATOM   1113  N   TYR  143      32.639  29.539  46.272  1.00 12.50      AAAA
ATOM   1114  CA  TYR  143      33.429  28.603  45.478  1.00 15.32      AAAA
ATOM   1115  CB  TYR  143      34.333  29.322  44.473  1.00 13.07      AAAA
ATOM   1116  CG  TYR  143      33.614  30.338  43.612  1.00 15.80      AAAA
ATOM   1117  CD1 TYR  143      33.396  31.636  44.071  1.00 15.48      AAAA
ATOM   1118  CE1 TYR  143      32.740  32.589  43.270  1.00 11.99      AAAA
ATOM   1119  CD2 TYR  143      33.157  29.999  42.336  1.00 14.60      AAAA
ATOM   1120  CE2 TYR  143      32.501  30.935  41.532  1.00 10.74      AAAA
ATOM   1121  CZ  TYR  143      32.301  32.229  42.008  1.00 20.89      AAAA
ATOM   1122  OH  TYR  143      31.698  33.177  41.208  1.00 18.87      AAAA
```

Fig. 16-17

| | | | | | | | | | |
|---|---|---|---|---|---|---|---|---|---|
| ATOM | 1123 | C | TYR | 143 | 34.310 | 27.723 | 46.358 | 1.00 17.35 | AAAA |
| ATOM | 1124 | O | TYR | 143 | 34.581 | 26.574 | 46.013 | 1.00 16.67 | AAAA |
| ATOM | 1125 | N | ILE | 144 | 34.763 | 28.262 | 47.489 | 1.00 14.93 | AAAA |
| ATOM | 1126 | CA | ILE | 144 | 35.599 | 27.500 | 48.408 | 1.00 14.17 | AAAA |
| ATOM | 1127 | CB | ILE | 144 | 37.018 | 28.069 | 48.440 | 1.00 14.87 | AAAA |
| ATOM | 1128 | CG2 | ILE | 144 | 37.864 | 27.332 | 49.474 | 1.00 13.55 | AAAA |
| ATOM | 1129 | CG1 | ILE | 144 | 37.611 | 28.027 | 47.021 | 1.00 16.98 | AAAA |
| ATOM | 1130 | CD1 | ILE | 144 | 39.052 | 28.537 | 46.901 | 1.00 17.42 | AAAA |
| ATOM | 1131 | C | ILE | 144 | 34.959 | 27.615 | 49.788 | 1.00 17.22 | AAAA |
| ATOM | 1132 | O | ILE | 144 | 34.606 | 28.716 | 50.220 | 1.00 14.72 | AAAA |
| ATOM | 1133 | N | ASN | 145 | 34.798 | 26.486 | 50.474 | 1.00 13.46 | AAAA |
| ATOM | 1134 | CA | ASN | 145 | 34.170 | 26.493 | 51.797 | 1.00 16.09 | AAAA |
| ATOM | 1135 | CB | ASN | 145 | 33.401 | 25.178 | 51.988 | 1.00 14.50 | AAAA |
| ATOM | 1136 | CG | ASN | 145 | 32.428 | 25.239 | 53.148 | 1.00 15.64 | AAAA |
| ATOM | 1137 | OD1 | ASN | 145 | 32.800 | 25.587 | 54.263 | 1.00 14.97 | AAAA |
| ATOM | 1138 | ND2 | ASN | 145 | 31.170 | 24.916 | 52.882 | 1.00 16.74 | AAAA |
| ATOM | 1139 | C | ASN | 145 | 35.266 | 26.639 | 52.873 | 1.00 15.04 | AAAA |
| ATOM | 1140 | O | ASN | 145 | 35.812 | 25.637 | 53.338 | 1.00 15.72 | AAAA |
| ATOM | 1141 | N | ASN | 146 | 35.599 | 27.865 | 53.282 | 1.00 12.34 | AAAA |
| ATOM | 1142 | CA | ASN | 146 | 36.685 | 28.006 | 54.262 | 1.00 15.31 | AAAA |
| ATOM | 1143 | CB | ASN | 146 | 37.161 | 29.464 | 54.354 | 1.00 15.81 | AAAA |
| ATOM | 1144 | CG | ASN | 146 | 36.101 | 30.396 | 54.865 | 1.00 15.25 | AAAA |
| ATOM | 1145 | OD1 | ASN | 146 | 36.113 | 30.757 | 56.034 | 1.00 13.57 | AAAA |
| ATOM | 1146 | ND2 | ASN | 146 | 35.156 | 30.775 | 53.996 | 1.00 10.85 | AAAA |
| ATOM | 1147 | C | ASN | 146 | 36.306 | 27.400 | 55.613 | 1.00 13.04 | AAAA |
| ATOM | 1148 | O | ASN | 146 | 37.160 | 26.865 | 56.314 | 1.00 14.76 | AAAA |
| ATOM | 1149 | N | PRO | 147 | 35.025 | 27.489 | 56.016 | 1.00 14.28 | AAAA |
| ATOM | 1150 | CD | PRO | 147 | 33.817 | 28.175 | 55.515 | 1.00 7.62 | AAAA |
| ATOM | 1151 | CA | PRO | 147 | 34.750 | 26.843 | 57.307 | 1.00 13.51 | AAAA |
| ATOM | 1152 | CB | PRO | 147 | 33.251 | 27.058 | 57.482 | 1.00 14.44 | AAAA |
| ATOM | 1153 | CG | PRO | 147 | 33.056 | 28.436 | 56.827 | 1.00 12.32 | AAAA |
| ATOM | 1154 | C | PRO | 147 | 35.118 | 25.330 | 57.278 | 1.00 18.86 | AAAA |
| ATOM | 1155 | O | PRO | 147 | 35.678 | 24.796 | 58.251 | 1.00 16.24 | AAAA |
| ATOM | 1156 | N | ALA | 148 | 34.818 | 24.642 | 56.171 | 1.00 15.01 | AAAA |
| ATOM | 1157 | CA | ALA | 148 | 35.122 | 23.200 | 56.080 | 1.00 15.58 | AAAA |
| ATOM | 1158 | CB | ALA | 148 | 34.402 | 22.561 | 54.882 | 1.00 12.93 | AAAA |
| ATOM | 1159 | C | ALA | 148 | 36.624 | 22.956 | 55.984 | 1.00 14.94 | AAAA |
| ATOM | 1160 | O | ALA | 148 | 37.138 | 21.999 | 56.560 | 1.00 14.69 | AAAA |
| ATOM | 1161 | N | VAL | 149 | 37.328 | 23.817 | 55.263 | 1.00 12.49 | AAAA |
| ATOM | 1162 | CA | VAL | 149 | 38.778 | 23.708 | 55.163 | 1.00 15.31 | AAAA |
| ATOM | 1163 | CB | VAL | 149 | 39.364 | 24.797 | 54.243 | 1.00 14.77 | AAAA |
| ATOM | 1164 | CG1 | VAL | 149 | 40.899 | 24.870 | 54.369 | 1.00 14.68 | AAAA |
| ATOM | 1165 | CG2 | VAL | 149 | 38.981 | 24.501 | 52.808 | 1.00 12.50 | AAAA |
| ATOM | 1166 | C | VAL | 149 | 39.323 | 23.887 | 56.572 | 1.00 20.14 | AAAA |
| ATOM | 1167 | O | VAL | 149 | 40.172 | 23.109 | 57.028 | 1.00 17.32 | AAAA |
| ATOM | 1168 | N | GLY | 150 | 38.815 | 24.899 | 57.271 | 1.00 15.45 | AAAA |
| ATOM | 1169 | CA | GLY | 150 | 39.284 | 25.168 | 58.622 | 1.00 20.96 | AAAA |
| ATOM | 1170 | C | GLY | 150 | 39.030 | 24.053 | 59.621 | 1.00 24.16 | AAAA |
| ATOM | 1171 | O | GLY | 150 | 39.888 | 23.738 | 60.458 | 1.00 19.50 | AAAA |
| ATOM | 1172 | N | ILE | 151 | 37.842 | 23.465 | 59.557 | 1.00 16.67 | AAAA |
| ATOM | 1173 | CA | ILE | 151 | 37.490 | 22.375 | 60.461 | 1.00 19.56 | AAAA |
| ATOM | 1174 | CB | ILE | 151 | 35.992 | 22.052 | 60.348 | 1.00 16.46 | AAAA |
| ATOM | 1175 | CG2 | ILE | 151 | 35.667 | 20.709 | 61.036 | 1.00 17.93 | AAAA |
| ATOM | 1176 | CG1 | ILE | 151 | 35.180 | 23.209 | 60.959 | 1.00 12.31 | AAAA |
| ATOM | 1177 | CD1 | ILE | 151 | 33.686 | 23.123 | 60.672 | 1.00 18.71 | AAAA |
| ATOM | 1178 | C | ILE | 151 | 38.352 | 21.148 | 60.164 | 1.00 22.66 | AAAA |
| ATOM | 1179 | O | ILE | 151 | 38.796 | 20.472 | 61.087 | 1.00 20.08 | AAAA |
| ATOM | 1180 | N | GLU | 152 | 38.599 | 20.861 | 58.888 | 1.00 19.71 | AAAA |
| ATOM | 1181 | CA | GLU | 152 | 39.434 | 19.718 | 58.533 | 1.00 13.85 | AAAA |
| ATOM | 1182 | CB | GLU | 152 | 39.362 | 19.437 | 57.033 | 1.00 20.21 | AAAA |
| ATOM | 1183 | CG | GLU | 152 | 38.033 | 18.833 | 56.624 | 1.00 22.16 | AAAA |
| ATOM | 1184 | CD | GLU | 152 | 37.838 | 17.430 | 57.166 | 1.00 26.94 | AAAA |
| ATOM | 1185 | OE1 | GLU | 152 | 36.720 | 16.906 | 57.035 | 1.00 25.03 | AAAA |
| ATOM | 1186 | OE2 | GLU | 152 | 38.800 | 16.846 | 57.708 | 1.00 24.95 | AAAA |
| ATOM | 1187 | C | GLU | 152 | 40.865 | 20.010 | 58.942 | 1.00 16.85 | AAAA |
| ATOM | 1188 | O | GLU | 152 | 41.629 | 19.110 | 59.289 | 1.00 19.25 | AAAA |

Fig. 16-18

| | | | | | | | | | |
|---|---|---|---|---|---|---|---|---|---|
| ATOM | 1189 | N | TYR | 153 | 41.228 | 21.290 | 58.931 | 1.00 14.74 | AAAA |
| ATOM | 1190 | CA | TYR | 153 | 42.574 | 21.672 | 59.350 | 1.00 17.71 | AAAA |
| ATOM | 1191 | CB | TYR | 153 | 42.757 | 23.193 | 59.179 | 1.00 13.26 | AAAA |
| ATOM | 1192 | CG | TYR | 153 | 44.059 | 23.727 | 59.729 | 1.00 16.36 | AAAA |
| ATOM | 1193 | CD1 | TYR | 153 | 45.234 | 23.726 | 58.967 | 1.00 18.41 | AAAA |
| ATOM | 1194 | CE1 | TYR | 153 | 46.438 | 24.219 | 59.511 | 1.00 21.03 | AAAA |
| ATOM | 1195 | CD2 | TYR | 153 | 44.115 | 24.220 | 61.028 | 1.00 21.16 | AAAA |
| ATOM | 1196 | CE2 | TYR | 153 | 45.288 | 24.705 | 61.570 | 1.00 19.76 | AAAA |
| ATOM | 1197 | CZ | TYR | 153 | 46.440 | 24.711 | 60.824 | 1.00 25.97 | AAAA |
| ATOM | 1198 | OH | TYR | 153 | 47.571 | 25.235 | 61.410 | 1.00 23.15 | AAAA |
| ATOM | 1199 | C | TYR | 153 | 42.712 | 21.274 | 60.828 | 1.00 20.00 | AAAA |
| ATOM | 1200 | O | TYR | 153 | 43.722 | 20.698 | 61.247 | 1.00 19.61 | AAAA |
| ATOM | 1201 | N | LEU | 154 | 41.683 | 21.569 | 61.616 | 1.00 17.78 | AAAA |
| ATOM | 1202 | CA | LEU | 154 | 41.698 | 21.239 | 63.042 | 1.00 17.26 | AAAA |
| ATOM | 1203 | CB | LEU | 154 | 40.511 | 21.913 | 63.744 | 1.00 20.44 | AAAA |
| ATOM | 1204 | CG | LEU | 154 | 40.636 | 23.434 | 63.942 | 1.00 19.57 | AAAA |
| ATOM | 1205 | CD1 | LEU | 154 | 39.277 | 24.046 | 64.309 | 1.00 22.48 | AAAA |
| ATOM | 1206 | CD2 | LEU | 154 | 41.692 | 23.709 | 65.044 | 1.00 20.84 | AAAA |
| ATOM | 1207 | C | LEU | 154 | 41.669 | 19.715 | 63.262 | 1.00 19.69 | AAAA |
| ATOM | 1208 | O | LEU | 154 | 42.357 | 19.191 | 64.149 | 1.00 22.91 | AAAA |
| ATOM | 1209 | N | ARG | 155 | 40.878 | 18.996 | 62.469 | 1.00 20.88 | AAAA |
| ATOM | 1210 | CA | ARG | 155 | 40.840 | 17.539 | 62.622 | 1.00 22.64 | AAAA |
| ATOM | 1211 | CB | ARG | 155 | 39.829 | 16.905 | 61.652 | 1.00 25.69 | AAAA |
| ATOM | 1212 | CG | ARG | 155 | 38.384 | 17.394 | 61.893 | 1.00 27.64 | AAAA |
| ATOM | 1213 | CD | ARG | 155 | 37.382 | 16.834 | 60.892 | 1.00 25.67 | AAAA |
| ATOM | 1214 | NE | ARG | 155 | 36.931 | 15.497 | 61.246 | 1.00 30.88 | AAAA |
| ATOM | 1215 | CZ | ARG | 155 | 36.135 | 14.753 | 60.488 | 1.00 36.28 | AAAA |
| ATOM | 1216 | NH1 | ARG | 155 | 35.705 | 15.218 | 59.318 | 1.00 26.96 | AAAA |
| ATOM | 1217 | NH2 | ARG | 155 | 35.737 | 13.562 | 60.923 | 1.00 27.33 | AAAA |
| ATOM | 1218 | C | ARG | 155 | 42.235 | 16.966 | 62.390 | 1.00 28.00 | AAAA |
| ATOM | 1219 | O | ARG | 155 | 42.674 | 16.070 | 63.119 | 1.00 28.05 | AAAA |
| ATOM | 1220 | N | LYS | 156 | 42.949 | 17.486 | 61.395 | 1.00 23.53 | AAAA |
| ATOM | 1221 | CA | LYS | 156 | 44.290 | 16.977 | 61.128 | 1.00 26.79 | AAAA |
| ATOM | 1222 | CB | LYS | 156 | 44.854 | 17.558 | 59.824 | 1.00 26.01 | AAAA |
| ATOM | 1223 | CG | LYS | 156 | 46.213 | 16.955 | 59.444 | 1.00 29.70 | AAAA |
| ATOM | 1224 | CD | LYS | 156 | 46.632 | 17.308 | 58.035 | 1.00 28.77 | AAAA |
| ATOM | 1225 | CE | LYS | 156 | 45.685 | 16.692 | 57.005 | 1.00 39.79 | AAAA |
| ATOM | 1226 | NZ | LYS | 156 | 45.671 | 15.192 | 57.058 | 1.00 36.33 | AAAA |
| ATOM | 1227 | C | LYS | 156 | 45.233 | 17.260 | 62.299 | 1.00 26.40 | AAAA |
| ATOM | 1228 | O | LYS | 156 | 46.188 | 16.511 | 62.529 | 1.00 26.19 | AAAA |
| ATOM | 1229 | N | LYS | 157 | 44.960 | 18.337 | 63.032 | 1.00 22.50 | AAAA |
| ATOM | 1230 | CA | LYS | 157 | 45.757 | 18.709 | 64.204 | 1.00 21.12 | AAAA |
| ATOM | 1231 | CB | LYS | 157 | 45.535 | 20.181 | 64.591 | 1.00 28.95 | AAAA |
| ATOM | 1232 | CG | LYS | 157 | 46.160 | 21.215 | 63.652 | 1.00 25.94 | AAAA |
| ATOM | 1233 | CD | LYS | 157 | 47.669 | 21.067 | 63.575 | 1.00 35.16 | AAAA |
| ATOM | 1234 | CE | LYS | 157 | 48.281 | 22.099 | 62.627 | 1.00 39.24 | AAAA |
| ATOM | 1235 | NZ | LYS | 157 | 49.742 | 21.869 | 62.406 | 1.00 40.01 | AAAA |
| ATOM | 1236 | C | LYS | 157 | 45.421 | 17.825 | 65.411 | 1.00 22.98 | AAAA |
| ATOM | 1237 | O | LYS | 157 | 46.085 | 17.903 | 66.444 | 1.00 27.77 | AAAA |
| ATOM | 1238 | N | GLY | 158 | 44.392 | 16.995 | 65.284 | 1.00 26.49 | AAAA |
| ATOM | 1239 | CA | GLY | 158 | 44.023 | 16.106 | 66.376 | 1.00 24.82 | AAAA |
| ATOM | 1240 | C | GLY | 158 | 42.771 | 16.459 | 67.161 | 1.00 33.13 | AAAA |
| ATOM | 1241 | O | GLY | 158 | 42.421 | 15.775 | 68.128 | 1.00 27.21 | AAAA |
| ATOM | 1242 | N | PHE | 159 | 42.085 | 17.529 | 66.781 | 1.00 27.47 | AAAA |
| ATOM | 1243 | CA | PHE | 159 | 40.866 | 17.861 | 67.502 | 1.00 24.15 | AAAA |
| ATOM | 1244 | CB | PHE | 159 | 40.410 | 19.285 | 67.186 | 1.00 27.53 | AAAA |
| ATOM | 1245 | CG | PHE | 159 | 41.264 | 20.343 | 67.827 | 1.00 27.26 | AAAA |
| ATOM | 1246 | CD1 | PHE | 159 | 42.439 | 20.785 | 67.220 | 1.00 28.12 | AAAA |
| ATOM | 1247 | CD2 | PHE | 159 | 40.926 | 20.842 | 69.076 | 1.00 21.10 | AAAA |
| ATOM | 1248 | CE1 | PHE | 159 | 43.264 | 21.714 | 67.866 | 1.00 26.24 | AAAA |
| ATOM | 1249 | CE2 | PHE | 159 | 41.738 | 21.768 | 69.736 | 1.00 26.07 | AAAA |
| ATOM | 1250 | CZ | PHE | 159 | 42.907 | 22.205 | 69.135 | 1.00 23.91 | AAAA |
| ATOM | 1251 | C | PHE | 159 | 39.792 | 16.854 | 67.120 | 1.00 28.02 | AAAA |
| ATOM | 1252 | O | PHE | 159 | 39.639 | 16.533 | 65.947 | 1.00 21.14 | AAAA |
| ATOM | 1253 | N | LYS | 160 | 39.056 | 16.361 | 68.110 | 1.00 24.79 | AAAA |
| ATOM | 1254 | CA | LYS | 160 | 38.011 | 15.366 | 67.881 | 1.00 24.26 | AAAA |

Fig. 16-19

| | | | | | | | | | |
|---|---|---|---|---|---|---|---|---|---|
| ATOM | 1255 | CB | LYS | 160 | 38.360 | 14.098 | 68.668 | 1.00 22.86 | AAAA |
| ATOM | 1256 | CG | LYS | 160 | 39.625 | 13.424 | 68.157 | 1.00 43.16 | AAAA |
| ATOM | 1257 | CD | LYS | 160 | 40.222 | 12.417 | 69.141 | 1.00 54.05 | AAAA |
| ATOM | 1258 | CE | LYS | 160 | 39.236 | 11.343 | 69.577 | 1.00 62.87 | AAAA |
| ATOM | 1259 | NZ | LYS | 160 | 38.154 | 11.890 | 70.446 | 1.00 68.11 | AAAA |
| ATOM | 1260 | C | LYS | 160 | 36.599 | 15.822 | 68.225 | 1.00 21.12 | AAAA |
| ATOM | 1261 | O | LYS | 160 | 35.632 | 15.072 | 68.051 | 1.00 22.43 | AAAA |
| ATOM | 1262 | N | ARG | 161 | 36.476 | 17.042 | 68.733 | 1.00 19.68 | AAAA |
| ATOM | 1263 | CA | ARG | 161 | 35.164 | 17.594 | 69.073 | 1.00 20.84 | AAAA |
| ATOM | 1264 | CB | ARG | 161 | 34.865 | 17.467 | 70.572 | 1.00 26.02 | AAAA |
| ATOM | 1265 | CG | ARG | 161 | 34.715 | 16.031 | 71.080 | 1.00 28.47 | AAAA |
| ATOM | 1266 | CD | ARG | 161 | 34.213 | 16.025 | 72.523 | 1.00 30.38 | AAAA |
| ATOM | 1267 | NE | ARG | 161 | 35.098 | 16.734 | 73.445 | 1.00 32.99 | AAAA |
| ATOM | 1268 | CZ | ARG | 161 | 36.272 | 16.278 | 73.883 | 1.00 40.49 | AAAA |
| ATOM | 1269 | NH1 | ARG | 161 | 36.724 | 15.094 | 73.489 | 1.00 31.49 | AAAA |
| ATOM | 1270 | NH2 | ARG | 161 | 37.003 | 17.014 | 74.712 | 1.00 38.54 | AAAA |
| ATOM | 1271 | C | ARG | 161 | 35.171 | 19.060 | 68.680 | 1.00 18.98 | AAAA |
| ATOM | 1272 | O | ARG | 161 | 35.552 | 19.932 | 69.460 | 1.00 23.57 | AAAA |
| ATOM | 1273 | N | ILE | 162 | 34.743 | 19.332 | 67.458 | 1.00 19.82 | AAAA |
| ATOM | 1274 | CA | ILE | 162 | 34.744 | 20.700 | 66.947 | 1.00 17.81 | AAAA |
| ATOM | 1275 | CB | ILE | 162 | 35.522 | 20.717 | 65.626 | 1.00 18.33 | AAAA |
| ATOM | 1276 | CG2 | ILE | 162 | 35.542 | 22.110 | 65.042 | 1.00 13.65 | AAAA |
| ATOM | 1277 | CG1 | ILE | 162 | 36.937 | 20.200 | 65.895 | 1.00 18.15 | AAAA |
| ATOM | 1278 | CD1 | ILE | 162 | 37.722 | 19.852 | 64.670 | 1.00 22.52 | AAAA |
| ATOM | 1279 | C | ILE | 162 | 33.316 | 21.184 | 66.724 | 1.00 14.71 | AAAA |
| ATOM | 1280 | O | ILE | 162 | 32.520 | 20.492 | 66.126 | 1.00 17.99 | AAAA |
| ATOM | 1281 | N | LEU | 163 | 32.996 | 22.374 | 67.217 | 1.00 16.93 | AAAA |
| ATOM | 1282 | CA | LEU | 163 | 31.653 | 22.902 | 67.061 | 1.00 20.73 | AAAA |
| ATOM | 1283 | CB | LEU | 163 | 31.115 | 23.376 | 68.421 | 1.00 18.45 | AAAA |
| ATOM | 1284 | CG | LEU | 163 | 29.846 | 24.236 | 68.463 | 1.00 19.99 | AAAA |
| ATOM | 1285 | CD1 | LEU | 163 | 28.657 | 23.408 | 67.975 | 1.00 15.66 | AAAA |
| ATOM | 1286 | CD2 | LEU | 163 | 29.609 | 24.751 | 69.870 | 1.00 18.74 | AAAA |
| ATOM | 1287 | C | LEU | 163 | 31.705 | 24.071 | 66.106 | 1.00 18.40 | AAAA |
| ATOM | 1288 | O | LEU | 163 | 32.607 | 24.889 | 66.188 | 1.00 18.65 | AAAA |
| ATOM | 1289 | N | TYR | 164 | 30.752 | 24.128 | 65.186 | 1.00 16.97 | AAAA |
| ATOM | 1290 | CA | TYR | 164 | 30.656 | 25.246 | 64.252 | 1.00 11.76 | AAAA |
| ATOM | 1291 | CB | TYR | 164 | 30.782 | 24.754 | 62.816 | 1.00 14.07 | AAAA |
| ATOM | 1292 | CG | TYR | 164 | 30.593 | 25.851 | 61.797 | 1.00 14.51 | AAAA |
| ATOM | 1293 | CD1 | TYR | 164 | 31.573 | 26.822 | 61.562 | 1.00 27.08 | AAAA |
| ATOM | 1294 | CE1 | TYR | 164 | 31.353 | 27.832 | 60.598 | 1.00 26.21 | AAAA |
| ATOM | 1295 | CD2 | TYR | 164 | 29.415 | 25.916 | 61.070 | 1.00 21.45 | AAAA |
| ATOM | 1296 | CE2 | TYR | 164 | 29.193 | 26.891 | 60.137 | 1.00 21.89 | AAAA |
| ATOM | 1297 | CZ | TYR | 164 | 30.148 | 27.839 | 59.896 | 1.00 16.35 | AAAA |
| ATOM | 1298 | OH | TYR | 164 | 29.857 | 28.764 | 58.913 | 1.00 27.44 | AAAA |
| ATOM | 1299 | C | TYR | 164 | 29.279 | 25.873 | 64.463 | 1.00 15.67 | AAAA |
| ATOM | 1300 | O | TYR | 164 | 28.760 | 25.177 | 64.455 | 1.00 16.07 | AAAA |
| ATOM | 1301 | N | ILE | 165 | 29..40 | 27.187 | 64.674 | 1.00 14.52 | AAAA |
| ATOM | 1302 | CA | ILE | 165 | 27.178 | 27.887 | 64.893 | 1.00 18.37 | AAAA |
| ATOM | 1303 | CB | ILE | 165 | 27.959 | 28.596 | 66.254 | 1.00 13.31 | AAAA |
| ATOM | 1304 | CG2 | ILE | 165 | 26.654 | 29.359 | 66.419 | 1.00 13.06 | AAAA |
| ATOM | 1305 | CG1 | ILE | 165 | 28.172 | 27.573 | 67.376 | 1.00 17.28 | AAAA |
| ATOM | 1306 | CD1 | ILE | 165 | 28.493 | 28.209 | 68.739 | 1.00 15.02 | AAAA |
| ATOM | 1307 | C | ILE | 165 | 27.853 | 28.926 | 63.779 | 1.00 20.75 | AAAA |
| ATOM | 1308 | O | ILE | 165 | 28.759 | 29.733 | 63.569 | 1.00 16.67 | AAAA |
| ATOM | 1309 | N | ASP | 166 | 26.725 | 28.901 | 63.084 | 1.00 15.37 | AAAA |
| ATOM | 1310 | CA | ASP | 166 | 26.503 | 29.779 | 61.942 | 1.00 15.63 | AAAA |
| ATOM | 1311 | CB | ASP | 166 | 26.276 | 28.885 | 60.698 | 1.00 12.31 | AAAA |
| ATOM | 1312 | CG | ASP | 166 | 26.279 | 29.666 | 59.393 | 1.00 16.37 | AAAA |
| ATOM | 1313 | OD1 | ASP | 166 | 25.378 | 30.508 | 59.213 | 1.00 13.41 | AAAA |
| ATOM | 1314 | OD2 | ASP | 166 | 27.187 | 29.428 | 58.551 | 1.00 16.06 | AAAA |
| ATOM | 1315 | C | ASP | 166 | 25.334 | 30.740 | 62.174 | 1.00 15.54 | AAAA |
| ATOM | 1316 | O | ASP | 166 | 24.160 | 30.355 | 62.137 | 1.00 12.60 | AAAA |
| ATOM | 1317 | N | LEU | 167 | 25.647 | 32.010 | 62.407 | 1.00 14.02 | AAAA |
| ATOM | 1318 | CA | LEU | 167 | 24.598 | 32.993 | 62.665 | 1.00 12.05 | AAAA |
| ATOM | 1319 | CB | LEU | 167 | 25.051 | 33.962 | 63.767 | 1.00 14.61 | AAAA |
| ATOM | 1320 | CG | LEU | 167 | 25.345 | 33.239 | 65.091 | 1.00 17.20 | AAAA |

Fig. 16-20

| | | | | | | | | | |
|---|---|---|---|---|---|---|---|---|---|
| ATOM | 1321 | CD1 | LEU | 167 | 25.635 | 34.271 | 66.169 | 1.00 28.82 | AAAA |
| ATOM | 1322 | CD2 | LEU | 167 | 24.148 | 32.372 | 65.513 | 1.00 18.59 | AAAA |
| ATOM | 1323 | C | LEU | 167 | 24.122 | 33.776 | 61.449 | 1.00 12.62 | AAAA |
| ATOM | 1324 | O | LEU | 167 | 23.288 | 34.678 | 61.570 | 1.00 15.00 | AAAA |
| ATOM | 1325 | N | ASP | 168 | 24.667 | 33.431 | 60.288 | 1.00 14.35 | AAAA |
| ATOM | 1326 | CA | ASP | 168 | 24.277 | 34.056 | 59.022 | 1.00 19.50 | AAAA |
| ATOM | 1327 | CB | ASP | 168 | 25.060 | 33.409 | 57.880 | 1.00 25.15 | AAAA |
| ATOM | 1328 | CG | ASP | 168 | 24.908 | 34.145 | 56.573 | 1.00 48.45 | AAAA |
| ATOM | 1329 | OD1 | ASP | 168 | 25.477 | 35.247 | 56.454 | 1.00 64.45 | AAAA |
| ATOM | 1330 | OD2 | ASP | 168 | 24.215 | 33.633 | 55.668 | 1.00 44.71 | AAAA |
| ATOM | 1331 | C | ASP | 168 | 22.787 | 33.751 | 58.834 | 1.00 16.30 | AAAA |
| ATOM | 1332 | O | ASP | 168 | 22.327 | 32.696 | 59.252 | 1.00 17.72 | AAAA |
| ATOM | 1333 | N | ALA | 169 | 22.059 | 34.657 | 58.175 | 1.00 14.11 | AAAA |
| ATOM | 1334 | CA | ALA | 169 | 20.618 | 34.503 | 57.934 | 1.00 19.61 | AAAA |
| ATOM | 1335 | CB | ALA | 169 | 20.006 | 35.856 | 57.470 | 1.00 13.56 | AAAA |
| ATOM | 1336 | C | ALA | 169 | 20.277 | 33.400 | 56.926 | 1.00 18.23 | AAAA |
| ATOM | 1337 | O | ALA | 169 | 19.105 | 33.159 | 56.641 | 1.00 17.20 | AAAA |
| ATOM | 1338 | N | HIS | 170 | 21.301 | 32.750 | 56.373 | 1.00 16.53 | AAAA |
| ATOM | 1339 | CA | HIS | 170 | 21.075 | 31.652 | 55.436 | 1.00 17.51 | AAAA |
| ATOM | 1340 | CB | HIS | 170 | 21.616 | 31.973 | 54.033 | 1.00 22.32 | AAAA |
| ATOM | 1341 | CG | HIS | 170 | 20.954 | 33.142 | 53.377 | 1.00 25.38 | AAAA |
| ATOM | 1342 | CD2 | HIS | 170 | 19.934 | 33.196 | 52.487 | 1.00 19.33 | AAAA |
| ATOM | 1343 | ND1 | HIS | 170 | 21.308 | 34.448 | 53.638 | 1.00 18.17 | AAAA |
| ATOM | 1344 | CE1 | HIS | 170 | 20.535 | 35.257 | 52.935 | 1.00 30.34 | AAAA |
| ATOM | 1345 | NE2 | HIS | 170 | 19.692 | 34.523 | 52.229 | 1.00 17.51 | AAAA |
| ATOM | 1346 | C | HIS | 170 | 21.781 | 30.413 | 55.967 | 1.00 16.72 | AAAA |
| ATOM | 1347 | O | HIS | 170 | 22.827 | 30.511 | 56.610 | 1.00 15.92 | AAAA |
| ATOM | 1348 | N | HIS | 171 | 21.209 | 29.245 | 55.682 | 1.00 15.28 | AAAA |
| ATOM | 1349 | CA | HIS | 171 | 21.751 | 27.961 | 56.123 | 1.00 12.53 | AAAA |
| ATOM | 1350 | CB | HIS | 171 | 20.702 | 26.878 | 55.814 | 1.00 14.09 | AAAA |
| ATOM | 1351 | CG | HIS | 171 | 21.180 | 25.468 | 55.980 | 1.00 17.27 | AAAA |
| ATOM | 1352 | CD2 | HIS | 171 | 21.249 | 24.447 | 55.090 | 1.00 12.48 | AAAA |
| ATOM | 1353 | ND1 | HIS | 171 | 21.622 | 24.956 | 57.181 | 1.00 26.73 | AAAA |
| ATOM | 1354 | CE1 | HIS | 171 | 21.948 | 23.685 | 57.021 | 1.00 15.98 | AAAA |
| ATOM | 1355 | NE2 | HIS | 171 | 21.729 | 23.352 | 55.761 | 1.00 20.03 | AAAA |
| ATOM | 1356 | C | HIS | 171 | 23.107 | 27.602 | 55.498 | 1.00 15.55 | AAAA |
| ATOM | 1357 | O | HIS | 171 | 23.318 | 27.784 | 54.298 | 1.00 17.03 | AAAA |
| ATOM | 1358 | N | CYS | 172 | 24.026 | 27.105 | 56.323 | 1.00 14.33 | AAAA |
| ATOM | 1359 | CA | CYS | 172 | 25.350 | 26.675 | 55.866 | 1.00 13.65 | AAAA |
| ATOM | 1360 | CB | CYS | 172 | 26.330 | 26.631 | 57.054 | 1.00 12.99 | AAAA |
| ATOM | 1361 | SG | CYS | 172 | 25.680 | 25.826 | 58.551 | 1.00 17.17 | AAAA |
| ATOM | 1362 | C | CYS | 172 | 25.212 | 25.274 | 55.257 | 1.00 16.52 | AAAA |
| ATOM | 1363 | O | CYS | 172 | 25.750 | 24.297 | 55.783 | 1.00 14.95 | AAAA |
| ATOM | 1364 | N | ASP | 173 | 24.516 | 25.173 | 54.130 | 1.00 15.42 | AAAA |
| ATOM | 1365 | CA | ASP | 173 | 24.302 | 23.865 | 53.531 | 1.00 14.75 | AAAA |
| ATOM | 1366 | CB | ASP | 173 | 23.339 | 23.956 | 52.332 | 1.00 17.73 | AAAA |
| ATOM | 1367 | CG | ASP | 173 | 23.765 | 24.966 | 51.283 | 1.00 22.84 | AAAA |
| ATOM | 1368 | OD1 | ASP | 173 | 23.106 | 24.998 | 50.216 | 1.00 18.68 | AAAA |
| ATOM | 1369 | OD2 | ASP | 173 | 24.730 | 25.728 | 51.504 | 1.00 15.34 | AAAA |
| ATOM | 1370 | C | ASP | 173 | 25.590 | 23.145 | 53.149 | 1.00 16.39 | AAAA |
| ATOM | 1371 | O | ASP | 173 | 25.684 | 21.922 | 53.279 | 1.00 16.48 | AAAA |
| ATOM | 1372 | N | GLY | 174 | 26.583 | 23.912 | 52.705 | 1.00 15.58 | AAAA |
| ATOM | 1373 | CA | GLY | 174 | 27.869 | 23.346 | 52.360 | 1.00 13.97 | AAAA |
| ATOM | 1374 | C | GLY | 174 | 28.508 | 22.723 | 53.595 | 1.00 18.44 | AAAA |
| ATOM | 1375 | O | GLY | 174 | 28.970 | 21.586 | 53.540 | 1.00 15.48 | AAAA |
| ATOM | 1376 | N | VAL | 175 | 28.554 | 23.456 | 54.706 | 1.00 16.84 | AAAA |
| ATOM | 1377 | CA | VAL | 175 | 29.136 | 22.923 | 55.946 | 1.00 16.54 | AAAA |
| ATOM | 1378 | CB | VAL | 175 | 29.201 | 24.031 | 57.037 | 1.00 15.88 | AAAA |
| ATOM | 1379 | CG1 | VAL | 175 | 29.927 | 23.507 | 58.307 | 1.00 15.35 | AAAA |
| ATOM | 1380 | CG2 | VAL | 175 | 29.923 | 25.258 | 56.476 | 1.00 15.62 | AAAA |
| ATOM | 1381 | C | VAL | 175 | 28.318 | 21.720 | 56.467 | 1.00 19.21 | AAAA |
| ATOM | 1382 | O | VAL | 175 | 28.876 | 20.735 | 56.961 | 1.00 17.75 | AAAA |
| ATOM | 1383 | N | GLN | 176 | 26.996 | 21.798 | 56.367 | 1.00 17.74 | AAAA |
| ATOM | 1384 | CA | GLN | 176 | 26.164 | 20.685 | 56.832 | 1.00 15.66 | AAAA |
| ATOM | 1385 | CB | GLN | 176 | 24.678 | 20.973 | 56.595 | 1.00 16.64 | AAAA |
| ATOM | 1386 | CG | GLN | 176 | 23.789 | 19.788 | 56.952 | 1.00 17.00 | AAAA |

Fig. 16-21

```
ATOM   1387  CD   GLN    176      22.325  20.106  56.884  1.00 21.52      AAAA
ATOM   1388  OE1  GLN    176      21.850  21.016  57.567  1.00 21.72      AAAA
ATOM   1389  NE2  GLN    176      21.581  19.348  56.064  1.00 20.30      AAAA
ATOM   1390  C    GLN    176      26.527  19.387  56.121  1.00 16.33      AAAA
ATOM   1391  O    GLN    176      26.751  18.354  56.748  1.00 17.46      AAAA
ATOM   1392  N    GLU    177      26.581  19.443  54.799  1.00 22.24      AAAA
ATOM   1393  CA   GLU    177      26.909  18.251  54.021  1.00 19.67      AAAA
ATOM   1394  CB   GLU    177      26.857  18.587  52.533  1.00 15.55      AAAA
ATOM   1395  CG   GLU    177      27.131  17.388  51.623  1.00 20.24      AAAA
ATOM   1396  CD   GLU    177      26.960  17.740  50.159  1.00 27.00      AAAA
ATOM   1397  OE1  GLU    177      27.974  17.935  49.450  1.00 30.23      AAAA
ATOM   1398  OE2  GLU    177      25.796  17.853  49.725  1.00 26.89      AAAA
ATOM   1399  C    GLU    177      28.284  17.713  54.376  1.00 20.42      AAAA
ATOM   1400  O    GLU    177      28.486  16.503  54.527  1.00 17.05      AAAA
ATOM   1401  N    ALA    178      29.233  18.626  54.527  1.00 19.67      AAAA
ATOM   1402  CA   ALA    178      30.611  18.259  54.839  1.00 18.18      AAAA
ATOM   1403  CB   ALA    178      31.464  19.519  54.918  1.00 12.76      AAAA
ATOM   1404  C    ALA    178      30.806  17.418  56.106  1.00 17.56      AAAA
ATOM   1405  O    ALA    178      31.690  16.555  56.167  1.00 17.72      AAAA
ATOM   1406  N    PHE    179      29.981  17.656  57.116  1.00 18.82      AAAA
ATOM   1407  CA   PHE    179      30.124  16.945  58.379  1.00 20.26      AAAA
ATOM   1408  CB   PHE    179      30.554  17.948  59.439  1.00 13.17      AAAA
ATOM   1409  CG   PHE    179      31.779  18.693  59.048  1.00 16.28      AAAA
ATOM   1410  CD1  PHE    179      31.705  20.017  58.610  1.00 13.77      AAAA
ATOM   1411  CD2  PHE    179      33.002  18.031  58.995  1.00 15.57      AAAA
ATOM   1412  CE1  PHE    179      32.845  20.673  58.114  1.00 20.03      AAAA
ATOM   1413  CE2  PHE    179      34.145  18.677  58.500  1.00 20.30      AAAA
ATOM   1414  CZ   PHE    179      34.060  20.002  58.058  1.00 19.51      AAAA
ATOM   1415  C    PHE    179      28.882  16.219  58.833  1.00 18.52      AAAA
ATOM   1416  O    PHE    179      28.773  15.828  60.000  1.00 20.21      AAAA
ATOM   1417  N    TYR    180      27.969  16.016  57.895  1.00 18.33      AAAA
ATOM   1418  CA   TYR    180      26.698  15.379  58.176  1.00 19.93      AAAA
ATOM   1419  CB   TYR    180      25.874  15.310  56.894  1.00 20.97      AAAA
ATOM   1420  CG   TYR    180      24.402  15.341  57.159  1.00 19.80      AAAA
ATOM   1421  CD1  TYR    180      23.565  14.337  56.686  1.00 23.87      AAAA
ATOM   1422  CE1  TYR    180      22.203  14.391  56.898  1.00 21.32      AAAA
ATOM   1423  CD2  TYR    180      23.831  16.416  57.865  1.00 19.02      AAAA
ATOM   1424  CE2  TYR    180      22.470  16.482  58.084  1.00 26.84      AAAA
ATOM   1425  CZ   TYR    180      21.659  15.462  57.594  1.00 30.54      AAAA
ATOM   1426  OH   TYR    180      20.310  15.514  57.794  1.00 22.81      AAAA
ATOM   1427  C    TYR    180      26.855  13.970  58.737  1.00 22.61      AAAA
ATOM   1428  O    TYR    180      26.064  13.526  59.579  1.00 23.44      AAAA
ATOM   1429  N    ASP    181      27.893  13.298  58.253  1.00 22.27      AAAA
ATOM   1430  CA   ASP    181      28.245  11.920  58.590  1.00 33.84      AAAA
ATOM   1431  CB   ASP    181      28.916  11.318  57.339  1.00 41.74      AAAA
ATOM   1432  CG   ASP    181      30.035  10.363  57.662  1.00 57.71      AAAA
ATOM   1433  OD1  ASP    181      30.999  10.780  58.340  1.00 61.40      AAAA
ATOM   1434  OD2  ASP    181      29.965   9.197  57.221  1.00 65.77      AAAA
ATOM   1435  C    ASP    181      29.107  11.654  59.838  1.00 30.21      AAAA
ATOM   1436  O    ASP    181      29.307  10.497  60.227  1.00 27.84      AAAA
ATOM   1437  N    THR    182      29.615  12.696  60.480  1.00 27.53      AAAA
ATOM   1438  CA   THR    182      30.472  12.466  61.634  1.00 21.19      AAAA
ATOM   1439  CB   THR    182      31.918  12.977  61.358  1.00 26.55      AAAA
ATOM   1440  OG1  THR    182      32.729  12.763  62.513  1.00 25.62      AAAA
ATOM   1441  CG2  THR    182      31.922  14.471  61.037  1.00 21.67      AAAA
ATOM   1442  C    THR    182      30.010  13.050  62.954  1.00 25.02      AAAA
ATOM   1443  O    THR    182      29.306  14.049  62.992  1.00 23.56      AAAA
ATOM   1444  N    ASP    183      30.434  12.424  64.042  1.00 19.66      AAAA
ATOM   1445  CA   ASP    183      30.086  12.894  65.371  1.00 21.52      AAAA
ATOM   1446  CB   ASP    183      29.735  11.700  66.275  1.00 28.52      AAAA
ATOM   1447  CG   ASP    183      30.920  10.783  66.523  1.00 32.30      AAAA
ATOM   1448  OD1  ASP    183      31.667  10.502  65.565  1.00 30.99      AAAA
ATOM   1449  OD2  ASP    183      31.095  10.326  67.675  1.00 48.65      AAAA
ATOM   1450  C    ASP    183      31.257  13.685  65.947  1.00 16.66      AAAA
ATOM   1451  O    ASP    183      31.236  14.092  67.104  1.00 23.37      AAAA
ATOM   1452  N    GLN    184      32.286  13.909  65.131  1.00 21.95      AAAA
```

Fig. 16-22

| ATOM | 1453 | CA | GLN | 184 | 33.437 | 14.672 | 65.590 | 1.00 | 17.65 | AAAA |
|------|------|------|------|-----|--------|--------|--------|------|-------|------|
| ATOM | 1454 | CB | GLN | 184 | 34.701 | 14.243 | 64.866 | 1.00 | 21.36 | AAAA |
| ATOM | 1455 | CG | GLN | 184 | 35.068 | 12.790 | 65.102 | 1.00 | 27.38 | AAAA |
| ATOM | 1456 | CD | GLN | 184 | 36.485 | 12.476 | 64.691 | 1.00 | 31.96 | AAAA |
| ATOM | 1457 | OE1 | GLN | 184 | 36.899 | 12.760 | 63.573 | 1.00 | 29.90 | AAAA |
| ATOM | 1458 | NE2 | GLN | 184 | 37.239 | 11.878 | 65.599 | 1.00 | 31.84 | AAAA |
| ATOM | 1459 | C | GLN | 184 | 33.207 | 16.165 | 65.382 | 1.00 | 18.54 | AAAA |
| ATOM | 1460 | O | GLN | 184 | 33.881 | 17.009 | 65.972 | 1.00 | 18.11 | AAAA |
| ATOM | 1461 | N | VAL | 185 | 32.258 | 16.481 | 64.519 | 1.00 | 19.18 | AAAA |
| ATOM | 1462 | CA | VAL | 185 | 31.934 | 17.872 | 64.267 | 1.00 | 21.57 | AAAA |
| ATOM | 1463 | CB | VAL | 185 | 32.261 | 18.264 | 62.807 | 1.00 | 22.64 | AAAA |
| ATOM | 1464 | CG1 | VAL | 185 | 31.994 | 19.768 | 62.591 | 1.00 | 16.26 | AAAA |
| ATOM | 1465 | CG2 | VAL | 185 | 33.722 | 17.924 | 62.500 | 1.00 | 16.77 | AAAA |
| ATOM | 1466 | C | VAL | 185 | 30.449 | 18.035 | 64.523 | 1.00 | 16.91 | AAAA |
| ATOM | 1467 | O | VAL | 185 | 29.658 | 17.156 | 64.179 | 1.00 | 20.79 | AAAA |
| ATOM | 1468 | N | PHE | 186 | 30.081 | 19.145 | 65.153 | 1.00 | 18.73 | AAAA |
| ATOM | 1469 | CA | PHE | 186 | 28.687 | 19.445 | 65.435 | 1.00 | 16.22 | AAAA |
| ATOM | 1470 | CB | PHE | 186 | 28.432 | 19.559 | 66.952 | 1.00 | 16.83 | AAAA |
| ATOM | 1471 | CG | PHE | 186 | 26.976 | 19.682 | 67.299 | 1.00 | 17.96 | AAAA |
| ATOM | 1472 | CD1 | PHE | 186 | 26.319 | 18.656 | 67.968 | 1.00 | 23.24 | AAAA |
| ATOM | 1473 | CD2 | PHE | 186 | 26.240 | 20.797 | 66.904 | 1.00 | 15.41 | AAAA |
| ATOM | 1474 | CE1 | PHE | 186 | 24.953 | 18.738 | 68.235 | 1.00 | 18.99 | AAAA |
| ATOM | 1475 | CE2 | PHE | 186 | 24.879 | 20.887 | 67.168 | 1.00 | 24.05 | AAAA |
| ATOM | 1476 | CZ | PHE | 186 | 24.234 | 19.846 | 67.838 | 1.00 | 22.93 | AAAA |
| ATOM | 1477 | C | PHE | 186 | 28.437 | 20.789 | 64.778 | 1.00 | 17.16 | AAAA |
| ATOM | 1478 | O | PHE | 186 | 29.192 | 21.725 | 64.993 | 1.00 | 19.37 | AAAA |
| ATOM | 1479 | N | VAL | 187 | 27.391 | 20.874 | 63.961 | 1.00 | 19.67 | AAAA |
| ATOM | 1480 | CA | VAL | 187 | 27.075 | 22.116 | 63.277 | 1.00 | 17.74 | AAAA |
| ATOM | 1481 | CB | VAL | 187 | 27.010 | 21.914 | 61.720 | 1.00 | 18.65 | AAAA |
| ATOM | 1482 | CG1 | VAL | 187 | 26.578 | 23.211 | 61.024 | 1.00 | 17.31 | AAAA |
| ATOM | 1483 | CG2 | VAL | 187 | 28.359 | 21.453 | 61.194 | 1.00 | 16.65 | AAAA |
| ATOM | 1484 | C | VAL | 187 | 25.732 | 22.637 | 63.746 | 1.00 | 18.46 | AAAA |
| ATOM | 1485 | O | VAL | 187 | 24.752 | 21.903 | 63.764 | 1.00 | 20.64 | AAAA |
| ATOM | 1486 | N | LEU | 188 | 25.708 | 23.899 | 64.150 | 1.00 | 14.42 | AAAA |
| ATOM | 1487 | CA | LEU | 188 | 24.482 | 24.563 | 64.567 | 1.00 | 16.68 | AAAA |
| ATOM | 1488 | CB | LEU | 188 | 24.568 | 25.070 | 66.009 | 1.00 | 13.98 | AAAA |
| ATOM | 1489 | CG | LEU | 188 | 23.522 | 26.119 | 66.450 | 1.00 | 13.66 | AAAA |
| ATOM | 1490 | CD1 | LEU | 188 | 22.103 | 25.556 | 66.401 | 1.00 | 15.55 | AAAA |
| ATOM | 1491 | CD2 | LEU | 188 | 23.844 | 26.585 | 67.861 | 1.00 | 16.40 | AAAA |
| ATOM | 1492 | C | LEU | 188 | 24.272 | 25.756 | 63.667 | 1.00 | 20.01 | AAAA |
| ATOM | 1493 | O | LEU | 188 | 25.164 | 26.595 | 63.506 | 1.00 | 18.86 | AAAA |
| ATOM | 1494 | N | SER | 189 | 23.106 | 25.845 | 63.057 | 1.00 | 14.46 | AAAA |
| ATOM | 1495 | CA | SER | 189 | 22.841 | 27.011 | 62.230 | 1.00 | 14.56 | AAAA |
| ATOM | 1496 | CB | SER | 189 | 22.896 | 26.668 | 60.737 | 1.00 | 15.55 | AAAA |
| ATOM | 1497 | OG | SER | 189 | 22.619 | 27.851 | 60.008 | 1.00 | 14.09 | AAAA |
| ATOM | 1498 | C | SER | 189 | 21.487 | 27.606 | 62.508 | 1.00 | 15.24 | AAAA |
| ATOM | 1499 | O | SER | 189 | 20.509 | 26.885 | 62.578 | 1.00 | 21.46 | AAAA |
| ATOM | 1500 | N | LEU | 190 | 21.423 | 28.921 | 62.690 | 1.00 | 14.92 | AAAA |
| ATOM | 1501 | CA | LEU | 190 | 20.128 | 29.572 | 62.826 | 1.00 | 15.54 | AAAA |
| ATOM | 1502 | CB | LEU | 190 | 20.084 | 30.663 | 63.906 | 1.00 | 21.02 | AAAA |
| ATOM | 1503 | CG | LEU | 190 | 20.594 | 30.532 | 65.339 | 1.00 | 30.17 | AAAA |
| ATOM | 1504 | CD1 | LEU | 190 | 19.736 | 31.437 | 66.210 | 1.00 | 19.75 | AAAA |
| ATOM | 1505 | CD2 | LEU | 190 | 20.547 | 29.130 | 65.831 | 1.00 | 19.08 | AAAA |
| ATOM | 1506 | C | LEU | 190 | 20.035 | 30.250 | 61.456 | 1.00 | 14.31 | AAAA |
| ATOM | 1507 | O | LEU | 190 | 21.031 | 30.752 | 60.951 | 1.00 | 15.43 | AAAA |
| ATOM | 1508 | N | HIS | 191 | 18.855 | 30.285 | 60.856 | 1.00 | 16.88 | AAAA |
| ATOM | 1509 | CA | HIS | 191 | 18.732 | 30.884 | 59.535 | 1.00 | 14.34 | AAAA |
| ATOM | 1510 | CB | HIS | 191 | 19.506 | 30.015 | 58.539 | 1.00 | 17.34 | AAAA |
| ATOM | 1511 | CG | HIS | 191 | 19.229 | 28.546 | 58.697 | 1.00 | 14.27 | AAAA |
| ATOM | 1512 | CD2 | HIS | 191 | 19.941 | 27.578 | 59.319 | 1.00 | 9.60 | AAAA |
| ATOM | 1513 | ND1 | HIS | 191 | 18.073 | 27.940 | 58.247 | 1.00 | 21.22 | AAAA |
| ATOM | 1514 | CE1 | HIS | 191 | 18.088 | 26.660 | 58.582 | 1.00 | 17.22 | AAAA |
| ATOM | 1515 | NE2 | HIS | 191 | 19.212 | 26.415 | 59.232 | 1.00 | 20.70 | AAAA |
| ATOM | 1516 | C | HIS | 191 | 17.277 | 31.026 | 59.110 | 1.00 | 16.19 | AAAA |
| ATOM | 1517 | O | HIS | 191 | 16.381 | 30.489 | 59.766 | 1.00 | 16.73 | AAAA |
| ATOM | 1518 | N | GLN | 192 | 17.044 | 31.796 | 58.045 | 1.00 | 14.78 | AAAA |

Fig. 16-23

| | | | | | | | | | |
|---|---|---|---|---|---|---|---|---|---|
| ATOM | 1519 | CA | GLN | 192 | 15.683 | 31.968 | 57.516 | 1.00 16.33 | AAAA |
| ATOM | 1520 | CB | GLN | 192 | 15.669 | 32.871 | 56.283 | 1.00 17.07 | AAAA |
| ATOM | 1521 | CG | GLN | 192 | 16.174 | 34.270 | 56.498 | 1.00 18.15 | AAAA |
| ATOM | 1522 | CD | GLN | 192 | 16.408 | 34.965 | 55.177 | 1.00 14.74 | AAAA |
| ATOM | 1523 | OE1 | GLN | 192 | 15.490 | 35.566 | 54.587 | 1.00 20.46 | AAAA |
| ATOM | 1524 | NE2 | GLN | 192 | 17.630 | 34.839 | 54.665 | 1.00 13.44 | AAAA |
| ATOM | 1525 | C | GLN | 192 | 15.262 | 30.584 | 57.072 | 1.00 15.06 | AAAA |
| ATOM | 1526 | O | GLN | 192 | 16.071 | 29.843 | 56.514 | 1.00 19.23 | AAAA |
| ATOM | 1527 | N | SER | 193 | 14.007 | 30.223 | 57.304 | 1.00 15.63 | AAAA |
| ATOM | 1528 | CA | SER | 193 | 13.561 | 28.907 | 56.877 | 1.00 13.84 | AAAA |
| ATOM | 1529 | CB | SER | 193 | 12.097 | 28.677 | 57.284 | 1.00 17.28 | AAAA |
| ATOM | 1530 | OG | SER | 193 | 11.639 | 27.439 | 56.750 | 1.00 17.58 | AAAA |
| ATOM | 1531 | C | SER | 193 | 13.687 | 28.704 | 55.350 | 1.00 11.80 | AAAA |
| ATOM | 1532 | O | SER | 193 | 13.400 | 29.601 | 54.569 | 1.00 18.44 | AAAA |
| ATOM | 1533 | N | PRO | 194 | 14.103 | 27.505 | 54.928 | 1.00 14.59 | AAAA |
| ATOM | 1534 | CD | PRO | 194 | 14.335 | 26.325 | 55.782 | 1.00 19.22 | AAAA |
| ATOM | 1535 | CA | PRO | 194 | 14.268 | 27.143 | 53.513 | 1.00 15.30 | AAAA |
| ATOM | 1536 | CB | PRO | 194 | 14.892 | 25.737 | 53.573 | 1.00 18.33 | AAAA |
| ATOM | 1537 | CG | PRO | 194 | 15.359 | 25.587 | 55.007 | 1.00 22.34 | AAAA |
| ATOM | 1538 | C | PRO | 194 | 12.880 | 27.104 | 52.866 | 1.00 16.40 | AAAA |
| ATOM | 1539 | O | PRO | 194 | 12.757 | 27.003 | 51.640 | 1.00 19.43 | AAAA |
| ATOM | 1540 | N | GLU | 195 | 11.828 | 27.151 | 53.681 | 1.00 20.57 | AAAA |
| ATOM | 1541 | CA | GLU | 195 | 10.483 | 27.161 | 53.099 | 1.00 30.15 | AAAA |
| ATOM | 1542 | CB | GLU | 195 | 9.386 | 27.037 | 54.173 | 1.00 31.91 | AAAA |
| ATOM | 1543 | CG | GLU | 195 | 8.987 | 28.325 | 54.879 | 1.00 45.60 | AAAA |
| ATOM | 1544 | CD | GLU | 195 | 7.880 | 29.119 | 54.174 | 1.00 34.45 | AAAA |
| ATOM | 1545 | OE1 | GLU | 195 | 7.635 | 30.259 | 54.612 | 1.00 43.98 | AAAA |
| ATOM | 1546 | OE2 | GLU | 195 | 7.241 | 28.627 | 53.210 | 1.00 38.39 | AAAA |
| ATOM | 1547 | C | GLU | 195 | 10.333 | 28.474 | 52.318 | 1.00 26.92 | AAAA |
| ATOM | 1548 | O | GLU | 195 | 9.522 | 28.557 | 51.395 | 1.00 24.59 | AAAA |
| ATOM | 1549 | N | TYR | 196 | 11.116 | 29.501 | 52.669 | 1.00 18.16 | AAAA |
| ATOM | 1550 | CA | TYR | 196 | 11.024 | 30.753 | 51.922 | 1.00 15.81 | AAAA |
| ATOM | 1551 | CB | TYR | 196 | 10.208 | 31.801 | 52.690 | 1.00 20.01 | AAAA |
| ATOM | 1552 | CG | TYR | 196 | 10.868 | 32.353 | 53.932 | 1.00 19.77 | AAAA |
| ATOM | 1553 | CD1 | TYR | 196 | 11.779 | 33.408 | 53.853 | 1.00 18.24 | AAAA |
| ATOM | 1554 | CE1 | TYR | 196 | 12.407 | 33.898 | 54.988 | 1.00 18.50 | AAAA |
| ATOM | 1555 | CD2 | TYR | 196 | 10.598 | 31.801 | 55.185 | 1.00 18.12 | AAAA |
| ATOM | 1556 | CE2 | TYR | 196 | 11.223 | 32.283 | 56.339 | 1.00 21.09 | AAAA |
| ATOM | 1557 | CZ | TYR | 196 | 12.125 | 33.326 | 56.235 | 1.00 20.39 | AAAA |
| ATOM | 1558 | OH | TYR | 196 | 12.759 | 33.784 | 57.367 | 1.00 16.20 | AAAA |
| ATOM | 1559 | C | TYR | 196 | 12.342 | 31.372 | 51.475 | 1.00 16.89 | AAAA |
| ATOM | 1560 | O | TYR | 196 | 12.336 | 32.347 | 50.718 | 1.00 23.08 | AAAA |
| ATOM | 1561 | N | ALA | 197 | 13.466 | 30.817 | 51.911 | 1.00 17.52 | AAAA |
| ATOM | 1562 | CA | ALA | 197 | 14.754 | 31.400 | 51.512 | 1.00 20.26 | AAAA |
| ATOM | 1563 | CB | ALA | 197 | 15.315 | 32.261 | 52.659 | 1.00 20.74 | AAAA |
| ATOM | 1564 | C | ALA | 197 | 15.814 | 30.392 | 51.074 | 1.00 13.51 | AAAA |
| ATOM | 1565 | O | ALA | 197 | 15.787 | 29.229 | 51.457 | 1.00 19.35 | AAAA |
| ATOM | 1566 | N | PHE | 198 | 16.757 | 30.869 | 50.257 | 1.00 18.01 | AAAA |
| ATOM | 1567 | CA | PHE | 198 | 17.861 | 30.049 | 49.782 | 1.00 17.97 | AAAA |
| ATOM | 1568 | CB | PHE | 198 | 18.929 | 30.933 | 49.119 | 1.00 20.38 | AAAA |
| ATOM | 1569 | CG | PHE | 198 | 20.094 | 30.162 | 48.545 | 1.00 23.61 | AAAA |
| ATOM | 1570 | CD1 | PHE | 198 | 20.039 | 29.660 | 47.245 | 1.00 29.71 | AAAA |
| ATOM | 1571 | CD2 | PHE | 198 | 21.229 | 29.899 | 49.321 | 1.00 19.06 | AAAA |
| ATOM | 1572 | CE1 | PHE | 198 | 21.091 | 28.908 | 46.719 | 1.00 30.39 | AAAA |
| ATOM | 1573 | CE2 | PHE | 198 | 22.290 | 29.145 | 48.807 | 1.00 23.17 | AAAA |
| ATOM | 1574 | CZ | PHE | 198 | 22.218 | 28.646 | 47.493 | 1.00 22.74 | AAAA |
| ATOM | 1575 | C | PHE | 198 | 18.453 | 29.419 | 51.032 | 1.00 16.02 | AAAA |
| ATOM | 1576 | O | PHE | 198 | 18.552 | 30.073 | 52.061 | 1.00 20.95 | AAAA |
| ATOM | 1577 | N | PRO | 199 | 18.941 | 28.176 | 50.937 | 1.00 19.92 | AAAA |
| ATOM | 1578 | CD | PRO | 199 | 19.600 | 27.508 | 52.074 | 1.00 17.86 | AAAA |
| ATOM | 1579 | CA | PRO | 199 | 18.990 | 27.318 | 49.744 | 1.00 23.54 | AAAA |
| ATOM | 1580 | CB | PRO | 199 | 20.108 | 26.344 | 50.095 | 1.00 22.70 | AAAA |
| ATOM | 1581 | CG | PRO | 199 | 19.813 | 26.087 | 51.534 | 1.00 23.16 | AAAA |
| ATOM | 1582 | C | PRO | 199 | 17.710 | 26.595 | 49.312 | 1.00 30.97 | AAAA |
| ATOM | 1583 | O | PRO | 199 | 17.733 | 25.855 | 48.322 | 1.00 23.25 | AAAA |
| ATOM | 1584 | N | PHE | 200 | 16.621 | 26.795 | 50.054 | 1.00 20.32 | AAAA |

Fig. 16-24

| | | | | | | | | | |
|---|---|---|---|---|---|---|---|---|---|
| ATOM | 1585 | CA | PHE | 200 | 15.319 | 26.166 | 49.752 | 1.00 20.27 | AAAA |
| ATOM | 1586 | CB | PHE | 200 | 14.840 | 26.533 | 48.346 | 1.00 19.77 | AAAA |
| ATOM | 1587 | CG | PHE | 200 | 14.752 | 27.999 | 48.082 | 1.00 18.06 | AAAA |
| ATOM | 1588 | CD1 | PHE | 200 | 15.742 | 28.644 | 47.346 | 1.00 18.97 | AAAA |
| ATOM | 1589 | CD2 | PHE | 200 | 13.654 | 28.736 | 48.519 | 1.00 19.06 | AAAA |
| ATOM | 1590 | CE1 | PHE | 200 | 15.635 | 30.003 | 47.042 | 1.00 21.67 | AAAA |
| ATOM | 1591 | CE2 | PHE | 200 | 13.539 | 30.101 | 48.221 | 1.00 22.60 | AAAA |
| ATOM | 1592 | CZ | PHE | 200 | 14.527 | 30.736 | 47.482 | 1.00 18.93 | AAAA |
| ATOM | 1593 | C | PHE | 200 | 15.294 | 24.637 | 49.845 | 1.00 18.44 | AAAA |
| ATOM | 1594 | O | PHE | 200 | 14.302 | 24.049 | 50.272 | 1.00 20.74 | AAAA |
| ATOM | 1595 | N | GLU | 201 | 16.384 | 24.004 | 49.418 | 1.00 20.77 | AAAA |
| ATOM | 1596 | CA | GLU | 201 | 16.522 | 22.542 | 49.399 | 1.00 27.34 | AAAA |
| ATOM | 1597 | CB | GLU | 201 | 17.498 | 22.146 | 48.284 | 1.00 28.99 | AAAA |
| ATOM | 1598 | CG | GLU | 201 | 17.024 | 22.458 | 46.881 | 1.00 34.82 | AAAA |
| ATOM | 1599 | CD | GLU | 201 | 18.123 | 22.265 | 45.848 | 1.00 32.40 | AAAA |
| ATOM | 1600 | OE1 | GLU | 201 | 18.701 | 21.155 | 45.769 | 1.00 38.28 | AAAA |
| ATOM | 1601 | OE2 | GLU | 201 | 18.405 | 23.230 | 45.111 | 1.00 40.08 | AAAA |
| ATOM | 1602 | C | GLU | 201 | 17.007 | 21.891 | 50.695 | 1.00 23.51 | AAAA |
| ATOM | 1603 | O | GLU | 201 | 16.845 | 20.689 | 50.886 | 1.00 23.17 | AAAA |
| ATOM | 1604 | N | LYS | 202 | 17.619 | 22.681 | 51.571 | 1.00 20.03 | AAAA |
| ATOM | 1605 | CA | LYS | 202 | 18.178 | 22.177 | 52.829 | 1.00 17.01 | AAAA |
| ATOM | 1606 | CB | LYS | 202 | 19.666 | 21.862 | 52.634 | 1.00 19.24 | AAAA |
| ATOM | 1607 | CG | LYS | 202 | 19.903 | 20.769 | 51.611 | 1.00 36.04 | AAAA |
| ATOM | 1608 | CD | LYS | 202 | 20.997 | 21.162 | 50.648 | 1.00 45.11 | AAAA |
| ATOM | 1609 | CE | LYS | 202 | 21.060 | 20.209 | 49.463 | 1.00 55.83 | AAAA |
| ATOM | 1610 | NZ | LYS | 202 | 22.024 | 20.662 | 48.422 | 1.00 28.09 | AAAA |
| ATOM | 1611 | C | LYS | 202 | 18.016 | 23.240 | 53.899 | 1.00 17.02 | AAAA |
| ATOM | 1612 | O | LYS | 202 | 17.705 | 24.381 | 53.585 | 1.00 20.20 | AAAA |
| ATOM | 1613 | N | GLY | 203 | 18.232 | 22.875 | 55.160 | 1.00 22.94 | AAAA |
| ATOM | 1614 | CA | GLY | 203 | 18.064 | 23.850 | 56.223 | 1.00 19.38 | AAAA |
| ATOM | 1615 | C | GLY | 203 | 16.874 | 23.564 | 57.128 | 1.00 20.48 | AAAA |
| ATOM | 1616 | O | GLY | 203 | 16.607 | 24.312 | 58.070 | 1.00 18.55 | AAAA |
| ATOM | 1617 | N | PHE | 204 | 16.150 | 22.484 | 56.852 | 1.00 15.42 | AAAA |
| ATOM | 1618 | CA | PHE | 204 | 14.983 | 22.143 | 57.670 | 1.00 20.73 | AAAA |
| ATOM | 1619 | CB | PHE | 204 | 14.018 | 21.212 | 56.903 | 1.00 19.97 | AAAA |
| ATOM | 1620 | CG | PHE | 204 | 13.441 | 21.838 | 55.667 | 1.00 19.63 | AAAA |
| ATOM | 1621 | CD1 | PHE | 204 | 14.137 | 21.801 | 54.459 | 1.00 24.96 | AAAA |
| ATOM | 1622 | CD2 | PHE | 204 | 12.230 | 22.523 | 55.725 | 1.00 18.92 | AAAA |
| ATOM | 1623 | CE1 | PHE | 204 | 13.636 | 22.438 | 53.327 | 1.00 20.66 | AAAA |
| ATOM | 1624 | CE2 | PHE | 204 | 11.720 | 23.169 | 54.597 | 1.00 24.86 | AAAA |
| ATOM | 1625 | CZ | PHE | 204 | 12.422 | 23.127 | 53.400 | 1.00 23.66 | AAAA |
| ATOM | 1626 | C | PHE | 204 | 15.376 | 21.513 | 59.006 | 1.00 18.73 | AAAA |
| ATOM | 1627 | O | PHE | 204 | 16.415 | 20.851 | 59.131 | 1.00 20.18 | AAAA |
| ATOM | 1628 | N | LEU | 205 | 14.518 | 21.726 | 59.994 | 1.00 19.46 | AAAA |
| ATOM | 1629 | CA | LEU | 205 | 14.727 | 21.244 | 61.356 | 1.00 21.09 | AAAA |
| ATOM | 1630 | CB | LEU | 205 | 13.547 | 21.674 | 62.233 | 1.00 23.44 | AAAA |
| ATOM | 1631 | CG | LEU | 205 | 13.506 | 21.222 | 63.693 | 1.00 23.23 | AAAA |
| ATOM | 1632 | CD1 | LEU | 205 | 14.717 | 21.736 | 64.445 | 1.00 24.06 | AAAA |
| ATOM | 1633 | CD2 | LEU | 205 | 12.224 | 21.743 | 64.312 | 1.00 30.63 | AAAA |
| ATOM | 1634 | C | LEU | 205 | 14.943 | 19.748 | 61.489 | 1.00 23.53 | AAAA |
| ATOM | 1635 | O | LEU | 205 | 15.659 | 19.315 | 62.381 | 1.00 21.28 | AAAA |
| ATOM | 1636 | N | GLU | 206 | 14.356 | 18.959 | 60.591 | 1.00 21.59 | AAAA |
| ATOM | 1637 | CA | GLU | 206 | 14.487 | 17.502 | 60.686 | 1.00 27.89 | AAAA |
| ATOM | 1638 | CB | GLU | 206 | 13.345 | 16.816 | 59.928 | 1.00 28.90 | AAAA |
| ATOM | 1639 | CG | GLU | 206 | 12.060 | 17.615 | 59.942 | 1.00 48.55 | AAAA |
| ATOM | 1640 | CD | GLU | 206 | 12.169 | 18.832 | 59.042 | 1.00 46.86 | AAAA |
| ATOM | 1641 | OE1 | GLU | 206 | 11.360 | 19.769 | 59.178 | 1.00 21.58 | AAAA |
| ATOM | 1642 | OE2 | GLU | 206 | 13.076 | 18.833 | 58.181 | 1.00 63.58 | AAAA |
| ATOM | 1643 | C | GLU | 206 | 15.819 | 16.955 | 60.188 | 1.00 22.86 | AAAA |
| ATOM | 1644 | O | GLU | 206 | 16.071 | 15.753 | 60.286 | 1.00 21.21 | AAAA |
| ATOM | 1645 | N | GLU | 207 | 16.666 | 17.816 | 59.631 | 1.00 25.04 | AAAA |
| ATOM | 1646 | CA | GLU | 207 | 17.976 | 17.373 | 59.152 | 1.00 19.61 | AAAA |
| ATOM | 1647 | CB | GLU | 207 | 18.483 | 18.322 | 58.055 | 1.00 20.75 | AAAA |
| ATOM | 1648 | CG | GLU | 207 | 17.682 | 18.222 | 56.753 | 1.00 18.44 | AAAA |
| ATOM | 1649 | CD | GLU | 207 | 17.687 | 19.514 | 55.983 | 1.00 24.75 | AAAA |
| ATOM | 1650 | OE1 | GLU | 207 | 18.738 | 20.182 | 55.948 | 1.00 22.17 | AAAA |

Fig. 16-25

| | | | | | | | | | |
|---|---|---|---|---|---|---|---|---|---|
| ATOM | 1651 | OE2 | GLU | 207 | 16.646 | 19.854 | 55.396 | 1.00 15.50 | AAAA |
| ATOM | 1652 | C | GLU | 207 | 18.921 | 17.379 | 60.350 | 1.00 28.83 | AAAA |
| ATOM | 1653 | O | GLU | 207 | 19.506 | 18.416 | 60.687 | 1.00 18.11 | AAAA |
| ATOM | 1654 | N | ILE | 208 | 19.081 | 16.218 | 60.988 | 1.00 21.60 | AAAA |
| ATOM | 1655 | CA | ILE | 208 | 19.930 | 16.138 | 62.168 | 1.00 22.37 | AAAA |
| ATOM | 1656 | CB | ILE | 208 | 19.113 | 15.652 | 63.403 | 1.00 28.84 | AAAA |
| ATOM | 1657 | CG2 | ILE | 208 | 19.968 | 15.693 | 64.653 | 1.00 43.26 | AAAA |
| ATOM | 1658 | CG1 | ILE | 208 | 17.905 | 16.561 | 63.625 | 1.00 21.61 | AAAA |
| ATOM | 1659 | CD1 | ILE | 208 | 17.029 | 16.160 | 64.786 | 1.00 41.40 | AAAA |
| ATOM | 1660 | C | ILE | 208 | 21.156 | 15.260 | 61.981 | 1.00 24.74 | AAAA |
| ATOM | 1661 | O | ILE | 208 | 21.785 | 14.850 | 62.943 | 1.00 22.68 | AAAA |
| ATOM | 1662 | N | GLY | 209 | 21.512 | 14.969 | 60.738 | 1.00 22.80 | AAAA |
| ATOM | 1663 | CA | GLY | 209 | 22.690 | 14.153 | 60.535 | 1.00 20.43 | AAAA |
| ATOM | 1664 | C | GLY | 209 | 22.342 | 12.769 | 60.037 | 1.00 25.56 | AAAA |
| ATOM | 1665 | O | GLY | 209 | 21.165 | 12.447 | 59.850 | 1.00 25.22 | AAAA |
| ATOM | 1666 | N | GLU | 210 | 23.373 | 11.944 | 59.888 | 1.00 26.07 | AAAA |
| ATOM | 1667 | CA | GLU | 210 | 23.235 | 10.601 | 59.348 | 1.00 25.78 | AAAA |
| ATOM | 1668 | CB | GLU | 210 | 23.404 | 10.731 | 57.835 | 1.00 28.27 | AAAA |
| ATOM | 1669 | CG | GLU | 210 | 23.041 | 9.569 | 56.965 | 1.00 56.41 | AAAA |
| ATOM | 1670 | CD | GLU | 210 | 23.170 | 9.952 | 55.495 | 1.00 65.37 | AAAA |
| ATOM | 1671 | OE1 | GLU | 210 | 24.290 | 10.327 | 55.075 | 1.00 62.00 | AAAA |
| ATOM | 1672 | OE2 | GLU | 210 | 22.153 | 9.894 | 54.768 | 1.00 73.24 | AAAA |
| ATOM | 1673 | C | GLU | 210 | 24.329 | 9.709 | 59.936 | 1.00 31.85 | AAAA |
| ATOM | 1674 | O | GLU | 210 | 25.447 | 10.170 | 60.217 | 1.00 28.85 | AAAA |
| ATOM | 1675 | N | GLY | 211 | 24.012 | 8.431 | 60.121 | 1.00 27.84 | AAAA |
| ATOM | 1676 | CA | GLY | 211 | 24.991 | 7.502 | 60.657 | 1.00 26.25 | AAAA |
| ATOM | 1677 | C | GLY | 211 | 25.545 | 7.942 | 61.995 | 1.00 27.79 | AAAA |
| ATOM | 1678 | O | GLY | 211 | 24.788 | 8.324 | 62.874 | 1.00 28.66 | AAAA |
| ATOM | 1679 | N | LYS | 212 | 26.865 | 7.880 | 62.150 | 1.00 34.62 | AAAA |
| ATOM | 1680 | CA | LYS | 212 | 27.512 | 8.287 | 63.393 | 1.00 34.39 | AAAA |
| ATOM | 1681 | CB | LYS | 212 | 29.029 | 8.132 | 63.273 | 1.00 40.40 | AAAA |
| ATOM | 1682 | CG | LYS | 212 | 29.505 | 6.712 | 62.996 | 1.00 53.97 | AAAA |
| ATOM | 1683 | CD | LYS | 212 | 29.139 | 5.770 | 64.131 | 1.00 61.93 | AAAA |
| ATOM | 1684 | CE | LYS | 212 | 29.612 | 4.347 | 63.863 | 1.00 62.74 | AAAA |
| ATOM | 1685 | NZ | LYS | 212 | 31.091 | 4.258 | 63.711 | 1.00 70.11 | AAAA |
| ATOM | 1686 | C | LYS | 212 | 27.181 | 9.741 | 63.725 | 1.00 36.04 | AAAA |
| ATOM | 1687 | O | LYS | 212 | 27.109 | 10.126 | 64.897 | 1.00 28.34 | AAAA |
| ATOM | 1688 | N | GLY | 213 | 26.959 | 10.543 | 62.688 | 1.00 31.47 | AAAA |
| ATOM | 1689 | CA | GLY | 213 | 26.648 | 11.948 | 62.898 | 1.00 31.68 | AAAA |
| ATOM | 1690 | C | GLY | 213 | 25.189 | 12.291 | 63.142 | 1.00 28.78 | AAAA |
| ATOM | 1691 | O | GLY | 213 | 24.840 | 13.460 | 63.259 | 1.00 22.56 | AAAA |
| ATOM | 1692 | N | LYS | 214 | 24.317 | 11.292 | 63.222 | 1.00 28.54 | AAAA |
| ATOM | 1693 | CA | LYS | 214 | 22.905 | 11.585 | 63.463 | 1.00 31.11 | AAAA |
| ATOM | 1694 | CB | LYS | 214 | 22.080 | 10.295 | 63.325 | 1.00 31.03 | AAAA |
| ATOM | 1695 | CG | LYS | 214 | 20.583 | 10.461 | 63.224 | 1.00 38.15 | AAAA |
| ATOM | 1696 | CD | LYS | 214 | 19.968 | 9.115 | 62.844 | 1.00 40.49 | AAAA |
| ATOM | 1697 | CE | LYS | 214 | 18.490 | 9.220 | 62.537 | 1.00 48.02 | AAAA |
| ATOM | 1698 | NZ | LYS | 214 | 17.927 | 7.924 | 62.064 | 1.00 44.99 | AAAA |
| ATOM | 1699 | C | LYS | 214 | 22.834 | 12.160 | 64.875 | 1.00 26.90 | AAAA |
| ATOM | 1700 | O | LYS | 214 | 23.260 | 11.524 | 65.831 | 1.00 33.33 | AAAA |
| ATOM | 1701 | N | GLY | 215 | 22.310 | 13.376 | 64.997 | 1.00 24.38 | AAAA |
| ATOM | 1702 | CA | GLY | 215 | 22.230 | 14.034 | 66.290 | 1.00 26.03 | AAAA |
| ATOM | 1703 | C | GLY | 215 | 23.298 | 15.115 | 66.447 | 1.00 27.03 | AAAA |
| ATOM | 1704 | O | GLY | 215 | 23.352 | 15.820 | 67.458 | 1.00 23.34 | AAAA |
| ATOM | 1705 | N | TYR | 216 | 24.152 | 15.260 | 65.439 | 1.00 22.79 | AAAA |
| ATOM | 1706 | CA | TYR | 216 | 25.217 | 16.257 | 65.512 | 1.00 25.51 | AAAA |
| ATOM | 1707 | CB | TYR | 216 | 26.592 | 15.576 | 65.406 | 1.00 20.54 | AAAA |
| ATOM | 1708 | CG | TYR | 216 | 26.900 | 14.671 | 66.581 | 1.00 26.47 | AAAA |
| ATOM | 1709 | CD1 | TYR | 216 | 26.221 | 13.464 | 66.757 | 1.00 28.96 | AAAA |
| ATOM | 1710 | CE1 | TYR | 216 | 26.455 | 12.660 | 67.872 | 1.00 33.08 | AAAA |
| ATOM | 1711 | CD2 | TYR | 216 | 27.832 | 15.052 | 67.552 | 1.00 24.21 | AAAA |
| ATOM | 1712 | CE2 | TYR | 216 | 28.074 | 14.254 | 68.675 | 1.00 34.45 | AAAA |
| ATOM | 1713 | CZ | TYR | 216 | 27.378 | 13.063 | 68.827 | 1.00 40.53 | AAAA |
| ATOM | 1714 | OH | TYR | 216 | 27.580 | 12.291 | 69.947 | 1.00 45.67 | AAAA |
| ATOM | 1715 | C | TYR | 216 | 25.104 | 17.391 | 64.493 | 1.00 22.57 | AAAA |
| ATOM | 1716 | O | TYR | 216 | 26.097 | 18.014 | 64.126 | 1.00 19.70 | AAAA |

Fig. 16-26

| | | | | | | | | | |
|---|---|---|---|---|---|---|---|---|---|
| ATOM | 1717 | N | ASN | 217 | 23.889 | 17.635 | 64.027 | 1.00 22.88 | AAAA |
| ATOM | 1718 | CA | ASN | 217 | 23.621 | 18.729 | 63.109 | 1.00 22.60 | AAAA |
| ATOM | 1719 | CB | ASN | 217 | 23.453 | 18.240 | 61.671 | 1.00 16.61 | AAAA |
| ATOM | 1720 | CG | ASN | 217 | 23.233 | 19.387 | 60.695 | 1.00 17.16 | AAAA |
| ATOM | 1721 | OD1 | ASN | 217 | 22.098 | 19.704 | 60.307 | 1.00 20.23 | AAAA |
| ATOM | 1722 | ND2 | ASN | 217 | 24.320 | 20.032 | 60.309 | 1.00 12.18 | AAAA |
| ATOM | 1723 | C | ASN | 217 | 22.311 | 19.296 | 63.630 | 1.00 17.65 | AAAA |
| ATOM | 1724 | O | ASN | 217 | 21.381 | 18.550 | 63.894 | 1.00 17.63 | AAAA |
| ATOM | 1725 | N | LEU | 218 | 22.236 | 20.610 | 63.793 | 1.00 21.68 | AAAA |
| ATOM | 1726 | CA | LEU | 218 | 21.014 | 21.197 | 64.320 | 1.00 21.20 | AAAA |
| ATOM | 1727 | CB | LEU | 218 | 21.186 | 21.547 | 65.808 | 1.00 17.73 | AAAA |
| ATOM | 1728 | CG | LEU | 218 | 19.906 | 21.702 | 66.647 | 1.00 32.30 | AAAA |
| ATOM | 1729 | CD1 | LEU | 218 | 20.228 | 22.427 | 67.944 | 1.00 24.51 | AAAA |
| ATOM | 1730 | CD2 | LEU | 218 | 18.862 | 22.464 | 65.903 | 1.00 40.08 | AAAA |
| ATOM | 1731 | C | LEU | 218 | 20.700 | 22.459 | 63.554 | 1.00 19.46 | AAAA |
| ATOM | 1732 | O | LEU | 218 | 21.467 | 23.425 | 63.615 | 1.00 16.70 | AAAA |
| ATOM | 1733 | N | ASN | 219 | 19.590 | 22.441 | 62.824 | 1.00 15.43 | AAAA |
| ATOM | 1734 | CA | ASN | 219 | 19.143 | 23.609 | 62.072 | 1.00 14.05 | AAAA |
| ATOM | 1735 | CB | ASN | 219 | 18.634 | 23.232 | 60.665 | 1.00 15.92 | AAAA |
| ATOM | 1736 | CG | ASN | 219 | 19.732 | 22.738 | 59.750 | 1.00 22.73 | AAAA |
| ATOM | 1737 | OD1 | ASN | 219 | 20.861 | 23.232 | 59.802 | 1.00 17.90 | AAAA |
| ATOM | 1738 | ND2 | ASN | 219 | 19.398 | 21.789 | 58.868 | 1.00 16.62 | AAAA |
| ATOM | 1739 | C | ASN | 219 | 17.990 | 24.256 | 62.821 | 1.00 21.98 | AAAA |
| ATOM | 1740 | O | ASN | 219 | 17.075 | 23.569 | 63.262 | 1.00 18.65 | AAAA |
| ATOM | 1741 | N | ILE | 220 | 18.025 | 25.580 | 62.952 | 1.00 16.82 | AAAA |
| ATOM | 1742 | CA | ILE | 220 | 16.951 | 26.298 | 63.640 | 1.00 13.22 | AAAA |
| ATOM | 1743 | CB | ILE | 220 | 17.522 | 27.115 | 64.823 | 1.00 15.70 | AAAA |
| ATOM | 1744 | CG2 | ILE | 220 | 16.411 | 27.912 | 65.479 | 1.00 15.18 | AAAA |
| ATOM | 1745 | CG1 | ILE | 220 | 18.246 | 26.193 | 65.823 | 1.00 19.11 | AAAA |
| ATOM | 1746 | CD1 | ILE | 220 | 17.350 | 25.259 | 66.632 | 1.00 22.75 | AAAA |
| ATOM | 1747 | C | ILE | 220 | 16.363 | 27.246 | 62.573 | 1.00 18.80 | AAAA |
| ATOM | 1748 | O | ILE | 220 | 16.810 | 28.386 | 62.419 | 1.00 15.52 | AAAA |
| ATOM | 1749 | N | PRO | 221 | 15.341 | 26.790 | 61.826 | 1.00 16.72 | AAAA |
| ATOM | 1750 | CD | PRO | 221 | 14.612 | 25.518 | 61.906 | 1.00 18.83 | AAAA |
| ATOM | 1751 | CA | PRO | 221 | 14.739 | 27.628 | 60.785 | 1.00 19.83 | AAAA |
| ATOM | 1752 | CB | PRO | 221 | 13.930 | 26.615 | 59.948 | 1.00 20.76 | AAAA |
| ATOM | 1753 | CG | PRO | 221 | 14.409 | 25.241 | 60.462 | 1.00 28.73 | AAAA |
| ATOM | 1754 | C | PRO | 221 | 13.849 | 28.664 | 61.444 | 1.00 21.26 | AAAA |
| ATOM | 1755 | O | PRO | 221 | 13.061 | 28.318 | 62.314 | 1.00 22.46 | AAAA |
| ATOM | 1756 | N | LEU | 222 | 13.977 | 29.926 | 61.028 | 1.00 19.70 | AAAA |
| ATOM | 1757 | CA | LEU | 222 | 13.209 | 31.018 | 61.612 | 1.00 21.62 | AAAA |
| ATOM | 1758 | CB | LEU | 222 | 14.163 | 31.972 | 62.319 | 1.00 16.46 | AAAA |
| ATOM | 1759 | CG | LEU | 222 | 14.868 | 31.232 | 63.466 | 1.00 18.65 | AAAA |
| ATOM | 1760 | CD1 | LEU | 222 | 16.026 | 32.072 | 64.014 | 1.00 21.32 | AAAA |
| ATOM | 1761 | CD2 | LEU | 222 | 13.857 | 30.925 | 64.555 | 1.00 19.98 | AAAA |
| ATOM | 1762 | C | LEU | 222 | 12.350 | 31.763 | 60.590 | 1.00 19.68 | AAAA |
| ATOM | 1763 | O | LEU | 222 | 12.687 | 31.830 | 59.412 | 1.00 18.07 | AAAA |
| ATOM | 1764 | N | PRO | 223 | 11.220 | 32.329 | 61.042 | 1.00 19.37 | AAAA |
| ATOM | 1765 | CD | PRO | 223 | 10.723 | 32.249 | 62.431 | 1.00 17.38 | AAAA |
| ATOM | 1766 | CA | PRO | 223 | 10.264 | 33.065 | 60.203 | 1.00 19.59 | AAAA |
| ATOM | 1767 | CB | PRO | 223 | 9.006 | 33.083 | 61.074 | 1.00 20.08 | AAAA |
| ATOM | 1768 | CG | PRO | 223 | 9.608 | 33.304 | 62.441 | 1.00 21.96 | AAAA |
| ATOM | 1769 | C | PRO | 223 | 10.606 | 34.458 | 59.723 | 1.00 23.15 | AAAA |
| ATOM | 1770 | O | PRO | 223 | 11.525 | 35.101 | 60.214 | 1.00 15.81 | AAAA |
| ATOM | 1771 | N | LYS | 224 | 9.830 | 34.912 | 58.745 | 1.00 16.41 | AAAA |
| ATOM | 1772 | CA | LYS | 224 | 9.975 | 36.254 | 58.200 | 1.00 16.11 | AAAA |
| ATOM | 1773 | CB | LYS | 224 | 9.002 | 36.446 | 57.039 | 1.00 20.34 | AAAA |
| ATOM | 1774 | CG | LYS | 224 | 9.163 | 35.441 | 55.900 | 1.00 19.33 | AAAA |
| ATOM | 1775 | CD | LYS | 224 | 8.109 | 35.687 | 54.807 | 1.00 25.49 | AAAA |
| ATOM | 1776 | CE | LYS | 224 | 8.209 | 34.624 | 53.704 | 1.00 24.14 | AAAA |
| ATOM | 1777 | NZ | LYS | 224 | 7.207 | 34.843 | 52.618 | 1.00 34.08 | AAAA |
| ATOM | 1778 | C | LYS | 224 | 9.638 | 37.289 | 59.284 | 1.00 15.77 | AAAA |
| ATOM | 1779 | O | LYS | 224 | 8.819 | 37.032 | 60.186 | 1.00 21.07 | AAAA |
| ATOM | 1780 | N | GLY | 225 | 10.239 | 38.469 | 59.171 | 1.00 20.77 | AAAA |
| ATOM | 1781 | CA | GLY | 225 | 9.974 | 39.527 | 60.129 | 1.00 20.30 | AAAA |
| ATOM | 1782 | C | GLY | 225 | 10.556 | 39.286 | 61.507 | 1.00 20.63 | AAAA |

Fig. 16-27

| ATOM | 1783 | O   | GLY | 225 | 10.128 | 39.912 | 62.468 | 1.00 | 20.66 | AAAA |
| ---- | ---- | --- | --- | --- | ------ | ------ | ------ | ---- | ----- | ---- |
| ATOM | 1784 | N   | LEU | 226 | 11.540 | 38.395 | 61.606 | 1.00 | 20.37 | AAAA |
| ATOM | 1785 | CA  | LEU | 226 | 12.154 | 38.063 | 62.893 | 1.00 | 18.71 | AAAA |
| ATOM | 1786 | CB  | LEU | 226 | 13.354 | 37.145 | 62.670 | 1.00 | 13.63 | AAAA |
| ATOM | 1787 | CG  | LEU | 226 | 13.836 | 36.443 | 63.939 | 1.00 | 18.44 | AAAA |
| ATOM | 1788 | CD1 | LEU | 226 | 12.834 | 35.329 | 64.243 | 1.00 | 18.09 | AAAA |
| ATOM | 1789 | CD2 | LEU | 226 | 15.232 | 35.844 | 63.741 | 1.00 | 17.96 | AAAA |
| ATOM | 1790 | C   | LEU | 226 | 12.649 | 39.309 | 63.642 | 1.00 | 19.84 | AAAA |
| ATOM | 1791 | O   | LEU | 226 | 13.320 | 40.151 | 63.052 | 1.00 | 18.13 | AAAA |
| ATOM | 1792 | N   | ASN | 227 | 12.336 | 39.421 | 64.932 | 1.00 | 23.30 | AAAA |
| ATOM | 1793 | CA  | ASN | 227 | 12.815 | 40.571 | 65.692 | 1.00 | 20.88 | AAAA |
| ATOM | 1794 | CB  | ASN | 227 | 11.682 | 41.261 | 66.485 | 1.00 | 21.73 | AAAA |
| ATOM | 1795 | CG  | ASN | 227 | 11.061 | 40.368 | 67.546 | 1.00 | 20.47 | AAAA |
| ATOM | 1796 | OD1 | ASN | 227 | 11.762 | 39.736 | 68.341 | 1.00 | 23.80 | AAAA |
| ATOM | 1797 | ND2 | ASN | 227 | 9.729  | 40.340 | 67.581 | 1.00 | 21.08 | AAAA |
| ATOM | 1798 | C   | ASN | 227 | 13.950 | 40.152 | 66.612 | 1.00 | 25.24 | AAAA |
| ATOM | 1799 | O   | ASN | 227 | 14.282 | 38.965 | 66.702 | 1.00 | 18.54 | AAAA |
| ATOM | 1800 | N   | ASP | 228 | 14.547 | 41.124 | 67.296 | 1.00 | 19.41 | AAAA |
| ATOM | 1801 | CA  | ASP | 228 | 15.682 | 40.844 | 68.169 | 1.00 | 22.15 | AAAA |
| ATOM | 1802 | CB  | ASP | 228 | 16.208 | 42.141 | 68.802 | 1.00 | 16.82 | AAAA |
| ATOM | 1803 | CG  | ASP | 228 | 16.852 | 43.060 | 67.796 | 1.00 | 30.68 | AAAA |
| ATOM | 1804 | OD1 | ASP | 228 | 17.182 | 42.576 | 66.690 | 1.00 | 23.87 | AAAA |
| ATOM | 1805 | OD2 | ASP | 228 | 17.053 | 44.256 | 68.123 | 1.00 | 25.02 | AAAA |
| ATOM | 1806 | C   | ASP | 228 | 15.440 | 39.835 | 69.265 | 1.00 | 18.83 | AAAA |
| ATOM | 1807 | O   | ASP | 228 | 16.298 | 39.002 | 69.536 | 1.00 | 16.28 | AAAA |
| ATOM | 1808 | N   | ASN | 229 | 14.291 | 39.930 | 69.928 | 1.00 | 20.73 | AAAA |
| ATOM | 1809 | CA  | ASN | 229 | 13.975 | 39.015 | 71.007 | 1.00 | 21.75 | AAAA |
| ATOM | 1810 | CB  | ASN | 229 | 12.706 | 39.483 | 71.712 | 1.00 | 19.46 | AAAA |
| ATOM | 1811 | CG  | ASN | 229 | 12.943 | 40.738 | 72.516 | 1.00 | 27.14 | AAAA |
| ATOM | 1812 | OD1 | ASN | 229 | 13.588 | 40.691 | 73.556 | 1.00 | 33.03 | AAAA |
| ATOM | 1813 | ND2 | ASN | 229 | 12.464 | 41.874 | 72.019 | 1.00 | 21.35 | AAAA |
| ATOM | 1814 | C   | ASN | 229 | 13.833 | 37.596 | 70.503 | 1.00 | 18.47 | AAAA |
| ATOM | 1815 | O   | ASN | 229 | 14.284 | 36.644 | 71.151 | 1.00 | 22.47 | AAAA |
| ATOM | 1816 | N   | GLU | 230 | 13.252 | 37.454 | 69.319 | 1.00 | 17.79 | AAAA |
| ATOM | 1817 | CA  | GLU | 230 | 13.081 | 36.125 | 68.748 | 1.00 | 21.18 | AAAA |
| ATOM | 1818 | CB  | GLU | 230 | 12.152 | 36.193 | 67.536 | 1.00 | 20.54 | AAAA |
| ATOM | 1819 | CG  | GLU | 230 | 10.765 | 36.714 | 67.890 | 1.00 | 28.98 | AAAA |
| ATOM | 1820 | CD  | GLU | 230 | 9.870  | 36.816 | 66.677 | 1.00 | 24.35 | AAAA |
| ATOM | 1821 | OE1 | GLU | 230 | 10.360 | 37.296 | 65.638 | 1.00 | 22.00 | AAAA |
| ATOM | 1822 | OE2 | GLU | 230 | 8.683  | 36.443 | 66.772 | 1.00 | 24.99 | AAAA |
| ATOM | 1823 | C   | GLU | 230 | 14.422 | 35.507 | 68.361 | 1.00 | 16.89 | AAAA |
| ATOM | 1824 | O   | GLU | 230 | 14.663 | 34.326 | 68.603 | 1.00 | 19.45 | AAAA |
| ATOM | 1825 | N   | PHE | 231 | 15.305 | 36.305 | 67.772 | 1.00 | 15.68 | AAAA |
| ATOM | 1826 | CA  | PHE | 231 | 16.616 | 35.788 | 67.389 | 1.00 | 15.78 | AAAA |
| ATOM | 1827 | CB  | PHE | 231 | 17.420 | 36.863 | 66.649 | 1.00 | 13.22 | AAAA |
| ATOM | 1828 | CG  | PHE | 231 | 18.719 | 36.361 | 66.069 | 1.00 | 20.63 | AAAA |
| ATOM | 1829 | CD1 | PHE | 231 | 18.723 | 35.445 | 65.016 | 1.00 | 18.42 | AAAA |
| ATOM | 1830 | CD2 | PHE | 231 | 19.936 | 36.804 | 66.568 | 1.00 | 21.10 | AAAA |
| ATOM | 1831 | CE1 | PHE | 231 | 19.918 | 34.983 | 64.471 | 1.00 | 17.67 | AAAA |
| ATOM | 1832 | CE2 | PHE | 231 | 21.144 | 36.346 | 66.029 | 1.00 | 28.29 | AAAA |
| ATOM | 1833 | CZ  | PHE | 231 | 21.130 | 35.431 | 64.976 | 1.00 | 27.85 | AAAA |
| ATOM | 1834 | C   | PHE | 231 | 17.385 | 35.332 | 68.636 | 1.00 | 18.54 | AAAA |
| ATOM | 1835 | O   | PHE | 231 | 17.869 | 34.201 | 68.702 | 1.00 | 18.86 | AAAA |
| ATOM | 1836 | N   | LEU | 232 | 17.495 | 36.204 | 69.636 | 1.00 | 19.07 | AAAA |
| ATOM | 1837 | CA  | LEU | 232 | 18.239 | 35.850 | 70.848 | 1.00 | 17.39 | AAAA |
| ATOM | 1838 | CB  | LEU | 232 | 18.415 | 37.078 | 71.737 | 1.00 | 24.53 | AAAA |
| ATOM | 1839 | CG  | LEU | 232 | 19.214 | 38.202 | 71.061 | 1.00 | 16.64 | AAAA |
| ATOM | 1840 | CD1 | LEU | 232 | 19.134 | 39.449 | 71.934 | 1.00 | 26.70 | AAAA |
| ATOM | 1841 | CD2 | LEU | 232 | 20.659 | 37.806 | 70.810 | 1.00 | 18.77 | AAAA |
| ATOM | 1842 | C   | LEU | 232 | 17.607 | 34.707 | 71.628 | 1.00 | 19.82 | AAAA |
| ATOM | 1843 | O   | LEU | 232 | 18.309 | 33.904 | 72.217 | 1.00 | 21.80 | AAAA |
| ATOM | 1844 | N   | PHE | 233 | 16.281 | 34.640 | 71.648 | 1.00 | 17.18 | AAAA |
| ATOM | 1845 | CA  | PHE | 233 | 15.587 | 33.537 | 72.309 | 1.00 | 23.34 | AAAA |
| ATOM | 1846 | CB  | PHE | 233 | 14.074 | 33.663 | 72.095 | 1.00 | 19.17 | AAAA |
| ATOM | 1847 | CG  | PHE | 233 | 13.289 | 32.447 | 72.523 | 1.00 | 21.40 | AAAA |
| ATOM | 1848 | CD1 | PHE | 233 | 12.863 | 32.302 | 73.841 | 1.00 | 29.62 | AAAA |

Fig. 16-28

| | | | | | | | | | |
|---|---|---|---|---|---|---|---|---|---|
| ATOM | 1849 | CD2 | PHE | 233 | 12.942 | 31.473 | 71.596 | 1.00 19.92 | AAAA |
| ATOM | 1850 | CE1 | PHE | 233 | 12.088 | 31.206 | 74.229 | 1.00 29.35 | AAAA |
| ATOM | 1851 | CE2 | PHE | 233 | 12.168 | 30.363 | 71.966 | 1.00 25.37 | AAAA |
| ATOM | 1852 | CZ | PHE | 233 | 11.737 | 30.231 | 73.283 | 1.00 30.28 | AAAA |
| ATOM | 1853 | C | PHE | 233 | 16.041 | 32.234 | 71.660 | 1.00 23.12 | AAAA |
| ATOM | 1854 | O | PHE | 233 | 16.433 | 31.273 | 72.332 | 1.00 18.35 | AAAA |
| ATOM | 1855 | N | ALA | 234 | 15.961 | 32.208 | 70.332 | 1.00 17.26 | AAAA |
| ATOM | 1856 | CA | ALA | 234 | 16.332 | 31.026 | 69.562 | 1.00 17.67 | AAAA |
| ATOM | 1857 | CB | ALA | 234 | 16.085 | 31.297 | 68.046 | 1.00 19.08 | AAAA |
| ATOM | 1858 | C | ALA | 234 | 17.786 | 30.641 | 69.800 | 1.00 16.31 | AAAA |
| ATOM | 1859 | O | ALA | 234 | 18.127 | 29.461 | 69.926 | 1.00 16.75 | AAAA |
| ATOM | 1860 | N | LEU | 235 | 18.646 | 31.643 | 69.846 | 1.00 16.73 | AAAA |
| ATOM | 1861 | CA | LEU | 235 | 20.074 | 31.411 | 70.051 | 1.00 19.14 | AAAA |
| ATOM | 1862 | CB | LEU | 235 | 20.823 | 32.742 | 69.956 | 1.00 21.72 | AAAA |
| ATOM | 1863 | CG | LEU | 235 | 22.226 | 32.790 | 69.345 | 1.00 36.73 | AAAA |
| ATOM | 1864 | CD1 | LEU | 235 | 23.026 | 33.844 | 70.105 | 1.00 20.69 | AAAA |
| ATOM | 1865 | CD2 | LEU | 235 | 22.917 | 31.426 | 69.393 | 1.00 22.96 | AAAA |
| ATOM | 1866 | C | LEU | 235 | 20.354 | 30.776 | 71.421 | 1.00 18.71 | AAAA |
| ATOM | 1867 | O | LEU | 235 | 21.028 | 29.747 | 71.522 | 1.00 18.59 | AAAA |
| ATOM | 1868 | N | GLU | 236 | 19.831 | 31.390 | 72.479 | 1.00 25.43 | AAAA |
| ATOM | 1869 | CA | GLU | 236 | 20.046 | 30.883 | 73.839 | 1.00 19.75 | AAAA |
| ATOM | 1870 | CB | GLU | 236 | 19.335 | 31.777 | 74.860 | 1.00 23.18 | AAAA |
| ATOM | 1871 | CG | GLU | 236 | 19.725 | 33.229 | 74.777 | 1.00 38.53 | AAAA |
| ATOM | 1872 | CD | GLU | 236 | 18.857 | 34.119 | 75.648 | 1.00 42.42 | AAAA |
| ATOM | 1873 | OE1 | GLU | 236 | 17.617 | 34.171 | 75.428 | 1.00 45.43 | AAAA |
| ATOM | 1874 | OE2 | GLU | 236 | 19.425 | 34.768 | 76.548 | 1.00 48.76 | AAAA |
| ATOM | 1875 | C | GLU | 236 | 19.541 | 29.452 | 74.011 | 1.00 25.85 | AAAA |
| ATOM | 1876 | O | GLU | 236 | 20.222 | 28.603 | 74.597 | 1.00 21.36 | AAAA |
| ATOM | 1877 | N | LYS | 237 | 18.343 | 29.193 | 73.501 | 1.00 23.16 | AAAA |
| ATOM | 1878 | CA | LYS | 237 | 17.752 | 27.871 | 73.610 | 1.00 17.06 | AAAA |
| ATOM | 1879 | CB | LYS | 237 | 16.282 | 27.943 | 73.193 | 1.00 26.98 | AAAA |
| ATOM | 1880 | CG | LYS | 237 | 15.483 | 26.711 | 73.519 | 1.00 52.00 | AAAA |
| ATOM | 1881 | CD | LYS | 237 | 14.078 | 27.110 | 73.932 | 1.00 56.40 | AAAA |
| ATOM | 1882 | CE | LYS | 237 | 14.131 | 27.979 | 75.183 | 1.00 52.03 | AAAA |
| ATOM | 1883 | NZ | LYS | 237 | 12.782 | 28.421 | 75.614 | 1.00 55.53 | AAAA |
| ATOM | 1884 | C | LYS | 237 | 18.502 | 26.827 | 72.785 | 1.00 18.46 | AAAA |
| ATOM | 1885 | O | LYS | 237 | 18.691 | 25.692 | 73.231 | 1.00 21.20 | AAAA |
| ATOM | 1886 | N | SER | 238 | 18.932 | 27.187 | 71.578 | 1.00 21.28 | AAAA |
| ATOM | 1887 | CA | SER | 238 | 19.649 | 26.208 | 70.776 | 1.00 16.47 | AAAA |
| ATOM | 1888 | CB | SER | 238 | 19.745 | 26.666 | 69.307 | 1.00 19.75 | AAAA |
| ATOM | 1889 | OG | SER | 238 | 20.475 | 27.858 | 69.160 | 1.00 22.52 | AAAA |
| ATOM | 1890 | C | SER | 238 | 21.039 | 25.923 | 71.361 | 1.00 18.79 | AAAA |
| ATOM | 1891 | O | SER | 238 | 21.521 | 24.788 | 71.312 | 1.00 20.60 | AAAA |
| ATOM | 1892 | N | LEU | 239 | 21.690 | 26.937 | 71.925 | 1.00 22.95 | AAAA |
| ATOM | 1893 | CA | LEU | 239 | 23.004 | 26.701 | 72.513 | 1.00 20.98 | AAAA |
| ATOM | 1894 | CB | LEU | 239 | 23.652 | 28.008 | 72.986 | 1.00 18.39 | AAAA |
| ATOM | 1895 | CG | LEU | 239 | 23.985 | 29.072 | 71.933 | 1.00 20.02 | AAAA |
| ATOM | 1896 | CD1 | LEU | 239 | 24.538 | 30.311 | 72.636 | 1.00 27.02 | AAAA |
| ATOM | 1897 | CD2 | LEU | 239 | 25.010 | 28.556 | 70.933 | 1.00 20.31 | AAAA |
| ATOM | 1898 | C | LEU | 239 | 22.882 | 25.735 | 73.680 | 1.00 25.16 | AAAA |
| ATOM | 1899 | O | LEU | 239 | 23.780 | 24.929 | 73.920 | 1.00 20.70 | AAAA |
| ATOM | 1900 | N | GLU | 240 | 21.768 | 25.800 | 74.398 | 1.00 24.93 | AAAA |
| ATOM | 1901 | CA | GLU | 240 | 21.570 | 24.912 | 75.536 | 1.00 25.72 | AAAA |
| ATOM | 1902 | CB | GLU | 240 | 20.331 | 25.356 | 76.337 | 1.00 29.10 | AAAA |
| ATOM | 1903 | CG | GLU | 240 | 20.042 | 24.531 | 77.581 | 1.00 49.56 | AAAA |
| ATOM | 1904 | CD | GLU | 240 | 19.053 | 25.212 | 78.515 | 1.00 63.15 | AAAA |
| ATOM | 1905 | OE1 | GLU | 240 | 17.935 | 25.550 | 78.067 | 1.00 69.26 | AAAA |
| ATOM | 1906 | OE2 | GLU | 240 | 19.400 | 25.410 | 79.703 | 1.00 66.68 | AAAA |
| ATOM | 1907 | C | GLU | 240 | 21.440 | 23.469 | 75.046 | 1.00 23.44 | AAAA |
| ATOM | 1908 | O | GLU | 240 | 21.951 | 22.535 | 75.674 | 1.00 23.10 | AAAA |
| ATOM | 1909 | N | ILE | 241 | 20.771 | 23.294 | 73.913 | 1.00 19.52 | AAAA |
| ATOM | 1910 | CA | ILE | 241 | 20.598 | 21.978 | 73.321 | 1.00 24.06 | AAAA |
| ATOM | 1911 | CB | ILE | 241 | 19.705 | 22.039 | 72.052 | 1.00 23.80 | AAAA |
| ATOM | 1912 | CG2 | ILE | 241 | 19.718 | 20.678 | 71.323 | 1.00 24.94 | AAAA |
| ATOM | 1913 | CG1 | ILE | 241 | 18.281 | 22.433 | 72.439 | 1.00 28.60 | AAAA |
| ATOM | 1914 | CD1 | ILE | 241 | 17.336 | 22.600 | 71.257 | 1.00 27.04 | AAAA |

Fig. 16-29

| | | | | | | | | | |
|---|---|---|---|---|---|---|---|---|---|
| ATOM | 1915 | C | ILE | 241 | 21.957 | 21.404 | 72.941 | 1.00 25.48 | AAAA |
| ATOM | 1916 | O | ILE | 241 | 22.244 | 20.234 | 73.195 | 1.00 19.43 | AAAA |
| ATOM | 1917 | N | VAL | 242 | 22.799 | 22.235 | 72.334 | 1.00 20.41 | AAAA |
| ATOM | 1918 | CA | VAL | 242 | 24.116 | 21.782 | 71.928 | 1.00 23.17 | AAAA |
| ATOM | 1919 | CB | VAL | 242 | 24.853 | 22.856 | 71.107 | 1.00 26.48 | AAAA |
| ATOM | 1920 | CG1 | VAL | 242 | 26.273 | 22.394 | 70.807 | 1.00 18.67 | AAAA |
| ATOM | 1921 | CG2 | VAL | 242 | 24.093 | 23.135 | 69.802 | 1.00 26.97 | AAAA |
| ATOM | 1922 | C | VAL | 242 | 24.962 | 21.456 | 73.154 | 1.00 24.81 | AAAA |
| ATOM | 1923 | O | VAL | 242 | 25.566 | 20.384 | 73.235 | 1.00 22.49 | AAAA |
| ATOM | 1924 | N | LYS | 243 | 24.989 | 22.387 | 74.102 | 1.00 26.06 | AAAA |
| ATOM | 1925 | CA | LYS | 243 | 25.775 | 22.202 | 75.311 | 1.00 32.57 | AAAA |
| ATOM | 1926 | CB | LYS | 243 | 25.599 | 23.379 | 76.272 | 1.00 28.53 | AAAA |
| ATOM | 1927 | CG | LYS | 243 | 26.386 | 23.183 | 77.568 | 1.00 43.21 | AAAA |
| ATOM | 1928 | CD | LYS | 243 | 26.022 | 24.191 | 78.653 | 1.00 53.10 | AAAA |
| ATOM | 1929 | CE | LYS | 243 | 26.407 | 25.607 | 78.287 | 1.00 50.30 | AAAA |
| ATOM | 1930 | NZ | LYS | 243 | 26.045 | 26.548 | 79.389 | 1.00 59.15 | AAAA |
| ATOM | 1931 | C | LYS | 243 | 25.433 | 20.917 | 76.046 | 1.00 30.38 | AAAA |
| ATOM | 1932 | O | LYS | 243 | 26.321 | 20.255 | 76.578 | 1.00 35.44 | AAAA |
| ATOM | 1933 | N | GLU | 244 | 24.161 | 20.542 | 76.076 | 1.00 28.12 | AAAA |
| ATOM | 1934 | CA | GLU | 244 | 23.798 | 19.320 | 76.798 | 1.00 37.54 | AAAA |
| ATOM | 1935 | CB | GLU | 244 | 22.288 | 19.260 | 77.048 | 1.00 35.34 | AAAA |
| ATOM | 1936 | CG | GLU | 244 | 21.735 | 20.459 | 77.816 | 1.00 55.88 | AAAA |
| ATOM | 1937 | CD | GLU | 244 | 20.281 | 20.275 | 78.230 | 1.00 57.89 | AAAA |
| ATOM | 1938 | OE1 | GLU | 244 | 19.673 | 21.246 | 78.738 | 1.00 60.60 | AAAA |
| ATOM | 1939 | OE2 | GLU | 244 | 19.753 | 19.152 | 78.062 | 1.00 57.73 | AAAA |
| ATOM | 1940 | C | GLU | 244 | 24.231 | 18.034 | 76.102 | 1.00 38.17 | AAAA |
| ATOM | 1941 | O | GLU | 244 | 24.294 | 16.978 | 76.727 | 1.00 38.46 | AAAA |
| ATOM | 1942 | N | VAL | 245 | 24.541 | 18.124 | 74.817 | 1.00 30.29 | AAAA |
| ATOM | 1943 | CA | VAL | 245 | 24.933 | 16.958 | 74.042 | 1.00 29.17 | AAAA |
| ATOM | 1944 | CB | VAL | 245 | 23.984 | 16.778 | 72.833 | 1.00 46.68 | AAAA |
| ATOM | 1945 | CG1 | VAL | 245 | 24.462 | 15.641 | 71.942 | 1.00 53.09 | AAAA |
| ATOM | 1946 | CG2 | VAL | 245 | 22.581 | 16.488 | 73.327 | 1.00 54.19 | AAAA |
| ATOM | 1947 | C | VAL | 245 | 26.364 | 16.982 | 73.508 | 1.00 34.90 | AAAA |
| ATOM | 1948 | O | VAL | 245 | 26.915 | 15.939 | 73.164 | 1.00 34.73 | AAAA |
| ATOM | 1949 | N | PHE | 246 | 26.980 | 18.156 | 73.465 | 1.00 29.22 | AAAA |
| ATOM | 1950 | CA | PHE | 246 | 28.324 | 18.256 | 72.897 | 1.00 29.17 | AAAA |
| ATOM | 1951 | CB | PHE | 246 | 28.178 | 18.800 | 71.464 | 1.00 30.42 | AAAA |
| ATOM | 1952 | CG | PHE | 246 | 29.384 | 18.588 | 70.585 | 1.00 25.62 | AAAA |
| ATOM | 1953 | CD1 | PHE | 246 | 29.695 | 17.326 | 70.097 | 1.00 28.89 | AAAA |
| ATOM | 1954 | CD2 | PHE | 246 | 30.167 | 19.668 | 70.196 | 1.00 25.17 | AAAA |
| ATOM | 1955 | CE1 | PHE | 246 | 30.771 | 17.138 | 69.222 | 1.00 23.43 | AAAA |
| ATOM | 1956 | CE2 | PHE | 246 | 31.248 | 19.495 | 69.322 | 1.00 22.40 | AAAA |
| ATOM | 1957 | CZ | PHE | 246 | 31.549 | 18.236 | 68.835 | 1.00 19.88 | AAAA |
| ATOM | 1958 | C | PHE | 246 | 29.233 | 19.176 | 73.712 | 1.00 23.38 | AAAA |
| ATOM | 1959 | O | PHE | 246 | 28.867 | 20.312 | 74.002 | 1.00 29.15 | AAAA |
| ATOM | 1960 | N | GLU | 247 | 30.410 | 18.682 | 74.094 | 1.00 29.73 | AAAA |
| ATOM | 1961 | CA | GLU | 247 | 31.395 | 19.481 | 74.841 | 1.00 28.10 | AAAA |
| ATOM | 1962 | CB | GLU | 247 | 31.912 | 18.726 | 76.074 | 1.00 35.75 | AAAA |
| ATOM | 1963 | CG | GLU | 247 | 30.972 | 18.707 | 77.286 | 1.00 60.78 | AAAA |
| ATOM | 1964 | CD | GLU | 247 | 29.700 | 17.892 | 77.077 | 1.00 70.07 | AAAA |
| ATOM | 1965 | OE1 | GLU | 247 | 28.913 | 18.220 | 76.165 | 1.00 79.95 | AAAA |
| ATOM | 1966 | OE2 | GLU | 247 | 29.481 | 16.920 | 77.835 | 1.00 76.80 | AAAA |
| ATOM | 1967 | C | GLU | 247 | 32.554 | 19.741 | 73.876 | 1.00 28.90 | AAAA |
| ATOM | 1968 | O | GLU | 247 | 33.490 | 18.946 | 73.778 | 1.00 23.67 | AAAA |
| ATOM | 1969 | N | PRO | 248 | 32.531 | 20.891 | 73.181 | 1.00 25.02 | AAAA |
| ATOM | 1970 | CD | PRO | 248 | 31.574 | 22.003 | 73.310 | 1.00 27.23 | AAAA |
| ATOM | 1971 | CA | PRO | 248 | 33.566 | 21.249 | 72.209 | 1.00 28.06 | AAAA |
| ATOM | 1972 | CB | PRO | 248 | 33.050 | 22.575 | 71.639 | 1.00 28.11 | AAAA |
| ATOM | 1973 | CG | PRO | 248 | 31.551 | 22.512 | 71.897 | 1.00 34.57 | AAAA |
| ATOM | 1974 | C | PRO | 248 | 34.968 | 21.416 | 72.770 | 1.00 23.87 | AAAA |
| ATOM | 1975 | O | PRO | 248 | 35.132 | 21.897 | 73.887 | 1.00 24.05 | AAAA |
| ATOM | 1976 | N | GLU | 249 | 35.965 | 21.013 | 71.983 | 1.00 24.34 | AAAA |
| ATOM | 1977 | CA | GLU | 249 | 37.366 | 21.195 | 72.355 | 1.00 25.98 | AAAA |
| ATOM | 1978 | CB | GLU | 249 | 38.275 | 20.166 | 71.679 | 1.00 22.07 | AAAA |
| ATOM | 1979 | CG | GLU | 249 | 38.046 | 18.726 | 72.116 | 1.00 33.40 | AAAA |
| ATOM | 1980 | CD | GLU | 249 | 39.005 | 17.767 | 71.445 | 1.00 29.15 | AAAA |

Fig. 16-30

```
ATOM   1981  OE1 GLU   249      39.071  17.770  70.199  1.00 27.62      AAAA
ATOM   1982  OE2 GLU   249      39.694  17.004  72.161  1.00 26.19      AAAA
ATOM   1983  C   GLU   249      37.692  22.561  71.786  1.00 26.04      AAAA
ATOM   1984  O   GLU   249      38.582  23.271  72.262  1.00 26.39      AAAA
ATOM   1985  N   VAL   250      36.953  22.921  70.744  1.00 23.83      AAAA
ATOM   1986  CA  VAL   250      37.151  24.197  70.086  1.00 19.67      AAAA
ATOM   1987  CB  VAL   250      38.438  24.178  69.210  1.00 20.88      AAAA
ATOM   1988  CG1 VAL   250      38.348  23.117  68.128  1.00 18.18      AAAA
ATOM   1989  CG2 VAL   250      38.647  25.530  68.591  1.00 16.71      AAAA
ATOM   1990  C   VAL   250      35.946  24.483  69.207  1.00 20.78      AAAA
ATOM   1991  O   VAL   250      35.299  23.556  68.746  1.00 19.60      AAAA
ATOM   1992  N   TYR   251      35.633  25.757  69.000  1.00 18.75      AAAA
ATOM   1993  CA  TYR   251      34.497  26.109  68.153  1.00 22.44      AAAA
ATOM   1994  CB  TYR   251      33.261  26.437  69.022  1.00 16.57      AAAA
ATOM   1995  CG  TYR   251      33.207  27.856  69.575  1.00 22.36      AAAA
ATOM   1996  CD1 TYR   251      32.654  28.896  68.823  1.00 18.12      AAAA
ATOM   1997  CE1 TYR   251      32.612  30.185  69.308  1.00 20.40      AAAA
ATOM   1998  CD2 TYR   251      33.715  28.160  70.842  1.00 20.04      AAAA
ATOM   1999  CE2 TYR   251      33.676  29.475  71.349  1.00 16.60      AAAA
ATOM   2000  CZ  TYR   251      33.128  30.473  70.573  1.00 14.68      AAAA
ATOM   2001  OH  TYR   251      33.100  31.780  71.011  1.00 21.79      AAAA
ATOM   2002  C   TYR   251      34.811  27.294  67.236  1.00 20.28      AAAA
ATOM   2003  O   TYR   251      35.695  28.107  67.525  1.00 19.91      AAAA
ATOM   2004  N   LEU   252      34.097  27.360  66.109  1.00 17.90      AAAA
ATOM   2005  CA  LEU   252      34.216  28.466  65.161  1.00 18.58      AAAA
ATOM   2006  CB  LEU   252      34.679  28.001  63.767  1.00 17.55      AAAA
ATOM   2007  CG  LEU   252      36.028  27.290  63.718  1.00 23.36      AAAA
ATOM   2008  CD1 LEU   252      35.819  25.820  64.017  1.00 27.78      AAAA
ATOM   2009  CD2 LEU   252      36.631  27.440  62.331  1.00 27.29      AAAA
ATOM   2010  C   LEU   252      32.816  29.049  65.052  1.00 15.49      AAAA
ATOM   2011  O   LEU   252      31.819  28.320  65.120  1.00 18.82      AAAA
ATOM   2012  N   LEU   253      32.756  30.360  64.891  1.00 16.80      AAAA
ATOM   2013  CA  LEU   253      31.498  31.105  64.817  1.00 17.50      AAAA
ATOM   2014  CB  LEU   253      31.379  31.987  66.073  1.00 15.49      AAAA
ATOM   2015  CG  LEU   253      30.326  33.085  66.165  1.00 17.75      AAAA
ATOM   2016  CD1 LEU   253      28.946  32.438  66.172  1.00 20.85      AAAA
ATOM   2017  CD2 LEU   253      30.536  33.897  67.464  1.00 19.05      AAAA
ATOM   2018  C   LEU   253      31.516  31.985  63.580  1.00 20.22      AAAA
ATOM   2019  O   LEU   253      32.474  32.727  63.371  1.00 18.14      AAAA
ATOM   2020  N   GLN   254      30.466  31.913  62.765  1.00 16.50      AAAA
ATOM   2021  CA  GLN   254      30.411  32.730  61.556  1.00 16.48      AAAA
ATOM   2022  CB  GLN   254      30.085  31.863  60.312  1.00 25.58      AAAA
ATOM   2023  CG  GLN   254      28.647  31.798  59.871  1.00 36.40      AAAA
ATOM   2024  CD  GLN   254      28.337  32.728  58.701  1.00 33.18      AAAA
ATOM   2025  OE1 GLN   254      28.744  32.487  57.546  1.00 21.05      AAAA
ATOM   2026  NE2 GLN   254      27.613  33.799  58.992  1.00 22.85      AAAA
ATOM   2027  C   GLN   254      29.384  33.816  61.832  1.00 16.12      AAAA
ATOM   2028  O   GLN   254      28.282  33.577  62.364  1.00 13.97      AAAA
ATOM   2029  N   LEU   255      29.768  35.032  61.468  1.00 14.42      AAAA
ATOM   2030  CA  LEU   255      28.988  36.215  61.763  1.00 17.99      AAAA
ATOM   2031  CB  LEU   255      29.834  37.070  62.719  1.00 20.68      AAAA
ATOM   2032  CG  LEU   255      30.240  36.283  63.964  1.00 22.90      AAAA
ATOM   2033  CD1 LEU   255      31.446  36.906  64.635  1.00 29.36      AAAA
ATOM   2034  CD2 LEU   255      29.042  36.214  64.900  1.00 14.80      AAAA
ATOM   2035  C   LEU   255      28.541  37.060  60.594  1.00 19.32      AAAA
ATOM   2036  O   LEU   255      28.838  38.260  60.561  1.00 21.23      AAAA
ATOM   2037  N   GLY   256      27.827  36.467  59.639  1.00 17.21      AAAA
ATOM   2038  CA  GLY   256      27.347  37.259  58.516  1.00 15.64      AAAA
ATOM   2039  C   GLY   256      26.413  38.348  59.028  1.00 17.31      AAAA
ATOM   2040  O   GLY   256      25.717  38.150  60.027  1.00 15.62      AAAA
ATOM   2041  N   THR   257      26.389  39.494  58.348  1.00 19.72      AAAA
ATOM   2042  CA  THR   257      25.536  40.598  58.776  1.00 19.88      AAAA
ATOM   2043  CB  THR   257      26.242  41.973  58.589  1.00 14.02      AAAA
ATOM   2044  OG1 THR   257      26.538  42.187  57.206  1.00 17.58      AAAA
ATOM   2045  CG2 THR   257      27.543  42.009  59.392  1.00 19.67      AAAA
ATOM   2046  C   THR   257      24.199  40.634  58.053  1.00 20.58      AAAA
```

Fig. 16-31

| | | | | | | | | | | |
|---|---|---|---|---|---|---|---|---|---|---|
| ATOM | 2047 | O   | THR | 257 | 23.403 | 41.545 | 58.266 | 1.00 | 14.59 | AAAA |
| ATOM | 2048 | N   | ASP | 258 | 23.927 | 39.639 | 57.213 | 1.00 | 16.56 | AAAA |
| ATOM | 2049 | CA  | ASP | 258 | 22.651 | 39.646 | 56.525 | 1.00 | 16.39 | AAAA |
| ATOM | 2050 | CB  | ASP | 258 | 22.604 | 38.611 | 55.388 | 1.00 | 18.38 | AAAA |
| ATOM | 2051 | CG  | ASP | 258 | 23.037 | 37.229 | 55.811 | 1.00 | 25.85 | AAAA |
| ATOM | 2052 | OD1 | ASP | 258 | 23.222 | 36.995 | 57.022 | 1.00 | 22.32 | AAAA |
| ATOM | 2053 | OD2 | ASP | 258 | 23.187 | 36.370 | 54.909 | 1.00 | 18.12 | AAAA |
| ATOM | 2054 | C   | ASP | 258 | 21.396 | 39.563 | 57.397 | 1.00 | 21.25 | AAAA |
| ATOM | 2055 | O   | ASP | 258 | 20.300 | 39.781 | 56.897 | 1.00 | 22.52 | AAAA |
| ATOM | 2056 | N   | PRO | 259 | 21.510 | 39.172 | 58.680 | 1.00 | 18.17 | AAAA |
| ATOM | 2057 | CD  | PRO | 259 | 22.614 | 38.528 | 59.422 | 1.00 | 25.88 | AAAA |
| ATOM | 2058 | CA  | PRO | 259 | 20.281 | 39.139 | 59.482 | 1.00 | 21.24 | AAAA |
| ATOM | 2059 | CB  | PRO | 259 | 20.710 | 38.363 | 60.735 | 1.00 | 21.18 | AAAA |
| ATOM | 2060 | CG  | PRO | 259 | 22.174 | 38.707 | 60.846 | 1.00 | 36.11 | AAAA |
| ATOM | 2061 | C   | PRO | 259 | 19.705 | 40.534 | 59.820 | 1.00 | 20.88 | AAAA |
| ATOM | 2062 | O   | PRO | 259 | 18.572 | 40.647 | 60.280 | 1.00 | 19.25 | AAAA |
| ATOM | 2063 | N   | LEU | 260 | 20.473 | 41.591 | 59.571 | 1.00 | 18.75 | AAAA |
| ATOM | 2064 | CA  | LEU | 260 | 20.023 | 42.949 | 59.875 | 1.00 | 22.16 | AAAA |
| ATOM | 2065 | CB  | LEU | 260 | 21.202 | 43.935 | 59.778 | 1.00 | 20.35 | AAAA |
| ATOM | 2066 | CG  | LEU | 260 | 22.403 | 43.640 | 60.682 | 1.00 | 21.82 | AAAA |
| ATOM | 2067 | CD1 | LEU | 260 | 23.604 | 44.486 | 60.253 | 1.00 | 18.57 | AAAA |
| ATOM | 2068 | CD2 | LEU | 260 | 22.032 | 43.873 | 62.123 | 1.00 | 19.18 | AAAA |
| ATOM | 2069 | C   | LEU | 260 | 18.876 | 43.469 | 59.014 | 1.00 | 24.16 | AAAA |
| ATOM | 2070 | O   | LEU | 260 | 18.742 | 43.144 | 57.826 | 1.00 | 21.69 | AAAA |
| ATOM | 2071 | N   | LEU | 261 | 18.049 | 44.300 | 59.634 | 1.00 | 19.54 | AAAA |
| ATOM | 2072 | CA  | LEU | 261 | 16.903 | 44.913 | 58.965 | 1.00 | 17.34 | AAAA |
| ATOM | 2073 | CB  | LEU | 261 | 16.285 | 45.967 | 59.892 | 1.00 | 19.96 | AAAA |
| ATOM | 2074 | CG  | LEU | 261 | 15.204 | 46.879 | 59.300 | 1.00 | 29.99 | AAAA |
| ATOM | 2075 | CD1 | LEU | 261 | 14.080 | 46.040 | 58.732 | 1.00 | 33.66 | AAAA |
| ATOM | 2076 | CD2 | LEU | 261 | 14.682 | 47.819 | 60.376 | 1.00 | 44.71 | AAAA |
| ATOM | 2077 | C   | LEU | 261 | 17.262 | 45.550 | 57.620 | 1.00 | 18.11 | AAAA |
| ATOM | 2078 | O   | LEU | 261 | 16.539 | 45.386 | 56.634 | 1.00 | 19.02 | AAAA |
| ATOM | 2079 | N   | GLU | 262 | 18.391 | 46.249 | 57.566 | 1.00 | 22.68 | AAAA |
| ATOM | 2080 | CA  | GLU | 262 | 18.802 | 46.921 | 56.338 | 1.00 | 18.46 | AAAA |
| ATOM | 2081 | CB  | GLU | 262 | 19.875 | 47.965 | 56.641 | 1.00 | 22.01 | AAAA |
| ATOM | 2082 | CG  | GLU | 262 | 19.365 | 49.136 | 57.443 | 1.00 | 22.94 | AAAA |
| ATOM | 2083 | CD  | GLU | 262 | 19.434 | 48.902 | 58.927 | 1.00 | 23.11 | AAAA |
| ATOM | 2084 | OE1 | GLU | 262 | 19.668 | 47.748 | 59.357 | 1.00 | 24.58 | AAAA |
| ATOM | 2085 | OE2 | GLU | 262 | 19.238 | 49.883 | 59.667 | 1.00 | 27.06 | AAAA |
| ATOM | 2086 | C   | GLU | 262 | 19.281 | 46.034 | 55.197 | 1.00 | 25.65 | AAAA |
| ATOM | 2087 | O   | GLU | 262 | 19.446 | 46.510 | 54.070 | 1.00 | 25.49 | AAAA |
| ATOM | 2088 | N   | ASP | 263 | 19.501 | 44.750 | 55.467 | 1.00 | 22.45 | AAAA |
| ATOM | 2089 | CA  | ASP | 263 | 19.959 | 43.851 | 54.418 | 1.00 | 15.93 | AAAA |
| ATOM | 2090 | CB  | ASP | 263 | 20.981 | 42.859 | 54.988 | 1.00 | 18.99 | AAAA |
| ATOM | 2091 | CG  | ASP | 263 | 21.706 | 42.081 | 53.907 | 1.00 | 22.21 | AAAA |
| ATOM | 2092 | OD1 | ASP | 263 | 22.876 | 41.730 | 54.139 | 1.00 | 23.19 | AAAA |
| ATOM | 2093 | OD2 | ASP | 263 | 21.112 | 41.809 | 52.838 | 1.00 | 25.02 | AAAA |
| ATOM | 2094 | C   | ASP | 263 | 18.733 | 43.165 | 53.837 | 1.00 | 22.32 | AAAA |
| ATOM | 2095 | O   | ASP | 263 | 18.012 | 42.419 | 54.519 | 1.00 | 18.50 | AAAA |
| ATOM | 2096 | N   | TYR | 264 | 18.500 | 43.447 | 52.564 | 1.00 | 25.21 | AAAA |
| ATOM | 2097 | CA  | TYR | 264 | 17.339 | 42.936 | 51.865 | 1.00 | 29.92 | AAAA |
| ATOM | 2098 | CB  | TYR | 264 | 17.077 | 43.776 | 50.596 | 1.00 | 38.48 | AAAA |
| ATOM | 2099 | CG  | TYR | 264 | 17.910 | 43.431 | 49.379 | 1.00 | 54.09 | AAAA |
| ATOM | 2100 | CD1 | TYR | 264 | 17.677 | 42.249 | 48.660 | 1.00 | 69.38 | AAAA |
| ATOM | 2101 | CE1 | TYR | 264 | 18.420 | 41.930 | 47.526 | 1.00 | 68.71 | AAAA |
| ATOM | 2102 | CD2 | TYR | 264 | 18.915 | 44.286 | 48.928 | 1.00 | 66.09 | AAAA |
| ATOM | 2103 | CE2 | TYR | 264 | 19.670 | 43.975 | 47.788 | 1.00 | 74.50 | AAAA |
| ATOM | 2104 | CZ  | TYR | 264 | 19.415 | 42.794 | 47.094 | 1.00 | 72.57 | AAAA |
| ATOM | 2105 | OH  | TYR | 264 | 20.154 | 42.472 | 45.975 | 1.00 | 71.96 | AAAA |
| ATOM | 2106 | C   | TYR | 264 | 17.445 | 41.461 | 51.532 | 1.00 | 29.55 | AAAA |
| ATOM | 2107 | O   | TYR | 264 | 16.448 | 40.839 | 51.190 | 1.00 | 30.11 | AAAA |
| ATOM | 2108 | N   | LEU | 265 | 18.639 | 40.891 | 51.629 | 1.00 | 24.45 | AAAA |
| ATOM | 2109 | CA  | LEU | 265 | 18.753 | 39.476 | 51.337 | 1.00 | 25.36 | AAAA |
| ATOM | 2110 | CB  | LEU | 265 | 20.186 | 39.089 | 50.969 | 1.00 | 29.81 | AAAA |
| ATOM | 2111 | CG  | LEU | 265 | 20.509 | 39.510 | 49.531 | 1.00 | 34.43 | AAAA |
| ATOM | 2112 | CD1 | LEU | 265 | 21.847 | 38.930 | 49.100 | 1.00 | 44.38 | AAAA |

Fig. 16-32

| | | | | | | | | | |
|---|---|---|---|---|---|---|---|---|---|
| ATOM | 2113 | CD2 | LEU | 265 | 19.422 | 38.990 | 48.603 | 1.00 46.72 | AAAA |
| ATOM | 2114 | C | LEU | 265 | 18.209 | 38.585 | 52.447 | 1.00 22.33 | AAAA |
| ATOM | 2115 | O | LEU | 265 | 18.279 | 37.364 | 52.348 | 1.00 23.48 | AAAA |
| ATOM | 2116 | N | SER | 266 | 17.677 | 39.194 | 53.508 | 1.00 17.50 | AAAA |
| ATOM | 2117 | CA | SER | 266 | 17.055 | 38.398 | 54.569 | 1.00 19.69 | AAAA |
| ATOM | 2118 | CB | SER | 266 | 17.912 | 38.314 | 55.845 | 1.00 20.73 | AAAA |
| ATOM | 2119 | OG | SER | 266 | 17.696 | 39.442 | 56.684 | 1.00 22.81 | AAAA |
| ATOM | 2120 | C | SER | 266 | 15.739 | 39.048 | 54.950 | 1.00 19.75 | AAAA |
| ATOM | 2121 | O | SER | 266 | 15.572 | 40.265 | 54.840 | 1.00 23.66 | AAAA |
| ATOM | 2122 | N | LYS | 267 | 14.799 | 38.229 | 55.402 | 1.00 18.40 | AAAA |
| ATOM | 2123 | CA | LYS | 267 | 13.527 | 38.759 | 55.851 | 1.00 20.64 | AAAA |
| ATOM | 2124 | CB | LYS | 267 | 12.397 | 37.787 | 55.513 | 1.00 20.96 | AAAA |
| ATOM | 2125 | CG | LYS | 267 | 12.269 | 37.536 | 54.025 | 1.00 25.60 | AAAA |
| ATOM | 2126 | CD | LYS | 267 | 12.095 | 38.823 | 53.259 | 1.00 33.47 | AAAA |
| ATOM | 2127 | CE | LYS | 267 | 11.985 | 38.540 | 51.772 | 1.00 38.49 | AAAA |
| ATOM | 2128 | NZ | LYS | 267 | 11.954 | 39.793 | 50.991 | 1.00 33.11 | AAAA |
| ATOM | 2129 | C | LYS | 267 | 13.601 | 38.987 | 57.365 | 1.00 20.63 | AAAA |
| ATOM | 2130 | O | LYS | 267 | 12.584 | 39.192 | 58.017 | 1.00 25.38 | AAAA |
| ATOM | 2131 | N | PHE | 268 | 14.814 | 38.937 | 57.915 | 1.00 18.98 | AAAA |
| ATOM | 2132 | CA | PHE | 268 | 15.034 | 39.182 | 59.345 | 1.00 18.50 | AAAA |
| ATOM | 2133 | CB | PHE | 268 | 16.328 | 38.510 | 59.833 | 1.00 20.91 | AAAA |
| ATOM | 2134 | CG | PHE | 268 | 16.252 | 37.006 | 59.967 | 1.00 16.96 | AAAA |
| ATOM | 2135 | CD1 | PHE | 268 | 17.374 | 36.290 | 60.415 | 1.00 16.61 | AAAA |
| ATOM | 2136 | CD2 | PHE | 268 | 15.081 | 36.303 | 59.682 | 1.00 18.13 | AAAA |
| ATOM | 2137 | CE1 | PHE | 268 | 17.331 | 34.904 | 60.581 | 1.00 14.81 | AAAA |
| ATOM | 2138 | CE2 | PHE | 268 | 15.027 | 34.900 | 59.849 | 1.00 17.45 | AAAA |
| ATOM | 2139 | CZ | PHE | 268 | 16.144 | 34.208 | 60.296 | 1.00 16.01 | AAAA |
| ATOM | 2140 | C | PHE | 268 | 15.179 | 40.699 | 59.510 | 1.00 18.33 | AAAA |
| ATOM | 2141 | O | PHE | 268 | 15.733 | 41.371 | 58.644 | 1.00 18.28 | AAAA |
| ATOM | 2142 | N | ASN | 269 | 14.679 | 41.236 | 60.613 | 1.00 21.04 | AAAA |
| ATOM | 2143 | CA | ASN | 269 | 14.763 | 42.675 | 60.859 | 1.00 22.89 | AAAA |
| ATOM | 2144 | CB | ASN | 269 | 13.365 | 43.298 | 60.940 | 1.00 20.55 | AAAA |
| ATOM | 2145 | CG | ASN | 269 | 12.551 | 43.071 | 59.686 | 1.00 26.13 | AAAA |
| ATOM | 2146 | OD1 | ASN | 269 | 13.060 | 43.192 | 58.571 | 1.00 29.17 | AAAA |
| ATOM | 2147 | ND2 | ASN | 269 | 11.268 | 42.767 | 59.860 | 1.00 28.26 | AAAA |
| ATOM | 2148 | C | ASN | 269 | 15.493 | 42.967 | 62.159 | 1.00 19.00 | AAAA |
| ATOM | 2149 | O | ASN | 269 | 14.984 | 43.683 | 63.019 | 1.00 21.85 | AAAA |
| ATOM | 2150 | N | LEU | 270 | 16.695 | 42.435 | 62.298 | 1.00 17.71 | AAAA |
| ATOM | 2151 | CA | LEU | 270 | 17.441 | 42.642 | 63.521 | 1.00 18.57 | AAAA |
| ATOM | 2152 | CB | LEU | 270 | 18.441 | 41.507 | 63.712 | 1.00 18.95 | AAAA |
| ATOM | 2153 | CG | LEU | 270 | 17.945 | 40.058 | 63.631 | 1.00 20.54 | AAAA |
| ATOM | 2154 | CD1 | LEU | 270 | 19.070 | 39.174 | 64.152 | 1.00 14.19 | AAAA |
| ATOM | 2155 | CD2 | LEU | 270 | 16.679 | 39.853 | 64.465 | 1.00 19.05 | AAAA |
| ATOM | 2156 | C | LEU | 270 | 18.203 | 43.971 | 63.583 | 1.00 22.83 | AAAA |
| ATOM | 2157 | O | LEU | 270 | 18.409 | 44.643 | 62.560 | 1.00 18.25 | AAAA |
| ATOM | 2158 | N | SER | 271 | 18.621 | 44.318 | 64.799 | 1.00 20.95 | AAAA |
| ATOM | 2159 | CA | SER | 271 | 19.414 | 45.518 | 65.081 | 1.00 18.28 | AAAA |
| ATOM | 2160 | CB | SER | 271 | 18.985 | 45.150 | 66.409 | 1.00 18.73 | AAAA |
| ATOM | 2161 | OG | SER | 271 | 19.347 | 45.327 | 67.512 | 1.00 22.28 | AAAA |
| ATOM | 2162 | C | SER | 271 | 20.875 | 45.073 | 65.224 | 1.00 19.98 | AAAA |
| ATOM | 2163 | O | SER | 271 | 21.122 | 43.899 | 65.537 | 1.00 18.82 | AAAA |
| ATOM | 2164 | N | ASN | 272 | 21.828 | 45.994 | 65.020 | 1.00 16.17 | AAAA |
| ATOM | 2165 | CA | ASN | 272 | 23.270 | 45.695 | 65.145 | 1.00 20.70 | AAAA |
| ATOM | 2166 | CB | ASN | 272 | 24.176 | 46.903 | 64.884 | 1.00 37.49 | AAAA |
| ATOM | 2167 | CG | ASN | 272 | 24.161 | 47.378 | 63.483 | 1.00 54.53 | AAAA |
| ATOM | 2168 | OD1 | ASN | 272 | 24.702 | 48.454 | 63.199 | 1.00 45.61 | AAAA |
| ATOM | 2169 | ND2 | ASN | 272 | 23.576 | 46.594 | 62.579 | 1.00 60.55 | AAAA |
| ATOM | 2170 | C | ASN | 272 | 23.586 | 45.343 | 66.580 | 1.00 18.03 | AAAA |
| ATOM | 2171 | O | ASN | 272 | 24.545 | 44.625 | 66.854 | 1.00 18.58 | AAAA |
| ATOM | 2172 | N | VAL | 273 | 22.831 | 45.938 | 67.500 | 1.00 19.57 | AAAA |
| ATOM | 2173 | CA | VAL | 273 | 23.053 | 45.698 | 68.919 | 1.00 22.12 | AAAA |
| ATOM | 2174 | CB | VAL | 273 | 22.345 | 46.765 | 69.765 | 1.00 26.91 | AAAA |
| ATOM | 2175 | CG1 | VAL | 273 | 22.440 | 46.421 | 71.233 | 1.00 39.69 | AAAA |
| ATOM | 2176 | CG2 | VAL | 273 | 23.034 | 48.115 | 69.531 | 1.00 34.73 | AAAA |
| ATOM | 2177 | C | VAL | 273 | 22.636 | 44.295 | 69.341 | 1.00 22.06 | AAAA |
| ATOM | 2178 | O | VAL | 273 | 23.249 | 43.708 | 70.217 | 1.00 16.89 | AAAA |

Fig. 16-33

```
ATOM   2179  N    ALA   274      21.601  43.747  68.713  1.00 21.79      AAAA
ATOM   2180  CA   ALA   274      21.207  42.383  69.035  1.00 21.31      AAAA
ATOM   2181  CB   ALA   274      19.806  42.092  68.475  1.00 18.95      AAAA
ATOM   2182  C    ALA   274      22.259  41.451  68.400  1.00 17.83      AAAA
ATOM   2183  O    ALA   274      22.569  40.389  68.947  1.00 20.38      AAAA
ATOM   2184  N    PHE   275      22.798  41.859  67.245  1.00 16.01      AAAA
ATOM   2185  CA   PHE   275      23.828  41.089  66.536  1.00 16.46      AAAA
ATOM   2186  CB   PHE   275      24.220  41.835  65.253  1.00 24.56      AAAA
ATOM   2187  CG   PHE   275      25.363  41.222  64.492  1.00 23.01      AAAA
ATOM   2188  CD1  PHE   275      25.209  40.035  63.788  1.00 23.88      AAAA
ATOM   2189  CD2  PHE   275      26.590  41.877  64.443  1.00 22.40      AAAA
ATOM   2190  CE1  PHE   275      26.266  39.510  63.038  1.00 28.74      AAAA
ATOM   2191  CE2  PHE   275      27.654  41.365  63.700  1.00 35.03      AAAA
ATOM   2192  CZ   PHE   275      27.489  40.181  62.996  1.00 24.63      AAAA
ATOM   2193  C    PHE   275      25.030  40.964  67.469  1.00 25.06      AAAA
ATOM   2194  O    PHE   275      25.619  39.888  67.632  1.00 19.71      AAAA
ATOM   2195  N    LEU   276      25.366  42.080  68.101  1.00 17.49      AAAA
ATOM   2196  CA   LEU   276      26.482  42.139  69.030  1.00 24.23      AAAA
ATOM   2197  CB   LEU   276      26.736  43.606  69.416  1.00 20.44      AAAA
ATOM   2198  CG   LEU   276      28.001  43.967  70.211  1.00 39.65      AAAA
ATOM   2199  CD1  LEU   276      27.948  45.447  70.589  1.00 29.65      AAAA
ATOM   2200  CD2  LEU   276      28.102  43.143  71.460  1.00 32.41      AAAA
ATOM   2201  C    LEU   276      26.180  41.278  70.262  1.00 18.86      AAAA
ATOM   2202  O    LEU   276      27.045  40.529  70.727  1.00 17.99      AAAA
ATOM   2203  N    LYS   277      24.968  41.374  70.805  1.00 19.67      AAAA
ATOM   2204  CA   LYS   277      24.644  40.552  71.964  1.00 21.33      AAAA
ATOM   2205  CB   LYS   277      23.265  40.888  72.532  1.00 23.84      AAAA
ATOM   2206  CG   LYS   277      23.247  42.126  73.366  1.00 40.87      AAAA
ATOM   2207  CD   LYS   277      22.069  42.086  74.325  1.00 54.73      AAAA
ATOM   2208  CE   LYS   277      22.172  40.884  75.254  1.00 58.85      AAAA
ATOM   2209  NZ   LYS   277      21.051  40.844  76.228  1.00 55.34      AAAA
ATOM   2210  C    LYS   277      24.695  39.068  71.660  1.00 22.12      AAAA
ATOM   2211  O    LYS   277      25.074  38.264  72.513  1.00 22.19      AAAA
ATOM   2212  N    ALA   278      24.311  38.700  70.441  1.00 20.23      AAAA
ATOM   2213  CA   ALA   278      24.325  37.291  70.039  1.00 17.06      AAAA
ATOM   2214  CB   ALA   278      23.798  37.154  68.589  1.00 19.27      AAAA
ATOM   2215  C    ALA   278      25.760  36.767  70.127  1.00 16.94      AAAA
ATOM   2216  O    ALA   278      26.035  35.676  70.648  1.00 14.93      AAAA
ATOM   2217  N    PHE   279      26.679  37.564  69.606  1.00 18.88      AAAA
ATOM   2218  CA   PHE   279      28.099  37.231  69.626  1.00 21.01      AAAA
ATOM   2219  CB   PHE   279      28.880  38.392  68.998  1.00 16.79      AAAA
ATOM   2220  CG   PHE   279      30.370  38.264  69.120  1.00 20.23      AAAA
ATOM   2221  CD1  PHE   279      31.062  37.272  68.423  1.00 21.61      AAAA
ATOM   2222  CD2  PHE   279      31.088  39.159  69.905  1.00 23.24      AAAA
ATOM   2223  CE1  PHE   279      32.461  37.185  68.509  1.00 30.98      AAAA
ATOM   2224  CE2  PHE   279      32.480  39.081  69.995  1.00 24.82      AAAA
ATOM   2225  CZ   PHE   279      33.169  38.095  69.295  1.00 30.27      AAAA
ATOM   2226  C    PHE   279      28.576  36.995  71.067  1.00 25.48      AAAA
ATOM   2227  O    PHE   279      29.275  36.016  71.362  1.00 16.30      AAAA
ATOM   2228  N    ASN   280      28.194  37.898  71.962  1.00 22.30      AAAA
ATOM   2229  CA   ASN   280      28.599  37.777  73.352  1.00 24.49      AAAA
ATOM   2230  CB   ASN   280      28.391  39.109  74.080  1.00 27.17      AAAA
ATOM   2231  CG   ASN   280      29.344  40.183  73.578  1.00 20.88      AAAA
ATOM   2232  OD1  ASN   280      30.503  39.897  73.273  1.00 22.95      AAAA
ATOM   2233  ND2  ASN   280      28.875  41.421  73.522  1.00 27.85      AAAA
ATOM   2234  C    ASN   280      27.928  36.636  74.095  1.00 23.01      AAAA
ATOM   2235  O    ASN   280      28.510  36.062  75.016  1.00 21.91      AAAA
ATOM   2236  N    ILE   281      26.711  36.300  73.689  1.00 18.74      AAAA
ATOM   2237  CA   ILE   281      26.005  35.179  74.294  1.00 18.37      AAAA
ATOM   2238  CB   ILE   281      24.566  35.067  73.758  1.00 19.31      AAAA
ATOM   2239  CG2  ILE   281      23.977  33.725  74.135  1.00 28.87      AAAA
ATOM   2240  CG1  ILE   281      23.710  36.206  74.308  1.00 23.51      AAAA
ATOM   2241  CD1  ILE   281      22.279  36.193  73.776  1.00 26.47      AAAA
ATOM   2242  C    ILE   281      26.743  33.876  73.965  1.00 18.54      AAAA
ATOM   2243  O    ILE   281      26.830  32.973  74.801  1.00 19.69      AAAA
ATOM   2244  N    VAL   282      27.258  33.765  72.744  1.00 17.72      AAAA
```

Fig. 16-34

| | | | | | | | | | |
|---|---|---|---|---|---|---|---|---|---|
| ATOM | 2245 | CA | VAL | 282 | 27.976 | 32.553 | 72.352 | 1.00 14.89 | AAAA |
| ATOM | 2246 | CB | VAL | 282 | 28.359 | 32.565 | 70.852 | 1.00 18.50 | AAAA |
| ATOM | 2247 | CG1 | VAL | 282 | 29.342 | 31.440 | 70.567 | 1.00 20.73 | AAAA |
| ATOM | 2248 | CG2 | VAL | 282 | 27.105 | 32.363 | 69.994 | 1.00 17.49 | AAAA |
| ATOM | 2249 | C | VAL | 282 | 29.241 | 32.433 | 73.198 | 1.00 21.79 | AAAA |
| ATOM | 2250 | O | VAL | 282 | 29.568 | 31.360 | 73.715 | 1.00 25.80 | AAAA |
| ATOM | 2251 | N | ARG | 283 | 29.935 | 33.549 | 73.361 | 1.00 19.14 | AAAA |
| ATOM | 2252 | CA | ARG | 283 | 31.161 | 33.548 | 74.150 | 1.00 23.51 | AAAA |
| ATOM | 2253 | CB | ARG | 283 | 31.851 | 34.898 | 74.023 | 1.00 20.64 | AAAA |
| ATOM | 2254 | CG | ARG | 283 | 32.338 | 35.200 | 72.607 | 1.00 19.65 | AAAA |
| ATOM | 2255 | CD | ARG | 283 | 32.754 | 36.645 | 72.474 | 1.00 25.70 | AAAA |
| ATOM | 2256 | NE | ARG | 283 | 33.970 | 36.944 | 73.215 | 1.00 36.05 | AAAA |
| ATOM | 2257 | CZ | ARG | 283 | 34.277 | 38.147 | 73.681 | 1.00 34.61 | AAAA |
| ATOM | 2258 | NH1 | ARG | 283 | 33.448 | 39.169 | 73.488 | 1.00 35.23 | AAAA |
| ATOM | 2259 | NH2 | ARG | 283 | 35.419 | 38.332 | 74.326 | 1.00 29.30 | AAAA |
| ATOM | 2260 | C | ARG | 283 | 30.911 | 33.219 | 75.622 | 1.00 25.44 | AAAA |
| ATOM | 2261 | O | ARG | 283 | 31.754 | 32.600 | 76.272 | 1.00 23.12 | AAAA |
| ATOM | 2262 | N | GLU | 284 | 29.765 | 33.632 | 76.151 | 1.00 26.79 | AAAA |
| ATOM | 2263 | CA | GLU | 284 | 29.462 | 33.338 | 77.553 | 1.00 31.77 | AAAA |
| ATOM | 2264 | CB | GLU | 284 | 28.243 | 34.115 | 78.033 | 1.00 30.96 | AAAA |
| ATOM | 2265 | CG | GLU | 284 | 28.399 | 35.605 | 77.957 | 1.00 50.56 | AAAA |
| ATOM | 2266 | CD | GLU | 284 | 27.137 | 36.320 | 78.365 | 1.00 63.75 | AAAA |
| ATOM | 2267 | OE1 | GLU | 284 | 26.085 | 36.067 | 77.738 | 1.00 68.93 | AAAA |
| ATOM | 2268 | OE2 | GLU | 284 | 27.198 | 37.133 | 79.309 | 1.00 72.01 | AAAA |
| ATOM | 2269 | C | GLU | 284 | 29.181 | 31.862 | 77.733 | 1.00 31.57 | AAAA |
| ATOM | 2270 | O | GLU | 284 | 29.410 | 31.310 | 78.803 | 1.00 33.08 | AAAA |
| ATOM | 2271 | N | VAL | 285 | 28.673 | 31.221 | 76.686 | 1.00 23.37 | AAAA |
| ATOM | 2272 | CA | VAL | 285 | 28.354 | 29.807 | 76.774 | 1.00 23.25 | AAAA |
| ATOM | 2273 | CB | VAL | 285 | 27.221 | 29.407 | 75.789 | 1.00 24.77 | AAAA |
| ATOM | 2274 | CG1 | VAL | 285 | 26.952 | 27.913 | 75.881 | 1.00 26.98 | AAAA |
| ATOM | 2275 | CG2 | VAL | 285 | 25.940 | 30.181 | 76.107 | 1.00 24.98 | AAAA |
| ATOM | 2276 | C | VAL | 285 | 29.567 | 28.942 | 76.479 | 1.00 31.41 | AAAA |
| ATOM | 2277 | O | VAL | 285 | 29.833 | 27.983 | 77.195 | 1.00 25.34 | AAAA |
| ATOM | 2278 | N | PHE | 286 | 30.316 | 29.276 | 75.431 | 1.00 27.27 | AAAA |
| ATOM | 2279 | CA | PHE | 286 | 31.463 | 28.457 | 75.086 | 1.00 22.47 | AAAA |
| ATOM | 2280 | CB | PHE | 286 | 31.289 | 27.904 | 73.667 | 1.00 22.26 | AAAA |
| ATOM | 2281 | CG | PHE | 286 | 30.168 | 26.918 | 73.536 | 1.00 25.71 | AAAA |
| ATOM | 2282 | CD1 | PHE | 286 | 28.971 | 27.274 | 72.917 | 1.00 22.88 | AAAA |
| ATOM | 2283 | CD2 | PHE | 286 | 30.294 | 25.631 | 74.069 | 1.00 24.49 | AAAA |
| ATOM | 2284 | CE1 | PHE | 286 | 27.919 | 26.365 | 72.829 | 1.00 19.85 | AAAA |
| ATOM | 2285 | CE2 | PHE | 286 | 29.246 | 24.714 | 73.987 | 1.00 27.48 | AAAA |
| ATOM | 2286 | CZ | PHE | 286 | 28.056 | 25.081 | 73.367 | 1.00 24.59 | AAAA |
| ATOM | 2287 | C | PHE | 286 | 32.854 | 29.059 | 75.225 | 1.00 21.53 | AAAA |
| ATOM | 2288 | O | PHE | 286 | 33.849 | 28.417 | 74.873 | 1.00 27.12 | AAAA |
| ATOM | 2289 | N | GLY | 287 | 32.937 | 30.272 | 75.754 | 1.00 23.76 | AAAA |
| ATOM | 2290 | CA | GLY | 287 | 34.237 | 30.896 | 75.901 | 1.00 24.17 | AAAA |
| ATOM | 2291 | C | GLY | 287 | 34.705 | 31.419 | 74.562 | 1.00 27.05 | AAAA |
| ATOM | 2292 | O | GLY | 287 | 33.888 | 31.670 | 73.667 | 1.00 18.06 | AAAA |
| ATOM | 2293 | N | GLU | 288 | 36.017 | 31.576 | 74.414 | 1.00 23.21 | AAAA |
| ATOM | 2294 | CA | GLU | 288 | 36.583 | 32.085 | 73.170 | 1.00 24.87 | AAAA |
| ATOM | 2295 | CB | GLU | 288 | 37.968 | 32.682 | 73.410 | 1.00 29.25 | AAAA |
| ATOM | 2296 | CG | GLU | 288 | 37.984 | 33.933 | 74.291 | 1.00 42.63 | AAAA |
| ATOM | 2297 | CD | GLU | 288 | 37.114 | 35.052 | 73.745 | 1.00 43.77 | AAAA |
| ATOM | 2298 | OE1 | GLU | 288 | 37.235 | 35.380 | 72.544 | 1.00 36.82 | AAAA |
| ATOM | 2299 | OE2 | GLU | 288 | 36.317 | 35.617 | 74.521 | 1.00 51.56 | AAAA |
| ATOM | 2300 | C | GLU | 288 | 36.693 | 31.028 | 72.072 | 1.00 20.85 | AAAA |
| ATOM | 2301 | O | GLU | 288 | 36.995 | 29.856 | 72.332 | 1.00 18.10 | AAAA |
| ATOM | 2302 | N | GLY | 289 | 36.447 | 31.468 | 70.843 | 1.00 26.12 | AAAA |
| ATOM | 2303 | CA | GLY | 289 | 36.517 | 30.588 | 69.692 | 1.00 20.71 | AAAA |
| ATOM | 2304 | C | GLY | 289 | 37.126 | 31.318 | 68.510 | 1.00 18.56 | AAAA |
| ATOM | 2305 | O | GLY | 289 | 37.669 | 32.404 | 68.679 | 1.00 16.59 | AAAA |
| ATOM | 2306 | N | VAL | 290 | 37.032 | 30.724 | 67.322 | 1.00 19.86 | AAAA |
| ATOM | 2307 | CA | VAL | 290 | 37.572 | 31.312 | 66.103 | 1.00 19.70 | AAAA |
| ATOM | 2308 | CB | VAL | 290 | 38.150 | 30.192 | 65.184 | 1.00 19.04 | AAAA |
| ATOM | 2309 | CG1 | VAL | 290 | 38.667 | 30.769 | 63.853 | 1.00 15.54 | AAAA |
| ATOM | 2310 | CG2 | VAL | 290 | 39.296 | 29.483 | 65.920 | 1.00 20.40 | AAAA |

Fig. 16-35

| | | | | | | | | | |
|---|---|---|---|---|---|---|---|---|---|
| ATOM | 2311 | C | VAL | 290 | 36.408 | 32.040 | 65.427 | 1.00 20.90 | AAAA |
| ATOM | 2312 | O | VAL | 290 | 35.351 | 31.439 | 65.193 | 1.00 19.33 | AAAA |
| ATOM | 2313 | N | TYR | 291 | 36.598 | 33.325 | 65.125 | 1.00 15.37 | AAAA |
| ATOM | 2314 | CA | TYR | 291 | 35.543 | 34.140 | 64.524 | 1.00 16.79 | AAAA |
| ATOM | 2315 | CB | TYR | 291 | 35.412 | 35.438 | 65.317 | 1.00 16.42 | AAAA |
| ATOM | 2316 | CG | TYR | 291 | 35.375 | 35.181 | 66.808 | 1.00 18.60 | AAAA |
| ATOM | 2317 | CD1 | TYR | 291 | 36.366 | 35.688 | 67.659 | 1.00 21.77 | AAAA |
| ATOM | 2318 | CE1 | TYR | 291 | 36.368 | 35.385 | 69.030 | 1.00 22.55 | AAAA |
| ATOM | 2319 | CD2 | TYR | 291 | 34.388 | 34.374 | 67.361 | 1.00 17.34 | AAAA |
| ATOM | 2320 | CE2 | TYR | 291 | 34.381 | 34.066 | 68.718 | 1.00 20.24 | AAAA |
| ATOM | 2321 | CZ | TYR | 291 | 35.367 | 34.568 | 69.545 | 1.00 25.85 | AAAA |
| ATOM | 2322 | OH | TYR | 291 | 35.338 | 34.246 | 70.885 | 1.00 25.57 | AAAA |
| ATOM | 2323 | C | TYR | 291 | 35.720 | 34.446 | 63.031 | 1.00 14.97 | AAAA |
| ATOM | 2324 | O | TYR | 291 | 36.773 | 34.921 | 62.586 | 1.00 15.21 | AAAA |
| ATOM | 2325 | N | LEU | 292 | 34.660 | 34.189 | 62.273 | 1.00 14.06 | AAAA |
| ATOM | 2326 | CA | LEU | 292 | 34.674 | 34.392 | 60.824 | 1.00 15.03 | AAAA |
| ATOM | 2327 | CB | LEU | 292 | 34.461 | 33.046 | 60.108 | 1.00 13.66 | AAAA |
| ATOM | 2328 | CG | LEU | 292 | 35.342 | 31.856 | 60.496 | 1.00 19.04 | AAAA |
| ATOM | 2329 | CD1 | LEU | 292 | 34.909 | 30.615 | 59.665 | 1.00 15.17 | AAAA |
| ATOM | 2330 | CD2 | LEU | 292 | 36.792 | 32.190 | 60.252 | 1.00 19.18 | AAAA |
| ATOM | 2331 | C | LEU | 292 | 33.564 | 35.327 | 60.396 | 1.00 16.62 | AAAA |
| ATOM | 2332 | O | LEU | 292 | 32.575 | 35.488 | 61.107 | 1.00 14.76 | AAAA |
| ATOM | 2333 | N | GLY | 293 | 33.724 | 35.932 | 59.216 | 1.00 18.62 | AAAA |
| ATOM | 2334 | CA | GLY | 293 | 32.696 | 36.816 | 58.699 | 1.00 17.10 | AAAA |
| ATOM | 2335 | C | GLY | 293 | 31.611 | 35.954 | 58.068 | 1.00 23.44 | AAAA |
| ATOM | 2336 | O | GLY | 293 | 31.407 | 34.798 | 58.459 | 1.00 23.60 | AAAA |
| ATOM | 2337 | N | GLY | 294 | 30.915 | 36.501 | 57.085 | 1.00 24.96 | AAAA |
| ATOM | 2338 | CA | GLY | 294 | 29.871 | 35.738 | 56.434 | 1.00 27.07 | AAAA |
| ATOM | 2339 | C | GLY | 294 | 29.132 | 36.632 | 55.474 | 1.00 28.41 | AAAA |
| ATOM | 2340 | O | GLY | 294 | 29.605 | 37.722 | 55.167 | 1.00 25.66 | AAAA |
| ATOM | 2341 | N | GLY | 295 | 27.972 | 36.168 | 55.011 | 1.00 20.33 | AAAA |
| ATOM | 2342 | CA | GLY | 295 | 27.164 | 36.936 | 54.085 | 1.00 20.14 | AAAA |
| ATOM | 2343 | C | GLY | 295 | 26.742 | 38.244 | 54.730 | 1.00 25.34 | AAAA |
| ATOM | 2344 | O | GLY | 295 | 26.550 | 38.317 | 55.942 | 1.00 28.89 | AAAA |
| ATOM | 2345 | N | GLY | 296 | 26.614 | 39.274 | 53.909 | 1.00 28.52 | AAAA |
| ATOM | 2346 | CA | GLY | 296 | 26.230 | 40.598 | 54.367 | 1.00 23.21 | AAAA |
| ATOM | 2347 | C | GLY | 296 | 26.314 | 41.342 | 53.059 | 1.00 26.34 | AAAA |
| ATOM | 2348 | O | GLY | 296 | 27.359 | 41.324 | 52.414 | 1.00 26.05 | AAAA |
| ATOM | 2349 | N | TYR | 297 | 25.235 | 42.008 | 52.662 | 1.00 22.61 | AAAA |
| ATOM | 2350 | CA | TYR | 297 | 25.228 | 42.644 | 51.360 | 1.00 22.58 | AAAA |
| ATOM | 2351 | CB | TYR | 297 | 24.265 | 41.861 | 50.457 | 1.00 23.68 | AAAA |
| ATOM | 2352 | CG | TYR | 297 | 24.502 | 40.352 | 50.521 | 1.00 25.14 | AAAA |
| ATOM | 2353 | CD1 | TYR | 297 | 23.981 | 39.571 | 51.568 | 1.00 28.31 | AAAA |
| ATOM | 2354 | CE1 | TYR | 297 | 24.269 | 38.196 | 51.662 | 1.00 24.18 | AAAA |
| ATOM | 2355 | CD2 | TYR | 297 | 25.307 | 39.725 | 49.577 | 1.00 29.74 | AAAA |
| ATOM | 2356 | CE2 | TYR | 297 | 25.598 | 38.362 | 49.664 | 1.00 27.09 | AAAA |
| ATOM | 2357 | CZ | TYR | 297 | 25.085 | 37.606 | 50.696 | 1.00 28.68 | AAAA |
| ATOM | 2358 | OH | TYR | 297 | 25.407 | 36.261 | 50.739 | 1.00 28.17 | AAAA |
| ATOM | 2359 | C | TYR | 297 | 24.916 | 44.138 | 51.320 | 1.00 24.98 | AAAA |
| ATOM | 2360 | O | TYR | 297 | 24.841 | 44.714 | 50.237 | 1.00 26.51 | AAAA |
| ATOM | 2361 | N | HIS | 298 | 24.740 | 44.752 | 52.491 | 1.00 23.80 | AAAA |
| ATOM | 2362 | CA | HIS | 298 | 24.480 | 46.188 | 52.591 | 1.00 23.44 | AAAA |
| ATOM | 2363 | CB | HIS | 298 | 23.325 | 46.494 | 53.536 | 1.00 23.37 | AAAA |
| ATOM | 2364 | CG | HIS | 298 | 22.956 | 47.945 | 53.551 | 1.00 32.94 | AAAA |
| ATOM | 2365 | CD2 | HIS | 298 | 23.491 | 48.983 | 54.232 | 1.00 24.31 | AAAA |
| ATOM | 2366 | ND1 | HIS | 298 | 22.011 | 48.487 | 52.707 | 1.00 38.29 | AAAA |
| ATOM | 2367 | CE1 | HIS | 298 | 21.978 | 49.797 | 52.868 | 1.00 26.60 | AAAA |
| ATOM | 2368 | NE2 | HIS | 298 | 22.867 | 50.125 | 53.788 | 1.00 36.57 | AAAA |
| ATOM | 2369 | C | HIS | 298 | 25.757 | 46.775 | 53.184 | 1.00 23.11 | AAAA |
| ATOM | 2370 | O | HIS | 298 | 26.135 | 46.439 | 54.306 | 1.00 22.64 | AAAA |
| ATOM | 2371 | N | PRO | 299 | 26.430 | 47.673 | 52.445 | 1.00 21.07 | AAAA |
| ATOM | 2372 | CD | PRO | 299 | 26.078 | 48.207 | 51.117 | 1.00 27.42 | AAAA |
| ATOM | 2373 | CA | PRO | 299 | 27.676 | 48.286 | 52.910 | 1.00 26.62 | AAAA |
| ATOM | 2374 | CB | PRO | 299 | 28.041 | 49.228 | 51.755 | 1.00 38.95 | AAAA |
| ATOM | 2375 | CG | PRO | 299 | 26.678 | 49.600 | 51.196 | 1.00 35.16 | AAAA |
| ATOM | 2376 | C | PRO | 299 | 27.644 | 48.991 | 54.262 | 1.00 25.75 | AAAA |

Fig. 16-36

```
ATOM  2377  O    PRO  299   28.565  48.845  55.068  1.00  24.36      AAAA
ATOM  2378  N    TYR  300   26.602  49.769  54.504  1.00  24.48      AAAA
ATOM  2379  CA   TYR  300   26.495  50.478  55.766  1.00  22.94      AAAA
ATOM  2380  CB   TYR  300   25.317  51.442  55.734  1.00  25.24      AAAA
ATOM  2381  CG   TYR  300   25.411  52.599  54.762  1.00  30.44      AAAA
ATOM  2382  CD1  TYR  300   26.366  52.634  53.746  1.00  26.01      AAAA
ATOM  2383  CE1  TYR  300   26.389  53.676  52.819  1.00  29.66      AAAA
ATOM  2384  CD2  TYR  300   24.490  53.640  54.827  1.00  31.37      AAAA
ATOM  2385  CE2  TYR  300   24.501  54.677  53.916  1.00  35.88      AAAA
ATOM  2386  CZ   TYR  300   25.448  54.689  52.913  1.00  38.44      AAAA
ATOM  2387  OH   TYR  300   25.417  55.700  51.990  1.00  33.41      AAAA
ATOM  2388  C    TYR  300   26.280  49.515  56.921  1.00  22.80      AAAA
ATOM  2389  O    TYR  300   26.895  49.643  57.983  1.00  19.14      AAAA
ATOM  2390  N    ALA  301   25.374  48.568  56.705  1.00  23.08      AAAA
ATOM  2391  CA   ALA  301   25.009  47.589  57.719  1.00  21.68      AAAA
ATOM  2392  CB   ALA  301   23.893  46.687  57.198  1.00  19.52      AAAA
ATOM  2393  C    ALA  301   26.216  46.762  58.098  1.00  23.49      AAAA
ATOM  2394  O    ALA  301   26.507  46.570  59.274  1.00  21.21      AAAA
ATOM  2395  N    LEU  302   26.904  46.275  57.072  1.00  23.19      AAAA
ATOM  2396  CA   LEU  302   28.090  45.463  57.234  1.00  20.66      AAAA
ATOM  2397  CB   LEU  302   28.602  45.057  55.844  1.00  23.31      AAAA
ATOM  2398  CG   LEU  302   29.932  44.335  55.611  1.00  36.66      AAAA
ATOM  2399  CD1  LEU  302   29.979  43.849  54.170  1.00  38.41      AAAA
ATOM  2400  CD2  LEU  302   31.104  45.255  55.879  1.00  28.52      AAAA
ATOM  2401  C    LEU  302   29.165  46.204  58.012  1.00  22.08      AAAA
ATOM  2402  O    LEU  302   29.653  45.713  59.020  1.00  20.43      AAAA
ATOM  2403  N    ALA  303   29.517  47.401  57.549  1.00  19.58      AAAA
ATOM  2404  CA   ALA  303   30.567  48.173  58.197  1.00  19.77      AAAA
ATOM  2405  CB   ALA  303   30.816  49.460  57.432  1.00  21.69      AAAA
ATOM  2406  C    ALA  303   30.324  48.485  59.657  1.00  19.19      AAAA
ATOM  2407  O    ALA  303   31.216  48.310  60.489  1.00  22.51      AAAA
ATOM  2408  N    ARG  304   29.128  48.954  59.993  1.00  20.12      AAAA
ATOM  2409  CA   ARG  304   28.872  49.296  61.377  1.00  18.04      AAAA
ATOM  2410  CB   ARG  304   27.566  50.114  61.511  1.00  21.09      AAAA
ATOM  2411  CG   ARG  304   27.532  51.481  60.792  1.00  24.34      AAAA
ATOM  2412  CD   ARG  304   26.259  52.259  61.206  1.00  27.09      AAAA
ATOM  2413  NE   ARG  304   25.090  51.398  61.116  1.00  45.73      AAAA
ATOM  2414  CZ   ARG  304   23.965  51.549  61.808  1.00  39.82      AAAA
ATOM  2415  NH1  ARG  304   23.813  52.550  62.677  1.00  28.40      AAAA
ATOM  2416  NH2  ARG  304   22.991  50.667  61.647  1.00  41.77      AAAA
ATOM  2417  C    ARG  304   28.794  48.073  62.280  1.00  21.00      AAAA
ATOM  2418  O    ARG  304   29.313  48.087  63.397  1.00  19.45      AAAA
ATOM  2419  N    ALA  305   28.159  47.008  61.796  1.00  19.93      AAAA
ATOM  2420  CA   ALA  305   28.002  45.809  62.610  1.00  18.70      AAAA
ATOM  2421  CB   ALA  305   26.998  44.830  61.933  1.00  18.26      AAAA
ATOM  2422  C    ALA  305   29.311  45.109  62.915  1.00  16.46      AAAA
ATOM  2423  O    ALA  305   29.564  44.736  64.061  1.00  19.49      AAAA
ATOM  2424  N    TRP  306   30.152  44.909  61.905  1.00  21.92      AAAA
ATOM  2425  CA   TRP  306   31.423  44.268  62.183  1.00  18.99      AAAA
ATOM  2426  CB   TRP  306   32.151  43.865  60.902  1.00  17.96      AAAA
ATOM  2427  CG   TRP  306   31.632  42.564  60.333  1.00  21.34      AAAA
ATOM  2428  CD2  TRP  306   31.852  42.058  59.014  1.00  16.55      AAAA
ATOM  2429  CE2  TRP  306   31.243  40.785  58.949  1.00  19.37      AAAA
ATOM  2430  CE3  TRP  306   32.507  42.556  57.878  1.00  17.80      AAAA
ATOM  2431  CD1  TRP  306   30.919  41.610  60.995  1.00  19.88      AAAA
ATOM  2432  NE1  TRP  306   30.680  40.535  60.170  1.00  15.95      AAAA
ATOM  2433  CZ2  TRP  306   31.270  40.002  57.787  1.00  24.85      AAAA
ATOM  2434  CZ3  TRP  306   32.534  41.781  56.725  1.00  29.69      AAAA
ATOM  2435  CH2  TRP  306   31.917  40.513  56.691  1.00  17.04      AAAA
ATOM  2436  C    TRP  306   32.289  45.168  63.018  1.00  20.26      AAAA
ATOM  2437  O    TRP  306   33.159  44.726  63.752  1.00  21.20      AAAA
ATOM  2438  N    THR  307   32.061  46.491  62.911  1.00  18.60      AAAA
ATOM  2439  CA   THR  307   32.843  47.412  63.722  1.00  16.88      AAAA
ATOM  2440  CB   THR  307   32.579  48.885  63.312  1.00  22.05      AAAA
ATOM  2441  OG1  THR  307   33.218  49.132  62.051  1.00  21.58      AAAA
ATOM  2442  CG2  THR  307   33.126  49.857  64.356  1.00  24.86      AAAA
```

Fig. 16-37

| | | | | | | | | | | |
|---|---|---|---|---|---|---|---|---|---|---|
| ATOM | 2443 | C | THR | 307 | 32.493 | 47.146 | 65.187 | 1.00 | 17.47 | AAAA |
| ATOM | 2444 | O | THR | 307 | 33.377 | 47.142 | 66.039 | 1.00 | 18.94 | AAAA |
| ATOM | 2445 | N | LEU | 308 | 31.216 | 46.901 | 65.487 | 1.00 | 19.97 | AAAA |
| ATOM | 2446 | CA | LEU | 308 | 30.834 | 46.587 | 66.866 | 1.00 | 22.54 | AAAA |
| ATOM | 2447 | CB | LEU | 308 | 29.318 | 46.365 | 66.989 | 1.00 | 21.13 | AAAA |
| ATOM | 2448 | CG | LEU | 308 | 28.415 | 47.579 | 66.751 | 1.00 | 22.82 | AAAA |
| ATOM | 2449 | CD1 | LEU | 308 | 26.937 | 47.219 | 67.023 | 1.00 | 25.01 | AAAA |
| ATOM | 2450 | CD2 | LEU | 308 | 28.870 | 48.710 | 67.685 | 1.00 | 29.09 | AAAA |
| ATOM | 2451 | C | LEU | 308 | 31.578 | 45.331 | 67.336 | 1.00 | 22.98 | AAAA |
| ATOM | 2452 | O | LEU | 308 | 32.056 | 45.250 | 68.479 | 1.00 | 22.27 | AAAA |
| ATOM | 2453 | N | ILE | 309 | 31.677 | 44.342 | 66.454 | 1.00 | 22.54 | AAAA |
| ATOM | 2454 | CA | ILE | 309 | 32.377 | 43.114 | 66.801 | 1.00 | 17.09 | AAAA |
| ATOM | 2455 | CB | ILE | 309 | 32.318 | 42.073 | 65.664 | 1.00 | 18.12 | AAAA |
| ATOM | 2456 | CG2 | ILE | 309 | 33.170 | 40.870 | 66.033 | 1.00 | 24.16 | AAAA |
| ATOM | 2457 | CG1 | ILE | 309 | 30.871 | 41.655 | 65.399 | 1.00 | 18.26 | AAAA |
| ATOM | 2458 | CD1 | ILE | 309 | 30.205 | 40.989 | 66.586 | 1.00 | 26.57 | AAAA |
| ATOM | 2459 | C | ILE | 309 | 33.849 | 43.410 | 67.067 | 1.00 | 20.84 | AAAA |
| ATOM | 2460 | O | ILE | 309 | 34.426 | 42.905 | 68.031 | 1.00 | 25.20 | AAAA |
| ATOM | 2461 | N | TRP | 310 | 34.466 | 44.223 | 66.214 | 1.00 | 16.86 | AAAA |
| ATOM | 2462 | CA | TRP | 310 | 35.888 | 44.517 | 66.411 | 1.00 | 17.86 | AAAA |
| ATOM | 2463 | CB | TRP | 310 | 36.439 | 45.319 | 65.235 | 1.00 | 14.83 | AAAA |
| ATOM | 2464 | CG | TRP | 310 | 37.879 | 45.648 | 65.397 | 1.00 | 16.63 | AAAA |
| ATOM | 2465 | CD2 | TRP | 310 | 38.967 | 44.718 | 65.560 | 1.00 | 18.62 | AAAA |
| ATOM | 2466 | CE2 | TRP | 310 | 40.131 | 45.478 | 65.799 | 1.00 | 25.60 | AAAA |
| ATOM | 2467 | CE3 | TRP | 310 | 39.069 | 43.319 | 65.529 | 1.00 | 24.06 | AAAA |
| ATOM | 2468 | CD1 | TRP | 310 | 38.418 | 46.895 | 65.533 | 1.00 | 19.82 | AAAA |
| ATOM | 2469 | NE1 | TRP | 310 | 39.768 | 46.801 | 65.777 | 1.00 | 25.84 | AAAA |
| ATOM | 2470 | CZ2 | TRP | 310 | 41.383 | 44.887 | 66.006 | 1.00 | 26.14 | AAAA |
| ATOM | 2471 | CZ3 | TRP | 310 | 40.308 | 42.730 | 65.735 | 1.00 | 24.89 | AAAA |
| ATOM | 2472 | CH2 | TRP | 310 | 41.452 | 43.515 | 65.971 | 1.00 | 24.96 | AAAA |
| ATOM | 2473 | C | TRP | 310 | 36.112 | 45.263 | 67.733 | 1.00 | 20.86 | AAAA |
| ATOM | 2474 | O | TRP | 310 | 37.050 | 44.957 | 68.478 | 1.00 | 21.38 | AAAA |
| ATOM | 2475 | N | CYS | 311 | 35.242 | 46.226 | 68.030 | 1.00 | 24.22 | AAAA |
| ATOM | 2476 | CA | CYS | 311 | 35.349 | 46.971 | 69.280 | 1.00 | 27.66 | AAAA |
| ATOM | 2477 | CB | CYS | 311 | 34.297 | 48.097 | 69.343 | 1.00 | 25.37 | AAAA |
| ATOM | 2478 | SG | CYS | 311 | 34.618 | 49.528 | 68.253 | 1.00 | 27.22 | AAAA |
| ATOM | 2479 | C | CYS | 311 | 35.224 | 46.042 | 70.490 | 1.00 | 22.95 | AAAA |
| ATOM | 2480 | O | CYS | 311 | 35.986 | 46.180 | 71.441 | 1.00 | 25.47 | AAAA |
| ATOM | 2481 | N | GLU | 312 | 34.284 | 45.089 | 70.457 | 1.00 | 17.03 | AAAA |
| ATOM | 2482 | CA | GLU | 312 | 34.120 | 44.129 | 71.569 | 1.00 | 22.44 | AAAA |
| ATOM | 2483 | CB | GLU | 312 | 33.011 | 43.110 | 71.280 | 1.00 | 20.81 | AAAA |
| ATOM | 2484 | CG | GLU | 312 | 31.856 | 43.048 | 72.258 | 1.00 | 43.65 | AAAA |
| ATOM | 2485 | CD | GLU | 312 | 32.265 | 42.971 | 73.717 | 1.00 | 29.63 | AAAA |
| ATOM | 2486 | OE1 | GLU | 312 | 33.022 | 42.059 | 74.119 | 1.00 | 38.85 | AAAA |
| ATOM | 2487 | OE2 | GLU | 312 | 31.804 | 43.844 | 74.473 | 1.00 | 53.21 | AAAA |
| ATOM | 2488 | C | GLU | 312 | 35.395 | 43.309 | 71.778 | 1.00 | 27.47 | AAAA |
| ATOM | 2489 | O | GLU | 312 | 35.899 | 43.178 | 72.895 | 1.00 | 22.33 | AAAA |
| ATOM | 2490 | N | LEU | 313 | 35.899 | 42.723 | 70.696 | 1.00 | 23.82 | AAAA |
| ATOM | 2491 | CA | LEU | 313 | 37.101 | 41.889 | 70.771 | 1.00 | 20.72 | AAAA |
| ATOM | 2492 | CB | LEU | 313 | 37.380 | 41.222 | 69.422 | 1.00 | 27.82 | AAAA |
| ATOM | 2493 | CG | LEU | 313 | 36.403 | 40.167 | 68.903 | 1.00 | 33.55 | AAAA |
| ATOM | 2494 | CD1 | LEU | 313 | 36.839 | 39.738 | 67.512 | 1.00 | 24.03 | AAAA |
| ATOM | 2495 | CD2 | LEU | 313 | 36.379 | 38.981 | 69.846 | 1.00 | 28.20 | AAAA |
| ATOM | 2496 | C | LEU | 313 | 38.343 | 42.670 | 71.181 | 1.00 | 18.21 | AAAA |
| ATOM | 2497 | O | LEU | 313 | 39.119 | 42.205 | 72.017 | 1.00 | 21.48 | AAAA |
| ATOM | 2498 | N | SER | 314 | 38.492 | 43.848 | 70.580 | 1.00 | 19.41 | AAAA |
| ATOM | 2499 | CA | SER | 314 | 39.627 | 44.753 | 70.775 | 1.00 | 28.26 | AAAA |
| ATOM | 2500 | CB | SER | 314 | 39.625 | 45.821 | 69.663 | 1.00 | 22.55 | AAAA |
| ATOM | 2501 | OG | SER | 314 | 40.732 | 46.696 | 69.759 | 1.00 | 61.92 | AAAA |
| ATOM | 2502 | C | SER | 314 | 39.619 | 45.429 | 72.144 | 1.00 | 30.18 | AAAA |
| ATOM | 2503 | O | SER | 314 | 40.631 | 45.969 | 72.590 | 1.00 | 25.04 | AAAA |
| ATOM | 2504 | N | GLY | 315 | 38.477 | 45.407 | 72.806 | 1.00 | 28.04 | AAAA |
| ATOM | 2505 | CA | GLY | 315 | 38.393 | 46.009 | 74.119 | 1.00 | 33.84 | AAAA |
| ATOM | 2506 | C | GLY | 315 | 38.324 | 47.518 | 74.105 | 1.00 | 36.93 | AAAA |
| ATOM | 2507 | O | GLY | 315 | 38.811 | 48.178 | 75.022 | 1.00 | 37.00 | AAAA |
| ATOM | 2508 | N | ARG | 316 | 37.739 | 48.090 | 73.065 | 1.00 | 31.33 | AAAA |

Fig. 16-38

```
ATOM   2509  CA   ARG  316      37.631  49.536  73.042  1.00  39.10      AAAA
ATOM   2510  CB   ARG  316      38.347  50.108  71.830  1.00  45.15      AAAA
ATOM   2511  CG   ARG  316      37.722  49.834  70.501  1.00  46.02      AAAA
ATOM   2512  CD   ARG  316      38.620  50.459  69.449  1.00  44.83      AAAA
ATOM   2513  NE   ARG  316      39.898  49.767  69.357  1.00  37.91      AAAA
ATOM   2514  CZ   ARG  316      40.945  50.219  68.674  1.00  27.39      AAAA
ATOM   2515  NH1  ARG  316      40.854  51.371  68.034  1.00  50.24      AAAA
ATOM   2516  NH2  ARG  316      42.054  49.493  68.572  1.00  34.51      AAAA
ATOM   2517  C    ARG  316      36.179  49.984  73.058  1.00  35.43      AAAA
ATOM   2518  O    ARG  316      35.292  49.271  72.596  1.00  30.71      AAAA
ATOM   2519  N    GLU  317      35.931  51.162  73.612  1.00  34.06      AAAA
ATOM   2520  CA   GLU  317      34.569  51.663  73.671  1.00  37.96      AAAA
ATOM   2521  CB   GLU  317      34.481  52.914  74.552  1.00  43.60      AAAA
ATOM   2522  CG   GLU  317      33.961  52.630  75.960  1.00  60.36      AAAA
ATOM   2523  CD   GLU  317      34.768  51.575  76.701  1.00  70.70      AAAA
ATOM   2524  OE1  GLU  317      34.375  51.217  77.832  1.00  76.71      AAAA
ATOM   2525  OE2  GLU  317      35.793  51.104  76.162  1.00  78.36      AAAA
ATOM   2526  C    GLU  317      34.068  51.958  72.280  1.00  35.65      AAAA
ATOM   2527  O    GLU  317      34.843  52.322  71.390  1.00  32.91      AAAA
ATOM   2528  N    VAL  318      32.767  51.772  72.094  1.00  30.52      AAAA
ATOM   2529  CA   VAL  318      32.138  52.012  70.808  1.00  37.04      AAAA
ATOM   2530  CB   VAL  318      30.877  51.138  70.638  1.00  36.48      AAAA
ATOM   2531  CG1  VAL  318      30.278  51.366  69.268  1.00  40.43      AAAA
ATOM   2532  CG2  VAL  318      31.222  49.674  70.846  1.00  33.75      AAAA
ATOM   2533  C    VAL  318      31.719  53.465  70.737  1.00  28.96      AAAA
ATOM   2534  O    VAL  318      30.930  53.915  71.556  1.00  33.56      AAAA
ATOM   2535  N    PRO  319      32.258  54.229  69.773  1.00  29.20      AAAA
ATOM   2536  CD   PRO  319      33.243  53.924  68.726  1.00  31.62      AAAA
ATOM   2537  CA   PRO  319      31.858  55.637  69.684  1.00  28.99      AAAA
ATOM   2538  CB   PRO  319      32.709  56.154  68.528  1.00  32.17      AAAA
ATOM   2539  CG   PRO  319      32.850  54.926  67.664  1.00  41.36      AAAA
ATOM   2540  C    PRO  319      30.365  55.680  69.377  1.00  36.95      AAAA
ATOM   2541  O    PRO  319      29.847  54.795  68.695  1.00  32.86      AAAA
ATOM   2542  N    GLU  320      29.646  56.683  69.855  1.00  34.61      AAAA
ATOM   2543  CA   GLU  320      28.230  56.657  69.544  1.00  35.13      AAAA
ATOM   2544  CB   GLU  320      27.419  57.416  70.595  1.00  52.97      AAAA
ATOM   2545  CG   GLU  320      27.751  58.875  70.738  1.00  56.06      AAAA
ATOM   2546  CD   GLU  320      26.822  59.558  71.721  1.00  65.58      AAAA
ATOM   2547  OE1  GLU  320      25.604  59.619  71.444  1.00  64.27      AAAA
ATOM   2548  OE2  GLU  320      27.306  60.022  72.775  1.00  72.99      AAAA
ATOM   2549  C    GLU  320      27.943  57.192  68.153  1.00  35.13      AAAA
ATOM   2550  O    GLU  320      26.916  56.879  67.565  1.00  37.43      AAAA
ATOM   2551  N    LYS  321      28.880  57.953  67.604  1.00  28.22      AAAA
ATOM   2552  CA   LYS  321      28.700  58.555  66.289  1.00  35.58      AAAA
ATOM   2553  CB   LYS  321      28.666  60.071  66.454  1.00  44.87      AAAA
ATOM   2554  CG   LYS  321      29.987  60.606  67.023  1.00  55.73      AAAA
ATOM   2555  CD   LYS  321      30.305  60.020  68.410  1.00  57.27      AAAA
ATOM   2556  CE   LYS  321      31.733  60.310  68.840  1.00  54.59      AAAA
ATOM   2557  NZ   LYS  321      32.024  61.774  68.848  1.00  67.47      AAAA
ATOM   2558  C    LYS  321      29.823  58.211  65.315  1.00  34.44      AAAA
ATOM   2559  O    LYS  321      30.912  57.818  65.731  1.00  33.83      AAAA
ATOM   2560  N    LEU  322      29.549  58.354  64.019  1.00  30.21      AAAA
ATOM   2561  CA   LEU  322      30.575  58.135  62.998  1.00  29.45      AAAA
ATOM   2562  CB   LEU  322      29.966  57.677  61.677  1.00  32.21      AAAA
ATOM   2563  CG   LEU  322      29.240  56.338  61.651  1.00  38.94      AAAA
ATOM   2564  CD1  LEU  322      29.008  55.977  60.186  1.00  38.44      AAAA
ATOM   2565  CD2  LEU  322      30.072  55.261  62.337  1.00  42.11      AAAA
ATOM   2566  C    LEU  322      31.228  59.503  62.783  1.00  33.28      AAAA
ATOM   2567  O    LEU  322      30.544  60.519  62.872  1.00  31.45      AAAA
ATOM   2568  N    ASN  323      32.533  59.539  62.519  1.00  34.38      AAAA
ATOM   2569  CA   ASN  323      33.208  60.824  62.294  1.00  36.53      AAAA
ATOM   2570  CB   ASN  323      34.701  60.737  62.600  1.00  42.85      AAAA
ATOM   2571  CG   ASN  323      35.484  60.081  61.480  1.00  50.51      AAAA
ATOM   2572  OD1  ASN  323      35.215  58.942  61.109  1.00  51.23      AAAA
ATOM   2573  ND2  ASN  323      36.455  60.807  60.928  1.00  60.23      AAAA
ATOM   2574  C    ASN  323      33.027  61.171  60.822  1.00  34.69      AAAA
```

Fig. 16-39

| | | | | | | | | | |
|---|---|---|---|---|---|---|---|---|---|
| ATOM | 2575 | O | ASN | 323 | 32.429 | 60.395 | 60.075 | 1.00 34.06 | AAAA |
| ATOM | 2576 | N | ASN | 324 | 33.551 | 62.317 | 60.390 | 1.00 23.73 | AAAA |
| ATOM | 2577 | CA | ASN | 324 | 33.385 | 62.720 | 58.995 | 1.00 31.06 | AAAA |
| ATOM | 2578 | CB | ASN | 324 | 33.868 | 64.155 | 58.784 | 1.00 36.07 | AAAA |
| ATOM | 2579 | CG | ASN | 324 | 32.974 | 65.163 | 59.450 | 1.00 45.77 | AAAA |
| ATOM | 2580 | OD1 | ASN | 324 | 31.765 | 65.189 | 59.206 | 1.00 39.55 | AAAA |
| ATOM | 2581 | ND2 | ASN | 324 | 33.555 | 66.008 | 60.291 | 1.00 39.12 | AAAA |
| ATOM | 2582 | C | ASN | 324 | 34.047 | 61.810 | 57.971 | 1.00 24.87 | AAAA |
| ATOM | 2583 | O | ASN | 324 | 33.451 | 61.483 | 56.941 | 1.00 31.91 | AAAA |
| ATOM | 2584 | N | LYS | 325 | 35.276 | 61.405 | 58.250 | 1.00 27.73 | AAAA |
| ATOM | 2585 | CA | LYS | 325 | 35.991 | 60.538 | 57.333 | 1.00 29.55 | AAAA |
| ATOM | 2586 | CB | LYS | 325 | 37.351 | 60.182 | 57.929 | 1.00 37.43 | AAAA |
| ATOM | 2587 | CG | LYS | 325 | 38.250 | 59.396 | 57.004 | 1.00 44.84 | AAAA |
| ATOM | 2588 | CD | LYS | 325 | 39.684 | 59.435 | 57.502 | 1.00 50.89 | AAAA |
| ATOM | 2589 | CE | LYS | 325 | 40.191 | 60.873 | 57.561 | 1.00 54.82 | AAAA |
| ATOM | 2590 | NZ | LYS | 325 | 41.621 | 60.980 | 57.969 | 1.00 65.70 | AAAA |
| ATOM | 2591 | C | LYS | 325 | 35.161 | 59.279 | 57.078 | 1.00 27.99 | AAAA |
| ATOM | 2592 | O | LYS | 325 | 35.016 | 58.836 | 55.938 | 1.00 31.80 | AAAA |
| ATOM | 2593 | N | ALA | 326 | 34.602 | 58.721 | 58.142 | 1.00 26.07 | AAAA |
| ATOM | 2594 | CA | ALA | 326 | 33.781 | 57.506 | 58.030 | 1.00 24.38 | AAAA |
| ATOM | 2595 | CB | ALA | 326 | 33.470 | 56.982 | 59.428 | 1.00 27.34 | AAAA |
| ATOM | 2596 | C | ALA | 326 | 32.478 | 57.709 | 57.231 | 1.00 25.78 | AAAA |
| ATOM | 2597 | O | ALA | 326 | 32.131 | 56.890 | 56.369 | 1.00 27.37 | AAAA |
| ATOM | 2598 | N | LYS | 327 | 31.749 | 58.790 | 57.496 | 1.00 27.31 | AAAA |
| ATOM | 2599 | CA | LYS | 327 | 30.502 | 59.027 | 56.758 | 1.00 28.56 | AAAA |
| ATOM | 2600 | CB | LYS | 327 | 29.759 | 60.251 | 57.313 | 1.00 28.87 | AAAA |
| ATOM | 2601 | CG | LYS | 327 | 29.491 | 60.209 | 58.812 | 1.00 36.72 | AAAA |
| ATOM | 2602 | CD | LYS | 327 | 28.643 | 61.407 | 59.255 | 1.00 40.34 | AAAA |
| ATOM | 2603 | CE | LYS | 327 | 28.645 | 61.594 | 60.769 | 1.00 38.91 | AAAA |
| ATOM | 2604 | NZ | LYS | 327 | 28.163 | 60.429 | 61.556 | 1.00 47.67 | AAAA |
| ATOM | 2605 | C | LYS | 327 | 30.792 | 59.244 | 55.269 | 1.00 29.15 | AAAA |
| ATOM | 2606 | O | LYS | 327 | 30.097 | 58.719 | 54.393 | 1.00 27.76 | AAAA |
| ATOM | 2607 | N | GLU | 328 | 31.829 | 60.015 | 54.972 | 1.00 31.59 | AAAA |
| ATOM | 2608 | CA | GLU | 328 | 32.167 | 60.265 | 53.581 | 1.00 28.93 | AAAA |
| ATOM | 2609 | CB | GLU | 328 | 33.257 | 61.332 | 53.515 | 1.00 32.30 | AAAA |
| ATOM | 2610 | CG | GLU | 328 | 32.745 | 62.652 | 54.067 | 1.00 47.50 | AAAA |
| ATOM | 2611 | CD | GLU | 328 | 33.764 | 63.772 | 54.032 | 1.00 46.67 | AAAA |
| ATOM | 2612 | OE1 | GLU | 328 | 34.325 | 64.037 | 52.951 | 1.00 56.88 | AAAA |
| ATOM | 2613 | OE2 | GLU | 328 | 33.984 | 64.402 | 55.087 | 1.00 42.24 | AAAA |
| ATOM | 2614 | C | GLU | 328 | 32.575 | 58.975 | 52.871 | 1.00 30.46 | AAAA |
| ATOM | 2615 | O | GLU | 328 | 32.226 | 58.753 | 51.704 | 1.00 26.29 | AAAA |
| ATOM | 2616 | N | LEU | 329 | 33.292 | 58.112 | 53.584 | 1.00 24.93 | AAAA |
| ATOM | 2617 | CA | LEU | 329 | 33.701 | 56.828 | 53.017 | 1.00 24.80 | AAAA |
| ATOM | 2618 | CB | LEU | 329 | 34.478 | 56.003 | 54.053 | 1.00 25.70 | AAAA |
| ATOM | 2619 | CG | LEU | 329 | 34.730 | 54.522 | 53.703 | 1.00 19.71 | AAAA |
| ATOM | 2620 | CD1 | LEU | 329 | 35.569 | 54.413 | 52.430 | 1.00 25.26 | AAAA |
| ATOM | 2621 | CD2 | LEU | 329 | 35.412 | 53.833 | 54.863 | 1.00 24.73 | AAAA |
| ATOM | 2622 | C | LEU | 329 | 32.443 | 56.059 | 52.603 | 1.00 23.50 | AAAA |
| ATOM | 2623 | O | LEU | 329 | 32.310 | 55.650 | 51.453 | 1.00 25.60 | AAAA |
| ATOM | 2624 | N | LEU | 330 | 31.516 | 55.881 | 53.539 | 1.00 23.02 | AAAA |
| ATOM | 2625 | CA | LEU | 330 | 30.289 | 55.145 | 53.242 | 1.00 23.85 | AAAA |
| ATOM | 2626 | CB | LEU | 330 | 29.414 | 55.030 | 54.484 | 1.00 21.74 | AAAA |
| ATOM | 2627 | CG | LEU | 330 | 30.039 | 54.252 | 55.642 | 1.00 25.29 | AAAA |
| ATOM | 2628 | CD1 | LEU | 330 | 28.984 | 54.053 | 56.724 | 1.00 30.58 | AAAA |
| ATOM | 2629 | CD2 | LEU | 330 | 30.538 | 52.905 | 55.168 | 1.00 22.44 | AAAA |
| ATOM | 2630 | C | LEU | 330 | 29.491 | 55.769 | 52.113 | 1.00 26.94 | AAAA |
| ATOM | 2631 | O | LEU | 330 | 28.968 | 55.060 | 51.252 | 1.00 26.65 | AAAA |
| ATOM | 2632 | N | LYS | 331 | 29.404 | 57.097 | 52.111 | 1.00 30.82 | AAAA |
| ATOM | 2633 | CA | LYS | 331 | 28.667 | 57.795 | 51.066 | 1.00 29.53 | AAAA |
| ATOM | 2634 | CB | LYS | 331 | 28.537 | 59.292 | 51.407 | 1.00 29.67 | AAAA |
| ATOM | 2635 | CG | LYS | 331 | 27.814 | 59.567 | 52.714 | 1.00 36.06 | AAAA |
| ATOM | 2636 | CD | LYS | 331 | 27.688 | 61.055 | 52.990 | 1.00 42.75 | AAAA |
| ATOM | 2637 | CE | LYS | 331 | 26.828 | 61.737 | 51.939 | 1.00 53.98 | AAAA |
| ATOM | 2638 | NZ | LYS | 331 | 26.634 | 63.185 | 52.234 | 1.00 67.57 | AAAA |
| ATOM | 2639 | C | LYS | 331 | 29.315 | 57.628 | 49.692 | 1.00 30.07 | AAAA |
| ATOM | 2640 | O | LYS | 331 | 28.634 | 57.759 | 48.672 | 1.00 36.20 | AAAA |

Fig. 16-40

| | | | | | | | | | | |
|---|---|---|---|---|---|---|---|---|---|---|
| ATOM | 2641 | N | SER | 332 | 30.608 | 57.305 | 49.657 | 1.00 | 30.08 | AAAA |
| ATOM | 2642 | CA | SER | 332 | 31.322 | 57.153 | 48.385 | 1.00 | 33.35 | AAAA |
| ATOM | 2643 | CB | SER | 332 | 32.834 | 57.312 | 48.590 | 1.00 | 40.36 | AAAA |
| ATOM | 2644 | OG | SER | 332 | 33.396 | 56.169 | 49.219 | 1.00 | 34.04 | AAAA |
| ATOM | 2645 | C | SER | 332 | 31.061 | 55.821 | 47.693 | 1.00 | 37.72 | AAAA |
| ATOM | 2646 | O | SER | 332 | 31.354 | 55.661 | 46.507 | 1.00 | 30.78 | AAAA |
| ATOM | 2647 | N | ILE | 333 | 30.521 | 54.865 | 48.440 | 1.00 | 30.61 | AAAA |
| ATOM | 2648 | CA | ILE | 333 | 30.219 | 53.547 | 47.899 | 1.00 | 37.59 | AAAA |
| ATOM | 2649 | CB | ILE | 333 | 29.901 | 52.551 | 49.022 | 1.00 | 33.59 | AAAA |
| ATOM | 2650 | CG2 | ILE | 333 | 29.738 | 51.146 | 48.442 | 1.00 | 37.05 | AAAA |
| ATOM | 2651 | CG1 | ILE | 333 | 31.015 | 52.564 | 50.065 | 1.00 | 38.95 | AAAA |
| ATOM | 2652 | CD1 | ILE | 333 | 30.706 | 51.727 | 51.282 | 1.00 | 46.83 | AAAA |
| ATOM | 2653 | C | ILE | 333 | 28.990 | 53.620 | 46.998 | 1.00 | 43.41 | AAAA |
| ATOM | 2654 | O | ILE | 333 | 27.889 | 53.876 | 47.479 | 1.00 | 46.24 | AAAA |
| ATOM | 2655 | N | ASP | 334 | 29.158 | 53.423 | 45.696 | 1.00 | 47.97 | AAAA |
| ATOM | 2656 | CA | ASP | 334 | 27.976 | 53.447 | 44.847 | 1.00 | 53.47 | AAAA |
| ATOM | 2657 | CB | ASP | 334 | 28.333 | 53.535 | 43.358 | 1.00 | 61.52 | AAAA |
| ATOM | 2658 | CG | ASP | 334 | 29.223 | 52.406 | 42.897 | 1.00 | 64.75 | AAAA |
| ATOM | 2659 | OD1 | ASP | 334 | 29.379 | 52.248 | 41.666 | 1.00 | 66.93 | AAAA |
| ATOM | 2660 | OD2 | ASP | 334 | 29.779 | 51.691 | 43.758 | 1.00 | 65.93 | AAAA |
| ATOM | 2661 | C | ASP | 334 | 27.248 | 52.144 | 45.161 | 1.00 | 51.83 | AAAA |
| ATOM | 2662 | O | ASP | 334 | 27.626 | 51.067 | 44.699 | 1.00 | 46.80 | AAAA |
| ATOM | 2663 | N | PHE | 335 | 26.215 | 52.249 | 45.986 | 1.00 | 54.96 | AAAA |
| ATOM | 2664 | CA | PHE | 335 | 25.455 | 51.080 | 46.392 | 1.00 | 50.60 | AAAA |
| ATOM | 2665 | CB | PHE | 335 | 25.413 | 51.003 | 47.920 | 1.00 | 39.55 | AAAA |
| ATOM | 2666 | CG | PHE | 335 | 24.380 | 50.054 | 48.440 | 1.00 | 37.98 | AAAA |
| ATOM | 2667 | CD1 | PHE | 335 | 24.389 | 48.715 | 48.054 | 1.00 | 46.72 | AAAA |
| ATOM | 2668 | CD2 | PHE | 335 | 23.362 | 50.506 | 49.262 | 1.00 | 34.23 | AAAA |
| ATOM | 2669 | CE1 | PHE | 335 | 23.389 | 47.842 | 48.478 | 1.00 | 49.80 | AAAA |
| ATOM | 2670 | CE2 | PHE | 335 | 22.361 | 49.644 | 49.689 | 1.00 | 48.51 | AAAA |
| ATOM | 2671 | CZ | PHE | 335 | 22.373 | 48.309 | 49.296 | 1.00 | 40.44 | AAAA |
| ATOM | 2672 | C | PHE | 335 | 24.033 | 51.000 | 45.839 | 1.00 | 54.52 | AAAA |
| ATOM | 2673 | O | PHE | 335 | 23.603 | 49.939 | 45.379 | 1.00 | 59.24 | AAAA |
| ATOM | 2674 | N | GLU | 336 | 23.302 | 52.108 | 45.888 | 1.00 | 50.94 | AAAA |
| ATOM | 2675 | CA | GLU | 336 | 21.923 | 52.119 | 45.406 | 1.00 | 57.05 | AAAA |
| ATOM | 2676 | CB | GLU | 336 | 21.853 | 51.751 | 43.924 | 1.00 | 60.27 | AAAA |
| ATOM | 2677 | CG | GLU | 336 | 20.430 | 51.627 | 43.422 | 1.00 | 68.55 | AAAA |
| ATOM | 2678 | CD | GLU | 336 | 20.352 | 51.126 | 42.001 | 1.00 | 80.03 | AAAA |
| ATOM | 2679 | OE1 | GLU | 336 | 20.860 | 50.013 | 41.735 | 1.00 | 84.64 | AAAA |
| ATOM | 2680 | OE2 | GLU | 336 | 19.777 | 51.841 | 41.153 | 1.00 | 80.68 | AAAA |
| ATOM | 2681 | C | GLU | 336 | 21.065 | 51.135 | 46.201 | 1.00 | 55.73 | AAAA |
| ATOM | 2682 | O | GLU | 336 | 21.219 | 49.917 | 46.089 | 1.00 | 51.33 | AAAA |
| ATOM | 2683 | N | GLU | 337 | 20.151 | 51.679 | 46.992 | 1.00 | 49.54 | AAAA |
| ATOM | 2684 | CA | GLU | 337 | 19.267 | 50.880 | 47.821 | 1.00 | 48.19 | AAAA |
| ATOM | 2685 | CB | GLU | 337 | 18.510 | 51.822 | 48.764 | 1.00 | 47.73 | AAAA |
| ATOM | 2686 | CG | GLU | 337 | 18.084 | 51.205 | 50.077 | 1.00 | 55.69 | AAAA |
| ATOM | 2687 | CD | GLU | 337 | 19.269 | 50.720 | 50.904 | 1.00 | 50.17 | AAAA |
| ATOM | 2688 | OE1 | GLU | 337 | 20.111 | 51.548 | 51.345 | 1.00 | 36.03 | AAAA |
| ATOM | 2689 | OE2 | GLU | 337 | 19.358 | 49.494 | 51.105 | 1.00 | 51.25 | AAAA |
| ATOM | 2690 | C | GLU | 337 | 18.294 | 50.083 | 46.936 | 1.00 | 49.13 | AAAA |
| ATOM | 2691 | O | GLU | 337 | 17.816 | 50.588 | 45.916 | 1.00 | 48.61 | AAAA |
| ATOM | 2692 | N | PHE | 338 | 18.015 | 48.837 | 47.313 | 1.00 | 48.15 | AAAA |
| ATOM | 2693 | CA | PHE | 338 | 17.092 | 48.000 | 46.547 | 1.00 | 48.12 | AAAA |
| ATOM | 2694 | CB | PHE | 338 | 16.870 | 46.658 | 47.249 | 1.00 | 54.54 | AAAA |
| ATOM | 2695 | CG | PHE | 338 | 15.883 | 45.777 | 46.548 | 1.00 | 57.22 | AAAA |
| ATOM | 2696 | CD1 | PHE | 338 | 16.115 | 45.366 | 45.243 | 1.00 | 60.01 | AAAA |
| ATOM | 2697 | CD2 | PHE | 338 | 14.699 | 45.398 | 47.171 | 1.00 | 55.04 | AAAA |
| ATOM | 2698 | CE1 | PHE | 338 | 15.185 | 44.597 | 44.566 | 1.00 | 60.84 | AAAA |
| ATOM | 2699 | CE2 | PHE | 338 | 13.758 | 44.624 | 46.497 | 1.00 | 59.41 | AAAA |
| ATOM | 2700 | CZ | PHE | 338 | 14.002 | 44.224 | 45.189 | 1.00 | 57.18 | AAAA |
| ATOM | 2701 | C | PHE | 338 | 15.755 | 48.714 | 46.380 | 1.00 | 45.46 | AAAA |
| ATOM | 2702 | O | PHE | 338 | 15.274 | 48.900 | 45.263 | 1.00 | 51.11 | AAAA |
| ATOM | 2703 | N | ASP | 339 | 15.154 | 49.098 | 47.501 | 1.00 | 40.38 | AAAA |
| ATOM | 2704 | CA | ASP | 339 | 13.890 | 49.820 | 47.488 | 1.00 | 49.97 | AAAA |
| ATOM | 2705 | CB | ASP | 339 | 13.270 | 49.821 | 48.886 | 1.00 | 53.23 | AAAA |
| ATOM | 2706 | CG | ASP | 339 | 12.000 | 50.659 | 48.968 | 1.00 | 57.40 | AAAA |

Fig. 16-41

```
ATOM  2707  OD1  ASP  339   12.039  51.858  48.616  1.00  53.79   AAAA
ATOM  2708  OD2  ASP  339   10.963  50.118  49.401  1.00  51.15   AAAA
ATOM  2709  C    ASP  339   14.215  51.248  47.076  1.00  55.06   AAAA
ATOM  2710  O    ASP  339   14.994  51.922  47.748  1.00  56.47   AAAA
ATOM  2711  N    ASP  340   13.623  51.708  45.978  1.00  58.46   AAAA
ATOM  2712  CA   ASP  340   13.874  53.059  45.484  1.00  67.72   AAAA
ATOM  2713  CB   ASP  340   12.683  53.559  44.664  1.00  71.52   AAAA
ATOM  2714  CG   ASP  340   12.611  52.913  43.295  1.00  79.72   AAAA
ATOM  2715  OD1  ASP  340   12.528  51.667  43.224  1.00  86.74   AAAA
ATOM  2716  OD2  ASP  340   12.640  53.655  42.288  1.00  83.40   AAAA
ATOM  2717  C    ASP  340   14.209  54.072  46.572  1.00  69.65   AAAA
ATOM  2718  O    ASP  340   15.204  54.794  46.463  1.00  70.13   AAAA
ATOM  2719  N    GLU  341   13.392  54.130  47.620  1.00  67.11   AAAA
ATOM  2720  CA   GLU  341   13.668  55.077  48.689  1.00  67.87   AAAA
ATOM  2721  CB   GLU  341   13.195  56.478  48.278  1.00  74.87   AAAA
ATOM  2722  CG   GLU  341   13.502  57.576  49.298  1.00  82.72   AAAA
ATOM  2723  CD   GLU  341   13.162  58.974  48.790  1.00  90.80   AAAA
ATOM  2724  OE1  GLU  341   11.988  59.215  48.431  1.00  90.38   AAAA
ATOM  2725  OE2  GLU  341   14.072  59.835  48.752  1.00  93.36   AAAA
ATOM  2726  C    GLU  341   13.101  54.719  50.058  1.00  60.22   AAAA
ATOM  2727  O    GLU  341   11.929  54.955  50.347  1.00  58.81   AAAA
ATOM  2728  N    VAL  342   13.956  54.144  50.897  1.00  57.28   AAAA
ATOM  2729  CA   VAL  342   13.694  53.781  52.262  1.00  52.09   AAAA
ATOM  2730  CB   VAL  342   14.195  52.419  52.669  1.00  53.17   AAAA
ATOM  2731  CG1  VAL  342   13.730  52.042  54.070  1.00  46.16   AAAA
ATOM  2732  CG2  VAL  342   13.815  51.356  51.663  1.00  59.09   AAAA
ATOM  2733  C    VAL  342   14.263  54.843  53.124  1.00  53.31   AAAA
ATOM  2734  O    VAL  342   13.763  55.230  54.185  1.00  57.79   AAAA
ATOM  2735  N    ASP  343   15.398  55.306  52.610  1.00  46.24   AAAA
ATOM  2736  CA   ASP  343   16.268  56.289  53.243  1.00  42.60   AAAA
ATOM  2737  CB   ASP  343   15.521  57.510  53.781  1.00  43.88   AAAA
ATOM  2738  CG   ASP  343   16.480  58.581  54.290  1.00  46.82   AAAA
ATOM  2739  OD1  ASP  343   16.028  59.581  54.887  1.00  46.16   AAAA
ATOM  2740  OD2  ASP  343   17.700  58.414  54.075  1.00  33.01   AAAA
ATOM  2741  C    ASP  343   17.012  55.636  54.395  1.00  35.45   AAAA
ATOM  2742  O    ASP  343   16.487  55.480  55.502  1.00  29.39   AAAA
ATOM  2743  N    ARG  344   18.247  55.249  54.124  1.00  30.51   AAAA
ATOM  2744  CA   ARG  344   19.059  54.613  55.140  1.00  29.43   AAAA
ATOM  2745  CB   ARG  344   19.736  53.377  54.561  1.00  30.10   AAAA
ATOM  2746  CG   ARG  344   18.803  52.258  54.180  1.00  33.95   AAAA
ATOM  2747  CD   ARG  344   17.981  51.770  55.365  1.00  20.92   AAAA
ATOM  2748  NE   ARG  344   17.120  50.673  54.936  1.00  29.72   AAAA
ATOM  2749  CZ   ARG  344   16.110  50.176  55.639  1.00  29.13   AAAA
ATOM  2750  NH1  ARG  344   15.805  50.668  56.835  1.00  29.63   AAAA
ATOM  2751  NH2  ARG  344   15.379  49.198  55.120  1.00  27.19   AAAA
ATOM  2752  C    ARG  344   20.116  55.769  55.660  1.00  34.31   AAAA
ATOM  2753  O    ARG  344   21.005  55.157  56.391  1.00  29.09   AAAA
ATOM  2754  N    SER  345   20.011  56.145  55.294  1.00  28.34   AAAA
ATOM  2755  CA   SER  345   20.999  57.839  55.715  1.00  30.95   AAAA
ATOM  2756  CB   SER  345   20.669  59.199  55.109  1.00  29.56   AAAA
ATOM  2757  OG   SER  345   19.429  59.648  55.610  1.00  29.38   AAAA
ATOM  2758  C    SER  345   21.137  57.988  57.230  1.00  30.92   AAAA
ATOM  2759  O    SER  345   22.155  58.488  57.718  1.00  31.15   AAAA
ATOM  2760  N    TYR  346   20.116  57.576  57.975  1.00  25.64   AAAA
ATOM  2761  CA   TYR  346   20.158  57.659  59.433  1.00  26.81   AAAA
ATOM  2762  CB   TYR  346   18.823  57.189  60.006  1.00  34.41   AAAA
ATOM  2763  CG   TYR  346   18.529  55.723  59.716  1.00  27.35   AAAA
ATOM  2764  CD1  TYR  346   19.003  54.708  60.556  1.00  24.87   AAAA
ATOM  2765  CE1  TYR  346   18.744  53.352  60.278  1.00  28.05   AAAA
ATOM  2766  CD2  TYR  346   17.795  55.358  58.588  1.00  27.70   AAAA
ATOM  2767  CE2  TYR  346   17.533  54.008  58.297  1.00  26.59   AAAA
ATOM  2768  CZ   TYR  346   18.008  53.015  59.145  1.00  33.75   AAAA
ATOM  2769  OH   TYR  346   17.737  51.691  58.855  1.00  26.06   AAAA
ATOM  2770  C    TYR  346   21.277  56.766  59.977  1.00  25.57   AAAA
ATOM  2771  O    TYR  346   21.769  56.970  61.085  1.00  28.07   AAAA
ATOM  2772  N    MET  347   21.666  55.761  59.198  1.00  29.08   AAAA
```

Fig. 16-42

| ATOM | 2773 | CA  | MET | 347 | 22.720 | 54.837 | 59.622 | 1.00 | 24.19 | AAAA |
| ATOM | 2774 | CB  | MET | 347 | 22.844 | 53.678 | 58.628 | 1.00 | 24.87 | AAAA |
| ATOM | 2775 | CG  | MET | 347 | 21.609 | 52.806 | 58.543 | 1.00 | 23.66 | AAAA |
| ATOM | 2776 | SD  | MET | 347 | 21.780 | 51.503 | 57.267 | 1.00 | 27.02 | AAAA |
| ATOM | 2777 | CE  | MET | 347 | 22.115 | 52.375 | 55.896 | 1.00 | 37.69 | AAAA |
| ATOM | 2778 | C   | MET | 347 | 24.054 | 55.540 | 59.737 | 1.00 | 29.45 | AAAA |
| ATOM | 2779 | O   | MET | 347 | 24.937 | 55.092 | 60.479 | 1.00 | 28.08 | AAAA |
| ATOM | 2780 | N   | LEU | 348 | 24.188 | 56.650 | 59.007 | 1.00 | 23.71 | AAAA |
| ATOM | 2781 | CA  | LEU | 348 | 25.418 | 57.446 | 58.998 | 1.00 | 34.11 | AAAA |
| ATOM | 2782 | CB  | LEU | 348 | 25.463 | 58.351 | 57.757 | 1.00 | 25.37 | AAAA |
| ATOM | 2783 | CG  | LEU | 348 | 25.320 | 57.785 | 56.344 | 1.00 | 30.38 | AAAA |
| ATOM | 2784 | CD1 | LEU | 348 | 25.307 | 58.944 | 55.340 | 1.00 | 27.44 | AAAA |
| ATOM | 2785 | CD2 | LEU | 348 | 26.459 | 56.814 | 56.041 | 1.00 | 36.44 | AAAA |
| ATOM | 2786 | C   | LEU | 348 | 25.507 | 58.332 | 60.237 | 1.00 | 36.09 | AAAA |
| ATOM | 2787 | O   | LEU | 348 | 26.561 | 58.894 | 60.539 | 1.00 | 33.30 | AAAA |
| ATOM | 2788 | N   | GLU | 349 | 24.394 | 58.445 | 60.953 | 1.00 | 30.51 | AAAA |
| ATOM | 2789 | CA  | GLU | 349 | 24.313 | 59.292 | 62.136 | 1.00 | 35.53 | AAAA |
| ATOM | 2790 | CB  | GLU | 349 | 22.908 | 59.896 | 62.217 | 1.00 | 31.35 | AAAA |
| ATOM | 2791 | CG  | GLU | 349 | 22.518 | 60.717 | 61.006 | 1.00 | 29.09 | AAAA |
| ATOM | 2792 | CD  | GLU | 349 | 23.481 | 61.859 | 60.746 | 1.00 | 31.78 | AAAA |
| ATOM | 2793 | OE1 | GLU | 349 | 23.937 | 62.476 | 61.730 | 1.00 | 30.98 | AAAA |
| ATOM | 2794 | OE2 | GLU | 349 | 23.766 | 62.155 | 59.569 | 1.00 | 30.67 | AAAA |
| ATOM | 2795 | C   | GLU | 349 | 24.663 | 58.633 | 63.471 | 1.00 | 38.48 | AAAA |
| ATOM | 2796 | O   | GLU | 349 | 24.727 | 59.303 | 64.502 | 1.00 | 40.12 | AAAA |
| ATOM | 2797 | N   | THR | 350 | 24.878 | 57.326 | 63.461 | 1.00 | 33.58 | AAAA |
| ATOM | 2798 | CA  | THR | 350 | 25.221 | 56.612 | 64.681 | 1.00 | 29.74 | AAAA |
| ATOM | 2799 | CB  | THR | 350 | 23.992 | 56.363 | 65.559 | 1.00 | 35.91 | AAAA |
| ATOM | 2800 | OG1 | THR | 350 | 23.421 | 57.615 | 65.952 | 1.00 | 45.03 | AAAA |
| ATOM | 2801 | CG2 | THR | 350 | 24.382 | 55.586 | 66.806 | 1.00 | 49.48 | AAAA |
| ATOM | 2802 | C   | THR | 350 | 25.821 | 55.267 | 64.330 | 1.00 | 30.63 | AAAA |
| ATOM | 2803 | O   | THR | 350 | 25.535 | 54.709 | 63.274 | 1.00 | 26.62 | AAAA |
| ATOM | 2804 | N   | LEU | 351 | 26.644 | 54.740 | 65.225 | 1.00 | 29.07 | AAAA |
| ATOM | 2805 | CA  | LEU | 351 | 27.271 | 53.461 | 64.972 | 1.00 | 24.59 | AAAA |
| ATOM | 2806 | CB  | LEU | 351 | 28.584 | 53.367 | 65.757 | 1.00 | 29.91 | AAAA |
| ATOM | 2807 | CG  | LEU | 351 | 29.591 | 52.327 | 65.267 | 1.00 | 39.62 | AAAA |
| ATOM | 2808 | CD1 | LEU | 351 | 30.887 | 52.467 | 66.039 | 1.00 | 37.09 | AAAA |
| ATOM | 2809 | CD2 | LEU | 351 | 29.024 | 50.935 | 65.415 | 1.00 | 54.03 | AAAA |
| ATOM | 2810 | C   | LEU | 351 | 26.314 | 52.336 | 65.377 | 1.00 | 29.71 | AAAA |
| ATOM | 2811 | O   | LEU | 351 | 26.130 | 51.364 | 64.641 | 1.00 | 30.53 | AAAA |
| ATOM | 2812 | N   | LYS | 352 | 25.697 | 52.481 | 66.543 | 1.00 | 28.64 | AAAA |
| ATOM | 2813 | CA  | LYS | 352 | 24.763 | 51.479 | 67.061 | 1.00 | 32.72 | AAAA |
| ATOM | 2814 | CB  | LYS | 352 | 24.913 | 51.381 | 68.581 | 1.00 | 27.37 | AAAA |
| ATOM | 2815 | CG  | LYS | 352 | 26.230 | 50.787 | 69.034 | 1.00 | 43.48 | AAAA |
| ATOM | 2816 | CD  | LYS | 352 | 26.536 | 51.068 | 70.504 | 1.00 | 46.77 | AAAA |
| ATOM | 2817 | CE  | LYS | 352 | 25.484 | 50.538 | 71.451 | 1.00 | 51.52 | AAAA |
| ATOM | 2818 | NZ  | LYS | 352 | 25.850 | 50.859 | 72.866 | 1.00 | 62.08 | AAAA |
| ATOM | 2819 | C   | LYS | 352 | 23.330 | 51.856 | 66.731 | 1.00 | 32.49 | AAAA |
| ATOM | 2820 | O   | LYS | 352 | 22.953 | 53.010 | 66.882 | 1.00 | 31.90 | AAAA |
| ATOM | 2821 | N   | ASP | 353 | 22.525 | 50.916 | 66.244 | 1.00 | 31.44 | AAAA |
| ATOM | 2822 | CA  | ASP | 353 | 21.136 | 51.286 | 66.012 | 1.00 | 26.50 | AAAA |
| ATOM | 2823 | CB  | ASP | 353 | 20.543 | 50.635 | 64.746 | 1.00 | 50.09 | AAAA |
| ATOM | 2824 | CG  | ASP | 353 | 20.880 | 49.176 | 64.604 | 1.00 | 52.79 | AAAA |
| ATOM | 2825 | OD1 | ASP | 353 | 21.980 | 48.861 | 64.109 | 1.00 | 58.55 | AAAA |
| ATOM | 2826 | OD2 | ASP | 353 | 20.040 | 48.339 | 64.984 | 1.00 | 73.19 | AAAA |
| ATOM | 2827 | C   | ASP | 353 | 20.328 | 50.930 | 67.257 | 1.00 | 26.41 | AAAA |
| ATOM | 2828 | O   | ASP | 353 | 20.806 | 50.214 | 68.136 | 1.00 | 25.73 | AAAA |
| ATOM | 2829 | N   | PRO | 354 | 19.118 | 51.481 | 67.385 | 1.00 | 30.12 | AAAA |
| ATOM | 2830 | CD  | PRO | 354 | 18.428 | 52.429 | 66.495 | 1.00 | 35.38 | AAAA |
| ATOM | 2831 | CA  | PRO | 354 | 18.276 | 51.190 | 68.547 | 1.00 | 34.02 | AAAA |
| ATOM | 2832 | CB  | PRO | 354 | 17.091 | 52.129 | 68.340 | 1.00 | 32.25 | AAAA |
| ATOM | 2833 | CG  | PRO | 354 | 16.974 | 52.139 | 66.833 | 1.00 | 44.48 | AAAA |
| ATOM | 2834 | C   | PRO | 354 | 17.838 | 49.736 | 68.512 | 1.00 | 34.00 | AAAA |
| ATOM | 2835 | O   | PRO | 354 | 17.829 | 49.111 | 67.452 | 1.00 | 28.28 | AAAA |
| ATOM | 2836 | N   | TRP | 355 | 17.484 | 49.190 | 69.664 | 1.00 | 23.89 | AAAA |
| ATOM | 2837 | CA  | TRP | 355 | 17.010 | 47.818 | 69.669 | 1.00 | 33.84 | AAAA |
| ATOM | 2838 | CB  | TRP | 355 | 16.653 | 47.363 | 71.076 | 1.00 | 33.84 | AAAA |

Fig. 16-43

| | | | | | | | | | |
|---|---|---|---|---|---|---|---|---|---|
| ATOM | 2839 | CG | TRP | 355 | 17.844 | 46.946 | 71.832 | 1.00 49.97 | AAAA |
| ATOM | 2840 | CD2 | TRP | 355 | 18.364 | 45.622 | 71.905 | 1.00 46.60 | AAAA |
| ATOM | 2841 | CE2 | TRP | 355 | 19.567 | 45.682 | 72.639 | 1.00 54.73 | AAAA |
| ATOM | 2842 | CE3 | TRP | 355 | 17.931 | 44.386 | 71.419 | 1.00 46.90 | AAAA |
| ATOM | 2843 | CD1 | TRP | 355 | 18.723 | 47.746 | 72.507 | 1.00 56.10 | AAAA |
| ATOM | 2844 | NE1 | TRP | 355 | 19.765 | 46.991 | 72.997 | 1.00 56.07 | AAAA |
| ATOM | 2845 | CZ2 | TRP | 355 | 20.340 | 44.552 | 72.897 | 1.00 55.25 | AAAA |
| ATOM | 2846 | CZ3 | TRP | 355 | 18.696 | 43.267 | 71.674 | 1.00 50.74 | AAAA |
| ATOM | 2847 | CH2 | TRP | 355 | 19.887 | 43.356 | 72.405 | 1.00 50.68 | AAAA |
| ATOM | 2848 | C | TRP | 355 | 15.789 | 47.712 | 68.776 | 1.00 33.12 | AAAA |
| ATOM | 2849 | O | TRP | 355 | 15.096 | 48.705 | 68.550 | 1.00 29.41 | AAAA |
| ATOM | 2850 | N | ARG | 356 | 15.547 | 46.508 | 68.263 | 1.00 23.90 | AAAA |
| ATOM | 2851 | CA | ARG | 356 | 14.413 | 46.237 | 67.387 | 1.00 23.96 | AAAA |
| ATOM | 2852 | CB | ARG | 356 | 14.892 | 46.096 | 65.935 | 1.00 22.66 | AAAA |
| ATOM | 2853 | CG | ARG | 356 | 15.505 | 47.385 | 65.393 | 1.00 29.06 | AAAA |
| ATOM | 2854 | CD | ARG | 356 | 16.291 | 47.212 | 64.108 | 1.00 28.92 | AAAA |
| ATOM | 2855 | NE | ARG | 356 | 16.833 | 48.503 | 63.686 | 1.00 24.73 | AAAA |
| ATOM | 2856 | CZ | ARG | 356 | 17.733 | 48.668 | 62.724 | 1.00 23.57 | AAAA |
| ATOM | 2857 | NH1 | ARG | 356 | 18.209 | 47.616 | 62.066 | 1.00 22.15 | AAAA |
| ATOM | 2858 | NH2 | ARG | 356 | 18.153 | 49.891 | 62.418 | 1.00 22.69 | AAAA |
| ATOM | 2859 | C | ARG | 356 | 13.781 | 44.944 | 67.878 | 1.00 24.89 | AAAA |
| ATOM | 2860 | O | ARG | 356 | 13.785 | 43.925 | 67.189 | 1.00 22.25 | AAAA |
| ATOM | 2861 | N | GLY | 357 | 13.231 | 44.993 | 69.085 | 1.00 23.91 | AAAA |
| ATOM | 2862 | CA | GLY | 357 | 12.631 | 43.805 | 69.657 | 1.00 26.72 | AAAA |
| ATOM | 2863 | C | GLY | 357 | 11.138 | 43.671 | 69.465 | 1.00 26.90 | AAAA |
| ATOM | 2864 | O | GLY | 357 | 10.536 | 44.330 | 68.619 | 1.00 29.87 | AAAA |
| ATOM | 2865 | N | GLY | 358 | 10.544 | 42.797 | 70.265 | 1.00 28.22 | AAAA |
| ATOM | 2866 | CA | GLY | 358 | 9.118 | 42.561 | 70.188 | 1.00 30.96 | AAAA |
| ATOM | 2867 | C | GLY | 358 | 8.800 | 41.274 | 70.920 | 1.00 30.03 | AAAA |
| ATOM | 2868 | O | GLY | 358 | 9.626 | 40.757 | 71.663 | 1.00 24.03 | AAAA |
| ATOM | 2869 | N | GLU | 359 | 7.601 | 40.747 | 70.715 | 1.00 28.34 | AAAA |
| ATOM | 2870 | CA | GLU | 359 | 7.218 | 39.509 | 71.366 | 1.00 24.37 | AAAA |
| ATOM | 2871 | CB | GLU | 359 | 5.699 | 39.372 | 71.375 | 1.00 32.52 | AAAA |
| ATOM | 2872 | CG | GLU | 359 | 4.981 | 40.327 | 72.299 | 1.00 45.44 | AAAA |
| ATOM | 2873 | CD | GLU | 359 | 3.472 | 40.250 | 72.132 | 1.00 50.43 | AAAA |
| ATOM | 2874 | OE1 | GLU | 359 | 2.924 | 39.125 | 72.151 | 1.00 42.92 | AAAA |
| ATOM | 2875 | OE2 | GLU | 359 | 2.839 | 41.316 | 71.987 | 1.00 40.72 | AAAA |
| ATOM | 2876 | C | GLU | 359 | 7.804 | 38.323 | 70.628 | 1.00 27.35 | AAAA |
| ATOM | 2877 | O | GLU | 359 | 8.138 | 38.415 | 69.449 | 1.00 22.94 | AAAA |
| ATOM | 2878 | N | VAL | 360 | 7.944 | 37.208 | 71.325 | 1.00 19.68 | AAAA |
| ATOM | 2879 | CA | VAL | 360 | 8.441 | 36.017 | 70.672 | 1.00 21.28 | AAAA |
| ATOM | 2880 | CB | VAL | 360 | 9.300 | 35.188 | 71.621 | 1.00 26.71 | AAAA |
| ATOM | 2881 | CG1 | VAL | 360 | 9.783 | 33.917 | 70.912 | 1.00 20.64 | AAAA |
| ATOM | 2882 | CG2 | VAL | 360 | 10.486 | 36.038 | 72.113 | 1.00 25.79 | AAAA |
| ATOM | 2883 | C | VAL | 360 | 7.228 | 35.202 | 70.197 | 1.00 25.51 | AAAA |
| ATOM | 2884 | O | VAL | 360 | 6.442 | 34.700 | 71.011 | 1.00 19.75 | AAAA |
| ATOM | 2885 | N | ARG | 361 | 7.065 | 35.094 | 68.873 | 1.00 18.48 | AAAA |
| ATOM | 2886 | CA | ARG | 361 | 5.947 | 34.337 | 68.301 | 1.00 22.01 | AAAA |
| ATOM | 2887 | CB | ARG | 361 | 5.988 | 34.389 | 66.772 | 1.00 19.31 | AAAA |
| ATOM | 2888 | CG | ARG | 361 | 5.446 | 35.671 | 66.204 | 1.00 30.86 | AAAA |
| ATOM | 2889 | CD | ARG | 361 | 5.735 | 35.730 | 64.723 | 1.00 37.95 | AAAA |
| ATOM | 2890 | NE | ARG | 361 | 7.111 | 36.148 | 64.460 | 1.00 30.73 | AAAA |
| ATOM | 2891 | CZ | ARG | 361 | 7.616 | 36.275 | 63.242 | 1.00 22.89 | AAAA |
| ATOM | 2892 | NH1 | ARG | 361 | 6.851 | 36.006 | 62.186 | 1.00 19.02 | AAAA |
| ATOM | 2893 | NH2 | ARG | 361 | 8.861 | 36.704 | 63.081 | 1.00 23.47 | AAAA |
| ATOM | 2894 | C | ARG | 361 | 5.897 | 32.879 | 68.714 | 1.00 26.11 | AAAA |
| ATOM | 2895 | O | ARG | 361 | 6.926 | 32.255 | 68.968 | 1.00 21.79 | AAAA |
| ATOM | 2896 | N | LYS | 362 | 4.681 | 32.338 | 68.763 | 1.00 24.89 | AAAA |
| ATOM | 2897 | CA | LYS | 362 | 4.479 | 30.938 | 69.125 | 1.00 28.63 | AAAA |
| ATOM | 2898 | CB | LYS | 362 | 2.981 | 30.570 | 69.070 | 1.00 22.91 | AAAA |
| ATOM | 2899 | CG | LYS | 362 | 2.145 | 31.200 | 70.168 | 1.00 50.86 | AAAA |
| ATOM | 2900 | CD | LYS | 362 | 2.290 | 32.715 | 70.157 | 1.00 57.51 | AAAA |
| ATOM | 2901 | CE | LYS | 362 | 1.923 | 33.278 | 68.799 | 1.00 50.87 | AAAA |
| ATOM | 2902 | NZ | LYS | 362 | 2.307 | 34.683 | 68.711 | 1.00 22.99 | AAAA |
| ATOM | 2903 | C | LYS | 362 | 5.269 | 30.014 | 68.202 | 1.00 16.77 | AAAA |
| ATOM | 2904 | O | LYS | 362 | 5.808 | 29.007 | 68.647 | 1.00 22.90 | AAAA |

Fig. 16-44

| | | | | | | | | | |
|---|---|---|---|---|---|---|---|---|---|
| ATOM | 2905 | N | GLU | 363 | 5.311 | 30.355 | 66.913 | 1.00 25.24 | AAAA |
| ATOM | 2906 | CA | GLU | 363 | 6.055 | 29.577 | 65.910 | 1.00 26.29 | AAAA |
| ATOM | 2907 | CB | GLU | 363 | 6.207 | 30.342 | 64.608 | 1.00 33.50 | AAAA |
| ATOM | 2908 | CG | GLU | 363 | 4.999 | 30.639 | 63.824 | 1.00 48.73 | AAAA |
| ATOM | 2909 | CD | GLU | 363 | 5.368 | 31.494 | 62.633 | 1.00 42.01 | AAAA |
| ATOM | 2910 | OE1 | GLU | 363 | 6.299 | 31.087 | 61.895 | 1.00 28.50 | AAAA |
| ATOM | 2911 | OE2 | GLU | 363 | 4.738 | 32.558 | 62.461 | 1.00 44.91 | AAAA |
| ATOM | 2912 | C | GLU | 363 | 7.481 | 29.326 | 66.349 | 1.00 19.00 | AAAA |
| ATOM | 2913 | O | GLU | 363 | 8.011 | 28.218 | 66.226 | 1.00 18.66 | AAAA |
| ATOM | 2914 | N | VAL | 364 | 8.121 | 30.399 | 66.790 | 1.00 20.69 | AAAA |
| ATOM | 2915 | CA | VAL | 364 | 9.501 | 30.303 | 67.219 | 1.00 23.13 | AAAA |
| ATOM | 2916 | CB | VAL | 364 | 10.096 | 31.681 | 67.510 | 1.00 16.98 | AAAA |
| ATOM | 2917 | CG1 | VAL | 364 | 11.515 | 31.513 | 68.010 | 1.00 22.32 | AAAA |
| ATOM | 2918 | CG2 | VAL | 364 | 10.082 | 32.548 | 66.242 | 1.00 23.99 | AAAA |
| ATOM | 2919 | C | VAL | 364 | 9.625 | 29.415 | 68.448 | 1.00 19.28 | AAAA |
| ATOM | 2920 | O | VAL | 364 | 10.507 | 28.548 | 68.510 | 1.00 20.17 | AAAA |
| ATOM | 2921 | N | LYS | 365 | 8.735 | 29.600 | 69.417 | 1.00 21.11 | AAAA |
| ATOM | 2922 | CA | LYS | 365 | 8.780 | 28.768 | 70.612 | 1.00 18.15 | AAAA |
| ATOM | 2923 | CB | LYS | 365 | 7.711 | 29.210 | 71.626 | 1.00 25.22 | AAAA |
| ATOM | 2924 | CG | LYS | 365 | 7.921 | 30.611 | 72.167 | 1.00 32.99 | AAAA |
| ATOM | 2925 | CD | LYS | 365 | 6.901 | 30.949 | 73.253 | 1.00 36.09 | AAAA |
| ATOM | 2926 | CE | LYS | 365 | 7.121 | 32.357 | 73.790 | 1.00 28.99 | AAAA |
| ATOM | 2927 | NZ | LYS | 365 | 6.178 | 32.736 | 74.882 | 1.00 38.98 | AAAA |
| ATOM | 2928 | C | LYS | 365 | 8.574 | 27.305 | 70.236 | 1.00 19.49 | AAAA |
| ATOM | 2929 | O | LYS | 365 | 9.255 | 26.417 | 70.758 | 1.00 22.04 | AAAA |
| ATOM | 2930 | N | ASP | 366 | 7.635 | 27.048 | 69.327 | 1.00 22.45 | AAAA |
| ATOM | 2931 | CA | ASP | 366 | 7.386 | 25.669 | 68.915 | 1.00 22.62 | AAAA |
| ATOM | 2932 | CB | ASP | 366 | 6.173 | 25.574 | 67.967 | 1.00 21.69 | AAAA |
| ATOM | 2933 | CG | ASP | 366 | 4.870 | 25.987 | 68.634 | 1.00 27.75 | AAAA |
| ATOM | 2934 | OD1 | ASP | 366 | 4.763 | 25.890 | 69.881 | 1.00 31.01 | AAAA |
| ATOM | 2935 | OD2 | ASP | 366 | 3.938 | 26.382 | 67.907 | 1.00 33.20 | AAAA |
| ATOM | 2936 | C | ASP | 366 | 8.606 | 25.034 | 68.237 | 1.00 24.53 | AAAA |
| ATOM | 2937 | O | ASP | 366 | 8.924 | 23.871 | 68.480 | 1.00 21.13 | AAAA |
| ATOM | 2938 | N | THR | 367 | 9.281 | 25.787 | 67.380 | 1.00 26.19 | AAAA |
| ATOM | 2939 | CA | THR | 367 | 10.462 | 25.252 | 66.694 | 1.00 21.68 | AAAA |
| ATOM | 2940 | CB | THR | 367 | 11.035 | 26.301 | 65.742 | 1.00 14.56 | AAAA |
| ATOM | 2941 | OG1 | THR | 367 | 10.085 | 26.545 | 64.697 | 1.00 21.76 | AAAA |
| ATOM | 2942 | CG2 | THR | 367 | 12.340 | 25.825 | 65.138 | 1.00 19.83 | AAAA |
| ATOM | 2943 | C | THR | 367 | 11.523 | 24.822 | 67.710 | 1.00 19.02 | AAAA |
| ATOM | 2944 | O | THR | 367 | 12.071 | 23.717 | 67.625 | 1.00 21.79 | AAAA |
| ATOM | 2945 | N | LEU | 368 | 11.802 | 25.684 | 68.683 | 1.00 18.42 | AAAA |
| ATOM | 2946 | CA | LEU | 368 | 12.797 | 25.348 | 69.700 | 1.00 21.02 | AAAA |
| ATOM | 2947 | CB | LEU | 368 | 13.148 | 26.569 | 70.560 | 1.00 17.34 | AAAA |
| ATOM | 2948 | CG | LEU | 368 | 14.206 | 27.518 | 69.959 | 1.00 17.45 | AAAA |
| ATOM | 2949 | CD1 | LEU | 368 | 15.525 | 26.758 | 69.817 | 1.00 16.83 | AAAA |
| ATOM | 2950 | CD2 | LEU | 368 | 13.756 | 28.041 | 68.593 | 1.00 19.49 | AAAA |
| ATOM | 2951 | C | LEU | 368 | 12.361 | 24.189 | 70.589 | 1.00 23.17 | AAAA |
| ATOM | 2952 | O | LEU | 368 | 13.203 | 23.420 | 71.052 | 1.00 24.81 | AAAA |
| ATOM | 2953 | N | GLU | 369 | 11.059 | 24.055 | 70.839 | 1.00 23.97 | AAAA |
| ATOM | 2954 | CA | GLU | 369 | 10.597 | 22.929 | 71.653 | 1.00 19.36 | AAAA |
| ATOM | 2955 | CB | GLU | 369 | 9.127 | 23.113 | 72.063 | 1.00 21.81 | AAAA |
| ATOM | 2956 | CG | GLU | 369 | 8.913 | 24.225 | 73.100 | 1.00 40.15 | AAAA |
| ATOM | 2957 | CD | GLU | 369 | 7.450 | 24.416 | 73.487 | 1.00 49.38 | AAAA |
| ATOM | 2958 | OE1 | GLU | 369 | 6.806 | 23.429 | 73.905 | 1.00 43.26 | AAAA |
| ATOM | 2959 | OE2 | GLU | 369 | 6.948 | 25.556 | 73.382 | 1.00 57.31 | AAAA |
| ATOM | 2960 | C | GLU | 369 | 10.778 | 21.623 | 70.859 | 1.00 24.29 | AAAA |
| ATOM | 2961 | O | GLU | 369 | 11.172 | 20.605 | 71.420 | 1.00 25.96 | AAAA |
| ATOM | 2962 | N | LYS | 370 | 10.488 | 21.643 | 69.560 | 1.00 22.98 | AAAA |
| ATOM | 2963 | CA | LYS | 370 | 10.665 | 20.437 | 68.746 | 1.00 23.19 | AAAA |
| ATOM | 2964 | CB | LYS | 370 | 10.051 | 20.596 | 67.347 | 1.00 26.83 | AAAA |
| ATOM | 2965 | CG | LYS | 370 | 8.537 | 20.461 | 67.287 | 1.00 36.68 | AAAA |
| ATOM | 2966 | CD | LYS | 370 | 8.056 | 20.431 | 65.832 | 1.00 39.85 | AAAA |
| ATOM | 2967 | CE | LYS | 370 | 6.567 | 20.105 | 65.740 | 1.00 56.23 | AAAA |
| ATOM | 2968 | NZ | LYS | 370 | 6.082 | 19.996 | 64.326 | 1.00 56.10 | AAAA |
| ATOM | 2969 | C | LYS | 370 | 12.148 | 20.123 | 68.602 | 1.00 31.63 | AAAA |
| ATOM | 2970 | O | LYS | 370 | 12.549 | 18.958 | 68.587 | 1.00 36.88 | AAAA |

Fig. 16-45

| | | | | | | | | | |
|---|---|---|---|---|---|---|---|---|---|
| ATOM | 2971 | N | ALA | 371 | 12.961 | 21.170 | 68.491 | 1.00 26.25 | AAAA |
| ATOM | 2972 | CA | ALA | 371 | 14.407 | 21.009 | 68.360 | 1.00 27.33 | AAAA |
| ATOM | 2973 | CB | ALA | 371 | 15.079 | 22.370 | 68.188 | 1.00 23.70 | AAAA |
| ATOM | 2974 | C | ALA | 371 | 14.989 | 20.308 | 69.581 | 1.00 26.74 | AAAA |
| ATOM | 2975 | O | ALA | 371 | 15.892 | 19.482 | 69.452 | 1.00 29.52 | AAAA |
| ATOM | 2976 | N | ALA | 372 | 14.484 | 20.652 | 70.764 | 1.00 24.83 | AAAA |
| ATOM | 2977 | CA | ALA | 372 | 14.959 | 20.055 | 72.012 | 1.00 34.24 | AAAA |
| ATOM | 2978 | CB | ALA | 372 | 14.305 | 20.750 | 73.214 | 1.00 37.17 | AAAA |
| ATOM | 2979 | C | ALA | 372 | 14.663 | 18.564 | 72.061 | 1.00 45.62 | AAAA |
| ATOM | 2980 | O | ALA | 372 | 15.563 | 17.741 | 72.280 | 1.00 35.52 | AAAA |
| ATOM | 2981 | N | ALA | 373 | 13.394 | 18.216 | 71.869 | 1.00 44.50 | AAAA |
| ATOM | 2982 | CA | ALA | 373 | 13.004 | 16.813 | 71.892 | 1.00 49.88 | AAAA |
| ATOM | 2983 | CB | ALA | 373 | 11.506 | 16.681 | 71.628 | 1.00 49.32 | AAAA |
| ATOM | 2984 | C | ALA | 373 | 13.807 | 16.072 | 70.825 | 1.00 44.64 | AAAA |
| ATOM | 2985 | O | ALA | 373 | 14.669 | 15.250 | 71.201 | 1.00 58.19 | AAAA |
| ATOM | 2986 | OXT | ALA | 373 | 13.591 | 16.337 | 69.626 | 1.00 41.63 | AAAA |
| HETATM | 2987 | OH2 | WAT | 1 | 36.368 | 43.907 | 49.242 | 1.00 13.03 | SOLV |
| HETATM | 2988 | OH2 | WAT | 2 | 23.107 | 30.584 | 59.802 | 1.00 11.42 | SOLV |
| HETATM | 2989 | OH2 | WAT | 3 | 20.594 | 33.744 | 61.457 | 1.00 14.73 | SOLV |
| HETATM | 2990 | OH2 | WAT | 4 | 31.359 | 16.551 | 51.590 | 1.00 19.84 | SOLV |
| HETATM | 2991 | OH2 | WAT | 5 | 30.389 | 18.140 | 45.769 | 1.00 19.94 | SOLV |
| HETATM | 2992 | OH2 | WAT | 6 | 16.925 | 41.748 | 56.551 | 1.00 13.33 | SOLV |
| HETATM | 2993 | OH2 | WAT | 7 | 28.448 | 16.084 | 62.316 | 1.00 14.08 | SOLV |
| HETATM | 2994 | OH2 | WAT | 8 | 40.375 | 38.476 | 55.678 | 1.00 19.10 | SOLV |
| HETATM | 2995 | OH2 | WAT | 9 | 18.455 | 29.667 | 54.797 | 1.00 18.81 | SOLV |
| HETATM | 2996 | OH2 | WAT | 10 | 26.305 | 18.390 | 59.507 | 1.00 16.65 | SOLV |
| HETATM | 2997 | OH2 | WAT | 11 | 50.145 | 32.063 | 58.142 | 1.00 16.53 | SOLV |
| HETATM | 2998 | OH2 | WAT | 12 | 45.935 | 30.996 | 40.672 | 1.00 25.08 | SOLV |
| HETATM | 2999 | OH2 | WAT | 13 | 26.358 | 43.110 | 74.179 | 1.00 22.91 | SOLV |
| HETATM | 3000 | OH2 | WAT | 14 | 48.727 | 24.720 | 56.917 | 1.00 25.49 | SOLV |
| HETATM | 3001 | OH2 | WAT | 15 | 30.244 | 18.663 | 50.165 | 1.00 25.78 | SOLV |
| HETATM | 3002 | OH2 | WAT | 16 | 10.615 | 28.799 | 63.631 | 1.00 22.40 | SOLV |
| HETATM | 3003 | OH2 | WAT | 17 | 18.401 | 20.018 | 62.704 | 1.00 21.46 | SOLV |
| HETATM | 3004 | OH2 | WAT | 18 | 22.195 | 47.791 | 60.896 | 1.00 26.19 | SOLV |
| HETATM | 3005 | OH2 | WAT | 19 | 3.278 | 32.141 | 65.350 | 1.00 20.38 | SOLV |
| HETATM | 3006 | OH2 | WAT | 20 | 23.643 | 22.897 | 59.512 | 1.00 21.27 | SOLV |
| HETATM | 3007 | OH2 | WAT | 21 | 50.287 | 23.101 | 48.818 | 1.00 19.73 | SOLV |
| HETATM | 3008 | OH2 | WAT | 22 | 44.725 | 34.256 | 46.541 | 1.00 18.74 | SOLV |
| HETATM | 3009 | OH2 | WAT | 23 | 8.346 | 30.527 | 49.922 | 1.00 22.33 | SOLV |
| HETATM | 3010 | OH2 | WAT | 24 | 39.855 | 33.795 | 67.390 | 1.00 20.43 | SOLV |
| HETATM | 3011 | OH2 | WAT | 25 | 7.827 | 32.763 | 57.779 | 1.00 19.24 | SOLV |
| HETATM | 3012 | OH2 | WAT | 26 | 45.388 | 34.567 | 36.246 | 1.00 20.86 | SOLV |
| HETATM | 3013 | OH2 | WAT | 27 | 47.636 | 32.244 | 33.388 | 1.00 20.41 | SOLV |
| HETATM | 3014 | OH2 | WAT | 28 | 32.514 | 35.684 | 41.278 | 1.00 24.76 | SOLV |
| HETATM | 3015 | OH2 | WAT | 29 | 26.188 | 15.341 | 61.913 | 1.00 19.63 | SOLV |
| HETATM | 3016 | OH2 | WAT | 30 | 14.957 | 43.169 | 56.333 | 1.00 23.80 | SOLV |
| HETATM | 3017 | OH2 | WAT | 31 | 24.483 | 43.556 | 55.704 | 1.00 27.25 | SOLV |
| HETATM | 3018 | OH2 | WAT | 32 | 41.141 | 16.376 | 48.456 | 1.00 25.99 | SOLV |
| HETATM | 3019 | OH2 | WAT | 33 | 23.104 | 17.625 | 54.086 | 1.00 26.37 | SOLV |
| HETATM | 3020 | OH2 | WAT | 34 | 51.301 | 28.602 | 57.694 | 1.00 32.78 | SOLV |
| HETATM | 3021 | OH2 | WAT | 35 | 51.376 | 29.469 | 53.156 | 1.00 24.27 | SOLV |
| HETATM | 3022 | OH2 | WAT | 36 | 12.518 | 22.131 | 49.816 | 1.00 23.60 | SOLV |
| HETATM | 3023 | OH2 | WAT | 37 | 6.521 | 27.442 | 50.861 | 1.00 25.87 | SOLV |
| HETATM | 3024 | OH2 | WAT | 38 | 30.390 | 33.757 | 34.190 | 1.00 19.87 | SOLV |
| HETATM | 3025 | OH2 | WAT | 39 | 8.328 | 29.586 | 62.062 | 1.00 32.01 | SOLV |
| HETATM | 3026 | OH2 | WAT | 40 | 30.180 | 24.235 | 30.724 | 1.00 22.61 | SOLV |
| HETATM | 3027 | OH2 | WAT | 41 | 44.521 | 30.663 | 38.395 | 1.00 27.52 | SOLV |
| HETATM | 3028 | OH2 | WAT | 42 | 30.981 | 18.043 | 41.186 | 1.00 23.45 | SOLV |
| HETATM | 3029 | OH2 | WAT | 43 | 14.632 | 37.127 | 73.830 | 1.00 29.36 | SOLV |
| HETATM | 3030 | OH2 | WAT | 44 | 39.332 | 25.953 | 72.230 | 1.00 21.87 | SOLV |
| HETATM | 3031 | OH2 | WAT | 45 | 7.597 | 37.592 | 51.896 | 1.00 39.62 | SOLV |
| HETATM | 3032 | OH2 | WAT | 46 | 15.027 | 18.079 | 54.827 | 1.00 26.65 | SOLV |
| HETATM | 3033 | OH2 | WAT | 47 | 11.076 | 45.493 | 66.435 | 1.00 38.18 | SOLV |
| HETATM | 3034 | OH2 | WAT | 48 | 42.124 | 18.055 | 37.233 | 1.00 28.62 | SOLV |
| HETATM | 3035 | OH2 | WAT | 49 | 48.736 | 25.764 | 64.149 | 1.00 31.88 | SOLV |
| HETATM | 3036 | OH2 | WAT | 50 | 50.383 | 27.254 | 54.972 | 1.00 24.36 | SOLV |

Fig. 16-46

| | | | | | | | | | |
|---|---|---|---|---|---|---|---|---|---|
| HETATM | 3037 | OH2 | WAT | 51 | 48.659 | 36.025 | 68.226 | 1.00 33.89 | SOLV |
| HETATM | 3038 | OH2 | WAT | 52 | 36.998 | 27.228 | 71.440 | 1.00 21.03 | SOLV |
| HETATM | 3039 | OH2 | WAT | 53 | 41.303 | 16.309 | 55.307 | 1.00 32.23 | SOLV |
| HETATM | 3040 | OH2 | WAT | 54 | 33.242 | 39.524 | 49.454 | 1.00 29.77 | SOLV |
| HETATM | 3041 | OH2 | WAT | 55 | 45.004 | 25.973 | 35.031 | 1.00 21.59 | SOLV |
| HETATM | 3042 | OH2 | WAT | 56 | 19.039 | 25.829 | 45.793 | 1.00 33.48 | SOLV |
| HETATM | 3043 | OH2 | WAT | 57 | 17.922 | 35.542 | 50.154 | 1.00 37.51 | SOLV |
| HETATM | 3044 | OH2 | WAT | 58 | 10.409 | 26.864 | 73.166 | 1.00 26.54 | SOLV |
| HETATM | 3045 | OH2 | WAT | 59 | 11.835 | 22.805 | 59.408 | 1.00 20.83 | SOLV |
| HETATM | 3046 | OH2 | WAT | 60 | 18.254 | 48.699 | 53.224 | 1.00 28.41 | SOLV |
| HETATM | 3047 | OH2 | WAT | 61 | 10.426 | 26.647 | 60.447 | 1.00 32.72 | SOLV |
| HETATM | 3048 | OH2 | WAT | 62 | 21.304 | 55.086 | 63.510 | 1.00 28.84 | SOLV |
| HETATM | 3049 | OH2 | WAT | 63 | 32.532 | 51.211 | 45.469 | 1.00 32.48 | SOLV |
| HETATM | 3050 | OH2 | WAT | 64 | 22.658 | 61.079 | 57.420 | 1.00 27.32 | SOLV |
| HETATM | 3051 | OH2 | WAT | 65 | 16.734 | 24.334 | 74.721 | 1.00 27.44 | SOLV |
| HETATM | 3052 | OH2 | WAT | 66 | 32.758 | 37.824 | 54.391 | 1.00 25.07 | SOLV |
| HETATM | 3053 | OH2 | WAT | 67 | 11.142 | 25.859 | 49.706 | 1.00 29.66 | SOLV |
| HETATM | 3054 | OH2 | WAT | 68 | 24.192 | 15.261 | 53.236 | 1.00 30.21 | SOLV |
| HETATM | 3055 | OH2 | WAT | 69 | 19.816 | 17.916 | 66.357 | 1.00 30.50 | SOLV |
| HETATM | 3056 | OH2 | WAT | 70 | 50.347 | 23.975 | 53.197 | 1.00 28.08 | SOLV |
| HETATM | 3057 | OH2 | WAT | 71 | 50.258 | 30.918 | 51.113 | 1.00 20.19 | SOLV |
| HETATM | 3058 | OH2 | WAT | 72 | 21.047 | 17.624 | 68.693 | 1.00 41.23 | SOLV |
| HETATM | 3059 | OH2 | WAT | 73 | 26.782 | 33.756 | 49.995 | 1.00 25.80 | SOLV |
| HETATM | 3060 | OH2 | WAT | 74 | 12.570 | 43.844 | 64.441 | 1.00 31.03 | SOLV |
| HETATM | 3061 | OH2 | WAT | 75 | 35.555 | 41.287 | 50.852 | 1.00 24.03 | SOLV |
| HETATM | 3062 | OH2 | WAT | 76 | 27.764 | 18.231 | 61.827 | 1.00 18.28 | SOLV |
| HETATM | 3063 | OH2 | WAT | 77 | 26.715 | 29.236 | 38.391 | 1.00 23.18 | SOLV |
| HETATM | 3064 | OH2 | WAT | 78 | 21.461 | 23.245 | 48.872 | 1.00 23.80 | SOLV |
| HETATM | 3065 | OH2 | WAT | 79 | 49.246 | 28.263 | 65.477 | 1.00 21.52 | SOLV |
| HETATM | 3066 | OH2 | WAT | 80 | 31.785 | 13.301 | 69.606 | 1.00 31.11 | SOLV |
| HETATM | 3067 | OH2 | WAT | 81 | 49.811 | 34.740 | 59.229 | 1.00 31.76 | SOLV |
| HETATM | 3068 | OH2 | WAT | 82 | 45.670 | 33.188 | 42.470 | 1.00 23.13 | SOLV |
| HETATM | 3069 | OH2 | WAT | 83 | 9.408 | 39.751 | 55.872 | 1.00 31.53 | SOLV |
| HETATM | 3070 | OH2 | WAT | 84 | 35.166 | 35.878 | 29.899 | 1.00 37.32 | SOLV |
| HETATM | 3071 | OH2 | WAT | 85 | 41.927 | 22.970 | 73.694 | 1.00 44.07 | SOLV |
| HETATM | 3072 | OH2 | WAT | 86 | 22.125 | 34.577 | 49.199 | 1.00 44.65 | SOLV |
| HETATM | 3073 | OH2 | WAT | 87 | 43.984 | 33.541 | 37.965 | 1.00 24.88 | SOLV |
| HETATM | 3074 | OH2 | WAT | 88 | 11.997 | 17.962 | 56.312 | 1.00 34.85 | SOLV |
| HETATM | 3075 | OH2 | WAT | 89 | 42.194 | 14.737 | 59.766 | 1.00 25.91 | SOLV |
| HETATM | 3076 | OH2 | WAT | 90 | 49.313 | 24.200 | 41.684 | 1.00 29.29 | SOLV |
| HETATM | 3077 | OH2 | WAT | 91 | 48.504 | 33.595 | 61.519 | 1.00 30.32 | SOLV |
| HETATM | 3078 | OH2 | WAT | 92 | 24.773 | 18.356 | 33.365 | 1.00 53.13 | SOLV |
| HETATM | 3079 | OH2 | WAT | 93 | 35.160 | 35.656 | 47.470 | 1.00 41.41 | SOLV |
| HETATM | 3080 | OH2 | WAT | 94 | 44.682 | 36.658 | 39.962 | 1.00 29.24 | SOLV |
| HETATM | 3081 | OH2 | WAT | 95 | 9.576 | 41.033 | 52.549 | 1.00 51.83 | SOLV |
| HETATM | 3082 | OH2 | WAT | 96 | 47.199 | 20.112 | 42.102 | 1.00 40.39 | SOLV |
| HETATM | 3083 | OH2 | WAT | 97 | 49.254 | 26.331 | 59.641 | 1.00 37.03 | SOLV |
| HETATM | 3084 | OH2 | WAT | 98 | 26.808 | 37.600 | 38.172 | 1.00 28.74 | SOLV |
| HETATM | 3085 | OH2 | WAT | 99 | 40.749 | 14.572 | 64.635 | 1.00 33.42 | SOLV |
| HETATM | 3086 | OH2 | WAT | 100 | 24.850 | 44.161 | 47.775 | 1.00 27.89 | SOLV |
| HETATM | 3087 | OH2 | WAT | 101 | 34.326 | 42.063 | 46.714 | 1.00 42.22 | SOLV |
| HETATM | 3088 | OH2 | WAT | 102 | 30.226 | 34.544 | 52.026 | 1.00 30.77 | SOLV |
| HETATM | 3089 | OH2 | WAT | 103 | 47.824 | 39.054 | 78.097 | 1.00 52.16 | SOLV |
| HETATM | 3090 | OH2 | WAT | 104 | 19.665 | 18.953 | 47.438 | 1.00 51.70 | SOLV |
| HETATM | 3091 | OH2 | WAT | 105 | 46.857 | 36.525 | 46.232 | 1.00 23.65 | SOLV |
| HETATM | 3092 | OH2 | WAT | 106 | 48.069 | 19.460 | 67.360 | 1.00 37.56 | SOLV |
| HETATM | 3093 | OH2 | WAT | 107 | 15.553 | 56.850 | 61.838 | 1.00 46.95 | SOLV |
| HETATM | 3094 | OH2 | WAT | 108 | 44.026 | 19.119 | 70.671 | 1.00 39.55 | SOLV |
| HETATM | 3095 | OH2 | WAT | 109 | 8.139 | 42.064 | 65.674 | 1.00 42.61 | SOLV |
| HETATM | 3096 | OH2 | WAT | 110 | 50.624 | 36.591 | 65.779 | 1.00 31.59 | SOLV |
| HETATM | 3097 | OH2 | WAT | 111 | 51.398 | 26.073 | 61.043 | 1.00 49.09 | SOLV |
| HETATM | 3098 | OH2 | WAT | 112 | 26.174 | 33.692 | 33.551 | 1.00 36.61 | SOLV |
| HETATM | 3099 | OH2 | WAT | 113 | 23.545 | 20.203 | 53.001 | 1.00 24.34 | SOLV |
| HETATM | 3100 | OH2 | WAT | 114 | 9.083 | 42.965 | 57.697 | 1.00 33.65 | SOLV |
| HETATM | 3101 | OH2 | WAT | 115 | 8.442 | 39.898 | 64.594 | 1.00 31.21 | SOLV |
| HETATM | 3102 | OH2 | WAT | 116 | 15.219 | 35.897 | 51.951 | 1.00 26.59 | SOLV |

Fig. 16-47

| | | | | | | | | | |
|---|---|---|---|---|---|---|---|---|---|
| HETATM | 3103 | OH2 | WAT | 117 | 15.417 | 38.438 | 50.473 | 1.00 34.46 | SOLV |
| HETATM | 3104 | OH2 | WAT | 118 | 40.757 | 26.310 | 29.206 | 1.00 29.12 | SOLV |
| HETATM | 3105 | OH2 | WAT | 119 | 27.717 | 18.542 | 46.553 | 1.00 28.17 | SOLV |
| HETATM | 3106 | OH2 | WAT | 120 | 18.612 | 13.786 | 56.845 | 1.00 38.56 | SOLV |
| HETATM | 3107 | OH2 | WAT | 121 | 43.198 | 31.377 | 72.139 | 1.00 26.31 | SOLV |
| HETATM | 3108 | OH2 | WAT | 122 | 44.188 | 35.704 | 33.802 | 1.00 29.81 | SOLV |
| HETATM | 3109 | OH2 | WAT | 123 | 50.736 | 40.909 | 58.456 | 1.00 32.40 | SOLV |
| HETATM | 3110 | OH2 | WAT | 124 | 31.302 | 33.760 | 31.742 | 1.00 30.84 | SOLV |
| HETATM | 3111 | OH2 | WAT | 125 | 36.895 | 21.264 | 34.198 | 1.00 34.67 | SOLV |
| HETATM | 3112 | OH2 | WAT | 126 | 47.474 | 22.252 | 67.427 | 1.00 34.35 | SOLV |
| HETATM | 3113 | OH2 | WAT | 127 | 7.178 | 25.936 | 64.063 | 1.00 31.77 | SOLV |
| HETATM | 3114 | OH2 | WAT | 128 | 36.362 | 66.647 | 54.021 | 1.00 36.88 | SOLV |
| HETATM | 3115 | OH2 | WAT | 129 | 42.486 | 35.503 | 30.348 | 1.00 26.61 | SOLV |
| HETATM | 3116 | OH2 | WAT | 130 | 8.432 | 34.383 | 50.442 | 1.00 37.45 | SOLV |
| HETATM | 3117 | OH2 | WAT | 131 | 37.644 | 49.018 | 48.946 | 1.00 37.33 | SOLV |
| HETATM | 3118 | OH2 | WAT | 132 | 50.273 | 41.645 | 63.380 | 1.00 37.33 | SOLV |
| HETATM | 3119 | OH2 | WAT | 133 | 7.518 | 26.633 | 61.571 | 1.00 45.42 | SOLV |
| HETATM | 3120 | OH2 | WAT | 134 | 31.483 | 46.197 | 72.538 | 1.00 28.02 | SOLV |
| HETATM | 3121 | OH2 | WAT | 135 | 41.501 | 16.604 | 58.054 | 1.00 32.78 | SOLV |
| HETATM | 3122 | OH2 | WAT | 136 | 45.898 | 47.740 | 55.185 | 1.00 43.47 | SOLV |
| HETATM | 3123 | OH2 | WAT | 137 | 16.300 | 33.614 | 49.519 | 1.00 30.37 | SOLV |
| HETATM | 3124 | OH2 | WAT | 138 | 51.148 | 36.946 | 55.148 | 1.00 46.34 | SOLV |
| HETATM | 3125 | OH2 | WAT | 139 | 21.525 | 53.761 | 50.892 | 1.00 38.27 | SOLV |
| HETATM | 3126 | OH2 | WAT | 140 | 21.603 | 54.580 | 68.690 | 1.00 33.10 | SOLV |
| HETATM | 3127 | OH2 | WAT | 141 | 10.191 | 29.237 | 60.325 | 1.00 30.24 | SOLV |
| HETATM | 3128 | OH2 | WAT | 142 | 16.951 | 18.120 | 66.901 | 1.00 40.85 | SOLV |
| HETATM | 3129 | OH2 | WAT | 143 | 4.943 | 24.912 | 51.199 | 1.00 49.13 | SOLV |
| HETATM | 3130 | OH2 | WAT | 144 | 10.711 | 25.291 | 58.177 | 1.00 30.72 | SOLV |
| HETATM | 3131 | OH2 | WAT | 145 | 30.815 | 43.398 | 36.040 | 1.00 42.23 | SOLV |
| HETATM | 3132 | OH2 | WAT | 146 | 21.763 | 24.512 | 46.695 | 1.00 28.31 | SOLV |
| HETATM | 3133 | OH2 | WAT | 147 | 51.788 | 33.122 | 50.887 | 1.00 26.15 | SOLV |
| HETATM | 3134 | OH2 | WAT | 148 | 24.531 | 44.741 | 72.420 | 1.00 27.99 | SOLV |
| HETATM | 3135 | OH2 | WAT | 149 | 50.938 | 23.483 | 60.422 | 1.00 38.20 | SOLV |
| HETATM | 3136 | OH2 | WAT | 150 | 24.860 | 47.932 | 61.067 | 1.00 18.89 | SOLV |
| HETATM | 3137 | OH2 | WAT | 151 | 27.336 | 37.304 | 35.642 | 1.00 33.58 | SOLV |
| HETATM | 3138 | OH2 | WAT | 152 | 38.680 | 35.535 | 35.974 | 1.00 26.89 | SOLV |
| HETATM | 3139 | OH2 | WAT | 153 | 24.441 | 16.097 | 33.317 | 1.00 48.33 | SOLV |
| HETATM | 3140 | OH2 | WAT | 154 | 20.343 | 18.124 | 73.416 | 1.00 36.28 | SOLV |
| HETATM | 3141 | OH2 | WAT | 155 | 49.765 | 37.948 | 74.801 | 1.00 48.41 | SOLV |
| HETATM | 3142 | OH2 | WAT | 156 | 34.329 | 31.169 | 47.547 | 1.00 25.33 | SOLV |
| HETATM | 3143 | OH2 | WAT | 157 | 43.028 | 24.554 | 72.536 | 1.00 41.54 | SOLV |
| HETATM | 3144 | OH2 | WAT | 158 | 39.888 | 15.082 | 42.035 | 1.00 28.76 | SOLV |
| HETATM | 3145 | OH2 | WAT | 159 | 41.886 | 20.780 | 73.179 | 1.00 51.03 | SOLV |
| HETATM | 3146 | OH2 | WAT | 160 | 22.962 | 49.969 | 58.518 | 1.00 35.04 | SOLV |
| HETATM | 3147 | OH2 | WAT | 161 | 14.696 | 15.261 | 68.016 | 1.00 55.47 | SOLV |
| HETATM | 3148 | OH2 | WAT | 162 | 14.915 | 18.181 | 64.866 | 1.00 42.00 | SOLV |
| HETATM | 3149 | OH2 | WAT | 163 | 30.608 | 49.029 | 52.612 | 1.00 47.32 | SOLV |
| HETATM | 3150 | OH2 | WAT | 164 | 52.566 | 30.906 | 57.612 | 1.00 36.71 | SOLV |
| HETATM | 3151 | OH2 | WAT | 165 | 23.699 | 27.331 | 77.729 | 1.00 32.22 | SOLV |
| HETATM | 3152 | OH2 | WAT | 166 | 36.971 | 59.046 | 63.272 | 1.00 43.05 | SOLV |
| HETATM | 3153 | OH2 | WAT | 167 | 46.053 | 45.927 | 52.876 | 1.00 33.66 | SOLV |
| HETATM | 3154 | OH2 | WAT | 168 | 42.780 | 49.151 | 58.106 | 1.00 44.63 | SOLV |
| HETATM | 3155 | OH2 | WAT | 169 | 15.100 | 44.506 | 72.183 | 1.00 45.43 | SOLV |
| HETATM | 3156 | OH2 | WAT | 170 | 31.677 | 60.998 | 50.050 | 1.00 34.51 | SOLV |
| HETATM | 3157 | OH2 | WAT | 171 | 25.336 | 45.674 | 45.578 | 1.00 55.85 | SOLV |
| HETATM | 3158 | OH2 | WAT | 172 | 17.481 | 18.266 | 49.018 | 1.00 32.73 | SOLV |
| HETATM | 3159 | OH2 | WAT | 173 | 26.112 | 18.147 | 31.404 | 1.00 49.94 | SOLV |
| HETATM | 3160 | OH2 | WAT | 174 | 45.874 | 43.142 | 70.985 | 1.00 32.89 | SOLV |
| HETATM | 3161 | OH2 | WAT | 175 | 34.517 | 17.884 | 33.278 | 1.00 42.20 | SOLV |
| HETATM | 3162 | OH2 | WAT | 176 | 16.330 | 54.886 | 50.466 | 1.00 40.74 | SOLV |
| HETATM | 3163 | OH2 | WAT | 177 | 31.400 | 51.087 | 74.689 | 1.00 38.56 | SOLV |
| HETATM | 3164 | OH2 | WAT | 178 | 50.971 | 27.079 | 67.130 | 1.00 44.49 | SOLV |
| HETATM | 3165 | OH2 | WAT | 179 | 7.933 | 23.412 | 54.691 | 1.00 42.84 | SOLV |
| HETATM | 3166 | OH2 | WAT | 180 | 33.498 | 47.596 | 73.612 | 1.00 35.99 | SOLV |
| HETATM | 3167 | OH2 | WAT | 181 | 26.016 | 19.583 | 44.954 | 1.00 51.31 | SOLV |
| HETATM | 3168 | OH2 | WAT | 182 | 40.139 | 17.026 | 74.920 | 1.00 43.64 | SOLV |

Fig. 16-48

| | | | | | | | | | |
|---|---|---|---|---|---|---|---|---|---|
| HETATM | 3169 | OH2 | WAT | 183 | 10.441 | 42.659 | 62.744 | 1.00 34.51 | SOLV |
| HETATM | 3170 | OH2 | WAT | 184 | 2.095 | 34.482 | 65.810 | 1.00 36.49 | SOLV |
| HETATM | 3171 | OH2 | WAT | 185 | 45.749 | 18.286 | 51.615 | 1.00 28.19 | SOLV |
| HETATM | 3172 | OH2 | WAT | 186 | 25.771 | 38.332 | 76.707 | 1.00 45.53 | SOLV |
| HETATM | 3173 | OH2 | WAT | 187 | 7.228 | 40.382 | 57.542 | 1.00 48.91 | SOLV |
| HETATM | 3174 | OH2 | WAT | 188 | 42.972 | 52.824 | 67.739 | 1.00 39.99 | SOLV |
| HETATM | 3175 | OH2 | WAT | 189 | 20.137 | 13.189 | 73.277 | 1.00 44.91 | SOLV |
| HETATM | 3176 | OH2 | WAT | 190 | 48.945 | 19.193 | 47.581 | 1.00 52.88 | SOLV |
| HETATM | 3177 | OH2 | WAT | 191 | 14.549 | 34.547 | 47.665 | 1.00 49.15 | SOLV |
| HETATM | 3178 | OH2 | WAT | 192 | 31.765 | 20.567 | 26.536 | 1.00 42.23 | SOLV |
| HETATM | 3179 | OH2 | WAT | 193 | 9.784 | 39.303 | 74.222 | 1.00 32.10 | SOLV |
| HETATM | 3180 | OH2 | WAT | 194 | 28.865 | 12.481 | 52.375 | 1.00 50.98 | SOLV |
| HETATM | 3181 | OH2 | WAT | 195 | 24.030 | 12.804 | 70.409 | 1.00 52.43 | SOLV |
| HETATM | 3182 | OH2 | WAT | 196 | 47.209 | 39.536 | 50.698 | 1.00 43.03 | SOLV |
| HETATM | 3183 | OH2 | WAT | 197 | 35.618 | 18.114 | 27.306 | 1.00 41.11 | SOLV |
| HETATM | 3184 | OH2 | WAT | 198 | 23.625 | 48.145 | 43.853 | 1.00 48.20 | SOLV |
| HETATM | 3185 | OH2 | WAT | 199 | 37.090 | 59.044 | 54.185 | 1.00 34.99 | SOLV |
| HETATM | 3186 | OH2 | WAT | 200 | 34.478 | 12.208 | 59.080 | 1.00 36.58 | SOLV |
| HETATM | 3187 | OH2 | WAT | 201 | 22.142 | 29.583 | 76.228 | 1.00 33.95 | SOLV |
| HETATM | 3188 | OH2 | WAT | 202 | 13.608 | 42.619 | 53.973 | 1.00 40.44 | SOLV |
| HETATM | 3189 | OH2 | WAT | 203 | 42.647 | 18.701 | 72.526 | 1.00 55.64 | SOLV |
| HETATM | 3190 | OH2 | WAT | 204 | 37.005 | 35.993 | 77.480 | 1.00 34.82 | SOLV |
| HETATM | 3191 | OH2 | WAT | 205 | 34.154 | 20.512 | 33.327 | 1.00 31.00 | SOLV |
| HETATM | 3192 | OH2 | WAT | 206 | 37.264 | 57.546 | 47.642 | 1.00 49.58 | SOLV |
| HETATM | 3193 | OH2 | WAT | 207 | 17.924 | 35.195 | 79.003 | 1.00 38.45 | SOLV |
| HETATM | 3194 | OH2 | WAT | 208 | 51.172 | 31.581 | 62.378 | 1.00 35.37 | SOLV |
| HETATM | 3195 | OH2 | WAT | 209 | 50.503 | 36.726 | 79.224 | 1.00 39.95 | SOLV |
| HETATM | 3196 | OH2 | WAT | 210 | 18.382 | 13.162 | 63.852 | 1.00 52.08 | SOLV |
| HETATM | 3197 | OH2 | WAT | 211 | 27.245 | 8.351 | 55.199 | 1.00 39.12 | SOLV |
| HETATM | 3198 | OH2 | WAT | 212 | 18.354 | 13.545 | 59.540 | 1.00 30.15 | SOLV |
| HETATM | 3199 | OH2 | WAT | 213 | 49.088 | 51.744 | 63.388 | 1.00 36.69 | SOLV |
| HETATM | 3200 | OH2 | WAT | 214 | 23.251 | 33.160 | 50.871 | 1.00 42.11 | SOLV |
| HETATM | 3201 | OH2 | WAT | 215 | 12.989 | 35.073 | 50.651 | 1.00 38.63 | SOLV |
| HETATM | 3202 | OH2 | WAT | 216 | 24.414 | 44.460 | 43.239 | 1.00 37.93 | SOLV |
| HETATM | 3203 | OH2 | WAT | 217 | 24.690 | 47.590 | 73.117 | 1.00 34.17 | SOLV |
| HETATM | 3204 | OH2 | WAT | 218 | 19.844 | 17.949 | 81.360 | 1.00 40.74 | SOLV |
| HETATM | 3205 | OH2 | WAT | 219 | 40.169 | 27.215 | 74.247 | 1.00 37.83 | SOLV |
| HETATM | 3206 | OH2 | WAT | 220 | 38.737 | 39.516 | 73.171 | 1.00 49.20 | SOLV |
| HETATM | 3207 | OH2 | WAT | 221 | 50.628 | 21.408 | 46.879 | 1.00 45.57 | SOLV |
| HETATM | 3208 | OH2 | WAT | 222 | 35.436 | 43.288 | 75.660 | 1.00 37.33 | SOLV |
| HETATM | 3209 | OH2 | WAT | 223 | 34.390 | 16.963 | 55.285 | 1.00 35.10 | SOLV |
| HETATM | 3210 | OH2 | WAT | 224 | 21.800 | 35.454 | 34.475 | 1.00 46.29 | SOLV |
| HETATM | 3211 | OH2 | WAT | 225 | 15.751 | 40.989 | 46.787 | 1.00 62.75 | SOLV |
| HETATM | 3212 | OH2 | WAT | 226 | 23.844 | 48.662 | 66.295 | 1.00 38.35 | SOLV |
| HETATM | 3213 | OH2 | WAT | 227 | 47.225 | 20.562 | 55.117 | 1.00 49.99 | SOLV |
| HETATM | 3214 | OH2 | WAT | 228 | 23.126 | 19.272 | 50.565 | 1.00 30.07 | SOLV |

Fig. 16-49

|      |    |     |     |   | Residue # | X | Y | Z | OCC. | B | Segment ID |
|------|----|-----|-----|---|-----------|--------|--------|--------|------|-------|---|
| ATOM | 1  | CB  | ALA | A | 2  | 43.739 | 36.862 | 75.052 | 1.00 | 64.01 | 6 |
| ATOM | 2  | C   | ALA | A | 2  | 44.405 | 38.106 | 72.971 | 1.00 | 60.02 | 6 |
| ATOM | 3  | O   | ALA | A | 2  | 43.251 | 38.536 | 72.908 | 1.00 | 57.94 | 8 |
| ATOM | 4  | N   | ALA | A | 2  | 46.142 | 37.179 | 74.497 | 1.00 | 62.88 | 7 |
| ATOM | 5  | CA  | ALA | A | 2  | 44.776 | 36.966 | 73.923 | 1.00 | 63.02 | 6 |
| ATOM | 6  | N   | LYS | A | 3  | 45.398 | 38.588 | 72.233 | 1.00 | 55.40 | 7 |
| ATOM | 7  | CA  | LYS | A | 3  | 45.196 | 39.671 | 71.287 | 1.00 | 53.02 | 6 |
| ATOM | 8  | CB  | LYS | A | 3  | 46.443 | 39.830 | 70.421 | 1.00 | 53.11 | 6 |
| ATOM | 9  | CG  | LYS | A | 3  | 47.703 | 40.093 | 71.217 | 1.00 | 57.36 | 6 |
| ATOM | 10 | CD  | LYS | A | 3  | 48.941 | 39.976 | 70.349 | 1.00 | 60.94 | 6 |
| ATOM | 11 | CE  | LYS | A | 3  | 48.909 | 40.957 | 69.196 | 1.00 | 63.48 | 6 |
| ATOM | 12 | NZ  | LYS | A | 3  | 50.075 | 40.765 | 68.294 | 1.00 | 66.87 | 7 |
| ATOM | 13 | C   | LYS | A | 3  | 43.986 | 39.401 | 70.399 | 1.00 | 50.49 | 6 |
| ATOM | 14 | O   | LYS | A | 3  | 43.691 | 38.255 | 70.063 | 1.00 | 52.50 | 8 |
| ATOM | 15 | N   | VAL | A | 4  | 43.281 | 40.464 | 70.034 | 1.00 | 45.96 | 7 |
| ATOM | 16 | CA  | VAL | A | 4  | 42.122 | 40.352 | 69.167 | 1.00 | 41.16 | 6 |
| ATOM | 17 | CB  | VAL | A | 4  | 40.983 | 41.272 | 69.638 | 1.00 | 41.53 | 6 |
| ATOM | 18 | CG1 | VAL | A | 4  | 39.734 | 41.028 | 68.797 | 1.00 | 40.07 | 6 |
| ATOM | 19 | CG2 | VAL | A | 4  | 40.705 | 41.033 | 71.115 | 1.00 | 38.31 | 6 |
| ATOM | 20 | C   | VAL | A | 4  | 42.619 | 40.796 | 67.796 | 1.00 | 39.96 | 6 |
| ATOM | 21 | O   | VAL | A | 4  | 43.123 | 41.914 | 67.645 | 1.00 | 39.15 | 8 |
| ATOM | 22 | N   | LYS | A | 5  | 42.486 | 39.916 | 66.807 | 1.00 | 36.24 | 7 |
| ATOM | 23 | CA  | LYS | A | 5  | 42.956 | 40.186 | 65.449 | 1.00 | 35.66 | 6 |
| ATOM | 24 | CB  | LYS | A | 5  | 43.930 | 39.088 | 65.024 | 1.00 | 37.33 | 6 |
| ATOM | 25 | CG  | LYS | A | 5  | 45.197 | 38.978 | 65.860 | 1.00 | 38.24 | 6 |
| ATOM | 26 | CD  | LYS | A | 5  | 46.113 | 40.179 | 65.659 | 1.00 | 35.41 | 6 |
| ATOM | 27 | CE  | LYS | A | 5  | 47.436 | 39.957 | 66.369 | 1.00 | 37.46 | 6 |
| ATOM | 28 | NZ  | LYS | A | 5  | 48.345 | 41.121 | 66.245 | 1.00 | 35.63 | 7 |
| ATOM | 29 | C   | LYS | A | 5  | 41.840 | 40.254 | 64.415 | 1.00 | 34.40 | 6 |
| ATOM | 30 | O   | LYS | A | 5  | 40.788 | 39.641 | 64.588 | 1.00 | 33.92 | 8 |
| ATOM | 31 | N   | LEU | A | 6  | 42.082 | 40.983 | 63.329 | 1.00 | 32.52 | 7 |
| ATOM | 32 | CA  | LEU | A | 6  | 41.097 | 41.094 | 62.253 | 1.00 | 33.64 | 6 |
| ATOM | 33 | CB  | LEU | A | 6  | 40.589 | 42.532 | 62.114 | 1.00 | 31.83 | 6 |
| ATOM | 34 | CG  | LEU | A | 6  | 39.346 | 42.823 | 61.248 | 1.00 | 32.93 | 6 |
| ATOM | 35 | CD1 | LEU | A | 6  | 39.356 | 44.295 | 60.899 | 1.00 | 28.95 | 6 |
| ATOM | 36 | CD2 | LEU | A | 6  | 39.336 | 42.031 | 59.964 | 1.00 | 32.87 | 6 |
| ATOM | 37 | C   | LEU | A | 6  | 41.802 | 40.721 | 60.955 | 1.00 | 35.09 | 6 |
| ATOM | 38 | O   | LEU | A | 6  | 42.631 | 41.491 | 60.468 | 1.00 | 36.93 | 8 |
| ATOM | 39 | N   | ILE | A | 7  | 41.494 | 39.561 | 60.382 | 1.00 | 35.52 | 7 |
| ATOM | 40 | CA  | ILE | A | 7  | 42.145 | 39.199 | 59.129 | 1.00 | 35.14 | 6 |
| ATOM | 41 | CB  | ILE | A | 7  | 42.062 | 37.711 | 58.850 | 1.00 | 33.68 | 6 |
| ATOM | 42 | CG2 | ILE | A | 7  | 42.731 | 37.409 | 57.517 | 1.00 | 32.87 | 6 |
| ATOM | 43 | CG1 | ILE | A | 7  | 42.746 | 36.941 | 59.975 | 1.00 | 33.32 | 6 |
| ATOM | 44 | CD1 | ILE | A | 7  | 42.744 | 35.451 | 59.755 | 1.00 | 35.09 | 6 |
| ATOM | 45 | C   | ILE | A | 7  | 41.487 | 39.935 | 57.971 | 1.00 | 37.13 | 6 |
| ATOM | 46 | O   | ILE | A | 7  | 40.258 | 39.933 | 57.855 | 1.00 | 35.21 | 8 |
| ATOM | 47 | N   | GLY | A | 8  | 42.304 | 40.563 | 57.124 | 1.00 | 37.25 | 7 |
| ATOM | 48 | CA  | GLY | A | 8  | 41.771 | 41.305 | 55.994 | 1.00 | 38.69 | 6 |
| ATOM | 49 | C   | GLY | A | 8  | 42.809 | 41.939 | 55.079 | 1.00 | 39.73 | 6 |
| ATOM | 50 | O   | GLY | A | 8  | 44.015 | 41.827 | 55.321 | 1.00 | 39.21 | 8 |
| ATOM | 51 | N   | THR | A | 9  | 42.335 | 42.622 | 54.033 | 1.00 | 39.41 | 7 |
| ATOM | 52 | CA  | THR | A | 9  | 43.212 | 43.268 | 53.057 | 1.00 | 38.69 | 6 |
| ATOM | 53 | CB  | THR | A | 9  | 44.132 | 42.210 | 52.390 | 1.00 | 37.27 | 6 |
| ATOM | 54 | OG1 | THR | A | 9  | 44.754 | 42.771 | 51.230 | 1.00 | 36.82 | 8 |
| ATOM | 55 | CG2 | THR | A | 9  | 43.332 | 40.972 | 52.001 | 1.00 | 38.59 | 6 |
| ATOM | 56 | C   | THR | A | 9  | 42.447 | 44.045 | 51.970 | 1.00 | 38.60 | 6 |
| ATOM | 57 | O   | THR | A | 9  | 41.434 | 43.569 | 51.452 | 1.00 | 37.30 | 8 |
| ATOM | 58 | N   | LEU | A | 10 | 42.939 | 45.238 | 51.628 | 1.00 | 38.14 | 7 |
| ATOM | 59 | CA  | LEU | A | 10 | 42.304 | 46.077 | 50.609 | 1.00 | 39.39 | 6 |
| ATOM | 60 | CB  | LEU | A | 10 | 43.026 | 47.418 | 50.456 | 1.00 | 38.98 | 6 |
| ATOM | 61 | CG  | LEU | A | 10 | 42.836 | 48.506 | 51.510 | 1.00 | 39.68 | 6 |
| ATOM | 62 | CD1 | LEU | A | 10 | 41.343 | 48.830 | 51.594 | 1.00 | 40.22 | 6 |
| ATOM | 63 | CD2 | LEU | A | 10 | 43.382 | 48.057 | 52.857 | 1.00 | 40.11 | 6 |
| ATOM | 64 | C   | LEU | A | 10 | 42.238 | 45.432 | 49.239 | 1.00 | 41.66 | 6 |
| ATOM | 65 | O   | LEU | A | 10 | 41.462 | 45.863 | 48.381 | 1.00 | 42.08 | 8 |
| ATOM | 66 | N   | ASP | A | 11 | 43.052 | 44.408 | 49.025 | 1.00 | 43.51 | 7 |

Fig. 17-1

| ATOM | 67 | CA | ASP | A | 11 | 43.071 | 43.731 | 47.737 | 1.00 | 47.27 | 6 |
|---|---|---|---|---|---|---|---|---|---|---|---|
| ATOM | 68 | CB | ASP | A | 11 | 44.250 | 42.765 | 47.694 | 1.00 | 51.03 | 6 |
| ATOM | 69 | CG | ASP | A | 11 | 45.579 | 43.479 | 47.858 | 1.00 | 54.10 | 6 |
| ATOM | 70 | OD1 | ASP | A | 11 | 45.944 | 44.282 | 46.975 | 1.00 | 55.93 | 8 |
| ATOM | 71 | OD2 | ASP | A | 11 | 46.255 | 43.251 | 48.879 | 1.00 | 57.79 | 8 |
| ATOM | 72 | C | ASP | A | 11 | 41.756 | 43.016 | 47.423 | 1.00 | 46.36 | 6 |
| ATOM | 73 | O | ASP | A | 11 | 41.472 | 42.702 | 46.266 | 1.00 | 43.49 | 8 |
| ATOM | 74 | N | TYR | A | 12 | 40.954 | 42.767 | 48.456 | 1.00 | 46.80 | 7 |
| ATOM | 75 | CA | TYR | A | 12 | 39.654 | 42.116 | 48.284 | 1.00 | 45.92 | 6 |
| ATOM | 76 | CB | TYR | A | 12 | 38.953 | 41.942 | 49.638 | 1.00 | 41.38 | 6 |
| ATOM | 77 | CG | TYR | A | 12 | 39.358 | 40.697 | 50.390 | 1.00 | 38.82 | 6 |
| ATOM | 78 | CD1 | TYR | A | 12 | 39.531 | 40.720 | 51.775 | 1.00 | 37.95 | 6 |
| ATOM | 79 | CE1 | TYR | A | 12 | 39.869 | 39.560 | 52.476 | 1.00 | 36.18 | 6 |
| ATOM | 80 | CD2 | TYR | A | 12 | 39.533 | 39.479 | 49.721 | 1.00 | 37.69 | 6 |
| ATOM | 81 | CE2 | TYR | A | 12 | 39.868 | 38.316 | 50.415 | 1.00 | 35.83 | 6 |
| ATOM | 82 | CZ | TYR | A | 12 | 40.032 | 38.365 | 51.787 | 1.00 | 34.10 | 6 |
| ATOM | 83 | OH | TYR | A | 12 | 40.339 | 37.216 | 52.470 | 1.00 | 36.31 | 8 |
| ATOM | 84 | C | TYR | A | 12 | 38.786 | 42.966 | 47.378 | 1.00 | 46.56 | 6 |
| ATOM | 85 | O | TYR | A | 12 | 37.821 | 42.476 | 46.791 | 1.00 | 47.38 | 8 |
| ATOM | 86 | N | GLY | A | 13 | 39.138 | 44.247 | 47.278 | 1.00 | 47.28 | 7 |
| ATOM | 87 | CA | GLY | A | 13 | 38.385 | 45.164 | 46.442 | 1.00 | 46.53 | 6 |
| ATOM | 88 | C | GLY | A | 13 | 38.650 | 44.934 | 44.968 | 1.00 | 45.60 | 6 |
| ATOM | 89 | O | GLY | A | 13 | 37.895 | 45.401 | 44.117 | 1.00 | 43.68 | 8 |
| ATOM | 90 | N | LYS | A | 14 | 39.725 | 44.210 | 44.672 | 1.00 | 46.52 | 7 |
| ATOM | 91 | CA | LYS | A | 14 | 40.112 | 43.908 | 43.296 | 1.00 | 47.28 | 6 |
| ATOM | 92 | CB | LYS | A | 14 | 41.629 | 43.748 | 43.201 | 1.00 | 50.22 | 6 |
| ATOM | 93 | CG | LYS | A | 14 | 42.396 | 45.044 | 43.307 | 1.00 | 57.12 | 6 |
| ATOM | 94 | CD | LYS | A | 14 | 42.038 | 46.004 | 42.161 | 1.00 | 63.60 | 6 |
| ATOM | 95 | CE | LYS | A | 14 | 42.349 | 45.422 | 40.768 | 1.00 | 66.65 | 6 |
| ATOM | 96 | NZ | LYS | A | 14 | 41.529 | 44.220 | 40.387 | 1.00 | 67.70 | 7 |
| ATOM | 97 | C | LYS | A | 14 | 39.460 | 42.643 | 42.769 | 1.00 | 44.18 | 6 |
| ATOM | 98 | O | LYS | A | 14 | 39.564 | 42.325 | 41.585 | 1.00 | 40.33 | 8 |
| ATOM | 99 | N | TYR | A | 15 | 38.790 | 41.926 | 43.661 | 1.00 | 43.25 | 7 |
| ATOM | 100 | CA | TYR | A | 15 | 38.145 | 40.665 | 43.317 | 1.00 | 43.18 | 6 |
| ATOM | 101 | CB | TYR | A | 15 | 38.789 | 39.547 | 44.142 | 1.00 | 36.88 | 6 |
| ATOM | 102 | CG | TYR | A | 15 | 40.302 | 39.560 | 44.053 | 1.00 | 32.96 | 6 |
| ATOM | 103 | CD1 | TYR | A | 15 | 41.084 | 39.107 | 45.108 | 1.00 | 30.90 | 6 |
| ATOM | 104 | CE1 | TYR | A | 15 | 42.476 | 39.144 | 45.035 | 1.00 | 30.94 | 6 |
| ATOM | 105 | CD2 | TYR | A | 15 | 40.952 | 40.049 | 42.912 | 1.00 | 33.01 | 6 |
| ATOM | 106 | CE2 | TYR | A | 15 | 42.341 | 40.092 | 42.826 | 1.00 | 29.68 | 6 |
| ATOM | 107 | CZ | TYR | A | 15 | 43.098 | 39.639 | 43.890 | 1.00 | 30.99 | 6 |
| ATOM | 108 | OH | TYR | A | 15 | 44.471 | 39.673 | 43.809 | 1.00 | 28.02 | 8 |
| ATOM | 109 | C | TYR | A | 15 | 36.661 | 40.778 | 43.621 | 1.00 | 45.56 | 6 |
| ATOM | 110 | O | TYR | A | 15 | 36.149 | 40.153 | 44.552 | 1.00 | 45.22 | 8 |
| ATOM | 111 | N | ARG | A | 16 | 35.981 | 41.599 | 42.830 | 1.00 | 48.81 | 7 |
| ATOM | 112 | CA | ARG | A | 16 | 34.553 | 41.819 | 42.999 | 1.00 | 53.22 | 6 |
| ATOM | 113 | CB | ARG | A | 16 | 34.193 | 43.263 | 42.654 | 1.00 | 57.11 | 6 |
| ATOM | 114 | CG | ARG | A | 16 | 34.852 | 44.330 | 43.490 | 1.00 | 61.66 | 6 |
| ATOM | 115 | CD | ARG | A | 16 | 34.280 | 44.408 | 44.886 | 1.00 | 67.04 | 6 |
| ATOM | 116 | NE | ARG | A | 16 | 34.798 | 45.590 | 45.569 | 1.00 | 73.59 | 7 |
| ATOM | 117 | CZ | ARG | A | 16 | 34.612 | 46.837 | 45.141 | 1.00 | 75.03 | 6 |
| ATOM | 118 | NH1 | ARG | A | 16 | 33.917 | 47.065 | 44.033 | 1.00 | 73.03 | 7 |
| ATOM | 119 | NH2 | ARG | A | 16 | 35.142 | 47.856 | 45.808 | 1.00 | 75.79 | 7 |
| ATOM | 120 | C | ARG | A | 16 | 33.757 | 40.903 | 42.080 | 1.00 | 51.79 | 6 |
| ATOM | 121 | O | ARG | A | 16 | 34.192 | 40.593 | 40.970 | 1.00 | 50.89 | 8 |
| ATOM | 122 | N | TYR | A | 17 | 32.596 | 40.463 | 42.552 | 1.00 | 50.19 | 7 |
| ATOM | 123 | CA | TYR | A | 17 | 31.737 | 39.634 | 41.733 | 1.00 | 49.60 | 6 |
| ATOM | 124 | CB | TYR | A | 17 | 30.534 | 39.119 | 42.528 | 1.00 | 45.80 | 6 |
| ATOM | 125 | CG | TYR | A | 17 | 30.803 | 37.894 | 43.365 | 1.00 | 42.01 | 6 |
| ATOM | 126 | CD1 | TYR | A | 17 | 31.689 | 37.932 | 44.438 | 1.00 | 42.45 | 6 |
| ATOM | 127 | CE1 | TYR | A | 17 | 31.960 | 36.780 | 45.193 | 1.00 | 43.36 | 6 |
| ATOM | 128 | CD2 | TYR | A | 17 | 30.185 | 36.680 | 43.062 | 1.00 | 39.89 | 6 |
| ATOM | 129 | CE2 | TYR | A | 17 | 30.443 | 35.526 | 43.803 | 1.00 | 40.56 | 6 |
| ATOM | 130 | CZ | TYR | A | 17 | 31.333 | 35.578 | 44.869 | 1.00 | 41.98 | 6 |
| ATOM | 131 | OH | TYR | A | 17 | 31.600 | 34.438 | 45.598 | 1.00 | 34.66 | 8 |
| ATOM | 132 | C | TYR | A | 17 | 31.245 | 40.547 | 40.622 | 1.00 | 51.88 | 6 |

Fig. 17-2

| ATOM | 133 | O | TYR | A | 17 | 31.332 | 41.772 | 40.726 | 1.00 | 47.86 | 8 |
|---|---|---|---|---|---|---|---|---|---|---|---|
| ATOM | 134 | N | PRO | A | 18 | 30.730 | 39.964 | 39.534 | 1.00 | 54.38 | 7 |
| ATOM | 135 | CD | PRO | A | 18 | 30.548 | 38.545 | 39.190 | 1.00 | 54.21 | 6 |
| ATOM | 136 | CA | PRO | A | 18 | 30.243 | 40.809 | 38.449 | 1.00 | 56.43 | 6 |
| ATOM | 137 | CB | PRO | A | 18 | 29.601 | 39.792 | 37.496 | 1.00 | 56.84 | 6 |
| ATOM | 138 | CG | PRO | A | 18 | 29.260 | 38.613 | 38.426 | 1.00 | 56.46 | 6 |
| ATOM | 139 | C | PRO | A | 18 | 29.273 | 41.891 | 38.932 | 1.00 | 58.74 | 6 |
| ATOM | 140 | O | PRO | A | 18 | 28.791 | 41.861 | 40.066 | 1.00 | 55.72 | 8 |
| ATOM | 141 | N | LYS | A | 19 | 29.017 | 42.851 | 38.052 | 1.00 | 62.10 | 7 |
| ATOM | 142 | CA | LYS | A | 19 | 28.127 | 43.973 | 38.314 | 1.00 | 64.85 | 6 |
| ATOM | 143 | CB | LYS | A | 19 | 27.972 | 44.781 | 37.022 | 1.00 | 69.74 | 6 |
| ATOM | 144 | CG | LYS | A | 19 | 28.008 | 43.925 | 35.740 | 1.00 | 74.99 | 6 |
| ATOM | 145 | CD | LYS | A | 19 | 26.895 | 42.881 | 35.668 | 1.00 | 78.18 | 6 |
| ATOM | 146 | CE | LYS | A | 19 | 26.981 | 42.010 | 34.420 | 1.00 | 80.24 | 6 |
| ATOM | 147 | NZ | LYS | A | 19 | 25.867 | 41.010 | 34.361 | 1.00 | 81.13 | 7 |
| ATOM | 148 | C | LYS | A | 19 | 26.750 | 43.619 | 38.869 | 1.00 | 64.77 | 6 |
| ATOM | 149 | O | LYS | A | 19 | 26.414 | 43.961 | 40.001 | 1.00 | 66.50 | 8 |
| ATOM | 150 | N | ASN | A | 20 | 25.957 | 42.933 | 38.062 | 1.00 | 63.75 | 7 |
| ATOM | 151 | CA | ASN | A | 20 | 24.612 | 42.556 | 38.439 | 1.00 | 62.96 | 6 |
| ATOM | 152 | CB | ASN | A | 20 | 23.870 | 42.031 | 37.208 | 1.00 | 67.42 | 6 |
| ATOM | 153 | CG | ASN | A | 20 | 22.392 | 41.833 | 37.459 | 1.00 | 72.29 | 6 |
| ATOM | 154 | OD1 | ASN | A | 20 | 21.666 | 42.785 | 37.772 | 1.00 | 75.25 | 8 |
| ATOM | 155 | ND2 | ASN | A | 20 | 21.931 | 40.594 | 37.322 | 1.00 | 74.38 | 7 |
| ATOM | 156 | C | ASN | A | 20 | 24.602 | 41.512 | 39.547 | 1.00 | 61.30 | 6 |
| ATOM | 157 | O | ASN | A | 20 | 23.629 | 40.773 | 39.698 | 1.00 | 61.49 | 8 |
| ATOM | 158 | N | HIS | A | 21 | 25.681 | 41.444 | 40.321 | 1.00 | 57.30 | 7 |
| ATOM | 159 | CA | HIS | A | 21 | 25.755 | 40.480 | 41.418 | 1.00 | 54.68 | 6 |
| ATOM | 160 | CB | HIS | A | 21 | 27.071 | 39.700 | 41.373 | 1.00 | 52.63 | 6 |
| ATOM | 161 | CG | HIS | A | 21 | 27.058 | 38.449 | 42.195 | 1.00 | 49.39 | 6 |
| ATOM | 162 | CD2 | HIS | A | 21 | 27.336 | 38.236 | 43.503 | 1.00 | 49.39 | 6 |
| ATOM | 163 | ND1 | HIS | A | 21 | 26.664 | 37.229 | 41.686 | 1.00 | 48.27 | 7 |
| ATOM | 164 | CE1 | HIS | A | 21 | 26.704 | 36.320 | 42.643 | 1.00 | 48.16 | 6 |
| ATOM | 165 | NE2 | HIS | A | 21 | 27.108 | 36.905 | 43.757 | 1.00 | 47.33 | 7 |
| ATOM | 166 | C | HIS | A | 21 | 25.664 | 41.215 | 42.760 | 1.00 | 52.89 | 6 |
| ATOM | 167 | O | HIS | A | 21 | 26.295 | 42.256 | 42.947 | 1.00 | 52.52 | 8 |
| ATOM | 168 | N | PRO | A | 22 | 24.880 | 40.679 | 43.713 | 1.00 | 50.81 | 7 |
| ATOM | 169 | CD | PRO | A | 22 | 24.076 | 39.444 | 43.661 | 1.00 | 48.50 | 6 |
| ATOM | 170 | CA | PRO | A | 22 | 24.734 | 41.310 | 45.029 | 1.00 | 48.02 | 6 |
| ATOM | 171 | CB | PRO | A | 22 | 23.860 | 40.308 | 45.783 | 1.00 | 47.45 | 6 |
| ATOM | 172 | CG | PRO | A | 22 | 22.990 | 39.754 | 44.667 | 1.00 | 47.76 | 6 |
| ATOM | 173 | C | PRO | A | 22 | 26.074 | 41.558 | 45.727 | 1.00 | 46.48 | 6 |
| ATOM | 174 | O | PRO | A | 22 | 26.164 | 42.405 | 46.615 | 1.00 | 45.69 | 8 |
| ATOM | 175 | N | LEU | A | 23 | 27.107 | 40.816 | 45.318 | 1.00 | 44.97 | 7 |
| ATOM | 176 | CA | LEU | A | 23 | 28.441 | 40.949 | 45.906 | 1.00 | 41.31 | 6 |
| ATOM | 177 | CB | LEU | A | 23 | 29.076 | 39.569 | 46.131 | 1.00 | 39.22 | 6 |
| ATOM | 178 | CG | LEU | A | 23 | 28.264 | 38.561 | 46.953 | 1.00 | 37.71 | 6 |
| ATOM | 179 | CD1 | LEU | A | 23 | 29.075 | 37.288 | 47.157 | 1.00 | 35.07 | 6 |
| ATOM | 180 | CD2 | LEU | A | 23 | 27.896 | 39.165 | 48.292 | 1.00 | 36.90 | 6 |
| ATOM | 181 | C | LEU | A | 23 | 29.334 | 41.789 | 45.003 | 1.00 | 40.14 | 6 |
| ATOM | 182 | O | LEU | A | 23 | 30.556 | 41.614 | 44.951 | 1.00 | 39.00 | 8 |
| ATOM | 183 | N | LYS | A | 24 | 28.706 | 42.705 | 44.284 | 1.00 | 39.67 | 7 |
| ATOM | 184 | CA | LYS | A | 24 | 29.430 | 43.590 | 43.398 | 1.00 | 42.88 | 6 |
| ATOM | 185 | CB | LYS | A | 24 | 28.480 | 44.120 | 42.323 | 1.00 | 40.24 | 6 |
| ATOM | 186 | CG | LYS | A | 24 | 28.949 | 45.362 | 41.610 | 1.00 | 44.08 | 6 |
| ATOM | 187 | CD | LYS | A | 24 | 28.247 | 46.600 | 42.166 | 1.00 | 44.47 | 6 |
| ATOM | 188 | CE | LYS | A | 24 | 26.732 | 46.492 | 41.968 | 1.00 | 43.23 | 6 |
| ATOM | 189 | NZ | LYS | A | 24 | 25.989 | 47.717 | 42.362 | 1.00 | 39.79 | 7 |
| ATOM | 190 | C | LYS | A | 24 | 30.031 | 44.723 | 44.217 | 1.00 | 43.70 | 6 |
| ATOM | 191 | O | LYS | A | 24 | 31.027 | 45.332 | 43.817 | 1.00 | 47.22 | 8 |
| ATOM | 192 | N | ILE | A | 25 | 29.431 | 44.976 | 45.378 | 1.00 | 42.27 | 7 |
| ATOM | 193 | CA | ILE | A | 25 | 29.870 | 46.035 | 46.289 | 1.00 | 39.86 | 6 |
| ATOM | 194 | CB | ILE | A | 25 | 28.763 | 46.407 | 47.306 | 1.00 | 37.72 | 6 |
| ATOM | 195 | CG2 | ILE | A | 25 | 27.539 | 46.953 | 46.580 | 1.00 | 39.67 | 6 |
| ATOM | 196 | CG1 | ILE | A | 25 | 28.410 | 45.168 | 48.145 | 1.00 | 35.25 | 6 |
| ATOM | 197 | CD1 | ILE | A | 25 | 27.301 | 45.368 | 49.151 | 1.00 | 31.74 | 6 |
| ATOM | 198 | C | ILE | A | 25 | 31.078 | 45.625 | 47.112 | 1.00 | 40.23 | 6 |

Fig. 17-3

```
ATOM  199  O    ILE A  25     31.419  44.441  47.198  1.00 38.90      8
ATOM  200  N    PRO A  26     31.762  46.616  47.709  1.00 40.18      7
ATOM  201  CD   PRO A  26     31.523  48.051  47.533  1.00 40.58      6
ATOM  202  CA   PRO A  26     32.939  46.437  48.558  1.00 38.31      6
ATOM  203  CB   PRO A  26     33.478  47.860  48.688  1.00 37.14      6
ATOM  204  CG   PRO A  26     32.940  48.537  47.458  1.00 38.77      6
ATOM  205  C    PRO A  26     32.433  45.903  49.891  1.00 37.32      6
ATOM  206  O    PRO A  26     31.416  46.372  50.412  1.00 32.70      8
ATOM  207  N    ARG A  27     33.134  44.930  50.452  1.00 36.54      7
ATOM  208  CA   ARG A  27     32.685  44.359  51.711  1.00 37.39      6
ATOM  209  CB   ARG A  27     32.116  42.952  51.455  1.00 35.29      6
ATOM  210  CG   ARG A  27     31.047  42.956  50.355  1.00 32.69      6
ATOM  211  CD   ARG A  27     30.507  41.573  49.956  1.00 33.87      6
ATOM  212  NE   ARG A  27     29.757  40.909  51.021  1.00 36.16      7
ATOM  213  CZ   ARG A  27     30.293  40.132  51.959  1.00 37.11      6
ATOM  214  NH1  ARG A  27     31.604  39.903  51.976  1.00 34.42      7
ATOM  215  NH2  ARG A  27     29.516  39.597  52.896  1.00 33.67      7
ATOM  216  C    ARG A  27     33.813  44.329  52.732  1.00 36.35      6
ATOM  217  O    ARG A  27     33.881  45.188  53.610  1.00 35.77      8
ATOM  218  N    VAL A  28     34.703  43.351  52.607  1.00 34.93      7
ATOM  219  CA   VAL A  28     35.810  43.230  53.537  1.00 34.00      6
ATOM  220  CB   VAL A  28     36.633  41.954  53.252  1.00 36.21      6
ATOM  221  CG1  VAL A  28     37.574  41.652  54.424  1.00 33.59      6
ATOM  222  CG2  VAL A  28     35.696  40.790  52.992  1.00 37.05      6
ATOM  223  C    VAL A  28     36.712  44.454  53.423  1.00 31.91      6
ATOM  224  O    VAL A  28     37.216  44.959  54.427  1.00 31.45      8
ATOM  225  N    SER A  29     36.908  44.936  52.199  1.00 33.12      7
ATOM  226  CA   SER A  29     37.751  46.111  51.967  1.00 32.03      6
ATOM  227  CB   SER A  29     38.205  46.181  50.499  1.00 31.77      6
ATOM  228  OG   SER A  29     37.113  46.223  49.600  1.00 30.80      8
ATOM  229  C    SER A  29     37.003  47.380  52.353  1.00 30.16      6
ATOM  230  O    SER A  29     37.604  48.404  52.650  1.00 28.70      8
ATOM  231  N    LEU A  30     35.682  47.310  52.352  1.00 32.43      7
ATOM  232  CA   LEU A  30     34.900  48.465  52.745  1.00 34.56      6
ATOM  233  CB   LEU A  30     33.463  48.358  52.221  1.00 36.44      6
ATOM  234  CG   LEU A  30     32.508  49.513  52.560  1.00 36.79      6
ATOM  235  CD1  LEU A  30     32.070  49.446  54.012  1.00 36.73      6
ATOM  236  CD2  LEU A  30     33.202  50.840  52.256  1.00 37.84      6
ATOM  237  C    LEU A  30     34.902  48.527  54.262  1.00 34.89      6
ATOM  238  O    LEU A  30     35.033  49.601  54.841  1.00 37.58      8
ATOM  239  N    LEU A  31     34.761  47.366  54.897  1.00 34.07      7
ATOM  240  CA   LEU A  31     34.743  47.276  56.350  1.00 34.85      6
ATOM  241  CB   LEU A  31     34.768  45.808  56.791  1.00 36.37      6
ATOM  242  CG   LEU A  31     34.459  45.471  58.261  1.00 36.04      6
ATOM  243  CD1  LEU A  31     34.841  44.027  58.532  1.00 35.13      6
ATOM  244  CD2  LEU A  31     35.228  46.357  59.194  1.00 35.86      6
ATOM  245  C    LEU A  31     35.976  47.994  56.894  1.00 36.43      6
ATOM  246  O    LEU A  31     35.855  49.035  57.544  1.00 35.87      8
ATOM  247  N    LEU A  32     37.157  47.426  56.635  1.00 37.76      7
ATOM  248  CA   LEU A  32     38.420  48.015  57.087  1.00 36.82      6
ATOM  249  CB   LEU A  32     39.611  47.318  56.418  1.00 36.37      6
ATOM  250  CG   LEU A  32     40.030  45.888  56.774  1.00 39.11      6
ATOM  251  CD1  LEU A  32     41.117  45.420  55.815  1.00 35.16      6
ATOM  252  CD2  LEU A  32     40.538  45.830  58.214  1.00 37.73      6
ATOM  253  C    LEU A  32     38.500  49.513  56.780  1.00 34.84      6
ATOM  254  O    LEU A  32     38.846  50.326  57.644  1.00 36.58      8
ATOM  255  N    ARG A  33     38.184  49.877  55.545  1.00 31.37      7
ATOM  256  CA   ARG A  33     38.247  51.270  55.150  1.00 32.53      6
ATOM  257  CB   ARG A  33     37.927  51.398  53.662  1.00 31.52      6
ATOM  258  CG   ARG A  33     38.481  52.652  53.042  1.00 35.88      6
ATOM  259  CD   ARG A  33     38.107  52.752  51.581  1.00 43.44      6
ATOM  260  NE   ARG A  33     38.521  51.583  50.811  1.00 48.37      7
ATOM  261  CZ   ARG A  33     38.348  51.469  49.497  1.00 52.27      6
ATOM  262  NH1  ARG A  33     37.771  52.459  48.823  1.00 51.75      7
ATOM  263  NH2  ARG A  33     38.739  50.369  48.858  1.00 51.08      7
ATOM  264  C    ARG A  33     37.274  52.102  55.989  1.00 32.32      6
```

Fig. 17-4

| | | | | | | | | | | |
|---|---|---|---|---|---|---|---|---|---|---|
| ATOM | 265 | O | ARG | A | 33 | 37.471 | 53.299 | 56.196 | 1.00 29.23 | 8 |
| ATOM | 266 | N | PHE | A | 34 | 36.231 | 51.445 | 56.484 | 1.00 32.58 | 7 |
| ATOM | 267 | CA | PHE | A | 34 | 35.216 | 52.096 | 57.304 | 1.00 32.69 | 6 |
| ATOM | 268 | CB | PHE | A | 34 | 33.952 | 51.232 | 57.359 | 1.00 31.22 | 6 |
| ATOM | 269 | CG | PHE | A | 34 | 32.838 | 51.825 | 58.183 | 1.00 28.74 | 6 |
| ATOM | 270 | CD1 | PHE | A | 34 | 32.085 | 52.888 | 57.700 | 1.00 22.76 | 6 |
| ATOM | 271 | CD2 | PHE | A | 34 | 32.551 | 51.322 | 59.456 | 1.00 28.09 | 6 |
| ATOM | 272 | CE1 | PHE | A | 34 | 31.061 | 53.441 | 58.472 | 1.00 23.70 | 6 |
| ATOM | 273 | CE2 | PHE | A | 34 | 31.524 | 51.873 | 60.235 | 1.00 24.59 | 6 |
| ATOM | 274 | CZ | PHE | A | 34 | 30.781 | 52.929 | 59.741 | 1.00 21.39 | 6 |
| ATOM | 275 | C | PHE | A | 34 | 35.734 | 52.319 | 58.719 | 1.00 33.45 | 6 |
| ATOM | 276 | O | PHE | A | 34 | 35.635 | 53.425 | 59.258 | 1.00 35.49 | 8 |
| ATOM | 277 | N | LYS | A | 35 | 36.276 | 51.264 | 59.323 | 1.00 34.52 | 7 |
| ATOM | 278 | CA | LYS | A | 35 | 36.805 | 51.360 | 60.678 | 1.00 36.51 | 6 |
| ATOM | 279 | CB | LYS | A | 35 | 37.118 | 49.977 | 61.235 | 1.00 36.47 | 6 |
| ATOM | 280 | CG | LYS | A | 35 | 35.912 | 49.074 | 61.343 | 1.00 40.81 | 5 |
| ATOM | 281 | CD | LYS | A | 35 | 36.246 | 47.801 | 62.090 | 1.00 44.10 | 6 |
| ATOM | 282 | CE | LYS | A | 35 | 37.347 | 47.029 | 61.402 | 1.00 47.46 | 6 |
| ATOM | 283 | NZ | LYS | A | 35 | 38.601 | 47.823 | 61.276 | 1.00 53.53 | 7 |
| ATOM | 284 | C | LYS | A | 35 | 38.054 | 52.222 | 60.735 | 1.00 36.61 | 6 |
| ATOM | 285 | O | LYS | A | 35 | 38.352 | 52.824 | 61.766 | 1.00 36.78 | 8 |
| ATOM | 286 | N | ASP | A | 36 | 38.794 | 52.267 | 59.635 | 1.00 36.27 | 7 |
| ATOM | 287 | CA | ASP | A | 36 | 39.980 | 53.090 | 59.592 | 1.00 39.71 | 6 |
| ATOM | 288 | CB | ASP | A | 36 | 40.679 | 52.937 | 58.239 | 1.00 44.78 | 6 |
| ATOM | 289 | CG | ASP | A | 36 | 41.863 | 53.892 | 58.075 | 1.00 47.10 | 6 |
| ATOM | 290 | OD1 | ASP | A | 36 | 42.803 | 53.352 | 58.906 | 1.00 44.02 | 8 |
| ATOM | 291 | OD2 | ASP | A | 36 | 41.843 | 54.682 | 57.106 | 1.00 48.43 | 8 |
| ATOM | 292 | C | ASP | A | 36 | 39.508 | 54.530 | 59.789 | 1.00 39.99 | 6 |
| ATOM | 293 | O | ASP | A | 36 | 40.023 | 55.258 | 60.636 | 1.00 40.76 | 8 |
| ATOM | 294 | N | ALA | A | 37 | 38.506 | 54.919 | 59.007 | 1.00 38.59 | 7 |
| ATOM | 295 | CA | ALA | A | 37 | 37.939 | 56.258 | 59.066 | 1.00 37.14 | 6 |
| ATOM | 296 | CB | ALA | A | 37 | 36.857 | 56.402 | 58.000 | 1.00 35.85 | 5 |
| ATOM | 297 | C | ALA | A | 37 | 37.354 | 56.549 | 60.446 | 1.00 38.34 | 6 |
| ATOM | 298 | O | ALA | A | 37 | 37.391 | 57.687 | 60.928 | 1.00 37.32 | 8 |
| ATOM | 299 | N | MET | A | 38 | 36.809 | 55.518 | 61.079 | 1.00 36.19 | 7 |
| ATOM | 300 | CA | MET | A | 38 | 36.213 | 55.674 | 62.397 | 1.00 36.80 | 6 |
| ATOM | 301 | CB | MET | A | 38 | 35.141 | 54.598 | 62.606 | 1.00 37.38 | 6 |
| ATOM | 302 | CG | MET | A | 38 | 33.938 | 54.717 | 61.673 | 1.00 37.60 | 6 |
| ATOM | 303 | SD | MET | A | 38 | 32.887 | 56.165 | 61.999 | 1.00 33.61 | 16 |
| ATOM | 304 | CE | MET | A | 38 | 32.398 | 55.824 | 63.680 | 1.00 35.60 | 6 |
| ATOM | 305 | C | MET | A | 38 | 37.262 | 55.582 | 63.502 | 1.00 35.84 | 6 |
| ATOM | 306 | O | MET | A | 38 | 36.937 | 55.688 | 64.692 | 1.00 34.89 | 8 |
| ATOM | 307 | N | ASN | A | 39 | 38.518 | 55.400 | 63.100 | 1.00 33.83 | 7 |
| ATOM | 308 | CA | ASN | A | 39 | 39.626 | 55.264 | 64.044 | 1.00 34.94 | 6 |
| ATOM | 309 | CB | ASN | A | 39 | 39.897 | 56.582 | 64.775 | 1.00 32.48 | 6 |
| ATOM | 310 | CG | ASN | A | 39 | 40.213 | 57.717 | 63.825 | 1.00 32.34 | 6 |
| ATOM | 311 | OD1 | ASN | A | 39 | 41.128 | 57.621 | 63.009 | 1.00 31.85 | 8 |
| ATOM | 312 | ND2 | ASN | A | 39 | 39.455 | 58.800 | 63.924 | 1.00 30.92 | 7 |
| ATOM | 313 | C | ASN | A | 39 | 39.253 | 54.183 | 65.045 | 1.00 36.87 | 6 |
| ATOM | 314 | O | ASN | A | 39 | 39.403 | 54.357 | 66.260 | 1.00 36.60 | 8 |
| ATOM | 315 | N | LEU | A | 40 | 38.752 | 53.067 | 64.518 | 1.00 37.48 | 7 |
| ATOM | 316 | CA | LEU | A | 40 | 38.341 | 51.933 | 65.336 | 1.00 39.66 | 6 |
| ATOM | 317 | CB | LEU | A | 40 | 36.863 | 51.622 | 65.086 | 1.00 41.35 | 6 |
| ATOM | 318 | CG | LEU | A | 40 | 35.858 | 52.712 | 65.476 | 1.00 42.69 | 6 |
| ATOM | 319 | CD1 | LEU | A | 40 | 34.448 | 52.261 | 65.111 | 1.00 45.05 | 6 |
| ATOM | 320 | CD2 | LEU | A | 40 | 35.951 | 52.989 | 66.966 | 1.00 39.44 | 6 |
| ATOM | 321 | C | LEU | A | 40 | 39.184 | 50.687 | 65.058 | 1.00 39.79 | 6 |
| ATOM | 322 | O | LEU | A | 40 | 38.804 | 49.575 | 65.434 | 1.00 36.88 | 8 |
| ATOM | 323 | N | ILE | A | 41 | 40.337 | 50.889 | 64.420 | 1.00 40.50 | 7 |
| ATOM | 324 | CA | ILE | A | 41 | 41.237 | 49.790 | 64.068 | 1.00 41.39 | 6 |
| ATOM | 325 | CB | ILE | A | 41 | 40.780 | 49.141 | 62.724 | 1.00 39.24 | 6 |
| ATOM | 326 | CG2 | ILE | A | 41 | 41.017 | 50.103 | 61.564 | 1.00 36.97 | 6 |
| ATOM | 327 | CG1 | ILE | A | 41 | 41.513 | 47.824 | 62.482 | 1.00 36.76 | 6 |
| ATOM | 328 | CD1 | ILE | A | 41 | 41.085 | 46.715 | 63.403 | 1.00 35.59 | 6 |
| ATOM | 329 | C | ILE | A | 41 | 42.684 | 50.295 | 63.913 | 1.00 44.37 | 6 |
| ATOM | 330 | O | ILE | A | 41 | 42.927 | 51.328 | 63.277 | 1.00 46.01 | 8 |

Fig. 17-5

| | | | | | | | | | |
|---|---|---|---|---|---|---|---|---|---|
| ATOM | 331 | N   | ASP | A | 42 | 43.646 | 49.582 | 64.497 | 1.00 45.19 | 7 |
| ATOM | 332 | CA  | ASP | A | 42 | 45.049 | 49.982 | 64.372 | 1.00 45.62 | 6 |
| ATOM | 333 | CB  | ASP | A | 42 | 45.716 | 50.090 | 65.742 | 1.00 45.17 | 6 |
| ATOM | 334 | CG  | ASP | A | 42 | 44.966 | 51.005 | 66.682 | 1.00 44.43 | 6 |
| ATOM | 335 | OD1 | ASP | A | 42 | 44.731 | 52.177 | 66.322 | 1.00 39.84 | 8 |
| ATOM | 336 | OD2 | ASP | A | 42 | 44.612 | 50.546 | 67.787 | 1.00 48.50 | 8 |
| ATOM | 337 | C   | ASP | A | 42 | 45.750 | 48.915 | 63.551 | 1.00 48.47 | 6 |
| ATOM | 338 | O   | ASP | A | 42 | 45.316 | 47.757 | 63.547 | 1.00 49.85 | 8 |
| ATOM | 339 | N   | GLU | A | 43 | 46.830 | 49.288 | 62.864 | 1.00 49.24 | 7 |
| ATOM | 340 | CA  | GLU | A | 43 | 47.553 | 48.325 | 62.028 | 1.00 50.79 | 6 |
| ATOM | 341 | CB  | GLU | A | 43 | 48.820 | 48.956 | 61.431 | 1.00 49.90 | 6 |
| ATOM | 342 | CG  | GLU | A | 43 | 48.544 | 50.029 | 60.378 | 1.00 57.20 | 6 |
| ATOM | 343 | CD  | GLU | A | 43 | 49.808 | 50.537 | 59.690 | 1.00 59.56 | 6 |
| ATOM | 344 | OE1 | GLU | A | 43 | 50.517 | 49.721 | 59.061 | 1.00 65.05 | 8 |
| ATOM | 345 | OE2 | GLU | A | 43 | 50.095 | 51.750 | 59.772 | 1.00 57.82 | 8 |
| ATOM | 346 | C   | GLU | A | 43 | 47.918 | 47.020 | 62.733 | 1.00 49.73 | 6 |
| ATOM | 347 | O   | GLU | A | 43 | 47.813 | 45.943 | 62.149 | 1.00 49.18 | 8 |
| ATOM | 348 | N   | LYS | A | 44 | 48.324 | 47.118 | 63.992 | 1.00 49.40 | 7 |
| ATOM | 349 | CA  | LYS | A | 44 | 48.730 | 45.949 | 64.762 | 1.00 49.09 | 6 |
| ATOM | 350 | CB  | LYS | A | 44 | 49.317 | 46.418 | 66.093 | 1.00 52.46 | 6 |
| ATOM | 351 | CG  | LYS | A | 44 | 50.448 | 47.421 | 65.899 | 1.00 55.75 | 6 |
| ATOM | 352 | CD  | LYS | A | 44 | 51.167 | 47.749 | 67.201 | 1.00 58.74 | 6 |
| ATOM | 353 | CE  | LYS | A | 44 | 52.327 | 48.704 | 66.949 | 1.00 58.48 | 6 |
| ATOM | 354 | NZ  | LYS | A | 44 | 53.122 | 48.968 | 68.176 | 1.00 58.95 | 7 |
| ATOM | 355 | C   | LYS | A | 44 | 47.638 | 44.897 | 64.994 | 1.00 47.63 | 6 |
| ATOM | 356 | O   | LYS | A | 44 | 47.932 | 43.738 | 65.290 | 1.00 45.13 | 8 |
| ATOM | 357 | N   | GLU | A | 45 | 46.379 | 45.298 | 64.854 | 1.00 45.25 | 7 |
| ATOM | 358 | CA  | GLU | A | 45 | 45.268 | 44.374 | 65.046 | 1.00 43.09 | 6 |
| ATOM | 359 | CB  | GLU | A | 45 | 44.024 | 45.143 | 65.514 | 1.00 41.19 | 6 |
| ATOM | 360 | CG  | GLU | A | 45 | 44.192 | 45.859 | 66.844 | 1.00 36.83 | 6 |
| ATOM | 361 | CD  | GLU | A | 45 | 43.003 | 46.741 | 67.204 | 1.00 38.92 | 6 |
| ATOM | 362 | OE1 | GLU | A | 45 | 42.707 | 47.701 | 66.447 | 1.00 37.30 | 8 |
| ATOM | 363 | OE2 | GLU | A | 45 | 42.368 | 46.479 | 68.253 | 1.00 36.33 | 8 |
| ATOM | 364 | C   | GLU | A | 45 | 44.969 | 43.660 | 63.726 | 1.00 43.04 | 6 |
| ATOM | 365 | O   | GLU | A | 45 | 44.480 | 42.523 | 63.699 | 1.00 45.03 | 8 |
| ATOM | 366 | N   | LEU | A | 46 | 45.282 | 44.341 | 62.632 | 1.00 40.29 | 7 |
| ATOM | 367 | CA  | LEU | A | 46 | 45.042 | 43.823 | 61.299 | 1.00 37.16 | 6 |
| ATOM | 368 | CB  | LEU | A | 46 | 44.910 | 44.990 | 60.331 | 1.00 37.86 | 6 |
| ATOM | 369 | CG  | LEU | A | 46 | 44.822 | 44.658 | 58.845 | 1.00 39.22 | 6 |
| ATOM | 370 | CD1 | LEU | A | 46 | 43.655 | 43.726 | 58.563 | 1.00 40.68 | 6 |
| ATOM | 371 | CD2 | LEU | A | 46 | 44.673 | 45.964 | 58.080 | 1.00 41.62 | 6 |
| ATOM | 372 | C   | LEU | A | 46 | 46.090 | 42.860 | 60.774 | 1.00 36.54 | 6 |
| ATOM | 373 | O   | LEU | A | 46 | 47.275 | 43.192 | 60.698 | 1.00 39.86 | 8 |
| ATOM | 374 | N   | ILE | A | 47 | 45.646 | 41.662 | 60.406 | 1.00 33.49 | 7 |
| ATOM | 375 | CA  | ILE | A | 47 | 46.540 | 40.657 | 59.844 | 1.00 30.51 | 6 |
| ATOM | 376 | CB  | ILE | A | 47 | 46.333 | 39.253 | 60.491 | 1.00 34.31 | 6 |
| ATOM | 377 | CG2 | ILE | A | 47 | 47.346 | 38.262 | 59.930 | 1.00 32.16 | 6 |
| ATOM | 378 | CG1 | ILE | A | 47 | 46.504 | 39.328 | 62.010 | 1.00 32.65 | 6 |
| ATOM | 379 | CD1 | ILE | A | 47 | 47.858 | 39.846 | 62.448 | 1.00 38.97 | 6 |
| ATOM | 380 | C   | ILE | A | 47 | 46.196 | 40.570 | 58.362 | 1.00 28.36 | 6 |
| ATOM | 381 | O   | ILE | A | 47 | 45.037 | 40.342 | 58.003 | 1.00 26.11 | 8 |
| ATOM | 382 | N   | LYS | A | 48 | 47.194 | 40.772 | 57.504 | 1.00 27.77 | 7 |
| ATOM | 383 | CA  | LYS | A | 48 | 46.985 | 40.713 | 56.056 | 1.00 25.80 | 6 |
| ATOM | 384 | CB  | LYS | A | 48 | 48.258 | 41.087 | 55.308 | 1.00 23.91 | 6 |
| ATOM | 385 | CG  | LYS | A | 48 | 48.056 | 41.273 | 53.811 | 1.00 24.90 | 6 |
| ATOM | 386 | CD  | LYS | A | 48 | 49.389 | 41.352 | 53.091 | 1.00 26.39 | 6 |
| ATOM | 387 | CE  | LYS | A | 48 | 49.233 | 41.864 | 51.679 | 1.00 27.71 | 6 |
| ATOM | 388 | NZ  | LYS | A | 48 | 48.774 | 43.275 | 51.696 | 1.00 32.59 | 7 |
| ATOM | 389 | C   | LYS | A | 48 | 46.595 | 39.299 | 55.654 | 1.00 26.32 | 6 |
| ATOM | 390 | O   | LYS | A | 48 | 47.072 | 38.325 | 56.235 | 1.00 27.85 | 8 |
| ATOM | 391 | N   | SER | A | 49 | 45.735 | 39.183 | 54.653 | 1.00 24.73 | 7 |
| ATOM | 392 | CA  | SER | A | 49 | 45.299 | 37.876 | 54.205 | 1.00 27.36 | 6 |
| ATOM | 393 | CB  | SER | A | 49 | 43.952 | 37.979 | 53.479 | 1.00 25.04 | 6 |
| ATOM | 394 | OG  | SER | A | 49 | 42.911 | 38.329 | 54.373 | 1.00 26.94 | 8 |
| ATOM | 395 | C   | SER | A | 49 | 46.322 | 37.211 | 53.293 | 1.00 28.97 | 6 |
| ATOM | 396 | O   | SER | A | 49 | 47.095 | 37.885 | 52.612 | 1.00 31.89 | 8 |

Fig. 17-6

```
ATOM    397  N   ARG A  50      46.315  35.879  53.296  1.00 29.71      7
ATOM    398  CA  ARG A  50      47.211  35.087  52.463  1.00 25.78      6
ATOM    399  CB  ARG A  50      48.249  34.351  53.318  1.00 26.20      6
ATOM    400  CG  ARG A  50      47.687  33.204  54.172  1.00 22.71      6
ATOM    401  CD  ARG A  50      48.818  32.468  54.890  1.00 22.95      6
ATOM    402  NE  ARG A  50      48.359  31.385  55.762  1.00 19.20      7
ATOM    403  CZ  ARG A  50      47.708  30.306  55.345  1.00 16.85      6
ATOM    404  NH1 ARG A  50      47.430  30.151  54.055  1.00 17.77      7
ATOM    405  NH2 ARG A  50      47.334  29.385  56.223  1.00 14.56      7
ATOM    406  C   ARG A  50      46.370  34.051  51.723  1.00 23.30      6
ATOM    407  O   ARG A  50      45.319  33.635  52.206  1.00 16.92      8
ATOM    408  N   PRO A  51      46.823  33.628  50.534  1.00 21.06      7
ATOM    409  CD  PRO A  51      48.021  34.038  49.789  1.00 20.50      6
ATOM    410  CA  PRO A  51      46.086  32.633  49.761  1.00 22.69      6
ATOM    411  CB  PRO A  51      46.862  32.592  48.451  1.00 21.57      6
ATOM    412  CG  PRO A  51      47.503  33.984  48.392  1.00 20.57      6
ATOM    413  C   PRO A  51      46.153  31.300  50.498  1.00 26.71      6
ATOM    414  O   PRO A  51      47.071  31.066  51.293  1.00 31.32      8
ATOM    415  N   ALA A  52      45.176  30.435  50.250  1.00 26.02      7
ATOM    416  CA  ALA A  52      45.151  29.121  50.876  1.00 25.76      6
ATOM    417  CB  ALA A  52      43.720  28.585  50.933  1.00 21.42      6
ATOM    418  C   ALA A  52      46.013  28.227  50.000  1.00 26.31      6
ATOM    419  O   ALA A  52      45.878  28.239  48.780  1.00 30.31      8
ATOM    420  N   THR A  53      46.909  27.464  50.608  1.00 26.80      7
ATOM    421  CA  THR A  53      47.759  26.578  49.831  1.00 27.52      6
ATOM    422  CB  THR A  53      48.845  25.975  50.717  1.00 26.27      6
ATOM    423  OG1 THR A  53      48.255  25.053  51.641  1.00 29.51      8
ATOM    424  CG2 THR A  53      49.522  27.076  51.502  1.00 24.66      6
ATOM    425  C   THR A  53      46.908  25.462  49.209  1.00 26.58      6
ATOM    426  O   THR A  53      45.778  25.228  49.634  1.00 21.98      8
ATOM    427  N   LYS A  54      47.455  24.782  48.203  1.00 29.62      7
ATOM    428  CA  LYS A  54      46.739  23.713  47.507  1.00 32.62      6
ATOM    429  CB  LYS A  54      47.601  23.151  46.370  1.00 31.99      6
ATOM    430  CG  LYS A  54      46.985  21.967  45.629  1.00 36.62      6
ATOM    431  CD  LYS A  54      45.733  22.352  44.866  1.00 40.69      6
ATOM    432  CE  LYS A  54      46.058  23.173  43.625  1.00 46.44      6
ATOM    433  NZ  LYS A  54      46.844  22.393  42.614  1.00 50.68      7
ATOM    434  C   LYS A  54      46.348  22.595  48.465  1.00 36.00      6
ATOM    435  O   LYS A  54      45.277  21.991  48.330  1.00 34.77      8
ATOM    436  N   GLU A  55      47.216  22.336  49.443  1.00 37.91      7
ATOM    437  CA  GLU A  55      46.979  21.290  50.433  1.00 36.96      6
ATOM    438  CB  GLU A  55      48.240  21.100  51.281  1.00 40.29      6
ATOM    439  CG  GLU A  55      48.216  19.887  52.195  1.00 47.95      6
ATOM    440  CD  GLU A  55      49.552  19.654  52.891  1.00 51.01      6
ATOM    441  OE1 GLU A  55      49.659  18.688  53.679  1.00 52.65      8
ATOM    442  OE2 GLU A  55      50.497  20.437  52.646  1.00 51.27      8
ATOM    443  C   GLU A  55      45.771  21.609  51.322  1.00 34.10      6
ATOM    444  O   GLU A  55      44.892  20.769  51.496  1.00 33.08      8
ATOM    445  N   GLU A  56      45.723  22.827  51.866  1.00 32.39      7
ATOM    446  CA  GLU A  56      44.621  23.256  52.733  1.00 30.13      6
ATOM    447  CB  GLU A  56      44.824  24.714  53.177  1.00 25.28      6
ATOM    448  CG  GLU A  56      46.204  24.994  53.758  1.00 28.82      6
ATOM    449  CD  GLU A  56      46.421  26.450  54.181  1.00 30.74      6
ATOM    450  OE1 GLU A  56      46.072  27.369  53.398  1.00 29.77      8
ATOM    451  OE2 GLU A  56      46.969  26.674  55.288  1.00 25.98      8
ATOM    452  C   GLU A  56      43.264  23.114  52.024  1.00 29.63      6
ATOM    453  O   GLU A  56      42.299  22.584  52.595  1.00 29.90      8
ATOM    454  N   LEU A  57      43.188  23.581  50.780  1.00 26.76      7
ATOM    455  CA  LEU A  57      41.944  23.490  50.020  1.00 25.29      6
ATOM    456  CB  LEU A  57      42.132  24.103  48.629  1.00 22.68      6
ATOM    457  CG  LEU A  57      42.402  25.612  48.572  1.00 22.39      6
ATOM    458  CD1 LEU A  57      42.654  26.045  47.123  1.00 20.77      6
ATOM    459  CD2 LEU A  57      41.211  26.366  49.156  1.00 17.66      6
ATOM    460  C   LEU A  57      41.479  22.037  49.896  1.00 26.02      6
ATOM    461  O   LEU A  57      40.284  21.741  50.014  1.00 23.41      8
ATOM    462  N   LEU A  58      42.444  21.143  49.675  1.00 24.82      7
```

Fig. 17-7

| | | | | | | | | | | |
|---|---|---|---|---|---|---|---|---|---|---|
| ATOM | 463 | CA | LEU | A | 58 | 42.194 | 19.718 | 49.526 | 1.00 22.44 | 6 |
| ATOM | 464 | CB | LEU | A | 58 | 43.434 | 19.027 | 48.965 | 1.00 21.02 | 6 |
| ATOM | 465 | CG | LEU | A | 58 | 43.838 | 19.471 | 47.558 | 1.00 22.94 | 6 |
| ATOM | 466 | CD1 | LEU | A | 58 | 45.212 | 18.908 | 47.176 | 1.00 20.35 | 6 |
| ATOM | 467 | CD2 | LEU | A | 58 | 42.755 | 19.033 | 46.587 | 1.00 23.28 | 6 |
| ATOM | 468 | C | LEU | A | 58 | 41.797 | 19.054 | 50.835 | 1.00 25.20 | 6 |
| ATOM | 469 | O | LEU | A | 58 | 41.456 | 17.867 | 50.854 | 1.00 26.55 | 8 |
| ATOM | 470 | N | LEU | A | 59 | 41.858 | 19.794 | 51.938 | 1.00 25.44 | 7 |
| ATOM | 471 | CA | LEU | A | 59 | 41.446 | 19.212 | 53.211 | 1.00 25.24 | 6 |
| ATOM | 472 | CB | LEU | A | 59 | 41.559 | 20.229 | 54.350 | 1.00 24.68 | 6 |
| ATOM | 473 | CG | LEU | A | 59 | 42.956 | 20.490 | 54.912 | 1.00 27.05 | 6 |
| ATOM | 474 | CD1 | LEU | A | 59 | 42.912 | 21.565 | 56.001 | 1.00 24.76 | 6 |
| ATOM | 475 | CD2 | LEU | A | 59 | 43.492 | 19.184 | 55.474 | 1.00 26.99 | 6 |
| ATOM | 476 | C | LEU | A | 59 | 39.991 | 18.807 | 53.045 | 1.00 24.22 | 6 |
| ATOM | 477 | O | LEU | A | 59 | 39.548 | 17.794 | 53.581 | 1.00 21.18 | 8 |
| ATOM | 478 | N | PHE | A | 60 | 39.270 | 19.615 | 52.270 | 1.00 25.00 | 7 |
| ATOM | 479 | CA | PHE | A | 60 | 37.859 | 19.403 | 52.011 | 1.00 25.00 | 6 |
| ATOM | 480 | CB | PHE | A | 60 | 37.054 | 20.560 | 52.605 | 1.00 26.34 | 6 |
| ATOM | 481 | CG | PHE | A | 60 | 35.600 | 20.555 | 52.223 | 1.00 29.37 | 6 |
| ATOM | 482 | CD1 | PHE | A | 60 | 34.811 | 19.422 | 52.427 | 1.00 27.57 | 6 |
| ATOM | 483 | CD2 | PHE | A | 60 | 35.015 | 21.692 | 51.661 | 1.00 27.33 | 6 |
| ATOM | 484 | CE1 | PHE | A | 60 | 33.466 | 19.419 | 52.077 | 1.00 27.00 | 6 |
| ATOM | 485 | CE2 | PHE | A | 60 | 33.670 | 21.699 | 51.306 | 1.00 28.08 | 6 |
| ATOM | 486 | CZ | PHE | A | 60 | 32.893 | 20.559 | 51.513 | 1.00 29.48 | 6 |
| ATOM | 487 | C | PHE | A | 60 | 37.506 | 19.214 | 50.538 | 1.00 27.78 | 6 |
| ATOM | 488 | O | PHE | A | 60 | 37.022 | 18.143 | 50.158 | 1.00 31.57 | 8 |
| ATOM | 489 | N | HIS | A | 61 | 37.734 | 20.220 | 49.696 | 1.00 26.76 | 7 |
| ATOM | 490 | CA | HIS | A | 61 | 37.376 | 20.056 | 48.287 | 1.00 28.84 | 6 |
| ATOM | 491 | CB | HIS | A | 61 | 37.365 | 21.405 | 47.561 | 1.00 27.76 | 6 |
| ATOM | 492 | CG | HIS | A | 61 | 36.385 | 22.396 | 48.117 | 1.00 30.54 | 6 |
| ATOM | 493 | CD2 | HIS | A | 61 | 35.056 | 22.549 | 47.907 | 1.00 33.74 | 6 |
| ATOM | 494 | ND1 | HIS | A | 61 | 36.750 | 23.401 | 48.987 | 1.00 34.02 | 7 |
| ATOM | 495 | CE1 | HIS | A | 61 | 35.691 | 24.135 | 49.286 | 1.00 32.07 | 6 |
| ATOM | 496 | NE2 | HIS | A | 61 | 34.649 | 23.638 | 48.644 | 1.00 34.10 | 7 |
| ATOM | 497 | C | HIS | A | 61 | 38.278 | 19.056 | 47.539 | 1.00 28.38 | 6 |
| ATOM | 498 | O | HIS | A | 61 | 39.287 | 18.604 | 48.072 | 1.00 25.81 | 8 |
| ATOM | 499 | N | THR | A | 62 | 37.895 | 18.705 | 46.310 | 1.00 32.88 | 7 |
| ATOM | 500 | CA | THR | A | 62 | 38.658 | 17.749 | 45.488 | 1.00 34.68 | 6 |
| ATOM | 501 | CB | THR | A | 62 | 37.715 | 16.739 | 44.778 | 1.00 34.36 | 6 |
| ATOM | 502 | OG1 | THR | A | 62 | 36.942 | 17.415 | 43.778 | 1.00 34.81 | 8 |
| ATOM | 503 | CG2 | THR | A | 62 | 36.759 | 16.112 | 45.778 | 1.00 34.33 | 6 |
| ATOM | 504 | C | THR | A | 62 | 39.485 | 18.454 | 44.408 | 1.00 35.60 | 6 |
| ATOM | 505 | O | THR | A | 62 | 39.017 | 19.418 | 43.790 | 1.00 30.85 | 8 |
| ATOM | 506 | N | GLU | A | 63 | 40.700 | 17.958 | 44.166 | 1.00 37.38 | 7 |
| ATOM | 507 | CA | GLU | A | 63 | 41.587 | 18.555 | 43.165 | 1.00 40.68 | 6 |
| ATOM | 508 | CB | GLU | A | 63 | 42.759 | 17.626 | 42.840 | 1.00 43.75 | 6 |
| ATOM | 509 | CG | GLU | A | 63 | 43.719 | 17.389 | 43.987 | 1.00 50.68 | 6 |
| ATOM | 510 | CD | GLU | A | 63 | 45.026 | 16.760 | 43.529 | 1.00 55.36 | 6 |
| ATOM | 511 | OE1 | GLU | A | 63 | 45.789 | 17.441 | 42.808 | 1.00 53.03 | 8 |
| ATOM | 512 | OE2 | GLU | A | 63 | 45.285 | 15.585 | 43.883 | 1.00 59.56 | 8 |
| ATOM | 513 | C | GLU | A | 63 | 40.894 | 18.939 | 41.860 | 1.00 39.26 | 6 |
| ATOM | 514 | O | GLU | A | 63 | 40.771 | 20.116 | 41.535 | 1.00 42.33 | 8 |
| ATOM | 515 | N | ASP | A | 64 | 40.453 | 17.948 | 41.102 | 1.00 37.07 | 7 |
| ATOM | 516 | CA | ASP | A | 64 | 39.782 | 18.224 | 39.845 | 1.00 36.98 | 6 |
| ATOM | 517 | CB | ASP | A | 64 | 38.957 | 17.000 | 39.426 | 1.00 42.19 | 6 |
| ATOM | 518 | CG | ASP | A | 64 | 38.037 | 16.501 | 40.533 | 1.00 47.66 | 6 |
| ATOM | 519 | OD1 | ASP | A | 64 | 37.039 | 17.193 | 40.851 | 1.00 47.95 | 8 |
| ATOM | 520 | OD2 | ASP | A | 64 | 38.325 | 15.413 | 41.091 | 1.00 50.07 | 8 |
| ATOM | 521 | C | ASP | A | 64 | 38.908 | 19.480 | 39.906 | 1.00 33.40 | 6 |
| ATOM | 522 | O | ASP | A | 64 | 38.927 | 20.293 | 38.986 | 1.00 33.64 | 8 |
| ATOM | 523 | N | TYR | A | 65 | 38.156 | 19.641 | 40.990 | 1.00 30.57 | 7 |
| ATOM | 524 | CA | TYR | A | 65 | 37.286 | 20.806 | 41.157 | 1.00 29.65 | 6 |
| ATOM | 525 | CB | TYR | A | 65 | 36.300 | 20.560 | 42.316 | 1.00 30.16 | 6 |
| ATOM | 526 | CG | TYR | A | 65 | 35.557 | 21.790 | 42.810 | 1.00 28.49 | 6 |
| ATOM | 527 | CD1 | TYR | A | 65 | 34.791 | 22.572 | 41.944 | 1.00 30.25 | 6 |
| ATOM | 528 | CE1 | TYR | A | 65 | 34.126 | 23.715 | 42.399 | 1.00 28.36 | 6 |

Fig. 17-8

| | | | | | | | | | | |
|---|---|---|---|---|---|---|---|---|---|---|
| ATOM | 529 | CD2 | TYR | A | 65 | 35.638 | 22.181 | 44.150 | 1.00 28.28 | 6 |
| ATOM | 530 | CE2 | TYR | A | 65 | 34.980 | 23.320 | 44.617 | 1.00 26.96 | 6 |
| ATOM | 531 | CZ | TYR | A | 65 | 34.227 | 24.082 | 43.740 | 1.00 29.79 | 6 |
| ATOM | 532 | OH | TYR | A | 65 | 33.568 | 25.201 | 44.207 | 1.00 28.53 | 8 |
| ATOM | 533 | C | TYR | A | 65 | 38.118 | 22.061 | 41.418 | 1.00 29.15 | 6 |
| ATOM | 534 | O | TYR | A | 65 | 37.860 | 23.128 | 40.857 | 1.00 30.45 | 8 |
| ATOM | 535 | N | ILE | A | 66 | 39.122 | 21.926 | 42.270 | 1.00 26.61 | 7 |
| ATOM | 536 | CA | ILE | A | 66 | 39.986 | 23.041 | 42.597 | 1.00 26.35 | 6 |
| ATOM | 537 | CB | ILE | A | 66 | 40.998 | 22.652 | 43.687 | 1.00 26.25 | 6 |
| ATOM | 538 | CG2 | ILE | A | 66 | 42.009 | 23.753 | 43.869 | 1.00 21.20 | 6 |
| ATOM | 539 | CG1 | ILE | A | 66 | 40.264 | 22.341 | 44.992 | 1.00 29.30 | 6 |
| ATOM | 540 | CD1 | ILE | A | 66 | 39.478 | 23.517 | 45.555 | 1.00 30.52 | 6 |
| ATOM | 541 | C | ILE | A | 66 | 40.761 | 23.504 | 41.381 | 1.00 28.07 | 6 |
| ATOM | 542 | O | ILE | A | 66 | 41.039 | 24.696 | 41.225 | 1.00 31.26 | 8 |
| ATOM | 543 | N | ASN | A | 67 | 41.125 | 22.559 | 40.521 | 1.00 28.47 | 7 |
| ATOM | 544 | CA | ASN | A | 67 | 41.902 | 22.898 | 39.337 | 1.00 30.15 | 6 |
| ATOM | 545 | CB | ASN | A | 67 | 42.563 | 21.656 | 38.726 | 1.00 34.20 | 6 |
| ATOM | 546 | CG | ASN | A | 67 | 43.712 | 21.118 | 39.578 | 1.00 38.78 | 6 |
| ATOM | 547 | OD1 | ASN | A | 67 | 44.674 | 21.841 | 39.878 | 1.00 43.34 | 8 |
| ATOM | 548 | ND2 | ASN | A | 67 | 43.626 | 19.845 | 39.956 | 1.00 37.14 | 7 |
| ATOM | 549 | C | ASN | A | 67 | 41.020 | 23.554 | 38.314 | 1.00 28.41 | 6 |
| ATOM | 550 | O | ASN | A | 67 | 41.494 | 24.354 | 37.499 | 1.00 28.05 | 8 |
| ATOM | 551 | N | THR | A | 68 | 39.733 | 23.221 | 38.361 | 1.00 25.32 | 7 |
| ATOM | 552 | CA | THR | A | 68 | 38.787 | 23.791 | 37.416 | 1.00 21.75 | 6 |
| ATOM | 553 | CB | THR | A | 68 | 37.438 | 23.111 | 37.500 | 1.00 16.99 | 6 |
| ATOM | 554 | OG1 | THR | A | 68 | 37.620 | 21.695 | 37.371 | 1.00 16.99 | 8 |
| ATOM | 555 | CG2 | THR | A | 68 | 36.549 | 23.591 | 36.359 | 1.00 17.59 | 6 |
| ATOM | 556 | C | THR | A | 68 | 38.633 | 25.263 | 37.732 | 1.00 22.13 | 6 |
| ATOM | 557 | O | THR | A | 68 | 38.529 | 26.088 | 36.830 | 1.00 21.97 | 8 |
| ATOM | 558 | N | LEU | A | 69 | 38.645 | 25.582 | 39.023 | 1.00 22.32 | 7 |
| ATOM | 559 | CA | LEU | A | 69 | 38.535 | 26.956 | 39.482 | 1.00 23.97 | 6 |
| ATOM | 560 | CB | LEU | A | 69 | 38.376 | 26.982 | 41.000 | 1.00 24.99 | 6 |
| ATOM | 561 | CG | LEU | A | 69 | 37.023 | 26.527 | 41.548 | 1.00 29.08 | 6 |
| ATOM | 562 | CD1 | LEU | A | 69 | 37.087 | 26.415 | 43.066 | 1.00 30.99 | 6 |
| ATOM | 563 | CD2 | LEU | A | 69 | 35.942 | 27.528 | 41.120 | 1.00 28.69 | 6 |
| ATOM | 564 | C | LEU | A | 69 | 39.772 | 27.757 | 39.088 | 1.00 24.90 | 6 |
| ATOM | 565 | O | LEU | A | 69 | 39.683 | 28.921 | 38.674 | 1.00 25.04 | 8 |
| ATOM | 566 | N | MET | A | 70 | 40.932 | 27.128 | 39.218 | 1.00 24.67 | 7 |
| ATOM | 567 | CA | MET | A | 70 | 42.183 | 27.794 | 38.897 | 1.00 23.62 | 6 |
| ATOM | 568 | CB | MET | A | 70 | 43.358 | 26.953 | 39.380 | 1.00 26.92 | 6 |
| ATOM | 569 | CG | MET | A | 70 | 43.418 | 26.751 | 40.884 | 1.00 26.69 | 6 |
| ATOM | 570 | SD | MET | A | 70 | 44.970 | 25.929 | 41.325 | 1.00 30.71 | 16 |
| ATOM | 571 | CE | MET | A | 70 | 46.137 | 27.077 | 40.642 | 1.00 23.20 | 6 |
| ATOM | 572 | C | MET | A | 70 | 42.324 | 28.040 | 37.412 | 1.00 21.62 | 6 |
| ATOM | 573 | O | MET | A | 70 | 42.903 | 29.041 | 36.982 | 1.00 18.99 | 8 |
| ATOM | 574 | N | GLU | A | 71 | 41.769 | 27.122 | 36.632 | 1.00 23.93 | 7 |
| ATOM | 575 | CA | GLU | A | 71 | 41.859 | 27.204 | 35.189 | 1.00 24.41 | 6 |
| ATOM | 576 | CB | GLU | A | 71 | 41.681 | 25.814 | 34.582 | 1.00 26.22 | 6 |
| ATOM | 577 | CG | GLU | A | 71 | 42.224 | 25.695 | 33.167 | 1.00 31.75 | 6 |
| ATOM | 578 | CD | GLU | A | 71 | 43.737 | 25.905 | 33.099 | 1.00 33.00 | 6 |
| ATOM | 579 | OE1 | GLU | A | 71 | 44.288 | 25.855 | 31.983 | 1.00 35.84 | 8 |
| ATOM | 580 | OE2 | GLU | A | 71 | 44.377 | 26.116 | 34.154 | 1.00 30.13 | 8 |
| ATOM | 581 | C | GLU | A | 71 | 40.845 | 28.160 | 34.592 | 1.00 21.86 | 6 |
| ATOM | 582 | O | GLU | A | 71 | 41.144 | 28.851 | 33.626 | 1.00 21.54 | 8 |
| ATOM | 583 | N | ALA | A | 72 | 39.649 | 28.197 | 35.169 | 1.00 19.22 | 7 |
| ATOM | 584 | CA | ALA | A | 72 | 38.589 | 29.067 | 34.684 | 1.00 19.39 | 6 |
| ATOM | 585 | CB | ALA | A | 72 | 37.298 | 28.743 | 35.397 | 1.00 19.23 | 6 |
| ATOM | 586 | C | ALA | A | 72 | 38.931 | 30.536 | 34.899 | 1.00 26.72 | 6 |
| ATOM | 587 | O | ALA | A | 72 | 38.711 | 31.383 | 34.016 | 1.00 26.12 | 8 |
| ATOM | 588 | N | GLU | A | 73 | 39.470 | 30.835 | 36.079 | 1.00 28.44 | 7 |
| ATOM | 589 | CA | GLU | A | 73 | 39.820 | 32.202 | 36.436 | 1.00 29.44 | 6 |
| ATOM | 590 | CB | GLU | A | 73 | 40.157 | 32.282 | 37.931 | 1.00 25.84 | 6 |
| ATOM | 591 | CG | GLU | A | 73 | 40.646 | 33.655 | 38.349 | 1.00 27.51 | 6 |
| ATOM | 592 | CD | GLU | A | 73 | 40.840 | 33.806 | 39.841 | 1.00 29.38 | 6 |
| ATOM | 593 | OE1 | GLU | A | 73 | 39.841 | 33.776 | 40.582 | 1.00 32.49 | 8 |
| ATOM | 594 | OE2 | GLU | A | 73 | 41.996 | 33.960 | 40.277 | 1.00 31.77 | 8 |

Fig. 17-9

| | | | | | | | | | |
|---|---|---|---|---|---|---|---|---|---|
| ATOM | 595 | C | GLU | A | 73 | 40.946 | 32.840 | 35.615 | 1.00 31.83 | 6 |
| ATOM | 596 | O | GLU | A | 73 | 40.859 | 34.024 | 35.259 | 1.00 33.52 | 8 |
| ATOM | 597 | N | ARG | A | 74 | 41.992 | 32.071 | 35.309 | 1.00 31.45 | 7 |
| ATOM | 598 | CA | ARG | A | 74 | 43.128 | 32.611 | 34.557 | 1.00 30.65 | 6 |
| ATOM | 599 | CB | ARG | A | 74 | 44.405 | 31.826 | 34.874 | 1.00 32.12 | 6 |
| ATOM | 600 | CG | ARG | A | 74 | 44.514 | 30.467 | 34.205 | 1.00 31.42 | 6 |
| ATOM | 601 | CD | ARG | A | 74 | 45.702 | 29.714 | 34.754 | 1.00 30.73 | 6 |
| ATOM | 602 | NE | ARG | A | 74 | 46.041 | 28.561 | 33.933 | 1.00 34.18 | 7 |
| ATOM | 603 | CZ | ARG | A | 74 | 46.646 | 28.634 | 32.748 | 1.00 35.55 | 6 |
| ATOM | 604 | NH1 | ARG | A | 74 | 46.989 | 29.818 | 32.232 | 1.00 29.64 | 7 |
| ATOM | 605 | NH2 | ARG | A | 74 | 46.906 | 27.514 | 32.079 | 1.00 34.07 | 7 |
| ATOM | 606 | C | ARG | A | 74 | 42.894 | 32.623 | 33.051 | 1.00 28.61 | 6 |
| ATOM | 607 | O | ARG | A | 74 | 43.431 | 33.465 | 32.338 | 1.00 24.38 | 8 |
| ATOM | 608 | N | CYS | A | 75 | 42.107 | 31.673 | 32.566 | 1.00 28.32 | 7 |
| ATOM | 609 | CA | CYS | A | 75 | 41.796 | 31.619 | 31.148 | 1.00 32.42 | 6 |
| ATOM | 610 | CB | CYS | A | 75 | 41.687 | 30.167 | 30.682 | 1.00 32.91 | 6 |
| ATOM | 611 | SG | CYS | A | 75 | 43.281 | 29.296 | 30.777 | 1.00 37.09 | 16 |
| ATOM | 612 | C | CYS | A | 75 | 40.489 | 32.382 | 30.956 | 1.00 33.10 | 6 |
| ATOM | 613 | O | CYS | A | 75 | 40.029 | 32.598 | 29.834 | 1.00 30.74 | 8 |
| ATOM | 614 | N | GLN | A | 76 | 39.914 | 32.787 | 32.088 | 1.00 34.42 | 7 |
| ATOM | 615 | CA | GLN | A | 76 | 38.691 | 33.575 | 32.144 | 1.00 33.20 | 6 |
| ATOM | 616 | CB | GLN | A | 76 | 38.986 | 34.962 | 31.578 | 1.00 32.09 | 6 |
| ATOM | 617 | CG | GLN | A | 76 | 38.089 | 36.064 | 32.094 | 1.00 39.46 | 6 |
| ATOM | 618 | CD | GLN | A | 76 | 38.479 | 36.541 | 33.480 | 1.00 41.47 | 6 |
| ATOM | 619 | OE1 | GLN | A | 76 | 38.574 | 35.755 | 34.426 | 1.00 45.02 | 8 |
| ATOM | 620 | NE2 | GLN | A | 76 | 38.703 | 37.846 | 33.606 | 1.00 42.22 | 7 |
| ATOM | 621 | C | GLN | A | 76 | 37.561 | 32.920 | 31.358 | 1.00 33.20 | 6 |
| ATOM | 622 | O | GLN | A | 76 | 36.732 | 33.598 | 30.760 | 1.00 34.19 | 8 |
| ATOM | 623 | N | CYS | A | 77 | 37.522 | 31.598 | 31.370 | 1.00 31.81 | 7 |
| ATOM | 624 | CA | CYS | A | 77 | 36.511 | 30.862 | 30.627 | 1.00 31.47 | 6 |
| ATOM | 625 | CB | CYS | A | 77 | 37.187 | 30.181 | 29.454 | 1.00 30.25 | 6 |
| ATOM | 626 | SG | CYS | A | 77 | 38.479 | 29.071 | 30.044 | 1.00 33.94 | 16 |
| ATOM | 627 | C | CYS | A | 77 | 35.851 | 29.795 | 31.498 | 1.00 31.97 | 6 |
| ATOM | 628 | O | CYS | A | 77 | 36.335 | 29.503 | 32.590 | 1.00 35.15 | 8 |
| ATOM | 629 | N | VAL | A | 78 | 34.750 | 29.216 | 31.018 | 1.00 30.78 | 7 |
| ATOM | 630 | CA | VAL | A | 78 | 34.069 | 28.139 | 31.747 | 1.00 30.55 | 6 |
| ATOM | 631 | CB | VAL | A | 78 | 32.539 | 28.287 | 31.720 | 1.00 30.06 | 6 |
| ATOM | 632 | CG1 | VAL | A | 78 | 31.881 | 27.030 | 32.293 | 1.00 28.23 | 6 |
| ATOM | 633 | CG2 | VAL | A | 78 | 32.129 | 29.503 | 32.526 | 1.00 30.67 | 6 |
| ATOM | 634 | C | VAL | A | 78 | 34.420 | 26.794 | 31.110 | 1.00 29.80 | 6 |
| ATOM | 635 | O | VAL | A | 78 | 33.851 | 26.422 | 30.077 | 1.00 29.65 | 8 |
| ATOM | 636 | N | PRO | A | 79 | 35.337 | 26.033 | 31.739 | 1.00 28.55 | 7 |
| ATOM | 637 | CD | PRO | A | 79 | 35.985 | 26.335 | 33.025 | 1.00 24.39 | 6 |
| ATOM | 638 | CA | PRO | A | 79 | 35.793 | 24.724 | 31.261 | 1.00 28.89 | 6 |
| ATOM | 639 | CB | PRO | A | 79 | 36.622 | 24.218 | 32.434 | 1.00 24.49 | 6 |
| ATOM | 640 | CG | PRO | A | 79 | 37.239 | 25.500 | 32.922 | 1.00 25.68 | 6 |
| ATOM | 641 | C | PRO | A | 79 | 34.668 | 23.776 | 30.881 | 1.00 30.13 | 6 |
| ATOM | 642 | O | PRO | A | 79 | 33.697 | 23.624 | 31.615 | 1.00 30.87 | 8 |
| ATOM | 643 | N | LYS | A | 80 | 34.796 | 23.136 | 29.727 | 1.00 33.44 | 7 |
| ATOM | 644 | CA | LYS | A | 80 | 33.758 | 22.216 | 29.303 | 1.00 38.52 | 6 |
| ATOM | 645 | CB | LYS | A | 80 | 34.202 | 21.421 | 28.076 | 1.00 45.18 | 6 |
| ATOM | 646 | CG | LYS | A | 80 | 35.450 | 20.589 | 28.278 | 1.00 55.18 | 6 |
| ATOM | 647 | CD | LYS | A | 80 | 35.788 | 19.827 | 27.000 | 1.00 60.80 | 6 |
| ATOM | 648 | CE | LYS | A | 80 | 37.035 | 18.976 | 27.168 | 1.00 64.25 | 6 |
| ATOM | 649 | NZ | LYS | A | 80 | 37.367 | 18.252 | 25.911 | 1.00 68.95 | 7 |
| ATOM | 650 | C | LYS | A | 80 | 33.411 | 21.267 | 30.443 | 1.00 36.56 | 6 |
| ATOM | 651 | O | LYS | A | 80 | 34.293 | 20.775 | 31.164 | 1.00 31.61 | 8 |
| ATOM | 652 | N | GLY | A | 81 | 32.112 | 21.035 | 30.602 | 1.00 32.57 | 7 |
| ATOM | 653 | CA | GLY | A | 81 | 31.634 | 20.155 | 31.648 | 1.00 29.81 | 6 |
| ATOM | 654 | C | GLY | A | 81 | 31.477 | 20.884 | 32.965 | 1.00 28.30 | 6 |
| ATOM | 655 | O | GLY | A | 81 | 30.544 | 20.612 | 33.723 | 1.00 25.49 | 8 |
| ATOM | 656 | N | ALA | A | 82 | 32.380 | 21.830 | 33.218 | 1.00 25.99 | 7 |
| ATOM | 657 | CA | ALA | A | 82 | 32.384 | 22.602 | 34.458 | 1.00 26.72 | 6 |
| ATOM | 658 | CB | ALA | A | 82 | 33.485 | 23.674 | 34.406 | 1.00 22.64 | 6 |
| ATOM | 659 | C | ALA | A | 82 | 31.066 | 23.245 | 34.886 | 1.00 27.84 | 6 |
| ATOM | 660 | O | ALA | A | 82 | 30.729 | 23.224 | 36.068 | 1.00 30.00 | 8 |

Fig. 17-10

```
ATOM    661  N    ARG A   83      30.310  23.811  33.951  1.00 31.15      7
ATOM    662  CA   ARG A   83      29.071  24.462  34.345  1.00 32.50      6
ATOM    663  CB   ARG A   83      28.285  24.941  33.127  1.00 37.19      6
ATOM    664  CG   ARG A   83      27.439  26.189  33.408  1.00 42.23      6
ATOM    665  CD   ARG A   83      26.480  26.020  34.585  1.00 48.02      6
ATOM    666  NE   ARG A   83      25.904  27.303  34.996  1.00 53.00      7
ATOM    667  CZ   ARG A   83      25.045  27.460  36.005  1.00 56.84      6
ATOM    668  NH1  ARG A   83      24.649  26.413  36.724  1.00 53.05      7
ATOM    669  NH2  ARG A   83      24.588  28.672  36.304  1.00 58.03      7
ATOM    670  C    ARG A   83      28.208  23.531  35.189  1.00 31.50      6
ATOM    671  O    ARG A   83      28.056  23.749  36.386  1.00 29.62      8
ATOM    672  N    GLU A   84      27.648  22.491  34.581  1.00 33.06      7
ATOM    673  CA   GLU A   84      26.819  21.568  35.343  1.00 35.40      6
ATOM    674  CB   GLU A   84      26.112  20.562  34.417  1.00 37.35      6
ATOM    675  CG   GLU A   84      26.989  19.684  33.496  1.00 40.01      6
ATOM    676  CD   GLU A   84      27.551  20.418  32.267  1.00 44.49      6
ATOM    677  OE1  GLU A   84      27.925  19.723  31.292  1.00 41.12      8
ATOM    678  OE2  GLU A   84      27.636  21.671  32.270  1.00 41.01      8
ATOM    679  C    GLU A   84      27.617  20.623  36.417  1.00 35.42      6
ATOM    680  O    GLU A   84      27.246  20.816  37.594  1.00 34.66      8
ATOM    681  N    LYS A   85      28.727  20.226  36.002  1.00 35.21      7
ATOM    682  CA   LYS A   85      29.604  19.450  36.878  1.00 37.93      6
ATOM    683  CB   LYS A   85      30.841  19.030  36.076  1.00 40.61      6
ATOM    684  CG   LYS A   85      31.739  17.977  36.706  1.00 42.63      6
ATOM    685  CD   LYS A   85      31.038  16.640  36.872  1.00 45.48      6
ATOM    686  CE   LYS A   85      32.054  15.523  37.078  1.00 45.60      6
ATOM    687  NZ   LYS A   85      33.032  15.833  38.154  1.00 46.16      7
ATOM    688  C    LYS A   85      30.032  20.159  38.175  1.00 37.56      6
ATOM    689  O    LYS A   85      30.161  19.516  39.222  1.00 38.40      8
ATOM    690  N    TYR A   86      30.254  21.472  38.116  1.00 35.60      7
ATOM    691  CA   TYR A   86      30.671  22.216  39.307  1.00 32.67      6
ATOM    692  CB   TYR A   86      32.151  22.610  39.200  1.00 32.09      6
ATOM    693  CG   TYR A   86      33.065  21.424  38.995  1.00 33.63      6
ATOM    694  CD1  TYR A   86      33.120  20.393  39.932  1.00 32.12      6
ATOM    695  CE1  TYR A   86      33.918  19.266  39.723  1.00 33.59      6
ATOM    696  CD2  TYR A   86      33.839  21.306  37.841  1.00 33.82      6
ATOM    697  CE2  TYR A   86      34.645  20.178  37.623  1.00 34.55      6
ATOM    698  CZ   TYR A   86      34.675  19.162  38.566  1.00 32.38      6
ATOM    699  OH   TYR A   86      35.431  18.034  38.336  1.00 29.17      8
ATOM    700  C    TYR A   86      29.831  23.455  39.597  1.00 30.21      6
ATOM    701  O    TYR A   86      30.192  24.265  40.445  1.00 29.12      8
ATOM    702  N    ASN A   87      28.712  23.594  38.893  1.00 29.44      7
ATOM    703  CA   ASN A   87      27.797  24.717  39.086  1.00 28.58      6
ATOM    704  CB   ASN A   87      27.154  24.618  40.470  1.00 25.63      6
ATOM    705  CG   ASN A   87      25.871  25.428  40.596  1.00 28.05      6
ATOM    706  OD1  ASN A   87      25.275  25.477  41.672  1.00 31.32      8
ATOM    707  ND2  ASN A   87      25.434  26.055  39.506  1.00 28.35      7
ATOM    708  C    ASN A   87      28.580  26.015  38.963  1.00 30.35      6
ATOM    709  O    ASN A   87      28.319  26.981  39.677  1.00 32.07      8
ATOM    710  N    ILE A   88      29.545  26.019  38.051  1.00 32.05      7
ATOM    711  CA   ILE A   88      30.407  27.173  37.809  1.00 33.77      6
ATOM    712  CB   ILE A   88      31.894  26.734  37.776  1.00 36.13      6
ATOM    713  CG2  ILE A   88      32.759  27.831  37.201  1.00 37.80      6
ATOM    714  CG1  ILE A   88      32.357  26.342  39.178  1.00 38.92      6
ATOM    715  CD1  ILE A   88      32.350  27.483  40.176  1.00 41.44      6
ATOM    716  C    ILE A   88      30.085  27.857  36.482  1.00 32.28      6
ATOM    717  O    ILE A   88      29.708  27.196  35.520  1.00 32.72      8
ATOM    718  N    GLY A   89      30.237  29.179  36.438  1.00 31.56      7
ATOM    719  CA   GLY A   89      29.994  29.915  35.207  1.00 30.84      6
ATOM    720  C    GLY A   89      28.696  30.689  35.093  1.00 32.17      6
ATOM    721  O    GLY A   89      28.628  31.670  34.349  1.00 30.42      8
ATOM    722  N    GLY A   90      27.670  30.257  35.821  1.00 31.51      7
ATOM    723  CA   GLY A   90      26.387  30.937  35.756  1.00 32.92      6
ATOM    724  C    GLY A   90      26.316  32.246  36.524  1.00 34.32      6
ATOM    725  O    GLY A   90      27.302  32.671  37.129  1.00 33.97      8
ATOM    726  N    TYR A   91      25.144  32.882  36.504  1.00 33.88      7
```

Fig. 17-11

| | | | | | | | | | |
|---|---|---|---|---|---|---|---|---|---|
| ATOM | 727 | CA | TYR A | 91 | 24.924 | 34.146 | 37.206 | 1.00 35.76 | 6 |
| ATOM | 728 | CB | TYR A | 91 | 23.465 | 34.589 | 37.058 | 1.00 38.10 | 6 |
| ATOM | 729 | CG | TYR A | 91 | 23.089 | 35.733 | 37.990 | 1.00 42.40 | 6 |
| ATOM | 730 | CD1 | TYR A | 91 | 23.417 | 37.057 | 37.688 | 1.00 43.57 | 6 |
| ATOM | 731 | CE1 | TYR A | 91 | 23.105 | 38.106 | 38.577 | 1.00 42.44 | 6 |
| ATOM | 732 | CD2 | TYR A | 91 | 22.444 | 35.484 | 39.205 | 1.00 44.07 | 6 |
| ATOM | 733 | CE2 | TYR A | 91 | 22.132 | 36.526 | 40.097 | 1.00 42.67 | 6 |
| ATOM | 734 | CZ | TYR A | 91 | 22.462 | 37.825 | 39.775 | 1.00 42.41 | 6 |
| ATOM | 735 | OH | TYR A | 91 | 22.130 | 38.835 | 40.646 | 1.00 43.69 | 8 |
| ATOM | 736 | C | TYR A | 91 | 25.242 | 34.082 | 38.701 | 1.00 34.15 | 6 |
| ATOM | 737 | O | TYR A | 91 | 25.821 | 35.014 | 39.266 | 1.00 29.52 | 8 |
| ATOM | 738 | N | GLU A | 92 | 24.837 | 32.986 | 39.333 | 1.00 34.78 | 7 |
| ATOM | 739 | CA | GLU A | 92 | 25.024 | 32.797 | 40.767 | 1.00 38.46 | 6 |
| ATOM | 740 | CB | GLU A | 92 | 24.233 | 31.564 | 41.211 | 1.00 43.99 | 6 |
| ATOM | 741 | CG | GLU A | 92 | 23.932 | 31.489 | 42.700 | 1.00 52.10 | 6 |
| ATOM | 742 | CD | GLU A | 92 | 23.294 | 30.161 | 43.097 | 1.00 58.00 | 6 |
| ATOM | 743 | OE1 | GLU A | 92 | 24.001 | 29.126 | 43.058 | 1.00 60.63 | 8 |
| ATOM | 744 | OE2 | GLU A | 92 | 22.087 | 30.149 | 43.434 | 1.00 59.58 | 8 |
| ATOM | 745 | C | GLU A | 92 | 26.492 | 32.669 | 41.208 | 1.00 36.42 | 6 |
| ATOM | 746 | O | GLU A | 92 | 26.902 | 33.287 | 42.193 | 1.00 32.92 | 8 |
| ATOM | 747 | N | ASN A | 93 | 27.280 | 31.883 | 40.473 | 1.00 34.12 | 7 |
| ATOM | 748 | CA | ASN A | 93 | 28.693 | 31.671 | 40.808 | 1.00 33.24 | 6 |
| ATOM | 749 | CB | ASN A | 93 | 28.871 | 30.259 | 41.364 | 1.00 28.52 | 6 |
| ATOM | 750 | CG | ASN A | 93 | 27.734 | 29.859 | 42.299 | 1.00 27.45 | 6 |
| ATOM | 751 | OD1 | ASN A | 93 | 27.547 | 30.457 | 43.355 | 1.00 21.76 | 8 |
| ATOM | 752 | ND2 | ASN A | 93 | 26.956 | 28.853 | 41.895 | 1.00 21.79 | 7 |
| ATOM | 753 | C | ASN A | 93 | 29.529 | 31.843 | 39.535 | 1.00 35.04 | 6 |
| ATOM | 754 | O | ASN A | 93 | 30.160 | 30.898 | 39.059 | 1.00 33.81 | 8 |
| ATOM | 755 | N | PRO A | 94 | 29.583 | 33.081 | 39.010 | 1.00 36.19 | 7 |
| ATOM | 756 | CD | PRO A | 94 | 28.970 | 34.231 | 39.690 | 1.00 34.62 | 6 |
| ATOM | 757 | CA | PRO A | 94 | 30.274 | 33.560 | 37.808 | 1.00 34.80 | 6 |
| ATOM | 758 | CB | PRO A | 94 | 29.924 | 35.050 | 37.791 | 1.00 33.94 | 6 |
| ATOM | 759 | CG | PRO A | 94 | 28.619 | 35.095 | 38.516 | 1.00 36.13 | 6 |
| ATOM | 760 | C | PRO A | 94 | 31.775 | 33.379 | 37.733 | 1.00 34.63 | 6 |
| ATOM | 761 | O | PRO A | 94 | 32.443 | 33.103 | 38.730 | 1.00 34.72 | 8 |
| ATOM | 762 | N | VAL A | 95 | 32.299 | 33.556 | 36.526 | 1.00 33.57 | 7 |
| ATOM | 763 | CA | VAL A | 95 | 33.735 | 33.499 | 36.307 | 1.00 30.31 | 6 |
| ATOM | 764 | CB | VAL A | 95 | 34.085 | 33.171 | 34.841 | 1.00 29.88 | 6 |
| ATOM | 765 | CG1 | VAL A | 95 | 35.561 | 33.453 | 34.574 | 1.00 29.53 | 6 |
| ATOM | 766 | CG2 | VAL A | 95 | 33.795 | 31.713 | 34.563 | 1.00 28.05 | 6 |
| ATOM | 767 | C | VAL A | 95 | 34.195 | 34.910 | 36.624 | 1.00 29.86 | 6 |
| ATOM | 768 | O | VAL A | 95 | 33.524 | 35.879 | 36.272 | 1.00 29.07 | 8 |
| ATOM | 769 | N | SER A | 96 | 35.318 | 35.019 | 37.317 | 1.00 30.89 | 7 |
| ATOM | 770 | CA | SER A | 96 | 35.889 | 36.310 | 37.687 | 1.00 32.27 | 6 |
| ATOM | 771 | CB | SER A | 96 | 34.885 | 37.145 | 38.501 | 1.00 30.16 | 6 |
| ATOM | 772 | OG | SER A | 96 | 34.600 | 36.545 | 39.756 | 1.00 26.77 | 8 |
| ATOM | 773 | C | SER A | 96 | 37.111 | 35.993 | 38.537 | 1.00 32.96 | 6 |
| ATOM | 774 | O | SER A | 96 | 37.603 | 34.865 | 38.511 | 1.00 33.77 | 8 |
| ATOM | 775 | N | TYR A | 97 | 37.609 | 36.973 | 39.282 | 1.00 32.66 | 7 |
| ATOM | 776 | CA | TYR A | 97 | 38.753 | 36.712 | 40.132 | 1.00 31.95 | 6 |
| ATOM | 777 | CB | TYR A | 97 | 39.838 | 37.766 | 39.923 | 1.00 31.81 | 6 |
| ATOM | 778 | CG | TYR A | 97 | 40.416 | 37.729 | 38.525 | 1.00 30.39 | 6 |
| ATOM | 779 | CD1 | TYR A | 97 | 39.820 | 38.434 | 37.479 | 1.00 30.65 | 6 |
| ATOM | 780 | CE1 | TYR A | 97 | 40.327 | 38.358 | 36.178 | 1.00 28.49 | 6 |
| ATOM | 781 | CD2 | TYR A | 97 | 41.536 | 36.945 | 38.236 | 1.00 28.43 | 6 |
| ATOM | 782 | CE2 | TYR A | 97 | 42.046 | 36.858 | 36.942 | 1.00 24.73 | 6 |
| ATOM | 783 | CZ | TYR A | 97 | 41.437 | 37.565 | 35.919 | 1.00 27.27 | 6 |
| ATOM | 784 | OH | TYR A | 97 | 41.915 | 37.455 | 34.633 | 1.00 26.70 | 8 |
| ATOM | 785 | C | TYR A | 97 | 38.350 | 36.618 | 41.596 | 1.00 31.10 | 6 |
| ATOM | 786 | O | TYR A | 97 | 39.178 | 36.735 | 42.495 | 1.00 33.01 | 8 |
| ATOM | 787 | N | ALA A | 98 | 37.059 | 36.398 | 41.818 | 1.00 31.11 | 7 |
| ATOM | 788 | CA | ALA A | 98 | 36.510 | 36.241 | 43.160 | 1.00 30.06 | 6 |
| ATOM | 789 | CB | ALA A | 98 | 35.141 | 36.920 | 43.256 | 1.00 27.71 | 6 |
| ATOM | 790 | C | ALA A | 98 | 36.350 | 34.736 | 43.357 | 1.00 31.24 | 6 |
| ATOM | 791 | O | ALA A | 98 | 36.335 | 34.238 | 44.487 | 1.00 29.66 | 8 |
| ATOM | 792 | N | MET A | 99 | 36.249 | 34.030 | 42.230 | 1.00 29.50 | 7 |

Fig. 17-12

```
ATOM    793  CA   MET A  99      36.048  32.589  42.207  1.00 29.89           6
ATOM    794  CB   MET A  99      35.774  32.123  40.778  1.00 30.48           6
ATOM    795  CG   MET A  99      36.942  32.265  39.822  1.00 29.63           6
ATOM    796  SD   MET A  99      36.426  31.939  38.126  1.00 29.78          16
ATOM    797  CE   MET A  99      35.629  30.273  38.347  1.00 25.05           6
ATOM    798  C    MET A  99      37.199  31.800  42.783  1.00 30.81           6
ATOM    799  O    MET A  99      36.993  30.757  43.406  1.00 30.59           8
ATOM    800  N    PHE A 100      38.417  32.274  42.569  1.00 32.09           7
ATOM    801  CA   PHE A 100      39.554  31.557  43.114  1.00 33.87           6
ATOM    802  CB   PHE A 100      40.322  30.817  42.029  1.00 33.95           6
ATOM    803  CG   PHE A 100      41.434  29.979  42.578  1.00 41.14           6
ATOM    804  CD1  PHE A 100      41.152  28.862  43.364  1.00 41.84           6
ATOM    805  CD2  PHE A 100      42.768  30.339  42.372  1.00 42.18           6
ATOM    806  CE1  PHE A 100      42.185  28.115  43.941  1.00 41.63           6
ATOM    807  CE2  PHE A 100      43.808  29.600  42.944  1.00 40.50           6
ATOM    808  CZ   PHE A 100      43.517  28.487  43.729  1.00 39.89           6
ATOM    809  C    PHE A 100      40.519  32.438  43.895  1.00 33.98           6
ATOM    810  O    PHE A 100      40.706  32.231  45.088  1.00 38.21           8
ATOM    811  N    THR A 101      41.137  33.415  43.245  1.00 28.09           7
ATOM    812  CA   THR A 101      42.063  34.261  43.969  1.00 22.19           6
ATOM    813  CB   THR A 101      42.623  35.378  43.072  1.00 22.48           6
ATOM    814  OG1  THR A 101      43.441  34.795  42.052  1.00 21.99           8
ATOM    815  CG2  THR A 101      43.468  36.335  43.876  1.00 15.00           6
ATOM    816  C    THR A 101      41.408  34.860  45.205  1.00 21.71           6
ATOM    817  O    THR A 101      41.988  34.845  46.282  1.00 23.82           8
ATOM    818  N    GLY A 102      40.197  35.377  45.068  1.00 21.79           7
ATOM    819  CA   GLY A 102      39.533  35.947  46.231  1.00 21.23           6
ATOM    820  C    GLY A 102      39.072  34.833  47.153  1.00 23.03           6
ATOM    821  O    GLY A 102      39.209  34.909  48.378  1.00 20.41           8
ATOM    822  N    SER A 103      38.512  33.792  46.544  1.00 22.59           7
ATOM    823  CA   SER A 103      38.028  32.640  47.276  1.00 26.51           6
ATOM    824  CB   SER A 103      37.454  31.598  46.314  1.00 28.10           6
ATOM    825  OG   SER A 103      36.314  32.099  45.639  1.00 32.01           8
ATOM    826  C    SER A 103      39.188  32.040  48.032  1.00 27.73           6
ATOM    827  O    SER A 103      39.019  31.544  49.144  1.00 30.61           8
ATOM    828  N    SER A 104      40.364  32.080  47.410  1.00 28.76           7
ATOM    829  CA   SER A 104      41.590  31.552  48.008  1.00 28.55           6
ATOM    830  CB   SER A 104      42.769  31.683  47.039  1.00 28.74           6
ATOM    831  OG   SER A 104      42.501  31.044  45.804  1.00 35.04           8
ATOM    832  C    SER A 104      41.870  32.401  49.226  1.00 25.57           6
ATOM    833  O    SER A 104      42.026  31.897  50.338  1.00 25.17           8
ATOM    834  N    LEU A 105      41.909  33.705  48.986  1.00 23.91           7
ATOM    835  CA   LEU A 105      42.163  34.698  50.008  1.00 23.01           6
ATOM    836  CB   LEU A 105      42.049  36.082  49.382  1.00 23.57           6
ATOM    837  CG   LEU A 105      43.158  37.091  49.672  1.00 25.30           6
ATOM    838  CD1  LEU A 105      44.502  36.551  49.178  1.00 22.38           6
ATOM    839  CD2  LEU A 105      42.823  38.413  48.984  1.00 27.36           6
ATOM    840  C    LEU A 105      41.187  34.559  51.182  1.00 23.48           6
ATOM    841  O    LEU A 105      41.604  34.448  52.331  1.00 21.60           8
ATOM    842  N    ALA A 106      39.887  34.556  50.897  1.00 25.32           7
ATOM    843  CA   ALA A 106      38.884  34.423  51.957  1.00 26.04           6
ATOM    844  CB   ALA A 106      37.471  34.423  51.358  1.00 24.28           6
ATOM    845  C    ALA A 106      39.088  33.158  52.790  1.00 25.76           6
ATOM    846  O    ALA A 106      38.953  33.186  54.015  1.00 22.75           8
ATOM    847  N    THR A 107      39.410  32.057  52.111  1.00 25.65           7
ATOM    848  CA   THR A 107      39.620  30.760  52.754  1.00 25.54           6
ATOM    849  CB   THR A 107      39.706  29.637  51.713  1.00 21.92           6
ATOM    850  OG1  THR A 107      38.559  29.688  50.868  1.00 26.40           8
ATOM    851  CG2  THR A 107      39.742  28.295  52.387  1.00 17.36           6
ATOM    852  C    THR A 107      40.901  30.720  53.583  1.00 28.16           6
ATOM    853  O    THR A 107      40.906  30.254  54.727  1.00 28.07           8
ATOM    854  N    GLY A 108      41.994  31.191  52.996  1.00 28.51           7
ATOM    855  CA   GLY A 108      43.247  31.187  53.718  1.00 28.37           6
ATOM    856  C    GLY A 108      43.027  31.921  55.019  1.00 30.26           6
ATOM    857  O    GLY A 108      43.502  31.499  56.076  1.00 32.98           8
ATOM    858  N    SER A 109      42.283  33.018  54.942  1.00 24.81           7
```

Fig. 17-13

| ATOM | 859 | CA | SER | A | 109 | 42.002 | 33.810 | 56.119 | 1.00 | 24.86 | 6 |
| ATOM | 860 | CB | SER | A | 109 | 41.222 | 35.066 | 55.727 | 1.00 | 24.74 | 6 |
| ATOM | 861 | OG | SER | A | 109 | 41.992 | 35.898 | 54.872 | 1.00 | 21.07 | 8 |
| ATOM | 862 | C | SER | A | 109 | 41.240 | 32.996 | 57.173 | 1.00 | 27.89 | 6 |
| ATOM | 863 | O | SER | A | 109 | 41.424 | 33.214 | 58.377 | 1.00 | 30.92 | 8 |
| ATOM | 864 | N | THR | A | 110 | 40.389 | 32.064 | 56.744 | 1.00 | 23.91 | 7 |
| ATOM | 865 | CA | THR | A | 110 | 39.676 | 31.259 | 57.721 | 1.00 | 24.80 | 6 |
| ATOM | 866 | CB | THR | A | 110 | 38.641 | 30.290 | 57.074 | 1.00 | 29.65 | 6 |
| ATOM | 867 | OG1 | THR | A | 110 | 37.469 | 31.016 | 56.669 | 1.00 | 30.45 | 8 |
| ATOM | 868 | CG2 | THR | A | 110 | 38.228 | 29.205 | 58.067 | 1.00 | 29.00 | 6 |
| ATOM | 869 | C | THR | A | 110 | 40.712 | 30.449 | 58.478 | 1.00 | 24.34 | 6 |
| ATOM | 870 | O | THR | A | 110 | 40.615 | 30.282 | 59.699 | 1.00 | 24.74 | 8 |
| ATOM | 871 | N | VAL | A | 111 | 41.715 | 29.954 | 57.764 | 1.00 | 23.01 | 7 |
| ATOM | 872 | CA | VAL | A | 111 | 42.759 | 29.173 | 58.416 | 1.00 | 24.13 | 6 |
| ATOM | 873 | CB | VAL | A | 111 | 43.695 | 28.495 | 57.391 | 1.00 | 25.77 | 6 |
| ATOM | 874 | CG1 | VAL | A | 111 | 44.845 | 27.773 | 58.121 | 1.00 | 22.51 | 6 |
| ATOM | 875 | CG2 | VAL | A | 111 | 42.888 | 27.502 | 56.534 | 1.00 | 22.67 | 6 |
| ATOM | 876 | C | VAL | A | 111 | 43.576 | 30.071 | 59.329 | 1.00 | 23.14 | 6 |
| ATOM | 877 | O | VAL | A | 111 | 43.720 | 29.793 | 60.518 | 1.00 | 24.11 | 8 |
| ATOM | 878 | N | GLN | A | 112 | 44.101 | 31.156 | 58.772 | 1.00 | 24.94 | 7 |
| ATOM | 879 | CA | GLN | A | 112 | 44.895 | 32.100 | 59.554 | 1.00 | 25.12 | 6 |
| ATOM | 880 | CB | GLN | A | 112 | 45.082 | 33.413 | 58.779 | 1.00 | 25.14 | 6 |
| ATOM | 881 | CG | GLN | A | 112 | 45.545 | 33.224 | 57.330 | 1.00 | 28.51 | 6 |
| ATOM | 882 | CD | GLN | A | 112 | 45.789 | 34.534 | 56.594 | 1.00 | 29.13 | 6 |
| ATOM | 883 | OE1 | GLN | A | 112 | 46.779 | 35.219 | 56.837 | 1.00 | 31.22 | 8 |
| ATOM | 884 | NE2 | GLN | A | 112 | 44.877 | 34.890 | 55.694 | 1.00 | 29.31 | 7 |
| ATOM | 885 | C | GLN | A | 112 | 44.107 | 32.362 | 60.827 | 1.00 | 24.62 | 6 |
| ATOM | 886 | O | GLN | A | 112 | 44.647 | 32.311 | 61.939 | 1.00 | 21.10 | 8 |
| ATOM | 887 | N | ALA | A | 113 | 42.813 | 32.622 | 60.644 | 1.00 | 24.41 | 7 |
| ATOM | 888 | CA | ALA | A | 113 | 41.914 | 32.904 | 61.751 | 1.00 | 23.33 | 6 |
| ATOM | 889 | CB | ALA | A | 113 | 40.516 | 33.183 | 61.224 | 1.00 | 19.80 | 6 |
| ATOM | 890 | C | ALA | A | 113 | 41.901 | 31.733 | 62.729 | 1.00 | 25.34 | 6 |
| ATOM | 891 | O | ALA | A | 113 | 41.925 | 31.930 | 63.946 | 1.00 | 27.52 | 8 |
| ATOM | 892 | N | ILE | A | 114 | 41.859 | 30.509 | 62.211 | 1.00 | 24.39 | 7 |
| ATOM | 893 | CA | ILE | A | 114 | 41.867 | 29.356 | 63.106 | 1.00 | 24.49 | 6 |
| ATOM | 894 | CB | ILE | A | 114 | 41.524 | 28.042 | 62.371 | 1.00 | 23.46 | 6 |
| ATOM | 895 | CG2 | ILE | A | 114 | 41.902 | 26.855 | 63.227 | 1.00 | 18.97 | 6 |
| ATOM | 896 | CG1 | ILE | A | 114 | 40.030 | 28.015 | 62.034 | 1.00 | 21.17 | 6 |
| ATOM | 897 | CD1 | ILE | A | 114 | 39.598 | 26.791 | 61.239 | 1.00 | 22.51 | 6 |
| ATOM | 898 | C | ILE | A | 114 | 43.230 | 29.227 | 63.757 | 1.00 | 24.32 | 6 |
| ATOM | 899 | O | ILE | A | 114 | 43.328 | 28.817 | 64.907 | 1.00 | 24.74 | 8 |
| ATOM | 900 | N | GLU | A | 115 | 44.280 | 29.580 | 63.019 | 1.00 | 26.58 | 7 |
| ATOM | 901 | CA | GLU | A | 115 | 45.638 | 29.518 | 63.551 | 1.00 | 25.89 | 6 |
| ATOM | 902 | CB | GLU | A | 115 | 46.639 | 29.992 | 62.508 | 1.00 | 22.63 | 6 |
| ATOM | 903 | CG | GLU | A | 115 | 46.554 | 29.264 | 61.192 | 1.00 | 20.39 | 6 |
| ATOM | 904 | CD | GLU | A | 115 | 47.668 | 29.670 | 60.244 | 1.00 | 21.39 | 6 |
| ATOM | 905 | OE1 | GLU | A | 115 | 47.848 | 30.887 | 60.016 | 1.00 | 19.60 | 8 |
| ATOM | 906 | OE2 | GLU | A | 115 | 48.362 | 28.769 | 59.722 | 1.00 | 22.53 | 8 |
| ATOM | 907 | C | GLU | A | 115 | 45.724 | 30.422 | 64.774 | 1.00 | 27.56 | 6 |
| ATOM | 908 | O | GLU | A | 115 | 46.173 | 30.005 | 65.837 | 1.00 | 25.98 | 8 |
| ATOM | 909 | N | GLU | A | 116 | 45.267 | 31.660 | 64.615 | 1.00 | 31.19 | 7 |
| ATOM | 910 | CA | GLU | A | 116 | 45.282 | 32.631 | 65.705 | 1.00 | 35.80 | 6 |
| ATOM | 911 | CB | GLU | A | 116 | 44.676 | 33.959 | 65.237 | 1.00 | 36.91 | 6 |
| ATOM | 912 | CG | GLU | A | 116 | 45.434 | 34.605 | 64.069 | 1.00 | 41.14 | 6 |
| ATOM | 913 | CD | GLU | A | 116 | 46.872 | 34.982 | 64.420 | 1.00 | 43.09 | 6 |
| ATOM | 914 | OE1 | GLU | A | 116 | 47.072 | 35.886 | 65.267 | 1.00 | 43.42 | 8 |
| ATOM | 915 | OE2 | GLU | A | 116 | 47.802 | 34.369 | 63.849 | 1.00 | 41.76 | 8 |
| ATOM | 916 | C | GLU | A | 116 | 44.543 | 32.131 | 66.947 | 1.00 | 35.11 | 6 |
| ATOM | 917 | O | GLU | A | 116 | 45.054 | 32.228 | 68.061 | 1.00 | 37.26 | 8 |
| ATOM | 918 | N | PHE | A | 117 | 43.343 | 31.598 | 66.761 | 1.00 | 34.30 | 7 |
| ATOM | 919 | CA | PHE | A | 117 | 42.577 | 31.096 | 67.893 | 1.00 | 34.44 | 6 |
| ATOM | 920 | CB | PHE | A | 117 | 41.300 | 30.399 | 67.415 | 1.00 | 35.45 | 6 |
| ATOM | 921 | CG | PHE | A | 117 | 40.383 | 29.979 | 68.533 | 1.00 | 37.14 | 6 |
| ATOM | 922 | CD1 | PHE | A | 117 | 39.705 | 30.930 | 69.290 | 1.00 | 35.80 | 6 |
| ATOM | 923 | CD2 | PHE | A | 117 | 40.196 | 28.630 | 68.832 | 1.00 | 41.05 | 6 |
| ATOM | 924 | CE1 | PHE | A | 117 | 38.853 | 30.549 | 70.323 | 1.00 | 38.08 | 6 |

Fig. 17-14

| | | | | | | | | | |
|---|---|---|---|---|---|---|---|---|---|
| ATOM | 925 | CE2 | PHE A 117 | 39.338 | 28.234 | 69.874 | 1.00 | 40.44 | 6 |
| ATOM | 926 | CZ | PHE A 117 | 38.668 | 29.198 | 70.617 | 1.00 | 38.64 | 6 |
| ATOM | 927 | C | PHE A 117 | 43.424 | 30.094 | 68.669 | 1.00 | 34.24 | 6 |
| ATOM | 928 | O | PHE A 117 | 43.490 | 30.136 | 69.898 | 1.00 | 33.54 | 8 |
| ATOM | 929 | N | LEU A 118 | 44.069 | 29.194 | 67.933 | 1.00 | 33.14 | 7 |
| ATOM | 930 | CA | LEU A 118 | 44.898 | 28.158 | 68.523 | 1.00 | 32.62 | 6 |
| ATOM | 931 | CB | LEU A 118 | 45.155 | 27.056 | 67.488 | 1.00 | 30.59 | 6 |
| ATOM | 932 | CG | LEU A 118 | 43.900 | 26.297 | 67.038 | 1.00 | 27.87 | 6 |
| ATOM | 933 | CD1 | LEU A 118 | 44.244 | 25.232 | 65.996 | 1.00 | 20.81 | 6 |
| ATOM | 934 | CD2 | LEU A 118 | 43.259 | 25.662 | 68.257 | 1.00 | 28.37 | 6 |
| ATOM | 935 | C | LEU A 118 | 46.216 | 28.696 | 69.084 | 1.00 | 34.37 | 6 |
| ATOM | 936 | O | LEU A 118 | 46.983 | 27.964 | 69.708 | 1.00 | 36.15 | 8 |
| ATOM | 937 | N | LYS A 119 | 46.481 | 29.974 | 68.843 | 1.00 | 34.75 | 7 |
| ATOM | 938 | CA | LYS A 119 | 47.679 | 30.609 | 69.365 | 1.00 | 34.34 | 6 |
| ATOM | 939 | CB | LYS A 119 | 48.143 | 31.739 | 68.448 | 1.00 | 33.52 | 6 |
| ATOM | 940 | CG | LYS A 119 | 48.614 | 31.270 | 67.100 | 1.00 | 37.98 | 6 |
| ATOM | 941 | CD | LYS A 119 | 49.111 | 32.430 | 66.263 | 1.00 | 43.40 | 6 |
| ATOM | 942 | CE | LYS A 119 | 49.691 | 31.928 | 64.949 | 1.00 | 46.52 | 6 |
| ATOM | 943 | NZ | LYS A 119 | 50.167 | 33.050 | 64.092 | 1.00 | 51.48 | 7 |
| ATOM | 944 | C | LYS A 119 | 47.273 | 31.191 | 70.705 | 1.00 | 34.85 | 6 |
| ATOM | 945 | O | LYS A 119 | 48.112 | 31.465 | 71.562 | 1.00 | 38.12 | 8 |
| ATOM | 946 | N | GLY A 120 | 45.967 | 31.372 | 70.869 | 1.00 | 34.15 | 7 |
| ATOM | 947 | CA | GLY A 120 | 45.431 | 31.927 | 72.094 | 1.00 | 36.25 | 6 |
| ATOM | 948 | C | GLY A 120 | 44.860 | 33.310 | 71.851 | 1.00 | 39.02 | 6 |
| ATOM | 949 | O | GLY A 120 | 44.640 | 34.072 | 72.796 | 1.00 | 40.23 | 8 |
| ATOM | 950 | N | ASN A 121 | 44.619 | 33.644 | 70.586 | 1.00 | 38.48 | 7 |
| ATOM | 951 | CA | ASN A 121 | 44.079 | 34.956 | 70.247 | 1.00 | 37.47 | 6 |
| ATOM | 952 | CB | ASN A 121 | 44.928 | 35.624 | 69.170 | 1.00 | 39.57 | 6 |
| ATOM | 953 | CG | ASN A 121 | 46.340 | 35.871 | 69.622 | 1.00 | 41.81 | 6 |
| ATOM | 954 | OD1 | ASN A 121 | 47.078 | 34.938 | 69.926 | 1.00 | 47.67 | 8 |
| ATOM | 955 | ND2 | ASN A 121 | 46.727 | 37.134 | 69.675 | 1.00 | 43.63 | 7 |
| ATOM | 956 | C | ASN A 121 | 42.637 | 34.893 | 69.772 | 1.00 | 36.59 | 6 |
| ATOM | 957 | O | ASN A 121 | 42.037 | 33.818 | 69.704 | 1.00 | 34.08 | 8 |
| ATOM | 958 | N | VAL A 122 | 42.092 | 36.061 | 69.446 | 1.00 | 33.53 | 7 |
| ATOM | 959 | CA | VAL A 122 | 40.720 | 36.166 | 68.976 | 1.00 | 34.77 | 6 |
| ATOM | 960 | CB | VAL A 122 | 39.861 | 37.064 | 69.898 | 1.00 | 38.20 | 6 |
| ATOM | 961 | CG1 | VAL A 122 | 38.418 | 37.096 | 69.388 | 1.00 | 37.55 | 6 |
| ATOM | 962 | CG2 | VAL A 122 | 39.918 | 36.553 | 71.342 | 1.00 | 37.77 | 6 |
| ATOM | 963 | C | VAL A 122 | 40.731 | 36.781 | 67.596 | 1.00 | 31.08 | 6 |
| ATOM | 964 | O | VAL A 122 | 40.991 | 37.967 | 67.441 | 1.00 | 34.19 | 8 |
| ATOM | 965 | N | ALA A 123 | 40.451 | 35.975 | 66.588 | 1.00 | 31.14 | 7 |
| ATOM | 966 | CA | ALA A 123 | 40.451 | 36.476 | 65.231 | 1.00 | 30.26 | 6 |
| ATOM | 967 | CB | ALA A 123 | 41.307 | 35.588 | 64.327 | 1.00 | 32.14 | 6 |
| ATOM | 968 | C | ALA A 123 | 39.038 | 36.533 | 64.716 | 1.00 | 28.26 | 6 |
| ATOM | 969 | O | ALA A 123 | 38.132 | 35.924 | 65.281 | 1.00 | 29.28 | 8 |
| ATOM | 970 | N | PHE A 124 | 38.875 | 37.276 | 63.631 | 1.00 | 28.70 | 7 |
| ATOM | 971 | CA | PHE A 124 | 37.601 | 37.475 | 62.976 | 1.00 | 28.38 | 6 |
| ATOM | 972 | CB | PHE A 124 | 36.920 | 38.713 | 63.563 | 1.00 | 29.16 | 6 |
| ATOM | 973 | CG | PHE A 124 | 35.645 | 39.099 | 62.874 | 1.00 | 31.20 | 6 |
| ATOM | 974 | CD1 | PHE A 124 | 34.679 | 38.139 | 62.564 | 1.00 | 32.00 | 6 |
| ATOM | 975 | CD2 | PHE A 124 | 35.378 | 40.435 | 62.579 | 1.00 | 29.53 | 6 |
| ATOM | 976 | CE1 | PHE A 124 | 33.463 | 38.510 | 61.973 | 1.00 | 30.74 | 6 |
| ATOM | 977 | CE2 | PHE A 124 | 34.165 | 40.813 | 61.988 | 1.00 | 27.45 | 6 |
| ATOM | 978 | CZ | PHE A 124 | 33.207 | 39.847 | 61.686 | 1.00 | 28.72 | 6 |
| ATOM | 979 | C | PHE A 124 | 37.880 | 37.671 | 61.496 | 1.00 | 30.19 | 6 |
| ATOM | 980 | O | PHE A 124 | 38.427 | 38.695 | 61.095 | 1.00 | 32.10 | 8 |
| ATOM | 981 | N | ASN A 125 | 37.545 | 36.663 | 60.696 | 1.00 | 32.16 | 7 |
| ATOM | 982 | CA | ASN A 125 | 37.731 | 36.728 | 59.251 | 1.00 | 30.10 | 6 |
| ATOM | 983 | CB | ASN A 125 | 38.247 | 35.393 | 58.712 | 1.00 | 32.02 | 6 |
| ATOM | 984 | CG | ASN A 125 | 38.281 | 35.360 | 57.195 | 1.00 | 33.79 | 6 |
| ATOM | 985 | OD1 | ASN A 125 | 38.754 | 36.306 | 56.556 | 1.00 | 31.85 | 8 |
| ATOM | 986 | ND2 | ASN A 125 | 37.790 | 34.268 | 56.609 | 1.00 | 30.51 | 7 |
| ATOM | 987 | C | ASN A 125 | 36.403 | 37.083 | 58.584 | 1.00 | 29.80 | 6 |
| ATOM | 988 | O | ASN A 125 | 35.626 | 36.205 | 58.179 | 1.00 | 27.24 | 8 |
| ATOM | 989 | N | PRO A 126 | 36.135 | 38.386 | 58.451 | 1.00 | 28.25 | 7 |
| ATOM | 990 | CD | PRO A 126 | 36.997 | 39.516 | 58.833 | 1.00 | 29.22 | 6 |

Fig. 17-15

| | | | | | | | | | |
|---|---|---|---|---|---|---|---|---|---|
| ATOM | 991 | CA | PRO | A | 126 | 34.909 | 38.891 | 57.844 | 1.00 27.92 | 6 |
| ATOM | 992 | CB | PRO | A | 126 | 35.139 | 40.407 | 57.856 | 1.00 29.07 | 6 |
| ATOM | 993 | CG | PRO | A | 126 | 36.649 | 40.520 | 57.775 | 1.00 26.54 | 6 |
| ATOM | 994 | C | PRO | A | 126 | 34.651 | 38.339 | 56.448 | 1.00 27.54 | 6 |
| ATOM | 995 | O | PRO | A | 126 | 33.532 | 38.402 | 55.949 | 1.00 28.66 | 8 |
| ATOM | 996 | N | ALA | A | 127 | 35.687 | 37.795 | 55.820 | 1.00 26.99 | 7 |
| ATOM | 997 | CA | ALA | A | 127 | 35.548 | 37.244 | 54.477 | 1.00 26.54 | 6 |
| ATOM | 998 | CB | ALA | A | 127 | 36.822 | 37.505 | 53.684 | 1.00 22.43 | 6 |
| ATOM | 999 | C | ALA | A | 127 | 35.225 | 35.744 | 54.480 | 1.00 27.38 | 6 |
| ATOM | 1000 | O | ALA | A | 127 | 35.038 | 35.140 | 53.423 | 1.00 29.04 | 8 |
| ATOM | 1001 | N | GLY | A | 128 | 35.166 | 35.142 | 55.663 | 1.00 26.97 | 7 |
| ATOM | 1002 | CA | GLY | A | 128 | 34.874 | 33.724 | 55.737 | 1.00 25.65 | 6 |
| ATOM | 1003 | C | GLY | A | 128 | 33.389 | 33.486 | 55.880 | 1.00 26.17 | 6 |
| ATOM | 1004 | O | GLY | A | 128 | 32.600 | 34.428 | 55.804 | 1.00 27.39 | 8 |
| ATOM | 1005 | N | GLY | A | 129 | 32.998 | 32.234 | 56.083 | 1.00 23.87 | 7 |
| ATOM | 1006 | CA | GLY | A | 129 | 31.588 | 31.936 | 56.236 | 1.00 25.17 | 6 |
| ATOM | 1007 | C | GLY | A | 129 | 30.847 | 31.674 | 54.937 | 1.00 25.88 | 6 |
| ATOM | 1008 | O | GLY | A | 129 | 29.643 | 31.908 | 54.848 | 1.00 25.07 | 8 |
| ATOM | 1009 | N | MET | A | 130 | 31.566 | 31.198 | 53.927 | 1.00 25.69 | 7 |
| ATOM | 1010 | CA | MET | A | 130 | 30.981 | 30.872 | 52.622 | 1.00 26.48 | 6 |
| ATOM | 1011 | CB | MET | A | 130 | 32.103 | 30.907 | 51.567 | 1.00 28.53 | 6 |
| ATOM | 1012 | CG | MET | A | 130 | 32.795 | 32.288 | 51.467 | 1.00 26.54 | 6 |
| ATOM | 1013 | SD | MET | A | 130 | 34.413 | 32.366 | 50.613 | 1.00 26.29 | 16 |
| ATOM | 1014 | CE | MET | A | 130 | 34.080 | 31.512 | 49.062 | 1.00 25.85 | 6 |
| ATOM | 1015 | C | MET | A | 130 | 30.355 | 29.463 | 52.768 | 1.00 24.47 | 6 |
| ATOM | 1016 | O | MET | A | 130 | 30.761 | 28.502 | 52.113 | 1.00 17.67 | 8 |
| ATOM | 1017 | N | HIS | A | 131 | 29.347 | 29.389 | 53.636 | 1.00 23.28 | 7 |
| ATOM | 1018 | CA | HIS | A | 131 | 28.647 | 28.161 | 54.019 | 1.00 26.33 | 6 |
| ATOM | 1019 | CB | HIS | A | 131 | 27.685 | 28.485 | 55.180 | 1.00 26.98 | 6 |
| ATOM | 1020 | CG | HIS | A | 131 | 26.663 | 29.540 | 54.862 | 1.00 28.50 | 6 |
| ATOM | 1021 | CD2 | HIS | A | 131 | 26.225 | 30.030 | 53.677 | 1.00 28.65 | 6 |
| ATOM | 1022 | ND1 | HIS | A | 131 | 25.906 | 30.166 | 55.831 | 1.00 33.04 | 7 |
| ATOM | 1023 | CE1 | HIS | A | 131 | 25.051 | 30.995 | 55.259 | 1.00 27.75 | 6 |
| ATOM | 1024 | NE2 | HIS | A | 131 | 25.224 | 30.932 | 53.952 | 1.00 26.97 | 7 |
| ATOM | 1025 | C | HIS | A | 131 | 27.917 | 27.284 | 53.017 | 1.00 28.44 | 6 |
| ATOM | 1026 | O | HIS | A | 131 | 27.434 | 26.214 | 53.390 | 1.00 31.15 | 8 |
| ATOM | 1027 | N | HIS | A | 132 | 27.861 | 27.694 | 51.756 | 1.00 30.64 | 7 |
| ATOM | 1028 | CA | HIS | A | 132 | 27.111 | 26.938 | 50.746 | 1.00 28.71 | 6 |
| ATOM | 1029 | CB | HIS | A | 132 | 26.321 | 27.941 | 49.890 | 1.00 27.21 | 6 |
| ATOM | 1030 | CG | HIS | A | 132 | 25.408 | 28.819 | 50.693 | 1.00 28.83 | 6 |
| ATOM | 1031 | CD2 | HIS | A | 132 | 25.111 | 30.137 | 50.578 | 1.00 28.92 | 6 |
| ATOM | 1032 | ND1 | HIS | A | 132 | 24.686 | 28.360 | 51.773 | 1.00 31.80 | 7 |
| ATOM | 1033 | CE1 | HIS | A | 132 | 23.981 | 29.353 | 52.285 | 1.00 29.95 | 6 |
| ATOM | 1034 | NE2 | HIS | A | 132 | 24.222 | 30.443 | 51.579 | 1.00 28.21 | 7 |
| ATOM | 1035 | C | HIS | A | 132 | 27.889 | 25.970 | 49.851 | 1.00 28.51 | 6 |
| ATOM | 1036 | O | HIS | A | 132 | 27.399 | 24.375 | 49.533 | 1.00 23.44 | 8 |
| ATOM | 1037 | N | ALA | A | 133 | 29.093 | 26.379 | 49.455 | 1.00 27.94 | 7 |
| ATOM | 1038 | CA | ALA | A | 133 | 29.958 | 25.586 | 48.579 | 1.00 26.99 | 6 |
| ATOM | 1039 | CB | ALA | A | 133 | 31.295 | 26.303 | 48.392 | 1.00 21.87 | 6 |
| ATOM | 1040 | C | ALA | A | 133 | 30.199 | 24.164 | 49.078 | 1.00 26.69 | 6 |
| ATOM | 1041 | O | ALA | A | 133 | 30.703 | 23.973 | 50.182 | 1.00 28.25 | 8 |
| ATOM | 1042 | N | PHE | A | 134 | 29.850 | 23.174 | 48.255 | 1.00 26.73 | 7 |
| ATOM | 1043 | CA | PHE | A | 134 | 30.046 | 21.773 | 48.615 | 1.00 25.04 | 6 |
| ATOM | 1044 | CB | PHE | A | 134 | 29.070 | 20.855 | 47.875 | 1.00 19.20 | 6 |
| ATOM | 1045 | CG | PHE | A | 134 | 27.629 | 21.199 | 48.100 | 1.00 15.75 | 6 |
| ATOM | 1046 | CD1 | PHE | A | 134 | 26.929 | 21.960 | 47.169 | 1.00 14.83 | 6 |
| ATOM | 1047 | CD2 | PHE | A | 134 | 26.985 | 20.814 | 49.273 | 1.00 14.03 | 6 |
| ATOM | 1048 | CE1 | PHE | A | 134 | 25.614 | 22.336 | 47.404 | 1.00 14.84 | 6 |
| ATOM | 1049 | CE2 | PHE | A | 134 | 25.670 | 21.184 | 49.519 | 1.00 12.07 | 6 |
| ATOM | 1050 | CZ | PHE | A | 134 | 24.985 | 21.949 | 48.581 | 1.00 14.59 | 6 |
| ATOM | 1051 | C | PHE | A | 134 | 31.460 | 21.310 | 48.319 | 1.00 29.48 | 6 |
| ATOM | 1052 | O | PHE | A | 134 | 32.291 | 22.066 | 47.822 | 1.00 33.19 | 8 |
| ATOM | 1053 | N | LYS | A | 135 | 31.713 | 20.045 | 48.620 | 1.00 31.52 | 7 |
| ATOM | 1054 | CA | LYS | A | 135 | 33.012 | 19.427 | 48.427 | 1.00 29.15 | 6 |
| ATOM | 1055 | CB | LYS | A | 135 | 32.923 | 17.971 | 48.885 | 1.00 29.45 | 6 |
| ATOM | 1056 | CG | LYS | A | 135 | 34.152 | 17.131 | 48.638 | 1.00 32.46 | 6 |

Fig. 17-16

| | | | | | | | | | |
|---|---|---|---|---|---|---|---|---|---|
| ATOM | 1057 | CD | LYS | A 135 | 33.965 | 15.734 | 49.221 | 1.00 29.67 | 6 |
| ATOM | 1058 | CE | LYS | A 135 | 34.234 | 15.703 | 50.716 | 1.00 30.09 | 6 |
| ATOM | 1059 | NZ | LYS | A 135 | 35.679 | 15.973 | 51.001 | 1.00 26.25 | 7 |
| ATOM | 1060 | C | LYS | A 135 | 33.513 | 19.516 | 46.993 | 1.00 30.22 | 6 |
| ATOM | 1061 | O | LYS | A 135 | 34.714 | 19.672 | 46.763 | 1.00 30.00 | 8 |
| ATOM | 1062 | N | SER | A 136 | 32.600 | 19.434 | 46.028 | 1.00 31.69 | 7 |
| ATOM | 1063 | CA | SER | A 136 | 32.995 | 19.489 | 44.619 | 1.00 32.88 | 6 |
| ATOM | 1064 | CB | SER | A 136 | 33.038 | 18.077 | 44.040 | 1.00 31.41 | 6 |
| ATOM | 1065 | OG | SER | A 136 | 33.882 | 17.241 | 44.810 | 1.00 35.41 | 8 |
| ATOM | 1066 | C | SER | A 136 | 32.397 | 20.347 | 43.727 | 1.00 33.55 | 6 |
| ATOM | 1067 | O | SER | A 136 | 31.921 | 20.031 | 42.553 | 1.00 36.11 | 8 |
| ATOM | 1068 | N | ARG | A 137 | 31.536 | 21.425 | 44.262 | 1.00 30.61 | 7 |
| ATOM | 1069 | CA | ARG | A 137 | 30.664 | 22.272 | 43.459 | 1.00 32.28 | 6 |
| ATOM | 1070 | CB | ARG | A 137 | 29.324 | 21.554 | 43.202 | 1.00 35.91 | 6 |
| ATOM | 1071 | CG | ARG | A 137 | 28.224 | 22.458 | 42.627 | 1.00 43.90 | 6 |
| ATOM | 1072 | CD | ARG | A 137 | 26.819 | 21.836 | 42.751 | 1.00 48.28 | 6 |
| ATOM | 1073 | NE | ARG | A 137 | 26.571 | 20.767 | 41.787 | 1.00 53.38 | 7 |
| ATOM | 1074 | CZ | ARG | A 137 | 26.150 | 20.960 | 40.538 | 1.00 55.30 | 6 |
| ATOM | 1075 | NH1 | ARG | A 137 | 25.921 | 22.185 | 40.090 | 1.00 54.06 | 7 |
| ATOM | 1076 | NH2 | ARG | A 137 | 25.969 | 19.922 | 39.728 | 1.00 58.96 | 7 |
| ATOM | 1077 | C | ARG | A 137 | 30.405 | 23.631 | 44.113 | 1.00 30.24 | 6 |
| ATOM | 1078 | O | ARG | A 137 | 30.380 | 23.748 | 45.338 | 1.00 23.11 | 8 |
| ATOM | 1079 | N | ALA | A 138 | 30.219 | 24.653 | 43.279 | 1.00 27.33 | 7 |
| ATOM | 1080 | CA | ALA | A 138 | 29.944 | 26.000 | 43.757 | 1.00 27.36 | 6 |
| ATOM | 1081 | CB | ALA | A 138 | 30.149 | 26.997 | 42.645 | 1.00 27.57 | 6 |
| ATOM | 1082 | C | ALA | A 138 | 28.496 | 26.003 | 44.213 | 1.00 26.45 | 6 |
| ATOM | 1083 | O | ALA | A 138 | 27.747 | 25.083 | 43.865 | 1.00 27.30 | 8 |
| ATOM | 1084 | N | ASN | A 139 | 28.090 | 27.021 | 44.975 | 1.00 22.47 | 7 |
| ATOM | 1085 | CA | ASN | A 139 | 26.711 | 27.063 | 45.471 | 1.00 23.85 | 6 |
| ATOM | 1086 | CB | ASN | A 139 | 26.406 | 25.738 | 46.218 | 1.00 16.82 | 6 |
| ATOM | 1087 | CG | ASN | A 139 | 25.040 | 25.718 | 46.900 | 1.00 14.45 | 6 |
| ATOM | 1088 | OD1 | ASN | A 139 | 24.019 | 26.084 | 46.319 | 1.00 13.39 | 8 |
| ATOM | 1089 | ND2 | ASN | A 139 | 25.018 | 25.249 | 48.139 | 1.00 20.08 | 7 |
| ATOM | 1090 | C | ASN | A 139 | 26.444 | 28.277 | 46.368 | 1.00 26.09 | 6 |
| ATOM | 1091 | O | ASN | A 139 | 27.239 | 28.600 | 47.260 | 1.00 27.50 | 8 |
| ATOM | 1092 | N | GLY | A 140 | 25.326 | 28.954 | 46.114 | 1.00 24.83 | 7 |
| ATOM | 1093 | CA | GLY | A 140 | 24.965 | 30.106 | 46.916 | 1.00 22.24 | 6 |
| ATOM | 1094 | C | GLY | A 140 | 25.991 | 31.211 | 46.890 | 1.00 22.35 | 6 |
| ATOM | 1095 | O | GLY | A 140 | 26.256 | 31.843 | 47.910 | 1.00 23.50 | 8 |
| ATOM | 1096 | N | PHE | A 141 | 26.570 | 31.437 | 45.717 | 1.00 25.60 | 7 |
| ATOM | 1097 | CA | PHE | A 141 | 27.582 | 32.476 | 45.518 | 1.00 26.47 | 6 |
| ATOM | 1098 | CB | PHE | A 141 | 27.204 | 33.765 | 46.258 | 1.00 28.05 | 6 |
| ATOM | 1099 | CG | PHE | A 141 | 25.925 | 34.391 | 45.792 | 1.00 28.61 | 6 |
| ATOM | 1100 | CD1 | PHE | A 141 | 25.352 | 35.428 | 46.518 | 1.00 30.74 | 6 |
| ATOM | 1101 | CD2 | PHE | A 141 | 25.312 | 33.975 | 44.620 | 1.00 29.10 | 6 |
| ATOM | 1102 | CE1 | PHE | A 141 | 24.193 | 36.044 | 46.087 | 1.00 29.33 | 6 |
| ATOM | 1103 | CE2 | PHE | A 141 | 24.150 | 34.583 | 44.177 | 1.00 31.03 | 6 |
| ATOM | 1104 | CZ | PHE | A 141 | 23.589 | 35.621 | 44.912 | 1.00 32.59 | 6 |
| ATOM | 1105 | C | PHE | A 141 | 28.954 | 32.038 | 45.991 | 1.00 24.63 | 6 |
| ATOM | 1106 | O | PHE | A 141 | 29.938 | 32.727 | 45.733 | 1.00 29.72 | 8 |
| ATOM | 1107 | N | CYS | A 142 | 29.025 | 30.897 | 46.667 | 1.00 21.11 | 7 |
| ATOM | 1108 | CA | CYS | A 142 | 30.296 | 30.399 | 47.192 | 1.00 22.30 | 6 |
| ATOM | 1109 | CB | CYS | A 142 | 30.062 | 29.787 | 48.567 | 1.00 21.31 | 6 |
| ATOM | 1110 | SG | CYS | A 142 | 28.943 | 30.748 | 49.582 | 1.00 22.93 | 16 |
| ATOM | 1111 | C | CYS | A 142 | 31.017 | 29.366 | 46.326 | 1.00 22.13 | 6 |
| ATOM | 1112 | O | CYS | A 142 | 30.408 | 28.389 | 45.878 | 1.00 22.97 | 8 |
| ATOM | 1113 | N | TYR | A 143 | 32.317 | 29.573 | 46.111 | 1.00 23.09 | 7 |
| ATOM | 1114 | CA | TYR | A 143 | 33.129 | 28.632 | 45.335 | 1.00 23.05 | 6 |
| ATOM | 1115 | CB | TYR | A 143 | 34.063 | 29.365 | 44.375 | 1.00 21.60 | 6 |
| ATOM | 1116 | CG | TYR | A 143 | 33.377 | 30.379 | 43.487 | 1.00 24.09 | 6 |
| ATOM | 1117 | CD1 | TYR | A 143 | 32.969 | 31.609 | 43.999 | 1.00 23.29 | 6 |
| ATOM | 1118 | CE1 | TYR | A 143 | 32.365 | 32.555 | 43.199 | 1.00 23.26 | 6 |
| ATOM | 1119 | CD2 | TYR | A 143 | 33.154 | 30.117 | 42.135 | 1.00 22.52 | 6 |
| ATOM | 1120 | CE2 | TYR | A 143 | 32.544 | 31.061 | 41.317 | 1.00 24.82 | 6 |
| ATOM | 1121 | CZ | TYR | A 143 | 32.153 | 32.281 | 41.857 | 1.00 27.55 | 6 |
| ATOM | 1122 | OH | TYR | A 143 | 31.553 | 33.241 | 41.064 | 1.00 32.35 | 8 |

Fig. 17-17

| | | | | | | | | | |
|---|---|---|---|---|---|---|---|---|---|
| ATOM | 1123 | C | TYR | A | 143 | 33.960 | 27.766 | 46.290 | 1.00 24.22 6 |
| ATOM | 1124 | O | TYR | A | 143 | 34.266 | 26.606 | 45.998 | 1.00 24.58 8 |
| ATOM | 1125 | N | ILE | A | 144 | 34.327 | 28.329 | 47.437 | 1.00 23.83 7 |
| ATOM | 1126 | CA | ILE | A | 144 | 35.086 | 27.566 | 48.425 | 1.00 20.24 6 |
| ATOM | 1127 | CB | ILE | A | 144 | 36.547 | 27.982 | 48.453 | 1.00 17.27 6 |
| ATOM | 1128 | CG2 | ILE | A | 144 | 37.231 | 27.354 | 49.662 | 1.00 11.03 6 |
| ATOM | 1129 | CG1 | ILE | A | 144 | 37.185 | 27.603 | 47.110 | 1.00 14.93 6 |
| ATOM | 1130 | CD1 | ILE | A | 144 | 38.601 | 28.028 | 46.946 | 1.00 19.68 6 |
| ATOM | 1131 | C | ILE | A | 144 | 34.495 | 27.703 | 49.815 | 1.00 21.77 6 |
| ATOM | 1132 | O | ILE | A | 144 | 34.288 | 28.811 | 50.318 | 1.00 21.19 8 |
| ATOM | 1133 | N | ASN | A | 145 | 34.212 | 26.555 | 50.424 | 1.00 23.00 7 |
| ATOM | 1134 | CA | ASN | A | 145 | 33.616 | 26.508 | 51.750 | 1.00 20.92 6 |
| ATOM | 1135 | CB | ASN | A | 145 | 32.902 | 25.170 | 51.935 | 1.00 17.08 6 |
| ATOM | 1136 | CG | ASN | A | 145 | 32.079 | 25.125 | 53.203 | 1.00 21.04 6 |
| ATOM | 1137 | OD1 | ASN | A | 145 | 32.549 | 25.508 | 54.276 | 1.00 20.97 8 |
| ATOM | 1138 | ND2 | ASN | A | 145 | 30.844 | 24.640 | 53.093 | 1.00 20.93 7 |
| ATOM | 1139 | C | ASN | A | 145 | 34.706 | 26.669 | 52.806 | 1.00 19.68 6 |
| ATOM | 1140 | O | ASN | A | 145 | 35.201 | 25.679 | 53.351 | 1.00 20.64 8 |
| ATOM | 1141 | N | ASN | A | 146 | 35.079 | 27.911 | 53.100 | 1.00 16.28 7 |
| ATOM | 1142 | CA | ASN | A | 146 | 36.123 | 28.143 | 54.088 | 1.00 19.34 6 |
| ATOM | 1143 | CB | ASN | A | 146 | 36.428 | 29.651 | 54.207 | 1.00 20.27 6 |
| ATOM | 1144 | CG | ASN | A | 146 | 35.292 | 30.444 | 54.795 | 1.00 18.05 6 |
| ATOM | 1145 | OD1 | ASN | A | 146 | 35.079 | 30.421 | 55.999 | 1.00 25.83 8 |
| ATOM | 1146 | ND2 | ASN | A | 146 | 34.552 | 31.149 | 53.948 | 1.00 16.04 7 |
| ATOM | 1147 | C | ASN | A | 146 | 35.775 | 27.504 | 55.443 | 1.00 20.48 6 |
| ATOM | 1148 | O | ASN | A | 146 | 36.663 | 27.027 | 56.151 | 1.00 19.88 8 |
| ATOM | 1149 | N | PRO | A | 147 | 34.482 | 27.485 | 55.819 | 1.00 19.38 7 |
| ATOM | 1150 | CD | PRO | A | 147 | 33.312 | 28.068 | 55.135 | 1.00 17.48 6 |
| ATOM | 1151 | CA | PRO | A | 147 | 34.058 | 26.877 | 57.087 | 1.00 22.25 6 |
| ATOM | 1152 | CB | PRO | A | 147 | 32.539 | 27.065 | 57.057 | 1.00 20.15 6 |
| ATOM | 1153 | CG | PRO | A | 147 | 32.407 | 28.378 | 56.305 | 1.00 20.81 6 |
| ATOM | 1154 | C | PRO | A | 147 | 34.443 | 25.383 | 57.188 | 1.00 26.89 6 |
| ATOM | 1155 | O | PRO | A | 147 | 35.066 | 24.954 | 58.169 | 1.00 29.10 8 |
| ATOM | 1156 | N | ALA | A | 148 | 34.070 | 24.596 | 56.176 | 1.00 25.88 7 |
| ATOM | 1157 | CA | ALA | A | 148 | 34.372 | 23.164 | 56.174 | 1.00 25.47 6 |
| ATOM | 1158 | CB | ALA | A | 148 | 33.670 | 22.468 | 55.009 | 1.00 21.84 6 |
| ATOM | 1159 | C | ALA | A | 148 | 35.870 | 22.916 | 56.100 | 1.00 25.94 6 |
| ATOM | 1160 | O | ALA | A | 148 | 36.382 | 21.971 | 56.701 | 1.00 27.19 8 |
| ATOM | 1161 | N | VAL | A | 149 | 36.574 | 23.756 | 55.349 | 1.00 26.11 7 |
| ATOM | 1162 | CA | VAL | A | 149 | 38.017 | 23.609 | 55.233 | 1.00 24.04 6 |
| ATOM | 1163 | CB | VAL | A | 149 | 38.622 | 24.663 | 54.267 | 1.00 26.16 6 |
| ATOM | 1164 | CG1 | VAL | A | 149 | 40.135 | 24.476 | 54.158 | 1.00 25.36 6 |
| ATOM | 1165 | CG2 | VAL | A | 149 | 37.970 | 24.544 | 52.886 | 1.00 26.81 6 |
| ATOM | 1166 | C | VAL | A | 149 | 38.516 | 23.870 | 56.640 | 1.00 23.57 6 |
| ATOM | 1167 | O | VAL | A | 149 | 39.453 | 23.228 | 57.122 | 1.00 19.75 8 |
| ATOM | 1168 | N | GLY | A | 150 | 37.850 | 24.815 | 57.299 | 1.00 22.20 7 |
| ATOM | 1169 | CA | GLY | A | 150 | 38.210 | 25.175 | 58.654 | 1.00 25.43 6 |
| ATOM | 1170 | C | GLY | A | 150 | 38.130 | 23.975 | 59.568 | 1.00 27.19 6 |
| ATOM | 1171 | O | GLY | A | 150 | 39.112 | 23.620 | 60.221 | 1.00 27.05 8 |
| ATOM | 1172 | N | ILE | A | 151 | 36.959 | 23.348 | 59.618 | 1.00 25.56 7 |
| ATOM | 1173 | CA | ILE | A | 151 | 36.775 | 22.176 | 60.457 | 1.00 28.24 6 |
| ATOM | 1174 | CB | ILE | A | 151 | 35.317 | 21.654 | 60.389 | 1.00 29.41 6 |
| ATOM | 1175 | CG2 | ILE | A | 151 | 35.251 | 20.215 | 60.869 | 1.00 26.02 6 |
| ATOM | 1176 | CG1 | ILE | A | 151 | 34.394 | 22.540 | 61.240 | 1.00 33.31 6 |
| ATOM | 1177 | CD1 | ILE | A | 151 | 34.255 | 23.967 | 60.759 | 1.00 36.83 6 |
| ATOM | 1178 | C | ILE | A | 151 | 37.723 | 21.039 | 60.075 | 1.00 29.32 6 |
| ATOM | 1179 | O | ILE | A | 151 | 38.340 | 20.420 | 60.947 | 1.00 29.08 8 |
| ATOM | 1180 | N | GLU | A | 152 | 37.843 | 20.769 | 58.778 | 1.00 29.91 7 |
| ATOM | 1181 | CA | GLU | A | 152 | 38.704 | 19.690 | 58.315 | 1.00 32.58 6 |
| ATOM | 1182 | CB | GLU | A | 152 | 38.575 | 19.526 | 56.802 | 1.00 35.07 6 |
| ATOM | 1183 | CG | GLU | A | 152 | 37.269 | 18.848 | 56.393 | 1.00 38.51 6 |
| ATOM | 1184 | CD | GLU | A | 152 | 37.120 | 17.440 | 56.987 | 1.00 41.41 6 |
| ATOM | 1185 | OE1 | GLU | A | 152 | 36.089 | 16.779 | 56.718 | 1.00 45.64 8 |
| ATOM | 1186 | OE2 | GLU | A | 152 | 38.030 | 16.992 | 57.723 | 1.00 40.09 8 |
| ATOM | 1187 | C | GLU | A | 152 | 40.145 | 19.903 | 58.721 | 1.00 32.97 6 |
| ATOM | 1188 | O | GLU | A | 152 | 40.879 | 18.946 | 58.978 | 1.00 30.15 8 |

Fig. 17-18

| | | | | | | | | | |
|---|---|---|---|---|---|---|---|---|---|
| ATOM | 1189 | N | TYR | A | 153 | 40.541 | 21.170 | 58.765 | 1.00 33.90 | 7 |
| ATOM | 1190 | CA | TYR | A | 153 | 41.875 | 21.563 | 59.193 | 1.00 32.04 | 6 |
| ATOM | 1191 | CB | TYR | A | 153 | 42.019 | 23.074 | 59.058 | 1.00 34.88 | 6 |
| ATOM | 1192 | CG | TYR | A | 153 | 43.280 | 23.667 | 59.639 | 1.00 38.03 | 6 |
| ATOM | 1193 | CD1 | TYR | A | 153 | 44.498 | 23.611 | 58.948 | 1.00 42.34 | 6 |
| ATOM | 1194 | CE1 | TYR | A | 153 | 45.658 | 24.207 | 59.475 | 1.00 43.38 | 6 |
| ATOM | 1195 | CD2 | TYR | A | 153 | 43.250 | 24.321 | 60.869 | 1.00 37.19 | 6 |
| ATOM | 1196 | CE2 | TYR | A | 153 | 44.387 | 24.913 | 61.401 | 1.00 41.09 | 6 |
| ATOM | 1197 | CZ | TYR | A | 153 | 45.587 | 24.860 | 60.704 | 1.00 43.34 | 6 |
| ATOM | 1198 | OH | TYR | A | 153 | 46.696 | 25.480 | 61.241 | 1.00 44.86 | 8 |
| ATOM | 1199 | C | TYR | A | 153 | 41.919 | 21.168 | 60.667 | 1.00 32.59 | 6 |
| ATOM | 1200 | O | TYR | A | 153 | 42.867 | 20.518 | 61.120 | 1.00 32.24 | 8 |
| ATOM | 1201 | N | LEU | A | 154 | 40.869 | 21.556 | 61.397 | 1.00 30.10 | 7 |
| ATOM | 1202 | CA | LEU | A | 154 | 40.730 | 21.261 | 62.823 | 1.00 29.38 | 6 |
| ATOM | 1203 | CB | LEU | A | 154 | 39.443 | 21.889 | 63.378 | 1.00 28.60 | 6 |
| ATOM | 1204 | CG | LEU | A | 154 | 39.399 | 23.407 | 63.618 | 1.00 31.20 | 6 |
| ATOM | 1205 | CD1 | LEU | A | 154 | 37.991 | 23.833 | 64.041 | 1.00 28.53 | 6 |
| ATOM | 1206 | CD2 | LEU | A | 154 | 40.418 | 23.787 | 64.691 | 1.00 24.95 | 6 |
| ATOM | 1207 | C | LEU | A | 154 | 40.732 | 19.772 | 63.146 | 1.00 29.56 | 6 |
| ATOM | 1208 | O | LEU | A | 154 | 41.223 | 19.363 | 64.196 | 1.00 28.36 | 8 |
| ATOM | 1209 | N | ARG | A | 155 | 40.174 | 18.958 | 62.256 | 1.00 31.95 | 7 |
| ATOM | 1210 | CA | ARG | A | 155 | 40.134 | 17.522 | 62.499 | 1.00 33.00 | 6 |
| ATOM | 1211 | CB | ARG | A | 155 | 39.127 | 16.847 | 61.561 | 1.00 33.13 | 6 |
| ATOM | 1212 | CG | ARG | A | 155 | 37.708 | 17.368 | 61.769 | 1.00 32.84 | 6 |
| ATOM | 1213 | CD | ARG | A | 155 | 36.678 | 16.719 | 60.863 | 1.00 32.92 | 6 |
| ATOM | 1214 | NE | ARG | A | 155 | 36.152 | 15.451 | 61.363 | 1.00 33.98 | 7 |
| ATOM | 1215 | CZ | ARG | A | 155 | 35.195 | 14.760 | 60.741 | 1.00 37.93 | 6 |
| ATOM | 1216 | NH1 | ARG | A | 155 | 34.671 | 15.215 | 59.605 | 1.00 38.39 | 7 |
| ATOM | 1217 | NH2 | ARG | A | 155 | 34.732 | 13.631 | 61.259 | 1.00 38.67 | 7 |
| ATOM | 1218 | C | ARG | A | 155 | 41.521 | 16.929 | 62.331 | 1.00 33.97 | 6 |
| ATOM | 1219 | O | ARG | A | 155 | 41.869 | 15.941 | 62.965 | 1.00 32.95 | 8 |
| ATOM | 1220 | N | LYS | A | 156 | 42.318 | 17.548 | 61.467 | 1.00 34.20 | 7 |
| ATOM | 1221 | CA | LYS | A | 156 | 43.679 | 17.081 | 61.243 | 1.00 36.32 | 6 |
| ATOM | 1222 | CB | LYS | A | 156 | 44.249 | 17.662 | 59.942 | 1.00 37.57 | 6 |
| ATOM | 1223 | CG | LYS | A | 156 | 45.673 | 17.187 | 59.638 | 1.00 40.32 | 6 |
| ATOM | 1224 | CD | LYS | A | 156 | 46.116 | 17.532 | 58.220 | 1.00 40.33 | 6 |
| ATOM | 1225 | CE | LYS | A | 156 | 45.180 | 16.909 | 57.184 | 1.00 41.27 | 6 |
| ATOM | 1226 | NZ | LYS | A | 156 | 45.015 | 15.435 | 57.364 | 1.00 37.92 | 7 |
| ATOM | 1227 | C | LYS | A | 156 | 44.539 | 17.501 | 62.428 | 1.00 36.17 | 6 |
| ATOM | 1228 | O | LYS | A | 156 | 45.582 | 16.905 | 62.699 | 1.00 34.53 | 8 |
| ATOM | 1229 | N | LYS | A | 157 | 44.093 | 18.537 | 63.132 | 1.00 36.71 | 7 |
| ATOM | 1230 | CA | LYS | A | 157 | 44.820 | 19.026 | 64.294 | 1.00 37.09 | 6 |
| ATOM | 1231 | CB | LYS | A | 157 | 44.495 | 20.501 | 64.566 | 1.00 37.02 | 6 |
| ATOM | 1232 | CG | LYS | A | 157 | 44.982 | 21.435 | 63.477 | 1.00 36.22 | 6 |
| ATOM | 1233 | CD | LYS | A | 157 | 46.468 | 21.231 | 63.239 | 1.00 37.91 | 6 |
| ATOM | 1234 | CE | LYS | A | 157 | 46.993 | 22.100 | 62.107 | 1.00 39.35 | 6 |
| ATOM | 1235 | NZ | LYS | A | 157 | 48.434 | 21.815 | 61.842 | 1.00 38.78 | 7 |
| ATOM | 1236 | C | LYS | A | 157 | 44.498 | 18.178 | 65.515 | 1.00 35.61 | 6 |
| ATOM | 1237 | O | LYS | A | 157 | 45.204 | 18.232 | 66.518 | 1.00 36.38 | 8 |
| ATOM | 1238 | N | GLY | A | 158 | 43.433 | 17.392 | 65.431 | 1.00 34.37 | 7 |
| ATOM | 1239 | CA | GLY | A | 158 | 43.097 | 16.537 | 66.552 | 1.00 38.08 | 6 |
| ATOM | 1240 | C | GLY | A | 158 | 41.782 | 16.781 | 67.267 | 1.00 38.78 | 6 |
| ATOM | 1241 | O | GLY | A | 158 | 41.460 | 16.053 | 68.208 | 1.00 41.07 | 8 |
| ATOM | 1242 | N | PHE | A | 159 | 41.023 | 17.791 | 66.855 | 1.00 36.75 | 7 |
| ATOM | 1243 | CA | PHE | A | 159 | 39.743 | 18.046 | 67.505 | 1.00 33.83 | 6 |
| ATOM | 1244 | CB | PHE | A | 159 | 39.246 | 19.459 | 67.213 | 1.00 32.65 | 6 |
| ATOM | 1245 | CG | PHE | A | 159 | 40.115 | 20.521 | 57.787 | 1.00 29.97 | 6 |
| ATOM | 1246 | CD1 | PHE | A | 159 | 41.404 | 20.724 | 67.297 | 1.00 30.20 | 6 |
| ATOM | 1247 | CD2 | PHE | A | 159 | 39.672 | 21.289 | 68.853 | 1.00 29.28 | 6 |
| ATOM | 1248 | CE1 | PHE | A | 159 | 42.241 | 21.680 | 67.862 | 1.00 28.96 | 6 |
| ATOM | 1249 | CE2 | PHE | A | 159 | 40.498 | 22.246 | 69.428 | 1.00 29.67 | 5 |
| ATOM | 1250 | CZ | PHE | A | 159 | 41.785 | 22.442 | 68.931 | 1.00 30.59 | 6 |
| ATOM | 1251 | C | PHE | A | 159 | 38.732 | 17.026 | 67.025 | 1.00 33.41 | 6 |
| ATOM | 1252 | O | PHE | A | 159 | 38.664 | 16.716 | 65.838 | 1.00 31.61 | 8 |
| ATOM | 1253 | N | LYS | A | 160 | 37.951 | 16.506 | 67.966 | 1.00 35.13 | 7 |
| ATOM | 1254 | CA | LYS | A | 160 | 36.947 | 15.493 | 67.677 | 1.00 35.39 | 6 |

Fig. 17-19

| | | | | | | | | | |
|---|---|---|---|---|---|---|---|---|---|
| ATOM | 1255 | CB | LYS | A | 160 | 37.342 | 14.198 | 68.389 | 1.00 36.43 | 6 |
| ATOM | 1256 | CG | LYS | A | 160 | 38.535 | 13.502 | 67.708 | 1.00 40.67 | 6 |
| ATOM | 1257 | CD | LYS | A | 160 | 39.312 | 12.538 | 68.615 | 1.00 44.68 | 6 |
| ATOM | 1258 | CE | LYS | A | 160 | 38.425 | 11.536 | 69.345 | 1.00 49.23 | 6 |
| ATOM | 1259 | NZ | LYS | A | 160 | 37.593 | 12.182 | 70.411 | 1.00 50.63 | 7 |
| ATOM | 1260 | C | LYS | A | 160 | 35.524 | 15.927 | 68.027 | 1.00 35.94 | 6 |
| ATOM | 1261 | O | LYS | A | 160 | 34.561 | 15.241 | 67.691 | 1.00 35.72 | 8 |
| ATOM | 1262 | N | ARG | A | 161 | 35.399 | 17.058 | 68.718 | 1.00 34.35 | 7 |
| ATOM | 1263 | CA | ARG | A | 161 | 34.091 | 17.618 | 69.044 | 1.00 34.95 | 6 |
| ATOM | 1264 | CB | ARG | A | 161 | 33.771 | 17.525 | 70.535 | 1.00 33.94 | 6 |
| ATOM | 1265 | CG | ARG | A | 161 | 33.427 | 16.132 | 70.992 | 1.00 38.25 | 6 |
| ATOM | 1266 | CD | ARG | A | 161 | 32.823 | 16.131 | 72.386 | 1.00 41.17 | 6 |
| ATOM | 1267 | NE | ARG | A | 161 | 33.719 | 16.722 | 73.378 | 1.00 47.64 | 7 |
| ATOM | 1268 | CZ | ARG | A | 161 | 34.912 | 16.233 | 73.705 | 1.00 47.92 | 6 |
| ATOM | 1269 | NH1 | ARG | A | 161 | 35.372 | 15.131 | 73.121 | 1.00 47.56 | 7 |
| ATOM | 1270 | NH2 | ARG | A | 161 | 35.648 | 16.858 | 74.616 | 1.00 46.95 | 7 |
| ATOM | 1271 | C | ARG | A | 161 | 34.113 | 19.076 | 68.598 | 1.00 34.58 | 6 |
| ATOM | 1272 | O | ARG | A | 161 | 34.468 | 19.980 | 69.357 | 1.00 33.77 | 8 |
| ATOM | 1273 | N | ILE | A | 162 | 33.741 | 19.280 | 67.341 | 1.00 31.74 | 7 |
| ATOM | 1274 | CA | ILE | A | 162 | 33.735 | 20.594 | 66.735 | 1.00 29.83 | 6 |
| ATOM | 1275 | CB | ILE | A | 162 | 34.429 | 20.542 | 65.362 | 1.00 29.96 | 6 |
| ATOM | 1276 | CG2 | ILE | A | 162 | 34.580 | 21.942 | 64.784 | 1.00 30.57 | 6 |
| ATOM | 1277 | CG1 | ILE | A | 162 | 35.801 | 19.891 | 65.522 | 1.00 28.81 | 6 |
| ATOM | 1278 | CD1 | ILE | A | 162 | 36.537 | 19.685 | 64.224 | 1.00 33.05 | 6 |
| ATOM | 1279 | C | ILE | A | 162 | 32.300 | 21.050 | 66.560 | 1.00 29.66 | 6 |
| ATOM | 1280 | O | ILE | A | 162 | 31.416 | 20.241 | 66.266 | 1.00 25.24 | 8 |
| ATOM | 1281 | N | LEU | A | 163 | 32.081 | 22.351 | 66.745 | 1.00 30.00 | 7 |
| ATOM | 1282 | CA | LEU | A | 163 | 30.754 | 22.945 | 66.617 | 1.00 30.48 | 6 |
| ATOM | 1283 | CB | LEU | A | 163 | 30.236 | 23.406 | 67.992 | 1.00 32.25 | 6 |
| ATOM | 1284 | CG | LEU | A | 163 | 28.934 | 24.229 | 68.044 | 1.00 31.21 | 6 |
| ATOM | 1285 | CD1 | LEU | A | 163 | 27.804 | 23.494 | 67.326 | 1.00 31.58 | 6 |
| ATOM | 1286 | CD2 | LEU | A | 163 | 28.569 | 24.502 | 69.493 | 1.00 25.00 | 6 |
| ATOM | 1287 | C | LEU | A | 163 | 30.717 | 24.122 | 65.659 | 1.00 29.23 | 6 |
| ATOM | 1288 | O | LEU | A | 163 | 31.596 | 24.980 | 65.654 | 1.00 29.72 | 8 |
| ATOM | 1289 | N | TYR | A | 164 | 29.675 | 24.157 | 64.846 | 1.00 29.68 | 7 |
| ATOM | 1290 | CA | TYR | A | 164 | 29.500 | 25.244 | 63.899 | 1.00 29.89 | 6 |
| ATOM | 1291 | CB | TYR | A | 164 | 29.512 | 24.688 | 62.470 | 1.00 27.81 | 6 |
| ATOM | 1292 | CG | TYR | A | 164 | 29.377 | 25.742 | 61.399 | 1.00 27.79 | 6 |
| ATOM | 1293 | CD1 | TYR | A | 164 | 30.390 | 26.670 | 61.168 | 1.00 24.82 | 6 |
| ATOM | 1294 | CE1 | TYR | A | 164 | 30.247 | 27.655 | 60.198 | 1.00 24.51 | 6 |
| ATOM | 1295 | CD2 | TYR | A | 164 | 28.216 | 25.827 | 60.631 | 1.00 27.61 | 6 |
| ATOM | 1296 | CE2 | TYR | A | 164 | 28.065 | 26.808 | 59.662 | 1.00 25.67 | 6 |
| ATOM | 1297 | CZ | TYR | A | 164 | 29.078 | 27.718 | 59.451 | 1.00 25.63 | 6 |
| ATOM | 1298 | OH | TYR | A | 164 | 28.898 | 28.704 | 58.506 | 1.00 27.10 | 8 |
| ATOM | 1299 | C | TYR | A | 164 | 28.149 | 25.907 | 64.218 | 1.00 28.38 | 6 |
| ATOM | 1300 | O | TYR | A | 164 | 27.119 | 25.225 | 64.277 | 1.00 29.43 | 8 |
| ATOM | 1301 | N | ILE | A | 165 | 28.166 | 27.217 | 64.464 | 1.00 24.30 | 7 |
| ATOM | 1302 | CA | ILE | A | 165 | 26.941 | 27.969 | 64.754 | 1.00 22.93 | 6 |
| ATOM | 1303 | CB | ILE | A | 165 | 26.985 | 28.649 | 66.143 | 1.00 22.00 | 6 |
| ATOM | 1304 | CG2 | ILE | A | 165 | 25.765 | 29.559 | 66.312 | 1.00 16.15 | 6 |
| ATOM | 1305 | CG1 | ILE | A | 165 | 27.033 | 27.567 | 67.240 | 1.00 20.78 | 6 |
| ATOM | 1306 | CD1 | ILE | A | 165 | 27.185 | 28.101 | 68.650 | 1.00 15.49 | 6 |
| ATOM | 1307 | C | ILE | A | 165 | 26.784 | 29.010 | 63.657 | 1.00 24.45 | 6 |
| ATOM | 1308 | O | ILE | A | 165 | 27.605 | 29.921 | 63.506 | 1.00 23.17 | 8 |
| ATOM | 1309 | N | ASP | A | 166 | 25.709 | 28.871 | 62.895 | 1.00 24.20 | 7 |
| ATOM | 1310 | CA | ASP | A | 166 | 25.478 | 29.726 | 61.749 | 1.00 20.78 | 6 |
| ATOM | 1311 | CB | ASP | A | 166 | 25.314 | 28.809 | 60.548 | 1.00 17.64 | 6 |
| ATOM | 1312 | CG | ASP | A | 166 | 25.410 | 29.529 | 59.256 | 1.00 19.93 | 6 |
| ATOM | 1313 | OD1 | ASP | A | 166 | 24.536 | 30.391 | 59.004 | 1.00 20.20 | 8 |
| ATOM | 1314 | OD2 | ASP | A | 166 | 26.366 | 29.231 | 58.491 | 1.00 17.64 | 8 |
| ATOM | 1315 | C | ASP | A | 166 | 24.290 | 30.670 | 61.895 | 1.00 22.79 | 6 |
| ATOM | 1316 | O | ASP | A | 166 | 23.134 | 30.256 | 61.826 | 1.00 22.70 | 8 |
| ATOM | 1317 | N | LEU | A | 167 | 24.583 | 31.952 | 62.085 | 1.00 26.40 | 7 |
| ATOM | 1318 | CA | LEU | A | 167 | 23.536 | 32.954 | 62.250 | 1.00 25.76 | 6 |
| ATOM | 1319 | CB | LEU | A | 167 | 23.963 | 33.991 | 63.288 | 1.00 26.65 | 6 |
| ATOM | 1320 | CG | LEU | A | 167 | 24.364 | 33.463 | 64.674 | 1.00 26.75 | 6 |

Fig. 17-20

| | | | | | | | | | |
|---|---|---|---|---|---|---|---|---|---|
| ATOM | 1321 | CD1 | LEU | A | 167 | 24.741 | 34.647 | 65.552 | 1.00 26.24 | 6 |
| ATOM | 1322 | CD2 | LEU | A | 167 | 23.225 | 32.661 | 65.302 | 1.00 23.45 | 6 |
| ATOM | 1323 | C | LEU | A | 167 | 23.162 | 33.660 | 60.951 | 1.00 26.37 | 6 |
| ATOM | 1324 | O | LEU | A | 167 | 22.386 | 34.613 | 60.971 | 1.00 25.95 | 8 |
| ATOM | 1325 | N | ASP | A | 168 | 23.726 | 33.208 | 59.828 | 1.00 29.66 | 7 |
| ATOM | 1326 | CA | ASP | A | 168 | 23.410 | 33.787 | 58.520 | 1.00 28.35 | 6 |
| ATOM | 1327 | CB | ASP | A | 168 | 24.057 | 32.987 | 57.390 | 1.00 33.29 | 6 |
| ATOM | 1328 | CG | ASP | A | 168 | 23.937 | 33.676 | 56.037 | 1.00 35.38 | 6 |
| ATOM | 1329 | OD1 | ASP | A | 168 | 24.892 | 34.388 | 55.659 | 1.00 39.48 | 8 |
| ATOM | 1330 | OD2 | ASP | A | 168 | 22.893 | 33.531 | 55.364 | 1.00 33.40 | 8 |
| ATOM | 1331 | C | ASP | A | 168 | 21.906 | 33.614 | 58.408 | 1.00 28.74 | 6 |
| ATOM | 1332 | O | ASP | A | 168 | 21.354 | 32.648 | 58.948 | 1.00 26.21 | 8 |
| ATOM | 1333 | N | ALA | A | 169 | 21.239 | 34.524 | 57.711 | 1.00 26.16 | 7 |
| ATOM | 1334 | CA | ALA | A | 169 | 19.793 | 34.415 | 57.579 | 1.00 24.39 | 6 |
| ATOM | 1335 | CB | ALA | A | 169 | 19.233 | 35.640 | 56.879 | 1.00 22.75 | 6 |
| ATOM | 1336 | C | ALA | A | 169 | 19.420 | 33.157 | 56.813 | 1.00 24.37 | 6 |
| ATOM | 1337 | O | ALA | A | 169 | 18.266 | 32.752 | 56.824 | 1.00 22.34 | 8 |
| ATOM | 1338 | N | HIS | A | 170 | 20.405 | 32.542 | 56.156 | 1.00 25.78 | 7 |
| ATOM | 1339 | CA | HIS | A | 170 | 20.180 | 31.327 | 55.375 | 1.00 25.20 | 6 |
| ATOM | 1340 | CB | HIS | A | 170 | 20.667 | 31.501 | 53.936 | 1.00 25.76 | 6 |
| ATOM | 1341 | CG | HIS | A | 170 | 20.122 | 32.711 | 53.245 | 1.00 29.08 | 6 |
| ATOM | 1342 | CD2 | HIS | A | 170 | 19.338 | 32.834 | 52.147 | 1.00 30.59 | 6 |
| ATOM | 1343 | ND1 | HIS | A | 170 | 20.384 | 33.995 | 53.675 | 1.00 30.77 | 7 |
| ATOM | 1344 | CE1 | HIS | A | 170 | 19.784 | 34.858 | 52.873 | 1.00 29.07 | 6 |
| ATOM | 1345 | NE2 | HIS | A | 170 | 19.143 | 34.180 | 51.939 | 1.00 32.19 | 7 |
| ATOM | 1346 | C | HIS | A | 170 | 20.895 | 30.113 | 55.958 | 1.00 26.00 | 6 |
| ATOM | 1347 | O | HIS | A | 170 | 21.913 | 30.234 | 56.637 | 1.00 25.76 | 8 |
| ATOM | 1348 | N | HIS | A | 171 | 20.349 | 28.939 | 55.658 | 1.00 27.29 | 7 |
| ATOM | 1349 | CA | HIS | A | 171 | 20.893 | 27.655 | 56.090 | 1.00 25.01 | 6 |
| ATOM | 1350 | CB | HIS | A | 171 | 19.934 | 26.532 | 55.663 | 1.00 24.93 | 6 |
| ATOM | 1351 | CG | HIS | A | 171 | 20.468 | 25.148 | 55.889 | 1.00 26.56 | 6 |
| ATOM | 1352 | CD2 | HIS | A | 171 | 20.674 | 24.123 | 55.028 | 1.00 22.34 | 6 |
| ATOM | 1353 | ND1 | HIS | A | 171 | 20.823 | 24.678 | 57.137 | 1.00 25.35 | 7 |
| ATOM | 1354 | CE1 | HIS | A | 171 | 21.222 | 23.424 | 57.036 | 1.00 22.68 | 6 |
| ATOM | 1355 | NE2 | HIS | A | 171 | 21.140 | 23.062 | 55.767 | 1.00 24.13 | 7 |
| ATOM | 1356 | C | HIS | A | 171 | 22.267 | 27.413 | 55.471 | 1.00 24.74 | 6 |
| ATOM | 1357 | O | HIS | A | 171 | 22.540 | 27.863 | 54.356 | 1.00 28.22 | 8 |
| ATOM | 1358 | N | CYS | A | 172 | 23.131 | 26.705 | 56.190 | 1.00 23.03 | 7 |
| ATOM | 1359 | CA | CYS | A | 172 | 24.467 | 26.389 | 55.683 | 1.00 23.41 | 6 |
| ATOM | 1360 | CB | CYS | A | 172 | 25.497 | 26.474 | 56.812 | 1.00 19.31 | 6 |
| ATOM | 1361 | SG | CYS | A | 172 | 25.005 | 25.631 | 58.318 | 1.00 16.78 | 16 |
| ATOM | 1362 | C | CYS | A | 172 | 24.484 | 24.997 | 55.048 | 1.00 25.45 | 6 |
| ATOM | 1363 | O | CYS | A | 172 | 25.203 | 24.098 | 55.483 | 1.00 24.47 | 8 |
| ATOM | 1364 | N | ASP | A | 173 | 23.664 | 24.839 | 54.015 | 1.00 26.67 | 7 |
| ATOM | 1365 | CA | ASP | A | 173 | 23.542 | 23.593 | 53.269 | 1.00 26.47 | 6 |
| ATOM | 1366 | CB | ASP | A | 173 | 22.735 | 23.857 | 51.993 | 1.00 26.33 | 6 |
| ATOM | 1367 | CG | ASP | A | 173 | 23.281 | 25.030 | 51.179 | 1.00 27.06 | 6 |
| ATOM | 1368 | OD1 | ASP | A | 173 | 22.539 | 25.558 | 50.330 | 1.00 23.43 | 8 |
| ATOM | 1369 | OD2 | ASP | A | 173 | 24.454 | 25.417 | 51.372 | 1.00 29.38 | 8 |
| ATOM | 1370 | C | ASP | A | 173 | 24.872 | 22.932 | 52.922 | 1.00 26.65 | 6 |
| ATOM | 1371 | O | ASP | A | 173 | 24.940 | 21.708 | 52.784 | 1.00 28.38 | 8 |
| ATOM | 1372 | N | GLY | A | 174 | 25.926 | 23.737 | 52.793 | 1.00 25.24 | 7 |
| ATOM | 1373 | CA | GLY | A | 174 | 27.227 | 23.198 | 52.447 | 1.00 23.11 | 6 |
| ATOM | 1374 | C | GLY | A | 174 | 27.896 | 22.505 | 53.612 | 1.00 25.64 | 6 |
| ATOM | 1375 | O | GLY | A | 174 | 28.443 | 21.408 | 53.462 | 1.00 27.67 | 8 |
| ATOM | 1376 | N | VAL | A | 175 | 27.848 | 23.144 | 54.778 | 1.00 24.29 | 7 |
| ATOM | 1377 | CA | VAL | A | 175 | 28.459 | 22.602 | 55.989 | 1.00 22.20 | 6 |
| ATOM | 1378 | CB | VAL | A | 175 | 28.536 | 23.672 | 57.101 | 1.00 20.15 | 6 |
| ATOM | 1379 | CG1 | VAL | A | 175 | 29.449 | 23.192 | 58.218 | 1.00 20.11 | 6 |
| ATOM | 1380 | CG2 | VAL | A | 175 | 29.015 | 24.989 | 56.530 | 1.00 18.74 | 6 |
| ATOM | 1381 | C | VAL | A | 175 | 27.647 | 21.409 | 56.505 | 1.00 22.85 | 6 |
| ATOM | 1382 | O | VAL | A | 175 | 28.173 | 20.512 | 57.173 | 1.00 20.07 | 8 |
| ATOM | 1383 | N | GLN | A | 176 | 26.356 | 21.404 | 56.203 | 1.00 24.12 | 7 |
| ATOM | 1384 | CA | GLN | A | 176 | 25.518 | 20.303 | 56.629 | 1.00 27.18 | 6 |
| ATOM | 1385 | CB | GLN | A | 176 | 24.045 | 20.611 | 56.355 | 1.00 32.86 | 6 |
| ATOM | 1386 | CG | GLN | A | 176 | 23.084 | 19.483 | 56.726 | 1.00 36.04 | 6 |

Fig. 17-21

```
ATOM   1387  CD   GLN A 176      21.620  19.862  56.537  1.00 38.36      6
ATOM   1388  OE1  GLN A 176      21.113  20.782  57.185  1.00 38.59      8
ATOM   1389  NE2  GLN A 176      20.934  19.151  55.649  1.00 38.81      7
ATOM   1390  C    GLN A 176      25.956  19.083  55.841  1.00 27.70      6
ATOM   1391  O    GLN A 176      26.326  18.066  56.416  1.00 26.89      8
ATOM   1392  N    GLU A 177      25.951  19.194  54.519  1.00 27.96      7
ATOM   1393  CA   GLU A 177      26.343  18.062  53.698  1.00 31.16      6
ATOM   1394  CB   GLU A 177      26.395  18.460  52.220  1.00 30.37      6
ATOM   1395  CG   GLU A 177      26.353  17.256  51.287  1.00 36.20      6
ATOM   1396  CD   GLU A 177      26.273  17.626  49.818  1.00 40.70      6
ATOM   1397  OE1  GLU A 177      27.322  17.967  49.234  1.00 46.78      8
ATOM   1398  OE2  GLU A 177      25.155  17.590  49.250  1.00 39.39      8
ATOM   1399  C    GLU A 177      27.702  17.516  54.137  1.00 31.66      6
ATOM   1400  O    GLU A 177      27.868  16.317  54.356  1.00 32.81      8
ATOM   1401  N    ALA A 178      28.663  18.419  54.287  1.00 33.39      7
ATOM   1402  CA   ALA A 178      30.026  18.072  54.673  1.00 31.63      6
ATOM   1403  CB   ALA A 178      30.830  19.338  54.856  1.00 30.96      6
ATOM   1404  C    ALA A 178      30.204  17.185  55.897  1.00 30.63      6
ATOM   1405  O    ALA A 178      31.032  16.276  55.876  1.00 27.95      8
ATOM   1406  N    PHE A 179      29.444  17.444  56.961  1.00 31.01      7
ATOM   1407  CA   PHE A 179      29.590  16.656  58.184  1.00 31.34      6
ATOM   1408  CB   PHE A 179      30.147  17.532  59.310  1.00 30.13      6
ATOM   1409  CG   PHE A 179      31.189  18.505  58.858  1.00 27.78      6
ATOM   1410  CD1  PHE A 179      30.827  19.790  58.466  1.00 28.24      6
ATOM   1411  CD2  PHE A 179      32.522  18.124  58.766  1.00 28.33      6
ATOM   1412  CE1  PHE A 179      31.778  20.688  57.988  1.00 26.68      6
ATOM   1413  CE2  PHE A 179      33.487  19.013  58.285  1.00 28.79      6
ATOM   1414  CZ   PHE A 179      33.111  20.300  57.895  1.00 28.67      6
ATOM   1415  C    PHE A 179      28.300  16.003  58.664  1.00 32.06      6
ATOM   1416  O    PHE A 179      28.218  15.542  59.803  1.00 30.58      8
ATOM   1417  N    TYR A 180      27.305  15.960  57.787  1.00 34.25      7
ATOM   1418  CA   TYR A 180      26.001  15.377  58.099  1.00 38.60      6
ATOM   1419  CB   TYR A 180      25.062  15.605  56.911  1.00 38.99      6
ATOM   1420  CG   TYR A 180      23.593  15.453  57.220  1.00 37.91      6
ATOM   1421  CD1  TYR A 180      22.938  14.232  57.064  1.00 35.83      6
ATOM   1422  CE1  TYR A 180      21.589  14.103  57.373  1.00 39.20      6
ATOM   1423  CD2  TYR A 180      22.861  16.543  57.694  1.00 37.56      6
ATOM   1424  CE2  TYR A 180      21.518  16.430  58.007  1.00 40.28      6
ATOM   1425  CZ   TYR A 180      20.882  15.211  57.848  1.00 41.92      6
ATOM   1426  OH   TYR A 180      19.549  15.110  58.188  1.00 43.41      8
ATOM   1427  C    TYR A 180      26.133  13.884  58.382  1.00 40.28      6
ATOM   1428  O    TYR A 180      25.158  13.192  58.680  1.00 39.27      8
ATOM   1429  N    ASP A 181      27.363  13.402  58.319  1.00 43.51      7
ATOM   1430  CA   ASP A 181      27.638  11.994  58.519  1.00 45.89      6
ATOM   1431  CB   ASP A 181      28.414  11.487  57.303  1.00 51.00      6
ATOM   1432  CG   ASP A 181      28.830  10.050  57.436  1.00 56.84      6
ATOM   1433  OD1  ASP A 181      29.637   9.750  58.345  1.00 59.47      8
ATOM   1434  OD2  ASP A 181      28.348   9.221  56.629  1.00 60.73      8
ATOM   1435  C    ASP A 181      28.398  11.665  59.804  1.00 44.75      6
ATOM   1436  O    ASP A 181      28.257  10.568  60.350  1.00 44.69      8
ATOM   1437  N    THR A 182      29.194  12.606  60.298  1.00 41.26      7
ATOM   1438  CA   THR A 182      29.975  12.337  61.495  1.00 39.51      6
ATOM   1439  CB   THR A 182      31.408  12.881  61.355  1.00 39.19      6
ATOM   1440  OG1  THR A 182      32.171  12.508  62.505  1.00 37.82      8
ATOM   1441  CG2  THR A 182      31.395  14.397  61.232  1.00 40.12      6
ATOM   1442  C    THR A 182      29.370  12.910  62.759  1.00 38.58      6
ATOM   1443  O    THR A 182      28.609  13.876  62.716  1.00 41.24      8
ATOM   1444  N    ASP A 183      29.712  12.304  63.890  1.00 37.39      7
ATOM   1445  CA   ASP A 183      29.211  12.773  65.171  1.00 39.24      6
ATOM   1446  CB   ASP A 183      28.824  11.588  66.061  1.00 40.31      6
ATOM   1447  CG   ASP A 183      30.010  10.723  66.433  1.00 41.64      6
ATOM   1448  OD1  ASP A 183      30.725  10.268  65.520  1.00 42.53      8
ATOM   1449  OD2  ASP A 183      30.221  10.494  67.640  1.00 42.46      8
ATOM   1450  C    ASP A 183      30.286  13.621  65.853  1.00 40.34      6
ATOM   1451  O    ASP A 183      30.109  14.071  66.983  1.00 42.07      8
ATOM   1452  N    GLN A 184      31.400  13.830  65.154  1.00 39.29      7
```

Fig. 17-22

| | | | | | | | | | |
|---|---|---|---|---|---|---|---|---|---|
| ATOM | 1453 | CA | GLN | A | 184 | 32.506 | 14.635 | 65.671 | 1.00 37.08 6 |
| ATOM | 1454 | CB | GLN | A | 184 | 33.830 | 14.252 | 64.994 | 1.00 33.77 6 |
| ATOM | 1455 | CG | GLN | A | 184 | 34.229 | 12.804 | 65.166 | 1.00 33.63 6 |
| ATOM | 1456 | CD | GLN | A | 184 | 35.599 | 12.499 | 64.593 | 1.00 32.74 6 |
| ATOM | 1457 | OE1 | GLN | A | 184 | 35.853 | 12.704 | 63.413 | 1.00 31.17 8 |
| ATOM | 1458 | NE2 | GLN | A | 184 | 36.490 | 11.999 | 65.436 | 1.00 36.58 7 |
| ATOM | 1459 | C | GLN | A | 184 | 32.222 | 16.110 | 65.403 | 1.00 36.42 6 |
| ATOM | 1460 | O | GLN | A | 184 | 32.803 | 16.994 | 66.034 | 1.00 37.41 8 |
| ATOM | 1461 | N | VAL | A | 185 | 31.329 | 16.372 | 64.456 | 1.00 33.14 7 |
| ATOM | 1462 | CA | VAL | A | 185 | 30.984 | 17.740 | 64.119 | 1.00 32.40 6 |
| ATOM | 1463 | CB | VAL | A | 185 | 31.308 | 18.052 | 62.641 | 1.00 33.03 6 |
| ATOM | 1464 | CG1 | VAL | A | 185 | 31.009 | 19.520 | 62.331 | 1.00 29.27 6 |
| ATOM | 1465 | CG2 | VAL | A | 185 | 32.773 | 17.738 | 62.357 | 1.00 34.58 6 |
| ATOM | 1466 | C | VAL | A | 185 | 29.508 | 17.972 | 64.360 | 1.00 31.51 6 |
| ATOM | 1467 | O | VAL | A | 185 | 28.680 | 17.124 | 64.038 | 1.00 31.71 8 |
| ATOM | 1468 | N | PHE | A | 186 | 29.185 | 19.119 | 64.946 | 1.00 30.98 7 |
| ATOM | 1469 | CA | PHE | A | 186 | 27.798 | 19.463 | 65.207 | 1.00 31.44 6 |
| ATOM | 1470 | CB | PHE | A | 186 | 27.524 | 19.532 | 66.716 | 1.00 30.96 6 |
| ATOM | 1471 | CG | PHE | A | 186 | 26.059 | 19.617 | 67.066 | 1.00 31.59 6 |
| ATOM | 1472 | CD1 | PHE | A | 186 | 25.552 | 18.901 | 68.153 | 1.00 30.54 6 |
| ATOM | 1473 | CD2 | PHE | A | 186 | 25.179 | 20.395 | 66.308 | 1.00 31.50 6 |
| ATOM | 1474 | CE1 | PHE | A | 186 | 24.191 | 18.951 | 68.478 | 1.00 33.28 6 |
| ATOM | 1475 | CE2 | PHE | A | 186 | 23.815 | 20.457 | 66.622 | 1.00 33.04 6 |
| ATOM | 1476 | CZ | PHE | A | 186 | 23.318 | 19.733 | 67.708 | 1.00 32.35 6 |
| ATOM | 1477 | C | PHE | A | 186 | 27.490 | 20.798 | 64.551 | 1.00 30.37 6 |
| ATOM | 1478 | O | PHE | A | 186 | 28.189 | 21.789 | 64.751 | 1.00 31.32 8 |
| ATOM | 1479 | N | VAL | A | 187 | 26.435 | 20.809 | 63.752 | 1.00 31.14 7 |
| ATOM | 1480 | CA | VAL | A | 187 | 26.024 | 22.015 | 63.063 | 1.00 32.05 6 |
| ATOM | 1481 | CB | VAL | A | 187 | 26.018 | 21.805 | 61.525 | 1.00 33.54 6 |
| ATOM | 1482 | CG1 | VAL | A | 187 | 25.574 | 23.081 | 60.813 | 1.00 32.07 6 |
| ATOM | 1483 | CG2 | VAL | A | 187 | 27.420 | 21.389 | 61.056 | 1.00 35.44 6 |
| ATOM | 1484 | C | VAL | A | 187 | 24.638 | 22.439 | 63.524 | 1.00 31.47 6 |
| ATOM | 1485 | O | VAL | A | 187 | 23.666 | 21.686 | 63.410 | 1.00 29.06 8 |
| ATOM | 1486 | N | LEU | A | 188 | 24.579 | 23.638 | 64.090 | 1.00 29.44 7 |
| ATOM | 1487 | CA | LEU | A | 188 | 23.336 | 24.228 | 64.551 | 1.00 29.39 6 |
| ATOM | 1488 | CB | LEU | A | 188 | 23.433 | 24.665 | 66.009 | 1.00 29.62 6 |
| ATOM | 1489 | CG | LEU | A | 188 | 22.293 | 25.589 | 66.458 | 1.00 27.92 6 |
| ATOM | 1490 | CD1 | LEU | A | 188 | 20.970 | 24.844 | 66.414 | 1.00 25.87 5 |
| ATOM | 1491 | CD2 | LEU | A | 188 | 22.574 | 26.107 | 67.861 | 1.00 27.69 6 |
| ATOM | 1492 | C | LEU | A | 188 | 23.161 | 25.454 | 63.675 | 1.00 31.89 6 |
| ATOM | 1493 | O | LEU | A | 188 | 24.130 | 26.175 | 63.388 | 1.00 31.50 8 |
| ATOM | 1494 | N | SER | A | 189 | 21.929 | 25.700 | 63.250 | 1.00 29.93 7 |
| ATOM | 1495 | CA | SER | A | 189 | 21.682 | 26.831 | 62.390 | 1.00 24.65 6 |
| ATOM | 1496 | CB | SER | A | 189 | 21.873 | 26.411 | 60.942 | 1.00 22.40 6 |
| ATOM | 1497 | OG | SER | A | 189 | 21.585 | 27.485 | 60.083 | 1.00 19.12 8 |
| ATOM | 1498 | C | SER | A | 189 | 20.716 | 27.462 | 62.540 | 1.00 27.00 6 |
| ATOM | 1499 | O | SER | A | 189 | 19.996 | 26.774 | 62.577 | 1.00 26.72 8 |
| ATOM | 1500 | N | LEU | A | 190 | 20.221 | 28.783 | 62.669 | 1.00 27.41 7 |
| ATOM | 1501 | CA | LEU | A | 190 | 19.096 | 29.554 | 62.735 | 1.00 29.68 6 |
| ATOM | 1502 | CB | LEU | A | 190 | 19.185 | 30.682 | 63.771 | 1.00 29.84 6 |
| ATOM | 1503 | CG | LEU | A | 190 | 19.108 | 30.366 | 65.264 | 1.00 26.79 6 |
| ATOM | 1504 | CD1 | LEU | A | 190 | 19.020 | 31.662 | 66.045 | 1.00 23.44 6 |
| ATOM | 1505 | CD2 | LEU | A | 190 | 17.881 | 29.549 | 65.546 | 1.00 27.63 6 |
| ATOM | 1506 | C | LEU | A | 190 | 19.046 | 30.141 | 61.329 | 1.00 29.58 6 |
| ATOM | 1507 | O | LEU | A | 190 | 20.084 | 30.525 | 60.790 | 1.00 32.40 8 |
| ATOM | 1508 | N | HIS | A | 191 | 17.864 | 30.206 | 60.727 | 1.00 29.61 7 |
| ATOM | 1509 | CA | HIS | A | 191 | 17.766 | 30.726 | 59.368 | 1.00 29.72 6 |
| ATOM | 1510 | CB | HIS | A | 191 | 18.595 | 29.839 | 58.432 | 1.00 26.47 6 |
| ATOM | 1511 | CG | HIS | A | 191 | 18.225 | 28.392 | 58.504 | 1.00 28.18 6 |
| ATOM | 1512 | CD2 | HIS | A | 191 | 18.918 | 27.313 | 58.940 | 1.00 28.88 6 |
| ATOM | 1513 | ND1 | HIS | A | 191 | 16.989 | 27.921 | 58.118 | 1.00 31.00 7 |
| ATOM | 1514 | CE1 | HIS | A | 191 | 16.938 | 26.614 | 58.312 | 1.00 30.54 6 |
| ATOM | 1515 | NE2 | HIS | A | 191 | 18.095 | 26.220 | 58.810 | 1.00 27.21 7 |
| ATOM | 1516 | C | HIS | A | 191 | 16.329 | 30.812 | 58.856 | 1.00 28.05 6 |
| ATOM | 1517 | O | HIS | A | 191 | 15.385 | 30.411 | 59.535 | 1.00 27.81 8 |
| ATOM | 1518 | N | GLN | A | 192 | 16.183 | 31.346 | 57.649 | 1.00 29.39 7 |

Fig. 17-23

```
ATOM  1519  CA   GLN A 192    14.886  31.494  57.008  1.00  28.21    6
ATOM  1520  CB   GLN A 192    15.016  32.416  55.796  1.00  24.94    6
ATOM  1521  CG   GLN A 192    15.622  33.773  56.124  1.00  21.66    6
ATOM  1522  CD   GLN A 192    15.701  34.690  54.921  1.00  22.22    6
ATOM  1523  OE1  GLN A 192    14.684  35.173  54.428  1.00  23.38    8
ATOM  1524  NE2  GLN A 192    16.914  34.925  54.434  1.00  22.97    7
ATOM  1525  C    GLN A 192    14.435  30.104  56.570  1.00  32.71    6
ATOM  1526  O    GLN A 192    15.157  29.403  55.853  1.00  33.85    8
ATOM  1527  N    SER A 193    13.249  29.694  57.011  1.00  34.44    7
ATOM  1528  CA   SER A 193    12.751  28.376  56.650  1.00  33.28    6
ATOM  1529  CB   SER A 193    11.264  28.249  56.961  1.00  33.25    6
ATOM  1530  OG   SER A 193    10.786  26.987  56.540  1.00  31.52    8
ATOM  1531  C    SER A 193    12.974  28.150  55.171  1.00  34.79    6
ATOM  1532  O    SER A 193    12.775  29.051  54.356  1.00  33.74    8
ATOM  1533  N    PRO A 194    13.404  26.938  54.803  1.00  37.57    7
ATOM  1534  CD   PRO A 194    13.689  25.775  55.658  1.00  38.89    6
ATOM  1535  CA   PRO A 194    13.654  26.600  53.403  1.00  37.81    6
ATOM  1536  CB   PRO A 194    14.248  25.194  53.498  1.00  39.30    6
ATOM  1537  CG   PRO A 194    14.840  25.163  54.916  1.00  39.09    6
ATOM  1538  C    PRO A 194    12.340  26.617  52.638  1.00  36.81    6
ATOM  1539  O    PRO A 194    12.317  26.443  51.425  1.00  34.09    8
ATOM  1540  N    GLU A 195    11.246  26.835  53.364  1.00  39.25    7
ATOM  1541  CA   GLU A 195     9.928  26.866  52.750  1.00  41.54    6
ATOM  1542  CB   GLU A 195     8.843  26.600  53.812  1.00  45.84    6
ATOM  1543  CG   GLU A 195     8.360  27.811  54.608  1.00  53.30    6
ATOM  1544  CD   GLU A 195     7.160  28.502  53.960  1.00  55.91    6
ATOM  1545  OE1  GLU A 195     6.735  29.571  54.461  1.00  55.14    8
ATOM  1546  OE2  GLU A 195     6.631  27.966  52.956  1.00  57.75    8
ATOM  1547  C    GLU A 195     9.700  28.208  52.047  1.00  39.50    6
ATOM  1548  O    GLU A 195     8.651  28.431  51.452  1.00  40.21    8
ATOM  1549  N    TYR A 196    10.689  29.096  52.098  1.00  37.13    7
ATOM  1550  CA   TYR A 196    10.549  30.379  51.434  1.00  35.50    6
ATOM  1551  CB   TYR A 196     9.602  31.274  52.245  1.00  36.36    6
ATOM  1552  CG   TYR A 196    10.175  31.816  53.538  1.00  37.28    6
ATOM  1553  CD1  TYR A 196    11.120  32.848  53.527  1.00  35.42    6
ATOM  1554  CE1  TYR A 196    11.637  33.366  54.706  1.00  33.10    6
ATOM  1555  CD2  TYR A 196     9.764  31.311  54.776  1.00  36.75    6
ATOM  1556  CE2  TYR A 196    10.279  31.825  55.968  1.00  35.26    6
ATOM  1557  CZ   TYR A 196    11.213  32.856  55.922  1.00  35.84    6
ATOM  1558  OH   TYR A 196    11.704  33.401  57.087  1.00  37.09    8
ATOM  1559  C    TYR A 196    11.878  31.097  51.188  1.00  34.89    6
ATOM  1560  O    TYR A 196    11.896  32.256  50.764  1.00  31.61    8
ATOM  1561  N    ALA A 197    12.991  30.416  51.437  1.00  34.39    7
ATOM  1562  CA   ALA A 197    14.297  31.041  51.242  1.00  34.82    6
ATOM  1563  CB   ALA A 197    14.684  31.826  52.489  1.00  32.48    6
ATOM  1564  C    ALA A 197    15.418  30.075  50.887  1.00  36.59    6
ATOM  1565  O    ALA A 197    15.407  28.903  51.291  1.00  37.46    8
ATOM  1566  N    PHE A 198    16.388  30.584  50.133  1.00  36.22    7
ATOM  1567  CA   PHE A 198    17.548  29.802  49.722  1.00  37.68    6
ATOM  1568  CB   PHE A 198    18.597  30.729  49.109  1.00  40.89    6
ATOM  1569  CG   PHE A 198    19.810  30.013  48.578  1.00  43.59    6
ATOM  1570  CD1  PHE A 198    19.783  29.404  47.325  1.00  44.74    6
ATOM  1571  CD2  PHE A 198    20.970  29.929  49.336  1.00  41.86    6
ATOM  1572  CE1  PHE A 198    20.894  28.729  46.833  1.00  41.42    6
ATOM  1573  CE2  PHE A 198    22.079  29.251  48.849  1.00  43.30    6
ATOM  1574  CZ   PHE A 198    22.040  28.652  47.595  1.00  41.86    6
ATOM  1575  C    PHE A 198    18.139  29.140  50.967  1.00  37.00    6
ATOM  1576  O    PHE A 198    18.166  29.754  52.036  1.00  36.43    8
ATOM  1577  N    PRO A 199    18.641  27.892  50.848  1.00  37.63    7
ATOM  1578  CD   PRO A 199    19.298  27.238  51.997  1.00  35.29    6
ATOM  1579  CA   PRO A 199    18.727  27.008  49.673  1.00  36.52    6
ATOM  1580  CB   PRO A 199    19.702  25.936  50.138  1.00  34.96    6
ATOM  1581  CG   PRO A 199    19.281  25.770  51.565  1.00  34.57    6
ATOM  1582  C    PRO A 199    17.409  26.380  49.222  1.00  35.72    6
ATOM  1583  O    PRO A 199    17.386  25.663  48.225  1.00  37.36    8
ATOM  1584  N    PHE A 200    16.331  26.638  49.962  1.00  33.78    7
```

Fig. 17-24

```
ATOM   1585  CA   PHE A 200      15.004  26.090  49.662  1.00 32.15      6
ATOM   1586  CB   PHE A 200      14.562  26.381  48.222  1.00 28.39      6
ATOM   1587  CG   PHE A 200      14.600  27.827  47.835  1.00 26.29      6
ATOM   1588  CD1  PHE A 200      15.749  28.385  47.296  1.00 24.82      6
ATOM   1589  CD2  PHE A 200      13.466  28.623  47.966  1.00 28.04      6
ATOM   1590  CE1  PHE A 200      15.767  29.712  46.882  1.00 25.68      6
ATOM   1591  CE2  PHE A 200      13.475  29.955  47.557  1.00 27.03      6
ATOM   1592  CZ   PHE A 200      14.626  30.498  47.013  1.00 24.90      6
ATOM   1593  C    PHE A 200      14.947  24.574  49.842  1.00 32.66      6
ATOM   1594  O    PHE A 200      13.925  24.033  50.264  1.00 31.22      8
ATOM   1595  N    GLU A 201      16.043  23.896  49.499  1.00 33.60      7
ATOM   1596  CA   GLU A 201      16.128  22.438  49.585  1.00 30.86      6
ATOM   1597  CB   GLU A 201      17.213  21.931  48.637  1.00 32.98      6
ATOM   1598  CG   GLU A 201      16.879  22.182  47.175  1.00 33.52      6
ATOM   1599  CD   GLU A 201      18.012  21.864  46.232  1.00 34.56      6
ATOM   1600  OE1  GLU A 201      18.396  20.678  46.117  1.00 36.35      8
ATOM   1601  OE2  GLU A 201      18.523  22.814  45.605  1.00 36.52      8
ATOM   1602  C    GLU A 201      16.369  21.911  50.981  1.00 28.52      6
ATOM   1603  O    GLU A 201      15.537  21.199  51.520  1.00 28.91      8
ATOM   1604  N    LYS A 202      17.511  22.239  51.566  1.00 31.64      7
ATOM   1605  CA   LYS A 202      17.795  21.780  52.917  1.00 32.34      6
ATOM   1606  CB   LYS A 202      19.276  21.432  53.092  1.00 36.91      6
ATOM   1607  CG   LYS A 202      19.789  20.226  52.307  1.00 43.74      6
ATOM   1608  CD   LYS A 202      20.212  20.590  50.891  1.00 49.31      6
ATOM   1609  CE   LYS A 202      20.952  19.428  50.227  1.00 49.34      6
ATOM   1610  NZ   LYS A 202      21.504  19.802  48.895  1.00 49.89      7
ATOM   1611  C    LYS A 202      17.421  22.849  53.937  1.00 30.55      6
ATOM   1612  O    LYS A 202      16.877  23.890  53.586  1.00 26.55      8
ATOM   1613  N    GLY A 203      17.710  22.571  55.203  1.00 30.59      7
ATOM   1614  CA   GLY A 203      17.422  23.519  56.259  1.00 30.24      6
ATOM   1615  C    GLY A 203      16.216  23.210  57.125  1.00 29.23      6
ATOM   1616  O    GLY A 203      15.915  23.975  58.041  1.00 32.90      8
ATOM   1617  N    PHE A 204      15.526  22.104  56.866  1.00 26.32      7
ATOM   1618  CA   PHE A 204      14.344  21.779  57.657  1.00 23.25      6
ATOM   1619  CB   PHE A 204      13.366  20.917  56.863  1.00 21.25      6
ATOM   1620  CG   PHE A 204      12.855  21.573  55.635  1.00 18.60      6
ATOM   1621  CD1  PHE A 204      13.605  21.560  54.461  1.00 16.43      6
ATOM   1622  CD2  PHE A 204      11.654  22.273  55.664  1.00 14.82      6
ATOM   1623  CE1  PHE A 204      13.168  22.245  53.333  1.00 16.91      6
ATOM   1624  CE2  PHE A 204      11.206  22.962  54.544  1.00 15.28      6
ATOM   1625  CZ   PHE A 204      11.965  22.952  53.375  1.00 18.34      6
ATOM   1626  C    PHE A 204      14.626  21.094  58.979  1.00 23.72      6
ATOM   1627  O    PHE A 204      15.578  20.318  59.118  1.00 22.68      8
ATOM   1628  N    LEU A 205      13.760  21.376  59.942  1.00 20.94      7
ATOM   1629  CA   LEU A 205      13.877  20.818  61.272  1.00 24.83      6
ATOM   1630  CB   LEU A 205      12.678  21.259  62.110  1.00 21.29      6
ATOM   1631  CG   LEU A 205      12.672  20.811  63.568  1.00 22.67      6
ATOM   1632  CD1  LEU A 205      14.011  21.182  64.245  1.00 19.76      6
ATOM   1633  CD2  LEU A 205      11.478  21.456  64.275  1.00 20.62      6
ATOM   1634  C    LEU A 205      14.002  19.293  61.303  1.00 28.79      6
ATOM   1635  O    LEU A 205      14.443  18.730  62.310  1.00 28.59      8
ATOM   1636  N    GLU A 206      13.625  18.628  60.211  1.00 33.52      7
ATOM   1637  CA   GLU A 206      13.693  17.166  60.142  1.00 39.79      6
ATOM   1638  CB   GLU A 206      12.736  16.616  59.070  1.00 44.37      6
ATOM   1639  CG   GLU A 206      11.284  17.060  59.204  1.00 50.75      6
ATOM   1640  CD   GLU A 206      11.014  18.390  58.512  1.00 55.31      6
ATOM   1641  OE1  GLU A 206       9.972  19.027  58.797  1.00 55.36      8
ATOM   1642  OE2  GLU A 206      11.839  18.786  57.661  1.00 56.48      8
ATOM   1643  C    GLU A 206      15.114  16.674  59.847  1.00 40.00      6
ATOM   1644  O    GLU A 206      15.483  15.541  60.180  1.00 39.35      8
ATOM   1645  N    GLU A 207      15.903  17.536  59.217  1.00 39.38      7
ATOM   1646  CA   GLU A 207      17.286  17.219  58.873  1.00 37.90      6
ATOM   1647  CB   GLU A 207      17.776  18.242  57.854  1.00 37.36      6
ATOM   1648  CG   GLU A 207      16.983  18.158  56.556  1.00 37.29      6
ATOM   1649  CD   GLU A 207      16.978  19.452  55.773  1.00 38.15      6
ATOM   1650  OE1  GLU A 207      18.071  20.016  55.537  1.00 35.44      8
```

Fig. 17-25

| | | | | | | | | |
|---|---|---|---|---|---|---|---|---|
| ATOM | 1651 | OE2 | GLU A 207 | 15.870 | 19.891 | 55.389 | 1.00 34.62 | 8 |
| ATOM | 1652 | C | GLU A 207 | 18.139 | 17.239 | 60.134 | 1.00 36.18 | 6 |
| ATOM | 1653 | O | GLU A 207 | 18.560 | 18.303 | 60.590 | 1.00 34.81 | 8 |
| ATOM | 1654 | N | ILE A 208 | 18.381 | 16.059 | 60.701 | 1.00 34.45 | 7 |
| ATOM | 1655 | CA | ILE A 208 | 19.164 | 15.965 | 61.932 | 1.00 38.53 | 6 |
| ATOM | 1656 | CB | ILE A 208 | 18.260 | 15.511 | 63.117 | 1.00 41.12 | 6 |
| ATOM | 1657 | CG2 | ILE A 208 | 19.097 | 15.273 | 64.375 | 1.00 41.36 | 6 |
| ATOM | 1658 | CG1 | ILE A 208 | 17.193 | 16.581 | 63.383 | 1.00 42.21 | 6 |
| ATOM | 1659 | CD1 | ILE A 208 | 16.291 | 16.286 | 64.560 | 1.00 44.81 | 6 |
| ATOM | 1660 | C | ILE A 208 | 20.407 | 15.074 | 61.876 | 1.00 36.66 | 6 |
| ATOM | 1661 | O | ILE A 208 | 21.243 | 15.110 | 62.775 | 1.00 34.03 | 8 |
| ATOM | 1662 | N | GLY A 209 | 20.540 | 14.284 | 60.822 | 1.00 36.80 | 7 |
| ATOM | 1663 | CA | GLY A 209 | 21.703 | 13.428 | 60.728 | 1.00 38.99 | 6 |
| ATOM | 1664 | C | GLY A 209 | 21.509 | 12.246 | 59.805 | 1.00 40.93 | 6 |
| ATOM | 1665 | O | GLY A 209 | 20.477 | 12.124 | 59.145 | 1.00 40.26 | 8 |
| ATOM | 1666 | N | GLU A 210 | 22.508 | 11.370 | 59.775 | 1.00 42.16 | 7 |
| ATOM | 1667 | CA | GLU A 210 | 22.492 | 10.185 | 58.930 | 1.00 43.30 | 6 |
| ATOM | 1668 | CB | GLU A 210 | 22.810 | 10.586 | 57.488 | 1.00 47.08 | 6 |
| ATOM | 1669 | CG | GLU A 210 | 22.826 | 9.453 | 56.478 | 1.00 53.90 | 6 |
| ATOM | 1670 | CD | GLU A 210 | 23.256 | 9.915 | 55.089 | 1.00 56.27 | 6 |
| ATOM | 1671 | OE1 | GLU A 210 | 24.412 | 10.371 | 54.941 | 1.00 56.19 | 8 |
| ATOM | 1672 | OE2 | GLU A 210 | 22.437 | 9.826 | 54.145 | 1.00 60.28 | 8 |
| ATOM | 1673 | C | GLU A 210 | 23.583 | 9.276 | 59.473 | 1.00 41.47 | 6 |
| ATOM | 1674 | O | GLU A 210 | 24.750 | 9.457 | 59.152 | 1.00 43.97 | 8 |
| ATOM | 1675 | N | GLY A 211 | 23.203 | 8.307 | 60.299 | 1.00 39.97 | 7 |
| ATOM | 1676 | CA | GLY A 211 | 24.181 | 7.405 | 60.885 | 1.00 37.34 | 6 |
| ATOM | 1677 | C | GLY A 211 | 24.642 | 7.952 | 62.224 | 1.00 37.84 | 6 |
| ATOM | 1678 | O | GLY A 211 | 23.820 | 8.408 | 63.019 | 1.00 37.30 | 8 |
| ATOM | 1679 | N | LYS A 212 | 25.948 | 7.910 | 62.485 | 1.00 38.52 | 7 |
| ATOM | 1680 | CA | LYS A 212 | 26.490 | 8.440 | 63.733 | 1.00 38.29 | 6 |
| ATOM | 1681 | CB | LYS A 212 | 28.020 | 8.359 | 63.731 | 1.00 40.54 | 6 |
| ATOM | 1682 | CG | LYS A 212 | 28.570 | 6.950 | 63.675 | 1.00 46.39 | 6 |
| ATOM | 1683 | CD | LYS A 212 | 28.149 | 6.147 | 64.910 | 1.00 51.59 | 6 |
| ATOM | 1684 | CE | LYS A 212 | 28.556 | 4.676 | 64.809 | 1.00 52.77 | 6 |
| ATOM | 1685 | NZ | LYS A 212 | 30.030 | 4.478 | 64.662 | 1.00 55.48 | 7 |
| ATOM | 1686 | C | LYS A 212 | 26.061 | 9.897 | 63.866 | 1.00 37.68 | 6 |
| ATOM | 1687 | O | LYS A 212 | 25.814 | 10.389 | 64.962 | 1.00 34.75 | 8 |
| ATOM | 1688 | N | GLY A 213 | 25.956 | 10.574 | 62.728 | 1.00 38.89 | 7 |
| ATOM | 1689 | CA | GLY A 213 | 25.577 | 11.975 | 62.724 | 1.00 43.58 | 6 |
| ATOM | 1690 | C | GLY A 213 | 24.126 | 12.295 | 63.020 | 1.00 43.99 | 6 |
| ATOM | 1691 | O | GLY A 213 | 23.737 | 13.464 | 63.024 | 1.00 44.67 | 8 |
| ATOM | 1692 | N | LYS A 214 | 23.321 | 11.268 | 63.265 | 1.00 46.02 | 7 |
| ATOM | 1693 | CA | LYS A 214 | 21.907 | 11.467 | 63.562 | 1.00 45.61 | 6 |
| ATOM | 1694 | CB | LYS A 214 | 21.168 | 10.130 | 63.469 | 1.00 47.77 | 6 |
| ATOM | 1695 | CG | LYS A 214 | 19.675 | 10.252 | 63.249 | 1.00 49.25 | 6 |
| ATOM | 1696 | CD | LYS A 214 | 19.078 | 8.901 | 62.911 | 1.00 51.64 | 6 |
| ATOM | 1697 | CE | LYS A 214 | 17.637 | 9.038 | 62.440 | 1.00 54.30 | 6 |
| ATOM | 1698 | NZ | LYS A 214 | 17.030 | 7.727 | 62.034 | 1.00 56.09 | 7 |
| ATOM | 1699 | C | LYS A 214 | 21.809 | 12.047 | 64.970 | 1.00 44.22 | 6 |
| ATOM | 1700 | O | LYS A 214 | 22.210 | 11.410 | 65.942 | 1.00 45.04 | 8 |
| ATOM | 1701 | N | GLY A 215 | 21.292 | 13.266 | 65.074 | 1.00 42.89 | 7 |
| ATOM | 1702 | CA | GLY A 215 | 21.193 | 13.904 | 66.373 | 1.00 40.20 | 6 |
| ATOM | 1703 | C | GLY A 215 | 22.295 | 14.931 | 66.600 | 1.00 39.90 | 6 |
| ATOM | 1704 | O | GLY A 215 | 22.356 | 15.548 | 67.668 | 1.00 40.12 | 8 |
| ATOM | 1705 | N | TYR A 216 | 23.175 | 15.111 | 65.612 | 1.00 38.49 | 7 |
| ATOM | 1706 | CA | TYR A 216 | 24.261 | 16.086 | 65.726 | 1.00 35.91 | 6 |
| ATOM | 1707 | CB | TYR A 216 | 25.632 | 15.421 | 65.618 | 1.00 36.47 | 6 |
| ATOM | 1708 | CG | TYR A 216 | 25.935 | 14.461 | 66.738 | 1.00 39.54 | 6 |
| ATOM | 1709 | CD1 | TYR A 216 | 25.296 | 13.220 | 66.810 | 1.00 40.62 | 6 |
| ATOM | 1710 | CE1 | TYR A 216 | 25.561 | 12.333 | 67.849 | 1.00 41.58 | 6 |
| ATOM | 1711 | CD2 | TYR A 216 | 26.852 | 14.795 | 67.739 | 1.00 39.20 | 6 |
| ATOM | 1712 | CE2 | TYR A 216 | 27.124 | 13.915 | 68.786 | 1.00 40.87 | 6 |
| ATOM | 1713 | CZ | TYR A 216 | 26.475 | 12.685 | 68.833 | 1.00 41.86 | 6 |
| ATOM | 1714 | OH | TYR A 216 | 26.743 | 11.802 | 69.852 | 1.00 43.04 | 8 |
| ATOM | 1715 | C | TYR A 216 | 24.182 | 17.215 | 64.709 | 1.00 34.21 | 6 |
| ATOM | 1716 | O | TYR A 216 | 25.194 | 17.832 | 64.375 | 1.00 33.37 | 8 |

Fig. 17-26

```
ATOM   1717  N    ASN A 217      22.976  17.471  64.212  1.00 33.83      7
ATOM   1718  CA   ASN A 217      22.726  18.558  63.267  1.00 30.20      6
ATOM   1719  CB   ASN A 217      22.699  18.057  61.823  1.00 27.74      6
ATOM   1720  CG   ASN A 217      22.457  19.177  60.826  1.00 25.61      6
ATOM   1721  OD1  ASN A 217      21.354  19.705  60.719  1.00 25.00      8
ATOM   1722  ND2  ASN A 217      23.501  19.558  60.103  1.00 30.43      7
ATOM   1723  C    ASN A 217      21.369  19.116  63.645  1.00 29.09      6
ATOM   1724  O    ASN A 217      20.433  18.351  63.885  1.00 26.93      8
ATOM   1725  N    LEU A 218      21.263  20.440  63.710  1.00 27.19      7
ATOM   1726  CA   LEU A 218      20.010  21.071  64.089  1.00 25.33      6
ATOM   1727  CB   LEU A 218      20.026  21.379  65.590  1.00 23.23      6
ATOM   1728  CG   LEU A 218      18.729  21.704  66.346  1.00 21.00      6
ATOM   1729  CD1  LEU A 218      19.100  22.313  67.695  1.00 18.62      6
ATOM   1730  CD2  LEU A 218      17.872  22.675  65.583  1.00 18.48      6
ATOM   1731  C    LEU A 218      19.785  22.368  63.325  1.00 25.04      6
ATOM   1732  O    LEU A 218      20.596  23.287  63.415  1.00 25.23      8
ATOM   1733  N    ASN A 219      18.681  22.436  62.584  1.00 28.44      7
ATOM   1734  CA   ASN A 219      18.310  23.636  61.829  1.00 28.76      6
ATOM   1735  CB   ASN A 219      17.809  23.298  60.417  1.00 25.69      6
ATOM   1736  CG   ASN A 219      18.748  22.408  59.646  1.00 26.10      6
ATOM   1737  OD1  ASN A 219      19.927  22.708  59.505  1.00 28.53      8
ATOM   1738  ND2  ASN A 219      18.220  21.311  59.114  1.00 26.97      7
ATOM   1739  C    ASN A 219      17.129  24.248  62.582  1.00 31.96      6
ATOM   1740  O    ASN A 219      16.373  23.539  63.246  1.00 34.84      8
ATOM   1741  N    ILE A 220      16.952  25.556  62.472  1.00 32.96      7
ATOM   1742  CA   ILE A 220      15.826  26.196  63.129  1.00 32.50      6
ATOM   1743  CB   ILE A 220      16.259  27.037  64.350  1.00 32.32      6
ATOM   1744  CG2  ILE A 220      15.029  27.644  65.014  1.00 29.46      6
ATOM   1745  CG1  ILE A 220      16.978  26.160  65.374  1.00 29.65      6
ATOM   1746  CD1  ILE A 220      16.080  25.138  66.027  1.00 28.65      6
ATOM   1747  C    ILE A 220      15.140  27.106  62.123  1.00 35.36      6
ATOM   1748  O    ILE A 220      15.469  28.290  62.009  1.00 35.52      8
ATOM   1749  N    PRO A 221      14.185  26.553  61.359  1.00 36.87      7
ATOM   1750  CD   PRO A 221      13.718  25.158  61.359  1.00 35.12      6
ATOM   1751  CA   PRO A 221      13.445  27.318  60.356  1.00 35.41      6
ATOM   1752  CB   PRO A 221      12.509  26.262  59.767  1.00 35.68      6
ATOM   1753  CG   PRO A 221      13.319  24.992  59.911  1.00 33.86      6
ATOM   1754  C    PRO A 221      12.696  28.437  61.053  1.00 34.37      6
ATOM   1755  O    PRO A 221      12.014  28.199  62.043  1.00 38.79      8
ATOM   1756  N    LEU A 222      12.815  29.655  60.547  1.00 34.76      7
ATOM   1757  CA   LEU A 222      12.138  30.796  61.166  1.00 33.87      6
ATOM   1758  CB   LEU A 222      13.173  31.735  61.798  1.00 35.13      6
ATOM   1759  CG   LEU A 222      14.104  31.163  62.876  1.00 33.07      6
ATOM   1760  CD1  LEU A 222      15.234  32.150  63.154  1.00 34.04      6
ATOM   1761  CD2  LEU A 222      13.312  30.856  64.141  1.00 32.39      6
ATOM   1762  C    LEU A 222      11.287  31.567  60.157  1.00 32.15      6
ATOM   1763  O    LEU A 222      11.669  31.740  59.000  1.00 31.32      8
ATOM   1764  N    PRO A 223      10.127  32.060  60.601  1.00 30.97      7
ATOM   1765  CD   PRO A 223       9.606  31.913  61.972  1.00 32.34      6
ATOM   1766  CA   PRO A 223       9.173  32.818  59.789  1.00 30.55      6
ATOM   1767  CB   PRO A 223       7.957  32.893  60.702  1.00 29.44      6
ATOM   1768  CG   PRO A 223       8.626  33.068  62.046  1.00 31.02      6
ATOM   1769  C    PRO A 223       9.645  34.205  59.366  1.00 29.20      6
ATOM   1770  O    PRO A 223      10.694  34.680  59.796  1.00 31.95      8
ATOM   1771  N    LYS A 224       8.841  34.841  58.521  1.00 26.14      7
ATOM   1772  CA   LYS A 224       9.115  36.172  58.026  1.00 23.54      6
ATOM   1773  CB   LYS A 224       8.285  36.443  56.766  1.00 24.71      6
ATOM   1774  CG   LYS A 224       8.563  35.500  55.619  1.00 23.83      6
ATOM   1775  CD   LYS A 224       7.737  35.800  54.394  1.00 20.59      6
ATOM   1776  CE   LYS A 224       8.065  34.769  53.329  1.00 27.03      6
ATOM   1777  NZ   LYS A 224       7.198  34.849  52.122  1.00 30.48      7
ATOM   1778  C    LYS A 224       8.702  37.151  59.111  1.00 25.48      6
ATOM   1779  O    LYS A 224       7.999  36.780  60.055  1.00 22.67      8
ATOM   1780  N    GLY A 225       9.124  38.404  58.960  1.00 26.88      7
ATOM   1781  CA   GLY A 225       8.777  39.432  59.925  1.00 29.80      6
ATOM   1782  C    GLY A 225       9.396  39.188  61.286  1.00 32.96      6
```

Fig. 17-27

| ATOM | 1783 | O   | GLY A 225 | 9.068  | 39.861 | 62.271 | 1.00 | 31.20 | 8 |
| ATOM | 1784 | N   | LEU A 226 | 10.299 | 38.216 | 61.338 | 1.00 | 32.86 | 7 |
| ATOM | 1785 | CA  | LEU A 226 | 10.975 | 37.877 | 62.575 | 1.00 | 34.55 | 6 |
| ATOM | 1786 | CB  | LEU A 226 | 12.149 | 36.958 | 62.255 | 1.00 | 34.46 | 6 |
| ATOM | 1787 | CG  | LEU A 226 | 12.982 | 36.413 | 63.407 | 1.00 | 34.48 | 6 |
| ATOM | 1788 | CD1 | LEU A 226 | 12.146 | 35.425 | 64.212 | 1.00 | 33.18 | 6 |
| ATOM | 1789 | CD2 | LEU A 226 | 14.207 | 35.724 | 62.847 | 1.00 | 31.39 | 6 |
| ATOM | 1790 | C   | LEU A 226 | 11.481 | 39.160 | 63.255 | 1.00 | 36.29 | 6 |
| ATOM | 1791 | O   | LEU A 226 | 12.156 | 39.970 | 62.613 | 1.00 | 33.87 | 8 |
| ATOM | 1792 | N   | ASN A 227 | 11.131 | 39.358 | 64.531 | 1.00 | 37.31 | 7 |
| ATOM | 1793 | CA  | ASN A 227 | 11.592 | 40.536 | 65.279 | 1.00 | 37.26 | 6 |
| ATOM | 1794 | CB  | ASN A 227 | 10.444 | 41.212 | 66.053 | 1.00 | 35.57 | 6 |
| ATOM | 1795 | CG  | ASN A 227 | 9.920  | 40.368 | 67.208 | 1.00 | 36.07 | 6 |
| ATOM | 1796 | OD1 | ASN A 227 | 10.678 | 39.940 | 68.089 | 1.00 | 35.08 | 8 |
| ATOM | 1797 | ND2 | ASN A 227 | 8.611  | 40.143 | 67.218 | 1.00 | 32.33 | 7 |
| ATOM | 1798 | C   | ASN A 227 | 12.688 | 40.096 | 66.259 | 1.00 | 37.95 | 6 |
| ATOM | 1799 | O   | ASN A 227 | 12.869 | 38.890 | 66.473 | 1.00 | 37.08 | 8 |
| ATOM | 1800 | N   | ASP A 228 | 13.403 | 41.063 | 66.832 | 1.00 | 36.07 | 7 |
| ATOM | 1801 | CA  | ASP A 228 | 14.505 | 40.754 | 67.751 | 1.00 | 37.63 | 6 |
| ATOM | 1802 | CB  | ASP A 228 | 14.996 | 42.007 | 68.486 | 1.00 | 36.48 | 6 |
| ATOM | 1803 | CG  | ASP A 228 | 15.480 | 43.088 | 67.545 | 1.00 | 37.52 | 6 |
| ATOM | 1804 | OD1 | ASP A 228 | 15.936 | 42.752 | 66.427 | 1.00 | 35.28 | 8 |
| ATOM | 1805 | OD2 | ASP A 228 | 15.426 | 44.274 | 67.937 | 1.00 | 39.01 | 8 |
| ATOM | 1806 | C   | ASP A 228 | 14.204 | 39.678 | 68.783 | 1.00 | 37.56 | 6 |
| ATOM | 1807 | O   | ASP A 228 | 14.921 | 38.678 | 68.869 | 1.00 | 39.53 | 8 |
| ATOM | 1808 | N   | ASN A 229 | 13.155 | 39.889 | 69.572 | 1.00 | 38.37 | 7 |
| ATOM | 1809 | CA  | ASN A 229 | 12.766 | 38.935 | 70.605 | 1.00 | 37.49 | 6 |
| ATOM | 1810 | CB  | ASN A 229 | 11.422 | 39.352 | 71.200 | 1.00 | 37.38 | 6 |
| ATOM | 1811 | CG  | ASN A 229 | 11.490 | 40.709 | 71.877 | 1.00 | 40.47 | 6 |
| ATOM | 1812 | OD1 | ASN A 229 | 12.041 | 40.840 | 72.973 | 1.00 | 41.76 | 8 |
| ATOM | 1813 | ND2 | ASN A 229 | 10.960 | 41.735 | 71.212 | 1.00 | 36.50 | 7 |
| ATOM | 1814 | C   | ASN A 229 | 12.680 | 37.530 | 70.017 | 1.00 | 37.64 | 6 |
| ATOM | 1815 | O   | ASN A 229 | 13.446 | 36.634 | 70.395 | 1.00 | 35.76 | 8 |
| ATOM | 1816 | N   | GLU A 230 | 11.758 | 37.351 | 69.076 | 1.00 | 36.01 | 7 |
| ATOM | 1817 | CA  | GLU A 230 | 11.574 | 36.062 | 68.425 | 1.00 | 34.74 | 6 |
| ATOM | 1818 | CB  | GLU A 230 | 10.753 | 36.242 | 67.153 | 1.00 | 35.55 | 6 |
| ATOM | 1819 | CG  | GLU A 230 | 9.382  | 36.820 | 67.407 | 1.00 | 36.95 | 6 |
| ATOM | 1820 | CD  | GLU A 230 | 8.580  | 36.960 | 66.144 | 1.00 | 35.30 | 6 |
| ATOM | 1821 | OE1 | GLU A 230 | 9.042  | 37.670 | 65.229 | 1.00 | 36.98 | 8 |
| ATOM | 1822 | OE2 | GLU A 230 | 7.490  | 36.361 | 66.065 | 1.00 | 36.71 | 8 |
| ATOM | 1823 | C   | GLU A 230 | 12.916 | 35.421 | 68.082 | 1.00 | 33.92 | 6 |
| ATOM | 1824 | O   | GLU A 230 | 13.143 | 34.238 | 68.346 | 1.00 | 32.74 | 8 |
| ATOM | 1825 | N   | PHE A 231 | 13.804 | 36.207 | 67.487 | 1.00 | 32.03 | 7 |
| ATOM | 1826 | CA  | PHE A 231 | 15.116 | 35.712 | 67.123 | 1.00 | 30.55 | 6 |
| ATOM | 1827 | CB  | PHE A 231 | 15.932 | 36.821 | 66.460 | 1.00 | 33.86 | 6 |
| ATOM | 1828 | CG  | PHE A 231 | 17.295 | 36.381 | 66.012 | 1.00 | 36.97 | 6 |
| ATOM | 1829 | CD1 | PHE A 231 | 17.438 | 35.334 | 65.102 | 1.00 | 40.41 | 6 |
| ATOM | 1830 | CD2 | PHE A 231 | 18.436 | 37.021 | 66.480 | 1.00 | 36.58 | 6 |
| ATOM | 1831 | CE1 | PHE A 231 | 18.709 | 34.932 | 64.661 | 1.00 | 43.00 | 6 |
| ATOM | 1832 | CE2 | PHE A 231 | 19.711 | 36.632 | 66.049 | 1.00 | 39.07 | 6 |
| ATOM | 1833 | CZ  | PHE A 231 | 19.849 | 35.586 | 65.137 | 1.00 | 40.52 | 6 |
| ATOM | 1834 | C   | PHE A 231 | 15.835 | 35.232 | 68.376 | 1.00 | 30.63 | 6 |
| ATOM | 1835 | O   | PHE A 231 | 16.177 | 34.042 | 68.497 | 1.00 | 29.66 | 8 |
| ATOM | 1836 | N   | LEU A 232 | 16.049 | 36.162 | 69.310 | 1.00 | 24.94 | 7 |
| ATOM | 1837 | CA  | LEU A 232 | 16.742 | 35.857 | 70.556 | 1.00 | 22.82 | 6 |
| ATOM | 1838 | CB  | LEU A 232 | 16.724 | 37.084 | 71.468 | 1.00 | 24.96 | 6 |
| ATOM | 1839 | CG  | LEU A 232 | 17.507 | 38.282 | 70.890 | 1.00 | 29.34 | 6 |
| ATOM | 1840 | CD1 | LEU A 232 | 17.316 | 39.549 | 71.746 | 1.00 | 24.38 | 6 |
| ATOM | 1841 | CD2 | LEU A 232 | 18.991 | 37.903 | 70.787 | 1.00 | 27.39 | 6 |
| ATOM | 1842 | C   | LEU A 232 | 16.150 | 34.638 | 71.261 | 1.00 | 22.44 | 6 |
| ATOM | 1843 | O   | LEU A 232 | 16.882 | 33.793 | 71.767 | 1.00 | 20.37 | 8 |
| ATOM | 1844 | N   | PHE A 233 | 14.825 | 34.552 | 71.289 | 1.00 | 24.81 | 7 |
| ATOM | 1845 | CA  | PHE A 233 | 14.131 | 33.422 | 71.905 | 1.00 | 25.81 | 6 |
| ATOM | 1846 | CB  | PHE A 233 | 12.623 | 33.535 | 71.641 | 1.00 | 24.37 | 6 |
| ATOM | 1847 | CG  | PHE A 233 | 11.811 | 32.373 | 72.157 | 1.00 | 24.18 | 6 |
| ATOM | 1848 | CD1 | PHE A 233 | 11.491 | 32.264 | 73.503 | 1.00 | 25.59 | 6 |

Fig. 17-28

| | | | | | | | | |
|---|---|---|---|---|---|---|---|---|
| ATOM | 1849 | CD2 | PHE A 233 | 11.339 | 31.397 | 71.284 | 1.00 25.75 | 6 |
| ATOM | 1850 | CE1 | PHE A 233 | 10.698 | 31.198 | 73.974 | 1.00 25.33 | 6 |
| ATOM | 1851 | CE2 | PHE A 233 | 10.548 | 30.327 | 71.747 | 1.00 24.02 | 6 |
| ATOM | 1852 | CZ | PHE A 233 | 10.228 | 30.232 | 73.093 | 1.00 22.77 | 6 |
| ATOM | 1853 | C | PHE A 233 | 14.661 | 32.133 | 71.275 | 1.00 26.64 | 6 |
| ATOM | 1854 | O | PHE A 233 | 15.094 | 31.209 | 71.971 | 1.00 28.34 | 8 |
| ATOM | 1855 | N | ALA A 234 | 14.624 | 32.087 | 69.949 | 1.00 27.27 | 7 |
| ATOM | 1856 | CA | ALA A 234 | 15.080 | 30.921 | 69.209 | 1.00 30.24 | 6 |
| ATOM | 1857 | CB | ALA A 234 | 14.797 | 31.107 | 67.720 | 1.00 33.38 | 6 |
| ATOM | 1858 | C | ALA A 234 | 16.563 | 30.645 | 69.433 | 1.00 30.76 | 6 |
| ATOM | 1859 | O | ALA A 234 | 16.981 | 29.491 | 69.488 | 1.00 30.04 | 8 |
| ATOM | 1860 | N | LEU A 235 | 17.363 | 31.695 | 69.563 | 1.00 31.84 | 7 |
| ATOM | 1861 | CA | LEU A 235 | 18.789 | 31.486 | 69.790 | 1.00 32.83 | 6 |
| ATOM | 1862 | CB | LEU A 235 | 19.548 | 32.819 | 69.703 | 1.00 34.12 | 6 |
| ATOM | 1863 | CG | LEU A 235 | 21.039 | 32.745 | 69.316 | 1.00 36.33 | 6 |
| ATOM | 1864 | CD1 | LEU A 235 | 21.625 | 34.156 | 69.205 | 1.00 36.44 | 6 |
| ATOM | 1865 | CD2 | LEU A 235 | 21.803 | 31.939 | 70.330 | 1.00 35.64 | 6 |
| ATOM | 1866 | C | LEU A 235 | 18.970 | 30.846 | 71.176 | 1.00 30.75 | 6 |
| ATOM | 1867 | O | LEU A 235 | 19.648 | 29.835 | 71.312 | 1.00 30.12 | 8 |
| ATOM | 1868 | N | GLU A 236 | 18.347 | 31.435 | 72.192 | 1.00 29.03 | 7 |
| ATOM | 1869 | CA | GLU A 236 | 18.418 | 30.931 | 73.561 | 1.00 33.32 | 6 |
| ATOM | 1870 | CB | GLU A 236 | 17.479 | 31.730 | 74.452 | 1.00 35.06 | 6 |
| ATOM | 1871 | CG | GLU A 236 | 17.843 | 33.176 | 74.635 | 1.00 42.35 | 6 |
| ATOM | 1872 | CD | GLU A 236 | 16.610 | 34.022 | 74.843 | 1.00 47.12 | 6 |
| ATOM | 1873 | OE1 | GLU A 236 | 15.686 | 33.557 | 75.556 | 1.00 48.91 | 8 |
| ATOM | 1874 | OE2 | GLU A 236 | 16.572 | 35.150 | 74.297 | 1.00 49.07 | 8 |
| ATOM | 1875 | C | GLU A 236 | 17.988 | 29.473 | 73.639 | 1.00 34.65 | 6 |
| ATOM | 1876 | O | GLU A 236 | 18.715 | 28.593 | 74.116 | 1.00 30.43 | 8 |
| ATOM | 1877 | N | LYS A 237 | 16.767 | 29.250 | 73.176 | 1.00 35.67 | 7 |
| ATOM | 1878 | CA | LYS A 237 | 16.138 | 27.943 | 73.175 | 1.00 35.51 | 6 |
| ATOM | 1879 | CB | LYS A 237 | 14.791 | 28.060 | 72.452 | 1.00 37.01 | 6 |
| ATOM | 1880 | CG | LYS A 237 | 13.745 | 27.032 | 72.848 | 1.00 39.65 | 6 |
| ATOM | 1881 | CD | LYS A 237 | 12.712 | 27.605 | 73.821 | 1.00 40.66 | 6 |
| ATOM | 1882 | CE | LYS A 237 | 13.312 | 28.054 | 75.153 | 1.00 40.58 | 6 |
| ATOM | 1883 | NZ | LYS A 237 | 12.250 | 28.556 | 76.083 | 1.00 32.05 | 7 |
| ATOM | 1884 | C | LYS A 237 | 17.025 | 26.891 | 72.485 | 1.00 35.07 | 6 |
| ATOM | 1885 | O | LYS A 237 | 17.315 | 25.833 | 73.061 | 1.00 30.60 | 8 |
| ATOM | 1886 | N | SER A 238 | 17.455 | 27.200 | 71.259 | 1.00 33.59 | 7 |
| ATOM | 1887 | CA | SER A 238 | 18.279 | 26.293 | 70.452 | 1.00 32.18 | 6 |
| ATOM | 1888 | CB | SER A 238 | 18.453 | 26.867 | 69.042 | 1.00 32.01 | 6 |
| ATOM | 1889 | OG | SER A 238 | 19.014 | 28.168 | 69.075 | 1.00 37.80 | 8 |
| ATOM | 1890 | C | SER A 238 | 19.650 | 25.928 | 71.032 | 1.00 31.94 | 6 |
| ATOM | 1891 | O | SER A 238 | 20.064 | 24.758 | 70.990 | 1.00 26.88 | 8 |
| ATOM | 1892 | N | LEU A 239 | 20.357 | 26.920 | 71.564 | 1.00 31.19 | 7 |
| ATOM | 1893 | CA | LEU A 239 | 21.660 | 26.650 | 72.147 | 1.00 30.82 | 6 |
| ATOM | 1894 | CB | LEU A 239 | 22.293 | 27.914 | 72.720 | 1.00 28.03 | 6 |
| ATOM | 1895 | CG | LEU A 239 | 22.650 | 29.087 | 71.817 | 1.00 24.31 | 6 |
| ATOM | 1896 | CD1 | LEU A 239 | 23.210 | 30.189 | 72.695 | 1.00 24.63 | 6 |
| ATOM | 1897 | CD2 | LEU A 239 | 23.663 | 28.681 | 70.770 | 1.00 23.11 | 6 |
| ATOM | 1898 | C | LEU A 239 | 21.463 | 25.666 | 73.275 | 1.00 31.99 | 6 |
| ATOM | 1899 | O | LEU A 239 | 22.279 | 24.764 | 73.473 | 1.00 32.57 | 8 |
| ATOM | 1900 | N | GLU A 240 | 20.367 | 25.835 | 74.009 | 1.00 33.86 | 7 |
| ATOM | 1901 | CA | GLU A 240 | 20.094 | 24.965 | 75.136 | 1.00 38.61 | 6 |
| ATOM | 1902 | CB | GLU A 240 | 18.799 | 25.369 | 75.842 | 1.00 43.21 | 6 |
| ATOM | 1903 | CG | GLU A 240 | 18.500 | 24.468 | 77.045 | 1.00 53.52 | 6 |
| ATOM | 1904 | CD | GLU A 240 | 19.677 | 24.383 | 78.022 | 1.00 56.39 | 5 |
| ATOM | 1905 | OE1 | GLU A 240 | 19.969 | 25.399 | 78.701 | 1.00 57.81 | 8 |
| ATOM | 1906 | OE2 | GLU A 240 | 20.318 | 23.304 | 78.093 | 1.00 55.12 | 8 |
| ATOM | 1907 | C | GLU A 240 | 20.033 | 23.507 | 74.722 | 1.00 39.28 | 6 |
| ATOM | 1908 | O | GLU A 240 | 20.532 | 22.630 | 75.437 | 1.00 38.83 | 8 |
| ATOM | 1909 | N | ILE A 241 | 19.423 | 23.252 | 73.567 | 1.00 40.74 | 7 |
| ATOM | 1910 | CA | ILE A 241 | 19.310 | 21.896 | 73.035 | 1.00 38.08 | 6 |
| ATOM | 1911 | CB | ILE A 241 | 18.465 | 21.871 | 71.734 | 1.00 33.57 | 6 |
| ATOM | 1912 | CG2 | ILE A 241 | 18.536 | 20.506 | 71.086 | 1.00 31.39 | 6 |
| ATOM | 1913 | CG1 | ILE A 241 | 17.012 | 22.226 | 72.056 | 1.00 31.06 | 6 |
| ATOM | 1914 | CD1 | ILE A 241 | 16.147 | 22.478 | 70.843 | 1.00 27.53 | 6 |

Fig. 17-29

```
ATOM   1915  C    ILE A 241      20.713  21.372  72.747  1.00 39.56       6
ATOM   1916  O    ILE A 241      20.984  20.189  72.936  1.00 40.82       8
ATOM   1917  N    VAL A 242      21.605  22.254  72.299  1.00 41.93       7
ATOM   1918  CA   VAL A 242      22.979  21.842  72.015  1.00 45.09       6
ATOM   1919  CB   VAL A 242      23.808  22.959  71.329  1.00 45.76       6
ATOM   1920  CG1  VAL A 242      25.242  22.479  71.116  1.00 43.09       6
ATOM   1921  CG2  VAL A 242      23.182  23.334  69.991  1.00 46.41       6
ATOM   1922  C    VAL A 242      23.698  21.453  73.300  1.00 45.69       6
ATOM   1923  O    VAL A 242      24.191  20.331  73.423  1.00 46.30       8
ATOM   1924  N    LYS A 243      23.750  22.373  74.259  1.00 44.60       7
ATOM   1925  CA   LYS A 243      24.427  22.088  75.513  1.00 46.96       6
ATOM   1926  CB   LYS A 243      24.214  23.217  76.527  1.00 49.49       6
ATOM   1927  CG   LYS A 243      25.061  23.023  77.795  1.00 54.90       6
ATOM   1928  CD   LYS A 243      24.652  23.934  78.939  1.00 58.95       6
ATOM   1929  CE   LYS A 243      24.782  25.399  78.577  1.00 64.13       6
ATOM   1930  NZ   LYS A 243      24.274  26.283  79.676  1.00 66.93       7
ATOM   1931  C    LYS A 243      23.965  20.767  76.135  1.00 47.06       6
ATOM   1932  O    LYS A 243      24.735  20.113  76.845  1.00 46.39       8
ATOM   1933  N    GLU A 244      22.716  20.380  75.878  1.00 47.51       7
ATOM   1934  CA   GLU A 244      22.172  19.136  76.429  1.00 51.33       6
ATOM   1935  CB   GLU A 244      20.650  19.061  76.259  1.00 54.49       6
ATOM   1936  CG   GLU A 244      19.843  20.199  76.842  1.00 62.61       6
ATOM   1937  CD   GLU A 244      18.360  20.089  76.489  1.00 65.15       6
ATOM   1938  OE1  GLU A 244      17.572  20.980  76.888  1.00 66.49       8
ATOM   1939  OE2  GLU A 244      17.986  19.108  75.807  1.00 64.82       8
ATOM   1940  C    GLU A 244      22.745  17.936  75.698  1.00 50.17       6
ATOM   1941  O    GLU A 244      22.866  16.846  76.259  1.00 51.54       8
ATOM   1942  N    VAL A 245      23.104  18.148  74.441  1.00 47.70       7
ATOM   1943  CA   VAL A 245      23.587  17.063  73.611  1.00 45.43       6
ATOM   1944  CB   VAL A 245      22.704  16.980  72.336  1.00 48.47       6
ATOM   1945  CG1  VAL A 245      23.082  15.765  71.499  1.00 51.87       6
ATOM   1946  CG2  VAL A 245      21.226  16.934  72.731  1.00 45.65       6
ATOM   1947  C    VAL A 245      25.056  17.070  73.185  1.00 43.01       6
ATOM   1948  O    VAL A 245      25.620  16.005  72.946  1.00 39.28       8
ATOM   1949  N    PHE A 246      25.682  18.245  73.109  1.00 40.53       7
ATOM   1950  CA   PHE A 246      27.063  18.321  72.633  1.00 38.56       6
ATOM   1951  CB   PHE A 246      27.023  18.700  71.154  1.00 36.85       6
ATOM   1952  CG   PHE A 246      28.315  18.487  70.415  1.00 36.46       6
ATOM   1953  CD1  PHE A 246      28.749  17.201  70.098  1.00 32.95       6
ATOM   1954  CD2  PHE A 246      29.064  19.582  69.967  1.00 35.51       6
ATOM   1955  CE1  PHE A 246      29.903  17.004  69.337  1.00 33.80       6
ATOM   1956  CE2  PHE A 246      30.222  19.397  69.206  1.00 34.46       6
ATOM   1957  CZ   PHE A 246      30.640  18.103  68.889  1.00 35.54       6
ATOM   1958  C    PHE A 246      27.970  19.311  73.371  1.00 40.83       6
ATOM   1959  O    PHE A 246      27.613  20.478  73.549  1.00 40.32       8
ATOM   1960  N    GLU A 247      29.141  18.839  73.802  1.00 42.54       7
ATOM   1961  CA   GLU A 247      30.128  19.695  74.467  1.00 43.93       6
ATOM   1962  CB   GLU A 247      30.655  19.075  75.770  1.00 45.67       6
ATOM   1963  CG   GLU A 247      29.763  19.243  77.005  1.00 51.63       6
ATOM   1964  CD   GLU A 247      28.478  18.424  76.962  1.00 57.42       6
ATOM   1965  OE1  GLU A 247      27.645  18.644  76.058  1.00 62.12       8
ATOM   1966  OE2  GLU A 247      28.296  17.557  77.845  1.00 59.43       8
ATOM   1967  C    GLU A 247      31.268  19.839  73.464  1.00 43.62       6
ATOM   1968  O    GLU A 247      32.077  18.931  73.294  1.00 44.25       8
ATOM   1969  N    PRO A 248      31.342  20.988  72.780  1.00 43.65       7
ATOM   1970  CD   PRO A 248      30.439  22.143  72.863  1.00 42.73       6
ATOM   1971  CA   PRO A 248      32.371  21.260  71.779  1.00 43.28       6
ATOM   1972  CB   PRO A 248      31.802  22.480  71.042  1.00 43.03       6
ATOM   1973  CG   PRO A 248      30.317  22.474  71.415  1.00 43.02       6
ATOM   1974  C    PRO A 248      33.759  21.552  72.331  1.00 43.37       6
ATOM   1975  O    PRO A 248      33.896  22.286  73.305  1.00 45.44       8
ATOM   1976  N    GLU A 249      34.788  20.982  71.710  1.00 42.38       7
ATOM   1977  CA   GLU A 249      36.151  21.263  72.136  1.00 41.56       6
ATOM   1978  CB   GLU A 249      37.148  20.275  71.528  1.00 42.06       6
ATOM   1979  CG   GLU A 249      36.935  18.816  71.887  1.00 44.28       6
ATOM   1980  CD   GLU A 249      38.015  17.908  71.295  1.00 44.79       6
```

Fig. 17-30

```
ATOM   1981  OE1 GLU A 249      38.208  17.938  70.054  1.00 42.47      8
ATOM   1982  OE2 GLU A 249      38.666  17.168  72.072  1.00 39.73      8
ATOM   1983  C   GLU A 249      36.443  22.654  71.583  1.00 40.99      6
ATOM   1984  O   GLU A 249      37.150  23.450  72.204  1.00 42.83      8
ATOM   1985  N   VAL A 250      35.879  22.936  70.407  1.00 37.65      7
ATOM   1986  CA  VAL A 250      36.059  24.221  69.728  1.00 34.87      6
ATOM   1987  CB  VAL A 250      37.294  24.203  68.789  1.00 34.53      6
ATOM   1988  CG1 VAL A 250      37.129  23.113  67.728  1.00 32.76      6
ATOM   1989  CG2 VAL A 250      37.487  25.581  68.144  1.00 29.62      6
ATOM   1990  C   VAL A 250      34.830  24.527  68.891  1.00 32.67      6
ATOM   1991  O   VAL A 250      34.162  23.610  68.421  1.00 33.96      8
ATOM   1992  N   TYR A 251      34.539  25.810  68.690  1.00 29.71      7
ATOM   1993  CA  TYR A 251      33.368  26.183  67.916  1.00 27.07      6
ATOM   1994  CB  TYR A 251      32.185  26.451  68.860  1.00 29.11      6
ATOM   1995  CG  TYR A 251      32.080  27.872  69.406  1.00 31.46      6
ATOM   1996  CD1 TYR A 251      31.553  28.903  68.622  1.00 31.14      6
ATOM   1997  CE1 TYR A 251      31.439  30.196  69.106  1.00 31.66      6
ATOM   1998  CD2 TYR A 251      32.494  28.181  70.696  1.00 30.20      6
ATOM   1999  CE2 TYR A 251      32.384  29.477  71.193  1.00 33.89      6
ATOM   2000  CZ  TYR A 251      31.854  30.482  70.391  1.00 34.75      6
ATOM   2001  OH  TYR A 251      31.743  31.773  70.867  1.00 33.52      8
ATOM   2002  C   TYR A 251      33.570  27.384  66.992  1.00 27.48      6
ATOM   2003  O   TYR A 251      34.167  28.402  67.366  1.00 24.78      8
ATOM   2004  N   LEU A 252      33.063  27.254  65.773  1.00 24.80      7
ATOM   2005  CA  LEU A 252      33.150  28.332  64.815  1.00 23.40      6
ATOM   2006  CB  LEU A 252      33.631  27.810  63.451  1.00 21.32      6
ATOM   2007  CG  LEU A 252      35.126  27.456  63.385  1.00 21.84      6
ATOM   2008  CD1 LEU A 252      35.457  26.373  64.395  1.00 22.51      6
ATOM   2009  CD2 LEU A 252      35.499  26.999  61.986  1.00 22.07      6
ATOM   2010  C   LEU A 252      31.762  28.959  64.729  1.00 22.56      6
ATOM   2011  O   LEU A 252      30.750  28.266  64.856  1.00 21.99      8
ATOM   2012  N   LEU A 253      31.734  30.277  64.554  1.00 21.01      7
ATOM   2013  CA  LEU A 253      30.498  31.047  64.461  1.00 18.89      6
ATOM   2014  CB  LEU A 253      30.352  31.944  65.695  1.00 20.05      6
ATOM   2015  CG  LEU A 253      29.198  32.942  65.842  1.00 21.61      6
ATOM   2016  CD1 LEU A 253      27.849  32.220  65.860  1.00 22.23      6
ATOM   2017  CD2 LEU A 253      29.395  33.716  67.145  1.00 22.90      6
ATOM   2018  C   LEU A 253      30.539  31.901  63.198  1.00 20.05      6
ATOM   2019  O   LEU A 253      31.466  32.691  62.987  1.00 18.17      8
ATOM   2020  N   GLN A 254      29.544  31.720  62.340  1.00 19.40      7
ATOM   2021  CA  GLN A 254      29.488  32.490  61.115  1.00 18.17      6
ATOM   2022  CB  GLN A 254      29.017  31.592  59.969  1.00  9.67      6
ATOM   2023  CG  GLN A 254      27.584  31.713  59.601  1.00 18.43      6
ATOM   2024  CD  GLN A 254      27.368  32.766  58.549  1.00 19.97      6
ATOM   2025  OE1 GLN A 254      27.917  32.677  57.450  1.00 22.54      8
ATOM   2026  NE2 GLN A 254      26.564  33.769  58.869  1.00 22.89      7
ATOM   2027  C   GLN A 254      28.520  33.634  61.444  1.00 19.75      6
ATOM   2028  O   GLN A 254      27.470  33.415  62.060  1.00 18.77      8
ATOM   2029  N   LEU A 255      28.905  34.854  61.067  1.00 23.02      7
ATOM   2030  CA  LEU A 255      28.132  36.052  61.369  1.00 23.77      6
ATOM   2031  CB  LEU A 255      28.963  36.993  62.242  1.00 26.84      6
ATOM   2032  CG  LEU A 255      29.226  36.556  63.684  1.00 29.34      6
ATOM   2033  CD1 LEU A 255      30.196  37.520  64.331  1.00 30.65      6
ATOM   2034  CD2 LEU A 255      27.902  36.506  64.456  1.00 28.42      6
ATOM   2035  C   LEU A 255      27.605  36.842  60.197  1.00 24.84      6
ATOM   2036  O   LEU A 255      27.774  38.066  60.149  1.00 24.94      8
ATOM   2037  N   GLY A 256      26.969  36.158  59.254  1.00 25.07      7
ATOM   2038  CA  GLY A 256      26.408  36.858  58.117  1.00 26.11      6
ATOM   2039  C   GLY A 256      25.506  37.956  58.644  1.00 27.11      6
ATOM   2040  O   GLY A 256      24.742  37.734  59.584  1.00 25.67      8
ATOM   2041  N   THR A 257      25.599  39.150  58.072  1.00 27.85      7
ATOM   2042  CA  THR A 257      24.757  40.244  58.536  1.00 29.28      6
ATOM   2043  CB  THR A 257      25.517  41.597  58.545  1.00 27.98      6
ATOM   2044  OG1 THR A 257      26.002  41.895  57.232  1.00 31.91      8
ATOM   2045  CG2 THR A 257      26.686  41.541  59.510  1.00 26.45      6
ATOM   2046  C   THR A 257      23.477  40.392  57.722  1.00 28.39      6
```

Fig. 17-31

```
ATOM  2047  O    THR A 257    22.747  41.370  57.879  1.00  29.49    8
ATOM  2048  N    ASP A 258    23.192  39.414  56.867  1.00  29.13    7
ATOM  2049  CA   ASP A 258    21.977  39.471  56.065  1.00  30.49    6
ATOM  2050  CB   ASP A 258    22.004  38.432  54.933  1.00  28.22    6
ATOM  2051  CG   ASP A 258    22.337  37.033  55.416  1.00  29.39    6
ATOM  2052  OD1  ASP A 258    21.893  36.653  56.520  1.00  30.16    8
ATOM  2053  OD2  ASP A 258    23.019  36.292  54.667  1.00  29.97    8
ATOM  2054  C    ASP A 258    20.646  39.355  56.826  1.00  30.50    6
ATOM  2055  O    ASP A 258    19.601  39.622  56.248  1.00  32.87    8
ATOM  2056  N    PRO A 259    20.650  38.912  58.101  1.00  30.76    7
ATOM  2057  CD   PRO A 259    21.711  38.338  58.952  1.00  33.56    6
ATOM  2058  CA   PRO A 259    19.366  38.821  58.806  1.00  31.73    6
ATOM  2059  CB   PRO A 259    19.705  37.912  59.987  1.00  31.87    6
ATOM  2060  CG   PRO A 259    21.067  38.373  60.333  1.00  31.73    6
ATOM  2061  C    PRO A 259    18.817  40.184  59.260  1.00  30.86    6
ATOM  2062  O    PRO A 259    17.736  40.270  59.845  1.00  29.78    8
ATOM  2063  N    LEU A 260    19.565  41.245  58.980  1.00  29.58    7
ATOM  2064  CA   LEU A 260    19.161  42.592  59.375  1.00  29.15    6
ATOM  2065  CB   LEU A 260    20.367  43.542  59.275  1.00  27.14    6
ATOM  2066  CG   LEU A 260    21.543  43.286  60.234  1.00  22.17    6
ATOM  2067  CD1  LEU A 260    22.794  43.919  59.684  1.00  15.79    6
ATOM  2068  CD2  LEU A 260    21.211  43.793  61.633  1.00  16.25    6
ATOM  2069  C    LEU A 260    17.992  43.165  58.576  1.00  28.09    6
ATOM  2070  O    LEU A 260    17.787  42.834  57.410  1.00  29.61    8
ATOM  2071  N    LEU A 261    17.237  44.044  59.223  1.00  29.29    7
ATOM  2072  CA   LEU A 261    16.097  44.693  58.596  1.00  29.71    6
ATOM  2073  CB   LEU A 261    15.540  45.788  59.513  1.00  29.62    6
ATOM  2074  CG   LEU A 261    14.406  46.664  58.950  1.00  28.14    6
ATOM  2075  CD1  LEU A 261    13.144  45.819  58.803  1.00  24.82    6
ATOM  2076  CD2  LEU A 261    14.139  47.859  59.882  1.00  25.45    6
ATOM  2077  C    LEU A 261    16.461  45.322  57.259  1.00  29.50    6
ATOM  2078  O    LEU A 261    15.717  45.198  56.295  1.00  31.67    8
ATOM  2079  N    GLU A 262    17.603  45.998  57.201  1.00  31.54    7
ATOM  2080  CA   GLU A 262    18.015  46.664  55.973  1.00  31.93    6
ATOM  2081  CB   GLU A 262    19.049  47.758  56.279  1.00  29.34    6
ATOM  2082  CG   GLU A 262    18.496  48.931  57.086  1.00  28.52    6
ATOM  2083  CD   GLU A 262    18.449  48.687  58.589  1.00  29.76    6
ATOM  2084  OE1  GLU A 262    18.175  47.548  59.029  1.00  30.12    8
ATOM  2085  OE2  GLU A 262    18.661  49.661  59.338  1.00  27.69    8
ATOM  2086  C    GLU A 262    18.526  45.754  54.857  1.00  34.29    6
ATOM  2087  O    GLU A 262    18.690  46.199  53.722  1.00  35.20    8
ATOM  2088  N    ASP A 263    18.778  44.486  55.158  1.00  36.55    7
ATOM  2089  CA   ASP A 263    19.245  43.582  54.117  1.00  39.50    6
ATOM  2090  CB   ASP A 263    20.354  42.672  54.641  1.00  38.42    6
ATOM  2091  CG   ASP A 263    20.982  41.847  53.538  1.00  39.33    6
ATOM  2092  OD1  ASP A 263    22.064  41.263  53.762  1.00  38.86    8
ATOM  2093  OD2  ASP A 263    20.384  41.779  52.443  1.00  39.50    8
ATOM  2094  C    ASP A 263    18.046  42.775  53.634  1.00  42.83    6
ATOM  2095  O    ASP A 263    17.474  41.966  54.381  1.00  44.22    8
ATOM  2096  N    TYR A 264    17.673  43.002  52.377  1.00  44.14    7
ATOM  2097  CA   TYR A 264    16.508  42.357  51.796  1.00  46.67    6
ATOM  2098  CB   TYR A 264    16.031  43.149  50.568  1.00  54.61    6
ATOM  2099  CG   TYR A 264    16.824  42.939  49.294  1.00  63.02    6
ATOM  2100  CD1  TYR A 264    16.510  41.897  48.412  1.00  65.73    6
ATOM  2101  CE1  TYR A 264    17.230  41.709  47.226  1.00  68.35    6
ATOM  2102  CD2  TYR A 264    17.882  43.786  48.962  1.00  66.23    6
ATOM  2103  CE2  TYR A 264    18.611  43.606  47.780  1.00  68.63    6
ATOM  2104  CZ   TYR A 264    18.279  42.570  46.918  1.00  69.08    6
ATOM  2105  OH   TYR A 264    18.989  42.411  45.746  1.00  69.01    8
ATOM  2106  C    TYR A 264    16.665  40.888  51.451  1.00  43.89    6
ATOM  2107  O    TYR A 264    15.663  40.185  51.293  1.00  44.80    8
ATOM  2108  N    LEU A 265    17.897  40.400  51.333  1.00  40.37    7
ATOM  2109  CA   LEU A 265    18.051  38.984  51.016  1.00  38.06    6
ATOM  2110  CB   LEU A 265    19.474  38.646  50.538  1.00  33.48    6
ATOM  2111  CG   LEU A 265    19.905  39.211  49.172  1.00  32.43    6
ATOM  2112  CD1  LEU A 265    21.176  38.535  48.703  1.00  26.97    6
```

Fig. 17-32

| | | | | | | | | | |
|---|---|---|---|---|---|---|---|---|---|
| ATOM | 2113 | CD2 | LEU A 265 | 18.828 | 38.954 | 48.141 | 1.00 | 34.41 | 6 |
| ATOM | 2114 | C | LEU A 265 | 17.665 | 38.131 | 52.219 | 1.00 | 37.41 | 6 |
| ATOM | 2115 | O | LEU A 265 | 18.125 | 37.000 | 52.370 | 1.00 | 37.96 | 8 |
| ATOM | 2116 | N | SER A 266 | 16.804 | 38.694 | 53.066 | 1.00 | 36.21 | 7 |
| ATOM | 2117 | CA | SER A 266 | 16.294 | 38.013 | 54.253 | 1.00 | 36.46 | 6 |
| ATOM | 2118 | CB | SER A 266 | 17.263 | 38.136 | 55.427 | 1.00 | 37.22 | 6 |
| ATOM | 2119 | OG | SER A 266 | 17.190 | 39.440 | 55.991 | 1.00 | 37.41 | 8 |
| ATOM | 2120 | C | SER A 266 | 14.997 | 38.705 | 54.653 | 1.00 | 35.55 | 6 |
| ATOM | 2121 | O | SER A 266 | 14.889 | 39.927 | 54.568 | 1.00 | 37.09 | 8 |
| ATOM | 2122 | N | LYS A 267 | 14.018 | 37.928 | 55.093 | 1.00 | 34.33 | 7 |
| ATOM | 2123 | CA | LYS A 267 | 12.750 | 38.493 | 55.532 | 1.00 | 36.13 | 6 |
| ATOM | 2124 | CB | LYS A 267 | 11.596 | 37.548 | 55.183 | 1.00 | 36.11 | 6 |
| ATOM | 2125 | CG | LYS A 267 | 11.503 | 37.222 | 53.705 | 1.00 | 36.79 | 6 |
| ATOM | 2126 | CD | LYS A 267 | 11.453 | 38.487 | 52.869 | 1.00 | 38.55 | 6 |
| ATOM | 2127 | CE | LYS A 267 | 11.369 | 38.170 | 51.389 | 1.00 | 41.60 | 6 |
| ATOM | 2128 | NZ | LYS A 267 | 11.503 | 39.413 | 50.569 | 1.00 | 42.07 | 7 |
| ATOM | 2129 | C | LYS A 267 | 12.791 | 38.738 | 57.043 | 1.00 | 34.90 | 6 |
| ATOM | 2130 | O | LYS A 267 | 11.758 | 38.867 | 57.694 | 1.00 | 37.18 | 8 |
| ATOM | 2131 | N | PHE A 268 | 13.998 | 38.775 | 57.595 | 1.00 | 32.82 | 7 |
| ATOM | 2132 | CA | PHE A 268 | 14.192 | 39.021 | 59.016 | 1.00 | 31.50 | 6 |
| ATOM | 2133 | CB | PHE A 268 | 15.477 | 38.337 | 59.495 | 1.00 | 34.05 | 6 |
| ATOM | 2134 | CG | PHE A 268 | 15.379 | 36.839 | 59.604 | 1.00 | 34.54 | 6 |
| ATOM | 2135 | CD1 | PHE A 268 | 16.506 | 36.087 | 59.940 | 1.00 | 35.04 | 6 |
| ATOM | 2136 | CD2 | PHE A 268 | 14.161 | 36.178 | 59.429 | 1.00 | 34.57 | 6 |
| ATOM | 2137 | CE1 | PHE A 268 | 16.423 | 34.691 | 60.108 | 1.00 | 35.44 | 6 |
| ATOM | 2138 | CE2 | PHE A 268 | 14.066 | 34.784 | 59.594 | 1.00 | 36.00 | 6 |
| ATOM | 2139 | CZ | PHE A 268 | 15.201 | 34.040 | 59.936 | 1.00 | 34.68 | 6 |
| ATOM | 2140 | C | PHE A 268 | 14.319 | 40.530 | 59.190 | 1.00 | 30.94 | 6 |
| ATOM | 2141 | O | PHE A 268 | 14.983 | 41.192 | 58.394 | 1.00 | 30.27 | 8 |
| ATOM | 2142 | N | ASN A 269 | 13.693 | 41.081 | 60.222 | 1.00 | 32.53 | 7 |
| ATOM | 2143 | CA | ASN A 269 | 13.760 | 42.527 | 60.448 | 1.00 | 35.83 | 6 |
| ATOM | 2144 | CB | ASN A 269 | 12.344 | 43.115 | 60.570 | 1.00 | 37.23 | 6 |
| ATOM | 2145 | CG | ASN A 269 | 11.478 | 42.809 | 59.360 | 1.00 | 40.75 | 6 |
| ATOM | 2146 | OD1 | ASN A 269 | 11.830 | 43.148 | 58.227 | 1.00 | 43.88 | 8 |
| ATOM | 2147 | ND2 | ASN A 269 | 10.335 | 42.165 | 59.594 | 1.00 | 39.61 | 7 |
| ATOM | 2148 | C | ASN A 269 | 14.553 | 42.854 | 61.710 | 1.00 | 35.45 | 6 |
| ATOM | 2149 | O | ASN A 269 | 14.095 | 43.621 | 62.560 | 1.00 | 41.47 | 8 |
| ATOM | 2150 | N | LEU A 270 | 15.747 | 42.285 | 61.827 | 1.00 | 33.27 | 7 |
| ATOM | 2151 | CA | LEU A 270 | 16.571 | 42.510 | 63.004 | 1.00 | 30.68 | 6 |
| ATOM | 2152 | CB | LEU A 270 | 17.638 | 41.431 | 63.114 | 1.00 | 27.41 | 6 |
| ATOM | 2153 | CG | LEU A 270 | 17.140 | 40.002 | 62.988 | 1.00 | 23.76 | 6 |
| ATOM | 2154 | CD1 | LEU A 270 | 18.222 | 39.106 | 63.543 | 1.00 | 27.14 | 6 |
| ATOM | 2155 | CD2 | LEU A 270 | 15.855 | 39.801 | 63.772 | 1.00 | 28.00 | 6 |
| ATOM | 2156 | C | LEU A 270 | 17.258 | 43.856 | 63.033 | 1.00 | 32.30 | 6 |
| ATOM | 2157 | O | LEU A 270 | 17.347 | 44.554 | 62.017 | 1.00 | 36.27 | 8 |
| ATOM | 2158 | N | SER A 271 | 17.749 | 44.207 | 64.216 | 1.00 | 30.33 | 7 |
| ATOM | 2159 | CA | SER A 271 | 18.465 | 45.457 | 64.424 | 1.00 | 30.79 | 6 |
| ATOM | 2160 | CB | SER A 271 | 17.816 | 46.249 | 65.562 | 1.00 | 29.53 | 6 |
| ATOM | 2161 | OG | SER A 271 | 17.712 | 45.471 | 66.739 | 1.00 | 30.43 | 8 |
| ATOM | 2162 | C | SER A 271 | 19.911 | 45.109 | 64.768 | 1.00 | 33.09 | 6 |
| ATOM | 2163 | O | SER A 271 | 20.194 | 43.972 | 65.172 | 1.00 | 29.64 | 8 |
| ATOM | 2164 | N | ASN A 272 | 20.821 | 46.069 | 64.586 | 1.00 | 32.36 | 7 |
| ATOM | 2165 | CA | ASN A 272 | 22.234 | 45.846 | 64.896 | 1.00 | 31.65 | 6 |
| ATOM | 2166 | CB | ASN A 272 | 23.036 | 47.141 | 64.771 | 1.00 | 33.76 | 6 |
| ATOM | 2167 | CG | ASN A 272 | 23.101 | 47.658 | 63.361 | 1.00 | 37.76 | 6 |
| ATOM | 2168 | OD1 | ASN A 272 | 23.719 | 48.686 | 63.100 | 1.00 | 36.12 | 8 |
| ATOM | 2169 | ND2 | ASN A 272 | 22.460 | 46.952 | 62.437 | 1.00 | 44.79 | 7 |
| ATOM | 2170 | C | ASN A 272 | 22.369 | 45.333 | 66.321 | 1.00 | 32.61 | 6 |
| ATOM | 2171 | O | ASN A 272 | 22.970 | 44.283 | 66.565 | 1.00 | 27.95 | 8 |
| ATOM | 2172 | N | VAL A 273 | 21.803 | 46.091 | 67.257 | 1.00 | 33.22 | 7 |
| ATOM | 2173 | CA | VAL A 273 | 21.839 | 45.741 | 68.668 | 1.00 | 35.52 | 6 |
| ATOM | 2174 | CB | VAL A 273 | 20.928 | 46.660 | 69.481 | 1.00 | 37.80 | 6 |
| ATOM | 2175 | CG1 | VAL A 273 | 20.987 | 46.276 | 70.964 | 1.00 | 39.00 | 6 |
| ATOM | 2176 | CG2 | VAL A 273 | 21.356 | 48.112 | 69.275 | 1.00 | 38.88 | 6 |
| ATOM | 2177 | C | VAL A 273 | 21.416 | 44.300 | 68.908 | 1.00 | 34.26 | 6 |
| ATOM | 2178 | O | VAL A 273 | 22.060 | 43.580 | 69.679 | 1.00 | 35.96 | 8 |

Fig. 17-33

| | | | | | | | | | |
|---|---|---|---|---|---|---|---|---|---|
| ATOM | 2179 | N | ALA | A | 274 | 20.328 | 43.889 | 68.262 | 1.00 32.36 7 |
| ATOM | 2180 | CA | ALA | A | 274 | 19.834 | 42.521 | 68.385 | 1.00 31.09 6 |
| ATOM | 2181 | CB | ALA | A | 274 | 18.574 | 42.356 | 67.578 | 1.00 28.88 6 |
| ATOM | 2182 | C | ALA | A | 274 | 20.923 | 41.588 | 67.861 | 1.00 31.74 6 |
| ATOM | 2183 | O | ALA | A | 274 | 21.323 | 40.634 | 68.533 | 1.00 31.54 8 |
| ATOM | 2184 | N | PHE | A | 275 | 21.401 | 41.879 | 66.655 | 1.00 30.05 7 |
| ATOM | 2185 | CA | PHE | A | 275 | 22.467 | 41.102 | 66.036 | 1.00 31.30 6 |
| ATOM | 2186 | CB | PHE | A | 275 | 22.932 | 41.810 | 64.751 | 1.00 31.54 6 |
| ATOM | 2187 | CG | PHE | A | 275 | 23.938 | 41.029 | 63.941 | 1.00 31.76 6 |
| ATOM | 2188 | CD1 | PHE | A | 275 | 23.597 | 39.809 | 63.365 | 1.00 32.40 6 |
| ATOM | 2189 | CD2 | PHE | A | 275 | 25.219 | 41.529 | 63.729 | 1.00 34.04 6 |
| ATOM | 2190 | CE1 | PHE | A | 275 | 24.513 | 39.100 | 62.586 | 1.00 32.27 6 |
| ATOM | 2191 | CE2 | PHE | A | 275 | 26.149 | 40.828 | 62.950 | 1.00 33.90 6 |
| ATOM | 2192 | CZ | PHE | A | 275 | 25.793 | 39.613 | 62.378 | 1.00 34.50 6 |
| ATOM | 2193 | C | PHE | A | 275 | 23.632 | 40.999 | 67.040 | 1.00 29.98 6 |
| ATOM | 2194 | O | PHE | A | 275 | 24.252 | 39.950 | 67.200 | 1.00 29.41 8 |
| ATOM | 2195 | N | LEU | A | 276 | 23.908 | 42.099 | 67.726 | 1.00 31.22 7 |
| ATOM | 2196 | CA | LEU | A | 276 | 24.988 | 42.144 | 68.698 | 1.00 32.29 6 |
| ATOM | 2197 | CB | LEU | A | 276 | 25.221 | 43.594 | 69.141 | 1.00 33.44 6 |
| ATOM | 2198 | CG | LEU | A | 276 | 26.415 | 43.908 | 70.050 | 1.00 36.01 6 |
| ATOM | 2199 | CD1 | LEU | A | 276 | 26.683 | 45.391 | 70.025 | 1.00 35.02 6 |
| ATOM | 2200 | CD2 | LEU | A | 276 | 26.147 | 43.433 | 71.467 | 1.00 39.09 6 |
| ATOM | 2201 | C | LEU | A | 276 | 24.682 | 41.244 | 69.894 | 1.00 32.79 6 |
| ATOM | 2202 | O | LEU | A | 276 | 25.560 | 40.530 | 70.371 | 1.00 30.74 8 |
| ATOM | 2203 | N | LYS | A | 277 | 23.445 | 41.273 | 70.384 | 1.00 33.95 7 |
| ATOM | 2204 | CA | LYS | A | 277 | 23.086 | 40.413 | 71.505 | 1.00 36.56 6 |
| ATOM | 2205 | CB | LYS | A | 277 | 21.623 | 40.588 | 71.902 | 1.00 35.76 6 |
| ATOM | 2206 | CG | LYS | A | 277 | 21.343 | 41.842 | 72.687 | 1.00 42.31 6 |
| ATOM | 2207 | CD | LYS | A | 277 | 20.743 | 41.508 | 74.049 | 1.00 45.72 6 |
| ATOM | 2208 | CE | LYS | A | 277 | 21.665 | 40.601 | 74.865 | 1.00 47.87 6 |
| ATOM | 2209 | NZ | LYS | A | 277 | 21.140 | 40.378 | 76.244 | 1.00 44.36 7 |
| ATOM | 2210 | C | LYS | A | 277 | 23.302 | 38.974 | 71.092 | 1.00 37.98 6 |
| ATOM | 2211 | O | LYS | A | 277 | 23.875 | 38.179 | 71.845 | 1.00 37.54 8 |
| ATOM | 2212 | N | ALA | A | 278 | 22.832 | 38.654 | 69.886 | 1.00 37.17 7 |
| ATOM | 2213 | CA | ALA | A | 278 | 22.952 | 37.311 | 69.323 | 1.00 34.51 6 |
| ATOM | 2214 | CB | ALA | A | 278 | 22.638 | 37.341 | 67.820 | 1.00 35.38 6 |
| ATOM | 2215 | C | ALA | A | 278 | 24.368 | 36.831 | 69.550 | 1.00 30.63 6 |
| ATOM | 2216 | O | ALA | A | 278 | 24.605 | 35.790 | 70.167 | 1.00 27.62 8 |
| ATOM | 2217 | N | PHE | A | 279 | 25.303 | 37.624 | 69.049 | 1.00 29.24 7 |
| ATOM | 2218 | CA | PHE | A | 279 | 26.722 | 37.347 | 69.167 | 1.00 31.48 6 |
| ATOM | 2219 | CB | PHE | A | 279 | 27.490 | 38.558 | 68.645 | 1.00 33.25 6 |
| ATOM | 2220 | CG | PHE | A | 279 | 28.974 | 38.396 | 68.663 | 1.00 39.28 6 |
| ATOM | 2221 | CD1 | PHE | A | 279 | 29.578 | 37.337 | 68.000 | 1.00 41.15 6 |
| ATOM | 2222 | CD2 | PHE | A | 279 | 29.776 | 39.328 | 69.315 | 1.00 40.66 6 |
| ATOM | 2223 | CE1 | PHE | A | 279 | 30.960 | 37.209 | 67.987 | 1.00 44.22 6 |
| ATOM | 2224 | CE2 | PHE | A | 279 | 31.153 | 39.213 | 69.308 | 1.00 41.38 6 |
| ATOM | 2225 | CZ | PHE | A | 279 | 31.750 | 38.152 | 68.614 | 1.00 44.52 6 |
| ATOM | 2226 | C | PHE | A | 279 | 27.116 | 37.043 | 70.611 | 1.00 31.81 6 |
| ATOM | 2227 | O | PHE | A | 279 | 27.627 | 35.953 | 70.935 | 1.00 27.51 8 |
| ATOM | 2228 | N | ASN | A | 280 | 26.860 | 38.005 | 71.503 | 1.00 29.32 7 |
| ATOM | 2229 | CA | ASN | A | 280 | 27.192 | 37.851 | 72.907 | 1.00 29.26 6 |
| ATOM | 2230 | CB | ASN | A | 280 | 26.927 | 39.153 | 73.660 | 1.00 30.39 6 |
| ATOM | 2231 | CG | ASN | A | 280 | 27.907 | 40.245 | 73.278 | 1.00 30.68 6 |
| ATOM | 2232 | OD1 | ASN | A | 280 | 29.117 | 40.030 | 73.303 | 1.00 33.34 8 |
| ATOM | 2233 | ND2 | ASN | A | 280 | 27.395 | 41.419 | 72.931 | 1.00 27.00 7 |
| ATOM | 2234 | C | ASN | A | 280 | 26.524 | 36.680 | 73.616 | 1.00 30.01 6 |
| ATOM | 2235 | O | ASN | A | 280 | 27.167 | 36.004 | 74.419 | 1.00 29.58 8 |
| ATOM | 2236 | N | ILE | A | 281 | 25.252 | 36.423 | 73.335 | 1.00 30.46 7 |
| ATOM | 2237 | CA | ILE | A | 281 | 24.594 | 35.291 | 73.983 | 1.00 33.71 6 |
| ATOM | 2238 | CB | ILE | A | 281 | 23.107 | 35.161 | 73.569 | 1.00 36.14 6 |
| ATOM | 2239 | CG2 | ILE | A | 281 | 22.541 | 33.820 | 74.032 | 1.00 36.18 6 |
| ATOM | 2240 | CG1 | ILE | A | 281 | 22.298 | 36.307 | 74.177 | 1.00 33.52 6 |
| ATOM | 2241 | CD1 | ILE | A | 281 | 20.835 | 36.243 | 73.834 | 1.00 37.16 6 |
| ATOM | 2242 | C | ILE | A | 281 | 25.330 | 34.006 | 73.631 | 1.00 34.06 6 |
| ATOM | 2243 | O | ILE | A | 281 | 25.385 | 33.071 | 74.437 | 1.00 31.94 8 |
| ATOM | 2244 | N | VAL | A | 282 | 25.896 | 33.960 | 72.427 | 1.00 35.31 7 |

Fig. 17-34

```
ATOM   2245  CA  VAL A 282      26.654  32.785  72.005  1.00 36.45      6
ATOM   2246  CB  VAL A 282      27.084  32.871  70.524  1.00 35.62      6
ATOM   2247  CG1 VAL A 282      27.829  31.604  70.126  1.00 31.20      6
ATOM   2248  CG2 VAL A 282      25.880  33.080  69.646  1.00 34.51      6
ATOM   2249  C   VAL A 282      27.919  32.723  72.857  1.00 37.80      6
ATOM   2250  O   VAL A 282      28.182  31.722  73.532  1.00 36.12      8
ATOM   2251  N   ARG A 283      28.693  33.808  72.821  1.00 38.45      7
ATOM   2252  CA  ARG A 283      29.929  33.884  73.587  1.00 40.06      6
ATOM   2253  CB  ARG A 283      30.551  35.272  73.449  1.00 39.38      6
ATOM   2254  CG  ARG A 283      30.974  35.625  72.027  1.00 41.90      6
ATOM   2255  CD  ARG A 283      31.492  37.048  71.968  1.00 41.36      6
ATOM   2256  NE  ARG A 283      32.647  37.206  72.840  1.00 43.35      7
ATOM   2257  CZ  ARG A 283      33.162  38.373  73.215  1.00 42.55      6
ATOM   2258  NH1 ARG A 283      32.628  39.516  72.797  1.00 39.95      7
ATOM   2259  NH2 ARG A 283      34.220  38.392  74.014  1.00 41.72      7
ATOM   2260  C   ARG A 283      29.614  33.587  75.044  1.00 40.01      6
ATOM   2261  O   ARG A 283      30.350  32.862  75.716  1.00 39.01      8
ATOM   2262  N   GLU A 284      28.506  34.141  75.520  1.00 40.30      7
ATOM   2263  CA  GLU A 284      28.084  33.923  76.894  1.00 43.19      6
ATOM   2264  CB  GLU A 284      26.753  34.647  77.165  1.00 47.53      6
ATOM   2265  CG  GLU A 284      26.875  36.176  77.090  1.00 56.10      6
ATOM   2266  CD  GLU A 284      25.542  36.923  77.179  1.00 60.77      6
ATOM   2267  OE1 GLU A 284      24.659  36.682  76.329  1.00 61.41      8
ATOM   2268  OE2 GLU A 284      25.383  37.763  78.096  1.00 62.21      8
ATOM   2269  C   GLU A 284      27.953  32.429  77.179  1.00 40.72      6
ATOM   2270  O   GLU A 284      28.565  31.922  78.120  1.00 45.29      8
ATOM   2271  N   VAL A 285      27.186  31.721  76.354  1.00 34.82      7
ATOM   2272  CA  VAL A 285      26.975  30.288  76.551  1.00 30.84      6
ATOM   2273  CB  VAL A 285      25.842  29.752  75.647  1.00 27.74      6
ATOM   2274  CG1 VAL A 285      25.698  28.253  75.831  1.00 22.95      6
ATOM   2275  CG2 VAL A 285      24.545  30.433  75.982  1.00 26.26      6
ATOM   2276  C   VAL A 285      28.181  29.366  76.341  1.00 31.93      6
ATOM   2277  O   VAL A 285      28.492  28.556  77.214  1.00 33.46      8
ATOM   2278  N   PHE A 286      28.845  29.466  75.191  1.00 29.43      7
ATOM   2279  CA  PHE A 286      29.973  28.586  74.907  1.00 24.26      6
ATOM   2280  CB  PHE A 286      29.830  27.957  73.519  1.00 22.57      6
ATOM   2281  CG  PHE A 286      28.607  27.095  73.345  1.00 23.46      6
ATOM   2282  CD1 PHE A 286      27.409  27.639  72.885  1.00 23.90      6
ATOM   2283  CD2 PHE A 286      28.664  25.718  73.608  1.00 21.95      6
ATOM   2284  CE1 PHE A 286      26.281  26.814  72.681  1.00 24.90      6
ATOM   2285  CE2 PHE A 286      27.547  24.892  73.411  1.00 18.06      6
ATOM   2286  CZ  PHE A 286      26.357  25.437  72.945  1.00 20.23      6
ATOM   2287  C   PHE A 286      31.368  29.200  74.991  1.00 25.14      6
ATOM   2288  O   PHE A 286      32.338  28.566  74.560  1.00 23.16      8
ATOM   2289  N   GLY A 287      31.480  30.416  75.525  1.00 25.51      7
ATOM   2290  CA  GLY A 287      32.783  31.065  75.614  1.00 26.86      6
ATOM   2291  C   GLY A 287      33.353  31.511  74.270  1.00 26.28      6
ATOM   2292  O   GLY A 287      32.644  31.549  73.271  1.00 26.29      8
ATOM   2293  N   GLU A 288      34.637  31.849  74.238  1.00 27.17      7
ATOM   2294  CA  GLU A 288      35.274  32.291  72.996  1.00 33.20      6
ATOM   2295  CB  GLU A 288      36.680  32.828  73.269  1.00 35.09      6
ATOM   2296  CG  GLU A 288      36.726  34.104  74.083  1.00 41.67      6
ATOM   2297  CD  GLU A 288      35.970  35.231  73.421  1.00 43.13      6
ATOM   2298  OE1 GLU A 288      36.221  35.493  72.228  1.00 45.39      8
ATOM   2299  OE2 GLU A 288      35.130  35.858  74.097  1.00 47.64      8
ATOM   2300  C   GLU A 288      35.386  31.204  71.930  1.00 32.87      6
ATOM   2301  O   GLU A 288      35.596  30.029  72.247  1.00 31.59      8
ATOM   2302  N   GLY A 289      35.268  31.619  70.668  1.00 31.93      7
ATOM   2303  CA  GLY A 289      35.373  30.698  69.545  1.00 29.58      6
ATOM   2304  C   GLY A 289      35.948  31.372  68.307  1.00 27.42      6
ATOM   2305  O   GLY A 289      36.556  32.437  68.398  1.00 26.27      8
ATOM   2306  N   VAL A 290      35.764  30.758  67.143  1.00 27.64      7
ATOM   2307  CA  VAL A 290      36.277  31.349  65.907  1.00 27.17      6
ATOM   2308  CB  VAL A 290      37.014  30.301  65.037  1.00 25.25      6
ATOM   2309  CG1 VAL A 290      37.616  30.976  63.813  1.00 22.41      6
ATOM   2310  CG2 VAL A 290      38.100  29.632  65.852  1.00 17.33      6
```

Fig. 17-35

| ATOM | 2311 | C | VAL A 290 | 35.137 | 31.975 | 65.105 | 1.00 | 25.97 | 6 |
|---|---|---|---|---|---|---|---|---|---|
| ATOM | 2312 | O | VAL A 290 | 34.218 | 31.279 | 64.672 | 1.00 | 22.32 | 8 |
| ATOM | 2313 | N | TYR A 291 | 35.217 | 33.293 | 64.914 | 1.00 | 27.33 | 7 |
| ATOM | 2314 | CA | TYR A 291 | 34.188 | 34.052 | 64.203 | 1.00 | 26.69 | 6 |
| ATOM | 2315 | CB | TYR A 291 | 33.925 | 35.356 | 64.939 | 1.00 | 25.51 | 6 |
| ATOM | 2316 | CG | TYR A 291 | 33.935 | 35.178 | 66.435 | 1.00 | 28.73 | 6 |
| ATOM | 2317 | CD1 | TYR A 291 | 35.025 | 35.596 | 67.191 | 1.00 | 29.72 | 6 |
| ATOM | 2318 | CE1 | TYR A 291 | 35.059 | 35.414 | 68.563 | 1.00 | 29.53 | 6 |
| ATOM | 2319 | CD2 | TYR A 291 | 32.874 | 34.565 | 67.094 | 1.00 | 27.39 | 6 |
| ATOM | 2320 | CE2 | TYR A 291 | 32.898 | 34.377 | 68.466 | 1.00 | 31.03 | 6 |
| ATOM | 2321 | CZ | TYR A 291 | 33.997 | 34.808 | 69.194 | 1.00 | 31.85 | 6 |
| ATOM | 2322 | OH | TYR A 291 | 34.030 | 34.647 | 70.562 | 1.00 | 38.03 | 8 |
| ATOM | 2323 | C | TYR A 291 | 34.527 | 34.345 | 62.745 | 1.00 | 27.99 | 6 |
| ATOM | 2324 | O | TYR A 291 | 35.608 | 34.843 | 62.415 | 1.00 | 24.83 | 8 |
| ATOM | 2325 | N | LEU A 292 | 33.567 | 34.042 | 61.880 | 1.00 | 30.17 | 7 |
| ATOM | 2326 | CA | LEU A 292 | 33.726 | 34.220 | 60.441 | 1.00 | 28.26 | 6 |
| ATOM | 2327 | CB | LEU A 292 | 33.561 | 32.861 | 59.741 | 1.00 | 27.70 | 6 |
| ATOM | 2328 | CG | LEU A 292 | 34.191 | 31.643 | 60.435 | 1.00 | 24.64 | 6 |
| ATOM | 2329 | CD1 | LEU A 292 | 33.867 | 30.380 | 59.661 | 1.00 | 24.66 | 6 |
| ATOM | 2330 | CD2 | LEU A 292 | 35.686 | 31.825 | 60.553 | 1.00 | 23.19 | 6 |
| ATOM | 2331 | C | LEU A 292 | 32.649 | 35.175 | 59.944 | 1.00 | 25.59 | 6 |
| ATOM | 2332 | O | LEU A 292 | 31.640 | 35.394 | 60.611 | 1.00 | 18.11 | 8 |
| ATOM | 2333 | N | GLY A 293 | 32.869 | 35.749 | 58.770 | 1.00 | 28.55 | 7 |
| ATOM | 2334 | CA | GLY A 293 | 31.878 | 36.653 | 58.223 | 1.00 | 31.26 | 6 |
| ATOM | 2335 | C | GLY A 293 | 30.722 | 35.815 | 57.714 | 1.00 | 34.84 | 6 |
| ATOM | 2336 | O | GLY A 293 | 30.463 | 34.724 | 58.234 | 1.00 | 34.11 | 8 |
| ATOM | 2337 | N | GLY A 294 | 30.036 | 36.312 | 56.689 | 1.00 | 35.34 | 7 |
| ATOM | 2338 | CA | GLY A 294 | 28.918 | 35.581 | 56.124 | 1.00 | 34.84 | 6 |
| ATOM | 2339 | C | GLY A 294 | 28.142 | 36.445 | 55.155 | 1.00 | 34.79 | 6 |
| ATOM | 2340 | O | GLY A 294 | 28.644 | 37.473 | 54.699 | 1.00 | 37.05 | 8 |
| ATOM | 2341 | N | GLY A 295 | 26.917 | 36.035 | 54.842 | 1.00 | 31.87 | 7 |
| ATOM | 2342 | CA | GLY A 295 | 26.102 | 36.806 | 53.925 | 1.00 | 27.78 | 6 |
| ATOM | 2343 | C | GLY A 295 | 25.969 | 38.245 | 54.378 | 1.00 | 27.09 | 6 |
| ATOM | 2344 | O | GLY A 295 | 26.192 | 38.558 | 55.546 | 1.00 | 27.03 | 8 |
| ATOM | 2345 | N | GLY A 296 | 25.596 | 39.119 | 53.450 | 1.00 | 24.67 | 7 |
| ATOM | 2346 | CA | GLY A 296 | 25.440 | 40.527 | 53.757 | 1.00 | 25.28 | 6 |
| ATOM | 2347 | C | GLY A 296 | 25.562 | 41.262 | 52.446 | 1.00 | 27.64 | 6 |
| ATOM | 2348 | O | GLY A 296 | 26.591 | 41.163 | 51.771 | 1.00 | 26.65 | 8 |
| ATOM | 2349 | N | TYR A 297 | 24.526 | 42.009 | 52.078 | 1.00 | 30.21 | 7 |
| ATOM | 2350 | CA | TYR A 297 | 24.543 | 42.704 | 50.801 | 1.00 | 30.62 | 6 |
| ATOM | 2351 | CB | TYR A 297 | 23.560 | 42.011 | 49.859 | 1.00 | 29.50 | 6 |
| ATOM | 2352 | CG | TYR A 297 | 23.717 | 40.516 | 49.953 | 1.00 | 30.33 | 6 |
| ATOM | 2353 | CD1 | TYR A 297 | 23.174 | 39.810 | 51.031 | 1.00 | 30.86 | 6 |
| ATOM | 2354 | CE1 | TYR A 297 | 23.450 | 38.449 | 51.226 | 1.00 | 30.74 | 6 |
| ATOM | 2355 | CD2 | TYR A 297 | 24.538 | 39.824 | 49.062 | 1.00 | 31.20 | 6 |
| ATOM | 2356 | CE2 | TYR A 297 | 24.821 | 38.460 | 49.247 | 1.00 | 32.08 | 6 |
| ATOM | 2357 | CZ | TYR A 297 | 24.275 | 37.781 | 50.332 | 1.00 | 30.92 | 6 |
| ATOM | 2358 | OH | TYR A 297 | 24.539 | 36.440 | 50.509 | 1.00 | 29.60 | 8 |
| ATOM | 2359 | C | TYR A 297 | 24.267 | 44.195 | 50.875 | 1.00 | 32.07 | 6 |
| ATOM | 2360 | O | TYR A 297 | .134 | 44.849 | 49.840 | 1.00 | 33.83 | 8 |
| ATOM | 2361 | N | HIS A 298 | .180 | 44.725 | 52.094 | 1.00 | 31.41 | 7 |
| ATOM | 2362 | CA | HIS A 298 | .961 | 46.153 | 52.289 | 1.00 | 33.94 | 6 |
| ATOM | 2363 | CB | HIS A 298 | 22.761 | 46.430 | 53.194 | 1.00 | 34.75 | 6 |
| ATOM | 2364 | CG | HIS A 298 | 22.379 | 47.880 | 53.256 | 1.00 | 35.16 | 6 |
| ATOM | 2365 | CD2 | HIS A 298 | 22.558 | 48.809 | 54.224 | 1.00 | 35.72 | 6 |
| ATOM | 2366 | ND1 | HIS A 298 | 21.779 | 48.538 | 52.205 | 1.00 | 34.10 | 7 |
| ATOM | 2367 | CE1 | HIS A 298 | 21.605 | 49.809 | 52.522 | 1.00 | 31.84 | 6 |
| ATOM | 2368 | NE2 | HIS A 298 | 22.069 | 50.000 | 53.742 | 1.00 | 35.46 | 7 |
| ATOM | 2369 | C | HIS A 298 | 25.213 | 46.697 | 52.962 | 1.00 | 36.21 | 6 |
| ATOM | 2370 | O | HIS A 298 | 25.471 | 46.405 | 54.133 | 1.00 | 33.83 | 8 |
| ATOM | 2371 | N | PRO A 299 | 25.992 | 47.519 | 52.234 | 1.00 | 36.69 | 7 |
| ATOM | 2372 | CD | PRO A 299 | 25.680 | 47.997 | 50.881 | 1.00 | 35.57 | 6 |
| ATOM | 2373 | CA | PRO A 299 | 27.238 | 48.142 | 52.689 | 1.00 | 35.17 | 6 |
| ATOM | 2374 | CB | PRO A 299 | 27.586 | 49.073 | 51.525 | 1.00 | 37.75 | 6 |
| ATOM | 2375 | CG | PRO A 299 | 26.216 | 49.399 | 50.954 | 1.00 | 37.76 | 6 |
| ATOM | 2376 | C | PRO A 299 | 27.045 | 48.886 | 54.000 | 1.00 | 34.47 | 6 |

Fig. 17-36

```
ATOM   2377  O    PRO A 299      27.781  48.670  54.963  1.00 33.67      8
ATOM   2378  N    TYR A 300      26.051  49.763  54.026  1.00 32.69      7
ATOM   2379  CA   TYR A 300      25.745  50.521  55.227  1.00 32.97      6
ATOM   2380  CB   TYR A 300      24.496  51.377  55.009  1.00 35.56      6
ATOM   2381  CG   TYR A 300      24.648  52.524  54.028  1.00 35.96      6
ATOM   2382  CD1  TYR A 300      25.370  52.367  52.842  1.00 39.37      6
ATOM   2383  CE1  TYR A 300      25.461  53.405  51.907  1.00 39.92      6
ATOM   2384  CD2  TYR A 300      24.016  53.752  54.259  1.00 35.92      6
ATOM   2385  CE2  TYR A 300      24.098  54.793  53.334  1.00 36.78      6
ATOM   2386  CZ   TYR A 300      24.823  54.612  52.161  1.00 38.09      6
ATOM   2387  OH   TYR A 300      24.927  55.634  51.251  1.00 37.68      8
ATOM   2388  C    TYR A 300      25.497  49.546  56.369  1.00 31.10      6
ATOM   2389  O    TYR A 300      26.062  49.692  57.440  1.00 30.62      8
ATOM   2390  N    ALA A 301      24.661  48.541  56.125  1.00 32.55      7
ATOM   2391  CA   ALA A 301      24.323  47.541  57.145  1.00 31.64      6
ATOM   2392  CB   ALA A 301      23.216  46.602  56.624  1.00 24.69      6
ATOM   2393  C    ALA A 301      25.539  46.727  57.552  1.00 30.06      6
ATOM   2394  O    ALA A 301      25.848  46.579  58.734  1.00 31.91      8
ATOM   2395  N    LEU A 302      26.223  46.192  56.557  1.00 28.94      7
ATOM   2396  CA   LEU A 302      27.404  45.383  56.795  1.00 30.55      6
ATOM   2397  CB   LEU A 302      28.012  45.002  55.441  1.00 31.83      6
ATOM   2398  CG   LEU A 302      29.315  44.223  55.323  1.00 30.01      6
ATOM   2399  CD1  LEU A 302      29.491  43.781  53.888  1.00 32.09      6
ATOM   2400  CD2  LEU A 302      30.475  45.077  55.762  1.00 32.23      6
ATOM   2401  C    LEU A 302      28.418  46.136  57.663  1.00 29.79      6
ATOM   2402  O    LEU A 302      28.796  45.676  58.746  1.00 27.68      8
ATOM   2403  N    ALA A 303      28.842  47.299  57.179  1.00 27.92      7
ATOM   2404  CA   ALA A 303      29.818  48.119  57.877  1.00 25.00      6
ATOM   2405  CB   ALA A 303      30.026  49.424  57.137  1.00 23.62      6
ATOM   2406  C    ALA A 303      29.397  48.397  59.305  1.00 25.06      6
ATOM   2407  O    ALA A 303      30.088  48.015  60.248  1.00 26.90      8
ATOM   2408  N    ARG A 304      28.258  49.054  59.472  1.00 24.06      7
ATOM   2409  CA   ARG A 304      27.794  49.382  60.810  1.00 24.37      6
ATOM   2410  CB   ARG A 304      26.420  50.052  60.758  1.00 23.99      6
ATOM   2411  CG   ARG A 304      26.328  51.257  59.815  1.00 28.77      6
ATOM   2412  CD   ARG A 304      25.106  52.089  60.156  1.00 29.96      6
ATOM   2413  NE   ARG A 304      23.943  51.233  60.369  1.00 36.43      7
ATOM   2414  CZ   ARG A 304      22.893  51.573  61.110  1.00 37.01      6
ATOM   2415  NH1  ARG A 304      22.854  52.757  61.713  1.00 36.37      7
ATOM   2416  NH2  ARG A 304      21.896  50.719  61.269  1.00 34.36      7
ATOM   2417  C    ARG A 304      27.727  48.142  61.691  1.00 24.24      6
ATOM   2418  O    ARG A 304      28.343  48.099  62.762  1.00 22.34      8
ATOM   2419  N    ALA A 305      26.994  47.132  61.221  1.00 24.51      7
ATOM   2420  CA   ALA A 305      26.801  45.883  61.959  1.00 22.70      6
ATOM   2421  CB   ALA A 305      25.880  44.960  61.175  1.00 18.13      6
ATOM   2422  C    ALA A 305      28.089  45.142  62.351  1.00 23.33      6
ATOM   2423  O    ALA A 305      28.237  44.725  63.506  1.00 21.51      8
ATOM   2424  N    TRP A 306      29.016  44.961  61.411  1.00 22.79      7
ATOM   2425  CA   TRP A 306      30.244  44.270  61.764  1.00 24.33      6
ATOM   2426  CB   TRP A 306      31.029  43.842  60.524  1.00 26.93      6
ATOM   2427  CG   TRP A 306      30.604  42.503  59.952  1.00 27.96      6
ATOM   2428  CD2  TRP A 306      30.861  42.013  58.629  1.00 26.38      6
ATOM   2429  CE2  TRP A 306      30.366  40.688  58.570  1.00 24.96      6
ATOM   2430  CE3  TRP A 306      31.462  42.563  57.490  1.00 23.00      6
ATOM   2431  CD1  TRP A 306      29.983  41.484  60.620  1.00 28.53      6
ATOM   2432  NE1  TRP A 306      29.837  40.392  59.797  1.00 25.62      7
ATOM   2433  CZ2  TRP A 306      30.450  39.904  57.414  1.00 24.51      6
ATOM   2434  CZ3  TRP A 306      31.548  41.784  56.343  1.00 25.37      6
ATOM   2435  CH2  TRP A 306      31.042  40.465  56.315  1.00 24.20      6
ATOM   2436  C    TRP A 306      31.129  45.108  62.676  1.00 26.51      6
ATOM   2437  O    TRP A 306      31.908  44.570  63.464  1.00 25.07      8
ATOM   2438  N    THR A 307      31.003  46.427  62.575  1.00 28.08      7
ATOM   2439  CA   THR A 307      31.785  47.323  63.415  1.00 27.91      6
ATOM   2440  CB   THR A 307      31.484  48.796  63.100  1.00 27.86      6
ATOM   2441  OG1  THR A 307      31.994  49.119  61.799  1.00 30.17      8
ATOM   2442  CG2  THR A 307      32.120  49.704  64.137  1.00 24.72      6
```

Fig. 17-37

| ATOM | 2443 | C   | THR A 307 | 31.441 | 47.041 | 64.863 | 1.00 | 29.35 | 6 |
|------|------|-----|-----------|--------|--------|--------|------|-------|----|
| ATOM | 2444 | O   | THR A 307 | 32.316 | 46.989 | 65.725 | 1.00 | 32.56 | 8 |
| ATOM | 2445 | N   | LEU A 308 | 30.159 | 46.857 | 65.135 | 1.00 | 30.60 | 7 |
| ATOM | 2446 | CA  | LEU A 308 | 29.740 | 46.555 | 66.490 | 1.00 | 33.69 | 6 |
| ATOM | 2447 | CB  | LEU A 308 | 28.256 | 46.215 | 66.525 | 1.00 | 34.48 | 6 |
| ATOM | 2448 | CG  | LEU A 308 | 27.338 | 47.337 | 66.058 | 1.00 | 34.79 | 6 |
| ATOM | 2449 | CD1 | LEU A 308 | 25.903 | 46.887 | 66.153 | 1.00 | 31.98 | 6 |
| ATOM | 2450 | CD2 | LEU A 308 | 27.569 | 48.542 | 66.924 | 1.00 | 36.96 | 6 |
| ATOM | 2451 | C   | LEU A 308 | 30.531 | 45.353 | 66.965 | 1.00 | 34.57 | 6 |
| ATOM | 2452 | O   | LEU A 308 | 31.230 | 45.417 | 67.975 | 1.00 | 33.75 | 8 |
| ATOM | 2453 | N   | ILE A 309 | 30.423 | 44.262 | 66.208 | 1.00 | 35.78 | 7 |
| ATOM | 2454 | CA  | ILE A 309 | 31.108 | 43.017 | 66.540 | 1.00 | 35.87 | 6 |
| ATOM | 2455 | CB  | ILE A 309 | 30.939 | 41.949 | 65.431 | 1.00 | 34.95 | 6 |
| ATOM | 2456 | CG2 | ILE A 309 | 31.733 | 40.695 | 65.799 | 1.00 | 31.21 | 6 |
| ATOM | 2457 | CG1 | ILE A 309 | 29.445 | 41.631 | 65.212 | 1.00 | 34.25 | 6 |
| ATOM | 2458 | CD1 | ILE A 309 | 28.726 | 41.014 | 66.407 | 1.00 | 25.04 | 6 |
| ATOM | 2459 | C   | ILE A 309 | 32.589 | 43.238 | 66.772 | 1.00 | 35.81 | 6 |
| ATOM | 2460 | O   | ILE A 309 | 33.183 | 42.617 | 67.657 | 1.00 | 38.19 | 8 |
| ATOM | 2461 | N   | TRP A 310 | 33.197 | 44.111 | 65.977 | 1.00 | 36.10 | 7 |
| ATOM | 2462 | CA  | TRP A 310 | 34.612 | 44.384 | 66.169 | 1.00 | 35.26 | 6 |
| ATOM | 2463 | CB  | TRP A 310 | 35.150 | 45.311 | 65.075 | 1.00 | 32.61 | 6 |
| ATOM | 2464 | CG  | TRP A 310 | 36.619 | 45.588 | 65.220 | 1.00 | 30.79 | 6 |
| ATOM | 2465 | CD2 | TRP A 310 | 37.679 | 44.620 | 65.274 | 1.00 | 29.93 | 6 |
| ATOM | 2466 | CE2 | TRP A 310 | 38.882 | 45.330 | 65.474 | 1.00 | 28.42 | 6 |
| ATOM | 2467 | CE3 | TRP A 310 | 37.731 | 43.224 | 65.174 | 1.00 | 31.59 | 6 |
| ATOM | 2468 | CD1 | TRP A 310 | 37.206 | 46.804 | 65.380 | 1.00 | 30.62 | 6 |
| ATOM | 2469 | NE1 | TRP A 310 | 38.565 | 46.659 | 65.536 | 1.00 | 29.37 | 7 |
| ATOM | 2470 | CZ2 | TRP A 310 | 40.126 | 44.691 | 65.578 | 1.00 | 27.91 | 6 |
| ATOM | 2471 | CZ3 | TRP A 310 | 38.978 | 42.585 | 65.279 | 1.00 | 28.06 | 6 |
| ATOM | 2472 | CH2 | TRP A 310 | 40.150 | 43.322 | 65.479 | 1.00 | 26.50 | 6 |
| ATOM | 2473 | C   | TRP A 310 | 34.744 | 45.040 | 67.545 | 1.00 | 36.00 | 6 |
| ATOM | 2474 | O   | TRP A 310 | 35.365 | 44.476 | 68.440 | 1.00 | 36.24 | 8 |
| ATOM | 2475 | N   | CYS A 311 | 34.134 | 46.213 | 67.715 | 1.00 | 34.57 | 7 |
| ATOM | 2476 | CA  | CYS A 311 | 34.183 | 46.937 | 68.985 | 1.00 | 32.82 | 6 |
| ATOM | 2477 | CB  | CYS A 311 | 33.169 | 48.085 | 68.996 | 1.00 | 35.62 | 6 |
| ATOM | 2478 | SG  | CYS A 311 | 33.439 | 49.401 | 67.796 | 1.00 | 32.36 | 16 |
| ATOM | 2479 | C   | CYS A 311 | 33.912 | 46.061 | 70.206 | 1.00 | 32.01 | 6 |
| ATOM | 2480 | O   | CYS A 311 | 34.452 | 46.313 | 71.280 | 1.00 | 29.82 | 8 |
| ATOM | 2481 | N   | GLU A 312 | 33.062 | 45.049 | 70.053 | 1.00 | 32.57 | 7 |
| ATOM | 2482 | CA  | GLU A 312 | 32.731 | 44.159 | 71.171 | 1.00 | 33.86 | 6 |
| ATOM | 2483 | CB  | GLU A 312 | 31.557 | 43.252 | 70.807 | 1.00 | 34.19 | 6 |
| ATOM | 2484 | CG  | GLU A 312 | 30.442 | 43.185 | 71.844 | 1.00 | 40.27 | 6 |
| ATOM | 2485 | CD  | GLU A 312 | 30.923 | 42.821 | 73.239 | 1.00 | 43.80 | 6 |
| ATOM | 2486 | OE1 | GLU A 312 | 31.685 | 41.831 | 73.383 | 1.00 | 44.81 | 8 |
| ATOM | 2487 | OE2 | GLU A 312 | 30.516 | 43.522 | 74.195 | 1.00 | 41.54 | 8 |
| ATOM | 2488 | C   | GLU A 312 | 33.953 | 43.298 | 71.456 | 1.00 | 33.77 | 6 |
| ATOM | 2489 | O   | GLU A 312 | 34.253 | 42.957 | 72.603 | 1.00 | 32.07 | 8 |
| ATOM | 2490 | N   | LEU A 313 | 34.647 | 42.945 | 70.382 | 1.00 | 33.45 | 7 |
| ATOM | 2491 | CA  | LEU A 313 | 35.848 | 42.135 | 70.473 | 1.00 | 32.89 | 6 |
| ATOM | 2492 | CB  | LEU A 313 | 36.172 | 41.513 | 69.115 | 1.00 | 32.14 | 6 |
| ATOM | 2493 | CG  | LEU A 313 | 35.154 | 40.493 | 68.626 | 1.00 | 27.73 | 6 |
| ATOM | 2494 | CD1 | LEU A 313 | 35.587 | 39.956 | 67.269 | 1.00 | 30.39 | 6 |
| ATOM | 2495 | CD2 | LEU A 313 | 35.053 | 39.367 | 69.648 | 1.00 | 27.87 | 6 |
| ATOM | 2496 | C   | LEU A 313 | 36.976 | 43.031 | 70.903 | 1.00 | 31.64 | 6 |
| ATOM | 2497 | O   | LEU A 313 | 37.605 | 42.793 | 71.925 | 1.00 | 31.74 | 8 |
| ATOM | 2498 | N   | SER A 314 | 37.206 | 44.064 | 70.099 | 1.00 | 33.49 | 7 |
| ATOM | 2499 | CA  | SER A 314 | 38.232 | 45.067 | 70.328 | 1.00 | 35.59 | 6 |
| ATOM | 2500 | CB  | SER A 314 | 38.107 | 46.154 | 69.256 | 1.00 | 36.47 | 6 |
| ATOM | 2501 | OG  | SER A 314 | 39.141 | 47.120 | 69.353 | 1.00 | 44.55 | 8 |
| ATOM | 2502 | C   | SER A 314 | 38.046 | 45.661 | 71.730 | 1.00 | 37.82 | 6 |
| ATOM | 2503 | O   | SER A 314 | 39.015 | 46.043 | 72.395 | 1.00 | 37.32 | 8 |
| ATOM | 2504 | N   | GLY A 315 | 36.794 | 45.725 | 72.175 | 1.00 | 38.05 | 7 |
| ATOM | 2505 | CA  | GLY A 315 | 36.506 | 46.243 | 73.498 | 1.00 | 42.42 | 6 |
| ATOM | 2506 | C   | GLY A 315 | 36.295 | 47.744 | 73.568 | 1.00 | 46.80 | 6 |
| ATOM | 2507 | O   | GLY A 315 | 35.923 | 48.276 | 74.618 | 1.00 | 47.85 | 8 |
| ATOM | 2508 | N   | ARG A 316 | 36.518 | 48.438 | 72.458 | 1.00 | 48.90 | 7 |

Fig. 17-38

```
ATOM   2509  CA   ARG A 316      36.346  49.885  72.448  1.00 52.27      6
ATOM   2510  CB   ARG A 316      37.144  50.479  71.283  1.00 53.60      6
ATOM   2511  CG   ARG A 316      36.730  50.007  69.900  1.00 52.11      6
ATOM   2512  CD   ARG A 316      37.734  50.514  68.870  1.00 53.76      6
ATOM   2513  NE   ARG A 316      39.028  49.854  69.019  1.00 53.67      7
ATOM   2514  CZ   ARG A 316      40.135  50.221  68.383  1.00 55.34      6
ATOM   2515  NH1  ARG A 316      40.110  51.253  67.552  1.00 55.44      7
ATOM   2516  NH2  ARG A 316      41.266  49.546  68.569  1.00 55.80      7
ATOM   2517  C    ARG A 316      34.882  50.343  72.391  1.00 52.06      6
ATOM   2518  O    ARG A 316      34.075  49.781  71.652  1.00 54.96      8
ATOM   2519  N    GLU A 317      34.547  51.361  73.182  1.00 51.87      7
ATOM   2520  CA   GLU A 317      33.185  51.900  73.222  1.00 52.67      6
ATOM   2521  CB   GLU A 317      33.111  53.139  74.123  1.00 54.70      6
ATOM   2522  CG   GLU A 317      32.549  52.901  75.527  1.00 60.94      6
ATOM   2523  CD   GLU A 317      33.353  51.912  76.361  1.00 64.62      6
ATOM   2524  OE1  GLU A 317      33.025  51.741  77.556  1.00 64.59      8
ATOM   2525  OE2  GLU A 317      34.305  51.302  75.832  1.00 68.64      8
ATOM   2526  C    GLU A 317      32.642  52.256  71.843  1.00 51.27      6
ATOM   2527  O    GLU A 317      33.270  52.983  71.077  1.00 49.34      8
ATOM   2528  N    VAL A 318      31.457  51.733  71.548  1.00 51.30      7
ATOM   2529  CA   VAL A 318      30.780  51.962  70.280  1.00 48.80      6
ATOM   2530  CB   VAL A 318      29.522  51.071  70.169  1.00 47.11      6
ATOM   2531  CG1  VAL A 318      28.875  51.237  68.808  1.00 45.53      6
ATOM   2532  CG2  VAL A 318      29.895  49.631  70.424  1.00 47.05      6
ATOM   2533  C    VAL A 318      30.349  53.411  70.178  1.00 47.64      6
ATOM   2534  O    VAL A 318      29.511  53.867  70.953  1.00 47.61      8
ATOM   2535  N    PRO A 319      30.925  54.165  69.234  1.00 48.14      7
ATOM   2536  CD   PRO A 319      31.960  53.836  68.247  1.00 48.87      6
ATOM   2537  CA   PRO A 319      30.538  55.569  69.093  1.00 52.54      6
ATOM   2538  CB   PRO A 319      31.438  56.051  67.954  1.00 49.96      6
ATOM   2539  CG   PRO A 319      31.612  54.802  67.141  1.00 50.17      6
ATOM   2540  C    PRO A 319      29.052  55.679  68.764  1.00 55.84      6
ATOM   2541  O    PRO A 319      28.531  54.913  67.953  1.00 56.06      8
ATOM   2542  N    GLU A 320      28.369  56.624  69.402  1.00 59.20      7
ATOM   2543  CA   GLU A 320      26.942  56.804  69.167  1.00 62.61      6
ATOM   2544  CB   GLU A 320      26.302  57.588  70.313  1.00 65.59      6
ATOM   2545  CG   GLU A 320      26.727  59.042  70.365  1.00 73.01      6
ATOM   2546  CD   GLU A 320      26.007  59.823  71.451  1.00 76.93      6
ATOM   2547  OE1  GLU A 320      24.755  59.832  71.446  1.00 77.37      8
ATOM   2548  OE2  GLU A 320      26.697  60.431  72.303  1.00 79.46      8
ATOM   2549  C    GLU A 320      26.698  57.551  67.863  1.00 61.40      6
ATOM   2550  O    GLU A 320      25.663  58.197  67.699  1.00 62.33      8
ATOM   2551  N    LYS A 321      27.650  57.463  66.939  1.00 59.47      7
ATOM   2552  CA   LYS A 321      27.519  58.150  65.662  1.00 59.54      6
ATOM   2553  CB   LYS A 321      27.340  59.648  65.897  1.00 61.36      6
ATOM   2554  CG   LYS A 321      23.620  60.323  66.366  1.00 65.23      6
ATOM   2555  CD   LYS A 321      29.169  59.691  67.643  1.00 66.59      6
ATOM   2556  CE   LYS A 321      20.564  60.215  67.960  1.00 67.34      6
ATOM   2557  NZ   LYS A 321      30.591  61.699  68.100  1.00 68.58      7
ATOM   2558  C    LYS A 321      28.766  57.941  64.806  1.00 59.24      6
ATOM   2559  O    LYS A 321      29.845  57.623  65.319  1.00 58.70      8
ATOM   2560  N    LEU A 322      28.608  58.146  63.500  1.00 57.55      7
ATOM   2561  CA   LEU A 322      29.702  58.002  62.543  1.00 54.72      6
ATOM   2562  CB   LEU A 322      29.171  57.450  61.214  1.00 52.96      6
ATOM   2563  CG   LEU A 322      28.141  56.316  61.295  1.00 52.97      6
ATOM   2564  CD1  LEU A 322      27.708  55.932  59.899  1.00 49.01      6
ATOM   2565  CD2  LEU A 322      28.716  55.115  62.035  1.00 54.73      6
ATOM   2566  C    LEU A 322      30.250  59.406  62.313  1.00 53.47      6
ATOM   2567  O    LEU A 322      29.512  60.383  62.464  1.00 53.39      8
ATOM   2568  N    ASN A 323      31.530  59.521  61.965  1.00 51.43      7
ATOM   2569  CA   ASN A 323      32.089  60.842  61.706  1.00 50.32      6
ATOM   2570  CB   ASN A 323      33.591  60.905  62.035  1.00 52.31      6
ATOM   2571  CG   ASN A 323      34.428  59.964  61.189  1.00 55.06      6
ATOM   2572  OD1  ASN A 323      34.386  58.744  61.363  1.00 55.77      8
ATOM   2573  ND2  ASN A 323      35.195  60.530  60.259  1.00 52.71      7
ATOM   2574  C    ASN A 323      31.843  61.199  60.243  1.00 48.63      6
```

Fig. 17-39

```
ATOM   2575  O    ASN A 323      31.135  60.479  59.538  1.00 47.52      8
ATOM   2576  N    ASN A 324      32.426  62.304  59.792  1.00 47.66      7
ATOM   2577  CA   ASN A 324      32.242  62.769  58.419  1.00 49.25      6
ATOM   2578  CB   ASN A 324      32.758  64.200  58.292  1.00 50.73      6
ATOM   2579  CG   ASN A 324      32.025  65.154  59.205  1.00 53.83      6
ATOM   2580  OD1  ASN A 324      30.812  65.314  59.096  1.00 56.90      8
ATOM   2581  ND2  ASN A 324      32.755  65.789  60.119  1.00 54.93      7
ATOM   2582  C    ASN A 324      32.906  61.891  57.367  1.00 49.34      6
ATOM   2583  O    ASN A 324      32.275  61.502  56.379  1.00 47.22      8
ATOM   2584  N    LYS A 325      34.182  61.590  57.586  1.00 48.27      7
ATOM   2585  CA   LYS A 325      34.957  60.759  56.676  1.00 46.57      6
ATOM   2586  CB   LYS A 325      36.314  60.453  57.305  1.00 49.94      6
ATOM   2587  CG   LYS A 325      37.299  59.737  56.399  1.00 54.75      6
ATOM   2588  CD   LYS A 325      38.562  59.329  57.173  1.00 58.22      6
ATOM   2589  CE   LYS A 325      39.236  60.521  57.844  1.00 58.35      6
ATOM   2590  NZ   LYS A 325      40.473  60.128  58.566  1.00 59.81      7
ATOM   2591  C    LYS A 325      34.202  59.458  56.410  1.00 44.85      6
ATOM   2592  O    LYS A 325      34.065  59.027  55.263  1.00 43.59      8
ATOM   2593  N    ALA A 326      33.712  58.843  57.483  1.00 42.27      7
ATOM   2594  CA   ALA A 326      32.964  57.597  57.387  1.00 40.91      6
ATOM   2595  CB   ALA A 326      32.663  57.067  58.773  1.00 36.86      6
ATOM   2596  C    ALA A 326      31.666  57.803  56.612  1.00 43.30      6
ATOM   2597  O    ALA A 326      31.342  57.028  55.705  1.00 42.83      8
ATOM   2598  N    LYS A 327      30.918  58.843  56.977  1.00 45.56      7
ATOM   2599  CA   LYS A 327      29.657  59.146  56.306  1.00 47.23      6
ATOM   2600  CB   LYS A 327      29.023  60.407  56.892  1.00 49.59      6
ATOM   2601  CG   LYS A 327      28.547  60.263  58.329  1.00 54.63      6
ATOM   2602  CD   LYS A 327      28.024  61.591  58.862  1.00 55.89      6
ATOM   2603  CE   LYS A 327      27.529  61.483  60.299  1.00 58.28      6
ATOM   2604  NZ   LYS A 327      26.304  60.644  60.426  1.00 59.91      7
ATOM   2605  C    LYS A 327      29.888  59.347  54.816  1.00 46.97      6
ATOM   2606  O    LYS A 327      29.090  58.913  53.990  1.00 48.10      8
ATOM   2607  N    GLU A 328      30.986  60.012  54.480  1.00 44.99      7
ATOM   2608  CA   GLU A 328      31.325  60.264  53.091  1.00 43.18      6
ATOM   2609  CB   GLU A 328      32.417  61.326  53.027  1.00 47.93      6
ATOM   2610  CG   GLU A 328      31.993  62.621  53.710  1.00 53.65      6
ATOM   2611  CD   GLU A 328      33.112  63.630  53.831  1.00 55.79      6
ATOM   2612  OE1  GLU A 328      33.642  64.060  52.783  1.00 58.73      8
ATOM   2613  OE2  GLU A 328      33.459  63.991  54.979  1.00 58.13      8
ATOM   2614  C    GLU A 328      31.789  58.971  52.437  1.00 41.56      6
ATOM   2615  O    GLU A 328      31.537  58.743  51.255  1.00 39.41      8
ATOM   2616  N    LEU A 329      32.465  58.123  53.211  1.00 40.64      7
ATOM   2617  CA   LEU A 329      32.940  56.844  52.695  1.00 36.45      6
ATOM   2618  CB   LEU A 329      33.623  56.032  53.801  1.00 34.70      6
ATOM   2619  CG   LEU A 329      34.100  54.610  53.433  1.00 35.69      6
ATOM   2620  CD1  LEU A 329      35.195  54.642  52.359  1.00 30.11      6
ATOM   2621  CD2  LEU A 329      34.619  53.926  54.683  1.00 34.63      6
ATOM   2622  C    LEU A 329      31.746  56.064  52.157  1.00 35.77      6
ATOM   2623  O    LEU A 329      31.692  55.746  50.975  1.00 34.94      8
ATOM   2624  N    LEU A 330      30.784  55.770  53.029  1.00 34.78      7
ATOM   2625  CA   LEU A 330      29.599  55.028  52.630  1.00 34.95      6
ATOM   2626  CB   LEU A 330      28.631  54.914  53.803  1.00 30.95      6
ATOM   2627  CG   LEU A 330      29.164  54.115  54.991  1.00 32.66      6
ATOM   2628  CD1  LEU A 330      28.051  53.904  56.022  1.00 31.74      6
ATOM   2629  CD2  LEU A 330      29.674  52.769  54.509  1.00 30.73      6
ATOM   2630  C    LEU A 330      28.877  55.631  51.428  1.00 37.28      6
ATOM   2631  O    LEU A 330      28.395  54.901  50.557  1.00 40.56      8
ATOM   2632  N    LYS A 331      28.806  56.957  51.383  1.00 38.24      7
ATOM   2633  CA   LYS A 331      28.140  57.661  50.294  1.00 39.59      6
ATOM   2634  CB   LYS A 331      27.994  59.146  50.643  1.00 42.31      6
ATOM   2635  CG   LYS A 331      27.129  59.399  51.873  1.00 45.93      6
ATOM   2636  CD   LYS A 331      27.017  60.879  52.244  1.00 49.72      6
ATOM   2637  CE   LYS A 331      26.271  61.698  51.193  1.00 53.66      6
ATOM   2638  NZ   LYS A 331      26.053  63.114  51.640  1.00 54.22      7
ATOM   2639  C    LYS A 331      28.863  57.514  48.958  1.00 41.02      6
ATOM   2640  O    LYS A 331      28.220  57.485  47.904  1.00 39.58      8
```

Fig. 17-40

```
ATOM   2641  N    SER A 332      30.192  57.413  49.005  1.00 42.69      7
ATOM   2642  CA   SER A 332      30.998  57.274  47.792  1.00 46.02      6
ATOM   2643  CB   SER A 332      32.494  57.243  48.124  1.00 47.51      6
ATOM   2644  OG   SER A 332      32.862  56.066  48.823  1.00 50.97      8
ATOM   2645  C    SER A 332      30.634  56.007  47.040  1.00 48.51      6
ATOM   2646  O    SER A 332      30.706  55.959  45.811  1.00 49.45      8
ATOM   2647  N    ILE A 333      30.241  54.982  47.786  1.00 51.56      7
ATOM   2648  CA   ILE A 333      29.869  53.713  47.187  1.00 54.86      6
ATOM   2649  CB   ILE A 333      29.657  52.626  48.246  1.00 55.80      6
ATOM   2650  CG2  ILE A 333      29.388  51.285  47.559  1.00 52.34      6
ATOM   2651  CG1  ILE A 333      30.892  52.522  49.140  1.00 56.89      6
ATOM   2652  CD1  ILE A 333      30.766  51.456  50.204  1.00 60.31      6
ATOM   2653  C    ILE A 333      28.579  53.813  46.396  1.00 57.07      6
ATOM   2654  O    ILE A 333      27.572  54.321  46.897  1.00 55.59      8
ATOM   2655  N    ASP A 334      28.623  53.320  45.160  1.00 61.14      7
ATOM   2656  CA   ASP A 334      27.456  53.300  44.281  1.00 65.55      6
ATOM   2657  CB   ASP A 334      27.888  53.259  42.811  1.00 69.19      6
ATOM   2658  CG   ASP A 334      28.784  52.073  42.491  1.00 70.21      6
ATOM   2659  OD1  ASP A 334      29.097  51.875  41.298  1.00 71.47      8
ATOM   2660  OD2  ASP A 334      29.181  51.344  43.427  1.00 70.91      8
ATOM   2661  C    ASP A 334      26.660  52.041  44.627  1.00 65.65      6
ATOM   2662  O    ASP A 334      26.797  50.996  43.990  1.00 63.91      8
ATOM   2663  N    PHE A 335      25.822  52.153  45.649  1.00 65.73      7
ATOM   2664  CA   PHE A 335      25.041  51.021  46.104  1.00 63.44      6
ATOM   2665  CB   PHE A 335      24.980  51.034  47.632  1.00 58.05      6
ATOM   2666  CG   PHE A 335      24.039  50.028  48.195  1.00 53.82      6
ATOM   2667  CD1  PHE A 335      24.178  48.679  47.886  1.00 52.40      6
ATOM   2668  CD2  PHE A 335      22.978  50.429  48.989  1.00 51.33      6
ATOM   2669  CE1  PHE A 335      23.265  47.742  48.356  1.00 52.73      6
ATOM   2670  CE2  PHE A 335      22.062  49.503  49.462  1.00 53.20      6
ATOM   2671  CZ   PHE A 335      22.204  48.151  49.144  1.00 51.76      6
ATOM   2672  C    PHE A 335      23.629  50.893  45.535  1.00 65.55      6
ATOM   2673  O    PHE A 335      23.230  49.810  45.097  1.00 67.33      8
ATOM   2674  N    GLU A 336      22.874  51.986  45.537  1.00 66.47      7
ATOM   2675  CA   GLU A 336      21.497  51.948  45.048  1.00 67.43      6
ATOM   2676  CB   GLU A 336      21.422  51.379  43.626  1.00 71.79      6
ATOM   2677  CG   GLU A 336      19.982  51.245  43.116  1.00 78.77      6
ATOM   2678  CD   GLU A 336      19.868  50.505  41.789  1.00 82.67      6
ATOM   2679  OE1  GLU A 336      20.232  49.306  41.734  1.00 83.29      8
ATOM   2680  OE2  GLU A 336      19.410  51.126  40.801  1.00 84.26      8
ATOM   2681  C    GLU A 336      20.655  51.069  45.971  1.00 64.72      6
ATOM   2682  O    GLU A 336      20.686  49.840  45.876  1.00 59.84      8
ATOM   2683  N    GLU A 337      19.901  51.710  46.858  1.00 64.47      7
ATOM   2684  CA   GLU A 337      19.045  51.003  47.805  1.00 65.83      6
ATOM   2685  CB   GLU A 337      18.398  52.003  48.759  1.00 64.20      6
ATOM   2686  CG   GLU A 337      17.753  51.370  49.964  1.00 64.26      6
ATOM   2687  CD   GLU A 337      18.774  50.630  50.850  1.00 64.04      6
ATOM   2688  OE1  GLU A 337      19.741  51.312  51.261  1.00 61.66      8
ATOM   2689  OE2  GLU A 337      18.608  49.483  51.132  1.00 63.64      8
ATOM   2690  C    GLU A 337      17.950  50.239  47.063  1.00 67.13      6
ATOM   2691  O    GLU A 337      17.269  50.807  46.205  1.00 68.27      8
ATOM   2692  N    PHE A 338      17.779  48.960  47.394  1.00 67.22      7
ATOM   2693  CA   PHE A 338      16.764  48.129  46.748  1.00 68.05      6
ATOM   2694  CB   PHE A 338      16.445  46.919  47.626  1.00 69.68      6
ATOM   2695  CG   PHE A 338      15.228  46.158  47.187  1.00 72.35      6
ATOM   2696  CD1  PHE A 338      15.122  45.674  45.888  1.00 72.37      6
ATOM   2697  CD2  PHE A 338      14.172  45.941  48.074  1.00 73.61      6
ATOM   2698  CE1  PHE A 338      13.980  44.984  45.478  1.00 73.39      6
ATOM   2699  CE2  PHE A 338      13.024  45.250  47.672  1.00 73.26      6
ATOM   2700  CZ   PHE A 338      12.929  44.771  46.369  1.00 73.34      6
ATOM   2701  C    PHE A 338      15.481  48.902  46.434  1.00 68.45      6
ATOM   2702  O    PHE A 338      15.286  49.367  45.310  1.00 67.92      8
ATOM   2703  N    ASP A 339      14.606  49.026  47.426  1.00 68.98      7
ATOM   2704  CA   ASP A 339      13.358  49.759  47.261  1.00 70.68      6
ATOM   2705  CB   ASP A 339      12.596  49.758  48.588  1.00 71.06      6
ATOM   2706  CG   ASP A 339      11.381  50.678  48.581  1.00 72.05      6
```

Fig. 17-41

```
ATOM   2707  OD1 ASP A 339      11.548  51.893  48.320  1.00 72.29    8
ATOM   2708  OD2 ASP A 339      10.262  50.188  48.858  1.00 71.03    8
ATOM   2709  C   ASP A 339      13.715  51.183  46.853  1.00 73.18    6
ATOM   2710  O   ASP A 339      14.407  51.884  47.592  1.00 73.78    8
ATOM   2711  N   ASP A 340      13.247  51.600  45.677  1.00 76.36    7
ATOM   2712  CA  ASP A 340      13.518  52.943  45.152  1.00 78.34    6
ATOM   2713  CB  ASP A 340      12.410  53.385  44.189  1.00 77.55    6
ATOM   2714  CG  ASP A 340      12.462  52.655  42.864  1.00 78.90    6
ATOM   2715  OD1 ASP A 340      12.348  51.408  42.855  1.00 78.38    8
ATOM   2716  OD2 ASP A 340      12.620  53.336  41.830  1.00 78.74    8
ATOM   2717  C   ASP A 340      13.687  54.017  46.214  1.00 79.51    6
ATOM   2718  O   ASP A 340      14.587  54.856  46.117  1.00 80.19    8
ATOM   2719  N   GLU A 341      12.824  54.000  47.224  1.00 79.64    7
ATOM   2720  CA  GLU A 341      12.922  54.998  48.271  1.00 80.05    6
ATOM   2721  CB  GLU A 341      12.269  56.301  47.811  1.00 83.75    6
ATOM   2722  CG  GLU A 341      12.411  57.442  48.806  1.00 89.02    6
ATOM   2723  CD  GLU A 341      11.756  58.724  48.328  1.00 91.52    6
ATOM   2724  OE1 GLU A 341      10.515  58.738  48.175  1.00 93.33    8
ATOM   2725  OE2 GLU A 341      12.484  59.716  48.102  1.00 92.65    8
ATOM   2726  C   GLU A 341      12.317  54.578  49.597  1.00 77.98    6
ATOM   2727  O   GLU A 341      11.102  54.610  49.777  1.00 79.82    8
ATOM   2728  N   VAL A 342      13.179  54.181  50.523  1.00 74.49    7
ATOM   2729  CA  VAL A 342      12.745  53.793  51.859  1.00 71.55    6
ATOM   2730  CB  VAL A 342      13.224  52.383  52.245  1.00 72.40    6
ATOM   2731  CG1 VAL A 342      12.672  52.004  53.610  1.00 71.16    6
ATOM   2732  CG2 VAL A 342      12.797  51.391  51.207  1.00 74.35    6
ATOM   2733  C   VAL A 342      13.454  54.778  52.766  1.00 68.46    6
ATOM   2734  O   VAL A 342      12.952  55.154  53.829  1.00 68.96    8
ATOM   2735  N   ASP A 343      14.636  55.184  52.311  1.00 61.61    7
ATOM   2736  CA  ASP A 343      15.486  56.114  53.029  1.00 54.91    6
ATOM   2737  CB  ASP A 343      14.678  57.303  53.543  1.00 55.06    6
ATOM   2738  CG  ASP A 343      15.556  58.390  54.114  1.00 54.44    6
ATOM   2739  OD1 ASP A 343      15.002  59.351  54.694  1.00 56.20    8
ATOM   2740  OD2 ASP A 343      16.795  58.287  53.969  1.00 49.32    8
ATOM   2741  C   ASP A 343      16.152  55.401  54.198  1.00 50.85    6
ATOM   2742  O   ASP A 343      15.557  55.209  55.257  1.00 49.32    8
ATOM   2743  N   ARG A 344      17.396  55.004  53.980  1.00 47.84    7
ATOM   2744  CA  ARG A 344      18.195  54.321  54.981  1.00 45.34    6
ATOM   2745  CB  ARG A 344      18.883  53.099  54.358  1.00 45.00    6
ATOM   2746  CG  ARG A 344      17.950  51.969  53.974  1.00 39.03    6
ATOM   2747  CD  ARG A 344      17.185  51.531  55.188  1.00 35.83    6
ATOM   2748  NE  ARG A 344      16.278  50.439  54.885  1.00 39.20    7
ATOM   2749  CZ  ARG A 344      15.350  49.993  55.724  1.00 39.89    6
ATOM   2750  NH1 ARG A 344      15.217  50.561  56.917  1.00 40.17    7
ATOM   2751  NH2 ARG A 344      14.566  48.976  55.375  1.00 40.75    7
ATOM   2752  C   ARG A 344      19.250  55.278  55.515  1.00 44.72    6
ATOM   2753  O   ARG A 344      20.170  54.869  56.223  1.00 46.97    8
ATOM   2754  N   SER A 345      19.113  56.552  55.157  1.00 45.81    7
ATOM   2755  CA  SER A 345      20.045  57.596  55.577  1.00 43.66    6
ATOM   2756  CB  SER A 345      19.538  58.960  55.115  1.00 43.44    6
ATOM   2757  OG  SER A 345      18.292  59.260  55.722  1.00 45.62    8
ATOM   2758  C   SER A 345      20.258  57.627  57.089  1.00 42.79    6
ATOM   2759  O   SER A 345      21.364  57.902  57.552  1.00 42.62    8
ATOM   2760  N   TYR A 346      19.200  57.354  57.851  1.00 40.55    7
ATOM   2761  CA  TYR A 346      19.280  57.352  59.308  1.00 41.05    6
ATOM   2762  CB  TYR A 346      17.971  56.819  59.905  1.00 41.74    6
ATOM   2763  CG  TYR A 346      17.668  55.355  59.630  1.00 43.47    6
ATOM   2764  CD1 TYR A 346      18.331  54.333  60.328  1.00 44.45    6
ATOM   2765  CE1 TYR A 346      18.044  52.983  60.088  1.00 41.02    6
ATOM   2766  CD2 TYR A 346      16.710  54.988  58.682  1.00 42.08    6
ATOM   2767  CE2 TYR A 346      16.416  53.644  58.434  1.00 40.59    6
ATOM   2768  CZ  TYR A 346      17.086  52.649  59.139  1.00 41.66    5
ATOM   2769  OH  TYR A 346      16.806  51.324  58.884  1.00 39.60    8
ATOM   2770  C   TYR A 346      20.466  56.517  59.796  1.00 42.92    6
ATOM   2771  O   TYR A 346      21.101  56.844  60.799  1.00 42.65    8
ATOM   2772  N   MET A 347      20.757  55.443  59.067  1.00 44.59    7
```

Fig. 17-42

| | | | | | | | | | |
|---|---|---|---|---|---|---|---|---|---|
| ATOM | 2773 | CA | MET | A | 347 | 21.859 | 54.546 | 59.388 | 1.00 45.89 | 6 |
| ATOM | 2774 | CB | MET | A | 347 | 21.950 | 53.433 | 58.353 | 1.00 45.51 | 6 |
| ATOM | 2775 | CG | MET | A | 347 | 20.727 | 52.567 | 58.244 | 1.00 45.01 | 6 |
| ATOM | 2776 | SD | MET | A | 347 | 21.062 | 51.258 | 57.066 | 1.00 47.13 | 16 |
| ATOM | 2777 | CE | MET | A | 347 | 21.545 | 52.237 | 55.676 | 1.00 44.55 | 6 |
| ATOM | 2778 | C | MET | A | 347 | 23.188 | 55.286 | 59.404 | 1.00 48.47 | 6 |
| ATOM | 2779 | O | MET | A | 347 | 24.129 | 54.888 | 60.098 | 1.00 49.49 | 8 |
| ATOM | 2780 | N | LEU | A | 348 | 23.259 | 56.351 | 58.610 | 1.00 49.03 | 7 |
| ATOM | 2781 | CA | LEU | A | 348 | 24.458 | 57.178 | 58.499 | 1.00 48.86 | 6 |
| ATOM | 2782 | CB | LEU | A | 348 | 24.355 | 58.082 | 57.269 | 1.00 45.51 | 6 |
| ATOM | 2783 | CG | LEU | A | 348 | 24.280 | 57.424 | 55.895 | 1.00 44.47 | 6 |
| ATOM | 2784 | CD1 | LEU | A | 348 | 23.908 | 58.476 | 54.859 | 1.00 43.62 | 6 |
| ATOM | 2785 | CD2 | LEU | A | 348 | 25.618 | 56.757 | 55.565 | 1.00 42.53 | 6 |
| ATOM | 2786 | C | LEU | A | 348 | 24.644 | 58.049 | 59.738 | 1.00 49.33 | 6 |
| ATOM | 2787 | O | LEU | A | 348 | 25.765 | 58.369 | 60.123 | 1.00 49.78 | 8 |
| ATOM | 2788 | N | GLU | A | 349 | 23.537 | 58.428 | 60.358 | 1.00 48.34 | 7 |
| ATOM | 2789 | CA | GLU | A | 349 | 23.591 | 59.279 | 61.533 | 1.00 49.24 | 6 |
| ATOM | 2790 | CB | GLU | A | 349 | 22.198 | 59.848 | 61.811 | 1.00 48.36 | 6 |
| ATOM | 2791 | CG | GLU | A | 349 | 21.628 | 60.584 | 60.607 | 1.00 45.52 | 6 |
| ATOM | 2792 | CD | GLU | A | 349 | 22.598 | 61.619 | 60.065 | 1.00 42.94 | 6 |
| ATOM | 2793 | OE1 | GLU | A | 349 | 22.934 | 62.560 | 60.812 | 1.00 40.82 | 8 |
| ATOM | 2794 | OE2 | GLU | A | 349 | 23.028 | 61.483 | 58.900 | 1.00 38.30 | 8 |
| ATOM | 2795 | C | GLU | A | 349 | 24.119 | 58.531 | 62.745 | 1.00 48.32 | 6 |
| ATOM | 2796 | O | GLU | A | 349 | 25.226 | 58.783 | 63.219 | 1.00 47.87 | 8 |
| ATOM | 2797 | N | THR | A | 350 | 23.325 | 57.602 | 63.248 | 1.00 48.97 | 7 |
| ATOM | 2798 | CA | THR | A | 350 | 23.744 | 56.832 | 64.398 | 1.00 50.70 | 6 |
| ATOM | 2799 | CB | THR | A | 350 | 22.558 | 56.596 | 65.342 | 1.00 51.02 | 6 |
| ATOM | 2800 | OG1 | THR | A | 350 | 22.071 | 57.865 | 65.803 | 1.00 49.11 | 8 |
| ATOM | 2801 | CG2 | THR | A | 350 | 22.983 | 55.763 | 66.537 | 1.00 51.58 | 6 |
| ATOM | 2802 | C | THR | A | 350 | 24.361 | 55.507 | 63.954 | 1.00 49.56 | 6 |
| ATOM | 2803 | O | THR | A | 350 | 23.979 | 54.947 | 62.923 | 1.00 50.55 | 8 |
| ATOM | 2804 | N | LEU | A | 351 | 25.333 | 55.028 | 64.725 | 1.00 46.88 | 7 |
| ATOM | 2805 | CA | LEU | A | 351 | 26.018 | 53.781 | 64.417 | 1.00 45.35 | 6 |
| ATOM | 2806 | CB | LEU | A | 351 | 27.342 | 53.726 | 65.185 | 1.00 47.05 | 6 |
| ATOM | 2807 | CG | LEU | A | 351 | 28.257 | 52.502 | 65.072 | 1.00 49.54 | 6 |
| ATOM | 2808 | CD1 | LEU | A | 351 | 29.575 | 52.777 | 65.766 | 1.00 51.50 | 6 |
| ATOM | 2809 | CD2 | LEU | A | 351 | 27.603 | 51.302 | 65.692 | 1.00 48.35 | 6 |
| ATOM | 2810 | C | LEU | A | 351 | 25.145 | 52.584 | 64.772 | 1.00 44.79 | 6 |
| ATOM | 2811 | O | LEU | A | 351 | 25.131 | 51.578 | 64.061 | 1.00 41.45 | 8 |
| ATOM | 2812 | N | LYS | A | 352 | 24.420 | 52.711 | 65.880 | 1.00 45.27 | 7 |
| ATOM | 2813 | CA | LYS | A | 352 | 23.531 | 51.662 | 66.375 | 1.00 44.62 | 6 |
| ATOM | 2814 | CB | LYS | A | 352 | 23.764 | 51.464 | 67.873 | 1.00 42.23 | 6 |
| ATOM | 2815 | CG | LYS | A | 352 | 25.197 | 51.075 | 68.187 | 1.00 44.94 | 6 |
| ATOM | 2816 | CD | LYS | A | 352 | 25.572 | 51.262 | 69.650 | 1.00 46.80 | 6 |
| ATOM | 2817 | CE | LYS | A | 352 | 24.765 | 50.389 | 70.581 | 1.00 45.79 | 6 |
| ATOM | 2818 | NZ | LYS | A | 352 | 25.236 | 50.586 | 71.975 | 1.00 47.31 | 7 |
| ATOM | 2819 | C | LYS | A | 352 | 22.096 | 52.087 | 66.116 | 1.00 45.12 | 6 |
| ATOM | 2820 | O | LYS | A | 352 | 21.837 | 53.236 | 65.756 | 1.00 47.07 | 8 |
| ATOM | 2821 | N | ASP | A | 353 | 21.162 | 51.161 | 66.285 | 1.00 44.62 | 7 |
| ATOM | 2822 | CA | ASP | A | 353 | 19.761 | 51.474 | 66.060 | 1.00 46.43 | 6 |
| ATOM | 2823 | CB | ASP | A | 353 | 19.302 | 50.943 | 64.692 | 1.00 49.38 | 6 |
| ATOM | 2824 | CG | ASP | A | 353 | 19.813 | 49.546 | 64.396 | 1.00 51.52 | 6 |
| ATOM | 2825 | OD1 | ASP | A | 353 | 21.028 | 49.396 | 64.158 | 1.00 55.36 | 8 |
| ATOM | 2826 | OD2 | ASP | A | 353 | 19.005 | 48.596 | 64.398 | 1.00 52.35 | 8 |
| ATOM | 2827 | C | ASP | A | 353 | 18.841 | 50.968 | 67.165 | 1.00 45.90 | 6 |
| ATOM | 2828 | O | ASP | A | 353 | 19.152 | 50.001 | 67.854 | 1.00 45.98 | 8 |
| ATOM | 2829 | N | PRO | A | 354 | 17.687 | 51.629 | 67.348 | 1.00 45.86 | 7 |
| ATOM | 2830 | CD | PRO | A | 354 | 17.162 | 52.775 | 66.587 | 1.00 45.36 | 6 |
| ATOM | 2831 | CA | PRO | A | 354 | 16.723 | 51.243 | 68.378 | 1.00 45.52 | 6 |
| ATOM | 2832 | CB | PRO | A | 354 | 15.585 | 52.245 | 68.159 | 1.00 44.77 | 6 |
| ATOM | 2833 | CG | PRO | A | 354 | 15.681 | 52.513 | 66.664 | 1.00 45.06 | 6 |
| ATOM | 2834 | C | PRO | A | 354 | 16.277 | 49.804 | 68.188 | 1.00 44.13 | 6 |
| ATOM | 2835 | O | PRO | A | 354 | 16.352 | 49.271 | 67.078 | 1.00 42.90 | 8 |
| ATOM | 2836 | N | TRP | A | 355 | 15.821 | 49.174 | 69.267 | 1.00 42.77 | 7 |
| ATOM | 2837 | CA | TRP | A | 355 | 15.358 | 47.801 | 69.168 | 1.00 43.35 | 6 |
| ATOM | 2838 | CB | TRP | A | 355 | 14.982 | 47.225 | 70.539 | 1.00 47.11 | 6 |

Fig. 17-43

| | | | | | | | | | |
|---|---|---|---|---|---|---|---|---|---|
| ATOM | 2839 | CG | TRP | A | 355 | 16.168 | 46.752 | 71.322 | 1.00 52.43 | 6 |
| ATOM | 2840 | CD2 | TRP | A | 355 | 16.574 | 45.391 | 71.519 | 1.00 53.15 | 6 |
| ATOM | 2841 | CE2 | TRP | A | 355 | 17.789 | 45.416 | 72.238 | 1.00 54.97 | 6 |
| ATOM | 2842 | CE3 | TRP | A | 355 | 16.031 | 44.153 | 71.155 | 1.00 53.39 | 6 |
| ATOM | 2843 | CD1 | TRP | A | 355 | 17.125 | 47.526 | 71.916 | 1.00 54.39 | 6 |
| ATOM | 2844 | NE1 | TRP | A | 355 | 18.103 | 46.731 | 72.468 | 1.00 57.31 | 7 |
| ATOM | 2845 | CZ2 | TRP | A | 355 | 18.469 | 44.249 | 72.602 | 1.00 54.97 | 6 |
| ATOM | 2846 | CZ3 | TRP | A | 355 | 16.706 | 42.995 | 71.518 | 1.00 55.77 | 6 |
| ATOM | 2847 | CH2 | TRP | A | 355 | 17.913 | 43.052 | 72.234 | 1.00 54.84 | 6 |
| ATOM | 2848 | C | TRP | A | 355 | 14.177 | 47.690 | 68.230 | 1.00 41.94 | 6 |
| ATOM | 2849 | O | TRP | A | 355 | 13.508 | 48.677 | 67.915 | 1.00 41.39 | 8 |
| ATOM | 2850 | N | ARG | A | 356 | 13.942 | 46.471 | 67.775 | 1.00 38.60 | 7 |
| ATOM | 2851 | CA | ARG | A | 356 | 12.855 | 46.185 | 66.866 | 1.00 36.55 | 6 |
| ATOM | 2852 | CB | ARG | A | 356 | 13.413 | 46.044 | 65.451 | 1.00 35.06 | 6 |
| ATOM | 2853 | CG | ARG | A | 356 | 14.120 | 47.308 | 64.976 | 1.00 32.47 | 6 |
| ATOM | 2854 | CD | ARG | A | 356 | 14.969 | 47.082 | 63.733 | 1.00 29.54 | 6 |
| ATOM | 2855 | NE | ARG | A | 356 | 15.600 | 48.323 | 63.296 | 1.00 28.91 | 7 |
| ATOM | 2856 | CZ | ARG | A | 356 | 16.514 | 48.403 | 62.335 | 1.00 30.60 | 6 |
| ATOM | 2857 | NH1 | ARG | A | 356 | 16.916 | 47.305 | 61.702 | 1.00 33.52 | 7 |
| ATOM | 2858 | NH2 | ARG | A | 356 | 17.020 | 49.582 | 61.996 | 1.00 30.10 | 7 |
| ATOM | 2859 | C | ARG | A | 356 | 12.270 | 44.879 | 67.361 | 1.00 36.01 | 6 |
| ATOM | 2860 | O | ARG | A | 356 | 12.447 | 43.831 | 66.742 | 1.00 38.38 | 8 |
| ATOM | 2861 | N | GLY | A | 357 | 11.587 | 44.949 | 68.499 | 1.00 36.04 | 7 |
| ATOM | 2862 | CA | GLY | A | 357 | 11.001 | 43.758 | 69.085 | 1.00 36.08 | 6 |
| ATOM | 2863 | C | GLY | A | 357 | 9.514 | 43.596 | 68.851 | 1.00 34.51 | 6 |
| ATOM | 2864 | O | GLY | A | 357 | 8.943 | 44.196 | 67.943 | 1.00 36.77 | 8 |
| ATOM | 2865 | N | GLY | A | 358 | 8.892 | 42.772 | 69.687 | 1.00 36.04 | 7 |
| ATOM | 2866 | CA | GLY | A | 358 | 7.466 | 42.506 | 69.593 | 1.00 32.26 | 6 |
| ATOM | 2867 | C | GLY | A | 358 | 7.106 | 41.263 | 70.385 | 1.00 29.85 | 6 |
| ATOM | 2868 | O | GLY | A | 358 | 7.832 | 40.839 | 71.288 | 1.00 28.86 | 8 |
| ATOM | 2869 | N | GLU | A | 359 | 5.975 | 40.667 | 70.055 | 1.00 30.88 | 7 |
| ATOM | 2870 | CA | GLU | A | 359 | 5.550 | 39.455 | 70.743 | 1.00 32.58 | 6 |
| ATOM | 2871 | CB | GLU | A | 359 | 4.034 | 39.289 | 70.604 | 1.00 38.60 | 6 |
| ATOM | 2872 | CG | GLU | A | 359 | 3.230 | 40.435 | 71.222 | 1.00 47.44 | 6 |
| ATOM | 2873 | CD | GLU | A | 359 | 1.957 | 40.762 | 70.445 | 1.00 50.93 | 6 |
| ATOM | 2874 | OE1 | GLU | A | 359 | 1.123 | 39.852 | 70.221 | 1.00 52.13 | 8 |
| ATOM | 2875 | OE2 | GLU | A | 359 | 1.798 | 41.942 | 70.061 | 1.00 51.03 | 8 |
| ATOM | 2876 | C | GLU | A | 359 | 6.250 | 38.275 | 70.091 | 1.00 28.29 | 6 |
| ATOM | 2877 | O | GLU | A | 359 | 6.790 | 38.382 | 68.997 | 1.00 27.88 | 8 |
| ATOM | 2878 | N | VAL | A | 360 | 6.263 | 37.147 | 70.772 | 1.00 27.97 | 7 |
| ATOM | 2879 | CA | VAL | A | 360 | 6.859 | 35.957 | 70.193 | 1.00 25.86 | 6 |
| ATOM | 2880 | CB | VAL | A | 360 | 7.673 | 35.168 | 71.237 | 1.00 22.02 | 6 |
| ATOM | 2881 | CG1 | VAL | A | 360 | 8.155 | 33.849 | 70.641 | 1.00 19.45 | 6 |
| ATOM | 2882 | CG2 | VAL | A | 360 | 8.850 | 36.009 | 71.698 | 1.00 17.88 | 6 |
| ATOM | 2883 | C | VAL | A | 360 | 5.703 | 35.099 | 69.670 | 1.00 28.04 | 6 |
| ATOM | 2884 | C | VAL | A | 360 | 4.842 | 34.655 | 70.440 | 1.00 27.34 | 8 |
| ATOM | 2885 | N | ARG | A | 361 | 5.663 | 34.898 | 68.358 | 1.00 27.70 | 7 |
| ATOM | 2886 | C.. | ARG | A | 361 | 4.612 | 34.091 | 67.765 | 1.00 32.85 | 6 |
| ATOM | 2887 | CB | ARG | A | 361 | 4.693 | 34.164 | 66.242 | 1.00 32.30 | 6 |
| ATOM | 2888 | CG | ARG | A | 361 | 4.243 | 35.504 | 65.687 | 1.00 38.81 | 6 |
| ATOM | 2889 | CD | ARG | A | 361 | 4.546 | 35.653 | 64.201 | 1.00 40.09 | 6 |
| ATOM | 2890 | NE | ARG | A | 361 | 5.974 | 35.812 | 63.961 | 1.00 38.77 | 7 |
| ATOM | 2891 | CZ | ARG | A | 361 | 6.514 | 35.989 | 62.763 | 1.00 39.21 | 6 |
| ATOM | 2892 | NH1 | ARG | A | 361 | 5.748 | 36.027 | 61.685 | 1.00 40.79 | 7 |
| ATOM | 2893 | NH2 | ARG | A | 361 | 7.822 | 36.145 | 62.643 | 1.00 42.94 | 7 |
| ATOM | 2894 | C | ARG | A | 361 | 4.689 | 32.638 | 68.222 | 1.00 35.65 | 6 |
| ATOM | 2895 | O | ARG | A | 361 | 5.768 | 32.097 | 68.471 | 1.00 37.08 | 8 |
| ATOM | 2896 | N | LYS | A | 362 | 3.526 | 32.017 | 68.347 | 1.00 37.80 | 7 |
| ATOM | 2897 | CA | LYS | A | 362 | 3.436 | 30.626 | 68.757 | 1.00 39.91 | 6 |
| ATOM | 2898 | CB | LYS | A | 362 | 1.982 | 30.152 | 68.648 | 1.00 43.43 | 6 |
| ATOM | 2899 | CG | LYS | A | 362 | 1.014 | 30.803 | 69.640 | 1.00 45.11 | 6 |
| ATOM | 2900 | CD | LYS | A | 362 | 1.117 | 32.346 | 69.673 | 1.00 49.43 | 6 |
| ATOM | 2901 | CE | LYS | A | 362 | 0.813 | 33.022 | 68.327 | 1.00 45.02 | 6 |
| ATOM | 2902 | NZ | LYS | A | 362 | 0.962 | 34.509 | 68.422 | 1.00 41.08 | 7 |
| ATOM | 2903 | C | LYS | A | 362 | 4.320 | 29.809 | 67.831 | 1.00 39.25 | 6 |
| ATOM | 2904 | O | LYS | A | 362 | 4.953 | 28.835 | 68.248 | 1.00 35.45 | 8 |

Fig. 17-44

| ATOM | 2905 | N   | GLU A 363 | 4.358  | 30.229 | 66.568 | 1.00 | 41.13 | 7 |
| ATOM | 2906 | CA  | GLU A 363 | 5.147  | 29.554 | 65.539 | 1.00 | 43.96 | 6 |
| ATOM | 2907 | CB  | GLU A 363 | 5.225  | 30.416 | 64.278 | 1.00 | 45.90 | 6 |
| ATOM | 2908 | CG  | GLU A 363 | 3.892  | 30.876 | 63.741 | 1.00 | 50.68 | 6 |
| ATOM | 2909 | CD  | GLU A 363 | 4.045  | 31.738 | 62.507 | 1.00 | 54.11 | 6 |
| ATOM | 2910 | OE1 | GLU A 363 | 4.571  | 31.224 | 61.494 | 1.00 | 53.90 | 8 |
| ATOM | 2911 | OE2 | GLU A 363 | 3.648  | 32.927 | 62.552 | 1.00 | 56.05 | 8 |
| ATOM | 2912 | C   | GLU A 363 | 6.558  | 29.296 | 66.046 | 1.00 | 42.39 | 6 |
| ATOM | 2913 | O   | GLU A 363 | 7.062  | 28.169 | 65.989 | 1.00 | 41.48 | 8 |
| ATOM | 2914 | N   | VAL A 364 | 7.183  | 30.360 | 66.540 | 1.00 | 37.27 | 7 |
| ATOM | 2915 | CA  | VAL A 364 | 8.535  | 30.291 | 67.064 | 1.00 | 35.30 | 6 |
| ATOM | 2916 | CB  | VAL A 364 | 9.038  | 31.696 | 67.469 | 1.00 | 36.88 | 6 |
| ATOM | 2917 | CG1 | VAL A 364 | 10.444 | 31.599 | 68.043 | 1.00 | 37.77 | 6 |
| ATOM | 2918 | CG2 | VAL A 364 | 9.018  | 32.628 | 66.252 | 1.00 | 34.78 | 6 |
| ATOM | 2919 | C   | VAL A 364 | 8.650  | 29.361 | 68.268 | 1.00 | 33.01 | 6 |
| ATOM | 2920 | O   | VAL A 364 | 9.622  | 28.614 | 68.379 | 1.00 | 31.55 | 8 |
| ATOM | 2921 | N   | LYS A 365 | 7.664  | 29.409 | 69.165 | 1.00 | 32.61 | 7 |
| ATOM | 2922 | CA  | LYS A 365 | 7.674  | 28.567 | 70.362 | 1.00 | 30.96 | 6 |
| ATOM | 2923 | CB  | LYS A 365 | 6.598  | 29.010 | 71.358 | 1.00 | 30.13 | 6 |
| ATOM | 2924 | CG  | LYS A 365 | 6.826  | 30.409 | 71.899 | 1.00 | 36.02 | 6 |
| ATOM | 2925 | CD  | LYS A 365 | 5.837  | 30.781 | 72.995 | 1.00 | 38.94 | 6 |
| ATOM | 2926 | CE  | LYS A 365 | 6.120  | 32.187 | 73.509 | 1.00 | 41.58 | 6 |
| ATOM | 2927 | NZ  | LYS A 365 | 5.191  | 32.611 | 74.585 | 1.00 | 44.29 | 7 |
| ATOM | 2928 | C   | LYS A 365 | 7.452  | 27.114 | 70.007 | 1.00 | 30.32 | 6 |
| ATOM | 2929 | O   | LYS A 365 | 8.195  | 26.237 | 70.442 | 1.00 | 31.32 | 8 |
| ATOM | 2930 | N   | ASP A 366 | 6.427  | 26.863 | 69.209 | 1.00 | 29.85 | 7 |
| ATOM | 2931 | CA  | ASP A 366 | 6.115  | 25.509 | 68.807 | 1.00 | 32.07 | 6 |
| ATOM | 2932 | CB  | ASP A 366 | 4.948  | 25.522 | 67.818 | 1.00 | 35.98 | 6 |
| ATOM | 2933 | CG  | ASP A 366 | 3.711  | 26.206 | 68.381 | 1.00 | 39.88 | 6 |
| ATOM | 2934 | OD1 | ASP A 366 | 3.124  | 25.692 | 69.359 | 1.00 | 40.16 | 8 |
| ATOM | 2935 | OD2 | ASP A 366 | 3.326  | 27.266 | 67.848 | 1.00 | 43.21 | 8 |
| ATOM | 2936 | C   | ASP A 366 | 7.343  | 24.866 | 68.161 | 1.00 | 33.07 | 6 |
| ATOM | 2937 | O   | ASP A 366 | 7.753  | 23.763 | 68.540 | 1.00 | 32.64 | 8 |
| ATOM | 2938 | N   | THR A 367 | 7.932  | 25.565 | 67.193 | 1.00 | 31.89 | 7 |
| ATOM | 2939 | CA  | THR A 367 | 9.088  | 25.045 | 66.490 | 1.00 | 31.17 | 6 |
| ATOM | 2940 | CB  | THR A 367 | 9.712  | 26.070 | 65.572 | 1.00 | 31.55 | 6 |
| ATOM | 2941 | OG1 | THR A 367 | 8.707  | 26.620 | 64.714 | 1.00 | 34.37 | 8 |
| ATOM | 2942 | CG2 | THR A 367 | 10.780 | 25.404 | 64.723 | 1.00 | 33.55 | 6 |
| ATOM | 2943 | C   | THR A 367 | 10.146 | 24.633 | 67.472 | 1.00 | 33.09 | 6 |
| ATOM | 2944 | O   | THR A 367 | 10.586 | 23.476 | 67.485 | 1.00 | 38.62 | 8 |
| ATOM | 2945 | N   | LEU A 368 | 10.570 | 25.579 | 68.298 | 1.00 | 31.85 | 7 |
| ATOM | 2946 | CA  | LEU A 368 | 11.582 | 25.264 | 69.288 | 1.00 | 32.87 | 6 |
| ATOM | 2947 | CB  | LEU A 368 | 11.848 | 26.478 | 70.179 | 1.00 | 27.73 | 6 |
| ATOM | 2948 | CG  | LEU A 368 | 12.887 | 27.449 | 69.588 | 1.00 | 29.05 | 6 |
| ATOM | 2949 | CD1 | LEU A 368 | 14.260 | 26.777 | 69.541 | 1.00 | 23.05 | 6 |
| ATOM | 2950 | CD2 | LEU A 368 | 12.473 | 27.896 | 68.193 | 1.00 | 26.53 | 6 |
| ATOM | 2951 | C   | LEU A 368 | 11.157 | 24.053 | 70.107 | 1.00 | 35.16 | 6 |
| ATOM | 2952 | O   | LEU A 368 | 11.910 | 23.077 | 70.217 | 1.00 | 35.18 | 8 |
| ATOM | 2953 | N   | GLU A 369 | 9.942  | 24.101 | 70.649 | 1.00 | 37.56 | 7 |
| ATOM | 2954 | CA  | GLU A 369 | 9.431  | 22.993 | 71.442 | 1.00 | 40.23 | 6 |
| ATOM | 2955 | CB  | GLU A 369 | 7.956  | 23.216 | 71.770 | 1.00 | 42.07 | 6 |
| ATOM | 2956 | CG  | GLU A 369 | 7.722  | 24.460 | 72.617 | 1.00 | 48.51 | 6 |
| ATOM | 2957 | CD  | GLU A 369 | 6.281  | 24.616 | 73.067 | 1.00 | 51.93 | 6 |
| ATOM | 2958 | OE1 | GLU A 369 | 5.777  | 23.724 | 73.782 | 1.00 | 52.84 | 8 |
| ATOM | 2959 | OE2 | GLU A 369 | 5.652  | 25.636 | 72.710 | 1.00 | 58.33 | 8 |
| ATOM | 2960 | C   | GLU A 369 | 9.633  | 21.672 | 70.701 | 1.00 | 41.14 | 6 |
| ATOM | 2961 | O   | GLU A 369 | 10.087 | 20.684 | 71.286 | 1.00 | 41.87 | 8 |
| ATOM | 2962 | N   | LYS A 370 | 9.309  | 21.653 | 69.411 | 1.00 | 39.65 | 7 |
| ATOM | 2963 | CA  | LYS A 370 | 9.497  | 20.443 | 68.636 | 1.00 | 38.26 | 6 |
| ATOM | 2964 | CB  | LYS A 370 | 9.144  | 20.654 | 67.166 | 1.00 | 40.63 | 6 |
| ATOM | 2965 | CG  | LYS A 370 | 7.675  | 20.597 | 66.854 | 1.00 | 44.49 | 6 |
| ATOM | 2966 | CD  | LYS A 370 | 7.495  | 20.358 | 65.363 | 1.00 | 49.95 | 6 |
| ATOM | 2967 | CE  | LYS A 370 | 6.052  | 20.023 | 65.015 | 1.00 | 54.28 | 6 |
| ATOM | 2968 | NZ  | LYS A 370 | 5.890  | 19.679 | 63.574 | 1.00 | 55.44 | 7 |
| ATOM | 2969 | C   | LYS A 370 | 10.948 | 20.034 | 68.730 | 1.00 | 37.85 | 6 |
| ATOM | 2970 | O   | LYS A 370 | 11.261 | 18.930 | 69.156 | 1.00 | 37.95 | 8 |

Fig. 17-45

| | | | | | | | | | |
|---|---|---|---|---|---|---|---|---|---|
| ATOM | 2971 | N | ALA | A | 371 | 11.827 | 20.944 | 68.325 | 1.00 37.78 7 |
| ATOM | 2972 | CA | ALA | A | 371 | 13.264 | 20.704 | 68.340 | 1.00 36.39 6 |
| ATOM | 2973 | CB | ALA | A | 371 | 14.007 | 22.030 | 68.200 | 1.00 37.73 6 |
| ATOM | 2974 | C | ALA | A | 371 | 13.719 | 19.972 | 69.603 | 1.00 35.42 6 |
| ATOM | 2975 | O | ALA | A | 371 | 14.424 | 18.964 | 69.525 | 1.00 32.06 8 |
| ATOM | 2976 | N | ALA | A | 372 | 13.317 | 20.478 | 70.766 | 1.00 33.96 7 |
| ATOM | 2977 | CA | ALA | A | 372 | 13.695 | 19.848 | 72.024 | 1.00 32.22 6 |
| ATOM | 2978 | CB | ALA | A | 372 | 12.946 | 20.486 | 73.165 | 1.00 28.27 6 |
| ATOM | 2979 | C | ALA | A | 372 | 13.372 | 18.362 | 71.953 | 1.00 31.75 6 |
| ATOM | 2980 | O | ALA | A | 372 | 14.183 | 17.517 | 72.338 | 1.00 31.56 8 |
| ATOM | 2981 | N | ALA | A | 373 | 12.187 | 18.059 | 71.432 | 1.00 32.72 7 |
| ATOM | 2982 | CA | ALA | A | 373 | 11.710 | 16.684 | 71.305 | 1.00 32.32 6 |
| ATOM | 2983 | CB | ALA | A | 373 | 10.206 | 16.689 | 71.103 | 1.00 30.18 6 |
| ATOM | 2984 | C | ALA | A | 373 | 12.385 | 15.921 | 70.172 | 1.00 33.13 6 |
| ATOM | 2985 | OT1 | ALA | A | 373 | 13.078 | 14.926 | 70.468 | 1.00 35.87 8 |
| ATOM | 2986 | OT2 | ALA | A | 373 | 12.218 | 16.320 | 69.003 | 1.00 34.11 8 |
| ATOM | 2987 | ZN | ZN | Z | 951 | 22.693 | 34.497 | 53.990 | 1.00 36.45 6 |
| ATOM | 2988 | OH2 | WAT | S | 1 | 35.654 | 44.211 | 49.416 | 1.00 9.27 8 |
| ATOM | 2989 | OH2 | WAT | S | 2 | 24.480 | 33.130 | 53.069 | 1.00 21.27 8 |
| ATOM | 2990 | OH2 | WAT | S | 3 | 22.124 | 30.277 | 59.314 | 1.00 14.69 8 |
| ATOM | 2991 | OH2 | WAT | S | 4 | 13.839 | 20.611 | 75.741 | 1.00 27.94 8 |
| ATOM | 2992 | OH2 | WAT | S | 5 | 34.033 | 41.903 | 46.522 | 1.00 44.54 8 |
| ATOM | 2993 | OH2 | WAT | S | 6 | 15.039 | 42.130 | 55.781 | 1.00 23.79 8 |
| ATOM | 2994 | OH2 | WAT | S | 7 | 32.737 | 41.397 | 75.900 | 1.00 15.80 8 |
| ATOM | 2995 | OH2 | WAT | S | 8 | 11.367 | 22.606 | 58.814 | 1.00 23.37 8 |
| ATOM | 2996 | OH2 | WAT | S | 9 | 13.909 | 18.160 | 65.105 | 1.00 29.93 8 |
| ATOM | 2997 | OH2 | WAT | S | 10 | 29.655 | 56.108 | 58.029 | 1.00 50.54 8 |
| ATOM | 2998 | OH2 | WAT | S | 11 | 45.405 | 17.964 | 51.885 | 1.00 -9.28 8 |
| ATOM | 2999 | OH2 | WAT | S | 12 | 21.870 | 35.873 | 34.515 | 1.00 32.78 8 |
| ATOM | 3000 | OH2 | WAT | S | 13 | 43.504 | 35.670 | 33.779 | 1.00 28.85 8 |
| ATOM | 3001 | OH2 | WAT | S | 14 | 2.054 | 37.997 | 68.430 | 1.00 40.53 8 |
| ATOM | 3002 | OH2 | WAT | S | 15 | 49.730 | 28.024 | 55.966 | 1.00 21.42 8 |
| ATOM | 3003 | OH2 | WAT | S | 16 | 47.503 | 32.289 | 34.336 | 1.00 26.13 8 |
| ATOM | 3004 | OH2 | WAT | S | 17 | 6.101 | 26.102 | 64.434 | 1.00 21.69 8 |
| ATOM | 3005 | OH2 | WAT | S | 18 | 10.761 | 46.748 | 45.836 | 1.00 15.79 8 |
| ATOM | 3006 | OH2 | WAT | S | 19 | 9.146 | 16.861 | 61.441 | 1.00 16.68 8 |
| ATOM | 3007 | OH2 | WAT | S | 20 | 5.684 | 34.080 | 76.599 | 1.00 37.53 8 |
| ATOM | 3008 | OH2 | WAT | S | 21 | 14.896 | 33.163 | 49.117 | 1.00 34.17 8 |
| ATOM | 3009 | OH2 | WAT | S | 22 | 43.346 | 40.839 | 36.825 | 1.00 35.64 8 |
| ATOM | 3010 | OH2 | WAT | S | 23 | 0.516 | 27.705 | 69.174 | 1.00 21.02 8 |
| ATOM | 3011 | OH2 | WAT | S | 24 | 41.270 | 25.444 | 29.717 | 1.00 29.80 8 |
| ATOM | 3012 | OH2 | WAT | S | 25 | 17.818 | 29.142 | 54.584 | 1.00 27.92 8 |
| ATOM | 3013 | OH2 | WAT | S | 26 | 21.512 | 60.572 | 56.912 | 1.00 16.77 8 |
| ATOM | 3014 | OH2 | WAT | S | 27 | 21.211 | 33.582 | 48.347 | 1.00 23.93 8 |
| ATOM | 3015 | OH2 | WAT | S | 28 | 47.805 | 24.638 | 56.619 | 1.00 23.73 8 |
| ATOM | 3016 | OH2 | WAT | S | 29 | 44.624 | 50.302 | 58.154 | 1.00 16.79 8 |
| ATOM | 3017 | OH2 | WAT | S | 30 | 31.096 | 16.437 | 51.311 | 1.00 26.61 8 |
| ATOM | 3018 | OH2 | WAT | S | 31 | 39.837 | 38.833 | 55.145 | 1.00 32.28 8 |
| ATOM | 3019 | OH2 | WAT | S | 32 | 11.660 | 43.601 | 63.704 | 1.00 22.94 8 |
| ATOM | 3020 | OH2 | WAT | S | 33 | 49.899 | 23.474 | 53.058 | 1.00 26.85 8 |
| ATOM | 3021 | OH2 | WAT | S | 34 | 34.624 | 17.734 | 32.228 | 1.00 21.18 8 |
| ATOM | 3022 | OH2 | WAT | S | 35 | 26.926 | 15.913 | 62.444 | 1.00 27.01 8 |
| ATOM | 3023 | OH2 | WAT | S | 36 | 8.893 | 28.686 | 63.905 | 1.00 27.68 8 |
| ATOM | 3024 | OH2 | WAT | S | 37 | 23.381 | 26.634 | 43.532 | 1.00 24.42 8 |
| ATOM | 3025 | OH2 | WAT | S | 38 | 48.484 | 27.990 | 65.270 | 1.00 34.86 8 |
| ATOM | 3026 | OH2 | WAT | S | 39 | 43.382 | 28.410 | 74.379 | 1.00 25.68 8 |
| ATOM | 3027 | OH2 | WAT | S | 40 | 42.904 | 18.967 | 70.272 | 1.00 29.45 8 |
| ATOM | 3028 | OH2 | WAT | S | 41 | 20.521 | 53.828 | 50.298 | 1.00 22.35 8 |
| ATOM | 3029 | OH2 | WAT | S | 42 | 13.310 | 38.921 | 48.404 | 1.00 23.32 8 |
| ATOM | 3030 | OH2 | WAT | S | 43 | 9.787 | 46.265 | 60.012 | 1.00 33.51 8 |
| ATOM | 3031 | OH2 | WAT | S | 44 | 36.089 | 30.416 | 51.377 | 1.00 47.75 8 |
| ATOM | 3032 | OH2 | WAT | S | 45 | 14.831 | 48.131 | 42.151 | 1.00 50.96 8 |
| ATOM | 3033 | OH2 | WAT | S | 46 | 54.162 | 48.194 | 60.971 | 1.00 22.66 8 |
| ATOM | 3034 | OH2 | WAT | S | 47 | 38.943 | 61.290 | 63.509 | 1.00 33.73 8 |
| ATOM | 3035 | OH2 | WAT | S | 48 | 29.980 | 18.112 | 33.130 | 1.00 35.80 8 |
| ATOM | 3036 | OH2 | WAT | S | 49 | 31.879 | 50.673 | 44.528 | 1.00 24.39 8 |

Fig. 17-46

| | | | | | | | | | |
|---|---|---|---|---|---|---|---|---|---|
| ATOM | 3037 | OH2 | WAT | S | 50 | 39.863 | 14.629 | 64.307 | 1.00 24.19 | 8 |
| ATOM | 3038 | OH2 | WAT | S | 51 | 26.119 | 29.471 | 38.549 | 1.00 27.78 | 8 |
| ATOM | 3039 | OH2 | WAT | S | 52 | 48.070 | 41.589 | 44.011 | 1.00 36.38 | 8 |
| ATOM | 3040 | OH2 | WAT | S | 53 | 50.802 | 29.649 | 52.495 | 1.00 31.04 | 8 |
| ATOM | 3041 | OH2 | WAT | S | 54 | 49.540 | 35.532 | 71.585 | 1.00 20.96 | 8 |
| ATOM | 3042 | OH2 | WAT | S | 55 | 6.887 | 23.426 | 64.961 | 1.00 17.49 | 8 |
| ATOM | 3043 | OH2 | WAT | S | 56 | 25.698 | 39.891 | 37.674 | 1.00 51.51 | 8 |
| ATOM | 3044 | OH2 | WAT | S | 57 | 45.498 | 44.101 | 55.393 | 1.00 37.34 | 8 |
| ATOM | 3045 | OH2 | WAT | S | 58 | 44.661 | 34.733 | 46.902 | 1.00 44.52 | 8 |
| ATOM | 3046 | OH2 | WAT | S | 59 | 21.912 | 21.320 | 79.233 | 1.00 26.96 | 8 |
| ATOM | 3047 | OH2 | WAT | S | 60 | 27.290 | 21.016 | 77.320 | 1.00 27.74 | 8 |
| ATOM | 3048 | OH2 | WAT | S | 61 | 19.809 | 49.810 | 61.716 | 1.00 46.14 | 8 |
| ATOM | 3049 | OH2 | WAT | S | 62 | 30.843 | 18.035 | 41.441 | 1.00 42.23 | 8 |
| ATOM | 3050 | OH2 | WAT | S | 63 | 19.055 | 33.379 | 60.511 | 1.00 28.99 | 8 |
| ATOM | 3051 | OH2 | WAT | S | 64 | 47.925 | 33.253 | 61.470 | 1.00 34.93 | 8 |
| ATOM | 3052 | OH2 | WAT | S | 65 | 32.500 | 36.000 | 41.000 | 1.00 35.33 | 8 |
| ATOM | 3053 | OH2 | WAT | S | 66 | 27.245 | 56.551 | 44.579 | 1.00 34.19 | 8 |
| ATOM | 3054 | OH2 | WAT | S | 67 | 5.176 | 32.914 | 54.669 | 1.00 41.89 | 8 |
| ATOM | 3055 | OH2 | WAT | S | 68 | 41.159 | 51.018 | 49.348 | 1.00 27.31 | 8 |
| ATOM | 3056 | OH2 | WAT | S | 69 | 12.869 | 50.298 | 61.877 | 1.00 31.30 | 8 |
| ATOM | 3057 | OH2 | WAT | S | 70 | 17.499 | 12.826 | 63.854 | 1.00 24.91 | 8 |
| ATOM | 3058 | OH2 | WAT | S | 71 | 27.152 | 12.189 | 53.999 | 1.00 18.76 | 8 |
| ATOM | 3059 | OH2 | WAT | S | 72 | 25.213 | 54.809 | 67.866 | 1.00 61.35 | 8 |
| ATOM | 3060 | OH2 | WAT | S | 73 | 17.671 | 48.515 | 53.188 | 1.00 37.63 | 8 |
| ATOM | 3061 | OH2 | WAT | S | 74 | 23.765 | 60.846 | 66.579 | 1.00 21.81 | 8 |
| ATOM | 3062 | OH2 | WAT | S | 75 | 35.535 | 27.040 | 70.698 | 1.00 34.04 | 8 |
| ATOM | 3063 | OH2 | WAT | S | 76 | 26.280 | 16.065 | 76.564 | 1.00 32.20 | 8 |
| ATOM | 3064 | OH2 | WAT | S | 77 | 18.451 | 25.555 | 45.150 | 1.00 28.55 | 8 |
| ATOM | 3065 | OH2 | WAT | S | 78 | 10.446 | 61.273 | 48.633 | 1.00 44.74 | 8 |
| ATOM | 3066 | OH2 | WAT | S | 79 | 13.256 | 24.051 | 73.017 | 1.00 35.45 | 8 |
| ATOM | 3067 | OH2 | WAT | S | 80 | 23.571 | 13.292 | 69.937 | 1.00 49.49 | 8 |
| ATOM | 3068 | OH2 | WAT | S | 81 | 29.891 | 18.071 | 46.109 | 1.00 22.84 | 8 |
| ATOM | 3069 | OH2 | WAT | S | 82 | 12.886 | 42.723 | 75.807 | 1.00 35.31 | 8 |
| ATOM | 3070 | OH2 | WAT | S | 83 | 41.348 | 15.471 | 45.004 | 1.00 47.24 | 8 |
| ATOM | 3071 | OH2 | WAT | S | 84 | 13.406 | 44.647 | 71.349 | 1.00 49.67 | 8 |
| ATOM | 3072 | OH2 | WAT | S | 85 | 30.444 | 35.217 | 51.882 | 1.00 38.15 | 8 |
| ATOM | 3073 | OH2 | WAT | S | 86 | 5.217 | 40.817 | 61.244 | 1.00 19.51 | 8 |
| ATOM | 3074 | OH2 | WAT | S | 87 | 8.891 | 21.532 | 56.838 | 1.00 30.72 | 8 |
| ATOM | 3075 | OH2 | WAT | S | 88 | 41.816 | 25.022 | 72.452 | 1.00 22.92 | 8 |
| ATOM | 3076 | OH2 | WAT | S | 89 | 50.621 | 36.644 | 60.248 | 1.00 29.29 | 8 |
| ATOM | 3077 | OH2 | WAT | S | 90 | 26.008 | 34.532 | 49.627 | 1.00 45.42 | 8 |
| ATOM | 3078 | OH2 | WAT | S | 91 | 8.131 | 39.168 | 54.903 | 1.00 31.50 | 8 |
| ATOM | 3079 | OH2 | WAT | S | 92 | 16.591 | 58.091 | 57.551 | 1.00 34.73 | 8 |
| ATOM | 3080 | OH2 | WAT | S | 93 | 34.773 | 54.065 | 69.382 | 1.00 36.05 | 8 |
| ATOM | 3081 | OH2 | WAT | S | 94 | 42.105 | 31.720 | 71.257 | 1.00 35.49 | 8 |
| ATOM | 3082 | OH2 | WAT | S | 95 | 29.684 | 52.077 | 73.172 | 1.00 35.17 | 8 |
| ATOM | 3083 | OH2 | WAT | S | 96 | 26.411 | 37.426 | 38.934 | 1.00 41.68 | 8 |
| ATOM | 3084 | OH2 | WAT | S | 97 | 41.183 | 52.989 | 62.927 | 1.00 50.77 | 8 |
| ATOM | 3085 | OH2 | WAT | S | 98 | 21.167 | 6.202 | 63.102 | 1.00 33.36 | 8 |
| ATOM | 3086 | OH2 | WAT | S | 99 | 25.060 | 18.985 | 36.669 | 1.00 46.63 | 8 |
| ATOM | 3087 | OH2 | WAT | S | 100 | 37.304 | 39.027 | 73.722 | 1.00 25.99 | 8 |
| ATOM | 3088 | OH2 | WAT | S | 101 | 15.911 | 54.635 | 39.343 | 1.00 29.88 | 8 |
| ATOM | 3089 | OH2 | WAT | S | 102 | 48.730 | 25.803 | 59.572 | 1.00 37.97 | 8 |
| ATOM | 3090 | OH2 | WAT | S | 103 | 24.029 | 42.997 | 74.111 | 1.00 25.23 | 8 |
| ATOM | 3091 | OH2 | WAT | S | 104 | 42.477 | 21.773 | 46.986 | 1.00 49.05 | 8 |
| ATOM | 3092 | OH2 | WAT | S | 105 | 29.984 | 22.945 | 31.397 | 1.00 44.21 | 8 |
| ATOM | 3093 | OH2 | WAT | S | 106 | 40.850 | 36.936 | 31.885 | 1.00 43.26 | 8 |
| ATOM | 3094 | OH2 | WAT | S | 107 | 9.750 | 32.487 | 48.823 | 1.00 35.71 | 8 |
| ATOM | 3095 | OH2 | WAT | S | 108 | 7.618 | 30.171 | 58.896 | 1.00 40.03 | 8 |
| ATOM | 3096 | OH2 | WAT | S | 109 | 17.603 | 13.771 | 59.767 | 1.00 50.33 | 8 |
| ATOM | 3097 | OH2 | WAT | S | 110 | 22.590 | 8.744 | 67.501 | 1.00 34.81 | 8 |
| ATOM | 3098 | OH2 | WAT | S | 111 | 21.034 | 29.771 | 76.056 | 1.00 30.02 | 8 |
| ATOM | 3099 | OH2 | WAT | S | 112 | 24.791 | 14.674 | 50.081 | 1.00 51.96 | 8 |
| ATOM | 3100 | OH2 | WAT | S | 113 | 40.750 | 47.494 | 54.056 | 1.00 46.98 | 8 |
| ATOM | 3101 | OH2 | WAT | S | 114 | 7.708 | 42.479 | 58.027 | 1.00 34.08 | 8 |
| ATOM | 3102 | OH2 | WAT | S | 115 | 32.375 | 49.136 | 77.566 | 1.00 27.53 | 8 |

Fig. 17-47

| | | | | | | | | | |
|---|---|---|---|---|---|---|---|---|---|
| ATOM | 3103 | OH2 | WAT | S | 116 | 5.596 | 17.009 | 64.551 | 1.00 39.15 | 8 |
| ATOM | 3104 | OH2 | WAT | S | 117 | 20.194 | 50.998 | 70.563 | 1.00 19.73 | 8 |
| ATOM | 3105 | OH2 | WAT | S | 118 | 23.853 | 64.927 | 64.164 | 1.00 27.16 | 8 |
| ATOM | 3106 | OH2 | WAT | S | 119 | 9.277 | 43.601 | 46.279 | 1.00 32.31 | 8 |
| ATOM | 3107 | OH2 | WAT | S | 120 | 15.613 | 24.398 | 46.723 | 1.00 55.20 | 8 |
| ATOM | 3108 | OH2 | WAT | S | 121 | 33.110 | 16.122 | 54.229 | 1.00 35.91 | 8 |
| ATOM | 3109 | OH2 | WAT | S | 122 | 26.772 | 34.085 | 33.852 | 1.00 37.49 | 8 |
| ATOM | 3110 | OH2 | WAT | S | 123 | 28.654 | 37.783 | 75.829 | 1.00 47.30 | 8 |
| ATOM | 3111 | OH2 | WAT | S | 124 | 49.180 | 22.653 | 59.678 | 1.00 37.33 | 8 |
| ATOM | 3112 | OH2 | WAT | S | 125 | 20.561 | 27.788 | 65.975 | 1.00 67.86 | 8 |
| ATOM | 3113 | OH2 | WAT | S | 126 | 34.251 | 13.344 | 57.366 | 1.00 36.18 | 8 |
| ATOM | 3114 | OH2 | WAT | S | 127 | 49.215 | 36.854 | 48.117 | 1.00 33.63 | 8 |
| ATOM | 3115 | OH2 | WAT | S | 128 | 45.826 | 19.588 | 41.601 | 1.00 44.07 | 8 |
| ATOM | 3116 | OH2 | WAT | S | 129 | 18.693 | 56.382 | 64.014 | 1.00 47.77 | 8 |
| ATOM | 3117 | OH2 | WAT | S | 130 | 44.181 | 24.202 | 36.963 | 1.00 32.70 | 8 |
| ATOM | 3118 | OH2 | WAT | S | 131 | 19.160 | 51.901 | 38.133 | 1.00 54.07 | 8 |
| ATOM | 3119 | OH2 | WAT | S | 132 | 16.904 | 36.558 | 48.679 | 1.00 42.21 | 8 |
| ATOM | 3120 | OH2 | WAT | S | 133 | 46.851 | 26.029 | 34.353 | 1.00 56.33 | 8 |
| ATOM | 3121 | OH2 | WAT | S | 134 | 3.925 | 41.533 | 68.647 | 1.00 45.99 | 8 |
| ATOM | 3122 | OH2 | WAT | S | 135 | 44.590 | 38.382 | 78.167 | 1.00 44.50 | 8 |
| ATOM | 3123 | OH2 | WAT | S | 136 | 6.384 | 19.317 | 71.166 | 1.00 28.17 | 8 |
| ATOM | 3124 | OH2 | WAT | S | 137 | 17.982 | 39.823 | 66.487 | 1.00 49.31 | 8 |
| ATOM | 3125 | OH2 | WAT | S | 138 | 8.317 | 22.286 | 61.863 | 1.00 43.42 | 8 |
| ATOM | 3126 | OH2 | WAT | S | 139 | 29.248 | 14.196 | 55.622 | 1.00 35.55 | 8 |
| ATOM | 3127 | OH2 | WAT | S | 140 | 30.377 | 33.180 | 80.320 | 1.00 43.94 | 8 |
| ATOM | 3128 | OH2 | WAT | S | 141 | 41.842 | 32.906 | 27.392 | 1.00 24.82 | 8 |
| ATOM | 3129 | OH2 | WAT | S | 142 | 33.971 | 3.859 | 64.002 | 1.00 41.93 | 8 |
| ATOM | 3130 | OH2 | WAT | S | 143 | 27.314 | 8.087 | 70.916 | 1.00 49.03 | 8 |
| ATOM | 3131 | OH2 | WAT | S | 144 | 4.310 | 39.006 | 64.550 | 1.00 32.70 | 8 |
| ATOM | 3132 | OH2 | WAT | S | 145 | 2.940 | 19.950 | 63.265 | 1.00 33.24 | 8 |
| ATOM | 3133 | OH2 | WAT | S | 146 | 24.134 | 47.625 | 60.121 | 1.00 44.24 | 8 |
| ATOM | 3134 | OH2 | WAT | S | 147 | 25.035 | 53.746 | 42.337 | 1.00 47.82 | 8 |
| ATOM | 3135 | OH2 | WAT | S | 148 | 32.767 | 38.897 | 49.651 | 1.00 21.86 | 8 |
| ATOM | 3136 | OH2 | WAT | S | 149 | 37.145 | 57.288 | 47.392 | 1.00 36.13 | 8 |
| ATOM | 3137 | OH2 | WAT | S | 150 | 25.171 | 18.011 | 32.273 | 1.00 38.04 | 8 |
| ATOM | 3138 | OH2 | WAT | S | 151 | 24.054 | 43.182 | 55.583 | 1.00 41.68 | 8 |
| ATOM | 3139 | OH2 | WAT | S | 152 | 27.686 | 64.936 | 52.937 | 1.00 60.62 | 8 |
| ATOM | 3140 | OH2 | WAT | S | 153 | 24.084 | 39.543 | 76.589 | 1.00 22.62 | 8 |
| ATOM | 3141 | OH2 | WAT | S | 154 | 42.110 | 10.159 | 68.662 | 1.00 46.98 | 8 |
| ATOM | 3142 | OH2 | WAT | S | 155 | 9.675 | 22.905 | 75.335 | 1.00 26.45 | 8 |
| ATOM | 3143 | OH2 | WAT | S | 156 | 4.506 | 34.799 | 52.857 | 1.00 33.84 | 8 |
| ATOM | 3144 | OH2 | WAT | S | 157 | 32.583 | 35.051 | 76.446 | 1.00 36.27 | 8 |
| ATOM | 3145 | OH2 | WAT | S | 158 | 40.341 | 58.311 | 60.390 | 1.00 54.69 | 8 |
| ATOM | 3146 | OH2 | WAT | S | 159 | 29.473 | 58.378 | 71.881 | 1.00 28.59 | 8 |
| ATOM | 3147 | OH2 | WAT | S | 160 | 11.829 | 60.543 | 56.138 | 1.00 37.67 | 8 |
| ATOM | 3148 | OH2 | WAT | S | 161 | 24.241 | 48.010 | 67.935 | 1.00 56.62 | 8 |
| ATOM | 3149 | OH2 | WAT | S | 162 | 12.853 | 33.929 | 77.503 | 1.00 29.88 | 8 |
| ATOM | 3150 | OH2 | WAT | S | 163 | 9.491 | 26.168 | 59.687 | 1.00 15.42 | 8 |
| ATOM | 3151 | OH2 | WAT | S | 164 | 27.424 | 16.480 | 38.895 | 1.00 36.86 | 8 |
| ATOM | 3152 | OH2 | WAT | S | 165 | 8.512 | 56.634 | 49.614 | 1.00 30.08 | 8 |
| ATOM | 3153 | OH2 | WAT | S | 166 | 30.721 | 13.394 | 57.919 | 1.00 39.47 | 8 |
| ATOM | 3154 | OH2 | WAT | S | 167 | 49.594 | 38.223 | 73.903 | 1.00 29.50 | 8 |
| ATOM | 3155 | OH2 | WAT | S | 168 | 41.994 | 48.023 | 74.119 | 1.00 38.12 | 8 |
| ATOM | 3156 | OH2 | WAT | S | 169 | 42.092 | 39.503 | 33.116 | 1.00 24.47 | 8 |
| ATOM | 3157 | OH2 | WAT | S | 170 | 34.547 | 12.749 | 38.054 | 1.00 38.65 | 8 |
| ATOM | 3158 | OH2 | WAT | S | 171 | 15.377 | 60.862 | 50.791 | 1.00 32.82 | 8 |
| ATOM | 3159 | OH2 | WAT | S | 172 | 31.854 | 42.110 | 62.950 | 1.00 42.43 | 8 |
| ATOM | 3160 | OH2 | WAT | S | 173 | 48.743 | 44.073 | 57.626 | 1.00 34.04 | 8 |
| ATOM | 3161 | OH2 | WAT | S | 174 | 8.723 | 50.038 | 42.232 | 1.00 32.87 | 8 |
| ATOM | 3162 | OH2 | WAT | S | 175 | 14.257 | 18.280 | 53.455 | 1.00 40.51 | 8 |
| ATOM | 3163 | OH2 | WAT | S | 176 | 31.917 | 37.509 | 53.943 | 1.00 40.43 | 8 |
| ATOM | 3164 | OH2 | WAT | S | 177 | 23.921 | 47.029 | 70.642 | 1.00 47.97 | 8 |
| ATOM | 3165 | OH2 | WAT | S | 178 | 27.974 | 47.778 | 69.949 | 1.00 62.12 | 8 |
| ATOM | 3166 | OH2 | WAT | S | 179 | 7.850 | 25.093 | 51.345 | 1.00 50.13 | 8 |
| ATOM | 3167 | OH2 | WAT | S | 180 | 22.080 | 48.840 | 66.463 | 1.00 53.81 | 8 |
| ATOM | 3168 | OH2 | WAT | S | 181 | 34.780 | 48.220 | 77.419 | 1.00 30.86 | 8 |

Fig. 17-48

```
ATOM   3169  OH2 WAT S 182      43.893  35.526  52.018  1.00 47.14      8
ATOM   3170  OH2 WAT S 183      29.166  21.424  28.950  1.00 45.08      8
ATOM   3171  OH2 WAT S 184      51.175  51.545  62.599  1.00 33.88      8
ATOM   3172  OH2 WAT S 185      18.520  46.208  42.323  1.00 50.85      8
ATOM   3173  OH2 WAT S 186      44.774  30.219  38.653  1.00 45.36      8
ATOM   3174  OH2 WAT S 187      30.770   9.460  69.837  1.00 32.44      8
ATOM   3175  OH2 WAT S 188      22.157  39.535  78.736  1.00 37.01      8
ATOM   3176  OH2 WAT S 189      11.778  50.526  68.987  1.00 41.34      8
ATOM   3177  OH2 WAT S 190      31.339  60.910  49.439  1.00 21.88      8
ATOM   3178  OH2 WAT S 191      31.165  14.244  74.907  1.00 27.47      8
ATOM   3179  OH2 WAT S 192      39.705  15.398  70.464  1.00 47.05      8
ATOM   3180  OH2 WAT S 193       3.668  34.304  72.937  1.00 39.82      8
ATOM   3181  OH2 WAT S 194      25.256   9.360  67.925  1.00 33.21      8
ATOM   3182  OH2 WAT S 195      47.575  17.667  48.773  1.00 40.79      8
ATOM   3183  OH2 WAT S 196      32.017  13.045  34.633  1.00 37.00      8
ATOM   3184  OH2 WAT S 197      35.476   7.006  64.436  1.00 49.59      8
ATOM   3185  OH2 WAT S 198      12.180  16.270  56.288  1.00 47.22      8
ATOM   3186  OH2 WAT S 199      37.133  21.226  75.963  1.00 38.59      8
ATOM   3187  OH2 WAT S 200      40.268  15.712  48.199  1.00 39.24      8
ATOM   3188  OH2 WAT S 201      25.159  17.768  46.858  1.00 49.88      8
ATOM   3189  OH2 WAT S 202      24.593  27.104  65.727  1.00 53.46      8
ATOM   3190  OH2 WAT S 203      36.741  20.267  33.858  1.00 41.90      8
ATOM   3191  OH2 WAT S 204      10.013  53.930  47.546  1.00 48.06      8
ATOM   3192  OH2 WAT S 205      22.305  16.731  54.471  1.00 27.07      8
ATOM   3193  OH2 WAT S 206      47.454  34.778  74.101  1.00 47.44      8
ATOM   3194  OH2 WAT S 207      35.189  55.767  45.193  1.00 59.49      8
ATOM   3195  OH2 WAT S 208      37.827  18.151  36.382  1.00 45.31      8
ATOM   3196  OH2 WAT S 209       6.823  37.405  51.989  1.00 58.23      8
ATOM   3197  OH2 WAT S 210      32.040  43.551  36.157  1.00 30.78      8
ATOM   3198  OH2 WAT S 211      17.038  52.360  63.283  1.00 34.08      8
ATOM   3199  OH2 WAT S 212      30.001  18.471  49.568  1.00 33.92      8
ATOM   3200  OH2 WAT S 213      23.045  28.615  33.729  1.00 44.22      8
ATOM   3201  OH2 WAT S 214      26.130  61.496  75.246  1.00 40.49      8
ATOM   3202  OH2 WAT S 215      33.881  32.473  46.604  1.00 39.35      8
ATOM   3203  OH2 WAT S 216      23.887  45.987  44.362  1.00 36.50      8
ATOM   3204  OH2 WAT S 217       6.925  42.281  65.917  1.00 34.22      8
ATOM   3205  OH2 WAT S 218      32.823   8.977  59.213  1.00 27.03      8
END
```

Fig. 17-49

|      |    |     |     |   | Residue # | X | Y | Z | B | Segment ID |
|------|----|-----|-----|---|-----------|--------|---------|---------|------|-------|
| ATOM | 1  | CB  | ALA | A | 2  | 46.725 | 14.971  | 138.208 | 1.00 | 56.80 |
| ATOM | 2  | C   | ALA | A | 2  | 47.943 | 12.813  | 138.561 | 1.00 | 58.93 |
| ATOM | 3  | O   | ALA | A | 2  | 48.857 | 13.292  | 137.884 | 1.00 | 60.99 |
| ATOM | 4  | N   | ALA | A | 2  | 46.995 | 14.046  | 140.488 | 1.00 | 56.88 |
| ATOM | 5  | CA  | ALA | A | 2  | 46.801 | 13.697  | 139.052 | 1.00 | 59.41 |
| ATOM | 6  | N   | LYS | A | 3  | 47.890 | 11.525  | 138.903 | 1.00 | 53.81 |
| ATOM | 7  | CA  | LYS | A | 3  | 48.937 | 10.591  | 138.492 | 1.00 | 53.62 |
| ATOM | 8  | CB  | LYS | A | 3  | 48.736 | 9.229   | 139.156 | 1.00 | 50.26 |
| ATOM | 9  | CG  | LYS | A | 3  | 48.917 | 9.279   | 140.665 | 1.00 | 56.64 |
| ATOM | 10 | CD  | LYS | A | 3  | 48.950 | 7.891   | 141.285 | 1.00 | 57.18 |
| ATOM | 11 | CE  | LYS | A | 3  | 49.160 | 7.964   | 142.796 | 1.00 | 56.74 |
| ATOM | 12 | NZ  | LYS | A | 3  | 50.423 | 8.663   | 143.165 | 1.00 | 54.86 |
| ATOM | 13 | C   | LYS | A | 3  | 49.063 | 10.430  | 136.986 | 1.00 | 49.95 |
| ATOM | 14 | O   | LYS | A | 3  | 48.088 | 10.562  | 136.248 | 1.00 | 44.34 |
| ATOM | 15 | N   | VAL | A | 4  | 50.287 | 10.147  | 136.550 | 1.00 | 46.01 |
| ATOM | 16 | CA  | VAL | A | 4  | 50.609 | 9.985   | 135.142 | 1.00 | 42.48 |
| ATOM | 17 | CB  | VAL | A | 4  | 51.901 | 10.755  | 134.809 | 1.00 | 43.42 |
| ATOM | 18 | CG1 | VAL | A | 4  | 52.179 | 10.713  | 133.307 | 1.00 | 39.20 |
| ATOM | 19 | CG2 | VAL | A | 4  | 51.773 | 12.186  | 135.310 | 1.00 | 39.34 |
| ATOM | 20 | C   | VAL | A | 4  | 50.787 | 8.510   | 134.806 | 1.00 | 38.41 |
| ATOM | 21 | O   | VAL | A | 4  | 51.659 | 7.839   | 135.351 | 1.00 | 37.08 |
| ATOM | 22 | N   | LYS | A | 5  | 49.959 | 8.011   | 133.899 | 1.00 | 37.79 |
| ATOM | 23 | CA  | LYS | A | 5  | 50.016 | 6.610   | 133.515 | 1.00 | 38.17 |
| ATOM | 24 | CB  | LYS | A | 5  | 48.700 | 5.915   | 133.887 | 1.00 | 38.40 |
| ATOM | 25 | CG  | LYS | A | 5  | 48.411 | 5.803   | 135.385 | 1.00 | 42.84 |
| ATOM | 26 | CD  | LYS | A | 5  | 49.384 | 4.855   | 136.070 | 1.00 | 44.10 |
| ATOM | 27 | CE  | LYS | A | 5  | 49.017 | 4.632   | 137.534 | 1.00 | 45.97 |
| ATOM | 28 | NZ  | LYS | A | 5  | 49.045 | 5.894   | 138.322 | 1.00 | 51.78 |
| ATOM | 29 | C   | LYS | A | 5  | 50.275 | 6.392   | 132.030 | 1.00 | 38.31 |
| ATOM | 30 | O   | LYS | A | 5  | 49.992 | 7.253   | 131.201 | 1.00 | 38.13 |
| ATOM | 31 | N   | LEU | A | 6  | 50.817 | 5.220   | 131.717 | 1.00 | 35.05 |
| ATOM | 32 | CA  | LEU | A | 6  | 51.082 | 4.818   | 130.346 | 1.00 | 31.46 |
| ATOM | 33 | CB  | LEU | A | 6  | 52.582 | 4.592   | 130.133 | 1.00 | 28.46 |
| ATOM | 34 | CG  | LEU | A | 6  | 53.094 | 4.256   | 128.720 | 1.00 | 30.91 |
| ATOM | 35 | CD1 | LEU | A | 6  | 52.618 | 2.884   | 128.295 | 1.00 | 33.05 |
| ATOM | 36 | CD2 | LEU | A | 6  | 52.630 | 5.312   | 127.744 | 1.00 | 21.96 |
| ATOM | 37 | C   | LEU | A | 6  | 50.307 | 3.512   | 130.164 | 1.00 | 30.50 |
| ATOM | 38 | O   | LEU | A | 6  | 50.453 | 2.581   | 130.955 | 1.00 | 32.82 |
| ATOM | 39 | N   | ILE | A | 7  | 49.459 | 3.456   | 129.145 | 1.00 | 26.94 |
| ATOM | 40 | CA  | ILE | A | 7  | 48.676 | 2.255   | 128.893 | 1.00 | 28.29 |
| ATOM | 41 | CB  | ILE | A | 7  | 47.218 | 2.598   | 128.493 | 1.00 | 28.94 |
| ATOM | 42 | CG2 | ILE | A | 7  | 46.499 | 1.343   | 128.041 | 1.00 | 32.57 |
| ATOM | 43 | CG1 | ILE | A | 7  | 46.447 | 3.172   | 129.688 | 1.00 | 36.59 |
| ATOM | 44 | CD1 | ILE | A | 7  | 46.979 | 4.468   | 130.236 | 1.00 | 46.80 |
| ATOM | 45 | C   | ILE | A | 7  | 49.341 | 1.470   | 127.770 | 1.00 | 31.09 |
| ATOM | 46 | O   | ILE | A | 7  | 49.600 | 2.009   | 126.695 | 1.00 | 27.65 |
| ATOM | 47 | N   | GLY | A | 8  | 49.538 | 0.201   | 128.029 | 1.00 | 27.30 |
| ATOM | 48 | CA  | GLY | A | 8  | 50.277 | -0.614  | 127.016 | 1.00 | 25.50 |
| ATOM | 49 | C   | GLY | A | 8  | 50.578 | -2.024  | 127.480 | 1.00 | 30.66 |
| ATOM | 50 | O   | GLY | A | 8  | 50.224 | -2.421  | 128.592 | 1.00 | 30.02 |
| ATOM | 51 | N   | THR | A | 9  | 51.238 | -2.777  | 126.611 | 1.00 | 28.94 |
| ATOM | 52 | CA  | THR | A | 9  | 51.614 | -4.156  | 126.877 | 1.00 | 33.63 |
| ATOM | 53 | CB  | THR | A | 9  | 50.393 | -5.083  | 126.857 | 1.00 | 36.19 |
| ATOM | 54 | OG1 | THR | A | 9  | 50.827 | -6.441  | 126.992 | 1.00 | 34.87 |
| ATOM | 55 | CG2 | THR | A | 9  | 49.633 | -4.931  | 125.548 | 1.00 | 36.49 |
| ATOM | 56 | C   | THR | A | 9  | 52.567 | -4.637  | 125.794 | 1.00 | 34.83 |
| ATOM | 57 | O   | THR | A | 9  | 52.545 | -4.133  | 124.677 | 1.00 | 36.91 |
| ATOM | 58 | N   | LEU | A | 10 | 53.407 | -5.609  | 126.129 | 1.00 | 39.15 |
| ATOM | 59 | CA  | LEU | A | 10 | 54.345 | -6.167  | 125.164 | 1.00 | 40.21 |
| ATOM | 60 | CB  | LEU | A | 10 | 55.402 | -7.009  | 125.881 | 1.00 | 42.40 |
| ATOM | 61 | CG  | LEU | A | 10 | 56.482 | -6.282  | 126.687 | 1.00 | 42.29 |
| ATOM | 62 | CD1 | LEU | A | 10 | 55.870 | -5.293  | 127.647 | 1.00 | 42.92 |
| ATOM | 63 | CD2 | LEU | A | 10 | 57.319 | -7.306  | 127.424 | 1.00 | 40.29 |
| ATOM | 64 | C   | LEU | A | 10 | 53.591 | -7.039  | 124.159 | 1.00 | 41.70 |
| ATOM | 65 | O   | LEU | A | 10 | 54.055 | -7.266  | 123.044 | 1.00 | 37.13 |
| ATOM | 66 | N   | ASP | A | 11 | 52.419 | -7.519  | 124.557 | 1.00 | 47.28 |

Fig. 18-1

| ATOM | 67 | CA | ASP | A | 11 | 51.617 | -8.369 | 123.683 | 1.00 | 53.30 |
| ATOM | 68 | CB | ASP | A | 11 | 50.230 | -8.608 | 124.287 | 1.00 | 52.35 |
| ATOM | 69 | CG | ASP | A | 11 | 50.295 | -9.331 | 125.610 | 1.00 | 53.33 |
| ATOM | 70 | OD1 | ASP | A | 11 | 51.004 | -10.358 | 125.685 | 1.00 | 52.21 |
| ATOM | 71 | OD2 | ASP | A | 11 | 49.630 | -8.883 | 126.567 | 1.00 | 58.48 |
| ATOM | 72 | C | ASP | A | 11 | 51.459 | -7.840 | 122.257 | 1.00 | 53.33 |
| ATOM | 73 | O | ASP | A | 11 | 51.360 | -8.626 | 121.311 | 1.00 | 54.31 |
| ATOM | 74 | N | TYR | A | 12 | 51.424 | -6.521 | 122.092 | 1.00 | 51.92 |
| ATOM | 75 | CA | TYR | A | 12 | 51.275 | -5.970 | 120.749 | 1.00 | 51.41 |
| ATOM | 76 | CB | TYR | A | 12 | 51.328 | -4.437 | 120.755 | 1.00 | 49.05 |
| ATOM | 77 | CG | TYR | A | 12 | 50.164 | -3.729 | 121.421 | 1.00 | 45.48 |
| ATOM | 78 | CD1 | TYR | A | 12 | 50.296 | -3.157 | 122.686 | 1.00 | 47.08 |
| ATOM | 79 | CE1 | TYR | A | 12 | 49.252 | -2.430 | 123.263 | 1.00 | 47.53 |
| ATOM | 80 | CD2 | TYR | A | 12 | 48.952 | -3.565 | 120.749 | 1.00 | 43.77 |
| ATOM | 81 | CE2 | TYR | A | 12 | 47.906 | -2.847 | 121.310 | 1.00 | 44.16 |
| ATOM | 82 | CZ | TYR | A | 12 | 48.061 | -2.279 | 122.566 | 1.00 | 48.67 |
| ATOM | 83 | OH | TYR | A | 12 | 47.030 | -1.548 | 123.116 | 1.00 | 48.65 |
| ATOM | 84 | C | TYR | A | 12 | 52.367 | -6.503 | 119.816 | 1.00 | 50.01 |
| ATOM | 85 | O | TYR | A | 12 | 52.197 | -6.525 | 118.596 | 1.00 | 45.56 |
| ATOM | 86 | N | GLY | A | 13 | 53.484 | -6.931 | 120.396 | 1.00 | 48.72 |
| ATOM | 87 | CA | GLY | A | 13 | 54.574 | -7.458 | 119.599 | 1.00 | 50.56 |
| ATOM | 88 | C | GLY | A | 13 | 54.196 | -8.727 | 118.857 | 1.00 | 53.32 |
| ATOM | 89 | O | GLY | A | 13 | 54.931 | -9.184 | 117.982 | 1.00 | 52.64 |
| ATOM | 90 | N | LYS | A | 14 | 53.045 | -9.294 | 119.207 | 1.00 | 53.37 |
| ATOM | 91 | CA | LYS | A | 14 | 52.555 | -10.518 | 118.579 | 1.00 | 54.56 |
| ATOM | 92 | CB | LYS | A | 14 | 52.022 | -11.475 | 119.653 | 1.00 | 58.02 |
| ATOM | 93 | CG | LYS | A | 14 | 53.086 | -12.062 | 120.591 | 1.00 | 62.81 |
| ATOM | 94 | CD | LYS | A | 14 | 53.934 | -13.154 | 119.918 | 1.00 | 61.61 |
| ATOM | 95 | CE | LYS | A | 14 | 54.747 | -12.638 | 118.734 | 1.00 | 61.77 |
| ATOM | 96 | NZ | LYS | A | 14 | 55.514 | -13.713 | 118.045 | 1.00 | 58.35 |
| ATOM | 97 | C | LYS | A | 14 | 51.455 | -10.231 | 117.559 | 1.00 | 52.03 |
| ATOM | 98 | O | LYS | A | 14 | 50.911 | -11.145 | 116.942 | 1.00 | 51.71 |
| ATOM | 99 | N | TYR | A | 15 | 51.143 | -8.955 | 117.372 | 1.00 | 46.92 |
| ATOM | 100 | CA | TYR | A | 15 | 50.091 | -8.563 | 116.449 | 1.00 | 47.99 |
| ATOM | 101 | CB | TYR | A | 15 | 48.959 | -7.915 | 117.253 | 1.00 | 50.40 |
| ATOM | 102 | CG | TYR | A | 15 | 48.456 | -8.793 | 118.386 | 1.00 | 53.01 |
| ATOM | 103 | CD1 | TYR | A | 15 | 48.166 | -8.255 | 119.637 | 1.00 | 52.10 |
| ATOM | 104 | CE1 | TYR | A | 15 | 47.722 | -9.053 | 120.685 | 1.00 | 51.72 |
| ATOM | 105 | CD2 | TYR | A | 15 | 48.283 | -10.166 | 118.208 | 1.00 | 54.67 |
| ATOM | 106 | CE2 | TYR | A | 15 | 47.838 | -10.976 | 119.250 | 1.00 | 55.69 |
| ATOM | 107 | CZ | TYR | A | 15 | 47.561 | -10.412 | 120.485 | 1.00 | 54.18 |
| ATOM | 108 | OH | TYR | A | 15 | 47.130 | -11.208 | 121.520 | 1.00 | 55.42 |
| ATOM | 109 | C | TYR | A | 15 | 50.592 | -7.617 | 115.353 | 1.00 | 46.20 |
| ATOM | 110 | O | TYR | A | 15 | 49.933 | -6.635 | 115.018 | 1.00 | 43.72 |
| ATOM | 111 | N | ARG | A | 16 | 51.758 | -7.924 | 114.791 | 1.00 | 46.29 |
| ATOM | 112 | CA | ARG | A | 16 | 52.347 | -7.109 | 113.727 | 1.00 | 45.66 |
| ATOM | 113 | CB | ARG | A | 16 | 53.779 | -7.545 | 113.441 | 1.00 | 50.56 |
| ATOM | 114 | CG | ARG | A | 16 | 54.677 | -7.698 | 114.636 | 1.00 | 56.90 |
| ATOM | 115 | CD | ARG | A | 16 | 54.992 | -6.388 | 115.315 | 1.00 | 60.72 |
| ATOM | 116 | NE | ARG | A | 16 | 56.021 | -6.602 | 116.328 | 1.00 | 66.70 |
| ATOM | 117 | CZ | ARG | A | 16 | 57.211 | -7.141 | 116.070 | 1.00 | 66.68 |
| ATOM | 118 | NH1 | ARG | A | 16 | 57.520 | -7.519 | 114.834 | 1.00 | 65.68 |
| ATOM | 119 | NH2 | ARG | A | 16 | 58.093 | -7.314 | 117.046 | 1.00 | 66.33 |
| ATOM | 120 | C | ARG | A | 16 | 51.573 | -7.298 | 112.429 | 1.00 | 44.20 |
| ATOM | 121 | O | ARG | A | 16 | 50.871 | -8.293 | 112.254 | 1.00 | 43.41 |
| ATOM | 122 | N | TYR | A | 17 | 51.715 | -6.346 | 111.514 | 1.00 | 39.23 |
| ATOM | 123 | CA | TYR | A | 17 | 51.067 | -6.453 | 110.215 | 1.00 | 38.71 |
| ATOM | 124 | CB | TYR | A | 17 | 50.913 | -5.072 | 109.565 | 1.00 | 33.83 |
| ATOM | 125 | CG | TYR | A | 17 | 49.744 | -4.255 | 110.084 | 1.00 | 27.35 |
| ATOM | 126 | CD1 | TYR | A | 17 | 49.598 | -3.982 | 111.443 | 1.00 | 27.25 |
| ATOM | 127 | CE1 | TYR | A | 17 | 48.540 | -3.184 | 111.909 | 1.00 | 27.16 |
| ATOM | 128 | CD2 | TYR | A | 17 | 48.807 | -3.720 | 109.204 | 1.00 | 25.78 |
| ATOM | 129 | CE2 | TYR | A | 17 | 47.752 | -2.925 | 109.656 | 1.00 | 26.34 |
| ATOM | 130 | CZ | TYR | A | 17 | 47.626 | -2.659 | 111.009 | 1.00 | 27.28 |
| ATOM | 131 | OH | TYR | A | 17 | 46.602 | -1.842 | 111.450 | 1.00 | 22.04 |
| ATOM | 132 | C | TYR | A | 17 | 51.972 | -7.350 | 109.368 | 1.00 | 41.52 |

Fig. 18-2

| ATOM | 133 | O | TYR | A | 17 | 53.150 | -7.525 | 109.683 | 1.00 | 35.63 |
|---|---|---|---|---|---|---|---|---|---|---|
| ATOM | 134 | N | PRO | A | 18 | 51.440 | -7.925 | 108.278 | 1.00 | 46.68 |
| ATOM | 135 | CD | PRO | A | 18 | 50.076 | -7.765 | 107.755 | 1.00 | 47.16 |
| ATOM | 136 | CA | PRO | A | 18 | 52.205 | -8.812 | 107.392 | 1.00 | 48.87 |
| ATOM | 137 | CB | PRO | A | 18 | 51.213 | -9.091 | 106.262 | 1.00 | 48.14 |
| ATOM | 138 | CG | PRO | A | 18 | 50.343 | -7.837 | 106.274 | 1.00 | 55.13 |
| ATOM | 139 | C | PRO | A | 18 | 53.556 | -8.303 | 106.885 | 1.00 | 49.67 |
| ATOM | 140 | O | PRO | A | 18 | 53.788 | -7.101 | 106.766 | 1.00 | 49.33 |
| ATOM | 141 | N | LYS | A | 19 | 54.432 | -9.261 | 106.592 | 1.00 | 53.22 |
| ATOM | 142 | CA | LYS | A | 19 | 55.800 | -9.044 | 106.114 | 1.00 | 57.00 |
| ATOM | 143 | CB | LYS | A | 19 | 56.223 | -10.242 | 105.252 | 1.00 | 62.34 |
| ATOM | 144 | CG | LYS | A | 19 | 55.069 | -10.929 | 104.537 | 1.00 | 67.94 |
| ATOM | 145 | CD | LYS | A | 19 | 54.239 | -9.963 | 103.714 | 1.00 | 70.76 |
| ATOM | 146 | CE | LYS | A | 19 | 53.004 | -10.653 | 103.162 | 1.00 | 73.70 |
| ATOM | 147 | NZ | LYS | A | 19 | 52.116 | -9.701 | 102.442 | 1.00 | 79.01 |
| ATOM | 148 | C | LYS | A | 19 | 56.229 | -7.757 | 105.405 | 1.00 | 55.93 |
| ATOM | 149 | O | LYS | A | 19 | 57.230 | -7.150 | 105.796 | 1.00 | 59.86 |
| ATOM | 150 | N | ASN | A | 20 | 55.515 | -7.338 | 104.367 | 1.00 | 49.62 |
| ATOM | 151 | CA | ASN | A | 20 | 55.925 | -6.130 | 103.652 | 1.00 | 50.02 |
| ATOM | 152 | CB | ASN | A | 20 | 55.829 | -6.359 | 102.143 | 1.00 | 50.62 |
| ATOM | 153 | CG | ASN | A | 20 | 56.729 | -7.487 | 101.670 | 1.00 | 51.26 |
| ATOM | 154 | OD1 | ASN | A | 20 | 57.948 | -7.437 | 101.843 | 1.00 | 46.88 |
| ATOM | 155 | ND2 | ASN | A | 20 | 56.130 | -8.513 | 101.074 | 1.00 | 50.85 |
| ATOM | 156 | C | ASN | A | 20 | 55.167 | -4.862 | 104.023 | 1.00 | 45.50 |
| ATOM | 157 | O | ASN | A | 20 | 55.481 | -3.778 | 103.533 | 1.00 | 45.35 |
| ATOM | 158 | N | HIS | A | 21 | 54.182 | -4.997 | 104.899 | 1.00 | 37.46 |
| ATOM | 159 | CA | HIS | A | 21 | 53.374 | -3.863 | 105.321 | 1.00 | 32.39 |
| ATOM | 160 | CB | HIS | A | 21 | 52.198 | -4.355 | 106.162 | 1.00 | 29.34 |
| ATOM | 161 | CG | HIS | A | 21 | 51.118 | -3.339 | 106.348 | 1.00 | 30.50 |
| ATOM | 162 | CD2 | HIS | A | 21 | 50.999 | -2.314 | 107.223 | 1.00 | 22.88 |
| ATOM | 163 | ND1 | HIS | A | 21 | 49.993 | -3.298 | 105.552 | 1.00 | 30.15 |
| ATOM | 164 | CE1 | HIS | A | 21 | 49.226 | -2.293 | 105.933 | 1.00 | 30.96 |
| ATOM | 165 | NE2 | HIS | A | 21 | 49.814 | -1.680 | 106.945 | 1.00 | 36.41 |
| ATOM | 166 | C | HIS | A | 21 | 54.194 | -2.879 | 106.155 | 1.00 | 29.18 |
| ATOM | 167 | O | HIS | A | 21 | 55.030 | -3.279 | 106.963 | 1.00 | 26.92 |
| ATOM | 168 | N | PRO | A | 22 | 53.965 | -1.572 | 105.969 | 1.00 | 31.12 |
| ATOM | 169 | CD | PRO | A | 22 | 53.027 | -0.912 | 105.043 | 1.00 | 29.46 |
| ATOM | 170 | CA | PRO | A | 22 | 54.702 | -0.567 | 106.739 | 1.00 | 29.27 |
| ATOM | 171 | CB | PRO | A | 22 | 54.012 | 0.732 | 106.326 | 1.00 | 26.00 |
| ATOM | 172 | CG | PRO | A | 22 | 53.670 | 0.434 | 104.875 | 1.00 | 31.52 |
| ATOM | 173 | C | PRO | A | 22 | 54.624 | -0.822 | 108.253 | 1.00 | 29.96 |
| ATOM | 174 | O | PRO | A | 22 | 55.575 | -0.538 | 108.981 | 1.00 | 27.47 |
| ATOM | 175 | N | LEU | A | 23 | 53.501 | -1.371 | 108.715 | 1.00 | 26.64 |
| ATOM | 176 | CA | LEU | A | 23 | 53.309 | -1.644 | 110.144 | 1.00 | 30.44 |
| ATOM | 177 | CB | LEU | A | 23 | 51.833 | -1.428 | 110.515 | 1.00 | 24.09 |
| ATOM | 178 | CG | LEU | A | 23 | 51.356 | 0.029 | 110.479 | 1.00 | 25.30 |
| ATOM | 179 | CD1 | LEU | A | 23 | 49.836 | 0.103 | 110.668 | 1.00 | 17.72 |
| ATOM | 180 | CD2 | LEU | A | 23 | 52.086 | 0.816 | 111.574 | 1.00 | 24.15 |
| ATOM | 181 | C | LEU | A | 23 | 53.775 | -3.015 | 110.662 | 1.00 | 31.64 |
| ATOM | 182 | O | LEU | A | 23 | 53.252 | -3.512 | 111.667 | 1.00 | 31.00 |
| ATOM | 183 | N | LYS | A | 24 | 54.753 | -3.636 | 110.012 | 1.00 | 28.25 |
| ATOM | 184 | CA | LYS | A | 24 | 55.200 | -4.929 | 110.513 | 1.00 | 30.90 |
| ATOM | 185 | CB | LYS | A | 24 | 55.718 | -5.810 | 109.372 | 1.00 | 36.59 |
| ATOM | 186 | CG | LYS | A | 24 | 57.178 | -5.650 | 108.982 | 1.00 | 40.77 |
| ATOM | 187 | CD | LYS | A | 24 | 57.546 | -4.259 | 108.535 | 1.00 | 44.61 |
| ATOM | 188 | CE | LYS | A | 24 | 58.858 | -4.303 | 107.755 | 1.00 | 50.44 |
| ATOM | 189 | NZ | LYS | A | 24 | 59.959 | -4.990 | 108.487 | 1.00 | 51.30 |
| ATOM | 190 | C | LYS | A | 24 | 56.282 | -4.736 | 111.581 | 1.00 | 32.57 |
| ATOM | 191 | O | LYS | A | 24 | 56.695 | -5.683 | 112.245 | 1.00 | 29.83 |
| ATOM | 192 | N | ILE | A | 25 | 56.729 | -3.497 | 111.750 | 1.00 | 27.06 |
| ATOM | 193 | CA | ILE | A | 25 | 57.755 | -3.200 | 112.739 | 1.00 | 30.45 |
| ATOM | 194 | CB | ILE | A | 25 | 58.416 | -1.822 | 112.499 | 1.00 | 33.37 |
| ATOM | 195 | CG2 | ILE | A | 25 | 59.056 | -1.757 | 111.120 | 1.00 | 33.22 |
| ATOM | 196 | CG1 | ILE | A | 25 | 57.361 | -0.722 | 112.662 | 1.00 | 30.45 |
| ATOM | 197 | CD1 | ILE | A | 25 | 57.930 | 0.689 | 112.700 | 1.00 | 33.12 |
| ATOM | 198 | C | ILE | A | 25 | 57.156 | -3.129 | 114.141 | 1.00 | 32.10 |

Fig. 18-3

| | | | | | | | | | |
|---|---|---|---|---|---|---|---|---|---|
| ATOM | 199 | O | ILE | A | 25 | 55.967 | -2.851 | 114.310 | 1.00 28.15 |
| ATOM | 200 | N | PRO | A | 26 | 57.979 | -3.382 | 115.168 | 1.00 31.64 |
| ATOM | 201 | CD | PRO | A | 26 | 59.395 | -3.768 | 115.139 | 1.00 31.11 |
| ATOM | 202 | CA | PRO | A | 26 | 57.507 | -3.322 | 116.556 | 1.00 31.04 |
| ATOM | 203 | CB | PRO | A | 26 | 58.709 | -3.840 | 117.347 | 1.00 32.41 |
| ATOM | 204 | CG | PRO | A | 26 | 59.454 | -4.691 | 116.324 | 1.00 39.33 |
| ATOM | 205 | C | PRO | A | 26 | 57.265 | -1.840 | 116.827 | 1.00 28.42 |
| ATOM | 206 | O | PRO | A | 26 | 58.001 | -0.994 | 116.315 | 1.00 22.23 |
| ATOM | 207 | N | ARG | A | 27 | 56.251 | -1.514 | 117.614 | 1.00 24.16 |
| ATOM | 208 | CA | ARG | A | 27 | 55.977 | -0.116 | 117.899 | 1.00 28.53 |
| ATOM | 209 | CB | ARG | A | 27 | 54.787 | 0.358 | 117.048 | 1.00 29.77 |
| ATOM | 210 | CG | ARG | A | 27 | 55.075 | 0.191 | 115.554 | 1.00 29.64 |
| ATOM | 211 | CD | ARG | A | 27 | 53.918 | 0.538 | 114.620 | 1.00 26.61 |
| ATOM | 212 | NE | ARG | A | 27 | 53.622 | 1.965 | 114.517 | 1.00 28.52 |
| ATOM | 213 | CZ | ARG | A | 27 | 52.649 | 2.591 | 115.173 | 1.00 29.70 |
| ATOM | 214 | NH1 | ARG | A | 27 | 51.857 | 1.924 | 115.999 | 1.00 30.17 |
| ATOM | 215 | NH2 | ARG | A | 27 | 52.451 | 3.889 | 114.983 | 1.00 23.25 |
| ATOM | 216 | C | ARG | A | 27 | 55.746 | 0.114 | 119.387 | 1.00 30.71 |
| ATOM | 217 | O | ARG | A | 27 | 56.679 | 0.490 | 120.113 | 1.00 24.60 |
| ATOM | 218 | N | VAL | A | 28 | 54.529 | -0.117 | 119.863 | 1.00 23.51 |
| ATOM | 219 | CA | VAL | A | 28 | 54.282 | 0.093 | 121.282 | 1.00 29.33 |
| ATOM | 220 | CB | VAL | A | 28 | 52.800 | -0.124 | 121.635 | 1.00 34.56 |
| ATOM | 221 | CG1 | VAL | A | 28 | 52.599 | 0.002 | 123.142 | 1.00 32.42 |
| ATOM | 222 | CG2 | VAL | A | 28 | 51.947 | 0.908 | 120.903 | 1.00 33.77 |
| ATOM | 223 | C | VAL | A | 28 | 55.158 | -0.816 | 122.145 | 1.00 29.75 |
| ATOM | 224 | O | VAL | A | 28 | 55.673 | -0.394 | 123.182 | 1.00 32.49 |
| ATOM | 225 | N | SER | A | 29 | 55.341 | -2.059 | 121.718 | 1.00 26.09 |
| ATOM | 226 | CA | SER | A | 29 | 56.162 | -2.982 | 122.483 | 1.00 31.39 |
| ATOM | 227 | CB | SER | A | 29 | 56.058 | -4.399 | 121.905 | 1.00 26.92 |
| ATOM | 228 | OG | SER | A | 29 | 56.562 | -4.464 | 120.579 | 1.00 33.85 |
| ATOM | 229 | C | SER | A | 29 | 57.609 | -2.482 | 122.453 | 1.00 34.77 |
| ATOM | 230 | O | SER | A | 29 | 58.378 | -2.718 | 123.391 | 1.00 29.39 |
| ATOM | 231 | N | LEU | A | 30 | 57.967 | -1.778 | 121.380 | 1.00 31.20 |
| ATOM | 232 | CA | LEU | A | 30 | 59.317 | -1.234 | 121.240 | 1.00 32.03 |
| ATOM | 233 | CB | LEU | A | 30 | 59.554 | -0.668 | 119.829 | 1.00 30.86 |
| ATOM | 234 | CG | LEU | A | 30 | 61.008 | -0.550 | 119.333 | 1.00 33.22 |
| ATOM | 235 | CD1 | LEU | A | 30 | 61.066 | 0.484 | 118.224 | 1.00 28.76 |
| ATOM | 236 | CD2 | LEU | A | 30 | 61.948 | -0.135 | 120.441 | 1.00 35.11 |
| ATOM | 237 | C | LEU | A | 30 | 59.423 | -0.089 | 122.236 | 1.00 30.29 |
| ATOM | 238 | O | LEU | A | 30 | 60.397 | 0.019 | 122.984 | 1.00 27.69 |
| ATOM | 239 | N | LEU | A | 31 | 58.408 | 0.769 | 122.232 | 1.00 27.38 |
| ATOM | 240 | CA | LEU | A | 31 | 58.372 | 1.915 | 123.126 | 1.00 24.94 |
| ATOM | 241 | CB | LEU | A | 31 | 57.008 | 2.596 | 123.042 | 1.00 24.92 |
| ATOM | 242 | CG | LEU | A | 31 | 56.918 | 4.069 | 123.460 | 1.00 30.49 |
| ATOM | 243 | CD1 | LEU | A | 31 | 55.492 | 4.390 | 123.881 | 1.00 24.71 |
| ATOM | 244 | CD2 | LEU | A | 31 | 57.851 | 4.355 | 124.603 | 1.00 27.32 |
| ATOM | 245 | C | LEU | A | 31 | 58.610 | 1.429 | 124.564 | 1.00 28.18 |
| ATOM | 246 | O | LEU | A | 31 | 59.489 | 1.928 | 125.263 | 1.00 33.64 |
| ATOM | 247 | N | LEU | A | 32 | 57.831 | 0.445 | 125.000 | 1.00 30.17 |
| ATOM | 248 | CA | LEU | A | 32 | 57.965 | -0.084 | 126.357 | 1.00 30.59 |
| ATOM | 249 | CB | LEU | A | 32 | 56.944 | -1.206 | 126.601 | 1.00 30.55 |
| ATOM | 250 | CG | LEU | A | 32 | 55.458 | -0.879 | 126.402 | 1.00 29.50 |
| ATOM | 251 | CD1 | LEU | A | 32 | 54.611 | -2.107 | 126.727 | 1.00 28.31 |
| ATOM | 252 | CD2 | LEU | A | 32 | 55.058 | 0.273 | 127.287 | 1.00 31.92 |
| ATOM | 253 | C | LEU | A | 32 | 59.376 | -0.597 | 126.657 | 1.00 33.56 |
| ATOM | 254 | O | LEU | A | 32 | 59.961 | -0.243 | 127.682 | 1.00 36.51 |
| ATOM | 255 | N | ARG | A | 33 | 59.926 | -1.429 | 125.777 | 1.00 29.75 |
| ATOM | 256 | CA | ARG | A | 33 | 61.271 | -1.953 | 125.999 | 1.00 33.49 |
| ATOM | 257 | CB | ARG | A | 33 | 61.630 | -3.003 | 124.945 | 1.00 39.50 |
| ATOM | 258 | CG | ARG | A | 33 | 60.814 | -4.283 | 125.024 | 1.00 44.40 |
| ATOM | 259 | CD | ARG | A | 33 | 61.237 | -5.256 | 123.933 | 1.00 53.68 |
| ATOM | 260 | NE | ARG | A | 33 | 60.515 | -6.522 | 124.007 | 1.00 56.66 |
| ATOM | 261 | CZ | ARG | A | 33 | 60.611 | -7.384 | 125.014 | 1.00 58.73 |
| ATOM | 262 | NH1 | ARG | A | 33 | 61.402 | -7.121 | 126.045 | 1.00 59.32 |
| ATOM | 263 | NH2 | ARG | A | 33 | 59.911 | -8.511 | 124.991 | 1.00 57.91 |
| ATOM | 264 | C | ARG | A | 33 | 62.314 | -0.845 | 125.978 | 1.00 31.45 |

Fig. 18-4

| | | | | | | | | | |
|---|---|---|---|---|---|---|---|---|---|
| ATOM | 265 | O | ARG | A | 33 | 63.288 | -0.885 | 126.722 | 1.00 26.49 |
| ATOM | 266 | N | PHE | A | 34 | 62.103 | 0.146 | 125.123 | 1.00 32.42 |
| ATOM | 267 | CA | PHE | A | 34 | 63.042 | 1.253 | 125.000 | 1.00 33.37 |
| ATOM | 268 | CB | PHE | A | 34 | 62.617 | 2.180 | 123.858 | 1.00 31.68 |
| ATOM | 269 | CG | PHE | A | 34 | 63.653 | 3.202 | 123.486 | 1.00 29.05 |
| ATOM | 270 | CD1 | PHE | A | 34 | 64.825 | 2.819 | 122.838 | 1.00 29.21 |
| ATOM | 271 | CD2 | PHE | A | 34 | 63.458 | 4.546 | 123.781 | 1.00 28.25 |
| ATOM | 272 | CE1 | PHE | A | 34 | 65.793 | 3.763 | 122.484 | 1.00 29.35 |
| ATOM | 273 | CE2 | PHE | A | 34 | 64.416 | 5.501 | 123.435 | 1.00 32.67 |
| ATOM | 274 | CZ | PHE | A | 34 | 65.589 | 5.108 | 122.783 | 1.00 29.08 |
| ATOM | 275 | C | PHE | A | 34 | 63.083 | 2.042 | 126.305 | 1.00 33.47 |
| ATOM | 276 | O | PHE | A | 34 | 64.155 | 2.294 | 126.852 | 1.00 27.49 |
| ATOM | 277 | N | LYS | A | 35 | 61.912 | 2.432 | 126.802 | 1.00 29.34 |
| ATOM | 278 | CA | LYS | A | 35 | 61.848 | 3.191 | 128.042 | 1.00 31.48 |
| ATOM | 279 | CB | LYS | A | 35 | 60.406 | 3.576 | 128.374 | 1.00 30.82 |
| ATOM | 280 | CG | LYS | A | 35 | 59.803 | 4.552 | 127.395 | 1.00 32.98 |
| ATOM | 281 | CD | LYS | A | 35 | 58.404 | 4.974 | 127.790 | 1.00 40.93 |
| ATOM | 282 | CE | LYS | A | 35 | 57.410 | 3.827 | 127.688 | 1.00 44.56 |
| ATOM | 283 | NZ | LYS | A | 35 | 57.754 | 2.656 | 128.548 | 1.00 55.10 |
| ATOM | 284 | C | LYS | A | 35 | 62.443 | 2.387 | 129.183 | 1.00 34.47 |
| ATOM | 285 | O | LYS | A | 35 | 63.136 | 2.933 | 130.043 | 1.00 32.01 |
| ATOM | 286 | N | ASP | A | 36 | 62.180 | 1.086 | 129.190 | 1.00 36.28 |
| ATOM | 287 | CA | ASP | A | 36 | 62.710 | 0.233 | 130.242 | 1.00 37.93 |
| ATOM | 288 | CB | ASP | A | 36 | 62.145 | -1.178 | 130.126 | 1.00 41.27 |
| ATOM | 289 | CG | ASP | A | 36 | 62.731 | -2.117 | 131.157 | 1.00 43.77 |
| ATOM | 290 | OD1 | ASP | A | 36 | 62.660 | -1.793 | 132.360 | 1.00 43.92 |
| ATOM | 291 | OD2 | ASP | A | 36 | 63.261 | -3.178 | 130.765 | 1.00 45.78 |
| ATOM | 292 | C | ASP | A | 36 | 64.227 | 0.181 | 130.174 | 1.00 38.74 |
| ATOM | 293 | O | ASP | A | 36 | 64.902 | 0.187 | 131.201 | 1.00 36.23 |
| ATOM | 294 | N | ALA | A | 37 | 64.760 | 0.127 | 128.958 | 1.00 37.96 |
| ATOM | 295 | CA | ALA | A | 37 | 66.201 | 0.080 | 128.768 | 1.00 39.49 |
| ATOM | 296 | CB | ALA | A | 37 | 66.525 | -0.158 | 127.299 | 1.00 39.74 |
| ATOM | 297 | C | ALA | A | 37 | 66.832 | 1.386 | 129.244 | 1.00 40.09 |
| ATOM | 298 | O | ALA | A | 37 | 67.962 | 1.402 | 129.714 | 1.00 38.80 |
| ATOM | 299 | N | MET | A | 38 | 66.085 | 2.477 | 129.131 | 1.00 39.04 |
| ATOM | 300 | CA | MET | A | 38 | 66.567 | 3.789 | 129.545 | 1.00 38.71 |
| ATOM | 301 | CB | MET | A | 38 | 65.965 | 4.863 | 128.640 | 1.00 36.66 |
| ATOM | 302 | CG | MET | A | 38 | 66.335 | 4.744 | 127.173 | 1.00 39.16 |
| ATOM | 303 | SD | MET | A | 38 | 68.005 | 5.298 | 126.840 | 1.00 37.55 |
| ATOM | 304 | CE | MET | A | 38 | 67.892 | 7.033 | 127.287 | 1.00 35.74 |
| ATOM | 305 | C | MET | A | 38 | 66.187 | 4.094 | 130.995 | 1.00 40.58 |
| ATOM | 306 | O | MET | A | 38 | 66.484 | 5.173 | 131.502 | 1.00 38.12 |
| ATOM | 307 | N | ASN | A | 39 | 65.530 | 3.147 | 131.657 | 1.00 38.41 |
| ATOM | 308 | CA | ASN | A | 39 | 65.094 | 3.346 | 133.039 | 1.00 42.46 |
| ATOM | 309 | CB | ASN | A | 39 | 66.298 | 3.494 | 133.979 | 1.00 46.06 |
| ATOM | 310 | CG | ASN | A | 39 | 67.125 | 2.224 | 134.074 | 1.00 51.69 |
| ATOM | 311 | OD1 | ASN | A | 39 | 66.625 | 1.175 | 134.487 | 1.00 54.33 |
| ATOM | 312 | ND2 | ASN | A | 39 | 68.396 | 2.313 | 133.695 | 1.00 49.13 |
| ATOM | 313 | C | ASN | A | 39 | 64.222 | 4.594 | 133.134 | 1.00 41.19 |
| ATOM | 314 | O | ASN | A | 39 | 64.375 | 5.402 | 134.050 | 1.00 42.74 |
| ATOM | 315 | N | LEU | A | 40 | 63.301 | 4.746 | 132.188 | 1.00 40.22 |
| ATOM | 316 | CA | LEU | A | 40 | 62.427 | 5.909 | 132.170 | 1.00 39.85 |
| ATOM | 317 | CB | LEU | A | 40 | 62.524 | 6.610 | 130.812 | 1.00 40.42 |
| ATOM | 318 | CG | LEU | A | 40 | 63.940 | 7.074 | 130.447 | 1.00 40.40 |
| ATOM | 319 | CD1 | LEU | A | 40 | 63.916 | 7.753 | 129.088 | 1.00 32.75 |
| ATOM | 320 | CD2 | LEU | A | 40 | 64.470 | 8.031 | 131.513 | 1.00 38.89 |
| ATOM | 321 | C | LEU | A | 40 | 60.967 | 5.610 | 132.505 | 1.00 38.97 |
| ATOM | 322 | O | LEU | A | 40 | 60.076 | 6.409 | 132.213 | 1.00 32.32 |
| ATOM | 323 | N | ILE | A | 41 | 60.720 | 4.461 | 133.124 | 1.00 38.57 |
| ATOM | 324 | CA | ILE | A | 41 | 59.363 | 4.109 | 133.520 | 1.00 42.43 |
| ATOM | 325 | CB | ILE | A | 41 | 58.536 | 3.575 | 132.330 | 1.00 39.13 |
| ATOM | 326 | CG2 | ILE | A | 41 | 59.137 | 2.271 | 131.820 | 1.00 36.51 |
| ATOM | 327 | CG1 | ILE | A | 41 | 57.082 | 3.367 | 132.774 | 1.00 38.71 |
| ATOM | 328 | CD1 | ILE | A | 41 | 56.147 | 2.920 | 131.676 | 1.00 44.09 |
| ATOM | 329 | C | ILE | A | 41 | 59.376 | 3.056 | 134.619 | 1.00 42.40 |
| ATOM | 330 | O | ILE | A | 41 | 60.255 | 2.195 | 134.654 | 1.00 43.05 |

Fig. 18-5

| | | | | | | | | |
|---|---|---|---|---|---|---|---|---|
| ATOM | 331 | N | ASP | A | 42 | 58.414 | 3.148 | 135.532 | 1.00 47.83 |
| ATOM | 332 | CA | ASP | A | 42 | 58.301 | 2.183 | 136.620 | 1.00 49.23 |
| ATOM | 333 | CB | ASP | A | 42 | 58.243 | 2.880 | 137.984 | 1.00 46.60 |
| ATOM | 334 | CG | ASP | A | 42 | 59.493 | 3.688 | 138.284 | 1.00 52.63 |
| ATOM | 335 | OD1 | ASP | A | 42 | 60.614 | 3.146 | 138.141 | 1.00 49.28 |
| ATOM | 336 | OD2 | ASP | A | 42 | 59.355 | 4.866 | 138.678 | 1.00 52.47 |
| ATOM | 337 | C | ASP | A | 42 | 57.034 | 1.368 | 136.405 | 1.00 51.22 |
| ATOM | 338 | O | ASP | A | 42 | 56.048 | 1.866 | 135.864 | 1.00 48.07 |
| ATOM | 339 | N | GLU | A | 43 | 57.072 | 0.111 | 136.832 | 1.00 51.41 |
| ATOM | 340 | CA | GLU | A | 43 | 55.945 | -0.792 | 136.673 | 1.00 50.67 |
| ATOM | 341 | CB | GLU | A | 43 | 56.234 | -2.094 | 137.412 | 1.00 54.49 |
| ATOM | 342 | CG | GLU | A | 43 | 55.208 | -3.178 | 137.185 | 1.00 60.55 |
| ATOM | 343 | CD | GLU | A | 43 | 55.524 | -4.432 | 137.974 | 1.00 66.12 |
| ATOM | 344 | OE1 | GLU | A | 43 | 54.761 | -5.417 | 137.861 | 1.00 70.33 |
| ATOM | 345 | OE2 | GLU | A | 43 | 56.536 | -4.427 | 138.711 | 1.00 67.39 |
| ATOM | 346 | C | GLU | A | 43 | 54.645 | -0.178 | 137.178 | 1.00 50.20 |
| ATOM | 347 | O | GLU | A | 43 | 53.567 | -0.475 | 136.658 | 1.00 48.27 |
| ATOM | 348 | N | LYS | A | 44 | 54.755 | 0.683 | 138.186 | 1.00 49.04 |
| ATOM | 349 | CA | LYS | A | 44 | 53.601 | 1.356 | 138.778 | 1.00 47.56 |
| ATOM | 350 | CB | LYS | A | 44 | 54.013 | 2.004 | 140.112 | 1.00 54.73 |
| ATOM | 351 | CG | LYS | A | 44 | 53.190 | 3.229 | 140.542 | 1.00 58.07 |
| ATOM | 352 | CD | LYS | A | 44 | 53.705 | 4.500 | 139.853 | 1.00 61.24 |
| ATOM | 353 | CE | LYS | A | 44 | 52.849 | 5.727 | 140.151 | 1.00 61.93 |
| ATOM | 354 | NZ | LYS | A | 44 | 51.501 | 5.644 | 139.519 | 1.00 62.80 |
| ATOM | 355 | C | LYS | A | 44 | 52.929 | 2.387 | 137.875 | 1.00 44.52 |
| ATOM | 356 | O | LYS | A | 44 | 51.752 | 2.701 | 138.052 | 1.00 45.31 |
| ATOM | 357 | N | GLU | A | 45 | 53.674 | 2.915 | 136.914 | 1.00 41.03 |
| ATOM | 358 | CA | GLU | A | 45 | 53.140 | 3.914 | 135.994 | 1.00 41.23 |
| ATOM | 359 | CB | GLU | A | 45 | 54.271 | 4.810 | 135.500 | 1.00 38.52 |
| ATOM | 360 | CG | GLU | A | 45 | 54.973 | 5.572 | 136.589 | 1.00 40.30 |
| ATOM | 361 | CD | GLU | A | 45 | 56.241 | 6.222 | 136.096 | 1.00 38.06 |
| ATOM | 362 | OE1 | GLU | A | 45 | 57.170 | 5.478 | 135.715 | 1.00 36.93 |
| ATOM | 363 | OE2 | GLU | A | 45 | 56.306 | 7.467 | 136.084 | 1.00 32.57 |
| ATOM | 364 | C | GLU | A | 45 | 52.479 | 3.253 | 134.791 | 1.00 40.69 |
| ATOM | 365 | O | GLU | A | 45 | 51.783 | 3.907 | 134.015 | 1.00 39.77 |
| ATOM | 366 | N | LEU | A | 46 | 52.700 | 1.953 | 134.645 | 1.00 36.90 |
| ATOM | 367 | CA | LEU | A | 46 | 52.165 | 1.207 | 133.517 | 1.00 40.46 |
| ATOM | 368 | CB | LEU | A | 46 | 53.222 | 0.219 | 133.034 | 1.00 35.52 |
| ATOM | 369 | CG | LEU | A | 46 | 52.873 | -0.619 | 131.811 | 1.00 43.75 |
| ATOM | 370 | CD1 | LEU | A | 46 | 52.571 | 0.292 | 130.630 | 1.00 42.06 |
| ATOM | 371 | CD2 | LEU | A | 46 | 54.035 | -1.544 | 131.500 | 1.00 42.90 |
| ATOM | 372 | C | LEU | A | 46 | 50.852 | 0.467 | 133.780 | 1.00 40.03 |
| ATOM | 373 | O | LEU | A | 46 | 50.741 | -0.306 | 134.730 | 1.00 39.37 |
| ATOM | 374 | N | ILE | A | 47 | 49.861 | 0.718 | 132.928 | 1.00 34.03 |
| ATOM | 375 | CA | ILE | A | 47 | 48.560 | 0.068 | 133.033 | 1.00 32.12 |
| ATOM | 376 | CB | ILE | A | 47 | 47.413 | 1.087 | 132.937 | 1.00 32.35 |
| ATOM | 377 | CG2 | ILE | A | 47 | 46.069 | 0.360 | 132.833 | 1.00 30.60 |
| ATOM | 378 | CG1 | ILE | A | 47 | 47.448 | 2.015 | 134.156 | 1.00 36.56 |
| ATOM | 379 | CD1 | ILE | A | 47 | 46.372 | 3.080 | 134.162 | 1.00 35.46 |
| ATOM | 380 | C | ILE | A | 47 | 48.428 | -0.920 | 131.882 | 1.00 33.67 |
| ATOM | 381 | O | ILE | A | 47 | 48.505 | -0.532 | 130.717 | 1.00 27.64 |
| ATOM | 382 | N | LYS | A | 48 | 48.231 | -2.195 | 132.205 | 1.00 32.98 |
| ATOM | 383 | CA | LYS | A | 48 | 48.102 | -3.224 | 131.176 | 1.00 30.98 |
| ATOM | 384 | CB | LYS | A | 48 | 48.038 | -4.609 | 131.821 | 1.00 39.21 |
| ATOM | 385 | CG | LYS | A | 48 | 47.956 | -5.747 | 130.819 | 1.00 46.81 |
| ATOM | 386 | CD | LYS | A | 48 | 47.989 | -7.102 | 131.509 | 1.00 50.75 |
| ATOM | 387 | CE | LYS | A | 48 | 47.967 | -8.240 | 130.492 | 1.00 54.43 |
| ATOM | 388 | NZ | LYS | A | 48 | 49.151 | -8.199 | 129.580 | 1.00 50.43 |
| ATOM | 389 | C | LYS | A | 48 | 46.869 | -3.006 | 130.310 | 1.00 29.55 |
| ATOM | 390 | O | LYS | A | 48 | 45.764 | -2.840 | 130.820 | 1.00 29.65 |
| ATOM | 391 | N | SER | A | 49 | 47.071 | -2.992 | 128.996 | 1.00 30.69 |
| ATOM | 392 | CA | SER | A | 49 | 45.989 | -2.802 | 128.033 | 1.00 29.32 |
| ATOM | 393 | CB | SER | A | 49 | 46.551 | -2.805 | 126.609 | 1.00 31.53 |
| ATOM | 394 | OG | SER | A | 49 | 47.571 | -1.834 | 126.443 | 1.00 30.74 |
| ATOM | 395 | C | SER | A | 49 | 44.952 | -3.916 | 128.147 | 1.00 31.31 |
| ATOM | 396 | O | SER | A | 49 | 45.295 | -5.059 | 128.436 | 1.00 34.44 |

Fig. 18-6

| | | | | | | | | | |
|---|---|---|---|---|---|---|---|---|---|
| ATOM | 397 | N | ARG | A | 50 | 43.688 | -3.582 | 127.922 | 1.00 32.87 |
| ATOM | 398 | CA | ARG | A | 50 | 42.632 | -4.582 | 127.960 | 1.00 31.45 |
| ATOM | 399 | CB | ARG | A | 50 | 41.636 | -4.325 | 129.101 | 1.00 28.35 |
| ATOM | 400 | CG | ARG | A | 50 | 40.729 | -3.103 | 128.915 | 1.00 32.05 |
| ATOM | 401 | CD | ARG | A | 50 | 39.653 | -3.055 | 130.008 | 1.00 30.46 |
| ATOM | 402 | NE | ARG | A | 50 | 38.821 | -1.850 | 129.964 | 1.00 25.21 |
| ATOM | 403 | CZ | ARG | A | 50 | 37.930 | -1.569 | 129.016 | 1.00 28.32 |
| ATOM | 404 | NH1 | ARG | A | 50 | 37.726 | -2.406 | 128.001 | 1.00 25.45 |
| ATOM | 405 | NH2 | ARG | A | 50 | 37.238 | -0.439 | 129.087 | 1.00 24.92 |
| ATOM | 406 | C | ARG | A | 50 | 41.894 | -4.470 | 126.638 | 1.00 31.12 |
| ATOM | 407 | O | ARG | A | 50 | 41.895 | -3.406 | 126.019 | 1.00 24.62 |
| ATOM | 408 | N | PRO | A | 51 | 41.264 | -5.566 | 126.181 | 1.00 32.55 |
| ATOM | 409 | CD | PRO | A | 51 | 41.164 | -6.921 | 126.751 | 1.00 32.40 |
| ATOM | 410 | CA | PRO | A | 51 | 40.534 | -5.506 | 124.917 | 1.00 30.36 |
| ATOM | 411 | CB | PRO | A | 51 | 40.138 | -6.967 | 124.683 | 1.00 33.95 |
| ATOM | 412 | CG | PRO | A | 51 | 41.173 | -7.750 | 125.499 | 1.00 32.85 |
| ATOM | 413 | C | PRO | A | 51 | 39.309 | -4.630 | 125.134 | 1.00 31.61 |
| ATOM | 414 | O | PRO | A | 51 | 38.877 | -4.431 | 126.267 | 1.00 29.84 |
| ATOM | 415 | N | ALA | A | 52 | 38.755 | -4.093 | 124.058 | 1.00 29.09 |
| ATOM | 416 | CA | ALA | A | 52 | 37.556 | -3.294 | 124.183 | 1.00 29.61 |
| ATOM | 417 | CB | ALA | A | 52 | 37.365 | -2.447 | 122.956 | 1.00 28.67 |
| ATOM | 418 | C | ALA | A | 52 | 36.437 | -4.321 | 124.288 | 1.00 32.39 |
| ATOM | 419 | O | ALA | A | 52 | 36.603 | -5.453 | 123.844 | 1.00 30.40 |
| ATOM | 420 | N | THR | A | 53 | 35.318 | -3.947 | 124.896 | 1.00 32.98 |
| ATOM | 421 | CA | THR | A | 53 | 34.192 | -4.868 | 124.997 | 1.00 36.61 |
| ATOM | 422 | CB | THR | A | 53 | 33.253 | -4.514 | 126.166 | 1.00 34.22 |
| ATOM | 423 | OG1 | THR | A | 53 | 32.734 | -3.193 | 125.970 | 1.00 29.52 |
| ATOM | 424 | CG2 | THR | A | 53 | 33.998 | -4.579 | 127.493 | 1.00 36.45 |
| ATOM | 425 | C | THR | A | 53 | 33.411 | -4.700 | 123.702 | 1.00 38.94 |
| ATOM | 426 | O | THR | A | 53 | 33.559 | -3.689 | 123.012 | 1.00 32.67 |
| ATOM | 427 | N | LYS | A | 54 | 32.577 | -5.679 | 123.372 | 1.00 39.19 |
| ATOM | 428 | CA | LYS | A | 54 | 31.792 | -5.595 | 122.152 | 1.00 40.71 |
| ATOM | 429 | CB | LYS | A | 54 | 30.933 | -6.851 | 121.994 | 1.00 41.68 |
| ATOM | 430 | CG | LYS | A | 54 | 30.367 | -7.034 | 120.597 | 1.00 49.42 |
| ATOM | 431 | CD | LYS | A | 54 | 29.541 | -8.310 | 120.508 | 1.00 51.82 |
| ATOM | 432 | CE | LYS | A | 54 | 29.075 | -8.588 | 119.087 | 1.00 52.94 |
| ATOM | 433 | NZ | LYS | A | 54 | 30.216 | -8.879 | 118.182 | 1.00 54.26 |
| ATOM | 434 | C | LYS | A | 54 | 30.913 | -4.347 | 122.237 | 1.00 39.46 |
| ATOM | 435 | O | LYS | A | 54 | 30.719 | -3.637 | 121.249 | 1.00 37.19 |
| ATOM | 436 | N | GLU | A | 55 | 30.404 | -4.075 | 123.434 | 1.00 36.71 |
| ATOM | 437 | CA | GLU | A | 55 | 29.554 | -2.913 | 123.665 | 1.00 36.18 |
| ATOM | 438 | CB | GLU | A | 55 | 29.109 | -2.877 | 125.127 | 1.00 42.16 |
| ATOM | 439 | CG | GLU | A | 55 | 28.223 | -1.694 | 125.476 | 1.00 46.04 |
| ATOM | 440 | CD | GLU | A | 55 | 27.873 | -1.639 | 126.953 | 1.00 51.15 |
| ATOM | 441 | OE1 | GLU | A | 55 | 27.092 | -0.748 | 127.343 | 1.00 56.53 |
| ATOM | 442 | OE2 | GLU | A | 55 | 28.382 | -2.482 | 127.727 | 1.00 51.67 |
| ATOM | 443 | C | GLU | A | 55 | 30.278 | -1.607 | 123.322 | 1.00 35.45 |
| ATOM | 444 | O | GLU | A | 55 | 29.721 | -0.729 | 122.667 | 1.00 29.11 |
| ATOM | 445 | N | GLU | A | 56 | 31.518 | -1.476 | 123.776 | 1.00 27.82 |
| ATOM | 446 | CA | GLU | A | 56 | 32.289 | -0.269 | 123.497 | 1.00 34.70 |
| ATOM | 447 | CB | GLU | A | 56 | 33.635 | -0.329 | 124.232 | 1.00 30.71 |
| ATOM | 448 | CG | GLU | A | 56 | 33.474 | -0.484 | 125.746 | 1.00 35.09 |
| ATOM | 449 | CD | GLU | A | 56 | 34.787 | -0.675 | 126.479 | 1.00 32.29 |
| ATOM | 450 | OE1 | GLU | A | 56 | 35.645 | -1.434 | 125.986 | 1.00 34.54 |
| ATOM | 451 | OE2 | GLU | A | 56 | 34.951 | -0.094 | 127.569 | 1.00 33.25 |
| ATOM | 452 | C | GLU | A | 56 | 32.495 | -0.104 | 121.988 | 1.00 32.51 |
| ATOM | 453 | O | GLU | A | 56 | 32.341 | 0.990 | 121.444 | 1.00 29.59 |
| ATOM | 454 | N | LEU | A | 57 | 32.827 | -1.196 | 121.311 | 1.00 35.58 |
| ATOM | 455 | CA | LEU | A | 57 | 33.039 | -1.147 | 119.871 | 1.00 35.70 |
| ATOM | 456 | CB | LEU | A | 57 | 33.475 | -2.512 | 119.334 | 1.00 35.25 |
| ATOM | 457 | CG | LEU | A | 57 | 34.829 | -3.030 | 119.814 | 1.00 36.19 |
| ATOM | 458 | CD1 | LEU | A | 57 | 35.095 | -4.390 | 119.183 | 1.00 33.69 |
| ATOM | 459 | CD2 | LEU | A | 57 | 35.925 | -2.041 | 119.433 | 1.00 32.61 |
| ATOM | 460 | C | LEU | A | 57 | 31.772 | -0.717 | 119.157 | 1.00 36.02 |
| ATOM | 461 | O | LEU | A | 57 | 31.828 | 0.067 | 118.205 | 1.00 32.72 |
| ATOM | 462 | N | LEU | A | 58 | 30.631 | -1.228 | 119.620 | 1.00 32.35 |

Fig. 18-7

| ATOM | 463 | CA  | LEU | A | 58 | 29.353 | -0.898 | 119.004 | 1.00 | 33.21 |
| ATOM | 464 | CB  | LEU | A | 58 | 28.260 | -1.844 | 119.495 | 1.00 | 35.17 |
| ATOM | 465 | CG  | LEU | A | 58 | 28.504 | -3.296 | 119.077 | 1.00 | 33.71 |
| ATOM | 466 | CD1 | LEU | A | 58 | 27.338 | -4.166 | 119.524 | 1.00 | 36.80 |
| ATOM | 467 | CD2 | LEU | A | 58 | 28.665 | -3.364 | 117.570 | 1.00 | 36.50 |
| ATOM | 468 | C   | LEU | A | 58 | 28.940 | 0.543  | 119.222 | 1.00 | 30.99 |
| ATOM | 469 | O   | LEU | A | 58 | 27.915 | 0.985  | 118.700 | 1.00 | 35.50 |
| ATOM | 470 | N   | LEU | A | 59 | 29.733 | 1.279  | 119.993 | 1.00 | 32.55 |
| ATOM | 471 | CA  | LEU | A | 59 | 29.443 | 2.687  | 120.217 | 1.00 | 30.37 |
| ATOM | 472 | CB  | LEU | A | 59 | 30.387 | 3.279  | 121.268 | 1.00 | 28.01 |
| ATOM | 473 | CG  | LEU | A | 59 | 30.174 | 2.828  | 122.716 | 1.00 | 32.19 |
| ATOM | 474 | CD1 | LEU | A | 59 | 31.248 | 3.427  | 123.604 | 1.00 | 24.85 |
| ATOM | 475 | CD2 | LEU | A | 59 | 28.785 | 3.263  | 123.192 | 1.00 | 25.65 |
| ATOM | 476 | C   | LEU | A | 59 | 29.632 | 3.405  | 118.890 | 1.00 | 31.26 |
| ATOM | 477 | O   | LEU | A | 59 | 29.020 | 4.442  | 118.652 | 1.00 | 31.80 |
| ATOM | 478 | N   | PHE | A | 60 | 30.482 | 2.850  | 118.026 | 1.00 | 29.79 |
| ATOM | 479 | CA  | PHE | A | 60 | 30.726 | 3.454  | 116.716 | 1.00 | 30.24 |
| ATOM | 480 | CB  | PHE | A | 60 | 32.131 | 4.055  | 116.637 | 1.00 | 29.99 |
| ATOM | 481 | CG  | PHE | A | 60 | 32.443 | 4.691  | 115.299 | 1.00 | 28.88 |
| ATOM | 482 | CD1 | PHE | A | 60 | 31.706 | 5.780  | 114.845 | 1.00 | 25.58 |
| ATOM | 483 | CD2 | PHE | A | 60 | 33.448 | 4.178  | 114.479 | 1.00 | 24.00 |
| ATOM | 484 | CE1 | PHE | A | 60 | 31.959 | 6.351  | 113.592 | 1.00 | 26.12 |
| ATOM | 485 | CE2 | PHE | A | 60 | 33.709 | 4.740  | 113.226 | 1.00 | 25.98 |
| ATOM | 486 | CZ  | PHE | A | 60 | 32.963 | 5.828  | 112.781 | 1.00 | 24.53 |
| ATOM | 487 | C   | PHE | A | 60 | 30.536 | 2.520  | 115.529 | 1.00 | 30.30 |
| ATOM | 488 | O   | PHE | A | 60 | 29.810 | 2.854  | 114.602 | 1.00 | 32.82 |
| ATOM | 489 | N   | HIS | A | 61 | 31.195 | 1.363  | 115.543 | 1.00 | 32.85 |
| ATOM | 490 | CA  | HIS | A | 61 | 31.075 | 0.418  | 114.431 | 1.00 | 34.59 |
| ATOM | 491 | CB  | HIS | A | 61 | 32.296 | -0.492 | 114.361 | 1.00 | 32.89 |
| ATOM | 492 | CG  | HIS | A | 61 | 33.576 | 0.238  | 114.116 | 1.00 | 34.25 |
| ATOM | 493 | CD2 | HIS | A | 61 | 34.225 | 0.532  | 112.967 | 1.00 | 34.67 |
| ATOM | 494 | ND1 | HIS | A | 61 | 34.328 | 0.786  | 115.133 | 1.00 | 37.78 |
| ATOM | 495 | CE1 | HIS | A | 61 | 35.390 | 1.382  | 114.619 | 1.00 | 37.50 |
| ATOM | 496 | NE2 | HIS | A | 61 | 35.350 | 1.243  | 113.307 | 1.00 | 37.91 |
| ATOM | 497 | C   | HIS | A | 61 | 29.824 | -0.449 | 114.480 | 1.00 | 38.44 |
| ATOM | 498 | O   | HIS | A | 61 | 29.213 | -0.612 | 115.538 | 1.00 | 35.78 |
| ATOM | 499 | N   | THR | A | 62 | 29.462 | -1.015 | 113.327 | 1.00 | 39.73 |
| ATOM | 500 | CA  | THR | A | 62 | 28.278 | -1.868 | 113.218 | 1.00 | 38.05 |
| ATOM | 501 | CB  | THR | A | 62 | 27.682 | -1.825 | 111.804 | 1.00 | 37.22 |
| ATOM | 502 | OG1 | THR | A | 62 | 28.631 | -2.345 | 110.867 | 1.00 | 41.15 |
| ATOM | 503 | CG2 | THR | A | 62 | 27.348 | -0.404 | 111.418 | 1.00 | 38.27 |
| ATOM | 504 | C   | THR | A | 62 | 28.598 | -3.317 | 113.551 | 1.00 | 39.06 |
| ATOM | 505 | O   | THR | A | 62 | 29.731 | -3.768 | 113.392 | 1.00 | 39.32 |
| ATOM | 506 | N   | GLU | A | 63 | 27.582 | -4.034 | 114.017 | 1.00 | 40.92 |
| ATOM | 507 | CA  | GLU | A | 63 | 27.696 | -5.441 | 114.393 | 1.00 | 40.68 |
| ATOM | 508 | CB  | GLU | A | 63 | 26.303 | -6.000 | 114.704 | 1.00 | 43.19 |
| ATOM | 509 | CG  | GLU | A | 63 | 26.269 | -7.451 | 115.171 | 1.00 | 46.90 |
| ATOM | 510 | CD  | GLU | A | 63 | 26.472 | -7.593 | 116.665 | 1.00 | 53.11 |
| ATOM | 511 | OE1 | GLU | A | 63 | 26.601 | -8.739 | 117.152 | 1.00 | 52.78 |
| ATOM | 512 | OE2 | GLU | A | 63 | 26.487 | -6.556 | 117.358 | 1.00 | 57.24 |
| ATOM | 513 | C   | GLU | A | 63 | 28.320 | -6.263 | 113.268 | 1.00 | 36.19 |
| ATOM | 514 | O   | GLU | A | 63 | 29.272 | -7.011 | 113.481 | 1.00 | 29.70 |
| ATOM | 515 | N   | ASP | A | 64 | 27.755 | -6.119 | 112.074 | 1.00 | 35.85 |
| ATOM | 516 | CA  | ASP | A | 64 | 28.198 | -6.841 | 110.886 | 1.00 | 37.61 |
| ATOM | 517 | CB  | ASP | A | 64 | 27.363 | -6.382 | 109.697 | 1.00 | 43.30 |
| ATOM | 518 | CG  | ASP | A | 64 | 27.313 | -4.872 | 109.582 | 1.00 | 53.38 |
| ATOM | 519 | OD1 | ASP | A | 64 | 28.290 | -4.269 | 109.089 | 1.00 | 52.15 |
| ATOM | 520 | OD2 | ASP | A | 64 | 26.298 | -4.285 | 110.018 | 1.00 | 53.97 |
| ATOM | 521 | C   | ASP | A | 64 | 29.673 | -6.660 | 110.594 | 1.00 | 35.04 |
| ATOM | 522 | O   | ASP | A | 64 | 30.379 | -7.625 | 110.303 | 1.00 | 33.60 |
| ATOM | 523 | N   | TYR | A | 65 | 30.144 | -5.423 | 110.671 | 1.00 | 33.88 |
| ATOM | 524 | CA  | TYR | A | 65 | 31.554 | -5.153 | 110.419 | 1.00 | 32.91 |
| ATOM | 525 | CB  | TYR | A | 65 | 31.793 | -3.637 | 110.375 | 1.00 | 34.80 |
| ATOM | 526 | CG  | TYR | A | 65 | 33.247 | -3.253 | 110.219 | 1.00 | 35.19 |
| ATOM | 527 | CD1 | TYR | A | 65 | 34.009 | -3.751 | 109.163 | 1.00 | 28.43 |
| ATOM | 528 | CE1 | TYR | A | 65 | 35.352 | -3.411 | 109.024 | 1.00 | 32.52 |

Fig. 18-8

| | | | | | | | | | |
|---|---|---|---|---|---|---|---|---|---|
| ATOM | 529 | CD2 | TYR | A | 65 | 33.863 | -2.398 | 111.134 | 1.00 34.08 |
| ATOM | 530 | CE2 | TYR | A | 65 | 35.211 | -2.050 | 111.002 | 1.00 29.89 |
| ATOM | 531 | CZ | TYR | A | 65 | 35.949 | -2.560 | 109.948 | 1.00 35.29 |
| ATOM | 532 | OH | TYR | A | 65 | 37.286 | -2.231 | 109.825 | 1.00 29.81 |
| ATOM | 533 | C | TYR | A | 65 | 32.405 | -5.813 | 111.504 | 1.00 27.65 |
| ATOM | 534 | O | TYR | A | 65 | 33.339 | -6.557 | 111.209 | 1.00 27.65 |
| ATOM | 535 | N | ILE | A | 66 | 32.070 | -5.559 | 112.765 | 1.00 27.32 |
| ATOM | 536 | CA | ILE | A | 66 | 32.822 | -6.153 | 113.858 | 1.00 25.82 |
| ATOM | 537 | CB | ILE | A | 66 | 32.227 | -5.764 | 115.217 | 1.00 32.25 |
| ATOM | 538 | CG2 | ILE | A | 66 | 33.029 | -6.403 | 116.338 | 1.00 28.85 |
| ATOM | 539 | CG1 | ILE | A | 66 | 32.226 | -4.242 | 115.364 | 1.00 31.48 |
| ATOM | 540 | CD1 | ILE | A | 66 | 33.607 | -3.612 | 115.282 | 1.00 38.02 |
| ATOM | 541 | C | ILE | A | 66 | 32.836 | -7.677 | 113.736 | 1.00 31.21 |
| ATOM | 542 | O | ILE | A | 66 | 33.891 | -8.305 | 113.844 | 1.00 30.25 |
| ATOM | 543 | N | ASN | A | 67 | 31.672 | -8.279 | 113.507 | 1.00 33.28 |
| ATOM | 544 | CA | ASN | A | 67 | 31.627 | -9.731 | 113.372 | 1.00 35.87 |
| ATOM | 545 | CB | ASN | A | 67 | 30.190 | -10.242 | 113.177 | 1.00 33.07 |
| ATOM | 546 | CG | ASN | A | 67 | 29.338 | -10.072 | 114.421 | 1.00 37.34 |
| ATOM | 547 | OD1 | ASN | A | 67 | 29.807 | -10.296 | 115.535 | 1.00 35.20 |
| ATOM | 548 | ND2 | ASN | A | 67 | 28.071 | -9.709 | 114.236 | 1.00 34.83 |
| ATOM | 549 | C | ASN | A | 67 | 32.499 | -10.198 | 112.219 | 1.00 31.00 |
| ATOM | 550 | O | ASN | A | 67 | 33.132 | -11.248 | 112.306 | 1.00 37.26 |
| ATOM | 551 | N | THR | A | 68 | 32.543 | -9.426 | 111.140 | 1.00 30.91 |
| ATOM | 552 | CA | THR | A | 68 | 33.368 | -9.814 | 109.997 | 1.00 31.04 |
| ATOM | 553 | CB | THR | A | 68 | 33.133 | -8.894 | 108.792 | 1.00 34.01 |
| ATOM | 554 | OG1 | THR | A | 68 | 31.780 | -9.037 | 108.352 | 1.00 33.26 |
| ATOM | 555 | CG2 | THR | A | 68 | 34.072 | -9.256 | 107.646 | 1.00 30.84 |
| ATOM | 556 | C | THR | A | 68 | 34.844 | -9.794 | 110.378 | 1.00 33.31 |
| ATOM | 557 | O | THR | A | 68 | 35.591 | -10.708 | 110.024 | 1.00 32.52 |
| ATOM | 558 | N | LEU | A | 69 | 35.267 | -8.768 | 111.117 | 1.00 30.30 |
| ATOM | 559 | CA | LEU | A | 69 | 36.669 | -8.686 | 111.534 | 1.00 28.20 |
| ATOM | 560 | CB | LEU | A | 69 | 36.938 | -7.409 | 112.351 | 1.00 28.25 |
| ATOM | 561 | CG | LEU | A | 69 | 36.859 | -6.049 | 111.647 | 1.00 30.18 |
| ATOM | 562 | CD1 | LEU | A | 69 | 37.154 | -4.929 | 112.647 | 1.00 31.08 |
| ATOM | 563 | CD2 | LEU | A | 69 | 37.868 | -6.004 | 110.505 | 1.00 27.85 |
| ATOM | 564 | C | LEU | A | 69 | 37.036 | -9.902 | 112.372 | 1.00 31.65 |
| ATOM | 565 | O | LEU | A | 69 | 38.084 | -10.519 | 112.165 | 1.00 23.95 |
| ATOM | 566 | N | MET | A | 70 | 36.169 | -10.243 | 113.321 | 1.00 30.78 |
| ATOM | 567 | CA | MET | A | 70 | 36.411 | -11.383 | 114.193 | 1.00 34.50 |
| ATOM | 568 | CB | MET | A | 70 | 35.318 | -11.486 | 115.258 | 1.00 31.96 |
| ATOM | 569 | CG | MET | A | 70 | 35.203 | -10.259 | 116.147 | 1.00 36.26 |
| ATOM | 570 | SD | MET | A | 70 | 33.948 | -10.454 | 117.431 | 1.00 37.52 |
| ATOM | 571 | CE | MET | A | 70 | 34.633 | -11.815 | 118.403 | 1.00 37.36 |
| ATOM | 572 | C | MET | A | 70 | 36.484 | -12.685 | 113.401 | 1.00 33.33 |
| ATOM | 573 | O | MET | A | 70 | 37.392 | -13.488 | 113.607 | 1.00 31.47 |
| ATOM | 574 | N | GLU | A | 71 | 35.534 | -12.887 | 112.494 | 1.00 35.37 |
| ATOM | 575 | CA | GLU | A | 71 | 35.516 | -14.098 | 111.681 | 1.00 36.6 |
| ATOM | 576 | CB | GLU | A | 71 | 34.245 | -14.160 | 110.834 | 1.00 37.3 |
| ATOM | 577 | CG | GLU | A | 71 | 34.206 | -15.359 | 109.897 | 1.00 46.37 |
| ATOM | 578 | CD | GLU | A | 71 | 34.257 | -16.693 | 110.633 | 1.00 46.37 |
| ATOM | 579 | OE1 | GLU | A | 71 | 34.355 | -17.733 | 109.952 | 1.00 48.94 |
| ATOM | 580 | OE2 | GLU | A | 71 | 34.190 | -16.705 | 111.882 | 1.00 45.53 |
| ATOM | 581 | C | GLU | A | 71 | 36.732 | -14.169 | 110.769 | 1.00 35.96 |
| ATOM | 582 | O | GLU | A | 71 | 37.342 | -15.228 | 110.617 | 1.00 32.99 |
| ATOM | 583 | N | ALA | A | 72 | 37.079 | -13.039 | 110.159 | 1.00 36.50 |
| ATOM | 584 | CA | ALA | A | 72 | 38.225 | -12.981 | 109.264 | 1.00 33.98 |
| ATOM | 585 | CB | ALA | A | 72 | 38.366 | -11.580 | 108.675 | 1.00 33.23 |
| ATOM | 586 | C | ALA | A | 72 | 39.498 | -13.362 | 109.998 | 1.00 34.60 |
| ATOM | 587 | O | ALA | A | 72 | 40.337 | -14.094 | 109.466 | 1.00 31.53 |
| ATOM | 588 | N | GLU | A | 73 | 39.647 | -12.873 | 111.224 | 1.00 30.87 |
| ATOM | 589 | CA | GLU | A | 73 | 40.847 | -13.177 | 111.985 | 1.00 29.66 |
| ATOM | 590 | CB | GLU | A | 73 | 41.004 | -12.224 | 113.180 | 1.00 33.33 |
| ATOM | 591 | CG | GLU | A | 73 | 42.234 | -12.545 | 114.033 | 1.00 32.80 |
| ATOM | 592 | CD | GLU | A | 73 | 42.390 | -11.634 | 115.233 | 1.00 40.07 |
| ATOM | 593 | OE1 | GLU | A | 73 | 42.601 | -10.418 | 115.044 | 1.00 41.02 |
| ATOM | 594 | OE2 | GLU | A | 73 | 42.298 | -12.138 | 116.372 | 1.00 41.21 |

Fig. 18-9

```
ATOM    595  C    GLU A   73      40.906 -14.615 112.485  1.00 31.73
ATOM    596  O    GLU A   73      41.957 -15.249 112.409  1.00 32.96
ATOM    597  N    ARG A   74      39.798 -15.145 112.992  1.00 35.85
ATOM    598  CA   ARG A   74      39.847 -16.511 113.502  1.00 43.24
ATOM    599  CB   ARG A   74      38.548 -16.892 114.216  1.00 43.63
ATOM    600  CG   ARG A   74      37.450 -17.349 113.294  1.00 51.20
ATOM    601  CD   ARG A   74      36.366 -18.087 114.063  1.00 51.13
ATOM    602  NE   ARG A   74      35.534 -18.871 113.158  1.00 57.40
ATOM    603  CZ   ARG A   74      35.991 -19.870 112.403  1.00 56.36
ATOM    604  NH1  ARG A   74      37.273 -20.208 112.446  1.00 51.10
ATOM    605  NH2  ARG A   74      35.172 -20.517 111.586  1.00 58.75
ATOM    606  C    ARG A   74      40.125 -17.506 112.372  1.00 43.06
ATOM    607  O    ARG A   74      40.916 -18.429 112.541  1.00 42.52
ATOM    608  N    SER A   75      39.485 -17.305 111.222  1.00 43.63
ATOM    609  CA   SER A   75      39.670 -18.186 110.066  1.00 44.93
ATOM    610  CB   SER A   75      38.485 -18.089 109.113  1.00 42.05
ATOM    611  OG   SER A   75      38.420 -16.799 108.532  1.00 38.43
ATOM    612  C    SER A   75      40.910 -17.797 109.282  1.00 46.44
ATOM    613  O    SER A   75      41.339 -18.522 108.383  1.00 45.17
ATOM    614  N    GLN A   76      41.466 -16.638 109.618  1.00 46.18
ATOM    615  CA   GLN A   76      42.642 -16.116 108.936  1.00 44.73
ATOM    616  CB   GLN A   76      43.868 -16.973 109.226  1.00 37.36
ATOM    617  CG   GLN A   76      45.162 -16.208 109.045  1.00 43.96
ATOM    618  CD   GLN A   76      45.415 -15.214 110.176  1.00 41.86
ATOM    619  OE1  GLN A   76      44.499 -14.537 110.655  1.00 37.78
ATOM    620  NE2  GLN A   76      46.669 -15.111 110.591  1.00 45.00
ATOM    621  C    GLN A   76      42.374 -16.120 107.429  1.00 44.17
ATOM    622  O    GLN A   76      43.233 -16.495 106.630  1.00 40.49
ATOM    623  N    SER A   77      41.168 -15.713 107.053  1.00 43.11
ATOM    624  CA   SER A   77      40.784 -15.667 105.649  1.00 44.66
ATOM    625  CB   SER A   77      40.182 -17.004 105.220  1.00 44.56
ATOM    626  OG   SER A   77      38.974 -17.246 105.925  1.00 42.58
ATOM    627  C    SER A   77      39.747 -14.573 105.448  1.00 44.80
ATOM    628  O    SER A   77      39.096 -14.142 106.395  1.00 45.11
ATOM    629  N    VAL A   78      39.590 -14.137 104.207  1.00 46.06
ATOM    630  CA   VAL A   78      38.632 -13.095 103.888  1.00 47.65
ATOM    631  CB   VAL A   78      39.107 -12.245 102.701  1.00 49.63
ATOM    632  CG1  VAL A   78      38.076 -11.167 102.391  1.00 51.25
ATOM    633  CG2  VAL A   78      40.454 -11.627 103.017  1.00 53.00
ATOM    634  C    VAL A   78      37.275 -13.682 103.530  1.00 48.07
ATOM    635  O    VAL A   78      37.111 -14.301 102.480  1.00 42.31
ATOM    636  N    PRO A   79      36.282 -13.492 104.407  1.00 49.82
ATOM    637  CD   PRO A   79      36.347 -12.782 105.696  1.00 50.81
ATOM    638  CA   PRO A   79      34.927 -13.998 104.186  1.00 51.31
ATOM    639  CB   PRO A   79      34.170 -13.450 105.396  1.00 53.13
ATOM    640  CG   PRO A   79      35.244 -13.469 106.469  1.00 53.50
ATOM    641  C    PRO A   79      34.343 -13.517 102.858  1.00 52.42
ATOM    642  O    PRO A   79      34.670 -12.428 102.382  1.00 55.73
ATOM    643  N    LYS A   80      33.482 -14.343 102.273  1.00 49.63
ATOM    644  CA   LYS A   80      32.824 -14.053 101.002  1.00 51.62
ATOM    645  CB   LYS A   80      31.632 -15.004 100.822  1.00 53.92
ATOM    646  CG   LYS A   80      30.817 -14.808  99.545  1.00 56.27
ATOM    647  CD   LYS A   80      29.586 -15.712  99.560  1.00 56.61
ATOM    648  CE   LYS A   80      28.744 -15.579  98.298  1.00 56.04
ATOM    649  NZ   LYS A   80      29.471 -16.036  97.081  1.00 58.90
ATOM    650  C    LYS A   80      32.338 -12.607 100.874  1.00 51.10
ATOM    651  O    LYS A   80      31.539 -12.140 101.689  1.00 49.22
ATOM    652  N    GLY A   81      32.821 -11.914  99.842  1.00 51.14
ATOM    653  CA   GLY A   81      32.418 -10.537  99.592  1.00 47.07
ATOM    654  C    GLY A   81      32.876  -9.496 100.599  1.00 46.90
ATOM    655  O    GLY A   81      32.671  -8.301 100.397  1.00 43.90
ATOM    656  N    ALA A   82      33.504  -9.942 101.681  1.00 44.50
ATOM    657  CA   ALA A   82      33.973  -9.029 102.715  1.00 44.69
ATOM    658  CB   ALA A   82      34.497  -9.825 103.903  1.00 44.62
ATOM    659  C    ALA A   82      35.049  -8.073 102.215  1.00 41.82
ATOM    660  O    ALA A   82      35.132  -6.925 102.662  1.00 35.92
```

Fig. 18-10

| ATOM | 661 | N | ARG | A | 83 | 35.874 | -8.549 | 101.289 | 1.00 | 43.30 |
| ATOM | 662 | CA | ARG | A | 83 | 36.959 | -7.742 | 100.741 | 1.00 | 43.25 |
| ATOM | 663 | CB | ARG | A | 83 | 37.715 | -8.533 | 99.677 | 1.00 | 46.60 |
| ATOM | 664 | CG | ARG | A | 83 | 38.988 | -7.865 | 99.222 | 1.00 | 51.32 |
| ATOM | 665 | CD | ARG | A | 83 | 39.636 | -8.632 | 98.086 | 1.00 | 55.55 |
| ATOM | 666 | NE | ARG | A | 83 | 40.995 | -8.164 | 97.810 | 1.00 | 64.08 |
| ATOM | 667 | CZ | ARG | A | 83 | 41.330 | -6.905 | 97.540 | 1.00 | 63.01 |
| ATOM | 668 | NH1 | ARG | A | 83 | 40.403 | -5.954 | 97.504 | 1.00 | 62.76 |
| ATOM | 669 | NH2 | ARG | A | 83 | 42.599 | -6.600 | 97.304 | 1.00 | 59.66 |
| ATOM | 670 | C | ARG | A | 83 | 36.453 | -6.435 | 100.134 | 1.00 | 44.58 |
| ATOM | 671 | O | ARG | A | 83 | 37.002 | -5.365 | 100.395 | 1.00 | 38.05 |
| ATOM | 672 | N | GLU | A | 84 | 35.404 | -6.528 | 99.323 | 1.00 | 41.82 |
| ATOM | 673 | CA | GLU | A | 84 | 34.824 | -5.356 | 98.678 | 1.00 | 41.44 |
| ATOM | 674 | CB | GLU | A | 84 | 34.145 | -5.765 | 97.367 | 1.00 | 46.27 |
| ATOM | 675 | CG | GLU | A | 84 | 33.621 | -7.185 | 97.388 | 1.00 | 52.61 |
| ATOM | 676 | CD | GLU | A | 84 | 34.749 | -8.198 | 97.308 | 1.00 | 54.12 |
| ATOM | 677 | OE1 | GLU | A | 84 | 34.555 | -9.344 | 97.764 | 1.00 | 59.66 |
| ATOM | 678 | OE2 | GLU | A | 84 | 35.823 | -7.850 | 96.769 | 1.00 | 50.30 |
| ATOM | 679 | C | GLU | A | 84 | 33.831 | -4.595 | 99.545 | 1.00 | 37.36 |
| ATOM | 680 | O | GLU | A | 84 | 33.592 | -3.379 | 99.416 | 1.00 | 34.30 |
| ATOM | 681 | N | LYS | A | 85 | 33.138 | -5.301 | 100.427 | 1.00 | 36.00 |
| ATOM | 682 | CA | LYS | A | 85 | 32.154 | -4.646 | 101.280 | 1.00 | 36.95 |
| ATOM | 683 | CB | LYS | A | 85 | 31.089 | -5.649 | 101.725 | 1.00 | 36.60 |
| ATOM | 684 | CG | LYS | A | 85 | 29.975 | -5.042 | 102.570 | 1.00 | 40.72 |
| ATOM | 685 | CD | LYS | A | 85 | 28.939 | -6.092 | 102.963 | 1.00 | 46.21 |
| ATOM | 686 | CE | LYS | A | 85 | 27.839 | -5.487 | 103.827 | 1.00 | 49.06 |
| ATOM | 687 | NZ | LYS | A | 85 | 26.859 | -6.513 | 104.287 | 1.00 | 52.72 |
| ATOM | 688 | C | LYS | A | 85 | 32.785 | -4.008 | 102.513 | 1.00 | 36.48 |
| ATOM | 689 | O | LYS | A | 85 | 32.353 | -2.949 | 102.966 | 1.00 | 32.97 |
| ATOM | 690 | N | TYR | A | 86 | 33.819 | -4.649 | 103.041 | 1.00 | 33.69 |
| ATOM | 691 | CA | TYR | A | 86 | 34.468 | -4.169 | 104.250 | 1.00 | 35.23 |
| ATOM | 692 | CB | TYR | A | 86 | 34.410 | -5.281 | 105.300 | 1.00 | 33.65 |
| ATOM | 693 | CG | TYR | A | 86 | 32.990 | -5.665 | 105.680 | 1.00 | 35.09 |
| ATOM | 694 | CD1 | TYR | A | 86 | 32.165 | -4.765 | 106.351 | 1.00 | 34.06 |
| ATOM | 695 | CE1 | TYR | A | 86 | 30.866 | -5.100 | 106.704 | 1.00 | 34.32 |
| ATOM | 696 | CD2 | TYR | A | 86 | 32.470 | -6.923 | 105.365 | 1.00 | 33.17 |
| ATOM | 697 | CE2 | TYR | A | 86 | 31.162 | -7.271 | 105.716 | 1.00 | 33.91 |
| ATOM | 698 | CZ | TYR | A | 86 | 30.369 | -6.350 | 106.386 | 1.00 | 34.21 |
| ATOM | 699 | OH | TYR | A | 86 | 29.079 | -6.658 | 106.738 | 1.00 | 35.20 |
| ATOM | 700 | C | TYR | A | 86 | 35.901 | -3.672 | 104.046 | 1.00 | 36.09 |
| ATOM | 701 | O | TYR | A | 86 | 36.552 | -3.208 | 104.984 | 1.00 | 36.06 |
| ATOM | 702 | N | ASN | A | 87 | 36.382 | -3.777 | 102.814 | 1.00 | 36.46 |
| ATOM | 703 | CA | ASN | A | 87 | 37.712 | -3.313 | 102.441 | 1.00 | 32.71 |
| ATOM | 704 | CB | ASN | A | 87 | 37.768 | -1.791 | 102.576 | 1.00 | 36.26 |
| ATOM | 705 | CG | ASN | A | 87 | 38.989 | -1.199 | 101.926 | 1.00 | 37.25 |
| ATOM | 706 | OD1 | ASN | A | 87 | 39.305 | -1.518 | 100.784 | 1.00 | 36.29 |
| ATOM | 707 | ND2 | ASN | A | 87 | 39.675 | -0.320 | 102.640 | 1.00 | 45.25 |
| ATOM | 708 | C | ASN | A | 87 | 38.855 | -3.956 | 103.217 | 1.00 | 34.73 |
| ATOM | 709 | O | ASN | A | 87 | 39.868 | -3.315 | 103.512 | 1.00 | 33.23 |
| ATOM | 710 | N | ILE | A | 88 | 38.687 | -5.237 | 103.523 | 1.00 | 32.48 |
| ATOM | 711 | CA | ILE | A | 88 | 39.676 | -6.018 | 104.248 | 1.00 | 33.65 |
| ATOM | 712 | CB | ILE | A | 88 | 39.030 | -6.732 | 105.445 | 1.00 | 38.66 |
| ATOM | 713 | CG2 | ILE | A | 88 | 40.021 | -7.680 | 106.081 | 1.00 | 41.31 |
| ATOM | 714 | CG1 | ILE | A | 88 | 38.536 | -5.707 | 106.461 | 1.00 | 40.45 |
| ATOM | 715 | CD1 | ILE | A | 88 | 39.641 | -4.953 | 107.124 | 1.00 | 42.25 |
| ATOM | 716 | C | ILE | A | 88 | 40.251 | -7.090 | 103.318 | 1.00 | 37.36 |
| ATOM | 717 | O | ILE | A | 88 | 39.555 | -7.587 | 102.431 | 1.00 | 35.47 |
| ATOM | 718 | N | GLY | A | 89 | 41.517 | -7.446 | 103.520 | 1.00 | 31.52 |
| ATOM | 719 | CA | GLY | A | 89 | 42.124 | -8.477 | 102.698 | 1.00 | 33.53 |
| ATOM | 720 | C | GLY | A | 89 | 43.134 | -7.994 | 101.675 | 1.00 | 34.50 |
| ATOM | 721 | O | GLY | A | 89 | 43.951 | -8.777 | 101.186 | 1.00 | 32.81 |
| ATOM | 722 | N | GLY | A | 90 | 43.071 | -6.710 | 101.335 | 1.00 | 31.39 |
| ATOM | 723 | CA | GLY | A | 90 | 44.005 | -6.158 | 100.371 | 1.00 | 23.90 |
| ATOM | 724 | C | GLY | A | 90 | 45.340 | -5.893 | 101.040 | 1.00 | 28.78 |
| ATOM | 725 | O | GLY | A | 90 | 45.563 | -6.339 | 102.163 | 1.00 | 21.71 |
| ATOM | 726 | N | TYR | A | 91 | 46.221 | -5.155 | 100.367 | 1.00 | 28.26 |

Fig. 18-11

| | | | | | | | | | |
|---|---|---|---|---|---|---|---|---|---|
| ATOM | 727 | CA | TYR | A | 91 | 47.539 | -4.850 | 100.918 | 1.00 27.34 |
| ATOM | 728 | CB | TYR | A | 91 | 48.477 | -4.365 | 99.805 | 1.00 22.62 |
| ATOM | 729 | CG | TYR | A | 91 | 48.066 | -3.039 | 99.194 | 1.00 24.28 |
| ATOM | 730 | CD1 | TYR | A | 91 | 48.374 | -1.829 | 99.822 | 1.00 21.55 |
| ATOM | 731 | CE1 | TYR | A | 91 | 47.970 | -0.609 | 99.275 | 1.00 24.69 |
| ATOM | 732 | CD2 | TYR | A | 91 | 47.341 | -2.997 | 98.002 | 1.00 24.86 |
| ATOM | 733 | CE2 | TYR | A | 91 | 46.931 | -1.786 | 97.447 | 1.00 29.92 |
| ATOM | 734 | CZ | TYR | A | 91 | 47.250 | -0.597 | 98.086 | 1.00 29.04 |
| ATOM | 735 | OH | TYR | A | 91 | 46.861 | 0.593 | 97.516 | 1.00 29.51 |
| ATOM | 736 | C | TYR | A | 91 | 47.452 | -3.777 | 101.998 | 1.00 27.52 |
| ATOM | 737 | O | TYR | A | 91 | 48.314 | -3.689 | 102.869 | 1.00 27.20 |
| ATOM | 738 | N | GLU | A | 92 | 46.402 | -2.971 | 101.938 | 1.00 26.75 |
| ATOM | 739 | CA | GLU | A | 92 | 46.232 | -1.879 | 102.882 | 1.00 28.38 |
| ATOM | 740 | CB | GLU | A | 92 | 45.234 | -0.881 | 102.310 | 1.00 28.57 |
| ATOM | 741 | CG | GLU | A | 92 | 45.232 | 0.471 | 102.982 | 1.00 36.94 |
| ATOM | 742 | CD | GLU | A | 92 | 44.178 | 1.395 | 102.396 | 1.00 37.40 |
| ATOM | 743 | OE1 | GLU | A | 92 | 42.999 | 1.293 | 102.794 | 1.00 31.22 |
| ATOM | 744 | OE2 | GLU | A | 92 | 44.527 | 2.209 | 101.516 | 1.00 40.54 |
| ATOM | 745 | C | GLU | A | 92 | 45.770 | -2.343 | 104.259 | 1.00 29.20 |
| ATOM | 746 | O | GLU | A | 92 | 46.389 | -2.015 | 105.268 | 1.00 21.86 |
| ATOM | 747 | N | ASN | A | 93 | 44.687 | -3.117 | 104.286 | 1.00 26.51 |
| ATOM | 748 | CA | ASN | A | 93 | 44.109 | -3.613 | 105.527 | 1.00 24.02 |
| ATOM | 749 | CB | ASN | A | 93 | 42.727 | -2.988 | 105.690 | 1.00 24.51 |
| ATOM | 750 | CG | ASN | A | 93 | 42.738 | -1.488 | 105.405 | 1.00 28.61 |
| ATOM | 751 | OD1 | ASN | A | 93 | 43.428 | -0.727 | 106.079 | 1.00 25.30 |
| ATOM | 752 | ND2 | ASN | A | 93 | 41.987 | -1.063 | 104.393 | 1.00 20.45 |
| ATOM | 753 | C | ASN | A | 93 | 43.999 | -5.132 | 105.407 | 1.00 24.79 |
| ATOM | 754 | O | ASN | A | 93 | 42.905 | -5.680 | 105.291 | 1.00 21.89 |
| ATOM | 755 | N | PRO | A | 94 | 45.142 | -5.828 | 105.429 | 1.00 24.60 |
| ATOM | 756 | CD | PRO | A | 94 | 46.493 | -5.246 | 105.540 | 1.00 22.93 |
| ATOM | 757 | CA | PRO | A | 94 | 45.241 | -7.285 | 105.312 | 1.00 27.23 |
| ATOM | 758 | CB | PRO | A | 94 | 46.730 | -7.488 | 105.093 | 1.00 25.46 |
| ATOM | 759 | CG | PRO | A | 94 | 47.299 | -6.431 | 106.046 | 1.00 26.20 |
| ATOM | 760 | C | PRO | A | 94 | 44.743 | -8.112 | 106.489 | 1.00 31.04 |
| ATOM | 761 | O | PRO | A | 94 | 44.411 | -7.589 | 107.558 | 1.00 29.10 |
| ATOM | 762 | N | VAL | A | 95 | 44.696 | -9.422 | 106.266 | 1.00 28.27 |
| ATOM | 763 | CA | VAL | A | 95 | 44.299 | -10.367 | 107.291 | 1.00 28.82 |
| ATOM | 764 | CB | VAL | A | 95 | 43.938 | -11.737 | 106.677 | 1.00 30.75 |
| ATOM | 765 | CG1 | VAL | A | 95 | 43.745 | -12.766 | 107.776 | 1.00 33.60 |
| ATOM | 766 | CG2 | VAL | A | 95 | 42.679 | -11.611 | 105.849 | 1.00 24.87 |
| ATOM | 767 | C | VAL | A | 95 | 45.503 | -10.549 | 108.204 | 1.00 29.98 |
| ATOM | 768 | O | VAL | A | 95 | 46.637 | -10.649 | 107.729 | 1.00 31.36 |
| ATOM | 769 | N | SER | A | 96 | 45.264 | -10.572 | 109.510 | 1.00 29.38 |
| ATOM | 770 | CA | SER | A | 96 | 46.335 | -10.766 | 110.485 | 1.00 32.56 |
| ATOM | 771 | CB | SER | A | 96 | 47.325 | -9.600 | 110.454 | 1.00 34.15 |
| ATOM | 772 | OG | SER | A | 96 | 46.758 | -8.448 | 111.051 | 1.00 28.33 |
| ATOM | 773 | C | SER | A | 96 | 45.681 | -10.804 | 111.854 | 1.00 32.10 |
| ATOM | 774 | O | SER | A | 96 | 44.458 | -10.839 | 111.950 | 1.00 37.91 |
| ATOM | 775 | N | TYR | A | 97 | 46.484 | -10.795 | 112.913 | 1.00 32.57 |
| ATOM | 776 | CA | TYR | A | 97 | 45.914 | -10.801 | 114.248 | 1.00 34.95 |
| ATOM | 777 | CB | TYR | A | 97 | 46.685 | -11.735 | 115.182 | 1.00 35.47 |
| ATOM | 778 | CG | TYR | A | 97 | 46.492 | -13.187 | 114.817 | 1.00 40.65 |
| ATOM | 779 | CD1 | TYR | A | 97 | 47.319 | -13.812 | 113.882 | 1.00 40.63 |
| ATOM | 780 | CE1 | TYR | A | 97 | 47.083 | -15.121 | 113.475 | 1.00 42.16 |
| ATOM | 781 | CD2 | TYR | A | 97 | 45.421 | -13.910 | 115.338 | 1.00 38.82 |
| ATOM | 782 | CE2 | TYR | A | 97 | 45.175 | -15.219 | 114.936 | 1.00 42.82 |
| ATOM | 783 | CZ | TYR | A | 97 | 46.010 | -15.816 | 114.005 | 1.00 42.56 |
| ATOM | 784 | OH | TYR | A | 97 | 45.772 | -17.105 | 113.601 | 1.00 46.03 |
| ATOM | 785 | C | TYR | A | 97 | 45.862 | -9.394 | 114.813 | 1.00 37.56 |
| ATOM | 786 | O | TYR | A | 97 | 45.601 | -9.195 | 115.998 | 1.00 39.06 |
| ATOM | 787 | N | ALA | A | 98 | 46.115 | -8.418 | 113.948 | 1.00 31.96 |
| ATOM | 788 | CA | ALA | A | 98 | 46.048 | -7.024 | 114.341 | 1.00 30.43 |
| ATOM | 789 | CB | ALA | A | 98 | 47.105 | -6.211 | 113.600 | 1.00 29.64 |
| ATOM | 790 | C | ALA | A | 98 | 44.658 | -6.533 | 113.962 | 1.00 30.35 |
| ATOM | 791 | O | ALA | A | 98 | 44.099 | -5.655 | 114.612 | 1.00 31.82 |
| ATOM | 792 | N | MET | A | 99 | 44.094 | -7.130 | 112.915 | 1.00 30.40 |

Fig. 18-12

| | | | | | | | | | |
|---|---|---|---|---|---|---|---|---|---|
| ATOM | 793 | CA | MET | A | 99 | 42.788 | -6.730 | 112.420 | 1.00 27.54 |
| ATOM | 794 | CB | MET | A | 99 | 42.370 | -7.620 | 111.238 | 1.00 30.55 |
| ATOM | 795 | CG | MET | A | 99 | 42.052 | -9.071 | 111.565 | 1.00 31.59 |
| ATOM | 796 | SD | MET | A | 99 | 41.902 | -10.077 | 110.053 | 1.00 30.13 |
| ATOM | 797 | CE | MET | A | 99 | 40.770 | -9.086 | 109.085 | 1.00 28.02 |
| ATOM | 798 | C | MET | A | 99 | 41.703 | -6.696 | 113.490 | 1.00 28.02 |
| ATOM | 799 | O | MET | A | 99 | 40.818 | -5.842 | 113.446 | 1.00 24.53 |
| ATOM | 800 | N | PHE | A | 100 | 41.752 | -7.614 | 114.449 | 1.00 26.07 |
| ATOM | 801 | CA | PHE | A | 100 | 40.759 | -7.583 | 115.516 | 1.00 30.47 |
| ATOM | 802 | CB | PHE | A | 100 | 39.738 | -8.718 | 115.404 | 1.00 30.29 |
| ATOM | 803 | CG | PHE | A | 100 | 38.693 | -8.657 | 116.475 | 1.00 29.35 |
| ATOM | 804 | CD1 | PHE | A | 100 | 37.722 | -7.662 | 116.455 | 1.00 27.01 |
| ATOM | 805 | CD2 | PHE | A | 100 | 38.756 | -9.506 | 117.575 | 1.00 30.68 |
| ATOM | 806 | CE1 | PHE | A | 100 | 36.834 | -7.507 | 117.519 | 1.00 31.41 |
| ATOM | 807 | CE2 | PHE | A | 100 | 37.873 | -9.356 | 118.644 | 1.00 28.39 |
| ATOM | 808 | CZ | PHE | A | 100 | 36.913 | -8.355 | 118.618 | 1.00 24.06 |
| ATOM | 809 | C | PHE | A | 100 | 41.345 | -7.616 | 116.922 | 1.00 29.67 |
| ATOM | 810 | O | PHE | A | 100 | 41.028 | -6.751 | 117.740 | 1.00 29.67 |
| ATOM | 811 | N | THR | A | 101 | 42.181 | -8.610 | 117.222 | 1.00 31.30 |
| ATOM | 812 | CA | THR | A | 101 | 42.770 | -8.701 | 118.562 | 1.00 31.37 |
| ATOM | 813 | CB | THR | A | 101 | 43.610 | -9.977 | 118.732 | 1.00 31.63 |
| ATOM | 814 | OG1 | THR | A | 101 | 42.777 | -11.119 | 118.532 | 1.00 31.64 |
| ATOM | 815 | CG2 | THR | A | 101 | 44.197 | -10.045 | 120.137 | 1.00 27.38 |
| ATOM | 816 | C | THR | A | 101 | 43.647 | -7.493 | 118.884 | 1.00 31.66 |
| ATOM | 817 | O | THR | A | 101 | 43.502 | -6.875 | 119.942 | 1.00 30.71 |
| ATOM | 818 | N | GLY | A | 102 | 44.562 | -7.166 | 117.976 | 1.00 27.40 |
| ATOM | 819 | CA | GLY | A | 102 | 45.430 | -6.018 | 118.193 | 1.00 27.19 |
| ATOM | 820 | C | GLY | A | 102 | 44.631 | -4.728 | 118.266 | 1.00 27.26 |
| ATOM | 821 | O | GLY | A | 102 | 44.785 | -3.940 | 119.201 | 1.00 27.68 |
| ATOM | 822 | N | SER | A | 103 | 43.767 | -4.515 | 117.279 | 1.00 30.52 |
| ATOM | 823 | CA | SER | A | 103 | 42.941 | -3.314 | 117.216 | 1.00 31.91 |
| ATOM | 824 | CB | SER | A | 103 | 42.085 | -3.334 | 115.949 | 1.00 34.63 |
| ATOM | 825 | OG | SER | A | 103 | 42.896 | -3.265 | 114.791 | 1.00 35.94 |
| ATOM | 826 | C | SER | A | 103 | 42.046 | -3.163 | 118.441 | 1.00 32.44 |
| ATOM | 827 | O | SER | A | 103 | 41.891 | -2.065 | 118.984 | 1.00 25.78 |
| ATOM | 828 | N | SER | A | 104 | 41.455 | -4.270 | 118.871 | 1.00 30.47 |
| ATOM | 829 | CA | SER | A | 104 | 40.584 | -4.251 | 120.038 | 1.00 30.22 |
| ATOM | 830 | CB | SER | A | 104 | 39.978 | -5.633 | 120.265 | 1.00 23.88 |
| ATOM | 831 | OG | SER | A | 104 | 39.078 | -5.595 | 121.358 | 1.00 36.91 |
| ATOM | 832 | C | SER | A | 104 | 41.367 | -3.841 | 121.282 | 1.00 28.13 |
| ATOM | 833 | O | SER | A | 104 | 40.872 | -3.098 | 122.130 | 1.00 25.16 |
| ATOM | 834 | N | LEU | A | 105 | 42.594 | -4.336 | 121.386 | 1.00 29.39 |
| ATOM | 835 | CA | LEU | A | 105 | 43.445 | -4.034 | 122.530 | 1.00 29.52 |
| ATOM | 836 | CB | LEU | A | 105 | 44.684 | -4.922 | 122.471 | 1.00 32.90 |
| ATOM | 837 | CG | LEU | A | 105 | 45.461 | -5.176 | 123.754 | 1.00 40.34 |
| ATOM | 838 | CD1 | LEU | A | 105 | 44.520 | -5.723 | 124.828 | 1.00 35.95 |
| ATOM | 839 | CD2 | LEU | A | 105 | 46.582 | -6.178 | 123.462 | 1.00 40.23 |
| ATOM | 840 | C | LEU | A | 105 | 43.834 | -2.552 | 122.511 | 1.00 32.09 |
| ATOM | 841 | O | LEU | A | 105 | 43.896 | -1.894 | 123.554 | 1.00 30.38 |
| ATOM | 842 | N | ALA | A | 106 | 44.081 | -2.029 | 121.314 | 1.00 30.26 |
| ATOM | 843 | CA | ALA | A | 106 | 44.448 | -0.626 | 121.151 | 1.00 28.31 |
| ATOM | 844 | CB | ALA | A | 106 | 44.958 | -0.386 | 119.738 | 1.00 23.88 |
| ATOM | 845 | C | ALA | A | 106 | 43.243 | 0.268 | 121.434 | 1.00 26.04 |
| ATOM | 846 | O | ALA | A | 106 | 43.380 | 1.376 | 121.952 | 1.00 20.63 |
| ATOM | 847 | N | THR | A | 107 | 42.058 | -0.224 | 121.099 | 1.00 26.86 |
| ATOM | 848 | CA | THR | A | 107 | 40.841 | 0.542 | 121.322 | 1.00 25.04 |
| ATOM | 849 | CB | THR | A | 107 | 39.706 | 0.007 | 120.443 | 1.00 26.50 |
| ATOM | 850 | OG1 | THR | A | 107 | 40.111 | 0.092 | 119.069 | 1.00 24.62 |
| ATOM | 851 | CG2 | THR | A | 107 | 38.439 | 0.824 | 120.629 | 1.00 19.80 |
| ATOM | 852 | C | THR | A | 107 | 40.450 | 0.503 | 122.798 | 1.00 27.90 |
| ATOM | 853 | O | THR | A | 107 | 40.039 | 1.515 | 123.361 | 1.00 29.04 |
| ATOM | 854 | N | GLY | A | 108 | 40.585 | -0.662 | 123.422 | 1.00 24.01 |
| ATOM | 855 | CA | GLY | A | 108 | 40.256 | -0.767 | 124.832 | 1.00 24.86 |
| ATOM | 856 | C | GLY | A | 108 | 41.181 | 0.155 | 125.603 | 1.00 23.86 |
| ATOM | 857 | O | GLY | A | 108 | 40.771 | 0.790 | 126.572 | 1.00 26.97 |
| ATOM | 858 | N | SER | A | 109 | 42.434 | 0.236 | 125.158 | 1.00 23.07 |

Fig. 18-13

| ATOM | 859 | CA | SER | A | 109 | 43.421 | 1.090 | 125.807 | 1.00 | 20.96 |
| --- | --- | --- | --- | --- | --- | --- | --- | --- | --- | --- |
| ATOM | 860 | CB | SER | A | 109 | 44.795 | 0.910 | 125.160 | 1.00 | 24.84 |
| ATOM | 861 | OG | SER | A | 109 | 45.294 | -0.393 | 125.402 | 1.00 | 25.84 |
| ATOM | 862 | C | SER | A | 109 | 43.008 | 2.552 | 125.759 | 1.00 | 21.13 |
| ATOM | 863 | O | SER | A | 109 | 43.323 | 3.312 | 126.672 | 1.00 | 23.17 |
| ATOM | 864 | N | THR | A | 110 | 42.311 | 2.949 | 124.698 | 1.00 | 20.83 |
| ATOM | 865 | CA | THR | A | 110 | 41.841 | 4.327 | 124.583 | 1.00 | 21.84 |
| ATOM | 866 | CB | THR | A | 110 | 41.332 | 4.648 | 123.161 | 1.00 | 24.33 |
| ATOM | 867 | OG1 | THR | A | 110 | 42.452 | 4.769 | 122.276 | 1.00 | 25.38 |
| ATOM | 868 | CG2 | THR | A | 110 | 40.543 | 5.954 | 123.144 | 1.00 | 21.18 |
| ATOM | 869 | C | THR | A | 110 | 40.725 | 4.561 | 125.600 | 1.00 | 28.52 |
| ATOM | 870 | O | THR | A | 110 | 40.632 | 5.637 | 126.197 | 1.00 | 28.27 |
| ATOM | 871 | N | VAL | A | 111 | 39.882 | 3.558 | 125.809 | 1.00 | 26.88 |
| ATOM | 872 | CA | VAL | A | 111 | 38.811 | 3.706 | 126.793 | 1.00 | 30.04 |
| ATOM | 873 | CB | VAL | A | 111 | 37.820 | 2.519 | 126.742 | 1.00 | 29.94 |
| ATOM | 874 | CG1 | VAL | A | 111 | 36.737 | 2.693 | 127.802 | 1.00 | 27.07 |
| ATOM | 875 | CG2 | VAL | A | 111 | 37.193 | 2.431 | 125.355 | 1.00 | 25.26 |
| ATOM | 876 | C | VAL | A | 111 | 39.440 | 3.797 | 128.187 | 1.00 | 28.10 |
| ATOM | 877 | O | VAL | A | 111 | 38.968 | 4.539 | 129.039 | 1.00 | 26.06 |
| ATOM | 878 | N | GLN | A | 112 | 40.521 | 3.056 | 128.415 | 1.00 | 23.92 |
| ATOM | 879 | CA | GLN | A | 112 | 41.188 | 3.097 | 129.711 | 1.00 | 30.27 |
| ATOM | 880 | CB | GLN | A | 112 | 42.268 | 2.020 | 129.804 | 1.00 | 28.61 |
| ATOM | 881 | CG | GLN | A | 112 | 41.777 | 0.629 | 129.481 | 1.00 | 28.90 |
| ATOM | 882 | CD | GLN | A | 112 | 42.883 | -0.397 | 129.564 | 1.00 | 28.60 |
| ATOM | 883 | OE1 | GLN | A | 112 | 43.344 | -0.740 | 130.653 | 1.00 | 29.68 |
| ATOM | 884 | NE2 | GLN | A | 112 | 43.333 | -0.880 | 128.409 | 1.00 | 22.13 |
| ATOM | 885 | C | GLN | A | 112 | 41.834 | 4.461 | 129.931 | 1.00 | 29.99 |
| ATOM | 886 | O | GLN | A | 112 | 41.791 | 5.006 | 131.035 | 1.00 | 28.43 |
| ATOM | 887 | N | ALA | A | 113 | 42.453 | 5.004 | 128.885 | 1.00 | 28.64 |
| ATOM | 888 | CA | ALA | A | 113 | 43.083 | 6.315 | 129.001 | 1.00 | 26.62 |
| ATOM | 889 | CB | ALA | A | 113 | 43.693 | 6.732 | 127.684 | 1.00 | 23.49 |
| ATOM | 890 | C | ALA | A | 113 | 42.005 | 7.307 | 129.407 | 1.00 | 24.63 |
| ATOM | 891 | O | ALA | A | 113 | 42.232 | 8.183 | 130.240 | 1.00 | 26.38 |
| ATOM | 892 | N | ILE | A | 114 | 40.824 | 7.163 | 128.822 | 1.00 | 25.26 |
| ATOM | 893 | CA | ILE | A | 114 | 39.728 | 8.063 | 129.145 | 1.00 | 27.05 |
| ATOM | 894 | CB | ILE | A | 114 | 38.554 | 7.887 | 128.156 | 1.00 | 26.93 |
| ATOM | 895 | CG2 | ILE | A | 114 | 37.387 | 8.770 | 128.576 | 1.00 | 25.86 |
| ATOM | 896 | CG1 | ILE | A | 114 | 39.008 | 8.259 | 126.739 | 1.00 | 28.38 |
| ATOM | 897 | CD1 | ILE | A | 114 | 37.938 | 8.105 | 125.669 | 1.00 | 28.64 |
| ATOM | 898 | C | ILE | A | 114 | 39.239 | 7.823 | 130.578 | 1.00 | 31.36 |
| ATOM | 899 | O | ILE | A | 114 | 38.898 | 8.770 | 131.291 | 1.00 | 24.56 |
| ATOM | 900 | N | GLU | A | 115 | 39.210 | 6.563 | 131.005 | 1.00 | 31.17 |
| ATOM | 901 | CA | GLU | A | 115 | 38.750 | 6.257 | 132.358 | 1.00 | 32.12 |
| ATOM | 902 | CB | GLU | A | 115 | 38.729 | 4.744 | 132.607 | 1.00 | 32.15 |
| ATOM | 903 | CG | GLU | A | 115 | 37.904 | 3.947 | 131.598 | 1.00 | 32.84 |
| ATOM | 904 | CD | GLU | A | 115 | 37.875 | 2.459 | 131.912 | 1.00 | 34.12 |
| ATOM | 905 | OE1 | GLU | A | 115 | 38.910 | 1.910 | 132.345 | 1.00 | 30.36 |
| ATOM | 906 | OE2 | GLU | A | 115 | 36.826 | 1.827 | 131.699 | 1.00 | 31.38 |
| ATOM | 907 | C | GLU | A | 115 | 39.675 | 6.932 | 133.357 | 1.00 | 31.65 |
| ATOM | 908 | O | GLU | A | 115 | 39.224 | 7.446 | 134.383 | 1.00 | 29.25 |
| ATOM | 909 | N | GLU | A | 116 | 40.970 | 6.933 | 133.053 | 1.00 | 31.50 |
| ATOM | 910 | CA | GLU | A | 116 | 41.942 | 7.564 | 133.934 | 1.00 | 32.34 |
| ATOM | 911 | CB | GLU | A | 116 | 43.367 | 7.285 | 133.457 | 1.00 | 33.29 |
| ATOM | 912 | CG | GLU | A | 116 | 43.805 | 5.842 | 133.633 | 1.00 | 32.29 |
| ATOM | 913 | CD | GLU | A | 116 | 43.701 | 5.378 | 135.079 | 1.00 | 36.87 |
| ATOM | 914 | OE1 | GLU | A | 116 | 44.329 | 6.003 | 135.961 | 1.00 | 34.07 |
| ATOM | 915 | OE2 | GLU | A | 116 | 42.993 | 4.385 | 135.335 | 1.00 | 35.00 |
| ATOM | 916 | C | GLU | A | 116 | 41.702 | 9.067 | 134.006 | 1.00 | 36.69 |
| ATOM | 917 | O | GLU | A | 116 | 41.863 | 9.678 | 135.066 | 1.00 | 34.39 |
| ATOM | 918 | N | PHE | A | 117 | 41.317 | 9.661 | 132.881 | 1.00 | 31.19 |
| ATOM | 919 | CA | PHE | A | 117 | 41.038 | 11.091 | 132.841 | 1.00 | 28.43 |
| ATOM | 920 | CB | PHE | A | 117 | 40.593 | 11.509 | 131.444 | 1.00 | 30.14 |
| ATOM | 921 | CG | PHE | A | 117 | 40.044 | 12.908 | 131.381 | 1.00 | 35.78 |
| ATOM | 922 | CD1 | PHE | A | 117 | 40.882 | 14.006 | 131.501 | 1.00 | 33.39 |
| ATOM | 923 | CD2 | PHE | A | 117 | 38.675 | 13.123 | 131.225 | 1.00 | 38.90 |
| ATOM | 924 | CE1 | PHE | A | 117 | 40.372 | 15.299 | 131.466 | 1.00 | 30.65 |

Fig. 18-14

```
ATOM    925  CE2 PHE A 117      38.153  14.412 131.190  1.00 36.50
ATOM    926  CZ  PHE A 117      39.003  15.501 131.310  1.00 35.41
ATOM    927  C   PHE A 117      39.908  11.401 133.811  1.00 32.78
ATOM    928  O   PHE A 117      39.966  12.377 134.566  1.00 29.82
ATOM    929  N   LEU A 118      38.874  10.568 133.771  1.00 28.61
ATOM    930  CA  LEU A 118      37.720  10.751 134.632  1.00 32.00
ATOM    931  CB  LEU A 118      36.621   9.748 134.263  1.00 29.19
ATOM    932  CG  LEU A 118      36.098   9.830 132.820  1.00 34.47
ATOM    933  CD1 LEU A 118      34.962   8.836 132.622  1.00 32.69
ATOM    934  CD2 LEU A 118      35.612  11.240 132.522  1.00 32.24
ATOM    935  C   LEU A 118      38.123  10.590 136.094  1.00 31.17
ATOM    936  O   LEU A 118      37.576  11.260 136.964  1.00 28.32
ATOM    937  N   LYS A 119      39.083   9.707 136.363  1.00 27.23
ATOM    938  CA  LYS A 119      39.531   9.497 137.733  1.00 30.95
ATOM    939  CB  LYS A 119      40.203   8.130 137.884  1.00 26.35
ATOM    940  CG  LYS A 119      39.293   6.954 137.540  1.00 32.44
ATOM    941  CD  LYS A 119      39.895   5.624 137.986  1.00 33.31
ATOM    942  CE  LYS A 119      41.280   5.385 137.411  1.00 33.47
ATOM    943  NZ  LYS A 119      41.874   4.102 137.904  1.00 33.40
ATOM    944  C   LYS A 119      40.493  10.594 138.173  1.00 32.65
ATOM    945  O   LYS A 119      41.050  10.548 139.270  1.00 28.83
ATOM    946  N   GLY A 120      40.689  11.583 137.308  1.00 33.77
ATOM    947  CA  GLY A 120      41.571  12.677 137.652  1.00 33.84
ATOM    948  C   GLY A 120      43.035  12.448 137.340  1.00 34.27
ATOM    949  O   GLY A 120      43.880  13.227 137.776  1.00 36.80
ATOM    950  N   ASN A 121      43.347  11.384 136.606  1.00 30.77
ATOM    951  CA  ASN A 121      44.731  11.122 136.244  1.00 31.73
ATOM    952  CB  ASN A 121      45.089   9.646 136.437  1.00 29.34
ATOM    953  CG  ASN A 121      44.856   9.170 137.851  1.00 35.83
ATOM    954  OD1 ASN A 121      45.190   9.861 138.816  1.00 32.74
ATOM    955  ND2 ASN A 121      44.304   7.970 137.986  1.00 33.20
ATOM    956  C   ASN A 121      44.954  11.506 134.790  1.00 32.59
ATOM    957  O   ASN A 121      44.031  11.952 134.110  1.00 34.69
ATOM    958  N   VAL A 122      46.186  11.334 134.322  1.00 32.74
ATOM    959  CA  VAL A 122      46.540  11.653 132.946  1.00 33.59
ATOM    960  CB  VAL A 122      47.571  12.790 132.882  1.00 36.05
ATOM    961  CG1 VAL A 122      47.884  13.121 131.438  1.00 37.58
ATOM    962  CG2 VAL A 122      47.029  14.021 133.602  1.00 37.19
ATOM    963  C   VAL A 122      47.147  10.397 132.352  1.00 34.47
ATOM    964  O   VAL A 122      48.053   9.801 132.939  1.00 31.28
ATOM    965  N   ALA A 123      46.646   9.989 131.196  1.00 28.06
ATOM    966  CA  ALA A 123      47.142   8.784 130.563  1.00 30.73
ATOM    967  CB  ALA A 123      46.133   7.666 130.727  1.00 32.69
ATOM    968  C   ALA A 123      47.466   8.969 129.088  1.00 30.55
ATOM    969  O   ALA A 123      46.909   9.830 128.406  1.00 32.89
ATOM    970  N   PHE A 124      48.380   8.136 128.613  1.00 27.53
ATOM    971  CA  PHE A 124      48.807   8.157 127.229  1.00 26.56
ATOM    972  CB  PHE A 124      50.261   8.660 127.157  1.00 25.32
ATOM    973  CG  PHE A 124      50.903   8.544 125.793  1.00 27.84
ATOM    974  CD1 PHE A 124      50.179   8.785 124.629  1.00 24.77
ATOM    975  CD2 PHE A 124      52.266   8.266 125.686  1.00 21.79
ATOM    976  CE1 PHE A 124      50.802   8.753 123.385  1.00 29.19
ATOM    977  CE2 PHE A 124      52.894   8.235 124.449  1.00 27.38
ATOM    978  CZ  PHE A 124      52.164   8.478 123.296  1.00 20.91
ATOM    979  C   PHE A 124      48.671   6.749 126.675  1.00 21.13
ATOM    980  O   PHE A 124      49.181   5.795 127.260  1.00 25.38
ATOM    981  N   ASN A 125      47.933   6.624 125.580  1.00 18.87
ATOM    982  CA  ASN A 125      47.750   5.342 124.905  1.00 25.05
ATOM    983  CB  ASN A 125      46.271   4.982 124.756  1.00 22.99
ATOM    984  CG  ASN A 125      46.073   3.784 123.856  1.00 24.08
ATOM    985  OD1 ASN A 125      46.916   2.888 123.822  1.00 20.46
ATOM    986  ND2 ASN A 125      44.960   3.748 123.138  1.00 16.10
ATOM    987  C   ASN A 125      48.380   5.410 123.518  1.00 23.43
ATOM    988  O   ASN A 125      47.718   5.749 122.542  1.00 23.48
ATOM    989  N   PRO A 126      49.680   5.103 123.423  1.00 24.55
ATOM    990  CD  PRO A 126      50.589   4.730 124.519  1.00 22.87
```

Fig. 18-15

```
ATOM    991   CA  PRO A 126      50.413    5.130 122.160   1.00 22.39
ATOM    992   CB  PRO A 126      51.829    4.751 122.594   1.00 18.20
ATOM    993   CG  PRO A 126      51.564    3.849 123.798   1.00 25.43
ATOM    994   C   PRO A 126      49.867    4.224 121.058   1.00 23.18
ATOM    995   O   PRO A 126      50.173    4.436 119.893   1.00 20.12
ATOM    996   N   ALA A 127      49.058    3.232 121.423   1.00 23.27
ATOM    997   CA  ALA A 127      48.493    2.306 120.444   1.00 23.89
ATOM    998   CB  ALA A 127      48.176    0.967 121.118   1.00 24.82
ATOM    999   C   ALA A 127      47.241    2.864 119.778   1.00 24.76
ATOM   1000   O   ALA A 127      46.806    2.360 118.745   1.00 28.99
ATOM   1001   N   GLY A 128      46.666    3.906 120.367   1.00 22.12
ATOM   1002   CA  GLY A 128      45.461    4.494 119.809   1.00 21.43
ATOM   1003   C   GLY A 128      45.732    5.521 118.725   1.00 23.55
ATOM   1004   O   GLY A 128      46.875    5.695 118.291   1.00 23.25
ATOM   1005   N   GLY A 129      44.680    6.199 118.283   1.00 18.03
ATOM   1006   CA  GLY A 129      44.822    7.205 117.243   1.00 24.99
ATOM   1007   C   GLY A 129      44.600    6.655 115.847   1.00 25.11
ATOM   1008   O   GLY A 129      44.963    7.293 114.857   1.00 24.99
ATOM   1009   N   MET A 130      44.002    5.470 115.765   1.00 20.01
ATOM   1010   CA  MET A 130      43.729    4.825 114.481   1.00 23.63
ATOM   1011   CB  MET A 130      43.360    3.361 114.744   1.00 22.77
ATOM   1012   CG  MET A 130      44.455    2.661 115.563   1.00 26.30
ATOM   1013   SD  MET A 130      44.198    0.913 115.989   1.00 26.57
ATOM   1014   CE  MET A 130      42.665    1.030 116.936   1.00 27.59
ATOM   1015   C   MET A 130      42.580    5.617 113.869   1.00 23.70
ATOM   1016   O   MET A 130      41.421    5.199 113.901   1.00 26.28
ATOM   1017   N   HIS A 131      42.926    6.766 113.294   1.00 20.66
ATOM   1018   CA  HIS A 131      41.933    7.687 112.775   1.00 20.99
ATOM   1019   CB  HIS A 131      42.474    9.125 112.891   1.00 21.01
ATOM   1020   CG  HIS A 131      43.699    9.391 112.069   1.00 28.30
ATOM   1021   CD2 HIS A 131      44.498    8.549 111.373   1.00 19.65
ATOM   1022   ND1 HIS A 131      44.246   10.649 111.917   1.00 27.76
ATOM   1023   CE1 HIS A 131      45.328   10.567 111.163   1.00 20.48
ATOM   1024   NE2 HIS A 131      45.503    9.302 110.820   1.00 24.18
ATOM   1025   C   HIS A 131      41.280    7.513 111.416   1.00 23.76
ATOM   1026   O   HIS A 131      40.453    8.341 111.051   1.00 21.95
ATOM   1027   N   HIS A 132      41.600    6.449 110.682   1.00 25.12
ATOM   1028   CA  HIS A 132      41.006    6.257 109.354   1.00 23.32
ATOM   1029   CB  HIS A 132      42.060    5.715 108.388   1.00 17.87
ATOM   1030   CG  HIS A 132      43.148    6.689 108.072   1.00 24.79
ATOM   1031   CD2 HIS A 132      44.496    6.574 108.144   1.00 21.72
ATOM   1032   ND1 HIS A 132      42.896    7.944 107.556   1.00 13.58
ATOM   1033   CE1 HIS A 132      44.044    8.558 107.323   1.00 15.41
ATOM   1034   NE2 HIS A 132      45.028    7.748 107.668   1.00 15.27
ATOM   1035   C   HIS A 132      39.752    5.386 109.208   1.00 23.38
ATOM   1036   O   HIS A 132      38.947    5.615 108.304   1.00 24.70
ATOM   1037   N   ALA A 133      39.587    4.388 110.070   1.00 23.34
ATOM   1038   CA  ALA A 133      38.453    3.471 109.953   1.00 23.77
ATOM   1039   CB  ALA A 133      38.515    2.417 111.053   1.00 27.49
ATOM   1040   C   ALA A 133      37.093    4.145 109.966   1.00 23.02
ATOM   1041   O   ALA A 133      36.878    5.117 110.691   1.00 25.98
ATOM   1042   N   PHE A 134      36.179    3.633 109.148   1.00 18.90
ATOM   1043   CA  PHE A 134      34.831    4.173 109.103   1.00 23.73
ATOM   1044   CB  PHE A 134      34.317    4.296 107.663   1.00 24.29
ATOM   1045   CG  PHE A 134      35.119    5.225 106.801   1.00 26.67
ATOM   1046   CD1 PHE A 134      36.025    4.724 105.867   1.00 28.69
ATOM   1047   CD2 PHE A 134      34.975    6.605 106.921   1.00 32.49
ATOM   1048   CE1 PHE A 134      36.775    5.582 105.063   1.00 28.65
ATOM   1049   CE2 PHE A 134      35.724    7.479 106.119   1.00 27.86
ATOM   1050   CZ  PHE A 134      36.623    6.967 105.188   1.00 23.93
ATOM   1051   C   PHE A 134      33.894    3.260 109.884   1.00 25.91
ATOM   1052   O   PHE A 134      34.270    2.172 110.319   1.00 27.20
ATOM   1053   N   LYS A 135      32.670    3.728 110.062   1.00 29.14
ATOM   1054   CA  LYS A 135      31.638    2.984 110.765   1.00 35.26
ATOM   1055   CB  LYS A 135      30.294    3.628 110.429   1.00 35.86
ATOM   1056   CG  LYS A 135      29.072    2.779 110.667   1.00 46.26
```

Fig. 18-16

| | | | | | | | | | |
|---|---|---|---|---|---|---|---|---|---|
| ATOM | 1057 | CD | LYS | A | 135 | 27.834 | 3.542 | 110.211 | 1.00 47.72 |
| ATOM | 1058 | CE | LYS | A | 135 | 26.610 | 2.645 | 110.169 | 1.00 53.65 |
| ATOM | 1059 | NZ | LYS | A | 135 | 26.788 | 1.549 | 109.167 | 1.00 53.27 |
| ATOM | 1060 | C | LYS | A | 135 | 31.617 | 1.490 | 110.414 | 1.00 35.62 |
| ATOM | 1061 | O | LYS | A | 135 | 31.609 | 0.635 | 111.301 | 1.00 32.58 |
| ATOM | 1062 | N | SER | A | 136 | 31.629 | 1.180 | 109.122 | 1.00 35.97 |
| ATOM | 1063 | CA | SER | A | 136 | 31.555 | -0.211 | 108.684 | 1.00 38.99 |
| ATOM | 1064 | CB | SER | A | 136 | 30.172 | -0.474 | 108.083 | 1.00 38.87 |
| ATOM | 1065 | OG | SER | A | 136 | 29.146 | -0.072 | 108.975 | 1.00 43.54 |
| ATOM | 1066 | C | SER | A | 136 | 32.608 | -0.616 | 107.660 | 1.00 37.84 |
| ATOM | 1067 | O | SER | A | 136 | 32.350 | -1.491 | 106.828 | 1.00 36.33 |
| ATOM | 1068 | N | ARG | A | 137 | 33.788 | -0.008 | 107.705 | 1.00 33.23 |
| ATOM | 1069 | CA | ARG | A | 137 | 34.797 | -0.368 | 106.724 | 1.00 30.89 |
| ATOM | 1070 | CB | ARG | A | 137 | 34.456 | 0.291 | 105.385 | 1.00 33.88 |
| ATOM | 1071 | CG | ARG | A | 137 | 35.009 | -0.465 | 104.201 | 1.00 44.41 |
| ATOM | 1072 | CD | ARG | A | 137 | 34.809 | 0.261 | 102.880 | 1.00 46.27 |
| ATOM | 1073 | NE | ARG | A | 137 | 35.091 | -0.645 | 101.768 | 1.00 48.87 |
| ATOM | 1074 | CZ | ARG | A | 137 | 35.352 | -0.261 | 100.526 | 1.00 48.64 |
| ATOM | 1075 | NH1 | ARG | A | 137 | 35.372 | 1.029 | 100.220 | 1.00 51.82 |
| ATOM | 1076 | NH2 | ARG | A | 137 | 35.592 | -1.169 | 99.589 | 1.00 49.01 |
| ATOM | 1077 | C | ARG | A | 137 | 36.209 | 0.021 | 107.143 | 1.00 31.84 |
| ATOM | 1078 | O | ARG | A | 137 | 36.428 | 1.079 | 107.742 | 1.00 30.36 |
| ATOM | 1079 | N | ALA | A | 138 | 37.156 | -0.845 | 106.828 | 1.00 30.06 |
| ATOM | 1080 | CA | ALA | A | 138 | 38.560 | -0.588 | 107.158 | 1.00 32.24 |
| ATOM | 1081 | CB | ALA | A | 138 | 39.367 | -1.864 | 107.048 | 1.00 31.25 |
| ATOM | 1082 | C | ALA | A | 138 | 39.095 | 0.449 | 106.187 | 1.00 29.49 |
| ATOM | 1083 | O | ALA | A | 138 | 38.612 | 0.551 | 105.063 | 1.00 26.11 |
| ATOM | 1084 | N | ASN | A | 139 | 40.099 | 1.206 | 106.615 | 1.00 29.54 |
| ATOM | 1085 | CA | ASN | A | 139 | 40.673 | 2.241 | 105.767 | 1.00 26.99 |
| ATOM | 1086 | CB | ASN | A | 139 | 39.685 | 3.415 | 105.662 | 1.00 24.10 |
| ATOM | 1087 | CG | ASN | A | 139 | 40.209 | 4.556 | 104.811 | 1.00 28.02 |
| ATOM | 1088 | OD1 | ASN | A | 139 | 40.729 | 4.334 | 103.727 | 1.00 26.90 |
| ATOM | 1089 | ND2 | ASN | A | 139 | 40.050 | 5.789 | 105.293 | 1.00 23.55 |
| ATOM | 1090 | C | ASN | A | 139 | 42.027 | 2.713 | 106.285 | 1.00 30.17 |
| ATOM | 1091 | O | ASN | A | 139 | 42.245 | 2.827 | 107.497 | 1.00 27.55 |
| ATOM | 1092 | N | GLY | A | 140 | 42.944 | 2.959 | 105.354 | 1.00 31.82 |
| ATOM | 1093 | CA | GLY | A | 140 | 44.277 | 3.428 | 105.702 | 1.00 24.90 |
| ATOM | 1094 | C | GLY | A | 140 | 45.000 | 2.696 | 106.816 | 1.00 27.79 |
| ATOM | 1095 | O | GLY | A | 140 | 45.560 | 3.339 | 107.705 | 1.00 23.85 |
| ATOM | 1096 | N | PHE | A | 141 | 45.006 | 1.365 | 106.768 | 1.00 24.35 |
| ATOM | 1097 | CA | PHE | A | 141 | 45.679 | 0.538 | 107.783 | 1.00 24.53 |
| ATOM | 1098 | CB | PHE | A | 141 | 47.031 | 1.146 | 108.197 | 1.00 26.40 |
| ATOM | 1099 | CG | PHE | A | 141 | 47.997 | 1.366 | 107.062 | 1.00 30.31 |
| ATOM | 1100 | CD1 | PHE | A | 141 | 49.145 | 2.125 | 107.269 | 1.00 31.60 |
| ATOM | 1101 | CD2 | PHE | A | 141 | 47.781 | 0.811 | 105.802 | 1.00 29.44 |
| ATOM | 1102 | CE1 | PHE | A | 141 | 50.066 | 2.331 | 106.243 | 1.00 30.44 |
| ATOM | 1103 | CE2 | PHE | A | 141 | 48.694 | 1.008 | 104.770 | 1.00 27.91 |
| ATOM | 1104 | CZ | PHE | A | 141 | 49.840 | 1.771 | 104.991 | 1.00 29.38 |
| ATOM | 1105 | C | PHE | A | 141 | 44.846 | 0.387 | 109.056 | 1.00 23.53 |
| ATOM | 1106 | O | PHE | A | 141 | 45.194 | -0.399 | 109.941 | 1.00 23.09 |
| ATOM | 1107 | N | CYS | A | 142 | 43.760 | 1.143 | 109.159 | 1.00 22.86 |
| ATOM | 1108 | CA | CYS | A | 142 | 42.925 | 1.099 | 110.356 | 1.00 23.87 |
| ATOM | 1109 | CB | CYS | A | 142 | 42.472 | 2.516 | 110.723 | 1.00 22.51 |
| ATOM | 1110 | SG | CYS | A | 142 | 43.828 | 3.683 | 111.072 | 1.00 27.62 |
| ATOM | 1111 | C | CYS | A | 142 | 41.694 | 0.205 | 110.233 | 1.00 24.20 |
| ATOM | 1112 | O | CYS | A | 142 | 40.932 | 0.307 | 109.272 | 1.00 24.12 |
| ATOM | 1113 | N | TYR | A | 143 | 41.498 | -0.663 | 111.219 | 1.00 23.84 |
| ATOM | 1114 | CA | TYR | A | 143 | 40.335 | -1.546 | 111.236 | 1.00 26.07 |
| ATOM | 1115 | CB | TYR | A | 143 | 40.728 | -2.958 | 111.680 | 1.00 27.89 |
| ATOM | 1116 | CG | TYR | A | 143 | 41.829 | -3.582 | 110.855 | 1.00 27.30 |
| ATOM | 1117 | CD1 | TYR | A | 143 | 43.169 | -3.329 | 111.137 | 1.00 25.76 |
| ATOM | 1118 | CE1 | TYR | A | 143 | 44.185 | -3.875 | 110.346 | 1.00 25.77 |
| ATOM | 1119 | CD2 | TYR | A | 143 | 41.526 | -4.394 | 109.762 | 1.00 25.87 |
| ATOM | 1120 | CE2 | TYR | A | 143 | 42.531 | -4.941 | 108.967 | 1.00 23.10 |
| ATOM | 1121 | CZ | TYR | A | 143 | 43.854 | -4.679 | 109.262 | 1.00 22.93 |
| ATOM | 1122 | OH | TYR | A | 143 | 44.849 | -5.217 | 108.476 | 1.00 20.64 |

Fig. 18-17

```
ATOM   1123  C    TYR A 143      39.281  -0.991 112.193  1.00 24.56
ATOM   1124  O    TYR A 143      38.085  -1.030 111.905  1.00 24.88
ATOM   1125  N    ILE A 144      39.734  -0.471 113.331  1.00 23.77
ATOM   1126  CA   ILE A 144      38.833   0.102 114.335  1.00 27.11
ATOM   1127  CB   ILE A 144      38.871  -0.729 115.643  1.00 24.56
ATOM   1128  CG2  ILE A 144      37.941  -0.120 116.690  1.00 23.47
ATOM   1129  CG1  ILE A 144      38.430  -2.169 115.346  1.00 28.51
ATOM   1130  CD1  ILE A 144      38.535  -3.113 116.539  1.00 28.70
ATOM   1131  C    ILE A 144      39.248   1.550 114.627  1.00 24.15
ATOM   1132  O    ILE A 144      40.428   1.843 114.800  1.00 24.42
ATOM   1133  N    ASN A 145      38.277   2.453 114.669  1.00 22.04
ATOM   1134  CA   ASN A 145      38.555   3.866 114.920  1.00 21.31
ATOM   1135  CB   ASN A 145      37.559   4.732 114.133  1.00 18.87
ATOM   1136  CG   ASN A 145      37.956   6.205 114.091  1.00 22.21
ATOM   1137  OD1  ASN A 145      38.223   6.823 115.124  1.00 22.47
ATOM   1138  ND2  ASN A 145      37.978   6.776 112.892  1.00 23.78
ATOM   1139  C    ASN A 145      38.417   4.141 116.418  1.00 22.63
ATOM   1140  O    ASN A 145      37.338   4.535 116.880  1.00 22.45
ATOM   1141  N    ASN A 146      39.495   3.941 117.178  1.00 16.63
ATOM   1142  CA   ASN A 146      39.423   4.160 118.628  1.00 23.57
ATOM   1143  CB   ASN A 146      40.708   3.678 119.320  1.00 19.80
ATOM   1144  CG   ASN A 146      41.924   4.508 118.967  1.00 27.81
ATOM   1145  OD1  ASN A 146      42.299   5.421 119.704  1.00 19.55
ATOM   1146  ND2  ASN A 146      42.544   4.202 117.827  1.00 19.55
ATOM   1147  C    ASN A 146      39.079   5.602 119.023  1.00 26.32
ATOM   1148  O    ASN A 146      38.452   5.827 120.059  1.00 28.34
ATOM   1149  N    PRO A 147      39.512   6.605 118.231  1.00 28.46
ATOM   1150  CD   PRO A 147      40.383   6.637 117.042  1.00 27.18
ATOM   1151  CA   PRO A 147      39.150   7.972 118.618  1.00 24.15
ATOM   1152  CB   PRO A 147      39.859   8.815 117.558  1.00 25.13
ATOM   1153  CG   PRO A 147      41.081   7.959 117.235  1.00 30.05
ATOM   1154  C    PRO A 147      37.618   8.136 118.578  1.00 26.71
ATOM   1155  O    PRO A 147      37.017   8.760 119.456  1.00 24.93
ATOM   1156  N    ALA A 148      36.989   7.557 117.562  1.00 21.42
ATOM   1157  CA   ALA A 148      35.536   7.633 117.416  1.00 21.03
ATOM   1158  CB   ALA A 148      35.112   7.044 116.072  1.00 19.98
ATOM   1159  C    ALA A 148      34.838   6.891 118.552  1.00 20.49
ATOM   1160  O    ALA A 148      33.822   7.344 119.067  1.00 21.44
ATOM   1161  N    VAL A 149      35.381   5.739 118.928  1.00 19.20
ATOM   1162  CA   VAL A 149      34.818   4.950 120.016  1.00 24.61
ATOM   1163  CB   VAL A 149      35.570   3.608 120.181  1.00 25.96
ATOM   1164  CG1  VAL A 149      35.158   2.918 121.485  1.00 26.58
ATOM   1165  CG2  VAL A 149      35.262   2.704 118.995  1.00 25.67
ATOM   1166  C    VAL A 149      34.947   5.752 121.304  1.00 23.56
ATOM   1167  O    VAL A 149      33.990   5.887 122.064  1.00 22.52
ATOM   1168  N    GLY A 150      36.143   6.287 121.536  1.00 24.65
ATOM   1169  CA   GLY A 150      36.390   7.074 122.731  1.00 22.82
ATOM   1170  C    GLY A 150      35.477   8.281 122.838  1.00 25.46
ATOM   1171  O    GLY A 150      34.919   8.564 123.904  1.00 23.17
ATOM   1172  N    ILE A 151      35.327   9.001 121.733  1.00 24.38
ATOM   1173  CA   ILE A 151      34.481  10.180 121.716  1.00 22.85
ATOM   1174  CB   ILE A 151      34.610  10.928 120.371  1.00 24.45
ATOM   1175  CG2  ILE A 151      33.598  12.077 120.306  1.00 24.71
ATOM   1176  CG1  ILE A 151      36.041  11.462 120.222  1.00 28.02
ATOM   1177  CD1  ILE A 151      36.354  12.056 118.854  1.00 27.10
ATOM   1178  C    ILE A 151      33.018   9.806 121.987  1.00 28.19
ATOM   1179  O    ILE A 151      32.337  10.482 122.763  1.00 26.37
ATOM   1180  N    GLU A 152      32.532   8.734 121.364  1.00 26.32
ATOM   1181  CA   GLU A 152      31.149   8.314 121.601  1.00 30.07
ATOM   1182  CB   GLU A 152      30.758   7.161 120.672  1.00 29.37
ATOM   1183  CG   GLU A 152      30.609   7.543 119.194  1.00 27.68
ATOM   1184  CD   GLU A 152      29.455   8.504 118.946  1.00 31.82
ATOM   1185  OE1  GLU A 152      29.139   8.777 117.773  1.00 33.51
ATOM   1186  OE2  GLU A 152      28.862   9.009 119.918  1.00 34.73
ATOM   1187  C    GLU A 152      31.009   7.879 123.055  1.00 28.00
ATOM   1188  O    GLU A 152      29.980   8.096 123.683  1.00 31.23
```

Fig. 18-18

| | | | | | | | | | |
|---|---|---|---|---|---|---|---|---|---|
| ATOM | 1189 | N | TYR | A | 153 | 32.054 | 7.253 | 123.583 | 1.00 28.72 |
| ATOM | 1190 | CA | TYR | A | 153 | 32.066 | 6.805 | 124.971 | 1.00 31.35 |
| ATOM | 1191 | CB | TYR | A | 153 | 33.427 | 6.204 | 125.307 | 1.00 31.56 |
| ATOM | 1192 | CG | TYR | A | 153 | 33.617 | 5.839 | 126.759 | 1.00 33.17 |
| ATOM | 1193 | CD1 | TYR | A | 153 | 33.111 | 4.647 | 127.280 | 1.00 35.43 |
| ATOM | 1194 | CE1 | TYR | A | 153 | 33.321 | 4.298 | 128.619 | 1.00 33.52 |
| ATOM | 1195 | CD2 | TYR | A | 153 | 34.329 | 6.677 | 127.611 | 1.00 34.29 |
| ATOM | 1196 | CE2 | TYR | A | 153 | 34.544 | 6.342 | 128.944 | 1.00 35.34 |
| ATOM | 1197 | CZ | TYR | A | 153 | 34.041 | 5.154 | 129.444 | 1.00 37.50 |
| ATOM | 1198 | OH | TYR | A | 153 | 34.260 | 4.835 | 130.767 | 1.00 30.10 |
| ATOM | 1199 | C | TYR | A | 153 | 31.828 | 8.022 | 125.857 | 1.00 32.71 |
| ATOM | 1200 | O | TYR | A | 153 | 31.026 | 7.988 | 126.787 | 1.00 29.14 |
| ATOM | 1201 | N | LEU | A | 154 | 32.538 | 9.102 | 125.552 | 1.00 29.65 |
| ATOM | 1202 | CA | LEU | A | 154 | 32.413 | 10.332 | 126.310 | 1.00 32.87 |
| ATOM | 1203 | CB | LEU | A | 154 | 33.477 | 11.329 | 125.847 | 1.00 31.46 |
| ATOM | 1204 | CG | LEU | A | 154 | 34.910 | 11.053 | 126.324 | 1.00 29.68 |
| ATOM | 1205 | CD1 | LEU | A | 154 | 35.898 | 11.953 | 125.605 | 1.00 29.29 |
| ATOM | 1206 | CD2 | LEU | A | 154 | 34.989 | 11.278 | 127.829 | 1.00 27.19 |
| ATOM | 1207 | C | LEU | A | 154 | 31.020 | 10.952 | 126.232 | 1.00 34.63 |
| ATOM | 1208 | O | LEU | A | 154 | 30.475 | 11.379 | 127.250 | 1.00 32.58 |
| ATOM | 1209 | N | ARG | A | 155 | 30.443 | 10.999 | 125.035 | 1.00 36.63 |
| ATOM | 1210 | CA | ARG | A | 155 | 29.107 | 11.569 | 124.869 | 1.00 38.36 |
| ATOM | 1211 | CB | ARG | A | 155 | 28.661 | 11.502 | 123.405 | 1.00 36.32 |
| ATOM | 1212 | CG | ARG | A | 155 | 29.581 | 12.253 | 122.460 | 1.00 43.15 |
| ATOM | 1213 | CD | ARG | A | 155 | 29.100 | 12.201 | 121.023 | 1.00 41.10 |
| ATOM | 1214 | NE | ARG | A | 155 | 27.936 | 13.047 | 120.768 | 1.00 44.00 |
| ATOM | 1215 | CZ | ARG | A | 155 | 27.331 | 13.140 | 119.583 | 1.00 54.07 |
| ATOM | 1216 | NH1 | ARG | A | 155 | 27.772 | 12.441 | 118.540 | 1.00 51.61 |
| ATOM | 1217 | NH2 | ARG | A | 155 | 26.291 | 13.948 | 119.424 | 1.00 51.76 |
| ATOM | 1218 | C | ARG | A | 155 | 28.112 | 10.821 | 125.745 | 1.00 36.25 |
| ATOM | 1219 | O | ARG | A | 155 | 27.270 | 11.433 | 126.397 | 1.00 39.00 |
| ATOM | 1220 | N | LYS | A | 156 | 28.213 | 9.496 | 125.765 | 1.00 36.48 |
| ATOM | 1221 | CA | LYS | A | 156 | 27.315 | 8.698 | 126.587 | 1.00 39.06 |
| ATOM | 1222 | CB | LYS | A | 156 | 27.460 | 7.213 | 126.256 | 1.00 41.88 |
| ATOM | 1223 | CG | LYS | A | 156 | 26.672 | 6.816 | 125.020 | 1.00 51.15 |
| ATOM | 1224 | CD | LYS | A | 156 | 27.169 | 7.505 | 123.781 | 1.00 55.56 |
| ATOM | 1225 | CE | LYS | A | 156 | 26.117 | 7.502 | 122.676 | 1.00 55.63 |
| ATOM | 1226 | NZ | LYS | A | 156 | 24.993 | 8.425 | 123.013 | 1.00 49.15 |
| ATOM | 1227 | C | LYS | A | 156 | 27.527 | 8.932 | 128.076 | 1.00 39.91 |
| ATOM | 1228 | O | LYS | A | 156 | 26.636 | 8.658 | 128.876 | 1.00 37.01 |
| ATOM | 1229 | N | LYS | A | 157 | 28.703 | 9.431 | 128.448 | 1.00 37.73 |
| ATOM | 1230 | CA | LYS | A | 157 | 28.985 | 9.725 | 129.847 | 1.00 36.52 |
| ATOM | 1231 | CB | LYS | A | 157 | 30.493 | 9.700 | 130.122 | 1.00 35.64 |
| ATOM | 1232 | CG | LYS | A | 157 | 31.094 | 8.308 | 130.174 | 1.00 35.44 |
| ATOM | 1233 | CD | LYS | A | 157 | 30.509 | 7.510 | 131.335 | 1.00 31.28 |
| ATOM | 1234 | CE | LYS | A | 157 | 31.077 | 6.106 | 131.388 | 1.00 31.48 |
| ATOM | 1235 | NZ | LYS | A | 157 | 30.464 | 5.310 | 132.493 | 1.00 36.39 |
| ATOM | 1236 | C | LYS | A | 157 | 28.423 | 11.097 | 130.197 | 1.00 38.12 |
| ATOM | 1237 | O | LYS | A | 157 | 28.531 | 11.547 | 131.336 | 1.00 37.61 |
| ATOM | 1238 | N | GLY | A | 158 | 27.842 | 11.768 | 129.205 | 1.00 36.27 |
| ATOM | 1239 | CA | GLY | A | 158 | 27.257 | 13.074 | 129.452 | 1.00 34.31 |
| ATOM | 1240 | C | GLY | A | 158 | 27.972 | 14.293 | 128.894 | 1.00 36.36 |
| ATOM | 1241 | O | GLY | A | 158 | 27.438 | 15.399 | 128.963 | 1.00 32.96 |
| ATOM | 1242 | N | PHE | A | 159 | 29.170 | 14.117 | 128.344 | 1.00 33.89 |
| ATOM | 1243 | CA | PHE | A | 159 | 29.892 | 15.260 | 127.796 | 1.00 30.29 |
| ATOM | 1244 | CB | PHE | A | 159 | 31.346 | 14.892 | 127.504 | 1.00 28.62 |
| ATOM | 1245 | CG | PHE | A | 159 | 32.137 | 14.555 | 128.730 | 1.00 28.80 |
| ATOM | 1246 | CD1 | PHE | A | 159 | 32.043 | 13.300 | 129.310 | 1.00 30.41 |
| ATOM | 1247 | CD2 | PHE | A | 159 | 32.951 | 15.513 | 129.327 | 1.00 29.37 |
| ATOM | 1248 | CE1 | PHE | A | 159 | 32.749 | 12.996 | 130.472 | 1.00 34.42 |
| ATOM | 1249 | CE2 | PHE | A | 159 | 33.661 | 15.223 | 130.488 | 1.00 31.10 |
| ATOM | 1250 | CZ | PHE | A | 159 | 33.561 | 13.963 | 131.062 | 1.00 32.32 |
| ATOM | 1251 | C | PHE | A | 159 | 29.224 | 15.786 | 126.536 | 1.00 28.88 |
| ATOM | 1252 | O | PHE | A | 159 | 28.765 | 15.003 | 125.705 | 1.00 27.71 |
| ATOM | 1253 | N | LYS | A | 160 | 29.180 | 17.110 | 126.402 | 1.00 30.20 |
| ATOM | 1254 | CA | LYS | A | 160 | 28.550 | 17.766 | 125.254 | 1.00 33.98 |

Fig. 18-19

| ATOM | 1255 | CB | LYS | A | 160 | 27.390 | 18.653 | 125.719 | 1.00 | 36.87 |
| --- | --- | --- | --- | --- | --- | --- | --- | --- | --- | --- |
| ATOM | 1256 | CG | LYS | A | 160 | 26.273 | 17.914 | 126.419 | 1.00 | 39.48 |
| ATOM | 1257 | CD | LYS | A | 160 | 25.105 | 18.850 | 126.723 | 1.00 | 48.58 |
| ATOM | 1258 | CE | LYS | A | 160 | 25.500 | 20.003 | 127.651 | 1.00 | 50.81 |
| ATOM | 1259 | NZ | LYS | A | 160 | 25.924 | 19.534 | 129.008 | 1.00 | 49.79 |
| ATOM | 1260 | C | LYS | A | 160 | 29.484 | 18.616 | 124.394 | 1.00 | 32.59 |
| ATOM | 1261 | O | LYS | A | 160 | 29.093 | 19.085 | 123.327 | 1.00 | 30.98 |
| ATOM | 1262 | N | ARG | A | 161 | 30.700 | 18.846 | 124.867 | 1.00 | 31.43 |
| ATOM | 1263 | CA | ARG | A | 161 | 31.665 | 19.626 | 124.108 | 1.00 | 29.97 |
| ATOM | 1264 | CB | ARG | A | 161 | 31.781 | 21.048 | 124.673 | 1.00 | 34.45 |
| ATOM | 1265 | CG | ARG | A | 161 | 30.476 | 21.854 | 124.610 | 1.00 | 37.63 |
| ATOM | 1266 | CD | ARG | A | 161 | 30.705 | 23.321 | 124.956 | 1.00 | 39.01 |
| ATOM | 1267 | NE | ARG | A | 161 | 31.158 | 23.503 | 126.341 | 1.00 | 43.76 |
| ATOM | 1268 | CZ | ARG | A | 161 | 30.389 | 23.337 | 127.414 | 1.00 | 43.33 |
| ATOM | 1269 | NH1 | ARG | A | 161 | 29.117 | 22.985 | 127.274 | 1.00 | 45.95 |
| ATOM | 1270 | NH2 | ARG | A | 161 | 30.893 | 23.518 | 128.627 | 1.00 | 43.74 |
| ATOM | 1271 | C | ARG | A | 161 | 33.009 | 18.910 | 124.161 | 1.00 | 32.71 |
| ATOM | 1272 | O | ARG | A | 161 | 33.792 | 19.090 | 125.092 | 1.00 | 28.53 |
| ATOM | 1273 | N | ILE | A | 162 | 33.257 | 18.087 | 123.149 | 1.00 | 32.50 |
| ATOM | 1274 | CA | ILE | A | 162 | 34.485 | 17.313 | 123.049 | 1.00 | 28.52 |
| ATOM | 1275 | CB | ILE | A | 162 | 34.146 | 15.821 | 122.820 | 1.00 | 31.42 |
| ATOM | 1276 | CG2 | ILE | A | 162 | 35.407 | 14.976 | 122.898 | 1.00 | 24.95 |
| ATOM | 1277 | CG1 | ILE | A | 162 | 33.147 | 15.355 | 123.879 | 1.00 | 30.25 |
| ATOM | 1278 | CD1 | ILE | A | 162 | 32.564 | 13.977 | 123.635 | 1.00 | 34.27 |
| ATOM | 1279 | C | ILE | A | 162 | 35.353 | 17.816 | 121.886 | 1.00 | 26.46 |
| ATOM | 1280 | O | ILE | A | 162 | 34.876 | 17.973 | 120.762 | 1.00 | 27.88 |
| ATOM | 1281 | N | LEU | A | 163 | 36.626 | 18.067 | 122.168 | 1.00 | 23.13 |
| ATOM | 1282 | CA | LEU | A | 163 | 37.575 | 18.534 | 121.156 | 1.00 | 25.74 |
| ATOM | 1283 | CB | LEU | A | 163 | 38.384 | 19.729 | 121.681 | 1.00 | 26.25 |
| ATOM | 1284 | CG | LEU | A | 163 | 39.626 | 20.138 | 120.862 | 1.00 | 24.39 |
| ATOM | 1285 | CD1 | LEU | A | 163 | 39.213 | 20.591 | 119.473 | 1.00 | 26.25 |
| ATOM | 1286 | CD2 | LEU | A | 163 | 40.361 | 21.252 | 121.560 | 1.00 | 27.76 |
| ATOM | 1287 | C | LEU | A | 163 | 38.547 | 17.416 | 120.792 | 1.00 | 27.09 |
| ATOM | 1288 | O | LEU | A | 163 | 39.053 | 16.721 | 121.674 | 1.00 | 25.25 |
| ATOM | 1289 | N | TYR | A | 164 | 38.808 | 17.257 | 119.496 | 1.00 | 26.97 |
| ATOM | 1290 | CA | TYR | A | 164 | 39.747 | 16.241 | 119.010 | 1.00 | 26.97 |
| ATOM | 1291 | CB | TYR | A | 164 | 39.021 | 15.181 | 118.179 | 1.00 | 23.38 |
| ATOM | 1292 | CG | TYR | A | 164 | 39.944 | 14.146 | 117.565 | 1.00 | 21.76 |
| ATOM | 1293 | CD1 | TYR | A | 164 | 40.563 | 13.179 | 118.353 | 1.00 | 22.49 |
| ATOM | 1294 | CE1 | TYR | A | 164 | 41.419 | 12.224 | 117.794 | 1.00 | 22.90 |
| ATOM | 1295 | CD2 | TYR | A | 164 | 40.202 | 14.142 | 116.194 | 1.00 | 18.74 |
| ATOM | 1296 | CE2 | TYR | A | 164 | 41.060 | 13.190 | 115.616 | 1.00 | 23.36 |
| ATOM | 1297 | CZ | TYR | A | 164 | 41.663 | 12.235 | 116.426 | 1.00 | 21.50 |
| ATOM | 1298 | OH | TYR | A | 164 | 42.506 | 11.296 | 115.878 | 1.00 | 18.41 |
| ATOM | 1299 | C | TYR | A | 164 | 40.798 | 16.923 | 118.138 | 1.00 | 21.67 |
| ATOM | 1300 | O | TYR | A | 164 | 40.473 | 17.511 | 117.112 | 1.00 | 19.75 |
| ATOM | 1301 | N | ILE | A | 165 | 42.057 | 16.843 | 118.551 | 1.00 | 25.61 |
| ATOM | 1302 | CA | ILE | A | 165 | 43.149 | 17.462 | 117.804 | 1.00 | 24.43 |
| ATOM | 1303 | CB | ILE | A | 165 | 43.963 | 18.396 | 118.717 | 1.00 | 26.41 |
| ATOM | 1304 | CG2 | ILE | A | 165 | 45.127 | 19.017 | 117.937 | 1.00 | 19.36 |
| ATOM | 1305 | CG1 | ILE | A | 165 | 43.035 | 19.482 | 119.274 | 1.00 | 23.36 |
| ATOM | 1306 | CD1 | ILE | A | 165 | 43.685 | 20.402 | 120.299 | 1.00 | 25.05 |
| ATOM | 1307 | C | ILE | A | 165 | 44.040 | 16.365 | 117.234 | 1.00 | 26.91 |
| ATOM | 1308 | O | ILE | A | 165 | 44.538 | 15.505 | 117.971 | 1.00 | 21.91 |
| ATOM | 1309 | N | ASP | A | 166 | 44.242 | 16.408 | 115.920 | 1.00 | 24.20 |
| ATOM | 1310 | CA | ASP | A | 166 | 45.022 | 15.386 | 115.228 | 1.00 | 27.11 |
| ATOM | 1311 | CB | ASP | A | 166 | 44.140 | 14.765 | 114.137 | 1.00 | 28.56 |
| ATOM | 1312 | CG | ASP | A | 166 | 44.699 | 13.461 | 113.599 | 1.00 | 34.59 |
| ATOM | 1313 | OD1 | ASP | A | 166 | 45.831 | 13.456 | 113.068 | 1.00 | 30.37 |
| ATOM | 1314 | OD2 | ASP | A | 166 | 43.995 | 12.437 | 113.717 | 1.00 | 23.27 |
| ATOM | 1315 | C | ASP | A | 166 | 46.319 | 15.924 | 114.614 | 1.00 | 24.47 |
| ATOM | 1316 | O | ASP | A | 166 | 46.295 | 16.613 | 113.591 | 1.00 | 23.19 |
| ATOM | 1317 | N | LEU | A | 167 | 47.452 | 15.597 | 115.227 | 1.00 | 23.43 |
| ATOM | 1318 | CA | LEU | A | 167 | 48.738 | 16.068 | 114.722 | 1.00 | 24.67 |
| ATOM | 1319 | CB | LEU | A | 167 | 49.682 | 16.382 | 115.887 | 1.00 | 21.90 |
| ATOM | 1320 | CG | LEU | A | 167 | 49.143 | 17.444 | 116.858 | 1.00 | 26.62 |

Fig. 18-20

| ATOM | 1321 | CD1 | LEU | A | 167 | 50.249 | 17.845 | 117.821 | 1.00 | 25.88 |
| ATOM | 1322 | CD2 | LEU | A | 167 | 48.658 | 18.668 | 116.092 | 1.00 | 22.40 |
| ATOM | 1323 | C | LEU | A | 167 | 49.405 | 15.092 | 113.755 | 1.00 | 25.82 |
| ATOM | 1324 | O | LEU | A | 167 | 50.504 | 15.345 | 113.262 | 1.00 | 21.89 |
| ATOM | 1325 | N | ASP | A | 168 | 48.736 | 13.977 | 113.488 | 1.00 | 24.69 |
| ATOM | 1326 | CA | ASP | A | 168 | 49.244 | 12.975 | 112.555 | 1.00 | 24.59 |
| ATOM | 1327 | CB | ASP | A | 168 | 48.209 | 11.852 | 112.410 | 1.00 | 27.12 |
| ATOM | 1328 | CG | ASP | A | 168 | 48.722 | 10.669 | 111.608 | 1.00 | 28.11 |
| ATOM | 1329 | C | ASP | A | 168 | 49.423 | 13.686 | 111.209 | 1.00 | 24.17 |
| ATOM | 1330 | O | ASP | A | 168 | 48.629 | 14.559 | 110.865 | 1.00 | 17.18 |
| ATOM | 1331 | OD1 | ASP | A | 168 | 49.085 | 9.644 | 112.227 | 1.00 | 25.40 |
| ATOM | 1332 | OD2 | ASP | A | 168 | 48.777 | 10.750 | 110.364 | 1.00 | 34.72 |
| ATOM | 1333 | N | ALA | A | 169 | 50.448 | 13.312 | 110.446 | 1.00 | 21.29 |
| ATOM | 1334 | CA | ALA | A | 169 | 50.693 | 13.927 | 109.140 | 1.00 | 25.00 |
| ATOM | 1335 | CB | ALA | A | 169 | 52.068 | 13.498 | 108.601 | 1.00 | 21.17 |
| ATOM | 1336 | C | ALA | A | 169 | 49.612 | 13.636 | 108.093 | 1.00 | 26.57 |
| ATOM | 1337 | O | ALA | A | 169 | 49.641 | 14.204 | 107.000 | 1.00 | 26.90 |
| ATOM | 1338 | N | HIS | A | 170 | 48.673 | 12.746 | 108.406 | 1.00 | 21.63 |
| ATOM | 1339 | CA | HIS | A | 170 | 47.592 | 12.445 | 107.468 | 1.00 | 24.79 |
| ATOM | 1340 | C | HIS | A | 170 | 46.243 | 12.867 | 108.045 | 1.00 | 20.98 |
| ATOM | 1341 | O | HIS | A | 170 | 46.044 | 12.849 | 109.255 | 1.00 | 24.12 |
| ATOM | 1342 | CB | HIS | A | 170 | 47.550 | 10.950 | 107.131 | 1.00 | 23.17 |
| ATOM | 1343 | CG | HIS | A | 170 | 48.830 | 10.420 | 106.570 | 1.00 | 30.28 |
| ATOM | 1344 | ND1 | HIS | A | 170 | 49.842 | 9.982 | 107.385 | 1.00 | 31.00 |
| ATOM | 1345 | CE1 | HIS | A | 170 | 50.825 | 9.634 | 106.577 | 1.00 | 24.33 |
| ATOM | 1346 | CD2 | HIS | A | 170 | 49.224 | 10.329 | 105.273 | 1.00 | 22.88 |
| ATOM | 1347 | NE2 | HIS | A | 170 | 50.502 | 9.828 | 105.285 | 1.00 | 21.89 |
| ATOM | 1348 | N | HIS | A | 171 | 45.317 | 13.231 | 107.171 | 1.00 | 21.14 |
| ATOM | 1349 | CA | HIS | A | 171 | 43.993 | 13.661 | 107.591 | 1.00 | 25.57 |
| ATOM | 1350 | CB | HIS | A | 171 | 43.234 | 14.242 | 106.404 | 1.00 | 22.47 |
| ATOM | 1351 | CG | HIS | A | 171 | 41.857 | 14.719 | 106.746 | 1.00 | 29.75 |
| ATOM | 1352 | CD2 | HIS | A | 171 | 41.433 | 15.648 | 107.634 | 1.00 | 25.58 |
| ATOM | 1353 | ND1 | HIS | A | 171 | 40.721 | 14.201 | 106.160 | 1.00 | 28.90 |
| ATOM | 1354 | CE1 | HIS | A | 171 | 39.656 | 14.787 | 106.676 | 1.00 | 25.35 |
| ATOM | 1355 | NE2 | HIS | A | 171 | 40.060 | 15.669 | 107.573 | 1.00 | 32.40 |
| ATOM | 1356 | C | HIS | A | 171 | 43.169 | 12.533 | 108.204 | 1.00 | 29.61 |
| ATOM | 1357 | O | HIS | A | 171 | 43.169 | 11.411 | 107.698 | 1.00 | 27.62 |
| ATOM | 1358 | N | CYS | A | 172 | 42.461 | 12.852 | 109.286 | 1.00 | 26.52 |
| ATOM | 1359 | CA | CYS | A | 172 | 41.610 | 11.897 | 109.987 | 1.00 | 24.82 |
| ATOM | 1360 | CB | CYS | A | 172 | 41.460 | 12.322 | 111.456 | 1.00 | 29.47 |
| ATOM | 1361 | SG | CYS | A | 172 | 40.959 | 14.065 | 111.717 | 1.00 | 25.69 |
| ATOM | 1362 | C | CYS | A | 172 | 40.237 | 11.797 | 109.314 | 1.00 | 28.21 |
| ATOM | 1363 | O | CYS | A | 172 | 39.211 | 12.131 | 109.914 | 1.00 | 26.78 |
| ATOM | 1364 | N | ASP | A | 173 | 40.213 | 11.332 | 108.066 | 1.00 | 22.05 |
| ATOM | 1365 | CA | ASP | A | 173 | 38.949 | 11.217 | 107.350 | 1.00 | 27.39 |
| ATOM | 1366 | CB | ASP | A | 173 | 39.167 | 10.646 | 105.931 | 1.00 | 30.47 |
| ATOM | 1367 | CG | ASP | A | 173 | 39.824 | 9.264 | 105.922 | 1.00 | 29.77 |
| ATOM | 1368 | OD1 | ASP | A | 173 | 39.886 | 8.658 | 104.830 | 1.00 | 21.14 |
| ATOM | 1369 | OD2 | ASP | A | 173 | 40.288 | 8.787 | 106.978 | 1.00 | 30.04 |
| ATOM | 1370 | C | ASP | A | 173 | 37.895 | 10.400 | 108.105 | 1.00 | 27.86 |
| ATOM | 1371 | O | ASP | A | 173 | 36.720 | 10.762 | 108.120 | 1.00 | 23.47 |
| ATOM | 1372 | N | GLY | A | 174 | 38.309 | 9.315 | 108.753 | 1.00 | 25.84 |
| ATOM | 1373 | CA | GLY | A | 174 | 37.344 | 8.513 | 109.490 | 1.00 | 28.49 |
| ATOM | 1374 | C | GLY | A | 174 | 36.694 | 9.296 | 110.619 | 1.00 | 26.14 |
| ATOM | 1375 | O | GLY | A | 174 | 35.475 | 9.287 | 110.780 | 1.00 | 21.39 |
| ATOM | 1376 | N | VAL | A | 175 | 37.510 | 9.984 | 111.409 | 1.00 | 27.24 |
| ATOM | 1377 | CA | VAL | A | 175 | 36.995 | 10.773 | 112.523 | 1.00 | 25.53 |
| ATOM | 1378 | CB | VAL | A | 175 | 38.137 | 11.299 | 113.401 | 1.00 | 30.54 |
| ATOM | 1379 | CG1 | VAL | A | 175 | 37.565 | 12.105 | 114.566 | 1.00 | 28.02 |
| ATOM | 1380 | CG2 | VAL | A | 175 | 38.973 | 10.129 | 113.911 | 1.00 | 21.30 |
| ATOM | 1381 | C | VAL | A | 175 | 36.163 | 11.955 | 112.035 | 1.00 | 25.01 |
| ATOM | 1382 | O | VAL | A | 175 | 35.130 | 12.282 | 112.623 | 1.00 | 21.60 |
| ATOM | 1383 | N | GLN | A | 176 | 36.601 | 12.594 | 110.957 | 1.00 | 25.43 |
| ATOM | 1384 | CA | GLN | A | 176 | 35.854 | 13.730 | 110.426 | 1.00 | 26.12 |
| ATOM | 1385 | CB | GLN | A | 176 | 36.554 | 14.336 | 109.205 | 1.00 | 24.71 |
| ATOM | 1386 | CG | GLN | A | 176 | 35.682 | 15.349 | 108.469 | 1.00 | 26.68 |

Fig. 18-21

| | | | | | | | | |
|---|---|---|---|---|---|---|---|---|
| ATOM | 1387 | CD | GLN | A | 176 | 36.385 | 16.002 | 107.306 | 1.00 29.54 |
| ATOM | 1388 | OE1 | GLN | A | 176 | 37.382 | 16.704 | 107.486 | 1.00 26.93 |
| ATOM | 1389 | NE2 | GLN | A | 176 | 35.872 | 15.776 | 106.099 | 1.00 27.58 |
| ATOM | 1390 | C | GLN | A | 176 | 34.446 | 13.316 | 110.029 | 1.00 27.63 |
| ATOM | 1391 | O | GLN | A | 176 | 33.481 | 14.021 | 110.319 | 1.00 25.93 |
| ATOM | 1392 | N | GLU | A | 177 | 34.330 | 12.173 | 109.362 | 1.00 32.21 |
| ATOM | 1393 | CA | GLU | A | 177 | 33.027 | 11.696 | 108.915 | 1.00 32.72 |
| ATOM | 1394 | CB | GLU | A | 177 | 33.181 | 10.445 | 108.053 | 1.00 34.20 |
| ATOM | 1395 | CG | GLU | A | 177 | 31.905 | 10.069 | 107.329 | 1.00 39.40 |
| ATOM | 1396 | CD | GLU | A | 177 | 32.060 | 8.819 | 106.497 | 1.00 41.42 |
| ATOM | 1397 | OE1 | GLU | A | 177 | 32.056 | 7.712 | 107.075 | 1.00 45.91 |
| ATOM | 1398 | OE2 | GLU | A | 177 | 32.206 | 8.947 | 105.264 | 1.00 42.35 |
| ATOM | 1399 | C | GLU | A | 177 | 32.128 | 11.377 | 110.099 | 1.00 30.54 |
| ATOM | 1400 | O | GLU | A | 177 | 30.945 | 11.697 | 110.093 | 1.00 25.39 |
| ATOM | 1401 | N | ALA | A | 178 | 32.707 | 10.750 | 111.114 | 1.00 27.03 |
| ATOM | 1402 | CA | ALA | A | 178 | 31.971 | 10.365 | 112.303 | 1.00 30.67 |
| ATOM | 1403 | CB | ALA | A | 178 | 32.905 | 9.658 | 113.289 | 1.00 30.49 |
| ATOM | 1404 | C | ALA | A | 178 | 31.261 | 11.519 | 113.003 | 1.00 33.21 |
| ATOM | 1405 | O | ALA | A | 178 | 30.145 | 11.355 | 113.493 | 1.00 28.64 |
| ATOM | 1406 | N | PHE | A | 179 | 31.888 | 12.688 | 113.055 | 1.00 29.27 |
| ATOM | 1407 | CA | PHE | A | 179 | 31.256 | 13.801 | 113.751 | 1.00 30.49 |
| ATOM | 1408 | CB | PHE | A | 179 | 32.071 | 14.128 | 115.001 | 1.00 24.44 |
| ATOM | 1409 | CG | PHE | A | 179 | 32.469 | 12.909 | 115.781 | 1.00 24.43 |
| ATOM | 1410 | CD1 | PHE | A | 179 | 33.749 | 12.375 | 115.657 | 1.00 25.04 |
| ATOM | 1411 | CD2 | PHE | A | 179 | 31.536 | 12.233 | 116.563 | 1.00 23.09 |
| ATOM | 1412 | CE1 | PHE | A | 179 | 34.103 | 11.184 | 116.293 | 1.00 16.56 |
| ATOM | 1413 | CE2 | PHE | A | 179 | 31.881 | 11.038 | 117.204 | 1.00 26.38 |
| ATOM | 1414 | CZ | PHE | A | 179 | 33.170 | 10.515 | 117.067 | 1.00 20.30 |
| ATOM | 1415 | C | PHE | A | 179 | 31.079 | 15.037 | 112.891 | 1.00 31.00 |
| ATOM | 1416 | O | PHE | A | 179 | 31.006 | 16.152 | 113.399 | 1.00 31.32 |
| ATOM | 1417 | N | TYR | A | 180 | 30.980 | 14.828 | 111.584 | 1.00 31.68 |
| ATOM | 1418 | CA | TYR | A | 180 | 30.829 | 15.925 | 110.646 | 1.00 32.76 |
| ATOM | 1419 | CB | TYR | A | 180 | 30.931 | 15.378 | 109.213 | 1.00 35.12 |
| ATOM | 1420 | CG | TYR | A | 180 | 31.331 | 16.406 | 108.172 | 1.00 36.27 |
| ATOM | 1421 | CD1 | TYR | A | 180 | 30.427 | 16.846 | 107.204 | 1.00 37.31 |
| ATOM | 1422 | CE1 | TYR | A | 180 | 30.801 | 17.791 | 106.244 | 1.00 34.81 |
| ATOM | 1423 | CD2 | TYR | A | 180 | 32.624 | 16.937 | 108.154 | 1.00 36.32 |
| ATOM | 1424 | CE2 | TYR | A | 180 | 33.007 | 17.879 | 107.203 | 1.00 37.83 |
| ATOM | 1425 | CZ | TYR | A | 180 | 32.088 | 18.304 | 106.250 | 1.00 36.05 |
| ATOM | 1426 | OH | TYR | A | 180 | 32.446 | 19.255 | 105.323 | 1.00 28.04 |
| ATOM | 1427 | C | TYR | A | 180 | 29.518 | 16.696 | 110.825 | 1.00 30.94 |
| ATOM | 1428 | O | TYR | A | 180 | 29.459 | 17.894 | 110.560 | 1.00 30.42 |
| ATOM | 1429 | N | ASP | A | 181 | 28.473 | 16.026 | 111.299 | 1.00 31.56 |
| ATOM | 1430 | CA | ASP | A | 181 | 27.180 | 16.691 | 111.444 | 1.00 37.30 |
| ATOM | 1431 | CB | ASP | A | 181 | 26.086 | 15.833 | 110.807 | 1.00 37.68 |
| ATOM | 1432 | CG | ASP | A | 181 | 25.645 | 14.689 | 111.705 | 1.00 39.86 |
| ATOM | 1433 | OD1 | ASP | A | 181 | 26.505 | 13.963 | 112.233 | 1.00 43.25 |
| ATOM | 1434 | OD2 | ASP | A | 181 | 24.425 | 14.504 | 111.871 | 1.00 46.56 |
| ATOM | 1435 | C | ASP | A | 181 | 26.754 | 17.044 | 112.866 | 1.00 36.81 |
| ATOM | 1436 | O | ASP | A | 181 | 25.571 | 17.286 | 113.109 | 1.00 33.91 |
| ATOM | 1437 | N | THR | A | 182 | 27.689 | 17.066 | 113.810 | 1.00 40.86 |
| ATOM | 1438 | CA | THR | A | 182 | 27.327 | 17.412 | 115.184 | 1.00 38.27 |
| ATOM | 1439 | CB | THR | A | 182 | 27.433 | 16.201 | 116.133 | 1.00 37.99 |
| ATOM | 1440 | OG1 | THR | A | 182 | 27.013 | 16.595 | 117.448 | 1.00 35.64 |
| ATOM | 1441 | CG2 | THR | A | 182 | 28.869 | 15.684 | 116.194 | 1.00 35.61 |
| ATOM | 1442 | C | THR | A | 182 | 28.177 | 18.546 | 115.746 | 1.00 39.51 |
| ATOM | 1443 | O | THR | A | 182 | 29.365 | 18.673 | 115.433 | 1.00 40.07 |
| ATOM | 1444 | N | ASP | A | 183 | 27.557 | 19.369 | 116.582 | 1.00 37.01 |
| ATOM | 1445 | CA | ASP | A | 183 | 28.250 | 20.497 | 117.181 | 1.00 37.74 |
| ATOM | 1446 | CB | ASP | A | 183 | 27.313 | 21.706 | 117.228 | 1.00 35.56 |
| ATOM | 1447 | CG | ASP | A | 183 | 26.136 | 21.493 | 118.155 | 1.00 38.01 |
| ATOM | 1448 | OD1 | ASP | A | 183 | 25.614 | 20.357 | 118.210 | 1.00 34.94 |
| ATOM | 1449 | OD2 | ASP | A | 183 | 25.720 | 22.470 | 118.814 | 1.00 38.17 |
| ATOM | 1450 | C | ASP | A | 183 | 28.762 | 20.161 | 118.578 | 1.00 35.27 |
| ATOM | 1451 | O | ASP | A | 183 | 29.337 | 21.015 | 119.251 | 1.00 35.16 |
| ATOM | 1452 | N | GLN | A | 184 | 28.562 | 18.917 | 119.012 | 1.00 35.10 |

Fig. 18-22

```
ATOM  1453 CA  GLN A 184    29.030 18.505 120.333  1.00 35.16
ATOM  1454 CB  GLN A 184    28.155 17.382 120.906  1.00 36.94
ATOM  1455 CG  GLN A 184    26.663 17.718 120.988  1.00 38.34
ATOM  1456 CD  GLN A 184    25.881 16.725 121.838  1.00 43.68
ATOM  1457 OE1 GLN A 184    26.027 15.512 121.696  1.00 35.48
ATOM  1458 NE2 GLN A 184    25.036 17.243 122.723  1.00 51.06
ATOM  1459 C   GLN A 184    30.479 18.035 120.253  1.00 36.32
ATOM  1460 O   GLN A 184    31.135 17.825 121.275  1.00 34.24
ATOM  1461 N   VAL A 185    30.976 17.883 119.028  1.00 34.51
ATOM  1462 CA  VAL A 185    32.348 17.443 118.804  1.00 33.59
ATOM  1463 CB  VAL A 185    32.393 15.990 118.259  1.00 35.11
ATOM  1464 CG1 VAL A 185    33.834 15.567 118.003  1.00 23.80
ATOM  1465 CG2 VAL A 185    31.731 15.045 119.242  1.00 26.00
ATOM  1466 C   VAL A 185    33.053 18.354 117.803  1.00 33.11
ATOM  1467 O   VAL A 185    32.545 18.593 116.714  1.00 27.73
ATOM  1468 N   PHE A 186    34.215 18.872 118.184  1.00 31.49
ATOM  1469 CA  PHE A 186    34.985 19.729 117.291  1.00 30.63
ATOM  1470 CB  PHE A 186    35.420 21.023 117.991  1.00 30.34
ATOM  1471 CG  PHE A 186    36.008 22.047 117.051  1.00 30.22
ATOM  1472 CD1 PHE A 186    35.265 23.156 116.656  1.00 32.23
ATOM  1473 CD2 PHE A 186    37.284 21.879 116.524  1.00 29.37
ATOM  1474 CE1 PHE A 186    35.785 24.078 115.748  1.00 27.87
ATOM  1475 CE2 PHE A 186    37.813 22.794 115.615  1.00 28.54
ATOM  1476 CZ  PHE A 186    37.064 23.892 115.227  1.00 30.80
ATOM  1477 C   PHE A 186    36.232 18.952 116.879  1.00 33.38
ATOM  1478 O   PHE A 186    36.952 18.426 117.729  1.00 28.30
ATOM  1479 N   VAL A 187    36.478 18.877 115.574  1.00 32.00
ATOM  1480 CA  VAL A 187    37.645 18.171 115.060  1.00 29.70
ATOM  1481 CB  VAL A 187    37.252 17.095 114.019  1.00 30.03
ATOM  1482 CG1 VAL A 187    38.510 16.488 113.405  1.00 27.77
ATOM  1483 CG2 VAL A 187    36.410 16.003 114.672  1.00 25.98
ATOM  1484 C   VAL A 187    38.604 19.153 114.392  1.00 31.03
ATOM  1485 O   VAL A 187    38.215 19.895 113.491  1.00 31.88
ATOM  1486 N   LEU A 188    39.850 19.157 114.857  1.00 24.88
ATOM  1487 CA  LEU A 188    40.899 20.010 114.304  1.00 26.92
ATOM  1488 CB  LEU A 188    41.468 20.959 115.361  1.00 27.04
ATOM  1489 CG  LEU A 188    42.823 21.565 114.963  1.00 25.15
ATOM  1490 CD1 LEU A 188    42.686 22.315 113.648  1.00 18.53
ATOM  1491 CD2 LEU A 188    43.330 22.485 116.068  1.00 28.81
ATOM  1492 C   LEU A 188    42.022 19.113 113.815  1.00 31.22
ATOM  1493 O   LEU A 188    42.579 18.333 114.587  1.00 25.83
ATOM  1494 N   SER A 189    42.369 19.230 112.540  1.00 30.53
ATOM  1495 CA  SER A 189    43.429 18.399 112.007  1.00 30.13
ATOM  1496 CB  SER A 189    42.821 17.249 111.199  1.00 33.41
ATOM  1497 OG  SER A 189    43.837 16.474 110.588  1.00 32.98
ATOM  1498 C   SER A 189    44.448 19.120 111.143  1.00 27.94
ATOM  1499 O   SER A 189    44.084 19.891 110.253  1.00 22.14
ATOM  1500 N   LEU A 190    45.728 18.877 111.423  1.00 24.80
ATOM  1501 CA  LEU A 190    46.805 19.438 110.614  1.00 22.23
ATOM  1502 CB  LEU A 190    47.955 20.000 111.459  1.00 23.69
ATOM  1503 CG  LEU A 190    47.733 21.075 112.522  1.00 28.92
ATOM  1504 CD1 LEU A 190    49.070 21.780 112.740  1.00 23.01
ATOM  1505 CD2 LEU A 190    46.691 22.093 112.087  1.00 28.11
ATOM  1506 C   LEU A 190    47.300 18.210 109.872  1.00 22.69
ATOM  1507 O   LEU A 190    47.416 17.141 110.465  1.00 16.55
ATOM  1508 N   HIS A 191    47.599 18.353 108.587  1.00 19.22
ATOM  1509 CA  HIS A 191    48.046 17.210 107.804  1.00 23.28
ATOM  1510 CB  HIS A 191    46.870 16.242 107.650  1.00 15.58
ATOM  1511 CG  HIS A 191    45.591 16.915 107.256  1.00 24.16
ATOM  1512 CD2 HIS A 191    45.034 17.124 106.038  1.00 17.71
ATOM  1513 ND1 HIS A 191    44.695 17.419 108.176  1.00 23.76
ATOM  1514 CE1 HIS A 191    43.644 17.913 107.545  1.00 19.78
ATOM  1515 NE2 HIS A 191    43.823 17.746 106.246  1.00 27.87
ATOM  1516 C   HIS A 191    48.570 17.620 106.434  1.00 23.65
ATOM  1517 O   HIS A 191    48.419 18.761 106.017  1.00 23.89
ATOM  1518 N   GLN A 192    49.209 16.681 105.746  1.00 23.49
```

Fig. 18-23

| ATOM | 1519 | CA | GLN | A | 192 | 49.718 | 16.950 | 104.412 | 1.00 | 20.55 |
|---|---|---|---|---|---|---|---|---|---|---|
| ATOM | 1520 | CB | GLN | A | 192 | 50.474 | 15.738 | 103.864 | 1.00 | 23.63 |
| ATOM | 1521 | CG | GLN | A | 192 | 51.528 | 15.181 | 104.797 | 1.00 | 24.07 |
| ATOM | 1522 | CD | GLN | A | 192 | 52.110 | 13.876 | 104.293 | 1.00 | 26.90 |
| ATOM | 1523 | OE1 | GLN | A | 192 | 52.986 | 13.860 | 103.421 | 1.00 | 20.21 |
| ATOM | 1524 | NE2 | GLN | A | 192 | 51.605 | 12.765 | 104.828 | 1.00 | 23.52 |
| ATOM | 1525 | C | GLN | A | 192 | 48.478 | 17.174 | 103.570 | 1.00 | 21.41 |
| ATOM | 1526 | O | GLN | A | 192 | 47.478 | 16.466 | 103.726 | 1.00 | 20.15 |
| ATOM | 1527 | N | SER | A | 193 | 48.528 | 18.167 | 102.692 | 1.00 | 24.36 |
| ATOM | 1528 | CA | SER | A | 193 | 47.397 | 18.448 | 101.821 | 1.00 | 23.98 |
| ATOM | 1529 | CB | SER | A | 193 | 47.760 | 19.537 | 100.820 | 1.00 | 24.60 |
| ATOM | 1530 | OG | SER | A | 193 | 46.729 | 19.660 | 99.861 | 1.00 | 25.83 |
| ATOM | 1531 | C | SER | A | 193 | 46.985 | 17.200 | 101.045 | 1.00 | 23.74 |
| ATOM | 1532 | O | SER | A | 193 | 47.829 | 16.492 | 100.506 | 1.00 | 19.80 |
| ATOM | 1533 | N | PRO | A | 194 | 45.674 | 16.936 | 100.953 | 1.00 | 24.85 |
| ATOM | 1534 | CD | PRO | A | 194 | 44.561 | 17.719 | 101.507 | 1.00 | 25.08 |
| ATOM | 1535 | CA | PRO | A | 194 | 45.151 | 15.772 | 100.235 | 1.00 | 29.25 |
| ATOM | 1536 | CB | PRO | A | 194 | 43.641 | 15.901 | 100.444 | 1.00 | 30.51 |
| ATOM | 1537 | CG | PRO | A | 194 | 43.554 | 16.643 | 101.758 | 1.00 | 30.21 |
| ATOM | 1538 | C | PRO | A | 194 | 45.527 | 15.825 | 98.756 | 1.00 | 30.75 |
| ATOM | 1539 | O | PRO | A | 194 | 45.420 | 14.830 | 98.041 | 1.00 | 30.04 |
| ATOM | 1540 | N | GLU | A | 195 | 45.967 | 16.991 | 98.298 | 1.00 | 26.28 |
| ATOM | 1541 | CA | GLU | A | 195 | 46.343 | 17.127 | 96.898 | 1.00 | 31.11 |
| ATOM | 1542 | CB | GLU | A | 195 | 46.738 | 18.570 | 96.571 | 1.00 | 29.52 |
| ATOM | 1543 | CG | GLU | A | 195 | 45.680 | 19.600 | 96.933 | 1.00 | 38.32 |
| ATOM | 1544 | CD | GLU | A | 195 | 45.976 | 20.972 | 96.352 | 1.00 | 44.15 |
| ATOM | 1545 | OE1 | GLU | A | 195 | 47.139 | 21.425 | 96.434 | 1.00 | 44.23 |
| ATOM | 1546 | OE2 | GLU | A | 195 | 45.037 | 21.605 | 95.825 | 1.00 | 45.06 |
| ATOM | 1547 | C | GLU | A | 195 | 47.499 | 16.193 | 96.552 | 1.00 | 30.81 |
| ATOM | 1548 | O | GLU | A | 195 | 47.582 | 15.705 | 95.426 | 1.00 | 37.17 |
| ATOM | 1549 | N | TYR | A | 196 | 48.377 | 15.922 | 97.515 | 1.00 | 25.01 |
| ATOM | 1550 | CA | TYR | A | 196 | 49.517 | 15.053 | 97.242 | 1.00 | 23.43 |
| ATOM | 1551 | CB | TYR | A | 196 | 50.810 | 15.881 | 97.223 | 1.00 | 26.67 |
| ATOM | 1552 | CG | TYR | A | 196 | 51.255 | 16.424 | 98.572 | 1.00 | 26.78 |
| ATOM | 1553 | CD1 | TYR | A | 196 | 51.957 | 15.625 | 99.476 | 1.00 | 26.08 |
| ATOM | 1554 | CE1 | TYR | A | 196 | 52.338 | 16.110 | 100.734 | 1.00 | 26.77 |
| ATOM | 1555 | CD2 | TYR | A | 196 | 50.944 | 17.731 | 98.958 | 1.00 | 27.55 |
| ATOM | 1556 | CE2 | TYR | A | 196 | 51.320 | 18.226 | 100.216 | 1.00 | 25.95 |
| ATOM | 1557 | CZ | TYR | A | 196 | 52.012 | 17.409 | 101.096 | 1.00 | 24.78 |
| ATOM | 1558 | OH | TYR | A | 196 | 52.356 | 17.879 | 102.345 | 1.00 | 25.50 |
| ATOM | 1559 | C | TYR | A | 196 | 49.670 | 13.906 | 98.229 | 1.00 | 27.05 |
| ATOM | 1560 | O | TYR | A | 196 | 50.585 | 13.088 | 98.096 | 1.00 | 24.02 |
| ATOM | 1561 | N | ALA | A | 197 | 48.785 | 13.822 | 99.214 | 1.00 | 22.10 |
| ATOM | 1562 | CA | ALA | A | 197 | 48.928 | 12.760 | 100.199 | 1.00 | 24.90 |
| ATOM | 1563 | CB | ALA | A | 197 | 49.627 | 13.307 | 101.437 | 1.00 | 27.83 |
| ATOM | 1564 | C | ALA | A | 197 | 47.644 | 12.069 | 100.608 | 1.00 | 26.20 |
| ATOM | 1565 | O | ALA | A | 197 | 46.553 | 12.617 | 100.484 | 1.00 | 22.82 |
| ATOM | 1566 | N | PHE | A | 198 | 47.795 | 10.849 | 101.102 | 1.00 | 31.74 |
| ATOM | 1567 | CA | PHE | A | 198 | 46.663 | 10.072 | 101.580 | 1.00 | 28.74 |
| ATOM | 1568 | CB | PHE | A | 198 | 47.130 | 8.691 | 102.036 | 1.00 | 30.66 |
| ATOM | 1569 | CG | PHE | A | 198 | 46.009 | 7.766 | 102.399 | 1.00 | 29.61 |
| ATOM | 1570 | CD1 | PHE | A | 198 | 45.496 | 6.879 | 101.463 | 1.00 | 28.76 |
| ATOM | 1571 | CD2 | PHE | A | 198 | 45.426 | 7.822 | 103.657 | 1.00 | 28.43 |
| ATOM | 1572 | CE1 | PHE | A | 198 | 44.415 | 6.057 | 101.773 | 1.00 | 35.72 |
| ATOM | 1573 | CE2 | PHE | A | 198 | 44.340 | 7.004 | 103.970 | 1.00 | 34.62 |
| ATOM | 1574 | CZ | PHE | A | 198 | 43.837 | 6.121 | 103.029 | 1.00 | 35.73 |
| ATOM | 1575 | C | PHE | A | 198 | 46.121 | 10.814 | 102.802 | 1.00 | 28.95 |
| ATOM | 1576 | O | PHE | A | 198 | 46.892 | 11.347 | 103.596 | 1.00 | 25.72 |
| ATOM | 1577 | N | PRO | A | 199 | 44.792 | 10.905 | 102.941 | 1.00 | 28.27 |
| ATOM | 1578 | CD | PRO | A | 199 | 44.100 | 11.499 | 104.099 | 1.00 | 33.97 |
| ATOM | 1579 | CA | PRO | A | 199 | 43.313 | 10.364 | 102.008 | 1.00 | 32.80 |
| ATOM | 1580 | CB | PRO | A | 199 | 42.550 | 10.312 | 102.858 | 1.00 | 29.84 |
| ATOM | 1581 | CG | PRO | A | 199 | 42.665 | 11.612 | 103.592 | 1.00 | 37.32 |
| ATOM | 1582 | C | PRO | A | 199 | 43.773 | 11.476 | 100.965 | 1.00 | 35.02 |
| ATOM | 1583 | O | PRO | A | 199 | 44.052 | 12.631 | 101.280 | 1.00 | 48.84 |
| ATOM | 1584 | N | PHE | A | 200 | 43.441 | 11.156 | 99.734 | 1.00 | 33.64 |

Fig. 18-24

| ATOM | 1585 | CA  | PHE | A | 200 | 43.418 | 12.179 | 98.718  | 1.00 | 28.12 |
| ATOM | 1586 | CB  | PHE | A | 200 | 43.927 | 11.579 | 97.411  | 1.00 | 26.69 |
| ATOM | 1587 | CG  | PHE | A | 200 | 45.226 | 10.833 | 97.561  | 1.00 | 27.33 |
| ATOM | 1588 | CD1 | PHE | A | 200 | 45.239 | 9.510  | 97.995  | 1.00 | 29.79 |
| ATOM | 1589 | CD2 | PHE | A | 200 | 46.439 | 11.461 | 97.302  | 1.00 | 24.38 |
| ATOM | 1590 | CE1 | PHE | A | 200 | 46.444 | 8.820  | 98.168  | 1.00 | 29.45 |
| ATOM | 1591 | CE2 | PHE | A | 200 | 47.651 | 10.782 | 97.473  | 1.00 | 31.41 |
| ATOM | 1592 | CZ  | PHE | A | 200 | 47.653 | 9.458  | 97.906  | 1.00 | 29.64 |
| ATOM | 1593 | C   | PHE | A | 200 | 42.042 | 12.795 | 98.518  | 1.00 | 26.15 |
| ATOM | 1594 | O   | PHE | A | 200 | 41.935 | 13.889 | 97.986  | 1.00 | 27.96 |
| ATOM | 1595 | N   | GLU | A | 201 | 41.002 | 12.101 | 98.979  | 1.00 | 28.52 |
| ATOM | 1596 | CA  | GLU | A | 201 | 39.614 | 12.534 | 98.806  | 1.00 | 35.04 |
| ATOM | 1597 | CB  | GLU | A | 201 | 38.695 | 11.316 | 98.818  | 1.00 | 33.61 |
| ATOM | 1598 | CG  | GLU | A | 201 | 39.087 | 10.240 | 97.838  | 1.00 | 37.80 |
| ATOM | 1599 | CD  | GLU | A | 201 | 38.222 | 9.016  | 97.997  | 1.00 | 43.48 |
| ATOM | 1600 | OE1 | GLU | A | 201 | 36.992 | 9.142  | 97.825  | 1.00 | 40.96 |
| ATOM | 1601 | OE2 | GLU | A | 201 | 38.772 | 7.937  | 98.298  | 1.00 | 44.17 |
| ATOM | 1602 | C   | GLU | A | 201 | 39.077 | 13.516 | 99.837  | 1.00 | 36.30 |
| ATOM | 1603 | O   | GLU | A | 201 | 38.087 | 14.206 | 99.592  | 1.00 | 36.47 |
| ATOM | 1604 | N   | LYS | A | 202 | 39.693 | 13.552 | 101.007 | 1.00 | 34.63 |
| ATOM | 1605 | CA  | LYS | A | 202 | 39.229 | 14.460 | 102.030 | 1.00 | 34.09 |
| ATOM | 1606 | CB  | LYS | A | 202 | 38.294 | 13.729 | 102.992 | 1.00 | 40.88 |
| ATOM | 1607 | CG  | LYS | A | 202 | 37.011 | 13.318 | 102.292 | 1.00 | 43.17 |
| ATOM | 1608 | CD  | LYS | A | 202 | 35.935 | 12.854 | 103.230 | 1.00 | 47.39 |
| ATOM | 1609 | CE  | LYS | A | 202 | 34.628 | 12.663 | 102.469 | 1.00 | 47.74 |
| ATOM | 1610 | NZ  | LYS | A | 202 | 33.504 | 12.290 | 103.378 | 1.00 | 53.56 |
| ATOM | 1611 | C   | LYS | A | 202 | 40.382 | 15.101 | 102.753 | 1.00 | 36.27 |
| ATOM | 1612 | O   | LYS | A | 202 | 41.520 | 14.666 | 102.613 | 1.00 | 28.06 |
| ATOM | 1613 | N   | GLY | A | 203 | 40.080 | 16.152 | 103.509 | 1.00 | 31.91 |
| ATOM | 1614 | CA  | GLY | A | 203 | 41.115 | 16.862 | 104.228 | 1.00 | 33.75 |
| ATOM | 1615 | C   | GLY | A | 203 | 41.288 | 18.288 | 103.729 | 1.00 | 30.54 |
| ATOM | 1616 | O   | GLY | A | 203 | 42.174 | 18.996 | 104.200 | 1.00 | 28.04 |
| ATOM | 1617 | N   | PHE | A | 204 | 40.458 | 18.713 | 102.778 | 1.00 | 29.93 |
| ATOM | 1618 | CA  | PHE | A | 204 | 40.557 | 20.077 | 102.260 | 1.00 | 35.76 |
| ATOM | 1619 | CB  | PHE | A | 204 | 39.863 | 20.217 | 100.901 | 1.00 | 31.41 |
| ATOM | 1620 | CG  | PHE | A | 204 | 40.498 | 19.416 | 99.803  | 1.00 | 31.06 |
| ATOM | 1621 | CD1 | PHE | A | 204 | 40.169 | 18.075 | 99.618  | 1.00 | 35.66 |
| ATOM | 1622 | CD2 | PHE | A | 204 | 41.431 | 20.002 | 98.955  | 1.00 | 30.79 |
| ATOM | 1623 | CE1 | PHE | A | 204 | 40.761 | 17.329 | 98.597  | 1.00 | 35.20 |
| ATOM | 1624 | CE2 | PHE | A | 204 | 42.033 | 19.267 | 97.931  | 1.00 | 36.08 |
| ATOM | 1625 | CZ  | PHE | A | 204 | 41.697 | 17.928 | 97.751  | 1.00 | 36.54 |
| ATOM | 1626 | C   | PHE | A | 204 | 39.967 | 21.103 | 103.231 | 1.00 | 37.30 |
| ATOM | 1627 | O   | PHE | A | 204 | 39.088 | 20.786 | 104.040 | 1.00 | 33.56 |
| ATOM | 1628 | N   | LEU | A | 205 | 40.451 | 22.337 | 103.128 | 1.00 | 38.52 |
| ATOM | 1629 | CA  | LEU | A | 205 | 40.012 | 23.427 | 103.993 | 1.00 | 36.81 |
| ATOM | 1630 | CB  | LEU | A | 205 | 40.801 | 24.695 | 103.659 | 1.00 | 34.73 |
| ATOM | 1631 | CG  | LEU | A | 205 | 40.496 | 25.954 | 104.479 | 1.00 | 40.98 |
| ATOM | 1632 | CD1 | LEU | A | 205 | 40.690 | 25.677 | 105.965 | 1.00 | 39.87 |
| ATOM | 1633 | CD2 | LEU | A | 205 | 41.415 | 27.079 | 104.032 | 1.00 | 39.94 |
| ATOM | 1634 | C   | LEU | A | 205 | 38.520 | 23.728 | 103.925 | 1.00 | 36.58 |
| ATOM | 1635 | O   | LEU | A | 205 | 37.931 | 24.178 | 104.905 | 1.00 | 40.98 |
| ATOM | 1636 | N   | GLU | A | 206 | 37.909 | 23.477 | 102.774 | 1.00 | 36.07 |
| ATOM | 1637 | CA  | GLU | A | 206 | 36.486 | 23.748 | 102.586 | 1.00 | 36.30 |
| ATOM | 1638 | CB  | GLU | A | 206 | 36.107 | 23.597 | 101.105 | 1.00 | 39.98 |
| ATOM | 1639 | CG  | GLU | A | 206 | 36.890 | 24.473 | 100.131 | 1.00 | 48.04 |
| ATOM | 1640 | CD  | GLU | A | 206 | 38.307 | 23.980 | 99.868  | 1.00 | 51.87 |
| ATOM | 1641 | OE1 | GLU | A | 206 | 39.146 | 23.993 | 100.792 | 1.00 | 50.32 |
| ATOM | 1642 | OE2 | GLU | A | 206 | 38.581 | 23.569 | 98.716  | 1.00 | 56.69 |
| ATOM | 1643 | C   | GLU | A | 206 | 35.572 | 22.852 | 103.427 | 1.00 | 33.85 |
| ATOM | 1644 | O   | GLU | A | 206 | 34.433 | 23.213 | 103.718 | 1.00 | 26.22 |
| ATOM | 1645 | N   | GLU | A | 207 | 36.071 | 21.679 | 103.805 | 1.00 | 31.68 |
| ATOM | 1646 | CA  | GLU | A | 207 | 35.297 | 20.726 | 104.599 | 1.00 | 31.65 |
| ATOM | 1647 | CB  | GLU | A | 207 | 36.000 | 19.369 | 104.566 | 1.00 | 34.15 |
| ATOM | 1648 | CG  | GLU | A | 207 | 36.044 | 18.741 | 103.179 | 1.00 | 33.80 |
| ATOM | 1649 | CD  | GLU | A | 207 | 37.182 | 17.751 | 103.022 | 1.00 | 33.85 |
| ATOM | 1650 | OE1 | GLU | A | 207 | 37.487 | 17.025 | 103.995 | 1.00 | 33.22 |

Fig. 18-25

```
ATOM   1651  OE2 GLU A 207      37.760  17.688 101.916  1.00 35.48
ATOM   1652  C   GLU A 207      35.182  21.229 106.033  1.00 35.06
ATOM   1653  O   GLU A 207      36.009  20.894 106.887  1.00 34.16
ATOM   1654  N   ILE A 208      34.150  22.024 106.302  1.00 35.99
ATOM   1655  CA  ILE A 208      33.968  22.604 107.634  1.00 38.96
ATOM   1656  CB  ILE A 208      33.737  24.134 107.529  1.00 42.74
ATOM   1657  CG2 ILE A 208      33.717  24.762 108.914  1.00 48.29
ATOM   1658  CG1 ILE A 208      34.841  24.795 106.700  1.00 40.34
ATOM   1659  CD1 ILE A 208      36.207  24.758 107.335  1.00 46.23
ATOM   1660  C   ILE A 208      32.821  21.998 108.452  1.00 38.32
ATOM   1661  O   ILE A 208      32.558  22.434 109.571  1.00 40.08
ATOM   1662  N   GLY A 209      32.142  20.997 107.901  1.00 34.36
ATOM   1663  CA  GLY A 209      31.047  20.374 108.620  1.00 33.32
ATOM   1664  C   GLY A 209      29.699  20.673 107.993  1.00 37.87
ATOM   1665  O   GLY A 209      29.579  21.581 107.173  1.00 40.56
ATOM   1666  N   GLU A 210      28.676  19.917 108.380  1.00 37.38
ATOM   1667  CA  GLU A 210      27.337  20.118 107.831  1.00 42.34
ATOM   1668  CB  GLU A 210      27.008  19.012 106.823  1.00 42.73
ATOM   1669  CG  GLU A 210      26.860  17.636 107.460  1.00 47.38
ATOM   1670  CD  GLU A 210      26.633  16.532 106.443  1.00 52.68
ATOM   1671  OE1 GLU A 210      26.385  15.379 106.860  1.00 50.59
ATOM   1672  OE2 GLU A 210      26.711  16.810 105.226  1.00 53.78
ATOM   1673  C   GLU A 210      26.287  20.114 108.938  1.00 42.90
ATOM   1674  O   GLU A 210      26.516  19.577 110.022  1.00 45.94
ATOM   1675  N   GLY A 211      25.130  20.702 108.654  1.00 43.16
ATOM   1676  CA  GLY A 211      24.068  20.751 109.642  1.00 43.98
ATOM   1677  C   GLY A 211      24.514  21.450 110.911  1.00 45.01
ATOM   1678  O   GLY A 211      25.186  22.479 110.858  1.00 48.15
ATOM   1679  N   LYS A 212      24.145  20.896 112.059  1.00 41.63
ATOM   1680  CA  LYS A 212      24.528  21.495 113.328  1.00 45.07
ATOM   1681  CB  LYS A 212      23.913  20.715 114.490  1.00 46.59
ATOM   1682  CG  LYS A 212      22.386  20.591 114.462  1.00 55.31
ATOM   1683  CD  LYS A 212      21.651  21.945 114.481  1.00 57.42
ATOM   1684  CE  LYS A 212      21.749  22.696 113.151  1.00 59.71
ATOM   1685  NZ  LYS A 212      21.051  24.017 113.178  1.00 57.43
ATOM   1686  C   LYS A 212      26.046  21.513 113.469  1.00 42.08
ATOM   1687  O   LYS A 212      26.598  22.326 114.207  1.00 40.03
ATOM   1688  N   GLY A 213      26.713  20.615 112.751  1.00 39.51
ATOM   1689  CA  GLY A 213      28.163  20.538 112.817  1.00 40.11
ATOM   1690  C   GLY A 213      28.888  21.519 111.916  1.00 38.25
ATOM   1691  O   GLY A 213      30.122  21.575 111.913  1.00 34.70
ATOM   1692  N   LYS A 214      28.131  22.295 111.143  1.00 37.31
ATOM   1693  CA  LYS A 214      28.736  23.274 110.250  1.00 39.58
ATOM   1694  CB  LYS A 214      27.656  24.017 109.463  1.00 44.69
ATOM   1695  CG  LYS A 214      28.189  25.030 108.461  1.00 44.53
ATOM   1696  CD  LYS A 214      27.047  25.704 107.720  1.00 47.71
ATOM   1697  CE  LYS A 214      27.553  26.759 106.754  1.00 52.94
ATOM   1698  NZ  LYS A 214      28.453  26.183 105.717  1.00 57.45
ATOM   1699  C   LYS A 214      29.547  24.259 111.085  1.00 40.16
ATOM   1700  O   LYS A 214      29.002  24.963 111.933  1.00 37.92
ATOM   1701  N   GLY A 215      30.851  24.295 110.846  1.00 36.57
ATOM   1702  CA  GLY A 215      31.716  25.183 111.593  1.00 35.03
ATOM   1703  C   GLY A 215      32.431  24.448 112.709  1.00 34.57
ATOM   1704  O   GLY A 215      33.216  25.039 113.454  1.00 33.76
ATOM   1705  N   TYR A 216      32.168  23.153 112.837  1.00 34.61
ATOM   1706  CA  TYR A 216      32.816  22.378 113.885  1.00 35.00
ATOM   1707  CB  TYR A 216      31.763  21.683 114.753  1.00 36.19
ATOM   1708  CG  TYR A 216      30.928  22.671 115.547  1.00 36.68
ATOM   1709  CD1 TYR A 216      29.961  23.462 114.925  1.00 35.83
ATOM   1710  CE1 TYR A 216      29.249  24.431 115.641  1.00 40.89
ATOM   1711  CD2 TYR A 216      31.163  22.869 116.910  1.00 41.50
ATOM   1712  CE2 TYR A 216      30.459  23.834 117.634  1.00 40.69
ATOM   1713  CZ  TYR A 216      29.505  24.612 116.994  1.00 40.17
ATOM   1714  OH  TYR A 216      28.816  25.566 117.708  1.00 38.09
ATOM   1715  C   TYR A 216      33.877  21.384 113.401  1.00 34.05
ATOM   1716  O   TYR A 216      34.263  20.462 114.127  1.00 31.87
```

Fig. 18-26

| | | | | | | | | |
|---|---|---|---|---|---|---|---|---|
| ATOM | 1717 | N | ASN | A | 217 | 34.343 | 21.580 | 112.170 | 1.00 | 29.90 |
| ATOM | 1718 | CA | ASN | A | 217 | 35.398 | 20.748 | 111.606 | 1.00 | 30.02 |
| ATOM | 1719 | CB | ASN | A | 217 | 34.833 | 19.727 | 110.615 | 1.00 | 26.46 |
| ATOM | 1720 | CG | ASN | A | 217 | 35.897 | 18.764 | 110.105 | 1.00 | 30.13 |
| ATOM | 1721 | OD1 | ASN | A | 217 | 36.558 | 19.022 | 109.097 | 1.00 | 29.80 |
| ATOM | 1722 | ND2 | ASN | A | 217 | 36.094 | 17.659 | 110.831 | 1.00 | 19.92 |
| ATOM | 1723 | C | ASN | A | 217 | 36.378 | 21.686 | 110.915 | 1.00 | 30.23 |
| ATOM | 1724 | O | ASN | A | 217 | 35.983 | 22.502 | 110.080 | 1.00 | 27.88 |
| ATOM | 1725 | N | LEU | A | 218 | 37.655 | 21.577 | 111.271 | 1.00 | 29.45 |
| ATOM | 1726 | CA | LEU | A | 218 | 38.670 | 22.451 | 110.698 | 1.00 | 28.76 |
| ATOM | 1727 | CB | LEU | A | 218 | 39.160 | 23.444 | 111.753 | 1.00 | 29.02 |
| ATOM | 1728 | CG | LEU | A | 218 | 39.513 | 24.867 | 111.307 | 1.00 | 34.69 |
| ATOM | 1729 | CD1 | LEU | A | 218 | 40.432 | 25.480 | 112.367 | 1.00 | 32.93 |
| ATOM | 1730 | CD2 | LEU | A | 218 | 40.197 | 24.873 | 109.954 | 1.00 | 30.69 |
| ATOM | 1731 | C | LEU | A | 218 | 39.870 | 21.657 | 110.207 | 1.00 | 26.65 |
| ATOM | 1732 | O | LEU | A | 218 | 40.527 | 20.981 | 110.999 | 1.00 | 25.25 |
| ATOM | 1733 | N | ASN | A | 219 | 40.151 | 21.752 | 108.909 | 1.00 | 25.21 |
| ATOM | 1734 | CA | ASN | A | 219 | 41.287 | 21.069 | 108.294 | 1.00 | 21.91 |
| ATOM | 1735 | CB | ASN | A | 219 | 40.875 | 20.314 | 107.018 | 1.00 | 23.69 |
| ATOM | 1736 | CG | ASN | A | 219 | 39.972 | 19.144 | 107.298 | 1.00 | 27.88 |
| ATOM | 1737 | OD1 | ASN | A | 219 | 40.153 | 18.440 | 108.289 | 1.00 | 29.28 |
| ATOM | 1738 | ND2 | ASN | A | 219 | 39.018 | 18.900 | 106.407 | 1.00 | 24.48 |
| ATOM | 1739 | C | ASN | A | 219 | 42.355 | 22.074 | 107.906 | 1.00 | 23.46 |
| ATOM | 1740 | O | ASN | A | 219 | 42.059 | 23.073 | 107.259 | 1.00 | 28.17 |
| ATOM | 1741 | N | ILE | A | 220 | 43.595 | 21.804 | 108.287 | 1.00 | 23.90 |
| ATOM | 1742 | CA | ILE | A | 220 | 44.702 | 22.684 | 107.945 | 1.00 | 23.22 |
| ATOM | 1743 | CB | ILE | A | 220 | 45.468 | 23.131 | 109.212 | 1.00 | 28.73 |
| ATOM | 1744 | CG2 | ILE | A | 220 | 46.601 | 24.078 | 108.831 | 1.00 | 26.01 |
| ATOM | 1745 | CG1 | ILE | A | 220 | 44.502 | 23.783 | 110.212 | 1.00 | 26.36 |
| ATOM | 1746 | CD1 | ILE | A | 220 | 43.771 | 25.004 | 109.688 | 1.00 | 25.74 |
| ATOM | 1747 | C | ILE | A | 220 | 45.669 | 21.929 | 107.018 | 1.00 | 25.29 |
| ATOM | 1748 | O | ILE | A | 220 | 46.631 | 21.315 | 107.477 | 1.00 | 20.44 |
| ATOM | 1749 | N | PRO | A | 221 | 45.396 | 21.924 | 105.703 | 1.00 | 26.34 |
| ATOM | 1750 | CD | PRO | A | 221 | 44.234 | 22.497 | 104.999 | 1.00 | 28.22 |
| ATOM | 1751 | CA | PRO | A | 221 | 46.271 | 21.234 | 104.747 | 1.00 | 26.92 |
| ATOM | 1752 | CB | PRO | A | 221 | 45.454 | 21.279 | 103.457 | 1.00 | 27.81 |
| ATOM | 1753 | CG | PRO | A | 221 | 44.774 | 22.622 | 103.582 | 1.00 | 30.62 |
| ATOM | 1754 | C | PRO | A | 221 | 47.595 | 21.977 | 104.625 | 1.00 | 27.45 |
| ATOM | 1755 | O | PRO | A | 221 | 47.603 | 23.199 | 104.457 | 1.00 | 31.21 |
| ATOM | 1756 | N | LEU | A | 222 | 48.704 | 21.242 | 104.703 | 1.00 | 26.01 |
| ATOM | 1757 | CA | LEU | A | 222 | 50.038 | 21.838 | 104.640 | 1.00 | 26.41 |
| ATOM | 1758 | CB | LEU | A | 222 | 50.726 | 21.650 | 105.997 | 1.00 | 26.12 |
| ATOM | 1759 | CG | LEU | A | 222 | 49.960 | 22.322 | 107.150 | 1.00 | 27.67 |
| ATOM | 1760 | CD1 | LEU | A | 222 | 50.531 | 21.899 | 108.497 | 1.00 | 30.97 |
| ATOM | 1761 | CD2 | LEU | A | 222 | 50.024 | 23.839 | 106.985 | 1.00 | 31.59 |
| ATOM | 1762 | C | LEU | A | 222 | 50.911 | 21.286 | 103.504 | 1.00 | 28.97 |
| ATOM | 1763 | O | LEU | A | 222 | 50.784 | 20.128 | 103.117 | 1.00 | 27.95 |
| ATOM | 1764 | N | PRO | A | 223 | 51.821 | 22.116 | 102.964 | 1.00 | 31.52 |
| ATOM | 1765 | CD | PRO | A | 223 | 52.059 | 23.518 | 103.358 | 1.00 | 29.08 |
| ATOM | 1766 | CA | PRO | A | 223 | 52.727 | 21.753 | 101.865 | 1.00 | 29.93 |
| ATOM | 1767 | CB | PRO | A | 223 | 53.265 | 23.109 | 101.428 | 1.00 | 29.16 |
| ATOM | 1768 | CG | PRO | A | 223 | 53.458 | 23.771 | 102.779 | 1.00 | 25.86 |
| ATOM | 1769 | C | PRO | A | 223 | 53.862 | 20.782 | 102.206 | 1.00 | 33.62 |
| ATOM | 1770 | O | PRO | A | 223 | 54.179 | 20.531 | 103.376 | 1.00 | 26.55 |
| ATOM | 1771 | N | LYS | A | 224 | 54.479 | 20.257 | 101.153 | 1.00 | 34.00 |
| ATOM | 1772 | CA | LYS | A | 224 | 55.595 | 19.320 | 101.264 | 1.00 | 32.88 |
| ATOM | 1773 | CB | LYS | A | 224 | 55.938 | 18.767 | 99.884 | 1.00 | 36.31 |
| ATOM | 1774 | CG | LYS | A | 224 | 54.761 | 18.204 | 99.115 | 1.00 | 39.37 |
| ATOM | 1775 | CD | LYS | A | 224 | 55.150 | 17.998 | 97.658 | 1.00 | 45.23 |
| ATOM | 1776 | CE | LYS | A | 224 | 53.989 | 17.478 | 96.835 | 1.00 | 47.90 |
| ATOM | 1777 | NZ | LYS | A | 224 | 54.331 | 17.441 | 95.388 | 1.00 | 46.60 |
| ATOM | 1778 | C | LYS | A | 224 | 56.817 | 20.054 | 101.798 | 1.00 | 29.43 |
| ATOM | 1779 | O | LYS | A | 224 | 56.933 | 21.270 | 101.640 | 1.00 | 24.10 |
| ATOM | 1780 | N | GLY | A | 225 | 57.735 | 19.305 | 102.403 | 1.00 | 25.00 |
| ATOM | 1781 | CA | GLY | A | 225 | 58.947 | 19.896 | 102.942 | 1.00 | 26.20 |
| ATOM | 1782 | C | GLY | A | 225 | 58.727 | 20.792 | 104.154 | 1.00 | 29.44 |

Fig. 18-27

| ATOM | 1783 | O   | GLY | A | 225 | 59.610 | 21.562 | 104.528 | 1.00 | 29.09 |
| --- | --- | --- | --- | --- | --- | --- | --- | --- | --- | --- |
| ATOM | 1784 | N   | LEU | A | 226 | 57.560 | 20.679 | 104.777 | 1.00 | 24.26 |
| ATOM | 1785 | CA  | LEU | A | 226 | 57.212 | 21.488 | 105.951 | 1.00 | 25.35 |
| ATOM | 1786 | CB  | LEU | A | 226 | 55.930 | 20.925 | 106.579 | 1.00 | 23.23 |
| ATOM | 1787 | CG  | LEU | A | 226 | 55.172 | 21.757 | 107.611 | 1.00 | 28.28 |
| ATOM | 1788 | CD1 | LEU | A | 226 | 54.596 | 22.972 | 106.911 | 1.00 | 28.07 |
| ATOM | 1789 | CD2 | LEU | A | 226 | 54.036 | 20.933 | 108.226 | 1.00 | 27.49 |
| ATOM | 1790 | C   | LEU | A | 226 | 58.333 | 21.501 | 106.998 | 1.00 | 24.79 |
| ATOM | 1791 | O   | LEU | A | 226 | 58.902 | 20.450 | 107.299 | 1.00 | 26.15 |
| ATOM | 1792 | N   | ASN | A | 227 | 58.664 | 22.674 | 107.548 | 1.00 | 23.94 |
| ATOM | 1793 | CA  | ASN | A | 227 | 59.702 | 22.733 | 108.578 | 1.00 | 24.89 |
| ATOM | 1794 | CB  | ASN | A | 227 | 60.751 | 23.823 | 108.269 | 1.00 | 27.43 |
| ATOM | 1795 | CG  | ASN | A | 227 | 60.190 | 25.231 | 108.334 | 1.00 | 31.62 |
| ATOM | 1796 | OD1 | ASN | A | 227 | 59.598 | 25.632 | 109.336 | 1.00 | 31.17 |
| ATOM | 1797 | ND2 | ASN | A | 227 | 60.395 | 25.998 | 107.267 | 1.00 | 28.06 |
| ATOM | 1798 | C   | ASN | A | 227 | 59.076 | 22.957 | 109.960 | 1.00 | 23.16 |
| ATOM | 1799 | O   | ASN | A | 227 | 57.873 | 23.206 | 110.065 | 1.00 | 18.45 |
| ATOM | 1800 | N   | ASP | A | 228 | 59.880 | 22.862 | 111.018 | 1.00 | 21.29 |
| ATOM | 1801 | CA  | ASP | A | 228 | 59.357 | 23.032 | 112.375 | 1.00 | 25.80 |
| ATOM | 1802 | CB  | ASP | A | 228 | 60.464 | 22.893 | 113.426 | 1.00 | 24.02 |
| ATOM | 1803 | CG  | ASP | A | 228 | 61.110 | 21.520 | 113.422 | 1.00 | 26.48 |
| ATOM | 1804 | OD1 | ASP | A | 228 | 60.410 | 20.530 | 113.135 | 1.00 | 29.55 |
| ATOM | 1805 | OD2 | ASP | A | 228 | 62.311 | 21.425 | 113.744 | 1.00 | 29.88 |
| ATOM | 1806 | C   | ASP | A | 228 | 58.628 | 24.341 | 112.620 | 1.00 | 27.83 |
| ATOM | 1807 | O   | ASP | A | 228 | 57.589 | 24.360 | 113.284 | 1.00 | 25.68 |
| ATOM | 1808 | N   | ASN | A | 229 | 59.167 | 25.437 | 112.098 | 1.00 | 25.78 |
| ATOM | 1809 | CA  | ASN | A | 229 | 58.537 | 26.739 | 112.297 | 1.00 | 27.75 |
| ATOM | 1810 | CB  | ASN | A | 229 | 59.453 | 27.850 | 111.770 | 1.00 | 32.77 |
| ATOM | 1811 | CG  | ASN | A | 229 | 60.707 | 28.020 | 112.621 | 1.00 | 30.35 |
| ATOM | 1812 | OD1 | ASN | A | 229 | 60.635 | 28.433 | 113.782 | 1.00 | 33.12 |
| ATOM | 1813 | ND2 | ASN | A | 229 | 61.856 | 27.691 | 112.053 | 1.00 | 28.11 |
| ATOM | 1814 | C   | ASN | A | 229 | 57.168 | 26.817 | 111.645 | 1.00 | 29.47 |
| ATOM | 1815 | O   | ASN | A | 229 | 56.230 | 27.387 | 112.202 | 1.00 | 26.75 |
| ATOM | 1816 | N   | GLU | A | 230 | 57.041 | 26.228 | 110.463 | 1.00 | 30.80 |
| ATOM | 1817 | CA  | GLU | A | 230 | 55.761 | 26.244 | 109.773 | 1.00 | 30.77 |
| ATOM | 1818 | CB  | GLU | A | 230 | 55.929 | 25.716 | 108.341 | 1.00 | 29.11 |
| ATOM | 1819 | CG  | GLU | A | 230 | 56.897 | 26.531 | 107.507 | 1.00 | 35.94 |
| ATOM | 1820 | CD  | GLU | A | 230 | 57.119 | 25.946 | 106.125 | 1.00 | 37.77 |
| ATOM | 1821 | OE1 | GLU | A | 230 | 57.465 | 24.748 | 106.039 | 1.00 | 38.98 |
| ATOM | 1822 | OE2 | GLU | A | 230 | 56.957 | 26.684 | 105.129 | 1.00 | 31.32 |
| ATOM | 1823 | C   | GLU | A | 230 | 54.723 | 25.407 | 110.527 | 1.00 | 30.13 |
| ATOM | 1824 | O   | GLU | A | 230 | 53.563 | 25.799 | 110.631 | 1.00 | 28.35 |
| ATOM | 1825 | N   | PHE | A | 231 | 55.141 | 24.262 | 111.060 | 1.00 | 32.49 |
| ATOM | 1826 | CA  | PHE | A | 231 | 54.223 | 23.386 | 111.790 | 1.00 | 28.54 |
| ATOM | 1827 | CB  | PHE | A | 231 | 54.913 | 22.075 | 112.191 | 1.00 | 31.22 |
| ATOM | 1828 | CG  | PHE | A | 231 | 53.974 | 21.050 | 112.781 | 1.00 | 28.41 |
| ATOM | 1829 | CD1 | PHE | A | 231 | 53.026 | 20.417 | 111.982 | 1.00 | 29.66 |
| ATOM | 1830 | CD2 | PHE | A | 231 | 54.036 | 20.723 | 114.130 | 1.00 | 28.38 |
| ATOM | 1831 | CE1 | PHE | A | 231 | 52.153 | 19.469 | 112.518 | 1.00 | 25.79 |
| ATOM | 1832 | CE2 | PHE | A | 231 | 53.166 | 19.774 | 114.681 | 1.00 | 31.40 |
| ATOM | 1833 | CZ  | PHE | A | 231 | 52.223 | 19.146 | 113.870 | 1.00 | 30.51 |
| ATOM | 1834 | C   | PHE | A | 231 | 53.693 | 24.065 | 113.045 | 1.00 | 26.85 |
| ATOM | 1835 | O   | PHE | A | 231 | 52.483 | 24.092 | 113.277 | 1.00 | 25.99 |
| ATOM | 1836 | N   | LEU | A | 232 | 54.598 | 24.607 | 113.858 | 1.00 | 26.75 |
| ATOM | 1837 | CA  | LEU | A | 232 | 54.193 | 25.283 | 115.092 | 1.00 | 27.25 |
| ATOM | 1838 | CB  | LEU | A | 232 | 55.422 | 25.617 | 115.933 | 1.00 | 25.15 |
| ATOM | 1839 | CG  | LEU | A | 232 | 56.176 | 24.372 | 116.420 | 1.00 | 28.11 |
| ATOM | 1840 | CD1 | LEU | A | 232 | 57.440 | 24.783 | 117.162 | 1.00 | 27.32 |
| ATOM | 1841 | CD2 | LEU | A | 232 | 55.268 | 23.540 | 117.328 | 1.00 | 27.87 |
| ATOM | 1842 | C   | LEU | A | 232 | 53.371 | 26.542 | 114.800 | 1.00 | 26.98 |
| ATOM | 1843 | O   | LEU | A | 232 | 52.449 | 26.866 | 115.544 | 1.00 | 23.34 |
| ATOM | 1844 | N   | PHE | A | 233 | 53.694 | 27.232 | 113.708 | 1.00 | 24.99 |
| ATOM | 1845 | CA  | PHE | A | 233 | 52.950 | 28.426 | 113.312 | 1.00 | 28.13 |
| ATOM | 1846 | CB  | PHE | A | 233 | 53.542 | 29.029 | 112.029 | 1.00 | 30.77 |
| ATOM | 1847 | CG  | PHE | A | 233 | 52.719 | 30.151 | 111.448 | 1.00 | 29.65 |
| ATOM | 1848 | CD1 | PHE | A | 233 | 52.803 | 31.441 | 111.962 | 1.00 | 32.80 |

Fig. 18-28

| | | | | | | | | |
|---|---|---|---|---|---|---|---|---|
| ATOM | 1849 | CD2 | PHE | A | 233 | 51.825 | 29.903 | 110.412 | 1.00 | 31.59 |
| ATOM | 1850 | CE1 | PHE | A | 233 | 52.008 | 32.468 | 111.452 | 1.00 | 33.90 |
| ATOM | 1851 | CE2 | PHE | A | 233 | 51.022 | 30.924 | 109.895 | 1.00 | 32.47 |
| ATOM | 1852 | CZ | PHE | A | 233 | 51.114 | 32.208 | 110.415 | 1.00 | 32.50 |
| ATOM | 1853 | C | PHE | A | 233 | 51.510 | 27.999 | 113.031 | 1.00 | 31.62 |
| ATOM | 1854 | O | PHE | A | 233 | 50.553 | 28.603 | 113.532 | 1.00 | 25.88 |
| ATOM | 1855 | N | ALA | A | 234 | 51.370 | 26.955 | 112.215 | 1.00 | 28.12 |
| ATOM | 1856 | CA | ALA | A | 234 | 50.056 | 26.436 | 111.853 | 1.00 | 25.68 |
| ATOM | 1857 | CB | ALA | A | 234 | 50.195 | 25.279 | 110.864 | 1.00 | 20.08 |
| ATOM | 1858 | C | ALA | A | 234 | 49.304 | 25.969 | 113.089 | 1.00 | 25.17 |
| ATOM | 1859 | O | ALA | A | 234 | 48.114 | 26.228 | 113.234 | 1.00 | 25.21 |
| ATOM | 1860 | N | LEU | A | 235 | 50.002 | 25.285 | 113.987 | 1.00 | 28.18 |
| ATOM | 1861 | CA | LEU | A | 235 | 49.367 | 24.781 | 115.195 | 1.00 | 33.70 |
| ATOM | 1862 | CB | LEU | A | 235 | 50.356 | 23.964 | 116.026 | 1.00 | 32.70 |
| ATOM | 1863 | CG | LEU | A | 235 | 49.772 | 22.788 | 116.820 | 1.00 | 36.89 |
| ATOM | 1864 | CD1 | LEU | A | 235 | 50.634 | 22.545 | 118.052 | 1.00 | 31.37 |
| ATOM | 1865 | CD2 | LEU | A | 235 | 48.344 | 23.072 | 117.231 | 1.00 | 31.47 |
| ATOM | 1866 | C | LEU | A | 235 | 48.841 | 25.925 | 116.062 | 1.00 | 33.38 |
| ATOM | 1867 | O | LEU | A | 235 | 47.673 | 25.926 | 116.455 | 1.00 | 28.13 |
| ATOM | 1868 | N | GLU | A | 236 | 49.710 | 26.888 | 116.362 | 1.00 | 34.02 |
| ATOM | 1869 | CA | GLU | A | 236 | 49.336 | 28.026 | 117.199 | 1.00 | 37.30 |
| ATOM | 1870 | CB | GLU | A | 236 | 50.528 | 28.972 | 117.400 | 1.00 | 41.51 |
| ATOM | 1871 | CG | GLU | A | 236 | 51.675 | 28.356 | 118.188 | 1.00 | 49.54 |
| ATOM | 1872 | CD | GLU | A | 236 | 52.811 | 29.334 | 118.451 | 1.00 | 55.02 |
| ATOM | 1873 | OE1 | GLU | A | 236 | 53.781 | 28.947 | 119.140 | 1.00 | 56.19 |
| ATOM | 1874 | OE2 | GLU | A | 236 | 52.735 | 30.486 | 117.968 | 1.00 | 54.84 |
| ATOM | 1875 | C | GLU | A | 236 | 48.163 | 28.803 | 116.638 | 1.00 | 33.98 |
| ATOM | 1876 | O | GLU | A | 236 | 47.211 | 29.098 | 117.362 | 1.00 | 37.01 |
| ATOM | 1877 | N | LYS | A | 237 | 48.223 | 29.137 | 115.354 | 1.00 | 33.94 |
| ATOM | 1878 | CA | LYS | A | 237 | 47.140 | 29.888 | 114.726 | 1.00 | 33.10 |
| ATOM | 1879 | CB | LYS | A | 237 | 47.505 | 30.244 | 113.281 | 1.00 | 36.08 |
| ATOM | 1880 | CG | LYS | A | 237 | 48.695 | 31.186 | 113.165 | 1.00 | 33.62 |
| ATOM | 1881 | CD | LYS | A | 237 | 48.395 | 32.508 | 113.856 | 1.00 | 37.99 |
| ATOM | 1882 | CE | LYS | A | 237 | 49.569 | 33.471 | 113.762 | 1.00 | 45.24 |
| ATOM | 1883 | NZ | LYS | A | 237 | 49.285 | 34.737 | 114.500 | 1.00 | 43.49 |
| ATOM | 1884 | C | LYS | A | 237 | 45.820 | 29.128 | 114.751 | 1.00 | 31.40 |
| ATOM | 1885 | O | LYS | A | 237 | 44.793 | 29.680 | 115.131 | 1.00 | 31.67 |
| ATOM | 1886 | N | SER | A | 238 | 45.841 | 27.861 | 114.354 | 1.00 | 28.72 |
| ATOM | 1887 | CA | SER | A | 238 | 44.610 | 27.080 | 114.335 | 1.00 | 31.74 |
| ATOM | 1888 | CB | SER | A | 238 | 44.834 | 25.720 | 113.660 | 1.00 | 28.90 |
| ATOM | 1889 | OG | SER | A | 238 | 45.760 | 24.924 | 114.372 | 1.00 | 25.18 |
| ATOM | 1890 | C | SER | A | 238 | 44.041 | 26.891 | 115.740 | 1.00 | 33.23 |
| ATOM | 1891 | O | SER | A | 238 | 42.823 | 26.875 | 115.916 | 1.00 | 34.79 |
| ATOM | 1892 | N | LEU | A | 239 | 44.907 | 26.742 | 116.741 | 1.00 | 35.27 |
| ATOM | 1893 | CA | LEU | A | 239 | 44.413 | 26.587 | 118.108 | 1.00 | 37.57 |
| ATOM | 1894 | CB | LEU | A | 239 | 45.554 | 26.307 | 119.090 | 1.00 | 38.58 |
| ATOM | 1895 | CG | LEU | A | 239 | 46.176 | 24.907 | 119.038 | 1.00 | 39.74 |
| ATOM | 1896 | CD1 | LEU | A | 239 | 47.276 | 24.797 | 120.075 | 1.00 | 35.82 |
| ATOM | 1897 | CD2 | LEU | A | 239 | 45.109 | 23.861 | 119.301 | 1.00 | 34.93 |
| ATOM | 1898 | C | LEU | A | 239 | 43.670 | 27.852 | 118.521 | 1.00 | 39.09 |
| ATOM | 1899 | O | LEU | A | 239 | 42.628 | 27.782 | 119.174 | 1.00 | 35.50 |
| ATOM | 1900 | N | GLU | A | 240 | 44.202 | 29.007 | 118.131 | 1.00 | 39.27 |
| ATOM | 1901 | CA | GLU | A | 240 | 43.561 | 30.281 | 118.450 | 1.00 | 40.15 |
| ATOM | 1902 | CB | GLU | A | 240 | 44.366 | 31.448 | 117.883 | 1.00 | 40.42 |
| ATOM | 1903 | CG | GLU | A | 240 | 45.661 | 31.747 | 118.602 | 1.00 | 43.91 |
| ATOM | 1904 | CD | GLU | A | 240 | 46.407 | 32.884 | 117.942 | 1.00 | 49.31 |
| ATOM | 1905 | OE1 | GLU | A | 240 | 45.772 | 33.925 | 117.665 | 1.00 | 49.00 |
| ATOM | 1906 | OE2 | GLU | A | 240 | 47.624 | 32.745 | 117.705 | 1.00 | 54.05 |
| ATOM | 1907 | C | GLU | A | 240 | 42.165 | 30.312 | 117.849 | 1.00 | 39.58 |
| ATOM | 1908 | O | GLU | A | 240 | 41.224 | 30.822 | 118.455 | 1.00 | 40.99 |
| ATOM | 1909 | N | ILE | A | 241 | 42.039 | 29.764 | 116.645 | 1.00 | 35.70 |
| ATOM | 1910 | CA | ILE | A | 241 | 40.754 | 29.726 | 115.964 | 1.00 | 38.23 |
| ATOM | 1911 | CB | ILE | A | 241 | 40.904 | 29.150 | 114.546 | 1.00 | 37.55 |
| ATOM | 1912 | CG2 | ILE | A | 241 | 39.535 | 29.005 | 113.895 | 1.00 | 37.30 |
| ATOM | 1913 | CG1 | ILE | A | 241 | 41.832 | 30.048 | 113.724 | 1.00 | 38.36 |
| ATOM | 1914 | CD1 | ILE | A | 241 | 42.106 | 29.541 | 112.320 | 1.00 | 36.15 |

Fig. 18-29

| | | | | | | | | |
|---|---|---|---|---|---|---|---|---|
| ATOM | 1915 | C | | ILE | A | 241 | 39.751 | 28.881 | 116.737 | 1.00 | 37.31 |
| ATOM | 1916 | O | | ILE | A | 241 | 38.591 | 29.264 | 116.884 | 1.00 | 37.91 |
| ATOM | 1917 | N | | VAL | A | 242 | 40.203 | 27.732 | 117.231 | 1.00 | 37.07 |
| ATOM | 1918 | CA | | VAL | A | 242 | 39.336 | 26.832 | 117.981 | 1.00 | 38.35 |
| ATOM | 1919 | CB | | VAL | A | 242 | 40.025 | 25.477 | 118.250 | 1.00 | 37.58 |
| ATOM | 1920 | CG1 | | VAL | A | 242 | 39.120 | 24.581 | 119.078 | 1.00 | 31.91 |
| ATOM | 1921 | CG2 | | VAL | A | 242 | 40.364 | 24.803 | 116.928 | 1.00 | 39.21 |
| ATOM | 1922 | C | | VAL | A | 242 | 38.930 | 27.451 | 119.305 | 1.00 | 40.40 |
| ATOM | 1923 | O | | VAL | A | 242 | 37.759 | 27.422 | 119.675 | 1.00 | 38.19 |
| ATOM | 1924 | N | | LYS | A | 243 | 39.905 | 28.008 | 120.014 | 1.00 | 45.47 |
| ATOM | 1925 | CA | | LYS | A | 243 | 39.661 | 28.654 | 121.301 | 1.00 | 48.74 |
| ATOM | 1926 | CB | | LYS | A | 243 | 40.945 | 29.319 | 121.801 | 1.00 | 51.01 |
| ATOM | 1927 | CG | | LYS | A | 243 | 41.853 | 28.426 | 122.614 | 1.00 | 56.09 |
| ATOM | 1928 | CD | | LYS | A | 243 | 41.250 | 28.149 | 123.991 | 1.00 | 57.39 |
| ATOM | 1929 | CE | | LYS | A | 243 | 41.054 | 29.436 | 124.783 | 1.00 | 59.53 |
| ATOM | 1930 | NZ | | LYS | A | 243 | 40.448 | 29.193 | 126.127 | 1.00 | 57.91 |
| ATOM | 1931 | C | | LYS | A | 243 | 38.559 | 29.705 | 121.260 | 1.00 | 51.67 |
| ATOM | 1932 | O | | LYS | A | 243 | 37.815 | 29.871 | 122.226 | 1.00 | 52.84 |
| ATOM | 1933 | N | | GLU | A | 244 | 38.451 | 30.410 | 120.140 | 1.00 | 53.77 |
| ATOM | 1934 | CA | | GLU | A | 244 | 37.460 | 31.471 | 120.004 | 1.00 | 54.74 |
| ATOM | 1935 | CB | | GLU | A | 244 | 37.954 | 32.497 | 118.986 | 1.00 | 55.15 |
| ATOM | 1936 | CG | | GLU | A | 244 | 37.068 | 33.717 | 118.865 | 1.00 | 60.63 |
| ATOM | 1937 | CD | | GLU | A | 244 | 37.602 | 34.714 | 117.868 | 1.00 | 65.87 |
| ATOM | 1938 | OE1 | | GLU | A | 244 | 38.746 | 35.181 | 118.053 | 1.00 | 70.36 |
| ATOM | 1939 | OE2 | | GLU | A | 244 | 36.879 | 35.031 | 116.900 | 1.00 | 67.09 |
| ATOM | 1940 | C | | GLU | A | 244 | 36.051 | 31.025 | 119.626 | 1.00 | 52.65 |
| ATOM | 1941 | O | | GLU | A | 244 | 35.127 | 31.838 | 119.606 | 1.00 | 55.59 |
| ATOM | 1942 | N | | VAL | A | 245 | 35.869 | 29.745 | 119.332 | 1.00 | 50.57 |
| ATOM | 1943 | CA | | VAL | A | 245 | 34.546 | 29.269 | 118.947 | 1.00 | 45.75 |
| ATOM | 1944 | CB | | VAL | A | 245 | 34.475 | 29.081 | 117.409 | 1.00 | 46.91 |
| ATOM | 1945 | CG1 | | VAL | A | 245 | 33.085 | 28.634 | 116.986 | 1.00 | 52.62 |
| ATOM | 1946 | CG2 | | VAL | A | 245 | 34.825 | 30.389 | 116.716 | 1.00 | 48.34 |
| ATOM | 1947 | C | | VAL | A | 245 | 34.130 | 27.969 | 119.642 | 1.00 | 42.67 |
| ATOM | 1948 | O | | VAL | A | 245 | 33.021 | 27.480 | 119.445 | 1.00 | 43.61 |
| ATOM | 1949 | N | | PHE | A | 246 | 35.001 | 27.417 | 120.477 | 1.00 | 40.87 |
| ATOM | 1950 | CA | | PHE | A | 246 | 34.662 | 26.168 | 121.139 | 1.00 | 37.47 |
| ATOM | 1951 | CB | | PHE | A | 246 | 35.106 | 24.991 | 120.257 | 1.00 | 37.00 |
| ATOM | 1952 | CG | | PHE | A | 246 | 34.450 | 23.685 | 120.604 | 1.00 | 33.22 |
| ATOM | 1953 | CD1 | | PHE | A | 246 | 33.111 | 23.467 | 120.302 | 1.00 | 33.93 |
| ATOM | 1954 | CD2 | | PHE | A | 246 | 35.168 | 22.674 | 121.234 | 1.00 | 32.13 |
| ATOM | 1955 | CE1 | | PHE | A | 246 | 32.493 | 22.260 | 120.621 | 1.00 | 37.75 |
| ATOM | 1956 | CE2 | | PHE | A | 246 | 34.561 | 21.459 | 121.561 | 1.00 | 35.92 |
| ATOM | 1957 | CZ | | PHE | A | 246 | 33.217 | 21.252 | 121.251 | 1.00 | 36.30 |
| ATOM | 1958 | C | | PHE | A | 246 | 35.322 | 26.065 | 122.509 | 1.00 | 38.93 |
| ATOM | 1959 | O | | PHE | A | 246 | 36.546 | 26.158 | 122.630 | 1.00 | 40.66 |
| ATOM | 1960 | N | | GLU | A | 247 | 34.500 | 25.870 | 123.537 | 1.00 | 38.59 |
| ATOM | 1961 | CA | | GLU | A | 247 | 34.970 | 25.733 | 124.918 | 1.00 | 44.60 |
| ATOM | 1962 | CB | | GLU | A | 247 | 34.146 | 25.615 | 125.865 | 1.00 | 47.07 |
| ATOM | 1963 | CG | | GLU | A | 247 | 33.161 | 27.569 | 125.185 | 1.00 | 56.16 |
| ATOM | 1964 | CD | | GLU | A | 247 | 31.944 | 26.865 | 124.577 | 1.00 | 62.03 |
| ATOM | 1965 | OE1 | | GLU | A | 247 | 32.096 | 26.088 | 123.607 | 1.00 | 61.85 |
| ATOM | 1966 | OE2 | | GLU | A | 247 | 30.822 | 27.094 | 125.083 | 1.00 | 64.59 |
| ATOM | 1967 | C | | GLU | A | 247 | 34.774 | 24.269 | 125.285 | 1.00 | 39.40 |
| ATOM | 1968 | O | | GLU | A | 247 | 33.727 | 23.879 | 125.794 | 1.00 | 39.91 |
| ATOM | 1969 | N | | PRO | A | 248 | 35.792 | 23.442 | 125.041 | 1.00 | 38.64 |
| ATOM | 1970 | CD | | PRO | A | 248 | 37.101 | 23.817 | 124.483 | 1.00 | 33.25 |
| ATOM | 1971 | CA | | PRO | A | 248 | 35.769 | 22.006 | 125.316 | 1.00 | 35.84 |
| ATOM | 1972 | CB | | PRO | A | 248 | 37.047 | 21.531 | 124.648 | 1.00 | 36.05 |
| ATOM | 1973 | CG | | PRO | A | 248 | 37.970 | 22.687 | 124.982 | 1.00 | 34.21 |
| ATOM | 1974 | C | | PRO | A | 248 | 35.736 | 21.611 | 126.779 | 1.00 | 33.94 |
| ATOM | 1975 | O | | PRO | A | 248 | 36.445 | 22.186 | 127.597 | 1.00 | 32.05 |
| ATOM | 1976 | N | | GLU | A | 249 | 34.914 | 20.616 | 127.096 | 1.00 | 29.39 |
| ATOM | 1977 | CA | | GLU | A | 249 | 34.841 | 20.105 | 128.459 | 1.00 | 33.12 |
| ATOM | 1978 | CB | | GLU | A | 249 | 33.521 | 19.361 | 128.693 | 1.00 | 30.36 |
| ATOM | 1979 | CG | | GLU | A | 249 | 32.284 | 20.212 | 128.564 | 1.00 | 35.98 |
| ATOM | 1980 | CD | | GLU | A | 249 | 31.026 | 19.388 | 128.668 | 1.00 | 40.52 |

Fig. 18-30

| | | | | | | | | | |
|---|---|---|---|---|---|---|---|---|---|
| ATOM | 1981 | OE1 | GLU | A | 249 | 30.817 | 18.509 | 127.804 | 1.00 40.27 |
| ATOM | 1982 | OE2 | GLU | A | 249 | 30.252 | 19.609 | 129.620 | 1.00 38.57 |
| ATOM | 1983 | C | GLU | A | 249 | 35.995 | 19.119 | 128.623 | 1.00 32.30 |
| ATOM | 1984 | O | GLU | A | 249 | 36.472 | 18.884 | 129.728 | 1.00 28.51 |
| ATOM | 1985 | N | VAL | A | 250 | 36.434 | 18.547 | 127.502 | 1.00 33.74 |
| ATOM | 1986 | CA | VAL | A | 250 | 37.516 | 17.563 | 127.494 | 1.00 29.31 |
| ATOM | 1987 | CB | VAL | A | 250 | 36.988 | 16.174 | 127.926 | 1.00 29.85 |
| ATOM | 1988 | CG1 | VAL | A | 250 | 35.908 | 15.711 | 126.958 | 1.00 24.36 |
| ATOM | 1989 | CG2 | VAL | A | 250 | 38.121 | 15.166 | 127.978 | 1.00 25.60 |
| ATOM | 1990 | C | VAL | A | 250 | 38.066 | 17.453 | 126.076 | 1.00 29.30 |
| ATOM | 1991 | O | VAL | A | 250 | 37.358 | 17.741 | 125.114 | 1.00 24.46 |
| ATOM | 1992 | N | TYR | A | 251 | 39.323 | 17.046 | 125.930 | 1.00 27.96 |
| ATOM | 1993 | CA | TYR | A | 251 | 39.865 | 16.913 | 124.585 | 1.00 30.06 |
| ATOM | 1994 | CB | TYR | A | 251 | 40.585 | 18.206 | 124.165 | 1.00 25.89 |
| ATOM | 1995 | CG | TYR | A | 251 | 41.998 | 18.370 | 124.692 | 1.00 29.90 |
| ATOM | 1996 | CD1 | TYR | A | 251 | 43.087 | 17.794 | 124.029 | 1.00 26.02 |
| ATOM | 1997 | CE1 | TYR | A | 251 | 44.390 | 17.953 | 124.507 | 1.00 29.20 |
| ATOM | 1998 | CD2 | TYR | A | 251 | 42.249 | 19.107 | 125.849 | 1.00 31.96 |
| ATOM | 1999 | CE2 | TYR | A | 251 | 43.551 | 19.271 | 126.338 | 1.00 31.54 |
| ATOM | 2000 | CZ | TYR | A | 251 | 44.614 | 18.694 | 125.664 | 1.00 31.46 |
| ATOM | 2001 | OH | TYR | A | 251 | 45.894 | 18.854 | 126.152 | 1.00 29.69 |
| ATOM | 2002 | C | TYR | A | 251 | 40.801 | 15.731 | 124.451 | 1.00 27.56 |
| ATOM | 2003 | O | TYR | A | 251 | 41.382 | 15.273 | 125.436 | 1.00 28.23 |
| ATOM | 2004 | N | LEU | A | 252 | 40.908 | 15.222 | 123.227 | 1.00 23.52 |
| ATOM | 2005 | CA | LEU | A | 252 | 41.806 | 14.117 | 122.919 | 1.00 26.53 |
| ATOM | 2006 | CB | LEU | A | 252 | 41.057 | 12.930 | 122.293 | 1.00 25.74 |
| ATOM | 2007 | CG | LEU | A | 252 | 40.266 | 12.001 | 123.221 | 1.00 28.49 |
| ATOM | 2008 | CD1 | LEU | A | 252 | 39.122 | 12.753 | 123.868 | 1.00 27.67 |
| ATOM | 2009 | CD2 | LEU | A | 252 | 39.727 | 10.835 | 122.414 | 1.00 32.00 |
| ATOM | 2010 | C | LEU | A | 252 | 42.842 | 14.638 | 121.932 | 1.00 27.53 |
| ATOM | 2011 | O | LEU | A | 252 | 42.528 | 15.444 | 121.055 | 1.00 24.42 |
| ATOM | 2012 | N | LEU | A | 253 | 44.075 | 14.176 | 122.078 | 1.00 24.60 |
| ATOM | 2013 | CA | LEU | A | 253 | 45.157 | 14.599 | 121.204 | 1.00 25.04 |
| ATOM | 2014 | CB | LEU | A | 253 | 46.176 | 15.400 | 122.017 | 1.00 22.48 |
| ATOM | 2015 | CG | LEU | A | 253 | 47.456 | 15.880 | 121.323 | 1.00 21.05 |
| ATOM | 2016 | CD1 | LEU | A | 253 | 47.105 | 16.833 | 120.175 | 1.00 23.05 |
| ATOM | 2017 | CD2 | LEU | A | 253 | 48.348 | 16.578 | 122.360 | 1.00 16.40 |
| ATOM | 2018 | C | LEU | A | 253 | 45.822 | 13.374 | 120.580 | 1.00 23.55 |
| ATOM | 2019 | O | LEU | A | 253 | 46.329 | 12.516 | 121.303 | 1.00 22.11 |
| ATOM | 2020 | N | GLN | A | 254 | 45.811 | 13.287 | 119.248 | 1.00 22.33 |
| ATOM | 2021 | CA | GLN | A | 254 | 46.417 | 12.150 | 118.552 | 1.00 19.84 |
| ATOM | 2022 | CB | GLN | A | 254 | 45.542 | 11.731 | 117.348 | 1.00 23.09 |
| ATOM | 2023 | CG | GLN | A | 254 | 46.075 | 12.038 | 115.963 | 1.00 35.49 |
| ATOM | 2024 | CD | GLN | A | 254 | 47.073 | 11.017 | 115.453 | 1.00 31.26 |
| ATOM | 2025 | OE1 | GLN | A | 254 | 46.712 | 9.937 | 114.961 | 1.00 33.69 |
| ATOM | 2026 | NE2 | GLN | A | 254 | 48.338 | 11.349 | 115.574 | 1.00 31.02 |
| ATOM | 2027 | C | GLN | A | 254 | 47.831 | 12.576 | 118.153 | 1.00 22.46 |
| ATOM | 2028 | O | GLN | A | 254 | 48.034 | 13.599 | 117.478 | 1.00 17.56 |
| ATOM | 2029 | N | LEU | A | 255 | 48.804 | 11.781 | 118.590 | 1.00 17.64 |
| ATOM | 2030 | CA | LEU | A | 255 | 50.213 | 12.079 | 118.383 | 1.00 17.04 |
| ATOM | 2031 | CB | LEU | A | 255 | 50.894 | 12.136 | 119.750 | 1.00 14.75 |
| ATOM | 2032 | CG | LEU | A | 255 | 50.277 | 13.196 | 120.670 | 1.00 25.02 |
| ATOM | 2033 | CD1 | LEU | A | 255 | 50.732 | 12.996 | 122.107 | 1.00 21.99 |
| ATOM | 2034 | CD2 | LEU | A | 255 | 50.636 | 14.578 | 120.149 | 1.00 18.30 |
| ATOM | 2035 | C | LEU | A | 255 | 51.023 | 11.169 | 117.476 | 1.00 21.34 |
| ATOM | 2036 | O | LEU | A | 255 | 52.089 | 10.705 | 117.875 | 1.00 18.73 |
| ATOM | 2037 | N | GLY | A | 256 | 50.543 | 10.928 | 116.259 | 1.00 22.75 |
| ATOM | 2038 | CA | GLY | A | 256 | 51.291 | 10.093 | 115.330 | 1.00 24.09 |
| ATOM | 2039 | C | GLY | A | 256 | 52.660 | 10.721 | 115.126 | 1.00 24.27 |
| ATOM | 2040 | O | GLY | A | 256 | 52.805 | 11.945 | 115.134 | 1.00 19.15 |
| ATOM | 2041 | N | THR | A | 257 | 53.680 | 9.903 | 114.948 | 1.00 24.14 |
| ATOM | 2042 | CA | THR | A | 257 | 55.014 | 10.440 | 114.765 | 1.00 21.32 |
| ATOM | 2043 | CB | THR | A | 257 | 56.048 | 9.582 | 115.511 | 1.00 17.24 |
| ATOM | 2044 | OG1 | THR | A | 257 | 56.009 | 8.248 | 115.004 | 1.00 17.48 |
| ATOM | 2045 | CG2 | THR | A | 257 | 55.728 | 9.532 | 117.016 | 1.00 15.73 |
| ATOM | 2046 | C | THR | A | 257 | 55.403 | 10.527 | 113.290 | 1.00 22.98 |

Fig. 18-31

```
ATOM   2047  O    THR A 257      56.517  10.941 112.974  1.00 20.39
ATOM   2048  N    ASP A 258      54.493  10.177 112.379  1.00 22.20
ATOM   2049  CA   ASP A 258      54.863  10.229 110.961  1.00 26.56
ATOM   2050  CB   ASP A 258      53.849   9.496 110.056  1.00 25.06
ATOM   2051  CG   ASP A 258      52.415   9.944 110.252  1.00 29.08
ATOM   2052  C    ASP A 258      55.222  11.596 110.364  1.00 27.87
ATOM   2053  O    ASP A 258      55.756  11.661 109.254  1.00 25.61
ATOM   2054  OD1  ASP A 258      52.173  11.070 110.742  1.00 29.86
ATOM   2055  OD2  ASP A 258      51.513   9.168 109.869  1.00 33.25
ATOM   2056  N    PRO A 259      54.884  12.710 111.045  1.00 31.06
ATOM   2057  CD   PRO A 259      54.019  12.928 112.220  1.00 28.59
ATOM   2058  CA   PRO A 259      55.268  14.006 110.469  1.00 30.95
ATOM   2059  CB   PRO A 259      54.447  14.993 111.296  1.00 35.06
ATOM   2060  CG   PRO A 259      54.418  14.320 112.636  1.00 35.26
ATOM   2061  C    PRO A 259      56.790  14.268 110.583  1.00 29.06
ATOM   2062  O    PRO A 259      57.300  15.251 110.044  1.00 29.70
ATOM   2063  N    LEU A 260      57.508  13.389 111.280  1.00 22.68
ATOM   2064  CA   LEU A 260      58.960  13.545 111.455  1.00 28.41
ATOM   2065  CB   LEU A 260      59.461  12.576 112.533  1.00 22.47
ATOM   2066  CG   LEU A 260      58.970  12.791 113.969  1.00 20.14
ATOM   2067  CD1  LEU A 260      59.352  11.599 114.826  1.00 22.83
ATOM   2068  CD2  LEU A 260      59.592  14.079 114.532  1.00 20.48
ATOM   2069  C    LEU A 260      59.770  13.344 110.160  1.00 27.95
ATOM   2070  O    LEU A 260      59.407  12.535 109.299  1.00 27.03
ATOM   2071  N    LEU A 261      60.874  14.081 110.040  1.00 26.76
ATOM   2072  CA   LEU A 261      61.742  14.010 108.865  1.00 26.56
ATOM   2073  CB   LEU A 261      63.067  14.737 109.137  1.00 23.06
ATOM   2074  CG   LEU A 261      64.131  14.615 108.025  1.00 29.52
ATOM   2075  CD1  LEU A 261      63.642  15.325 106.770  1.00 22.68
ATOM   2076  CD2  LEU A 261      65.460  15.219 108.475  1.00 26.71
ATOM   2077  C    LEU A 261      62.063  12.577 108.443  1.00 28.23
ATOM   2078  O    LEU A 261      61.880  12.198 107.289  1.00 26.52
ATOM   2079  N    GLU A 262      62.539  11.787 109.397  1.00 28.70
ATOM   2080  CA   GLU A 262      62.938  10.416 109.135  1.00 31.76
ATOM   2081  CB   GLU A 262      63.685   9.855 110.351  1.00 29.72
ATOM   2082  CG   GLU A 262      64.890  10.683 110.803  1.00 31.33
ATOM   2083  CD   GLU A 262      64.521  11.847 111.708  1.00 28.07
ATOM   2084  OE1  GLU A 262      63.324  12.195 111.789  1.00 28.75
ATOM   2085  OE2  GLU A 262      65.433  12.424 112.340  1.00 26.08
ATOM   2086  C    GLU A 262      61.847   9.429 108.721  1.00 28.63
ATOM   2087  O    GLU A 262      62.158   8.305 108.350  1.00 29.72
ATOM   2088  N    ASP A 263      60.582   9.825 108.785  1.00 28.07
ATOM   2089  CA   ASP A 263      59.513   8.902 108.412  1.00 26.85
ATOM   2090  CB   ASP A 263      58.305   9.099 109.333  1.00 25.26
ATOM   2091  CG   ASP A 263      57.261   7.998 109.185  1.00 33.14
ATOM   2092  OD1  ASP A 263      56.638   7.636 110.209  1.00 29.91
ATOM   2093  OD2  ASP A 263      57.042   7.509 108.051  1.00 26.56
ATOM   2094  C    ASP A 263      59.150   9.146 106.951  1.00 29.44
ATOM   2095  O    ASP A 263      58.740  10.247 106.594  1.00 24.70
ATOM   2096  N    TYR A 264      59.303   8.111 106.130  1.00 27.51
ATOM   2097  CA   TYR A 264      59.031   8.219 104.696  1.00 33.89
ATOM   2098  CB   TYR A 264      59.576   7.008 103.935  1.00 40.44
ATOM   2099  CG   TYR A 264      61.059   6.771 104.092  1.00 50.64
ATOM   2100  CD1  TYR A 264      61.565   6.087 105.199  1.00 54.67
ATOM   2101  CE1  TYR A 264      62.933   5.876 105.351  1.00 55.28
ATOM   2102  CD2  TYR A 264      61.960   7.242 103.140  1.00 53.79
ATOM   2103  CE2  TYR A 264      63.329   7.038 103.282  1.00 56.61
ATOM   2104  CZ   TYR A 264      63.809   6.354 104.388  1.00 56.22
ATOM   2105  OH   TYR A 264      65.161   6.147 104.524  1.00 55.90
ATOM   2106  C    TYR A 264      57.581   8.394 104.294  1.00 31.33
ATOM   2107  O    TYR A 264      57.311   8.825 103.178  1.00 27.15
ATOM   2108  N    LEU A 265      56.641   8.059 105.172  1.00 26.88
ATOM   2109  CA   LEU A 265      55.244   8.209 104.792  1.00 24.39
ATOM   2110  CB   LEU A 265      54.360   7.189 105.527  1.00 26.55
ATOM   2111  CG   LEU A 265      54.663   5.724 105.168  1.00 29.80
ATOM   2112  CD1  LEU A 265      53.464   4.836 105.503  1.00 21.17
```

Fig. 18-32

| | | | | | | | | |
|---|---|---|---|---|---|---|---|---|
| ATOM | 2113 | CD2 | LEU A 265 | 54.931 | 5.620 | 103.682 | 1.00 | 33.35 |
| ATOM | 2114 | C | LEU A 265 | 54.669 | 9.617 | 104.921 | 1.00 | 20.81 |
| ATOM | 2115 | O | LEU A 265 | 53.457 | 9.796 | 104.979 | 1.00 | 21.30 |
| ATOM | 2116 | N | SER A 266 | 55.540 | 10.622 | 104.959 | 1.00 | 23.23 |
| ATOM | 2117 | CA | SER A 266 | 55.084 | 12.011 | 105.008 | 1.00 | 26.30 |
| ATOM | 2118 | CB | SER A 266 | 54.856 | 12.502 | 106.444 | 1.00 | 25.16 |
| ATOM | 2119 | OG | SER A 266 | 56.074 | 12.845 | 107.084 | 1.00 | 22.92 |
| ATOM | 2120 | C | SER A 266 | 56.147 | 12.879 | 104.355 | 1.00 | 30.17 |
| ATOM | 2121 | O | SER A 266 | 57.334 | 12.555 | 104.385 | 1.00 | 31.65 |
| ATOM | 2122 | N | LYS A 267 | 55.731 | 13.985 | 103.757 | 1.00 | 31.56 |
| ATOM | 2123 | CA | LYS A 267 | 56.696 | 14.873 | 103.140 | 1.00 | 27.65 |
| ATOM | 2124 | CB | LYS A 267 | 56.140 | 15.425 | 101.834 | 1.00 | 30.54 |
| ATOM | 2125 | CG | LYS A 267 | 55.815 | 14.327 | 100.819 | 1.00 | 34.13 |
| ATOM | 2126 | CD | LYS A 267 | 57.039 | 13.463 | 100.549 | 1.00 | 29.09 |
| ATOM | 2127 | CE | LYS A 267 | 56.745 | 12.376 | 99.524 | 1.00 | 37.61 |
| ATOM | 2128 | NZ | LYS A 267 | 57.956 | 11.541 | 99.272 | 1.00 | 31.91 |
| ATOM | 2129 | C | LYS A 267 | 57.050 | 16.004 | 104.107 | 1.00 | 30.85 |
| ATOM | 2130 | O | LYS A 267 | 57.624 | 17.017 | 103.707 | 1.00 | 27.86 |
| ATOM | 2131 | N | PHE A 268 | 56.688 | 15.826 | 105.377 | 1.00 | 24.19 |
| ATOM | 2132 | CA | PHE A 268 | 57.009 | 16.808 | 106.412 | 1.00 | 25.34 |
| ATOM | 2133 | CB | PHE A 268 | 56.014 | 16.730 | 107.579 | 1.00 | 24.54 |
| ATOM | 2134 | CG | PHE A 268 | 54.636 | 17.256 | 107.257 | 1.00 | 21.68 |
| ATOM | 2135 | CD1 | PHE A 268 | 53.631 | 17.221 | 108.216 | 1.00 | 28.65 |
| ATOM | 2136 | CD2 | PHE A 268 | 54.346 | 17.806 | 106.011 | 1.00 | 25.14 |
| ATOM | 2137 | CE1 | PHE A 268 | 52.357 | 17.728 | 107.944 | 1.00 | 25.34 |
| ATOM | 2138 | CE2 | PHE A 268 | 53.077 | 18.315 | 105.730 | 1.00 | 23.79 |
| ATOM | 2139 | CZ | PHE A 268 | 52.082 | 18.275 | 106.702 | 1.00 | 28.13 |
| ATOM | 2140 | C | PHE A 268 | 58.410 | 16.470 | 106.908 | 1.00 | 25.66 |
| ATOM | 2141 | O | PHE A 268 | 58.778 | 15.299 | 106.994 | 1.00 | 28.44 |
| ATOM | 2142 | N | ASN A 269 | 59.194 | 17.490 | 107.230 | 1.00 | 25.81 |
| ATOM | 2143 | CA | ASN A 269 | 60.555 | 17.270 | 107.709 | 1.00 | 30.60 |
| ATOM | 2144 | CB | ASN A 269 | 61.566 | 17.938 | 106.767 | 1.00 | 31.97 |
| ATOM | 2145 | CG | ASN A 269 | 61.392 | 17.513 | 105.317 | 1.00 | 35.83 |
| ATOM | 2146 | OD1 | ASN A 269 | 61.235 | 16.332 | 105.020 | 1.00 | 33.93 |
| ATOM | 2147 | ND2 | ASN A 269 | 61.446 | 18.477 | 104.405 | 1.00 | 33.95 |
| ATOM | 2148 | C | ASN A 269 | 60.723 | 17.843 | 109.110 | 1.00 | 31.80 |
| ATOM | 2149 | O | ASN A 269 | 61.609 | 18.665 | 109.348 | 1.00 | 28.13 |
| ATOM | 2150 | N | LEU A 270 | 59.888 | 17.397 | 110.043 | 1.00 | 29.70 |
| ATOM | 2151 | CA | LEU A 270 | 59.954 | 17.918 | 111.406 | 1.00 | 26.87 |
| ATOM | 2152 | CB | LEU A 270 | 58.575 | 17.833 | 112.074 | 1.00 | 26.60 |
| ATOM | 2153 | CG | LEU A 270 | 57.392 | 18.425 | 111.297 | 1.00 | 29.62 |
| ATOM | 2154 | CD1 | LEU A 270 | 56.177 | 18.494 | 112.222 | 1.00 | 28.54 |
| ATOM | 2155 | CD2 | LEU A 270 | 57.740 | 19.825 | 110.790 | 1.00 | 29.40 |
| ATOM | 2156 | C | LEU A 270 | 60.979 | 17.242 | 112.301 | 1.00 | 26.83 |
| ATOM | 2157 | O | LEU A 270 | 61.490 | 16.158 | 111.990 | 1.00 | 19.60 |
| ATOM | 2158 | N | SER A 271 | 61.275 | 17.896 | 113.420 | 1.00 | 21.66 |
| ATOM | 2159 | CA | SER A 271 | 62.220 | 17.365 | 114.393 | 1.00 | 27.08 |
| ATOM | 2160 | CB | SER A 271 | 63.189 | 18.460 | 114.846 | 1.00 | 24.64 |
| ATOM | 2161 | OG | SER A 271 | 62.499 | 19.433 | 115.626 | 1.00 | 18.60 |
| ATOM | 2162 | C | SER A 271 | 61.454 | 16.868 | 115.618 | 1.00 | 23.70 |
| ATOM | 2163 | O | SER A 271 | 60.272 | 17.150 | 115.772 | 1.00 | 22.56 |
| ATOM | 2164 | N | ASN A 272 | 62.157 | 16.129 | 116.470 | 1.00 | 28.35 |
| ATOM | 2165 | CA | ASN A 272 | 61.649 | 15.593 | 117.739 | 1.00 | 31.03 |
| ATOM | 2166 | CB | ASN A 272 | 62.774 | 14.880 | 118.498 | 1.00 | 28.80 |
| ATOM | 2167 | CG | ASN A 272 | 62.854 | 13.428 | 118.180 | 1.00 | 36.65 |
| ATOM | 2168 | OD1 | ASN A 272 | 63.712 | 12.709 | 118.705 | 1.00 | 29.89 |
| ATOM | 2169 | ND2 | ASN A 272 | 61.953 | 12.969 | 117.319 | 1.00 | 40.80 |
| ATOM | 2170 | C | ASN A 272 | 61.167 | 16.695 | 118.661 | 1.00 | 31.83 |
| ATOM | 2171 | O | ASN A 272 | 60.090 | 16.618 | 119.261 | 1.00 | 27.50 |
| ATOM | 2172 | N | VAL A 273 | 62.032 | 17.693 | 118.804 | 1.00 | 31.49 |
| ATOM | 2173 | CA | VAL A 273 | 61.802 | 18.837 | 119.667 | 1.00 | 31.58 |
| ATOM | 2174 | CB | VAL A 273 | 63.069 | 19.709 | 119.725 | 1.00 | 35.80 |
| ATOM | 2175 | CG1 | VAL A 273 | 62.804 | 20.988 | 120.500 | 1.00 | 48.07 |
| ATOM | 2176 | CG2 | VAL A 273 | 64.198 | 18.914 | 120.381 | 1.00 | 42.81 |
| ATOM | 2177 | C | VAL A 273 | 60.608 | 19.665 | 119.234 | 1.00 | 30.13 |
| ATOM | 2178 | O | VAL A 273 | 59.872 | 20.174 | 120.072 | 1.00 | 31.44 |

Fig. 18-33

| ATOM | 2179 | N | ALA A 274 | 60.405 | 19.800 | 117.929 | 1.00 | 24.15 |
|---|---|---|---|---|---|---|---|---|
| ATOM | 2180 | CA | ALA A 274 | 59.258 | 20.558 | 117.455 | 1.00 | 26.27 |
| ATOM | 2181 | CB | ALA A 274 | 59.341 | 20.780 | 115.965 | 1.00 | 21.85 |
| ATOM | 2182 | C | ALA A 274 | 58.005 | 19.759 | 117.789 | 1.00 | 25.68 |
| ATOM | 2183 | O | ALA A 274 | 56.961 | 20.324 | 118.132 | 1.00 | 23.76 |
| ATOM | 2184 | N | PHE A 275 | 58.122 | 18.438 | 117.680 | 1.00 | 25.20 |
| ATOM | 2185 | CA | PHE A 275 | 57.015 | 17.538 | 117.974 | 1.00 | 25.89 |
| ATOM | 2186 | CB | PHE A 275 | 57.449 | 16.092 | 117.710 | 1.00 | 25.21 |
| ATOM | 2187 | CG | PHE A 275 | 56.340 | 15.088 | 117.870 | 1.00 | 28.85 |
| ATOM | 2188 | CD1 | PHE A 275 | 55.278 | 15.064 | 116.982 | 1.00 | 32.60 |
| ATOM | 2189 | CD2 | PHE A 275 | 56.365 | 14.166 | 118.910 | 1.00 | 28.93 |
| ATOM | 2190 | CE1 | PHE A 275 | 54.248 | 14.132 | 117.119 | 1.00 | 33.75 |
| ATOM | 2191 | CE2 | PHE A 275 | 55.343 | 13.231 | 119.059 | 1.00 | 30.83 |
| ATOM | 2192 | CZ | PHE A 275 | 54.282 | 13.214 | 118.160 | 1.00 | 34.19 |
| ATOM | 2193 | C | PHE A 275 | 56.607 | 17.712 | 119.445 | 1.00 | 24.63 |
| ATOM | 2194 | O | PHE A 275 | 55.428 | 17.877 | 119.767 | 1.00 | 22.40 |
| ATOM | 2195 | N | LEU A 276 | 57.594 | 17.673 | 120.331 | 1.00 | 25.45 |
| ATOM | 2196 | CA | LEU A 276 | 57.357 | 17.837 | 121.766 | 1.00 | 27.94 |
| ATOM | 2197 | CB | LEU A 276 | 58.667 | 17.692 | 122.534 | 1.00 | 26.11 |
| ATOM | 2198 | CG | LEU A 276 | 58.651 | 18.132 | 124.001 | 1.00 | 31.15 |
| ATOM | 2199 | CD1 | LEU A 276 | 57.609 | 17.351 | 124.761 | 1.00 | 29.37 |
| ATOM | 2200 | CD2 | LEU A 276 | 60.033 | 17.937 | 124.612 | 1.00 | 27.98 |
| ATOM | 2201 | C | LEU A 276 | 56.770 | 19.208 | 122.058 | 1.00 | 30.12 |
| ATOM | 2202 | O | LEU A 276 | 55.822 | 19.348 | 122.838 | 1.00 | 28.69 |
| ATOM | 2203 | N | LYS A 277 | 57.353 | 20.219 | 121.425 | 1.00 | 30.99 |
| ATOM | 2204 | CA | LYS A 277 | 56.913 | 21.593 | 121.603 | 1.00 | 27.04 |
| ATOM | 2205 | CB | LYS A 277 | 57.742 | 22.516 | 120.704 | 1.00 | 30.38 |
| ATOM | 2206 | CG | LYS A 277 | 57.941 | 23.934 | 121.237 | 1.00 | 36.46 |
| ATOM | 2207 | CD | LYS A 277 | 56.633 | 24.668 | 121.454 | 1.00 | 42.73 |
| ATOM | 2208 | CE | LYS A 277 | 56.870 | 26.059 | 122.049 | 1.00 | 45.70 |
| ATOM | 2209 | NZ | LYS A 277 | 57.528 | 26.004 | 123.390 | 1.00 | 44.64 |
| ATOM | 2210 | C | LYS A 277 | 55.432 | 21.683 | 121.242 | 1.00 | 30.26 |
| ATOM | 2211 | O | LYS A 277 | 54.640 | 22.284 | 121.972 | 1.00 | 27.55 |
| ATOM | 2212 | N | ALA A 278 | 55.057 | 21.078 | 120.115 | 1.00 | 30.15 |
| ATOM | 2213 | CA | ALA A 278 | 53.662 | 21.096 | 119.676 | 1.00 | 30.51 |
| ATOM | 2214 | CB | ALA A 278 | 53.496 | 20.270 | 118.406 | 1.00 | 28.96 |
| ATOM | 2215 | C | ALA A 278 | 52.789 | 20.527 | 120.786 | 1.00 | 30.99 |
| ATOM | 2216 | O | ALA A 278 | 51.735 | 21.067 | 121.108 | 1.00 | 30.36 |
| ATOM | 2217 | N | PHE A 279 | 53.245 | 19.422 | 121.360 | 1.00 | 27.85 |
| ATOM | 2218 | CA | PHE A 279 | 52.540 | 18.759 | 122.448 | 1.00 | 29.62 |
| ATOM | 2219 | CB | PHE A 279 | 53.343 | 17.534 | 122.886 | 1.00 | 26.83 |
| ATOM | 2220 | CG | PHE A 279 | 52.786 | 16.823 | 124.078 | 1.00 | 29.11 |
| ATOM | 2221 | CD1 | PHE A 279 | 51.556 | 16.176 | 124.015 | 1.00 | 28.86 |
| ATOM | 2222 | CD2 | PHE A 279 | 53.505 | 16.786 | 125.257 | 1.00 | 33.03 |
| ATOM | 2223 | CE1 | PHE A 279 | 51.054 | 15.500 | 125.121 | 1.00 | 37.90 |
| ATOM | 2224 | CE2 | PHE A 279 | 53.011 | 16.114 | 126.386 | 1.00 | 38.01 |
| ATOM | 2225 | CZ | PHE A 279 | 51.783 | 15.469 | 126.313 | 1.00 | 36.22 |
| ATOM | 2226 | C | PHE A 279 | 52.362 | 19.730 | 123.621 | 1.00 | 30.07 |
| ATOM | 2227 | O | PHE A 279 | 51.265 | 19.853 | 124.184 | 1.00 | 26.26 |
| ATOM | 2228 | N | ASN A 280 | 53.432 | 20.429 | 123.990 | 1.00 | 32.03 |
| ATOM | 2229 | CA | ASN A 280 | 53.339 | 21.373 | 125.104 | 1.00 | 30.54 |
| ATOM | 2230 | CB | ASN A 280 | 54.724 | 21.819 | 125.583 | 1.00 | 26.79 |
| ATOM | 2231 | CG | ASN A 280 | 55.508 | 20.695 | 126.227 | 1.00 | 33.68 |
| ATOM | 2232 | OD1 | ASN A 280 | 54.958 | 19.886 | 126.971 | 1.00 | 34.47 |
| ATOM | 2233 | ND2 | ASN A 280 | 56.809 | 20.680 | 125.973 | 1.00 | 33.59 |
| ATOM | 2234 | C | ASN A 280 | 52.493 | 22.587 | 124.781 | 1.00 | 30.46 |
| ATOM | 2235 | O | ASN A 280 | 51.899 | 23.182 | 125.677 | 1.00 | 27.66 |
| ATOM | 2236 | N | ILE A 281 | 52.429 | 22.960 | 123.509 | 1.00 | 27.32 |
| ATOM | 2237 | CA | ILE A 281 | 51.620 | 24.107 | 123.128 | 1.00 | 31.07 |
| ATOM | 2238 | CB | ILE A 281 | 51.878 | 24.517 | 121.666 | 1.00 | 35.08 |
| ATOM | 2239 | CG2 | ILE A 281 | 50.776 | 25.445 | 121.174 | 1.00 | 34.33 |
| ATOM | 2240 | CG1 | ILE A 281 | 53.253 | 25.185 | 121.562 | 1.00 | 33.53 |
| ATOM | 2241 | CD1 | ILE A 281 | 53.590 | 25.694 | 120.178 | 1.00 | 34.88 |
| ATOM | 2242 | C | ILE A 281 | 50.141 | 23.798 | 123.329 | 1.00 | 31.22 |
| ATOM | 2243 | O | ILE A 281 | 49.391 | 24.621 | 123.854 | 1.00 | 30.15 |
| ATOM | 2244 | N | VAL A 282 | 49.723 | 22.606 | 122.923 | 1.00 | 30.91 |

Fig. 18-34

```
ATOM  2245  CA   VAL A 282     48.332  22.214 123.081  1.00 30.76
ATOM  2246  CB   VAL A 282     48.075  20.797 122.523  1.00 35.10
ATOM  2247  CG1  VAL A 282     46.641  20.358 122.841  1.00 28.72
ATOM  2248  CG2  VAL A 282     48.313  20.781 121.018  1.00 28.66
ATOM  2249  C    VAL A 282     47.952  22.236 124.558  1.00 31.39
ATOM  2250  O    VAL A 282     46.884  22.715 124.917  1.00 32.70
ATOM  2251  N    ARG A 283     48.837  21.720 125.406  1.00 29.86
ATOM  2252  CA   ARG A 283     48.587  21.675 126.840  1.00 34.82
ATOM  2253  CB   ARG A 283     49.629  20.785 127.519  1.00 31.44
ATOM  2254  CG   ARG A 283     49.551  19.334 127.061  1.00 29.49
ATOM  2255  CD   ARG A 283     50.729  18.539 127.554  1.00 30.67
ATOM  2256  NE   ARG A 283     50.730  18.314 128.990  1.00 30.78
ATOM  2257  CZ   ARG A 283     51.826  18.351 129.742  1.00 35.27
ATOM  2258  NH1  ARG A 283     53.012  18.611 129.198  1.00 36.46
ATOM  2259  NH2  ARG A 283     51.742  18.100 131.035  1.00 35.90
ATOM  2260  C    ARG A 283     48.561  23.065 127.473  1.00 36.06
ATOM  2261  O    ARG A 283     47.830  23.302 128.439  1.00 35.04
ATOM  2262  N    GLU A 284     49.350  23.985 126.928  1.00 35.70
ATOM  2263  CA   GLU A 284     49.376  25.348 127.448  1.00 40.93
ATOM  2264  CB   GLU A 284     50.499  26.166 126.799  1.00 44.17
ATOM  2265  CG   GLU A 284     51.917  25.702 127.141  1.00 56.39
ATOM  2266  CD   GLU A 284     52.989  26.495 126.401  1.00 60.69
ATOM  2267  OE1  GLU A 284     53.012  27.738 126.542  1.00 63.13
ATOM  2268  OE2  GLU A 284     53.810  25.880 125.680  1.00 62.79
ATOM  2269  C    GLU A 284     48.039  26.014 127.148  1.00 39.24
ATOM  2270  O    GLU A 284     47.525  26.783 127.954  1.00 38.52
ATOM  2271  N    VAL A 285     47.472  25.704 125.986  1.00 33.75
ATOM  2272  CA   VAL A 285     46.205  26.294 125.592  1.00 35.82
ATOM  2273  CB   VAL A 285     46.039  26.291 124.062  1.00 34.14
ATOM  2274  CG1  VAL A 285     44.654  26.811 123.693  1.00 36.43
ATOM  2275  CG2  VAL A 285     47.114  27.153 123.419  1.00 37.26
ATOM  2276  C    VAL A 285     44.964  25.638 126.192  1.00 38.96
ATOM  2277  O    VAL A 285     44.043  26.336 126.611  1.00 41.83
ATOM  2278  N    PHE A 286     44.931  24.308 126.236  1.00 37.57
ATOM  2279  CA   PHE A 286     43.760  23.608 126.753  1.00 35.05
ATOM  2280  CB   PHE A 286     43.159  22.723 125.657  1.00 32.53
ATOM  2281  CG   PHE A 286     42.544  23.490 124.529  1.00 30.15
ATOM  2282  CD1  PHE A 286     43.104  23.459 123.256  1.00 33.96
ATOM  2283  CD2  PHE A 286     41.398  24.245 124.736  1.00 30.30
ATOM  2284  CE1  PHE A 286     42.527  24.170 122.202  1.00 32.96
ATOM  2285  CE2  PHE A 286     40.813  24.958 123.693  1.00 31.67
ATOM  2286  CZ   PHE A 286     41.381  24.919 122.419  1.00 31.66
ATOM  2287  C    PHE A 286     43.922  22.773 128.015  1.00 35.18
ATOM  2288  O    PHE A 286     42.984  22.080 128.409  1.00 36.97
ATOM  2289  N    GLY A 287     45.086  22.840 128.656  1.00 30.87
ATOM  2290  CA   GLY A 287     45.297  22.056 129.862  1.00 30.06
ATOM  2291  C    GLY A 287     45.525  20.590 129.527  1.00 34.44
ATOM  2292  O    GLY A 287     45.914  20.264 128.403  1.00 32.54
ATOM  2293  N    GLU A 288     45.288  19.710 130.500  1.00 28.42
ATOM  2294  CA   GLU A 288     45.464  18.273 130.310  1.00 32.23
ATOM  2295  CB   GLU A 288     45.613  17.576 131.663  1.00 37.02
ATOM  2296  CG   GLU A 288     46.910  17.864 132.411  1.00 45.36
ATOM  2297  CD   GLU A 288     48.140  17.455 131.622  1.00 45.65
ATOM  2298  OE1  GLU A 288     48.144  16.334 131.069  1.00 46.42
ATOM  2299  OE2  GLU A 288     49.106  18.245 131.571  1.00 50.78
ATOM  2300  C    GLU A 288     44.309  17.623 129.546  1.00 30.98
ATOM  2301  O    GLU A 288     43.144  17.957 129.762  1.00 28.67
ATOM  2302  N    GLY A 289     44.641  16.694 128.657  1.00 29.66
ATOM  2303  CA   GLY A 289     43.625  15.999 127.886  1.00 28.08
ATOM  2304  C    GLY A 289     43.922  14.510 127.861  1.00 30.45
ATOM  2305  O    GLY A 289     44.618  14.007 128.739  1.00 25.90
ATOM  2306  N    VAL A 290     43.384  13.807 126.868  1.00 26.21
ATOM  2307  CA   VAL A 290     43.612  12.373 126.718  1.00 27.31
ATOM  2308  CB   VAL A 290     42.288  11.626 126.412  1.00 26.53
ATOM  2309  CG1  VAL A 290     42.554  10.148 126.204  1.00 25.36
ATOM  2310  CG2  VAL A 290     41.308  11.822 127.565  1.00 24.38
```

Fig. 18-35

```
ATOM   2311  C    VAL A 290      44.580  12.248 125.550  1.00 24.52
ATOM   2312  O    VAL A 290      44.307  12.743 124.461  1.00 26.84
ATOM   2313  N    TYR A 291      45.716  11.597 125.775  1.00 23.56
ATOM   2314  CA   TYR A 291      46.729  11.478 124.732  1.00 23.74
ATOM   2315  CB   TYR A 291      48.092  11.817 125.342  1.00 18.40
ATOM   2316  CG   TYR A 291      48.040  13.113 126.118  1.00 21.60
ATOM   2317  CD1  TYR A 291      48.326  13.148 127.483  1.00 23.83
ATOM   2318  CE1  TYR A 291      48.200  14.331 128.214  1.00 24.57
ATOM   2319  CD2  TYR A 291      47.634  14.291 125.503  1.00 18.17
ATOM   2320  CE2  TYR A 291      47.504  15.476 126.220  1.00 26.36
ATOM   2321  CZ   TYR A 291      47.786  15.489 127.575  1.00 27.68
ATOM   2322  OH   TYR A 291      47.631  16.657 128.283  1.00 28.92
ATOM   2323  C    TYR A 291      46.768  10.118 124.044  1.00 23.03
ATOM   2324  O    TYR A 291      46.837   9.082 124.707  1.00 20.66
ATOM   2325  N    LEU A 292      46.755  10.142 122.711  1.00 23.96
ATOM   2326  CA   LEU A 292      46.767   8.924 121.902  1.00 20.69
ATOM   2327  CB   LEU A 292      45.482   8.842 121.076  1.00 22.13
ATOM   2328  CG   LEU A 292      44.162   9.063 121.814  1.00 23.78
ATOM   2329  CD1  LEU A 292      43.001   8.959 120.826  1.00 23.09
ATOM   2330  CD2  LEU A 292      44.008   8.050 122.930  1.00 16.01
ATOM   2331  C    LEU A 292      47.953   8.885 120.947  1.00 22.90
ATOM   2332  O    LEU A 292      48.527   9.923 120.617  1.00 22.31
ATOM   2333  N    GLY A 293      48.301   7.684 120.491  1.00 18.83
ATOM   2334  CA   GLY A 293      49.401   7.529 119.554  1.00 24.35
ATOM   2335  C    GLY A 293      48.908   7.846 118.154  1.00 24.22
ATOM   2336  O    GLY A 293      48.025   8.684 117.991  1.00 20.46
ATOM   2337  N    GLY A 294      49.459   7.177 117.148  1.00 24.63
ATOM   2338  CA   GLY A 294      49.035   7.423 115.779  1.00 22.03
ATOM   2339  C    GLY A 294      50.024   6.869 114.769  1.00 22.90
ATOM   2340  O    GLY A 294      50.956   6.150 115.136  1.00 24.10
ATOM   2341  N    GLY A 295      49.825   7.203 113.499  1.00 19.85
ATOM   2342  CA   GLY A 295      50.721   6.724 112.458  1.00 23.33
ATOM   2343  C    GLY A 295      52.185   7.010 112.740  1.00 19.01
ATOM   2344  O    GLY A 295      52.541   8.094 113.196  1.00 19.39
ATOM   2345  N    GLY A 296      53.035   6.026 112.472  1.00 25.85
ATOM   2346  CA   GLY A 296      54.468   6.162 112.690  1.00 22.65
ATOM   2347  C    GLY A 296      55.098   4.898 112.146  1.00 25.31
ATOM   2348  O    GLY A 296      54.778   3.798 112.609  1.00 25.86
ATOM   2349  N    TYR A 297      56.005   5.034 111.185  1.00 22.83
ATOM   2350  CA   TYR A 297      56.598   3.852 110.577  1.00 23.93
ATOM   2351  CB   TYR A 297      56.137   3.780 109.125  1.00 21.59
ATOM   2352  CG   TYR A 297      54.660   4.084 109.035  1.00 25.85
ATOM   2353  CD1  TYR A 297      54.203   5.402 109.017  1.00 22.28
ATOM   2354  CE1  TYR A 297      52.842   5.695 109.089  1.00 20.19
ATOM   2355  CD2  TYR A 297      53.713   3.062 109.116  1.00 25.28
ATOM   2356  CE2  TYR A 297      52.352   3.346 109.190  1.00 21.83
ATOM   2357  CZ   TYR A 297      51.927   4.666 109.181  1.00 21.81
ATOM   2358  OH   TYR A 297      50.588   4.972 109.305  1.00 19.51
ATOM   2359  C    TYR A 297      58.104   3.694 110.674  1.00 23.78
ATOM   2360  O    TYR A 297      58.665   2.724 110.154  1.00 22.07
ATOM   2361  N    HIS A 298      58.765   4.641 111.326  1.00 23.71
ATOM   2362  CA   HIS A 298      60.204   4.534 111.517  1.00 26.33
ATOM   2363  CB   HIS A 298      60.913   5.852 111.216  1.00 28.74
ATOM   2364  CG   HIS A 298      62.403   5.727 111.213  1.00 33.08
ATOM   2365  CD2  HIS A 298      63.273   5.465 112.215  1.00 31.83
ATOM   2366  ND1  HIS A 298      63.151   5.775 110.056  1.00 32.49
ATOM   2367  CE1  HIS A 298      64.419   5.547 110.345  1.00 29.10
ATOM   2368  NE2  HIS A 298      64.520   5.354 111.648  1.00 38.70
ATOM   2369  C    HIS A 298      60.371   4.188 112.996  1.00 27.81
ATOM   2370  O    HIS A 298      60.120   5.020 113.865  1.00 25.07
ATOM   2371  N    PRO A 299      60.829   2.963 113.297  1.00 29.37
ATOM   2372  CD   PRO A 299      61.285   1.932 112.352  1.00 26.09
ATOM   2373  CA   PRO A 299      61.024   2.491 114.669  1.00 29.46
ATOM   2374  CB   PRO A 299      61.675   1.118 114.465  1.00 29.03
ATOM   2375  CG   PRO A 299      62.411   1.306 113.137  1.00 27.34
ATOM   237   C    PRO A 299      61.849   3.403 115.570  1.00 31.88
```

Fig. 18-36

| | | | | | | | | | |
|---|---|---|---|---|---|---|---|---|---|
| ATOM | 2377 | O | PRO | A | 299 | 61.480 | 3.622 | 116.724 | 1.00 32.45 |
| ATOM | 2378 | N | TYR | A | 300 | 62.959 | 3.932 | 115.058 | 1.00 27.41 |
| ATOM | 2379 | CA | TYR | A | 300 | 63.803 | 4.801 | 115.878 | 1.00 27.34 |
| ATOM | 2380 | CB | TYR | A | 300 | 65.163 | 5.058 | 115.207 | 1.00 26.84 |
| ATOM | 2381 | CG | TYR | A | 300 | 65.912 | 3.821 | 114.738 | 1.00 29.09 |
| ATOM | 2382 | CD1 | TYR | A | 300 | 65.517 | 2.539 | 115.120 | 1.00 30.93 |
| ATOM | 2383 | CE1 | TYR | A | 300 | 66.214 | 1.411 | 114.682 | 1.00 30.68 |
| ATOM | 2384 | CD2 | TYR | A | 300 | 67.027 | 3.941 | 113.908 | 1.00 29.72 |
| ATOM | 2385 | CE2 | TYR | A | 300 | 67.730 | 2.829 | 113.466 | 1.00 30.76 |
| ATOM | 2386 | CZ | TYR | A | 300 | 67.320 | 1.568 | 113.854 | 1.00 33.89 |
| ATOM | 2387 | OH | TYR | A | 300 | 68.011 | 0.471 | 113.404 | 1.00 34.70 |
| ATOM | 2388 | C | TYR | A | 300 | 63.113 | 6.134 | 116.137 | 1.00 23.44 |
| ATOM | 2389 | O | TYR | A | 300 | 63.108 | 6.631 | 117.264 | 1.00 23.87 |
| ATOM | 2390 | N | ALA | A | 301 | 62.530 | 6.711 | 115.092 | 1.00 22.19 |
| ATOM | 2391 | CA | ALA | A | 301 | 61.839 | 7.993 | 115.216 | 1.00 26.50 |
| ATOM | 2392 | CB | ALA | A | 301 | 61.266 | 8.416 | 113.864 | 1.00 24.16 |
| ATOM | 2393 | C | ALA | A | 301 | 60.715 | 7.878 | 116.237 | 1.00 27.86 |
| ATOM | 2394 | O | ALA | A | 301 | 60.556 | 8.728 | 117.117 | 1.00 22.47 |
| ATOM | 2395 | N | LEU | A | 302 | 59.940 | 6.808 | 116.110 | 1.00 23.27 |
| ATOM | 2396 | CA | LEU | A | 302 | 58.818 | 6.566 | 116.996 | 1.00 26.50 |
| ATOM | 2397 | CB | LEU | A | 302 | 58.036 | 5.354 | 116.483 | 1.00 26.02 |
| ATOM | 2398 | CG | LEU | A | 302 | 56.866 | 4.798 | 117.291 | 1.00 29.73 |
| ATOM | 2399 | CD1 | LEU | A | 302 | 55.983 | 3.938 | 116.394 | 1.00 31.01 |
| ATOM | 2400 | CD2 | LEU | A | 302 | 57.394 | 4.001 | 118.465 | 1.00 32.99 |
| ATOM | 2401 | C | LEU | A | 302 | 59.246 | 6.373 | 118.451 | 1.00 27.49 |
| ATOM | 2402 | O | LEU | A | 302 | 58.648 | 6.946 | 119.358 | 1.00 25.22 |
| ATOM | 2403 | N | ALA | A | 303 | 60.289 | 5.580 | 118.672 | 1.00 27.85 |
| ATOM | 2404 | CA | ALA | A | 303 | 60.765 | 5.320 | 120.024 | 1.00 27.33 |
| ATOM | 2405 | CB | ALA | A | 303 | 61.854 | 4.269 | 119.990 | 1.00 29.17 |
| ATOM | 2406 | C | ALA | A | 303 | 61.279 | 6.580 | 120.714 | 1.00 26.64 |
| ATOM | 2407 | O | ALA | A | 303 | 60.944 | 6.849 | 121.875 | 1.00 23.18 |
| ATOM | 2408 | N | ARG | A | 304 | 62.092 | 7.354 | 120.003 | 1.00 27.48 |
| ATOM | 2409 | CA | ARG | A | 304 | 62.648 | 8.570 | 120.581 | 1.00 25.46 |
| ATOM | 2410 | CB | ARG | A | 304 | 63.773 | 9.136 | 119.704 | 1.00 21.31 |
| ATOM | 2411 | CG | ARG | A | 304 | 65.005 | 8.231 | 119.562 | 1.00 25.98 |
| ATOM | 2412 | CD | ARG | A | 304 | 66.153 | 9.042 | 118.951 | 1.00 27.87 |
| ATOM | 2413 | NE | ARG | A | 304 | 65.647 | 9.766 | 117.796 | 1.00 36.76 |
| ATOM | 2414 | CZ | ARG | A | 304 | 66.207 | 10.838 | 117.261 | 1.00 30.79 |
| ATOM | 2415 | NH1 | ARG | A | 304 | 67.323 | 11.345 | 117.768 | 1.00 30.11 |
| ATOM | 2416 | NH2 | ARG | A | 304 | 65.623 | 11.419 | 116.225 | 1.00 36.07 |
| ATOM | 2417 | C | ARG | A | 304 | 61.585 | 9.634 | 120.803 | 1.00 25.46 |
| ATOM | 2418 | O | ARG | A | 304 | 61.519 | 10.237 | 121.876 | 1.00 24.23 |
| ATOM | 2419 | N | ALA | A | 305 | 60.741 | 9.854 | 119.802 | 1.00 22.22 |
| ATOM | 2420 | CA | ALA | A | 305 | 59.700 | 10.868 | 119.910 | 1.00 26.70 |
| ATOM | 2421 | CB | ALA | A | 305 | 58.914 | 10.960 | 118.607 | 1.00 28.14 |
| ATOM | 2422 | C | ALA | A | 305 | 58.749 | 10.626 | 121.072 | 1.00 25.54 |
| ATOM | 2423 | O | ALA | A | 305 | 58.513 | 11.520 | 121.883 | 1.00 24.17 |
| ATOM | 2424 | N | TRP | A | 306 | 58.189 | 9.426 | 121.160 | 1.00 25.66 |
| ATOM | 2425 | CA | TRP | A | 306 | 57.270 | 9.157 | 122.253 | 1.00 28.01 |
| ATOM | 2426 | CB | TRP | A | 306 | 56.454 | 7.873 | 122.012 | 1.00 18.66 |
| ATOM | 2427 | CG | TRP | A | 306 | 55.382 | 8.052 | 120.973 | 1.00 21.80 |
| ATOM | 2428 | CD2 | TRP | A | 306 | 54.709 | 7.019 | 120.240 | 1.00 24.88 |
| ATOM | 2429 | CE2 | TRP | A | 306 | 53.725 | 7.646 | 119.442 | 1.00 23.98 |
| ATOM | 2430 | CE3 | TRP | A | 306 | 54.839 | 5.623 | 120.181 | 1.00 23.26 |
| ATOM | 2431 | CD1 | TRP | A | 306 | 54.795 | 9.228 | 120.599 | 1.00 20.24 |
| ATOM | 2432 | NE1 | TRP | A | 306 | 53.799 | 8.995 | 119.681 | 1.00 24.18 |
| ATOM | 2433 | CZ2 | TRP | A | 306 | 52.875 | 6.926 | 118.590 | 1.00 24.30 |
| ATOM | 2434 | CZ3 | TRP | A | 306 | 53.993 | 4.906 | 119.335 | 1.00 23.89 |
| ATOM | 2435 | CH2 | TRP | A | 306 | 53.024 | 5.562 | 118.550 | 1.00 24.12 |
| ATOM | 2436 | C | TRP | A | 306 | 57.969 | 9.113 | 123.605 | 1.00 27.93 |
| ATOM | 2437 | O | TRP | A | 306 | 57.330 | 9.319 | 124.637 | 1.00 28.58 |
| ATOM | 2438 | N | THR | A | 307 | 59.273 | 8.851 | 123.615 | 1.00 26.76 |
| ATOM | 2439 | CA | THR | A | 307 | 60.000 | 8.850 | 124.881 | 1.00 22.81 |
| ATOM | 2440 | CB | THR | A | 307 | 61.457 | 8.319 | 124.730 | 1.00 25.54 |
| ATOM | 2441 | OG1 | THR | A | 307 | 61.435 | 6.902 | 124.504 | 1.00 22.73 |
| ATOM | 2442 | CG2 | THR | A | 307 | 62.269 | 8.599 | 125.988 | 1.00 24.03 |

Fig. 18-37

| ATOM | 2443 | C   | THR A 307 | 60.027 | 10.288 | 125.396 | 1.00 | 26.54 |
|------|------|-----|-----------|--------|--------|---------|------|-------|
| ATOM | 2444 | O   | THR A 307 | 59.925 | 10.526 | 126.604 | 1.00 | 25.34 |
| ATOM | 2445 | N   | LEU A 308 | 60.152 | 11.247 | 124.478 | 1.00 | 21.65 |
| ATOM | 2446 | CA  | LEU A 308 | 60.172 | 12.657 | 124.862 | 1.00 | 21.41 |
| ATOM | 2447 | CB  | LEU A 308 | 60.442 | 13.558 | 123.642 | 1.00 | 19.20 |
| ATOM | 2448 | CG  | LEU A 308 | 61.797 | 13.386 | 122.938 | 1.00 | 21.31 |
| ATOM | 2449 | CD1 | LEU A 308 | 61.900 | 14.362 | 121.774 | 1.00 | 21.75 |
| ATOM | 2450 | CD2 | LEU A 308 | 62.937 | 13.622 | 123.915 | 1.00 | 19.26 |
| ATOM | 2451 | C   | LEU A 308 | 58.811 | 12.981 | 125.479 | 1.00 | 25.18 |
| ATOM | 2452 | O   | LEU A 308 | 58.731 | 13.565 | 126.561 | 1.00 | 21.35 |
| ATOM | 2453 | N   | ILE A 309 | 57.743 | 12.567 | 124.806 | 1.00 | 21.74 |
| ATOM | 2454 | CA  | ILE A 309 | 56.394 | 12.799 | 125.298 | 1.00 | 19.23 |
| ATOM | 2455 | CB  | ILE A 309 | 55.337 | 12.149 | 124.366 | 1.00 | 19.63 |
| ATOM | 2456 | CG2 | ILE A 309 | 53.945 | 12.321 | 124.948 | 1.00 | 19.54 |
| ATOM | 2457 | CG1 | ILE A 309 | 55.403 | 12.788 | 122.979 | 1.00 | 20.80 |
| ATOM | 2458 | CD1 | ILE A 309 | 55.118 | 14.274 | 122.988 | 1.00 | 20.08 |
| ATOM | 2459 | C   | ILE A 309 | 56.228 | 12.222 | 126.701 | 1.00 | 23.97 |
| ATOM | 2460 | O   | ILE A 309 | 55.731 | 12.894 | 127.602 | 1.00 | 21.38 |
| ATOM | 2461 | N   | TRP A 310 | 56.652 | 10.977 | 126.888 | 1.00 | 26.45 |
| ATOM | 2462 | CA  | TRP A 310 | 56.525 | 10.342 | 128.192 | 1.00 | 28.35 |
| ATOM | 2463 | CB  | TRP A 310 | 56.940 | 8.872  | 128.132 | 1.00 | 23.95 |
| ATOM | 2464 | CG  | TRP A 310 | 56.874 | 8.203  | 129.479 | 1.00 | 29.60 |
| ATOM | 2465 | CD2 | TRP A 310 | 55.697 | 7.967  | 130.263 | 1.00 | 31.40 |
| ATOM | 2466 | CE2 | TRP A 310 | 56.115 | 7.390  | 131.480 | 1.00 | 32.47 |
| ATOM | 2467 | CE3 | TRP A 310 | 54.329 | 8.189  | 130.055 | 1.00 | 32.30 |
| ATOM | 2468 | CD1 | TRP A 310 | 57.926 | 7.770  | 130.232 | 1.00 | 33.42 |
| ATOM | 2469 | NE1 | TRP A 310 | 57.480 | 7.282  | 131.436 | 1.00 | 30.09 |
| ATOM | 2470 | CZ2 | TRP A 310 | 55.213 | 7.030  | 132.492 | 1.00 | 29.93 |
| ATOM | 2471 | CZ3 | TRP A 310 | 53.432 | 7.831  | 131.062 | 1.00 | 29.72 |
| ATOM | 2472 | CH2 | TRP A 310 | 53.881 | 7.259  | 132.265 | 1.00 | 24.53 |
| ATOM | 2473 | C   | TRP A 310 | 57.308 | 11.048 | 129.293 | 1.00 | 33.49 |
| ATOM | 2474 | O   | TRP A 310 | 56.820 | 11.137 | 130.426 | 1.00 | 27.59 |
| ATOM | 2475 | N   | CYS A 311 | 58.512 | 11.535 | 128.984 | 1.00 | 29.34 |
| ATOM | 2476 | CA  | CYS A 311 | 59.305 | 12.247 | 129.994 | 1.00 | 30.06 |
| ATOM | 2477 | CB  | CYS A 311 | 60.722 | 12.538 | 129.479 | 1.00 | 30.08 |
| ATOM | 2478 | SG  | CYS A 311 | 61.804 | 11.084 | 129.327 | 1.00 | 33.17 |
| ATOM | 2479 | C   | CYS A 311 | 58.612 | 13.560 | 130.397 | 1.00 | 29.25 |
| ATOM | 2480 | O   | CYS A 311 | 58.612 | 13.940 | 131.570 | 1.00 | 28.80 |
| ATOM | 2481 | N   | GLU A 312 | 58.021 | 14.247 | 129.425 | 1.00 | 23.13 |
| ATOM | 2482 | CA  | GLU A 312 | 57.308 | 15.496 | 129.696 | 1.00 | 30.31 |
| ATOM | 2483 | CB  | GLU A 312 | 56.648 | 16.032 | 128.427 | 1.00 | 28.97 |
| ATOM | 2484 | CG  | GLU A 312 | 57.080 | 17.418 | 127.988 | 1.00 | 41.67 |
| ATOM | 2485 | CD  | GLU A 312 | 56.905 | 18.465 | 129.059 | 1.00 | 44.21 |
| ATOM | 2486 | OE1 | GLU A 312 | 55.813 | 18.534 | 129.658 | 1.00 | 54.15 |
| ATOM | 2487 | OE2 | GLU A 312 | 57.860 | 19.233 | 129.290 | 1.00 | 43.90 |
| ATOM | 2488 | C   | GLU A 312 | 56.204 | 15.225 | 130.712 | 1.00 | 28.03 |
| ATOM | 2489 | O   | GLU A 312 | 56.120 | 15.869 | 131.751 | 1.00 | 30.64 |
| ATOM | 2490 | N   | LEU A 313 | 55.343 | 14.270 | 130.388 | 1.00 | 31.06 |
| ATOM | 2491 | CA  | LEU A 313 | 54.231 | 13.918 | 131.266 | 1.00 | 36.21 |
| ATOM | 2492 | CB  | LEU A 313 | 53.337 | 12.873 | 130.604 | 1.00 | 28.83 |
| ATOM | 2493 | CG  | LEU A 313 | 52.493 | 13.342 | 129.429 | 1.00 | 34.62 |
| ATOM | 2494 | CD1 | LEU A 313 | 51.818 | 12.146 | 128.788 | 1.00 | 33.05 |
| ATOM | 2495 | CD2 | LEU A 313 | 51.471 | 14.357 | 129.914 | 1.00 | 27.27 |
| ATOM | 2496 | C   | LEU A 313 | 54.685 | 13.377 | 132.610 | 1.00 | 33.97 |
| ATOM | 2497 | O   | LEU A 313 | 54.131 | 13.730 | 133.644 | 1.00 | 37.26 |
| ATOM | 2498 | N   | SER A 314 | 55.688 | 12.508 | 132.577 | 1.00 | 33.72 |
| ATOM | 2499 | CA  | SER A 314 | 56.233 | 11.880 | 133.776 | 1.00 | 33.58 |
| ATOM | 2500 | CB  | SER A 314 | 57.183 | 10.743 | 133.388 | 1.00 | 35.88 |
| ATOM | 2501 | OG  | SER A 314 | 56.517 | 9.761  | 132.628 | 1.00 | 45.88 |
| ATOM | 2502 | C   | SER A 314 | 57.002 | 12.846 | 134.659 | 1.00 | 31.54 |
| ATOM | 2503 | O   | SER A 314 | 57.339 | 12.513 | 135.788 | 1.00 | 27.69 |
| ATOM | 2504 | N   | GLY A 315 | 57.312 | 14.021 | 134.130 | 1.00 | 35.50 |
| ATOM | 2505 | CA  | GLY A 315 | 58.057 | 14.996 | 134.905 | 1.00 | 36.31 |
| ATOM | 2506 | C   | GLY A 315 | 59.518 | 14.634 | 135.099 | 1.00 | 38.47 |
| ATOM | 2507 | O   | GLY A 315 | 60.138 | 15.049 | 136.078 | 1.00 | 41.57 |
| ATOM | 2508 | N   | ARG A 316 | 60.089 | 13.862 | 134.181 | 1.00 | 39.32 |

Fig. 18-38

```
ATOM   2509  CA   ARG A 316      61.490  13.501 134.332  1.00 39.06
ATOM   2510  CB   ARG A 316      61.641  11.982 134.413  1.00 39.16
ATOM   2511  CG   ARG A 316      61.233  11.226 133.184  1.00 39.11
ATOM   2512  CD   ARG A 316      61.426   9.744 133.429  1.00 41.21
ATOM   2513  NE   ARG A 316      60.461   9.229 134.389  1.00 40.97
ATOM   2514  CZ   ARG A 316      60.524   8.021 134.926  1.00 36.40
ATOM   2515  NH1  ARG A 316      61.511   7.209 134.598  1.00 38.93
ATOM   2516  NH2  ARG A 316      59.583   7.621 135.768  1.00 30.53
ATOM   2517  C    ARG A 316      62.369  14.083 133.230  1.00 40.17
ATOM   2518  O    ARG A 316      61.910  14.325 132.111  1.00 34.27
ATOM   2519  N    GLU A 317      63.633  14.325 133.564  1.00 41.26
ATOM   2520  CA   GLU A 317      64.580  14.905 132.619  1.00 44.42
ATOM   2521  CB   GLU A 317      65.901  15.249 133.317  1.00 46.84
ATOM   2522  CG   GLU A 317      65.756  15.996 134.629  1.00 57.66
ATOM   2523  CD   GLU A 317      65.212  15.113 135.743  1.00 65.46
ATOM   2524  OE1  GLU A 317      65.871  14.101 136.073  1.00 68.38
ATOM   2525  OE2  GLU A 317      64.129  15.425 136.287  1.00 67.24
ATOM   2526  C    GLU A 317      64.873  13.962 131.462  1.00 38.45
ATOM   2527  O    GLU A 317      64.977  12.748 131.636  1.00 38.84
ATOM   2528  N    VAL A 318      65.010  14.525 130.275  1.00 37.64
ATOM   2529  CA   VAL A 318      65.315  13.720 129.108  1.00 39.13
ATOM   2530  CB   VAL A 318      64.858  14.417 127.810  1.00 42.75
ATOM   2531  CG1  VAL A 318      65.192  13.544 126.610  1.00 41.84
ATOM   2532  CG2  VAL A 318      63.364  14.701 127.867  1.00 42.38
ATOM   2533  C    VAL A 318      66.822  13.495 129.037  1.00 38.45
ATOM   2534  O    VAL A 318      67.598  14.442 128.910  1.00 36.04
ATOM   2535  N    PRO A 319      67.261  12.236 129.156  1.00 39.54
ATOM   2536  CD   PRO A 319      66.512  10.994 129.397  1.00 40.47
ATOM   2537  CA   PRO A 319      68.695  11.949 129.088  1.00 43.85
ATOM   2538  CB   PRO A 319      68.745  10.439 129.319  1.00 44.12
ATOM   2539  CG   PRO A 319      67.419   9.986 128.745  1.00 46.48
ATOM   2540  C    PRO A 319      69.228  12.353 127.718  1.00 43.55
ATOM   2541  O    PRO A 319      68.563  12.141 126.708  1.00 43.45
ATOM   2542  N    GLU A 320      70.420  12.936 127.689  1.00 42.52
ATOM   2543  CA   GLU A 320      71.026  13.380 126.440  1.00 45.19
ATOM   2544  CB   GLU A 320      72.384  14.032 126.706  1.00 43.86
ATOM   2545  CG   GLU A 320      73.121  14.412 125.434  1.00 52.62
ATOM   2546  CD   GLU A 320      74.507  14.967 125.697  1.00 52.36
ATOM   2547  OE1  GLU A 320      75.219  15.271 124.720  1.00 56.25
ATOM   2548  OE2  GLU A 320      74.883  15.101 126.875  1.00 52.25
ATOM   2549  C    GLU A 320      71.223  12.266 125.421  1.00 43.52
ATOM   2550  O    GLU A 320      70.876  12.412 124.253  1.00 41.89
ATOM   2551  N    LYS A 321      71.781  11.150 125.867  1.00 43.35
ATOM   2552  CA   LYS A 321      72.059  10.041 124.969  1.00 43.53
ATOM   2553  CB   LYS A 321      73.561   9.808 124.879  1.00 42.78
ATOM   2554  CG   LYS A 321      74.238   9.340 126.180  1.00 49.38
ATOM   2555  CD   LYS A 321      74.272  10.396 127.307  1.00 57.82
ATOM   2556  CE   LYS A 321      72.978  10.497 128.129  1.00 53.81
ATOM   2557  NZ   LYS A 321      72.660   9.245 128.883  1.00 54.17
ATOM   2558  C    LYS A 321      71.407   8.731 125.345  1.00 41.52
ATOM   2559  O    LYS A 321      70.954   8.540 126.469  1.00 41.98
ATOM   2560  N    LEU A 322      71.378   7.820 124.382  1.00 38.64
ATOM   2561  CA   LEU A 322      70.815   6.508 124.613  1.00 40.46
ATOM   2562  CB   LEU A 322      70.442   5.845 123.289  1.00 42.22
ATOM   2563  CG   LEU A 322      69.595   6.632 122.287  1.00 42.92
ATOM   2564  CD1  LEU A 322      69.204   5.737 121.125  1.00 41.13
ATOM   2565  CD2  LEU A 322      68.361   7.148 122.967  1.00 44.41
ATOM   2566  C    LEU A 322      71.918   5.702 125.268  1.00 41.36
ATOM   2567  O    LEU A 322      73.079   5.825 124.884  1.00 44.16
ATOM   2568  N    ASN A 323      71.579   4.894 126.265  1.00 39.89
ATOM   2569  CA   ASN A 323      72.594   4.067 126.895  1.00 40.96
ATOM   2570  CB   ASN A 323      72.136   3.556 128.259  1.00 43.00
ATOM   2571  CG   ASN A 323      70.787   2.886 128.202  1.00 45.59
ATOM   2572  OD1  ASN A 323      70.482   2.151 127.264  1.00 45.71
ATOM   2573  ND2  ASN A 323      69.975   3.114 129.224  1.00 48.08
ATOM   2574  C    ASN A 323      72.828   2.894 125.954  1.00 44.88
```

Fig. 18-39

```
ATOM   2575  O    ASN A 323      72.124   2.739 124.955  1.00 46.41
ATOM   2576  N    ASN A 324      73.809   2.062 126.268  1.00 45.98
ATOM   2577  CA   ASN A 324      74.122   0.938 125.404  1.00 49.82
ATOM   2578  CB   ASN A 324      75.386   0.244 125.904  1.00 53.88
ATOM   2579  CG   ASN A 324      75.960  -0.711 124.888  1.00 60.09
ATOM   2580  OD1  ASN A 324      75.344  -1.723 124.550  1.00 66.99
ATOM   2581  ND2  ASN A 324      77.143  -0.386 124.378  1.00 58.06
ATOM   2582  C    ASN A 324      72.979  -0.070 125.267  1.00 47.12
ATOM   2583  O    ASN A 324      72.784  -0.644 124.197  1.00 43.63
ATOM   2584  N    LYS A 325      72.220  -0.276 126.339  1.00 46.39
ATOM   2585  CA   LYS A 325      71.106  -1.221 126.318  1.00 46.76
ATOM   2586  CB   LYS A 325      70.428  -1.328 127.695  1.00 47.65
ATOM   2587  CG   LYS A 325      71.292  -1.837 128.858  1.00 54.21
ATOM   2588  CD   LYS A 325      72.160  -0.750 129.526  1.00 56.87
ATOM   2589  CE   LYS A 325      73.329  -0.289 128.671  1.00 57.45
ATOM   2590  NZ   LYS A 325      74.091   0.816 129.307  1.00 58.32
ATOM   2591  C    LYS A 325      70.062  -0.791 125.296  1.00 45.17
ATOM   2592  O    LYS A 325      69.474  -1.625 124.601  1.00 42.73
ATOM   2593  N    ALA A 326      69.832   0.514 125.213  1.00 41.43
ATOM   2594  CA   ALA A 326      68.861   1.054 124.276  1.00 41.61
ATOM   2595  CB   ALA A 326      68.562   2.508 124.616  1.00 42.80
ATOM   2596  C    ALA A 326      69.365   0.940 122.838  1.00 43.80
ATOM   2597  O    ALA A 326      68.595   0.625 121.926  1.00 45.17
ATOM   2598  N    LYS A 327      70.658   1.191 122.637  1.00 43.46
ATOM   2599  CA   LYS A 327      71.235   1.120 121.296  1.00 43.26
ATOM   2600  CB   LYS A 327      72.723   1.484 121.311  1.00 44.77
ATOM   2601  CG   LYS A 327      73.037   2.892 121.800  1.00 50.87
ATOM   2602  CD   LYS A 327      74.544   3.168 121.747  1.00 52.74
ATOM   2603  CE   LYS A 327      74.916   4.508 122.377  1.00 51.30
ATOM   2604  NZ   LYS A 327      74.256   5.670 121.715  1.00 52.72
ATOM   2605  C    LYS A 327      71.063  -0.274 120.728  1.00 41.29
ATOM   2606  O    LYS A 327      70.625  -0.437 119.592  1.00 38.83
ATOM   2607  N    GLU A 328      71.403  -1.278 121.526  1.00 39.95
ATOM   2608  CA   GLU A 328      71.276  -2.660 121.090  1.00 42.40
ATOM   2609  CB   GLU A 328      71.875  -3.605 122.135  1.00 43.05
ATOM   2610  CG   GLU A 328      73.369  -3.432 122.295  1.00 48.81
ATOM   2611  CD   GLU A 328      74.096  -3.529 120.963  1.00 52.11
ATOM   2612  OE1  GLU A 328      73.972  -4.574 120.291  1.00 55.44
ATOM   2613  OE2  GLU A 328      74.785  -2.558 120.584  1.00 51.64
ATOM   2614  C    GLU A 328      69.825  -3.030 120.818  1.00 39.51
ATOM   2615  O    GLU A 328      69.536  -3.842 119.939  1.00 37.35
ATOM   2616  N    LEU A 329      68.911  -2.444 121.582  1.00 36.37
ATOM   2617  CA   LEU A 329      67.496  -2.717 121.380  1.00 36.03
ATOM   2618  CB   LEU A 329      66.646  -1.958 122.400  1.00 34.66
ATOM   2619  CG   LEU A 329      65.133  -2.110 122.213  1.00 33.88
ATOM   2620  CD1  LEU A 329      64.755  -3.572 122.351  1.00 36.21
ATOM   2621  CD2  LEU A 329      64.391  -1.268 123.240  1.00 34.00
ATOM   2622  C    LEU A 329      67.120  -2.268 119.971  1.00 33.64
ATOM   2623  O    LEU A 329      66.655  -3.061 119.162  1.00 31.29
ATOM   2624  N    LEU A 330      67.333  -0.990 119.681  1.00 33.78
ATOM   2625  CA   LEU A 330      67.004  -0.461 118.366  1.00 36.38
ATOM   2626  CB   LEU A 330      67.326   1.033 118.294  1.00 30.74
ATOM   2627  CG   LEU A 330      66.514   1.958 119.205  1.00 31.51
ATOM   2628  CD1  LEU A 330      66.857   3.404 118.894  1.00 22.11
ATOM   2629  CD2  LEU A 330      65.028   1.728 118.978  1.00 29.69
ATOM   2630  C    LEU A 330      67.729  -1.201 117.246  1.00 36.49
ATOM   2631  O    LEU A 330      67.142  -1.493 116.210  1.00 35.61
ATOM   2632  N    LYS A 331      69.005  -1.503 117.455  1.00 37.63
ATOM   2633  CA   LYS A 331      69.786  -2.205 116.446  1.00 41.32
ATOM   2634  CB   LYS A 331      71.256  -2.272 116.874  1.00 44.74
ATOM   2635  CG   LYS A 331      71.954  -0.919 116.869  1.00 44.68
ATOM   2636  CD   LYS A 331      73.350  -0.964 117.498  1.00 51.42
ATOM   2637  CE   LYS A 331      74.315  -1.889 116.765  1.00 53.71
ATOM   2638  NZ   LYS A 331      73.928  -3.327 116.855  1.00 56.15
ATOM   2639  C    LYS A 331      69.258  -3.612 116.173  1.00 42.35
ATOM   2640  O    LYS A 331      69.310  -4.086 115.042  1.00 42.68
```

Fig. 18-40

| | | | | | | | | | |
|---|---|---|---|---|---|---|---|---|---|
| ATOM | 2641 | N | SER | A | 332 | 68.734 | -4.270 | 117.200 | 1.00 41.56 |
| ATOM | 2642 | CA | SER | A | 332 | 68.226 | -5.629 | 117.039 | 1.00 46.88 |
| ATOM | 2643 | CB | SER | A | 332 | 68.045 | -6.298 | 118.400 | 1.00 42.19 |
| ATOM | 2644 | OG | SER | A | 332 | 66.959 | -5.714 | 119.096 | 1.00 39.55 |
| ATOM | 2645 | C | SER | A | 332 | 66.896 | -5.687 | 116.297 | 1.00 48.58 |
| ATOM | 2646 | O | SER | A | 332 | 66.393 | -6.774 | 116.017 | 1.00 45.78 |
| ATOM | 2647 | N | ILE | A | 333 | 66.325 | -4.531 | 115.979 | 1.00 48.27 |
| ATOM | 2648 | CA | ILE | A | 333 | 65.041 | -4.503 | 115.292 | 1.00 51.82 |
| ATOM | 2649 | CB | ILE | A | 333 | 64.378 | -3.119 | 115.402 | 1.00 52.16 |
| ATOM | 2650 | CG2 | ILE | A | 333 | 63.038 | -3.122 | 114.683 | 1.00 52.64 |
| ATOM | 2651 | CG1 | ILE | A | 333 | 64.163 | -2.765 | 116.871 | 1.00 52.70 |
| ATOM | 2652 | CD1 | ILE | A | 333 | 63.550 | -1.402 | 117.077 | 1.00 56.70 |
| ATOM | 2653 | C | ILE | A | 333 | 65.112 | -4.887 | 113.820 | 1.00 53.43 |
| ATOM | 2654 | O | ILE | A | 333 | 66.118 | -4.675 | 113.145 | 1.00 56.45 |
| ATOM | 2655 | N | ASP | A | 334 | 64.016 | -5.461 | 113.344 | 1.00 55.53 |
| ATOM | 2656 | CA | ASP | A | 334 | 63.865 | -5.892 | 111.962 | 1.00 59.58 |
| ATOM | 2657 | CB | ASP | A | 334 | 62.845 | -7.040 | 111.918 | 1.00 62.69 |
| ATOM | 2658 | CG | ASP | A | 334 | 61.546 | -6.712 | 112.664 | 1.00 66.23 |
| ATOM | 2659 | OD1 | ASP | A | 334 | 60.795 | -5.814 | 112.227 | 1.00 63.25 |
| ATOM | 2660 | OD2 | ASP | A | 334 | 61.277 | -7.354 | 113.704 | 1.00 63.45 |
| ATOM | 2661 | C | ASP | A | 334 | 63.385 | -4.705 | 111.125 | 1.00 60.81 |
| ATOM | 2662 | O | ASP | A | 334 | 62.239 | -4.673 | 110.681 | 1.00 59.47 |
| ATOM | 2663 | N | PHE | A | 335 | 64.266 | -3.736 | 110.889 | 1.00 60.00 |
| ATOM | 2664 | CA | PHE | A | 335 | 63.864 | -2.545 | 110.147 | 1.00 59.37 |
| ATOM | 2665 | CB | PHE | A | 335 | 64.247 | -1.298 | 110.952 | 1.00 53.38 |
| ATOM | 2666 | CG | PHE | A | 335 | 63.895 | -0.013 | 110.275 | 1.00 49.13 |
| ATOM | 2667 | CD1 | PHE | A | 335 | 62.618 | 0.189 | 109.770 | 1.00 44.32 |
| ATOM | 2668 | CD2 | PHE | A | 335 | 64.845 | 0.993 | 110.127 | 1.00 49.91 |
| ATOM | 2669 | CE1 | PHE | A | 335 | 62.288 | 1.373 | 109.122 | 1.00 42.74 |
| ATOM | 2670 | CE2 | PHE | A | 335 | 64.526 | 2.180 | 109.483 | 1.00 46.40 |
| ATOM | 2671 | CZ | PHE | A | 335 | 63.244 | 2.370 | 108.978 | 1.00 42.77 |
| ATOM | 2672 | C | PHE | A | 335 | 64.334 | -2.399 | 108.696 | 1.00 60.85 |
| ATOM | 2673 | O | PHE | A | 335 | 63.689 | -2.914 | 107.785 | 1.00 66.28 |
| ATOM | 2674 | N | GLU | A | 336 | 65.430 | -1.671 | 108.493 | 1.00 57.40 |
| ATOM | 2675 | CA | GLU | A | 336 | 66.015 | -1.411 | 107.174 | 1.00 58.96 |
| ATOM | 2676 | CB | GLU | A | 336 | 65.782 | -2.579 | 106.211 | 1.00 62.66 |
| ATOM | 2677 | CG | GLU | A | 336 | 66.417 | -2.377 | 104.846 | 1.00 68.51 |
| ATOM | 2678 | CD | GLU | A | 336 | 66.277 | -3.590 | 103.943 | 1.00 73.21 |
| ATOM | 2679 | OE1 | GLU | A | 336 | 66.753 | -4.678 | 104.333 | 1.00 73.30 |
| ATOM | 2680 | OE2 | GLU | A | 336 | 65.697 | -3.457 | 102.843 | 1.00 75.74 |
| ATOM | 2681 | C | GLU | A | 336 | 65.460 | -0.124 | 106.576 | 1.00 55.70 |
| ATOM | 2682 | O | GLU | A | 336 | 64.281 | -0.023 | 106.253 | 1.00 55.28 |
| ATOM | 2683 | N | GLU | A | 337 | 66.338 | 0.857 | 106.432 | 1.00 54.75 |
| ATOM | 2684 | CA | GLU | A | 337 | 65.986 | 2.167 | 105.905 | 1.00 55.99 |
| ATOM | 2685 | CB | GLU | A | 337 | 67.221 | 3.065 | 105.983 | 1.00 51.75 |
| ATOM | 2686 | CG | GLU | A | 337 | 66.926 | 4.536 | 106.092 | 1.00 52.28 |
| ATOM | 2687 | CD | GLU | A | 337 | 66.184 | 4.891 | 107.366 | 1.00 43.72 |
| ATOM | 2688 | OE1 | GLU | A | 337 | 66.705 | 4.640 | 108.474 | 1.00 42.21 |
| ATOM | 2689 | OE2 | GLU | A | 337 | 65.072 | 5.425 | 107.256 | 1.00 47.31 |
| ATOM | 2690 | C | GLU | A | 337 | 65.485 | 2.064 | 104.460 | 1.00 57.56 |
| ATOM | 2691 | O | GLU | A | 337 | 66.087 | 1.377 | 103.639 | 1.00 58.29 |
| ATOM | 2692 | N | PHE | A | 338 | 64.385 | 2.745 | 104.151 | 1.00 60.26 |
| ATOM | 2693 | CA | PHE | A | 338 | 63.814 | 2.710 | 102.805 | 1.00 61.69 |
| ATOM | 2694 | CB | PHE | A | 338 | 62.561 | 3.582 | 102.723 | 1.00 60.86 |
| ATOM | 2695 | CG | PHE | A | 338 | 61.845 | 3.493 | 101.401 | 1.00 61.92 |
| ATOM | 2696 | CD1 | PHE | A | 338 | 61.054 | 2.391 | 101.094 | 1.00 62.99 |
| ATOM | 2697 | CD2 | PHE | A | 338 | 61.970 | 4.508 | 100.458 | 1.00 62.74 |
| ATOM | 2698 | CE1 | PHE | A | 338 | 60.392 | 2.302 | 99.868 | 1.00 65.11 |
| ATOM | 2699 | CE2 | PHE | A | 338 | 61.315 | 4.428 | 99.228 | 1.00 64.62 |
| ATOM | 2700 | CZ | PHE | A | 338 | 60.523 | 3.322 | 98.934 | 1.00 63.87 |
| ATOM | 2701 | C | PHE | A | 338 | 64.818 | 3.208 | 101.773 | 1.00 64.33 |
| ATOM | 2702 | O | PHE | A | 338 | 64.803 | 2.781 | 100.616 | 1.00 62.45 |
| ATOM | 2703 | N | ASP | A | 339 | 65.677 | 4.130 | 102.194 | 1.00 64.11 |
| ATOM | 2704 | CA | ASP | A | 339 | 66.689 | 4.684 | 101.310 | 1.00 67.42 |
| ATOM | 2705 | CB | ASP | A | 339 | 66.565 | 6.206 | 101.248 | 1.00 67.20 |
| ATOM | 2706 | CG | ASP | A | 339 | 67.647 | 6.838 | 100.402 | 1.00 68.03 |

Fig. 18-41

```
ATOM   2707  OD1 ASP A 339      67.796   6.432  99.229  1.00 72.20
ATOM   2708  OD2 ASP A 339      68.346   7.740 100.904  1.00 64.15
ATOM   2709  C   ASP A 339      68.088   4.295 101.763  1.00 68.73
ATOM   2710  O   ASP A 339      68.511   4.628 102.869  1.00 68.17
ATOM   2711  N   ASP A 340      68.796   3.588 100.888  1.00 71.90
ATOM   2712  CA  ASP A 340      70.151   3.111 101.149  1.00 73.59
ATOM   2713  CB  ASP A 340      70.778   2.601  99.848  1.00 75.47
ATOM   2714  CG  ASP A 340      69.953   1.511  99.195  1.00 76.03
ATOM   2715  OD1 ASP A 340      69.761   0.449  99.823  1.00 76.90
ATOM   2716  OD2 ASP A 340      69.492   1.718  98.054  1.00 80.23
ATOM   2717  C   ASP A 340      71.069   4.155 101.766  1.00 72.77
ATOM   2718  O   ASP A 340      71.618   3.946 102.845  1.00 73.08
ATOM   2719  N   GLU A 341      71.242   5.275 101.074  1.00 73.15
ATOM   2720  CA  GLU A 341      72.112   6.341 101.557  1.00 74.56
ATOM   2721  CB  GLU A 341      72.917   6.924 100.390  1.00 77.06
ATOM   2722  CG  GLU A 341      73.878   8.034 100.792  1.00 82.57
ATOM   2723  CD  GLU A 341      74.924   7.571 101.794  1.00 85.34
ATOM   2724  OE1 GLU A 341      75.718   6.669 101.450  1.00 86.64
ATOM   2725  OE2 GLU A 341      74.951   8.106 102.924  1.00 85.37
ATOM   2726  C   GLU A 341      71.327   7.453 102.245  1.00 72.47
ATOM   2727  O   GLU A 341      70.822   8.364 101.589  1.00 76.75
ATOM   2728  N   VAL A 342      71.228   7.381 103.566  1.00 67.86
ATOM   2729  CA  VAL A 342      70.503   8.393 104.323  1.00 64.84
ATOM   2730  CB  VAL A 342      69.160   7.853 104.850  1.00 66.27
ATOM   2731  CG1 VAL A 342      68.256   7.494 103.701  1.00 67.95
ATOM   2732  CG2 VAL A 342      69.400   6.637 105.722  1.00 65.37
ATOM   2733  C   VAL A 342      71.305   8.871 105.520  1.00 61.75
ATOM   2734  O   VAL A 342      71.375  10.066 105.795  1.00 64.14
ATOM   2735  N   ASP A 343      71.912   7.925 106.225  1.00 56.79
ATOM   2736  CA  ASP A 343      72.692   8.229 107.417  1.00 54.53
ATOM   2737  CB  ASP A 343      73.707   9.340 107.158  1.00 56.31
ATOM   2738  CG  ASP A 343      74.531   9.660 108.388  1.00 58.81
ATOM   2739  OD1 ASP A 343      75.298  10.644 108.357  1.00 65.36
ATOM   2740  OD2 ASP A 343      74.420   8.918 109.387  1.00 54.29
ATOM   2741  C   ASP A 343      71.765   8.675 108.534  1.00 50.70
ATOM   2742  O   ASP A 343      71.442   9.859 108.651  1.00 46.00
ATOM   2743  N   ARG A 344      71.328   7.717 109.341  1.00 46.20
ATOM   2744  CA  ARG A 344      70.452   8.004 110.463  1.00 41.18
ATOM   2745  CB  ARG A 344      69.121   7.268 110.299  1.00 39.81
ATOM   2746  CG  ARG A 344      68.289   7.711 109.098  1.00 35.08
ATOM   2747  CD  ARG A 344      68.036   9.211 109.121  1.00 28.37
ATOM   2748  NE  ARG A 344      67.157   9.645 108.036  1.00 30.90
ATOM   2749  CZ  ARG A 344      67.013  10.909 107.649  1.00 31.05
ATOM   2750  NH1 ARG A 344      67.693  11.874 108.258  1.00 30.49
ATOM   2751  NH2 ARG A 344      66.201  11.212 106.646  1.00 31.76
ATOM   2752  C   ARG A 344      71.147   7.561 111.742  1.00 38.46
ATOM   2753  O   ARG A 344      70.516   7.370 112.773  1.00 34.99
ATOM   2754  N   SER A 345      72.464   7.418 111.662  1.00 33.97
ATOM   2755  CA  SER A 345      73.261   6.981 112.795  1.00 33.68
ATOM   2756  CB  SER A 345      74.742   6.972 112.404  1.00 39.11
ATOM   2757  OG  SER A 345      75.163   8.260 111.990  1.00 42.80
ATOM   2758  C   SER A 345      73.054   7.826 114.053  1.00 31.83
ATOM   2759  O   SER A 345      73.100   7.314 115.167  1.00 24.35
ATOM   2760  N   TYR A 346      72.819   9.119 113.877  1.00 33.10
ATOM   2761  CA  TYR A 346      72.614  10.003 115.015  1.00 34.50
ATOM   2762  CB  TYR A 346      72.397  11.437 114.522  1.00 35.16
ATOM   2763  CG  TYR A 346      71.168  11.615 113.659  1.00 39.69
ATOM   2764  CD1 TYR A 346      69.909  11.814 114.227  1.00 36.57
ATOM   2765  CE1 TYR A 346      68.767  11.940 113.424  1.00 40.23
ATOM   2766  CD2 TYR A 346      71.260  11.544 112.270  1.00 39.04
ATOM   2767  CE2 TYR A 346      70.131  11.667 111.463  1.00 38.65
ATOM   2768  CZ  TYR A 346      68.890  11.864 112.041  1.00 37.64
ATOM   2769  OH  TYR A 346      67.776  11.982 111.234  1.00 32.48
ATOM   2770  C   TYR A 346      71.432   9.560 115.874  1.00 37.72
ATOM   2771  O   TYR A 346      71.396   9.829 117.074  1.00 35.48
ATOM   2772  N   MET A 347      70.472   8.869 115.265  1.00 35.36
```

Fig. 18-42

| | | | | | | | | | |
|---|---|---|---|---|---|---|---|---|---|
| ATOM | 2773 | CA | MET | A | 347 | 69.295 | 8.418 | 116.004 | 1.00 36.97 |
| ATOM | 2774 | CB | MET | A | 347 | 68.226 | 7.868 | 115.052 | 1.00 33.45 |
| ATOM | 2775 | CG | MET | A | 347 | 67.853 | 8.809 | 113.921 | 1.00 28.09 |
| ATOM | 2776 | SD | MET | A | 347 | 66.471 | 8.194 | 112.943 | 1.00 32.14 |
| ATOM | 2777 | CE | MET | A | 347 | 67.058 | 6.647 | 112.457 | 1.00 39.25 |
| ATOM | 2778 | C | MET | A | 347 | 69.632 | 7.363 | 117.055 | 1.00 34.67 |
| ATOM | 2779 | O | MET | A | 347 | 68.890 | 7.187 | 118.016 | 1.00 33.46 |
| ATOM | 2780 | N | LEU | A | 348 | 70.747 | 6.663 | 116.880 | 1.00 36.42 |
| ATOM | 2781 | CA | LEU | A | 348 | 71.137 | 5.641 | 117.846 | 1.00 34.57 |
| ATOM | 2782 | CB | LEU | A | 348 | 71.841 | 4.476 | 117.152 | 1.00 34.16 |
| ATOM | 2783 | CG | LEU | A | 348 | 71.066 | 3.655 | 116.121 | 1.00 35.61 |
| ATOM | 2784 | CD1 | LEU | A | 348 | 72.010 | 2.660 | 115.469 | 1.00 36.58 |
| ATOM | 2785 | CD2 | LEU | A | 348 | 69.906 | 2.935 | 116.788 | 1.00 42.34 |
| ATOM | 2786 | C | LEU | A | 348 | 72.075 | 6.232 | 118.885 | 1.00 37.10 |
| ATOM | 2787 | O | LEU | A | 348 | 72.583 | 5.513 | 119.745 | 1.00 37.75 |
| ATOM | 2788 | N | GLU | A | 349 | 72.295 | 7.541 | 118.801 | 1.00 38.31 |
| ATOM | 2789 | CA | GLU | A | 349 | 73.192 | 8.231 | 119.726 | 1.00 42.86 |
| ATOM | 2790 | CB | GLU | A | 349 | 74.150 | 9.136 | 118.948 | 1.00 47.04 |
| ATOM | 2791 | CG | GLU | A | 349 | 74.942 | 8.426 | 117.867 | 1.00 53.27 |
| ATOM | 2792 | CD | GLU | A | 349 | 75.828 | 7.325 | 118.410 | 1.00 58.36 |
| ATOM | 2793 | OE1 | GLU | A | 349 | 76.681 | 7.619 | 119.279 | 1.00 59.59 |
| ATOM | 2794 | OE2 | GLU | A | 349 | 75.669 | 6.166 | 117.963 | 1.00 59.17 |
| ATOM | 2795 | C | GLU | A | 349 | 72.458 | 9.080 | 120.752 | 1.00 41.72 |
| ATOM | 2796 | O | GLU | A | 349 | 72.564 | 8.852 | 121.959 | 1.00 42.27 |
| ATOM | 2797 | N | THR | A | 350 | 71.716 | 10.067 | 120.261 | 1.00 37.05 |
| ATOM | 2798 | CA | THR | A | 350 | 70.992 | 10.976 | 121.135 | 1.00 40.78 |
| ATOM | 2799 | CB | THR | A | 350 | 71.468 | 12.418 | 120.900 | 1.00 41.69 |
| ATOM | 2800 | OG1 | THR | A | 350 | 71.359 | 12.733 | 119.508 | 1.00 43.25 |
| ATOM | 2801 | CG2 | THR | A | 350 | 72.918 | 12.575 | 121.325 | 1.00 44.11 |
| ATOM | 2802 | C | THR | A | 350 | 69.474 | 10.911 | 120.968 | 1.00 41.47 |
| ATOM | 2803 | O | THR | A | 350 | 68.968 | 10.608 | 119.884 | 1.00 39.72 |
| ATOM | 2804 | N | LEU | A | 351 | 68.760 | 11.199 | 122.054 | 1.00 38.68 |
| ATOM | 2805 | CA | LEU | A | 351 | 67.299 | 11.185 | 122.056 | 1.00 35.91 |
| ATOM | 2806 | CB | LEU | A | 351 | 66.763 | 11.210 | 123.487 | 1.00 35.94 |
| ATOM | 2807 | CG | LEU | A | 351 | 66.752 | 9.890 | 124.251 | 1.00 37.67 |
| ATOM | 2808 | CD1 | LEU | A | 351 | 66.290 | 10.118 | 125.677 | 1.00 40.11 |
| ATOM | 2809 | CD2 | LEU | A | 351 | 65.813 | 8.920 | 123.544 | 1.00 39.29 |
| ATOM | 2810 | C | LEU | A | 351 | 66.679 | 12.342 | 121.294 | 1.00 37.76 |
| ATOM | 2811 | O | LEU | A | 351 | 65.747 | 12.149 | 120.512 | 1.00 34.86 |
| ATOM | 2812 | N | LYS | A | 352 | 67.192 | 13.544 | 121.525 | 1.00 34.79 |
| ATOM | 2813 | CA | LYS | A | 352 | 66.651 | 14.724 | 120.870 | 1.00 38.73 |
| ATOM | 2814 | CB | LYS | A | 352 | 66.676 | 15.911 | 121.835 | 1.00 36.48 |
| ATOM | 2815 | CG | LYS | A | 352 | 66.062 | 15.580 | 123.179 | 1.00 42.08 |
| ATOM | 2816 | CD | LYS | A | 352 | 66.202 | 16.701 | 124.196 | 1.00 43.22 |
| ATOM | 2817 | CE | LYS | A | 352 | 65.349 | 17.901 | 123.845 | 1.00 49.81 |
| ATOM | 2818 | NZ | LYS | A | 352 | 65.342 | 18.880 | 124.972 | 1.00 52.70 |
| ATOM | 2819 | C | LYS | A | 352 | 67.425 | 15.063 | 119.610 | 1.00 38.77 |
| ATOM | 2820 | O | LYS | A | 352 | 68.654 | 15.098 | 119.601 | 1.00 36.21 |
| ATOM | 2821 | N | ASP | A | 353 | 66.697 | 15.293 | 118.530 | 1.00 37.69 |
| ATOM | 2822 | CA | ASP | A | 353 | 67.337 | 15.647 | 117.286 | 1.00 39.89 |
| ATOM | 2823 | CB | ASP | A | 353 | 66.532 | 15.075 | 116.110 | 1.00 43.53 |
| ATOM | 2824 | CG | ASP | A | 353 | 65.058 | 15.368 | 116.211 | 1.00 47.99 |
| ATOM | 2825 | OD1 | ASP | A | 353 | 64.253 | 14.623 | 115.593 | 1.00 38.06 |
| ATOM | 2826 | OD2 | ASP | A | 353 | 64.706 | 16.352 | 116.898 | 1.00 52.94 |
| ATOM | 2827 | C | ASP | A | 353 | 67.457 | 17.165 | 117.247 | 1.00 39.20 |
| ATOM | 2828 | O | ASP | A | 353 | 66.890 | 17.861 | 118.092 | 1.00 35.66 |
| ATOM | 2829 | N | PRO | A | 354 | 68.244 | 17.696 | 116.302 | 1.00 40.75 |
| ATOM | 2830 | CD | PRO | A | 354 | 69.047 | 17.005 | 115.279 | 1.00 40.05 |
| ATOM | 2831 | CA | PRO | A | 354 | 68.426 | 19.145 | 116.179 | 1.00 38.41 |
| ATOM | 2832 | CB | PRO | A | 354 | 69.534 | 19.250 | 115.140 | 1.00 36.24 |
| ATOM | 2833 | CG | PRO | A | 354 | 69.190 | 18.095 | 114.225 | 1.00 39.41 |
| ATOM | 2834 | C | PRO | A | 354 | 67.144 | 19.780 | 115.689 | 1.00 37.28 |
| ATOM | 2835 | O | PRO | A | 354 | 66.299 | 19.106 | 115.094 | 1.00 31.87 |
| ATOM | 2836 | N | TRP | A | 355 | 66.993 | 21.074 | 115.934 | 1.00 37.87 |
| ATOM | 2837 | CA | TRP | A | 355 | 65.804 | 21.757 | 115.472 | 1.00 40.04 |
| ATOM | 2838 | CB | TRP | A | 355 | 65.714 | 23.157 | 116.080 | 1.00 42.85 |

Fig. 18-43

```
ATOM   2839  CG   TRP A 355      64.333  23.471 116.569  1.00 53.01
ATOM   2840  CD2  TRP A 355      63.439  24.463 116.047  1.00 54.23
ATOM   2841  CE2  TRP A 355      62.234  24.368 116.783  1.00 52.59
ATOM   2842  CE3  TRP A 355      63.538  25.422 115.028  1.00 52.82
ATOM   2843  CD1  TRP A 355      63.655  22.836 117.575  1.00 51.80
ATOM   2844  NE1  TRP A 355      62.393  23.368 117.708  1.00 51.38
ATOM   2845  CZ2  TRP A 355      61.134  25.197 116.532  1.00 51.28
ATOM   2846  CZ3  TRP A 355      62.444  26.245 114.779  1.00 53.22
ATOM   2847  CH2  TRP A 355      61.257  26.126 115.531  1.00 50.50
ATOM   2848  C    TRP A 355      65.935  21.836 113.954  1.00 37.34
ATOM   2849  O    TRP A 355      67.041  21.929 113.422  1.00 39.01
ATOM   2850  N    ARG A 356      64.809  21.764 113.259  1.00 36.31
ATOM   2851  CA   ARG A 356      64.797  21.820 111.802  1.00 35.22
ATOM   2852  CB   ARG A 356      64.317  20.469 111.252  1.00 33.36
ATOM   2853  CG   ARG A 356      65.310  19.340 111.564  1.00 34.50
ATOM   2854  CD   ARG A 356      64.729  17.927 111.468  1.00 28.06
ATOM   2855  NE   ARG A 356      65.745  16.956 111.870  1.00 24.79
ATOM   2856  CZ   ARG A 356      65.499  15.703 112.236  1.00 27.56
ATOM   2857  NH1  ARG A 356      64.253  15.237 112.259  1.00 19.09
ATOM   2858  NH2  ARG A 356      66.502  14.918 112.604  1.00 21.34
ATOM   2859  C    ARG A 356      63.874  22.955 111.390  1.00 33.74
ATOM   2860  O    ARG A 356      62.746  22.732 110.950  1.00 34.68
ATOM   2861  N    GLY A 357      64.361  24.181 111.550  1.00 35.60
ATOM   2862  CA   GLY A 357      63.556  25.345 111.220  1.00 35.43
ATOM   2863  C    GLY A 357      63.719  25.932 109.830  1.00 38.08
ATOM   2864  O    GLY A 357      64.112  25.250 108.885  1.00 37.29
ATOM   2865  N    GLY A 358      63.406  27.218 109.721  1.00 39.67
ATOM   2866  CA   GLY A 358      63.493  27.925 108.457  1.00 36.36
ATOM   2867  C    GLY A 358      62.398  28.966 108.499  1.00 39.45
ATOM   2868  O    GLY A 358      61.763  29.131 109.539  1.00 37.58
ATOM   2869  N    GLU A 359      62.163  29.662 107.391  1.00 40.89
ATOM   2870  CA   GLU A 359      61.121  30.682 107.358  1.00 41.37
ATOM   2871  CB   GLU A 359      61.310  31.627 106.172  1.00 44.64
ATOM   2872  CG   GLU A 359      60.956  30.977 104.848  1.00 52.13
ATOM   2873  CD   GLU A 359      60.833  31.973 103.708  1.00 59.14
ATOM   2874  OE1  GLU A 359      60.448  31.551 102.593  1.00 60.47
ATOM   2875  OE2  GLU A 359      61.119  33.173 103.923  1.00 57.77
ATOM   2876  C    GLU A 359      59.770  30.006 107.200  1.00 38.02
ATOM   2877  O    GLU A 359      59.689  28.828 106.850  1.00 35.29
ATOM   2878  N    VAL A 360      58.708  30.762 107.441  1.00 36.81
ATOM   2879  CA   VAL A 360      57.363  30.237 107.291  1.00 35.97
ATOM   2880  CB   VAL A 360      56.401  30.789 108.368  1.00 34.90
ATOM   2881  CG1  VAL A 360      54.999  30.251 108.133  1.00 36.53
ATOM   2882  CG2  VAL A 360      56.888  30.393 109.755  1.00 37.06
ATOM   2883  C    VAL A 360      56.886  30.690 105.928  1.00 36.74
ATOM   2884  O    VAL A 360      56.661  31.881 105.712  1.00 34.90
ATOM   2885  N    ARG A 361      56.753  29.741 105.004  1.00 35.48
ATOM   2886  CA   ARG A 361      56.301  30.049 103.652  1.00 38.21
ATOM   2887  CB   ARG A 361      56.152  28.776 102.815  1.00 39.76
ATOM   2888  CG   ARG A 361      57.416  28.342 102.098  1.00 39.93
ATOM   2889  CD   ARG A 361      57.225  26.963 101.486  1.00 38.68
ATOM   2890  NE   ARG A 361      57.112  25.940 102.525  1.00 39.72
ATOM   2891  CZ   ARG A 361      56.952  24.643 102.286  1.00 38.79
ATOM   2892  NH1  ARG A 361      56.881  24.200 101.036  1.00 32.40
ATOM   2893  NH2  ARG A 361      56.899  23.785 103.297  1.00 36.58
ATOM   2894  C    ARG A 361      54.996  30.807 103.603  1.00 38.98
ATOM   2895  O    ARG A 361      54.120  30.636 104.452  1.00 39.07
ATOM   2896  N    LYS A 362      54.880  31.634 102.573  1.00 39.95
ATOM   2897  CA   LYS A 362      53.709  32.459 102.339  1.00 42.73
ATOM   2898  CB   LYS A 362      53.931  33.301 101.078  1.00 44.92
ATOM   2899  CG   LYS A 362      54.995  34.390 101.219  1.00 55.45
ATOM   2900  CD   LYS A 362      56.351  33.842 101.671  1.00 58.28
ATOM   2901  CE   LYS A 362      56.907  32.809 100.697  1.00 57.04
ATOM   2902  NZ   LYS A 362      58.224  32.283 101.151  1.00 58.75
ATOM   2903  C    LYS A 362      52.434  31.634 102.200  1.00 40.51
ATOM   2904  O    LYS A 362      51.391  31.996 102.748  1.00 36.10
```

Fig. 18-44

| | | | | | | | | | |
|---|---|---|---|---|---|---|---|---|---|
| ATOM | 2905 | N | GLU | A | 363 | 52.506 | 30.527 | 101.469 | 1.00 37.79 |
| ATOM | 2906 | CA | GLU | A | 363 | 51.313 | 29.705 | 101.295 | 1.00 40.96 |
| ATOM | 2907 | CB | GLU | A | 363 | 51.587 | 28.530 | 100.347 | 1.00 43.62 |
| ATOM | 2908 | CG | GLU | A | 363 | 52.729 | 27.616 | 100.739 | 1.00 47.01 |
| ATOM | 2909 | CD | GLU | A | 363 | 52.995 | 26.547 | 99.683 | 1.00 51.65 |
| ATOM | 2910 | OE1 | GLU | A | 363 | 52.080 | 25.737 | 99.409 | 1.00 45.63 |
| ATOM | 2911 | OE2 | GLU | A | 363 | 54.116 | 26.526 | 99.125 | 1.00 48.44 |
| ATOM | 2912 | C | GLU | A | 363 | 50.788 | 29.209 | 102.636 | 1.00 37.74 |
| ATOM | 2913 | O | GLU | A | 363 | 49.582 | 29.113 | 102.834 | 1.00 34.79 |
| ATOM | 2914 | N | VAL | A | 364 | 51.691 | 28.910 | 103.564 | 1.00 33.64 |
| ATOM | 2915 | CA | VAL | A | 364 | 51.274 | 28.455 | 104.886 | 1.00 32.39 |
| ATOM | 2916 | CB | VAL | A | 364 | 52.484 | 28.048 | 105.749 | 1.00 33.99 |
| ATOM | 2917 | CG1 | VAL | A | 364 | 52.018 | 27.676 | 107.160 | 1.00 36.90 |
| ATOM | 2918 | CG2 | VAL | A | 364 | 53.198 | 26.867 | 105.109 | 1.00 29.56 |
| ATOM | 2919 | C | VAL | A | 364 | 50.506 | 29.574 | 105.589 | 1.00 34.33 |
| ATOM | 2920 | O | VAL | A | 364 | 49.454 | 29.336 | 106.188 | 1.00 29.80 |
| ATOM | 2921 | N | LYS | A | 365 | 51.027 | 30.797 | 105.499 | 1.00 38.12 |
| ATOM | 2922 | CA | LYS | A | 365 | 50.381 | 31.952 | 106.119 | 1.00 36.77 |
| ATOM | 2923 | CB | LYS | A | 365 | 51.255 | 33.204 | 105.969 | 1.00 37.98 |
| ATOM | 2924 | CG | LYS | A | 365 | 52.629 | 33.084 | 106.610 | 1.00 37.99 |
| ATOM | 2925 | CD | LYS | A | 365 | 53.449 | 34.357 | 106.429 | 1.00 35.50 |
| ATOM | 2926 | CE | LYS | A | 365 | 54.837 | 34.190 | 107.032 | 1.00 40.35 |
| ATOM | 2927 | NZ | LYS | A | 365 | 55.674 | 35.407 | 106.877 | 1.00 43.74 |
| ATOM | 2928 | C | LYS | A | 365 | 49.025 | 32.191 | 105.468 | 1.00 36.62 |
| ATOM | 2929 | O | LYS | A | 365 | 48.038 | 32.469 | 106.148 | 1.00 33.53 |
| ATOM | 2930 | N | ASP | A | 366 | 48.968 | 32.073 | 104.147 | 1.00 37.05 |
| ATOM | 2931 | CA | ASP | A | 366 | 47.708 | 32.278 | 103.449 | 1.00 37.72 |
| ATOM | 2932 | CB | ASP | A | 366 | 47.906 | 32.237 | 101.929 | 1.00 40.57 |
| ATOM | 2933 | CG | ASP | A | 366 | 48.833 | 33.334 | 101.427 | 1.00 43.98 |
| ATOM | 2934 | OD1 | ASP | A | 366 | 49.078 | 34.304 | 102.176 | 1.00 38.51 |
| ATOM | 2935 | OD2 | ASP | A | 366 | 49.297 | 33.235 | 100.269 | 1.00 41.96 |
| ATOM | 2936 | C | ASP | A | 366 | 46.670 | 31.238 | 103.862 | 1.00 39.24 |
| ATOM | 2937 | O | ASP | A | 366 | 45.497 | 31.562 | 104.029 | 1.00 39.04 |
| ATOM | 2938 | N | THR | A | 367 | 47.096 | 29.990 | 104.031 | 1.00 38.99 |
| ATOM | 2939 | CA | THR | A | 367 | 46.167 | 28.935 | 104.432 | 1.00 36.80 |
| ATOM | 2940 | CB | THR | A | 367 | 46.868 | 27.560 | 104.527 | 1.00 33.84 |
| ATOM | 2941 | OG1 | THR | A | 367 | 47.332 | 27.167 | 103.232 | 1.00 34.92 |
| ATOM | 2942 | CG2 | THR | A | 367 | 45.904 | 26.509 | 105.046 | 1.00 35.11 |
| ATOM | 2943 | C | THR | A | 367 | 45.532 | 29.257 | 105.786 | 1.00 36.58 |
| ATOM | 2944 | O | THR | A | 367 | 44.307 | 29.202 | 105.931 | 1.00 30.18 |
| ATOM | 2945 | N | LEU | A | 368 | 46.363 | 29.581 | 106.776 | 1.00 35.32 |
| ATOM | 2946 | CA | LEU | A | 368 | 45.850 | 29.926 | 108.095 | 1.00 35.46 |
| ATOM | 2947 | CB | LEU | A | 368 | 46.997 | 30.169 | 109.077 | 1.00 34.03 |
| ATOM | 2948 | CG | LEU | A | 368 | 47.545 | 28.925 | 109.794 | 1.00 39.04 |
| ATOM | 2949 | CD1 | LEU | A | 368 | 46.449 | 28.358 | 110.688 | 1.00 37.35 |
| ATOM | 2950 | CD2 | LEU | A | 368 | 48.014 | 27.871 | 108.797 | 1.00 39.52 |
| ATOM | 2951 | C | LEU | A | 368 | 44.957 | 31.156 | 107.994 | 1.00 38.12 |
| ATOM | 2952 | O | LEU | A | 368 | 43.968 | 31.277 | 108.719 | 1.00 31.70 |
| ATOM | 2953 | N | GLU | A | 369 | 45.307 | 32.063 | 107.086 | 1.00 40.45 |
| ATOM | 2954 | CA | GLU | A | 369 | 44.509 | 33.261 | 106.866 | 1.00 45.36 |
| ATOM | 2955 | CB | GLU | A | 369 | 45.128 | 34.126 | 105.765 | 1.00 47.38 |
| ATOM | 2956 | CG | GLU | A | 369 | 46.020 | 35.228 | 106.283 | 1.00 53.81 |
| ATOM | 2957 | CD | GLU | A | 369 | 45.227 | 36.306 | 106.996 | 1.00 59.97 |
| ATOM | 2958 | OE1 | GLU | A | 369 | 45.846 | 37.252 | 107.526 | 1.00 60.65 |
| ATOM | 2959 | OE2 | GLU | A | 369 | 43.980 | 36.211 | 107.016 | 1.00 63.69 |
| ATOM | 2960 | C | GLU | A | 369 | 43.100 | 32.865 | 106.466 | 1.00 43.23 |
| ATOM | 2961 | O | GLU | A | 369 | 42.130 | 33.283 | 107.095 | 1.00 44.62 |
| ATOM | 2962 | N | LYS | A | 370 | 42.983 | 32.057 | 105.417 | 1.00 40.34 |
| ATOM | 2963 | CA | LYS | A | 370 | 41.666 | 31.631 | 104.977 | 1.00 43.36 |
| ATOM | 2964 | CB | LYS | A | 370 | 41.738 | 30.773 | 103.704 | 1.00 44.79 |
| ATOM | 2965 | CG | LYS | A | 370 | 42.032 | 31.546 | 102.419 | 1.00 48.93 |
| ATOM | 2966 | CD | LYS | A | 370 | 43.503 | 31.514 | 102.019 | 1.00 51.41 |
| ATOM | 2967 | CE | LYS | A | 370 | 43.921 | 30.116 | 101.561 | 1.00 51.14 |
| ATOM | 2968 | NZ | LYS | A | 370 | 45.339 | 30.062 | 101.091 | 1.00 50.34 |
| ATOM | 2969 | C | LYS | A | 370 | 40.959 | 30.848 | 106.069 | 1.00 43.09 |
| ATOM | 2970 | O | LYS | A | 370 | 39.745 | 30.977 | 106.248 | 1.00 41.34 |

Fig. 18-45

| | | | | | | | | |
|---|---|---|---|---|---|---|---|---|
| ATOM | 2971 | N | ALA | A | 371 | 41.715 | 30.037 | 106.802 | 1.00 39.56 |
| ATOM | 2972 | CA | ALA | A | 371 | 41.120 | 29.238 | 107.861 | 1.00 43.57 |
| ATOM | 2973 | CB | ALA | A | 371 | 42.193 | 28.440 | 108.594 | 1.00 39.11 |
| ATOM | 2974 | C | ALA | A | 371 | 40.365 | 30.132 | 108.837 | 1.00 46.10 |
| ATOM | 2975 | O | ALA | A | 371 | 39.230 | 29.829 | 109.210 | 1.00 46.07 |
| ATOM | 2976 | N | LYS | A | 372 | 40.981 | 31.239 | 109.227 | 1.00 46.62 |
| ATOM | 2977 | CA | LYS | A | 372 | 40.391 | 32.178 | 110.192 | 1.00 48.18 |
| ATOM | 2978 | C | LYS | A | 372 | 39.052 | 32.698 | 109.664 | 1.00 51.67 |
| ATOM | 2979 | O | LYS | A | 372 | 38.294 | 33.318 | 110.432 | 1.00 53.21 |
| ATOM | 2980 | CB | LYS | A | 372 | 41.334 | 33.364 | 110.413 | 1.00 47.22 |
| ATOM | 2981 | CG | LYS | A | 372 | 42.804 | 32.949 | 110.510 | 1.00 20.00 |
| ATOM | 2982 | CD | LYS | A | 372 | 43.746 | 34.131 | 110.752 | 1.00 20.00 |
| ATOM | 2983 | CE | LYS | A | 372 | 45.216 | 33.715 | 110.849 | 1.00 20.00 |
| ATOM | 2984 | NZ | LYS | A | 372 | 46.121 | 34.850 | 111.081 | 1.00 20.00 |
| ATOM | 2985 | N | ALA | A | 373 | 38.751 | 32.476 | 108.397 | 1.00 57.71 |
| ATOM | 2986 | CA | ALA | A | 373 | 37.492 | 32.933 | 107.806 | 1.00 58.67 |
| ATOM | 2987 | CB | ALA | A | 373 | 37.758 | 33.632 | 106.480 | 1.00 57.19 |
| ATOM | 2988 | C | ALA | A | 373 | 36.524 | 31.773 | 107.594 | 1.00 59.58 |
| ATOM | 2989 | O | ALA | A | 373 | 35.432 | 31.797 | 108.205 | 1.00 60.89 |
| ATOM | 2990 | OXT | ALA | A | 373 | 36.870 | 30.853 | 106.822 | 1.00 60.10 |
| ATOM | 3014 | CB | ALA | B | 2 | 54.881 | -4.431 | 56.836 | 1.00 55.77 |
| ATOM | 3015 | C | ALA | B | 2 | 53.960 | -2.137 | 56.480 | 1.00 57.58 |
| ATOM | 3016 | O | ALA | B | 2 | 54.920 | -1.720 | 57.131 | 1.00 56.75 |
| ATOM | 3017 | N | ALA | B | 2 | 54.263 | -3.672 | 54.557 | 1.00 58.22 |
| ATOM | 3018 | CA | ALA | B | 2 | 53.914 | -3.584 | 56.008 | 1.00 58.47 |
| ATOM | 3019 | N | LYS | B | 3 | 52.919 | -1.376 | 56.151 | 1.00 52.79 |
| ATOM | 3020 | CA | LYS | B | 3 | 52.855 | 0.022 | 56.543 | 1.00 49.68 |
| ATOM | 3021 | CB | LYS | B | 3 | 51.643 | 0.700 | 55.896 | 1.00 53.14 |
| ATOM | 3022 | CG | LYS | B | 3 | 51.751 | 0.785 | 54.377 | 1.00 53.37 |
| ATOM | 3023 | CD | LYS | B | 3 | 50.685 | 1.681 | 53.786 | 1.00 55.40 |
| ATOM | 3024 | CE | LYS | B | 3 | 50.808 | 1.783 | 52.277 | 1.00 59.51 |
| ATOM | 3025 | NZ | LYS | B | 3 | 52.140 | 2.323 | 51.884 | 1.00 56.88 |
| ATOM | 3026 | C | LYS | B | 3 | 52.849 | 0.238 | 58.059 | 1.00 46.83 |
| ATOM | 3027 | O | LYS | B | 3 | 52.389 | -0.607 | 58.830 | 1.00 41.63 |
| ATOM | 3028 | N | VAL | B | 4 | 53.376 | 1.385 | 58.467 | 1.00 41.46 |
| ATOM | 3029 | CA | VAL | B | 4 | 53.483 | 1.751 | 59.871 | 1.00 40.85 |
| ATOM | 3030 | CB | VAL | B | 4 | 54.893 | 2.288 | 60.163 | 1.00 39.55 |
| ATOM | 3031 | CG1 | VAL | B | 4 | 55.070 | 2.541 | 61.648 | 1.00 41.23 |
| ATOM | 3032 | CG2 | VAL | B | 4 | 55.916 | 1.306 | 59.652 | 1.00 38.96 |
| ATOM | 3033 | C | VAL | B | 4 | 52.451 | 2.813 | 60.230 | 1.00 38.92 |
| ATOM | 3034 | O | VAL | B | 4 | 52.472 | 3.916 | 59.691 | 1.00 42.80 |
| ATOM | 3035 | N | LYS | B | 5 | 51.559 | 2.479 | 61.157 | 1.00 34.90 |
| ATOM | 3036 | CA | LYS | B | 5 | 50.501 | 3.396 | 61.558 | 1.00 31.22 |
| ATOM | 3037 | CB | LYS | B | 5 | 49.133 | 2.796 | 61.215 | 1.00 33.76 |
| ATOM | 3038 | CG | LYS | B | 5 | 48.841 | 2.623 | 59.726 | 1.00 36.60 |
| ATOM | 3039 | CD | LYS | B | 5 | 48.667 | 3.964 | 59.032 | 1.00 41.48 |
| ATOM | 3040 | CE | LYS | B | 5 | 48.234 | 3.803 | 57.577 | 1.00 43.62 |
| ATOM | 3041 | NZ | LYS | B | 5 | 49.215 | 3.025 | 56.781 | 1.00 42.53 |
| ATOM | 3042 | C | LYS | B | 5 | 50.512 | 3.749 | 63.038 | 1.00 32.67 |
| ATOM | 3043 | O | LYS | B | 5 | 51.012 | 2.995 | 63.878 | 1.00 25.78 |
| ATOM | 3044 | N | LEU | B | 6 | 49.937 | 4.906 | 63.343 | 1.00 27.07 |
| ATOM | 3045 | CA | LEU | B | 6 | 49.821 | 5.379 | 64.712 | 1.00 31.09 |
| ATOM | 3046 | CB | LEU | B | 6 | 50.596 | 6.696 | 64.896 | 1.00 30.13 |
| ATOM | 3047 | CG | LEU | B | 6 | 50.691 | 7.340 | 66.285 | 1.00 28.09 |
| ATOM | 3048 | CD1 | LEU | B | 6 | 49.333 | 7.827 | 66.728 | 1.00 38.87 |
| ATOM | 3049 | CD2 | LEU | B | 6 | 51.248 | 6.338 | 67.282 | 1.00 24.87 |
| ATOM | 3050 | C | LEU | B | 6 | 48.324 | 5.594 | 64.924 | 1.00 29.52 |
| ATOM | 3051 | O | LEU | B | 6 | 47.669 | 6.287 | 64.149 | 1.00 33.36 |
| ATOM | 3052 | N | ILE | B | 7 | 47.777 | 4.975 | 65.960 | 1.00 28.02 |
| ATOM | 3053 | CA | ILE | B | 7 | 46.361 | 5.111 | 66.250 | 1.00 23.83 |
| ATOM | 3054 | CB | ILE | B | 7 | 45.736 | 3.761 | 66.670 | 1.00 25.11 |
| ATOM | 3055 | CG2 | ILE | B | 7 | 44.309 | 3.974 | 67.127 | 1.00 23.59 |
| ATOM | 3056 | CG1 | ILE | B | 7 | 45.690 | 2.794 | 65.477 | 1.00 31.00 |
| ATOM | 3057 | CD1 | ILE | B | 7 | 47.021 | 2.406 | 64.906 | 1.00 38.60 |
| ATOM | 3058 | C | ILE | B | 7 | 46.179 | 6.130 | 67.363 | 1.00 26.49 |
| ATOM | 3059 | O | ILE | B | 7 | 46.766 | 6.005 | 68.430 | 1.00 26.68 |

Fig. 18-46

| ATOM | 3060 | N | GLY | B | 8 | 45.372 | 7.151 | 67.106 | 1.00 | 29.51 |
| ATOM | 3061 | CA | GLY | B | 8 | 45.151 | 8.170 | 68.117 | 1.00 | 30.28 |
| ATOM | 3062 | C | GLY | B | 8 | 44.217 | 9.273 | 67.667 | 1.00 | 28.79 |
| ATOM | 3063 | O | GLY | B | 8 | 43.629 | 9.207 | 66.590 | 1.00 | 19.70 |
| ATOM | 3064 | N | THR | B | 9 | 44.088 | 10.291 | 68.509 | 1.00 | 26.46 |
| ATOM | 3065 | CA | THR | B | 9 | 43.234 | 11.438 | 68.238 | 1.00 | 29.37 |
| ATOM | 3066 | CB | THR | B | 9 | 41.748 | 11.064 | 68.311 | 1.00 | 32.64 |
| ATOM | 3067 | OG1 | THR | B | 9 | 40.959 | 12.253 | 68.218 | 1.00 | 30.35 |
| ATOM | 3068 | CG2 | THR | B | 9 | 41.431 | 10.383 | 69.637 | 1.00 | 33.42 |
| ATOM | 3069 | C | THR | B | 9 | 43.479 | 12.496 | 69.302 | 1.00 | 33.42 |
| ATOM | 3070 | O | THR | B | 9 | 43.884 | 12.173 | 70.416 | 1.00 | 30.46 |
| ATOM | 3071 | N | LEU | B | 10 | 43.228 | 13.754 | 68.961 | 1.00 | 32.05 |
| ATOM | 3072 | CA | LEU | B | 10 | 43.396 | 14.840 | 69.914 | 1.00 | 34.75 |
| ATOM | 3073 | CB | LEU | B | 10 | 43.381 | 16.189 | 69.190 | 1.00 | 38.02 |
| ATOM | 3074 | CG | LEU | B | 10 | 44.605 | 16.578 | 68.355 | 1.00 | 40.82 |
| ATOM | 3075 | CD1 | LEU | B | 10 | 44.961 | 15.472 | 67.394 | 1.00 | 43.62 |
| ATOM | 3076 | CD2 | LEU | B | 10 | 44.314 | 17.869 | 67.605 | 1.00 | 34.99 |
| ATOM | 3077 | C | LEU | B | 10 | 42.272 | 14.809 | 70.945 | 1.00 | 34.25 |
| ATOM | 3078 | O | LEU | B | 10 | 42.415 | 15.348 | 72.042 | 1.00 | 33.13 |
| ATOM | 3079 | N | ASP | B | 11 | 41.158 | 14.169 | 70.595 | 1.00 | 30.61 |
| ATOM | 3080 | CA | ASP | B | 11 | 40.011 | 14.098 | 71.501 | 1.00 | 33.08 |
| ATOM | 3081 | CB | ASP | B | 11 | 38.928 | 13.167 | 70.945 | 1.00 | 37.57 |
| ATOM | 3082 | CG | ASP | B | 11 | 38.372 | 13.643 | 69.621 | 1.00 | 43.14 |
| ATOM | 3083 | OD1 | ASP | B | 11 | 38.013 | 14.834 | 69.525 | 1.00 | 42.22 |
| ATOM | 3084 | OD2 | ASP | B | 11 | 38.281 | 12.825 | 68.681 | 1.00 | 45.58 |
| ATOM | 3085 | C | ASP | B | 11 | 40.358 | 13.654 | 72.919 | 1.00 | 32.19 |
| ATOM | 3086 | O | ASP | B | 11 | 39.688 | 14.053 | 73.875 | 1.00 | 23.44 |
| ATOM | 3087 | N | TYR | B | 12 | 41.386 | 12.822 | 73.066 | 1.00 | 28.02 |
| ATOM | 3088 | CA | TYR | B | 12 | 41.770 | 12.373 | 74.402 | 1.00 | 32.00 |
| ATOM | 3089 | CB | TYR | B | 12 | 43.011 | 11.476 | 74.363 | 1.00 | 28.67 |
| ATOM | 3090 | CG | TYR | B | 12 | 42.821 | 10.108 | 73.737 | 1.00 | 25.33 |
| ATOM | 3091 | CD1 | TYR | B | 12 | 43.338 | 9.823 | 72.475 | 1.00 | 23.74 |
| ATOM | 3092 | CE1 | TYR | B | 12 | 43.235 | 8.546 | 71.924 | 1.00 | 22.85 |
| ATOM | 3093 | CD2 | TYR | B | 12 | 42.183 | 9.077 | 74.436 | 1.00 | 21.93 |
| ATOM | 3094 | CE2 | TYR | B | 12 | 42.074 | 7.793 | 73.889 | 1.00 | 21.99 |
| ATOM | 3095 | CZ | TYR | B | 12 | 42.605 | 7.538 | 72.640 | 1.00 | 22.99 |
| ATOM | 3096 | OH | TYR | B | 12 | 42.532 | 6.273 | 72.109 | 1.00 | 18.79 |
| ATOM | 3097 | C | TYR | B | 12 | 42.054 | 13.567 | 75.319 | 1.00 | 32.74 |
| ATOM | 3098 | O | TYR | B | 12 | 41.986 | 13.450 | 76.542 | 1.00 | 23.85 |
| ATOM | 3099 | N | GLY | B | 13 | 42.374 | 14.710 | 74.720 | 1.00 | 26.96 |
| ATOM | 3100 | CA | GLY | B | 13 | 42.658 | 15.900 | 75.501 | 1.00 | 34.92 |
| ATOM | 3101 | C | GLY | B | 13 | 41.452 | 16.396 | 76.277 | 1.00 | 36.82 |
| ATOM | 3102 | O | GLY | B | 13 | 41.580 | 17.228 | 77.176 | 1.00 | 34.10 |
| ATOM | 3103 | N | LYS | B | 14 | 40.279 | 15.875 | 75.929 | 1.00 | 37.23 |
| ATOM | 3104 | CA | LYS | B | 14 | 39.031 | 16.247 | 76.584 | 1.00 | 41.77 |
| ATOM | 3105 | CB | LYS | B | 14 | 37.925 | 16.406 | 75.537 | 1.00 | 45.82 |
| ATOM | 3106 | CG | LYS | B | 14 | 38.110 | 17.585 | 74.579 | 1.00 | 51.38 |
| ATOM | 3107 | CD | LYS | B | 14 | 37.805 | 18.939 | 75.241 | 1.00 | 57.78 |
| ATOM | 3108 | CE | LYS | B | 14 | 38.752 | 19.285 | 76.388 | 1.00 | 58.82 |
| ATOM | 3109 | NZ | LYS | B | 14 | 38.387 | 20.568 | 77.070 | 1.00 | 55.06 |
| ATOM | 3110 | C | LYS | B | 14 | 38.591 | 15.226 | 77.627 | 1.00 | 39.50 |
| ATOM | 3111 | O | LYS | B | 14 | 37.546 | 15.385 | 78.252 | 1.00 | 35.54 |
| ATOM | 3112 | N | TYR | B | 15 | 39.395 | 14.186 | 77.815 | 1.00 | 40.97 |
| ATOM | 3113 | CA | TYR | B | 15 | 39.070 | 13.128 | 78.768 | 1.00 | 44.15 |
| ATOM | 3114 | CB | TYR | B | 15 | 38.863 | 11.827 | 77.990 | 1.00 | 44.42 |
| ATOM | 3115 | CG | TYR | B | 15 | 37.850 | 11.972 | 76.876 | 1.00 | 42.02 |
| ATOM | 3116 | CD1 | TYR | B | 15 | 38.064 | 11.389 | 75.634 | 1.00 | 41.06 |
| ATOM | 3117 | CE1 | TYR | B | 15 | 37.138 | 11.530 | 74.603 | 1.00 | 42.76 |
| ATOM | 3118 | CD2 | TYR | B | 15 | 36.678 | 12.703 | 77.065 | 1.00 | 42.99 |
| ATOM | 3119 | CE2 | TYR | B | 15 | 35.748 | 12.851 | 76.048 | 1.00 | 43.30 |
| ATOM | 3120 | CZ | TYR | B | 15 | 35.984 | 12.261 | 74.816 | 1.00 | 45.49 |
| ATOM | 3121 | OH | TYR | B | 15 | 35.066 | 12.403 | 73.801 | 1.00 | 45.69 |
| ATOM | 3122 | C | TYR | B | 15 | 40.151 | 12.944 | 79.838 | 1.00 | 43.48 |
| ATOM | 3123 | O | TYR | B | 15 | 40.519 | 11.819 | 80.167 | 1.00 | 41.20 |
| ATOM | 3124 | N | ARG | B | 16 | 40.647 | 14.052 | 80.381 | 1.00 | 43.01 |
| ATOM | 3125 | CA | ARG | B | 16 | 41.686 | 14.012 | 81.410 | 1.00 | 43.70 |

Fig. 18-47

| | | | | | | | | | |
|---|---|---|---|---|---|---|---|---|---|
| ATOM | 3126 | CB | ARG | B | 16 | 42.250 | 15.410 | 81.663 | 1.00 49.13 |
| ATOM | 3127 | CG | ARG | B | 16 | 42.656 | 16.197 | 80.447 | 1.00 54.22 |
| ATOM | 3128 | CD | ARG | B | 16 | 43.858 | 15.624 | 79.751 | 1.00 55.13 |
| ATOM | 3129 | NE | ARG | B | 16 | 44.303 | 16.549 | 78.718 | 1.00 62.87 |
| ATOM | 3130 | CZ | ARG | B | 16 | 44.628 | 17.818 | 78.951 | 1.00 64.92 |
| ATOM | 3131 | NH1 | ARG | B | 16 | 44.556 | 18.308 | 80.182 | 1.00 65.86 |
| ATOM | 3132 | NH2 | ARG | B | 16 | 45.022 | 18.600 | 77.954 | 1.00 67.15 |
| ATOM | 3133 | C | ARG | B | 16 | 41.093 | 13.531 | 82.728 | 1.00 42.97 |
| ATOM | 3134 | O | ARG | B | 16 | 39.882 | 13.593 | 82.927 | 1.00 38.44 |
| ATOM | 3135 | N | TYR | B | 17 | 41.949 | 13.056 | 83.628 | 1.00 39.36 |
| ATOM | 3136 | CA | TYR | B | 17 | 41.494 | 12.637 | 84.945 | 1.00 37.67 |
| ATOM | 3137 | CB | TYR | B | 17 | 42.500 | 11.679 | 85.584 | 1.00 31.69 |
| ATOM | 3138 | CG | TYR | B | 17 | 42.413 | 10.250 | 85.087 | 1.00 28.00 |
| ATOM | 3139 | CD1 | TYR | B | 17 | 42.530 | 9.944 | 83.732 | 1.00 22.89 |
| ATOM | 3140 | CE1 | TYR | B | 17 | 42.502 | 8.618 | 83.287 | 1.00 21.42 |
| ATOM | 3141 | CD2 | TYR | B | 17 | 42.258 | 9.196 | 85.984 | 1.00 24.67 |
| ATOM | 3142 | CE2 | TYR | B | 17 | 42.229 | 7.873 | 85.556 | 1.00 24.48 |
| ATOM | 3143 | CZ | TYR | B | 17 | 42.355 | 7.587 | 84.210 | 1.00 27.13 |
| ATOM | 3144 | OH | TYR | B | 17 | 42.371 | 6.271 | 83.796 | 1.00 19.94 |
| ATOM | 3145 | C | TYR | B | 17 | 41.377 | 13.927 | 85.765 | 1.00 38.94 |
| ATOM | 3146 | O | TYR | B | 17 | 41.947 | 14.951 | 85.391 | 1.00 39.65 |
| ATOM | 3147 | N | PRO | B | 18 | 40.647 | 13.893 | 86.891 | 1.00 41.27 |
| ATOM | 3148 | CD | PRO | B | 18 | 39.958 | 12.728 | 87.462 | 1.00 43.62 |
| ATOM | 3149 | CA | PRO | B | 18 | 40.448 | 15.058 | 87.762 | 1.00 45.33 |
| ATOM | 3150 | CB | PRO | B | 18 | 39.648 | 14.473 | 88.928 | 1.00 44.09 |
| ATOM | 3151 | CG | PRO | B | 18 | 40.096 | 13.015 | 88.933 | 1.00 49.22 |
| ATOM | 3152 | C | PRO | B | 18 | 41.702 | 15.809 | 88.221 | 1.00 45.86 |
| ATOM | 3153 | O | PRO | B | 18 | 42.789 | 15.244 | 88.317 | 1.00 45.44 |
| ATOM | 3154 | N | LYS | B | 19 | 41.506 | 17.095 | 88.507 | 1.00 48.42 |
| ATOM | 3155 | CA | LYS | B | 19 | 42.535 | 18.040 | 88.952 | 1.00 51.03 |
| ATOM | 3156 | CB | LYS | B | 19 | 41.873 | 19.122 | 89.814 | 1.00 56.35 |
| ATOM | 3157 | CG | LYS | B | 19 | 40.630 | 18.657 | 90.563 | 1.00 65.69 |
| ATOM | 3158 | CD | LYS | B | 19 | 40.894 | 17.441 | 91.423 | 1.00 68.96 |
| ATOM | 3159 | CE | LYS | B | 19 | 39.602 | 16.882 | 91.999 | 1.00 71.85 |
| ATOM | 3160 | NZ | LYS | B | 19 | 39.825 | 15.603 | 92.731 | 1.00 72.79 |
| ATOM | 3161 | C | LYS | B | 19 | 43.830 | 17.593 | 89.639 | 1.00 48.62 |
| ATOM | 3162 | O | LYS | B | 19 | 44.912 | 18.009 | 89.235 | 1.00 49.04 |
| ATOM | 3163 | N | ASN | B | 20 | 43.745 | 16.775 | 90.678 | 1.00 43.99 |
| ATOM | 3164 | CA | ASN | B | 20 | 44.957 | 16.356 | 91.375 | 1.00 43.86 |
| ATOM | 3165 | CB | ASN | B | 20 | 44.740 | 16.440 | 92.890 | 1.00 45.92 |
| ATOM | 3166 | CG | ASN | B | 20 | 44.418 | 17.848 | 93.355 | 1.00 49.44 |
| ATOM | 3167 | OD1 | ASN | B | 20 | 45.194 | 18.779 | 93.138 | 1.00 47.72 |
| ATOM | 3168 | ND2 | ASN | B | 20 | 43.268 | 18.011 | 93.999 | 1.00 49.42 |
| ATOM | 3169 | C | ASN | B | 20 | 45.460 | 14.960 | 91.008 | 1.00 39.49 |
| ATOM | 3170 | O | ASN | B | 20 | 46.496 | 14.521 | 91.494 | 1.00 38.24 |
| ATOM | 3171 | N | HIS | B | 21 | 44.729 | 14.274 | 90.140 | 1.00 36.93 |
| ATOM | 3172 | CA | HIS | B | 21 | 45.091 | 12.923 | 8 .723 | 1.00 33.57 |
| ATOM | 3173 | CB | HIS | B | 21 | 43.948 | 12.299 | 8 .924 | 1.00 28.67 |
| ATOM | 3174 | CG | HIS | B | 21 | 44.068 | 10.817 | 88.750 | 1.00 32.14 |
| ATOM | 3175 | CD2 | HIS | B | 21 | 44.779 | 10.076 | 87.867 | 1.00 26.15 |
| ATOM | 3176 | ND1 | HIS | B | 21 | 43.431 | 9.917 | 89.578 | 1.00 29.59 |
| ATOM | 3177 | CE1 | HIS | B | 21 | 43.743 | 8.686 | 89.212 | 1.00 23.65 |
| ATOM | 3178 | NE2 | HIS | B | 21 | 44.560 | 8.755 | 88.177 | 1.00 29.71 |
| ATOM | 3179 | C | HIS | B | 21 | 46.348 | 12.928 | 88.852 | 1.00 29.06 |
| ATOM | 3180 | O | HIS | B | 21 | 46.536 | 13.805 | 88.015 | 1.00 24.86 |
| ATOM | 3181 | N | PRO | B | 22 | 47.225 | 11.937 | 89.035 | 1.00 30.50 |
| ATOM | 3182 | CD | PRO | B | 22 | 47.187 | 10.802 | 89.976 | 1.00 31.51 |
| ATOM | 3183 | CA | PRO | B | 22 | 48.446 | 11.880 | 88.231 | 1.00 29.58 |
| ATOM | 3184 | CB | PRO | B | 22 | 49.055 | 10.549 | 88.656 | 1.00 33.72 |
| ATOM | 3185 | CG | PRO | B | 22 | 43.658 | 10.489 | 90.124 | 1.00 31.07 |
| ATOM | 3186 | C | PRO | B | 22 | 48.176 | 11.950 | 86.728 | 1.00 28.52 |
| ATOM | 3187 | O | PRO | B | 22 | 48.989 | 12.474 | 85.972 | 1.00 31.85 |
| ATOM | 3188 | N | LEU | B | 23 | 47.030 | 11.435 | 86.297 | 1.00 24.47 |
| ATOM | 3189 | CA | LEU | B | 23 | 46.685 | 11.434 | 84.874 | 1.00 27.80 |
| ATOM | 3190 | CB | LEU | B | 23 | 45.933 | 10.141 | 84.513 | 1.00 22.18 |
| ATOM | 3191 | CG | LEU | B | 23 | 46.760 | 8.852 | 84.556 | 1.00 29.32 |

Fig. 18-48

| | | | | | | | | | |
|---|---|---|---|---|---|---|---|---|---|
| M | 3192 | CD1 | LEU | B | 23 | 45.868 | 7.628 | 84.402 | 1.00 24.94 |
| M | 3193 | CD2 | LEU | B | 23 | 47.805 | 8.905 | 83.446 | 1.00 24.80 |
| M | 3194 | C | LEU | B | 23 | 45.891 | 12.638 | 84.367 | 1.00 27.95 |
| M | 3195 | O | LEU | B | 23 | 45.166 | 12.528 | 83.373 | 1.00 24.42 |
| M | 3196 | N | LYS | B | 24 | 46.011 | 13.793 | 85.018 | 1.00 31.01 |
| M | 3197 | CA | LYS | B | 24 | 45.261 | 14.946 | 84.530 | 1.00 29.40 |
| M | 3198 | CB | LYS | B | 24 | 44.934 | 15.923 | 85.665 | 1.00 33.03 |
| M | 3199 | CG | LYS | B | 24 | 45.979 | 16.969 | 85.999 | 1.00 33.54 |
| M | 3200 | CD | LYS | B | 24 | 47.300 | 16.397 | 86.422 | 1.00 39.10 |
| M | 3201 | CE | LYS | B | 24 | 48.109 | 17.466 | 87.152 | 1.00 45.49 |
| M | 3202 | NZ | LYS | B | 24 | 48.224 | 18.737 | 86.380 | 1.00 45.95 |
| M | 3203 | C | LYS | B | 24 | 46.039 | 15.653 | 83.425 | 1.00 30.02 |
| M | 3204 | O | LYS | B | 24 | 45.508 | 16.523 | 82.736 | 1.00 28.82 |
| M | 3205 | N | ILE | B | 25 | 47.298 | 15.262 | 83.246 | 1.00 25.93 |
| M | 3206 | CA | ILE | B | 25 | 48.139 | 15.858 | 82.212 | 1.00 29.48 |
| M | 3207 | CB | ILE | B | 25 | 49.641 | 15.528 | 82.409 | 1.00 33.61 |
| M | 3208 | CG2 | ILE | B | 25 | 50.126 | 16.033 | 83.775 | 1.00 32.27 |
| M | 3209 | CG1 | ILE | B | 25 | 49.851 | 14.014 | 82.263 | 1.00 28.17 |
| M | 3210 | CD1 | ILE | B | 25 | 51.310 | 13.584 | 82.188 | 1.00 36.32 |
| M | 3211 | C | ILE | B | 25 | 47.784 | 15.318 | 80.834 | 1.00 30.08 |
| M | 3212 | O | ILE | B | 25 | 47.263 | 14.210 | 80.704 | 1.00 25.37 |
| M | 3213 | N | PRO | B | 26 | 48.064 | 16.101 | 79.783 | 1.00 29.19 |
| M | 3214 | CD | PRO | B | 26 | 48.650 | 17.448 | 79.770 | 1.00 32.47 |
| M | 3215 | CA | PRO | B | 26 | 47.782 | 15.673 | 78.413 | 1.00 29.52 |
| M | 3216 | CB | PRO | B | 26 | 48.103 | 16.921 | 77.593 | 1.00 29.84 |
| M | 3217 | CG | PRO | B | 26 | 47.930 | 18.046 | 78.599 | 1.00 36.40 |
| M | 3218 | C | PRO | B | 26 | 48.789 | 14.561 | 78.137 | 1.00 27.64 |
| M | 3219 | O | PRO | B | 26 | 49.920 | 14.620 | 78.629 | 1.00 23.08 |
| M | 3220 | N | ARG | B | 27 | 48.403 | 13.557 | 77.360 | 1.00 23.09 |
| M | 3221 | CA | ARG | B | 27 | 49.326 | 12.469 | 77.072 | 1.00 23.00 |
| M | 3222 | CB | ARG | B | 27 | 48.987 | 11.264 | 77.962 | 1.00 26.21 |
| M | 3223 | CG | ARG | B | 27 | 49.101 | 11.617 | 79.449 | 1.00 17.03 |
| M | 3224 | CD | ARG | B | 27 | 48.663 | 10.507 | 80.416 | 1.00 26.83 |
| M | 3225 | NE | ARG | B | 27 | 49.586 | 9.375 | 80.502 | 1.00 22.99 |
| M | 3226 | CZ | ARG | B | 27 | 49.444 | 8.220 | 79.856 | 1.00 25.06 |
| M | 3227 | NH1 | ARG | B | 27 | 48.408 | 8.022 | 79.059 | 1.00 17.74 |
| M | 3228 | NH2 | ARG | B | 27 | 50.336 | 7.253 | 80.027 | 1.00 23.38 |
| M | 3229 | C | ARG | B | 27 | 49.329 | 12.097 | 75.595 | 1.00 22.54 |
| M | 3230 | O | ARG | B | 27 | 50.214 | 12.526 | 74.852 | 1.00 21.86 |
| M | 3231 | N | VAL | B | 28 | 48.352 | 11.318 | 75.148 | 1.00 20.64 |
| M | 3232 | CA | VAL | B | 28 | 48.337 | 10.954 | 73.739 | 1.00 26.57 |
| M | 3233 | CB | VAL | B | 28 | 47.242 | 9.917 | 73.424 | 1.00 30.92 |
| M | 3234 | CG1 | VAL | B | 28 | 47.195 | 9.645 | 71.925 | 1.00 27.04 |
| M | 3235 | CG2 | VAL | B | 28 | 47.535 | 8.616 | 74.172 | 1.00 25.45 |
| M | 3236 | C | VAL | B | 28 | 48.150 | 12.189 | 72.866 | 1.00 28.02 |
| M | 3237 | O | VAL | B | 28 | 48.780 | 12.311 | 71.808 | 1.00 30.88 |
| M | 3238 | N | SER | B | 29 | 47.298 | 13.112 | 73.304 | 1.00 24.30 |
| M | 3239 | CA | SER | B | 29 | 47.082 | 14.326 | 72.523 | 1.00 29.48 |
| M | 3240 | CB | SER | B | 29 | 45.939 | 15.169 | 73.110 | 1.00 31.72 |
| M | 3241 | OG | SER | B | 29 | 46.218 | 15.614 | 74.424 | 1.00 34.55 |
| M | 3242 | C | SER | B | 29 | 48.379 | 15.125 | 72.514 | 1.00 30.81 |
| M | 3243 | O | SER | B | 29 | 48.680 | 15.820 | 71.545 | 1.00 28.85 |
| M | 3244 | N | LEU | B | 30 | 49.157 | 15.003 | 73.589 | 1.00 29.63 |
| M | 3245 | CA | LEU | B | 30 | 50.427 | 15.721 | 73.679 | 1.00 31.59 |
| M | 3246 | CB | LEU | B | 30 | 51.046 | 15.593 | 75.079 | 1.00 29.49 |
| M | 3247 | CG | LEU | B | 30 | 52.066 | 16.660 | 75.513 | 1.00 34.37 |
| M | 3248 | CD1 | LEU | B | 30 | 52.937 | 16.083 | 76.610 | 1.00 30.15 |
| M | 3249 | CD2 | LEU | B | 30 | 52.951 | 17.098 | 74.357 | 1.00 32.90 |
| M | 3250 | C | LEU | B | 30 | 51.371 | 15.085 | 72.672 | 1.00 25.90 |
| M | 3251 | O | LEU | B | 30 | 52.052 | 15.777 | 71.913 | 1.00 25.10 |
| M | 3252 | N | LEU | B | 31 | 51.404 | 13.756 | 72.675 | 1.00 22.10 |
| M | 3253 | CA | LEU | B | 31 | 52.268 | 13.013 | 71.764 | 1.00 25.52 |
| M | 3254 | CB | LEU | B | 31 | 51.966 | 11.514 | 71.842 | 1.00 26.41 |
| M | 3255 | CG | LEU | B | 31 | 53.066 | 10.524 | 71.441 | 1.00 28.93 |
| M | 3256 | CD1 | LEU | B | 31 | 52.425 | 9.198 | 71.042 | 1.00 23.69 |
| M | 3257 | CD2 | LEU | B | 31 | 53.873 | 11.049 | 70.300 | 1.00 30.41 |

Fig. 18-49

```
ATOM   3258  C   LEU B  31      52.010  13.489  70.335  1.00 25.38
ATOM   3259  O   LEU B  31      52.940  13.851  69.614  1.00 21.03
ATOM   3260  N   LEU B  32      50.741  13.481  69.933  1.00 21.27
ATOM   3261  CA  LEU B  32      50.364  13.899  68.585  1.00 27.91
ATOM   3262  CB  LEU B  32      48.841  13.798  68.408  1.00 26.60
ATOM   3263  CG  LEU B  32      48.195  12.419  68.614  1.00 27.30
ATOM   3264  CD1 LEU B  32      46.699  12.504  68.321  1.00 31.60
ATOM   3265  CD2 LEU B  32      48.837  11.391  67.708  1.00 26.90
ATOM   3266  C   LEU B  32      50.835  15.317  68.242  1.00 26.07
ATOM   3267  O   LEU B  32      51.458  15.533  67.205  1.00 22.45
ATOM   3268  N   ARG B  33      50.545  16.282  69.111  1.00 28.19
ATOM   3269  CA  ARG B  33      50.962  17.660  68.865  1.00 31.77
ATOM   3270  CB  ARG B  33      50.395  18.601  69.930  1.00 34.22
ATOM   3271  CG  ARG B  33      48.887  18.740  69.904  1.00 40.33
ATOM   3272  CD  ARG B  33      48.420  19.713  70.970  1.00 47.67
ATOM   3273  NE  ARG B  33      46.977  19.931  70.924  1.00 56.24
ATOM   3274  CZ  ARG B  33      46.330  20.505  69.912  1.00 60.10
ATOM   3275  NH1 ARG B  33      46.997  20.929  68.845  1.00 63.11
ATOM   3276  NH2 ARG B  33      45.011  20.652  69.965  1.00 63.81
ATOM   3277  C   ARG B  33      52.476  17.791  68.852  1.00 30.12
ATOM   3278  O   ARG B  33      53.028  18.580  68.097  1.00 30.20
ATOM   3279  N   PHE B  34      53.147  17.012  69.694  1.00 30.70
ATOM   3280  CA  PHE B  34      54.600  17.060  69.774  1.00 29.42
ATOM   3281  CB  PHE B  34      55.096  16.176  70.920  1.00 30.46
ATOM   3282  CG  PHE B  34      56.556  16.358  71.248  1.00 28.56
ATOM   3283  CD1 PHE B  34      57.001  17.515  71.885  1.00 26.92
ATOM   3284  CD2 PHE B  34      57.481  15.373  70.932  1.00 28.88
ATOM   3285  CE1 PHE B  34      58.346  17.684  72.206  1.00 28.15
ATOM   3286  CE2 PHE B  34      58.831  15.530  71.246  1.00 31.47
ATOM   3287  CZ  PHE B  34      59.265  16.689  71.887  1.00 28.15
ATOM   3288  C   PHE B  34      55.202  16.583  68.460  1.00 33.78
ATOM   3289  O   PHE B  34      56.049  17.259  67.873  1.00 33.71
ATOM   3290  N   LYS B  35      54.770  15.413  67.999  1.00 28.65
ATOM   3291  CA  LYS B  35      55.294  14.880  66.753  1.00 34.33
ATOM   3292  CB  LYS B  35      54.684  13.509  66.454  1.00 32.97
ATOM   3293  CG  LYS B  35      55.141  12.423  67.414  1.00 34.93
ATOM   3294  CD  LYS B  35      54.580  11.066  67.047  1.00 41.43
ATOM   3295  CE  LYS B  35      53.070  11.004  67.205  1.00 44.04
ATOM   3296  NZ  LYS B  35      52.335  11.984  66.345  1.00 60.09
ATOM   3297  C   LYS B  35      55.015  15.842  65.608  1.00 35.78
ATOM   3298  O   LYS B  35      55.869  16.061  64.752  1.00 33.39
ATOM   3299  N   ASP B  36      53.823  16.426  65.602  1.00 32.32
ATOM   3300  CA  ASP B  36      53.468  17.365  64.552  1.00 36.31
ATOM   3301  CB  ASP B  36      52.015  17.800  64.698  1.00 42.56
ATOM   3302  CG  ASP B  36      51.617  18.822  63.661  1.00 43.03
ATOM   3303  OD1 ASP B  36      51.812  18.544  62.461  1.00 39.17
ATOM   3304  OD2 ASP B  36      51.111  19.897  64.043  1.00 44.34
ATOM   3305  C   ASP B  36      54.371  18.590  64.578  1.00 36.14
ATOM   3306  O   ASP B  36      54.764  19.099  63.534  1.00 32.40
ATOM   3307  N   ALA B  37      54.694  19.061  65.777  1.00 34.80
ATOM   3308  CA  ALA B  37      55.554  20.226  65.924  1.00 36.82
ATOM   3309  CB  ALA B  37      55.599  20.659  67.383  1.00 38.54
ATOM   3310  C   ALA B  37      56.959  19.901  65.429  1.00 37.66
ATOM   3311  O   ALA B  37      57.675  20.776  64.950  1.00 30.56
ATOM   3312  N   MET B  38      57.346  18.635  65.541  1.00 37.42
ATOM   3313  CA  MET B  38      58.670  18.192  65.107  1.00 36.25
ATOM   3314  CB  MET B  38      59.158  17.059  66.013  1.00 36.44
ATOM   3315  CG  MET B  38      59.341  17.438  67.474  1.00 37.68
ATOM   3316  SD  MET B  38      60.841  18.391  67.784  1.00 38.07
ATOM   3317  CE  MET B  38      62.093  17.228  67.300  1.00 30.98
ATOM   3318  C   MET B  38      58.639  17.690  63.663  1.00 35.86
ATOM   3319  O   MET B  38      59.659  17.262  63.130  1.00 32.69
ATOM   3320  N   ASN B  39      57.470  17.742  63.035  1.00 35.82
ATOM   3321  CA  ASN B  39      57.321  17.262  61.661  1.00 42.75
ATOM   3322  CB  ASN B  39      58.156  18.108  60.688  1.00 46.20
ATOM   3323  CG  ASN B  39      57.670  19.543  60.591  1.00 47.57
```

Fig. 18-50

| | | | | | | | | | |
|---|---|---|---|---|---|---|---|---|---|
| ATOM | 3324 | OD1 | ASN | B | 39 | 56.524 | 19.801 | 60.212 | 1.00 48.78 |
| ATOM | 3325 | ND2 | ASN | B | 39 | 58.540 | 20.486 | 60.933 | 1.00 46.52 |
| ATOM | 3326 | C | ASN | B | 39 | 57.759 | 15.804 | 61.569 | 1.00 39.12 |
| ATOM | 3327 | O | ASN | B | 39 | 58.465 | 15.416 | 60.639 | 1.00 35.75 |
| ATOM | 3328 | N | LEU | B | 40 | 57.332 | 14.997 | 62.535 | 1.00 34.64 |
| ATOM | 3329 | CA | LEU | B | 40 | 57.700 | 13.590 | 62.556 | 1.00 35.10 |
| ATOM | 3330 | CB | LEU | B | 40 | 58.347 | 13.248 | 63.898 | 1.00 35.97 |
| ATOM | 3331 | CG | LEU | B | 40 | 59.595 | 14.073 | 64.227 | 1.00 36.21 |
| ATOM | 3332 | CD1 | LEU | B | 40 | 60.148 | 13.648 | 65.573 | 1.00 36.57 |
| ATOM | 3333 | CD2 | LEU | B | 40 | 60.646 | 13.880 | 63.145 | 1.00 36.79 |
| ATOM | 3334 | C | LEU | B | 40 | 56.549 | 12.626 | 62.264 | 1.00 37.58 |
| ATOM | 3335 | O | LEU | B | 40 | 56.637 | 11.438 | 62.573 | 1.00 39.15 |
| ATOM | 3336 | N | ILE | B | 41 | 55.476 | 13.131 | 61.663 | 1.00 36.79 |
| ATOM | 3337 | CA | ILE | B | 41 | 54.340 | 12.290 | 61.314 | 1.00 35.42 |
| ATOM | 3338 | CB | ILE | B | 41 | 53.445 | 11.991 | 62.536 | 1.00 35.21 |
| ATOM | 3339 | CG2 | ILE | B | 41 | 52.793 | 13.271 | 63.047 | 1.00 31.89 |
| ATOM | 3340 | CG1 | ILE | B | 41 | 52.367 | 10.980 | 62.141 | 1.00 32.68 |
| ATOM | 3341 | CD1 | ILE | B | 41 | 51.470 | 10.550 | 63.285 | 1.00 36.46 |
| ATOM | 3342 | C | ILE | B | 41 | 53.492 | 12.937 | 60.229 | 1.00 37.52 |
| ATOM | 3343 | O | ILE | B | 41 | 53.352 | 14.157 | 60.183 | 1.00 40.24 |
| ATOM | 3344 | N | ASP | B | 42 | 52.943 | 12.114 | 59.345 | 1.00 39.55 |
| ATOM | 3345 | CA | ASP | B | 42 | 52.094 | 12.615 | 58.273 | 1.00 45.30 |
| ATOM | 3346 | CB | ASP | B | 42 | 52.569 | 12.119 | 56.901 | 1.00 45.93 |
| ATOM | 3347 | CG | ASP | B | 42 | 53.972 | 12.584 | 56.564 | 1.00 47.09 |
| ATOM | 3348 | OD1 | ASP | B | 42 | 54.244 | 13.799 | 56.686 | 1.00 46.60 |
| ATOM | 3349 | OD2 | ASP | B | 42 | 54.797 | 11.736 | 56.162 | 1.00 45.16 |
| ATOM | 3350 | C | ASP | B | 42 | 50.677 | 12.134 | 58.524 | 1.00 45.15 |
| ATOM | 3351 | O | ASP | B | 42 | 50.467 | 11.051 | 59.069 | 1.00 47.06 |
| ATOM | 3352 | N | GLU | B | 43 | 49.707 | 12.944 | 58.121 | 1.00 48.13 |
| ATOM | 3353 | CA | GLU | B | 43 | 48.303 | 12.618 | 58.312 | 1.00 50.50 |
| ATOM | 3354 | CB | GLU | B | 43 | 47.441 | 13.637 | 57.571 | 1.00 53.54 |
| ATOM | 3355 | CG | GLU | B | 43 | 45.961 | 13.505 | 57.840 | 1.00 59.52 |
| ATOM | 3356 | CD | GLU | B | 43 | 45.155 | 14.518 | 57.065 | 1.00 64.03 |
| ATOM | 3357 | OE1 | GLU | B | 43 | 43.914 | 14.535 | 57.215 | 1.00 68.54 |
| ATOM | 3358 | OE2 | GLU | B | 43 | 45.765 | 15.298 | 56.301 | 1.00 66.95 |
| ATOM | 3359 | C | GLU | B | 43 | 47.972 | 11.205 | 57.836 | 1.00 47.81 |
| ATOM | 3360 | O | GLU | B | 43 | 47.092 | 10.547 | 58.390 | 1.00 49.67 |
| ATOM | 3361 | N | LYS | B | 44 | 48.690 | 10.744 | 56.817 | 1.00 46.21 |
| ATOM | 3362 | CA | LYS | B | 44 | 48.484 | 9.409 | 56.251 | 1.00 48.28 |
| ATOM | 3363 | CB | LYS | B | 44 | 49.207 | 9.311 | 54.894 | 1.00 49.96 |
| ATOM | 3364 | CG | LYS | B | 44 | 49.639 | 7.903 | 54.470 | 1.00 52.18 |
| ATOM | 3365 | CD | LYS | B | 44 | 50.970 | 7.532 | 55.127 | 1.00 61.03 |
| ATOM | 3366 | CE | LYS | B | 44 | 51.399 | 6.095 | 54.844 | 1.00 62.80 |
| ATOM | 3367 | NZ | LYS | B | 44 | 50.511 | 5.098 | 55.510 | 1.00 65.34 |
| ATOM | 3368 | C | LYS | B | 44 | 48.899 | 8.249 | 57.161 | 1.00 45.92 |
| ATOM | 3369 | O | LYS | B | 44 | 48.418 | 7.127 | 57.009 | 1.00 41.30 |
| ATOM | 3370 | N | GLU | B | 45 | 49.797 | 8.517 | 58.100 | 1.00 42.18 |
| ATOM | 3371 | CA | GLU | B | 45 | 50.268 | 7.486 | 59.014 | 1.00 38.41 |
| ATOM | 3372 | CB | GLU | B | 45 | 51.684 | 7.812 | 59.468 | 1.00 33.73 |
| ATOM | 3373 | CG | GLU | B | 45 | 52.694 | 7.887 | 58.351 | 1.00 37.58 |
| ATOM | 3374 | CD | GLU | B | 45 | 53.998 | 8.504 | 58.813 | 1.00 34.34 |
| ATOM | 3375 | OE1 | GLU | B | 45 | 53.997 | 9.699 | 59.176 | 1.00 38.04 |
| ATOM | 3376 | OE2 | GLU | B | 45 | 55.020 | 7.799 | 58.821 | 1.00 33.37 |
| ATOM | 3377 | C | GLU | B | 45 | 49.368 | 7.403 | 60.238 | 1.00 36.86 |
| ATOM | 3378 | O | GLU | B | 45 | 49.461 | 6.462 | 61.032 | 1.00 34.98 |
| ATOM | 3379 | N | LEU | B | 46 | 48.489 | 8.386 | 60.386 | 1.00 30.86 |
| ATOM | 3380 | CA | LEU | B | 46 | 47.608 | 8.438 | 61.545 | 1.00 30.65 |
| ATOM | 3381 | CB | LEU | B | 46 | 47.501 | 9.889 | 62.019 | 1.00 32.74 |
| ATOM | 3382 | CG | LEU | B | 46 | 46.642 | 10.163 | 63.250 | 1.00 34.76 |
| ATOM | 3383 | CD1 | LEU | B | 46 | 47.189 | 9.379 | 64.425 | 1.00 32.24 |
| ATOM | 3384 | CD2 | LEU | B | 46 | 46.639 | 11.656 | 63.548 | 1.00 33.94 |
| ATOM | 3385 | C | LEU | B | 46 | 46.212 | 7.861 | 61.318 | 1.00 31.36 |
| ATOM | 3386 | O | LEU | B | 46 | 45.530 | 8.218 | 60.363 | 1.00 31.78 |
| ATOM | 3387 | N | ILE | B | 47 | 45.801 | 6.957 | 62.203 | 1.00 31.18 |
| ATOM | 3388 | CA | ILE | B | 47 | 44.479 | 6.338 | 62.139 | 1.00 29.36 |
| ATOM | 3389 | CB | ILE | B | 47 | 44.564 | 4.802 | 62.258 | 1.00 28.62 |

Fig. 18-51

| ATOM | 3390 | CG2 | ILE | B | 47 | 43.161 | 4.205 | 62.407 | 1.00 | 28.80 |
|---|---|---|---|---|---|---|---|---|---|---|
| ATOM | 3391 | CG1 | ILE | B | 47 | 45.266 | 4.230 | 61.028 | 1.00 | 29.42 |
| ATOM | 3392 | CD1 | ILE | B | 47 | 45.419 | 2.722 | 61.054 | 1.00 | 31.12 |
| ATOM | 3393 | C | ILE | B | 47 | 43.659 | 6.875 | 63.303 | 1.00 | 32.22 |
| ATOM | 3394 | O | ILE | B | 47 | 44.063 | 6.755 | 64.461 | 1.00 | 31.17 |
| ATOM | 3395 | N | LYS | B | 48 | 42.514 | 7.475 | 62.999 | 1.00 | 28.39 |
| ATOM | 3396 | CA | LYS | B | 48 | 41.662 | 8.037 | 64.040 | 1.00 | 32.37 |
| ATOM | 3397 | CB | LYS | B | 48 | 40.517 | 8.840 | 63.414 | 1.00 | 36.32 |
| ATOM | 3398 | CG | LYS | B | 48 | 39.607 | 9.514 | 64.430 | 1.00 | 43.08 |
| ATOM | 3399 | CD | LYS | B | 48 | 38.535 | 10.361 | 63.747 | 1.00 | 44.38 |
| ATOM | 3400 | CE | LYS | B | 48 | 37.657 | 11.074 | 64.768 | 1.00 | 45.91 |
| ATOM | 3401 | NZ | LYS | B | 48 | 38.451 | 11.991 | 65.643 | 1.00 | 42.66 |
| ATOM | 3402 | C | LYS | B | 48 | 41.095 | 6.943 | 64.937 | 1.00 | 31.08 |
| ATOM | 3403 | O | LYS | B | 48 | 40.524 | 5.962 | 64.457 | 1.00 | 26.24 |
| ATOM | 3404 | N | SER | B | 49 | 41.260 | 7.121 | 66.244 | 1.00 | 27.89 |
| ATOM | 3405 | CA | SER | B | 49 | 40.770 | 6.168 | 67.232 | 1.00 | 25.17 |
| ATOM | 3406 | CB | SER | B | 49 | 41.146 | 6.639 | 68.642 | 1.00 | 24.41 |
| ATOM | 3407 | OG | SER | B | 49 | 42.539 | 6.858 | 68.777 | 1.00 | 31.79 |
| ATOM | 3408 | C | SER | B | 49 | 39.248 | 6.054 | 67.160 | 1.00 | 29.07 |
| ATOM | 3409 | O | SER | B | 49 | 38.565 | 7.034 | 66.879 | 1.00 | 28.47 |
| ATOM | 3410 | N | ARG | B | 50 | 38.723 | 4.859 | 67.409 | 1.00 | 26.13 |
| ATOM | 3411 | CA | ARG | B | 50 | 37.278 | 4.658 | 67.430 | 1.00 | 24.24 |
| ATOM | 3412 | CB | ARG | B | 50 | 36.810 | 3.700 | 66.323 | 1.00 | 25.03 |
| ATOM | 3413 | CG | ARG | B | 50 | 37.231 | 2.233 | 66.507 | 1.00 | 26.54 |
| ATOM | 3414 | CD | ARG | B | 50 | 36.570 | 1.340 | 65.452 | 1.00 | 26.21 |
| ATOM | 3415 | NE | ARG | B | 50 | 37.006 | -0.058 | 65.504 | 1.00 | 25.13 |
| ATOM | 3416 | CZ | ARG | B | 50 | 36.700 | -0.924 | 66.468 | 1.00 | 26.09 |
| ATOM | 3417 | NH1 | ARG | B | 50 | 35.941 | -0.558 | 67.497 | 1.00 | 23.42 |
| ATOM | 3418 | NH2 | ARG | B | 50 | 37.157 | -2.168 | 66.402 | 1.00 | 23.91 |
| ATOM | 3419 | C | ARG | B | 50 | 36.937 | 4.037 | 68.775 | 1.00 | 23.83 |
| ATOM | 3420 | O | ARG | B | 50 | 37.782 | 3.392 | 69.403 | 1.00 | 21.60 |
| ATOM | 3421 | N | PRO | B | 51 | 35.700 | 4.223 | 69.243 | 1.00 | 22.99 |
| ATOM | 3422 | CD | PRO | B | 51 | 34.554 | 4.962 | 68.688 | 1.00 | 25.09 |
| ATOM | 3423 | CA | PRO | B | 51 | 35.338 | 3.628 | 70.530 | 1.00 | 25.48 |
| ATOM | 3424 | CB | PRO | B | 51 | 33.949 | 4.217 | 70.802 | 1.00 | 26.32 |
| ATOM | 3425 | CG | PRO | B | 51 | 33.936 | 5.503 | 69.953 | 1.00 | 28.65 |
| ATOM | 3426 | C | PRO | B | 51 | 35.264 | 2.118 | 70.325 | 1.00 | 26.73 |
| ATOM | 3427 | O | PRO | B | 51 | 35.142 | 1.646 | 69.194 | 1.00 | 18.87 |
| ATOM | 3428 | N | ALA | B | 52 | 35.355 | 1.359 | 71.408 | 1.00 | 23.64 |
| ATOM | 3429 | CA | ALA | B | 52 | 35.237 | -0.083 | 71.291 | 1.00 | 23.27 |
| ATOM | 3430 | CB | ALA | B | 52 | 35.811 | -0.757 | 72.521 | 1.00 | 26.31 |
| ATOM | 3431 | C | ALA | B | 52 | 33.733 | -0.324 | 71.223 | 1.00 | 25.25 |
| ATOM | 3432 | O | ALA | B | 52 | 32.950 | 0.515 | 71.677 | 1.00 | 22.78 |
| ATOM | 3433 | N | THR | B | 53 | 33.321 | -1.447 | 70.651 | 1.00 | 22.77 |
| ATOM | 3434 | CA | THR | B | 53 | 31.900 | -1.760 | 70.596 | 1.00 | 26.90 |
| ATOM | 3435 | CB | THR | B | 53 | 31.567 | -2.732 | 69.456 | 1.00 | 30.00 |
| ATOM | 3436 | OG1 | THR | B | 53 | 32.305 | -3.950 | 69.642 | 1.00 | 25.59 |
| ATOM | 3437 | CG2 | THR | B | 53 | 31.917 | -2.117 | 68.103 | 1.00 | 23.33 |
| ATOM | 3438 | C | THR | B | 53 | 31.579 | -2.445 | 71.916 | 1.00 | 30.41 |
| ATOM | 3439 | O | THR | B | 53 | 32.484 | -2.917 | 72.609 | 1.00 | 26.13 |
| ATOM | 3440 | N | LYS | B | 54 | 30.300 | -2.504 | 72.268 | 1.00 | 29.12 |
| ATOM | 3441 | CA | LYS | B | 54 | 29.909 | -3.140 | 73.514 | 1.00 | 30.24 |
| ATOM | 3442 | CB | LYS | B | 54 | 28.396 | -3.027 | 73.720 | 1.00 | 32.78 |
| ATOM | 3443 | CG | LYS | B | 54 | 27.947 | -3.351 | 75.131 | 1.00 | 34.85 |
| ATOM | 3444 | CD | LYS | B | 54 | 26.445 | -3.204 | 75.268 | 1.00 | 41.13 |
| ATOM | 3445 | CE | LYS | B | 54 | 26.008 | -3.366 | 76.709 | 1.00 | 43.39 |
| ATOM | 3446 | NZ | LYS | B | 54 | 26.464 | -2.257 | 77.582 | 1.00 | 47.39 |
| ATOM | 3447 | C | LYS | B | 54 | 30.329 | -4.603 | 73.442 | 1.00 | 29.10 |
| ATOM | 3448 | O | LYS | B | 54 | 30.779 | -5.183 | 74.430 | 1.00 | 26.71 |
| ATOM | 3449 | N | GLU | B | 55 | 30.196 | -5.187 | 72.256 | 1.00 | 23.97 |
| ATOM | 3450 | CA | GLU | B | 55 | 30.577 | -6.577 | 72.032 | 1.00 | 28.08 |
| ATOM | 3451 | CB | GLU | B | 55 | 30.288 | -6.965 | 70.579 | 1.00 | 24.82 |
| ATOM | 3452 | CG | GLU | B | 55 | 30.671 | -8.400 | 70.237 | 1.00 | 33.40 |
| ATOM | 3453 | CD | GLU | B | 55 | 30.453 | -8.737 | 68.767 | 1.00 | 38.49 |
| ATOM | 3454 | OE1 | GLU | B | 55 | 30.638 | -9.913 | 68.394 | 1.00 | 41.24 |
| ATOM | 3455 | OE2 | GLU | B | 55 | 30.101 | -7.833 | 67.984 | 1.00 | 40.02 |

Fig. 18-52

```
ATOM   3456  C   GLU B  55      32.066  -6.808  72.345  1.00 25.82
ATOM   3457  O   GLU B  55      32.429  -7.765  73.033  1.00 23.83
ATOM   3458  N   GLU B  56      32.931  -5.938  71.835  1.00 25.04
ATOM   3459  CA  GLU B  56      34.365  -6.079  72.093  1.00 25.30
ATOM   3460  CB  GLU B  56      35.141  -5.003  71.334  1.00 24.31
ATOM   3461  CG  GLU B  56      34.866  -5.039  69.836  1.00 32.15
ATOM   3462  CD  GLU B  56      35.512  -3.903  69.073  1.00 31.43
ATOM   3463  OE1 GLU B  56      35.486  -2.759  69.568  1.00 28.54
ATOM   3464  OE2 GLU B  56      36.012  -4.147  67.959  1.00 28.89
ATOM   3465  C   GLU B  56      34.653  -5.988  73.595  1.00 28.88
ATOM   3466  O   GLU B  56      35.450  -6.766  74.137  1.00 25.07
ATOM   3467  N   LEU B  57      33.996  -5.050  74.272  1.00 24.52
ATOM   3468  CA  LEU B  57      34.203  -4.891  75.702  1.00 27.34
ATOM   3469  CB  LEU B  57      33.416  -3.694  76.231  1.00 22.79
ATOM   3470  CG  LEU B  57      33.859  -2.320  75.722  1.00 23.57
ATOM   3471  CD1 LEU B  57      33.008  -1.247  76.366  1.00 22.27
ATOM   3472  CD2 LEU B  57      35.342  -2.089  76.061  1.00 17.24
ATOM   3473  C   LEU B  57      33.785  -6.144  76.452  1.00 26.92
ATOM   3474  O   LEU B  57      34.458  -6.568  77.396  1.00 24.06
ATOM   3475  N   LEU B  58      32.670  -6.732  76.029  1.00 23.35
ATOM   3476  CA  LEU B  58      32.154  -7.931  76.674  1.00 25.60
ATOM   3477  CB  LEU B  58      30.718  -8.207  76.221  1.00 28.50
ATOM   3478  CG  LEU B  58      29.734  -7.110  76.649  1.00 30.91
ATOM   3479  CD1 LEU B  58      28.323  -7.468  76.212  1.00 28.93
ATOM   3480  CD2 LEU B  58      29.794  -6.945  78.157  1.00 33.44
ATOM   3481  C   LEU B  58      33.027  -9.153  76.446  1.00 24.59
ATOM   3482  O   LEU B  58      32.760 -10.216  76.991  1.00 19.76
ATOM   3483  N   LEU B  59      34.065  -9.006  75.630  1.00 23.99
ATOM   3484  CA  LEU B  59      34.988 -10.108  75.411  1.00 25.11
ATOM   3485  CB  LEU B  59      36.018  -9.757  74.332  1.00 21.64
ATOM   3486  CG  LEU B  59      35.483  -9.652  72.905  1.00 24.24
ATOM   3487  CD1 LEU B  59      36.585  -9.177  71.975  1.00 24.25
ATOM   3488  CD2 LEU B  59      34.957 -11.014  72.468  1.00 19.91
ATOM   3489  C   LEU B  59      35.699 -10.371  76.733  1.00 23.84
ATOM   3490  O   LEU B  59      36.150 -11.489  76.992  1.00 19.39
ATOM   3491  N   PHE B  60      35.793  -9.344  77.577  1.00 21.80
ATOM   3492  CA  PHE B  60      36.462  -9.510  78.876  1.00 23.08
ATOM   3493  CB  PHE B  60      37.809  -8.770  78.908  1.00 18.22
ATOM   3494  CG  PHE B  60      38.544  -8.906  80.230  1.00 21.72
ATOM   3495  CD1 PHE B  60      38.975 -10.157  80.680  1.00 19.23
ATOM   3496  CD2 PHE B  60      38.757  -7.791  81.048  1.00 17.75
ATOM   3497  CE1 PHE B  60      39.602 -10.301  81.927  1.00 18.80
ATOM   3498  CE2 PHE B  60      39.384  -7.923  82.297  1.00 19.23
ATOM   3499  CZ  PHE B  60      39.807  -9.184  82.737  1.00 16.10
ATOM   3500  C   PHE B  60      35.648  -9.069  80.083  1.00 21.58
ATOM   3501  O   PHE B  60      35.508  -9.822  81.040  1.00 22.21
ATOM   3502  N   HIS B  61      35.128  -7.847  80.055  1.00 20.65
ATOM   3503  CA  HIS B  61      34.362  -7.336  81.184  1.00 23.32
ATOM   3504  CB  HIS B  61      34.422  -5.807  81.229  1.00 27.60
ATOM   3505  CG  HIS B  61      35.800  -5.259  81.440  1.00 31.83
ATOM   3506  CD2 HIS B  61      36.466  -4.940  82.575  1.00 26.86
ATOM   3507  ND1 HIS B  61      36.669  -5.003  80.401  1.00 34.35
ATOM   3508  CE1 HIS B  61      37.810  -4.546  80.887  1.00 34.78
ATOM   3509  NE2 HIS B  61      37.713  -4.499  82.204  1.00 36.27
ATOM   3510  C   HIS B  61      32.902  -7.775  81.198  1.00 28.04
ATOM   3511  O   HIS B  61      32.349  -8.167  80.176  1.00 25.70
ATOM   3512  N   THR B  62      32.276  -7.691  82.367  1.00 25.25
ATOM   3513  CA  THR B  62      30.882  -8.084  82.506  1.00 25.35
ATOM   3514  CB  THR B  62      30.578  -8.549  83.932  1.00 25.47
ATOM   3515  OG1 THR B  62      30.783  -7.462  84.843  1.00 28.62
ATOM   3516  CG2 THR B  62      31.482  -9.701  84.315  1.00 21.32
ATOM   3517  C   THR B  62      29.931  -6.942  82.162  1.00 26.06
ATOM   3518  O   THR B  62      30.287  -5.771  82.254  1.00 24.14
ATOM   3519  N   GLU B  63      28.718  -7.305  81.759  1.00 28.01
ATOM   3520  CA  GLU B  63      27.681  -6.349  81.389  1.00 30.77
ATOM   3521  CB  GLU B  63      26.374  -7.094  81.114  1.00 33.97
```

Fig. 18-53

| ATOM | 3522 | CG | GLU | B | 63 | 25.213 | -6.210 | 80.667 | 1.00 | 41.12 |
|------|------|------|------|---|----|--------|--------|--------|------|-------|
| ATOM | 3523 | CD | GLU | B | 63 | 25.189 | -5.987 | 79.168 | 1.00 | 44.47 |
| ATOM | 3524 | OE1 | GLU | B | 63 | 24.361 | -5.177 | 78.689 | 1.00 | 42.64 |
| ATOM | 3525 | OE2 | GLU | B | 63 | 25.992 | -6.640 | 78.465 | 1.00 | 45.96 |
| ATOM | 3526 | C | GLU | B | 63 | 27.436 | -5.326 | 82.498 | 1.00 | 27.29 |
| ATOM | 3527 | O | GLU | B | 63 | 27.381 | -4.118 | 82.252 | 1.00 | 25.13 |
| ATOM | 3528 | N | ASP | B | 64 | 27.272 | -5.834 | 83.713 | 1.00 | 24.38 |
| ATOM | 3529 | CA | ASP | B | 64 | 27.010 | -5.023 | 84.897 | 1.00 | 29.27 |
| ATOM | 3530 | CB | ASP | B | 64 | 26.887 | -5.944 | 86.112 | 1.00 | 36.30 |
| ATOM | 3531 | CG | ASP | B | 64 | 28.022 | -6.935 | 86.198 | 1.00 | 50.77 |
| ATOM | 3532 | OD1 | ASP | B | 64 | 29.128 | -6.540 | 86.630 | 1.00 | 52.71 |
| ATOM | 3533 | OD2 | ASP | B | 64 | 27.812 | -8.106 | 85.802 | 1.00 | 51.98 |
| ATOM | 3534 | C | ASP | B | 64 | 28.075 | -3.967 | 85.143 | 1.00 | 26.49 |
| ATOM | 3535 | O | ASP | B | 64 | 27.768 | -2.806 | 85.422 | 1.00 | 18.33 |
| ATOM | 3536 | N | TYR | B | 65 | 29.332 | -4.373 | 85.052 | 1.00 | 22.75 |
| ATOM | 3537 | CA | TYR | B | 65 | 30.420 | -3.435 | 85.251 | 1.00 | 19.32 |
| ATOM | 3538 | CB | TYR | B | 65 | 31.751 | -4.186 | 85.256 | 1.00 | 16.59 |
| ATOM | 3539 | CG | TYR | B | 65 | 32.949 | -3.285 | 85.366 | 1.00 | 19.19 |
| ATOM | 3540 | CD1 | TYR | B | 65 | 33.033 | -2.328 | 86.383 | 1.00 | 21.35 |
| ATOM | 3541 | CE1 | TYR | B | 65 | 34.135 | -1.489 | 86.489 | 1.00 | 18.32 |
| ATOM | 3542 | CD2 | TYR | B | 65 | 34.004 | -3.382 | 84.456 | 1.00 | 18.65 |
| ATOM | 3543 | CE2 | TYR | B | 65 | 35.116 | -2.544 | 84.554 | 1.00 | 21.01 |
| ATOM | 3544 | CZ | TYR | B | 65 | 35.172 | -1.601 | 85.573 | 1.00 | 20.61 |
| ATOM | 3545 | OH | TYR | B | 65 | 36.262 | -0.775 | 85.682 | 1.00 | 17.77 |
| ATOM | 3546 | C | TYR | B | 65 | 30.392 | -2.373 | 84.146 | 1.00 | 22.01 |
| ATOM | 3547 | O | TYR | B | 65 | 30.399 | -1.167 | 84.421 | 1.00 | 18.20 |
| ATOM | 3548 | N | ILE | B | 66 | 30.330 | -2.815 | 82.894 | 1.00 | 19.49 |
| ATOM | 3549 | CA | ILE | B | 66 | 30.305 | -1.870 | 81.786 | 1.00 | 19.68 |
| ATOM | 3550 | CB | ILE | B | 66 | 30.208 | -2.592 | 80.432 | 1.00 | 23.31 |
| ATOM | 3551 | CG2 | ILE | B | 66 | 30.200 | -1.571 | 79.303 | 1.00 | 21.30 |
| ATOM | 3552 | CG1 | ILE | B | 66 | 31.400 | -3.541 | 80.260 | 1.00 | 27.67 |
| ATOM | 3553 | CD1 | ILE | B | 66 | 32.758 | -2.839 | 80.291 | 1.00 | 29.29 |
| ATOM | 3554 | C | ILE | B | 66 | 29.128 | -0.909 | 81.940 | 1.00 | 26.99 |
| ATOM | 3555 | O | ILE | B | 66 | 29.294 | 0.309 | 81.848 | 1.00 | 23.36 |
| ATOM | 3556 | N | ASN | B | 67 | 27.939 | -1.447 | 82.198 | 1.00 | 24.98 |
| ATOM | 3557 | CA | ASN | B | 67 | 26.782 | -0.580 | 82.363 | 1.00 | 27.70 |
| ATOM | 3558 | CB | ASN | B | 67 | 25.492 | -1.389 | 82.580 | 1.00 | 25.58 |
| ATOM | 3559 | CG | ASN | B | 67 | 25.081 | -2.183 | 81.341 | 1.00 | 26.91 |
| ATOM | 3560 | OD1 | ASN | B | 67 | 25.199 | -1.701 | 80.220 | 1.00 | 31.48 |
| ATOM | 3561 | ND2 | ASN | B | 67 | 24.572 | -3.387 | 81.545 | 1.00 | 23.80 |
| ATOM | 3562 | C | ASN | B | 67 | 26.982 | 0.401 | 83.513 | 1.00 | 25.34 |
| ATOM | 3563 | O | ASN | B | 67 | 26.524 | 1.539 | 83.448 | 1.00 | 22.53 |
| ATOM | 3564 | N | THR | B | 68 | 27.664 | -0.031 | 84.568 | 1.00 | 23.65 |
| ATOM | 3565 | CA | THR | B | 68 | 27.903 | 0.863 | 85.696 | 1.00 | 25.25 |
| ATOM | 3566 | CB | THR | B | 68 | 28.516 | 0.119 | 86.891 | 1.00 | 29.08 |
| ATOM | 3567 | OG1 | THR | B | 68 | 27.561 | -0.826 | 87.396 | 1.00 | 25.94 |
| ATOM | 3568 | CG2 | THR | B | 68 | 28.894 | 1.100 | 88.002 | 1.00 | 22.90 |
| ATOM | 3569 | C | THR | B | 68 | 28.818 | 2.009 | 85.287 | 1.00 | 25.91 |
| ATOM | 3570 | O | THR | B | 68 | 28.576 | 3.156 | 85.661 | 1.00 | 28.47 |
| ATOM | 3571 | N | LEU | B | 69 | 29.861 | 1.702 | 84.519 | 1.00 | 25.13 |
| ATOM | 3572 | CA | LEU | B | 69 | 30.788 | 2.729 | 84.054 | 1.00 | 24.37 |
| ATOM | 3573 | CB | LEU | B | 69 | 31.915 | 2.122 | 83.201 | 1.00 | 21.32 |
| ATOM | 3574 | CG | LEU | B | 69 | 32.960 | 1.231 | 83.889 | 1.00 | 22.33 |
| ATOM | 3575 | CD1 | LEU | B | 69 | 34.006 | 0.786 | 82.859 | 1.00 | 22.57 |
| ATOM | 3576 | CD2 | LEU | B | 69 | 33.643 | 2.000 | 85.008 | 1.00 | 23.20 |
| ATOM | 3577 | C | LEU | B | 69 | 30.036 | 3.764 | 83.229 | 1.00 | 23.02 |
| ATOM | 3578 | O | LEU | B | 69 | 30.190 | 4.966 | 83.444 | 1.00 | 18.98 |
| ATOM | 3579 | N | MET | B | 70 | 29.218 | 3.290 | 82.294 | 1.00 | 19.62 |
| ATOM | 3580 | CA | MET | B | 70 | 28.449 | 4.181 | 81.434 | 1.00 | 25.87 |
| ATOM | 3581 | CB | MET | B | 70 | 27.660 | 3.371 | 80.401 | 1.00 | 24.80 |
| ATOM | 3582 | CG | MET | B | 70 | 28.531 | 2.511 | 79.490 | 1.00 | 30.37 |
| ATOM | 3583 | SD | MET | B | 70 | 27.592 | 1.599 | 78.227 | 1.00 | 30.35 |
| ATOM | 3584 | CE | MET | B | 70 | 26.922 | 2.986 | 77.245 | 1.00 | 30.20 |
| ATOM | 3585 | C | MET | B | 70 | 27.489 | 5.062 | 82.242 | 1.00 | 28.82 |
| ATOM | 3586 | O | MET | B | 70 | 27.391 | 6.273 | 82.009 | 1.00 | 24.09 |
| ATOM | 3587 | N | GLU | B | 71 | 26.786 | 4.458 | 83.194 | 1.00 | 28.21 |

Fig. 18-54

| | | | | | | | | | |
|---|---|---|---|---|---|---|---|---|---|
| ATOM | 3588 | CA | GLU | B | 71 | 25.837 | 5.207 | 84.008 | 1.00 27.45 |
| ATOM | 3589 | CB | GLU | B | 71 | 25.014 | 4.268 | 84.889 | 1.00 30.70 |
| ATOM | 3590 | CG | GLU | B | 71 | 24.072 | 5.005 | 85.832 | 1.00 33.61 |
| ATOM | 3591 | CD | GLU | B | 71 | 23.044 | 5.867 | 85.096 | 1.00 37.51 |
| ATOM | 3592 | OE1 | GLU | B | 71 | 22.333 | 6.638 | 85.773 | 1.00 35.47 |
| ATOM | 3593 | OE2 | GLU | B | 71 | 22.934 | 5.769 | 83.849 | 1.00 31.03 |
| ATOM | 3594 | C | GLU | B | 71 | 26.559 | 6.209 | 84.887 | 1.00 29.15 |
| ATOM | 3595 | O | GLU | B | 71 | 26.115 | 7.341 | 85.035 | 1.00 23.96 |
| ATOM | 3596 | N | ALA | B | 72 | 27.671 | 5.781 | 85.481 | 1.00 27.76 |
| ATOM | 3597 | CA | ALA | B | 72 | 28.454 | 6.662 | 86.340 | 1.00 27.58 |
| ATOM | 3598 | CB | ALA | B | 72 | 29.663 | 5.920 | 86.909 | 1.00 23.24 |
| ATOM | 3599 | C | ALA | B | 72 | 28.924 | 7.886 | 85.563 | 1.00 28.07 |
| ATOM | 3600 | O | ALA | B | 72 | 28.895 | 8.999 | 86.079 | 1.00 23.22 |
| ATOM | 3601 | N | GLU | B | 73 | 29.356 | 7.684 | 84.322 | 1.00 26.40 |
| ATOM | 3602 | CA | GLU | B | 73 | 29.846 | 8.801 | 83.529 | 1.00 29.06 |
| ATOM | 3603 | CB | GLU | B | 73 | 30.658 | 8.314 | 82.325 | 1.00 29.48 |
| ATOM | 3604 | CG | GLU | B | 73 | 31.162 | 9.466 | 81.443 | 1.00 31.00 |
| ATOM | 3605 | CD | GLU | B | 73 | 31.938 | 9.009 | 80.216 | 1.00 34.37 |
| ATOM | 3606 | OE1 | GLU | B | 73 | 33.059 | 8.461 | 80.356 | 1.00 28.41 |
| ATOM | 3607 | OE2 | GLU | B | 73 | 31.419 | 9.203 | 79.100 | 1.00 30.59 |
| ATOM | 3608 | C | GLU | B | 73 | 28.744 | 9.734 | 83.045 | 1.00 31.92 |
| ATOM | 3609 | O | GLU | B | 73 | 28.894 | 10.951 | 83.104 | 1.00 35.69 |
| ATOM | 3610 | N | ARG | B | 74 | 27.633 | 9.186 | 82.570 | 1.00 33.53 |
| ATOM | 3611 | CA | ARG | B | 74 | 26.583 | 10.067 | 82.081 | 1.00 38.64 |
| ATOM | 3612 | CB | ARG | B | 74 | 25.456 | 9.280 | 81.403 | 1.00 39.90 |
| ATOM | 3613 | CG | ARG | B | 74 | 24.448 | 8.706 | 82.363 | 1.00 46.67 |
| ATOM | 3614 | CD | ARG | B | 74 | 23.174 | 8.311 | 81.646 | 1.00 47.53 |
| ATOM | 3615 | NE | ARG | B | 74 | 22.076 | 8.153 | 82.594 | 1.00 55.58 |
| ATOM | 3616 | CZ | ARG | B | 74 | 21.609 | 9.136 | 83.362 | 1.00 56.04 |
| ATOM | 3617 | NH1 | ARG | B | 74 | 22.142 | 10.351 | 83.297 | 1.00 58.93 |
| ATOM | 3618 | NH2 | ARG | B | 74 | 20.601 | 8.910 | 84.192 | 1.00 53.62 |
| ATOM | 3619 | C | ARG | B | 74 | 26.008 | 10.914 | 83.222 | 1.00 35.84 |
| ATOM | 3620 | O | ARG | B | 74 | 25.778 | 12.107 | 83.048 | 1.00 29.44 |
| ATOM | 3621 | N | SER | B | 75 | 25.794 | 10.302 | 84.386 | 1.00 31.02 |
| ATOM | 3622 | CA | SER | B | 75 | 25.243 | 11.014 | 85.539 | 1.00 31.99 |
| ATOM | 3623 | CB | SER | B | 75 | 24.592 | 10.038 | 86.510 | 1.00 34.47 |
| ATOM | 3624 | OG | SER | B | 75 | 25.581 | 9.228 | 87.123 | 1.00 34.33 |
| ATOM | 3625 | C | SER | B | 75 | 26.339 | 11.754 | 86.288 | 1.00 35.42 |
| ATOM | 3626 | O | SER | B | 75 | 26.060 | 12.555 | 87.180 | 1.00 33.45 |
| ATOM | 3627 | N | GLN | B | 76 | 27.584 | 11.473 | 85.922 | 1.00 33.25 |
| ATOM | 3628 | CA | GLN | B | 76 | 28.739 | 12.082 | 86.565 | 1.00 35.61 |
| ATOM | 3629 | CB | GLN | B | 76 | 28.818 | 13.572 | 86.241 | 1.00 30.11 |
| ATOM | 3630 | CG | GLN | B | 76 | 30.216 | 14.112 | 86.390 | 1.00 39.13 |
| ATOM | 3631 | CD | GLN | B | 76 | 31.124 | 13.681 | 85.248 | 1.00 33.54 |
| ATOM | 3632 | OE1 | GLN | B | 76 | 31.052 | 12.546 | 84.761 | 1.00 29.21 |
| ATOM | 3633 | NE2 | GLN | B | 76 | 31.995 | 14.583 | 84.827 | 1.00 40.93 |
| ATOM | 3634 | C | GLN | B | 76 | 28.624 | 11.892 | 88.079 | 1.00 37.88 |
| ATOM | 3635 | O | GLN | B | 76 | 28.901 | 12.908 | 88.858 | 1.00 32.74 |
| ATOM | 3636 | N | SER | B | 77 | 28.209 | 10.697 | 88.488 | 1.00 34.72 |
| ATOM | 3637 | CA | SER | B | 77 | 28.047 | 10.382 | 89.901 | 1.00 37.07 |
| ATOM | 3638 | CB | SER | B | 77 | 26.635 | 10.738 | 90.371 | 1.00 39.61 |
| ATOM | 3639 | OG | SER | B | 77 | 25.678 | 9.941 | 89.688 | 1.00 39.03 |
| ATOM | 3640 | C | SER | B | 77 | 28.265 | 8.897 | 90.112 | 1.00 35.95 |
| ATOM | 3641 | O | SER | B | 77 | 28.177 | 8.108 | 89.173 | 1.00 36.60 |
| ATOM | 3642 | N | VAL | B | 78 | 28.528 | 8.518 | 91.355 | 1.00 33.03 |
| ATOM | 3643 | CA | VAL | B | 78 | 28.753 | 7.124 | 91.685 | 1.00 33.41 |
| ATOM | 3644 | CB | VAL | B | 78 | 29.742 | 6.979 | 92.848 | 1.00 36.91 |
| ATOM | 3645 | CG1 | VAL | B | 78 | 29.955 | 5.499 | 93.163 | 1.00 34.37 |
| ATOM | 3646 | CG2 | VAL | B | 78 | 31.055 | 7.658 | 92.496 | 1.00 34.19 |
| ATOM | 3647 | C | VAL | B | 78 | 27.461 | 6.431 | 92.082 | 1.00 34.93 |
| ATOM | 3648 | O | VAL | B | 78 | 26.897 | 6.703 | 93.143 | 1.00 28.25 |
| ATOM | 3649 | N | PRO | B | 79 | 26.971 | 5.521 | 91.228 | 1.00 36.73 |
| ATOM | 3650 | CD | PRO | B | 79 | 27.532 | 5.114 | 89.930 | 1.00 37.44 |
| ATOM | 3651 | CA | PRO | B | 79 | 25.738 | 4.779 | 91.493 | 1.00 38.33 |
| ATOM | 3652 | CB | PRO | B | 79 | 25.668 | 3.826 | 90.301 | 1.00 38.68 |
| ATOM | 3653 | CG | PRO | B | 79 | 26.293 | 4.664 | 89.201 | 1.00 37.41 |

Fig. 18-55

| | | | | | | | | | |
|---|---|---|---|---|---|---|---|---|---|
| ATOM | 3654 | C | PRO | B | 79 | 25.788 | 4.046 | 92.834 | 1.00 36.92 |
| ATOM | 3655 | O | PRO | B | 79 | 26.854 | 3.648 | 93.298 | 1.00 33.03 |
| ATOM | 3656 | N | LYS | B | 80 | 24.623 | 3.881 | 93.448 | 1.00 38.43 |
| ATOM | 3657 | CA | LYS | B | 80 | 24.482 | 3.206 | 94.736 | 1.00 39.73 |
| ATOM | 3658 | CB | LYS | B | 80 | 23.003 | 2.871 | 94.967 | 1.00 43.33 |
| ATOM | 3659 | CG | LYS | B | 80 | 22.679 | 2.129 | 96.262 | 1.00 44.60 |
| ATOM | 3660 | CD | LYS | B | 80 | 21.198 | 1.742 | 96.287 | 1.00 48.09 |
| ATOM | 3661 | CE | LYS | B | 80 | 20.805 | 1.014 | 97.559 | 1.00 50.12 |
| ATOM | 3662 | NZ | LYS | B | 80 | 20.932 | 1.890 | 98.760 | 1.00 53.16 |
| ATOM | 3663 | C | LYS | B | 80 | 25.315 | 1.928 | 94.854 | 1.00 40.35 |
| ATOM | 3664 | O | LYS | B | 80 | 25.181 | 1.011 | 94.047 | 1.00 36.67 |
| ATOM | 3665 | N | GLY | B | 81 | 26.173 | 1.880 | 95.869 | 1.00 38.26 |
| ATOM | 3666 | CA | GLY | B | 81 | 26.996 | 0.709 | 96.104 | 1.00 34.69 |
| ATOM | 3667 | C | GLY | B | 81 | 28.066 | 0.407 | 95.071 | 1.00 34.63 |
| ATOM | 3668 | O | GLY | B | 81 | 28.861 | -0.513 | 95.255 | 1.00 33.92 |
| ATOM | 3669 | N | ALA | B | 82 | 28.100 | 1.178 | 93.992- | 1.00 31.26 |
| ATOM | 3670 | CA | ALA | B | 82 | 29.082 | 0.963 | 92.936 | 1.00 34.88 |
| ATOM | 3671 | CB | ALA | B | 82 | 28.755 | 1.848 | 91.751 | 1.00 23.13 |
| ATOM | 3672 | C | ALA | B | 82 | 30.517 | 1.223 | 93.405 | 1.00 36.85 |
| ATOM | 3673 | O | ALA | B | 82 | 31.461 | 0.580 | 92.945 | 1.00 32.17 |
| ATOM | 3674 | N | ARG | B | 83 | 30.677 | 2.168 | 94.323 | 1.00 36.52 |
| ATOM | 3675 | CA | ARG | B | 83 | 31.994 | 2.522 | 94.830 | 1.00 38.75 |
| ATOM | 3676 | CB | ARG | B | 83 | 31.865 | 3.616 | 95.885 | 1.00 40.24 |
| ATOM | 3677 | CG | ARG | B | 83 | 33.187 | 4.180 | 96.330 | 1.00 49.12 |
| ATOM | 3678 | CD | ARG | B | 83 | 33.015 | 5.239 | 97.404 | 1.00 53.26 |
| ATOM | 3679 | NE | ARG | B | 83 | 34.240 | 6.010 | 97.624 | 1.00 59.30 |
| ATOM | 3680 | CZ | ARG | B | 83 | 35.437 | 5.486 | 97.883 | 1.00 61.56 |
| ATOM | 3681 | NH1 | ARG | B | 83 | 35.598 | 4.170 | 97.958 | 1.00 63.53 |
| ATOM | 3682 | NH2 | ARG | B | 83 | 36.479 | 6.285 | 98.073 | 1.00 62.02 |
| ATOM | 3683 | C | ARG | B | 83 | 32.719 | 1.326 | 95.426 | 1.00 37.75 |
| ATOM | 3684 | O | ARG | B | 83 | 33.893 | 1.094 | 95.146 | 1.00 37.18 |
| ATOM | 3685 | N | GLU | B | 84 | 32.011 | 0.564 | 96.249 | 1.00 35.29 |
| ATOM | 3686 | CA | GLU | B | 84 | 32.581 | -0.609 | 96.898 | 1.00 35.29 |
| ATOM | 3687 | CB | GLU | B | 84 | 31.876 | -0.855 | 98.236 | 1.00 40.14 |
| ATOM | 3688 | CG | GLU | B | 84 | 30.443 | -0.383 | 98.240 | 1.00 46.30 |
| ATOM | 3689 | CD | GLU | B | 84 | 30.356 | 1.132 | 98.293 | 1.00 48.30 |
| ATOM | 3690 | OE1 | GLU | B | 84 | 29.339 | 1.690 | 97.834 | 1.00 43.07 |
| ATOM | 3691 | OE2 | GLU | B | 84 | 31.306 | 1.762 | 98.814 | 1.00 50.07 |
| ATOM | 3692 | C | GLU | B | 84 | 32.527 | -1.880 | 96.055 | 1.00 32.90 |
| ATOM | 3693 | O | GLU | B | 84 | 33.371 | -2.765 | 96.193 | 1.00 28.68 |
| ATOM | 3694 | N | LYS | B | 85 | 31.533 | -1.984 | 95.187 | 1.00 27.12 |
| ATOM | 3695 | CA | LYS | B | 85 | 31.412 | -3.177 | 94.361 | 1.00 30.46 |
| ATOM | 3696 | CB | LYS | B | 85 | 29.950 | -3.401 | 93.967 | 1.00 30.01 |
| ATOM | 3697 | CG | LYS | B | 85 | 29.717 | -4.643 | 93.117 | 1.00 28.40 |
| ATOM | 3698 | CD | LYS | B | 85 | 28.234 | -4.807 | 92.775 | 1.00 32.87 |
| ATOM | 3699 | CE | LYS | B | 85 | 28.000 | -6.048 | 91.928 | 1.00 34.15 |
| ATOM | 3700 | NZ | LYS | B | 85 | 26.582 | -6.186 | 91.507 | 1.00 35.34 |
| ATOM | 3701 | C | LYS | B | 85 | 32.267 | -3.096 | 93.101 | 1.00 28.98 |
| ATOM | 3702 | O | LYS | B | 85 | 32.817 | -4.098 | 92.652 | 1.00 24.69 |
| ATOM | 3703 | N | TYR | B | 86 | 32.391 | -1.896 | 92.550 | 1.00 27.81 |
| ATOM | 3704 | CA | TYR | B | 86 | 33.141 | -1.692 | 91.319 | 1.00 27.56 |
| ATOM | 3705 | CB | TYR | B | 86 | 32.206 | -1.050 | 90.288 | 1.00 28.88 |
| ATOM | 3706 | CG | TYR | B | 86 | 31.008 | -1.927 | 89.951 | 1.00 31.29 |
| ATOM | 3707 | CD1 | TYR | B | 86 | 31.178 | -3.137 | 89.276 | 1.00 26.99 |
| ATOM | 3708 | CE1 | TYR | B | 86 | 30.095 | -3.955 | 88.965 | 1.00 26.97 |
| ATOM | 3709 | CD2 | TYR | B | 86 | 29.713 | -1.553 | 90.315 | 1.00 28.38 |
| ATOM | 3710 | CE2 | TYR | B | 86 | 28.611 | -2.370 | 90.008 | 1.00 24.19 |
| ATOM | 3711 | CZ | TYR | B | 86 | 28.815 | -3.569 | 89.331 | 1.00 28.46 |
| ATOM | 3712 | OH | TYR | B | 86 | 27.747 | -4.379 | 89.008 | 1.00 22.70 |
| ATOM | 3713 | C | TYR | B | 86 | 34.422 | -0.870 | 91.489 | 1.00 24.64 |
| ATOM | 3714 | O | TYR | B | 86 | 35.160 | -0.645 | 90.530 | 1.00 27.19 |
| ATOM | 3715 | N | ASN | B | 87 | 34.674 | -0.418 | 92.711 | 1.00 25.54 |
| ATOM | 3716 | CA | ASN | B | 87 | 35.881 | 0.341 | 93.032 | 1.00 29.30 |
| ATOM | 3717 | CB | ASN | B | 87 | 37.105 | -0.561 | 92.866 | 1.00 28.92 |
| ATOM | 3718 | CG | ASN | B | 87 | 38.343 | 0.019 | 93.506 | 1.00 34.72 |
| ATOM | 3719 | OD1 | ASN | B | 87 | 38.309 | 0.452 | 94.659 | 1.00 38.41 |

Fig. 18-56

| | | | | | | | | | |
|---|---|---|---|---|---|---|---|---|---|
| ATOM | 3720 | ND2 | ASN | B | 87 | 39.449 | 0.012 | 92.775 | 1.00 35.86 |
| ATOM | 3721 | C | ASN | B | 87 | 36.070 | 1.622 | 92.223 | 1.00 29.72 |
| ATOM | 3722 | O | ASN | B | 87 | 37.194 | 1.998 | 91.876 | 1.00 24.01 |
| ATOM | 3723 | N | ILE | B | 88 | 34.956 | 2.282 | 91.932 | 1.00 29.43 |
| ATOM | 3724 | CA | ILE | B | 88 | 34.945 | 3.536 | 91.196 | 1.00 30.64 |
| ATOM | 3725 | CB | ILE | B | 88 | 33.959 | 3.464 | 90.027 | 1.00 37.12 |
| ATOM | 3726 | CG2 | ILE | B | 88 | 33.821 | 4.829 | 89.379 | 1.00 40.62 |
| ATOM | 3727 | CG1 | ILE | B | 88 | 34.421 | 2.433 | 89.008 | 1.00 35.43 |
| ATOM | 3728 | CD1 | ILE | B | 88 | 35.684 | 2.821 | 88.324 | 1.00 41.80 |
| ATOM | 3729 | C | ILE | B | 88 | 34.483 | 4.669 | 92.118 | 1.00 31.90 |
| ATOM | 3730 | O | ILE | B | 88 | 33.681 | 4.445 | 93.024 | 1.00 28.86 |
| ATOM | 3731 | N | GLY | B | 89 | 34.977 | 5.881 | 91.875 | 1.00 30.36 |
| ATOM | 3732 | CA | GLY | B | 89 | 34.574 | 7.022 | 92.686 | 1.00 29.54 |
| ATOM | 3733 | C | GLY | B | 89 | 35.601 | 7.524 | 93.685 | 1.00 31.49 |
| ATOM | 3734 | O | GLY | B | 89 | 35.497 | 8.652 | 94.177 | 1.00 37.26 |
| ATOM | 3735 | N | GLY | B | 90 | 36.583 | 6.687 | 94.005 | 1.00 30.97 |
| ATOM | 3736 | CA | GLY | B | 90 | 37.612 | 7.086 | 94.949 | 1.00 31.03 |
| ATOM | 3737 | C | GLY | B | 90 | 38.655 | 7.936 | 94.247 | 1.00 34.78 |
| ATOM | 3738 | O | GLY | B | 90 | 38.455 | 8.344 | 93.103 | 1.00 32.73 |
| ATOM | 3739 | N | TYR | B | 91 | 39.772 | 8.201 | 94.915 | 1.00 29.39 |
| ATOM | 3740 | CA | TYR | B | 91 | 40.820 | 9.023 | 94.322 | 1.00 28.15 |
| ATOM | 3741 | CB | TYR | B | 91 | 41.810 | 9.463 | 95.405 | 1.00 27.29 |
| ATOM | 3742 | CG | TYR | B | 91 | 42.609 | 8.330 | 96.007 | 1.00 26.60 |
| ATOM | 3743 | CD1 | TYR | B | 91 | 43.738 | 7.823 | 95.359 | 1.00 28.55 |
| ATOM | 3744 | CE1 | TYR | B | 91 | 44.456 | 6.762 | 95.896 | 1.00 28.75 |
| ATOM | 3745 | CD2 | TYR | B | 91 | 42.219 | 7.741 | 97.208 | 1.00 28.35 |
| ATOM | 3746 | CE2 | TYR | B | 91 | 42.927 | 6.680 | 97.751 | 1.00 27.58 |
| ATOM | 3747 | CZ | TYR | B | 91 | 44.043 | 6.196 | 97.094 | 1.00 30.12 |
| ATOM | 3748 | OH | TYR | B | 91 | 44.753 | 5.154 | 97.637 | 1.00 36.59 |
| ATOM | 3749 | C | TYR | B | 91 | 41.563 | 8.271 | 93.226 | 1.00 29.27 |
| ATOM | 3750 | O | TYR | B | 91 | 42.109 | 8.874 | 92.308 | 1.00 25.22 |
| ATOM | 3751 | N | GLU | B | 92 | 41.568 | 6.948 | 93.318 | 1.00 28.32 |
| ATOM | 3752 | CA | GLU | B | 92 | 42.286 | 6.124 | 92.350 | 1.00 27.06 |
| ATOM | 3753 | CB | GLU | B | 92 | 42.474 | 4.726 | 92.924 | 1.00 23.35 |
| ATOM | 3754 | CG | GLU | B | 92 | 43.502 | 3.884 | 92.221 | 1.00 29.80 |
| ATOM | 3755 | CD | GLU | B | 92 | 43.585 | 2.500 | 92.826 | 1.00 35.34 |
| ATOM | 3756 | OE1 | GLU | B | 92 | 42.742 | 1.645 | 92.477 | 1.00 32.15 |
| ATOM | 3757 | OE2 | GLU | B | 92 | 44.475 | 2.278 | 93.678 | 1.00 31.61 |
| ATOM | 3758 | C | GLU | B | 92 | 41.594 | 6.024 | 90.997 | 1.00 23.42 |
| ATOM | 3759 | O | GLU | B | 92 | 42.204 | 6.260 | 89.962 | 1.00 20.47 |
| ATOM | 3760 | N | ASN | B | 93 | 40.314 | 5.677 | 91.017 | 1.00 18.85 |
| ATOM | 3761 | CA | ASN | B | 93 | 39.534 | 5.509 | 89.795 | 1.00 21.96 |
| ATOM | 3762 | CB | ASN | B | 93 | 39.165 | 4.033 | 89.664 | 1.00 23.90 |
| ATOM | 3763 | CG | ASN | B | 93 | 40.351 | 3.120 | 89.943 | 1.00 24.78 |
| ATOM | 3764 | OD1 | ASN | B | 93 | 41.362 | 3.160 | 89.239 | 1.00 22.35 |
| ATOM | 3765 | ND2 | ASN | B | 93 | 40.240 | 2.311 | 90.987 | 1.00 13.35 |
| ATOM | 3766 | C | ASN | B | 93 | 38.285 | 6.362 | 89.944 | 1.00 25.16 |
| ATOM | 3767 | O | ASN | B | 93 | 37.183 | 5.843 | 90.121 | 1.00 20.91 |
| ATOM | 3768 | N | PRO | B | 94 | 38.449 | 7.693 | 89.887 | 1.00 26.37 |
| ATOM | 3769 | CD | PRO | B | 94 | 39.738 | 8.389 | 89.716 | 1.00 19.35 |
| ATOM | 3770 | CA | PRO | B | 94 | 37.373 | 8.676 | 90.024 | 1.00 24.59 |
| ATOM | 3771 | CB | PRO | B | 94 | 38.147 | 9.972 | 90.200 | 1.00 25.95 |
| ATOM | 3772 | CG | PRO | B | 94 | 39.297 | 9.740 | 89.223 | 1.00 22.60 |
| ATOM | 3773 | C | PRO | B | 94 | 36.384 | 8.777 | 88.873 | 1.00 28.74 |
| ATOM | 3774 | O | PRO | B | 94 | 36.562 | 8.176 | 87.808 | 1.00 25.77 |
| ATOM | 3775 | N | VAL | B | 95 | 35.332 | 9.553 | 89.112 | 1.00 27.14 |
| ATOM | 3776 | CA | VAL | B | 95 | 34.317 | 9.812 | 88.103 | 1.00 25.94 |
| ATOM | 3777 | CB | VAL | B | 95 | 33.035 | 10.393 | 88.742 | 1.00 23.75 |
| ATOM | 3778 | CG1 | VAL | B | 95 | 32.067 | 10.855 | 87.662 | 1.00 26.34 |
| ATOM | 3779 | CG2 | VAL | B | 95 | 32.378 | 9.346 | 89.622 | 1.00 27.59 |
| ATOM | 3780 | C | VAL | B | 95 | 34.912 | 10.861 | 87.175 | 1.00 25.69 |
| ATOM | 3781 | O | VAL | B | 95 | 35.564 | 11.793 | 87.641 | 1.00 25.25 |
| ATOM | 3782 | N | SER | B | 96 | 34.708 | 10.699 | 85.871 | 1.00 28.02 |
| ATOM | 3783 | CA | SER | B | 96 | 35.199 | 11.647 | 84.868 | 1.00 24.82 |
| ATOM | 3784 | CB | SER | B | 96 | 36.729 | 11.705 | 84.850 | 1.00 25.90 |
| ATOM | 3785 | OG | SER | B | 96 | 37.274 | 10.548 | 84.229 | 1.00 23.99 |

Fig. 18-57

| | | | | | | | | | |
|---|---|---|---|---|---|---|---|---|---|
| ATOM | 3786 | C | SER | B | 96 | 34.726 | 11.127 | 83.519 | 1.00 26.22 |
| ATOM | 3787 | O | SER | B | 96 | 33.943 | 10.174 | 83.462 | 1.00 23.57 |
| ATOM | 3788 | N | TYR | B | 97 | 35.195 | 11.744 | 82.438 | 1.00 22.83 |
| ATOM | 3789 | CA | TYR | B | 97 | 34.818 | 11.279 | 81.110 | 1.00 28.59 |
| ATOM | 3790 | CB | TYR | B | 97 | 34.536 | 12.452 | 80.165 | 1.00 31.45 |
| ATOM | 3791 | CG | TYR | B | 97 | 33.279 | 13.203 | 80.548 | 1.00 35.09 |
| ATOM | 3792 | CD1 | TYR | B | 97 | 33.316 | 14.239 | 81.480 | 1.00 32.87 |
| ATOM | 3793 | CE1 | TYR | B | 97 | 32.148 | 14.863 | 81.911 | 1.00 37.73 |
| ATOM | 3794 | CD2 | TYR | B | 97 | 32.036 | 12.812 | 80.049 | 1.00 34.85 |
| ATOM | 3795 | CE2 | TYR | B | 97 | 30.858 | 13.430 | 80.475 | 1.00 38.61 |
| ATOM | 3796 | CZ | TYR | B | 97 | 30.924 | 14.453 | 81.408 | 1.00 39.45 |
| ATOM | 3797 | OH | TYR | B | 97 | 29.768 | 15.047 | 81.852 | 1.00 35.36 |
| ATOM | 3798 | C | TYR | B | 97 | 35.883 | 10.354 | 80.534 | 1.00 28.93 |
| ATOM | 3799 | O | TYR | B | 97 | 35.859 | 9.992 | 79.358 | 1.00 28.26 |
| ATOM | 3800 | N | ALA | B | 98 | 36.822 | 9.968 | 81.385 | 1.00 29.09 |
| ATOM | 3801 | CA | ALA | B | 98 | 37.866 | 9.044 | 80.980 | 1.00 26.88 |
| ATOM | 3802 | CB | ALA | B | 98 | 39.167 | 9.369 | 81.692 | 1.00 27.99 |
| ATOM | 3803 | C | ALA | B | 98 | 37.395 | 7.657 | 81.382 | 1.00 22.53 |
| ATOM | 3804 | O | ALA | B | 98 | 37.721 | 6.675 | 80.722 | 1.00 21.98 |
| ATOM | 3805 | N | MET | B | 99 | 36.603 | 7.595 | 82.453 | 1.00 23.51 |
| ATOM | 3806 | CA | MET | B | 99 | 36.106 | 6.326 | 82.986 | 1.00 26.36 |
| ATOM | 3807 | CB | MET | B | 99 | 35.179 | 6.568 | 84.185 | 1.00 24.05 |
| ATOM | 3808 | CG | MET | B | 99 | 33.822 | 7.188 | 83.875 | 1.00 28.37 |
| ATOM | 3809 | SD | MET | B | 99 | 32.966 | 7.704 | 85.406 | 1.00 27.91 |
| ATOM | 3810 | CE | MET | B | 99 | 33.106 | 6.227 | 86.409 | 1.00 22.12 |
| ATOM | 3811 | C | MET | B | 99 | 35.430 | 5.435 | 81.953 | 1.00 25.76 |
| ATOM | 3812 | O | MET | B | 99 | 35.544 | 4.212 | 82.031 | 1.00 26.11 |
| ATOM | 3813 | N | PHE | B | 100 | 34.724 | 6.027 | 80.992 | 1.00 22.17 |
| ATOM | 3814 | CA | PHE | B | 100 | 34.107 | 5.222 | 79.940 | 1.00 22.35 |
| ATOM | 3815 | CB | PHE | B | 100 | 32.582 | 5.133 | 80.088 | 1.00 22.01 |
| ATOM | 3816 | CG | PHE | B | 100 | 31.947 | 4.254 | 79.038 | 1.00 24.22 |
| ATOM | 3817 | CD1 | PHE | B | 100 | 32.143 | 2.872 | 79.061 | 1.00 26.61 |
| ATOM | 3818 | CD2 | PHE | B | 100 | 31.280 | 4.813 | 77.953 | 1.00 21.22 |
| ATOM | 3819 | CE1 | PHE | B | 100 | 31.691 | 2.059 | 78.012 | 1.00 26.91 |
| ATOM | 3820 | CE2 | PHE | B | 100 | 30.825 | 4.010 | 76.894 | 1.00 24.80 |
| ATOM | 3821 | CZ | PHE | B | 100 | 31.033 | 2.632 | 76.924 | 1.00 24.85 |
| ATOM | 3822 | C | PHE | B | 100 | 34.425 | 5.695 | 78.514 | 1.00 24.86 |
| ATOM | 3823 | O | PHE | B | 100 | 34.922 | 4.920 | 77.694 | 1.00 21.40 |
| ATOM | 3824 | N | THR | B | 101 | 34.131 | 6.957 | 78.204 | 1.00 24.24 |
| ATOM | 3825 | CA | THR | B | 101 | 34.390 | 7.469 | 76.854 | 1.00 24.54 |
| ATOM | 3826 | CB | THR | B | 101 | 33.914 | 8.926 | 76.708 | 1.00 24.46 |
| ATOM | 3827 | OG1 | THR | B | 101 | 32.504 | 8.985 | 76.953 | 1.00 27.64 |
| ATOM | 3828 | CG2 | THR | B | 101 | 34.191 | 9.445 | 75.297 | 1.00 22.19 |
| ATOM | 3829 | C | THR | B | 101 | 35.872 | 7.387 | 76.483 | 1.00 25.26 |
| ATOM | 3830 | O | THR | B | 101 | 36.231 | 6.856 | 75.430 | 1.00 25.47 |
| ATOM | 3831 | N | GLY | B | 102 | 36.725 | 7.916 | 77.350 | 1.00 23.74 |
| ATOM | 3832 | CA | GLY | B | 102 | 38.153 | 7.867 | 77.096 | 1.00 24.53 |
| ATOM | 3833 | C | GLY | B | 102 | 38.657 | 6.434 | 77.046 | 1.00 24.06 |
| ATOM | 3834 | O | GLY | B | 102 | 39.346 | 6.045 | 76.100 | 1.00 22.53 |
| ATOM | 3835 | N | SER | B | 103 | 38.316 | 5.651 | 78.067 | 1.00 22.02 |
| ATOM | 3836 | CA | SER | B | 103 | 38.730 | 4.253 | 78.146 | 1.00 20.45 |
| ATOM | 3837 | CB | SER | B | 103 | 38.193 | 3.613 | 79.427 | 1.00 25.21 |
| ATOM | 3838 | OG | SER | B | 103 | 38.820 | 4.166 | 80.567 | 1.00 26.48 |
| ATOM | 3839 | C | SER | B | 103 | 38.268 | 3.446 | 76.938 | 1.00 20.53 |
| ATOM | 3840 | O | SER | B | 103 | 39.034 | 2.669 | 76.372 | 1.00 16.82 |
| ATOM | 3841 | N | SER | B | 104 | 37.014 | 3.642 | 76.542 | 1.00 17.11 |
| ATOM | 3842 | CA | SER | B | 104 | 36.462 | 2.937 | 75.395 | 1.00 23.32 |
| ATOM | 3843 | CB | SER | B | 104 | 34.980 | 3.289 | 75.228 | 1.00 22.93 |
| ATOM | 3844 | OG | SER | B | 104 | 34.424 | 2.557 | 74.161 | 1.00 24.75 |
| ATOM | 3845 | C | SER | B | 104 | 37.221 | 3.288 | 74.116 | 1.00 21.97 |
| ATOM | 3846 | O | SER | B | 104 | 37.451 | 2.434 | 73.256 | 1.00 22.83 |
| ATOM | 3847 | N | LEU | B | 105 | 37.619 | 4.549 | 73.997 | 1.00 23.00 |
| ATOM | 3848 | CA | LEU | B | 105 | 38.354 | 5.007 | 72.825 | 1.00 25.12 |
| ATOM | 3849 | CB | LEU | B | 105 | 38.443 | 6.536 | 72.859 | 1.00 29.25 |
| ATOM | 3850 | CG | LEU | B | 105 | 38.702 | 7.289 | 71.553 | 1.00 34.27 |
| ATOM | 3851 | CD1 | LEU | B | 105 | 37.662 | 6.888 | 70.512 | 1.00 31.51 |

Fig. 18-58

| | | | | | | | | | |
|---|---|---|---|---|---|---|---|---|---|
| ATOM | 3852 | CD2 | LEU | B | 105 | 38.629 | 8.802 | 71.819 | 1.00 34.30 |
| ATOM | 3853 | C | LEU | B | 105 | 39.755 | 4.374 | 72.813 | 1.00 27.39 |
| ATOM | 3854 | O | LEU | B | 105 | 40.262 | 3.955 | 71.765 | 1.00 20.15 |
| ATOM | 3855 | N | ALA | B | 106 | 40.371 | 4.293 | 73.988 | 1.00 23.62 |
| ATOM | 3856 | CA | ALA | B | 106 | 41.704 | 3.692 | 74.115 | 1.00 22.73 |
| ATOM | 3857 | CB | ALA | B | 106 | 42.263 | 3.939 | 75.529 | 1.00 17.46 |
| ATOM | 3858 | C | ALA | B | 106 | 41.639 | 2.189 | 73.846 | 1.00 22.77 |
| ATOM | 3859 | O | ALA | B | 106 | 42.583 | 1.597 | 73.316 | 1.00 24.98 |
| ATOM | 3860 | N | THR | B | 107 | 40.523 | 1.567 | 74.224 | 1.00 23.54 |
| ATOM | 3861 | CA | THR | B | 107 | 40.355 | 0.132 | 74.033 | 1.00 19.76 |
| ATOM | 3862 | CB | THR | B | 107 | 39.236 | -0.410 | 74.947 | 1.00 22.85 |
| ATOM | 3863 | OG1 | THR | B | 107 | 39.572 | -0.128 | 76.306 | 1.00 16.29 |
| ATOM | 3864 | CG2 | THR | B | 107 | 39.085 | -1.917 | 74.787 | 1.00 17.21 |
| ATOM | 3865 | C | THR | B | 107 | 40.036 | -0.169 | 72.571 | 1.00 23.47 |
| ATOM | 3866 | O | THR | B | 107 | 40.540 | -1.138 | 72.001 | 1.00 19.25 |
| ATOM | 3867 | N | GLY | B | 108 | 39.191 | 0.656 | 71.959 | 1.00 24.87 |
| ATOM | 3868 | CA | GLY | B | 108 | 38.879 | 0.434 | 70.560 | 1.00 21.32 |
| ATOM | 3869 | C | GLY | B | 108 | 40.161 | 0.594 | 69.757 | 1.00 22.01 |
| ATOM | 3870 | O | GLY | B | 108 | 40.388 | -0.099 | 68.761 | 1.00 20.46 |
| ATOM | 3871 | N | SER | B | 109 | 41.018 | 1.508 | 70.197 | 1.00 19.89 |
| ATOM | 3872 | CA | SER | B | 109 | 42.274 | 1.749 | 69.499 | 1.00 19.37 |
| ATOM | 3873 | CB | SER | B | 109 | 42.993 | 2.956 | 70.107 | 1.00 18.28 |
| ATOM | 3874 | OG | SER | B | 109 | 42.250 | 4.145 | 69.882 | 1.00 21.29 |
| ATOM | 3875 | C | SER | B | 109 | 43.168 | 0.513 | 69.542 | 1.00 20.70 |
| ATOM | 3876 | O | SER | B | 109 | 43.940 | 0.261 | 68.617 | 1.00 20.69 |
| ATOM | 3877 | N | THR | B | 110 | 43.065 | -0.259 | 70.616 | 1.00 20.54 |
| ATOM | 3878 | CA | THR | B | 110 | 43.858 | -1.475 | 70.729 | 1.00 19.98 |
| ATOM | 3879 | CB | THR | B | 110 | 43.826 | -2.043 | 72.158 | 1.00 20.63 |
| ATOM | 3880 | OG1 | THR | B | 110 | 44.632 | -1.215 | 73.007 | 1.00 20.72 |
| ATOM | 3881 | CG2 | THR | B | 110 | 44.371 | -3.470 | 72.188 | 1.00 20.05 |
| ATOM | 3882 | C | THR | B | 110 | 43.333 | -2.507 | 69.738 | 1.00 21.61 |
| ATOM | 3883 | O | THR | B | 110 | 44.115 | -3.239 | 69.127 | 1.00 18.11 |
| ATOM | 3884 | N | VAL | B | 111 | 42.012 | -2.557 | 69.567 | 1.00 18.29 |
| ATOM | 3885 | CA | VAL | B | 111 | 41.432 | -3.486 | 68.608 | 1.00 20.36 |
| ATOM | 3886 | CB | VAL | B | 111 | 39.886 | -3.494 | 68.677 | 1.00 23.94 |
| ATOM | 3887 | CG1 | VAL | B | 111 | 39.324 | -4.442 | 67.619 | 1.00 24.37 |
| ATOM | 3888 | CG2 | VAL | B | 111 | 39.426 | -3.937 | 70.063 | 1.00 21.60 |
| ATOM | 3889 | C | VAL | B | 111 | 41.872 | -3.080 | 67.197 | 1.00 20.35 |
| ATOM | 3890 | O | VAL | B | 111 | 42.146 | -3.936 | 66.362 | 1.00 23.29 |
| ATOM | 3891 | N | GLN | B | 112 | 41.953 | -1.775 | 66.937 | 1.00 22.07 |
| ATOM | 3892 | CA | GLN | B | 112 | 42.367 | -1.290 | 65.617 | 1.00 22.34 |
| ATOM | 3893 | CB | GLN | B | 112 | 42.199 | 0.230 | 65.513 | 1.00 24.54 |
| ATOM | 3894 | CG | GLN | B | 112 | 40.810 | 0.729 | 65.843 | 1.00 20.63 |
| ATOM | 3895 | CD | GLN | B | 112 | 40.700 | 2.236 | 65.742 | 1.00 21.19 |
| ATOM | 3896 | OE1 | GLN | B | 112 | 40.664 | 2.794 | 64.645 | 1.00 26.73 |
| ATOM | 3897 | NE2 | GLN | B | 112 | 40.667 | 2.905 | 66.886 | 1.00 18.23 |
| ATOM | 3898 | C | GLN | B | 112 | 43.826 | -1.635 | 65.363 | 1.00 23.01 |
| ATOM | 3899 | O | GLN | B | 112 | 44.195 | -2.020 | 64.257 | 1.00 15.79 |
| ATOM | 3900 | N | ALA | B | 113 | 44.660 | -1.476 | 66.389 | 1.00 20.60 |
| ATOM | 3901 | CA | ALA | B | 113 | 46.070 | -1.790 | 66.249 | 1.00 18.02 |
| ATOM | 3902 | CB | ALA | B | 113 | 46.794 | -1.536 | 67.548 | 1.00 20.84 |
| ATOM | 3903 | C | ALA | B | 113 | 46.170 | -3.262 | 65.863 | 1.00 23.78 |
| ATOM | 3904 | O | ALA | B | 113 | 46.982 | -3.642 | 65.023 | 1.00 19.33 |
| ATOM | 3905 | N | ILE | B | 114 | 45.331 | -4.091 | 66.477 | 1.00 21.45 |
| ATOM | 3906 | CA | ILE | B | 114 | 45.344 | -5.511 | 66.168 | 1.00 24.26 |
| ATOM | 3907 | CB | ILE | B | 114 | 44.507 | -6.306 | 67.191 | 1.00 20.72 |
| ATOM | 3908 | CG2 | ILE | B | 114 | 44.476 | -7.779 | 66.800 | 1.00 21.92 |
| ATOM | 3909 | CG1 | ILE | B | 114 | 45.116 | -6.144 | 68.593 | 1.00 24.32 |
| ATOM | 3910 | CD1 | ILE | B | 114 | 44.364 | -6.872 | 69.694 | 1.00 19.01 |
| ATOM | 3911 | C | ILE | B | 114 | 44.808 | -5.765 | 64.753 | 1.00 26.75 |
| ATOM | 3912 | O | ILE | B | 114 | 45.305 | -6.640 | 64.032 | 1.00 20.18 |
| ATOM | 3913 | N | GLU | B | 115 | 43.792 | -5.009 | 64.347 | 1.00 24.69 |
| ATOM | 3914 | CA | GLU | B | 115 | 43.243 | -5.198 | 63.005 | 1.00 29.26 |
| ATOM | 3915 | CB | GLU | B | 115 | 42.043 | -4.278 | 62.770 | 1.00 29.07 |
| ATOM | 3916 | CG | GLU | B | 115 | 40.940 | -4.421 | 63.800 | 1.00 32.31 |
| ATOM | 3917 | CD | GLU | B | 115 | 39.757 | -3.519 | 63.516 | 1.00 38.14 |

Fig. 18-59

| ATOM | 3918 | OE1 | GLU | B | 115 | 39.980 | -2.374 | 63.072 | 1.00 | 40.63 |
| --- | --- | --- | --- | --- | --- | --- | --- | --- | --- | --- |
| ATOM | 3919 | OE2 | GLU | B | 115 | 38.607 | -3.940 | 63.758 | 1.00 | 39.86 |
| ATOM | 3920 | C | GLU | B | 115 | 44.334 | -4.906 | 61.974 | 1.00 | 31.52 |
| ATOM | 3921 | O | GLU | B | 115 | 44.444 | -5.603 | 60.964 | 1.00 | 26.43 |
| ATOM | 3922 | N | GLU | B | 116 | 45.141 | -3.879 | 62.234 | 1.00 | 26.04 |
| ATOM | 3923 | CA | GLU | B | 116 | 46.226 | -3.522 | 61.324 | 1.00 | 26.21 |
| ATOM | 3924 | CB | GLU | B | 116 | 46.909 | -2.227 | 61.775 | 1.00 | 23.21 |
| ATOM | 3925 | CG | GLU | B | 116 | 46.055 | -0.983 | 61.601 | 1.00 | 23.82 |
| ATOM | 3926 | CD | GLU | B | 116 | 45.576 | -0.817 | 60.163 | 1.00 | 31.43 |
| ATOM | 3927 | OE1 | GLU | B | 116 | 46.425 | -0.734 | 59.253 | 1.00 | 26.45 |
| ATOM | 3928 | OE2 | GLU | B | 116 | 44.349 | -0.771 | 59.945 | 1.00 | 24.59 |
| ATOM | 3929 | C | GLU | B | 116 | 47.256 | -4.644 | 61.243 | 1.00 | 28.60 |
| ATOM | 3930 | O | GLU | B | 116 | 47.857 | -4.884 | 60.189 | 1.00 | 25.01 |
| ATOM | 3931 | N | PHE | B | 117 | 47.470 | -5.324 | 62.363 | 1.00 | 26.22 |
| ATOM | 3932 | CA | PHE | B | 117 | 48.421 | -6.425 | 62.400 | 1.00 | 28.05 |
| ATOM | 3933 | CB | PHE | B | 117 | 48.516 | -7.007 | 63.805 | 1.00 | 32.15 |
| ATOM | 3934 | CG | PHE | B | 117 | 49.278 | -8.299 | 63.869 | 1.00 | 33.88 |
| ATOM | 3935 | CD1 | PHE | B | 117 | 50.656 | -8.321 | 63.713 | 1.00 | 33.52 |
| ATOM | 3936 | CD2 | PHE | B | 117 | 48.604 | -9.502 | 64.054 | 1.00 | 32.83 |
| ATOM | 3937 | CE1 | PHE | B | 117 | 51.356 | -9.521 | 63.740 | 1.00 | 31.67 |
| ATOM | 3938 | CE2 | PHE | B | 117 | 49.294 | -10.710 | 64.082 | 1.00 | 35.69 |
| ATOM | 3939 | CZ | PHE | B | 117 | 50.674 | -10.717 | 63.926 | 1.00 | 36.72 |
| ATOM | 3940 | C | PHE | B | 117 | 47.929 | -7.508 | 61.456 | 1.00 | 26.43 |
| ATOM | 3941 | O | PHE | B | 117 | 48.689 | -8.061 | 60.669 | 1.00 | 27.61 |
| ATOM | 3942 | N | LEU | B | 118 | 46.642 | -7.809 | 61.551 | 1.00 | 23.59 |
| ATOM | 3943 | CA | LEU | B | 118 | 46.048 | -8.820 | 60.705 | 1.00 | 29.15 |
| ATOM | 3944 | CB | LEU | B | 118 | 44.585 | -9.039 | 61.099 | 1.00 | 28.78 |
| ATOM | 3945 | CG | LEU | B | 118 | 44.375 | -9.478 | 62.557 | 1.00 | 35.24 |
| ATOM | 3946 | CD1 | LEU | B | 118 | 42.898 | -9.763 | 62.788 | 1.00 | 31.92 |
| ATOM | 3947 | CD2 | LEU | B | 118 | 45.205 | -10.723 | 62.856 | 1.00 | 33.40 |
| ATOM | 3948 | C | LEU | B | 118 | 46.153 | -8.422 | 59.236 | 1.00 | 30.15 |
| ATOM | 3949 | O | LEU | B | 118 | 46.350 | -9.276 | 58.379 | 1.00 | 27.04 |
| ATOM | 3950 | N | LYS | B | 119 | 46.035 | -7.128 | 58.947 | 1.00 | 27.96 |
| ATOM | 3951 | CA | LYS | B | 119 | 46.127 | -6.663 | 57.569 | 1.00 | 26.69 |
| ATOM | 3952 | CB | LYS | B | 119 | 45.470 | -5.291 | 57.412 | 1.00 | 23.94 |
| ATOM | 3953 | CG | LYS | B | 119 | 43.998 | -5.260 | 57.795 | 1.00 | 24.41 |
| ATOM | 3954 | CD | LYS | B | 119 | 43.327 | -3.970 | 57.350 | 1.00 | 27.53 |
| ATOM | 3955 | CE | LYS | B | 119 | 44.024 | -2.739 | 57.886 | 1.00 | 33.13 |
| ATOM | 3956 | NZ | LYS | B | 119 | 43.371 | -1.479 | 57.428 | 1.00 | 27.75 |
| ATOM | 3957 | C | LYS | B | 119 | 47.577 | -6.598 | 57.101 | 1.00 | 29.12 |
| ATOM | 3958 | O | LYS | B | 119 | 47.864 | -6.160 | 55.984 | 1.00 | 35.25 |
| ATOM | 3959 | N | GLY | B | 120 | 48.493 | -7.034 | 57.958 | 1.00 | 30.25 |
| ATOM | 3960 | CA | GLY | B | 120 | 49.896 | -7.037 | 57.585 | 1.00 | 28.38 |
| ATOM | 3961 | C | GLY | B | 120 | 50.642 | -5.751 | 57.861 | 1.00 | 27.91 |
| ATOM | 3962 | O | GLY | B | 120 | 51.775 | -5.582 | 57.403 | 1.00 | 22.25 |
| ATOM | 3963 | N | ASN | B | 121 | 50.024 | -4.836 | 58.600 | 1.00 | 25.42 |
| ATOM | 3964 | CA | ASN | B | 121 | 50.695 | -3.587 | 58.919 | 1.00 | 29.49 |
| ATOM | 3965 | CB | ASN | B | 121 | 49.758 | -2.389 | 58.727 | 1.00 | 30.07 |
| ATOM | 3966 | CG | ASN | B | 121 | 49.201 | -2.307 | 57.325 | 1.00 | 32.25 |
| ATOM | 3967 | OD1 | ASN | B | 121 | 49.924 | -2.491 | 56.350 | 1.00 | 35.44 |
| ATOM | 3968 | ND2 | ASN | B | 121 | 47.917 | -2.006 | 57.217 | 1.00 | 32.26 |
| ATOM | 3969 | C | ASN | B | 121 | 51.172 | -3.637 | 60.361 | 1.00 | 30.92 |
| ATOM | 3970 | O | ASN | B | 121 | 50.971 | -4.631 | 61.059 | 1.00 | 27.08 |
| ATOM | 3971 | N | VAL | B | 122 | 51.810 | -2.560 | 60.796 | 1.00 | 28.46 |
| ATOM | 3972 | CA | VAL | B | 122 | 52.309 | -2.457 | 62.155 | 1.00 | 29.48 |
| ATOM | 3973 | CB | VAL | B | 122 | 53.840 | -2.352 | 62.177 | 1.00 | 33.40 |
| ATOM | 3974 | CG1 | VAL | B | 122 | 54.334 | -2.294 | 63.611 | 1.00 | 32.22 |
| ATOM | 3975 | CG2 | VAL | B | 122 | 54.446 | -3.544 | 61.458 | 1.00 | 33.57 |
| ATOM | 3976 | C | VAL | B | 122 | 51.713 | -1.196 | 62.748 | 1.00 | 29.04 |
| ATOM | 3977 | O | VAL | B | 122 | 51.800 | -0.118 | 62.153 | 1.00 | 27.47 |
| ATOM | 3978 | N | ALA | B | 123 | 51.100 | -1.326 | 63.918 | 1.00 | 26.71 |
| ATOM | 3979 | CA | ALA | B | 123 | 50.477 | -0.177 | 64.559 | 1.00 | 25.62 |
| ATOM | 3980 | CB | ALA | B | 123 | 48.963 | -0.281 | 64.447 | 1.00 | 21.65 |
| ATOM | 3981 | C | ALA | B | 123 | 50.872 | -0.005 | 66.017 | 1.00 | 28.62 |
| ATOM | 3982 | O | ALA | B | 123 | 51.227 | -0.965 | 66.712 | 1.00 | 26.96 |
| ATOM | 3983 | N | PHE | B | 124 | 50.805 | 1.239 | 66.472 | 1.00 | 22.85 |

Fig. 18-60

| | | | | | | | | | |
|---|---|---|---|---|---|---|---|---|---|
| ATOM | 3984 | CA | PHE | B | 124 | 51.122 | 1.577 | 67.847 | 1.00 17.31 |
| ATOM | 3985 | CB | PHE | B | 124 | 52.419 | 2.404 | 67.876 | 1.00 16.88 |
| ATOM | 3986 | CG | PHE | B | 124 | 52.762 | 3.000 | 69.225 | 1.00 18.52 |
| ATOM | 3987 | CD1 | PHE | B | 124 | 52.533 | 2.304 | 70.403 | 1.00 17.52 |
| ATOM | 3988 | CD2 | PHE | B | 124 | 53.382 | 4.245 | 69.297 | 1.00 17.88 |
| ATOM | 3989 | CE1 | PHE | B | 124 | 52.914 | 2.837 | 71.638 | 1.00 25.77 |
| ATOM | 3990 | CE2 | PHE | B | 124 | 53.769 | 4.790 | 70.517 | 1.00 21.97 |
| ATOM | 3991 | CZ | PHE | B | 124 | 53.535 | 4.084 | 71.698 | 1.00 20.16 |
| ATOM | 3992 | C | PHE | B | 124 | 49.937 | 2.348 | 68.421 | 1.00 18.77 |
| ATOM | 3993 | O | PHE | B | 124 | 49.462 | 3.311 | 67.820 | 1.00 16.62 |
| ATOM | 3994 | N | ASN | B | 125 | 49.418 | 1.868 | 69.546 | 1.00 16.69 |
| ATOM | 3995 | CA | ASN | B | 125 | 48.320 | 2.528 | 70.238 | 1.00 16.22 |
| ATOM | 3996 | CB | ASN | B | 125 | 47.129 | 1.603 | 70.435 | 1.00 12.71 |
| ATOM | 3997 | CG | ASN | B | 125 | 46.095 | 2.209 | 71.346 | 1.00 19.79 |
| ATOM | 3998 | OD1 | ASN | B | 125 | 45.930 | 3.430 | 71.372 | 1.00 20.83 |
| ATOM | 3999 | ND2 | ASN | B | 125 | 45.376 | 1.371 | 72.087 | 1.00 12.31 |
| ATOM | 4000 | C | ASN | B | 125 | 48.790 | 3.004 | 71.600 | 1.00 19.19 |
| ATOM | 4001 | O | ASN | B | 125 | 48.687 | 2.280 | 72.585 | 1.00 20.99 |
| ATOM | 4002 | N | PRO | B | 126 | 49.335 | 4.226 | 71.668 | 1.00 19.02 |
| ATOM | 4003 | CD | PRO | B | 126 | 49.595 | 5.156 | 70.555 | 1.00 21.39 |
| ATOM | 4004 | CA | PRO | B | 126 | 49.833 | 4.805 | 72.917 | 1.00 21.60 |
| ATOM | 4005 | CB | PRO | B | 126 | 50.398 | 6.161 | 72.459 | 1.00 21.07 |
| ATOM | 4006 | CG | PRO | B | 126 | 49.530 | 6.487 | 71.269 | 1.00 17.70 |
| ATOM | 4007 | C | PRO | B | 126 | 48.808 | 4.942 | 74.034 | 1.00 20.69 |
| ATOM | 4008 | O | PRO | B | 126 | 49.178 | 5.053 | 75.198 | 1.00 19.79 |
| ATOM | 4009 | N | ALA | B | 127 | 47.525 | 4.937 | 73.689 | 1.00 16.67 |
| ATOM | 4010 | CA | ALA | B | 127 | 46.476 | 5.065 | 74.698 | 1.00 20.44 |
| ATOM | 4011 | CB | ALA | B | 127 | 45.198 | 5.609 | 74.066 | 1.00 19.56 |
| ATOM | 4012 | C | ALA | B | 127 | 46.169 | 3.747 | 75.401 | 1.00 20.80 |
| ATOM | 4013 | O | ALA | B | 127 | 45.555 | 3.742 | 76.472 | 1.00 19.47 |
| ATOM | 4014 | N | GLY | B | 128 | 46.587 | 2.634 | 74.800 | 1.00 20.52 |
| ATOM | 4015 | CA | GLY | B | 128 | 46.325 | 1.333 | 75.399 | 1.00 19.43 |
| ATOM | 4016 | C | GLY | B | 128 | 47.327 | 0.910 | 76.463 | 1.00 20.56 |
| ATOM | 4017 | O | GLY | B | 128 | 48.182 | 1.697 | 76.869 | 1.00 18.37 |
| ATOM | 4018 | N | GLY | B | 129 | 47.215 | -0.333 | 76.929 | 1.00 19.68 |
| ATOM | 4019 | CA | GLY | B | 129 | 48.136 | -0.820 | 77.943 | 1.00 19.93 |
| ATOM | 4020 | C | GLY | B | 129 | 47.620 | -0.619 | 79.358 | 1.00 25.25 |
| ATOM | 4021 | O | GLY | B | 129 | 48.383 | -0.686 | 80.329 | 1.00 18.98 |
| ATOM | 4022 | N | MET | B | 130 | 46.317 | -0.374 | 79.474 | 1.00 16.04 |
| ATOM | 4023 | CA | MET | B | 130 | 45.677 | -0.161 | 80.768 | 1.00 19.26 |
| ATOM | 4024 | CB | MET | B | 130 | 44.301 | 0.451 | 80.519 | 1.00 17.94 |
| ATOM | 4025 | CG | MET | B | 130 | 44.413 | 1.728 | 79.653 | 1.00 22.95 |
| ATOM | 4026 | SD | MET | B | 130 | 42.873 | 2.615 | 79.307 | 1.00 31.83 |
| ATOM | 4027 | CE | MET | B | 130 | 41.957 | 1.358 | 78.382 | 1.00 20.22 |
| ATOM | 4028 | C | MET | B | 130 | 45.598 | -1.548 | 81.421 | 1.00 22.63 |
| ATOM | 4029 | O | MET | B | 130 | 44.546 | -2.173 | 81.486 | 1.00 16.24 |
| ATOM | 4030 | N | HIS | B | 131 | 46.737 | -1.999 | 81.932 | 1.00 18.42 |
| ATOM | 4031 | CA | HIS | B | 131 | 46.853 | -3.343 | 82.472 | 1.00 17.07 |
| ATOM | 4032 | CB | HIS | B | 131 | 48.323 | -3.804 | 82.341 | 1.00 17.61 |
| ATOM | 4033 | CG | HIS | B | 131 | 49.316 | -2.979 | 83.106 | 1.00 14.01 |
| ATOM | 4034 | CD2 | HIS | B | 131 | 49.138 | -1.904 | 83.915 | 1.00 13.47 |
| ATOM | 4035 | ND1 | HIS | B | 131 | 50.680 | -3.190 | 83.051 | 1.00 18.00 |
| ATOM | 4036 | CE1 | HIS | B | 131 | 51.297 | -2.281 | 83.789 | 1.00 15.27 |
| ATOM | 4037 | NE2 | HIS | B | 131 | 50.384 | -1.489 | 84.324 | 1.00 17.21 |
| ATOM | 4038 | C | HIS | B | 131 | 46.329 | -3.724 | 83.852 | 1.00 16.41 |
| ATOM | 4039 | O | HIS | B | 131 | 46.452 | -4.883 | 84.236 | 1.00 19.37 |
| ATOM | 4040 | N | HIS | B | 132 | 45.721 | -2.794 | 84.586 | 1.00 18.64 |
| ATOM | 4041 | CA | HIS | B | 132 | 45.241 | -3.112 | 85.936 | 1.00 20.87 |
| ATOM | 4042 | CB | HIS | B | 132 | 45.513 | -1.935 | 86.885 | 1.00 18.85 |
| ATOM | 4043 | CG | HIS | B | 132 | 46.966 | -1.686 | 87.152 | 1.00 20.00 |
| ATOM | 4044 | CD2 | HIS | B | 132 | 47.715 | -0.563 | 87.030 | 1.00 15.74 |
| ATOM | 4045 | ND1 | HIS | B | 132 | 47.810 | -2.655 | 87.659 | 1.00 14.72 |
| ATOM | 4046 | CE1 | HIS | B | 132 | 49.014 | -2.139 | 87.837 | 1.00 14.64 |
| ATOM | 4047 | NE2 | HIS | B | 132 | 48.984 | -0.872 | 87.462 | 1.00 14.88 |
| ATOM | 4048 | C | HIS | B | 132 | 43.778 | -3.547 | 86.136 | 1.00 22.83 |
| ATOM | 4049 | O | HIS | B | 132 | 43.478 | -4.298 | 87.076 | 1.00 17.84 |

Fig. 18-61

| | | | | | | | | | |
|---|---|---|---|---|---|---|---|---|---|
| ATOM | 4050 | N | ALA | B | 133 | 42.878 | -3.088 | 85.271 | 1.00 16.54 |
| ATOM | 4051 | CA | ALA | B | 133 | 41.457 | -3.396 | 85.424 | 1.00 19.13 |
| ATOM | 4052 | CB | ALA | B | 133 | 40.654 | -2.704 | 84.328 | 1.00 23.56 |
| ATOM | 4053 | C | ALA | B | 133 | 41.127 | -4.883 | 85.439 | 1.00 23.12 |
| ATOM | 4054 | O | ALA | B | 133 | 41.718 | -5.677 | 84.696 | 1.00 18.03 |
| ATOM | 4055 | N | PHE | B | 134 | 40.181 | -5.257 | 86.294 | 1.00 19.69 |
| ATOM | 4056 | CA | PHE | B | 134 | 39.762 | -6.649 | 86.365 | 1.00 19.35 |
| ATOM | 4057 | CB | PHE | B | 134 | 39.583 | -7.122 | 87.818 | 1.00 21.26 |
| ATOM | 4058 | CG | PHE | B | 134 | 40.837 | -7.053 | 88.646 | 1.00 23.41 |
| ATOM | 4059 | CD1 | PHE | B | 134 | 41.041 | -6.009 | 89.544 | 1.00 24.25 |
| ATOM | 4060 | CD2 | PHE | B | 134 | 41.820 | -8.027 | 88.522 | 1.00 22.80 |
| ATOM | 4061 | CE1 | PHE | B | 134 | 42.207 | -5.935 | 90.311 | 1.00 23.36 |
| ATOM | 4062 | CE2 | PHE | B | 134 | 42.997 | -7.964 | 89.283 | 1.00 27.74 |
| ATOM | 4063 | CZ | PHE | B | 134 | 43.190 | -6.917 | 90.178 | 1.00 24.05 |
| ATOM | 4064 | C | PHE | B | 134 | 38.444 | -6.816 | 85.621 | 1.00 18.60 |
| ATOM | 4065 | O | PHE | B | 134 | 37.815 | -5.849 | 85.196 | 1.00 13.82 |
| ATOM | 4066 | N | LYS | B | 135 | 38.050 | -8.064 | 85.454 | 1.00 19.78 |
| ATOM | 4067 | CA | LYS | B | 135 | 36.813 | -8.421 | 84.782 | 1.00 28.09 |
| ATOM | 4068 | CB | LYS | B | 135 | 36.501 | -9.879 | 85.125 | 1.00 34.06 |
| ATOM | 4069 | CG | LYS | B | 135 | 35.077 | -10.310 | 84.953 | 1.00 42.76 |
| ATOM | 4070 | CD | LYS | B | 135 | 34.927 | -11.745 | 85.437 | 1.00 48.44 |
| ATOM | 4071 | CE | LYS | B | 135 | 33.462 | -12.152 | 85.531 | 1.00 55.66 |
| ATOM | 4072 | NZ | LYS | B | 135 | 32.727 | -11.332 | 86.544 | 1.00 51.65 |
| ATOM | 4073 | C | LYS | B | 135 | 35.639 | -7.512 | 85.172 | 1.00 28.27 |
| ATOM | 4074 | O | LYS | B | 135 | 34.927 | -6.999 | 84.309 | 1.00 24.86 |
| ATOM | 4075 | N | SER | B | 136 | 35.450 | -7.292 | 86.470 | 1.00 29.89 |
| ATOM | 4076 | CA | SER | B | 136 | 34.331 | -6.477 | 86.933 | 1.00 30.86 |
| ATOM | 4077 | CB | SER | B | 136 | 33.282 | -7.388 | 87.582 | 1.00 31.57 |
| ATOM | 4078 | OG | SER | B | 136 | 32.916 | -8.434 | 86.698 | 1.00 45.10 |
| ATOM | 4079 | C | SER | B | 136 | 34.705 | -5.380 | 87.923 | 1.00 31.50 |
| ATOM | 4080 | O | SER | B | 136 | 33.887 | -4.997 | 88.765 | 1.00 24.54 |
| ATOM | 4081 | N | ARG | B | 137 | 35.920 | -4.854 | 87.835 | 1.00 22.63 |
| ATOM | 4082 | CA | ARG | B | 137 | 36.291 | -3.826 | 88.794 | 1.00 25.51 |
| ATOM | 4083 | CB | ARG | B | 137 | 36.629 | -4.486 | 90.136 | 1.00 29.62 |
| ATOM | 4084 | CG | ARG | B | 137 | 36.391 | -3.578 | 91.318 | 1.00 36.21 |
| ATOM | 4085 | CD | ARG | B | 137 | 36.874 | -4.160 | 92.631 | 1.00 40.79 |
| ATOM | 4086 | NE | ARG | B | 137 | 36.365 | -3.357 | 93.744 | 1.00 45.95 |
| ATOM | 4087 | CZ | ARG | B | 137 | 36.863 | -3.369 | 94.973 | 1.00 41.97 |
| ATOM | 4088 | NH1 | ARG | B | 137 | 37.897 | -4.144 | 95.263 | 1.00 43.42 |
| ATOM | 4089 | NH2 | ARG | B | 137 | 36.322 | -2.604 | 95.913 | 1.00 46.65 |
| ATOM | 4090 | C | ARG | B | 137 | 37.461 | -2.956 | 88.339 | 1.00 24.73 |
| ATOM | 4091 | O | ARG | B | 137 | 38.420 | -3.441 | 87.734 | 1.00 19.32 |
| ATOM | 4092 | N | ALA | B | 138 | 37.372 | -1.663 | 88.631 | 1.00 16.77 |
| ATOM | 4093 | CA | ALA | B | 138 | 38.428 | -0.733 | 88.270 | 1.00 18.50 |
| ATOM | 4094 | CB | ALA | B | 138 | 37.939 | 0.694 | 88.401 | 1.00 17.24 |
| ATOM | 4095 | C | ALA | B | 138 | 39.597 | -0.964 | 89.216 | 1.00 22.62 |
| ATOM | 4096 | O | ALA | B | 138 | 39.411 | -1.419 | 90.346 | 1.00 18.98 |
| ATOM | 4097 | N | ASN | B | 139 | 40.301 | -0.641 | 88.759 | 1.00 20.82 |
| ATOM | 4098 | CA | ASN | B | 139 | 41.989 | -0.828 | 89.585 | 1.00 25.17 |
| ATOM | 4099 | CB | ASN | B | 139 | 42.311 | -2.329 | 89.689 | 1.00 20.59 |
| ATOM | 4100 | CG | ASN | B | 139 | 43.556 | -2.608 | 90.511 | 1.00 27.70 |
| ATOM | 4101 | OD1 | ASN | B | 139 | 43.726 | -2.057 | 91.592 | 1.00 22.43 |
| ATOM | 4102 | ND2 | ASN | B | 139 | 44.420 | -3.487 | 90.010 | 1.00 24.43 |
| ATOM | 4103 | C | ASN | B | 139 | 43.176 | -0.062 | 89.020 | 1.00 22.37 |
| ATOM | 4104 | O | ASN | B | 139 | 43.338 | 0.038 | 87.799 | 1.00 17.50 |
| ATOM | 4105 | N | GLY | B | 140 | 43.984 | 0.496 | 89.920 | 1.00 21.67 |
| ATOM | 4106 | CA | GLY | B | 140 | 45.166 | 1.249 | 89.524 | 1.00 23.06 |
| ATOM | 4107 | C | GLY | B | 140 | 45.005 | 2.268 | 88.402 | 1.00 26.29 |
| ATOM | 4108 | O | GLY | B | 140 | 45.827 | 2.301 | 87.479 | 1.00 22.47 |
| ATOM | 4109 | N | PHE | B | 141 | 43.958 | 3.093 | 88.473 | 1.00 22.33 |
| ATOM | 4110 | CA | PHE | B | 141 | 43.694 | 4.126 | 87.461 | 1.00 19.01 |
| ATOM | 4111 | CB | PHE | B | 141 | 44.996 | 4.806 | 86.997 | 1.00 22.90 |
| ATOM | 4112 | CG | PHE | B | 141 | 45.810 | 5.433 | 88.097 | 1.00 23.17 |
| ATOM | 4113 | CD1 | PHE | B | 141 | 47.114 | 5.851 | 87.842 | 1.00 22.17 |
| ATOM | 4114 | CD2 | PHE | B | 141 | 45.281 | 5.635 | 89.366 | 1.00 23.40 |
| ATOM | 4115 | CE1 | PHE | B | 141 | 47.876 | 6.462 | 88.833 | 1.00 24.02 |

Fig. 18-62

| | | | | | | | | | |
|---|---|---|---|---|---|---|---|---|---|
| ATOM | 4116 | CE2 | PHE | B | 141 | 46.033 | 6.244 | 90.361 | 1.00 23.03 |
| ATOM | 4117 | CZ | PHE | B | 141 | 47.335 | 6.658 | 90.092 | 1.00 25.15 |
| ATOM | 4118 | C | PHE | B | 141 | 43.029 | 3.538 | 86.214 | 1.00 23.69 |
| ATOM | 4119 | O | PHE | B | 141 | 42.596 | 4.283 | 85.335 | 1.00 18.88 |
| ATOM | 4120 | N | CYS | B | 142 | 42.962 | 2.211 | 86.122 | 1.00 15.03 |
| ATOM | 4121 | CA | CYS | B | 142 | 42.380 | 1.578 | 84.938 | 1.00 19.55 |
| ATOM | 4122 | CB | CYS | B | 142 | 43.193 | 0.336 | 84.552 | 1.00 20.38 |
| ATOM | 4123 | SG | CYS | B | 142 | 44.933 | 0.662 | 84.190 | 1.00 37.40 |
| ATOM | 4124 | C | CYS | B | 142 | 40.923 | 1.171 | 85.098 | 1.00 22.77 |
| ATOM | 4125 | O | CYS | B | 142 | 40.561 | 0.514 | 86.082 | 1.00 23.04 |
| ATOM | 4126 | N | TYR | B | 143 | 40.094 | 1.557 | 84.130 | 1.00 15.24 |
| ATOM | 4127 | CA | TYR | B | 143 | 38.675 | 1.194 | 84.155 | 1.00 21.97 |
| ATOM | 4128 | CB | TYR | B | 143 | 37.795 | 2.372 | 83.723 | 1.00 18.06 |
| ATOM | 4129 | CG | TYR | B | 143 | 38.016 | 3.622 | 84.535 | 1.00 24.34 |
| ATOM | 4130 | CD1 | TYR | B | 143 | 39.038 | 4.516 | 84.214 | 1.00 23.20 |
| ATOM | 4131 | CE1 | TYR | B | 143 | 39.265 | 5.658 | 84.991 | 1.00 27.42 |
| ATOM | 4132 | CD2 | TYR | B | 143 | 37.226 | 3.892 | 85.652 | 1.00 19.15 |
| ATOM | 4133 | CE2 | TYR | B | 143 | 37.441 | 5.023 | 86.432 | 1.00 21.92 |
| ATOM | 4134 | CZ | TYR | B | 143 | 38.458 | 5.900 | 86.099 | 1.00 23.94 |
| ATOM | 4135 | OH | TYR | B | 143 | 38.655 | 7.015 | 86.877 | 1.00 22.37 |
| ATOM | 4136 | C | TYR | B | 143 | 38.431 | 0.008 | 83.218 | 1.00 19.91 |
| ATOM | 4137 | O | TYR | B | 143 | 37.665 | -0.902 | 83.535 | 1.00 22.50 |
| ATOM | 4138 | N | ILE | B | 144 | 39.083 | 0.026 | 82.061 | 1.00 19.20 |
| ATOM | 4139 | CA | ILE | B | 144 | 38.938 | -1.055 | 81.082 | 1.00 19.68 |
| ATOM | 4140 | CB | ILE | B | 144 | 38.282 | -0.528 | 79.787 | 1.00 20.26 |
| ATOM | 4141 | CG2 | ILE | B | 144 | 38.151 | -1.649 | 78.760 | 1.00 15.37 |
| ATOM | 4142 | CG1 | ILE | B | 144 | 36.901 | 0.053 | 80.113 | 1.00 20.93 |
| ATOM | 4143 | CD1 | ILE | B | 144 | 36.198 | 0.697 | 78.917 | 1.00 23.75 |
| ATOM | 4144 | C | ILE | B | 144 | 40.320 | -1.627 | 80.774 | 1.00 22.78 |
| ATOM | 4145 | O | ILE | B | 144 | 41.281 | -0.873 | 80.600 | 1.00 22.01 |
| ATOM | 4146 | N | ASN | B | 145 | 40.422 | -2.956 | 80.723 | 1.00 23.18 |
| ATOM | 4147 | CA | ASN | B | 145 | 41.698 | -3.623 | 80.451 | 1.00 20.63 |
| ATOM | 4148 | CB | ASN | B | 145 | 41.778 | -4.935 | 81.243 | 1.00 17.81 |
| ATOM | 4149 | CG | ASN | B | 145 | 43.188 | -5.531 | 81.268 | 1.00 25.17 |
| ATOM | 4150 | OD1 | ASN | B | 145 | 43.804 | -5.742 | 80.227 | 1.00 23.63 |
| ATOM | 4151 | ND2 | ASN | B | 145 | 43.693 | -5.819 | 82.472 | 1.00 22.69 |
| ATOM | 4152 | C | ASN | B | 145 | 41.780 | -3.918 | 78.955 | 1.00 21.18 |
| ATOM | 4153 | O | ASN | B | 145 | 41.389 | -5.002 | 78.508 | 1.00 17.80 |
| ATOM | 4154 | N | ASN | B | 146 | 42.293 | -2.968 | 78.177 | 1.00 15.23 |
| ATOM | 4155 | CA | ASN | B | 146 | 42.367 | -3.175 | 76.733 | 1.00 19.71 |
| ATOM | 4156 | CB | ASN | B | 146 | 42.773 | -1.880 | 76.015 | 1.00 17.65 |
| ATOM | 4157 | CG | ASN | B | 146 | 44.196 | -1.458 | 76.306 | 1.00 19.86 |
| ATOM | 4158 | OD1 | ASN | B | 146 | 45.109 | -1.735 | 75.532 | 1.00 20.27 |
| ATOM | 4159 | ND2 | ASN | B | 146 | 44.395 | -0.798 | 77.435 | 1.00 11.85 |
| ATOM | 4160 | C | ASN | B | 146 | 43.277 | -4.342 | 76.331 | 1.00 19.07 |
| ATOM | 4161 | O | ASN | B | 146 | 43.030 | -4.996 | 75.328 | 1.00 18.61 |
| ATOM | 4162 | N | PRO | B | 147 | 44.358 | -4.598 | 77.082 | 1.00 17.78 |
| ATOM | 4163 | CD | PRO | B | 147 | 44.953 | -3.919 | 78.240 | 1.00 18.13 |
| ATOM | 4164 | CA | PRO | B | 147 | 45.197 | -5.735 | 76.678 | 1.00 19.98 |
| ATOM | 4165 | CB | PRO | B | 147 | 46.338 | -5.694 | 77.698 | 1.00 24.29 |
| ATOM | 4166 | CG | PRO | B | 147 | 46.425 | -4.201 | 78.020 | 1.00 26.27 |
| ATOM | 4167 | C | PRO | B | 147 | 44.377 | -7.041 | 76.757 | 1.00 20.91 |
| ATOM | 4168 | O | PRO | B | 147 | 44.461 | -7.892 | 75.871 | 1.00 17.58 |
| ATOM | 4169 | N | ALA | B | 148 | 43.568 | -7.172 | 77.809 | 1.00 15.81 |
| ATOM | 4170 | CA | ALA | B | 148 | 42.732 | -8.362 | 78.008 | 1.00 19.82 |
| ATOM | 4171 | CB | ALA | B | 148 | 42.049 | -8.312 | 79.372 | 1.00 17.50 |
| ATOM | 4172 | C | ALA | B | 148 | 41.683 | -8.473 | 76.903 | 1.00 22.58 |
| ATOM | 4173 | O | ALA | B | 148 | 41.419 | -9.567 | 76.404 | 1.00 18.38 |
| ATOM | 4174 | N | VAL | B | 149 | 41.080 | -7.341 | 76.540 | 1.00 22.48 |
| ATOM | 4175 | CA | VAL | B | 149 | 40.086 | -7.300 | 75.466 | 1.00 19.04 |
| ATOM | 4176 | CB | VAL | B | 149 | 39.503 | -5.877 | 75.281 | 1.00 18.96 |
| ATOM | 4177 | CG1 | VAL | B | 149 | 38.691 | -5.800 | 73.988 | 1.00 17.32 |
| ATOM | 4178 | CG2 | VAL | B | 149 | 38.621 | -5.531 | 76.462 | 1.00 15.33 |
| ATOM | 4179 | C | VAL | B | 149 | 40.763 | -7.709 | 74.166 | 1.00 22.12 |
| ATOM | 4180 | O | VAL | B | 149 | 40.240 | -8.535 | 73.421 | 1.00 21.83 |
| ATOM | 4181 | N | GLY | B | 150 | 41.927 | -7.120 | 73.903 | 1.00 19.51 |

Fig. 18-63

```
ATOM   4182  CA   GLY B 150      42.657   -7.433  72.689  1.00 19.32
ATOM   4183  C    GLY B 150      43.033   -8.901  72.606  1.00 19.59
ATOM   4184  O    GLY B 150      42.862   -9.550  71.568  1.00 22.28
ATOM   4185  N    ILE B 151      43.558   -9.435  73.700  1.00 19.51
ATOM   4186  CA   ILE B 151      43.958  -10.834  73.723  1.00 23.21
ATOM   4187  CB   ILE B 151      44.666  -11.175  75.053  1.00 23.50
ATOM   4188  CG2  ILE B 151      44.918  -12.679  75.158  1.00 20.01
ATOM   4189  CG1  ILE B 151      45.988  -10.394  75.129  1.00 21.98
ATOM   4190  CD1  ILE B 151      46.716  -10.502  76.457  1.00 21.24
ATOM   4191  C    ILE B 151      42.749  -11.741  73.490  1.00 28.40
ATOM   4192  O    ILE B 151      42.832  -12.692  72.706  1.00 22.96
ATOM   4193  N    GLU B 152      41.623  -11.450  74.144  1.00 27.32
ATOM   4194  CA   GLU B 152      40.417  -12.265  73.939  1.00 27.62
ATOM   4195  CB   GLU B 152      39.294  -11.845  74.886  1.00 26.46
ATOM   4196  CG   GLU B 152      39.533  -12.200  76.347  1.00 28.26
ATOM   4197  CD   GLU B 152      39.613  -13.708  76.592  1.00 31.10
ATOM   4198  OE1  GLU B 152      39.668  -14.123  77.767  1.00 29.55
ATOM   4199  OE2  GLU B 152      39.626  -14.481  75.617  1.00 30.51
ATOM   4200  C    GLU B 152      39.948  -12.125  72.497  1.00 30.30
ATOM   4201  O    GLU B 152      39.463  -13.082  71.893  1.00 25.58
ATOM   4202  N    TYR B 153      40.093  -10.923  71.948  1.00 26.23
ATOM   4203  CA   TYR B 153      39.720  -10.669  70.563  1.00 28.19
ATOM   4204  CB   TYR B 153      40.082   -9.235  70.190  1.00 27.94
ATOM   4205  CG   TYR B 153      39.879   -8.886  68.735  1.00 28.46
ATOM   4206  CD1  TYR B 153      38.618   -8.560  68.240  1.00 25.69
ATOM   4207  CE1  TYR B 153      38.447   -8.195  66.898  1.00 30.73
ATOM   4208  CD2  TYR B 153      40.962   -8.847  67.856  1.00 24.82
ATOM   4209  CE2  TYR B 153      40.801   -8.488  66.526  1.00 29.26
ATOM   4210  CZ   TYR B 153      39.547   -8.161  66.054  1.00 31.25
ATOM   4211  OH   TYR B 153      39.406   -7.803  64.735  1.00 34.22
ATOM   4212  C    TYR B 153      40.513  -11.627  69.674  1.00 28.11
ATOM   4213  O    TYR B 153      39.975  -12.248  68.759  1.00 22.06
ATOM   4214  N    LEU B 154      41.810  -11.725  69.944  1.00 26.77
ATOM   4215  CA   LEU B 154      42.681  -12.597  69.168  1.00 28.79
ATOM   4216  CB   LEU B 154      44.142  -12.386  69.592  1.00 28.06
ATOM   4217  CG   LEU B 154      44.789  -11.087  69.083  1.00 27.71
ATOM   4218  CD1  LEU B 154      46.119  -10.860  69.759  1.00 34.15
ATOM   4219  CD2  LEU B 154      44.968  -11.171  67.571  1.00 26.71
ATOM   4220  C    LEU B 154      42.299  -14.074  69.274  1.00 26.98
ATOM   4221  O    LEU B 154      42.282  -14.787  68.271  1.00 29.88
ATOM   4222  N    ARG B 155      41.996  -14.536  70.480  1.00 23.19
ATOM   4223  CA   ARG B 155      41.622  -15.936  70.669  1.00 29.47
ATOM   4224  CB   ARG B 155      41.339  -16.230  72.144  1.00 28.53
ATOM   4225  CG   ARG B 155      42.527  -15.965  73.053  1.00 35.03
ATOM   4226  CD   ARG B 155      42.212  -16.276  74.507  1.00 39.42
ATOM   4227  NE   ARG B 155      42.165  -17.706  74.792  1.00 30.99
ATOM   4228  CZ   ARG B 155      41.869  -18.209  75.986  1.00 41.33
ATOM   4229  NH1  ARG B 155      41.591  -17.394  77.002  1.00 38.47
ATOM   4230  NH2  ARG B 155      41.872  -19.523  76.178  1.00 40.67
ATOM   4231  C    ARG B 155      40.393  -16.260  69.832  1.00 29.07
ATOM   4232  O    ARG B 155      40.325  -17.311  69.203  1.00 25.31
ATOM   4233  N    LYS B 156      39.419  -15.357  69.828  1.00 28.99
ATOM   4234  CA   LYS B 156      38.216  -15.573  69.038  1.00 34.63
ATOM   4235  CB   LYS B 156      37.148  -14.534  69.386  1.00 36.63
ATOM   4236  CG   LYS B 156      36.393  -14.883  70.646  1.00 42.18
ATOM   4237  CD   LYS B 156      37.292  -14.900  71.868  1.00 51.38
ATOM   4238  CE   LYS B 156      36.685  -15.712  73.009  1.00 52.76
ATOM   4239  NZ   LYS B 156      36.561  -17.172  72.677  1.00 51.29
ATOM   4240  C    LYS B 156      38.504  -15.562  67.538  1.00 34.66
ATOM   4241  O    LYS B 156      37.722  -16.088  66.754  1.00 33.53
ATOM   4242  N    LYS B 157      39.625  -14.966  67.140  1.00 30.06
ATOM   4243  CA   LYS B 157      39.996  -14.945  65.734  1.00 31.36
ATOM   4244  CB   LYS B 157      40.888  -13.746  65.418  1.00 29.79
ATOM   4245  CG   LYS B 157      40.157  -12.426  65.359  1.00 31.52
ATOM   4246  CD   LYS B 157      39.132  -12.424  64.239  1.00 28.48
ATOM   4247  CE   LYS B 157      38.395  -11.101  64.171  1.00 31.90
```

Fig. 18-64

| | | | | | | | | | |
|---|---|---|---|---|---|---|---|---|---|
| ATOM | 4248 | NZ | LYS | B | 157 | 37.406 | -11.080 | 63.054 | 1.00 32.91 |
| ATOM | 4249 | C | LYS | B | 157 | 40.724 | -16.234 | 65.381 | 1.00 31.92 |
| ATOM | 4250 | O | LYS | B | 157 | 41.146 | -16.421 | 64.246 | 1.00 33.58 |
| ATOM | 4251 | N | GLY | B | 158 | 40.890 | -17.111 | 66.368 | 1.00 28.97 |
| ATOM | 4252 | CA | GLY | B | 158 | 41.546 | -18.379 | 66.112 | 1.00 28.98 |
| ATOM | 4253 | C | GLY | B | 158 | 42.962 | -18.569 | 66.622 | 1.00 33.33 |
| ATOM | 4254 | O | GLY | B | 158 | 43.503 | -19.672 | 66.522 | 1.00 30.58 |
| ATOM | 4255 | N | PHE | B | 159 | 43.578 | -17.521 | 67.164 | 1.00 32.80 |
| ATOM | 4256 | CA | PHE | B | 159 | 44.937 | -17.657 | 67.678 | 1.00 28.89 |
| ATOM | 4257 | CB | PHE | B | 159 | 45.560 | -16.286 | 67.934 | 1.00 30.33 |
| ATOM | 4258 | CG | PHE | B | 159 | 45.748 | -15.470 | 66.692 | 1.00 28.53 |
| ATOM | 4259 | CD1 | PHE | B | 159 | 44.682 | -14.787 | 66.121 | 1.00 24.58 |
| ATOM | 4260 | CD2 | PHE | B | 159 | 46.989 | -15.420 | 66.068 | 1.00 24.21 |
| ATOM | 4261 | CE1 | PHE | B | 159 | 44.849 | -14.066 | 64.948 | 1.00 25.26 |
| ATOM | 4262 | CE2 | PHE | B | 159 | 47.168 | -14.706 | 64.895 | 1.00 23.66 |
| ATOM | 4263 | CZ | PHE | B | 159 | 46.095 | -14.026 | 64.332 | 1.00 26.65 |
| ATOM | 4264 | C | PHE | B | 159 | 44.969 | -18.484 | 68.958 | 1.00 30.92 |
| ATOM | 4265 | O | PHE | B | 159 | 44.102 | -18.334 | 69.820 | 1.00 24.26 |
| ATOM | 4266 | N | LYS | B | 160 | 45.979 | -19.347 | 69.077 | 1.00 28.86 |
| ATOM | 4267 | CA | LYS | B | 160 | 46.123 | -20.224 | 70.237 | 1.00 30.27 |
| ATOM | 4268 | CB | LYS | B | 160 | 46.085 | -21.692 | 69.800 | 1.00 32.05 |
| ATOM | 4269 | CG | LYS | B | 160 | 44.806 | -22.117 | 69.113 | 1.00 41.13 |
| ATOM | 4270 | CD | LYS | B | 160 | 44.809 | -23.621 | 68.826 | 1.00 40.73 |
| ATOM | 4271 | CE | LYS | B | 160 | 45.945 | -24.031 | 67.904 | 1.00 43.16 |
| ATOM | 4272 | NZ | LYS | B | 160 | 45.812 | -23.408 | 66.554 | 1.00 48.69 |
| ATOM | 4273 | C | LYS | B | 160 | 47.394 | -19.997 | 71.048 | 1.00 28.23 |
| ATOM | 4274 | O | LYS | B | 160 | 47.552 | -20.561 | 72.130 | 1.00 25.29 |
| ATOM | 4275 | N | ARG | B | 161 | 48.320 | -19.206 | 70.520 | 1.00 28.51 |
| ATOM | 4276 | CA | ARG | B | 161 | 49.550 | -18.921 | 71.247 | 1.00 25.84 |
| ATOM | 4277 | CB | ARG | B | 161 | 50.724 | -19.719 | 70.667 | 1.00 25.33 |
| ATOM | 4278 | CG | ARG | B | 161 | 50.551 | -21.245 | 70.781 | 1.00 27.47 |
| ATOM | 4279 | CD | ARG | B | 161 | 51.833 | -21.985 | 70.394 | 1.00 32.27 |
| ATOM | 4280 | NE | ARG | B | 161 | 52.218 | -21.761 | 69.002 | 1.00 34.90 |
| ATOM | 4281 | CZ | ARG | B | 161 | 51.584 | -22.276 | 67.954 | 1.00 38.45 |
| ATOM | 4282 | NH1 | ARG | B | 161 | 50.527 | -23.056 | 68.130 | 1.00 38.77 |
| ATOM | 4283 | NH2 | ARG | B | 161 | 51.999 | -22.000 | 66.725 | 1.00 38.64 |
| ATOM | 4284 | C | ARG | B | 161 | 49.818 | -17.421 | 71.182 | 1.00 30.40 |
| ATOM | 4285 | O | ARG | B | 161 | 50.393 | -16.912 | 70.218 | 1.00 27.50 |
| ATOM | 4286 | N | ILE | B | 162 | 49.376 | -16.722 | 72.221 | 1.00 25.64 |
| ATOM | 4287 | CA | ILE | B | 162 | 49.515 | -15.273 | 72.303 | 1.00 27.44 |
| ATOM | 4288 | CB | ILE | B | 162 | 48.134 | -14.618 | 72.545 | 1.00 24.53 |
| ATOM | 4289 | CG2 | ILE | B | 162 | 48.249 | -13.101 | 72.473 | 1.00 25.49 |
| ATOM | 4290 | CG1 | ILE | B | 162 | 47.142 | -15.101 | 71.487 | 1.00 29.46 |
| ATOM | 4291 | CD1 | ILE | B | 162 | 45.688 | -14.707 | 71.758 | 1.00 31.94 |
| ATOM | 4292 | C | ILE | B | 162 | 50.465 | -14.868 | 73.429 | 1.00 22.68 |
| ATOM | 4293 | O | ILE | B | 162 | 50.311 | -15.302 | 74.568 | 1.00 24.25 |
| ATOM | 4294 | N | LEU | B | 163 | 51.454 | -14.042 | 73.100 | 1.00 19.49 |
| ATOM | 4295 | CA | LEU | B | 163 | 52.425 | -13.561 | 74.081 | 1.00 17.57 |
| ATOM | 4296 | CB | LEU | B | 163 | 53.850 | -13.686 | 73.528 | 1.00 20.54 |
| ATOM | 4297 | CG | LEU | B | 163 | 54.979 | -12.975 | 74.295 | 1.00 18.84 |
| ATOM | 4298 | CD1 | LEU | B | 163 | 55.102 | -13.538 | 75.690 | 1.00 20.55 |
| ATOM | 4299 | CD2 | LEU | B | 163 | 56.293 | -13.148 | 73.556 | 1.00 18.57 |
| ATOM | 4300 | C | LEU | B | 163 | 52.158 | -12.099 | 74.430 | 1.00 16.20 |
| ATOM | 4301 | O | LEU | B | 163 | 51.898 | -11.277 | 73.549 | 1.00 16.09 |
| ATOM | 4302 | N | TYR | B | 164 | 52.227 | -11.780 | 75.715 | 1.00 14.05 |
| ATOM | 4303 | CA | TYR | B | 164 | 52.027 | -10.411 | 76.191 | 1.00 16.21 |
| ATOM | 4304 | CB | TYR | B | 164 | 50.777 | -10.323 | 77.070 | 1.00 16.01 |
| ATOM | 4305 | CG | TYR | B | 164 | 50.534 | -8.948 | 77.667 | 1.00 15.08 |
| ATOM | 4306 | CD1 | TYR | B | 164 | 50.148 | -7.869 | 76.869 | 1.00 19.51 |
| ATOM | 4307 | CE1 | TYR | B | 164 | 49.948 | -6.597 | 77.418 | 1.00 12.88 |
| ATOM | 4308 | CD2 | TYR | B | 164 | 50.715 | -8.724 | 79.021 | 1.00 14.07 |
| ATOM | 4309 | CE2 | TYR | B | 164 | 50.520 | -7.463 | 79.583 | 1.00 13.66 |
| ATOM | 4310 | CZ | TYR | B | 164 | 50.139 | -6.407 | 78.782 | 1.00 14.72 |
| ATOM | 4311 | OH | TYR | B | 164 | 49.952 | -5.163 | 79.354 | 1.00 13.54 |
| ATOM | 4312 | C | TYR | B | 164 | 53.246 | -10.017 | 77.018 | 1.00 19.14 |
| ATOM | 4313 | O | TYR | B | 164 | 53.539 | -10.642 | 78.036 | 1.00 26.51 |

Fig. 18-65

| | | | | | | | | | |
|---|---|---|---|---|---|---|---|---|---|
| ATOM | 4314 | N | ILE | B | 165 | 53.964 | -8.992 | 76.573 | 1.00 22.40 |
| ATOM | 4315 | CA | ILE | B | 165 | 55.148 | -8.518 | 77.285 | 1.00 17.72 |
| ATOM | 4316 | CB | ILE | B | 165 | 56.352 | -8.465 | 76.343 | 1.00 22.51 |
| ATOM | 4317 | CG2 | ILE | B | 165 | 57.582 | -7.902 | 77.079 | 1.00 16.36 |
| ATOM | 4318 | CG1 | ILE | B | 165 | 56.632 | -9.880 | 75.818 | 1.00 19.82 |
| ATOM | 4319 | CD1 | ILE | B | 165 | 57.721 | -9.942 | 74.742 | 1.00 21.74 |
| ATOM | 4320 | C | ILE | B | 165 | 54.851 | -7.126 | 77.850 | 1.00 22.54 |
| ATOM | 4321 | O | ILE | B | 165 | 54.478 | -6.223 | 77.111 | 1.00 16.60 |
| ATOM | 4322 | N | ASP | B | 166 | 55.046 | -6.961 | 79.156 | 1.00 15.78 |
| ATOM | 4323 | CA | ASP | B | 166 | 54.740 | -5.704 | 79.840 | 1.00 20.62 |
| ATOM | 4324 | CB | ASP | B | 166 | 53.719 | -5.996 | 80.949 | 1.00 17.57 |
| ATOM | 4325 | CG | ASP | B | 166 | 53.063 | -4.742 | 81.486 | 1.00 25.39 |
| ATOM | 4326 | OD1 | ASP | B | 166 | 53.779 | -3.859 | 82.003 | 1.00 19.68 |
| ATOM | 4327 | OD2 | ASP | B | 166 | 51.824 | -4.637 | 81.377 | 1.00 29.22 |
| ATOM | 4328 | C | ASP | B | 166 | 55.976 | -5.002 | 80.423 | 1.00 19.01 |
| ATOM | 4329 | O | ASP | B | 166 | 56.509 | -5.412 | 81.456 | 1.00 19.74 |
| ATOM | 4330 | N | LEU | B | 167 | 56.414 | -3.923 | 79.775 | 1.00 17.88 |
| ATOM | 4331 | CA | LEU | B | 167 | 57.598 | -3.211 | 80.235 | 1.00 14.99 |
| ATOM | 4332 | CB | LEU | B | 167 | 58.412 | -2.710 | 79.044 | 1.00 19.22 |
| ATOM | 4333 | CG | LEU | B | 167 | 58.871 | -3.799 | 78.069 | 1.00 22.68 |
| ATOM | 4334 | CD1 | LEU | B | 167 | 59.835 | -3.179 | 77.074 | 1.00 25.35 |
| ATOM | 4335 | CD2 | LEU | B | 167 | 59.570 | -4.943 | 78.808 | 1.00 17.54 |
| ATOM | 4336 | C | LEU | B | 167 | 57.284 | -2.059 | 81.183 | 1.00 17.49 |
| ATOM | 4337 | O | LEU | B | 167 | 58.189 | -1.359 | 81.639 | 1.00 13.39 |
| ATOM | 4338 | N | ASP | B | 168 | 56.003 | -1.878 | 81.479 | 1.00 20.03 |
| ATOM | 4339 | CA | ASP | B | 168 | 55.549 | -0.848 | 82.412 | 1.00 21.98 |
| ATOM | 4340 | CB | ASP | B | 168 | 54.030 | -0.955 | 82.597 | 1.00 21.21 |
| ATOM | 4341 | CG | ASP | B | 168 | 53.453 | 0.186 | 83.428 | 1.00 24.92 |
| ATOM | 4342 | C | ASP | B | 168 | 56.241 | -1.139 | 83.753 | 1.00 22.98 |
| ATOM | 4343 | O | ASP | B | 168 | 56.447 | -2.304 | 84.091 | 1.00 18.36 |
| ATOM | 4344 | OD1 | ASP | B | 168 | 52.849 | 1.099 | 82.825 | 1.00 22.03 |
| ATOM | 4345 | OD2 | ASP | B | 168 | 53.606 | 0.189 | 84.676 | 1.00 18.43 |
| ATOM | 4346 | N | ALA | B | 169 | 56.581 | -0.095 | 84.514 | 1.00 15.46 |
| ATOM | 4347 | CA | ALA | B | 169 | 57.263 | -0.268 | 85.807 | 1.00 18.73 |
| ATOM | 4348 | CB | ALA | B | 169 | 57.764 | 1.084 | 86.323 | 1.00 11.98 |
| ATOM | 4349 | C | ALA | B | 169 | 56.400 | -0.940 | 86.886 | 1.00 21.82 |
| ATOM | 4350 | O | ALA | B | 169 | 56.886 | -1.262 | 87.980 | 1.00 22.51 |
| ATOM | 4351 | N | HIS | B | 170 | 55.120 | -1.134 | 86.600 | 1.00 18.75 |
| ATOM | 4352 | CA | HIS | B | 170 | 54.238 | -1.776 | 87.570 | 1.00 22.70 |
| ATOM | 4353 | C | HIS | B | 170 | 53.716 | -3.096 | 87.015 | 1.00 22.11 |
| ATOM | 4354 | O | HIS | B | 170 | 53.536 | -3.244 | 85.809 | 1.00 21.94 |
| ATOM | 4355 | CB | HIS | B | 170 | 53.050 | -0.867 | 87.927 | 1.00 21.28 |
| ATOM | 4356 | CG | HIS | B | 170 | 53.449 | 0.475 | 88.460 | 1.00 18.89 |
| ATOM | 4357 | ND1 | HIS | B | 170 | 53.695 | 1.539 | 87.626 | 1.00 19.13 |
| ATOM | 4358 | CE1 | HIS | B | 170 | 54.046 | 2.539 | 88.412 | 1.00 19.41 |
| ATOM | 4359 | CD2 | HIS | B | 170 | 53.660 | 0.854 | 89.746 | 1.00 19.02 |
| ATOM | 4360 | NE2 | HIS | B | 170 | 54.042 | 2.174 | 89.710 | 1.00 20.45 |
| ATOM | 4361 | N | HIS | B | 171 | 53.474 | -4.047 | 87.907 | 1.00 19.20 |
| ATOM | 4362 | CA | HIS | B | 171 | 52.961 | -5.352 | 87.519 | 1.00 21.20 |
| ATOM | 4363 | CB | HIS | B | 171 | 52.964 | -6.284 | 88.722 | 1.00 22.00 |
| ATOM | 4364 | CG | HIS | B | 171 | 52.541 | -7.683 | 88.400 | 1.00 24.64 |
| ATOM | 4365 | CD2 | HIS | B | 171 | 53.056 | -8.594 | 87.540 | 1.00 19.19 |
| ATOM | 4366 | ND1 | HIS | B | 171 | 51.441 | -8.279 | 88.979 | 1.00 25.71 |
| ATOM | 4367 | CE1 | HIS | B | 171 | 51.295 | -9.497 | 88.487 | 1.00 25.30 |
| ATOM | 4368 | NE2 | HIS | B | 171 | 52.261 | -9.713 | 87.612 | 1.00 24.71 |
| ATOM | 4369 | C | HIS | B | 171 | 51.549 | -5.306 | 86.943 | 1.00 23.91 |
| ATOM | 4370 | O | HIS | B | 171 | 50.677 | -4.620 | 87.479 | 1.00 18.93 |
| ATOM | 4371 | N | CYS | B | 172 | 51.332 | -6.062 | 85.865 | 1.00 15.36 |
| ATOM | 4372 | CA | CYS | B | 172 | 50.036 | -6.141 | 85.207 | 1.00 20.03 |
| ATOM | 4373 | CB | CYS | B | 172 | 50.240 | -6.534 | 83.732 | 1.00 22.46 |
| ATOM | 4374 | SG | CYS | B | 172 | 51.259 | -3.030 | 83.419 | 1.00 23.49 |
| ATOM | 4375 | C | CYS | B | 172 | 49.110 | -7.146 | 85.913 | 1.00 18.05 |
| ATOM | 4376 | O | CYS | B | 172 | 48.712 | -8.151 | 85.327 | 1.00 18.23 |
| ATOM | 4377 | N | ASP | B | 173 | 48.767 | -6.871 | 87.170 | 1.00 16.78 |
| ATOM | 4378 | CA | ASP | B | 173 | 47.909 | -7.776 | 87.928 | 1.00 18.81 |
| ATOM | 4379 | CB | ASP | B | 173 | 47.638 | -7.236 | 89.344 | 1.00 20.39 |

Fig. 18-66

| | | | | | | | | |
|---|---|---|---|---|---|---|---|---|
| ATOM | 4380 | CG | ASP | B | 173 | 46.961 | -5.871 | 89.354 | 1.00 23.40 |
| ATOM | 4381 | OD1 | ASP | B | 173 | 46.564 | -5.435 | 90.455 | 1.00 18.64 |
| ATOM | 4382 | OD2 | ASP | B | 173 | 46.834 | -5.231 | 88.291 | 1.00 19.24 |
| ATOM | 4383 | C | ASP | B | 173 | 46.595 | -8.116 | 87.219 | 1.00 17.46 |
| ATOM | 4384 | O | ASP | B | 173 | 46.162 | -9.272 | 87.224 | 1.00 15.53 |
| ATOM | 4385 | N | GLY | B | 174 | 45.978 | -7.130 | 86.580 | 1.00 13.46 |
| ATOM | 4386 | CA | GLY | B | 174 | 44.733 | -7.391 | 85.876 | 1.00 18.18 |
| ATOM | 4387 | C | GLY | B | 174 | 44.904 | -8.392 | 84.741 | 1.00 17.85 |
| ATOM | 4388 | O | GLY | B | 174 | 44.104 | -9.316 | 84.583 | 1.00 18.27 |
| ATOM | 4389 | N | VAL | B | 175 | 45.951 | -8.214 | 83.943 | 1.00 16.14 |
| ATOM | 4390 | CA | VAL | B | 175 | 46.206 | -9.111 | 82.829 | 1.00 17.00 |
| ATOM | 4391 | CB | VAL | B | 175 | 47.305 | -8.552 | 81.902 | 1.00 27.22 |
| ATOM | 4392 | CG1 | VAL | B | 175 | 47.533 | -9.507 | 80.731 | 1.00 19.75 |
| ATOM | 4393 | CG2 | VAL | B | 175 | 46.896 | -7.169 | 81.396 | 1.00 18.66 |
| ATOM | 4394 | C | VAL | B | 175 | 46.635 | -10.486 | 83.324 | 1.00 22.82 |
| ATOM | 4395 | O | VAL | B | 175 | 46.255 | -11.503 | 82.754 | 1.00 18.06 |
| ATOM | 4396 | N | GLN | B | 176 | 47.439 | -10.520 | 84.378 | 1.00 21.67 |
| ATOM | 4397 | CA | GLN | B | 176 | 47.889 | -11.798 | 84.911 | 1.00 21.55 |
| ATOM | 4398 | CB | GLN | B | 176 | 48.824 | -11.602 | 86.105 | 1.00 19.68 |
| ATOM | 4399 | CG | GLN | B | 176 | 49.088 | -12.905 | 86.862 | 1.00 20.17 |
| ATOM | 4400 | CD | GLN | B | 176 | 50.066 | -12.759 | 87.996 | 1.00 25.42 |
| ATOM | 4401 | OE1 | GLN | B | 176 | 51.243 | -12.442 | 87.786 | 1.00 21.56 |
| ATOM | 4402 | NE2 | GLN | B | 176 | 49.592 | -13.000 | 89.217 | 1.00 20.18 |
| ATOM | 4403 | C | GLN | B | 176 | 46.689 | -12.630 | 85.348 | 1.00 24.78 |
| ATOM | 4404 | O | GLN | B | 176 | 46.618 | -13.817 | 85.057 | 1.00 22.91 |
| ATOM | 4405 | N | GLU | B | 177 | 45.751 | -12.007 | 86.051 | 1.00 23.69 |
| ATOM | 4406 | CA | GLU | B | 177 | 44.571 | -12.727 | 86.523 | 1.00 27.01 |
| ATOM | 4407 | CB | GLU | B | 177 | 43.703 | -11.825 | 87.394 | 1.00 24.73 |
| ATOM | 4408 | CG | GLU | B | 177 | 42.633 | -12.581 | 88.138 | 1.00 37.46 |
| ATOM | 4409 | CD | GLU | B | 177 | 41.767 | -11.676 | 88.987 | 1.00 42.48 |
| ATOM | 4410 | OE1 | GLU | B | 177 | 40.875 | -11.002 | 88.432 | 1.00 44.35 |
| ATOM | 4411 | OE2 | GLU | B | 177 | 41.993 | -11.627 | 90.213 | 1.00 45.63 |
| ATOM | 4412 | C | GLU | B | 177 | 43.732 | -13.247 | 85.370 | 1.00 26.56 |
| ATOM | 4413 | O | GLU | B | 177 | 43.240 | -14.375 | 85.408 | 1.00 27.71 |
| ATOM | 4414 | N | ALA | B | 178 | 43.573 | -12.418 | 84.344 | 1.00 24.58 |
| ATOM | 4415 | CA | ALA | B | 178 | 42.776 | -12.775 | 83.174 | 1.00 25.86 |
| ATOM | 4416 | CB | ALA | B | 178 | 42.778 | -11.628 | 82.171 | 1.00 24.20 |
| ATOM | 4417 | C | ALA | B | 178 | 43.231 | -14.054 | 82.485 | 1.00 25.72 |
| ATOM | 4418 | O | ALA | B | 178 | 42.406 | -14.838 | 82.036 | 1.00 22.38 |
| ATOM | 4419 | N | PHE | B | 179 | 44.535 | -14.282 | 82.395 | 1.00 27.19 |
| ATOM | 4420 | CA | PHE | B | 179 | 44.990 | -15.489 | 81.703 | 1.00 27.05 |
| ATOM | 4421 | CB | PHE | B | 179 | 45.714 | -15.086 | 80.418 | 1.00 25.22 |
| ATOM | 4422 | CG | PHE | B | 179 | 44.992 | -14.020 | 79.644 | 1.00 20.36 |
| ATOM | 4423 | CD1 | PHE | B | 179 | 45.387 | -12.687 | 79.735 | 1.00 25.23 |
| ATOM | 4424 | CD2 | PHE | B | 179 | 43.860 | -14.332 | 78.902 | 1.00 19.22 |
| ATOM | 4425 | CE1 | PHE | B | 179 | 44.659 | -11.677 | 79.102 | 1.00 19.25 |
| ATOM | 4426 | CE2 | PHE | B | 179 | 43.128 | -13.315 | 78.272 | 1.00 20.65 |
| ATOM | 4427 | CZ | PHE | B | 179 | 43.528 | -12.001 | 78.374 | 1.00 25.64 |
| ATOM | 4428 | C | PHE | B | 179 | 45.866 | -16.398 | 82.556 | 1.00 23.50 |
| ATOM | 4429 | O | PHE | B | 179 | 46.652 | -17.182 | 82.038 | 1.00 18.26 |
| ATOM | 4430 | N | TYR | B | 180 | 45.689 | -16.313 | 83.868 | 1.00 23.24 |
| ATOM | 4431 | CA | TYR | B | 180 | 46.479 | -17.106 | 84.799 | 1.00 26.76 |
| ATOM | 4432 | CB | TYR | B | 180 | 46.150 | -16.665 | 86.231 | 1.00 25.72 |
| ATOM | 4433 | CG | TYR | B | 180 | 47.226 | -16.969 | 87.247 | 1.00 29.66 |
| ATOM | 4434 | CD1 | TYR | B | 180 | 47.037 | -17.942 | 88.237 | 1.00 27.07 |
| ATOM | 4435 | CE1 | TYR | B | 180 | 48.039 | -18.222 | 89.170 | 1.00 30.08 |
| ATOM | 4436 | CD2 | TYR | B | 180 | 48.444 | -16.283 | 87.216 | 1.00 29.68 |
| ATOM | 4437 | CE2 | TYR | B | 180 | 49.451 | -16.552 | 88.139 | 1.00 30.99 |
| ATOM | 4438 | CZ | TYR | B | 180 | 49.248 | -17.521 | 89.112 | 1.00 33.16 |
| ATOM | 4439 | OH | TYR | B | 180 | 50.262 | -17.791 | 90.006 | 1.00 28.47 |
| ATOM | 4440 | C | TYR | B | 180 | 46.256 | -18.619 | 84.649 | 1.00 29.13 |
| ATOM | 4441 | O | TYR | B | 180 | 47.163 | -19.416 | 84.922 | 1.00 23.43 |
| ATOM | 4442 | N | ASP | B | 181 | 45.073 | -19.021 | 84.190 | 1.00 25.67 |
| ATOM | 4443 | CA | ASP | B | 181 | 44.784 | -20.445 | 84.075 | 1.00 28.28 |
| ATOM | 4444 | CB | ASP | B | 181 | 43.446 | -20.759 | 84.757 | 1.00 32.13 |
| ATOM | 4445 | CG | ASP | B | 181 | 42.247 | -20.410 | 83.890 | 1.00 36.12 |

Fig. 18-67

| | | | | | | | | |
|---|---|---|---|---|---|---|---|---|
| ATOM | 4446 | OD1 | ASP | B | 181 | 42.202 | -19.300 | 83.329 | 1.00 41.04 |
| ATOM | 4447 | OD2 | ASP | B | 181 | 41.334 | -21.249 | 83.782 | 1.00 44.36 |
| ATOM | 4448 | C | ASP | B | 181 | 44.773 | -21.018 | 82.664 | 1.00 32.41 |
| ATOM | 4449 | O | ASP | B | 181 | 44.246 | -22.115 | 82.444 | 1.00 31.67 |
| ATOM | 4450 | N | THR | B | 182 | 45.345 | -20.302 | 81.702 | 1.00 29.24 |
| ATOM | 4451 | CA | THR | B | 182 | 45.363 | -20.823 | 80.340 | 1.00 30.57 |
| ATOM | 4452 | CB | THR | B | 182 | 44.468 | -20.008 | 79.397 | 1.00 30.03 |
| ATOM | 4453 | OG1 | THR | B | 182 | 44.516 | -20.598 | 78.095 | 1.00 28.22 |
| ATOM | 4454 | CG2 | THR | B | 182 | 44.947 | -18.561 | 79.310 | 1.00 26.55 |
| ATOM | 4455 | C | THR | B | 182 | 46.759 | -20.870 | 79.740 | 1.00 32.31 |
| ATOM | 4456 | O | THR | B | 182 | 47.591 | -20.007 | 80.008 | 1.00 27.27 |
| ATOM | 4457 | N | ASP | B | 183 | 46.999 | -21.878 | 78.909 | 1.00 29.94 |
| ATOM | 4458 | CA | ASP | B | 183 | 48.296 | -22.049 | 78.273 | 1.00 31.40 |
| ATOM | 4459 | CB | ASP | B | 183 | 48.648 | -23.536 | 78.228 | 1.00 33.36 |
| ATOM | 4460 | CG | ASP | B | 183 | 47.718 | -24.319 | 77.328 | 1.00 33.33 |
| ATOM | 4461 | OD1 | ASP | B | 183 | 46.513 | -23.988 | 77.287 | 1.00 28.06 |
| ATOM | 4462 | OD2 | ASP | B | 183 | 48.186 | -25.271 | 76.675 | 1.00 38.19 |
| ATOM | 4463 | C | ASP | B | 183 | 48.321 | -21.462 | 76.864 | 1.00 31.14 |
| ATOM | 4464 | O | ASP | B | 183 | 49.332 | -21.557 | 76.168 | 1.00 28.74 |
| ATOM | 4465 | N | GLN | B | 184 | 47.217 | -20.852 | 76.446 | 1.00 25.34 |
| ATOM | 4466 | CA | GLN | B | 184 | 47.151 | -20.251 | 75.118 | 1.00 28.59 |
| ATOM | 4467 | CB | GLN | B | 184 | 45.712 | -20.256 | 74.581 | 1.00 26.84 |
| ATOM | 4468 | CG | GLN | B | 184 | 45.060 | -21.632 | 74.529 | 1.00 34.86 |
| ATOM | 4469 | CD | GLN | B | 184 | 43.760 | -21.647 | 73.736 | 1.00 32.27 |
| ATOM | 4470 | OE1 | GLN | B | 184 | 42.897 | -20.789 | 73.912 | 1.00 35.43 |
| ATOM | 4471 | NE2 | GLN | B | 184 | 43.611 | -22.641 | 72.870 | 1.00 28.92 |
| ATOM | 4472 | C | GLN | B | 184 | 47.672 | -18.817 | 75.175 | 1.00 27.28 |
| ATOM | 4473 | O | GLN | B | 184 | 47.871 | -18.171 | 74.148 | 1.00 29.70 |
| ATOM | 4474 | N | VAL | B | 185 | 47.900 | -18.325 | 76.386 | 1.00 27.64 |
| ATOM | 4475 | CA | VAL | B | 185 | 48.400 | -16.972 | 76.575 | 1.00 26.26 |
| ATOM | 4476 | CB | VAL | B | 185 | 47.304 | -16.039 | 77.145 | 1.00 22.85 |
| ATOM | 4477 | CG1 | VAL | B | 185 | 47.879 | -14.642 | 77.395 | 1.00 23.10 |
| ATOM | 4478 | CG2 | VAL | B | 185 | 46.136 | -15.967 | 76.191 | 1.00 21.67 |
| ATOM | 4479 | C | VAL | B | 185 | 49.570 | -16.964 | 77.547 | 1.00 27.01 |
| ATOM | 4480 | O | VAL | B | 185 | 49.456 | -17.469 | 78.663 | 1.00 23.75 |
| ATOM | 4481 | N | PHE | B | 186 | 50.696 | -16.403 | 77.115 | 1.00 22.02 |
| ATOM | 4482 | CA | PHE | B | 186 | 51.868 | -16.301 | 77.978 | 1.00 21.83 |
| ATOM | 4483 | CB | PHE | B | 186 | 53.142 | -16.763 | 77.252 | 1.00 17.02 |
| ATOM | 4484 | CG | PHE | B | 186 | 54.336 | -16.921 | 78.170 | 1.00 24.84 |
| ATOM | 4485 | CD1 | PHE | B | 186 | 54.756 | -18.189 | 78.580 | 1.00 22.70 |
| ATOM | 4486 | CD2 | PHE | B | 186 | 55.004 | -15.805 | 78.670 | 1.00 20.26 |
| ATOM | 4487 | CE1 | PHE | B | 186 | 55.819 | -18.338 | 79.471 | 1.00 21.47 |
| ATOM | 4488 | CE2 | PHE | B | 186 | 56.071 | -15.941 | 79.563 | 1.00 20.01 |
| ATOM | 4489 | CZ | PHE | B | 186 | 56.481 | -17.206 | 79.968 | 1.00 17.84 |
| ATOM | 4490 | C | PHE | B | 186 | 52.032 | -14.827 | 78.368 | 1.00 18.12 |
| ATOM | 4491 | O | PHE | B | 186 | 52.038 | -13.946 | 77.508 | 1.00 15.92 |
| ATOM | 4492 | N | VAL | B | 187 | 52.161 | -14.565 | 79.661 | 1.00 18.06 |
| ATOM | 4493 | CA | VAL | B | 187 | 52.348 | -13.208 | 80.153 | 1.00 17.67 |
| ATOM | 4494 | CB | VAL | B | 187 | 51.282 | -12.839 | 81.225 | 1.00 22.85 |
| ATOM | 4495 | CG1 | VAL | B | 187 | 51.608 | -11.473 | 81.840 | 1.00 24.08 |
| ATOM | 4496 | CG2 | VAL | B | 187 | 49.882 | -12.808 | 80.598 | 1.00 18.82 |
| ATOM | 4497 | C | VAL | B | 187 | 53.735 | -13.060 | 80.788 | 1.00 18.32 |
| ATOM | 4498 | O | VAL | B | 187 | 54.092 | -13.807 | 81.707 | 1.00 18.82 |
| ATOM | 4499 | N | LEU | B | 188 | 54.503 | -12.103 | 80.282 | 1.00 14.70 |
| ATOM | 4500 | CA | LEU | B | 188 | 55.832 | -11.789 | 80.798 | 1.00 18.84 |
| ATOM | 4501 | CB | LEU | B | 188 | 56.900 | -11.948 | 79.716 | 1.00 18.64 |
| ATOM | 4502 | CG | LEU | B | 188 | 58.230 | -11.277 | 80.082 | 1.00 21.23 |
| ATOM | 4503 | CD1 | LEU | B | 188 | 58.769 | -11.832 | 81.395 | 1.00 18.55 |
| ATOM | 4504 | CD2 | LEU | B | 188 | 59.227 | -11.489 | 78.957 | 1.00 20.49 |
| ATOM | 4505 | C | LEU | B | 188 | 55.836 | -10.339 | 81.280 | 1.00 22.14 |
| ATOM | 4506 | O | LEU | B | 188 | 55.527 | -9.410 | 80.517 | 1.00 19.96 |
| ATOM | 4507 | N | SER | B | 189 | 56.187 | -10.133 | 82.540 | 1.00 21.08 |
| ATOM | 4508 | CA | SER | B | 189 | 56.203 | -8.782 | 83.061 | 1.00 21.85 |
| ATOM | 4509 | CB | SER | B | 189 | 54.956 | -8.543 | 83.908 | 1.00 25.95 |
| ATOM | 4510 | OG | SER | B | 189 | 54.988 | -7.252 | 84.475 | 1.00 21.91 |
| ATOM | 4511 | C | SER | B | 189 | 57.423 | -8.420 | 83.883 | 1.00 23.62 |

Fig. 18-68

| ATOM | 4512 | O | SER | B | 189 | 57.829 | -9.174 | 84.766 | 1.00 | 18.61 |
|---|---|---|---|---|---|---|---|---|---|---|
| ATOM | 4513 | N | LEU | B | 190 | 58.020 | -7.269 | 83.569 | 1.00 | 20.83 |
| ATOM | 4514 | CA | LEU | B | 190 | 59.149 | -6.767 | 84.347 | 1.00 | 21.85 |
| ATOM | 4515 | CB | LEU | B | 190 | 60.278 | -6.226 | 83.473 | 1.00 | 22.85 |
| ATOM | 4516 | CG | LEU | B | 190 | 60.964 | -7.089 | 82.413 | 1.00 | 32.59 |
| ATOM | 4517 | CD1 | LEU | B | 190 | 62.337 | -6.479 | 82.140 | 1.00 | 29.27 |
| ATOM | 4518 | CD2 | LEU | B | 190 | 61.136 | -8.511 | 82.879 | 1.00 | 31.88 |
| ATOM | 4519 | C | LEU | B | 190 | 58.505 | -5.613 | 85.085 | 1.00 | 21.28 |
| ATOM | 4520 | O | LEU | B | 190 | 57.695 | -4.897 | 84.501 | 1.00 | 15.72 |
| ATOM | 4521 | N | HIS | B | 191 | 58.857 | -5.421 | 86.351 | 1.00 | 18.16 |
| ATOM | 4522 | CA | HIS | B | 191 | 58.249 | -4.357 | 87.145 | 1.00 | 17.46 |
| ATOM | 4523 | CB | HIS | B | 191 | 56.759 | -4.690 | 87.369 | 1.00 | 16.00 |
| ATOM | 4524 | CG | HIS | B | 191 | 56.517 | -6.085 | 87.880 | 1.00 | 22.14 |
| ATOM | 4525 | CD2 | HIS | B | 191 | 56.341 | -6.551 | 89.143 | 1.00 | 12.25 |
| ATOM | 4526 | ND1 | HIS | B | 191 | 56.372 | -7.179 | 87.049 | 1.00 | 18.02 |
| ATOM | 4527 | CE1 | HIS | B | 191 | 56.119 | -8.256 | 87.775 | 1.00 | 8.17 |
| ATOM | 4528 | NE2 | HIS | B | 191 | 56.094 | -7.902 | 89.049 | 1.00 | 19.79 |
| ATOM | 4529 | C | HIS | B | 191 | 58.945 | -4.197 | 88.484 | 1.00 | 17.41 |
| ATOM | 4530 | O | HIS | B | 191 | 59.769 | -5.029 | 88.867 | 1.00 | 18.74 |
| ATOM | 4531 | N | GLN | B | 192 | 58.618 | -3.114 | 89.182 | 1.00 | 18.20 |
| ATOM | 4532 | CA | GLN | B | 192 | 59.173 | -2.854 | 90.502 | 1.00 | 18.41 |
| ATOM | 4533 | CB | GLN | B | 192 | 58.690 | -1.500 | 91.034 | 1.00 | 20.71 |
| ATOM | 4534 | CG | GLN | B | 192 | 58.871 | -0.334 | 90.072 | 1.00 | 21.49 |
| ATOM | 4535 | CD | GLN | B | 192 | 58.226 | 0.930 | 90.594 | 1.00 | 20.65 |
| ATOM | 4536 | OE1 | GLN | B | 192 | 58.775 | 1.615 | 91.459 | 1.00 | 21.52 |
| ATOM | 4537 | NE2 | GLN | B | 192 | 57.029 | 1.226 | 90.098 | 1.00 | 15.10 |
| ATOM | 4538 | C | GLN | B | 192 | 58.608 | -3.945 | 91.395 | 1.00 | 17.55 |
| ATOM | 4539 | O | GLN | B | 192 | 57.415 | -4.256 | 91.320 | 1.00 | 17.48 |
| ATOM | 4540 | N | SER | B | 193 | 59.447 | -4.522 | 92.240 | 1.00 | 15.71 |
| ATOM | 4541 | CA | SER | B | 193 | 58.986 | -5.574 | 93.143 | 1.00 | 20.58 |
| ATOM | 4542 | CB | SER | B | 193 | 60.093 | -5.963 | 94.120 | 1.00 | 20.71 |
| ATOM | 4543 | OG | SER | B | 193 | 59.571 | -6.804 | 95.138 | 1.00 | 22.55 |
| ATOM | 4544 | C | SER | B | 193 | 57.774 | -5.112 | 93.947 | 1.00 | 21.81 |
| ATOM | 4545 | O | SER | B | 193 | 57.769 | -4.003 | 94.486 | 1.00 | 20.82 |
| ATOM | 4546 | N | PRO | B | 194 | 56.745 | -5.967 | 94.063 | 1.00 | 21.80 |
| ATOM | 4547 | CD | PRO | B | 194 | 56.648 | -7.331 | 93.524 | 1.00 | 24.27 |
| ATOM | 4548 | CA | PRO | B | 194 | 55.524 | -5.643 | 94.812 | 1.00 | 23.58 |
| ATOM | 4549 | CB | PRO | B | 194 | 54.678 | -6.909 | 94.642 | 1.00 | 22.98 |
| ATOM | 4550 | CG | PRO | B | 194 | 55.168 | -7.458 | 93.317 | 1.00 | 26.35 |
| ATOM | 4551 | C | PRO | B | 194 | 55.841 | -5.366 | 96.283 | 1.00 | 25.79 |
| ATOM | 4552 | O | PRO | B | 194 | 55.009 | -4.831 | 97.022 | 1.00 | 27.26 |
| ATOM | 4553 | N | GLU | B | 195 | 57.045 | -5.736 | 96.710 | 1.00 | 23.20 |
| ATOM | 4554 | CA | GLU | B | 195 | 57.428 | -5.514 | 98.093 | 1.00 | 29.56 |
| ATOM | 4555 | CB | GLU | B | 195 | 58.816 | -6.090 | 98.379 | 1.00 | 32.38 |
| ATOM | 4556 | CG | GLU | B | 195 | 58.940 | -7.567 | 98.049 | 1.00 | 45.25 |
| ATOM | 4557 | CD | GLU | B | 195 | 60.206 | -8.189 | 98.613 | 1.00 | 50.44 |
| ATOM | 4558 | OE1 | GLU | B | 195 | 61.290 | -7.580 | 98.471 | 1.00 | 50.51 |
| ATOM | 4559 | OE2 | GLU | B | 195 | 60.118 | -9.297 | 99.184 | 1.00 | 49.77 |
| ATOM | 4560 | C | GLU | B | 195 | 57.414 | -4.035 | 98.425 | 1.00 | 25.11 |
| ATOM | 4561 | O | GLU | B | 195 | 57.095 | -3.659 | 99.551 | 1.00 | 29.05 |
| ATOM | 4562 | N | TYR | B | 196 | 57.729 | -3.191 | 97.445 | 1.00 | 22.90 |
| ATOM | 4563 | CA | TYR | B | 196 | 57.743 | -1.750 | 97.696 | 1.00 | 22.46 |
| ATOM | 4564 | CB | TYR | B | 196 | 59.188 | -1.223 | 97.668 | 1.00 | 22.72 |
| ATOM | 4565 | CG | TYR | B | 196 | 59.855 | -1.234 | 96.301 | 1.00 | 24.17 |
| ATOM | 4566 | CD1 | TYR | B | 196 | 59.639 | -0.203 | 95.385 | 1.00 | 20.87 |
| ATOM | 4567 | CE1 | TYR | B | 196 | 60.229 | -0.222 | 94.118 | 1.00 | 18.31 |
| ATOM | 4568 | CD2 | TYR | B | 196 | 60.684 | -2.289 | 95.916 | 1.00 | 24.63 |
| ATOM | 4569 | CE2 | TYR | B | 196 | 61.276 | -2.318 | 94.648 | 1.00 | 24.39 |
| ATOM | 4570 | CZ | TYR | B | 196 | 61.042 | -1.284 | 93.756 | 1.00 | 23.01 |
| ATOM | 4571 | OH | TYR | B | 196 | 61.592 | -1.328 | 92.492 | 1.00 | 19.86 |
| ATOM | 4572 | C | TYR | B | 196 | 56.896 | -0.938 | 96.725 | 1.00 | 23.54 |
| ATOM | 4573 | O | TYR | B | 196 | 56.779 | 0.275 | 96.869 | 1.00 | 17.53 |
| ATOM | 4574 | N | ALA | B | 197 | 56.293 | -1.589 | 95.740 | 1.00 | 22.11 |
| ATOM | 4575 | CA | ALA | B | 197 | 55.503 | -0.829 | 94.779 | 1.00 | 24.28 |
| ATOM | 4576 | CB | ALA | B | 197 | 56.310 | -0.616 | 93.513 | 1.00 | 23.03 |
| ATOM | 4577 | C | ALA | B | 197 | 54.153 | -1.412 | 94.413 | 1.00 | 22.80 |

Fig. 18-69

```
ATOM   4578  O    ALA B 197      53.910  -2.609  94.549  1.00 17.67
ATOM   4579  N    PHE B 198      53.278  -0.541  93.932  1.00 26.40
ATOM   4580  CA   PHE B 198      51.956  -0.950  93.495  1.00 28.19
ATOM   4581  CB   PHE B 198      51.152   0.263  93.035  1.00 29.51
ATOM   4582  CG   PHE B 198      49.721  -0.050  92.711  1.00 29.50
ATOM   4583  CD1  PHE B 198      48.732   0.100  93.674  1.00 32.77
ATOM   4584  CD2  PHE B 198      49.367  -0.533  91.455  1.00 25.82
ATOM   4585  CE1  PHE B 198      47.410  -0.223  93.394  1.00 36.70
ATOM   4586  CE2  PHE B 198      48.050  -0.858  91.170  1.00 29.29
ATOM   4587  CZ   PHE B 198      47.071  -0.703  92.141  1.00 33.05
ATOM   4588  C    PHE B 198      52.170  -1.858  92.284  1.00 28.28
ATOM   4589  O    PHE B 198      53.045  -1.602  91.456  1.00 27.15
ATOM   4590  N    PRO B 199      51.407  -2.952  92.185  1.00 31.37
ATOM   4591  CD   PRO B 199      51.440  -3.887  91.045  1.00 37.07
ATOM   4592  CA   PRO B 199      50.386  -3.369  93.144  1.00 35.32
ATOM   4593  CB   PRO B 199      49.545  -4.328  92.321  1.00 33.88
ATOM   4594  CG   PRO B 199      50.641  -5.068  91.578  1.00 36.75
ATOM   4595  C    PRO B 199      51.241  -4.082  94.184  1.00 36.93
ATOM   4596  O    PRO B 199      52.308  -4.603  93.860  1.00 50.93
ATOM   4597  N    PHE B 200      50.804  -4.127  95.422  1.00 37.04
ATOM   4598  CA   PHE B 200      51.644  -4.763  96.421  1.00 30.13
ATOM   4599  CB   PHE B 200      51.547  -3.968  97.723  1.00 28.70
ATOM   4600  CG   PHE B 200      51.760  -2.485  97.543  1.00 29.98
ATOM   4601  CD1  PHE B 200      50.717  -1.660  97.137  1.00 28.92
ATOM   4602  CD2  PHE B 200      53.016  -1.919  97.746  1.00 23.60
ATOM   4603  CE1  PHE B 200      50.922  -0.289  96.938  1.00 27.63
ATOM   4604  CE2  PHE B 200      53.229  -0.558  97.547  1.00 23.56
ATOM   4605  CZ   PHE B 200      52.182   0.260  97.143  1.00 28.37
ATOM   4606  C    PHE B 200      51.296  -6.227  96.658  1.00 25.51
ATOM   4607  O    PHE B 200      52.112  -6.984  97.167  1.00 20.92
ATOM   4608  N    GLU B 201      50.094  -6.618  96.252  1.00 27.41
ATOM   4609  CA   GLU B 201      49.576  -7.972  96.454  1.00 31.98
ATOM   4610  CB   GLU B 201      48.056  -7.928  96.487  1.00 31.57
ATOM   4611  CG   GLU B 201      47.486  -6.935  97.449  1.00 39.17
ATOM   4612  CD   GLU B 201      45.987  -6.853  97.316  1.00 40.31
ATOM   4613  OE1  GLU B 201      45.332  -7.902  97.500  1.00 38.90
ATOM   4614  OE2  GLU B 201      45.475  -5.751  97.019  1.00 35.04
ATOM   4615  C    GLU B 201      49.979  -9.018  95.422  1.00 30.83
ATOM   4616  O    GLU B 201      49.901 -10.219  95.690  1.00 26.34
ATOM   4617  N    LYS B 202      50.362  -8.573  94.234  1.00 24.95
ATOM   4618  CA   LYS B 202      50.764  -9.501  93.195  1.00 22.79
ATOM   4619  CB   LYS B 202      49.588  -9.773  92.258  1.00 25.12
ATOM   4620  CG   LYS B 202      48.484 -10.523  93.000  1.00 35.38
ATOM   4621  CD   LYS B 202      47.431 -11.099  92.103  1.00 38.67
ATOM   4622  CE   LYS B 202      46.498 -11.998  92.903  1.00 40.98
ATOM   4623  NZ   LYS B 202      45.491 -12.659  92.028  1.00 46.65
ATOM   4624  C    LYS B 202      51.975  -9.007  92.435  1.00 24.62
ATOM   4625  O    LYS B 202      52.355  -7.838  92.549  1.00 21.83
ATOM   4626  N    GLY B 203      52.598  -9.910  91.684  1.00 17.60
ATOM   4627  CA   GLY B 203      53.779  -9.545  90.928  1.00 19.41
ATOM   4628  C    GLY B 203      55.014 -10.297  91.396  1.00 20.36
ATOM   4629  O    GLY B 203      56.101 -10.070  90.888  1.00 23.83
ATOM   4630  N    PHE B 204      54.855 -11.201  92.358  1.00 24.82
ATOM   4631  CA   PHE B 204      55.992 -11.957  92.859  1.00 24.24
ATOM   4632  CB   PHE B 204      55.690 -12.567  94.236  1.00 22.72
ATOM   4633  CG   PHE B 204      55.485 -11.549  95.322  1.00 25.26
ATOM   4634  CD1  PHE B 204      54.235 -10.977  95.535  1.00 23.80
ATOM   4635  CD2  PHE B 204      56.551 -11.159  96.133  1.00 20.25
ATOM   4636  CE1  PHE B 204      54.048 -10.036  96.545  1.00 29.98
ATOM   4637  CE2  PHE B 204      56.377 -10.221  97.141  1.00 24.40
ATOM   4638  CZ   PHE B 204      55.124  -9.658  97.350  1.00 25.54
ATOM   4639  C    PHE B 204      56.412 -13.057  91.894  1.00 25.86
ATOM   4640  O    PHE B 204      55.613 -13.540  91.091  1.00 20.65
ATOM   4641  N    LEU B 205      57.676 -13.449  91.986  1.00 24.25
ATOM   4642  CA   LEU B 205      58.233 -14.472  91.114  1.00 30.66
ATOM   4643  CB   LEU B 205      59.723 -14.637  91.413  1.00 34.01
```

Fig. 18-70

| | | | | | | | | | |
|---|---|---|---|---|---|---|---|---|---|
| ATOM | 4644 | CG | LEU | B | 205 | 60.495 | -15.669 | 90.592 | 1.00 34.12 |
| ATOM | 4645 | CD1 | LEU | B | 205 | 60.356 | -15.382 | 89.109 | 1.00 32.95 |
| ATOM | 4646 | CD2 | LEU | B | 205 | 61.957 | -15.629 | 91.005 | 1.00 36.49 |
| ATOM | 4647 | C | LEU | B | 205 | 57.535 | -15.827 | 91.205 | 1.00 30.51 |
| ATOM | 4648 | O | LEU | B | 205 | 57.467 | -16.562 | 90.220 | 1.00 25.89 |
| ATOM | 4649 | N | GLU | B | 206 | 57.010 | -16.147 | 92.382 | 1.00 30.43 |
| ATOM | 4650 | CA | GLU | B | 206 | 56.338 | -17.423 | 92.605 | 1.00 30.64 |
| ATOM | 4651 | CB | GLU | B | 206 | 56.025 | -17.601 | 94.093 | 1.00 34.77 |
| ATOM | 4652 | CG | GLU | B | 206 | 57.227 | -17.512 | 95.033 | 1.00 42.50 |
| ATOM | 4653 | CD | GLU | B | 206 | 57.718 | -16.084 | 95.270 | 1.00 45.76 |
| ATOM | 4654 | OE1 | GLU | B | 206 | 58.228 | -15.438 | 94.333 | 1.00 42.62 |
| ATOM | 4655 | OE2 | GLU | B | 206 | 57.585 | -15.602 | 96.413 | 1.00 50.22 |
| ATOM | 4656 | C | GLU | B | 206 | 55.045 | -17.587 | 91.811 | 1.00 31.13 |
| ATOM | 4657 | O | GLU | B | 206 | 54.607 | -18.708 | 91.563 | 1.00 28.18 |
| ATOM | 4658 | N | GLU | B | 207 | 54.430 | -16.472 | 91.425 | 1.00 25.16 |
| ATOM | 4659 | CA | GLU | B | 207 | 53.178 | -16.499 | 90.664 | 1.00 28.78 |
| ATOM | 4660 | CB | GLU | B | 207 | 52.546 | -15.107 | 90.695 | 1.00 30.76 |
| ATOM | 4661 | CG | GLU | B | 207 | 52.121 | -14.659 | 92.093 | 1.00 29.39 |
| ATOM | 4662 | CD | GLU | B | 207 | 52.057 | -13.151 | 92.230 | 1.00 27.87 |
| ATOM | 4663 | OE1 | GLU | B | 207 | 51.656 | -12.477 | 91.261 | 1.00 24.38 |
| ATOM | 4664 | OE2 | GLU | B | 207 | 52.389 | -12.636 | 93.316 | 1.00 25.36 |
| ATOM | 4665 | C | GLU | B | 207 | 53.453 | -16.922 | 89.224 | 1.00 29.48 |
| ATOM | 4666 | O | GLU | B | 207 | 53.658 | -16.077 | 88.351 | 1.00 27.48 |
| ATOM | 4667 | N | ILE | B | 208 | 53.442 | -18.230 | 88.976 | 1.00 26.67 |
| ATOM | 4668 | CA | ILE | B | 208 | 53.735 | -18.754 | 87.646 | 1.00 32.60 |
| ATOM | 4669 | CB | ILE | B | 208 | 54.789 | -19.877 | 87.740 | 1.00 34.26 |
| ATOM | 4670 | CG2 | ILE | B | 208 | 55.239 | -20.296 | 86.352 | 1.00 41.65 |
| ATOM | 4671 | CG1 | ILE | B | 208 | 56.008 | -19.404 | 88.532 | 1.00 36.07 |
| ATOM | 4672 | CD1 | ILE | B | 208 | 56.814 | -18.338 | 87.851 | 1.00 45.18 |
| ATOM | 4673 | C | ILE | B | 208 | 52.522 | -19.289 | 86.870 | 1.00 32.26 |
| ATOM | 4674 | O | ILE | B | 208 | 52.668 | -19.799 | 85.759 | 1.00 27.43 |
| ATOM | 4675 | N | GLY | B | 209 | 51.328 | -19.165 | 87.442 | 1.00 32.60 |
| ATOM | 4676 | CA | GLY | B | 209 | 50.139 | -19.652 | 86.760 | 1.00 35.07 |
| ATOM | 4677 | C | GLY | B | 209 | 49.565 | -20.892 | 87.420 | 1.00 36.19 |
| ATOM | 4678 | O | GLY | B | 209 | 50.230 | -21.524 | 88.235 | 1.00 31.61 |
| ATOM | 4679 | N | GLU | B | 210 | 48.335 | -21.245 | 87.066 | 1.00 36.98 |
| ATOM | 4680 | CA | GLU | B | 210 | 47.677 | -22.412 | 87.647 | 1.00 40.60 |
| ATOM | 4681 | CB | GLU | B | 210 | 46.633 | -21.964 | 88.672 | 1.00 37.98 |
| ATOM | 4682 | CG | GLU | B | 210 | 45.446 | -21.234 | 88.058 | 1.00 42.78 |
| ATOM | 4683 | CD | GLU | B | 210 | 44.470 | -20.717 | 89.098 | 1.00 48.41 |
| ATOM | 4684 | OE1 | GLU | B | 210 | 43.400 | -20.202 | 88.709 | 1.00 51.03 |
| ATOM | 4685 | OE2 | GLU | B | 210 | 44.778 | -20.814 | 90.306 | 1.00 49.90 |
| ATOM | 4686 | C | GLU | B | 210 | 46.996 | -23.248 | 86.564 | 1.00 39.48 |
| ATOM | 4687 | O | GLU | B | 210 | 46.709 | -22.751 | 85.471 | 1.00 33.65 |
| ATOM | 4688 | N | GLY | B | 211 | 46.736 | -24.515 | 86.876 | 1.00 39.18 |
| ATOM | 4689 | CA | GLY | B | 211 | 46.087 | -25.399 | 85.923 | 1.00 38.43 |
| ATOM | 4690 | C | GLY | B | 211 | 46.877 | -25.500 | 84.637 | 1.00 40.29 |
| ATOM | 4691 | O | GLY | B | 211 | 48.101 | -25.610 | 84.666 | 1.00 39.39 |
| ATOM | 4692 | N | LYS | B | 212 | 46.187 | -25.458 | 83.504 | 1.00 40.90 |
| ATOM | 4693 | CA | LYS | B | 212 | 46.864 | -25.538 | 82.219 | 1.00 43.53 |
| ATOM | 4694 | CB | LYS | B | 212 | 45.842 | -25.548 | 81.080 | 1.00 47.87 |
| ATOM | 4695 | CG | LYS | B | 212 | 44.795 | -26.665 | 81.144 | 1.00 53.09 |
| ATOM | 4696 | CD | LYS | B | 212 | 45.398 | -28.076 | 81.130 | 1.00 58.61 |
| ATOM | 4697 | CE | LYS | B | 212 | 46.069 | -28.454 | 82.452 | 1.00 59.78 |
| ATOM | 4698 | NZ | LYS | B | 212 | 46.570 | -29.825 | 82.420 | 1.00 62.17 |
| ATOM | 4699 | C | LYS | B | 212 | 47.823 | -24.363 | 82.040 | 1.00 38.84 |
| ATOM | 4700 | O | LYS | B | 212 | 48.797 | -24.457 | 81.295 | 1.00 40.33 |
| ATOM | 4701 | N | GLY | B | 213 | 47.543 | -23.262 | 82.731 | 1.00 37.20 |
| ATOM | 4702 | CA | GLY | B | 213 | 48.384 | -22.081 | 82.627 | 1.00 34.66 |
| ATOM | 4703 | C | GLY | B | 213 | 49.625 | -22.107 | 83.505 | 1.00 37.09 |
| ATOM | 4704 | O | GLY | B | 213 | 50.425 | -21.165 | 83.489 | 1.00 25.85 |
| ATOM | 4705 | N | LYS | B | 214 | 49.794 | -23.180 | 84.273 | 1.00 33.33 |
| ATOM | 4706 | CA | LYS | B | 214 | 50.953 | -23.297 | 85.148 | 1.00 37.90 |
| ATOM | 4707 | CB | LYS | B | 214 | 50.886 | -24.598 | 85.954 | 1.00 38.89 |
| ATOM | 4708 | CG | LYS | B | 214 | 52.032 | -24.786 | 86.938 | 1.00 39.29 |
| ATOM | 4709 | CD | LYS | B | 214 | 51.876 | -26.094 | 87.704 | 1.00 43.60 |

Fig. 18-71

| | | | | | | | | | |
|---|---|---|---|---|---|---|---|---|---|
| ATOM | 4710 | CE | LYS | B | 214 | 53.047 | -26.334 | 88.640 | 1.00 47.36 |
| ATOM | 4711 | NZ | LYS | B | 214 | 53.165 | -25.264 | 89.666 | 1.00 54.03 |
| ATOM | 4712 | C | LYS | B | 214 | 52.209 | -23.275 | 84.291 | 1.00 34.16 |
| ATOM | 4713 | O | LYS | B | 214 | 52.404 | -24.136 | 83.438 | 1.00 34.70 |
| ATOM | 4714 | N | GLY | B | 215 | 53.057 | -22.279 | 84.523 | 1.00 33.58 |
| ATOM | 4715 | CA | GLY | B | 215 | 54.275 | -22.152 | 83.743 | 1.00 28.27 |
| ATOM | 4716 | C | GLY | B | 215 | 54.104 | -21.155 | 82.605 | 1.00 31.02 |
| ATOM | 4717 | O | GLY | B | 215 | 55.033 | -20.911 | 81.833 | 1.00 23.68 |
| ATOM | 4718 | N | TYR | B | 216 | 52.918 | -20.564 | 82.493 | 1.00 22.45 |
| ATOM | 4719 | CA | TYR | B | 216 | 52.683 | -19.605 | 81.426 | 1.00 24.03 |
| ATOM | 4720 | CB | TYR | B | 216 | 51.458 | -20.013 | 80.603 | 1.00 17.60 |
| ATOM | 4721 | CG | TYR | B | 216 | 51.682 | -21.291 | 79.806 | 1.00 25.96 |
| ATOM | 4722 | CD1 | TYR | B | 216 | 51.692 | -22.538 | 80.435 | 1.00 21.41 |
| ATOM | 4723 | CE1 | TYR | B | 216 | 51.988 | -23.704 | 79.729 | 1.00 23.78 |
| ATOM | 4724 | CD2 | TYR | B | 216 | 51.970 | -21.242 | 78.439 | 1.00 19.62 |
| ATOM | 4725 | CE2 | TYR | B | 216 | 52.269 | -22.402 | 77.722 | 1.00 26.39 |
| ATOM | 4726 | CZ | TYR | B | 216 | 52.277 | -23.630 | 78.379 | 1.00 29.35 |
| ATOM | 4727 | OH | TYR | B | 216 | 52.577 | -24.782 | 77.690 | 1.00 27.75 |
| ATOM | 4728 | C | TYR | B | 216 | 52.575 | -18.153 | 81.884 | 1.00 24.53 |
| ATOM | 4729 | O | TYR | B | 216 | 52.065 | -17.298 | 81.159 | 1.00 18.99 |
| ATOM | 4730 | N | ASN | B | 217 | 53.052 | -17.886 | 83.098 | 1.00 21.41 |
| ATOM | 4731 | CA | ASN | B | 217 | 53.073 | -16.534 | 83.642 | 1.00 21.23 |
| ATOM | 4732 | CB | ASN | B | 217 | 51.954 | -16.325 | 84.669 | 1.00 16.78 |
| ATOM | 4733 | CG | ASN | B | 217 | 51.882 | -14.889 | 85.162 | 1.00 22.07 |
| ATOM | 4734 | OD1 | ASN | B | 217 | 52.506 | -14.521 | 86.163 | 1.00 23.13 |
| ATOM | 4735 | ND2 | ASN | B | 217 | 51.146 | -14.058 | 84.435 | 1.00 19.26 |
| ATOM | 4736 | C | ASN | B | 217 | 54.437 | -16.339 | 84.291 | 1.00 19.40 |
| ATOM | 4737 | O | ASN | B | 217 | 54.857 | -17.145 | 85.124 | 1.00 19.28 |
| ATOM | 4738 | N | LEU | B | 218 | 55.130 | -15.273 | 83.905 | 1.00 18.65 |
| ATOM | 4739 | CA | LEU | B | 218 | 56.459 | -15.004 | 84.444 | 1.00 16.41 |
| ATOM | 4740 | CB | LEU | B | 218 | 57.512 | -15.244 | 83.368 | 1.00 18.29 |
| ATOM | 4741 | CG | LEU | B | 218 | 58.851 | -15.872 | 83.782 | 1.00 28.15 |
| ATOM | 4742 | CD1 | LEU | B | 218 | 59.873 | -15.563 | 82.695 | 1.00 20.50 |
| ATOM | 4743 | CD2 | LEU | B | 218 | 59.332 | -15.348 | 85.116 | 1.00 22.53 |
| ATOM | 4744 | C | LEU | B | 218 | 56.595 | -13.562 | 84.926 | 1.00 17.89 |
| ATOM | 4745 | O | LEU | B | 218 | 56.469 | -12.627 | 84.128 | 1.00 14.48 |
| ATOM | 4746 | N | ASN | B | 219 | 56.859 | -13.395 | 86.219 | 1.00 14.09 |
| ATOM | 4747 | CA | ASN | B | 219 | 57.044 | -12.075 | 86.821 | 1.00 18.41 |
| ATOM | 4748 | CB | ASN | B | 219 | 56.238 | -11.922 | 88.111 | 1.00 14.64 |
| ATOM | 4749 | CG | ASN | B | 219 | 54.748 | -11.898 | 87.868 | 1.00 27.12 |
| ATOM | 4750 | OD1 | ASN | B | 219 | 54.286 | -11.332 | 86.880 | 1.00 20.21 |
| ATOM | 4751 | ND2 | ASN | B | 219 | 53.982 | -12.480 | 88.787 | 1.00 23.62 |
| ATOM | 4752 | C | ASN | B | 219 | 58.504 | -11.843 | 87.172 | 1.00 20.39 |
| ATOM | 4753 | O | ASN | B | 219 | 59.115 | -12.672 | 87.841 | 1.00 20.41 |
| ATOM | 4754 | N | ILE | B | 220 | 59.056 | -10.717 | 86.729 | 1.00 15.11 |
| ATOM | 4755 | CA | ILE | B | 220 | 60.441 | -10.394 | 87.033 | 1.00 17.16 |
| ATOM | 4756 | CB | ILE | B | 220 | 61.250 | -10.083 | 85.740 | 1.00 20.78 |
| ATOM | 4757 | CG2 | ILE | B | 220 | 62.736 | -9.821 | 86.094 | 1.00 18.08 |
| ATOM | 4758 | CG1 | ILE | B | 220 | 61.138 | -11.250 | 84.748 | 1.00 17.62 |
| ATOM | 4759 | CD1 | ILE | B | 220 | 61.646 | -12.590 | 85.273 | 1.00 20.72 |
| ATOM | 4760 | C | ILE | B | 220 | 60.475 | -9.161 | 87.947 | 1.00 21.17 |
| ATOM | 4761 | O | ILE | B | 220 | 60.565 | -8.036 | 87.470 | 1.00 16.03 |
| ATOM | 4762 | N | PRO | B | 221 | 60.367 | -9.357 | 89.274 | 1.00 21.74 |
| ATOM | 4763 | CD | PRO | B | 221 | 60.135 | -10.619 | 90.000 | 1.00 22.96 |
| ATOM | 4764 | CA | PRO | B | 221 | 60.394 | -8.225 | 90.213 | 1.00 19.16 |
| ATOM | 4765 | CB | PRO | B | 221 | 59.947 | -8.869 | 91.523 | 1.00 19.40 |
| ATOM | 4766 | CG | PRO | B | 221 | 60.564 | -10.251 | 91.407 | 1.00 23.02 |
| ATOM | 4767 | C | PRO | B | 221 | 61.799 | -7.634 | 90.289 | 1.00 22.42 |
| ATOM | 4768 | O | PRO | B | 221 | 62.780 | -8.369 | 90.425 | 1.00 20.71 |
| ATOM | 4769 | N | LEU | B | 222 | 61.899 | -6.309 | 90.202 | 1.00 22.74 |
| ATOM | 4770 | CA | LEU | B | 222 | 63.198 | -5.643 | 90.223 | 1.00 21.18 |
| ATOM | 4771 | CB | LEU | B | 222 | 63.453 | -4.993 | 88.850 | 1.00 17.21 |
| ATOM | 4772 | CG | LEU | B | 222 | 63.467 | -6.027 | 87.721 | 1.00 20.26 |
| ATOM | 4773 | CD1 | LEU | B | 222 | 63.453 | -5.354 | 86.361 | 1.00 20.00 |
| ATOM | 4774 | CD2 | LEU | B | 222 | 64.696 | -6.908 | 87.881 | 1.00 21.93 |
| ATOM | 4775 | C | LEU | B | 222 | 63.335 | -4.616 | 91.353 | 1.00 20.04 |

Fig. 18-72

| | | | | | | | | | |
|---|---|---|---|---|---|---|---|---|---|
| ATOM | 4776 | O   | LEU | B | 222 | 62.350 | -4.030 | 91.806 | 1.00 17.58 |
| ATOM | 4777 | N   | PRO | B | 223 | 64.571 | -4.394 | 91.830 | 1.00 19.48 |
| ATOM | 4778 | CD  | PRO | B | 223 | 65.806 | -5.072 | 91.400 | 1.00 16.80 |
| ATOM | 4779 | CA  | PRO | B | 223 | 64.873 | -3.454 | 92.915 | 1.00 20.38 |
| ATOM | 4780 | CB  | PRO | B | 223 | 66.274 | -3.881 | 93.327 | 1.00 26.11 |
| ATOM | 4781 | CG  | PRO | B | 223 | 66.884 | -4.161 | 91.973 | 1.00 19.74 |
| ATOM | 4782 | C   | PRO | B | 223 | 64.818 | -1.971 | 92.553 | 1.00 21.39 |
| ATOM | 4783 | O   | PRO | B | 223 | 64.815 | -1.598 | 91.380 | 1.00 17.16 |
| ATOM | 4784 | N   | LYS | B | 224 | 64.798 | -1.142 | 93.589 | 1.00 20.65 |
| ATOM | 4785 | CA  | LYS | B | 224 | 64.755 | 0.311  | 93.462 | 1.00 27.00 |
| ATOM | 4786 | CB  | LYS | B | 224 | 64.577 | 0.938  | 94.844 | 1.00 36.47 |
| ATOM | 4787 | CG  | LYS | B | 224 | 63.415 | 0.389  | 95.651 | 1.00 37.72 |
| ATOM | 4788 | CD  | LYS | B | 224 | 63.541 | 0.833  | 97.101 | 1.00 42.06 |
| ATOM | 4789 | CE  | LYS | B | 224 | 62.420 | 0.276  | 97.955 | 1.00 45.18 |
| ATOM | 4790 | NZ  | LYS | B | 224 | 62.645 | 0.570  | 99.399 | 1.00 46.30 |
| ATOM | 4791 | C   | LYS | B | 224 | 66.071 | 0.808  | 92.874 | 1.00 27.01 |
| ATOM | 4792 | O   | LYS | B | 224 | 67.098 | 0.139  | 92.995 | 1.00 21.54 |
| ATOM | 4793 | N   | GLY | B | 225 | 66.038 | 1.989  | 92.259 | 1.00 22.66 |
| ATOM | 4794 | CA  | GLY | B | 225 | 67.239 | 2.565  | 91.669 | 1.00 25.67 |
| ATOM | 4795 | C   | GLY | B | 225 | 67.768 | 1.809  | 90.459 | 1.00 24.95 |
| ATOM | 4796 | O   | GLY | B | 225 | 68.917 | 1.975  | 90.069 | 1.00 26.83 |
| ATOM | 4797 | N   | LEU | B | 226 | 66.926 | 0.980  | 89.855 | 1.00 21.79 |
| ATOM | 4798 | CA  | LEU | B | 226 | 67.319 | 0.180  | 88.692 | 1.00 22.91 |
| ATOM | 4799 | CB  | LEU | B | 226 | 66.067 | -0.473 | 88.099 | 1.00 23.29 |
| ATOM | 4800 | CG  | LEU | B | 226 | 66.238 | -1.605 | 87.091 | 1.00 26.71 |
| ATOM | 4801 | CD1 | LEU | B | 226 | 66.846 | -2.804 | 87.813 | 1.00 26.44 |
| ATOM | 4802 | CD2 | LEU | B | 226 | 64.877 | -1.997 | 86.508 | 1.00 22.96 |
| ATOM | 4803 | C   | LEU | B | 226 | 68.008 | 1.017  | 87.603 | 1.00 22.66 |
| ATOM | 4804 | O   | LEU | B | 226 | 67.517 | 2.087  | 87.250 | 1.00 20.19 |
| ATOM | 4805 | N   | ASN | B | 227 | 69.134 | 0.549  | 87.060 | 1.00 15.52 |
| ATOM | 4806 | CA  | ASN | B | 227 | 69.794 | 1.317  | 85.998 | 1.00 19.49 |
| ATOM | 4807 | CB  | ASN | B | 227 | 71.304 | 1.474  | 86.270 | 1.00 20.43 |
| ATOM | 4808 | CG  | ASN | B | 227 | 72.062 | 0.161  | 86.206 | 1.00 28.97 |
| ATOM | 4809 | OD1 | ASN | B | 227 | 72.015 | -0.546 | 85.199 | 1.00 24.30 |
| ATOM | 4810 | ND2 | ASN | B | 227 | 72.786 | -0.160 | 87.276 | 1.00 20.88 |
| ATOM | 4811 | C   | ASN | B | 227 | 69.548 | 0.671  | 84.630 | 1.00 21.26 |
| ATOM | 4812 | O   | ASN | B | 227 | 69.004 | -0.432 | 84.555 | 1.00 18.90 |
| ATOM | 4813 | N   | ASP | B | 228 | 69.949 | 1.347  | 83.552 | 1.00 20.98 |
| ATOM | 4814 | CA  | ASP | B | 228 | 69.720 | 0.817  | 82.208 | 1.00 22.61 |
| ATOM | 4815 | CB  | ASP | B | 228 | 70.270 | 1.753  | 81.126 | 1.00 23.46 |
| ATOM | 4816 | CG  | ASP | B | 228 | 69.596 | 3.113  | 81.119 | 1.00 26.12 |
| ATOM | 4817 | OD1 | ASP | B | 228 | 68.387 | 3.193  | 81.415 | 1.00 26.75 |
| ATOM | 4818 | OD2 | ASP | B | 228 | 70.276 | 4.101  | 80.773 | 1.00 30.22 |
| ATOM | 4819 | C   | ASP | B | 228 | 70.286 | -0.573 | 81.952 | 1.00 23.49 |
| ATOM | 4820 | O   | ASP | B | 228 | 69.651 | -1.390 | 81.288 | 1.00 19.31 |
| ATOM | 4821 | N   | ASN | B | 229 | 71.484 | -0.836 | 82.453 | 1.00 22.24 |
| ATOM | 4822 | CA  | ASN | B | 229 | 72.111 | -2.135 | 82.250 | 1.00 23.30 |
| ATOM | 4823 | CB  | ASN | B | 229 | 73.562 | -2.101 | 82.737 | 1.00 20.99 |
| ATOM | 4824 | CG  | ASN | B | 229 | 74.441 | -1.237 | 81.859 | 1.00 25.71 |
| ATOM | 4825 | OD1 | ASN | B | 229 | 74.644 | -1.538 | 80.678 | 1.00 26.40 |
| ATOM | 4826 | ND2 | ASN | B | 229 | 74.955 | -0.151 | 82.417 | 1.00 27.44 |
| ATOM | 4827 | C   | ASN | B | 229 | 71.341 | -3.252 | 82.943 | 1.00 23.74 |
| ATOM | 4828 | O   | ASN | B | 229 | 71.207 | -4.346 | 82.402 | 1.00 20.51 |
| ATOM | 4829 | N   | GLU | B | 230 | 70.832 | -2.976 | 84.139 | 1.00 23.06 |
| ATOM | 4830 | CA  | GLU | B | 230 | 70.069 | -3.977 | 84.874 | 1.00 23.01 |
| ATOM | 4831 | CB  | GLU | B | 230 | 69.799 | -3.480 | 86.297 | 1.00 24.73 |
| ATOM | 4832 | CG  | GLU | B | 230 | 71.069 | -3.201 | 87.087 | 1.00 27.28 |
| ATOM | 4833 | CD  | GLU | B | 230 | 70.792 | -2.649 | 88.470 | 1.00 27.47 |
| ATOM | 4834 | OE1 | GLU | B | 230 | 70.086 | -1.625 | 88.569 | 1.00 27.87 |
| ATOM | 4835 | OE2 | GLU | B | 230 | 71.286 | -3.232 | 89.455 | 1.00 26.79 |
| ATOM | 4836 | C   | GLU | B | 230 | 68.749 | -4.281 | 84.146 | 1.00 24.25 |
| ATOM | 4837 | O   | GLU | B | 230 | 68.347 | -5.445 | 84.022 | 1.00 15.89 |
| ATOM | 4838 | N   | PHE | B | 231 | 68.091 | -3.242 | 83.637 | 1.00 21.46 |
| ATOM | 4839 | CA  | PHE | B | 231 | 66.814 | -3.429 | 82.933 | 1.00 22.84 |
| ATOM | 4840 | CB  | PHE | B | 231 | 66.210 | -2.079 | 82.529 | 1.00 23.96 |
| ATOM | 4841 | CG  | PHE | B | 231 | 64.803 | -2.182 | 81.975 | 1.00 26.13 |

Fig. 18-73

```
ATOM   4842  CD1  PHE B 231      63.738   -2.514  82.805  1.00 25.00
ATOM   4843  CD2  PHE B 231      64.550   -1.956  80.627  1.00 22.93
ATOM   4844  CE1  PHE B 231      62.440   -2.618  82.304  1.00 25.03
ATOM   4845  CE2  PHE B 231      63.250   -2.059  80.114  1.00 27.46
ATOM   4846  CZ   PHE B 231      62.196   -2.390  80.957  1.00 20.25
ATOM   4847  C    PHE B 231      66.978   -4.288  81.677  1.00 23.14
ATOM   4848  O    PHE B 231      66.221   -5.239  81.464  1.00 20.02
ATOM   4849  N    LEU B 232      67.963   -3.952  80.845  1.00 22.02
ATOM   4850  CA   LEU B 232      68.200   -4.697  79.614  1.00 19.97
ATOM   4851  CB   LEU B 232      69.192   -3.942  78.734  1.00 24.99
ATOM   4852  CG   LEU B 232      68.665   -2.581  78.263  1.00 29.73
ATOM   4853  CD1  LEU B 232      69.746   -1.856  77.454  1.00 28.11
ATOM   4854  CD2  LEU B 232      67.409   -2.784  77.414  1.00 26.54
ATOM   4855  C    LEU B 232      68.688   -6.119  79.898  1.00 19.25
ATOM   4856  O    LEU B 232      68.365   -7.051  79.162  1.00 19.49
ATOM   4857  N    PHE B 233      69.468   -6.280  80.962  1.00 20.50
ATOM   4858  CA   PHE B 233      69.950   -7.599  81.378  1.00 20.70
ATOM   4859  CB   PHE B 233      70.825   -7.471  82.632  1.00 23.75
ATOM   4860  CG   PHE B 233      71.217   -8.790  83.239  1.00 28.58
ATOM   4861  CD1  PHE B 233      72.285   -9.519  82.731  1.00 30.48
ATOM   4862  CD2  PHE B 233      70.481   -9.328  84.294  1.00 25.32
ATOM   4863  CE1  PHE B 233      72.617  -10.762  83.262  1.00 31.87
ATOM   4864  CE2  PHE B 233      70.803  -10.573  84.832  1.00 31.26
ATOM   4865  CZ   PHE B 233      71.871  -11.292  84.317  1.00 32.29
ATOM   4866  C    PHE B 233      68.712   -8.439  81.727  1.00 20.23
ATOM   4867  O    PHE B 233      68.553   -9.567  81.270  1.00 21.56
ATOM   4868  N    ALA B 234      67.842   -7.878  82.560  1.00 21.26
ATOM   4869  CA   ALA B 234      66.626   -8.576  82.963  1.00 19.60
ATOM   4870  CB   ALA B 234      65.835   -7.733  83.950  1.00 19.25
ATOM   4871  C    ALA B 234      65.772   -8.898  81.749  1.00 18.87
ATOM   4872  O    ALA B 234      65.253  -10.010  81.624  1.00 21.91
ATOM   4873  N    LEU B 235      65.634   -7.934  80.845  1.00 20.29
ATOM   4874  CA   LEU B 235      64.822   -8.141  79.652  1.00 19.53
ATOM   4875  CB   LEU B 235      64.773   -6.874  78.795  1.00 24.07
ATOM   4876  CG   LEU B 235      63.465   -6.607  78.024  1.00 27.87
ATOM   4877  CD1  LEU B 235      63.783   -5.813  76.770  1.00 20.77
ATOM   4878  CD2  LEU B 235      62.761   -7.897  77.664  1.00 26.94
ATOM   4879  C    LEU B 235      65.376   -9.276  78.795  1.00 20.79
ATOM   4880  O    LEU B 235      64.648  -10.205  78.431  1.00 18.25
ATOM   4881  N    GLU B 236      66.665   -9.191  78.462  1.00 19.33
ATOM   4882  CA   GLU B 236      67.303  -10.206  77.629  1.00 27.93
ATOM   4883  CB   GLU B 236      68.777   -9.853  77.384  1.00 31.06
ATOM   4884  CG   GLU B 236      68.969   -8.597  76.548  1.00 43.60
ATOM   4885  CD   GLU B 236      70.428   -8.292  76.259  1.00 45.19
ATOM   4886  OE1  GLU B 236      70.697   -7.309  75.538  1.00 48.77
ATOM   4887  OE2  GLU B 236      71.305   -9.032  76.751  1.00 52.72
ATOM   4888  C    GLU B 236      67.205  -11.607  78.209  1.00 24.89
ATOM   4889  O    GLU B 236      66.865  -12.552  77.501  1.00 22.06
ATOM   4890  N    LYS B 237      67.520  -11.748  79.492  1.00 24.20
ATOM   4891  CA   LYS B 237      67.449  -13.058  80.130  1.00 27.10
ATOM   4892  CB   LYS B 237      67.989  -12.984  81.562  1.00 23.43
ATOM   4893  CG   LYS B 237      69.466  -12.641  81.650  1.00 29.46
ATOM   4894  CD   LYS B 237      70.305  -13.683  80.924  1.00 31.65
ATOM   4895  CE   LYS B 237      71.782  -13.356  80.993  1.00 39.70
ATOM   4896  NZ   LYS B 237      72.580  -14.363  80.242  1.00 46.74
ATOM   4897  C    LYS B 237      66.019  -13.615  80.143  1.00 30.92
ATOM   4898  O    LYS B 237      65.789  -14.766  79.763  1.00 31.42
ATOM   4899  N    SER B 238      65.057  -12.806  80.573  1.00 25.86
ATOM   4900  CA   SER B 238      63.677  -13.280  80.620  1.00 27.98
ATOM   4901  CB   SER B 238      62.776  -12.241  81.289  1.00 23.89
ATOM   4902  OG   SER B 238      62.756  -11.028  80.565  1.00 29.27
ATOM   4903  C    SER B 238      63.145  -13.642  79.229  1.00 28.32
ATOM   4904  O    SER B 238      62.387  -14.605  79.089  1.00 29.65
ATOM   4905  N    LEU B 239      63.536  -12.886  78.203  1.00 27.39
ATOM   4906  CA   LEU B 239      63.079  -13.192  76.846  1.00 32.52
ATOM   4907  CB   LEU B 239      63.544  -12.129  75.837  1.00 30.53
```

Fig. 18-74

```
ATOM   4908  CG  LEU B 239      62.833 -10.772  75.895  1.00 36.06
ATOM   4909  CD1 LEU B 239      63.404  -9.836  74.842  1.00 29.64
ATOM   4910  CD2 LEU B 239      61.338 -10.976  75.667  1.00 30.73
ATOM   4911  C   LEU B 239      63.598 -14.563  76.430  1.00 34.15
ATOM   4912  O   LEU B 239      62.879 -15.340  75.803  1.00 33.23
ATOM   4913  N   GLU B 240      64.844 -14.859  76.788  1.00 31.39
ATOM   4914  CA  GLU B 240      65.434 -16.152  76.472  1.00 33.79
ATOM   4915  CB  GLU B 240      66.859 -16.238  77.011  1.00 38.51
ATOM   4916  CG  GLU B 240      67.878 -15.407  76.275  1.00 40.56
ATOM   4917  CD  GLU B 240      69.256 -15.532  76.903  1.00 48.20
ATOM   4918  OE1 GLU B 240      69.685 -16.679  77.161  1.00 45.36
ATOM   4919  OE2 GLU B 240      69.912 -14.492  77.130  1.00 48.21
ATOM   4920  C   GLU B 240      64.604 -17.258  77.108  1.00 33.23
ATOM   4921  O   GLU B 240      64.391 -18.310  76.510  1.00 32.15
ATOM   4922  N   ILE B 241      64.146 -17.017  78.331  1.00 29.72
ATOM   4923  CA  ILE B 241      63.328 -17.989  79.047  1.00 29.85
ATOM   4924  CB  ILE B 241      63.006 -17.489  80.466  1.00 30.42
ATOM   4925  CG2 ILE B 241      62.049 -18.456  81.162  1.00 29.88
ATOM   4926  CG1 ILE B 241      64.309 -17.311  81.254  1.00 29.77
ATOM   4927  CD1 ILE B 241      64.118 -16.760  82.654  1.00 32.92
ATOM   4928  C   ILE B 241      62.016 -18.247  78.298  1.00 34.65
ATOM   4929  O   ILE B 241      61.592 -19.396  78.149  1.00 30.22
ATOM   4930  N   VAL B 242      61.379 -17.178  77.823  1.00 31.16
ATOM   4931  CA  VAL B 242      60.114 -17.312  77.105  1.00 34.55
ATOM   4932  CB  VAL B 242      59.476 -15.937  76.825  1.00 30.77
ATOM   4933  CG1 VAL B 242      58.191 -16.113  76.038  1.00 32.18
ATOM   4934  CG2 VAL B 242      59.201 -15.214  78.140  1.00 31.57
ATOM   4935  C   VAL B 242      60.320 -18.042  75.787  1.00 36.56
ATOM   4936  O   VAL B 242      59.572 -18.959  75.453  1.00 33.93
ATOM   4937  N   LYS B 243      61.337 -17.627  75.042  1.00 38.64
ATOM   4938  CA  LYS B 243      61.659 -18.241  73.760  1.00 44.36
ATOM   4939  CB  LYS B 243      62.966 -17.659  73.214  1.00 48.33
ATOM   4940  CG  LYS B 243      62.810 -16.399  72.386  1.00 53.88
ATOM   4941  CD  LYS B 243      62.185 -16.718  71.036  1.00 53.72
ATOM   4942  CE  LYS B 243      63.056 -17.681  70.242  1.00 54.69
ATOM   4943  NZ  LYS B 243      62.456 -18.025  68.923  1.00 57.75
ATOM   4944  C   LYS B 243      61.793 -19.755  73.824  1.00 43.21
ATOM   4945  O   LYS B 243      61.432 -20.455  72.884  1.00 42.92
ATOM   4946  N   GLU B 244      62.312 -20.257  74.935  1.00 45.77
ATOM   4947  CA  GLU B 244      62.528 -21.687  75.085  1.00 47.72
ATOM   4948  CB  GLU B 244      63.669 -21.925  76.075  1.00 50.89
ATOM   4949  CG  GLU B 244      64.080 -23.378  76.208  1.00 57.16
ATOM   4950  CD  GLU B 244      65.223 -23.564  77.173  1.00 57.74
ATOM   4951  OE1 GLU B 244      66.295 -22.967  76.942  1.00 60.18
ATOM   4952  OE2 GLU B 244      65.049 -24.308  78.160  1.00 61.59
ATOM   4953  C   GLU B 244      61.312 -22.507  75.505  1.00 47.78
ATOM   4954  O   GLU B 244      61.376 -23.736  75.544  1.00 51.39
ATOM   4955  N   VAL B 245      60.200 -21.851  75.805  1.00 43.31
ATOM   4956  CA  VAL B 245      59.019 -22.589  76.230  1.00 43.55
ATOM   4957  CB  VAL B 245      58.867 -22.514  77.771  1.00 45.89
ATOM   4958  CG1 VAL B 245      57.665 -23.322  78.231  1.00 49.90
ATOM   4959  CG2 VAL B 245      60.131 -23.040  78.435  1.00 46.37
ATOM   4960  C   VAL B 245      57.727 -22.115  75.565  1.00 41.01
ATOM   4961  O   VAL B 245      56.659 -22.676  75.798  1.00 39.36
ATOM   4962  N   PHE B 246      57.814 -21.101  74.716  1.00 34.37
ATOM   4963  CA  PHE B 246      56.610 -20.602  74.077  1.00 34.36
ATOM   4964  CB  PHE B 246      55.986 -19.517  74.958  1.00 30.80
ATOM   4965  CG  PHE B 246      54.542 -19.230  74.644  1.00 32.57
ATOM   4966  CD1 PHE B 246      53.548 -20.142  74.989  1.00 27.72
ATOM   4967  CD2 PHE B 246      54.174 -18.048  74.003  1.00 28.20
ATOM   4968  CE1 PHE B 246      52.207 -19.878  74.704  1.00 26.71
ATOM   4969  CE2 PHE B 246      52.836 -17.773  73.713  1.00 29.27
ATOM   4970  CZ  PHE B 246      51.850 -18.689  74.065  1.00 26.18
ATOM   4971  C   PHE B 246      56.904 -20.040  72.682  1.00 35.32
ATOM   4972  O   PHE B 246      57.740 -19.153  72.517  1.00 31.73
ATOM   4973  N   GLU B 247      56.205 -20.568  71.683  1.00 37.00
```

Fig. 18-75

```
ATOM   4974  CA  GLU B 247      56.363  -20.137  70.296  1.00 40.73
ATOM   4975  CB  GLU B 247      56.518  -21.347  69.370  1.00 43.38
ATOM   4976  CG  GLU B 247      56.670  -22.702  70.073  1.00 51.49
ATOM   4977  CD  GLU B 247      55.381  -23.214  70.718  1.00 55.29
ATOM   4978  OE1 GLU B 247      54.887  -22.601  71.691  1.00 49.08
ATOM   4979  OE2 GLU B 247      54.859  -24.246  70.241  1.00 60.95
ATOM   4980  C   GLU B 247      55.090  -19.379  69.939  1.00 39.04
ATOM   4981  O   GLU B 247      54.129  -19.960  69.436  1.00 39.49
ATOM   4982  N   PRO B 248      55.076  -18.064  70.182  1.00 35.13
ATOM   4983  CD  PRO B 248      56.188  -17.270  70.733  1.00 33.57
ATOM   4984  CA  PRO B 248      53.935  -17.188  69.916  1.00 36.03
ATOM   4985  CB  PRO B 248      54.375  -15.878  70.562  1.00 35.33
ATOM   4986  CG  PRO B 248      55.844  -15.880  70.233  1.00 32.85
ATOM   4987  C   PRO B 248      53.563  -16.990  68.457  1.00 33.44
ATOM   4988  O   PRO B 248      54.427  -16.808  67.604  1.00 29.38
ATOM   4989  N   GLU B 249      52.263  -17.012  68.182  1.00 32.23
ATOM   4990  CA  GLU B 249      51.773  -16.782  66.828  1.00 29.35
ATOM   4991  CB  GLU B 249      50.374  -17.366  66.645  1.00 31.87
ATOM   4992  CG  GLU B 249      50.284  -18.867  66.787  1.00 28.64
ATOM   4993  CD  GLU B 249      48.847  -19.338  66.747  1.00 33.37
ATOM   4994  OE1 GLU B 249      48.069  -18.917  67.630  1.00 26.38
ATOM   4995  OE2 GLU B 249      48.494  -20.115  65.835  1.00 37.71
ATOM   4996  C   GLU B 249      51.700  -15.273  66.650  1.00 28.25
ATOM   4997  O   GLU B 249      51.776  -14.765  65.537  1.00 21.47
ATOM   4998  N   VAL B 250      51.561  -14.564  67.768  1.00 21.77
ATOM   4999  CA  VAL B 250      51.459  -13.110  67.756  1.00 21.41
ATOM   5000  CB  VAL B 250      50.027  -12.676  67.357  1.00 26.42
ATOM   5001  CG1 VAL B 250      49.037  -13.196  68.378  1.00 20.96
ATOM   5002  CG2 VAL B 250      49.931  -11.166  67.243  1.00 24.68
ATOM   5003  C   VAL B 250      51.757  -12.608  69.168  1.00 22.88
ATOM   5004  O   VAL B 250      51.592  -13.354  70.133  1.00 18.00
ATOM   5005  N   TYR B 251      52.201  -11.359  69.295  1.00 20.28
ATOM   5006  CA  TYR B 251      52.481  -10.823  70.620  1.00 22.33
ATOM   5007  CB  TYR B 251      53.956  -11.043  70.999  1.00 20.67
ATOM   5008  CG  TYR B 251      54.948  -10.045  70.427  1.00 21.89
ATOM   5009  CD1 TYR B 251      55.198   -8.834  71.072  1.00 19.31
ATOM   5010  CE1 TYR B 251      56.129   -7.922  70.562  1.00 23.73
ATOM   5011  CD2 TYR B 251      55.651  -10.321  69.254  1.00 18.72
ATOM   5012  CE2 TYR B 251      56.580   -9.417  68.734  1.00 22.71
ATOM   5013  CZ  TYR B 251      56.813   -8.220  69.390  1.00 27.33
ATOM   5014  OH  TYR B 251      57.705   -7.308  68.865  1.00 23.18
ATOM   5015  C   TYR B 251      52.134   -9.349  70.732  1.00 25.71
ATOM   5016  O   TYR B 251      52.095   -8.622  69.728  1.00 20.14
ATOM   5017  N   LEU B 252      51.834   -8.930  71.958  1.00 21.13
ATOM   5018  CA  LEU B 252      51.533   -7.532  72.252  1.00 24.61
ATOM   5019  CB  LEU B 252      50.154   -7.373  72.897  1.00 22.88
ATOM   5020  CG  LEU B 252      48.915   -7.435  71.996  1.00 23.73
ATOM   5021  CD1 LEU B 252      48.779   -8.792  71.360  1.00 23.18
ATOM   5022  CD2 LEU B 252      47.697   -7.119  72.833  1.00 29.06
ATOM   5023  C   LEU B 252      52.610   -7.044  73.217  1.00 24.77
ATOM   5024  O   LEU B 252      53.064   -7.797  74.076  1.00 23.33
ATOM   5025  N   LEU B 253      53.011   -5.786  73.071  1.00 20.14
ATOM   5026  CA  LEU B 253      54.057   -5.209  73.911  1.00 20.33
ATOM   5027  CB  LEU B 253      55.304   -4.946  73.051  1.00 15.18
ATOM   5028  CG  LEU B 253      56.490   -4.210  73.688  1.00 18.34
ATOM   5029  CD1 LEU B 253      57.062   -5.044  74.829  1.00 14.11
ATOM   5030  CD2 LEU B 253      57.552   -3.953  72.624  1.00 19.60
ATOM   5031  C   LEU B 253      53.550   -3.913  74.536  1.00 20.54
ATOM   5032  O   LEU B 253      53.200   -2.974  73.821  1.00 22.80
ATOM   5033  N   GLN B 254      53.495   -3.858  75.865  1.00 20.37
ATOM   5034  CA  GLN B 254      53.000   -2.654  76.539  1.00 21.77
ATOM   5035  CB  GLN B 254      52.129   -3.040  77.755  1.00 17.85
ATOM   5036  CG  GLN B 254      52.724   -2.815  79.124  1.00 32.51
ATOM   5037  CD  GLN B 254      52.563   -1.396  79.609  1.00 28.19
ATOM   5038  OE1 GLN B 254      51.507   -0.996  80.124  1.00 26.96
ATOM   5039  NE2 GLN B 254      53.603   -0.619  79.432  1.00 16.80
```

Fig. 18-76

| ATOM | 5040 | C | GLN | B | 254 | 54.211 | -1.793 | 76.887 | 1.00 | 20.15 |
|------|------|------|-----|---|-----|--------|--------|--------|------|-------|
| ATOM | 5041 | O | GLN | B | 254 | 55.186 | -2.254 | 77.497 | 1.00 | 20.11 |
| ATOM | 5042 | N | LEU | B | 255 | 54.146 | -0.532 | 76.468 | 1.00 | 19.46 |
| ATOM | 5043 | CA | LEU | B | 255 | 55.268 | 0.386 | 76.614 | 1.00 | 15.99 |
| ATOM | 5044 | CB | LEU | B | 255 | 55.692 | 0.831 | 75.211 | 1.00 | 18.15 |
| ATOM | 5045 | CG | LEU | B | 255 | 56.143 | -0.316 | 74.296 | 1.00 | 21.80 |
| ATOM | 5046 | CD1 | LEU | B | 255 | 56.215 | 0.159 | 72.850 | 1.00 | 16.70 |
| ATOM | 5047 | CD2 | LEU | B | 255 | 57.501 | -0.843 | 74.771 | 1.00 | 13.76 |
| ATOM | 5048 | C | LEU | B | 255 | 55.083 | 1.614 | 77.492 | 1.00 | 21.41 |
| ATOM | 5049 | O | LEU | B | 255 | 55.379 | 2.741 | 77.065 | 1.00 | 18.40 |
| ATOM | 5050 | N | GLY | B | 256 | 54.618 | 1.408 | 78.718 | 1.00 | 16.80 |
| ATOM | 5051 | CA | GLY | B | 256 | 54.456 | 2.519 | 79.634 | 1.00 | 19.90 |
| ATOM | 5052 | C | GLY | B | 256 | 55.816 | 3.181 | 79.818 | 1.00 | 17.68 |
| ATOM | 5053 | O | GLY | B | 256 | 56.854 | 2.514 | 79.841 | 1.00 | 13.96 |
| ATOM | 5054 | N | THR | B | 257 | 55.824 | 4.497 | 79.936 | 1.00 | 19.55 |
| ATOM | 5055 | CA | THR | B | 257 | 57.081 | 5.205 | 80.098 | 1.00 | 19.47 |
| ATOM | 5056 | CB | THR | B | 257 | 57.044 | 6.547 | 79.340 | 1.00 | 21.49 |
| ATOM | 5057 | OG1 | THR | B | 257 | 55.989 | 7.365 | 79.858 | 1.00 | 17.43 |
| ATOM | 5058 | CG2 | THR | B | 257 | 56.780 | 6.311 | 77.850 | 1.00 | 22.49 |
| ATOM | 5059 | C | THR | B | 257 | 57.440 | 5.466 | 81.564 | 1.00 | 20.75 |
| ATOM | 5060 | O | THR | B | 257 | 58.480 | 5.054 | 81.843 | 1.00 | 25.01 |
| ATOM | 5061 | N | ASP | B | 258 | 56.618 | 5.004 | 82.504 | 1.00 | 17.23 |
| ATOM | 5062 | CA | ASP | B | 258 | 56.929 | 5.277 | 83.906 | 1.00 | 17.42 |
| ATOM | 5063 | CB | ASP | B | 258 | 55.744 | 4.940 | 84.846 | 1.00 | 12.75 |
| ATOM | 5064 | CG | ASP | B | 258 | 55.197 | 3.524 | 84.676 | 1.00 | 21.60 |
| ATOM | 5065 | C | ASP | B | 258 | 58.245 | 4.718 | 84.460 | 1.00 | 16.09 |
| ATOM | 5066 | O | ASP | B | 258 | 58.667 | 5.116 | 85.542 | 1.00 | 22.07 |
| ATOM | 5067 | OD1 | ASP | B | 258 | 55.901 | 2.642 | 84.150 | 1.00 | 17.74 |
| ATOM | 5068 | OD2 | ASP | B | 258 | 54.041 | 3.281 | 85.109 | 1.00 | 18.68 |
| ATOM | 5069 | N | PRO | B | 259 | 58.879 | 3.746 | 83.779 | 1.00 | 20.98 |
| ATOM | 5070 | CD | PRO | B | 259 | 58.474 | 2.901 | 82.641 | 1.00 | 17.75 |
| ATOM | 5071 | CA | PRO | B | 259 | 60.154 | 3.257 | 84.321 | 1.00 | 22.63 |
| ATOM | 5072 | CB | PRO | B | 259 | 60.395 | 1.988 | 83.506 | 1.00 | 23.46 |
| ATOM | 5073 | CG | PRO | B | 259 | 59.800 | 2.343 | 82.199 | 1.00 | 27.08 |
| ATOM | 5074 | C | PRO | B | 259 | 61.305 | 4.284 | 84.172 | 1.00 | 23.86 |
| ATOM | 5075 | O | PRO | B | 259 | 62.406 | 4.082 | 84.698 | 1.00 | 24.24 |
| ATOM | 5076 | N | LEU | B | 260 | 61.054 | 5.387 | 83.465 | 1.00 | 20.49 |
| ATOM | 5077 | CA | LEU | B | 260 | 62.080 | 6.417 | 83.262 | 1.00 | 15.17 |
| ATOM | 5078 | CB | LEU | B | 260 | 61.626 | 7.408 | 82.185 | 1.00 | 17.03 |
| ATOM | 5079 | CG | LEU | B | 260 | 61.431 | 6.881 | 80.760 | 1.00 | 16.02 |
| ATOM | 5080 | CD1 | LEU | B | 260 | 60.703 | 7.915 | 79.901 | 1.00 | 17.03 |
| ATOM | 5081 | CD2 | LEU | B | 260 | 62.803 | 6.546 | 80.163 | 1.00 | 18.58 |
| ATOM | 5082 | C | LEU | B | 260 | 62.449 | 7.194 | 84.541 | 1.00 | 22.45 |
| ATOM | 5083 | O | LEU | B | 260 | 61.611 | 7.440 | 85.412 | 1.00 | 17.84 |
| ATOM | 5084 | N | LEU | B | 261 | 63.713 | 7.588 | 84.635 | 1.00 | 22.90 |
| ATOM | 5085 | CA | LEU | B | 261 | 64.219 | 8.332 | 85.782 | 1.00 | 26.34 |
| ATOM | 5086 | CB | LEU | B | 261 | 65.605 | 8.914 | 85.473 | 1.00 | 20.58 |
| ATOM | 5087 | CG | LEU | B | 261 | 66.180 | 9.850 | 86.553 | 1.00 | 28.44 |
| ATOM | 5088 | CD1 | LEU | B | 261 | 66.481 | 9.055 | 87.812 | 1.00 | 29.84 |
| ATOM | 5089 | CD2 | LEU | B | 261 | 67.462 | 10.522 | 86.057 | 1.00 | 32.10 |
| ATOM | 5090 | C | LEU | B | 261 | 63.315 | 9.475 | 86.227 | 1.00 | 27.61 |
| ATOM | 5091 | O | LEU | B | 261 | 62.978 | 9.586 | 87.408 | 1.00 | 24.02 |
| ATOM | 5092 | N | GLU | B | 262 | 62.934 | 10.315 | 85.269 | 1.00 | 23.33 |
| ATOM | 5093 | CA | GLU | B | 262 | 62.126 | 11.490 | 85.530 | 1.00 | 23.38 |
| ATOM | 5094 | CB | GLU | B | 262 | 62.115 | 12.415 | 84.302 | 1.00 | 23.17 |
| ATOM | 5095 | CG | GLU | B | 262 | 63.503 | 12.854 | 83.806 | 1.00 | 28.98 |
| ATOM | 5096 | CD | GLU | B | 262 | 64.179 | 11.831 | 82.902 | 1.00 | 32.26 |
| ATOM | 5097 | CE1 | GLU | B | 262 | 63.702 | 10.673 | 82.838 | 1.00 | 29.28 |
| ATOM | 5098 | OE2 | GLU | B | 262 | 65.201 | 12.186 | 82.264 | 1.00 | 25.42 |
| ATOM | 5099 | C | GLU | B | 262 | 60.693 | 11.249 | 85.976 | 1.00 | 23.25 |
| ATOM | 5100 | O | GLU | B | 262 | 60.013 | 12.192 | 86.368 | 1.00 | 27.63 |
| ATOM | 5101 | N | ASP | B | 263 | 60.219 | 10.011 | 85.927 | 1.00 | 22.25 |
| ATOM | 5102 | CA | ASP | B | 263 | 58.840 | 9.751 | 86.345 | 1.00 | 24.46 |
| ATOM | 5103 | CB | ASP | B | 263 | 58.214 | 8.659 | 85.465 | 1.00 | 20.94 |
| ATOM | 5104 | CG | ASP | B | 263 | 56.710 | 8.543 | 85.659 | 1.00 | 25.30 |
| ATOM | 5105 | OD1 | ASP | B | 263 | 55.995 | 8.318 | 84.656 | 1.00 | 21.82 |

Fig. 18-77

| | | | | | | | | | |
|---|---|---|---|---|---|---|---|---|---|
| ATOM | 5106 | OD2 | ASP | B | 263 | 56.239 | 8.666 | 86.811 | 1.00 18.31 |
| ATOM | 5107 | C | ASP | B | 263 | 58.834 | 9.339 | 87.814 | 1.00 26.39 |
| ATOM | 5108 | O | ASP | B | 263 | 59.437 | 8.335 | 88.179 | 1.00 22.11 |
| ATOM | 5109 | N | TYR | B | 264 | 58.155 | 10.124 | 88.648 | 1.00 25.81 |
| ATOM | 5110 | CA | TYR | B | 264 | 58.101 | 9.864 | 90.084 | 1.00 30.96 |
| ATOM | 5111 | CB | TYR | B | 264 | 57.511 | 11.055 | 90.841 | 1.00 36.80 |
| ATOM | 5112 | CG | TYR | B | 264 | 58.241 | 12.356 | 90.645 | 1.00 46.58 |
| ATOM | 5113 | CD1 | TYR | B | 264 | 57.984 | 13.166 | 89.542 | 1.00 47.03 |
| ATOM | 5114 | CE1 | TYR | B | 264 | 58.654 | 14.370 | 89.364 | 1.00 50.25 |
| ATOM | 5115 | CD2 | TYR | B | 264 | 59.197 | 12.779 | 91.565 | 1.00 50.94 |
| ATOM | 5116 | CE2 | TYR | B | 264 | 59.876 | 13.977 | 91.396 | 1.00 51.28 |
| ATOM | 5117 | CZ | TYR | B | 264 | 59.600 | 14.769 | 90.297 | 1.00 52.21 |
| ATOM | 5118 | OH | TYR | B | 264 | 60.268 | 15.961 | 90.142 | 1.00 49.65 |
| ATOM | 5119 | C | TYR | B | 264 | 57.340 | 8.628 | 90.525 | 1.00 31.04 |
| ATOM | 5120 | O | TYR | B | 264 | 57.514 | 8.181 | 91.657 | 1.00 24.50 |
| ATOM | 5121 | N | LEU | B | 265 | 56.491 | 8.074 | 89.666 | 1.00 26.68 |
| ATOM | 5122 | CA | LEU | B | 265 | 55.744 | 6.900 | 90.086 | 1.00 24.17 |
| ATOM | 5123 | CB | LEU | B | 265 | 54.371 | 6.838 | 89.390 | 1.00 24.69 |
| ATOM | 5124 | CG | LEU | B | 265 | 53.415 | 7.982 | 89.761 | 1.00 26.00 |
| ATOM | 5125 | CD1 | LEU | B | 265 | 51.970 | 7.583 | 89.460 | 1.00 22.21 |
| ATOM | 5126 | CD2 | LEU | B | 265 | 53.530 | 8.281 | 91.238 | 1.00 29.31 |
| ATOM | 5127 | C | LEU | B | 265 | 56.478 | 5.568 | 89.948 | 1.00 25.83 |
| ATOM | 5128 | O | LEU | B | 265 | 55.848 | 4.512 | 89.908 | 1.00 21.74 |
| ATOM | 5129 | N | SER | B | 266 | 57.808 | 5.618 | 89.867 | 1.00 23.30 |
| ATOM | 5130 | CA | SER | B | 266 | 58.608 | 4.398 | 89.813 | 1.00 20.75 |
| ATOM | 5131 | CB | SER | B | 266 | 58.820 | 3.900 | 88.378 | 1.00 19.67 |
| ATOM | 5132 | OG | SER | B | 266 | 59.863 | 4.615 | 87.739 | 1.00 18.11 |
| ATOM | 5133 | C | SER | B | 266 | 59.963 | 4.710 | 90.420 | 1.00 23.01 |
| ATOM | 5134 | O | SER | B | 266 | 60.437 | 5.845 | 90.345 | 1.00 17.74 |
| ATOM | 5135 | N | LYS | B | 267 | 60.590 | 3.707 | 91.023 | 1.00 24.25 |
| ATOM | 5136 | CA | LYS | B | 267 | 61.905 | 3.916 | 91.613 | 1.00 23.79 |
| ATOM | 5137 | CB | LYS | B | 267 | 62.027 | 3.153 | 92.929 | 1.00 23.71 |
| ATOM | 5138 | CG | LYS | B | 267 | 60.989 | 3.582 | 93.960 | 1.00 27.29 |
| ATOM | 5139 | CD | LYS | B | 267 | 61.059 | 5.088 | 94.207 | 1.00 30.33 |
| ATOM | 5140 | CE | LYS | B | 267 | 60.067 | 5.535 | 95.273 | 1.00 30.90 |
| ATOM | 5141 | NZ | LYS | B | 267 | 60.155 | 7.004 | 95.509 | 1.00 33.37 |
| ATOM | 5142 | C | LYS | B | 267 | 62.990 | 3.483 | 90.634 | 1.00 26.41 |
| ATOM | 5143 | O | LYS | B | 267 | 64.153 | 3.317 | 91.016 | 1.00 25.33 |
| ATOM | 5144 | N | PHE | B | 268 | 62.595 | 3.288 | 89.375 | 1.00 22.18 |
| ATOM | 5145 | CA | PHE | B | 268 | 63.529 | 2.919 | 88.318 | 1.00 22.78 |
| ATOM | 5146 | CB | PHE | B | 268 | 62.814 | 2.171 | 87.179 | 1.00 20.55 |
| ATOM | 5147 | CG | PHE | B | 268 | 62.389 | 0.761 | 87.526 | 1.00 19.23 |
| ATOM | 5148 | CD1 | PHE | B | 268 | 61.722 | -0.025 | 86.585 | 1.00 20.72 |
| ATOM | 5149 | CD2 | PHE | B | 268 | 62.673 | 0.207 | 88.773 | 1.00 18.17 |
| ATOM | 5150 | CE1 | PHE | B | 268 | 61.344 | -1.336 | 86.875 | 1.00 18.83 |
| ATOM | 5151 | CE2 | PHE | B | 268 | 62.300 | -1.105 | 89.073 | 1.00 20.05 |
| ATOM | 5152 | CZ | PHE | B | 268 | 61.634 | -1.879 | 88.122 | 1.00 19.70 |
| ATOM | 5153 | C | PHE | B | 268 | 64.114 | 4.222 | 87.785 | 1.00 23.66 |
| ATOM | 5154 | O | PHE | B | 268 | 63.412 | 5.232 | 87.692 | 1.00 19.40 |
| ATOM | 5155 | N | ASN | B | 269 | 65.396 | 4.203 | 87.437 | 1.00 21.96 |
| ATOM | 5156 | CA | ASN | B | 269 | 66.060 | 5.396 | 86.926 | 1.00 25.04 |
| ATOM | 5157 | CB | ASN | B | 269 | 67.243 | 5.783 | 87.824 | 1.00 25.68 |
| ATOM | 5158 | CG | ASN | B | 269 | 66.845 | 5.946 | 89.273 | 1.00 27.04 |
| ATOM | 5159 | OD1 | ASN | B | 269 | 65.832 | 6.557 | 89.579 | 1.00 28.81 |
| ATOM | 5160 | ND2 | ASN | B | 269 | 67.659 | 5.419 | 90.176 | 1.00 31.12 |
| ATOM | 5161 | C | ASN | B | 269 | 66.579 | 5.151 | 85.523 | 1.00 25.87 |
| ATOM | 5162 | O | ASN | B | 269 | 67.769 | 5.336 | 85.268 | 1.00 24.58 |
| ATOM | 5163 | N | LEU | B | 270 | 65.695 | 4.757 | 84.611 | 1.00 21.37 |
| ATOM | 5164 | CA | LEU | B | 270 | 66.116 | 4.462 | 83.241 | 1.00 16.35 |
| ATOM | 5165 | CB | LEU | B | 270 | 65.176 | 3.426 | 82.610 | 1.00 24.12 |
| ATOM | 5166 | CG | LEU | B | 270 | 64.909 | 2.144 | 83.412 | 1.00 27.89 |
| ATOM | 5167 | CD1 | LEU | B | 270 | 64.181 | 1.136 | 82.515 | 1.00 23.01 |
| ATOM | 5168 | CD2 | LEU | B | 270 | 66.221 | 1.547 | 83.904 | 1.00 23.92 |
| ATOM | 5169 | C | LEU | B | 270 | 66.184 | 5.682 | 82.337 | 1.00 20.06 |
| ATOM | 5170 | O | LEU | B | 270 | 65.654 | 6.761 | 82.663 | 1.00 16.34 |
| ATOM | 5171 | N | SER | B | 271 | 66.839 | 5.497 | 81.193 | 1.00 20.07 |

Fig. 18-78

| | | | | | | | | | |
|---|---|---|---|---|---|---|---|---|---|
| ATOM | 5172 | CA | SER | B | 271 | 66.989 | 6.546 | 80.200 | 1.00 21.20 |
| ATOM | 5173 | CB | SER | B | 271 | 68.437 | 6.621 | 79.714 | 1.00 21.80 |
| ATOM | 5174 | OG | SER | B | 271 | 68.772 | 5.485 | 78.921 | 1.00 21.47 |
| ATOM | 5175 | C | SER | B | 271 | 66.106 | 6.228 | 79.000 | 1.00 22.83 |
| ATOM | 5176 | O | SER | B | 271 | 65.631 | 5.102 | 78.854 | 1.00 16.12 |
| ATOM | 5177 | N | ASN | B | 272 | 65.916 | 7.238 | 78.154 | 1.00 20.84 |
| ATOM | 5178 | CA | ASN | B | 272 | 65.152 | 7.156 | 76.906 | 1.00 27.82 |
| ATOM | 5179 | CB | ASN | B | 272 | 65.263 | 8.478 | 76.123 | 1.00 30.30 |
| ATOM | 5180 | CG | ASN | B | 272 | 64.198 | 9.456 | 76.475 | 1.00 37.83 |
| ATOM | 5181 | OD1 | ASN | B | 272 | 64.167 | 10.575 | 75.946 | 1.00 37.72 |
| ATOM | 5182 | ND2 | ASN | B | 272 | 63.299 | 9.052 | 77.360 | 1.00 41.69 |
| ATOM | 5183 | C | ASN | B | 272 | 65.701 | 6.088 | 75.974 | 1.00 26.88 |
| ATOM | 5184 | O | ASN | B | 272 | 64.967 | 5.280 | 75.412 | 1.00 23.12 |
| ATOM | 5185 | N | VAL | B | 273 | 67.012 | 6.160 | 75.774 | 1.00 20.40 |
| ATOM | 5186 | CA | VAL | B | 273 | 67.745 | 5.260 | 74.899 | 1.00 27.34 |
| ATOM | 5187 | CB | VAL | B | 273 | 69.225 | 5.705 | 74.805 | 1.00 30.40 |
| ATOM | 5188 | CG1 | VAL | B | 273 | 70.036 | 4.691 | 74.029 | 1.00 34.98 |
| ATOM | 5189 | CG2 | VAL | B | 273 | 69.299 | 7.057 | 74.115 | 1.00 33.57 |
| ATOM | 5190 | C | VAL | B | 273 | 67.664 | 3.812 | 75.343 | 1.00 24.23 |
| ATOM | 5191 | O | VAL | B | 273 | 67.590 | 2.913 | 74.513 | 1.00 24.19 |
| ATOM | 5192 | N | ALA | B | 274 | 67.690 | 3.580 | 76.648 | 1.00 20.96 |
| ATOM | 5193 | CA | ALA | B | 274 | 67.589 | 2.220 | 77.151 | 1.00 18.12 |
| ATOM | 5194 | CB | ALA | B | 274 | 67.858 | 2.195 | 78.646 | 1.00 19.09 |
| ATOM | 5195 | C | ALA | B | 274 | 66.172 | 1.729 | 76.863 | 1.00 18.23 |
| ATOM | 5196 | O | ALA | B | 274 | 65.962 | 0.567 | 76.525 | 1.00 20.77 |
| ATOM | 5197 | N | PHE | B | 275 | 65.207 | 2.631 | 77.003 | 1.00 18.50 |
| ATOM | 5198 | CA | PHE | B | 275 | 63.802 | 2.310 | 76.761 | 1.00 21.25 |
| ATOM | 5199 | CB | PHE | B | 275 | 62.941 | 3.546 | 77.037 | 1.00 22.24 |
| ATOM | 5200 | CG | PHE | B | 275 | 61.466 | 3.303 | 76.921 | 1.00 24.72 |
| ATOM | 5201 | CD1 | PHE | B | 275 | 60.815 | 2.483 | 77.826 | 1.00 23.64 |
| ATOM | 5202 | CD2 | PHE | B | 275 | 60.732 | 3.893 | 75.907 | 1.00 27.31 |
| ATOM | 5203 | CE1 | PHE | B | 275 | 59.450 | 2.254 | 77.722 | 1.00 27.82 |
| ATOM | 5204 | CE2 | PHE | B | 275 | 59.365 | 3.670 | 75.795 | 1.00 27.62 |
| ATOM | 5205 | CZ | PHE | B | 275 | 58.727 | 2.851 | 76.701 | 1.00 25.78 |
| ATOM | 5206 | C | PHE | B | 275 | 63.642 | 1.860 | 75.305 | 1.00 24.47 |
| ATOM | 5207 | O | PHE | B | 275 | 63.045 | 0.821 | 75.030 | 1.00 22.68 |
| ATOM | 5208 | N | LEU | B | 276 | 64.183 | 2.648 | 74.378 | 1.00 23.85 |
| ATOM | 5209 | CA | LEU | B | 276 | 64.128 | 2.330 | 72.946 | 1.00 21.28 |
| ATOM | 5210 | CB | LEU | B | 276 | 64.814 | 3.421 | 72.134 | 1.00 19.87 |
| ATOM | 5211 | CG | LEU | B | 276 | 65.114 | 3.132 | 70.662 | 1.00 24.94 |
| ATOM | 5212 | CD1 | LEU | B | 276 | 63.818 | 2.852 | 69.936 | 1.00 24.81 |
| ATOM | 5213 | CD2 | LEU | B | 276 | 65.840 | 4.312 | 70.018 | 1.00 21.01 |
| ATOM | 5214 | C | LEU | B | 276 | 64.841 | 1.021 | 72.653 | 1.00 22.33 |
| ATOM | 5215 | O | LEU | B | 276 | 64.348 | 0.191 | 71.886 | 1.00 20.73 |
| ATOM | 5216 | N | LYS | B | 277 | 66.011 | 0.857 | 73.261 | 1.00 20.72 |
| ATOM | 5217 | CA | LYS | B | 277 | 66.823 | -0.335 | 73.076 | 1.00 24.36 |
| ATOM | 5218 | CB | LYS | B | 277 | 68.086 | -0.239 | 73.938 | 1.00 27.37 |
| ATOM | 5219 | CG | LYS | B | 277 | 69.303 | -0.973 | 73.381 | 1.00 35.58 |
| ATOM | 5220 | CD | LYS | B | 277 | 69.061 | -2.456 | 73.188 | 1.00 43.87 |
| ATOM | 5221 | CE | LYS | B | 277 | 70.283 | -3.137 | 72.580 | 1.00 44.87 |
| ATOM | 5222 | NZ | LYS | B | 277 | 70.616 | -2.586 | 71.230 | 1.00 49.66 |
| ATOM | 5223 | C | LYS | B | 277 | 66.000 | -1.554 | 73.482 | 1.00 24.22 |
| ATOM | 5224 | O | LYS | B | 277 | 65.987 | -2.568 | 72.777 | 1.00 19.90 |
| ATOM | 5225 | N | ALA | B | 278 | 65.319 | -1.454 | 74.624 | 1.00 22.32 |
| ATOM | 5226 | CA | ALA | B | 278 | 64.476 | -2.544 | 75.114 | 1.00 21.71 |
| ATOM | 5227 | CB | ALA | B | 278 | 63.752 | -2.117 | 76.381 | 1.00 17.34 |
| ATOM | 5228 | C | ALA | B | 278 | 63.459 | -2.896 | 74.031 | 1.00 22.68 |
| ATOM | 5229 | O | ALA | B | 278 | 63.231 | -4.068 | 73.723 | 1.00 19.27 |
| ATOM | 5230 | N | PHE | B | 279 | 62.849 | -1.862 | 73.464 | 1.00 24.79 |
| ATOM | 5231 | CA | PHE | B | 279 | 61.860 | -2.014 | 72.398 | 1.00 22.74 |
| ATOM | 5232 | CB | PHE | B | 279 | 61.395 | -0.629 | 71.955 | 1.00 22.46 |
| ATOM | 5233 | CG | PHE | B | 279 | 60.467 | -0.640 | 70.778 | 1.00 22.62 |
| ATOM | 5234 | CD1 | PHE | B | 279 | 59.196 | -1.182 | 70.882 | 1.00 21.74 |
| ATOM | 5235 | CD2 | PHE | B | 279 | 60.862 | -0.078 | 69.567 | 1.00 26.07 |
| ATOM | 5236 | CE1 | PHE | B | 279 | 58.325 | -1.162 | 69.799 | 1.00 27.02 |
| ATOM | 5237 | CE2 | PHE | B | 279 | 60.001 | -0.051 | 68.476 | 1.00 25.57 |

Fig. 18-79

| | | | | | | | | |
|---|---|---|---|---|---|---|---|---|
| ATOM | 5238 | CZ | PHE | B | 279 | 58.727 | -0.594 | 68.592 | 1.00 | 25.13 |
| ATOM | 5239 | C | PHE | B | 279 | 62.472 | -2.768 | 71.212 | 1.00 | 23.60 |
| ATOM | 5240 | O | PHE | B | 279 | 61.866 | -3.697 | 70.678 | 1.00 | 26.54 |
| ATOM | 5241 | N | ASN | B | 280 | 63.677 | -2.376 | 70.804 | 1.00 | 21.93 |
| ATOM | 5242 | CA | ASN | B | 280 | 64.318 | -3.046 | 69.680 | 1.00 | 23.70 |
| ATOM | 5243 | CB | ASN | B | 280 | 65.520 | -2.248 | 69.164 | 1.00 | 22.63 |
| ATOM | 5244 | CG | ASN | B | 280 | 65.107 | -0.937 | 68.505 | 1.00 | 30.83 |
| ATOM | 5245 | OD1 | ASN | B | 280 | 64.094 | -0.878 | 67.796 | 1.00 | 25.81 |
| ATOM | 5246 | ND2 | ASN | B | 280 | 65.900 | 0.112 | 68.714 | 1.00 | 26.54 |
| ATOM | 5247 | C | ASN | B | 280 | 64.746 | -4.466 | 70.009 | 1.00 | 26.10 |
| ATOM | 5248 | O | ASN | B | 280 | 64.775 | -5.321 | 69.124 | 1.00 | 26.16 |
| ATOM | 5249 | N | ILE | B | 281 | 65.080 | -4.724 | 71.272 | 1.00 | 26.10 |
| ATOM | 5250 | CA | ILE | B | 281 | 65.485 | -6.067 | 71.667 | 1.00 | 25.81 |
| ATOM | 5251 | CB | ILE | B | 281 | 66.006 | -6.098 | 73.124 | 1.00 | 28.50 |
| ATOM | 5252 | CG2 | ILE | B | 281 | 66.046 | -7.527 | 73.648 | 1.00 | 28.53 |
| ATOM | 5253 | CG1 | ILE | B | 281 | 67.392 | -5.454 | 73.173 | 1.00 | 32.07 |
| ATOM | 5254 | CD1 | ILE | B | 281 | 68.038 | -5.442 | 74.541 | 1.00 | 28.24 |
| ATOM | 5255 | C | ILE | B | 281 | 64.320 | -7.030 | 71.507 | 1.00 | 25.77 |
| ATOM | 5256 | O | ILE | B | 281 | 64.484 | -8.131 | 70.982 | 1.00 | 23.39 |
| ATOM | 5257 | N | VAL | B | 282 | 63.139 | -6.618 | 71.950 | 1.00 | 21.30 |
| ATOM | 5258 | CA | VAL | B | 282 | 61.961 | -7.465 | 71.813 | 1.00 | 22.90 |
| ATOM | 5259 | CB | VAL | B | 282 | 60.703 | -6.775 | 72.387 | 1.00 | 24.07 |
| ATOM | 5260 | CG1 | VAL | B | 282 | 59.464 | -7.611 | 72.093 | 1.00 | 22.28 |
| ATOM | 5261 | CG2 | VAL | B | 282 | 60.865 | -6.587 | 73.906 | 1.00 | 26.89 |
| ATOM | 5262 | C | VAL | B | 282 | 61.718 | -7.795 | 70.339 | 1.00 | 23.87 |
| ATOM | 5263 | O | VAL | B | 282 | 61.462 | -8.949 | 69.978 | 1.00 | 22.65 |
| ATOM | 5264 | N | ARG | B | 283 | 61.799 | -6.779 | 69.488 | 1.00 | 23.19 |
| ATOM | 5265 | CA | ARG | B | 283 | 61.576 | -6.971 | 68.060 | 1.00 | 27.95 |
| ATOM | 5266 | CB | ARG | B | 283 | 61.510 | -5.612 | 67.359 | 1.00 | 25.48 |
| ATOM | 5267 | CG | ARG | B | 283 | 60.337 | -4.760 | 67.838 | 1.00 | 26.55 |
| ATOM | 5268 | CD | ARG | B | 283 | 60.442 | -3.333 | 67.339 | 1.00 | 31.52 |
| ATOM | 5269 | NE | ARG | B | 283 | 60.210 | -3.208 | 65.908 | 1.00 | 24.43 |
| ATOM | 5270 | CZ | ARG | B | 283 | 60.915 | -2.414 | 65.116 | 1.00 | 26.45 |
| ATOM | 5271 | NH1 | ARG | B | 283 | 61.902 | -1.676 | 65.622 | 1.00 | 26.04 |
| ATOM | 5272 | NH2 | ARG | B | 283 | 60.634 | -2.356 | 63.825 | 1.00 | 29.64 |
| ATOM | 5273 | C | ARG | B | 283 | 62.634 | -7.855 | 67.402 | 1.00 | 32.04 |
| ATOM | 5274 | O | ARG | B | 283 | 62.341 | -8.552 | 66.431 | 1.00 | 29.76 |
| ATOM | 5275 | N | GLU | B | 284 | 63.859 | -7.821 | 67.923 | 1.00 | 31.50 |
| ATOM | 5276 | CA | GLU | B | 284 | 64.934 | -8.646 | 67.381 | 1.00 | 32.42 |
| ATOM | 5277 | CB | GLU | B | 284 | 66.289 | -8.260 | 67.992 | 1.00 | 38.31 |
| ATOM | 5278 | CG | GLU | B | 284 | 66.798 | -6.864 | 67.640 | 1.00 | 48.93 |
| ATOM | 5279 | CD | GLU | B | 284 | 68.102 | -6.518 | 68.362 | 1.00 | 56.28 |
| ATOM | 5280 | OE1 | GLU | B | 284 | 69.084 | -7.281 | 68.222 | 1.00 | 57.37 |
| ATOM | 5281 | OE2 | GLU | B | 284 | 68.150 | -5.485 | 69.069 | 1.00 | 55.42 |
| ATOM | 5282 | C | GLU | B | 284 | 64.638 | -10.105 | 67.714 | 1.00 | 31.93 |
| ATOM | 5283 | O | GLU | B | 284 | 64.899 | -11.001 | 66.913 | 1.00 | 28.26 |
| ATOM | 5284 | N | VAL | B | 285 | 64.089 | -10.340 | 68.901 | 1.00 | 28.09 |
| ATOM | 5285 | CA | VAL | B | 285 | 63.765 | -11.697 | 69.325 | 1.00 | 30.67 |
| ATOM | 5286 | CB | VAL | B | 285 | 63.687 | -11.802 | 70.863 | 1.00 | 28.33 |
| ATOM | 5287 | CG1 | VAL | B | 285 | 63.257 | -13.206 | 71.262 | 1.00 | 29.84 |
| ATOM | 5288 | CG2 | VAL | B | 285 | 65.037 | -11.470 | 71.478 | 1.00 | 26.93 |
| ATOM | 5289 | C | VAL | B | 285 | 62.460 | -12.265 | 68.758 | 1.00 | 31.19 |
| ATOM | 5290 | O | VAL | B | 285 | 62.422 | -13.423 | 68.349 | 1.00 | 31.38 |
| ATOM | 5291 | N | PHE | B | 286 | 61.398 | -11.460 | 68.729 | 1.00 | 28.21 |
| ATOM | 5292 | CA | PHE | B | 286 | 60.105 | -11.948 | 68.249 | 1.00 | 25.71 |
| ATOM | 5293 | CB | PHE | B | 286 | 59.064 | -11.853 | 69.374 | 1.00 | 24.57 |
| ATOM | 5294 | CG | PHE | B | 286 | 59.311 | -12.804 | 70.514 | 1.00 | 26.87 |
| ATOM | 5295 | CD1 | PHE | B | 286 | 59.651 | -12.331 | 71.779 | 1.00 | 25.16 |
| ATOM | 5296 | CD2 | PHE | B | 286 | 59.205 | -14.180 | 70.319 | 1.00 | 22.51 |
| ATOM | 5297 | CE1 | PHE | B | 286 | 59.880 | -13.213 | 72.833 | 1.00 | 22.92 |
| ATOM | 5298 | CE2 | PHE | B | 286 | 59.433 | -15.063 | 71.362 | 1.00 | 21.99 |
| ATOM | 5299 | CZ | PHE | B | 286 | 59.772 | -14.578 | 72.626 | 1.00 | 26.75 |
| ATOM | 5300 | C | PHE | B | 286 | 59.518 | -11.318 | 66.993 | 1.00 | 25.90 |
| ATOM | 5301 | O | PHE | B | 286 | 58.388 | -11.630 | 66.620 | 1.00 | 22.84 |
| ATOM | 5302 | N | GLY | B | 287 | 60.272 | -10.451 | 66.329 | 1.00 | 28.27 |
| ATOM | 5303 | CA | GLY | B | 287 | 59.756 | -9.814 | 65.130 | 1.00 | 23.38 |

Fig. 18-80

```
ATOM   5304  C   GLY B 287      58.765   -8.719   65.498  1.00 29.17
ATOM   5305  O   GLY B 287      58.786   -8.216   66.617  1.00 22.88
ATOM   5306  N   GLU B 288      57.896   -8.361   64.558  1.00 26.77
ATOM   5307  CA  GLU B 288      56.893   -7.324   64.754  1.00 25.38
ATOM   5308  CB  GLU B 288      56.405   -6.791   63.405  1.00 29.51
ATOM   5309  CG  GLU B 288      57.430   -6.003   62.605  1.00 36.06
ATOM   5310  CD  GLU B 288      57.906   -4.769   63.347  1.00 41.10
ATOM   5311  OE1 GLU B 288      57.058   -4.055   63.919  1.00 41.19
ATOM   5312  OE2 GLU B 288      59.125   -4.503   63.348  1.00 44.69
ATOM   5313  C   GLU B 288      55.682   -7.819   65.527  1.00 27.87
ATOM   5314  O   GLU B 288      55.209   -8.931   65.308  1.00 26.80
ATOM   5315  N   GLY B 289      55.176   -6.973   66.419  1.00 24.53
ATOM   5316  CA  GLY B 289      54.006   -7.326   67.204  1.00 29.17
ATOM   5317  C   GLY B 289      53.015   -6.171   67.244  1.00 30.46
ATOM   5318  O   GLY B 289      53.005   -5.326   66.358  1.00 26.17
ATOM   5319  N   VAL B 290      52.171   -6.142   68.268  1.00 23.95
ATOM   5320  CA  VAL B 290      51.194   -5.079   68.440  1.00 22.25
ATOM   5321  CB  VAL B 290      49.794   -5.655   68.783  1.00 18.71
ATOM   5322  CG1 VAL B 290      48.810   -4.525   69.047  1.00 22.67
ATOM   5323  CG2 VAL B 290      49.289   -6.504   67.629  1.00 19.26
ATOM   5324  C   VAL B 290      51.722   -4.232   69.593  1.00 21.55
ATOM   5325  O   VAL B 290      51.960   -4.741   70.687  1.00 21.32
ATOM   5326  N   TYR B 291      51.913   -2.941   69.346  1.00 21.06
ATOM   5327  CA  TYR B 291      52.479   -2.063   70.357  1.00 19.29
ATOM   5328  CB  TYR B 291      53.582   -1.216   69.711  1.00 20.40
ATOM   5329  CG  TYR B 291      54.553   -2.072   68.918  1.00 23.09
ATOM   5330  CD1 TYR B 291      54.740   -1.875   67.549  1.00 19.52
ATOM   5331  CE1 TYR B 291      55.580   -2.712   66.809  1.00 20.67
ATOM   5332  CD2 TYR B 291      55.234   -3.122   69.527  1.00 22.88
ATOM   5333  CE2 TYR B 291      56.070   -3.960   68.800  1.00 26.04
ATOM   5334  CZ  TYR B 291      56.235   -3.752   67.442  1.00 23.44
ATOM   5335  OH  TYR B 291      57.027   -4.612   66.722  1.00 28.02
ATOM   5336  C   TYR B 291      51.465   -1.180   71.068  1.00 26.89
ATOM   5337  O   TYR B 291      50.668   -0.479   70.429  1.00 20.26
ATOM   5338  N   LEU B 292      51.522   -1.204   72.399  1.00 21.75
ATOM   5339  CA  LEU B 292      50.604   -0.426   73.227  1.00 22.11
ATOM   5340  CB  LEU B 292      49.765   -1.369   74.088  1.00 20.92
ATOM   5341  CG  LEU B 292      49.091   -2.542   73.375  1.00 22.94
ATOM   5342  CD1 LEU B 292      48.328   -3.362   74.411  1.00 21.03
ATOM   5343  CD2 LEU B 292      48.149   -2.043   72.281  1.00 18.04
ATOM   5344  C   LEU B 292      51.330    0.557   74.147  1.00 21.59
ATOM   5345  O   LEU B 292      52.514    0.404   74.426  1.00 19.96
ATOM   5346  N   GLY B 293      50.606    1.571   74.613  1.00 23.31
ATOM   5347  CA  GLY B 293      51.195    2.537   75.521  1.00 20.76
ATOM   5348  C   GLY B 293      51.163    1.979   76.930  1.00 26.15
ATOM   5349  O   GLY B 293      51.263    0.765   77.133  1.00 20.96
ATOM   5350  N   GLY B 294      51.017    2.859   77.914  1.00 24.63
ATOM   5351  CA  GLY B 294      50.980    2.407   79.293  1.00 20.00
ATOM   5352  C   GLY B 294      51.176    3.538   80.285  1.00 22.59
ATOM   5353  O   GLY B 294      51.145    4.719   79.916  1.00 17.46
ATOM   5354  N   GLY B 295      51.373    3.179   81.551  1.00 17.10
ATOM   5355  CA  GLY B 295      51.577    4.180   82.582  1.00 16.52
ATOM   5356  C   GLY B 295      52.695    5.145   82.232  1.00 19.54
ATOM   5357  O   GLY B 295      53.738    4.737   81.732  1.00 16.31
ATOM   5358  N   GLY B 296      52.467    6.430   82.497  1.00 21.93
ATOM   5359  CA  GLY B 296      53.448    7.465   82.207  1.00 20.05
ATOM   5360  C   GLY B 296      52.869    8.750   82.759  1.00 22.20
ATOM   5361  O   GLY B 296      51.790    9.160   82.336  1.00 20.48
ATOM   5362  N   TYR B 297      53.573    9.402   83.682  1.00 20.93
ATOM   5363  CA  TYR B 297      53.025   10.598   84.306  1.00 23.25
ATOM   5364  CB  TYR B 297      52.731   10.284   85.774  1.00 19.93
ATOM   5365  CG  TYR B 297      52.041    8.944   85.900  1.00 24.76
ATOM   5366  CD1 TYR B 297      52.779    7.758   85.936  1.00 21.97
ATOM   5367  CE1 TYR B 297      52.148    6.514   85.912  1.00 19.79
ATOM   5368  CD2 TYR B 297      50.653    8.850   85.849  1.00 20.86
ATOM   5369  CE2 TYR B 297      50.012    7.612   85.822  1.00 19.57
```

Fig. 18-81

| ATOM | 5370 | CZ | TYR | B | 297 | 50.758 | 6.457 | 85.851 | 1.00 | 23.85 |
|------|------|-----|-----|---|-----|--------|--------|--------|------|-------|
| ATOM | 5371 | OH | TYR | B | 297 | 50.106 | 5.254 | 85.806 | 1.00 | 17.83 |
| ATOM | 5372 | C | TYR | B | 297 | 53.839 | 11.877 | 84.181 | 1.00 | 25.22 |
| ATOM | 5373 | O | TYR | B | 297 | 53.451 | 12.925 | 84.705 | 1.00 | 21.77 |
| ATOM | 5374 | N | HIS | B | 298 | 54.974 | 11.794 | 83.497 | 1.00 | 23.21 |
| ATOM | 5375 | CA | HIS | B | 298 | 55.787 | 12.976 | 83.270 | 1.00 | 25.62 |
| ATOM | 5376 | CB | HIS | B | 298 | 57.270 | 12.713 | 83.534 | 1.00 | 22.88 |
| ATOM | 5377 | CG | HIS | B | 298 | 58.097 | 13.956 | 83.502 | 1.00 | 25.13 |
| ATOM | 5378 | CD2 | HIS | B | 298 | 58.406 | 14.791 | 82.482 | 1.00 | 28.22 |
| ATOM | 5379 | ND1 | HIS | B | 298 | 58.617 | 14.536 | 84.641 | 1.00 | 32.76 |
| ATOM | 5380 | CE1 | HIS | B | 298 | 59.209 | 15.674 | 84.323 | 1.00 | 26.52 |
| ATOM | 5381 | NE2 | HIS | B | 298 | 59.094 | 15.852 | 83.019 | 1.00 | 32.15 |
| ATOM | 5382 | C | HIS | B | 298 | 55.589 | 13.307 | 81.795 | 1.00 | 25.66 |
| ATOM | 5383 | O | HIS | B | 298 | 56.087 | 12.589 | 80.923 | 1.00 | 25.84 |
| ATOM | 5384 | N | PRO | B | 299 | 54.901 | 14.424 | 81.496 | 1.00 | 27.02 |
| ATOM | 5385 | CD | PRO | B | 299 | 54.388 | 15.424 | 82.447 | 1.00 | 29.91 |
| ATOM | 5386 | CA | PRO | B | 299 | 54.616 | 14.864 | 80.127 | 1.00 | 26.53 |
| ATOM | 5387 | CB | PRO | B | 299 | 53.952 | 16.232 | 80.342 | 1.00 | 27.76 |
| ATOM | 5388 | CG | PRO | B | 299 | 54.583 | 16.696 | 81.656 | 1.00 | 27.97 |
| ATOM | 5389 | C | PRO | B | 299 | 55.815 | 14.930 | 79.194 | 1.00 | 27.08 |
| ATOM | 5390 | O | PRO | B | 299 | 55.738 | 14.472 | 78.057 | 1.00 | 28.58 |
| ATOM | 5391 | N | TYR | B | 300 | 56.925 | 15.484 | 79.668 | 1.00 | 27.30 |
| ATOM | 5392 | CA | TYR | B | 300 | 58.114 | 15.593 | 78.824 | 1.00 | 27.17 |
| ATOM | 5393 | CB | TYR | B | 300 | 59.173 | 16.496 | 79.466 | 1.00 | 31.65 |
| ATOM | 5394 | CG | TYR | B | 300 | 58.684 | 17.851 | 79.921 | 1.00 | 31.61 |
| ATOM | 5395 | CD1 | TYR | B | 300 | 57.414 | 18.318 | 79.582 | 1.00 | 32.71 |
| ATOM | 5396 | CE1 | TYR | B | 300 | 56.971 | 19.568 | 80.014 | 1.00 | 38.52 |
| ATOM | 5397 | CD2 | TYR | B | 300 | 59.499 | 18.670 | 80.701 | 1.00 | 30.92 |
| ATOM | 5398 | CE2 | TYR | B | 300 | 59.072 | 19.917 | 81.138 | 1.00 | 32.13 |
| ATOM | 5399 | CZ | TYR | B | 300 | 57.808 | 20.361 | 80.795 | 1.00 | 39.17 |
| ATOM | 5400 | OH | TYR | B | 300 | 57.374 | 21.585 | 81.252 | 1.00 | 43.90 |
| ATOM | 5401 | C | TYR | B | 300 | 58.731 | 14.218 | 78.572 | 1.00 | 25.20 |
| ATOM | 5402 | O | TYR | B | 300 | 59.106 | 13.894 | 77.445 | 1.00 | 25.15 |
| ATOM | 5403 | N | ALA | B | 301 | 58.845 | 13.419 | 79.628 | 1.00 | 20.55 |
| ATOM | 5404 | CA | ALA | B | 301 | 59.414 | 12.080 | 79.508 | 1.00 | 22.12 |
| ATOM | 5405 | CB | ALA | B | 301 | 59.417 | 11.388 | 80.874 | 1.00 | 17.09 |
| ATOM | 5406 | C | ALA | B | 301 | 58.608 | 11.260 | 78.505 | 1.00 | 15.20 |
| ATOM | 5407 | O | ALA | B | 301 | 59.161 | 10.629 | 77.613 | 1.00 | 17.12 |
| ATOM | 5408 | N | LEU | B | 302 | 57.295 | 11.290 | 78.667 | 1.00 | 18.02 |
| ATOM | 5409 | CA | LEU | B | 302 | 56.381 | 10.553 | 77.815 | 1.00 | 19.88 |
| ATOM | 5410 | CB | LEU | B | 302 | 54.957 | 10.702 | 78.362 | 1.00 | 21.72 |
| ATOM | 5411 | CG | LEU | B | 302 | 53.767 | 10.118 | 77.606 | 1.00 | 31.08 |
| ATOM | 5412 | CD1 | LEU | B | 302 | 52.576 | 9.980 | 78.549 | 1.00 | 31.35 |
| ATOM | 5413 | CD2 | LEU | B | 302 | 53.434 | 11.011 | 76.415 | 1.00 | 27.11 |
| ATOM | 5414 | C | LEU | B | 302 | 56.445 | 10.988 | 76.351 | 1.00 | 21.13 |
| ATOM | 5415 | O | LEU | B | 302 | 56.473 | 10.149 | 75.449 | 1.00 | 21.76 |
| ATOM | 5416 | N | ALA | B | 303 | 56.472 | 12.293 | 76.115 | 1.00 | 17.69 |
| ATOM | 5417 | CA | ALA | B | 303 | 56.516 | 12.811 | 74.755 | 1.00 | 17.79 |
| ATOM | 5418 | CB | ALA | B | 303 | 56.357 | 14.326 | 74.780 | 1.00 | 24.50 |
| ATOM | 5419 | C | ALA | B | 303 | 57.803 | 12.425 | 74.040 | 1.00 | 20.84 |
| ATOM | 5420 | O | ALA | B | 303 | 57.781 | 11.968 | 72.891 | 1.00 | 19.33 |
| ATOM | 5421 | N | ARG | B | 304 | 58.930 | 12.594 | 74.723 | 1.00 | 21.08 |
| ATOM | 5422 | CA | ARG | B | 304 | 60.215 | 12.269 | 74.120 | 1.00 | 25.56 |
| ATOM | 5423 | CB | ARG | B | 304 | 61.375 | 12.825 | 74.962 | 1.00 | 18.37 |
| ATOM | 5424 | CG | ARG | B | 304 | 61.427 | 14.356 | 75.072 | 1.00 | 23.12 |
| ATOM | 5425 | CD | ARG | B | 304 | 62.797 | 14.758 | 75.624 | 1.00 | 29.00 |
| ATOM | 5426 | NE | ARG | B | 304 | 63.073 | 13.938 | 76.789 | 1.00 | 33.28 |
| ATOM | 5427 | CZ | ARG | B | 304 | 64.271 | 13.689 | 77.283 | 1.00 | 30.24 |
| ATOM | 5428 | NH1 | ARG | B | 304 | 65.363 | 14.194 | 76.723 | 1.00 | 24.98 |
| ATOM | 5429 | NH2 | ARG | B | 304 | 64.365 | 12.896 | 78.333 | 1.00 | 36.15 |
| ATOM | 5430 | C | ARG | B | 304 | 60.406 | 10.775 | 73.922 | 1.00 | 20.46 |
| ATOM | 5431 | O | ARG | B | 304 | 60.850 | 10.338 | 72.868 | 1.00 | 18.70 |
| ATOM | 5432 | N | ALA | B | 305 | 60.070 | 9.988 | 74.937 | 1.00 | 22.48 |
| ATOM | 5433 | CA | ALA | B | 305 | 60.226 | 8.542 | 74.845 | 1.00 | 19.70 |
| ATOM | 5434 | CB | ALA | B | 305 | 59.847 | 7.894 | 76.174 | 1.00 | 24.24 |
| ATOM | 5435 | C | ALA | B | 305 | 59.407 | 7.930 | 73.711 | 1.00 | 15.82 |

Fig. 18-82

| | | | | | | | | | |
|---|---|---|---|---|---|---|---|---|---|
| ATOM | 5436 | O | ALA | B | 305 | 59.938 | 7.184 | 72.888 | 1.00 19.12 |
| ATOM | 5437 | N | TRP | B | 306 | 58.113 | 8.230 | 73.659 | 1.00 18.65 |
| ATOM | 5438 | CA | TRP | B | 306 | 57.298 | 7.668 | 72.600 | 1.00 19.57 |
| ATOM | 5439 | CB | TRP | B | 306 | 55.800 | 7.856 | 72.893 | 1.00 18.26 |
| ATOM | 5440 | CG | TRP | B | 306 | 55.301 | 6.911 | 73.953 | 1.00 20.71 |
| ATOM | 5441 | CD2 | TRP | B | 306 | 54.087 | 7.025 | 74.708 | 1.00 23.94 |
| ATOM | 5442 | CE2 | TRP | B | 306 | 53.988 | 5.870 | 75.513 | 1.00 24.73 |
| ATOM | 5443 | CE3 | TRP | B | 306 | 53.073 | 7.991 | 74.780 | 1.00 26.01 |
| ATOM | 5444 | CD1 | TRP | B | 306 | 55.872 | 5.721 | 74.326 | 1.00 20.04 |
| ATOM | 5445 | NE1 | TRP | B | 306 | 55.092 | 5.093 | 75.260 | 1.00 19.17 |
| ATOM | 5446 | CZ2 | TRP | B | 306 | 52.912 | 5.655 | 76.385 | 1.00 28.04 |
| ATOM | 5447 | CZ3 | TRP | B | 306 | 52.001 | 7.779 | 75.646 | 1.00 28.68 |
| ATOM | 5448 | CH2 | TRP | B | 306 | 51.930 | 6.619 | 76.437 | 1.00 31.22 |
| ATOM | 5449 | C | TRP | B | 306 | 57.665 | 8.223 | 71.226 | 1.00 23.48 |
| ATOM | 5450 | O | TRP | B | 306 | 57.416 | 7.574 | 70.212 | 1.00 22.38 |
| ATOM | 5451 | N | THR | B | 307 | 58.262 | 9.412 | 71.176 | 1.00 22.36 |
| ATOM | 5452 | CA | THR | B | 307 | 58.672 | 9.953 | 69.880 | 1.00 25.94 |
| ATOM | 5453 | CB | THR | B | 307 | 59.143 | 11.417 | 69.986 | 1.00 25.88 |
| ATOM | 5454 | OG1 | THR | B | 307 | 58.015 | 12.261 | 70.258 | 1.00 21.07 |
| ATOM | 5455 | CG2 | THR | B | 307 | 59.827 | 11.864 | 68.686 | 1.00 22.52 |
| ATOM | 5456 | C | THR | B | 307 | 59.815 | 9.078 | 69.350 | 1.00 30.09 |
| ATOM | 5457 | O | THR | B | 307 | 59.922 | 8.834 | 68.144 | 1.00 25.82 |
| ATOM | 5458 | N | LEU | B | 308 | 60.664 | 8.596 | 70.258 | 1.00 27.54 |
| ATOM | 5459 | CA | LEU | B | 308 | 61.773 | 7.734 | 69.857 | 1.00 26.76 |
| ATOM | 5460 | CB | LEU | B | 308 | 62.691 | 7.424 | 71.054 | 1.00 24.24 |
| ATOM | 5461 | CG | LEU | B | 308 | 63.420 | 8.614 | 71.718 | 1.00 31.16 |
| ATOM | 5462 | CD1 | LEU | B | 308 | 64.282 | 8.147 | 72.877 | 1.00 24.71 |
| ATOM | 5463 | CD2 | LEU | B | 308 | 64.289 | 9.325 | 70.700 | 1.00 24.59 |
| ATOM | 5464 | C | LEU | B | 308 | 61.184 | 6.443 | 69.287 | 1.00 27.20 |
| ATOM | 5465 | O | LEU | B | 308 | 61.609 | 5.961 | 68.234 | 1.00 23.52 |
| ATOM | 5466 | N | ILE | B | 309 | 60.190 | 5.898 | 69.980 | 1.00 25.10 |
| ATOM | 5467 | CA | ILE | B | 309 | 59.537 | 4.679 | 69.530 | 1.00 25.14 |
| ATOM | 5468 | CB | ILE | B | 309 | 58.387 | 4.266 | 70.485 | 1.00 27.05 |
| ATOM | 5469 | CG2 | ILE | B | 309 | 57.646 | 3.058 | 69.926 | 1.00 23.57 |
| ATOM | 5470 | CG1 | ILE | B | 309 | 58.952 | 3.947 | 71.868 | 1.00 22.98 |
| ATOM | 5471 | CD1 | ILE | B | 309 | 59.927 | 2.793 | 71.868 | 1.00 24.25 |
| ATOM | 5472 | C | ILE | B | 309 | 58.958 | 4.885 | 68.133 | 1.00 25.41 |
| ATOM | 5473 | O | ILE | B | 309 | 59.177 | 4.064 | 67.243 | 1.00 22.13 |
| ATOM | 5474 | N | TRP | B | 310 | 58.232 | 5.984 | 67.943 | 1.00 27.45 |
| ATOM | 5475 | CA | TRP | B | 310 | 57.618 | 6.266 | 66.648 | 1.00 29.27 |
| ATOM | 5476 | CB | TRP | B | 310 | 56.721 | 7.505 | 66.715 | 1.00 27.00 |
| ATOM | 5477 | CG | TRP | B | 310 | 56.112 | 7.847 | 65.378 | 1.00 28.26 |
| ATOM | 5478 | CD2 | TRP | B | 310 | 55.172 | 7.061 | 64.633 | 1.00 27.50 |
| ATOM | 5479 | CE2 | TRP | B | 310 | 54.947 | 7.729 | 63.408 | 1.00 30.47 |
| ATOM | 5480 | CE3 | TRP | B | 310 | 54.500 | 5.856 | 64.877 | 1.00 29.85 |
| ATOM | 5481 | CD1 | TRP | B | 310 | 56.406 | 8.929 | 64.597 | 1.00 29.76 |
| ATOM | 5482 | NE1 | TRP | B | 310 | 55.713 | .865 | 63.415 | 1.00 26.71 |
| ATOM | 5483 | CZ2 | TRP | B | 310 | 54.076 | .234 | 62.429 | 1.00 28.23 |
| ATOM | 5484 | CZ3 | TRP | B | 310 | 53.636 | 5.362 | 63.901 | 1.00 30.24 |
| ATOM | 5485 | CH2 | TRP | B | 310 | 53.433 | 6.053 | 62.692 | 1.00 27.63 |
| ATOM | 5486 | C | TRP | B | 310 | 58.629 | 6.424 | 65.520 | 1.00 30.16 |
| ATOM | 5487 | O | TRP | B | 310 | 58.378 | 5.964 | 64.410 | 1.00 30.04 |
| ATOM | 5488 | N | CYS | B | 311 | 59.762 | 7.069 | 65.793 | 1.00 24.26 |
| ATOM | 5489 | CA | CYS | B | 311 | 60.782 | 7.233 | 64.764 | 1.00 27.97 |
| ATOM | 5490 | CB | CYS | B | 311 | 61.893 | 8.157 | 65.252 | 1.00 28.21 |
| ATOM | 5491 | SG | CYS | B | 311 | 61.422 | 9.905 | 65.381 | 1.00 33.38 |
| ATOM | 5492 | C | CYS | B | 311 | 61.380 | 5.886 | 64.351 | 1.00 30.02 |
| ATOM | 5493 | O | CYS | B | 311 | 61.670 | 5.660 | 63.172 | 1.00 25.45 |
| ATOM | 5494 | N | GLU | B | 312 | 61.570 | 5.001 | 65.327 | 1.00 31.59 |
| ATOM | 5495 | CA | GLU | B | 312 | 62.111 | 3.669 | 65.067 | 1.00 33.48 |
| ATOM | 5496 | CB | GLU | B | 312 | 62.142 | 2.843 | 66.352 | 1.00 34.78 |
| ATOM | 5497 | CG | GLU | B | 312 | 63.487 | 2.307 | 66.758 | 1.00 39.45 |
| ATOM | 5498 | CD | GLU | B | 312 | 64.171 | 1.513 | 65.675 | 1.00 40.11 |
| ATOM | 5499 | OE1 | GLU | B | 312 | 63.539 | 0.614 | 65.081 | 1.00 43.69 |
| ATOM | 5500 | OE2 | GLU | B | 312 | 65.358 | 1.782 | 65.437 | 1.00 39.26 |
| ATOM | 5501 | C | GLU | B | 312 | 61.197 | 2.959 | 64.080 | 1.00 29.97 |

Fig. 18-83

| ATOM | 5502 | O | GLU | B | 312 | 61.640 | 2.497 | 63.035 | 1.00 | 31.38 |
|---|---|---|---|---|---|---|---|---|---|---|
| ATOM | 5503 | N | LEU | B | 313 | 59.919 | 2.865 | 64.438 | 1.00 | 26.70 |
| ATOM | 5504 | CA | LEU | B | 313 | 58.930 | 2.203 | 63.598 | 1.00 | 26.73 |
| ATOM | 5505 | CB | LEU | B | 313 | 57.571 | 2.173 | 64.297 | 1.00 | 25.83 |
| ATOM | 5506 | CG | LEU | B | 313 | 57.429 | 1.224 | 65.477 | 1.00 | 35.18 |
| ATOM | 5507 | CD1 | LEU | B | 313 | 56.063 | 1.434 | 66.130 | 1.00 | 32.49 |
| ATOM | 5508 | CD2 | LEU | B | 313 | 57.595 | -0.215 | 64.989 | 1.00 | 29.71 |
| ATOM | 5509 | C | LEU | B | 313 | 58.768 | 2.866 | 62.248 | 1.00 | 29.03 |
| ATOM | 5510 | O | LEU | B | 313 | 58.716 | 2.187 | 61.228 | 1.00 | 25.39 |
| ATOM | 5511 | N | SER | B | 314 | 58.677 | 4.194 | 62.263 | 1.00 | 30.13 |
| ATOM | 5512 | CA | SER | B | 314 | 58.498 | 5.006 | 61.060 | 1.00 | 34.06 |
| ATOM | 5513 | CB | SER | B | 314 | 58.206 | 6.456 | 61.445 | 1.00 | 31.15 |
| ATOM | 5514 | OG | SER | B | 314 | 57.041 | 6.537 | 62.234 | 1.00 | 48.58 |
| ATOM | 5515 | C | SER | B | 314 | 59.707 | 5.003 | 60.151 | 1.00 | 31.84 |
| ATOM | 5516 | O | SER | B | 314 | 59.632 | 5.469 | 59.026 | 1.00 | 34.15 |
| ATOM | 5517 | N | GLY | B | 315 | 60.831 | 4.515 | 60.655 | 1.00 | 31.81 |
| ATOM | 5518 | CA | GLY | B | 315 | 62.036 | 4.485 | 59.848 | 1.00 | 37.27 |
| ATOM | 5519 | C | GLY | B | 315 | 62.659 | 5.851 | 59.616 | 1.00 | 39.93 |
| ATOM | 5520 | O | GLY | B | 315 | 63.363 | 6.054 | 58.624 | 1.00 | 39.79 |
| ATOM | 5521 | N | ARG | B | 316 | 62.422 | 6.798 | 60.518 | 1.00 | 38.22 |
| ATOM | 5522 | CA | ARG | B | 316 | 63.004 | 8.121 | 60.336 | 1.00 | 38.66 |
| ATOM | 5523 | CB | ARG | B | 316 | 61.908 | 9.184 | 60.275 | 1.00 | 40.20 |
| ATOM | 5524 | CG | ARG | B | 316 | 61.089 | 9.345 | 61.520 | 1.00 | 39.00 |
| ATOM | 5525 | CD | ARG | B | 316 | 60.032 | 10.398 | 61.284 | 1.00 | 42.13 |
| ATOM | 5526 | NE | ARG | B | 316 | 59.002 | 9.954 | 60.352 | 1.00 | 45.09 |
| ATOM | 5527 | CZ | ARG | B | 316 | 58.075 | 10.754 | 59.838 | 1.00 | 40.84 |
| ATOM | 5528 | NH1 | ARG | B | 316 | 58.064 | 12.033 | 60.170 | 1.00 | 48.44 |
| ATOM | 5529 | NH2 | ARG | B | 316 | 57.150 | 10.278 | 59.014 | 1.00 | 35.96 |
| ATOM | 5530 | C | ARG | B | 316 | 64.031 | 8.467 | 61.408 | 1.00 | 39.03 |
| ATOM | 5531 | O | ARG | B | 316 | 63.952 | 7.988 | 62.539 | 1.00 | 34.34 |
| ATOM | 5532 | N | GLU | B | 317 | 65.003 | 9.296 | 61.035 | 1.00 | 39.58 |
| ATOM | 5533 | CA | GLU | B | 317 | 66.074 | 9.697 | 61.943 | 1.00 | 43.35 |
| ATOM | 5534 | CB | GLU | B | 317 | 67.142 | 10.509 | 61.203 | 1.00 | 49.34 |
| ATOM | 5535 | CG | GLU | B | 317 | 67.609 | 9.910 | 59.884 | 1.00 | 57.04 |
| ATOM | 5536 | CD | GLU | B | 317 | 66.546 | 10.009 | 58.798 | 1.00 | 62.79 |
| ATOM | 5537 | OE1 | GLU | B | 317 | 66.146 | 11.149 | 58.467 | 1.00 | 63.46 |
| ATOM | 5538 | OE2 | GLU | B | 317 | 66.108 | 8.954 | 58.280 | 1.00 | 64.46 |
| ATOM | 5539 | C | GLU | B | 317 | 65.555 | 10.528 | 63.100 | 1.00 | 41.58 |
| ATOM | 5540 | O | GLU | B | 317 | 64.658 | 11.356 | 62.939 | 1.00 | 39.74 |
| ATOM | 5541 | N | VAL | B | 318 | 66.118 | 10.301 | 64.278 | 1.00 | 35.38 |
| ATOM | 5542 | CA | VAL | B | 318 | 65.706 | 11.049 | 65.448 | 1.00 | 38.76 |
| ATOM | 5543 | CB | VAL | B | 318 | 66.000 | 10.265 | 66.750 | 1.00 | 42.28 |
| ATOM | 5544 | CG1 | VAL | B | 318 | 65.560 | 11.080 | 67.962 | 1.00 | 38.26 |
| ATOM | 5545 | CG2 | VAL | B | 318 | 65.287 | 8.916 | 66.722 | 1.00 | 39.99 |
| ATOM | 5546 | C | VAL | B | 318 | 66.459 | 12.370 | 65.478 | 1.00 | 41.82 |
| ATOM | 5547 | O | VAL | B | 318 | 67.689 | 12.395 | 65.570 | 1.00 | 37.20 |
| ATOM | 5548 | N | PRO | B | 319 | 65.735 | 13.491 | 65.356 | 1.00 | 43.18 |
| ATOM | 5549 | CD | PRO | B | 319 | 64.290 | 13.672 | 65.155 | 1.00 | 41.90 |
| ATOM | 5550 | CA | PRO | B | 319 | 66.402 | 14.792 | 65.388 | 1.00 | 44.31 |
| ATOM | 5551 | CB | PRO | B | 319 | 65.241 | 15.763 | 65.181 | 1.00 | 44.58 |
| ATOM | 5552 | CG | PRO | B | 319 | 64.079 | 15.011 | 65.795 | 1.00 | 43.34 |
| ATOM | 5553 | C | PRO | B | 319 | 67.086 | 14.965 | 66.741 | 1.00 | 44.62 |
| ATOM | 5554 | O | PRO | B | 319 | 66.541 | 14.565 | 67.771 | 1.00 | 43.75 |
| ATOM | 5555 | N | GLU | B | 320 | 68.277 | 15.552 | 66.735 | 1.00 | 44.16 |
| ATOM | 5556 | CA | GLU | B | 320 | 69.029 | 15.762 | 67.967 | 1.00 | 45.92 |
| ATOM | 5557 | CB | GLU | B | 320 | 70.381 | 16.406 | 67.663 | 1.00 | 50.87 |
| ATOM | 5558 | CG | GLU | B | 320 | 71.165 | 16.768 | 68.919 | 1.00 | 53.71 |
| ATOM | 5559 | CD | GLU | B | 320 | 72.455 | 17.505 | 68.620 | 1.00 | 57.75 |
| ATOM | 5560 | OE1 | GLU | B | 320 | 73.161 | 17.874 | 69.583 | 1.00 | 56.37 |
| ATOM | 5561 | OE2 | GLU | B | 320 | 72.762 | 17.714 | 67.427 | 1.00 | 60.07 |
| ATOM | 5562 | C | GLU | B | 320 | 68.311 | 16.625 | 68.995 | 1.00 | 44.42 |
| ATOM | 5563 | O | GLU | B | 320 | 68.244 | 16.279 | 70.168 | 1.00 | 42.32 |
| ATOM | 5564 | N | LYS | B | 321 | 67.778 | 17.753 | 68.550 | 1.00 | 42.50 |
| ATOM | 5565 | CA | LYS | B | 321 | 67.102 | 18.672 | 69.448 | 1.00 | 45.24 |
| ATOM | 5566 | CB | LYS | B | 321 | 67.853 | 20.000 | 69.503 | 1.00 | 46.43 |
| ATOM | 5567 | CG | LYS | B | 321 | 67.890 | 20.802 | 68.195 | 1.00 | 51.45 |

Fig. 18-84

| | | | | | | | | | |
|---|---|---|---|---|---|---|---|---|---|
| ATOM | 5568 | CD | LYS | B | 321 | 68.700 | 20.144 | 67.057 | 1.00 57.24 |
| ATOM | 5569 | CE | LYS | B | 321 | 67.936 | 19.062 | 66.280 | 1.00 55.24 |
| ATOM | 5570 | NZ | LYS | B | 321 | 66.738 | 19.588 | 65.558 | 1.00 55.31 |
| ATOM | 5571 | C | LYS | B | 321 | 65.662 | 18.971 | 69.098 | 1.00 43.44 |
| ATOM | 5572 | O | LYS | B | 321 | 65.211 | 18.736 | 67.978 | 1.00 43.03 |
| ATOM | 5573 | N | LEU | B | 322 | 64.947 | 19.512 | 70.076 | 1.00 39.45 |
| ATOM | 5574 | CA | LEU | B | 322 | 63.563 | 19.885 | 69.875 | 1.00 40.31 |
| ATOM | 5575 | CB | LEU | B | 322 | 62.846 | 20.034 | 71.215 | 1.00 40.88 |
| ATOM | 5576 | CG | LEU | B | 322 | 62.943 | 18.901 | 72.234 | 1.00 40.09 |
| ATOM | 5577 | CD1 | LEU | B | 322 | 62.001 | 19.175 | 73.388 | 1.00 38.17 |
| ATOM | 5578 | CD2 | LEU | B | 322 | 62.588 | 17.596 | 71.580 | 1.00 41.56 |
| ATOM | 5579 | C | LEU | B | 322 | 63.615 | 21.244 | 69.197 | 1.00 41.23 |
| ATOM | 5580 | O | LEU | B | 322 | 64.466 | 22.070 | 69.531 | 1.00 39.22 |
| ATOM | 5581 | N | ASN | B | 323 | 62.735 | 21.473 | 68.233 | 1.00 40.04 |
| ATOM | 5582 | CA | ASN | B | 323 | 62.703 | 22.771 | 67.582 | 1.00 43.32 |
| ATOM | 5583 | CB | ASN | B | 323 | 61.985 | 22.707 | 66.234 | 1.00 41.53 |
| ATOM | 5584 | CG | ASN | B | 323 | 60.617 | 22.085 | 66.335 | 1.00 41.89 |
| ATOM | 5585 | OD1 | ASN | B | 323 | 59.889 | 22.308 | 67.304 | 1.00 39.79 |
| ATOM | 5586 | ND2 | ASN | B | 323 | 60.243 | 21.317 | 65.317 | 1.00 40.43 |
| ATOM | 5587 | C | ASN | B | 323 | 61.949 | 23.690 | 68.532 | 1.00 44.76 |
| ATOM | 5588 | O | ASN | B | 323 | 61.402 | 23.237 | 69.539 | 1.00 45.80 |
| ATOM | 5589 | N | ASN | B | 324 | 61.902 | 24.973 | 68.210 | 1.00 46.85 |
| ATOM | 5590 | CA | ASN | B | 324 | 61.234 | 25.930 | 69.076 | 1.00 47.60 |
| ATOM | 5591 | CB | ASN | B | 324 | 61.460 | 27.348 | 68.549 | 1.00 50.87 |
| ATOM | 5592 | CG | ASN | B | 324 | 61.089 | 28.407 | 69.562 | 1.00 55.06 |
| ATOM | 5593 | OD1 | ASN | B | 324 | 59.925 | 28.565 | 69.919 | 1.00 60.68 |
| ATOM | 5594 | ND2 | ASN | B | 324 | 62.091 | 29.131 | 70.048 | 1.00 59.17 |
| ATOM | 5595 | C | ASN | B | 324 | 59.740 | 25.664 | 69.249 | 1.00 43.97 |
| ATOM | 5596 | O | ASN | B | 324 | 59.190 | 25.898 | 70.322 | 1.00 41.33 |
| ATOM | 5597 | N | LYS | B | 325 | 59.087 | 25.168 | 68.201 | 1.00 43.49 |
| ATOM | 5598 | CA | LYS | B | 325 | 57.655 | 24.892 | 68.264 | 1.00 45.95 |
| ATOM | 5599 | CB | LYS | B | 325 | 57.112 | 24.415 | 66.909 | 1.00 48.97 |
| ATOM | 5600 | CG | LYS | B | 325 | 57.212 | 25.400 | 65.731 | 1.00 53.41 |
| ATOM | 5601 | CD | LYS | B | 325 | 58.582 | 25.386 | 65.024 | 1.00 58.77 |
| ATOM | 5602 | CE | LYS | B | 325 | 59.700 | 26.013 | 65.846 | 1.00 58.10 |
| ATOM | 5603 | NZ | LYS | B | 325 | 61.024 | 25.906 | 65.178 | 1.00 53.38 |
| ATOM | 5604 | C | LYS | B | 325 | 57.368 | 23.822 | 69.309 | 1.00 45.79 |
| ATOM | 5605 | O | LYS | B | 325 | 56.375 | 23.891 | 70.034 | 1.00 43.91 |
| ATOM | 5606 | N | ALA | B | 326 | 58.245 | 22.829 | 69.381 | 1.00 44.28 |
| ATOM | 5607 | CA | ALA | B | 326 | 58.078 | 21.746 | 70.336 | 1.00 44.25 |
| ATOM | 5608 | CB | ALA | B | 326 | 59.013 | 20.589 | 69.986 | 1.00 41.44 |
| ATOM | 5609 | C | ALA | B | 326 | 58.342 | 22.233 | 71.757 | 1.00 40.92 |
| ATOM | 5610 | O | ALA | B | 326 | 57.639 | 21.843 | 72.688 | 1.00 39.02 |
| ATOM | 5611 | N | LYS | B | 327 | 59.352 | 23.085 | 71.922 | 1.00 38.14 |
| ATOM | 5612 | CA | LYS | B | 327 | 59.689 | 23.603 | 73.246 | 1.00 40.11 |
| ATOM | 5613 | CB | LYS | B | 327 | 60.892 | 24.552 | 73.178 | 1.00 42.36 |
| ATOM | 5614 | CG | LYS | B | 327 | 62.174 | 23.922 | 72.659 | 1.00 45.78 |
| ATOM | 5615 | CD | LYS | B | 327 | 63.325 | 24.926 | 72.675 | 1.00 48.46 |
| ATOM | 5616 | CE | LYS | B | 327 | 64.594 | 24.367 | 72.031 | 1.00 49.62 |
| ATOM | 5617 | NZ | LYS | B | 327 | 65.108 | 23.139 | 72.700 | 1.00 48.53 |
| ATOM | 5618 | C | LYS | B | 327 | 58.500 | 24.338 | 73.841 | 1.00 39.17 |
| ATOM | 5619 | O | LYS | B | 327 | 58.132 | 24.112 | 74.994 | 1.00 38.87 |
| ATOM | 5620 | N | GLU | B | 328 | 57.898 | 25.215 | 73.048 | 1.00 41.06 |
| ATOM | 5621 | CA | GLU | B | 328 | 56.750 | 25.986 | 73.512 | 1.00 42.35 |
| ATOM | 5622 | CB | GLU | B | 328 | 56.357 | 27.028 | 72.463 | 1.00 44.02 |
| ATOM | 5623 | CG | GLU | B | 328 | 57.434 | 28.084 | 72.258 | 1.00 44.80 |
| ATOM | 5624 | CD | GLU | B | 328 | 57.835 | 28.742 | 73.569 | 1.00 48.40 |
| ATOM | 5625 | OE1 | GLU | B | 328 | 56.949 | 29.317 | 74.237 | 1.00 51.20 |
| ATOM | 5626 | OE2 | GLU | B | 328 | 59.029 | 28.680 | 73.935 | 1.00 47.81 |
| ATOM | 5627 | C | GLU | B | 328 | 55.569 | 25.087 | 73.839 | 1.00 38.67 |
| ATOM | 5628 | O | GLU | B | 328 | 54.794 | 25.377 | 74.750 | 1.00 41.20 |
| ATOM | 5629 | N | LEU | B | 329 | 55.429 | 23.999 | 73.090 | 1.00 35.31 |
| ATOM | 5630 | CA | LEU | B | 329 | 54.349 | 23.056 | 73.334 | 1.00 32.69 |
| ATOM | 5631 | CB | LEU | B | 329 | 54.404 | 21.900 | 72.334 | 1.00 35.06 |
| ATOM | 5632 | CG | LEU | B | 329 | 53.344 | 20.813 | 72.544 | 1.00 35.01 |
| ATOM | 5633 | CD1 | LEU | B | 329 | 51.958 | 21.430 | 72.419 | 1.00 36.90 |

Fig. 18-85

| ATOM | 5634 | CD2 | LEU | B | 329 | 53.521 | 19.699 | 71.525 | 1.00 | 32.36 |
| ATOM | 5635 | C | LEU | B | 329 | 54.504 | 22.507 | 74.747 | 1.00 | 34.07 |
| ATOM | 5636 | O | LEU | B | 329 | 53.621 | 22.664 | 75.583 | 1.00 | 30.53 |
| ATOM | 5637 | N | LEU | B | 330 | 55.640 | 21.873 | 75.013 | 1.00 | 32.74 |
| ATOM | 5638 | CA | LEU | B | 330 | 55.889 | 21.311 | 76.330 | 1.00 | 34.99 |
| ATOM | 5639 | CB | LEU | B | 330 | 57.267 | 20.642 | 76.382 | 1.00 | 37.01 |
| ATOM | 5640 | CG | LEU | B | 330 | 57.466 | 19.428 | 75.470 | 1.00 | 34.91 |
| ATOM | 5641 | CD1 | LEU | B | 330 | 58.832 | 18.817 | 75.728 | 1.00 | 34.69 |
| ATOM | 5642 | CD2 | LEU | B | 330 | 56.369 | 18.396 | 75.742 | 1.00 | 34.10 |
| ATOM | 5643 | C | LEU | B | 330 | 55.789 | 22.363 | 77.429 | 1.00 | 37.12 |
| ATOM | 5644 | O | LEU | B | 330 | 55.210 | 22.110 | 78.482 | 1.00 | 34.19 |
| ATOM | 5645 | N | LYS | B | 331 | 56.353 | 23.540 | 77.186 | 1.00 | 34.34 |
| ATOM | 5646 | CA | LYS | B | 331 | 56.313 | 24.604 | 78.181 | 1.00 | 43.35 |
| ATOM | 5647 | CB | LYS | B | 331 | 57.162 | 25.788 | 77.712 | 1.00 | 46.25 |
| ATOM | 5648 | CG | LYS | B | 331 | 58.658 | 25.496 | 77.685 | 1.00 | 51.07 |
| ATOM | 5649 | CD | LYS | B | 331 | 59.482 | 26.610 | 77.021 | 1.00 | 49.96 |
| ATOM | 5650 | CE | LYS | B | 331 | 59.371 | 27.957 | 77.733 | 1.00 | 53.08 |
| ATOM | 5651 | NZ | LYS | B | 331 | 58.013 | 28.569 | 77.662 | 1.00 | 56.18 |
| ATOM | 5652 | C | LYS | B | 331 | 54.892 | 25.069 | 78.494 | 1.00 | 42.06 |
| ATOM | 5653 | O | LYS | B | 331 | 54.588 | 25.416 | 79.631 | 1.00 | 43.05 |
| ATOM | 5654 | N | SER | B | 332 | 54.018 | 25.056 | 77.492 | 1.00 | 44.54 |
| ATOM | 5655 | CA | SER | B | 332 | 52.639 | 25.502 | 77.679 | 1.00 | 46.58 |
| ATOM | 5656 | CB | SER | B | 332 | 51.975 | 25.751 | 76.329 | 1.00 | 48.75 |
| ATOM | 5657 | OG | SER | B | 332 | 51.769 | 24.527 | 75.646 | 1.00 | 49.55 |
| ATOM | 5658 | C | SER | B | 332 | 51.780 | 24.507 | 78.451 | 1.00 | 49.56 |
| ATOM | 5659 | O | SER | B | 332 | 50.618 | 24.791 | 78.749 | 1.00 | 46.67 |
| ATOM | 5660 | N | ILE | B | 333 | 52.341 | 23.345 | 78.770 | 1.00 | 50.55 |
| ATOM | 5661 | CA | ILE | B | 333 | 51.586 | 22.326 | 79.488 | 1.00 | 51.93 |
| ATOM | 5662 | CB | ILE | B | 333 | 52.259 | 20.945 | 79.376 | 1.00 | 51.82 |
| ATOM | 5663 | CG2 | ILE | B | 333 | 51.447 | 19.902 | 80.134 | 1.00 | 50.29 |
| ATOM | 5664 | CG1 | ILE | B | 333 | 52.359 | 20.539 | 77.905 | 1.00 | 52.18 |
| ATOM | 5665 | CD1 | ILE | B | 333 | 53.044 | 19.210 | 77.693 | 1.00 | 55.42 |
| ATOM | 5666 | C | ILE | B | 333 | 51.367 | 22.634 | 80.964 | 1.00 | 51.45 |
| ATOM | 5667 | O | ILE | B | 333 | 52.180 | 23.290 | 81.614 | 1.00 | 50.96 |
| ATOM | 5668 | N | ASP | B | 334 | 50.245 | 22.141 | 81.472 | 1.00 | 54.05 |
| ATOM | 5669 | CA | ASP | B | 334 | 49.850 | 22.306 | 82.865 | 1.00 | 58.15 |
| ATOM | 5670 | CB | ASP | B | 334 | 48.320 | 22.216 | 82.959 | 1.00 | 60.38 |
| ATOM | 5671 | CG | ASP | B | 334 | 47.751 | 20.972 | 82.262 | 1.00 | 63.85 |
| ATOM | 5672 | OD1 | ASP | B | 334 | 48.017 | 19.833 | 82.710 | 1.00 | 59.16 |
| ATOM | 5673 | OD2 | ASP | B | 334 | 47.033 | 21.138 | 81.252 | 1.00 | 59.71 |
| ATOM | 5674 | C | ASP | B | 334 | 50.506 | 21.207 | 83.701 | 1.00 | 55.47 |
| ATOM | 5675 | O | ASP | B | 334 | 49.833 | 20.291 | 84.171 | 1.00 | 54.08 |
| ATOM | 5676 | N | PHE | B | 335 | 51.816 | 21.307 | 83.906 | 1.00 | 54.60 |
| ATOM | 5677 | CA | PHE | B | 335 | 52.524 | 20.266 | 84.641 | 1.00 | 56.60 |
| ATOM | 5678 | CB | PHE | B | 335 | 53.718 | 19.784 | 83.811 | 1.00 | 53.01 |
| ATOM | 5679 | CG | PHE | B | 335 | 54.522 | 18.717 | 84.482 | 1.00 | 49.30 |
| ATOM | 5680 | CD1 | PHE | B | 335 | 53.898 | 17.589 | 85.008 | 1.00 | 45.61 |
| ATOM | 5681 | CD2 | PHE | B | 335 | 55.901 | 18.843 | 84.605 | 1.00 | 46.83 |
| ATOM | 5682 | CE1 | PHE | B | 335 | 54.637 | 16.600 | 85.651 | 1.00 | 45.95 |
| ATOM | 5683 | CE2 | PHE | B | 335 | 56.651 | 17.860 | 85.247 | 1.00 | 46.02 |
| ATOM | 5684 | CZ | PHE | B | 335 | 56.018 | 16.737 | 85.772 | 1.00 | 46.08 |
| ATOM | 5685 | C | PHE | B | 335 | 52.971 | 20.559 | 86.072 | 1.00 | 57.29 |
| ATOM | 5686 | O | PHE | B | 335 | 52.197 | 20.378 | 87.012 | 1.00 | 63.54 |
| ATOM | 5687 | N | GLU | B | 336 | 54.223 | 20.983 | 86.229 | 1.00 | 55.21 |
| ATOM | 5688 | CA | GLU | B | 336 | 54.818 | 21.286 | 87.535 | 1.00 | 60.30 |
| ATOM | 5689 | CB | GLU | B | 336 | 53.783 | 21.846 | 88.517 | 1.00 | 64.95 |
| ATOM | 5690 | CG | GLU | B | 336 | 54.375 | 22.225 | 89.867 | 1.00 | 71.50 |
| ATOM | 5691 | CD | GLU | B | 336 | 53.363 | 22.882 | 90.787 | 1.00 | 75.37 |
| ATOM | 5692 | OE1 | GLU | B | 336 | 52.796 | 23.925 | 90.394 | 1.00 | 75.32 |
| ATOM | 5693 | OE2 | GLU | B | 336 | 53.137 | 22.361 | 91.901 | 1.00 | 76.84 |
| ATOM | 5694 | C | GLU | B | 336 | 55.485 | 20.058 | 88.146 | 1.00 | 55.66 |
| ATOM | 5695 | O | GLU | B | 336 | 54.823 | 19.093 | 88.529 | 1.00 | 49.97 |
| ATOM | 5696 | N | GLU | B | 337 | 56.807 | 20.125 | 88.240 | 1.00 | 54.26 |
| ATOM | 5697 | CA | GLU | B | 337 | 57.630 | 19.047 | 88.767 | 1.00 | 54.35 |
| ATOM | 5698 | CB | GLU | B | 337 | 59.101 | 19.457 | 88.635 | 1.00 | 54.08 |
| ATOM | 5699 | CG | GLU | B | 337 | 60.074 | 18.315 | 88.514 | 1.00 | 54.15 |

Fig. 18-86

| | | | | | | | | | |
|---|---|---|---|---|---|---|---|---|---|
| ATOM | 5700 | CD | GLU | B | 337 | 59.856 | 17.496 | 87.259 | 1.00 48.94 |
| ATOM | 5701 | OE1 | GLU | B | 337 | 59.958 | 18.049 | 86.142 | 1.00 41.06 |
| ATOM | 5702 | OE2 | GLU | B | 337 | 59.581 | 16.292 | 87.391 | 1.00 50.23 |
| ATOM | 5703 | C | GLU | B | 337 | 57.278 | 18.740 | 90.227 | 1.00 55.08 |
| ATOM | 5704 | O | GLU | B | 337 | 57.130 | 19.651 | 91.039 | 1.00 54.51 |
| ATOM | 5705 | N | PHE | B | 338 | 57.140 | 17.458 | 90.557 | 1.00 56.20 |
| ATOM | 5706 | CA | PHE | B | 338 | 56.798 | 17.048 | 91.918 | 1.00 57.73 |
| ATOM | 5707 | CB | PHE | B | 338 | 56.713 | 15.527 | 92.020 | 1.00 58.47 |
| ATOM | 5708 | CG | PHE | B | 338 | 56.231 | 15.034 | 93.359 | 1.00 63.17 |
| ATOM | 5709 | CD1 | PHE | B | 338 | 54.882 | 15.096 | 93.696 | 1.00 64.86 |
| ATOM | 5710 | CD2 | PHE | B | 338 | 57.129 | 14.526 | 94.293 | 1.00 63.51 |
| ATOM | 5711 | CE1 | PHE | B | 338 | 54.434 | 14.656 | 94.943 | 1.00 65.25 |
| ATOM | 5712 | CE2 | PHE | B | 338 | 56.693 | 14.087 | 95.539 | 1.00 63.64 |
| ATOM | 5713 | CZ | PHE | B | 338 | 55.342 | 14.152 | 95.864 | 1.00 66.30 |
| ATOM | 5714 | C | PHE | B | 338 | 57.836 | 17.539 | 92.918 | 1.00 61.85 |
| ATOM | 5715 | O | PHE | B | 338 | 57.520 | 17.807 | 94.078 | 1.00 58.15 |
| ATOM | 5716 | N | ASP | B | 339 | 59.081 | 17.636 | 92.466 | 1.00 64.63 |
| ATOM | 5717 | CA | ASP | B | 339 | 60.167 | 18.099 | 93.316 | 1.00 67.53 |
| ATOM | 5718 | CB | ASP | B | 339 | 61.286 | 17.059 | 93.362 | 1.00 67.32 |
| ATOM | 5719 | CG | ASP | B | 339 | 62.474 | 17.524 | 94.174 | 1.00 68.13 |
| ATOM | 5720 | OD1 | ASP | B | 339 | 62.280 | 17.909 | 95.346 | 1.00 68.68 |
| ATOM | 5721 | OD2 | ASP | B | 339 | 63.603 | 17.502 | 93.646 | 1.00 69.03 |
| ATOM | 5722 | C | ASP | B | 339 | 60.718 | 19.435 | 92.829 | 1.00 69.03 |
| ATOM | 5723 | O | ASP | B | 339 | 61.211 | 19.545 | 91.708 | 1.00 67.54 |
| ATOM | 5724 | N | ASP | B | 340 | 60.626 | 20.442 | 93.693 | 1.00 72.19 |
| ATOM | 5725 | CA | ASP | B | 340 | 61.088 | 21.797 | 93.402 | 1.00 75.20 |
| ATOM | 5726 | CB | ASP | B | 340 | 61.113 | 22.623 | 94.689 | 1.00 77.04 |
| ATOM | 5727 | CG | ASP | B | 340 | 59.766 | 22.671 | 95.375 | 1.00 78.70 |
| ATOM | 5728 | OD1 | ASP | B | 340 | 58.803 | 23.181 | 94.763 | 1.00 79.66 |
| ATOM | 5729 | OD2 | ASP | B | 340 | 59.668 | 22.194 | 96.525 | 1.00 80.53 |
| ATOM | 5730 | C | ASP | B | 340 | 62.464 | 21.856 | 92.751 | 1.00 74.82 |
| ATOM | 5731 | O | ASP | B | 340 | 62.615 | 22.400 | 91.659 | 1.00 78.48 |
| ATOM | 5732 | N | GLU | B | 341 | 63.465 | 21.303 | 93.426 | 1.00 74.11 |
| ATOM | 5733 | CA | GLU | B | 341 | 64.827 | 21.312 | 92.907 | 1.00 76.25 |
| ATOM | 5734 | CB | GLU | B | 341 | 65.818 | 21.596 | 94.040 | 1.00 79.54 |
| ATOM | 5735 | CG | GLU | B | 341 | 67.277 | 21.653 | 93.596 | 1.00 82.33 |
| ATOM | 5736 | CD | GLU | B | 341 | 67.539 | 22.750 | 92.577 | 1.00 83.24 |
| ATOM | 5737 | OE1 | GLU | B | 341 | 67.333 | 23.937 | 92.910 | 1.00 85.25 |
| ATOM | 5738 | OE2 | GLU | B | 341 | 67.950 | 22.427 | 91.443 | 1.00 83.72 |
| ATOM | 5739 | C | GLU | B | 341 | 65.196 | 19.998 | 92.227 | 1.00 73.97 |
| ATOM | 5740 | O | GLU | B | 341 | 65.627 | 19.051 | 92.883 | 1.00 77.10 |
| ATOM | 5741 | N | VAL | B | 342 | 65.033 | 19.946 | 90.910 | 1.00 71.92 |
| ATOM | 5742 | CA | VAL | B | 342 | 65.354 | 18.744 | 90.151 | 1.00 68.51 |
| ATOM | 5743 | CB | VAL | B | 342 | 64.081 | 18.027 | 89.663 | 1.00 68.83 |
| ATOM | 5744 | CG1 | VAL | B | 342 | 63.268 | 17.552 | 90.837 | 1.00 67.57 |
| ATOM | 5745 | CG2 | VAL | B | 342 | 63.255 | 18.969 | 88.806 | 1.00 67.72 |
| ATOM | 5746 | C | VAL | B | 342 | 66.201 | 19.059 | 88.927 | 1.00 65.35 |
| ATOM | 5747 | O | VAL | B | 342 | 67.177 | 18.366 | 88.640 | 1.00 68.31 |
| ATOM | 5748 | N | ASP | B | 343 | 65.819 | 20.112 | 88.213 | 1.00 60.89 |
| ATOM | 5749 | CA | ASP | B | 343 | 66.514 | 20.520 | 86.998 | 1.00 58.89 |
| ATOM | 5750 | CB | ASP | B | 343 | 68.024 | 20.636 | 87.223 | 1.00 63.48 |
| ATOM | 5751 | CG | ASP | B | 343 | 68.763 | 21.070 | 85.966 | 1.00 66.69 |
| ATOM | 5752 | OD1 | ASP | B | 343 | 70.012 | 21.070 | 85.970 | 1.00 67.64 |
| ATOM | 5753 | OD2 | ASP | B | 343 | 68.089 | 21.420 | 84.973 | 1.00 65.42 |
| ATOM | 5754 | C | ASP | B | 343 | 66.264 | 19.499 | 85.900 | 1.00 53.17 |
| ATOM | 5755 | O | ASP | B | 343 | 66.993 | 18.516 | 85.766 | 1.00 49.70 |
| ATOM | 5756 | N | ARG | B | 344 | 65.216 | 19.735 | 85.124 | 1.00 50.24 |
| ATOM | 5757 | CA | ARG | B | 344 | 64.868 | 18.853 | 84.022 | 1.00 46.49 |
| ATOM | 5758 | CB | ARG | B | 344 | 63.467 | 18.269 | 84.228 | 1.00 42.41 |
| ATOM | 5759 | CG | ARG | B | 344 | 63.317 | 17.367 | 85.452 | 1.00 38.59 |
| ATOM | 5760 | CD | ARG | B | 344 | 64.344 | 16.246 | 85.432 | 1.00 37.12 |
| ATOM | 5761 | NE | ARG | B | 344 | 64.169 | 15.310 | 86.537 | 1.00 36.55 |
| ATOM | 5762 | CZ | ARG | B | 344 | 65.078 | 14.413 | 86.905 | 1.00 37.20 |
| ATOM | 5763 | NH1 | ARG | B | 344 | 66.234 | 14.331 | 86.259 | 1.00 33.53 |
| ATOM | 5764 | NH2 | ARG | B | 344 | 64.830 | 13.595 | 87.915 | 1.00 28.79 |
| ATOM | 5765 | C | ARG | B | 344 | 64.910 | 19.660 | 82.732 | 1.00 44.45 |

Fig. 18-87

```
ATOM   5766  O    ARG B 344      64.328  19.269  81.720  1.00 38.73
ATOM   5767  N    SER B 345      65.618  20.784  82.783  1.00 42.44
ATOM   5768  CA   SER B 345      65.740  21.677  81.637  1.00 41.74
ATOM   5769  CB   SER B 345      66.661  22.849  81.993  1.00 43.47
ATOM   5770  OG   SER B 345      67.956  22.388  82.351  1.00 46.96
ATOM   5771  C    SER B 345      66.244  20.981  80.375  1.00 36.32
ATOM   5772  O    SER B 345      65.840  21.333  79.273  1.00 35.70
ATOM   5773  N    TYR B 346      67.117  19.992  80.534  1.00 33.93
ATOM   5774  CA   TYR B 346      67.661  19.264  79.391  1.00 34.77
ATOM   5775  CB   TYR B 346      68.660  18.206  79.877  1.00 36.09
ATOM   5776  CG   TYR B 346      68.054  17.146  80.774  1.00 34.27
ATOM   5777  CD1  TYR B 346      67.433  16.013  80.240  1.00 37.62
ATOM   5778  CE1  TYR B 346      66.843  15.048  81.077  1.00 36.73
ATOM   5779  CD2  TYR B 346      68.072  17.294  82.157  1.00 36.40
ATOM   5780  CE2  TYR B 346      67.489 -16.344  82.999  1.00 36.54
ATOM   5781  CZ   TYR B 346      66.878  15.228  82.457  1.00 36.54
ATOM   5782  OH   TYR B 346      66.310  14.306  83.306  1.00 33.35
ATOM   5783  C    TYR B 346      66.563  18.599  78.570  1.00 36.26
ATOM   5784  O    TYR B 346      66.719  18.385  77.367  1.00 40.50
ATOM   5785  N    MET B 347      65.445  18.282  79.214  1.00 32.72
ATOM   5786  CA   MET B 347      64.346  17.628  78.516  1.00 35.43
ATOM   5787  CB   MET B 347      63.280  17.164  79.513  1.00 34.36
ATOM   5788  CG   MET B 347      63.819  16.292  80.635  1.00 28.32
ATOM   5789  SD   MET B 347      62.515  15.604  81.669  1.00 34.47
ATOM   5790  CE   MET B 347      61.654  17.027  82.142  1.00 39.60
ATOM   5791  C    MET B 347      63.701  18.525  77.465  1.00 39.04
ATOM   5792  O    MET B 347      63.060  18.029  76.540  1.00 37.38
ATOM   5793  N    LEU B 348      63.857  19.839  77.606  1.00 39.21
ATOM   5794  CA   LEU B 348      63.272  20.773  76.645  1.00 40.81
ATOM   5795  CB   LEU B 348      62.806  22.058  77.339  1.00 36.87
ATOM   5796  CG   LEU B 348      61.690  21.975  78.384  1.00 42.66
ATOM   5797  CD1  LEU B 348      61.507  23.337  79.032  1.00 43.41
ATOM   5798  CD2  LEU B 348      60.391  21.511  77.741  1.00 40.47
ATOM   5799  C    LEU B 348      64.289  21.133  75.573  1.00 41.13
ATOM   5800  O    LEU B 348      64.018  21.968  74.711  1.00 38.93
ATOM   5801  N    GLU B 349      65.455  20.495  75.632  1.00 37.70
ATOM   5802  CA   GLU B 349      66.527  20.757  74.681  1.00 42.48
ATOM   5803  CB   GLU B 349      67.856  20.953  75.422  1.00 45.02
ATOM   5804  CG   GLU B 349      67.834  22.035  76.493  1.00 53.82
ATOM   5805  CD   GLU B 349      67.483  23.402  75.938  1.00 57.46
ATOM   5806  OE1  GLU B 349      68.211  23.885  75.044  1.00 59.62
ATOM   5807  OE2  GLU B 349      66.480  23.993  76.397  1.00 57.91
ATOM   5808  C    GLU B 349      66.709  19.638  73.664  1.00 43.57
ATOM   5809  O    GLU B 349      66.577  19.849  72.459  1.00 41.26
ATOM   5810  N    THR B 350      67.027  18.448  74.161  1.00 41.95
ATOM   5811  CA   THR B 350      67.264  17.299  73.298  1.00 40.02
ATOM   5812  CB   THR B 350      68.689  16.775  73.504  1.00 43.08
ATOM   5813  OG1  THR B 350      68.894  16.490  74.894  1.00 41.07
ATOM   5814  CG2  THR B 350      69.703  17.816  73.049  1.00 45.05
ATOM   5815  C    THR B 350      66.278  16.154  73.510  1.00 37.56
ATOM   5816  O    THR B 350      65.754  15.966  74.611  1.00 33.64
ATOM   5817  N    LEU B 351      66.043  15.391  72.445  1.00 32.86
ATOM   5818  CA   LEU B 351      65.126  14.260  72.475  1.00 35.00
ATOM   5819  CB   LEU B 351      64.776  13.810  71.053  1.00 31.61
ATOM   5820  CG   LEU B 351      63.709  14.601  70.312  1.00 35.31
ATOM   5821  CD1  LEU B 351      63.552  14.064  68.904  1.00 37.88
ATOM   5822  CD2  LEU B 351      62.397  14.474  71.068  1.00 39.36
ATOM   5823  C    LEU B 351      65.662  13.065  73.240  1.00 33.33
ATOM   5824  O    LEU B 351      64.956  12.469  74.046  1.00 31.48
ATOM   5825  N    LYS B 352      66.915  12.720  72.981  1.00 29.58
ATOM   5826  CA   LYS B 352      67.527  11.576  73.633  1.00 36.77
ATOM   5827  CB   LYS B 352      68.457  10.864  72.647  1.00 34.32
ATOM   5828  CG   LYS B 352      67.777  10.563  71.326  1.00 39.29
ATOM   5829  CD   LYS B 352      68.703   9.949  70.294  1.00 42.25
ATOM   5830  CE   LYS B 352      69.110   8.541  70.655  1.00 46.22
ATOM   5831  NZ   LYS B 352      69.831   7.905  69.516  1.00 44.15
```

Fig. 18-88

| | | | | | | | | | |
|---|---|---|---|---|---|---|---|---|---|
| ATOM | 5832 | C | | LYS | B | 352 | 68.295 | 11.983 | 74.878 | 1.00 | 36.30 |
| ATOM | 5833 | O | | LYS | B | 352 | 69.086 | 12.931 | 74.865 | 1.00 | 36.65 |
| ATOM | 5834 | N | | ASP | B | 353 | 68.049 | 11.275 | 75.967 | 1.00 | 30.01 |
| ATOM | 5835 | CA | | ASP | B | 353 | 68.757 | 11.569 | 77.188 | 1.00 | 33.99 |
| ATOM | 5836 | CB | | ASP | B | 353 | 67.852 | 11.308 | 78.394 | 1.00 | 38.57 |
| ATOM | 5837 | CG | | ASP | B | 353 | 67.134 | 9.986 | 78.315 | 1.00 | 43.90 |
| ATOM | 5838 | OD1 | ASP | B | 353 | 66.034 | 9.851 | 78.926 | 1.00 | 22.39 |
| ATOM | 5839 | OD2 | ASP | B | 353 | 67.679 | 9.078 | 77.649 | 1.00 | 50.42 |
| ATOM | 5840 | C | | ASP | B | 353 | 70.022 | 10.723 | 77.202 | 1.00 | 35.83 |
| ATOM | 5841 | O | | ASP | B | 353 | 70.189 | 9.833 | 76.368 | 1.00 | 23.71 |
| ATOM | 5842 | N | | PRO | B | 354 | 70.954 | 11.025 | 78.116 | 1.00 | 36.36 |
| ATOM | 5843 | CD | | PRO | B | 354 | 70.928 | 12.093 | 79.132 | 1.00 | 38.28 |
| ATOM | 5844 | CA | | PRO | B | 354 | 72.205 | 10.277 | 78.212 | 1.00 | 33.62 |
| ATOM | 5845 | CB | | PRO | B | 354 | 73.003 | 11.104 | 79.213 | 1.00 | 34.46 |
| ATOM | 5846 | CG | | PRO | B | 354 | 71.896 | 11.556 | 80.164 | 1.00 | 38.08 |
| ATOM | 5847 | C | | PRO | B | 354 | 71.924 | 8.883 | 78.733 | 1.00 | 33.62 |
| ATOM | 5848 | O | | PRO | B | 354 | 70.894 | 8.643 | 79.366 | 1.00 | 24.82 |
| ATOM | 5849 | N | | TRP | B | 355 | 72.833 | 7.954 | 78.468 | 1.00 | 31.76 |
| ATOM | 5850 | CA | | TRP | B | 355 | 72.635 | 6.611 | 78.969 | 1.00 | 30.01 |
| ATOM | 5851 | CB | | TRP | B | 355 | 73.653 | 5.655 | 78.359 | 1.00 | 34.02 |
| ATOM | 5852 | CG | | TRP | B | 355 | 73.025 | 4.378 | 77.910 | 1.00 | 44.37 |
| ATOM | 5853 | CD2 | TRP | B | 355 | 73.263 | 3.072 | 78.436 | 1.00 | 45.39 |
| ATOM | 5854 | CE2 | TRP | B | 355 | 72.418 | 2.177 | 77.734 | 1.00 | 44.31 |
| ATOM | 5855 | CE3 | TRP | B | 355 | 74.107 | 2.569 | 79.432 | 1.00 | 47.19 |
| ATOM | 5856 | CD1 | TRP | B | 355 | 72.073 | 4.230 | 76.935 | 1.00 | 42.18 |
| ATOM | 5857 | NE1 | TRP | B | 355 | 71.704 | 2.910 | 76.826 | 1.00 | 37.84 |
| ATOM | 5858 | CZ2 | TRP | B | 355 | 72.395 | 0.808 | 77.999 | 1.00 | 44.97 |
| ATOM | 5859 | CZ3 | TRP | B | 355 | 74.084 | 1.207 | 79.694 | 1.00 | 50.83 |
| ATOM | 5860 | CH2 | TRP | B | 355 | 73.231 | 0.341 | 78.979 | 1.00 | 48.73 |
| ATOM | 5861 | C | | TRP | B | 355 | 72.819 | 6.685 | 80.485 | 1.00 | 30.87 |
| ATOM | 5862 | O | | TRP | B | 355 | 73.622 | 7.474 | 80.981 | 1.00 | 26.93 |
| ATOM | 5863 | N | | ARG | B | 356 | 72.061 | 5.880 | 81.218 | 1.00 | 24.96 |
| ATOM | 5864 | CA | | ARG | B | 356 | 72.147 | 5.848 | 82.671 | 1.00 | 23.57 |
| ATOM | 5865 | CB | | ARG | B | 356 | 70.811 | 6.319 | 83.257 | 1.00 | 24.71 |
| ATOM | 5866 | CG | | ARG | B | 356 | 70.534 | 7.795 | 82.941 | 1.00 | 23.66 |
| ATOM | 5867 | CD | | ARG | B | 356 | 69.067 | 8.212 | 83.055 | 1.00 | 20.14 |
| ATOM | 5868 | NE | | ARG | B | 356 | 68.926 | 9.610 | 82.642 | 1.00 | 20.59 |
| ATOM | 5869 | CZ | | ARG | B | 356 | 67.787 | 10.192 | 82.288 | 1.00 | 25.41 |
| ATOM | 5870 | NH1 | ARG | B | 356 | 66.644 | 9.508 | 82.287 | 1.00 | 17.01 |
| ATOM | 5871 | NH2 | ARG | B | 356 | 67.796 | 11.464 | 81.910 | 1.00 | 20.07 |
| ATOM | 5872 | C | | ARG | B | 356 | 72.481 | 4.410 | 83.085 | 1.00 | 26.57 |
| ATOM | 5873 | O | | ARG | B | 356 | 71.610 | 3.641 | 83.485 | 1.00 | 23.02 |
| ATOM | 5874 | N | | GLY | B | 357 | 73.761 | 4.063 | 82.978 | 1.00 | 23.92 |
| ATOM | 5875 | CA | | GLY | B | 357 | 74.186 | 2.712 | 83.294 | 1.00 | 25.54 |
| ATOM | 5876 | C | | GLY | B | 357 | 74.796 | 2.464 | 84.657 | 1.00 | 24.35 |
| ATOM | 5877 | O | | GLY | B | 357 | 74.523 | 3.161 | 85.628 | 1.00 | 25.88 |
| ATOM | 5878 | N | | GLY | B | 358 | 75.638 | 1.444 | 84.718 | 1.00 | 24.32 |
| ATOM | 5879 | CA | | GLY | B | 358 | 76.282 | 1.070 | 85.960 | 1.00 | 23.56 |
| ATOM | 5880 | C | | GLY | B | 358 | 76.412 | -0.441 | 85.924 | 1.00 | 29.26 |
| ATOM | 5881 | O | | GLY | B | 358 | 76.146 | -1.051 | 84.889 | 1.00 | 23.71 |
| ATOM | 5882 | N | | GLU | B | 359 | 76.814 | -1.051 | 87.033 | 1.00 | 27.64 |
| ATOM | 5883 | CA | | GLU | B | 359 | 76.955 | -2.503 | 87.078 | 1.00 | 32.16 |
| ATOM | 5884 | CB | | GLU | B | 359 | 77.822 | -2.936 | 88.265 | 1.00 | 30.40 |
| ATOM | 5885 | CG | | GLU | B | 359 | 77.125 | -2.772 | 89.601 | 1.00 | 31.23 |
| ATOM | 5886 | CD | | GLU | B | 359 | 77.844 | -3.479 | 90.741 | 1.00 | 37.96 |
| ATOM | 5887 | OE1 | GLU | B | 359 | 77.287 | -3.521 | 91.861 | 1.00 | 33.89 |
| ATOM | 5888 | OE2 | GLU | B | 359 | 78.959 | -3.990 | 90.520 | 1.00 | 37.40 |
| ATOM | 5889 | C | | GLU | B | 359 | 75.571 | -3.122 | 87.261 | 1.00 | 31.35 |
| ATOM | 5890 | O | | GLU | B | 359 | 74.612 | -2.429 | 87.588 | 1.00 | 25.15 |
| ATOM | 5891 | N | | VAL | B | 360 | 75.482 | -4.428 | 87.053 | 1.00 | 29.61 |
| ATOM | 5892 | CA | | VAL | B | 360 | 74.230 | -5.147 | 87.251 | 1.00 | 26.21 |
| ATOM | 5893 | CB | | VAL | B | 360 | 74.035 | -6.270 | 86.200 | 1.00 | 28.47 |
| ATOM | 5894 | CG1 | VAL | B | 360 | 72.764 | -7.045 | 86.492 | 1.00 | 22.74 |
| ATOM | 5895 | CG2 | VAL | B | 360 | 73.969 | -5.670 | 84.796 | 1.00 | 29.70 |
| ATOM | 5896 | C | | VAL | B | 360 | 74.342 | -5.784 | 88.625 | 1.00 | 26.00 |
| ATOM | 5897 | O | | VAL | B | 360 | 75.150 | -6.693 | 88.821 | 1.00 | 27.55 |

Fig. 18-89

| | | | | | | | | |
|---|---|---|---|---|---|---|---|---|
| ATOM | 5898 | N | ARG | B | 361 | 73.553 | -5.289 | 89.575 | 1.00 26.45 |
| ATOM | 5899 | CA | ARG | B | 361 | 73.558 | -5.821 | 90.935 | 1.00 28.47 |
| ATOM | 5900 | CB | ARG | B | 361 | 72.479 | -5.146 | 91.787 | 1.00 30.55 |
| ATOM | 5901 | CG | ARG | B | 361 | 72.937 | -3.877 | 92.485 | 1.00 32.61 |
| ATOM | 5902 | CD | ARG | B | 361 | 71.749 | -3.163 | 93.117 | 1.00 35.00 |
| ATOM | 5903 | NE | ARG | B | 361 | 70.858 | -2.617 | 92.094 | 1.00 30.31 |
| ATOM | 5904 | CZ | ARG | B | 361 | 69.753 | -1.925 | 92.350 | 1.00 29.45 |
| ATOM | 5905 | NH1 | ARG | B | 361 | 69.385 | -1.689 | 93.605 | 1.00 18.49 |
| ATOM | 5906 | NH2 | ARG | B | 361 | 69.041 | -1.428 | 91.348 | 1.00 30.49 |
| ATOM | 5907 | C | ARG | B | 361 | 73.351 | -7.322 | 91.001 | 1.00 30.17 |
| ATOM | 5908 | O | ARG | B | 361 | 72.665 | -7.910 | 90.168 | 1.00 23.60 |
| ATOM | 5909 | N | LYS | B | 362 | 73.949 | -7.922 | 92.022 | 1.00 33.09 |
| ATOM | 5910 | CA | LYS | B | 362 | 73.864 | -9.351 | 92.272 | 1.00 36.94 |
| ATOM | 5911 | CB | LYS | B | 362 | 74.687 | -9.706 | 93.513 | 1.00 40.24 |
| ATOM | 5912 | CG | LYS | B | 362 | 76.190 | -9.527 | 93.337 | 1.00 52.55 |
| ATOM | 5913 | CD | LYS | B | 362 | 76.571 | -8.126 | 92.849 | 1.00 56.65 |
| ATOM | 5914 | CE | LYS | B | 362 | 76.149 | -7.032 | 93.819 | 1.00 53.39 |
| ATOM | 5915 | NZ | LYS | B | 362 | 76.553 | -5.680 | 93.341 | 1.00 48.87 |
| ATOM | 5916 | C | LYS | B | 362 | 72.427 | -9.826 | 92.463 | 1.00 32.84 |
| ATOM | 5917 | O | LYS | B | 362 | 72.045 | -10.867 | 91.938 | 1.00 28.27 |
| ATOM | 5918 | N | GLU | B | 363 | 71.628 | -9.075 | 93.215 | 1.00 34.67 |
| ATOM | 5919 | CA | GLU | B | 363 | 70.245 | -9.493 | 93.435 | 1.00 35.72 |
| ATOM | 5920 | CB | GLU | B | 363 | 69.519 | -8.532 | 94.390 | 1.00 36.04 |
| ATOM | 5921 | CG | GLU | B | 363 | 69.502 | -7.077 | 93.977 | 1.00 44.81 |
| ATOM | 5922 | CD | GLU | B | 363 | 68.859 | -6.186 | 95.033 | 1.00 52.14 |
| ATOM | 5923 | OE1 | GLU | B | 363 | 67.661 | -6.370 | 95.341 | 1.00 48.46 |
| ATOM | 5924 | OE2 | GLU | B | 363 | 69.562 | -5.300 | 95.566 | 1.00 57.31 |
| ATOM | 5925 | C | GLU | B | 363 | 69.501 | -9.619 | 92.111 | 1.00 30.68 |
| ATOM | 5926 | O | GLU | B | 363 | 68.695 | -10.530 | 91.944 | 1.00 30.45 |
| ATOM | 5927 | N | VAL | B | 364 | 69.784 | -8.724 | 91.166 | 1.00 26.19 |
| ATOM | 5928 | CA | VAL | B | 364 | 69.138 | -8.789 | 89.852 | 1.00 24.65 |
| ATOM | 5929 | CB | VAL | B | 364 | 69.536 | -7.599 | 88.958 | 1.00 23.49 |
| ATOM | 5930 | CG1 | VAL | B | 364 | 68.924 | -7.770 | 87.563 | 1.00 21.01 |
| ATOM | 5931 | CG2 | VAL | B | 364 | 69.049 | -6.293 | 89.587 | 1.00 23.08 |
| ATOM | 5932 | C | VAL | B | 364 | 69.530 | -10.083 | 89.144 | 1.00 23.19 |
| ATOM | 5933 | O | VAL | B | 364 | 68.691 | -10.749 | 88.542 | 1.00 23.06 |
| ATOM | 5934 | N | LYS | B | 365 | 70.810 | -10.436 | 89.216 | 1.00 27.15 |
| ATOM | 5935 | CA | LYS | B | 365 | 71.296 | -11.668 | 88.594 | 1.00 29.18 |
| ATOM | 5936 | CB | LYS | B | 365 | 72.821 | -11.758 | 88.704 | 1.00 28.61 |
| ATOM | 5937 | CG | LYS | B | 365 | 73.554 | -10.617 | 88.030 | 1.00 30.27 |
| ATOM | 5938 | CD | LYS | B | 365 | 75.074 | -10.768 | 88.154 | 1.00 32.58 |
| ATOM | 5939 | CE | LYS | B | 365 | 75.790 | -9.587 | 87.516 | 1.00 29.13 |
| ATOM | 5940 | NZ | LYS | B | 365 | 77.271 | -9.689 | 87.606 | 1.00 35.17 |
| ATOM | 5941 | C | LYS | B | 365 | 70.666 | -12.879 | 89.276 | 1.00 25.30 |
| ATOM | 5942 | O | LYS | B | 365 | 70.282 | -13.837 | 88.613 | 1.00 26.81 |
| ATOM | 5943 | N | ASP | B | 366 | 70.559 | -12.831 | 90.604 | 1.00 26.10 |
| ATOM | 5944 | CA | ASP | B | 366 | 69.963 | -13.938 | 91.347 | 1.00 28.29 |
| ATOM | 5945 | CB | ASP | B | 366 | 70.105 | -13.731 | 92.859 | 1.00 29.44 |
| ATOM | 5946 | CG | ASP | B | 366 | 71.557 | -13.669 | 93.311 | 1.00 32.95 |
| ATOM | 5947 | OD1 | ASP | B | 366 | 72.446 | -14.099 | 92.551 | 1.00 26.37 |
| ATOM | 5948 | OD2 | ASP | B | 366 | 71.811 | -13.216 | 94.442 | 1.00 35.26 |
| ATOM | 5949 | C | ASP | B | 366 | 68.487 | -14.110 | 90.986 | 1.00 28.61 |
| ATOM | 5950 | O | ASP | B | 366 | 68.000 | -15.231 | 90.869 | 1.00 27.00 |
| ATOM | 5951 | N | THR | B | 367 | 67.777 | -13.002 | 90.801 | 1.00 28.63 |
| ATOM | 5952 | CA | THR | B | 367 | 66.365 | -13.080 | 90.438 | 1.00 27.35 |
| ATOM | 5953 | CB | THR | B | 367 | 65.726 | -11.683 | 90.359 | 1.00 27.63 |
| ATOM | 5954 | OG1 | THR | B | 367 | 65.771 | -11.068 | 91.656 | 1.00 28.12 |
| ATOM | 5955 | CG2 | THR | B | 367 | 64.280 | -11.786 | 89.890 | 1.00 22.94 |
| ATOM | 5956 | C | THR | B | 367 | 66.197 | -13.782 | 89.094 | 1.00 25.46 |
| ATOM | 5957 | O | THR | B | 367 | 65.389 | -14.693 | 88.964 | 1.00 24.48 |
| ATOM | 5958 | N | LEU | B | 368 | 66.962 | -13.361 | 88.092 | 1.00 23.33 |
| ATOM | 5959 | CA | LEU | B | 368 | 66.857 | -13.990 | 86.785 | 1.00 28.99 |
| ATOM | 5960 | CB | LEU | B | 368 | 67.719 | -13.256 | 85.759 | 1.00 27.67 |
| ATOM | 5961 | CG | LEU | B | 368 | 67.060 | -12.070 | 85.046 | 1.00 29.47 |
| ATOM | 5962 | CD1 | LEU | B | 368 | 65.923 | -12.607 | 84.195 | 1.00 32.45 |
| ATOM | 5963 | CD2 | LEU | B | 368 | 66.546 | -11.027 | 86.043 | 1.00 19.43 |

Fig. 18-90

| | | | | | | | | |
|---|---|---|---|---|---|---|---|---|
| ATOM | 5964 | C | LEU | B | 368 | 67.262 | -15.454 | 86.888 | 1.00 32.40 |
| ATOM | 5965 | O | LEU | B | 368 | 66.726 | -16.309 | 86.179 | 1.00 31.80 |
| ATOM | 5966 | N | GLU | B | 369 | 68.212 | -15.735 | 87.774 | 1.00 33.59 |
| ATOM | 5967 | CA | GLU | B | 369 | 68.656 | -17.101 | 88.003 | 1.00 39.68 |
| ATOM | 5968 | CB | GLU | B | 369 | 69.736 | -17.141 | 89.082 | 1.00 42.61 |
| ATOM | 5969 | CG | GLU | B | 369 | 71.133 | -17.138 | 88.537 | 1.00 50.65 |
| ATOM | 5970 | CD | GLU | B | 369 | 71.469 | -18.443 | 87.842 | 1.00 55.81 |
| ATOM | 5971 | OE1 | GLU | B | 369 | 72.589 | -18.561 | 87.299 | 1.00 57.42 |
| ATOM | 5972 | OE2 | GLU | B | 369 | 70.610 | -19.353 | 87.841 | 1.00 58.37 |
| ATOM | 5973 | C | GLU | B | 369 | 67.479 | -17.954 | 88.442 | 1.00 34.94 |
| ATOM | 5974 | O | GLU | B | 369 | 67.190 | -18.974 | 87.827 | 1.00 32.71 |
| ATOM | 5975 | N | LYS | B | 370 | 66.805 | -17.541 | 89.512 | 1.00 34.92 |
| ATOM | 5976 | CA | LYS | B | 370 | 65.656 | -18.295 | 89.993 | 1.00 35.12 |
| ATOM | 5977 | CB | LYS | B | 370 | 65.061 | -17.679 | 91.268 | 1.00 37.39 |
| ATOM | 5978 | CG | LYS | B | 370 | 65.879 | -17.916 | 92.532 | 1.00 44.70 |
| ATOM | 5979 | CD | LYS | B | 370 | 66.781 | -16.741 | 92.892 | 1.00 48.10 |
| ATOM | 5980 | CE | LYS | B | 370 | 65.956 | -15.537 | 93.346 | 1.00 47.82 |
| ATOM | 5981 | NZ | LYS | B | 370 | 66.804 | -14.387 | 93.786 | 1.00 45.41 |
| ATOM | 5982 | C | LYS | B | 370 | 64.581 | -18.375 | 88.930 | 1.00 33.21 |
| ATOM | 5983 | O | LYS | B | 370 | 63.937 | -19.409 | 88.773 | 1.00 29.52 |
| ATOM | 5984 | N | ALA | B | 371 | 64.390 | -17.288 | 88.191 | 1.00 31.62 |
| ATOM | 5985 | CA | ALA | B | 371 | 63.368 | -17.274 | 87.153 | 1.00 37.19 |
| ATOM | 5986 | CB | ALA | B | 371 | 63.392 | -15.938 | 86.403 | 1.00 35.65 |
| ATOM | 5987 | C | ALA | B | 371 | 63.572 | -18.431 | 86.181 | 1.00 37.79 |
| ATOM | 5988 | O | ALA | B | 371 | 62.627 | -19.137 | 85.838 | 1.00 34.46 |
| ATOM | 5989 | N | LYS | B | 372 | 64.810 | -18.644 | 85.759 | 1.00 40.10 |
| ATOM | 5990 | CA | LYS | B | 372 | 65.147 | -19.698 | 84.792 | 1.00 40.46 |
| ATOM | 5991 | C | LYS | B | 372 | 64.746 | -21.066 | 85.348 | 1.00 43.15 |
| ATOM | 5992 | O | LYS | B | 372 | 64.757 | -22.053 | 84.591 | 1.00 43.57 |
| ATOM | 5993 | CB | LYS | B | 372 | 66.654 | -19.694 | 84.517 | 1.00 40.51 |
| ATOM | 5994 | CG | LYS | B | 372 | 67.029 | -18.925 | 83.248 | 1.00 20.00 |
| ATOM | 5995 | CD | LYS | B | 372 | 68.352 | -19.390 | 82.635 | 1.00 20.00 |
| ATOM | 5996 | CE | LYS | B | 372 | 68.544 | -20.907 | 82.706 | 1.00 20.00 |
| ATOM | 5997 | NZ | LYS | B | 372 | 69.814 | -21.354 | 82.116 | 1.00 20.00 |
| ATOM | 5998 | N | ALA | B | 373 | 64.412 | -21.159 | 86.624 | 1.00 47.80 |
| ATOM | 5999 | CA | ALA | B | 373 | 64.014 | -22.425 | 87.239 | 1.00 49.71 |
| ATOM | 6000 | CB | ALA | B | 373 | 64.762 | -22.639 | 88.546 | 1.00 48.25 |
| ATOM | 6001 | C | ALA | B | 373 | 62.515 | -22.443 | 87.494 | 1.00 53.38 |
| ATOM | 6002 | O | ALA | B | 373 | 61.844 | -23.313 | 86.903 | 1.00 58.01 |
| ATOM | 6003 | OXT | ALA | B | 373 | 62.029 | -21.589 | 88.269 | 1.00 55.13 |
| HETATM | 2991 | ZN | ZN | C | 1 | 49.660 | 9.211 | 109.302 | 1.00 32.54 |
| HETATM | 2992 | O1 | TSA | D | 2 | 47.669 | 8.189 | 109.464 | 1.00 28.76 |
| HETATM | 2993 | O2 | TSA | D | 2 | 49.952 | 6.981 | 108.340 | 1.00 25.81 |
| HETATM | 2994 | O3 | TSA | D | 2 | 52.458 | 5.101 | 101.667 | 1.00 36.93 |
| HETATM | 2995 | N1 | TSA | D | 2 | 47.800 | 7.789 | 108.131 | 1.00 31.21 |
| HETATM | 2996 | N2 | TSA | D | 2 | 53.013 | -1.329 | 101.259 | 1.00 30.57 |
| HETATM | 2997 | C1 | TSA | D | 2 | 51.859 | 2.799 | 101.610 | 1.00 28.47 |
| HETATM | 2998 | C2 | TSA | D | 2 | 50.907 | 1.769 | 101.666 | 1.00 25.57 |
| HETATM | 2999 | C3 | TSA | D | 2 | 51.241 | 0.419 | 101.551 | 1.00 21.68 |
| HETATM | 3000 | C4 | TSA | D | 2 | 52.626 | 0.026 | 101.366 | 1.00 23.11 |
| HETATM | 3001 | C5 | TSA | D | 2 | 53.589 | 1.080 | 101.303 | 1.00 25.02 |
| HETATM | 3002 | C6 | TSA | D | 2 | 53.218 | 2.408 | 101.418 | 1.00 29.24 |
| HETATM | 3003 | C7 | TSA | D | 2 | 51.572 | 4.261 | 101.734 | 1.00 32.98 |
| HETATM | 3004 | C8 | TSA | D | 2 | 50.108 | 4.726 | 101.996 | 1.00 29.05 |
| HETATM | 3005 | C9 | TSA | D | 2 | 50.052 | 5.421 | 103.338 | 1.00 28.13 |
| HETATM | 3006 | C10 | TSA | D | 2 | 49.060 | 5.357 | 104.279 | 1.00 25.99 |
| HETATM | 3007 | C11 | TSA | D | 2 | 49.315 | 6.155 | 105.504 | 1.00 32.05 |
| HETATM | 3008 | C12 | TSA | D | 2 | 48.515 | 6.184 | 106.595 | 1.00 27.37 |
| HETATM | 3009 | C13 | TSA | D | 2 | 48.855 | 6.994 | 107.756 | 1.00 29.02 |
| HETATM | 3010 | C14 | TSA | D | 2 | 49.680 | 5.693 | 100.864 | 1.00 30.21 |
| HETATM | 3011 | C15 | TSA | D | 2 | 47.776 | 4.545 | 104.132 | 1.00 30.60 |
| HETATM | 3012 | C17 | TSA | D | 2 | 54.438 | -1.703 | 101.139 | 1.00 23.45 |
| HETATM | 3013 | C16 | TSA | D | 2 | 52.044 | -2.416 | 101.316 | 1.00 23.15 |
| HETATM | 6004 | ZN | ZN | E | 1 | 52.949 | 1.842 | 85.681 | 1.00 28.19 |
| HETATM | 6005 | O1 | TSA | F | 2 | 50.964 | 0.911 | 85.428 | 1.00 24.72 |
| HETATM | 6006 | O2 | TSA | F | 2 | 51.255 | 3.324 | 86.654 | 1.00 30.24 |

Fig. 18-91

| | | | | | | | | | |
|---|---|---|---|---|---|---|---|---|---|
| HETATM | 6007 | O3 | TSA | F | 2 | 51.569 | 6.512 | 93.219 | 1.00 27.89 |
| HETATM | 6008 | N1 | TSA | F | 2 | 50.347 | 1.221 | 86.634 | 1.00 27.23 |
| HETATM | 6009 | N2 | TSA | F | 2 | 47.061 | 11.139 | 93.713 | 1.00 16.24 |
| HETATM | 6010 | C1 | TSA | F | 2 | 49.443 | 7.579 | 93.304 | 1.00 27.18 |
| HETATM | 6011 | C2 | TSA | F | 2 | 48.035 | 7.529 | 93.267 | 1.00 25.98 |
| HETATM | 6012 | C3 | TSA | F | 2 | 47.227 | 8.657 | 93.398 | 1.00 24.59 |
| HETATM | 6013 | C4 | TSA | F | 2 | 47.837 | 9.971 | 93.583 | 1.00 25.75 |
| HETATM | 6014 | C5 | TSA | F | 2 | 49.274 | 10.017 | 93.626 | 1.00 26.53 |
| HETATM | 6015 | C6 | TSA | F | 2 | 50.041 | 8.869 | 93.495 | 1.00 28.36 |
| HETATM | 6016 | C7 | TSA | F | 2 | 50.349 | 6.405 | 93.167 | 1.00 25.27 |
| HETATM | 6017 | C8 | TSA | F | 2 | 49.716 | 5.006 | 92.905 | 1.00 24.18 |
| HETATM | 6018 | C9 | TSA | F | 2 | 50.134 | 4.552 | 91.518 | 1.00 27.20 |
| HETATM | 6019 | C10 | TSA | F | 2 | 49.419 | 3.807 | 90.616 | 1.00 30.21 |
| HETATM | 6020 | C11 | TSA | F | 2 | 50.118 | 3.553 | 89.327 | 1.00 27.18 |
| HETATM | 6021 | C12 | TSA | F | 2 | 49.762 | 2.624 | 88.409 | 1.00 23.47 |
| HETATM | 6022 | C13 | TSA | F | 2 | 50.529 | 2.462 | 87.170 | 1.00 28.28 |
| HETATM | 6023 | C14 | TSA | F | 2 | 50.208 | 4.019 | 93.994 | 1.00 28.83 |
| HETATM | 6024 | C15 | TSA | F | 2 | 48.013 | 3.270 | 90.863 | 1.00 26.16 |
| HETATM | 6025 | C17 | TSA | F | 2 | 47.699 | 12.456 | 93.883 | 1.00 27.37 |
| HETATM | 6026 | C16 | TSA | F | 2 | 45.610 | 11.107 | 93.679 | 1.00 25.36 |
| HETATM | 6027 | OH2 | WAT | G | 1 | 61.391 | 6.723 | 88.062 | 1.00 12.93 |
| HETATM | 6028 | OH2 | WAT | G | 2 | 55.595 | -4.443 | 83.558 | 1.00 7.53 |
| HETATM | 6029 | OH2 | WAT | G | 3 | 58.656 | 12.731 | 106.749 | 1.00 12.33 |
| HETATM | 6030 | OH2 | WAT | G | 4 | 46.347 | 15.263 | 111.460 | 1.00 14.54 |
| HETATM | 6031 | OH2 | WAT | G | 5 | 45.523 | 13.627 | 76.224 | 1.00 11.14 |
| HETATM | 6032 | OH2 | WAT | G | 6 | 24.466 | -6.064 | 85.688 | 1.00 22.41 |
| HETATM | 6033 | OH2 | WAT | G | 7 | 48.579 | -17.745 | 80.769 | 1.00 21.99 |
| HETATM | 6034 | OH2 | WAT | G | 8 | 56.344 | -15.640 | 87.809 | 1.00 26.67 |
| HETATM | 6035 | OH2 | WAT | G | 9 | 48.554 | -14.901 | 83.717 | 1.00 23.94 |
| HETATM | 6036 | OH2 | WAT | G | 10 | 57.540 | -7.620 | 122.771 | 1.00 26.96 |
| HETATM | 6037 | OH2 | WAT | G | 11 | 59.414 | -2.497 | 84.029 | 1.00 22.51 |
| HETATM | 6038 | OH2 | WAT | G | 12 | 31.671 | 18.074 | 114.616 | 1.00 32.15 |
| HETATM | 6039 | OH2 | WAT | G | 13 | 62.335 | 10.679 | 117.140 | 1.00 19.47 |
| HETATM | 6040 | OH2 | WAT | G | 14 | 45.565 | 9.469 | 79.366 | 1.00 18.81 |
| HETATM | 6041 | OH2 | WAT | G | 15 | 43.311 | 8.237 | 79.508 | 1.00 26.11 |
| HETATM | 6042 | OH2 | WAT | G | 16 | 46.628 | 13.883 | 104.423 | 1.00 24.28 |
| HETATM | 6043 | OH2 | WAT | G | 17 | 40.672 | 2.507 | 81.576 | 1.00 18.30 |
| HETATM | 6044 | OH2 | WAT | G | 18 | 61.830 | 10.923 | 77.709 | 1.00 22.27 |
| HETATM | 6045 | OH2 | WAT | G | 19 | 57.813 | 0.831 | 108.580 | 1.00 24.68 |
| HETATM | 6046 | OH2 | WAT | G | 20 | 48.885 | 5.660 | 77.823 | 1.00 30.00 |
| HETATM | 6047 | OH2 | WAT | G | 21 | 36.382 | -8.352 | 88.841 | 1.00 17.32 |
| HETATM | 6048 | OH2 | WAT | G | 22 | 39.316 | -10.091 | 86.422 | 1.00 27.38 |
| HETATM | 6049 | OH2 | WAT | G | 23 | 54.802 | -3.446 | 90.346 | 1.00 21.73 |
| HETATM | 6050 | OH2 | WAT | G | 24 | 49.292 | 12.112 | 140.537 | 1.00 34.17 |
| HETATM | 6051 | OH2 | WAT | G | 25 | 56.747 | 8.830 | 60.744 | 1.00 40.67 |
| HETATM | 6052 | OH2 | WAT | G | 26 | 41.952 | 9.79* | 100.118 | 1.00 27.92 |
| HETATM | 6053 | OH2 | WAT | G | 27 | 31.268 | 2.80; | 106.695 | 1.00 24.31 |
| HETATM | 6054 | OH2 | WAT | G | 28 | 68.342 | 17.79: | 111.076 | 1.00 30.93 |
| HETATM | 6055 | OH2 | WAT | G | 29 | 72.651 | -6.985 | 94.845 | 1.00 29.34 |
| HETATM | 6056 | OH2 | WAT | G | 30 | 39.287 | 9.257 | 85.623 | 1.00 22.61 |
| HETATM | 6057 | OH2 | WAT | G | 31 | 61.221 | 14.462 | 87.256 | 1.00 29.85 |
| HETATM | 6058 | OH2 | WAT | G | 32 | 38.167 | 22.692 | 107.435 | 1.00 36.40 |
| HETATM | 6059 | OH2 | WAT | G | 33 | 64.657 | -2.682 | 96.225 | 1.00 18.70 |
| HETATM | 6060 | OH2 | WAT | G | 34 | 44.059 | -2.698 | 99.805 | 1.00 30.02 |
| HETATM | 6061 | OH2 | WAT | G | 35 | 38.480 | 4.763 | 93.051 | 1.00 28.03 |
| HETATM | 6062 | OH2 | WAT | G | 36 | 57.899 | 7.654 | 112.976 | 1.00 26.46 |
| HETATM | 6063 | OH2 | WAT | G | 37 | 57.092 | 3.145 | 93.309 | 1.00 22.31 |
| HETATM | 6064 | OH2 | WAT | G | 38 | 52.194 | -1.400 | 118.878 | 1.00 30.83 |
| HETATM | 6065 | OH2 | WAT | G | 39 | 69.400 | 14.200 | 123.379 | 1.00 30.98 |
| HETATM | 6066 | OH2 | WAT | G | 40 | 24.024 | 6.540 | 79.852 | 1.00 38.13 |
| HETATM | 6067 | OH2 | WAT | G | 41 | 46.657 | -10.880 | 89.402 | 1.00 29.24 |
| HETATM | 6068 | OH2 | WAT | G | 42 | 24.976 | 13.489 | 109.692 | 1.00 46.34 |
| HETATM | 6069 | OH2 | WAT | G | 43 | 46.533 | -4.511 | 94.759 | 1.00 23.11 |
| HETATM | 6070 | OH2 | WAT | G | 44 | 51.448 | 13.833 | 86.306 | 1.00 27.08 |
| HETATM | 6071 | OH2 | WAT | G | 45 | 70.578 | 4.183 | 105.248 | 1.00 42.42 |
| HETATM | 6072 | OH2 | WAT | G | 46 | 53.938 | -9.936 | 116.021 | 1.00 38.97 |

Fig. 18-92

```
HETATM 6073  OH2 WAT G  47      38.458  -0.443  63.035  1.00 28.35
HETATM 6074  OH2 WAT G  48      64.786   7.930 107.466  1.00 34.46
HETATM 6075  OH2 WAT G  49      50.823  36.521 114.809  1.00 40.51
HETATM 6076  OH2 WAT G  50      33.963 -10.352  68.080  1.00 39.11
HETATM 6077  OH2 WAT G  51      71.328 -14.321  86.007  1.00 33.30
HETATM 6078  OH2 WAT G  52      63.272  10.210  79.836  1.00 35.75
HETATM 6079  OH2 WAT G  53      59.263 -12.096  94.306  1.00 29.57
HETATM 6080  OH2 WAT G  54      46.041  10.641  76.561  1.00 27.97
HETATM 6081  OH2 WAT G  55      46.614 -13.620  89.775  1.00 24.25
HETATM 6082  OH2 WAT G  56      76.600   0.622  89.097  1.00 29.19
HETATM 6083  OH2 WAT G  57      53.555   6.439  79.089  1.00 34.05
HETATM 6084  OH2 WAT G  58      71.301  11.026  83.310  1.00 35.02
HETATM 6085  OH2 WAT G  59      28.188  -9.956  81.594  1.00 33.21
HETATM 6086  OH2 WAT G  60      53.084  20.992  98.483  1.00 27.64
HETATM 6087  OH2 WAT G  61      59.484   8.630  93.423  1.00 30.30
HETATM 6088  OH2 WAT G  62      26.195  -3.809  95.805  1.00 33.04
HETATM 6089  OH2 WAT G  63      26.095  -0.121  89.620  1.00 37.39
HETATM 6090  OH2 WAT G  64      47.100  -6.141 109.711  1.00 20.88
HETATM 6091  OH2 WAT G  65      23.273   0.731  92.275  1.00 30.38
HETATM 6092  OH2 WAT G  66      45.340 -24.751  72.694  1.00 37.51
HETATM 6093  OH2 WAT G  67      33.754  16.234 111.676  1.00 34.63
HETATM 6094  OH2 WAT G  68      52.831  19.209 126.276  1.00 47.11
HETATM 6095  OH2 WAT G  69      50.218  16.953 111.099  1.00 26.24
HETATM 6096  OH2 WAT G  70      44.791   5.844  70.857  1.00 24.95
HETATM 6097  OH2 WAT G  71      49.517 -18.731  82.921  1.00 29.48
HETATM 6098  OH2 WAT G  72      76.379  10.131 116.550  1.00 48.70
HETATM 6099  OH2 WAT G  73      30.214  -8.086  87.873  1.00 46.35
HETATM 6100  OH2 WAT G  74      45.320  12.061  80.458  1.00 30.80
HETATM 6101  OH2 WAT G  75      72.881   5.360  86.249  1.00 29.04
HETATM 6102  OH2 WAT G  76      59.674 -23.046  87.252  1.00 41.96
HETATM 6103  OH2 WAT G  77      40.619   7.921 100.345  1.00 26.45
HETATM 6104  OH2 WAT G  78      41.666 -19.477  70.073  1.00 36.27
HETATM 6105  OH2 WAT G  79      46.408  -6.539  92.717  1.00 25.78
HETATM 6106  OH2 WAT G  80      35.743 -12.230  81.646  1.00 28.34
HETATM 6107  OH2 WAT G  81      28.268   8.745 121.961  1.00 41.15
HETATM 6108  OH2 WAT G  82      68.843   3.154  71.986  1.00 32.34
HETATM 6109  OH2 WAT G  83      52.125 -11.158  85.150  1.00 24.14
HETATM 6110  OH2 WAT G  84      75.374  -1.773  92.264  1.00 26.12
HETATM 6111  OH2 WAT G  85      46.957  12.230 142.271  1.00 37.07
HETATM 6112  OH2 WAT G  86      63.789   9.551  64.329  1.00 55.58
HETATM 6113  OH2 WAT G  87      60.672  21.185  72.215  1.00 58.55
HETATM 6114  OH2 WAT G  88      56.547   9.505  82.064  1.00 31.10
HETATM 6115  OH2 WAT G  89      26.366  -0.876  92.250  1.00 29.70
HETATM 6116  OH2 WAT G  90      67.604 -16.583  80.808  1.00 32.85
HETATM 6117  OH2 WAT G  91      23.910   1.899  82.068  1.00 42.95
HETATM 6118  OH2 WAT G  92      50.032   4.106 117.380  1.00 30.05
HETATM 6119  OH2 WAT G  93      26.774  -9.492  83.952  1.00 43.59
HETATM 6120  OH2 WAT G  94      42.714  -0.637 113.787  1.00 40.17
HETATM 6121  OH2 WAT G  95      57.966   7.989 134.170  1.00 47.82
HETATM 6122  OH2 WAT G  96      54.478  -3.550 119.086  1.00 36.62
HETATM 6123  OH2 WAT G  97      53.065  11.696 101.718  1.00 41.62
HETATM 6124  OH2 WAT G  98      58.286 -23.645  68.207  1.00 45.98
HETATM 6125  OH2 WAT G  99      54.855  -9.614 121.975  1.00 34.57
HETATM 6126  OH2 WAT G 100      57.408  -3.352  57.145  1.00 42.14
HETATM 6127  OH2 WAT G 101      63.590  20.353 123.667  1.00 33.87
HETATM 6128  OH2 WAT G 102      48.129 -23.143  72.392  1.00 30.23
HETATM 6129  OH2 WAT G 103      62.834   6.913  76.094  1.00 52.01
HETATM 6130  OH2 WAT G 104      34.566   6.529  73.089  1.00 36.29
HETATM 6131  OH2 WAT G 105      51.588  20.869  67.459  1.00 36.85
HETATM 6132  OH2 WAT G 106      28.160  18.020 129.379  1.00 42.87
HETATM 6133  OH2 WAT G 107      49.082 -11.452  57.603  1.00 43.62
HETATM 6134  OH2 WAT G 108      44.717  -8.605  93.281  1.00 41.95
HETATM 6135  OH2 WAT G 109      67.088 -11.900  94.019  1.00 35.71
HETATM 6136  OH2 WAT G 110      49.561  22.763 100.800  1.00 35.40
HETATM 6137  OH2 WAT G 111      75.853  10.960 124.536  1.00 56.20
HETATM 6138  OH2 WAT G 112      54.383   8.930 136.095  1.00 36.40
```

Fig. 18-93

```
HETATM 6139  OH2 WAT G 113    33.114   1.764  67.443  1.00 37.01
HETATM 6140  OH2 WAT G 114    42.618  -4.357 102.345  1.00 39.18
HETATM 6141  OH2 WAT G 115    53.605 -10.816  66.281  1.00 31.62
HETATM 6142  OH2 WAT G 116    73.410  -1.010  90.400  1.00 34.72
HETATM 6143  OH2 WAT G 117    68.899   3.789 110.221  1.00 35.69
HETATM 6144  OH2 WAT G 118    31.474  19.159 112.425  1.00 28.08
HETATM 6145  OH2 WAT G 119    39.749  -0.616 132.457  1.00 37.43
HETATM 6146  OH2 WAT G 120    44.921   1.089 137.137  1.00 40.80
HETATM 6147  OH2 WAT G 121    31.081   7.617  75.105  1.00 40.86
HETATM 6148  OH2 WAT G 122    35.554  12.017 105.965  1.00 33.58
HETATM 6149  OH2 WAT G 123    41.381 -23.534  70.872  1.00 38.10
HETATM 6150  OH2 WAT G 124    31.999   1.992  73.813  1.00 33.97
HETATM 6151  OH2 WAT G 125    55.761  10.285 101.654  1.00 47.66
HETATM 6152  OH2 WAT G 126    30.596  12.964 133.642  1.00 37.98
HETATM 6153  OH2 WAT G 127    59.611   5.347 136.114  1.00 46.39
HETATM 6154  OH2 WAT G 128    24.190  12.220 124.679  1.00 30.77
HETATM 6155  OH2 WAT G 129    70.078   4.455  86.283  1.00 36.11
HETATM 6156  OH2 WAT G 130    57.882  -4.314 125.597  1.00 41.40
HETATM 6157  OH2 WAT G 131    45.838 -20.690  65.884  1.00 35.98
HETATM 6158  OH2 WAT G 132    47.574   3.186  79.027  1.00 36.67
HETATM 6159  OH2 WAT G 133    46.856 -18.901  62.295  1.00 45.40
HETATM 6160  OH2 WAT G 134    40.164   5.047  95.358  1.00 31.38
HETATM 6161  OH2 WAT G 135    27.268  -0.405 122.461  1.00 38.16
HETATM 6162  OH2 WAT G 136    54.200 -20.155  66.212  1.00 37.55
HETATM 6163  OH2 WAT G 137    45.435 -10.534 103.626  1.00 37.96
HETATM 6164  OH2 WAT G 138    31.633  25.030 106.499  1.00 43.94
HETATM 6165  OH2 WAT G 139    79.029  -7.518  93.606  1.00 40.55
HETATM 6166  OH2 WAT G 140    68.597  20.711 111.685  1.00 33.25
HETATM 6167  OH2 WAT G 141    64.263   8.524 113.832  1.00 40.63
HETATM 6168  OH2 WAT G 143    49.387 -24.485  70.152  1.00 34.07
HETATM 6169  OH2 WAT G 144    23.383  -3.854  83.604  1.00 32.22
HETATM 6170  OH2 WAT G 145    42.360  -0.710  61.686  1.00 35.94
HETATM 6171  OH2 WAT G 146    34.421  -3.304  65.685  1.00 35.42
HETATM 6172  OH2 WAT G 147    31.506   3.409  89.579  1.00 39.86
HETATM 6173  OH2 WAT G 148    34.963  10.688  91.806  1.00 31.12
HETATM 6174  OH2 WAT G 149    54.859 -15.085  96.769  1.00 46.65
HETATM 6175  OH2 WAT G 150    34.695   2.391 131.273  1.00 39.22
HETATM 6176  OH2 WAT G 151    40.348   1.395  61.905  1.00 34.09
HETATM 6177  OH2 WAT G 152    66.912  17.666 127.489  1.00 45.19
HETATM 6178  OH2 WAT G 153    31.096  19.900 103.232  1.00 43.45
HETATM 6179  OH2 WAT G 154    28.074  -4.222  70.175  1.00 28.86
HETATM 6180  OH2 WAT G 155    63.586  -1.894  99.003  1.00 41.15
HETATM 6181  OH2 WAT G 156    54.145 -22.222  88.415  1.00 40.92
HETATM 6182  OH2 WAT G 157    62.443  13.765  89.547  1.00 33.69
HETATM 6183  OH2 WAT G 158    58.832   9.798 101.311  1.00 31.00
HETATM 6184  OH2 WAT G 159    37.701  -5.528 119.322  1 00 45.00
HETATM 6185  OH2 WAT G 160    43.599  13.442 131.274  1 00 38.43
HETATM 6186  OH2 WAT G 161    23.540  -1.137  96.111  1 00 51.83
HETATM 6187  OH2 WAT G 162    59.915  -4.318 110.873  1.00 41.92
HETATM 6188  OH2 WAT G 163    51.265  -8.264  60.546  1.00 31.25
HETATM 6189  OH2 WAT G 164    58.109   7.024  98.294  1.00 46.30
HETATM 6190  OH2 WAT G 165    46.553  18.195  74.179  1.00 37.53
HETATM 6191  OH2 WAT G 166    55.706 -21.025  92.515  1.00 43.91
HETATM 6192  OH2 WAT G 167    67.146  -1.958 109.704  1.00 43.13
HETATM 6193  OH2 WAT G 168    47.445  -3.047 134.746  1.00 27.99
HETATM 6194  OH2 WAT G 169    65.193   5.304  63.562  1.00 36.05
HETATM 6195  OH2 WAT G 170    36.176   8.979 102.024  1.00 39.63
HETATM 6196  OH2 WAT G 171    70.527   5.797  70.886  1.00 44.69
HETATM 6197  OH2 WAT G 172    67.166   8.735  74.628  1.00 51.41
HETATM 6198  OH2 WAT G 173    19.700   9.630  81.850  1.00 53.49
HETATM 6199  OH2 WAT G 174    55.875  11.277  87.176  1.00 38.63
HETATM 6200  OH2 WAT G 175    61.874   8.432  91.682  1.00 40.08
HETATM 6201  OH2 WAT G 176    36.771  -6.815 121.530  1.00 32.57
HETATM 6202  OH2 WAT G 177    63.224   7.776  89.317  1.00 29.83
HETATM 6203  OH2 WAT G 178    29.606  15.345 132.470  1.00 47.28
HETATM 6204  OH2 WAT G 179    52.811  11.799  98.957  1.00 36.09
```

Fig. 18-94

| | | | | | | | | |
|---|---|---|---|---|---|---|---|---|
| HETATM | 6205 | OH2 | WAT | G | 180 | 38.589 | 18.249 | 88.356 | 1.00 36.19 |
| HETATM | 6206 | OH2 | WAT | G | 181 | 43.734 | -15.681 | 61.135 | 1.00 34.24 |
| HETATM | 6207 | OH2 | WAT | G | 182 | 42.283 | 15.251 | 91.437 | 1.00 37.96 |
| HETATM | 6208 | OH2 | WAT | G | 183 | 57.121 | -11.129 | 126.206 | 1.00 45.78 |
| HETATM | 6209 | OH2 | WAT | G | 184 | 50.011 | -19.367 | 92.127 | 1.00 36.55 |
| HETATM | 6210 | OH2 | WAT | G | 185 | 56.880 | 2.453 | 95.969 | 1.00 39.12 |
| HETATM | 6211 | OH2 | WAT | G | 186 | 26.356 | 14.125 | 125.052 | 1.00 32.68 |
| HETATM | 6212 | OH2 | WAT | G | 187 | 24.631 | 20.230 | 122.650 | 1.00 45.67 |
| HETATM | 6213 | OH2 | WAT | G | 188 | 23.516 | 4.964 | 81.599 | 1.00 42.16 |
| HETATM | 6214 | OH2 | WAT | G | 189 | 55.017 | 14.964 | 62.948 | 1.00 50.18 |
| HETATM | 6215 | OH2 | WAT | G | 190 | 33.371 | 13.710 | 105.640 | 1.00 37.04 |
| HETATM | 6216 | OH2 | WAT | G | 191 | 44.466 | -10.386 | 91.144 | 1.00 36.62 |
| HETATM | 6217 | OH2 | WAT | G | 192 | 28.437 | 22.668 | 121.285 | 1.00 38.19 |
| HETATM | 6218 | OH2 | WAT | G | 193 | 29.786 | 24.957 | 122.112 | 1.00 42.05 |
| HETATM | 6219 | OH2 | WAT | G | 194 | 28.852 | 3.461 | 96.101 | 1.00 48.35 |
| HETATM | 6220 | OH2 | WAT | G | 195 | 41.681 | 11.318 | 92.011 | 1.00 32.60 |
| HETATM | 6221 | OH2 | WAT | G | 196 | 26.812 | -10.229 | 111.631 | 1.00 47.70 |
| HETATM | 6222 | OH2 | WAT | G | 197 | 42.432 | -23.250 | 76.629 | 1.00 48.86 |
| HETATM | 6223 | OH2 | WAT | G | 198 | 25.484 | 12.756 | 121.410 | 1.00 43.09 |
| HETATM | 6224 | OH2 | WAT | G | 199 | 43.514 | -20.514 | 111.706 | 1.00 46.80 |
| HETATM | 6225 | OH2 | WAT | G | 200 | 74.273 | -13.079 | 95.699 | 1.00 44.89 |
| HETATM | 6226 | OH2 | WAT | G | 201 | 59.982 | 24.381 | 103.984 | 1.00 40.63 |
| HETATM | 6227 | OH2 | WAT | G | 202 | 67.164 | -12.771 | 74.705 | 1.00 35.13 |
| HETATM | 6228 | OH2 | WAT | G | 203 | 28.708 | 9.211 | 79.238 | 1.00 33.53 |
| HETATM | 6229 | OH2 | WAT | G | 204 | 53.256 | -3.576 | 122.243 | 1.00 48.49 |
| HETATM | 6230 | OH2 | WAT | G | 205 | 50.706 | 16.208 | 87.357 | 1.00 41.26 |
| HETATM | 6231 | OH2 | WAT | G | 206 | 50.000 | 34.998 | 98.339 | 1.00 39.15 |
| HETATM | 6232 | OH2 | WAT | G | 207 | 68.078 | -16.236 | 83.621 | 1.00 29.70 |
| HETATM | 6233 | OH2 | WAT | G | 208 | 24.395 | -4.134 | 111.635 | 1.00 50.82 |
| HETATM | 6234 | OH2 | WAT | G | 209 | 53.384 | -2.664 | 114.289 | 1.00 44.49 |
| HETATM | 6235 | OH2 | WAT | G | 210 | 60.120 | -9.482 | 94.788 | 1.00 31.97 |
| HETATM | 6236 | OH2 | WAT | G | 211 | 23.405 | 17.472 | 111.744 | 1.00 44.97 |
| HETATM | 6237 | OH2 | WAT | G | 212 | 46.214 | 20.943 | 76.878 | 1.00 59.14 |
| HETATM | 6238 | OH2 | WAT | G | 213 | 29.754 | 6.983 | 97.109 | 1.00 41.78 |
| HETATM | 6239 | OH2 | WAT | G | 214 | 46.820 | -0.465 | 55.181 | 1.00 41.02 |
| HETATM | 6240 | OH2 | WAT | G | 215 | 59.143 | 22.096 | 124.775 | 1.00 38.42 |
| HETATM | 6241 | OH2 | WAT | G | 216 | 42.674 | 14.088 | 66.037 | 1.00 32.50 |
| HETATM | 6242 | OH2 | WAT | G | 217 | 55.009 | -7.248 | 98.186 | 1.00 56.50 |
| HETATM | 6243 | OH2 | WAT | G | 218 | 63.361 | -8.209 | 109.653 | 1.00 49.66 |
| HETATM | 6244 | OH2 | WAT | G | 219 | 66.583 | -8.146 | 94.671 | 1.00 50.91 |
| HETATM | 6245 | OH2 | WAT | G | 220 | 44.627 | -2.583 | 93.919 | 1.00 36.99 |
| HETATM | 6246 | OH2 | WAT | G | 221 | 24.470 | -8.606 | 79.502 | 1.00 47.24 |
| HETATM | 6247 | OH2 | WAT | G | 222 | 76.913 | -7.777 | 83.973 | 1.00 50.43 |
| HETATM | 6248 | OH2 | WAT | G | 223 | 32.788 | 0.651 | 129.136 | 1.00 42.47 |
| HETATM | 6249 | OH2 | WAT | G | 224 | 73.731 | -16.880 | 88.817 | 1.00 46.69 |
| HETATM | 6250 | OH2 | WAT | G | 225 | 78.567 | -2.802 | 93.970 | 1.00 43.17 |
| HETATM | 6251 | OH2 | WAT | G | 226 | 45.681 | 1.248 | 57.532 | 1.00 35.84 |
| HETATM | 6252 | OH2 | WAT | G | 227 | 38.263 | 15.236 | 84.711 | 1.00 42.39 |
| HETATM | 6253 | OH2 | WAT | G | 228 | 38.933 | 35.224 | 108.488 | 1.00 52.23 |
| HETATM | 6254 | OH2 | WAT | G | 229 | 33.755 | 14.939 | 70.228 | 1.00 46.56 |
| HETATM | 6255 | OH2 | WAT | G | 230 | 51.521 | 34.184 | 100.859 | 1.00 52.96 |
| HETATM | 6256 | OH2 | WAT | G | 231 | 34.140 | 0.565 | 63.039 | 1.00 31.02 |
| HETATM | 6257 | OH2 | WAT | G | 232 | 37.277 | 13.977 | 81.662 | 1.00 39.83 |
| HETATM | 6258 | OH2 | WAT | G | 233 | 57.307 | 5.947 | 93.216 | 1.00 28.55 |
| HETATM | 6259 | OH2 | WAT | G | 234 | 31.718 | 16.820 | 125.707 | 1.00 53.16 |
| HETATM | 6260 | OH2 | WAT | G | 235 | 60.624 | 31.119 | 110.067 | 1.00 51.02 |
| HETATM | 6261 | OH2 | WAT | G | 236 | 44.357 | 4.267 | 94.916 | 1.00 57.50 |
| HETATM | 6262 | OH2 | WAT | G | 237 | 68.454 | 1.072 | 70.111 | 1.00 38.65 |
| HETATM | 6263 | OH2 | WAT | G | 238 | 27.836 | 6.773 | 79.253 | 1.00 44.95 |
| HETATM | 6264 | OH2 | WAT | G | 239 | 54.933 | 23.344 | 81.087 | 1.00 42.95 |
| HETATM | 6265 | OH2 | WAT | G | 240 | 34.072 | -15.271 | 71.579 | 1.00 45.78 |
| HETATM | 6266 | OH2 | WAT | G | 241 | 35.966 | -1.059 | 61.973 | 1.00 38.91 |
| HETATM | 6267 | OH2 | WAT | G | 242 | 29.687 | 1.898 | 127.376 | 1.00 44.85 |
| HETATM | 6268 | OH2 | WAT | G | 243 | 49.534 | -10.150 | 113.501 | 1.00 38.32 |
| HETATM | 6269 | OH2 | WAT | G | 244 | 57.252 | 9.773 | 96.696 | 1.00 48.83 |
| HETATM | 6270 | OH2 | WAT | G | 245 | 62.310 | 13.262 | 80.972 | 1.00 38.54 |

Fig. 18-95

```
HETATM 6271  OH2 WAT G 246      50.248  -5.552 102.815  1.00 43.23
HETATM 6272  OH2 WAT G 247      47.966  21.564  79.321  1.00 36.79
HETATM 6273  OH2 WAT G 248      62.507  20.866 108.414  1.00 35.30
HETATM 6274  OH2 WAT G 249      53.971  19.763  61.067  1.00 47.49
HETATM 6275  OH2 WAT G 250      38.406   9.828  67.749  1.00 33.71
HETATM 6276  OH2 WAT G 251      35.304  -6.179  66.319  1.00 36.23
HETATM 6277  OH2 WAT G 252      39.218 -12.667  85.010  1.00 36.17
HETATM 6278  OH2 WAT G 253      56.350   5.089  97.225  1.00 46.38
HETATM 6279  OH2 WAT G 254      69.850   3.406 122.119  1.00 55.07
HETATM 6280  OH2 WAT G 255      75.703   2.630 128.600  1.00 30.64
HETATM 6281  OH2 WAT G 256      32.019 -12.973 113.965  1.00 34.48
HETATM 6282  OH2 WAT G 257      54.081   3.421  56.994  1.00 39.11
HETATM 6283  OH2 WAT G 258      32.801  -6.170  91.078  1.00 35.72
HETATM 6284  OH2 WAT G 259      45.040   0.301  95.449  1.00 36.57
HETATM 6285  OH2 WAT G 260      39.815  21.460 128.855  1.00 40.10
HETATM 6286  OH2 WAT G 261      28.763  10.408  93.790  1.00 44.39
HETATM 6287  OH2 WAT G 262      49.668 -12.050  60.539  1.00 50.89
HETATM 6288  OH2 WAT G 263      64.353  20.015 117.495  1.00 62.67
HETATM 6289  OH2 WAT G 264      75.183  13.021 128.124  1.00 50.42
HETATM 6290  OH2 WAT G 265      46.289   6.826  52.485  1.00 46.86
HETATM 6291  OH2 WAT G 266      68.708  13.973  70.958  1.00 37.90
HETATM 6292  OH2 WAT G 267      71.504  12.997 130.029  1.00 38.78
HETATM 6293  OH2 WAT G 268      36.309  -4.716 130.364  1.00 42.92
HETATM 6294  OH2 WAT G 269      65.973  12.195  79.625  1.00 51.68
HETATM 6295  OH2 WAT G 270      71.952  13.021  74.292  1.00 37.70
HETATM 6296  OH2 WAT G 271      44.433 -17.578  62.734  1.00 49.33
HETATM 6297  OH2 WAT G 272      26.917  15.038  89.067  1.00 38.07
HETATM 6298  OH2 WAT G 273      63.380  -5.416 126.550  1.00 41.73
HETATM 6299  OH2 WAT G 274      63.360  -5.356  95.641  1.00 37.54
HETATM 6300  OH2 WAT G 275      65.947 -13.015  97.485  1.00 37.42
HETATM 6301  OH2 WAT G 276      26.406  25.831 117.328  1.00 48.37
HETATM 6302  OH2 WAT G 277      41.893 -10.251  98.201  1.00 46.36
HETATM 6303  OH2 WAT G 278      30.343  -6.507 117.764  1.00 49.87
HETATM 6304  OH2 WAT G 279      45.135  32.419 111.056  1.00 43.93
HETATM 6305  OH2 WAT G 280      50.553  -1.365 120.511  1.00 54.02
HETATM 6306  OH2 WAT G 281      60.428  13.652 105.130  1.00 31.10
HETATM 6307  OH2 WAT G 282      30.342   2.204  70.246  1.00 45.19
HETATM 6308  OH2 WAT G 283      60.358  15.921 127.736  1.00 33.17
HETATM 6309  OH2 WAT G 284      64.193   3.421  62.117  1.00 45.81
HETATM 6310  OH2 WAT G 285      45.468   6.113 105.853  1.00 48.98
HETATM 6311  OH2 WAT G 286      47.514   3.808  98.279  1.00 46.45
HETATM 6312  OH2 WAT G 287      72.144  -6.345  77.930  1.00 40.04
HETATM 6313  OH2 WAT G 288      54.142  -5.100  99.674  1.00 43.62
HETATM 6314  OH2 WAT G 289      48.982  13.297  65.822  1.00 46.98
HETATM 6315  OH2 WAT G 290      41.171  34.107 115.807  1.00 51.76
HETATM 6316  OH2 WAT G 291      36.494  37.195 104.170  1.00 44.27
HETATM 6317  OH2 WAT G 292      48.580  23.117  85.456  1.00 40.96
HETATM 6318  OH2 WAT G 293      55.853  22.934  98.099  1.00 40.95
HETATM 6319  OH2 WAT G 294      61.720  11.077  89.427  1.00 41.21
HETATM 6320  OH2 WAT G 295      43.313 -18.552 114.112  1.00 42.32
HETATM 6321  OH2 WAT G 296      53.001  -6.305 129.052  1.00 37.41
HETATM 6322  OH2 WAT G 297      70.258  24.928  82.843  1.00 48.09
HETATM 6323  OH2 WAT G 298      77.493   0.940 130.507  1.00 51.77
HETATM 6324  OH2 WAT G 299      32.233  12.182  83.028  1.00 53.51
HETATM 6325  OH2 WAT G 300      40.666  12.878  65.747  1.00 46.49
HETATM 6326  OH2 WAT G 301      50.977  12.831 114.597  1.00 48.51
HETATM 6327  OH2 WAT G 302      54.236   3.817  92.196  1.00 41.15
HETATM 6328  OH2 WAT G 303      59.527  -1.343 107.471  1.00 36.71
HETATM 6329  OH2 WAT G 304      70.331   3.940  89.312  1.00 47.70
HETATM 6330  OH2 WAT G 305      60.626   6.969 127.780  1.00 41.96
HETATM 6331  OH2 WAT G 306      42.156  -0.139 133.156  1.00 32.19
HETATM 6332  OH2 WAT G 307      58.386  16.514  99.413  1.00 53.60
HETATM 6333  OH2 WAT G 308      67.617  -1.589  96.570  1.00 40.36
HETATM 6334  OH2 WAT G 309      35.868 -10.936  98.849  1.00 48.80
HETATM 6335  OH2 WAT G 310      45.576  25.388 131.914  1.00 48.99
HETATM 6336  OH2 WAT G 311      37.583  -6.243  64.257  1.00 37.06
```

Fig. 18-96

```
HETATM 6337  OH2 WAT G 312      66.759  16.408  94.600  1.00 45.07
HETATM 6338  OH2 WAT G 313      24.142  11.212 113.340  1.00 52.23
HETATM 6339  OH2 WAT G 314      69.409  16.702  64.230  1.00 39.88
HETATM 6340  OH2 WAT G 315      22.064  24.858 115.328  1.00 50.23
HETATM 6341  OH2 WAT G 316      50.171   9.551 100.345  1.00 37.32
HETATM 6342  OH2 WAT G 317      55.104  31.302 119.497  1.00 44.78
HETATM 6343  OH2 WAT G 318      65.333 -10.105  95.866  1.00 44.21
HETATM 6344  OH2 WAT G 319      31.415  -2.472 128.127  1.00 41.95
HETATM 6345  OH2 WAT G 320      37.423  13.143  88.069  1.00 44.79
HETATM 6346  OH2 WAT G 321      43.619  14.292  96.509  1.00 54.69
HETATM 6347  OH2 WAT G 322      68.048  14.555 126.016  1.00 42.75
HETATM 6348  OH2 WAT G 323      34.778  -2.509 130.204  1.00 37.06
HETATM 6349  OH2 WAT G 324      27.972  18.144 103.841  1.00 47.34
HETATM 6350  OH2 WAT G 325      53.550  23.610  97.592  1.00 38.03
HETATM 6351  OH2 WAT G 326      33.776   4.171 103.451  1.00 50.60
HETATM 6352  OH2 WAT G 327      37.862  35.632 114.870  1.00 48.34
HETATM 6353  OH2 WAT G 328      50.893  14.612  93.478  1.00 38.77
HETATM 6354  OH2 WAT G 329      71.422 -20.913  86.137  1.00 47.69
HETATM 6355  OH2 WAT G 330      50.310 -23.133  74.502  1.00 41.94
HETATM 6356  OH2 WAT G 331      41.520   7.269  60.583  1.00 54.93
HETATM 6357  OH2 WAT G 332      75.879  13.737 106.089  1.00 44.65
HETATM 6358  OH2 WAT G 333      51.923   9.027 138.493  1.00 41.08
HETATM 6359  OH2 WAT G 334      49.511  27.611  79.363  1.00 39.05
HETATM 6360  OH2 WAT G 335      69.385   0.852 110.192  1.00 41.42
HETATM 6361  OH2 WAT G 336      40.952   2.479 101.880  1.00 42.50
HETATM 6362  OH2 WAT G 337      32.998   7.200 103.784  1.00 54.22
HETATM 6363  OH2 WAT G 338      54.366  15.261 136.205  1.00 52.69
HETATM 6364  OH2 WAT G 339      35.674  13.727  89.792  1.00 35.83
HETATM 6365  OH2 WAT G 340      66.606 -21.361  87.138  1.00 46.26
HETATM 6366  OH2 WAT G 341      72.053   4.708 131.550  1.00 45.27
HETATM 6367  OH2 WAT G 342      28.072  -1.358  70.419  1.00 34.92
HETATM 6368  OH2 WAT G 343      23.611  -3.981  76.422  1.00 52.99
HETATM 6369  OH2 WAT G 344      53.684   2.564 122.150  1.00 58.16
HETATM 6370  OH2 WAT G 345      30.624  -6.528 125.556  1.00 34.71
HETATM 6371  OH2 WAT G 346      27.870  13.838 113.997  1.00 44.91
HETATM 6372  OH2 WAT G 347      31.903  -9.588 116.327  1.00 55.34
HETATM 6373  OH2 WAT G 348      71.763  15.094  63.739  1.00 48.99
HETATM 6374  OH2 WAT G 349      25.258  -2.536 114.760  1.00 37.19
HETATM 6375  OH2 WAT G 350      43.765  12.162  78.143  1.00 42.32
HETATM 6376  OH2 WAT G 351      32.452   5.338  73.909  1.00 33.70
HETATM 6377  OH2 WAT G 352      52.896  -5.770 101.894  1.00 46.40
HETATM 6378  OH2 WAT G 353      47.968   4.242 115.852  1.00 34.62
HETATM 6379  OH2 WAT G 354      38.561  -9.302  90.596  1.00 49.80
HETATM 6380  OH2 WAT G 355      63.791  17.454  74.354  1.00 56.40
HETATM 6381  OH2 WAT G 356      41.360   2.648 133.760  1.00 50.00
HETATM 6382  OH2 WAT G 357      42.467  -7.937 122.328  1.00 38.01
HETATM 6383  OH2 WAT G 358      50.890  -0.362 116.668  1.00 39.26
HETATM 6384  OH2 WAT G 359      54.217 -23.881  67.865  1.00 55.18
HETATM 6385  OH2 WAT G 360      64.959   9.539 105.032  1.00 38.83
HETATM 6386  OH2 WAT G 361      58.113 -19.846  82.288  1.00 38.60
HETATM 6387  OH2 WAT G 362      42.245  -1.140  93.572  1.00 31.47
HETATM 6388  OH2 WAT G 363      73.552  17.770 125.885  1.00 54.89
HETATM 6389  OH2 WAT G 364      68.769  15.898 106.810  1.00 45.53
HETATM 6390  OH2 WAT G 365      37.543  19.031  78.866  1.00 45.15
HETATM 6391  OH2 WAT G 366      55.583   6.906  95.087  1.00 44.99
HETATM 6392  OH2 WAT G 367      41.284   9.699  78.250  1.00 36.58
HETATM 6393  OH2 WAT G 368      25.203   5.332 126.362  1.00 46.60
HETATM 6394  OH2 WAT G 369      74.742  -5.006  95.104  1.00 47.85
HETATM 6395  OH2 WAT G 370      70.349  19.871  69.925  1.00 51.46
HETATM 6396  OH2 WAT G 371      42.936  20.631  94.720  1.00 38.66
HETATM 6397  OH2 WAT G 372      34.162 -16.114 114.141  1.00 44.01
HETATM 6398  OH2 WAT G 373      33.863  16.838 100.275  1.00 44.66
HETATM 6399  OH2 WAT G 374      21.613  12.569  86.140  1.00 43.89
HETATM 6400  OH2 WAT G 375      35.751 -13.302 100.583  1.00 53.53
HETATM 6401  OH2 WAT G 376      70.095  13.395 117.505  1.00 52.02
HETATM 6402  OH2 WAT G 377      41.853  19.108 131.799  1.00 46.47
```

Fig. 18-97

```
HETATM 6403  OH2 WAT G 378      55.780 -14.986  65.487  1.00 49.09
HETATM 6404  OH2 WAT G 379      40.990  21.205  91.611  1.00 41.02
HETATM 6405  OH2 WAT G 380      48.157   1.057 116.992  1.00 44.84
HETATM 6406  OH2 WAT G 381      37.954  -6.221 128.334  1.00 37.09
HETATM 6407  OH2 WAT G 382      30.221  27.743 109.194  1.00 39.92
HETATM 6408  OH2 WAT G 383      49.926 -12.826 118.421  1.00 58.95
HETATM 6409  OH2 WAT G 384      42.435 -17.636  81.477  1.00 48.47
HETATM 6410  OH2 WAT G 385      58.226 -25.990  71.378  1.00 48.18
HETATM 6411  OH2 WAT G 386      40.495  17.944 128.741  1.00 43.82
HETATM 6412  OH2 WAT G 387      31.943   6.301 109.475  1.00 35.53
HETATM 6413  OH2 WAT G 388      47.277   2.559 100.509  1.00 43.00
HETATM 6414  OH2 WAT G 389      38.862   9.112 102.620  1.00 31.70
HETATM 6415  OH2 WAT G 390      71.652  14.568 105.167  1.00 49.63
HETATM 6416  OH2 WAT G 391      68.554 -10.518  73.331  1.00 38.16
HETATM 6417  OH2 WAT G 392      70.496 -16.160  84.425  1.00 32.16
HETATM 6418  OH2 WAT G 393      44.698 -24.950  75.603  1.00 43.38
HETATM 6419  OH2 WAT G 394      56.172  15.369  55.027  1.00 47.44
HETATM 6420  OH2 WAT G 395      46.150  -9.441  99.999  1.00 47.98
HETATM 6421  OH2 WAT G 396      26.892  -8.356  89.057  1.00 34.99
HETATM 6422  OH2 WAT G 397      31.737  14.380  90.395  1.00 50.78
HETATM 6423  OH2 WAT G 398      36.261 -13.824  62.777  1.00 50.86
HETATM 6424  OH2 WAT G 399      37.312  15.242 134.977  1.00 43.57
HETATM 6425  OH2 WAT G 400      33.728  13.773 126.419  1.00 57.13
HETATM 6426  OH2 WAT G 401      45.269  27.937 130.311  1.00 49.55
HETATM 6427  OH2 WAT G 402      44.887 -17.414 111.508  1.00 54.29
HETATM 6428  OH2 WAT G 403      68.928   0.455 136.711  1.00 49.90
HETATM 6429  OH2 WAT G 404      43.271 -21.571  64.425  1.00 48.61
HETATM 6430  OH2 WAT G 405      24.243  -4.781 108.590  1.00 51.05
HETATM 6431  OH2 WAT G 406      54.828   5.311  59.009  1.00 43.43
HETATM 6432  OH2 WAT G 407      53.460  27.992 124.076  1.00 47.83
HETATM 6433  OH2 WAT G 408      70.833 -18.390  85.386  1.00 49.26
HETATM 6434  OH2 WAT G 409      71.497  15.287 113.071  1.00 34.52
HETATM 6435  OH2 WAT G 410      36.407 -18.480 110.466  1.00 55.43
HETATM 6436  OH2 WAT G 411      26.220  -9.551  78.158  1.00 47.69
HETATM 6437  OH2 WAT G 412      52.319  26.326  82.038  1.00 42.00
HETATM 6438  OH2 WAT G 413      76.173  14.097 122.253  1.00 44.90
HETATM 6439  OH2 WAT G 414      58.379   6.335 123.024  1.00 54.61
HETATM 6440  OH2 WAT G 415      72.162 -16.705  82.719  1.00 50.63
HETATM 6441  OH2 WAT G 416      63.557  26.152  65.944  1.00 39.83
HETATM 6442  OH2 WAT G 417      38.935  23.070 122.742  1.00 52.57
HETATM 6443  OH2 WAT G 418      55.256 -10.714 124.501  1.00 42.38
HETATM 6444  OH2 WAT G 419      55.443  -9.037 110.170  1.00 46.47
HETATM 6445  OH2 WAT G 420      73.873  16.578 123.288  1.00 46.54
HETATM 6446  OH2 WAT G 421      74.426  12.663 117.527  1.00 43.62
HETATM 6447  OH2 WAT G 422      52.374  -0.368  51.502  1.00 56.99
HETATM 6448  OH2 WAT G 423      60.339  20.215  84.713  1.00 36.27
HETATM 6449  OH2 WAT G 424      48.308   1.354  54.561  1.00 38.53
HETATM 6450  OH2 WAT G 425      61.757  21.606 115.976  1.00 61.09
HETATM 6451  OH2 WAT G 426      33.222 -14.916 119.528  1.00 51.12
HETATM 6452  OH2 WAT G 427      47.477   3.359 112.298  1.00 46.10
HETATM 6453  OH2 WAT G 428      39.909   2.272 138.388  1.00 35.33
HETATM 6454  OH2 WAT G 429      57.829  15.336 126.262  1.00 62.59
HETATM 6455  OH2 WAT G 430      48.917  -5.857 119.191  1.00 51.45
HETATM 6456  OH2 WAT G 431      44.139  -3.812 132.964  1.00 44.91
HETATM 6457  OH2 WAT G 432      38.885  18.594  95.398  1.00 50.23
HETATM 6458  OH2 WAT G 433      52.628  -7.064  55.271  1.00 38.96
HETATM 6459  OH2 WAT G 434      60.644  -0.731 101.129  1.00 47.30
HETATM 6460  OH2 WAT G 435      64.772   5.808  71.942  1.00 50.81
HETATM 6461  OH2 WAT G 436      39.571  16.705  80.180  1.00 34.07
HETATM 6462  OH2 WAT G 437      32.791  -0.551  65.371  1.00 41.40
HETATM 6463  OH2 WAT G 438      58.318  -7.989  60.087  1.00 46.94
HETATM 6464  OH2 WAT G 439      26.982   5.474 120.408  1.00 46.28
HETATM 6465  OH2 WAT G 440      72.138   1.233  90.050  1.00 50.13
HETATM 6466  OH2 WAT G 441      29.494  10.971 118.393  1.00 56.30
HETATM 6467  OH2 WAT G 442      69.232   5.594 113.941  1.00 58.17
HETATM 6468  OH2 WAT G 443      61.459  11.576  71.140  1.00 61.67
```

Fig. 18-98

```
HETATM 6469  OH2 WAT G 444      59.592    2.195  58.518  1.00 42.66
HETATM 6470  OH2 WAT G 445      47.407    6.152 111.310  1.00 45.14
HETATM 6471  OH2 WAT G 446      36.254   18.203  99.930  1.00 44.76
HETATM 6472  OH2 WAT G 447      49.525   32.050 116.235  1.00 47.72
HETATM 6473  OH2 WAT G 448      21.801   -5.358  81.109  1.00 42.07
HETATM 6474  OH2 WAT G 449      52.131  -14.007  95.380  1.00 40.76
HETATM 6475  OH2 WAT G 450      39.712  -19.983  72.499  1.00 51.69
HETATM 6476  OH2 WAT G 451      67.651    5.620  67.102  1.00 42.38
HETATM 6477  OH2 WAT G 452      77.344    1.313  79.207  1.00 63.64
HETATM 6478  OH2 WAT G 453      55.249  -29.426  86.187  1.00 44.98
HETATM 6479  OH2 WAT G 454      64.429  -11.004  98.104  1.00 49.12
HETATM 6480  OH2 WAT G 455      45.456   -0.814 129.510  1.00 61.60
HETATM 6481  OH2 WAT G 456      65.066  -14.790  68.028  1.00 40.08
HETATM 6482  OH2 WAT G 457      34.732    5.611  94.924  1.00 58.32
```

Fig. 18-99

| | | | | Residue # | X | Y | Z | B | Segment ID | |
|---|---|---|---|---|---|---|---|---|---|---|
| ATOM | 1 | CB | ALA A | 2 | 45.368 | 37.229 | 75.022 | 1.00 | 57.10 | AAAA |
| ATOM | 2 | C | ALA A | 2 | 46.761 | 38.761 | 73.244 | 1.00 | 55.49 | AAAA |
| ATOM | 3 | C | ALA A | 2 | 46.339 | 39.800 | 73.750 | 1.00 | 55.57 | AAAA |
| ATOM | 4 | N | ALA A | 2 | 48.280 | 37.746 | 74.937 | 1.00 | 57.26 | AAAA |
| ATOM | 5 | CA | ALA A | 2 | 47.062 | 37.537 | 74.110 | 1.00 | 56.37 | AAAA |
| ATOM | 6 | N | LYS A | 3 | 46.976 | 38.628 | 71.938 | 1.00 | 53.94 | AAAA |
| ATOM | 7 | CA | LYS A | 3 | 46.721 | 39.716 | 71.002 | 1.00 | 51.97 | AAAA |
| ATOM | 8 | CB | LYS A | 3 | 47.815 | 39.778 | 69.939 | 1.00 | 53.86 | AAAA |
| ATOM | 9 | CG | LYS A | 3 | 49.223 | 39.876 | 70.490 | 1.00 | 56.47 | AAAA |
| ATOM | 10 | CD | LYS A | 3 | 50.252 | 39.670 | 69.387 | 1.00 | 57.84 | AAAA |
| ATOM | 11 | CE | LYS A | 3 | 51.654 | 39.597 | 69.957 | 1.00 | 58.89 | AAAA |
| ATOM | 12 | NZ | LYS A | 3 | 52.643 | 39.283 | 68.895 | 1.00 | 59.83 | AAAA |
| ATOM | 13 | C | LYS A | 3 | 45.393 | 39.494 | 70.305 | 1.00 | 49.57 | AAAA |
| ATOM | 14 | O | LYS A | 3 | 44.894 | 38.373 | 70.246 | 1.00 | 49.33 | AAAA |
| ATOM | 15 | N | VAL A | 4 | 44.826 | 40.574 | 69.777 | 1.00 | 46.23 | AAAA |
| ATOM | 16 | CA | VAL A | 4 | 43.561 | 40.516 | 69.056 | 1.00 | 42.51 | AAAA |
| ATOM | 17 | CB | VAL A | 4 | 42.543 | 41.516 | 69.630 | 1.00 | 42.26 | AAAA |
| ATOM | 18 | CG1 | VAL A | 4 | 41.213 | 41.352 | 68.940 | 1.00 | 41.51 | AAAA |
| ATOM | 19 | CG2 | VAL A | 4 | 42.401 | 41.307 | 71.128 | 1.00 | 42.00 | AAAA |
| ATOM | 20 | C | VAL A | 4 | 43.918 | 40.913 | 67.638 | 1.00 | 39.94 | AAAA |
| ATOM | 21 | O | VAL A | 4 | 44.332 | 42.032 | 67.395 | 1.00 | 40.39 | AAAA |
| ATOM | 22 | N | LYS A | 5 | 43.766 | 40.001 | 66.695 | 1.00 | 36.94 | AAAA |
| ATOM | 23 | CA | LYS A | 5 | 44.142 | 40.305 | 65.323 | 1.00 | 34.10 | AAAA |
| ATOM | 24 | CB | LYS A | 5 | 45.179 | 39.290 | 64.846 | 1.00 | 35.02 | AAAA |
| ATOM | 25 | CG | LYS A | 5 | 46.424 | 39.182 | 65.698 | 1.00 | 34.07 | AAAA |
| ATOM | 26 | CD | LYS A | 5 | 47.233 | 40.452 | 65.652 | 1.00 | 33.44 | AAAA |
| ATOM | 27 | CE | LYS A | 5 | 48.565 | 40.239 | 66.333 | 1.00 | 32.38 | AAAA |
| ATOM | 28 | NZ | LYS A | 5 | 49.372 | 41.460 | 66.222 | 1.00 | 31.26 | AAAA |
| ATOM | 29 | C | LYS A | 5 | 42.997 | 40.293 | 64.333 | 1.00 | 31.38 | AAAA |
| ATOM | 30 | O | LYS A | 5 | 42.053 | 39.523 | 64.466 | 1.00 | 31.74 | AAAA |
| ATOM | 31 | N | LEU A | 6 | 43.090 | 41.142 | 63.326 | 1.00 | 28.60 | AAAA |
| ATOM | 32 | CA | LEU A | 6 | 42.075 | 41.167 | 62.289 | 1.00 | 26.90 | AAAA |
| ATOM | 33 | CB | LEU A | 6 | 41.530 | 42.580 | 62.067 | 1.00 | 26.43 | AAAA |
| ATOM | 34 | CG | LEU A | 6 | 40.321 | 42.748 | 61.129 | 1.00 | 25.89 | AAAA |
| ATOM | 35 | CD1 | LEU A | 6 | 40.108 | 44.224 | 60.826 | 1.00 | 25.50 | AAAA |
| ATOM | 36 | CD2 | LEU A | 6 | 40.550 | 42.032 | 59.828 | 1.00 | 26.64 | AAAA |
| ATOM | 37 | C | LEU A | 6 | 42.818 | 40.701 | 61.049 | 1.00 | 25.74 | AAAA |
| ATOM | 38 | O | LEU A | 6 | 43.877 | 41.226 | 60.717 | 1.00 | 24.60 | AAAA |
| ATOM | 39 | N | ILE A | 7 | 42.282 | 39.704 | 60.367 | 1.00 | 25.90 | AAAA |
| ATOM | 40 | CA | ILE A | 7 | 42.939 | 39.212 | 59.173 | 1.00 | 26.75 | AAAA |
| ATOM | 41 | CB | ILE A | 7 | 42.839 | 37.712 | 59.089 | 1.00 | 26.58 | AAAA |
| ATOM | 42 | CG2 | ILE A | 7 | 43.474 | 37.227 | 57.783 | 1.00 | 27.88 | AAAA |
| ATOM | 43 | CG1 | ILE A | 7 | 43.528 | 37.116 | 60.310 | 1.00 | 27.02 | AAAA |
| ATOM | 44 | CD1 | ILE A | 7 | 43.507 | 35.640 | 60.350 | 1.00 | 27.46 | AAAA |
| ATOM | 45 | C | ILE A | 7 | 42.339 | 39.814 | 57.929 | 1.00 | 26.70 | AAAA |
| ATOM | 46 | O | ILE A | 7 | 41.162 | 39.655 | 57.681 | 1.00 | 27.68 | AAAA |
| ATOM | 47 | N | GLY A | 8 | 43.144 | 40.509 | 57.142 | 1.00 | 27.94 | AA A |
| ATOM | 48 | CA | GLY A | 8 | 42.598 | 41.110 | 55.944 | 1.00 | 29.78 | AA A |
| ATOM | 49 | C | GLY A | 8 | 43.587 | 41.789 | 55.027 | 1.00 | 30.38 | AAAA |
| ATOM | 50 | O | GLY A | 8 | 44.785 | 41.765 | 55.264 | 1.00 | 29.39 | AAAA |
| ATOM | 51 | N | THR A | 9 | 43.051 | 42.395 | 53.971 | 1.00 | 31.84 | AAAA |
| ATOM | 52 | CA | THR A | 9 | 43.832 | 43.106 | 52.962 | 1.00 | 32.41 | AAAA |
| ATOM | 53 | CB | THR A | 9 | 44.606 | 42.112 | 52.064 | 1.00 | 31.12 | AAAA |
| ATOM | 54 | CG1 | THR A | 9 | 45.324 | 42.825 | 51.053 | 1.00 | 30.74 | AAAA |
| ATOM | 55 | CG2 | THR A | 9 | 43.654 | 41.140 | 51.411 | 1.00 | 30.27 | AAAA |
| ATOM | 56 | C | THR A | 9 | 42.886 | 43.939 | 52.091 | 1.00 | 32.94 | AAAA |
| ATOM | 57 | O | THR A | 9 | 41.705 | 43.625 | 51.993 | 1.00 | 33.62 | AAAA |
| ATOM | 58 | N | LEU A | 10 | 43.396 | 45.009 | 51.485 | 1.00 | 33.20 | AAAA |
| ATOM | 59 | CA | LEU A | 10 | 42.573 | 45.840 | 50.611 | 1.00 | 33.29 | AAAA |
| ATOM | 60 | CB | LEU A | 10 | 43.117 | 47.275 | 50.484 | 1.00 | 33.12 | AAAA |
| ATOM | 61 | CG | LEU A | 10 | 43.142 | 48.245 | 51.666 | 1.00 | 32.95 | AAAA |
| ATOM | 62 | CD1 | LEU A | 10 | 41.743 | 48.386 | 52.288 | 1.00 | 31.99 | AAAA |
| ATOM | 63 | CD2 | LEU A | 10 | 44.126 | 47.734 | 52.675 | 1.00 | 34.71 | AAAA |
| ATOM | 64 | C | LEU A | 10 | 42.527 | 45.231 | 49.218 | 1.00 | 33.18 | AAAA |
| ATOM | 65 | O | LEU A | 10 | 41.876 | 45.768 | 48.328 | 1.00 | 32.52 | AAAA |
| ATOM | 66 | N | ASP A | 11 | 43.230 | 44.121 | 49.022 | 1.00 | 33.56 | AAAA |

Fig. 19-1

```
ATOM    67  CA  ASP A  11      43.240  43.489  47.716  1.00 34.24      AAAA
ATOM    68  CB  ASP A  11      44.393  42.499  47.607  1.00 35.81      AAAA
ATOM    69  CG  ASP A  11      45.739  43.190  47.604  1.00 37.57      AAAA
ATOM    70  OD1 ASP A  11      45.890  44.178  46.855  1.00 37.95      AAAA
ATOM    71  OD2 ASP A  11      46.650  42.750  48.332  1.00 40.31      AAAA
ATOM    72  C   ASP A  11      41.929  42.813  47.341  1.00 34.03      AAAA
ATOM    73  O   ASP A  11      41.629  42.652  46.150  1.00 34.80      AAAA
ATOM    74  N   TYR A  12      41.142  42.417  48.335  1.00 32.34      AAAA
ATOM    75  CA  TYR A  12      39.871  41.803  48.017  1.00 32.53      AAAA
ATOM    76  CB  TYR A  12      39.043  41.569  49.290  1.00 31.32      AAAA
ATOM    77  CG  TYR A  12      39.551  40.438  50.162  1.00 29.95      AAAA
ATOM    78  CD1 TYR A  12      39.983  40.669  51.469  1.00 28.52      AAAA
ATOM    79  CE1 TYR A  12      40.413  39.614  52.279- 1.00 28.03      AAAA
ATOM    80  CD2 TYR A  12      39.568  39.128  49.688  1.00 28.47      AAAA
ATOM    81  CE2 TYR A  12      39.992  38.083  50.483  1.00 28.47      AAAA
ATOM    82  CZ  TYR A  12      40.408  38.330  51.775  1.00 28.43      AAAA
ATOM    83  OH  TYR A  12      40.786  37.277  52.569  1.00 29.86      AAAA
ATOM    84  C   TYR A  12      39.146  42.749  47.066  1.00 33.16      AAAA
ATOM    85  O   TYR A  12      38.554  42.324  46.082  1.00 33.36      AAAA
ATOM    86  N   GLY A  13      39.237  44.041  47.356  1.00 34.76      AAAA
ATOM    87  CA  GLY A  13      38.594  45.065  46.546  1.00 36.60      AAAA
ATOM    88  C   GLY A  13      38.814  44.961  45.052  1.00 37.85      AAAA
ATOM    89  O   GLY A  13      38.105  45.591  44.275  1.00 37.40      AAAA
ATOM    90  N   LYS A  14      39.799  44.171  44.647  1.00 39.55      AAAA
ATOM    91  CA  LYS A  14      40.091  43.981  43.231  1.00 40.66      AAAA
ATOM    92  CB  LYS A  14      41.605  43.977  42.995  1.00 42.26      AAAA
ATOM    93  CG  LYS A  14      42.300  45.309  43.239  1.00 44.54      AAAA
ATOM    94  CD  LYS A  14      41.820  46.445  42.304  1.00 46.32      AAAA
ATOM    95  CE  LYS A  14      42.033  46.158  40.810  1.00 46.64      AAAA
ATOM    96  NZ  LYS A  14      41.133  45.086  40.256  1.00 47.23      AAAA
ATOM    97  C   LYS A  14      39.499  42.675  42.707  1.00 40.35      AAAA
ATOM    98  O   LYS A  14      39.593  42.377  41.511  1.00 39.97      AAAA
ATOM    99  N   TYR A  15      38.897  41.901  43.605  1.00 39.95      AAAA
ATOM   100  CA  TYR A  15      38.300  40.617  43.245  1.00 40.30      AAAA
ATOM   101  CB  TYR A  15      38.962  39.490  44.050  1.00 38.46      AAAA
ATOM   102  CG  TYR A  15      40.472  39.519  44.021  1.00 37.01      AAAA
ATOM   103  CD1 TYR A  15      41.213  39.136  45.137  1.00 36.24      AAAA
ATOM   104  CE1 TYR A  15      42.604  39.220  45.144  1.00 35.73      AAAA
ATOM   105  CD2 TYR A  15      41.163  39.976  42.902  1.00 36.84      AAAA
ATOM   106  CE2 TYR A  15      42.556  40.064  42.898  1.00 36.53      AAAA
ATOM   107  CZ  TYR A  15      43.271  39.689  44.028  1.00 36.24      AAAA
ATOM   108  OH  TYR A  15      44.648  39.816  44.042  1.00 36.49      AAAA
ATOM   109  C   TYR A  15      36.802  40.647  43.556  1.00 41.98      AAAA
ATOM   110  O   TYR A  15      36.288  39.786  44.280  1.00 42.59      AAAA
ATOM   111  N   ARG A  16      36.101  41.638  43.014  1.00 42.81      AAAA
ATOM   112  CA  ARG A  16      34.670  41.753  43.257  1.00 43.47      AAAA
ATOM   113  CB  ARG A  16      34.205  43.197  43.111  1.00 45.27      AAAA
ATOM   114  CG  ARG A  16      35.021  44.234  43.833  1.00 48.06      AAAA
ATOM   115  CD  ARG A  16      34.891  44.196  45.339  1.00 49.63      AAAA
ATOM   116  NE  ARG A  16      35.632  45.322  45.905  1.00 51.65      AAAA
ATOM   117  CZ  ARG A  16      35.382  46.602  45.622  1.00 52.71      AAAA
ATOM   118  NH1 ARG A  16      34.406  46.931  44.781  1.00 53.28      AAAA
ATOM   119  NH2 ARG A  16      36.124  47.560  46.162  1.00 53.43      AAAA
ATOM   120  C   ARG A  16      33.913  40.929  42.230  1.00 42.86      AAAA
ATOM   121  O   ARG A  16      34.455  40.541  41.193  1.00 41.83      AAAA
ATOM   122  N   TYR A  17      32.651  40.668  42.523  1.00 42.42      AAAA
ATOM   123  CA  TYR A  17      31.818  39.942  41.590  1.00 42.76      AAAA
ATOM   124  CB  TYR A  17      30.675  39.254  42.333  1.00 40.11      AAAA
ATOM   125  CG  TYR A  17      31.097  38.061  43.180  1.00 38.35      AAAA
ATOM   126  CD1 TYR A  17      32.169  38.148  44.071  1.00 36.15      AAAA
ATOM   127  CE1 TYR A  17      32.519  37.069  44.874  1.00 34.76      AAAA
ATOM   128  CD2 TYR A  17      30.386  36.855  43.116  1.00 36.40      AAAA
ATOM   129  CE2 TYR A  17      30.726  35.776  43.912  1.00 35.31      AAAA
ATOM   130  CZ  TYR A  17      31.792  35.887  44.790  1.00 35.00      AAAA
ATOM   131  OH  TYR A  17      32.115  34.814  45.584  1.00 33.29      AAAA
ATOM   132  C   TYR A  17      31.296  41.000  40.613  1.00 44.43      AAAA
```

Fig. 19-2

| | | | | | | | | | |
|---|---|---|---|---|---|---|---|---|---|
| ATOM | 133 | O | TYR | A | 17 | 31.346 | 42.194 | 40.905 | 1.00 44.68 | AAAA |
| ATOM | 134 | N | PRO | A | 18 | 30.799 | 40.574 | 39.440 | 1.00 45.95 | AAAA |
| ATOM | 135 | CD | PRO | A | 18 | 30.707 | 39.175 | 38.994 | 1.00 46.08 | AAAA |
| ATOM | 136 | CA | PRO | A | 18 | 30.268 | 41.465 | 38.402 | 1.00 47.24 | AAAA |
| ATOM | 137 | CB | PRO | A | 18 | 29.854 | 40.482 | 37.312 | 1.00 47.69 | AAAA |
| ATOM | 138 | CG | PRO | A | 18 | 30.876 | 39.338 | 37.511 | 1.00 46.79 | AAAA |
| ATOM | 139 | C | PRO | A | 18 | 29.129 | 42.390 | 38.834 | 1.00 48.98 | AAAA |
| ATOM | 140 | O | PRO | A | 18 | 28.298 | 42.020 | 39.660 | 1.00 49.11 | AAAA |
| ATOM | 141 | N | LYS | A | 19 | 29.114 | 43.593 | 38.253 | 1.00 50.59 | AAAA |
| ATOM | 142 | CA | LYS | A | 19 | 28.125 | 44.654 | 38.519 | 1.00 52.10 | AAAA |
| ATOM | 143 | CB | LYS | A | 19 | 27.876 | 45.466 | 37.246 | 1.00 54.41 | AAAA |
| ATOM | 144 | CG | LYS | A | 19 | 29.120 | 45.911 | 36.498 | 1.00 57.78 | AAAA |
| ATOM | 145 | CD | LYS | A | 19 | 28.747 | 46.508 | 35.142 | 1.00 59.34 | AAAA |
| ATOM | 146 | CE | LYS | A | 19 | 29.978 | 46.774 | 34.288 | 1.00 60.33 | AAAA |
| ATOM | 147 | NZ | LYS | A | 19 | 29.616 | 47.277 | 32.932 | 1.00 61.03 | AAAA |
| ATOM | 148 | C | LYS | A | 19 | 26.764 | 44.162 | 39.012 | 1.00 51.53 | AAAA |
| ATOM | 149 | O | LYS | A | 19 | 26.281 | 44.556 | 40.071 | 1.00 51.54 | AAAA |
| ATOM | 150 | N | ASN | A | 20 | 26.146 | 43.314 | 38.203 | 1.00 50.13 | AAAA |
| ATOM | 151 | CA | ASN | A | 20 | 24.831 | 42.750 | 38.482 | 1.00 48.44 | AAAA |
| ATOM | 152 | CB | ASN | A | 20 | 24.336 | 42.061 | 37.209 | 1.00 49.67 | AAAA |
| ATOM | 153 | CG | ASN | A | 20 | 25.389 | 41.132 | 36.613 | 1.00 51.61 | AAAA |
| ATOM | 154 | OD1 | ASN | A | 20 | 25.677 | 40.064 | 37.154 | 1.00 51.70 | AAAA |
| ATOM | 155 | ND2 | ASN | A | 20 | 25.998 | 41.562 | 35.509 | 1.00 53.00 | AAAA |
| ATOM | 156 | C | ASN | A | 20 | 24.789 | 41.765 | 39.649 | 1.00 45.57 | AAAA |
| ATOM | 157 | O | ASN | A | 20 | 23.764 | 41.127 | 39.877 | 1.00 44.67 | AAAA |
| ATOM | 158 | N | HIS | A | 21 | 25.883 | 41.662 | 40.398 | 1.00 42.71 | AAAA |
| ATOM | 159 | CA | HIS | A | 21 | 25.958 | 40.709 | 41.506 | 1.00 40.69 | AAAA |
| ATOM | 160 | CB | HIS | A | 21 | 27.216 | 39.857 | 41.353 | 1.00 40.16 | AAAA |
| ATOM | 161 | CG | HIS | A | 21 | 27.186 | 38.587 | 42.140 | 1.00 39.93 | AAAA |
| ATOM | 162 | CD2 | HIS | A | 21 | 27.329 | 38.353 | 43.467 | 1.00 39.27 | AAAA |
| ATOM | 163 | ND1 | HIS | A | 21 | 26.951 | 37.359 | 41.557 | 1.00 39.47 | AAAA |
| ATOM | 164 | CE1 | HIS | A | 21 | 26.948 | 36.425 | 42.493 | 1.00 39.36 | AAAA |
| ATOM | 165 | NE2 | HIS | A | 21 | 27.174 | 37.003 | 43.660 | 1.00 39.44 | AAAA |
| ATOM | 166 | C | HIS | A | 21 | 25.974 | 41.349 | 42.892 | 1.00 38.93 | AAAA |
| ATOM | 167 | O | HIS | A | 21 | 26.660 | 42.338 | 43.116 | 1.00 38.78 | AAAA |
| ATOM | 168 | N | PRO | A | 22 | 25.229 | 40.778 | 43.853 | 1.00 37.11 | AAAA |
| ATOM | 169 | CD | PRO | A | 22 | 24.371 | 39.579 | 43.814 | 1.00 36.09 | AAAA |
| ATOM | 170 | CA | PRO | A | 22 | 25.224 | 41.361 | 45.199 | 1.00 35.81 | AAAA |
| ATOM | 171 | CB | PRO | A | 22 | 24.473 | 40.306 | 46.012 | 1.00 36.04 | AAAA |
| ATOM | 172 | CG | PRO | A | 22 | 23.464 | 39.810 | 45.003 | 1.00 36.19 | AAAA |
| ATOM | 173 | C | PRO | A | 22 | 26.638 | 41.637 | 45.751 | 1.00 34.39 | AAAA |
| ATOM | 174 | O | PRO | A | 22 | 26.867 | 42.653 | 46.417 | 1.00 34.09 | AAAA |
| ATOM | 175 | N | LEU | A | 23 | 27.572 | 40.731 | 45.451 | 1.00 31.98 | AAAA |
| ATOM | 176 | CA | LEU | A | 23 | 28.954 | 40.827 | 45.900 | 1.00 29.65 | AAAA |
| ATOM | 177 | CB | LEU | A | 23 | 29.564 | 39.432 | 46.014 | 1.00 27.88 | AAAA |
| ATOM | 178 | CG | LEU | A | 23 | 28.896 | 38.528 | 47.048 | 1.00 27.31 | AAAA |
| ATOM | 179 | CD1 | LEU | A | 23 | 29.656 | 37.217 | 47.149 | 1.00 26.64 | AAAA |
| ATOM | 180 | CD2 | LEU | A | 23 | 28.879 | 39.212 | 48.399 | 1.00 26.75 | AAAA |
| ATOM | 181 | C | LEU | A | 23 | 29.838 | 41.709 | 45.018 | 1.00 29.20 | AAAA |
| ATOM | 182 | O | LEU | A | 23 | 31.057 | 41.606 | 45.028 | 1.00 28.38 | AAAA |
| ATOM | 183 | N | LYS | A | 24 | 29.204 | 42.582 | 44.259 | 1.00 29.27 | AAAA |
| ATOM | 184 | CA | LYS | A | 24 | 29.903 | 43.512 | 43.389 | 1.00 29.30 | AAAA |
| ATOM | 185 | CB | LYS | A | 24 | 28.881 | 44.091 | 42.405 | 1.00 29.75 | AAAA |
| ATOM | 186 | CG | LYS | A | 24 | 29.328 | 45.265 | 41.601 | 1.00 32.55 | AAAA |
| ATOM | 187 | CD | LYS | A | 24 | 28.537 | 46.526 | 41.994 | 1.00 34.37 | AAAA |
| ATOM | 188 | CE | LYS | A | 24 | 27.025 | 46.337 | 41.835 | 1.00 34.32 | AAAA |
| ATOM | 189 | NZ | LYS | A | 24 | 26.221 | 47.542 | 42.208 | 1.00 34.37 | AAAA |
| ATOM | 190 | C | LYS | A | 24 | 30.580 | 44.620 | 44.224 | 1.00 28.14 | AAAA |
| ATOM | 191 | O | LYS | A | 24 | 31.617 | 45.162 | 43.840 | 1.00 27.93 | AAAA |
| ATOM | 192 | N | ILE | A | 25 | 29.990 | 44.919 | 45.377 | 1.00 27.07 | AAAA |
| ATOM | 193 | CA | ILE | A | 25 | 30.468 | 45.945 | 46.296 | 1.00 25.82 | AAAA |
| ATOM | 194 | CB | ILE | A | 25 | 29.425 | 46.262 | 47.364 | 1.00 25.37 | AAAA |
| ATOM | 195 | CG2 | ILE | A | 25 | 28.190 | 46.846 | 46.737 | 1.00 25.71 | AAAA |
| ATOM | 196 | CG1 | ILE | A | 25 | 29.142 | 44.979 | 48.157 | 1.00 25.26 | AAAA |
| ATOM | 197 | CD1 | ILE | A | 25 | 28.318 | 45.163 | 49.413 | 1.00 25.17 | AAAA |
| ATOM | 198 | C | ILE | A | 25 | 31.700 | 45.550 | 47.095 | 1.00 25.28 | AAAA |

Fig. 19-3

| | | | | | | | | | | |
|---|---|---|---|---|---|---|---|---|---|---|
| ATOM | 199 | O | ILE | A | 25 | 32.037 | 44.379 | 47.183 | 1.00 24.48 | AAAA |
| ATOM | 200 | N | PRO | A | 26 | 32.375 | 46.547 | 47.714 | 1.00 24.98 | AAAA |
| ATOM | 201 | CD | PRO | A | 26 | 32.062 | 47.980 | 47.638 | 1.00 24.98 | AAAA |
| ATOM | 202 | CA | PRO | A | 26 | 33.570 | 46.367 | 48.543 | 1.00 24.44 | AAAA |
| ATOM | 203 | CB | PRO | A | 26 | 34.094 | 47.792 | 48.701 | 1.00 24.75 | AAAA |
| ATOM | 204 | CG | PRO | A | 26 | 33.435 | 48.546 | 47.538 | 1.00 25.51 | AAAA |
| ATOM | 205 | C | PRO | A | 26 | 33.021 | 45.838 | 49.862 | 1.00 23.42 | AAAA |
| ATOM | 206 | O | PRO | A | 26 | 31.930 | 46.233 | 50.272 | 1.00 22.12 | AAAA |
| ATOM | 207 | N | ARG | A | 27 | 33.754 | 44.960 | 50.532 | 1.00 23.06 | AAAA |
| ATOM | 208 | CA | ARG | A | 27 | 33.244 | 44.421 | 51.776 | 1.00 23.04 | AAAA |
| ATOM | 209 | CB | ARG | A | 27 | 32.633 | 43.043 | 51.492 | 1.00 22.20 | AAAA |
| ATOM | 210 | CG | ARG | A | 27 | 31.463 | 43.152 | 50.503 | 1.00 19.84 | AAAA |
| ATOM | 211 | CD | ARG | A | 27 | 30.762 | 41.844 | 50.160 | 1.00 18.64 | AAAA |
| ATOM | 212 | NE | ARG | A | 27 | 30.181 | 41.168 | 51.315 | 1.00 16.51 | AAAA |
| ATOM | 213 | CZ | ARG | A | 27 | 30.774 | 40.188 | 51.982 | 1.00 16.57 | AAAA |
| ATOM | 214 | NH1 | ARG | A | 27 | 31.969 | 39.763 | 51.605 | 1.00 17.50 | AAAA |
| ATOM | 215 | NH2 | ARG | A | 27 | 30.185 | 39.643 | 53.038 | 1.00 16.45 | AAAA |
| ATOM | 216 | C | ARG | A | 27 | 34.265 | 44.381 | 52.905 | 1.00 23.62 | AAAA |
| ATOM | 217 | O | ARG | A | 27 | 34.107 | 45.077 | 53.919 | 1.00 23.69 | AAAA |
| ATOM | 218 | N | VAL | A | 28 | 35.305 | 43.570 | 52.736 | 1.00 24.25 | AAAA |
| ATOM | 219 | CA | VAL | A | 28 | 36.355 | 43.466 | 53.737 | 1.00 23.36 | AAAA |
| ATOM | 220 | CB | VAL | A | 28 | 37.022 | 42.062 | 53.671 | 1.00 22.75 | AAAA |
| ATOM | 221 | CG1 | VAL | A | 28 | 38.292 | 42.031 | 54.475 | 1.00 22.95 | AAAA |
| ATOM | 222 | CG2 | VAL | A | 28 | 36.061 | 41.011 | 54.249 | 1.00 22.20 | AAAA |
| ATOM | 223 | C | VAL | A | 28 | 37.363 | 44.609 | 53.511 | 1.00 23.70 | AAAA |
| ATOM | 224 | O | VAL | A | 28 | 37.943 | 45.156 | 54.455 | 1.00 22.62 | AAAA |
| ATOM | 225 | N | SER | A | 29 | 37.538 | 44.989 | 52.253 | 1.00 24.27 | AAAA |
| ATOM | 226 | CA | SER | A | 29 | 38.444 | 46.082 | 51.910 | 1.00 26.03 | AAAA |
| ATOM | 227 | CB | SER | A | 29 | 38.632 | 46.178 | 50.381 | 1.00 25.95 | AAAA |
| ATOM | 228 | OG | SER | A | 29 | 37.395 | 46.417 | 49.716 | 1.00 27.57 | AAAA |
| ATOM | 229 | C | SER | A | 29 | 37.793 | 47.354 | 52.440 | 1.00 25.52 | AAAA |
| ATOM | 230 | O | SER | A | 29 | 38.463 | 48.311 | 52.828 | 1.00 25.49 | AAAA |
| ATOM | 231 | N | LEU | A | 30 | 36.468 | 47.342 | 52.448 | 1.00 26.09 | AAAA |
| ATOM | 232 | CA | LEU | A | 30 | 35.692 | 48.471 | 52.926 | 1.00 26.39 | AAAA |
| ATOM | 233 | CB | LEU | A | 30 | 34.262 | 48.365 | 52.393 | 1.00 25.89 | AAAA |
| ATOM | 234 | CG | LEU | A | 30 | 33.265 | 49.470 | 52.755 | 1.00 27.15 | AAAA |
| ATOM | 235 | CD1 | LEU | A | 30 | 32.486 | 49.101 | 53.999 | 1.00 26.34 | AAAA |
| ATOM | 236 | CD2 | LEU | A | 30 | 34.015 | 50.813 | 52.897 | 1.00 25.81 | AAAA |
| ATOM | 237 | C | LEU | A | 30 | 35.713 | 48.534 | 54.453 | 1.00 26.26 | AAAA |
| ATOM | 238 | O | LEU | A | 30 | 35.731 | 49.612 | 55.037 | 1.00 27.50 | AAAA |
| ATOM | 239 | N | LEU | A | 31 | 35.730 | 47.379 | 55.097 | 1.00 25.57 | AAAA |
| ATOM | 240 | CA | LEU | A | 31 | 35.776 | 47.343 | 56.545 | 1.00 26.87 | AAAA |
| ATOM | 241 | CB | LEU | A | 31 | 35.752 | 45.900 | 57.029 | 1.00 27.28 | AAAA |
| ATOM | 242 | CG | LEU | A | 31 | 35.135 | 45.563 | 58.383 | 1.00 27.87 | AAAA |
| ATOM | 243 | CD1 | LEU | A | 31 | 35.855 | 44.313 | 58.906 | 1.00 27.01 | AAAA |
| ATOM | 244 | CD2 | LEU | A | 31 | 35.261 | 46.706 | 59.372 | 1.00 26.32 | AAAA |
| ATOM | 245 | C | LEU | A | 31 | 37.087 | 48.003 | 57.012 | 1.00 28.08 | AAAA |
| ATOM | 246 | O | LEU | A | 31 | 37.094 | 48.854 | 57.901 | 1.00 27.42 | AAAA |
| ATOM | 247 | N | LEU | A | 32 | 38.197 | 47.584 | 56.409 | 1.00 29.52 | AAAA |
| ATOM | 248 | CA | LEU | A | 32 | 39.508 | 48.121 | 56.750 | 1.00 30.96 | AAAA |
| ATOM | 249 | CB | LEU | A | 32 | 40.607 | 47.394 | 55.950 | 1.00 31.58 | AAAA |
| ATOM | 250 | CG | LEU | A | 32 | 40.792 | 45.904 | 56.293 | 1.00 31.63 | AAAA |
| ATOM | 251 | CD1 | LEU | A | 32 | 41.810 | 45.246 | 55.380 | 1.00 31.31 | AAAA |
| ATOM | 252 | CD2 | LEU | A | 32 | 41.232 | 45.780 | 57.743 | 1.00 32.23 | AAAA |
| ATOM | 253 | C | LEU | A | 32 | 39.599 | 49.635 | 56.543 | 1.00 31.59 | AAAA |
| ATOM | 254 | O | LEU | A | 32 | 40.081 | 50.345 | 57.416 | 1.00 31.70 | AAAA |
| ATOM | 255 | N | ARG | A | 33 | 39.140 | 50.129 | 55.398 | 1.00 32.72 | AAAA |
| ATOM | 256 | CA | ARG | A | 33 | 39.178 | 51.564 | 55.141 | 1.00 33.91 | AAAA |
| ATOM | 257 | CB | ARG | A | 33 | 38.643 | 51.903 | 53.743 | 1.00 35.10 | AAAA |
| ATOM | 258 | CG | ARG | A | 33 | 39.627 | 51.609 | 52.621 | 1.00 37.84 | AAAA |
| ATOM | 259 | CD | ARG | A | 33 | 39.310 | 52.412 | 51.374 | 1.00 39.33 | AAAA |
| ATOM | 260 | NE | ARG | A | 33 | 38.255 | 51.806 | 50.580 | 1.00 42.51 | AAAA |
| ATOM | 261 | CZ | ARG | A | 33 | 37.662 | 52.395 | 49.541 | 1.00 44.22 | AAAA |
| ATOM | 262 | NH1 | ARG | A | 33 | 38.016 | 53.617 | 49.163 | 1.00 44.61 | AAAA |
| ATOM | 263 | NH2 | ARG | A | 33 | 36.723 | 51.752 | 48.861 | 1.00 45.23 | AAAA |
| ATOM | 264 | C | ARG | A | 33 | 38.352 | 52.305 | 56.168 | 1.00 33.48 | AAAA |

Fig. 19-4

```
ATOM    265  O    ARG A  33      38.713  53.390  56.592  1.00 33.61      AAAA
ATOM    266  N    PHE A  34      37.247  51.682  56.562  1.00 33.78      AAAA
ATOM    267  CA   PHE A  34      36.292  52.233  57.517  1.00 33.79      AAAA
ATOM    268  CB   PHE A  34      35.065  51.310  57.573  1.00 33.88      AAAA
ATOM    269  CG   PHE A  34      33.925  51.840  58.405  1.00 33.16      AAAA
ATOM    270  CD1  PHE A  34      33.108  52.856  57.925  1.00 32.77      AAAA
ATOM    271  CD2  PHE A  34      33.668  51.315  59.672  1.00 33.05      AAAA
ATOM    272  CE1  PHE A  34      32.044  53.343  58.695  1.00 32.86      AAAA
ATOM    273  CE2  PHE A  34      32.607  51.797  60.454  1.00 33.07      AAAA
ATOM    274  CZ   PHE A  34      31.794  52.809  59.966  1.00 32.58      AAAA
ATOM    275  C    PHE A  34      36.881  52.414  58.918  1.00 34.01      AAAA
ATOM    276  O    PHE A  34      36.903  53.524  59.455  1.00 33.49      AAAA
ATOM    277  N    LYS A  35      37.350  51.324  59.516  1.00 34.00      AAAA
ATOM    278  CA   LYS A  35      37.928  51.401  60.843  1.00 33.90      AAAA
ATOM    279  CB   LYS A  35      38.230  50.010  61.362  1.00 34.07      AAAA
ATOM    280  CG   LYS A  35      37.000  49.190  61.662  1.00 33.94      AAAA
ATOM    281  CD   LYS A  35      37.414  47.810  62.106  1.00 35.31      AAAA
ATOM    282  CE   LYS A  35      38.062  47.072  60.948  1.00 35.91      AAAA
ATOM    283  NZ   LYS A  35      39.058  47.928  60.236  1.00 36.19      AAAA
ATOM    284  C    LYS A  35      39.185  52.255  60.881  1.00 34.19      AAAA
ATOM    285  O    LYS A  35      39.554  52.775  61.929  1.00 34.32      AAAA
ATOM    286  N    ASP A  36      39.853  52.384  59.745  1.00 33.99      AAAA
ATOM    287  CA   ASP A  36      41.034  53.216  59.680  1.00 35.17      AAAA
ATOM    288  CB   ASP A  36      41.812  52.943  58.388  1.00 37.40      AAAA
ATOM    289  CG   ASP A  36      42.964  53.908  58.186  1.00 38.64      AAAA
ATOM    290  OD1  ASP A  36      43.648  54.218  59.184  1.00 40.02      AAAA
ATOM    291  OD2  ASP A  36      43.201  54.341  57.035  1.00 38.74      AAAA
ATOM    292  C    ASP A  36      40.568  54.670  59.724  1.00 35.85      AAAA
ATOM    293  O    ASP A  36      41.231  55.527  60.306  1.00 36.88      AAAA
ATOM    294  N    ALA A  37      39.420  54.940  59.111  1.00 34.96      AAAA
ATOM    295  CA   ALA A  37      38.851  56.280  59.108  1.00 34.47      AAAA
ATOM    296  CB   ALA A  37      37.751  56.373  58.067  1.00 33.80      AAAA
ATOM    297  C    ALA A  37      38.291  56.617  60.499  1.00 34.66      AAAA
ATOM    298  O    ALA A  37      38.268  57.779  60.899  1.00 34.55      AAAA
ATOM    299  N    MET A  38      37.830  55.600  61.226  1.00 34.24      AAAA
ATOM    300  CA   MET A  38      37.287  55.794  62.572  1.00 33.07      AAAA
ATOM    301  CB   MET A  38      36.289  54.687  62.917  1.00 32.82      AAAA
ATOM    302  CG   MET A  38      35.084  54.559  61.996  1.00 32.72      AAAA
ATOM    303  SD   MET A  38      33.980  55.948  62.101  1.00 33.65      AAAA
ATOM    304  CE   MET A  38      33.550  55.878  63.849  1.00 33.77      AAAA
ATOM    305  C    MET A  38      38.430  55.724  63.583  1.00 33.12      AAAA
ATOM    306  O    MET A  38      38.226  55.930  64.777  1.00 32.82      AAAA
ATOM    307  N    ASN A  39      39.628  55.428  63.090  1.00 32.64      AAAA
ATOM    308  CA   ASN A  39      40.805  55.266  63.935  1.00 32.38      AAAA
ATOM    309  CB   ASN A  39      41.200  56.600  64.589  1.00 32.93      AAAA
ATOM    310  CG   ASN A  39      41.393  57.736  63.571  1.00 34.40      AAAA
ATOM    311  OD1  ASN A  39      42.180  57.624  62.630  1.00 34.98      AAAA
ATOM    312  ND2  ASN A  39      40.677  58.838  63.772  1.00 33.52      AAAA
ATOM    313  C    ASN A  39      40.483  54.212  65.009  1.00 31.69      AAAA
ATOM    314  O    ASN A  39      40.565  54.490  66.205  1.00 31.12      AAAA
ATOM    315  N    LEU A  40      40.095  53.010  64.570  1.00 31.76      AAAA
ATOM    316  CA   LEU A  40      39.750  51.898  65.474  1.00 32.48      AAAA
ATOM    317  CB   LEU A  40      38.259  51.559  65.386  1.00 32.55      AAAA
ATOM    318  CG   LEU A  40      37.231  52.581  65.879  1.00 32.84      AAAA
ATOM    319  CD1  LEU A  40      35.837  52.089  65.554  1.00 33.79      AAAA
ATOM    320  CD2  LEU A  40      37.372  52.798  67.376  1.00 32.45      AAAA
ATOM    321  C    LEU A  40      40.555  50.628  65.187  1.00 32.92      AAAA
ATOM    322  O    LEU A  40      40.196  49.530  65.618  1.00 31.64      AAAA
ATOM    323  N    ILE A  41      41.652  50.794  64.464  1.00 34.12      AAAA
ATOM    324  CA   ILE A  41      42.508  49.680  64.116  1.00 36.07      AAAA
ATOM    325  CB   ILE A  41      42.017  48.991  62.811  1.00 35.51      AAAA
ATOM    326  CG2  ILE A  41      42.070  49.952  61.636  1.00 33.37      AAAA
ATOM    327  CG1  ILE A  41      42.898  47.790  62.480  1.00 35.97      AAAA
ATOM    328  CD1  ILE A  41      42.854  46.701  63.500  1.00 37.19      AAAA
ATOM    329  C    ILE A  41      43.921  50.226  63.916  1.00 38.85      AAAA
ATOM    330  O    ILE A  41      44.106  51.346  63.413  1.00 38.98      AAAA
```

Fig. 19-5

```
ATOM    331  N    ASP A   42      44.914  49.446  64.329  1.00 40.61      AAAA
ATOM    332  CA   ASP A   42      46.309  49.843  64.181  1.00 42.57      AAAA
ATOM    333  CB   ASP A   42      46.973  50.021  65.553  1.00 42.42      AAAA
ATOM    334  CG   ASP A   42      46.316  51.110  66.381  1.00 42.27      AAAA
ATOM    335  OD1  ASP A   42      46.227  52.250  65.883  1.00 41.20      AAAA
ATOM    336  OD2  ASP A   42      45.891  50.833  67.526  1.00 43.36      AAAA
ATOM    337  C    ASP A   42      47.011  48.752  63.392  1.00 44.05      AAAA
ATOM    338  O    ASP A   42      46.525  47.620  63.333  1.00 44.88      AAAA
ATOM    339  N    GLU A   43      48.147  49.090  62.789  1.00 45.10      AAAA
ATOM    340  CA   GLU A   43      48.905  48.141  61.980  1.00 46.11      AAAA
ATOM    341  CB   GLU A   43      50.172  48.796  61.454  1.00 46.89      AAAA
ATOM    342  CG   GLU A   43      49.924  50.057  60.668  1.00 49.30      AAAA
ATOM    343  CD   GLU A   43      51.187  50.580  60.028  1.00 49.67      AAAA
ATOM    344  OE1  GLU A   43      51.760  49.839  59.201  1.00 50.60      AAAA
ATOM    345  OE2  GLU A   43      51.601  51.714  60.349  1.00 49.60      AAAA
ATOM    346  C    GLU A   43      49.290  46.859  62.701  1.00 46.27      AAAA
ATOM    347  O    GLU A   43      49.214  45.773  62.131  1.00 46.00      AAAA
ATOM    348  N    LYS A   44      49.708  46.986  63.954  1.00 46.52      AAAA
ATOM    349  CA   LYS A   44      50.135  45.832  64.730  1.00 46.31      AAAA
ATOM    350  CB   LYS A   44      50.762  46.306  66.048  1.00 48.16      AAAA
ATOM    351  CG   LYS A   44      51.977  47.215  65.799  1.00 51.59      AAAA
ATOM    352  CD   LYS A   44      52.641  47.734  67.071  1.00 52.87      AAAA
ATOM    353  CE   LYS A   44      53.851  48.601  66.727  1.00 53.34      AAAA
ATOM    354  NZ   LYS A   44      54.615  49.033  67.936  1.00 53.45      AAAA
ATOM    355  C    LYS A   44      49.029  44.828  64.996  1.00 44.74      AAAA
ATOM    356  O    LYS A   44      49.296  43.735  65.480  1.00 45.35      AAAA
ATOM    357  N    GLU A   45      47.793  45.190  64.659  1.00 42.49      AAAA
ATOM    358  CA   GLU A   45      46.638  44.320  64.894  1.00 40.54      AAAA
ATOM    359  CB   GLU A   45      45.493  45.125  65.517  1.00 40.55      AAAA
ATOM    360  CG   GLU A   45      45.788  45.731  66.882  1.00 38.87      AAAA
ATOM    361  CD   GLU A   45      44.663  46.618  67.360  1.00 37.57      AAAA
ATOM    362  OE1  GLU A   45      44.383  47.631  66.693  1.00 36.29      AAAA
ATOM    363  OE2  GLU A   45      44.056  46.300  68.399  1.00 38.44      AAAA
ATOM    364  C    GLU A   45      46.126  43.648  63.630  1.00 39.15      AAAA
ATOM    365  O    GLU A   45      45.301  42.737  63.681  1.00 39.29      AAAA
ATOM    366  N    LEU A   46      46.619  44.115  62.497  1.00 37.62      AAAA
ATOM    367  CA   LEU A   46      46.219  43.589  61.211  1.00 35.88      AAAA
ATOM    368  CB   LEU A   46      46.125  44.750  60.229  1.00 36.09      AAAA
ATOM    369  CG   LEU A   46      45.608  44.550  58.817  1.00 36.50      AAAA
ATOM    370  CD1  LEU A   46      44.182  44.021  58.843  1.00 36.66      AAAA
ATOM    371  CD2  LEU A   46      45.646  45.893  58.113  1.00 35.85      AAAA
ATOM    372  C    LEU A   46      47.211  42.542  60.714  1.00 34.97      AAAA
ATOM    373  O    LEU A   46      48.424  42.670  60.900  1.00 35.72      AAAA
ATOM    374  N    ILE A   47      46.680  41.484  60.118  1.00 33.25      AAAA
ATOM    375  CA   ILE A   47      47.497  40.411  59.560  1.00 30.92      AAAA
ATOM    376  CB   ILE A   47      47.144  39.024  60.167  1.00 31.22      AAAA
ATOM    377  CG2  ILE A   47      48.093  37.970  59.640  1.00 28.55      AAAA
ATOM    378  CG1  ILE A   47      47.220  39.063  61.694  1.00 32.04      AAAA
ATOM    379  CD1  ILE A   47      48.596  39.241  62.242  1.00 34.13      AAAA
ATOM    380  C    ILE A   47      47.138  40.381  58.076  1.00 29.70      AAAA
ATOM    381  O    ILE A   47      45.956  40.373  57.714  1.00 28.42      AAAA
ATOM    382  N    LYS A   48      48.150  40.380  57.221  1.00 28.78      AAAA
ATOM    383  CA   LYS A   48      47.920  40.349  55.784  1.00 28.42      AAAA
ATOM    384  CB   LYS A   48      49.203  40.727  55.055  1.00 27.53      AAAA
ATOM    385  CG   LYS A   48      49.116  40.695  53.556  1.00 28.97      AAAA
ATOM    386  CD   LYS A   48      50.464  41.104  52.941  1.00 29.67      AAAA
ATOM    387  CE   LYS A   48      50.493  40.893  51.432  1.00 29.41      AAAA
ATOM    388  NZ   LYS A   48      49.409  41.645  50.764  1.00 29.68      AAAA
ATOM    389  C    LYS A   48      47.449  38.950  55.375  1.00 27.81      AAAA
ATOM    390  O    LYS A   48      48.024  37.938  55.787  1.00 27.96      AAAA
ATOM    391  N    SER A   49      46.385  38.892  54.581  1.00 26.82      AAAA
ATOM    392  CA   SER A   49      45.854  37.611  54.141  1.00 26.41      AAAA
ATOM    393  CB   SER A   49      44.514  37.795  53.420  1.00 25.40      AAAA
ATOM    394  OG   SER A   49      43.541  38.349  54.276  1.00 25.58      AAAA
ATOM    395  C    SER A   49      46.814  36.891  53.207  1.00 26.03      AAAA
ATOM    396  O    SER A   49      47.462  37.513  52.373  1.00 26.98      AAAA
```

Fig. 19-6

| | | | | | | | | | | |
|---|---|---|---|---|---|---|---|---|---|---|
| ATOM | 397 | N | ARG | A | 50 | 46.910 | 35.576 | 53.354 | 1.00 25.51 | AAAA |
| ATOM | 398 | CA | ARG | A | 50 | 47.755 | 34.794 | 52.474 | 1.00 25.45 | AAAA |
| ATOM | 399 | CB | ARG | A | 50 | 48.807 | 33.985 | 53.252 | 1.00 25.85 | AAAA |
| ATOM | 400 | CG | ARG | A | 50 | 48.229 | 32.819 | 54.009 | 1.00 27.16 | AAAA |
| ATOM | 401 | CD | ARG | A | 50 | 49.280 | 31.995 | 54.720 | 1.00 27.57 | AAAA |
| ATOM | 402 | NE | ARG | A | 50 | 48.673 | 30.896 | 55.482 | 1.00 27.90 | AAAA |
| ATOM | 403 | CZ | ARG | A | 50 | 48.106 | 29.820 | 54.946 | 1.00 28.34 | AAAA |
| ATOM | 404 | NH1 | ARG | A | 50 | 48.055 | 29.672 | 53.630 | 1.00 28.19 | AAAA |
| ATOM | 405 | NH2 | ARG | A | 50 | 47.592 | 28.884 | 55.735 | 1.00 28.62 | AAAA |
| ATOM | 406 | C | ARG | A | 50 | 46.806 | 33.834 | 51.762 | 1.00 24.91 | AAAA |
| ATOM | 407 | O | ARG | A | 50 | 45.740 | 33.510 | 52.283 | 1.00 23.57 | AAAA |
| ATOM | 408 | N | PRO | A | 51 | 47.172 | 33.392 | 50.549 | 1.00 24.28 | AAAA |
| ATOM | 409 | CD | PRO | A | 51 | 48.361 | 33.761 | 49.770 | 1.00 24.13 | AAAA |
| ATOM | 410 | CA | PRO | A | 51 | 46.355 | 32.462 | 49.776 | 1.00 24.18 | AAAA |
| ATOM | 411 | CB | PRO | A | 51 | 47.012 | 32.512 | 48.390 | 1.00 24.24 | AAAA |
| ATOM | 412 | CG | PRO | A | 51 | 47.766 | 33.862 | 48.405 | 1.00 24.11 | AAAA |
| ATOM | 413 | C | PRO | A | 51 | 46.473 | 31.070 | 50.393 | 1.00 23.69 | AAAA |
| ATOM | 414 | O | PRO | A | 51 | 47.545 | 30.680 | 50.839 | 1.00 24.13 | AAAA |
| ATOM | 415 | N | ALA | A | 52 | 45.381 | 30.325 | 50.422 | 1.00 23.36 | AAAA |
| ATOM | 416 | CA | ALA | A | 52 | 45.419 | 28.972 | 50.952 | 1.00 23.64 | AAAA |
| ATOM | 417 | CB | ALA | A | 52 | 44.012 | 28.405 | 51.029 | 1.00 23.86 | AAAA |
| ATOM | 418 | C | ALA | A | 52 | 46.260 | 28.145 | 49.994 | 1.00 23.58 | AAAA |
| ATOM | 419 | O | ALA | A | 52 | 46.240 | 28.383 | 48.806 | 1.00 24.52 | AAAA |
| ATOM | 420 | N | THR | A | 53 | 47.009 | 27.185 | 50.501 | 1.00 24.41 | AAAA |
| ATOM | 421 | CA | THR | A | 53 | 47.815 | 26.352 | 49.628 | 1.00 26.26 | AAAA |
| ATOM | 422 | CB | THR | A | 53 | 48.933 | 25.642 | 50.405 | 1.00 26.37 | AAAA |
| ATOM | 423 | OG1 | THR | A | 53 | 48.355 | 24.763 | 51.375 | 1.00 26.51 | AAAA |
| ATOM | 424 | CG2 | THR | A | 53 | 49.810 | 26.648 | 51.106 | 1.00 24.48 | AAAA |
| ATOM | 425 | C | THR | A | 53 | 46.889 | 25.299 | 49.034 | 1.00 27.63 | AAAA |
| ATOM | 426 | O | THR | A | 53 | 45.870 | 24.982 | 49.620 | 1.00 29.22 | AAAA |
| ATOM | 427 | N | LYS | A | 54 | 47.240 | 24.776 | 47.867 | 1.00 29.31 | AAAA |
| ATOM | 428 | CA | LYS | A | 54 | 46.450 | 23.752 | 47.189 | 1.00 30.61 | AAAA |
| ATOM | 429 | CB | LYS | A | 54 | 47.249 | 23.182 | 46.015 | 1.00 31.68 | AAAA |
| ATOM | 430 | CG | LYS | A | 54 | 46.585 | 22.020 | 45.304 | 1.00 34.38 | AAAA |
| ATOM | 431 | CD | LYS | A | 54 | 45.449 | 22.464 | 44.417 | 1.00 36.00 | AAAA |
| ATOM | 432 | CE | LYS | A | 54 | 45.943 | 22.850 | 43.025 | 1.00 37.55 | AAAA |
| ATOM | 433 | NZ | LYS | A | 54 | 46.425 | 21.664 | 42.236 | 1.00 37.57 | AAAA |
| ATOM | 434 | C | LYS | A | 54 | 46.127 | 22.640 | 48.170 | 1.00 31.26 | AAAA |
| ATOM | 435 | O | LYS | A | 54 | 45.025 | 22.097 | 48.176 | 1.00 31.72 | AAAA |
| ATOM | 436 | N | GLU | A | 55 | 47.102 | 22.312 | 49.006 | 1.00 31.88 | AAAA |
| ATOM | 437 | CA | GLU | A | 55 | 46.961 | 21.260 | 50.011 | 1.00 32.29 | AAAA |
| ATOM | 438 | CB | GLU | A | 55 | 48.266 | 21.089 | 50.778 | 1.00 34.43 | AAAA |
| ATOM | 439 | CG | GLU | A | 55 | 48.265 | 19.901 | 51.706 | 1.00 38.39 | AAAA |
| ATOM | 440 | CD | GLU | A | 55 | 49.513 | 19.839 | 52.584 | 1.00 41.46 | AAAA |
| ATOM | 441 | OE1 | GLU | A | 55 | 49.745 | 18.770 | 53.200 | 1.00 43.30 | AAAA |
| ATOM | 442 | OE2 | GLU | A | 55 | 50.245 | 20.859 | 52.672 | 1.00 42.45 | AAAA |
| ATOM | 443 | C | GLU | A | 55 | 45.851 | 21.555 | 51.013 | 1.00 30.43 | AAAA |
| ATOM | 444 | O | GLU | A | 55 | 45.048 | 20.681 | 51.332 | 1.00 30.59 | AAAA |
| ATOM | 445 | N | GLU | A | 56 | 45.822 | 22.782 | 51.517 | 1.00 28.23 | AAAA |
| ATOM | 446 | CA | GLU | A | 56 | 44.812 | 23.164 | 52.488 | 1.00 27.69 | AAAA |
| ATOM | 447 | CB | GLU | A | 56 | 45.078 | 24.588 | 52.989 | 1.00 27.90 | AAAA |
| ATOM | 448 | CG | GLU | A | 56 | 46.434 | 24.721 | 53.670 | 1.00 26.64 | AAAA |
| ATOM | 449 | CD | GLU | A | 56 | 46.769 | 26.135 | 54.098 | 1.00 26.35 | AAAA |
| ATOM | 450 | OE1 | GLU | A | 56 | 46.615 | 27.057 | 53.265 | 1.00 25.12 | AAAA |
| ATOM | 451 | OE2 | GLU | A | 56 | 47.213 | 26.315 | 55.255 | 1.00 25.70 | AAAA |
| ATOM | 452 | C | GLU | A | 56 | 43.408 | 23.043 | 51.914 | 1.00 26.99 | AAAA |
| ATOM | 453 | O | GLU | A | 56 | 42.495 | 22.574 | 52.588 | 1.00 26.25 | AAAA |
| ATOM | 454 | N | LEU | A | 57 | 43.252 | 23.447 | 50.659 | 1.00 27.26 | AAAA |
| ATOM | 455 | CA | LEU | A | 57 | 41.965 | 23.389 | 49.967 | 1.00 27.17 | AAAA |
| ATOM | 456 | CB | LEU | A | 57 | 42.077 | 24.063 | 48.596 | 1.00 26.62 | AAAA |
| ATOM | 457 | CG | LEU | A | 57 | 42.491 | 25.545 | 48.656 | 1.00 27.64 | AAAA |
| ATOM | 458 | CD1 | LEU | A | 57 | 42.770 | 26.108 | 47.269 | 1.00 26.66 | AAAA |
| ATOM | 459 | CD2 | LEU | A | 57 | 41.389 | 26.341 | 49.349 | 1.00 26.92 | AAAA |
| ATOM | 460 | C | LEU | A | 57 | 41.552 | 21.946 | 49.796 | 1.00 27.26 | AAAA |
| ATOM | 461 | O | LEU | A | 57 | 40.363 | 21.612 | 49.816 | 1.00 27.53 | AAAA |
| ATOM | 462 | N | LEU | A | 58 | 42.547 | 21.085 | 49.641 | 1.00 27.42 | AAAA |

Fig. 19-7

| ATOM | 463 | CA | LEU | A | 58 | 42.293 | 19.675 | 49.457 | 1.00 | 26.10 | AAAA |
| ATOM | 464 | CB | LEU | A | 58 | 43.486 | 19.019 | 48.794 | 1.00 | 25.43 | AAAA |
| ATOM | 465 | CG | LEU | A | 58 | 43.623 | 19.577 | 47.385 | 1.00 | 26.66 | AAAA |
| ATOM | 466 | CD1 | LEU | A | 58 | 44.760 | 18.884 | 46.705 | 1.00 | 27.12 | AAAA |
| ATOM | 467 | CD2 | LEU | A | 58 | 42.334 | 19.355 | 46.600 | 1.00 | 26.43 | AAAA |
| ATOM | 468 | C | LEU | A | 58 | 41.938 | 18.956 | 50.731 | 1.00 | 25.79 | AAAA |
| ATOM | 469 | O | LEU | A | 58 | 41.648 | 17.763 | 50.692 | 1.00 | 26.50 | AAAA |
| ATOM | 470 | N | LEU | A | 59 | 41.977 | 19.666 | 51.858 | 1.00 | 24.91 | AAAA |
| ATOM | 471 | CA | LEU | A | 59 | 41.595 | 19.070 | 53.136 | 1.00 | 25.15 | AAAA |
| ATOM | 472 | CB | LEU | A | 59 | 41.958 | 19.991 | 54.322 | 1.00 | 25.44 | AAAA |
| ATOM | 473 | CG | LEU | A | 59 | 43.423 | 20.280 | 54.710 | 1.00 | 24.67 | AAAA |
| ATOM | 474 | CD1 | LEU | A | 59 | 43.502 | 21.461 | 55.652 | 1.00 | 23.70 | AAAA |
| ATOM | 475 | CD2 | LEU | A | 59 | 44.044 | 19.044 | 55.357 | 1.00 | 24.08 | AAAA |
| ATOM | 476 | C | LEU | A | 59 | 40.074 | 18.870 | 53.090 | 1.00 | 25.41 | AAAA |
| ATOM | 477 | O | LEU | A | 59 | 39.503 | 18.266 | 53.993 | 1.00 | 25.88 | AAAA |
| ATOM | 478 | N | PHE | A | 60 | 39.436 | 19.392 | 52.031 | 1.00 | 25.05 | AAAA |
| ATOM | 479 | CA | PHE | A | 60 | 37.983 | 19.276 | 51.823 | 1.00 | 24.11 | AAAA |
| ATOM | 480 | CB | PHE | A | 60 | 37.250 | 20.476 | 52.440 | 1.00 | 21.80 | AAAA |
| ATOM | 481 | CG | PHE | A | 60 | 35.778 | 20.534 | 52.098 | 1.00 | 20.07 | AAAA |
| ATOM | 482 | CD1 | PHE | A | 60 | 34.917 | 19.501 | 52.462 | 1.00 | 19.27 | AAAA |
| ATOM | 483 | CD2 | PHE | A | 60 | 35.249 | 21.628 | 51.399 | 1.00 | 19.82 | AAAA |
| ATOM | 484 | CE1 | PHE | A | 60 | 33.550 | 19.557 | 52.136 | 1.00 | 19.26 | AAAA |
| ATOM | 485 | CE2 | PHE | A | 60 | 33.890 | 21.688 | 51.071 | 1.00 | 17.45 | AAAA |
| ATOM | 486 | CZ | PHE | A | 60 | 33.042 | 20.652 | 51.440 | 1.00 | 17.92 | AAAA |
| ATOM | 487 | C | PHE | A | 60 | 37.557 | 19.139 | 50.345 | 1.00 | 24.02 | AAAA |
| ATOM | 488 | O | PHE | A | 60 | 36.846 | 18.201 | 49.974 | 1.00 | 23.27 | AAAA |
| ATOM | 489 | N | HIS | A | 61 | 37.982 | 20.079 | 49.511 | 1.00 | 24.40 | AAAA |
| ATOM | 490 | CA | HIS | A | 61 | 37.626 | 20.053 | 48.099 | 1.00 | 25.04 | AAAA |
| ATOM | 491 | CB | HIS | A | 61 | 37.768 | 21.449 | 47.494 | 1.00 | 24.19 | AAAA |
| ATOM | 492 | CG | HIS | A | 61 | 36.744 | 22.429 | 47.979 | 1.00 | 24.44 | AAAA |
| ATOM | 493 | CD2 | HIS | A | 61 | 35.429 | 22.559 | 47.683 | 1.00 | 24.12 | AAAA |
| ATOM | 494 | ND1 | HIS | A | 61 | 37.038 | 23.444 | 48.864 | 1.00 | 24.36 | AAAA |
| ATOM | 495 | CE1 | HIS | A | 61 | 35.952 | 24.159 | 49.089 | 1.00 | 23.18 | AAAA |
| ATOM | 496 | NE2 | HIS | A | 61 | 34.962 | 23.643 | 48.385 | 1.00 | 23.91 | AAAA |
| ATOM | 497 | C | HIS | A | 61 | 38.416 | 19.054 | 47.253 | 1.00 | 25.60 | AAAA |
| ATOM | 498 | O | HIS | A | 61 | 39.596 | 18.805 | 47.498 | 1.00 | 26.94 | AAAA |
| ATOM | 499 | N | THR | A | 62 | 37.754 | 18.496 | 46.244 | 1.00 | 26.68 | AAAA |
| ATOM | 500 | CA | THR | A | 62 | 38.369 | 17.522 | 45.333 | 1.00 | 28.17 | AAAA |
| ATOM | 501 | CB | THR | A | 62 | 37.290 | 16.695 | 44.614 | 1.00 | 28.15 | AAAA |
| ATOM | 502 | OG1 | THR | A | 62 | 36.544 | 17.541 | 43.731 | 1.00 | 28.10 | AAAA |
| ATOM | 503 | CG2 | THR | A | 62 | 36.334 | 16.094 | 45.629 | 1.00 | 28.24 | AAAA |
| ATOM | 504 | C | THR | A | 62 | 39.226 | 18.217 | 44.278 | 1.00 | 29.28 | AAAA |
| ATOM | 505 | O | THR | A | 62 | 38.876 | 19.286 | 43.792 | 1.00 | 29.52 | AAAA |
| ATOM | 506 | N | GLU | A | 63 | 40.344 | 17.606 | 43.912 | 1.00 | 31.33 | AAAA |
| ATOM | 507 | CA | GLU | A | 63 | 41.249 | 18.202 | 42.928 | 1.00 | 32.42 | AAAA |
| ATOM | 508 | CB | GLU | A | 63 | 42.333 | 17.219 | 42.536 | 1.00 | 34.37 | AAAA |
| ATOM | 509 | CG | GLU | A | 63 | 43.304 | 16.869 | 43.609 | 1.00 | 37.20 | AAAA |
| ATOM | 510 | CD | GLU | A | 63 | 44.427 | 16.022 | 43.052 | 1.00 | 38.79 | AAAA |
| ATOM | 511 | OE1 | GLU | A | 63 | 45.100 | 16.499 | 42.097 | 1.00 | 37.96 | AAAA |
| ATOM | 512 | OE2 | GLU | A | 63 | 44.619 | 14.892 | 43.564 | 1.00 | 39.68 | AAAA |
| ATOM | 513 | C | GLU | A | 63 | 40.607 | 18.687 | 41.639 | 1.00 | 31.96 | AAAA |
| ATOM | 514 | O | GLU | A | 63 | 40.824 | 19.816 | 41.215 | 1.00 | 32.10 | AAAA |
| ATOM | 515 | N | ASP | A | 64 | 39.845 | 17.814 | 40.998 | 1.00 | 31.52 | AAAA |
| ATOM | 516 | CA | ASP | A | 64 | 39.204 | 18.165 | 39.753 | 1.00 | 31.36 | AAAA |
| ATOM | 517 | CB | ASP | A | 64 | 38.301 | 17.018 | 39.295 | 1.00 | 33.99 | AAAA |
| ATOM | 518 | CG | ASP | A | 64 | 37.213 | 16.694 | 40.302 | 1.00 | 37.38 | AAAA |
| ATOM | 519 | OD1 | ASP | A | 64 | 36.375 | 15.801 | 40.027 | 1.00 | 39.80 | AAAA |
| ATOM | 520 | OD2 | ASP | A | 64 | 37.188 | 17.332 | 41.374 | 1.00 | 38.67 | AAAA |
| ATOM | 521 | C | ASP | A | 64 | 38.412 | 19.465 | 39.902 | 1.00 | 30.02 | AAAA |
| ATOM | 522 | O | ASP | A | 64 | 38.462 | 20.331 | 39.026 | 1.00 | 30.47 | AAAA |
| ATOM | 523 | N | TYR | A | 65 | 37.695 | 19.608 | 41.012 | 1.00 | 27.51 | AAAA |
| ATOM | 524 | CA | TYR | A | 65 | 36.918 | 20.814 | 41.248 | 1.00 | 26.03 | AAAA |
| ATOM | 525 | CB | TYR | A | 65 | 36.010 | 20.654 | 42.467 | 1.00 | 25.42 | AAAA |
| ATOM | 526 | CG | TYR | A | 65 | 35.339 | 21.946 | 42.866 | 1.00 | 24.90 | AAAA |
| ATOM | 527 | CD1 | TYR | A | 65 | 34.525 | 22.636 | 41.964 | 1.00 | 25.04 | AAAA |
| ATOM | 528 | CE1 | TYR | A | 65 | 33.914 | 23.823 | 42.308 | 1.00 | 25.01 | AAAA |

Fig. 19-8

```
ATOM    529  CD2 TYR A  65      35.525  22.486  44.136  1.00 24.65      AAAA
ATOM    530  CE2 TYR A  65      34.920  23.677  44.497  1.00 25.86      AAAA
ATOM    531  CZ  TYR A  65      34.110  24.349  43.576  1.00 26.69      AAAA
ATOM    532  OH  TYR A  65      33.499  25.543  43.924  1.00 27.20      AAAA
ATOM    533  C   TYR A  65      37.814  22.022  41.464  1.00 24.91      AAAA
ATOM    534  O   TYR A  65      37.460  23.129  41.096  1.00 25.62      AAAA
ATOM    535  N   ILE A  66      38.965  21.812  42.080  1.00 23.20      AAAA
ATOM    536  CA  ILE A  66      39.877  22.902  42.328  1.00 22.33      AAAA
ATOM    537  CB  ILE A  66      40.924  22.520  43.402  1.00 21.45      AAAA
ATOM    538  CG2 ILE A  66      41.927  23.652  43.617  1.00 20.00      AAAA
ATOM    539  CG1 ILE A  66      40.220  22.289  44.729  1.00 20.16      AAAA
ATOM    540  CD1 ILE A  66      39.528  23.523  45.228  1.00 19.68      AAAA
ATOM    541  C   ILE A  66      40.558  23.261  41.023  1.00 22.68      AAAA
ATOM    542  O   ILE A  66      40.636  24.425  40.665  1.00 23.19      AAAA
ATOM    543  N   ASN A  67      41.036  22.262  40.295  1.00 22.96      AAAA
ATOM    544  CA  ASN A  67      41.698  22.545  39.029  1.00 23.92      AAAA
ATOM    545  CB  ASN A  67      42.292  21.261  38.395  1.00 24.24      AAAA
ATOM    546  CG  ASN A  67      43.344  20.588  39.289  1.00 23.38      AAAA
ATOM    547  OD1 ASN A  67      44.196  21.256  39.859  1.00 23.47      AAAA
ATOM    548  ND2 ASN A  67      43.290  19.258  39.392  1.00 23.20      AAAA
ATOM    549  C   ASN A  67      40.717  23.216  38.063  1.00 23.82      AAAA
ATOM    550  O   ASN A  67      41.123  23.996  37.204  1.00 24.63      AAAA
ATOM    551  N   THR A  68      39.427  22.928  38.213  1.00 24.08      AAAA
ATOM    552  CA  THR A  68      38.428  23.534  37.343  1.00 25.28      AAAA
ATOM    553  CB  THR A  68      37.030  22.904  37.525  1.00 24.55      AAAA
ATOM    554  OG1 THR A  68      37.090  21.500  37.258  1.00 24.64      AAAA
ATOM    555  CG2 THR A  68      36.049  23.534  36.564  1.00 23.58      AAAA
ATOM    556  C   THR A  68      38.322  25.023  37.664  1.00 26.31      AAAA
ATOM    557  O   THR A  68      38.114  25.854  36.771  1.00 26.69      AAAA
ATOM    558  N   LEU A  69      38.462  25.351  38.945  1.00 26.59      AAAA
ATOM    559  CA  LEU A  69      38.381  26.729  39.378  1.00 27.05      AAAA
ATOM    560  CB  LEU A  69      38.321  26.807  40.904  1.00 27.15      AAAA
ATOM    561  CG  LEU A  69      37.003  26.397  41.551  1.00 25.68      AAAA
ATOM    562  CD1 LEU A  69      37.088  26.491  43.062  1.00 26.30      AAAA
ATOM    563  CD2 LEU A  69      35.933  27.316  41.044  1.00 26.14      AAAA
ATOM    564  C   LEU A  69      39.570  27.508  38.867  1.00 28.44      AAAA
ATOM    565  O   LEU A  69      39.425  28.619  38.356  1.00 28.59      AAAA
ATOM    566  N   MET A  70      40.748  26.914  39.009  1.00 29.31      AAAA
ATOM    567  CA  MET A  70      41.981  27.536  38.571  1.00 29.89      AAAA
ATOM    568  CB  MET A  70      43.160  26.692  39.044  1.00 31.04      AAAA
ATOM    569  CG  MET A  70      43.164  26.528  40.562  1.00 31.79      AAAA
ATOM    570  SD  MET A  70      44.608  25.684  41.183  1.00 32.58      AAAA
ATOM    571  CE  MET A  70      45.859  26.820  40.670  1.00 30.82      AAAA
ATOM    572  C   MET A  70      42.017  27.723  37.057  1.00 30.36      AAAA
ATOM    573  O   MET A  70      42.462  28.769  36.559  1.00 30.18      AAAA
ATOM    574  N   GLU A  71      41.538  26.719  36.328  1.00 30.34      AAAA
ATOM    575  CA  GLU A  71      41.519  26.795  34.874  1.00 30.73      AAAA
ATOM    576  CB  GLU A  71      41.140  25.442  34.266  1.00 33.47      AAAA
ATOM    577  CG  GLU A  71      41.122  25.430  32.731  1.00 37.11      AAAA
ATOM    578  CD  GLU A  71      42.513  25.676  32.093  1.00 40.49      AAAA
ATOM    579  OE1 GLU A  71      42.570  25.798  30.844  1.00 41.95      AAAA
ATOM    580  OE2 GLU A  71      43.541  25.738  32.825  1.00 40.74      AAAA
ATOM    581  C   GLU A  71      40.537  27.851  34.392  1.00 29.78      AAAA
ATOM    582  O   GLU A  71      40.852  28.642  33.508  1.00 27.82      AAAA
ATOM    583  N   ALA A  72      39.352  27.855  34.992  1.00 29.85      AAAA
ATOM    584  CA  ALA A  72      38.296  28.790  34.635  1.00 29.88      AAAA
ATOM    585  CB  ALA A  72      37.022  28.432  35.374  1.00 29.07      AAAA
ATOM    586  C   ALA A  72      38.667  30.238  34.907  1.00 30.78      AAAA
ATOM    587  O   ALA A  72      38.359  31.122  34.108  1.00 31.27      AAAA
ATOM    588  N   GLU A  73      39.336  30.491  36.023  1.00 31.07      AAAA
ATOM    589  CA  GLU A  73      39.710  31.856  36.346  1.00 31.65      AAAA
ATOM    590  CB  GLU A  73      40.243  31.954  37.785  1.00 30.52      AAAA
ATOM    591  CG  GLU A  73      40.643  33.370  38.198  1.00 28.73      AAAA
ATOM    592  CD  GLU A  73      41.076  33.484  39.651  1.00 28.77      AAAA
ATOM    593  OE1 GLU A  73      40.239  33.260  40.546  1.00 28.94      AAAA
ATOM    594  OE2 GLU A  73      42.258  33.795  39.906  1.00 28.57      AAAA
```

Fig. 19-9

| ATOM | 595 | C | GLU | A | 73 | 40.726 | 32.461 | 35.378 | 1.00 | 33.54 | AAAA |
|------|-----|-----|-----|---|----|--------|--------|--------|------|-------|------|
| ATOM | 596 | O | GLU | A | 73 | 40.456 | 33.499 | 34.767 | 1.00 | 34.93 | AAAA |
| ATOM | 597 | N | ARG | A | 74 | 41.885 | 31.832 | 35.214 | 1.00 | 34.35 | AAAA |
| ATOM | 598 | CA | ARG | A | 74 | 42.890 | 32.428 | 34.334 | 1.00 | 36.04 | AAAA |
| ATOM | 599 | CB | ARG | A | 74 | 44.238 | 31.710 | 34.482 | 1.00 | 36.92 | AAAA |
| ATOM | 600 | CG | ARG | A | 74 | 44.327 | 30.313 | 33.923 | 1.00 | 38.14 | AAAA |
| ATOM | 601 | CD | ARG | A | 74 | 45.508 | 29.589 | 34.543 | 1.00 | 39.55 | AAAA |
| ATOM | 602 | NE | ARG | A | 74 | 45.893 | 28.404 | 33.785 | 1.00 | 42.02 | AAAA |
| ATOM | 603 | CZ | ARG | A | 74 | 46.632 | 28.436 | 32.675 | 1.00 | 42.69 | AAAA |
| ATOM | 604 | NH1 | ARG | A | 74 | 47.071 | 29.593 | 32.191 | 1.00 | 42.76 | AAAA |
| ATOM | 605 | NH2 | ARG | A | 74 | 46.933 | 27.309 | 32.046 | 1.00 | 42.92 | AAAA |
| ATOM | 606 | C | ARG | A | 74 | 42.476 | 32.532 | 32.864 | 1.00 | 36.56 | AAAA |
| ATOM | 607 | O | ARG | A | 74 | 42.842 | 33.493 | 32.187 | 1.00 | 37.73 | AAAA |
| ATOM | 608 | N | SER | A | 75 | 41.711 | 31.567 | 32.367 | 1.00 | 36.60 | AAAA |
| ATOM | 609 | CA | SER | A | 75 | 41.248 | 31.622 | 30.987 | 1.00 | 36.82 | AAAA |
| ATOM | 610 | CB | SER | A | 75 | 40.916 | 30.218 | 30.478 | 1.00 | 36.10 | AAAA |
| ATOM | 611 | OG | SER | A | 75 | 39.736 | 29.723 | 31.083 | 1.00 | 36.39 | AAAA |
| ATOM | 612 | C | SER | A | 75 | 39.980 | 32.476 | 31.001 | 1.00 | 36.90 | AAAA |
| ATOM | 613 | O | SER | A | 75 | 39.401 | 32.791 | 29.963 | 1.00 | 36.25 | AAAA |
| ATOM | 614 | N | GLN | A | 76 | 39.568 | 32.845 | 32.208 | 1.00 | 37.62 | AAAA |
| ATOM | 615 | CA | GLN | A | 76 | 38.368 | 33.639 | 32.427 | 1.00 | 37.92 | AAAA |
| ATOM | 616 | CB | GLN | A | 76 | 38.613 | 35.100 | 32.049 | 1.00 | 38.23 | AAAA |
| ATOM | 617 | CG | GLN | A | 76 | 37.630 | 36.048 | 32.717 | 1.00 | 40.67 | AAAA |
| ATOM | 618 | CD | GLN | A | 76 | 37.929 | 36.298 | 34.199 | 1.00 | 41.40 | AAAA |
| ATOM | 619 | OE1 | GLN | A | 76 | 38.226 | 35.379 | 34.973 | 1.00 | 40.79 | AAAA |
| ATOM | 620 | NE2 | GLN | A | 76 | 37.833 | 37.556 | 34.597 | 1.00 | 42.32 | AAAA |
| ATOM | 621 | C | GLN | A | 76 | 37.223 | 33.064 | 31.600 | 1.00 | 37.75 | AAAA |
| ATOM | 622 | O | GLN | A | 76 | 36.521 | 33.789 | 30.901 | 1.00 | 38.13 | AAAA |
| ATOM | 623 | N | SER | A | 77 | 37.045 | 31.749 | 31.685 | 1.00 | 37.52 | AAAA |
| ATOM | 624 | CA | SER | A | 77 | 35.990 | 31.061 | 30.950 | 1.00 | 37.75 | AAAA |
| ATOM | 625 | CB | SER | A | 77 | 36.537 | 30.440 | 29.664 | 1.00 | 37.90 | AAAA |
| ATOM | 626 | OG | SER | A | 77 | 36.851 | 31.441 | 28.724 | 1.00 | 40.32 | AAAA |
| ATOM | 627 | C | SER | A | 77 | 35.338 | 29.960 | 31.757 | 1.00 | 37.55 | AAAA |
| ATOM | 628 | O | SER | A | 77 | 35.790 | 29.620 | 32.846 | 1.00 | 36.81 | AAAA |
| ATOM | 629 | N | VAL | A | 78 | 34.264 | 29.412 | 31.198 | 1.00 | 37.82 | AAAA |
| ATOM | 630 | CA | VAL | A | 78 | 33.538 | 28.309 | 31.812 | 1.00 | 37.99 | AAAA |
| ATOM | 631 | CB | VAL | A | 78 | 32.027 | 28.514 | 31.715 | 1.00 | 37.19 | AAAA |
| ATOM | 632 | CG1 | VAL | A | 78 | 31.310 | 27.439 | 32.497 | 1.00 | 36.84 | AAAA |
| ATOM | 633 | CG2 | VAL | A | 78 | 31.662 | 29.906 | 32.201 | 1.00 | 37.60 | AAAA |
| ATOM | 634 | C | VAL | A | 78 | 33.918 | 27.089 | 30.976 | 1.00 | 38.28 | AAAA |
| ATOM | 635 | O | VAL | A | 78 | 33.497 | 26.959 | 29.819 | 1.00 | 39.18 | AAAA |
| ATOM | 636 | N | PRO | A | 79 | 34.734 | 26.187 | 31.537 | 1.00 | 37.69 | AAAA |
| ATOM | 637 | CD | PRO | A | 79 | 35.347 | 26.167 | 32.869 | 1.00 | 37.65 | AAAA |
| ATOM | 638 | CA | PRO | A | 79 | 35.146 | 24.998 | 30.797 | 1.00 | 37.54 | AAAA |
| ATOM | 639 | CB | PRO | A | 79 | 36.127 | 24.325 | 31.759 | 1.00 | 37.45 | AAAA |
| ATOM | 640 | CG | PRO | A | 79 | 36.655 | 25.489 | 32.557 | 1.00 | 37.65 | AAAA |
| ATOM | 641 | C | PRO | A | 79 | 33.980 | 24.089 | 30.434 | 1.00 | 37.20 | AAAA |
| ATOM | 642 | O | PRO | A | 79 | 32.958 | 24.050 | 31.120 | 1.00 | 36.43 | AAAA |
| ATOM | 643 | N | LYS | A | 80 | 34.154 | 23.363 | 29.338 | 1.00 | 37.42 | AAAA |
| ATOM | 644 | CA | LYS | A | 80 | 33.160 | 22.423 | 28.855 | 1.00 | 37.35 | AAAA |
| ATOM | 645 | CB | LYS | A | 80 | 33.757 | 21.586 | 27.725 | 1.00 | 37.99 | AAAA |
| ATOM | 646 | CG | LYS | A | 80 | 32.928 | 20.379 | 27.280 | 1.00 | 38.94 | AAAA |
| ATOM | 647 | CD | LYS | A | 80 | 31.835 | 20.710 | 26.286 | 1.00 | 39.07 | AAAA |
| ATOM | 648 | CE | LYS | A | 80 | 31.320 | 19.402 | 25.688 | 1.00 | 40.43 | AAAA |
| ATOM | 649 | NZ | LYS | A | 80 | 30.498 | 19.543 | 24.450 | 1.00 | 40.48 | AAAA |
| ATOM | 650 | C | LYS | A | 80 | 32.752 | 21.515 | 30.003 | 1.00 | 36.85 | AAAA |
| ATOM | 651 | O | LYS | A | 80 | 33.610 | 20.942 | 30.676 | 1.00 | 36.56 | AAAA |
| ATOM | 652 | N | GLY | A | 81 | 31.443 | 21.408 | 30.217 | 1.00 | 35.94 | AAAA |
| ATOM | 653 | CA | GLY | A | 81 | 30.903 | 20.570 | 31.268 | 1.00 | 35.48 | AAAA |
| ATOM | 654 | C | GLY | A | 81 | 31.110 | 21.054 | 32.693 | 1.00 | 35.23 | AAAA |
| ATOM | 655 | O | GLY | A | 81 | 30.749 | 20.355 | 33.644 | 1.00 | 35.46 | AAAA |
| ATOM | 656 | N | ALA | A | 82 | 31.677 | 22.241 | 32.867 | 1.00 | 35.17 | AAAA |
| ATOM | 657 | CA | ALA | A | 82 | 31.919 | 22.743 | 34.213 | 1.00 | 35.02 | AAAA |
| ATOM | 658 | CB | ALA | A | 82 | 33.076 | 23.743 | 34.208 | 1.00 | 35.13 | AAAA |
| ATOM | 659 | C | ALA | A | 82 | 30.674 | 23.378 | 34.797 | 1.00 | 34.39 | AAAA |
| ATOM | 660 | O | ALA | A | 82 | 30.451 | 23.332 | 36.001 | 1.00 | 33.82 | AAAA |

Fig. 19-10

| | | | | | | | | | |
|---|---|---|---|---|---|---|---|---|---|
| ATOM | 661 | N | ARG | A | 83 | 29.858 | 23.960 | 33.932 | 1.00 34.77 | AAAA |
| ATOM | 662 | CA | ARG | A | 83 | 28.637 | 24.613 | 34.361 | 1.00 35.34 | AAAA |
| ATOM | 663 | CB | ARG | A | 83 | 27.899 | 25.180 | 33.150 | 1.00 36.26 | AAAA |
| ATOM | 664 | CG | ARG | A | 83 | 27.045 | 26.395 | 33.464 | 1.00 37.09 | AAAA |
| ATOM | 665 | CD | ARG | A | 83 | 26.209 | 26.141 | 34.686 | 1.00 37.48 | AAAA |
| ATOM | 666 | NE | ARG | A | 83 | 25.475 | 27.310 | 35.134 | 1.00 37.35 | AAAA |
| ATOM | 667 | CZ | ARG | A | 83 | 24.711 | 27.311 | 36.218 | 1.00 37.77 | AAAA |
| ATOM | 668 | NH1 | ARG | A | 83 | 24.606 | 26.204 | 36.940 | 1.00 37.29 | AAAA |
| ATOM | 669 | NH2 | ARG | A | 83 | 24.040 | 28.401 | 36.568 | 1.00 38.34 | AAAA |
| ATOM | 670 | C | ARG | A | 83 | 27.739 | 23.603 | 35.065 | 1.00 36.30 | AAAA |
| ATOM | 671 | O | ARG | A | 83 | 27.232 | 23.854 | 36.154 | 1.00 36.17 | AAAA |
| ATOM | 672 | N | GLU | A | 84 | 27.565 | 22.450 | 34.431 | 1.00 37.19 | AAAA |
| ATOM | 673 | CA | GLU | A | 84 | 26.721 | 21.382 | 34.948 | 1.00 37.80 | AAAA |
| ATOM | 674 | CB | GLU | A | 84 | 26.466 | 20.375 | 33.833 | 1.00 40.55 | AAAA |
| ATOM | 675 | CG | GLU | A | 84 | 25.643 | 19.171 | 34.232 | 1.00 43.12 | AAAA |
| ATOM | 676 | CD | GLU | A | 84 | 25.362 | 18.268 | 33.046 | 1.00 44.98 | AAAA |
| ATOM | 677 | OE1 | GLU | A | 84 | 24.573 | 17.301 | 33.195 | 1.00 46.36 | AAAA |
| ATOM | 678 | OE2 | GLU | A | 84 | 25.937 | 18.532 | 31.962 | 1.00 44.94 | AAAA |
| ATOM | 679 | C | GLU | A | 84 | 27.290 | 20.657 | 36.158 | 1.00 37.07 | AAAA |
| ATOM | 680 | O | GLU | A | 84 | 26.642 | 20.555 | 37.199 | 1.00 36.17 | AAAA |
| ATOM | 681 | N | LYS | A | 85 | 28.506 | 20.152 | 35.999 | 1.00 36.23 | AAAA |
| ATOM | 682 | CA | LYS | A | 85 | 29.202 | 19.412 | 37.043 | 1.00 35.36 | AAAA |
| ATOM | 683 | CB | LYS | A | 85 | 30.449 | 18.761 | 36.437 | 1.00 36.96 | AAAA |
| ATOM | 684 | CG | LYS | A | 85 | 31.394 | 18.158 | 37.465 | 1.00 39.04 | AAAA |
| ATOM | 685 | CD | LYS | A | 85 | 30.995 | 16.766 | 37.919 | 1.00 40.59 | AAAA |
| ATOM | 686 | CE | LYS | A | 85 | 31.508 | 15.719 | 36.933 | 1.00 41.88 | AAAA |
| ATOM | 687 | NZ | LYS | A | 85 | 32.998 | 15.817 | 36.757 | 1.00 42.00 | AAAA |
| ATOM | 688 | C | LYS | A | 85 | 29.620 | 20.202 | 38.289 | 1.00 33.86 | AAAA |
| ATOM | 689 | O | LYS | A | 85 | 29.576 | 19.679 | 39.404 | 1.00 33.82 | AAAA |
| ATOM | 690 | N | TYR | A | 86 | 30.014 | 21.458 | 38.097 | 1.00 32.06 | AAAA |
| ATOM | 691 | CA | TYR | A | 86 | 30.514 | 22.279 | 39.194 | 1.00 29.44 | AAAA |
| ATOM | 692 | CB | TYR | A | 86 | 31.956 | 22.683 | 38.875 | 1.00 29.97 | AAAA |
| ATOM | 693 | CG | TYR | A | 86 | 32.872 | 21.496 | 38.621 | 1.00 29.99 | AAAA |
| ATOM | 694 | CD1 | TYR | A | 86 | 33.281 | 20.666 | 39.666 | 1.00 29.24 | AAAA |
| ATOM | 695 | CE1 | TYR | A | 86 | 34.126 | 19.582 | 39.437 | 1.00 29.85 | AAAA |
| ATOM | 696 | CD2 | TYR | A | 86 | 33.329 | 21.204 | 37.329 | 1.00 30.16 | AAAA |
| ATOM | 697 | CE2 | TYR | A | 86 | 34.173 | 20.118 | 37.087 | 1.00 29.61 | AAAA |
| ATOM | 698 | CZ | TYR | A | 86 | 34.570 | 19.313 | 38.148 | 1.00 29.79 | AAAA |
| ATOM | 699 | OH | TYR | A | 86 | 35.414 | 18.253 | 37.923 | 1.00 29.48 | AAAA |
| ATOM | 700 | C | TYR | A | 86 | 29.705 | 23.509 | 39.572 | 1.00 27.81 | AAAA |
| ATOM | 701 | O | TYR | A | 86 | 30.052 | 24.202 | 40.524 | 1.00 27.56 | AAAA |
| ATOM | 702 | N | ASN | A | 87 | 28.642 | 23.784 | 38.828 | 1.00 26.60 | AAAA |
| ATOM | 703 | CA | ASN | A | 87 | 27.777 | 24.924 | 39.111 | 1.00 26.56 | AAAA |
| ATOM | 704 | CB | ASN | A | 87 | 27.172 | 24.772 | 40.508 | 1.00 26.39 | AAAA |
| ATOM | 705 | CG | ASN | A | 87 | 25.863 | 25.544 | 40.684 | 1.00 26.64 | AAAA |
| ATOM | 706 | OD1 | ASN | A | 87 | 25.335 | 25.632 | 41.790 | 1.00 26.84 | AAAA |
| ATOM | 707 | ND2 | ASN | A | 87 | 25.330 | 26.084 | 39.597 | 1.00 26.33 | AAAA |
| ATOM | 708 | C | ASN | A | 87 | 28.587 | 26.217 | 39.024 | 1.00 26.40 | AAAA |
| ATOM | 709 | O | ASN | A | 87 | 28.430 | 27.129 | 39.832 | 1.00 24.80 | AAAA |
| ATOM | 710 | N | ILE | A | 88 | 29.448 | 26.273 | 38.015 | 1.00 27.57 | AAAA |
| ATOM | 711 | CA | ILE | A | 88 | 30.330 | 27.409 | 37.767 | 1.00 27.88 | AAAA |
| ATOM | 712 | CB | ILE | A | 88 | 31.817 | 26.932 | 37.648 | 1.00 27.38 | AAAA |
| ATOM | 713 | CG2 | ILE | A | 88 | 32.684 | 27.994 | 36.986 | 1.00 26.34 | AAAA |
| ATOM | 714 | CG1 | ILE | A | 88 | 32.354 | 26.543 | 39.026 | 1.00 28.35 | AAAA |
| ATOM | 715 | CD1 | ILE | A | 88 | 32.356 | 27.671 | 40.042 | 1.00 27.78 | AAAA |
| ATOM | 716 | C | ILE | A | 88 | 29.946 | 28.110 | 36.472 | 1.00 29.17 | AAAA |
| ATOM | 717 | O | ILE | A | 88 | 29.530 | 27.469 | 35.515 | 1.00 29.75 | AAAA |
| ATOM | 718 | N | GLY | A | 89 | 30.092 | 29.429 | 36.443 | 1.00 29.96 | AAAA |
| ATOM | 719 | CA | GLY | A | 89 | 29.791 | 30.162 | 35.229 | 1.00 30.24 | AAAA |
| ATOM | 720 | C | GLY | A | 89 | 28.430 | 30.805 | 35.242 | 1.00 30.44 | AAAA |
| ATOM | 721 | O | GLY | A | 89 | 28.177 | 31.769 | 34.514 | 1.00 31.14 | AAAA |
| ATOM | 722 | N | GLY | A | 90 | 27.542 | 30.268 | 36.061 | 1.00 30.00 | AAAA |
| ATOM | 723 | CA | GLY | A | 90 | 26.221 | 30.841 | 36.129 | 1.00 30.52 | AAAA |
| ATOM | 724 | C | GLY | A | 90 | 26.283 | 32.262 | 36.661 | 1.00 31.09 | AAAA |
| ATOM | 725 | O | GLY | A | 90 | 27.356 | 32.795 | 36.962 | 1.00 30.34 | AAAA |
| ATOM | 726 | N | TYR | A | 91 | 25.112 | 32.873 | 36.768 | 1.00 31.09 | AAAA |

Fig. 19-11

| | | | | | | | | | | |
|---|---|---|---|---|---|---|---|---|---|---|
| ATOM | 727 | CA | TYR | A | 91 | 24.977 | 34.213 | 37.290 | 1.00 | 31.27 | AAAA |
| ATOM | 728 | CB | TYR | A | 91 | 23.515 | 34.634 | 37.195 | 1.00 | 31.82 | AAAA |
| ATOM | 729 | CG | TYR | A | 91 | 23.169 | 35.825 | 38.047 | 1.00 | 31.81 | AAAA |
| ATOM | 730 | CD1 | TYR | A | 91 | 23.536 | 37.108 | 37.670 | 1.00 | 32.44 | AAAA |
| ATOM | 731 | CE1 | TYR | A | 91 | 23.250 | 38.203 | 38.475 | 1.00 | 31.88 | AAAA |
| ATOM | 732 | CD2 | TYR | A | 91 | 22.505 | 35.663 | 39.254 | 1.00 | 32.63 | AAAA |
| ATOM | 733 | CE2 | TYR | A | 91 | 22.215 | 36.754 | 40.068 | 1.00 | 32.60 | AAAA |
| ATOM | 734 | CZ | TYR | A | 91 | 22.589 | 38.016 | 39.668 | 1.00 | 31.59 | AAAA |
| ATOM | 735 | OH | TYR | A | 91 | 22.283 | 39.094 | 40.450 | 1.00 | 31.94 | AAAA |
| ATOM | 736 | C | TYR | A | 91 | 25.384 | 34.202 | 38.753 | 1.00 | 31.56 | AAAA |
| ATOM | 737 | O | TYR | A | 91 | 26.075 | 35.105 | 39.233 | 1.00 | 31.21 | AAAA |
| ATOM | 738 | N | GLU | A | 92 | 24.925 | 33.158 | 39.438 | 1.00 | 31.51 | AAAA |
| ATOM | 739 | CA | GLU | A | 92 | 25.143 | 32.941 | 40.865 | 1.00 | 32.70 | AAAA |
| ATOM | 740 | CB | GLU | A | 92 | 24.463 | 31.626 | 41.268 | 1.00 | 33.55 | AAAA |
| ATOM | 741 | CG | GLU | A | 92 | 24.174 | 31.495 | 42.747 | 1.00 | 34.16 | AAAA |
| ATOM | 742 | CD | GLU | A | 92 | 23.311 | 30.278 | 43.087 | 1.00 | 35.31 | AAAA |
| ATOM | 743 | OE1 | GLU | A | 92 | 23.857 | 29.148 | 43.152 | 1.00 | 34.30 | AAAA |
| ATOM | 744 | OE2 | GLU | A | 92 | 22.076 | 30.466 | 43.275 | 1.00 | 35.36 | AAAA |
| ATOM | 745 | C | GLU | A | 92 | 26.619 | 32.902 | 41.248 | 1.00 | 33.02 | AAAA |
| ATOM | 746 | O | GLU | A | 92 | 27.073 | 33.623 | 42.140 | 1.00 | 32.91 | AAAA |
| ATOM | 747 | N | ASN | A | 93 | 27.358 | 32.049 | 40.550 | 1.00 | 32.84 | AAAA |
| ATOM | 748 | CA | ASN | A | 93 | 28.785 | 31.861 | 40.777 | 1.00 | 31.92 | AAAA |
| ATOM | 749 | CB | ASN | A | 93 | 29.015 | 30.437 | 41.278 | 1.00 | 31.18 | AAAA |
| ATOM | 750 | CG | ASN | A | 93 | 27.948 | 29.994 | 42.259 | 1.00 | 30.34 | AAAA |
| ATOM | 751 | OD1 | ASN | A | 93 | 27.723 | 30.642 | 43.271 | 1.00 | 31.20 | AAAA |
| ATOM | 752 | ND2 | ASN | A | 93 | 27.284 | 28.892 | 41.955 | 1.00 | 29.02 | AAAA |
| ATOM | 753 | C | ASN | A | 93 | 29.442 | 32.052 | 39.411 | 1.00 | 30.84 | AAAA |
| ATOM | 754 | O | ASN | A | 93 | 29.823 | 31.082 | 38.758 | 1.00 | 30.82 | AAAA |
| ATOM | 755 | N | PRO | A | 94 | 29.605 | 33.309 | 38.975 | 1.00 | 29.56 | AAAA |
| ATOM | 756 | CD | PRO | A | 94 | 29.312 | 34.590 | 39.626 | 1.00 | 29.03 | AAAA |
| ATOM | 757 | CA | PRO | A | 94 | 30.209 | 33.564 | 37.671 | 1.00 | 28.89 | AAAA |
| ATOM | 758 | CB | PRO | A | 94 | 29.890 | 35.045 | 37.416 | 1.00 | 28.22 | AAAA |
| ATOM | 759 | CG | PRO | A | 94 | 28.839 | 35.377 | 38.435 | 1.00 | 29.50 | AAAA |
| ATOM | 760 | C | PRO | A | 94 | 31.698 | 33.351 | 37.664 | 1.00 | 28.25 | AAAA |
| ATOM | 761 | O | PRO | A | 94 | 32.308 | 32.996 | 38.671 | 1.00 | 28.21 | AAAA |
| ATOM | 762 | N | VAL | A | 95 | 32.257 | 33.593 | 36.488 | 1.00 | 27.36 | AAAA |
| ATOM | 763 | CA | VAL | A | 95 | 33.676 | 33.530 | 36.247 | 1.00 | 26.24 | AAAA |
| ATOM | 764 | CB | VAL | A | 95 | 33.945 | 33.289 | 34.741 | 1.00 | 26.10 | AAAA |
| ATOM | 765 | CG1 | VAL | A | 95 | 35.373 | 33.717 | 34.357 | 1.00 | 25.47 | AAAA |
| ATOM | 766 | CG2 | VAL | A | 95 | 33.736 | 31.826 | 34.434 | 1.00 | 25.59 | AAAA |
| ATOM | 767 | C | VAL | A | 95 | 34.178 | 34.919 | 36.647 | 1.00 | 26.56 | AAAA |
| ATOM | 768 | O | VAL | A | 95 | 33.560 | 35.937 | 36.307 | 1.00 | 27.18 | AAAA |
| ATOM | 769 | N | SER | A | 96 | 35.280 | 34.966 | 37.382 | 1.00 | 25.23 | AAAA |
| ATOM | 770 | CA | SER | A | 96 | 35.858 | 36.237 | 37.790 | 1.00 | 24.51 | AAAA |
| ATOM | 771 | CB | SER | A | 96 | 34.935 | 36.961 | 38.774 | 1.00 | 23.22 | AAAA |
| ATOM | 772 | OG | SER | A | 96 | 34.941 | 36.297 | 40.014 | 1.00 | 19.76 | AAAA |
| ATOM | 773 | C | SER | A | 96 | 37.169 | 35.920 | 38.485 | 1.00 | 24.84 | AAAA |
| ATOM | 774 | O | SER | A | 96 | 37.590 | 34.764 | 38.530 | 1.00 | 25.97 | AAAA |
| ATOM | 775 | N | TYR | A | 97 | 37.824 | 36.933 | 39.030 | 1.00 | 24.02 | AAAA |
| ATOM | 776 | CA | TYR | A | 97 | 39.047 | 36.664 | 39.744 | 1.00 | 24.55 | AAAA |
| ATOM | 777 | CB | TYR | A | 97 | 40.071 | 37.762 | 39.504 | 1.00 | 23.94 | AAAA |
| ATOM | 778 | CG | TYR | A | 97 | 40.682 | 37.636 | 38.128 | 1.00 | 23.72 | AAAA |
| ATOM | 779 | CD1 | TYR | A | 97 | 40.177 | 38.341 | 37.039 | 1.00 | 23.11 | AAAA |
| ATOM | 780 | CE1 | TYR | A | 97 | 40.700 | 38.136 | 35.758 | 1.00 | 23.50 | AAAA |
| ATOM | 781 | CD2 | TYR | A | 97 | 41.717 | 36.735 | 37.903 | 1.00 | 22.25 | AAAA |
| ATOM | 782 | CE2 | TYR | A | 97 | 42.236 | 36.526 | 36.640 | 1.00 | 22.86 | AAAA |
| ATOM | 783 | CZ | TYR | A | 97 | 41.730 | 37.217 | 35.572 | 1.00 | 23.56 | AAAA |
| ATOM | 784 | OH | TYR | A | 97 | 42.232 | 36.941 | 34.318 | 1.00 | 24.06 | AAAA |
| ATOM | 785 | C | TYR | A | 97 | 38.800 | 36.436 | 41.228 | 1.00 | 25.08 | AAAA |
| ATOM | 786 | O | TYR | A | 97 | 39.739 | 36.266 | 42.009 | 1.00 | 26.91 | AAAA |
| ATOM | 787 | N | ALA | A | 98 | 37.522 | 36.406 | 41.589 | 1.00 | 24.73 | AAAA |
| ATOM | 788 | CA | ALA | A | 98 | 37.083 | 36.159 | 42.951 | 1.00 | 24.50 | AAAA |
| ATOM | 789 | CB | ALA | A | 98 | 35.800 | 36.925 | 43.235 | 1.00 | 24.48 | AAAA |
| ATOM | 790 | C | ALA | A | 98 | 36.824 | 34.661 | 43.088 | 1.00 | 23.95 | AAAA |
| ATOM | 791 | O | ALA | A | 98 | 36.929 | 34.100 | 44.171 | 1.00 | 24.21 | AAAA |
| ATOM | 792 | N | MET | A | 99 | 36.502 | 34.011 | 41.976 | 1.00 | 23.10 | AAAA |

Fig. 19-12

| | | | | | | | | | |
|---|---|---|---|---|---|---|---|---|---|
| ATOM | 793 | CA | MET | A | 99 | 36.208 | 32.584 | 42.000 | 1.00 22.61 | AAAA |
| ATOM | 794 | CB | MET | A | 99 | 35.855 | 32.089 | 40.597 | 1.00 23.25 | AAAA |
| ATOM | 795 | CG | MET | A | 99 | 37.009 | 32.063 | 39.607 | 1.00 23.22 | AAAA |
| ATOM | 796 | SD | MET | A | 99 | 36.360 | 31.808 | 37.952 | 1.00 25.21 | AAAA |
| ATOM | 797 | CE | MET | A | 99 | 35.328 | 30.374 | 38.258 | 1.00 22.04 | AAAA |
| ATOM | 798 | C | MET | A | 99 | 37.319 | 31.720 | 42.581 | 1.00 21.80 | AAAA |
| ATOM | 799 | O | MET | A | 99 | 37.052 | 30.695 | 43.199 | 1.00 21.29 | AAAA |
| ATOM | 800 | N | PHE | A | 100 | 38.567 | 32.111 | 42.380 | 1.00 21.87 | AAAA |
| ATOM | 801 | CA | PHE | A | 100 | 39.650 | 31.322 | 42.936 | 1.00 21.11 | AAAA |
| ATOM | 802 | CB | PHE | A | 100 | 40.388 | 30.552 | 41.841 | 1.00 20.25 | AAAA |
| ATOM | 803 | CG | PHE | A | 100 | 41.451 | 29.648 | 42.375 | 1.00 20.14 | AAAA |
| ATOM | 804 | CD1 | PHE | A | 100 | 41.114 | 28.462 | 43.010 | 1.00 20.49 | AAAA |
| ATOM | 805 | CD2 | PHE | A | 100 | 42.785 | 30.050 | 42.373 | 1.00 19.82 | AAAA |
| ATOM | 806 | CE1 | PHE | A | 100 | 42.090 | 27.695 | 43.646 | 1.00 19.54 | AAAA |
| ATOM | 807 | CE2 | PHE | A | 100 | 43.755 | 29.300 | 43.001 | 1.00 19.22 | AAAA |
| ATOM | 808 | CZ | PHE | A | 100 | 43.410 | 28.122 | 43.641 | 1.00 19.47 | AAAA |
| ATOM | 809 | C | PHE | A | 100 | 40.649 | 32.161 | 43.743 | 1.00 21.37 | AAAA |
| ATOM | 810 | O | PHE | A | 100 | 40.959 | 31.822 | 44.887 | 1.00 21.26 | AAAA |
| ATOM | 811 | N | THR | A | 101 | 41.142 | 33.252 | 43.161 | 1.00 20.94 | AAAA |
| ATOM | 812 | CA | THR | A | 101 | 42.119 | 34.097 | 43.847 | 1.00 21.95 | AAAA |
| ATOM | 813 | CB | THR | A | 101 | 42.691 | 35.181 | 42.905 | 1.00 22.21 | AAAA |
| ATOM | 814 | OG1 | THR | A | 101 | 43.511 | 34.552 | 41.917 | 1.00 22.90 | AAAA |
| ATOM | 815 | CG2 | THR | A | 101 | 43.535 | 36.186 | 43.667 | 1.00 21.38 | AAAA |
| ATOM | 816 | C | THR | A | 101 | 41.584 | 34.755 | 45.117 | 1.00 22.60 | AAAA |
| ATOM | 817 | O | THR | A | 101 | 42.248 | 34.723 | 46.147 | 1.00 23.38 | AAAA |
| ATOM | 818 | N | GLY | A | 102 | 40.394 | 35.343 | 45.049 | 1.00 22.13 | AAAA |
| ATOM | 819 | CA | GLY | A | 102 | 39.826 | 35.972 | 46.227 | 1.00 22.03 | AAAA |
| ATOM | 820 | C | GLY | A | 102 | 39.340 | 34.928 | 47.221 | 1.00 21.36 | AAAA |
| ATOM | 821 | O | GLY | A | 102 | 39.433 | 35.104 | 48.439 | 1.00 20.02 | AAAA |
| ATOM | 822 | N | SER | A | 103 | 38.816 | 33.833 | 46.677 | 1.00 21.86 | AAAA |
| ATOM | 823 | CA | SER | A | 103 | 38.311 | 32.719 | 47.466 | 1.00 21.68 | AAAA |
| ATOM | 824 | CB | SER | A | 103 | 37.699 | 31.668 | 46.557 | 1.00 21.56 | AAAA |
| ATOM | 825 | OG | SER | A | 103 | 36.604 | 32.216 | 45.857 | 1.00 23.67 | AAAA |
| ATOM | 826 | C | SER | A | 103 | 39.450 | 32.098 | 48.229 | 1.00 22.67 | AAAA |
| ATOM | 827 | O | SER | A | 103 | 39.314 | 31.806 | 49.412 | 1.00 22.44 | AAAA |
| ATOM | 828 | N | SER | A | 104 | 40.578 | 31.898 | 47.545 | 1.00 23.37 | AAAA |
| ATOM | 829 | CA | SER | A | 104 | 41.746 | 31.305 | 48.183 | 1.00 23.50 | AAAA |
| ATOM | 830 | CB | SER | A | 104 | 42.862 | 31.070 | 47.172 | 1.00 24.80 | AAAA |
| ATOM | 831 | OG | SER | A | 104 | 42.441 | 30.169 | 46.175 | 1.00 28.38 | AAAA |
| ATOM | 832 | C | SER | A | 104 | 42.254 | 32.230 | 49.256 | 1.00 22.79 | AAAA |
| ATOM | 833 | O | SER | A | 104 | 42.707 | 31.794 | 50.307 | 1.00 22.66 | AAAA |
| ATOM | 834 | N | LEU | A | 105 | 42.160 | 33.518 | 48.970 | 1.00 22.08 | AAAA |
| ATOM | 835 | CA | LEU | A | 105 | 42.626 | 34.541 | 49.870 | 1.00 21.70 | AAAA |
| ATOM | 836 | CB | LEU | A | 105 | 42.524 | 35.882 | 49.159 | 1.00 21.89 | AAAA |
| ATOM | 837 | CG | LEU | A | 105 | 43.332 | 37.038 | 49.718 | 1.00 23.64 | AAAA |
| ATOM | 838 | CD1 | LEU | A | 105 | 44.830 | 36.692 | 49.639 | 1.00 22.01 | AAAA |
| ATOM | 839 | CD2 | LEU | A | 105 | 43.004 | 38.304 | 48.919 | 1.00 23.60 | AAAA |
| ATOM | 840 | C | LEU | A | 105 | 41.767 | 34.525 | 51.131 | 1.00 22.29 | AAAA |
| ATOM | 841 | O | LEU | A | 105 | 42.277 | 34.595 | 52.249 | 1.00 21.95 | AAAA |
| ATOM | 842 | N | ALA | A | 106 | 40.458 | 34.429 | 50.934 | 1.00 22.23 | AAAA |
| ATOM | 843 | CA | ALA | A | 106 | 39.515 | 34.394 | 52.042 | 1.00 22.32 | AAAA |
| ATOM | 844 | CB | ALA | A | 106 | 38.068 | 34.472 | 51.526 | 1.00 22.05 | AAAA |
| ATOM | 845 | C | ALA | A | 106 | 39.704 | 33.126 | 52.840 | 1.00 21.99 | AAAA |
| ATOM | 846 | O | ALA | A | 106 | 39.578 | 33.145 | 54.061 | 1.00 23.18 | AAAA |
| ATOM | 847 | N | THR | A | 107 | 40.011 | 32.032 | 52.144 | 1.00 21.24 | AAAA |
| ATOM | 848 | CA | THR | A | 107 | 40.209 | 30.732 | 52.779 | 1.00 20.60 | AAAA |
| ATOM | 849 | CB | THR | A | 107 | 40.170 | 29.571 | 51.749 | 1.00 19.82 | AAAA |
| ATOM | 850 | CG1 | THR | A | 107 | 38.903 | 29.553 | 51.083 | 1.00 18.56 | AAAA |
| ATOM | 851 | CG2 | THR | A | 107 | 40.360 | 28.242 | 52.455 | 1.00 18.58 | AAAA |
| ATOM | 852 | C | THR | A | 107 | 41.516 | 30.630 | 53.561 | 1.00 21.41 | AAAA |
| ATOM | 853 | O | THR | A | 107 | 41.537 | 30.040 | 54.646 | 1.00 23.16 | AAAA |
| ATOM | 854 | N | GLY | A | 108 | 42.601 | 31.176 | 53.003 | 1.00 20.14 | AAAA |
| ATOM | 855 | CA | GLY | A | 108 | 43.878 | 31.145 | 53.684 | 1.00 18.20 | AAAA |
| ATOM | 856 | C | GLY | A | 108 | 43.739 | 31.933 | 54.972 | 1.00 18.43 | AAAA |
| ATOM | 857 | O | GLY | A | 108 | 44.335 | 31.600 | 55.998 | 1.00 17.52 | AAAA |
| ATOM | 858 | N | SER | A | 109 | 42.909 | 32.969 | 54.929 | 1.00 18.56 | AAAA |

Fig. 19-13

| | | | | | | | | | | |
|---|---|---|---|---|---|---|---|---|---|---|
| ATOM | 859 | CA | SER | A | 109 | 42.683 | 33.805 | 56.098 | 1.00 19.67 | AAAA |
| ATOM | 860 | CB | SER | A | 109 | 41.899 | 35.058 | 55.707 | 1.00 20.27 | AAAA |
| ATOM | 861 | OG | SER | A | 109 | 42.618 | 35.803 | 54.746 | 1.00 21.80 | AAAA |
| ATOM | 862 | C | SER | A | 109 | 41.955 | 33.066 | 57.219 | 1.00 19.61 | AAAA |
| ATOM | 863 | O | SER | A | 109 | 42.078 | 33.426 | 58.388 | 1.00 18.40 | AAAA |
| ATOM | 864 | N | THR | A | 110 | 41.186 | 32.042 | 56.866 | 1.00 19.88 | AAAA |
| ATOM | 865 | CA | THR | A | 110 | 40.493 | 31.288 | 57.891 | 1.00 20.51 | AAAA |
| ATOM | 866 | CB | THR | A | 110 | 39.365 | 30.438 | 57.304 | 1.00 20.62 | AAAA |
| ATOM | 867 | OG1 | THR | A | 110 | 38.236 | 31.284 | 57.050 | 1.00 20.80 | AAAA |
| ATOM | 868 | CG2 | THR | A | 110 | 38.974 | 29.313 | 58.262 | 1.00 20.53 | AAAA |
| ATOM | 869 | C | THR | A | 110 | 41.504 | 30.420 | 58.601 | 1.00 20.36 | AAAA |
| ATOM | 870 | O | THR | A | 110 | 41.455 | 30.268 | 59.822 | 1.00 20.78 | AAAA |
| ATOM | 871 | N | VAL | A | 111 | 42.431 | 29.855 | 57.832 | 1.00 20.85 | AAAA |
| ATOM | 872 | CA | VAL | A | 111 | 43.480 | 29.053 | 58.423 | 1.00 21.03 | AAAA |
| ATOM | 873 | CB | VAL | A | 111 | 44.318 | 28.323 | 57.345 | 1.00 21.05 | AAAA |
| ATOM | 874 | CG1 | VAL | A | 111 | 45.537 | 27.644 | 57.983 | 1.00 19.91 | AAAA |
| ATOM | 875 | CG2 | VAL | A | 111 | 43.460 | 27.281 | 56.648 | 1.00 18.39 | AAAA |
| ATOM | 876 | C | VAL | A | 111 | 44.374 | 30.005 | 59.232 | 1.00 21.84 | AAAA |
| ATOM | 877 | O | VAL | A | 111 | 44.825 | 29.671 | 60.331 | 1.00 22.73 | AAAA |
| ATOM | 878 | N | GLN | A | 112 | 44.612 | 31.204 | 58.712 | 1.00 21.62 | AAAA |
| ATOM | 879 | CA | GLN | A | 112 | 45.449 | 32.133 | 59.452 | 1.00 21.89 | AAAA |
| ATOM | 880 | CB | GLN | A | 112 | 45.630 | 33.450 | 58.690 | 1.00 22.50 | AAAA |
| ATOM | 881 | CG | GLN | A | 112 | 46.288 | 33.283 | 57.335 | 1.00 23.68 | AAAA |
| ATOM | 882 | CD | GLN | A | 112 | 46.414 | 34.578 | 56.569 | 1.00 23.18 | AAAA |
| ATOM | 883 | OE1 | GLN | A | 112 | 47.389 | 35.310 | 56.722 | 1.00 23.86 | AAAA |
| ATOM | 884 | NE2 | GLN | A | 112 | 45.413 | 34.879 | 55.752 | 1.00 21.90 | AAAA |
| ATOM | 885 | C | GLN | A | 112 | 44.766 | 32.383 | 60.774 | 1.00 21.84 | AAAA |
| ATOM | 886 | O | GLN | A | 112 | 45.389 | 32.316 | 61.835 | 1.00 22.47 | AAAA |
| ATOM | 887 | N | ALA | A | 113 | 43.468 | 32.651 | 60.700 | 1.00 21.34 | AAAA |
| ATOM | 888 | CA | ALA | A | 113 | 42.682 | 32.934 | 61.884 | 1.00 20.84 | AAAA |
| ATOM | 889 | CB | ALA | A | 113 | 41.244 | 33.172 | 61.504 | 1.00 18.52 | AAAA |
| ATOM | 890 | C | ALA | A | 113 | 42.795 | 31.782 | 62.865 | 1.00 21.75 | AAAA |
| ATOM | 891 | O | ALA | A | 113 | 42.880 | 31.985 | 64.084 | 1.00 22.24 | AAAA |
| ATOM | 892 | N | ILE | A | 114 | 42.797 | 30.569 | 62.329 | 1.00 22.54 | AAAA |
| ATOM | 893 | CA | ILE | A | 114 | 42.891 | 29.393 | 63.160 | 1.00 23.16 | AAAA |
| ATOM | 894 | CB | ILE | A | 114 | 42.557 | 28.146 | 62.352 | 1.00 23.33 | AAAA |
| ATOM | 895 | CG2 | ILE | A | 114 | 42.939 | 26.912 | 63.106 | 1.00 23.80 | AAAA |
| ATOM | 896 | CG1 | ILE | A | 114 | 41.058 | 28.130 | 62.047 | 1.00 23.48 | AAAA |
| ATOM | 897 | CD1 | ILE | A | 114 | 40.610 | 26.951 | 61.204 | 1.00 22.08 | AAAA |
| ATOM | 898 | C | ILE | A | 114 | 44.268 | 29.270 | 63.792 | 1.00 24.33 | AAAA |
| ATOM | 899 | O | ILE | A | 114 | 44.373 | 29.013 | 64.990 | 1.00 25.30 | AAAA |
| ATOM | 900 | N | GLU | A | 115 | 45.319 | 29.490 | 63.002 | 1.00 24.96 | AAAA |
| ATOM | 901 | CA | GLU | A | 115 | 46.699 | 29.395 | 63.503 | 1.00 26.61 | AAAA |
| ATOM | 902 | CB | GLU | A | 115 | 47.708 | 29.753 | 62.406 | 1.00 24.75 | AAAA |
| ATOM | 903 | CG | GLU | A | 115 | 47.444 | 29.033 | 61.103 | 1.00 25.80 | AAAA |
| ATOM | 904 | CD | GLU | A | 115 | 48.471 | 29.323 | 60.030 | 1.00 26.07 | AAAA |
| ATOM | 905 | OE1 | GLU | A | 115 | 48.911 | 30.484 | 59.940 | 1.00 27.15 | AAAA |
| ATOM | 906 | OE2 | GLU | A | 115 | 48.819 | 28.402 | 59.260 | 1.00 25.45 | AAAA |
| ATOM | 907 | C | GLU | A | 115 | 46.877 | 30.340 | 64.680 | 1.00 27.89 | AAAA |
| ATOM | 908 | O | GLU | A | 115 | 47.480 | 29.975 | 65.695 | 1.00 28.04 | AAAA |
| ATOM | 909 | N | GLU | A | 116 | 46.337 | 31.552 | 64.531 | 1.00 29.15 | AAAA |
| ATOM | 910 | CA | GLU | A | 116 | 46.408 | 32.579 | 65.563 | 1.00 29.42 | AAAA |
| ATOM | 911 | CB | GLU | A | 116 | 45.751 | 33.871 | 65.082 | 1.00 28.26 | AAAA |
| ATOM | 912 | CG | GLU | A | 116 | 46.482 | 34.529 | 63.945 | 1.00 28.93 | AAAA |
| ATOM | 913 | CD | GLU | A | 116 | 47.902 | 34.937 | 64.318 | 1.00 28.32 | AAAA |
| ATOM | 914 | OE1 | GLU | A | 116 | 48.081 | 35.878 | 65.123 | 1.00 27.68 | AAAA |
| ATOM | 915 | OE2 | GLU | A | 116 | 48.838 | 34.297 | 63.810 | 1.00 27.38 | AAAA |
| ATOM | 916 | C | GLU | A | 116 | 45.737 | 32.126 | 66.845 | 1.00 29.77 | AAAA |
| ATOM | 917 | O | GLU | A | 116 | 46.338 | 32.196 | 67.920 | 1.00 30.29 | AAAA |
| ATOM | 918 | N | PHE | A | 117 | 44.492 | 31.665 | 66.727 | 1.00 29.64 | AAAA |
| ATOM | 919 | CA | PHE | A | 117 | 43.741 | 31.204 | 67.887 | 1.00 29.33 | AAAA |
| ATOM | 920 | CB | PHE | A | 117 | 42.425 | 30.552 | 67.480 | 1.00 28.89 | AAAA |
| ATOM | 921 | CG | PHE | A | 117 | 41.604 | 30.087 | 68.651 | 1.00 28.93 | AAAA |
| ATOM | 922 | CD1 | PHE | A | 117 | 41.010 | 31.010 | 69.510 | 1.00 28.42 | AAAA |
| ATOM | 923 | CD2 | PHE | A | 117 | 41.441 | 28.723 | 68.910 | 1.00 29.06 | AAAA |
| ATOM | 924 | CE1 | PHE | A | 117 | 40.261 | 30.588 | 70.610 | 1.00 28.68 | AAAA |

Fig. 19-14

```
ATOM    925  CE2 PHE A 117      40.695  28.284  70.009  1.00 29.16      AAAA
ATOM    926  CZ  PHE A 117      40.103  29.227  70.862  1.00 29.03      AAAA
ATOM    927  C   PHE A 117      44.545  30.195  68.671  1.00 29.22      AAAA
ATOM    928  O   PHE A 117      44.677  30.315  69.884  1.00 30.29      AAAA
ATOM    929  N   LEU A 118      45.066  29.195  67.965  1.00 29.24      AAAA
ATOM    930  CA  LEU A 118      45.864  28.145  68.576  1.00 29.50      AAAA
ATOM    931  CB  LEU A 118      46.182  27.047  67.550  1.00 28.57      AAAA
ATOM    932  CG  LEU A 118      44.962  26.296  66.989  1.00 28.16      AAAA
ATOM    933  CD1 LEU A 118      45.421  25.090  66.191  1.00 25.58      AAAA
ATOM    934  CD2 LEU A 118      44.053  25.846  68.128  1.00 27.64      AAAA
ATOM    935  C   LEU A 118      47.150  28.649  69.227  1.00 30.14      AAAA
ATOM    936  O   LEU A 118      47.727  27.954  70.056  1.00 29.94      AAAA
ATOM    937  N   LYS A 119      47.602  29.845  68.847  1.00 31.36      AAAA
ATOM    938  CA  LYS A 119      48.798  30.451  69.448  1.00 32.52      AAAA
ATOM    939  CB  LYS A 119      49.396  31.539  68.559  1.00 32.38      AAAA
ATOM    940  CG  LYS A 119      49.882  31.108  67.199  1.00 33.03      AAAA
ATOM    941  CD  LYS A 119      50.371  32.321  66.411  1.00 32.74      AAAA
ATOM    942  CE  LYS A 119      50.681  31.939  64.972  1.00 33.94      AAAA
ATOM    943  NZ  LYS A 119      51.125  33.099  64.152  1.00 34.93      AAAA
ATOM    944  C   LYS A 119      48.385  31.143  70.744  1.00 33.74      AAAA
ATOM    945  O   LYS A 119      49.218  31.748  71.413  1.00 34.85      AAAA
ATOM    946  N   GLY A 120      47.096  31.079  71.073  1.00 33.68      AAAA
ATOM    947  CA  GLY A 120      46.600  31.736  72.263  1.00 33.69      AAAA
ATOM    948  C   GLY A 120      45.987  33.110  71.988  1.00 34.11      AAAA
ATOM    949  O   GLY A 120      45.588  33.802  72.932  1.00 33.65      AAAA
ATOM    950  N   ASN A 121      45.904  33.513  70.717  1.00 33.58      AAAA
ATOM    951  CA  ASN A 121      45.326  34.820  70.368  1.00 33.35      AAAA
ATOM    952  CB  ASN A 121      46.194  35.537  69.341  1.00 33.18      AAAA
ATOM    953  CG  ASN A 121      47.570  35.828  69.859  1.00 34.31      AAAA
ATOM    954  OD1 ASN A 121      48.333  34.921  70.154  1.00 35.67      AAAA
ATOM    955  ND2 ASN A 121      47.897  37.096  69.975  1.00 34.18      AAAA
ATOM    956  C   ASN A 121      43.888  34.805  69.839  1.00 32.85      AAAA
ATOM    957  O   ASN A 121      43.304  33.751  69.599  1.00 32.78      AAAA
ATOM    958  N   VAL A 122      43.338  36.003  69.655  1.00 32.47      AAAA
ATOM    959  CA  VAL A 122      41.980  36.200  69.148  1.00 30.89      AAAA
ATOM    960  CB  VAL A 122      41.182  37.145  70.070  1.00 31.05      AAAA
ATOM    961  CG1 VAL A 122      39.831  37.423  69.489  1.00 30.95      AAAA
ATOM    962  CG2 VAL A 122      41.038  36.516  71.440  1.00 31.19      AAAA
ATOM    963  C   VAL A 122      42.056  36.805  67.750  1.00 30.19      AAAA
ATOM    964  O   VAL A 122      42.694  37.840  67.535  1.00 31.28      AAAA
ATOM    965  N   ALA A 123      41.405  36.147  66.800  1.00 28.62      AAAA
ATOM    966  CA  ALA A 123      41.415  36.589  65.421  1.00 26.49      AAAA
ATOM    967  CB  ALA A 123      42.323  35.708  64.599  1.00 26.51      AAAA
ATOM    968  C   ALA A 123      40.038  36.570  64.836  1.00 25.59      AAAA
ATOM    969  O   ALA A 123      39.173  35.814  65.252  1.00 26.27      AAAA
ATOM    970  N   PHE A 124      39.848  37.421  63.847  1.00 25.44      AAAA
ATOM    971  CA  PHE A 124      38.590  37.534  63.156  1.00 23.87      AAAA
ATOM    972  CB  PHE A 124      37.832  38.779  63.646  1.00 23.58      AAAA
ATOM    973  CG  PHE A 124      36.591  39.119  62.841  1.00 23.71      AAAA
ATOM    974  CD1 PHE A 124      35.668  38.140  62.495  1.00 23.44      AAAA
ATOM    975  CD2 PHE A 124      36.311  40.449  62.498  1.00 23.75      AAAA
ATOM    976  CE1 PHE A 124      34.479  38.483  61.823  1.00 23.31      AAAA
ATOM    977  CE2 PHE A 124      35.131  40.796  61.833  1.00 21.71      AAAA
ATOM    978  CZ  PHE A 124      34.217  39.815  61.497  1.00 22.35      AAAA
ATOM    979  C   PHE A 124      38.951  37.673  61.700  1.00 23.26      AAAA
ATOM    980  O   PHE A 124      39.720  38.555  61.323  1.00 22.29      AAAA
ATOM    981  N   ASN A 125      38.427  36.759  60.897  1.00 23.24      AAAA
ATOM    982  CA  ASN A 125      38.622  36.785  59.457  1.00 21.08      AAAA
ATOM    983  CB  ASN A 125      39.181  35.470  58.951  1.00 19.90      AAAA
ATOM    984  CG  ASN A 125      39.098  35.360  57.454  1.00 20.64      AAAA
ATOM    985  OD1 ASN A 125      39.389  36.317  56.748  1.00 21.63      AAAA
ATOM    986  ND2 ASN A 125      38.721  34.190  56.956  1.00 19.93      AAAA
ATOM    987  C   ASN A 125      37.269  37.059  58.813  1.00 20.19      AAAA
ATOM    988  O   ASN A 125      36.469  36.148  58.579  1.00 19.21      AAAA
ATOM    989  N   PRO A 126      36.991  38.340  58.543  1.00 19.14      AAAA
ATOM    990  CD  PRO A 126      37.893  39.460  58.858  1.00 19.22      AAAA
```

Fig. 19-15

| | | | | | | | | | |
|---|---|---|---|---|---|---|---|---|---|
| ATOM | 991 | CA | PRO | A | 126 | 35.766 | 38.849 | 57.932 | 1.00 19.52 | AAAA |
| ATOM | 992 | CB | PRO | A | 126 | 36.005 | 40.359 | 57.941 | 1.00 18.55 | AAAA |
| ATOM | 993 | CG | PRO | A | 126 | 37.511 | 40.465 | 57.799 | 1.00 17.97 | AAAA |
| ATOM | 994 | C | PRO | A | 126 | 35.456 | 38.313 | 56.526 | 1.00 19.41 | AAAA |
| ATOM | 995 | O | PRO | A | 126 | 34.303 | 38.349 | 56.080 | 1.00 19.68 | AAAA |
| ATOM | 996 | N | ALA | A | 127 | 36.477 | 37.814 | 55.835 | 1.00 18.17 | AAAA |
| ATOM | 997 | CA | ALA | A | 127 | 36.283 | 37.314 | 54.481 | 1.00 17.66 | AAAA |
| ATOM | 998 | CB | ALA | A | 127 | 37.547 | 37.520 | 53.658 | 1.00 17.08 | AAAA |
| ATOM | 999 | C | ALA | A | 127 | 35.875 | 35.857 | 54.443 | 1.00 17.46 | AAAA |
| ATOM | 1000 | O | ALA | A | 127 | 35.438 | 35.359 | 53.409 | 1.00 18.92 | AAAA |
| ATOM | 1001 | N | GLY | A | 128 | 36.019 | 35.180 | 55.570 | 1.00 15.94 | AAAA |
| ATOM | 1002 | CA | GLY | A | 128 | 35.685 | 33.780 | 55.642 | 1.00 15.45 | AAAA |
| ATOM | 1003 | C | GLY | A | 128 | 34.226 | 33.593 | 55.955 | 1.00 16.08 | AAAA |
| ATOM | 1004 | O | GLY | A | 128 | 33.485 | 34.557 | 55.997 | 1.00 15.43 | AAAA |
| ATOM | 1005 | N | GLY | A | 129 | 33.821 | 32.353 | 56.198 | 1.00 16.77 | AAAA |
| ATOM | 1006 | CA | GLY | A | 129 | 32.426 | 32.082 | 56.462 | 1.00 17.82 | AAAA |
| ATOM | 1007 | C | GLY | A | 129 | 31.669 | 31.822 | 55.169 | 1.00 18.64 | AAAA |
| ATOM | 1008 | O | GLY | A | 129 | 30.469 | 32.051 | 55.108 | 1.00 18.48 | AAAA |
| ATOM | 1009 | N | MET | A | 130 | 32.380 | 31.368 | 54.137 | 1.00 20.45 | AAAA |
| ATOM | 1010 | CA | MET | A | 130 | 31.790 | 31.029 | 52.826 | 1.00 21.60 | AAAA |
| ATOM | 1011 | CB | MET | A | 130 | 32.866 | 31.117 | 51.744 | 1.00 22.02 | AAAA |
| ATOM | 1012 | CG | MET | A | 130 | 33.551 | 32.472 | 51.698 | 1.00 21.75 | AAAA |
| ATOM | 1013 | SD | MET | A | 130 | 34.971 | 32.567 | 50.599 | 1.00 24.75 | AAAA |
| ATOM | 1014 | CE | MET | A | 130 | 34.268 | 32.137 | 49.048 | 1.00 24.40 | AAAA |
| ATOM | 1015 | C | MET | A | 130 | 31.328 | 29.587 | 53.002 | 1.00 22.08 | AAAA |
| ATOM | 1016 | O | MET | A | 130 | 31.970 | 28.641 | 52.546 | 1.00 22.98 | AAAA |
| ATOM | 1017 | N | HIS | A | 131 | 30.184 | 29.452 | 53.659 | 1.00 22.25 | AAAA |
| ATOM | 1018 | CA | HIS | A | 131 | 29.618 | 28.171 | 54.062 | 1.00 20.49 | AAAA |
| ATOM | 1019 | CB | HIS | A | 131 | 28.832 | 28.421 | 55.342 | 1.00 20.00 | AAAA |
| ATOM | 1020 | CG | HIS | A | 131 | 27.679 | 29.360 | 55.161 | 1.00 17.93 | AAAA |
| ATOM | 1021 | CD2 | HIS | A | 131 | 27.091 | 29.846 | 54.043 | 1.00 17.88 | AAAA |
| ATOM | 1022 | ND1 | HIS | A | 131 | 26.952 | 29.854 | 56.219 | 1.00 19.33 | AAAA |
| ATOM | 1023 | CE1 | HIS | A | 131 | 25.968 | 30.607 | 55.758 | 1.00 16.99 | AAAA |
| ATOM | 1024 | NE2 | HIS | A | 131 | 26.031 | 30.617 | 54.441 | 1.00 17.43 | AAAA |
| ATOM | 1025 | C | HIS | A | 131 | 28.763 | 27.332 | 53.141 | 1.00 19.97 | AAAA |
| ATOM | 1026 | O | HIS | A | 131 | 28.330 | 26.262 | 53.541 | 1.00 19.61 | AAAA |
| ATOM | 1027 | N | HIS | A | 132 | 28.518 | 27.796 | 51.923 | 1.00 20.11 | AAAA |
| ATOM | 1028 | CA | HIS | A | 132 | 27.673 | 27.058 | 50.994 | 1.00 17.76 | AAAA |
| ATOM | 1029 | CB | HIS | A | 132 | 26.879 | 28.044 | 50.127 | 1.00 16.76 | AAAA |
| ATOM | 1030 | CG | HIS | A | 132 | 25.824 | 28.815 | 50.862 | 1.00 15.35 | AAAA |
| ATOM | 1031 | CD2 | HIS | A | 132 | 25.567 | 30.146 | 50.920 | 1.00 14.15 | AAAA |
| ATOM | 1032 | ND1 | HIS | A | 132 | 24.804 | 28.200 | 51.557 | 1.00 16.15 | AAAA |
| ATOM | 1033 | CE1 | HIS | A | 132 | 23.966 | 29.119 | 52.005 | 1.00 14.13 | AAAA |
| ATOM | 1034 | NE2 | HIS | A | 132 | 24.405 | 30.307 | 51.632 | 1.00 14.65 | AAAA |
| ATOM | 1035 | C | HIS | A | 132 | 28.355 | 26.051 | 50.065 | 1.00 17.99 | AAAA |
| ATOM | 1036 | O | HIS | A | 132 | 27.742 | 25.053 | 49.684 | 1.00 18.54 | AAAA |
| ATOM | 1037 | N | ALA | A | 133 | 29.604 | 26.305 | 49.690 | 1.00 17.82 | AAAA |
| ATOM | 1038 | CA | ALA | A | 133 | 30.300 | 25.441 | 48.742 | 1.00 18.38 | AAAA |
| ATOM | 1039 | CB | ALA | A | 133 | 31.684 | 25.961 | 48.507 | 1.00 17.53 | AAAA |
| ATOM | 1040 | C | ALA | A | 133 | 30.366 | 23.970 | 49.130 | 1.00 20.92 | AAAA |
| ATOM | 1041 | O | ALA | A | 133 | 30.578 | 23.633 | 50.298 | 1.00 21.79 | AAAA |
| ATOM | 1042 | N | PHE | A | 134 | 30.184 | 23.086 | 48.152 | 1.00 20.58 | AAAA |
| ATOM | 1043 | CA | PHE | A | 134 | 30.258 | 21.663 | 48.455 | 1.00 21.38 | AAAA |
| ATOM | 1044 | CB | PHE | A | 134 | 29.168 | 20.860 | 47.731 | 1.00 19.41 | AAAA |
| ATOM | 1045 | CG | PHE | A | 134 | 27.772 | 21.229 | 48.126 | 1.00 18.32 | AAAA |
| ATOM | 1046 | CD1 | PHE | A | 134 | 27.027 | 22.099 | 47.357 | 1.00 19.22 | AAAA |
| ATOM | 1047 | CD2 | PHE | A | 134 | 27.193 | 20.701 | 49.271 | 1.00 19.14 | AAAA |
| ATOM | 1048 | CE1 | PHE | A | 134 | 25.714 | 22.438 | 47.726 | 1.00 18.56 | AAAA |
| ATOM | 1049 | CE2 | PHE | A | 134 | 25.889 | 21.036 | 49.644 | 1.00 17.72 | AAAA |
| ATOM | 1050 | CZ | PHE | A | 134 | 25.158 | 21.903 | 48.866 | 1.00 18.01 | AAAA |
| ATOM | 1051 | C | PHE | A | 134 | 31.625 | 21.124 | 48.081 | 1.00 22.90 | AAAA |
| ATOM | 1052 | O | PHE | A | 134 | 32.459 | 21.833 | 47.544 | 1.00 23.37 | AAAA |
| ATOM | 1053 | N | LYS | A | 135 | 31.842 | 19.861 | 48.390 | 1.00 24.63 | AAAA |
| ATOM | 1054 | CA | LYS | A | 135 | 33.095 | 19.195 | 48.122 | 1.00 27.16 | AAAA |
| ATOM | 1055 | CB | LYS | A | 135 | 32.926 | 17.714 | 48.480 | 1.00 28.53 | AAAA |
| ATOM | 1056 | CG | LYS | A | 135 | 34.133 | 16.843 | 48.292 | 1.00 31.01 | AAAA |

Fig. 19-16

| | | | | | | | | | | |
|---|---|---|---|---|---|---|---|---|---|---|
| ATOM | 1057 | CD | LYS | A | 135 | 33.879 | 15.472 | 48.910 | 1.00 32.75 | AAAA |
| ATOM | 1058 | CE | LYS | A | 135 | 33.961 | 15.495 | 50.457 | 1.00 33.96 | AAAA |
| ATOM | 1059 | NZ | LYS | A | 135 | 35.371 | 15.664 | 50.976 | 1.00 33.04 | AAAA |
| ATOM | 1060 | C | LYS | A | 135 | 33.577 | 19.390 | 46.673 | 1.00 27.37 | AAAA |
| ATOM | 1061 | O | LYS | A | 135 | 34.769 | 19.596 | 46.437 | 1.00 27.35 | AAAA |
| ATOM | 1062 | N | SER | A | 136 | 32.658 | 19.354 | 45.714 | 1.00 27.32 | AAAA |
| ATOM | 1063 | CA | SER | A | 136 | 33.028 | 19.527 | 44.313 | 1.00 28.31 | AAAA |
| ATOM | 1064 | CB | SER | A | 136 | 33.093 | 18.162 | 43.626 | 1.00 28.56 | AAAA |
| ATOM | 1065 | OG | SER | A | 136 | 33.822 | 17.242 | 44.417 | 1.00 29.28 | AAAA |
| ATOM | 1066 | C | SER | A | 136 | 31.993 | 20.395 | 43.599 | 1.00 28.91 | AAAA |
| ATOM | 1067 | O | SER | A | 136 | 31.568 | 20.080 | 42.486 | 1.00 28.78 | AAAA |
| ATOM | 1068 | N | ARG | A | 137 | 31.595 | 21.502 | 44.212 | 1.00 29.08 | AAAA |
| ATOM | 1069 | CA | ARG | A | 137 | 30.574 | 22.311 | 43.576 | 1.00 29.66 | AAAA |
| ATOM | 1070 | CB | ARG | A | 137 | 29.259 | 21.528 | 43.657 | 1.00 31.65 | AAAA |
| ATOM | 1071 | CG | ARG | A | 137 | 27.989 | 22.273 | 43.355 | 1.00 33.89 | AAAA |
| ATOM | 1072 | CD | ARG | A | 137 | 26.862 | 21.267 | 43.373 | 1.00 35.93 | AAAA |
| ATOM | 1073 | NE | ARG | A | 137 | 26.961 | 20.366 | 42.228 | 1.00 36.31 | AAAA |
| ATOM | 1074 | CZ | ARG | A | 137 | 26.505 | 20.660 | 41.015 | 1.00 35.99 | AAAA |
| ATOM | 1075 | NH1 | ARG | A | 137 | 25.915 | 21.834 | 40.798 | 1.00 34.63 | AAAA |
| ATOM | 1076 | NH2 | ARG | A | 137 | 26.650 | 19.786 | 40.025 | 1.00 35.35 | AAAA |
| ATOM | 1077 | C | ARG | A | 137 | 30.402 | 23.723 | 44.116 | 1.00 28.53 | AAAA |
| ATOM | 1078 | O | ARG | A | 137 | 30.418 | 23.946 | 45.324 | 1.00 28.51 | AAAA |
| ATOM | 1079 | N | ALA | A | 138 | 30.247 | 24.673 | 43.202 | 1.00 27.53 | AAAA |
| ATOM | 1080 | CA | ALA | A | 138 | 30.039 | 26.063 | 43.581 | 1.00 27.64 | AAAA |
| ATOM | 1081 | CB | ALA | A | 138 | 30.236 | 26.984 | 42.381 | 1.00 27.87 | AAAA |
| ATOM | 1082 | C | ALA | A | 138 | 28.601 | 26.130 | 44.079 | 1.00 27.27 | AAAA |
| ATOM | 1083 | O | ALA | A | 138 | 27.769 | 25.321 | 43.671 | 1.00 28.30 | AAAA |
| ATOM | 1084 | N | ASN | A | 139 | 28.292 | 27.080 | 44.951 | 1.00 26.16 | AAAA |
| ATOM | 1085 | CA | ASN | A | 139 | 26.945 | 27.134 | 45.480 | 1.00 25.39 | AAAA |
| ATOM | 1086 | CB | ASN | A | 139 | 26.673 | 25.847 | 46.282 | 1.00 24.58 | AAAA |
| ATOM | 1087 | CG | ASN | A | 139 | 25.343 | 25.872 | 47.017 | 1.00 25.37 | AAAA |
| ATOM | 1088 | OD1 | ASN | A | 139 | 24.272 | 26.017 | 46.413 | 1.00 24.20 | AAAA |
| ATOM | 1089 | ND2 | ASN | A | 139 | 25.408 | 25.720 | 48.338 | 1.00 24.91 | AAAA |
| ATOM | 1090 | C | ASN | A | 139 | 26.683 | 28.358 | 46.341 | 1.00 24.90 | AAAA |
| ATOM | 1091 | O | ASN | A | 139 | 27.346 | 28.570 | 47.348 | 1.00 24.98 | AAAA |
| ATOM | 1092 | N | GLY | A | 140 | 25.702 | 29.145 | 45.916 | 1.00 24.46 | AAAA |
| ATOM | 1093 | CA | GLY | A | 140 | 25.294 | 30.336 | 46.625 | 1.00 22.96 | AAAA |
| ATOM | 1094 | C | GLY | A | 140 | 26.383 | 31.358 | 46.755 | 1.00 22.24 | AAAA |
| ATOM | 1095 | O | GLY | A | 140 | 26.663 | 31.817 | 47.867 | 1.00 23.09 | AAAA |
| ATOM | 1096 | N | PHE | A | 141 | 26.992 | 31.711 | 45.625 | 1.00 20.60 | AAAA |
| ATOM | 1097 | CA | PHE | A | 141 | 28.075 | 32.700 | 45.572 | 1.00 19.43 | AAAA |
| ATOM | 1098 | CB | PHE | A | 141 | 27.758 | 33.920 | 46.430 | 1.00 19.86 | AAAA |
| ATOM | 1099 | CG | PHE | A | 141 | 26.453 | 34.577 | 46.114 | 1.00 21.18 | AAAA |
| ATOM | 1100 | CD1 | PHE | A | 141 | 25.974 | 35.592 | 46.934 | 1.00 20.49 | AAAA |
| ATOM | 1101 | CD2 | PHE | A | 141 | 25.723 | 34.218 | 44.985 | 1.00 21.42 | AAAA |
| ATOM | 1102 | CE1 | PHE | A | 141 | 24.800 | 36.242 | 46.638 | 1.00 22.45 | AAAA |
| ATOM | 1103 | CE2 | PHE | A | 141 | 24.540 | 34.859 | 44.672 | 1.00 21.76 | AAAA |
| ATOM | 1104 | CZ | PHE | A | 141 | 24.072 | 35.881 | 45.499 | 1.00 23.05 | AAAA |
| ATOM | 1105 | C | PHE | A | 141 | 29.396 | 32.132 | 46.069 | 1.00 18.68 | AAAA |
| ATOM | 1106 | O | PHE | A | 141 | 30.438 | 32.784 | 45.944 | 1.00 19.19 | AAAA |
| ATOM | 1107 | N | CYS | A | 142 | 29.367 | 30.930 | 46.635 | 1.00 16.93 | AAAA |
| ATOM | 1108 | CA | CYS | A | 142 | 30.594 | 30.332 | 47.150 | 1.00 16.80 | AAAA |
| ATOM | 1109 | CB | CYS | A | 142 | 30.323 | 29.689 | 48.509 | 1.00 16.51 | AAAA |
| ATOM | 1110 | SG | CYS | A | 142 | 29.524 | 30.826 | 49.617 | 1.00 15.01 | AAAA |
| ATOM | 1111 | C | CYS | A | 142 | 31.227 | 29.315 | 46.221 | 1.00 16.45 | AAAA |
| ATOM | 1112 | O | CYS | A | 142 | 30.533 | 28.565 | 45.556 | 1.00 15.32 | AAAA |
| ATOM | 1113 | N | TYR | A | 143 | 32.558 | 29.311 | 46.190 | 1.00 18.39 | AAAA |
| ATOM | 1114 | CA | TYR | A | 143 | 33.340 | 28.394 | 45.362 | 1.00 18.63 | AAAA |
| ATOM | 1115 | CB | TYR | A | 143 | 34.298 | 29.154 | 44.438 | 1.00 19.48 | AAAA |
| ATOM | 1116 | CG | TYR | A | 143 | 33.664 | 30.214 | 43.571 | 1.00 19.55 | AAAA |
| ATOM | 1117 | CD1 | TYR | A | 143 | 33.480 | 31.510 | 44.043 | 1.00 20.27 | AAAA |
| ATOM | 1118 | CE1 | TYR | A | 143 | 32.856 | 32.473 | 43.261 | 1.00 21.63 | AAAA |
| ATOM | 1119 | CD2 | TYR | A | 143 | 33.212 | 29.910 | 42.292 | 1.00 20.14 | AAAA |
| ATOM | 1120 | CE2 | TYR | A | 143 | 32.588 | 30.863 | 41.507 | 1.00 20.82 | AAAA |
| ATOM | 1121 | CZ | TYR | A | 143 | 32.414 | 32.135 | 41.998 | 1.00 20.90 | AAAA |
| ATOM | 1122 | OH | TYR | A | 143 | 31.787 | 33.071 | 41.228 | 1.00 23.36 | AAAA |

Fig. 19-17

```
ATOM   1123  C    TYR A 143      34.162  27.490  46.283  1.00 19.06      AAAA
ATOM   1124  O    TYR A 143      34.319  26.289  46.032  1.00 18.40      AAAA
ATOM   1125  N    ILE A 144      34.695  28.087  47.344  1.00 19.15      AAAA
ATOM   1126  CA   ILE A 144      35.490  27.350  48.315  1.00 19.97      AAAA
ATOM   1127  CB   ILE A 144      36.952  27.861  48.355  1.00 19.74      AAAA
ATOM   1128  CG2  ILE A 144      37.757  27.088  49.410  1.00 18.03      AAAA
ATOM   1129  CG1  ILE A 144      37.584  27.671  46.965  1.00 20.12      AAAA
ATOM   1130  CD1  ILE A 144      39.053  28.072  46.846  1.00 21.05      AAAA
ATOM   1131  C    ILE A 144      34.833  27.532  49.665  1.00 20.22      AAAA
ATOM   1132  O    ILE A 144      34.357  28.626  49.981  1.00 19.94      AAAA
ATOM   1133  N    ASN A 145      34.787  26.451  50.440  1.00 20.57      AAAA
ATOM   1134  CA   ASN A 145      34.165  26.448  51.770  1.00 20.39      AAAA
ATOM   1135  CB   ASN A 145      33.450  25.114  51.990  1.00 19.39      AAAA
ATOM   1136  CG   ASN A 145      32.505  25.143  53.171  1.00 19.31      AAAA
ATOM   1137  OD1  ASN A 145      32.862  25.583  54.263  1.00 21.26      AAAA
ATOM   1138  ND2  ASN A 145      31.290  24.667  52.960  1.00 17.08      AAAA
ATOM   1139  C    ASN A 145      35.236  26.621  52.856  1.00 20.17      AAAA
ATOM   1140  O    ASN A 145      35.690  25.622  53.421  1.00 19.75      AAAA
ATOM   1141  N    ASN A 146      35.644  27.862  53.148  1.00 20.06      AAAA
ATOM   1142  CA   ASN A 146      36.671  28.075  54.166  1.00 20.98      AAAA
ATOM   1143  CB   ASN A 146      37.019  29.573  54.333  1.00 21.78      AAAA
ATOM   1144  CG   ASN A 146      35.876  30.411  54.882  1.00 22.78      AAAA
ATOM   1145  OD1  ASN A 146      35.651  30.465  56.091  1.00 22.83      AAAA
ATOM   1146  ND2  ASN A 146      35.144  31.078  53.983  1.00 23.70      AAAA
ATOM   1147  C    ASN A 146      36.307  27.413  55.496  1.00 21.18      AAAA
ATOM   1148  O    ASN A 146      37.169  26.823  56.139  1.00 21.48      AAAA
ATOM   1149  N    PRO A 147      35.031  27.476  55.922  1.00 20.88      AAAA
ATOM   1150  CD   PRO A 147      33.835  28.120  55.358  1.00 21.85      AAAA
ATOM   1151  CA   PRO A 147      34.674  26.831  57.183  1.00 21.42      AAAA
ATOM   1152  CB   PRO A 147      33.176  27.073  57.261  1.00 21.00      AAAA
ATOM   1153  CG   PRO A 147      33.052  28.408  56.605  1.00 20.47      AAAA
ATOM   1154  C    PRO A 147      35.015  25.334  57.174  1.00 22.79      AAAA
ATOM   1155  O    PRO A 147      35.650  24.833  58.099  1.00 25.69      AAAA
ATOM   1156  N    ALA A 148      34.603  24.616  56.136  1.00 22.34      AAAA
ATOM   1157  CA   ALA A 148      34.889  23.193  56.070  1.00 22.23      AAAA
ATOM   1158  CB   ALA A 148      34.260  22.561  54.825  1.00 22.87      AAAA
ATOM   1159  C    ALA A 148      36.378  22.998  56.054  1.00 22.33      AAAA
ATOM   1160  O    ALA A 148      36.912  22.249  56.861  1.00 23.42      AAAA
ATOM   1161  N    VAL A 149      37.050  23.661  55.122  1.00 22.50      AAAA
ATOM   1162  CA   VAL A 149      38.505  23.569  55.018  1.00 21.29      AAAA
ATOM   1163  CB   VAL A 149      39.066  24.581  54.002  1.00 20.46      AAAA
ATOM   1164  CG1  VAL A 149      40.578  24.607  54.085  1.00 19.36      AAAA
ATOM   1165  CG2  VAL A 149      38.608  24.229  52.593  1.00 20.03      AAAA
ATOM   1166  C    VAL A 149      39.164  23.848  56.367  1.00 21.48      AAAA
ATOM   1167  O    VAL A 149      40.147  23.197  56.735  1.00 22.11      AAAA
ATOM   1168  N    GLY A 150      38.628  24.826  57.088  1.00 21.19      AAAA
ATOM   1169  CA   GLY A 150      39.171  25.176  58.386  1.00 21.70      AAAA
ATOM   1170  C    GLY A 150      38.973  24.043  59.368  1.00 22.31      AAAA
ATOM   1171  O    GLY A 150      39.913  23.597  60.026  1.00 22.51      AAAA
ATOM   1172  N    ILE A 151      37.736  23.566  59.453  1.00 22.86      AAAA
ATOM   1173  CA   ILE A 151      37.388  22.474  60.346  1.00 22.26      AAAA
ATOM   1174  CB   ILE A 151      35.894  22.124  60.191  1.00 21.51      AAAA
ATOM   1175  CG2  ILE A 151      35.542  20.899  61.019  1.00 21.36      AAAA
ATOM   1176  CG1  ILE A 151      35.051  23.329  60.627  1.00 20.39      AAAA
ATOM   1177  CD1  ILE A 151      33.576  23.199  60.361  1.00 16.88      AAAA
ATOM   1178  C    ILE A 151      38.265  21.243  60.096  1.00 23.29      AAAA
ATOM   1179  O    ILE A 151      38.786  20.660  61.038  1.00 23.88      AAAA
ATOM   1180  N    GLU A 152      38.435  20.853  58.836  1.00 24.13      AAAA
ATOM   1181  CA   GLU A 152      39.267  19.697  58.517  1.00 25.01      AAAA
ATOM   1182  CB   GLU A 152      39.242  19.404  57.010  1.00 25.07      AAAA
ATOM   1183  CG   GLU A 152      37.910  18.886  56.526  1.00 24.56      AAAA
ATOM   1184  CD   GLU A 152      37.500  17.570  57.198  1.00 25.00      AAAA
ATOM   1185  OE1  GLU A 152      36.345  17.158  57.011  1.00 26.40      AAAA
ATOM   1186  OE2  GLU A 152      38.315  16.935  57.897  1.00 25.00      AAAA
ATOM   1187  C    GLU A 152      40.694  19.957  58.965  1.00 26.06      AAAA
ATOM   1188  O    GLU A 152      41.425  19.035  59.331  1.00 26.40      AAAA
```

Fig. 19-18

```
ATOM   1189  N    TYR A 153      41.085  21.225  58.925  1.00 27.30      AAAA
ATOM   1190  CA   TYR A 153      42.422  21.632  59.334  1.00 27.63      AAAA
ATOM   1191  CB   TYR A 153      42.532  23.153  59.268  1.00 26.99      AAAA
ATOM   1192  CG   TYR A 153      43.856  23.719  59.710  1.00 27.03      AAAA
ATOM   1193  CD1  TYR A 153      44.942  23.790  58.837  1.00 27.78      AAAA
ATOM   1194  CE1  TYR A 153      46.165  24.356  59.250  1.00 28.40      AAAA
ATOM   1195  CD2  TYR A 153      44.017  24.215  61.007  1.00 27.52      AAAA
ATOM   1196  CE2  TYR A 153      45.216  24.774  61.425  1.00 27.66      AAAA
ATOM   1197  CZ   TYR A 153      46.284  24.845  60.547  1.00 28.15      AAAA
ATOM   1198  OH   TYR A 153      47.457  25.407  60.974  1.00 28.83      AAAA
ATOM   1199  C    TYR A 153      42.618  21.172  60.769  1.00 27.82      AAAA
ATOM   1200  O    TYR A 153      43.613  20.552  61.110  1.00 27.15      AAAA
ATOM   1201  N    LEU A 154      41.636  21.487  61.604  1.00 29.25      AAAA
ATOM   1202  CA   LEU A 154      41.665  21.138  63.014  1.00 29.35      AAAA
ATOM   1203  CB   LEU A 154      40.507  21.829  63.715  1.00 30.25      AAAA
ATOM   1204  CG   LEU A 154      40.685  23.346  63.792  1.00 31.10      AAAA
ATOM   1205  CD1  LEU A 154      39.348  24.020  64.092  1.00 31.24      AAAA
ATOM   1206  CD2  LEU A 154      41.747  23.669  64.852  1.00 29.84      AAAA
ATOM   1207  C    LEU A 154      41.625  19.639  63.263  1.00 29.73      AAAA
ATOM   1208  O    LEU A 154      42.313  19.151  64.150  1.00 30.51      AAAA
ATOM   1209  N    ARG A 155      40.832  18.903  62.489  1.00 28.95      AAAA
ATOM   1210  CA   ARG A 155      40.771  17.459  62.671  1.00 28.94      AAAA
ATOM   1211  CB   ARG A 155      39.742  16.820  61.723  1.00 28.64      AAAA
ATOM   1212  CG   ARG A 155      38.312  17.312  61.952  1.00 27.82      AAAA
ATOM   1213  CD   ARG A 155      37.319  16.751  60.955  1.00 27.19      AAAA
ATOM   1214  NE   ARG A 155      36.804  15.444  61.338  1.00 28.86      AAAA
ATOM   1215  CZ   ARG A 155      35.939  14.742  60.612  1.00 28.93      AAAA
ATOM   1216  NH1  ARG A 155      35.500  15.227  59.459  1.00 29.47      AAAA
ATOM   1217  NH2  ARG A 155      35.486  13.574  61.053  1.00 28.76      AAAA
ATOM   1218  C    ARG A 155      42.158  16.853  62.438  1.00 30.20      AAAA
ATOM   1219  O    ARG A 155      42.572  15.949  63.164  1.00 30.74      AAAA
ATOM   1220  N    LYS A 156      42.890  17.362  61.447  1.00 30.32      AAAA
ATOM   1221  CA   LYS A 156      44.224  16.838  61.173  1.00 30.07      AAAA
ATOM   1222  CB   LYS A 156      44.771  17.373  59.847  1.00 30.26      AAAA
ATOM   1223  CG   LYS A 156      46.168  16.869  59.525  1.00 30.16      AAAA
ATOM   1224  CD   LYS A 156      46.686  17.368  58.181  1.00 31.19      AAAA
ATOM   1225  CE   LYS A 156      45.884  16.813  56.986  1.00 31.70      AAAA
ATOM   1226  NZ   LYS A 156      45.963  15.324  56.824  1.00 31.20      AAAA
ATOM   1227  C    LYS A 156      45.167  17.202  62.306  1.00 30.08      AAAA
ATOM   1228  O    LYS A 156      46.192  16.550  62.485  1.00 29.16      AAAA
ATOM   1229  N    LYS A 157      44.816  18.252  63.053  1.00 30.08      AAAA
ATOM   1230  CA   LYS A 157      45.608  18.691  64.196  1.00 31.03      AAAA
ATOM   1231  CB   LYS A 157      45.446  20.201  64.452  1.00 31.81      AAAA
ATOM   1232  CG   LYS A 157      46.067  21.134  63.419  1.00 32.12      AAAA
ATOM   1233  CD   LYS A 157      47.580  21.041  63.348  1.00 31.34      AAAA
ATOM   1234  CE   LYS A 157      48.080  21.941  62.226  1.00 32.66      AAAA
ATOM   1235  NZ   LYS A 157      49.556  21.921  61.996  1.00 32.74      AAAA
ATOM   1236  C    LYS A 157      45.196  17.923  65.458  1.00 31.73      AAAA
ATOM   1237  O    LYS A 157      45.652  18.230  66.558  1.00 31.93      AAAA
ATOM   1238  N    GLY A 158      44.312  16.942  65.299  1.00 32.41      AAAA
ATOM   1239  CA   GLY A 158      43.901  16.140  66.436  1.00 32.34      AAAA
ATOM   1240  C    GLY A 158      42.604  16.429  67.172  1.00 32.65      AAAA
ATOM   1241  O    GLY A 158      42.182  15.604  67.980  1.00 32.85      AAAA
ATOM   1242  N    PHE A 159      41.960  17.565  66.932  1.00 33.16      AAAA
ATOM   1243  CA   PHE A 159      40.712  17.842  67.650  1.00 34.16      AAAA
ATOM   1244  CB   PHE A 159      40.220  19.281  67.403  1.00 34.81      AAAA
ATOM   1245  CG   PHE A 159      41.134  20.343  67.965  1.00 34.01      AAAA
ATOM   1246  CD1  PHE A 159      42.327  20.669  67.329  1.00 34.18      AAAA
ATOM   1247  CD2  PHE A 159      40.821  20.981  69.166  1.00 34.61      AAAA
ATOM   1248  CE1  PHE A 159      43.197  21.610  67.874  1.00 33.65      AAAA
ATOM   1249  CE2  PHE A 159      41.689  21.924  69.718  1.00 34.52      AAAA
ATOM   1250  CZ   PHE A 159      42.878  22.236  69.065  1.00 33.90      AAAA
ATOM   1251  C    PHE A 159      39.645  16.840  67.239  1.00 34.04      AAAA
ATOM   1252  O    PHE A 159      39.568  16.456  66.068  1.00 34.98      AAAA
ATOM   1253  N    LYS A 160      38.839  16.403  68.202  1.00 33.36      AAAA
ATOM   1254  CA   LYS A 160      37.794  15.415  67.936  1.00 33.11      AAAA
```

Fig. 19-19

| | | | | | | | | | |
|---|---|---|---|---|---|---|---|---|---|
| ATOM | 1255 | CB | LYS A 160 | 38.060 | 14.140 | 68.763 | 1.00 | 33.97 | AAAA |
| ATOM | 1256 | CG | LYS A 160 | 39.410 | 13.491 | 68.457 | 1.00 | 35.31 | AAAA |
| ATOM | 1257 | CD | LYS A 160 | 39.833 | 12.364 | 69.429 | 1.00 | 36.48 | AAAA |
| ATOM | 1258 | CE | LYS A 160 | 39.095 | 11.037 | 69.243 | 1.00 | 37.97 | AAAA |
| ATOM | 1259 | NZ | LYS A 160 | 37.636 | 11.080 | 69.568 | 1.00 | 39.67 | AAAA |
| ATOM | 1260 | C | LYS A 160 | 36.385 | 15.941 | 68.210 | 1.00 | 31.68 | AAAA |
| ATOM | 1261 | O | LYS A 160 | 35.405 | 15.290 | 67.887 | 1.00 | 31.51 | AAAA |
| ATOM | 1262 | N | ARG A 161 | 36.291 | 17.114 | 68.819 | 1.00 | 31.11 | AAAA |
| ATOM | 1263 | CA | ARG A 161 | 35.003 | 17.719 | 69.114 | 1.00 | 30.92 | AAAA |
| ATOM | 1264 | CB | ARG A 161 | 34.655 | 17.592 | 70.604 | 1.00 | 31.78 | AAAA |
| ATOM | 1265 | CG | ARG A 161 | 34.451 | 16.157 | 71.102 | 1.00 | 32.91 | AAAA |
| ATOM | 1266 | CD | ARG A 161 | 33.994 | 16.126 | 72.570 | 1.00 | 33.26 | AAAA |
| ATOM | 1267 | NE | ARG A 161 | 34.929 | 16.797 | 73.476 | 1.00 | 34.01 | AAAA |
| ATOM | 1268 | CZ | ARG A 161 | 36.183 | 16.404 | 73.698 | 1.00 | 34.88 | AAAA |
| ATOM | 1269 | NH1 | ARG A 161 | 36.675 | 15.334 | 73.081 | 1.00 | 34.89 | AAAA |
| ATOM | 1270 | NH2 | ARG A 161 | 36.954 | 17.084 | 74.537 | 1.00 | 34.71 | AAAA |
| ATOM | 1271 | C | ARG A 161 | 35.061 | 19.185 | 68.714 | 1.00 | 30.28 | AAAA |
| ATOM | 1272 | O | ARG A 161 | 35.365 | 20.059 | 69.529 | 1.00 | 29.86 | AAAA |
| ATOM | 1273 | N | ILE A 162 | 34.774 | 19.433 | 67.437 | 1.00 | 28.86 | AAAA |
| ATOM | 1274 | CA | ILE A 162 | 34.788 | 20.774 | 66.862 | 1.00 | 26.41 | AAAA |
| ATOM | 1275 | CB | ILE A 162 | 35.443 | 20.762 | 65.464 | 1.00 | 26.87 | AAAA |
| ATOM | 1276 | CG2 | ILE A 162 | 35.453 | 22.160 | 64.872 | 1.00 | 26.91 | AAAA |
| ATOM | 1277 | CG1 | ILE A 162 | 36.877 | 20.234 | 65.578 | 1.00 | 28.19 | AAAA |
| ATOM | 1278 | CD1 | ILE A 162 | 37.614 | 20.090 | 64.240 | 1.00 | 28.24 | AAAA |
| ATOM | 1279 | C | ILE A 162 | 33.369 | 21.283 | 66.731 | 1.00 | 24.08 | AAAA |
| ATOM | 1280 | O | ILE A 162 | 32.485 | 20.572 | 66.267 | 1.00 | 24.40 | AAAA |
| ATOM | 1281 | N | LEU A 163 | 33.153 | 22.519 | 67.153 | 1.00 | 22.25 | AAAA |
| ATOM | 1282 | CA | LEU A 163 | 31.838 | 23.126 | 67.074 | 1.00 | 20.48 | AAAA |
| ATOM | 1283 | CB | LEU A 163 | 31.408 | 23.671 | 68.440 | 1.00 | 20.97 | AAAA |
| ATOM | 1284 | CG | LEU A 163 | 30.099 | 24.477 | 68.486 | 1.00 | 20.50 | AAAA |
| ATOM | 1285 | CD1 | LEU A 163 | 28.998 | 23.695 | 67.799 | 1.00 | 19.07 | AAAA |
| ATOM | 1286 | CD2 | LEU A 163 | 29.738 | 24.802 | 69.950 | 1.00 | 19.76 | AAAA |
| ATOM | 1287 | C | LEU A 163 | 31.801 | 24.241 | 66.055 | 1.00 | 18.76 | AAAA |
| ATOM | 1288 | O | LEU A 163 | 32.756 | 24.986 | 65.894 | 1.00 | 18.41 | AAAA |
| ATOM | 1289 | N | TYR A 164 | 30.677 | 24.344 | 65.368 | 1.00 | 17.85 | AAAA |
| ATOM | 1290 | CA | TYR A 164 | 30.496 | 25.372 | 64.373 | 1.00 | 17.16 | AAAA |
| ATOM | 1291 | CB | TYR A 164 | 30.644 | 24.768 | 62.983 | 1.00 | 17.45 | AAAA |
| ATOM | 1292 | CG | TYR A 164 | 30.484 | 25.783 | 61.900 | 1.00 | 17.70 | AAAA |
| ATOM | 1293 | CD1 | TYR A 164 | 31.444 | 26.772 | 61.701 | 1.00 | 16.23 | AAAA |
| ATOM | 1294 | CE1 | TYR A 164 | 31.280 | 27.734 | 60.721 | 1.00 | 17.35 | AAAA |
| ATOM | 1295 | CD2 | TYR A 164 | 29.350 | 25.781 | 61.092 | 1.00 | 17.95 | AAAA |
| ATOM | 1296 | CE2 | TYR A 164 | 29.173 | 26.746 | 60.103 | 1.00 | 18.03 | AAAA |
| ATOM | 1297 | CZ | TYR A 164 | 30.138 | 27.717 | 59.919 | 1.00 | 17.30 | AAAA |
| ATOM | 1298 | OH | TYR A 164 | 29.955 | 28.647 | 58.926 | 1.00 | 16.70 | AAAA |
| ATOM | 1299 | C | TYR A 164 | 29.123 | 26.016 | 64.514 | 1.00 | 15.85 | AAAA |
| ATOM | 1300 | O | TYR A 164 | 28.101 | 25.351 | 64.416 | 1.00 | 16.44 | AAAA |
| ATOM | 1301 | N | ILE A 165 | 29.115 | 27.319 | 64.743 | 1.00 | 15.54 | AAAA |
| ATOM | 1302 | CA | ILE A 165 | 27.878 | 28.088 | 64.897 | 1.00 | 15.71 | AAAA |
| ATOM | 1303 | CB | ILE A 165 | 27.869 | 28.819 | 66.250 | 1.00 | 15.18 | AAAA |
| ATOM | 1304 | CG2 | ILE A 165 | 26.621 | 29.685 | 66.374 | 1.00 | 13.94 | AAAA |
| ATOM | 1305 | CG1 | ILE A 165 | 28.000 | 27.797 | 67.386 | 1.00 | 13.94 | AAAA |
| ATOM | 1306 | CD1 | ILE A 165 | 28.356 | 28.421 | 68.747 | 1.00 | 13.94 | AAAA |
| ATOM | 1307 | C | ILE A 165 | 27.808 | 29.124 | 63.754 | 1.00 | 16.00 | AAAA |
| ATOM | 1308 | O | ILE A 165 | 28.711 | 29.941 | 63.576 | 1.00 | 16.56 | AAAA |
| ATOM | 1309 | N | ASP A 166 | 26.721 | 29.087 | 63.001 | 1.00 | 16.18 | AAAA |
| ATOM | 1310 | CA | ASP A 166 | 26.524 | 29.962 | 61.865 | 1.00 | 16.67 | AAAA |
| ATOM | 1311 | CB | ASP A 166 | 26.240 | 29.066 | 60.651 | 1.00 | 18.05 | AAAA |
| ATOM | 1312 | CG | ASP A 166 | 26.238 | 29.809 | 59.329 | 1.00 | 19.21 | AAAA |
| ATOM | 1313 | OD1 | ASP A 166 | 25.353 | 30.659 | 59.114 | 1.00 | 18.36 | AAAA |
| ATOM | 1314 | OD2 | ASP A 166 | 27.131 | 29.521 | 58.495 | 1.00 | 19.19 | AAAA |
| ATOM | 1315 | C | ASP A 166 | 25.342 | 30.904 | 62.169 | 1.00 | 17.57 | AAAA |
| ATOM | 1316 | O | ASP A 166 | 24.206 | 30.459 | 62.321 | 1.00 | 17.26 | AAAA |
| ATOM | 1317 | N | LEU A 167 | 25.605 | 32.202 | 62.274 | 1.00 | 16.67 | AAAA |
| ATOM | 1318 | CA | LEU A 167 | 24.526 | 33.135 | 62.562 | 1.00 | 16.89 | AAAA |
| ATOM | 1319 | CB | LEU A 167 | 24.923 | 34.116 | 63.663 | 1.00 | 17.27 | AAAA |
| ATOM | 1320 | CG | LEU A 167 | 25.499 | 33.529 | 64.954 | 1.00 | 18.37 | AAAA |

Fig. 19-20

| | | | | | | | | | |
|---|---|---|---|---|---|---|---|---|---|
| ATOM | 1321 | CD1 | LEU | A | 167 | 25.760 | 34.671 | 65.933 | 1.00 18.72 | AAAA |
| ATOM | 1322 | CD2 | LEU | A | 167 | 24.566 | 32.507 | 65.547 | 1.00 17.06 | AAAA |
| ATOM | 1323 | C | LEU | A | 167 | 24.146 | 33.897 | 61.307 | 1.00 17.18 | AAAA |
| ATOM | 1324 | O | LEU | A | 167 | 23.390 | 34.850 | 61.358 | 1.00 17.21 | AAAA |
| ATOM | 1325 | N | ASP | A | 168 | 24.683 | 33.457 | 60.178 | 1.00 17.83 | AAAA |
| ATOM | 1326 | CA | ASP | A | 168 | 24.382 | 34.067 | 58.904 | 1.00 17.84 | AAAA |
| ATOM | 1327 | CB | ASP | A | 168 | 25.178 | 33.397 | 57.807 | 1.00 20.42 | AAAA |
| ATOM | 1328 | CG | ASP | A | 168 | 25.140 | 34.162 | 56.529 | 1.00 21.41 | AAAA |
| ATOM | 1329 | C | ASP | A | 168 | 22.915 | 33.783 | 58.660 | 1.00 18.35 | AAAA |
| ATOM | 1330 | O | ASP | A | 168 | 22.419 | 32.722 | 59.032 | 1.00 19.62 | AAAA |
| ATOM | 1331 | OD1 | ASP | A | 168 | 26.066 | 34.972 | 56.330 | 1.00 22.42 | AAAA |
| ATOM | 1332 | OD2 | ASP | A | 168 | 24.186 | 33.971 | 55.746 | 1.00 21.79 | AAAA |
| ATOM | 1333 | N | ALA | A | 169 | 22.239 | 34.717 | 58.010 | 1.00 17.98 | AAAA |
| ATOM | 1334 | CA | ALA | A | 169 | 20.824 | 34.601 | 57.708 | 1.00 17.36 | AAAA |
| ATOM | 1335 | CB | ALA | A | 169 | 20.348 | 35.860 | 57.007 | 1.00 17.00 | AAAA |
| ATOM | 1336 | C | ALA | A | 169 | 20.439 | 33.377 | 56.887 | 1.00 18.64 | AAAA |
| ATOM | 1337 | O | ALA | A | 169 | 19.255 | 33.043 | 56.819 | 1.00 19.46 | AAAA |
| ATOM | 1338 | N | HIS | A | 170 | 21.412 | 32.712 | 56.262 | 1.00 18.71 | AAAA |
| ATOM | 1339 | CA | HIS | A | 170 | 21.107 | 31.518 | 55.464 | 1.00 18.43 | AAAA |
| ATOM | 1340 | C | HIS | A | 170 | 21.802 | 30.265 | 55.986 | 1.00 18.02 | AAAA |
| ATOM | 1341 | O | HIS | A | 170 | 22.910 | 30.332 | 56.514 | 1.00 17.20 | AAAA |
| ATOM | 1342 | CB | HIS | A | 170 | 21.539 | 31.678 | 54.004 | 1.00 18.79 | AAAA |
| ATOM | 1343 | CG | HIS | A | 170 | 21.137 | 32.968 | 53.386 | 1.00 17.65 | AAAA |
| ATOM | 1344 | ND1 | HIS | A | 170 | 21.644 | 34.162 | 53.828 | 1.00 18.08 | AAAA |
| ATOM | 1345 | CE1 | HIS | A | 170 | 21.112 | 35.081 | 53.054 | 1.00 18.95 | AAAA |
| ATOM | 1346 | CD2 | HIS | A | 170 | 20.301 | 33.194 | 52.348 | 1.00 18.81 | AAAA |
| ATOM | 1347 | NE2 | HIS | A | 170 | 20.291 | 34.544 | 52.140 | 1.00 19.66 | AAAA |
| ATOM | 1348 | N | HIS | A | 171 | 21.142 | 29.124 | 55.793 | 1.00 17.53 | AAAA |
| ATOM | 1349 | CA | HIS | A | 171 | 21.662 | 27.822 | 56.193 | 1.00 16.38 | AAAA |
| ATOM | 1350 | CB | HIS | A | 171 | 20.644 | 26.740 | 55.830 | 1.00 16.32 | AAAA |
| ATOM | 1351 | CG | HIS | A | 171 | 21.157 | 25.337 | 55.958 | 1.00 15.91 | AAAA |
| ATOM | 1352 | CD2 | HIS | A | 171 | 21.241 | 24.336 | 55.051 | 1.00 14.14 | AAAA |
| ATOM | 1353 | ND1 | HIS | A | 171 | 21.602 | 24.807 | 57.151 | 1.00 16.79 | AAAA |
| ATOM | 1354 | CE1 | HIS | A | 171 | 21.937 | 23.543 | 56.973 | 1.00 14.91 | AAAA |
| ATOM | 1355 | NE2 | HIS | A | 171 | 21.725 | 23.234 | 55.709 | 1.00 15.45 | AAAA |
| ATOM | 1356 | C | HIS | A | 171 | 22.982 | 27.522 | 55.509 | 1.00 16.94 | AAAA |
| ATOM | 1357 | O | HIS | A | 171 | 23.146 | 27.725 | 54.318 | 1.00 18.71 | AAAA |
| ATOM | 1358 | N | CYS | A | 172 | 23.926 | 27.019 | 56.279 | 1.00 16.99 | AAAA |
| ATOM | 1359 | CA | CYS | A | 172 | 25.237 | 26.670 | 55.778 | 1.00 16.23 | AAAA |
| ATOM | 1360 | CB | CYS | A | 172 | 26.219 | 26.721 | 56.947 | 1.00 17.89 | AAAA |
| ATOM | 1361 | SG | CYS | A | 172 | 25.638 | 25.773 | 58.397 | 1.00 17.89 | AAAA |
| ATOM | 1362 | C | CYS | A | 172 | 25.205 | 25.271 | 55.210 | 1.00 16.57 | AAAA |
| ATOM | 1363 | O | CYS | A | 172 | 25.947 | 24.413 | 55.670 | 1.00 17.66 | AAAA |
| ATOM | 1364 | N | ASP | A | 173 | 24.364 | 25.026 | 54.214 | 1.00 18.25 | AAAA |
| ATOM | 1365 | CA | ASP | A | 173 | 24.253 | 23.680 | 53.620 | 1.00 19.91 | AAAA |
| ATOM | 1366 | CB | ASP | A | 173 | 23.342 | 23.699 | 52.397 | 1.00 20.86 | AAAA |
| ATOM | 1367 | CG | ASP | A | 173 | 23.780 | 24.719 | 51.358 | 1.00 21.90 | AAAA |
| ATOM | 1368 | OD1 | ASP | A | 173 | 23.257 | 24.640 | 50.217 | 1.00 21.35 | AAAA |
| ATOM | 1369 | OD2 | ASP | A | 173 | 24.624 | 25.597 | 51.687 | 1.00 21.35 | AAAA |
| ATOM | 1370 | C | ASP | A | 173 | 25.573 | 23.021 | 53.227 | 1.00 21.02 | AAAA |
| ATOM | 1371 | O | ASP | A | 173 | 25.673 | 21.785 | 53.199 | 1.00 22.79 | AAAA |
| ATOM | 1372 | N | GLY | A | 174 | 26.579 | 23.832 | 52.912 | 1.00 20.03 | AAAA |
| ATOM | 1373 | CA | GLY | A | 174 | 27.870 | 23.277 | 52.553 | 1.00 19.72 | AAAA |
| ATOM | 1374 | C | GLY | A | 174 | 28.537 | 22.680 | 53.771 | 1.00 20.27 | AAAA |
| ATOM | 1375 | O | GLY | A | 174 | 29.110 | 21.599 | 53.711 | 1.00 19.77 | AAAA |
| ATOM | 1376 | N | VAL | A | 175 | 28.448 | 23.387 | 54.893 | 1.00 21.38 | AAAA |
| ATOM | 1377 | CA | VAL | A | 175 | 29.056 | 22.934 | 56.135 | 1.00 22.26 | AAAA |
| ATOM | 1378 | CB | VAL | A | 175 | 29.032 | 24.040 | 57.203 | 1.00 23.15 | AAAA |
| ATOM | 1379 | CG1 | VAL | A | 175 | 29.853 | 23.617 | 58.418 | 1.00 22.84 | AAAA |
| ATOM | 1380 | CG2 | VAL | A | 175 | 29.562 | 25.347 | 56.612 | 1.00 23.43 | AAAA |
| ATOM | 1381 | C | VAL | A | 175 | 28.302 | 21.724 | 56.654 | 1.00 23.51 | AAAA |
| ATOM | 1382 | O | VAL | A | 175 | 28.893 | 20.803 | 57.210 | 1.00 23.74 | AAAA |
| ATOM | 1383 | N | GLN | A | 176 | 26.993 | 21.721 | 56.452 | 1.00 24.80 | AAAA |
| ATOM | 1384 | CA | GLN | A | 176 | 26.171 | 20.601 | 56.893 | 1.00 25.41 | AAAA |
| ATOM | 1385 | CB | GLN | A | 176 | 24.689 | 20.913 | 56.694 | 1.00 24.77 | AAAA |
| ATOM | 1386 | CG | GLN | A | 176 | 23.799 | 19.735 | 57.036 | 1.00 26.23 | AAAA |

Fig. 19-21

| | | | | | | | | | |
|---|---|---|---|---|---|---|---|---|---|
| ATOM | 1387 | CD  | GLN | A | 176 | 22.334 | 20.094 | 57.069 | 1.00 27.17 | AAAA |
| ATOM | 1388 | OE1 | GLN | A | 176 | 21.902 | 20.879 | 57.911 | 1.00 28.24 | AAAA |
| ATOM | 1389 | NE2 | GLN | A | 176 | 21.556 | 19.522 | 56.151 | 1.00 26.54 | AAAA |
| ATOM | 1390 | C   | GLN | A | 176 | 26.512 | 19.293 | 56.180 | 1.00 25.67 | AAAA |
| ATOM | 1391 | O   | GLN | A | 176 | 26.789 | 18.285 | 56.820 | 1.00 26.98 | AAAA |
| ATOM | 1392 | N   | GLU | A | 177 | 26.490 | 19.309 | 54.853 | 1.00 26.34 | AAAA |
| ATOM | 1393 | CA  | GLU | A | 177 | 26.786 | 18.117 | 54.073 | 1.00 26.18 | AAAA |
| ATOM | 1394 | CB  | GLU | A | 177 | 26.746 | 18.468 | 52.580 | 1.00 27.13 | AAAA |
| ATOM | 1395 | CG  | GLU | A | 177 | 26.769 | 17.269 | 51.628 | 1.00 29.77 | AAAA |
| ATOM | 1396 | CD  | GLU | A | 177 | 26.623 | 17.660 | 50.147 | 1.00 31.29 | AAAA |
| ATOM | 1397 | OE1 | GLU | A | 177 | 27.655 | 17.935 | 49.500 | 1.00 31.35 | AAAA |
| ATOM | 1398 | OE2 | GLU | A | 177 | 25.471 | 17.703 | 49.636 | 1.00 32.05 | AAAA |
| ATOM | 1399 | C   | GLU | A | 177 | 28.160 | 17.556 | 54.460 | 1.00 26.38 | AAAA |
| ATOM | 1400 | O   | GLU | A | 177 | 28.338 | 16.349 | 54.595 | 1.00 25.41 | AAAA |
| ATOM | 1401 | N   | ALA | A | 178 | 29.115 | 18.458 | 54.659 | 1.00 27.58 | AAAA |
| ATOM | 1402 | CA  | ALA | A | 178 | 30.495 | 18.119 | 55.004 | 1.00 27.66 | AAAA |
| ATOM | 1403 | CB  | ALA | A | 178 | 31.345 | 19.385 | 54.994 | 1.00 26.20 | AAAA |
| ATOM | 1404 | C   | ALA | A | 178 | 30.713 | 17.370 | 56.318 | 1.00 28.33 | AAAA |
| ATOM | 1405 | O   | ALA | A | 178 | 31.685 | 16.626 | 56.439 | 1.00 29.44 | AAAA |
| ATOM | 1406 | N   | PHE | A | 179 | 29.849 | 17.564 | 57.308 | 1.00 28.25 | AAAA |
| ATOM | 1407 | CA  | PHE | A | 179 | 30.036 | 16.852 | 58.561 | 1.00 29.20 | AAAA |
| ATOM | 1408 | CB  | PHE | A | 179 | 30.570 | 17.794 | 59.624 | 1.00 29.35 | AAAA |
| ATOM | 1409 | CG  | PHE | A | 179 | 31.751 | 18.572 | 59.171 | 1.00 30.26 | AAAA |
| ATOM | 1410 | CD1 | PHE | A | 179 | 31.582 | 19.777 | 58.497 | 1.00 31.01 | AAAA |
| ATOM | 1411 | CD2 | PHE | A | 179 | 33.033 | 18.069 | 59.339 | 1.00 30.37 | AAAA |
| ATOM | 1412 | CE1 | PHE | A | 179 | 32.670 | 20.470 | 57.993 | 1.00 31.20 | AAAA |
| ATOM | 1413 | CE2 | PHE | A | 179 | 34.133 | 18.749 | 58.840 | 1.00 31.74 | AAAA |
| ATOM | 1414 | CZ  | PHE | A | 179 | 33.950 | 19.960 | 58.161 | 1.00 31.81 | AAAA |
| ATOM | 1415 | C   | PHE | A | 179 | 28.760 | 16.180 | 59.040 | 1.00 30.33 | AAAA |
| ATOM | 1416 | O   | PHE | A | 179 | 28.624 | 15.810 | 60.215 | 1.00 31.82 | AAAA |
| ATOM | 1417 | N   | TYR | A | 180 | 27.842 | 15.994 | 58.105 | 1.00 29.18 | AAAA |
| ATOM | 1418 | CA  | TYR | A | 180 | 26.564 | 15.379 | 58.389 | 1.00 28.99 | AAAA |
| ATOM | 1419 | CB  | TYR | A | 180 | 25.725 | 15.343 | 57.123 | 1.00 28.30 | AAAA |
| ATOM | 1420 | CG  | TYR | A | 180 | 24.244 | 15.422 | 57.384 | 1.00 28.27 | AAAA |
| ATOM | 1421 | CD1 | TYR | A | 180 | 23.392 | 14.386 | 57.021 | 1.00 27.05 | AAAA |
| ATOM | 1422 | CE1 | TYR | A | 180 | 22.029 | 14.491 | 57.197 | 1.00 28.51 | AAAA |
| ATOM | 1423 | CD2 | TYR | A | 180 | 23.686 | 16.573 | 57.942 | 1.00 29.34 | AAAA |
| ATOM | 1424 | CE2 | TYR | A | 180 | 22.316 | 16.691 | 58.125 | 1.00 29.27 | AAAA |
| ATOM | 1425 | CZ  | TYR | A | 180 | 21.495 | 15.645 | 57.746 | 1.00 29.33 | AAAA |
| ATOM | 1426 | OH  | TYR | A | 180 | 20.141 | 15.775 | 57.893 | 1.00 30.83 | AAAA |
| ATOM | 1427 | C   | TYR | A | 180 | 26.673 | 13.970 | 58.940 | 1.00 28.79 | AAAA |
| ATOM | 1428 | O   | TYR | A | 180 | 25.877 | 13.577 | 59.785 | 1.00 28.71 | AAAA |
| ATOM | 1429 | N   | ASP | A | 181 | 27.662 | 13.214 | 58.472 | 1.00 29.03 | AAAA |
| ATOM | 1430 | CA  | ASP | A | 181 | 27.813 | 11.828 | 58.914 | 1.00 28.49 | AAAA |
| ATOM | 1431 | CB  | ASP | A | 181 | 28.140 | 10.930 | 57.715 | 1.00 27.59 | AAAA |
| ATOM | 1432 | CG  | ASP | A | 181 | 29.548 | 11.122 | 57.229 | 1.00 28.82 | AAAA |
| ATOM | 1433 | OD1 | ASP | A | 181 | 29.981 | 12.292 | 57.183 | 1.00 29.25 | AAAA |
| ATOM | 1434 | OD2 | ASP | A | 181 | 30.216 | 10.119 | 56.887 | 1.00 28.68 | AAAA |
| ATOM | 1435 | C   | ASP | A | 181 | 28.863 | 11.631 | 60.009 | 1.00 27.67 | AAAA |
| ATOM | 1436 | O   | ASP | A | 181 | 29.271 | 10.504 | 60.293 | 1.00 27.57 | AAAA |
| ATOM | 1437 | N   | THR | A | 182 | 29.308 | 12.713 | 60.628 | 1.00 26.27 | AAAA |
| ATOM | 1438 | CA  | THR | A | 182 | 30.284 | 12.544 | 61.689 | 1.00 26.22 | AAAA |
| ATOM | 1439 | CB  | THR | A | 182 | 31.670 | 13.118 | 61.317 | 1.00 25.92 | AAAA |
| ATOM | 1440 | OG1 | THR | A | 182 | 32.564 | 12.935 | 62.416 | 1.00 25.06 | AAAA |
| ATOM | 1441 | CG2 | THR | A | 182 | 31.577 | 14.594 | 60.974 | 1.00 25.25 | AAAA |
| ATOM | 1442 | C   | THR | A | 182 | 29.792 | 13.223 | 62.934 | 1.00 25.87 | AAAA |
| ATOM | 1443 | O   | THR | A | 182 | 28.942 | 14.102 | 62.863 | 1.00 26.35 | AAAA |
| ATOM | 1444 | N   | ASP | A | 183 | 30.327 | 12.804 | 64.071 | 1.00 25.86 | AAAA |
| ATOM | 1445 | CA  | ASP | A | 183 | 29.953 | 13.370 | 65.355 | 1.00 26.12 | AAAA |
| ATOM | 1446 | CB  | ASP | A | 183 | 29.468 | 12.260 | 66.274 | 1.00 27.10 | AAAA |
| ATOM | 1447 | CG  | ASP | A | 183 | 30.515 | 11.194 | 66.488 | 1.00 28.80 | AAAA |
| ATOM | 1448 | OD1 | ASP | A | 183 | 31.063 | 10.691 | 65.480 | 1.00 29.78 | AAAA |
| ATOM | 1449 | OD2 | ASP | A | 183 | 30.781 | 10.852 | 67.657 | 1.00 29.21 | AAAA |
| ATOM | 1450 | C   | ASP | A | 183 | 31.126 | 14.120 | 65.995 | 1.00 26.77 | AAAA |
| ATOM | 1451 | O   | ASP | A | 183 | 31.034 | 14.566 | 67.146 | 1.00 26.65 | AAAA |
| ATOM | 1452 | N   | GLN | A | 184 | 32.229 | 14.254 | 65.254 | 1.00 26.05 | AAAA |

Fig. 19-22

| ATOM | 1453 | CA  | GLN | A | 184 | 33.381 | 14.983 | 65.766 | 1.00 | 25.85 | AAAA |
| ATOM | 1454 | CB  | GLN | A | 184 | 34.674 | 14.510 | 65.095 | 1.00 | 26.30 | AAAA |
| ATOM | 1455 | CG  | GLN | A | 184 | 34.920 | 13.030 | 65.303 | 1.00 | 27.42 | AAAA |
| ATOM | 1456 | CD  | GLN | A | 184 | 36.273 | 12.583 | 64.822 | 1.00 | 28.40 | AAAA |
| ATOM | 1457 | OE1 | GLN | A | 184 | 36.685 | 12.905 | 63.709 | 1.00 | 30.05 | AAAA |
| ATOM | 1458 | NE2 | GLN | A | 184 | 36.970 | 11.816 | 65.651 | 1.00 | 29.24 | AAAA |
| ATOM | 1459 | C   | GLN | A | 184 | 33.159 | 16.474 | 65.536 | 1.00 | 25.22 | AAAA |
| ATOM | 1460 | O   | GLN | A | 184 | 33.734 | 17.316 | 66.220 | 1.00 | 24.57 | AAAA |
| ATOM | 1461 | N   | VAL | A | 185 | 32.290 | 16.791 | 64.584 | 1.00 | 25.17 | AAAA |
| ATOM | 1462 | CA  | VAL | A | 185 | 31.975 | 18.182 | 64.291 | 1.00 | 24.49 | AAAA |
| ATOM | 1463 | CB  | VAL | A | 185 | 32.324 | 18.563 | 62.832 | 1.00 | 23.20 | AAAA |
| ATOM | 1464 | CG1 | VAL | A | 185 | 32.045 | 20.060 | 62.599 | 1.00 | 19.72 | AAAA |
| ATOM | 1465 | CG2 | VAL | A | 185 | 33.777 | 18.205 | 62.543 | 1.00 | 20.67 | AAAA |
| ATOM | 1466 | C   | VAL | A | 185 | 30.494 | 18.421 | 64.501 | 1.00 | 24.81 | AAAA |
| ATOM | 1467 | O   | VAL | A | 185 | 29.664 | 17.787 | 63.844 | 1.00 | 27.07 | AAAA |
| ATOM | 1468 | N   | PHE | A | 186 | 30.162 | 19.311 | 65.434 | 1.00 | 23.40 | AAAA |
| ATOM | 1469 | CA  | PHE | A | 186 | 28.768 | 19.645 | 65.684 | 1.00 | 20.31 | AAAA |
| ATOM | 1470 | CB  | PHE | A | 186 | 28.513 | 19.937 | 67.164 | 1.00 | 19.77 | AAAA |
| ATOM | 1471 | CG  | PHE | A | 186 | 27.057 | 20.037 | 67.500 | 1.00 | 18.55 | AAAA |
| ATOM | 1472 | CD1 | PHE | A | 186 | 26.359 | 18.918 | 67.945 | 1.00 | 17.70 | AAAA |
| ATOM | 1473 | CD2 | PHE | A | 186 | 26.358 | 21.213 | 67.263 | 1.00 | 17.46 | AAAA |
| ATOM | 1474 | CE1 | PHE | A | 186 | 24.999 | 18.964 | 68.147 | 1.00 | 17.35 | AAAA |
| ATOM | 1475 | CE2 | PHE | A | 186 | 24.997 | 21.271 | 67.459 | 1.00 | 18.83 | AAAA |
| ATOM | 1476 | CZ  | PHE | A | 186 | 24.308 | 20.138 | 67.905 | 1.00 | 18.67 | AAAA |
| ATOM | 1477 | C   | PHE | A | 186 | 28.464 | 20.911 | 64.895 | 1.00 | 19.18 | AAAA |
| ATOM | 1478 | O   | PHE | A | 186 | 29.079 | 21.940 | 65.129 | 1.00 | 18.82 | AAAA |
| ATOM | 1479 | N   | VAL | A | 187 | 27.520 | 20.834 | 63.964 | 1.00 | 18.34 | AAAA |
| ATOM | 1480 | CA  | VAL | A | 187 | 27.137 | 21.993 | 63.160 | 1.00 | 16.47 | AAAA |
| ATOM | 1481 | CB  | VAL | A | 187 | 27.006 | 21.630 | 61.655 | 1.00 | 14.30 | AAAA |
| ATOM | 1482 | CG1 | VAL | A | 187 | 26.628 | 22.869 | 60.828 | 1.00 | 10.34 | AAAA |
| ATOM | 1483 | CG2 | VAL | A | 187 | 28.314 | 21.031 | 61.160 | 1.00 | 12.07 | AAAA |
| ATOM | 1484 | C   | VAL | A | 187 | 25.806 | 22.511 | 63.665 | 1.00 | 17.43 | AAAA |
| ATOM | 1485 | O   | VAL | A | 187 | 24.852 | 21.746 | 63.792 | 1.00 | 16.95 | AAAA |
| ATOM | 1486 | N   | LEU | A | 188 | 25.763 | 23.809 | 63.960 | 1.00 | 18.66 | AAAA |
| ATOM | 1487 | CA  | LEU | A | 188 | 24.555 | 24.507 | 64.460 | 1.00 | 20.51 | AAAA |
| ATOM | 1488 | CB  | LEU | A | 188 | 24.752 | 24.995 | 65.914 | 1.00 | 21.24 | AAAA |
| ATOM | 1489 | CG  | LEU | A | 188 | 23.702 | 26.019 | 66.395 | 1.00 | 20.80 | AAAA |
| ATOM | 1490 | CD1 | LEU | A | 188 | 22.365 | 25.323 | 66.493 | 1.00 | 19.77 | AAAA |
| ATOM | 1491 | CD2 | LEU | A | 188 | 24.085 | 26.627 | 67.750 | 1.00 | 20.63 | AAAA |
| ATOM | 1492 | C   | LEU | A | 188 | 24.297 | 25.735 | 63.591 | 1.00 | 20.41 | AAAA |
| ATOM | 1493 | O   | LEU | A | 188 | 25.223 | 26.484 | 63.288 | 1.00 | 21.86 | AAAA |
| ATOM | 1494 | N   | SER | A | 189 | 23.049 | 25.987 | 63.233 | 1.00 | 19.32 | AAAA |
| ATOM | 1495 | CA  | SER | A | 189 | 22.786 | 27.130 | 62.381 | 1.00 | 18.06 | AAAA |
| ATOM | 1496 | CB  | SER | A | 189 | 22.970 | 26.715 | 60.906 | 1.00 | 18.54 | AAAA |
| ATOM | 1497 | OG  | SER | A | 189 | 22.559 | 27.731 | 59.998 | 1.00 | 17.47 | AAAA |
| ATOM | 1498 | C   | SER | A | 189 | 21.418 | 27.751 | 62.554 | 1.00 | 17.90 | AAAA |
| ATOM | 1499 | O   | SER | A | 189 | 20.404 | 27.051 | 62.540 | 1.00 | 19.54 | AAAA |
| ATOM | 1500 | N   | LEU | A | 190 | 21.386 | 29.067 | 62.722 | 1.00 | 16.97 | AAAA |
| ATOM | 1501 | CA  | LEU | A | 190 | 20.117 | 29.772 | 62.797 | 1.00 | 18.49 | AAAA |
| ATOM | 1502 | CB  | LEU | A | 190 | 20.097 | 30.865 | 63.886 | 1.00 | 17.78 | AAAA |
| ATOM | 1503 | CG  | LEU | A | 190 | 20.534 | 30.600 | 65.337 | 1.00 | 17.10 | AAAA |
| ATOM | 1504 | CD1 | LEU | A | 190 | 19.643 | 31.406 | 66.266 | 1.00 | 15.50 | AAAA |
| ATOM | 1505 | CD2 | LEU | A | 190 | 20.455 | 29.147 | 65.686 | 1.00 | 15.15 | AAAA |
| ATOM | 1506 | C   | LEU | A | 190 | 20.111 | 30.408 | 61.416 | 1.00 | 19.35 | AAAA |
| ATOM | 1507 | O   | LEU | A | 190 | 21.136 | 30.891 | 60.967 | 1.00 | 19.75 | AAAA |
| ATOM | 1508 | N   | HIS | A | 191 | 18.975 | 30.397 | 60.736 | 1.00 | 21.75 | AAAA |
| ATOM | 1509 | CA  | HIS | A | 191 | 18.897 | 30.955 | 59.383 | 1.00 | 23.55 | AAAA |
| ATOM | 1510 | CB  | HIS | A | 191 | 19.626 | 30.013 | 58.426 | 1.00 | 23.63 | AAAA |
| ATOM | 1511 | CG  | HIS | A | 191 | 19.157 | 28.597 | 58.533 | 1.00 | 24.26 | AAAA |
| ATOM | 1512 | CD2 | HIS | A | 191 | 19.770 | 27.485 | 59.009 | 1.00 | 23.78 | AAAA |
| ATOM | 1513 | ND1 | HIS | A | 191 | 17.869 | 28.217 | 58.217 | 1.00 | 24.73 | AAAA |
| ATOM | 1514 | CE1 | HIS | A | 191 | 17.709 | 26.935 | 58.491 | 1.00 | 23.90 | AAAA |
| ATOM | 1515 | NE2 | HIS | A | 191 | 18.849 | 26.467 | 58.973 | 1.00 | 24.51 | AAAA |
| ATOM | 1516 | C   | HIS | A | 191 | 17.446 | 31.119 | 58.926 | 1.00 | 24.10 | AAAA |
| ATOM | 1517 | O   | HIS | A | 191 | 16.519 | 30.658 | 59.596 | 1.00 | 24.94 | AAAA |
| ATOM | 1518 | N   | GLN | A | 192 | 17.249 | 31.789 | 57.794 | 1.00 | 24.33 | AAAA |

Fig. 19-23

```
ATOM   1519  CA   GLN A 192      15.899  31.959  57.269  1.00 25.77        AAAA
ATOM   1520  CB   GLN A 192      15.881  32.896  56.060  1.00 26.51        AAAA
ATOM   1521  CG   GLN A 192      16.467  34.271  56.325  1.00 26.99        AAAA
ATOM   1522  CD   GLN A 192      16.581  35.076  55.062  1.00 27.98        AAAA
ATOM   1523  OE1  GLN A 192      15.583  35.496  54.493  1.00 30.48        AAAA
ATOM   1524  NE2  GLN A 192      17.802  35.274  54.595  1.00 29.04        AAAA
ATOM   1525  C    GLN A 192      15.463  30.573  56.832  1.00 25.77        AAAA
ATOM   1526  O    GLN A 192      16.211  29.865  56.169  1.00 26.73        AAAA
ATOM   1527  N    SER A 193      14.259  30.184  57.214  1.00 25.48        AAAA
ATOM   1528  CA   SER A 193      13.750  28.877  56.863  1.00 24.51        AAAA
ATOM   1529  CB   SER A 193      12.288  28.788  57.286  1.00 23.77        AAAA
ATOM   1530  OG   SER A 193      11.753  27.517  57.010  1.00 24.81        AAAA
ATOM   1531  C    SER A 193      13.906  28.597  55.361  1.00 24.53        AAAA
ATOM   1532  O    SER A 193      13.736  29.479  54.522  1.00 22.32        AAAA
ATOM   1533  N    PRO A 194      14.226  27.348  55.007  1.00 25.69        AAAA
ATOM   1534  CD   PRO A 194      14.411  26.167  55.862  1.00 25.02        AAAA
ATOM   1535  CA   PRO A 194      14.399  26.976  53.604  1.00 27.05        AAAA
ATOM   1536  CB   PRO A 194      14.906  25.535  53.697  1.00 26.30        AAAA
ATOM   1537  CG   PRO A 194      15.479  25.466  55.124  1.00 26.44        AAAA
ATOM   1538  C    PRO A 194      13.076  27.057  52.849  1.00 27.79        AAAA
ATOM   1539  O    PRO A 194      13.066  27.057  51.625  1.00 28.82        AAAA
ATOM   1540  N    GLU A 195      11.966  27.133  53.582  1.00 28.29        AAAA
ATOM   1541  CA   GLU A 195      10.656  27.187  52.950  1.00 29.08        AAAA
ATOM   1542  CB   GLU A 195       9.534  27.030  54.001  1.00 31.08        AAAA
ATOM   1543  CG   GLU A 195       9.070  28.294  54.722  1.00 35.07        AAAA
ATOM   1544  CD   GLU A 195       7.850  28.980  54.064  1.00 38.05        AAAA
ATOM   1545  OE1  GLU A 195       7.389  30.017  54.601  1.00 38.80        AAAA
ATOM   1546  OE2  GLU A 195       7.342  28.487  53.024  1.00 39.20        AAAA
ATOM   1547  C    GLU A 195      10.483  28.471  52.150  1.00 28.05        AAAA
ATOM   1548  O    GLU A 195       9.722  28.512  51.189  1.00 28.57        AAAA
ATOM   1549  N    TYR A 196      11.223  29.510  52.514  1.00 27.39        AAAA
ATOM   1550  CA   TYR A 196      11.108  30.769  51.802  1.00 25.80        AAAA
ATOM   1551  CB   TYR A 196      10.275  31.743  52.645  1.00 24.97        AAAA
ATOM   1552  CG   TYR A 196      10.971  32.281  53.868  1.00 23.41        AAAA
ATOM   1553  CD1  TYR A 196      11.911  33.306  53.765  1.00 23.99        AAAA
ATOM   1554  CE1  TYR A 196      12.559  33.805  54.892  1.00 23.44        AAAA
ATOM   1555  CD2  TYR A 196      10.697  31.768  55.126  1.00 23.24        AAAA
ATOM   1556  CE2  TYR A 196      11.336  32.256  56.254  1.00 23.93        AAAA
ATOM   1557  CZ   TYR A 196      12.265  33.270  56.133  1.00 24.07        AAAA
ATOM   1558  OH   TYR A 196      12.913  33.731  57.247  1.00 25.06        AAAA
ATOM   1559  C    TYR A 196      12.450  31.406  51.411  1.00 24.97        AAAA
ATOM   1560  O    TYR A 196      12.475  32.495  50.840  1.00 25.14        AAAA
ATOM   1561  N    ALA A 197      13.563  30.737  51.686  1.00 23.81        AAAA
ATOM   1562  CA   ALA A 197      14.855  31.330  51.337  1.00 23.32        AAAA
ATOM   1563  CB   ALA A 197      15.350  32.220  52.488  1.00 23.33        AAAA
ATOM   1564  C    ALA A 197      15.952  30.356  50.957  1.00 22.74        AAAA
ATOM   1565  O    ALA A 197      15.951  29.207  51.371  1.00 22.47        AAAA
ATOM   1566  N    PHE A 198      16.900  30.852  50.16   1.00 23.23        AAAA
ATOM   1567  CA   PHE A 198      18.062  30.081  49.741  1.00 23.68        AAAA
ATOM   1568  CB   PHE A 198      19.083  31.006  49.069  1.00 23.33        AAAA
ATOM   1569  CG   PHE A 198      20.250  30.280  48.464  1.00 22.98        AAAA
ATOM   1570  CD1  PHE A 198      20.151  29.713  47.203  1.00 22.75        AAAA
ATOM   1571  CD2  PHE A 198      21.436  30.127  49.175  1.00 23.32        AAAA
ATOM   1572  CE1  PHE A 198      21.207  29.003  46.645  1.00 22.13        AAAA
ATOM   1573  CE2  PHE A 198      22.512  29.408  48.622  1.00 22.83        AAAA
ATOM   1574  CZ   PHE A 198      22.386  28.849  47.351  1.00 22.55        AAAA
ATOM   1575  C    PHE A 198      18.689  29.490  51.008  1.00 23.69        AAAA
ATOM   1576  O    PHE A 198      18.802  30.171  52.012  1.00 22.85        AAAA
ATOM   1577  N    PRO A 199      19.166  28.236  50.954  1.00 23.96        AAAA
ATOM   1578  CD   PRO A 199      19.833  27.639  52.123  1.00 24.26        AAAA
ATOM   1579  CA   PRO A 199      19.199  27.286  49.837  1.00 24.70        AAAA
ATOM   1580  CB   PRO A 199      20.163  26.222  50.357  1.00 23.30        AAAA
ATOM   1581  CG   PRO A 199      19.797  26.162  51.782  1.00 23.21        AAAA
ATOM   1582  C    PRO A 199      17.885  26.679  49.326  1.00 25.22        AAAA
ATOM   1583  O    PRO A 199      17.866  26.145  48.215  1.00 26.24        AAAA
ATOM   1584  N    PHE A 200      16.811  26.756  50.116  1.00 25.09        AAAA
```

Fig. 19-24

| ATOM | 1585 | CA | PHE | A | 200 | 15.497 | 26.190 | 49.763 | 1.00 | 26.29 | AAAA |
|------|------|-----|-----|---|-----|--------|--------|--------|------|-------|------|
| ATOM | 1586 | CB | PHE | A | 200 | 15.064 | 26.567 | 48.340 | 1.00 | 25.65 | AAAA |
| ATOM | 1587 | CG | PHE | A | 200 | 14.863 | 28.035 | 48.122 | 1.00 | 24.65 | AAAA |
| ATOM | 1588 | CD1 | PHE | A | 200 | 15.806 | 28.781 | 47.439 | 1.00 | 24.42 | AAAA |
| ATOM | 1589 | CD2 | PHE | A | 200 | 13.735 | 28.671 | 48.608 | 1.00 | 23.79 | AAAA |
| ATOM | 1590 | CE1 | PHE | A | 200 | 15.631 | 30.125 | 47.246 | 1.00 | 24.41 | AAAA |
| ATOM | 1591 | CE2 | PHE | A | 200 | 13.552 | 30.035 | 48.418 | 1.00 | 24.94 | AAAA |
| ATOM | 1592 | CZ | PHE | A | 200 | 14.499 | 30.760 | 47.738 | 1.00 | 24.57 | AAAA |
| ATOM | 1593 | C | PHE | A | 200 | 15.415 | 24.656 | 49.863 | 1.00 | 28.54 | AAAA |
| ATOM | 1594 | O | PHE | A | 200 | 14.386 | 24.096 | 50.251 | 1.00 | 28.76 | AAAA |
| ATOM | 1595 | N | GLU | A | 201 | 16.499 | 23.981 | 49.504 | 1.00 | 29.67 | AAAA |
| ATOM | 1596 | CA | GLU | A | 201 | 16.539 | 22.528 | 49.524 | 1.00 | 31.88 | AAAA |
| ATOM | 1597 | CB | GLU | A | 201 | 17.434 | 22.045 | 48.392 | 1.00 | 32.71 | AAAA |
| ATOM | 1598 | CG | GLU | A | 201 | 16.897 | 22.415 | 47.017 | 1.00 | 34.87 | AAAA |
| ATOM | 1599 | CD | GLU | A | 201 | 17.898 | 22.147 | 45.912 | 1.00 | 35.14 | AAAA |
| ATOM | 1600 | OE1 | GLU | A | 201 | 18.299 | 20.982 | 45.735 | 1.00 | 36.09 | AAAA |
| ATOM | 1601 | OE2 | GLU | A | 201 | 18.286 | 23.112 | 45.221 | 1.00 | 36.30 | AAAA |
| ATOM | 1602 | C | GLU | A | 201 | 16.997 | 21.894 | 50.835 | 1.00 | 32.77 | AAAA |
| ATOM | 1603 | O | GLU | A | 201 | 16.806 | 20.690 | 51.046 | 1.00 | 33.44 | AAAA |
| ATOM | 1604 | N | LYS | A | 202 | 17.599 | 22.690 | 51.711 | 1.00 | 32.31 | AAAA |
| ATOM | 1605 | CA | LYS | A | 202 | 18.101 | 22.168 | 52.974 | 1.00 | 32.09 | AAAA |
| ATOM | 1606 | CB | LYS | A | 202 | 19.565 | 21.750 | 52.811 | 1.00 | 33.02 | AAAA |
| ATOM | 1607 | CG | LYS | A | 202 | 19.836 | 20.847 | 51.623 | 1.00 | 34.95 | AAAA |
| ATOM | 1608 | CD | LYS | A | 202 | 21.334 | 20.619 | 51.436 | 1.00 | 37.92 | AAAA |
| ATOM | 1609 | CE | LYS | A | 202 | 21.655 | 19.804 | 50.169 | 1.00 | 39.19 | AAAA |
| ATOM | 1610 | NZ | LYS | A | 202 | 23.120 | 19.522 | 49.988 | 1.00 | 38.58 | AAAA |
| ATOM | 1611 | C | LYS | A | 202 | 17.995 | 23.241 | 54.037 | 1.00 | 30.85 | AAAA |
| ATOM | 1612 | O | LYS | A | 202 | 17.706 | 24.389 | 53.739 | 1.00 | 30.49 | AAAA |
| ATOM | 1613 | N | GLY | A | 203 | 18.238 | 22.867 | 55.281 | 1.00 | 30.81 | AAAA |
| ATOM | 1614 | CA | GLY | A | 203 | 18.159 | 23.831 | 56.356 | 1.00 | 30.86 | AAAA |
| ATOM | 1615 | C | GLY | A | 203 | 16.991 | 23.578 | 57.280 | 1.00 | 30.84 | AAAA |
| ATOM | 1616 | O | GLY | A | 203 | 16.828 | 24.285 | 58.272 | 1.00 | 31.58 | AAAA |
| ATOM | 1617 | N | PHE | A | 204 | 16.182 | 22.570 | 56.965 | 1.00 | 30.54 | AAAA |
| ATOM | 1618 | CA | PHE | A | 204 | 15.025 | 22.241 | 57.797 | 1.00 | 30.51 | AAAA |
| ATOM | 1619 | CB | PHE | A | 204 | 14.061 | 21.317 | 57.058 | 1.00 | 29.06 | AAAA |
| ATOM | 1620 | CG | PHE | A | 204 | 13.524 | 21.890 | 55.787 | 1.00 | 27.13 | AAAA |
| ATOM | 1621 | CD1 | PHE | A | 204 | 14.222 | 21.762 | 54.601 | 1.00 | 26.52 | AAAA |
| ATOM | 1622 | CD2 | PHE | A | 204 | 12.307 | 22.548 | 55.779 | 1.00 | 26.50 | AAAA |
| ATOM | 1623 | CE1 | PHE | A | 204 | 13.713 | 22.276 | 53.420 | 1.00 | 26.44 | AAAA |
| ATOM | 1624 | CE2 | PHE | A | 204 | 11.786 | 23.069 | 54.600 | 1.00 | 26.69 | AAAA |
| ATOM | 1625 | CZ | PHE | A | 204 | 12.490 | 22.931 | 53.416 | 1.00 | 25.65 | AAAA |
| ATOM | 1626 | C | PHE | A | 204 | 15.401 | 21.590 | 59.127 | 1.00 | 30.87 | AAAA |
| ATOM | 1627 | O | PHE | A | 204 | 16.395 | 20.875 | 59.228 | 1.00 | 31.12 | AAAA |
| ATOM | 1628 | N | LEU | A | 205 | 14.580 | 21.844 | 60.139 | 1.00 | 31.22 | AAAA |
| ATOM | 1629 | CA | LEU | A | 205 | 14.782 | 21.329 | 61.489 | 1.00 | 31.43 | AAAA |
| ATOM | 1630 | CB | LEU | A | 205 | 13.575 | 21.691 | 62.357 | 1.00 | 31.42 | AAAA |
| ATOM | 1631 | CG | LEU | A | 205 | 13.603 | 21.078 | 63.755 | 1.00 | 31.76 | AAAA |
| ATOM | 1632 | CD1 | LEU | A | 205 | 14.894 | 21.492 | 64.457 | 1.00 | 32.36 | AAAA |
| ATOM | 1633 | CD2 | LEU | A | 205 | 12.379 | 21.516 | 64.536 | 1.00 | 31.31 | AAAA |
| ATOM | 1634 | C | LEU | A | 205 | 15.026 | 19.829 | 61.625 | 1.00 | 31.35 | AAAA |
| ATOM | 1635 | O | LEU | A | 205 | 15.714 | 19.392 | 62.546 | 1.00 | 31.40 | AAAA |
| ATOM | 1636 | N | GLU | A | 206 | 14.448 | 19.059 | 60.707 | 1.00 | 31.79 | AAAA |
| ATOM | 1637 | CA | GLU | A | 206 | 14.509 | 17.603 | 60.706 | 1.00 | 32.08 | AAAA |
| ATOM | 1638 | CB | GLU | A | 206 | 13.485 | 17.054 | 59.716 | 1.00 | 33.18 | AAAA |
| ATOM | 1639 | CG | GLU | A | 206 | 12.069 | 17.651 | 59.829 | 1.00 | 34.20 | AAAA |
| ATOM | 1640 | CD | GLU | A | 206 | 11.973 | 19.136 | 59.453 | 1.00 | 33.44 | AAAA |
| ATOM | 1641 | OE1 | GLU | A | 206 | 10.854 | 19.675 | 59.422 | 1.00 | 33.32 | AAAA |
| ATOM | 1642 | OE2 | GLU | A | 206 | 13.005 | 19.777 | 59.194 | 1.00 | 35.12 | AAAA |
| ATOM | 1643 | C | GLU | A | 206 | 15.882 | 17.045 | 60.363 | 1.00 | 32.34 | AAAA |
| ATOM | 1644 | O | GLU | A | 206 | 16.209 | 15.909 | 60.706 | 1.00 | 31.83 | AAAA |
| ATOM | 1645 | N | GLU | A | 207 | 16.680 | 17.847 | 59.670 | 1.00 | 32.48 | AAAA |
| ATOM | 1646 | CA | GLU | A | 207 | 18.017 | 17.431 | 59.287 | 1.00 | 31.67 | AAAA |
| ATOM | 1647 | CB | GLU | A | 207 | 18.552 | 18.385 | 58.238 | 1.00 | 30.39 | AAAA |
| ATOM | 1648 | CG | GLU | A | 207 | 17.768 | 18.316 | 56.960 | 1.00 | 29.63 | AAAA |
| ATOM | 1649 | CD | GLU | A | 207 | 17.953 | 19.547 | 56.121 | 1.00 | 30.04 | AAAA |
| ATOM | 1650 | OE1 | GLU | A | 207 | 19.108 | 19.991 | 55.971 | 1.00 | 30.31 | AAAA |

Fig. 19-25

| | | | | | | | | | | |
|---|---|---|---|---|---|---|---|---|---|---|
| ATOM | 1651 | OE2 | GLU | A | 207 | 16.947 | 20.070 | 55.604 | 1.00 30.76 | AAAA |
| ATOM | 1652 | C | GLU | A | 207 | 18.879 | 17.433 | 60.537 | 1.00 32.04 | AAAA |
| ATOM | 1653 | O | GLU | A | 207 | 19.472 | 18.448 | 60.910 | 1.00 31.57 | AAAA |
| ATOM | 1654 | N | ILE | A | 208 | 18.935 | 16.272 | 61.178 | 1.00 32.57 | AAAA |
| ATOM | 1655 | CA | ILE | A | 208 | 19.674 | 16.111 | 62.408 | 1.00 33.37 | AAAA |
| ATOM | 1656 | CB | ILE | A | 208 | 18.709 | 15.647 | 63.519 | 1.00 33.65 | AAAA |
| ATOM | 1657 | CG2 | ILE | A | 208 | 19.443 | 15.380 | 64.806 | 1.00 34.11 | AAAA |
| ATOM | 1658 | CG1 | ILE | A | 208 | 17.673 | 16.742 | 63.757 | 1.00 33.94 | AAAA |
| ATOM | 1659 | CD1 | ILE | A | 208 | 16.628 | 16.386 | 64.794 | 1.00 37.00 | AAAA |
| ATOM | 1660 | C | ILE | A | 208 | 20.863 | 15.174 | 62.280 | 1.00 34.00 | AAAA |
| ATOM | 1661 | O | ILE | A | 208 | 21.506 | 14.829 | 63.265 | 1.00 34.40 | AAAA |
| ATOM | 1662 | N | GLY | A | 209 | 21.177 | 14.768 | 61.062 | 1.00 34.64 | AAAA |
| ATOM | 1663 | CA | GLY | A | 209 | 22.321 | 13.903 | 60.913 | 1.00 35.55 | AAAA |
| ATOM | 1664 | C | GLY | A | 209 | 22.164 | 12.671 | 60.057 | 1.00 36.80 | AAAA |
| ATOM | 1665 | O | GLY | A | 209 | 21.148 | 12.461 | 59.400 | 1.00 37.32 | AAAA |
| ATOM | 1666 | N | GLU | A | 210 | 23.199 | 11.836 | 60.100 | 1.00 37.78 | AAAA |
| ATOM | 1667 | CA | GLU | A | 210 | 23.256 | 10.621 | 59.315 | 1.00 38.04 | AAAA |
| ATOM | 1668 | CB | GLU | A | 210 | 23.600 | 11.013 | 57.892 | 1.00 38.54 | AAAA |
| ATOM | 1669 | CG | GLU | A | 210 | 23.469 | 9.960 | 56.858 | 1.00 38.99 | AAAA |
| ATOM | 1670 | CD | GLU | A | 210 | 24.118 | 10.412 | 55.580 | 1.00 40.10 | AAAA |
| ATOM | 1671 | OE1 | GLU | A | 210 | 25.365 | 10.437 | 55.555 | 1.00 40.86 | AAAA |
| ATOM | 1672 | OE2 | GLU | A | 210 | 23.396 | 10.767 | 54.619 | 1.00 40.41 | AAAA |
| ATOM | 1673 | C | GLU | A | 210 | 24.377 | 9.770 | 59.894 | 1.00 37.98 | AAAA |
| ATOM | 1674 | O | GLU | A | 210 | 25.498 | 10.244 | 60.041 | 1.00 38.52 | AAAA |
| ATOM | 1675 | N | GLY | A | 211 | 24.085 | 8.517 | 60.220 | 1.00 38.02 | AAAA |
| ATOM | 1676 | CA | GLY | A | 211 | 25.116 | 7.654 | 60.770 | 1.00 38.09 | AAAA |
| ATOM | 1677 | C | GLY | A | 211 | 25.542 | 8.075 | 62.164 | 1.00 38.26 | AAAA |
| ATOM | 1678 | O | GLY | A | 211 | 24.697 | 8.443 | 62.977 | 1.00 37.82 | AAAA |
| ATOM | 1679 | N | LYS | A | 212 | 26.848 | 8.030 | 62.434 | 1.00 38.20 | AAAA |
| ATOM | 1680 | CA | LYS | A | 212 | 27.396 | 8.399 | 63.743 | 1.00 37.56 | AAAA |
| ATOM | 1681 | CB | LYS | A | 212 | 28.921 | 8.209 | 63.766 | 1.00 38.86 | AAAA |
| ATOM | 1682 | CG | LYS | A | 212 | 29.416 | 6.810 | 63.385 | 1.00 40.93 | AAAA |
| ATOM | 1683 | CD | LYS | A | 212 | 29.001 | 5.746 | 64.405 | 1.00 42.04 | AAAA |
| ATOM | 1684 | CE | LYS | A | 212 | 29.251 | 4.318 | 63.891 | 1.00 42.80 | AAAA |
| ATOM | 1685 | NZ | LYS | A | 212 | 30.673 | 4.002 | 63.562 | 1.00 42.32 | AAAA |
| ATOM | 1686 | C | LYS | A | 212 | 27.093 | 9.859 | 64.054 | 1.00 37.08 | AAAA |
| ATOM | 1687 | O | LYS | A | 212 | 27.075 | 10.269 | 65.218 | 1.00 36.94 | AAAA |
| ATOM | 1688 | N | GLY | A | 213 | 26.854 | 10.636 | 63.002 | 1.00 35.41 | AAAA |
| ATOM | 1689 | CA | GLY | A | 213 | 26.592 | 12.054 | 63.170 | 1.00 34.24 | AAAA |
| ATOM | 1690 | C | GLY | A | 213 | 25.163 | 12.438 | 63.470 | 1.00 33.27 | AAAA |
| ATOM | 1691 | O | GLY | A | 213 | 24.861 | 13.611 | 63.666 | 1.00 33.29 | AAAA |
| ATOM | 1692 | N | LYS | A | 214 | 24.280 | 11.451 | 63.512 | 1.00 31.79 | AAAA |
| ATOM | 1693 | CA | LYS | A | 214 | 22.883 | 11.710 | 63.794 | 1.00 30.47 | AAAA |
| ATOM | 1694 | CB | LYS | A | 214 | 22.111 | 10.396 | 63.737 | 1.00 30.35 | AAAA |
| ATOM | 1695 | CG | LYS | A | 214 | 20.676 | 10.552 | 63.280 | 1.00 30.45 | AAAA |
| ATOM | 1696 | CD | LYS | A | 214 | 20.141 | 9.241 | 62.759 | 1.00 29.75 | AAAA |
| ATOM | 1697 | CE | LYS | A | 214 | 18.737 | 9.400 | 62.229 | 1.00 30.19 | AAAA |
| ATOM | 1698 | NZ | LYS | A | 214 | 18.179 | 8.138 | 61.671 | 1.00 31.35 | AAAA |
| ATOM | 1699 | C | LYS | A | 214 | 22.778 | 12.374 | 65.168 | 1.00 30.31 | AAAA |
| ATOM | 1700 | O | LYS | A | 214 | 23.193 | 11.814 | 66.177 | 1.00 30.44 | AAAA |
| ATOM | 1701 | N | GLY | A | 215 | 22.243 | 13.590 | 65.192 | 1.00 29.95 | AAAA |
| ATOM | 1702 | CA | GLY | A | 215 | 22.128 | 14.325 | 66.437 | 1.00 29.16 | AAAA |
| ATOM | 1703 | C | GLY | A | 215 | 23.222 | 15.379 | 66.582 | 1.00 28.54 | AAAA |
| ATOM | 1704 | O | GLY | A | 215 | 23.306 | 16.061 | 67.602 | 1.00 28.27 | AAAA |
| ATOM | 1705 | N | TYR | A | 216 | 24.063 | 15.521 | 65.561 | 1.00 27.35 | AAAA |
| ATOM | 1706 | CA | TYR | A | 216 | 25.150 | 16.497 | 65.616 | 1.00 27.08 | AAAA |
| ATOM | 1707 | CB | TYR | A | 216 | 26.516 | 15.800 | 65.531 | 1.00 28.38 | AAAA |
| ATOM | 1708 | CG | TYR | A | 216 | 26.786 | 14.966 | 66.757 | 1.00 30.21 | AAAA |
| ATOM | 1709 | CD1 | TYR | A | 216 | 26.138 | 13.735 | 66.955 | 1.00 29.81 | AAAA |
| ATOM | 1710 | CE1 | TYR | A | 216 | 26.311 | 13.014 | 68.138 | 1.00 30.03 | AAAA |
| ATOM | 1711 | CD2 | TYR | A | 216 | 27.619 | 15.450 | 67.774 | 1.00 29.71 | AAAA |
| ATOM | 1712 | CE2 | TYR | A | 216 | 27.798 | 14.741 | 68.957 | 1.00 29.96 | AAAA |
| ATOM | 1713 | CZ | TYR | A | 216 | 27.143 | 13.528 | 69.138 | 1.00 30.84 | AAAA |
| ATOM | 1714 | OH | TYR | A | 216 | 27.297 | 12.859 | 70.332 | 1.00 31.14 | AAAA |
| ATOM | 1715 | C | TYR | A | 216 | 25.055 | 17.599 | 64.581 | 1.00 25.40 | AAAA |
| ATOM | 1716 | O | TYR | A | 216 | 26.046 | 18.240 | 64.243 | 1.00 26.38 | AAAA |

Fig. 19-26

| | | | | | | | | | | |
|---|---|---|---|---|---|---|---|---|---|---|
| ATOM | 1717 | N | ASN | A | 217 | 23.845 | 17.791 | 64.076 | 1.00 23.55 | AAAA |
| ATOM | 1718 | CA | ASN | A | 217 | 23.549 | 18.830 | 63.119 | 1.00 21.52 | AAAA |
| ATOM | 1719 | CB | ASN | A | 217 | 23.431 | 18.282 | 61.699 | 1.00 20.64 | AAAA |
| ATOM | 1720 | CG | ASN | A | 217 | 23.202 | 19.386 | 60.669 | 1.00 20.29 | AAAA |
| ATOM | 1721 | OD1 | ASN | A | 217 | 22.089 | 19.888 | 60.499 | 1.00 18.03 | AAAA |
| ATOM | 1722 | ND2 | ASN | A | 217 | 24.274 | 19.790 | 60.004 | 1.00 19.95 | AAAA |
| ATOM | 1723 | C | ASN | A | 217 | 22.216 | 19.346 | 63.605 | 1.00 21.64 | AAAA |
| ATOM | 1724 | O | ASN | A | 217 | 21.263 | 18.576 | 63.757 | 1.00 20.34 | AAAA |
| ATOM | 1725 | N | LEU | A | 218 | 22.165 | 20.647 | 63.873 | 1.00 22.22 | AAAA |
| ATOM | 1726 | CA | LEU | A | 218 | 20.960 | 21.282 | 64.388 | 1.00 22.03 | AAAA |
| ATOM | 1727 | CB | LEU | A | 218 | 21.195 | 21.711 | 65.840 | 1.00 20.97 | AAAA |
| ATOM | 1728 | CG | LEU | A | 218 | 20.051 | 21.838 | 66.841 | 1.00 20.94 | AAAA |
| ATOM | 1729 | CD1 | LEU | A | 218 | 20.513 | 22.744 | 67.936 | 1.00 20.31 | AAAA |
| ATOM | 1730 | CD2 | LEU | A | 218 | 18.818 | 22.412 | 66.227 | 1.00 21.27 | AAAA |
| ATOM | 1731 | C | LEU | A | 218 | 20.669 | 22.513 | 63.547 | 1.00 22.70 | AAAA |
| ATOM | 1732 | O | LEU | A | 218 | 21.451 | 23.454 | 63.557 | 1.00 22.64 | AAAA |
| ATOM | 1733 | N | ASN | A | 219 | 19.564 | 22.491 | 62.808 | 1.00 24.00 | AAAA |
| ATOM | 1734 | CA | ASN | A | 219 | 19.166 | 23.626 | 61.990 | 1.00 25.33 | AAAA |
| ATOM | 1735 | CB | ASN | A | 219 | 18.656 | 23.190 | 60.614 | 1.00 26.94 | AAAA |
| ATOM | 1736 | CG | ASN | A | 219 | 19.737 | 22.601 | 59.749 | 1.00 26.68 | AAAA |
| ATOM | 1737 | OD1 | ASN | A | 219 | 20.812 | 23.169 | 59.626 | 1.00 28.06 | AAAA |
| ATOM | 1738 | ND2 | ASN | A | 219 | 19.446 | 21.471 | 59.117 | 1.00 26.26 | AAAA |
| ATOM | 1739 | C | ASN | A | 219 | 18.046 | 24.345 | 62.710 | 1.00 25.69 | AAAA |
| ATOM | 1740 | O | ASN | A | 219 | 17.118 | 23.706 | 63.210 | 1.00 27.51 | AAAA |
| ATOM | 1741 | N | ILE | A | 220 | 18.122 | 25.667 | 62.753 | 1.00 25.05 | AAAA |
| ATOM | 1742 | CA | ILE | A | 220 | 17.107 | 26.457 | 63.428 | 1.00 25.87 | AAAA |
| ATOM | 1743 | CB | ILE | A | 220 | 17.733 | 27.331 | 64.557 | 1.00 25.04 | AAAA |
| ATOM | 1744 | CG2 | ILE | A | 220 | 16.654 | 28.152 | 65.227 | 1.00 25.24 | AAAA |
| ATOM | 1745 | CG1 | ILE | A | 220 | 18.460 | 26.447 | 65.584 | 1.00 24.07 | AAAA |
| ATOM | 1746 | CD1 | ILE | A | 220 | 17.557 | 25.502 | 66.378 | 1.00 22.28 | AAAA |
| ATOM | 1747 | C | ILE | A | 220 | 16.430 | 27.370 | 62.414 | 1.00 26.20 | AAAA |
| ATOM | 1748 | O | ILE | A | 220 | 16.801 | 28.534 | 62.265 | 1.00 25.35 | AAAA |
| ATOM | 1749 | N | PRO | A | 221 | 15.421 | 26.850 | 61.704 | 1.00 26.70 | AAAA |
| ATOM | 1750 | CD | PRO | A | 221 | 14.840 | 25.501 | 61.778 | 1.00 27.17 | AAAA |
| ATOM | 1751 | CA | PRO | A | 221 | 14.706 | 27.640 | 60.703 | 1.00 27.67 | AAAA |
| ATOM | 1752 | CB | PRO | A | 221 | 13.771 | 26.613 | 60.064 | 1.00 26.81 | AAAA |
| ATOM | 1753 | CG | PRO | A | 221 | 14.473 | 25.293 | 60.346 | 1.00 27.36 | AAAA |
| ATOM | 1754 | C | PRO | A | 221 | 13.944 | 28.763 | 61.390 | 1.00 28.61 | AAAA |
| ATOM | 1755 | O | PRO | A | 221 | 13.218 | 28.515 | 62.363 | 1.00 29.91 | AAAA |
| ATOM | 1756 | N | LEU | A | 222 | 14.100 | 29.990 | 60.900 | 1.00 28.15 | AAAA |
| ATOM | 1757 | CA | LEU | A | 222 | 13.408 | 31.117 | 61.511 | 1.00 28.48 | AAAA |
| ATOM | 1758 | CB | LEU | A | 222 | 14.431 | 32.041 | 62.191 | 1.00 28.69 | AAAA |
| ATOM | 1759 | CG | LEU | A | 222 | 15.187 | 31.394 | 63.371 | 1.00 28.67 | AAAA |
| ATOM | 1760 | CD1 | LEU | A | 222 | 16.304 | 32.300 | 63.837 | 1.00 28.62 | AAAA |
| ATOM | 1761 | CD2 | LEU | A | 222 | 14.231 | 31.106 | 64.527 | 1.00 27.65 | AAAA |
| ATOM | 1762 | C | LEU | A | 222 | 12.726 | 31.882 | 60.518 | 1.00 28.44 | AAAA |
| ATOM | 1763 | O | LEU | A | 222 | 12.318 | 31.958 | 59.325 | 1.00 27.90 | AAAA |
| ATOM | 1764 | N | PRO | A | 223 | 11.113 | 32.441 | 61.009 | 1.00 28.79 | AAAA |
| ATOM | 1765 | CD | PRO | A | 223 | 10.966 | 32.357 | 62.410 | 1.00 29.20 | AAAA |
| ATOM | 1766 | CA | PRO | A | 223 | 10.437 | 33.202 | 60.227 | 1.00 29.36 | AAAA |
| ATOM | 1767 | CB | PRO | A | 223 | 9.256 | 33.287 | 61.183 | 1.00 28.98 | AAAA |
| ATOM | 1768 | CG | PRO | A | 223 | 9.965 | 33.502 | 62.485 | 1.00 28.68 | AAAA |
| ATOM | 1769 | C | PRO | A | 223 | 10.890 | 34.585 | 59.753 | 1.00 30.15 | AAAA |
| ATOM | 1770 | O | PRO | A | 223 | 11.864 | 35.152 | 60.253 | 1.00 30.18 | AAAA |
| ATOM | 1771 | N | LYS | A | 224 | 10.150 | 35.112 | 58.781 | 1.00 30.50 | AAAA |
| ATOM | 1772 | CA | LYS | A | 224 | 10.398 | 36.422 | 58.213 | 1.00 29.92 | AAAA |
| ATOM | 1773 | CB | LYS | A | 224 | 9.491 | 36.661 | 57.008 | 1.00 30.57 | AAAA |
| ATOM | 1774 | CG | LYS | A | 224 | 9.588 | 35.676 | 55.893 | 1.00 30.06 | AAAA |
| ATOM | 1775 | CD | LYS | A | 224 | 8.640 | 36.087 | 54.798 | 1.00 30.91 | AAAA |
| ATOM | 1776 | CE | LYS | A | 224 | 8.575 | 35.051 | 53.705 | 1.00 32.15 | AAAA |
| ATOM | 1777 | NZ | LYS | A | 224 | 7.628 | 35.476 | 52.648 | 1.00 32.75 | AAAA |
| ATOM | 1778 | C | LYS | A | 224 | 10.050 | 37.468 | 59.260 | 1.00 29.75 | AAAA |
| ATOM | 1779 | O | LYS | A | 224 | 9.308 | 37.193 | 60.196 | 1.00 29.84 | AAAA |
| ATOM | 1780 | N | GLY | A | 225 | 10.555 | 38.678 | 59.079 | 1.00 29.39 | AAAA |
| ATOM | 1781 | CA | GLY | A | 225 | 10.261 | 39.730 | 60.031 | 1.00 29.87 | AAAA |
| ATOM | 1782 | C | GLY | A | 225 | 10.809 | 39.447 | 61.415 | 1.00 29.85 | AAAA |

Fig. 19-27

```
ATOM   1783  O    GLY A 225      10.371  40.051  62.392  1.00 29.85      AAAA
ATOM   1784  N    LEU A 226      11.775  38.536  61.499  1.00 29.50      AAAA
ATOM   1785  CA   LEU A 226      12.374  38.175  62.778  1.00 29.80      AAAA
ATOM   1786  CB   LEU A 226      13.513  37.170  62.570  1.00 28.81      AAAA
ATOM   1787  CG   LEU A 226      14.097  36.514  63.820  1.00 27.29      AAAA
ATOM   1788  CD1  LEU A 226      13.132  35.452  64.275  1.00 26.06      AAAA
ATOM   1789  CD2  LEU A 226      15.455  35.888  63.538  1.00 27.03      AAAA
ATOM   1790  C    LEU A 226      12.936  39.428  63.448  1.00 30.68      AAAA
ATOM   1791  O    LEU A 226      13.636  40.217  62.804  1.00 30.57      AAAA
ATOM   1792  N    ASN A 227      12.624  39.617  64.729  1.00 31.46      AAAA
ATOM   1793  CA   ASN A 227      13.139  40.769  65.469  1.00 32.06      AAAA
ATOM   1794  CB   ASN A 227      12.012  41.507  66.217  1.00 31.74      AAAA
ATOM   1795  CG   ASN A 227      11.291  40.630  67.234  1.00 32.07      AAAA
ATOM   1796  OD1  ASN A 227      11.914  40.017  68.104  1.00 31.61      AAAA
ATOM   1797  ND2  ASN A 227       9.962  40.592  67.141  1.00 31.59      AAAA
ATOM   1798  C    ASN A 227      14.225  40.334  66.444  1.00 32.45      AAAA
ATOM   1799  O    ASN A 227      14.413  39.140  66.688  1.00 32.78      AAAA
ATOM   1800  N    ASP A 228      14.943  41.297  67.002  1.00 33.32      AAAA
ATOM   1801  CA   ASP A 228      16.017  40.976  67.928  1.00 34.75      AAAA
ATOM   1802  CB   ASP A 228      16.508  42.233  68.654  1.00 36.77      AAAA
ATOM   1803  CG   ASP A 228      17.154  43.238  67.714  1.00 37.28      AAAA
ATOM   1804  OD1  ASP A 228      17.662  42.816  66.652  1.00 37.78      AAAA
ATOM   1805  OD2  ASP A 228      17.180  44.443  68.054  1.00 37.21      AAAA
ATOM   1806  C    ASP A 228      15.707  39.892  68.964  1.00 34.93      AAAA
ATOM   1807  O    ASP A 228      16.448  38.919  69.056  1.00 36.92      AAAA
ATOM   1808  N    ASN A 229      14.635  40.054  69.741  1.00 33.90      AAAA
ATOM   1809  CA   ASN A 229      14.268  39.079  70.775  1.00 33.01      AAAA
ATOM   1810  CB   ASN A 229      12.965  39.481  71.455  1.00 33.79      AAAA
ATOM   1811  CG   ASN A 229      13.131  40.663  72.369  1.00 34.04      AAAA
ATOM   1812  OD1  ASN A 229      13.783  40.564  73.405  1.00 34.25      AAAA
ATOM   1813  ND2  ASN A 229      12.550  41.797  71.988  1.00 34.05      AAAA
ATOM   1814  C    ASN A 229      14.114  37.656  70.276  1.00 32.98      AAAA
ATOM   1815  O    ASN A 229      14.529  36.697  70.944  1.00 32.77      AAAA
ATOM   1816  N    GLU A 230      13.496  37.523  69.108  1.00 32.02      AAAA
ATOM   1817  CA   GLU A 230      13.277  36.227  68.516  1.00 30.72      AAAA
ATOM   1818  CB   GLU A 230      12.399  36.375  67.272  1.00 31.38      AAAA
ATOM   1819  CG   GLU A 230      11.006  36.896  67.583  1.00 31.02      AAAA
ATOM   1820  CD   GLU A 230      10.175  37.187  66.350  1.00 31.52      AAAA
ATOM   1821  OE1  GLU A 230      10.644  37.970  65.497  1.00 31.89      AAAA
ATOM   1822  OE2  GLU A 230       9.047  36.655  66.241  1.00 31.04      AAAA
ATOM   1823  C    GLU A 230      14.628  35.622  68.180  1.00 30.79      AAAA
ATOM   1824  O    GLU A 230      14.905  34.465  68.512  1.00 31.05      AAAA
ATOM   1825  N    PHE A 231      15.490  36.412  67.553  1.00 30.05      AAAA
ATOM   1826  CA   PHE A 231      16.811  35.920  67.191  1.00 28.94      AAAA
ATOM   1827  CB   PHE A 231      17.632  37.015  66.528  1.00 29.33      AAAA
ATOM   1828  CG   PHE A 231      18.949  36.537  65.972  1.00 28.79      AAAA
ATOM   1829  CD1  PHE A 231      18.982  35.585  64.957  1.00 28.93      AAAA
ATOM   1830  CD2  PHE A 231      20.152  37.067  66.436  1.00 28.55      AAAA
ATOM   1831  CE1  PHE A 231      20.195  35.160  64.397  1.00 28.32      AAAA
ATOM   1832  CE2  PHE A 231      21.376  36.657  65.888  1.00 28.97      AAAA
ATOM   1833  CZ   PHE A 231      21.397  35.695  64.860  1.00 28.81      AAAA
ATOM   1834  C    PHE A 231      17.559  35.443  68.413  1.00 28.25      AAAA
ATOM   1835  O    PHE A 231      17.999  34.302  68.485  1.00 27.97      AAAA
ATOM   1836  N    LEU A 232      17.691  36.329  69.384  1.00 27.93      AAAA
ATOM   1837  CA   LEU A 232      18.425  36.003  70.590  1.00 27.93      AAAA
ATOM   1838  CB   LEU A 232      18.521  37.234  71.484  1.00 28.16      AAAA
ATOM   1839  CG   LEU A 232      19.220  38.379  70.747  1.00 27.96      AAAA
ATOM   1840  CD1  LEU A 232      19.203  39.629  71.587  1.00 27.57      AAAA
ATOM   1841  CD2  LEU A 232      20.639  37.955  70.387  1.00 27.76      AAAA
ATOM   1842  C    LEU A 232      17.815  34.851  71.340  1.00 27.95      AAAA
ATOM   1843  O    LEU A 232      18.526  34.061  71.941  1.00 27.92      AAAA
ATOM   1844  N    PHE A 233      16.495  34.758  71.298  1.00 28.81      AAAA
ATOM   1845  CA   PHE A 233      15.786  33.685  71.972  1.00 30.27      AAAA
ATOM   1846  CB   PHE A 233      14.278  33.837  71.745  1.00 31.51      AAAA
ATOM   1847  CG   PHE A 233      13.465  32.710  72.308  1.00 32.38      AAAA
ATOM   1848  CD1  PHE A 233      13.257  32.599  73.677  1.00 33.66      AAAA
```

Fig. 19-28

| | | | | | | | | | | |
|---|---|---|---|---|---|---|---|---|---|---|
| ATOM | 1849 | CD2 | PHE | A | 233 | 12.928 | 31.741 | 71.467 | 1.00 33.51 | AAAA |
| ATOM | 1850 | CE1 | PHE | A | 233 | 12.518 | 31.537 | 74.201 | 1.00 35.10 | AAAA |
| ATOM | 1851 | CE2 | PHE | A | 233 | 12.193 | 30.677 | 71.975 | 1.00 34.21 | AAAA |
| ATOM | 1852 | CZ | PHE | A | 233 | 11.986 | 30.572 | 73.344 | 1.00 35.23 | AAAA |
| ATOM | 1853 | C | PHE | A | 233 | 16.219 | 32.301 | 71.483 | 1.00 30.55 | AAAA |
| ATOM | 1854 | O | PHE | A | 233 | 16.438 | 31.391 | 72.280 | 1.00 30.65 | AAAA |
| ATOM | 1855 | N | ALA | A | 234 | 16.317 | 32.151 | 70.165 | 1.00 30.21 | AAAA |
| ATOM | 1856 | CA | ALA | A | 234 | 16.698 | 30.892 | 69.549 | 1.00 28.97 | AAAA |
| ATOM | 1857 | CB | ALA | A | 234 | 16.398 | 30.942 | 68.065 | 1.00 30.40 | AAAA |
| ATOM | 1858 | C | ALA | A | 234 | 18.169 | 30.571 | 69.761 | 1.00 28.27 | AAAA |
| ATOM | 1859 | O | ALA | A | 234 | 18.564 | 29.401 | 69.830 | 1.00 26.69 | AAAA |
| ATOM | 1860 | N | LEU | A | 235 | 18.978 | 31.614 | 69.855 | 1.00 27.56 | AAAA |
| ATOM | 1861 | CA | LEU | A | 235 | 20.402 | 31.427 | 70.055 | 1.00 29.17 | AAAA |
| ATOM | 1862 | CB | LEU | A | 235 | 21.126 | 32.767 | 69.989 | 1.00 29.04 | AAAA |
| ATOM | 1863 | CG | LEU | A | 235 | 22.527 | 32.757 | 69.378 | 1.00 28.54 | AAAA |
| ATOM | 1864 | CD1 | LEU | A | 235 | 23.350 | 33.837 | 70.058 | 1.00 27.05 | AAAA |
| ATOM | 1865 | CD2 | LEU | A | 235 | 23.182 | 31.408 | 69.558 | 1.00 27.21 | AAAA |
| ATOM | 1866 | C | LEU | A | 235 | 20.637 | 30.799 | 71.429 | 1.00 30.99 | AAAA |
| ATOM | 1867 | O | LEU | A | 235 | 21.159 | 29.697 | 71.547 | 1.00 31.65 | AAAA |
| ATOM | 1868 | N | GLU | A | 236 | 20.242 | 31.514 | 72.471 | 1.00 31.88 | AAAA |
| ATOM | 1869 | CA | GLU | A | 236 | 20.409 | 31.042 | 73.838 | 1.00 32.99 | AAAA |
| ATOM | 1870 | CB | GLU | A | 236 | 19.689 | 31.990 | 74.790 | 1.00 34.63 | AAAA |
| ATOM | 1871 | CG | GLU | A | 236 | 19.980 | 33.449 | 74.531 | 1.00 36.79 | AAAA |
| ATOM | 1872 | CD | GLU | A | 236 | 19.044 | 34.360 | 75.294 | 1.00 38.99 | AAAA |
| ATOM | 1873 | OE1 | GLU | A | 236 | 17.803 | 34.303 | 75.070 | 1.00 39.03 | AAAA |
| ATOM | 1874 | OE2 | GLU | A | 236 | 19.559 | 35.132 | 76.126 | 1.00 41.56 | AAAA |
| ATOM | 1875 | C | GLU | A | 236 | 19.806 | 29.656 | 73.982 | 1.00 32.94 | AAAA |
| ATOM | 1876 | O | GLU | A | 236 | 20.379 | 28.753 | 74.595 | 1.00 31.76 | AAAA |
| ATOM | 1877 | N | LYS | A | 237 | 18.631 | 29.503 | 73.399 | 1.00 32.83 | AAAA |
| ATOM | 1878 | CA | LYS | A | 237 | 17.906 | 28.256 | 73.471 | 1.00 33.59 | AAAA |
| ATOM | 1879 | CB | LYS | A | 237 | 16.504 | 28.506 | 72.942 | 1.00 35.00 | AAAA |
| ATOM | 1880 | CG | LYS | A | 237 | 15.516 | 27.436 | 73.213 | 1.00 36.69 | AAAA |
| ATOM | 1881 | CD | LYS | A | 237 | 14.310 | 28.008 | 73.940 | 1.00 38.53 | AAAA |
| ATOM | 1882 | CE | LYS | A | 237 | 14.636 | 28.331 | 75.392 | 1.00 39.27 | AAAA |
| ATOM | 1883 | NZ | LYS | A | 237 | 13.398 | 28.531 | 76.204 | 1.00 39.42 | AAAA |
| ATOM | 1884 | C | LYS | A | 237 | 18.619 | 27.129 | 72.707 | 1.00 33.14 | AAAA |
| ATOM | 1885 | O | LYS | A | 237 | 18.850 | 26.051 | 73.260 | 1.00 33.29 | AAAA |
| ATOM | 1886 | N | SER | A | 238 | 18.985 | 27.374 | 71.452 | 1.00 32.13 | AAAA |
| ATOM | 1887 | CA | SER | A | 238 | 19.671 | 26.345 | 70.685 | 1.00 31.25 | AAAA |
| ATOM | 1888 | CB | SER | A | 238 | 19.740 | 26.717 | 69.194 | 1.00 30.52 | AAAA |
| ATOM | 1889 | OG | SER | A | 238 | 20.544 | 27.851 | 68.970 | 1.00 29.95 | AAAA |
| ATOM | 1890 | C | SER | A | 238 | 21.075 | 26.064 | 71.236 | 1.00 31.21 | AAAA |
| ATOM | 1891 | O | SER | A | 238 | 21.556 | 24.929 | 71.169 | 1.00 30.06 | AAAA |
| ATOM | 1892 | N | LEU | A | 239 | 21.740 | 27.077 | 71.782 | 1.00 31.71 | AAAA |
| ATOM | 1893 | CA | LEU | A | 239 | 23.070 | 26.842 | 72.351 | 1.00 33.47 | AAAA |
| ATOM | 1894 | CB | LEU | A | 239 | 23.698 | 28.130 | 72.900 | 1.00 31.25 | AAAA |
| ATOM | 1895 | CG | LEU | A | 239 | 23.988 | 29.301 | 71.977 | 1.00 29.80 | AAAA |
| ATOM | 1896 | CD1 | LEU | A | 239 | 24.589 | 30.414 | 72.787 | 1.00 29.05 | AAAA |
| ATOM | 1897 | CD2 | LEU | A | 239 | 24.919 | 28.903 | 70.872 | 1.00 29.36 | AAAA |
| ATOM | 1898 | C | LEU | A | 239 | 22.933 | 25.839 | 73.502 | 1.00 35.41 | AAAA |
| ATOM | 1899 | O | LEU | A | 239 | 23.812 | 25.012 | 73.735 | 1.00 36.25 | AAAA |
| ATOM | 1900 | N | GLU | A | 240 | 21.816 | 25.906 | 74.213 | 1.00 37.34 | AAAA |
| ATOM | 1901 | CA | GLU | A | 240 | 21.594 | 25.005 | 75.331 | 1.00 39.39 | AAAA |
| ATOM | 1902 | CB | GLU | A | 240 | 20.281 | 25.361 | 76.017 | 1.00 41.90 | AAAA |
| ATOM | 1903 | CG | GLU | A | 240 | 20.040 | 24.610 | 77.308 | 1.00 45.52 | AAAA |
| ATOM | 1904 | CD | GLU | A | 240 | 19.665 | 25.552 | 78.432 | 1.00 47.80 | AAAA |
| ATOM | 1905 | OE1 | GLU | A | 240 | 18.670 | 26.295 | 78.274 | 1.00 49.70 | AAAA |
| ATOM | 1906 | OE2 | GLU | A | 240 | 20.364 | 25.559 | 79.469 | 1.00 48.04 | AAAA |
| ATOM | 1907 | C | GLU | A | 240 | 21.583 | 23.555 | 74.875 | 1.00 38.80 | AAAA |
| ATOM | 1908 | O | GLU | A | 240 | 22.224 | 22.700 | 75.478 | 1.00 37.85 | AAAA |
| ATOM | 1909 | N | ILE | A | 241 | 20.847 | 23.293 | 73.804 | 1.00 39.66 | AAAA |
| ATOM | 1910 | CA | ILE | A | 241 | 20.751 | 21.955 | 73.223 | 1.00 40.81 | AAAA |
| ATOM | 1911 | CB | ILE | A | 241 | 19.912 | 21.994 | 71.917 | 1.00 41.10 | AAAA |
| ATOM | 1912 | CG2 | ILE | A | 241 | 19.850 | 20.621 | 71.287 | 1.00 40.88 | AAAA |
| ATOM | 1913 | CG1 | ILE | A | 241 | 18.502 | 22.514 | 72.220 | 1.00 41.45 | AAAA |
| ATOM | 1914 | CD1 | ILE | A | 241 | 17.641 | 22.745 | 70.992 | 1.00 41.14 | AAAA |

Fig. 19-29

```
ATOM   1915  C   ILE A 241    22.159  21.424  72.893  1.00 41.66      AAAA
ATOM   1916  O   ILE A 241    22.445  20.229  73.045  1.00 42.10      AAAA
ATOM   1917  N   VAL A 242    23.026  22.324  72.432  1.00 41.42      AAAA
ATOM   1918  CA  VAL A 242    24.394  21.977  72.076  1.00 41.23      AAAA
ATOM   1919  CB  VAL A 242    25.089  23.146  71.351  1.00 40.40      AAAA
ATOM   1920  CG1 VAL A 242    26.556  22.850  71.171  1.00 39.25      AAAA
ATOM   1921  CG2 VAL A 242    24.438  23.384  70.004  1.00 39.79      AAAA
ATOM   1922  C   VAL A 242    25.228  21.604  73.298  1.00 42.67      AAAA
ATOM   1923  O   VAL A 242    25.882  20.562  73.316  1.00 41.83      AAAA
ATOM   1924  N   LYS A 243    25.198  22.456  74.318  1.00 44.41      AAAA
ATOM   1925  CA  LYS A 243    25.972  22.215  75.523  1.00 46.51      AAAA
ATOM   1926  CB  LYS A 243    25.797  23.363  76.522  1.00 47.29      AAAA
ATOM   1927  CG  LYS A 243    26.820  23.312  77.664  1.00 48.40      AAAA
ATOM   1928  CD  LYS A 243    26.479  24.248  78.823  1.00 48.88      AAAA
ATOM   1929  CE  LYS A 243    26.355  25.691  78.380  1.00 49.62      AAAA
ATOM   1930  NZ  LYS A 243    25.926  26.576  79.505  1.00 50.11      AAAA
ATOM   1931  C   LYS A 243    25.639  20.891  76.209  1.00 47.59      AAAA
ATOM   1932  O   LYS A 243    26.537  20.216  76.711  1.00 48.17      AAAA
ATOM   1933  N   GLU A 244    24.362  20.517  76.237  1.00 48.86      AAAA
ATOM   1934  CA  GLU A 244    23.957  19.262  76.877  1.00 50.82      AAAA
ATOM   1935  CB  GLU A 244    22.432  19.208  77.103  1.00 52.08      AAAA
ATOM   1936  CG  GLU A 244    21.818  20.405  77.829  1.00 53.82      AAAA
ATOM   1937  CD  GLU A 244    20.359  20.174  78.230  1.00 54.49      AAAA
ATOM   1938  OE1 GLU A 244    19.666  21.158  78.595  1.00 55.15      AAAA
ATOM   1939  OE2 GLU A 244    19.912  19.006  78.200  1.00 54.98      AAAA
ATOM   1940  C   GLU A 244    24.338  18.046  76.033  1.00 51.06      AAAA
ATOM   1941  O   GLU A 244    24.206  16.905  76.477  1.00 51.68      AAAA
ATOM   1942  N   VAL A 245    24.810  18.292  74.820  1.00 51.12      AAAA
ATOM   1943  CA  VAL A 245    25.149  17.212  73.904  1.00 50.08      AAAA
ATOM   1944  CB  VAL A 245    24.217  17.263  72.677  1.00 50.22      AAAA
ATOM   1945  CG1 VAL A 245    24.615  16.217  71.651  1.00 51.07      AAAA
ATOM   1946  CG2 VAL A 245    22.794  17.049  73.118  1.00 50.79      AAAA
ATOM   1947  C   VAL A 245    26.578  17.254  73.397  1.00 49.43      AAAA
ATOM   1948  O   VAL A 245    27.101  16.250  72.917  1.00 48.65      AAAA
ATOM   1949  N   PHE A 246    27.220  18.408  73.522  1.00 48.65      AAAA
ATOM   1950  CA  PHE A 246    28.556  18.552  72.982  1.00 47.97      AAAA
ATOM   1951  CB  PHE A 246    28.420  19.212  71.607  1.00 46.45      AAAA
ATOM   1952  CG  PHE A 246    29.553  18.932  70.671  1.00 45.35      AAAA
ATOM   1953  CD1 PHE A 246    29.841  17.629  70.280  1.00 44.13      AAAA
ATOM   1954  CD2 PHE A 246    30.291  19.972  70.124  1.00 44.40      AAAA
ATOM   1955  CE1 PHE A 246    30.840  17.370  69.356  1.00 43.95      AAAA
ATOM   1956  CE2 PHE A 246    31.292  19.721  69.197  1.00 43.47      AAAA
ATOM   1957  CZ  PHE A 246    31.566  18.422  68.811  1.00 44.05      AAAA
ATOM   1958  C   PHE A 246    29.481  19.383  73.860  1.00 48.60      AAAA
ATOM   1959  O   PHE A 246    29.132  20.501  74.239  1.00 49.59      AAAA
ATOM   1960  N   GLU A 247    30.647  18.834  74.198  1.00 48.69      AAAA
ATOM   1961  CA  GLU A 247    31.644  19.578  74.977  1.00 49.45      AAAA
ATOM   1962  CB  GLU A 247    32.174  18.768  76.178  1.00 51.91      AAAA
ATOM   1963  CG  GLU A 247    31.257  18.659  77.398  1.00 54.39      AAAA
ATOM   1964  CD  GLU A 247    29.986  17.845  77.146  1.00 57.34      AAAA
ATOM   1965  OE1 GLU A 247    29.100  18.315  76.393  1.00 58.48      AAAA
ATOM   1966  OE2 GLU A 247    29.877  16.725  77.702  1.00 57.95      AAAA
ATOM   1967  C   GLU A 247    32.807  19.903  74.024  1.00 47.39      AAAA
ATOM   1968  O   GLU A 247    33.742  19.119  73.872  1.00 46.65      AAAA
ATOM   1969  N   PRO A 248    32.748  21.070  73.371  1.00 46.25      AAAA
ATOM   1970  CD  PRO A 248    31.651  22.033  73.543  1.00 46.49      AAAA
ATOM   1971  CA  PRO A 248    33.710  21.614  72.411  1.00 45.44      AAAA
ATOM   1972  CB  PRO A 248    33.063  22.948  72.017  1.00 45.57      AAAA
ATOM   1973  CG  PRO A 248    31.604  22.661  72.178  1.00 46.28      AAAA
ATOM   1974  C   PRO A 248    35.155  21.814  72.880  1.00 44.29      AAAA
ATOM   1975  O   PRO A 248    35.401  22.370  73.947  1.00 44.57      AAAA
ATOM   1976  N   GLU A 249    36.100  21.364  72.059  1.00 42.21      AAAA
ATOM   1977  CA  GLU A 249    37.522  21.526  72.340  1.00 39.87      AAAA
ATOM   1978  CB  GLU A 249    38.344  20.460  71.625  1.00 39.58      AAAA
ATOM   1979  CG  GLU A 249    37.960  19.030  71.957  1.00 41.32      AAAA
ATOM   1980  CD  GLU A 249    38.825  18.007  71.241  1.00 40.96      AAAA
```

Fig. 19-30

| | | | | | | | | | | |
|---|---|---|---|---|---|---|---|---|---|---|
| ATOM | 1981 | OE1 | GLU | A | 249 | 38.871 | 18.017 | 69.996 | 1.00 41.55 | AAAA |
| ATOM | 1982 | OE2 | GLU | A | 249 | 39.462 | 17.187 | 71.926 | 1.00 42.49 | AAAA |
| ATOM | 1983 | C | GLU | A | 249 | 37.840 | 22.873 | 71.718 | 1.00 38.81 | AAAA |
| ATOM | 1984 | O | GLU | A | 249 | 38.715 | 23.617 | 72.181 | 1.00 38.27 | AAAA |
| ATOM | 1985 | N | VAL | A | 250 | 37.109 | 23.160 | 70.644 | 1.00 36.60 | AAAA |
| ATOM | 1986 | CA | VAL | A | 250 | 37.242 | 24.402 | 69.890 | 1.00 34.20 | AAAA |
| ATOM | 1987 | CB | VAL | A | 250 | 38.379 | 24.321 | 68.862 | 1.00 33.73 | AAAA |
| ATOM | 1988 | CG1 | VAL | A | 250 | 38.085 | 23.209 | 67.864 | 1.00 33.26 | AAAA |
| ATOM | 1989 | CG2 | VAL | A | 250 | 38.546 | 25.678 | 68.153 | 1.00 33.75 | AAAA |
| ATOM | 1990 | C | VAL | A | 250 | 35.945 | 24.617 | 69.130 | 1.00 31.98 | AAAA |
| ATOM | 1991 | O | VAL | A | 250 | 35.205 | 23.658 | 68.904 | 1.00 32.36 | AAAA |
| ATOM | 1992 | N | TYR | A | 251 | 35.657 | 25.863 | 68.760 | 1.00 28.65 | AAAA |
| ATOM | 1993 | CA | TYR | A | 251 | 34.449 | 26.150 | 67.991 | 1.00 26.49 | AAAA |
| ATOM | 1994 | CB | TYR | A | 251 | 33.241 | 26.442 | 68.906 | 1.00 24.32 | AAAA |
| ATOM | 1995 | CG | TYR | A | 251 | 33.193 | 27.853 | 69.465 | 1.00 22.96 | AAAA |
| ATOM | 1996 | CD1 | TYR | A | 251 | 32.771 | 28.931 | 68.668 | 1.00 22.21 | AAAA |
| ATOM | 1997 | CE1 | TYR | A | 251 | 32.791 | 30.234 | 69.151 | 1.00 21.29 | AAAA |
| ATOM | 1998 | CD2 | TYR | A | 251 | 33.628 | 28.124 | 70.771 | 1.00 21.47 | AAAA |
| ATOM | 1999 | CE2 | TYR | A | 251 | 33.651 | 29.425 | 71.265 | 1.00 20.80 | AAAA |
| ATOM | 2000 | CZ | TYR | A | 251 | 33.237 | 30.475 | 70.449 | 1.00 20.77 | AAAA |
| ATOM | 2001 | OH | TYR | A | 251 | 33.309 | 31.768 | 70.913 | 1.00 21.41 | AAAA |
| ATOM | 2002 | C | TYR | A | 251 | 34.691 | 27.345 | 67.092 | 1.00 24.59 | AAAA |
| ATOM | 2003 | O | TYR | A | 251 | 35.504 | 28.216 | 67.410 | 1.00 25.87 | AAAA |
| ATOM | 2004 | N | LEU | A | 252 | 33.984 | 27.374 | 65.970 | 1.00 22.49 | AAAA |
| ATOM | 2005 | CA | LEU | A | 252 | 34.082 | 28.482 | 65.045 | 1.00 20.96 | AAAA |
| ATOM | 2006 | CB | LEU | A | 252 | 34.523 | 28.018 | 63.657 | 1.00 21.31 | AAAA |
| ATOM | 2007 | CG | LEU | A | 252 | 35.940 | 27.472 | 63.556 | 1.00 21.03 | AAAA |
| ATOM | 2008 | CD1 | LEU | A | 252 | 35.947 | 26.028 | 63.977 | 1.00 22.16 | AAAA |
| ATOM | 2009 | CD2 | LEU | A | 252 | 36.440 | 27.594 | 62.143 | 1.00 22.13 | AAAA |
| ATOM | 2010 | C | LEU | A | 252 | 32.731 | 29.159 | 64.959 | 1.00 19.60 | AAAA |
| ATOM | 2011 | O | LEU | A | 252 | 31.689 | 28.523 | 65.070 | 1.00 19.95 | AAAA |
| ATOM | 2012 | N | LEU | A | 253 | 32.748 | 30.461 | 64.756 | 1.00 17.95 | AAAA |
| ATOM | 2013 | CA | LEU | A | 253 | 31.521 | 31.222 | 64.675 | 1.00 17.33 | AAAA |
| ATOM | 2014 | CB | LEU | A | 253 | 31.441 | 32.142 | 65.900 | 1.00 16.31 | AAAA |
| ATOM | 2015 | CG | LEU | A | 253 | 30.266 | 33.070 | 66.153 | 1.00 15.81 | AAAA |
| ATOM | 2016 | CD1 | LEU | A | 253 | 28.990 | 32.267 | 66.377 | 1.00 14.74 | AAAA |
| ATOM | 2017 | CD2 | LEU | A | 253 | 30.602 | 33.925 | 67.368 | 1.00 15.83 | AAAA |
| ATOM | 2018 | C | LEU | A | 253 | 31.564 | 32.035 | 63.386 | 1.00 16.60 | AAAA |
| ATOM | 2019 | O | LEU | A | 253 | 32.548 | 32.722 | 63.132 | 1.00 16.40 | AAAA |
| ATOM | 2020 | N | GLN | A | 254 | 30.526 | 31.936 | 62.557 | 1.00 15.88 | AAAA |
| ATOM | 2021 | CA | GLN | A | 254 | 30.507 | 32.716 | 61.328 | 1.00 16.27 | AAAA |
| ATOM | 2022 | CB | GLN | A | 254 | 30.045 | 31.881 | 60.121 | 1.00 15.88 | AAAA |
| ATOM | 2023 | CG | GLN | A | 254 | 28.587 | 32.048 | 59.734 | 1.00 18.52 | AAAA |
| ATOM | 2024 | CD | GLN | A | 254 | 28.380 | 32.935 | 58.519 | 1.00 17.54 | AAAA |
| ATOM | 2025 | OE1 | GLN | A | 254 | 28.714 | 32.572 | 57.391 | 1.00 15.89 | AAAA |
| ATOM | 2026 | NE2 | GLN | A | 254 | 27.828 | 34.103 | 58.750 | 1.00 18.49 | AAAA |
| ATOM | 2027 | C | GLN | A | 254 | 29.527 | 33.825 | 61.650 | 1.00 16.91 | AAAA |
| ATOM | 2028 | O | GLN | A | 254 | 28.450 | 33.571 | 62.198 | 1.00 17.41 | AAAA |
| ATOM | 2029 | N | LEU | A | 255 | 29.911 | 35.053 | 61.319 | 1.00 16.68 | AAAA |
| ATOM | 2030 | CA | LEU | A | 255 | 29.102 | 36.215 | 61.619 | 1.00 16.42 | AAAA |
| ATOM | 2031 | CB | LEU | A | 255 | 29.861 | 37.080 | 62.616 | 1.00 14.93 | AAAA |
| ATOM | 2032 | CG | LEU | A | 255 | 30.269 | 36.301 | 63.860 | 1.00 13.90 | AAAA |
| ATOM | 2033 | CD1 | LEU | A | 255 | 31.494 | 36.924 | 64.515 | 1.00 12.24 | AAAA |
| ATOM | 2034 | CD2 | LEU | A | 255 | 29.083 | 36.202 | 64.774 | 1.00 12.80 | AAAA |
| ATOM | 2035 | C | LEU | A | 255 | 28.699 | 37.048 | 60.404 | 1.00 18.32 | AAAA |
| ATOM | 2036 | O | LEU | A | 255 | 29.170 | 38.177 | 60.216 | 1.00 17.59 | AAAA |
| ATOM | 2037 | N | GLY | A | 256 | 27.813 | 36.482 | 59.588 | 1.00 19.75 | AAAA |
| ATOM | 2038 | CA | GLY | A | 256 | 27.322 | 37.188 | 58.422 | 1.00 20.77 | AAAA |
| ATOM | 2039 | C | GLY | A | 256 | 26.422 | 38.302 | 58.927 | 1.00 21.73 | AAAA |
| ATOM | 2040 | O | GLY | A | 256 | 25.642 | 38.096 | 59.857 | 1.00 21.38 | AAAA |
| ATOM | 2041 | N | THR | A | 257 | 26.528 | 39.485 | 58.325 | 1.00 22.82 | AAAA |
| ATOM | 2042 | CA | THR | A | 257 | 25.721 | 40.622 | 58.746 | 1.00 23.85 | AAAA |
| ATOM | 2043 | CB | THR | A | 257 | 26.460 | 41.968 | 58.549 | 1.00 23.99 | AAAA |
| ATOM | 2044 | OG1 | THR | A | 257 | 26.729 | 42.169 | 57.153 | 1.00 25.54 | AAAA |
| ATOM | 2045 | CG2 | THR | A | 257 | 27.780 | 41.985 | 59.329 | 1.00 24.07 | AAAA |
| ATOM | 2046 | C | THR | A | 257 | 24.438 | 40.691 | 57.948 | 1.00 24.97 | AAAA |

Fig. 19-31

```
ATOM  2047  O    THR A 257      23.692  41.672  58.048  1.00 25.84      AAAA
ATOM  2048  N    ASP A 258      24.152  39.665  57.154  1.00 25.18      AAAA
ATOM  2049  CA   ASP A 258      22.935  39.753  56.379  1.00 26.18      AAAA
ATOM  2050  CB   ASP A 258      22.950  38.830  55.149  1.00 25.52      AAAA
ATOM  2051  CG   ASP A 258      23.211  37.392  55.494  1.00 26.33      AAAA
ATOM  2052  C    ASP A 258      21.649  39.574  57.178  1.00 26.74      AAAA
ATOM  2053. O    ASP A 258      20.571  39.823  56.643  1.00 26.57      AAAA
ATOM  2054  OD1  ASP A 258      23.014  37.029  56.675  1.00 26.85      AAAA
ATOM  2055  OD2  ASP A 258      23.585  36.623  54.572  1.00 24.06      AAAA
ATOM  2056  N    PRO A 259      21.727  39.114  58.449  1.00 26.95      AAAA
ATOM  2057  CD   PRO A 259      22.834  38.589  59.271  1.00 27.34      AAAA
ATOM  2058  CA   PRO A 259      20.467  38.976  59.190  1.00 27.05      AAAA
ATOM  2059  CB   PRO A 259      20.886  38.186  60.425  1.00 26.38      AAAA
ATOM  2060  CG   PRO A 259      22.247  38.718  60.669  1.00 27.84      AAAA
ATOM  2061  C    PRO A 259      19.914  40.365  59.547  1.00 27.32      AAAA
ATOM  2062  O    PRO A 259      18.739  40.510  59.871  1.00 27.29      AAAA
ATOM  2063  N    LEU A 260      20.771  41.383  59.452  1.00 26.97      AAAA
ATOM  2064  CA   LEU A 260      20.389  42.763  59.752  1.00 26.74      AAAA
ATOM  2065  CB   LEU A 260      21.621  43.680  59.680  1.00 27.21      AAAA
ATOM  2066  CG   LEU A 260      22.732  43.465  60.709  1.00 27.01      AAAA
ATOM  2067  CD1  LEU A 260      23.889  44.380  60.408  1.00 25.51      AAAA
ATOM  2068  CD2  LEU A 260      22.189  43.718  62.112  1.00 27.39      AAAA
ATOM  2069  C    LEU A 260      19.295  43.351  58.865  1.00 26.47      AAAA
ATOM  2070  O    LEU A 260      19.278  43.137  57.649  1.00 26.72      AAAA
ATOM  2071  N    LEU A 261      18.413  44.126  59.494  1.00 26.32      AAAA
ATOM  2072  CA   LEU A 261      17.283  44.808  58.846  1.00 27.20      AAAA
ATOM  2073  CB   LEU A 261      16.732  45.885  59.780  1.00 28.71      AAAA
ATOM  2074  CG   LEU A 261      15.644  46.789  59.190  1.00 29.24      AAAA
ATOM  2075  CD1  LEU A 261      14.433  45.954  58.883  1.00 29.44      AAAA
ATOM  2076  CD2  LEU A 261      15.284  47.906  60.162  1.00 29.72      AAAA
ATOM  2077  C    LEU A 261      17.506  45.454  57.473  1.00 27.90      AAAA
ATOM  2078  O    LEU A 261      16.675  45.294  56.577  1.00 28.21      AAAA
ATOM  2079  N    GLU A 262      18.597  46.202  57.310  1.00 27.61      AAAA
ATOM  2080  CA   GLU A 262      18.887  46.877  56.043  1.00 26.92      AAAA
ATOM  2081  CB   GLU A 262      19.949  47.955  56.241  1.00 25.85      AAAA
ATOM  2082  CG   GLU A 262      19.549  49.119  57.117  1.00 25.36      AAAA
ATOM  2083  CD   GLU A 262      19.552  48.787  58.580  1.00 25.78      AAAA
ATOM  2084  OE1  GLU A 262      19.859  47.631  58.938  1.00 24.64      AAAA
ATOM  2085  OE2  GLU A 262      19.255  49.694  59.381  1.00 25.82      AAAA
ATOM  2086  C    GLU A 262      19.346  45.995  54.882  1.00 28.79      AAAA
ATOM  2087  O    GLU A 262      19.354  46.439  53.724  1.00 28.70      AAAA
ATOM  2088  N    ASP A 263      19.743  44.758  55.179  1.00 29.57      AAAA
ATOM  2089  CA   ASP A 263      20.230  43.853  54.145  1.00 28.99      AAAA
ATOM  2090  CB   ASP A 263      21.160  42.802  54.760  1.00 27.89      AAAA
ATOM  2091  CG   ASP A 263      21.986  42.062  53.714  1.00 29.02      AAAA
ATOM  2092  OD1  ASP A 263      23.194  41.863  53.957  1.00 28.06      AAAA
ATOM  2093  OD2  ASP A 263      21.438  41.663  52.660  1.00 28.80      AAAA
ATOM  2094  C    ASP A 263      19.066  43.197  53.431  1.00 29.73      AAAA
ATOM  2095  O    ASP A 263      18.258  42.510  54.043  1.00 29.15      AAAA
ATOM  2096  N    TYR A 264      19.002  43.416  52.122  1.00 31.25      AAAA
ATOM  2097  CA   TYR A 264      17.925  42.888  51.306  1.00 32.43      AAAA
ATOM  2098  CB   TYR A 264      17.913  43.558  49.938  1.00 34.53      AAAA
ATOM  2099  CG   TYR A 264      17.627  45.038  49.997  1.00 38.21      AAAA
ATOM  2100  CD1  TYR A 264      18.664  45.968  49.983  1.00 39.87      AAAA
ATOM  2101  CE1  TYR A 264      18.409  47.335  50.068  1.00 41.74      AAAA
ATOM  2102  CD2  TYR A 264      16.316  45.511  50.103  1.00 40.10      AAAA
ATOM  2103  CE2  TYR A 264      16.044  46.877  50.191  1.00 41.50      AAAA
ATOM  2104  CZ   TYR A 264      17.095  47.786  50.170  1.00 42.75      AAAA
ATOM  2105  OH   TYR A 264      16.838  49.147  50.231  1.00 44.65      AAAA
ATOM  2106  C    TYR A 264      17.897  41.385  51.135  1.00 32.50      AAAA
ATOM  2107  O    TYR A 264      16.819  40.816  50.968  1.00 32.49      AAAA
ATOM  2108  N    LEU A 265      19.064  40.740  51.171  1.00 32.64      AAAA
ATOM  2109  CA   LEU A 265      19.122  39.281  51.036  1.00 31.92      AAAA
ATOM  2110  CB   LEU A 265      20.525  38.823  50.617  1.00 32.75      AAAA
ATOM  2111  CG   LEU A 265      20.808  39.010  49.127  1.00 32.95      AAAA
ATOM  2112  CD1  LEU A 265      22.213  38.588  48.771  1.00 31.59      AAAA
```

Fig. 19-32

```
ATOM   2113  CD2 LEU A 265      19.803  38.166  48.361  1.00 34.62      AAAA
ATOM   2114  C   LEU A 265      18.693  38.540  52.296  1.00 30.33      AAAA
ATOM   2115  O   LEU A 265      19.024  37.375  52.484  1.00 30.30      AAAA
ATOM   2116  N   SER A 266      17.945  39.230  53.147  1.00 29.23      AAAA
ATOM   2117  CA  SER A 266      17.434  38.649  54.371  1.00 29.72      AAAA
ATOM   2118  CB  SER A 266      18.398  38.894  55.519  1.00 32.09      AAAA
ATOM   2119  OG  SER A 266      17.728  38.810  56.771  1.00 33.43      AAAA
ATOM   2120  C   SER A 266      16.115  39.290  54.698  1.00 28.71      AAAA
ATOM   2121  O   SER A 266      15.924  40.473  54.444  1.00 29.67      AAAA
ATOM   2122  N   LYS A 267      15.209  38.517  55.276  1.00 27.82      AAAA
ATOM   2123  CA  LYS A 267      13.908  39.045  55.654  1.00 27.56      AAAA
ATOM   2124  CB  LYS A 267      12.821  38.076  55.222  1.00 28.75      AAAA
ATOM   2125  CG  LYS A 267      12.733  37.922  53.718  1.00 29.67      AAAA
ATOM   2126  CD  LYS A 267      12.343  39.223  53.053  1.00 30.13      AAAA
ATOM   2127  CE  LYS A 267      12.303  39.036  51.546  1.00 31.86      AAAA
ATOM   2128  NZ  LYS A 267      11.796  40.252  50.843  1.00 33.92      AAAA
ATOM   2129  C   LYS A 267      13.800  39.327  57.152  1.00 27.18      AAAA
ATOM   2130  O   LYS A 267      12.707  39.591  57.665  1.00 27.18      AAAA
ATOM   2131  N   PHE A 268      14.944  39.267  57.836  1.00 26.12      AAAA
ATOM   2132  CA  PHE A 268      15.048  39.532  59.271  1.00 25.72      AAAA
ATOM   2133  CB  PHE A 268      16.272  38.830  59.856  1.00 24.94      AAAA
ATOM   2134  CG  PHE A 268      16.167  37.334  59.896  1.00 25.07      AAAA
ATOM   2135  CD1 PHE A 268      17.271  36.565  60.267  1.00 24.56      AAAA
ATOM   2136  CD2 PHE A 268      14.955  36.687  59.629  1.00 23.76      AAAA
ATOM   2137  CE1 PHE A 268      17.174  35.169  60.384  1.00 23.71      AAAA
ATOM   2138  CE2 PHE A 268      14.850  35.303  59.739  1.00 23.86      AAAA
ATOM   2139  CZ  PHE A 268      15.966  34.542  60.121  1.00 23.68      AAAA
ATOM   2140  C   PHE A 268      15.190  41.030  59.513  1.00 25.77      AAAA
ATOM   2141  O   PHE A 268      15.811  41.734  58.726  1.00 25.81      AAAA
ATOM   2142  N   ASN A 269      14.606  41.524  60.595  1.00 26.02      AAAA
ATOM   2143  CA  ASN A 269      14.718  42.943  60.890  1.00 26.58      AAAA
ATOM   2144  CB  ASN A 269      13.330  43.584  61.058  1.00 25.47      AAAA
ATOM   2145  CG  ASN A 269      12.379  43.252  59.906  1.00 25.37      AAAA
ATOM   2146  OD1 ASN A 269      12.761  43.260  58.734  1.00 23.82      AAAA
ATOM   2147  ND2 ASN A 269      11.123  42.985  60.245  1.00 24.03      AAAA
ATOM   2148  C   ASN A 269      15.540  43.112  62.169  1.00 26.82      AAAA
ATOM   2149  O   ASN A 269      15.089  43.715  63.150  1.00 27.98      AAAA
ATOM   2150  N   LEU A 270      16.744  42.559  62.149  1.00 26.07      AAAA
ATOM   2151  CA  LEU A 270      17.639  42.642  63.289  1.00 25.97      AAAA
ATOM   2152  CB  LEU A 270      18.634  41.479  63.265  1.00 23.76      AAAA
ATOM   2153  CG  LEU A 270      18.048  40.070  63.225  1.00 23.36      AAAA
ATOM   2154  CD1 LEU A 270      19.115  39.090  63.710  1.00 21.90      AAAA
ATOM   2155  CD2 LEU A 270      16.824  39.971  64.122  1.00 22.05      AAAA
ATOM   2156  C   LEU A 270      18.420  43.961  63.360  1.00 27.13      AAAA
ATOM   2157  O   LEU A 270      18.475  44.750  62.399  1.00 25.99      AAAA
ATOM   2158  N   SER A 271      19.038  44.176  64.517  1.00 27.97      AAAA
ATOM   2159  CA  SER A 271      19.832  45.370  64.767  1.00 27.95      AAAA
ATOM   2160  CB  SER A 271      19.235  46.137  65.943  1.00 27.32      AAAA
ATOM   2161  OG  SER A 271      19.184  45.297  67.089  1.00 27.90      AAAA
ATOM   2162  C   SER A 271      21.276  44.987  65.084  1.00 28.15      AAAA
ATOM   2163  O   SER A 271      21.574  43.832  65.401  1.00 26.99      AAAA
ATOM   2164  N   ASN A 272      22.156  45.980  64.979  1.00 28.96      AAAA
ATOM   2165  CA  ASN A 272      23.590  45.861  65.266  1.00 29.54      AAAA
ATOM   2166  CB  ASN A 272      24.247  47.243  65.223  1.00 30.96      AAAA
ATOM   2167  CG  ASN A 272      24.647  47.640  63.850  1.00 31.20      AAAA
ATOM   2168  OD1 ASN A 272      24.960  48.794  63.594  1.00 31.73      AAAA
ATOM   2169  ND2 ASN A 272      24.670  46.674  62.948  1.00 31.93      AAAA
ATOM   2170  C   ASN A 272      23.821  45.309  66.645  1.00 29.63      AAAA
ATOM   2171  O   ASN A 272      24.574  44.361  66.843  1.00 29.85      AAAA
ATOM   2172  N   VAL A 273      23.180  45.959  67.600  1.00 29.77      AAAA
ATOM   2173  CA  VAL A 273      23.290  45.602  68.994  1.00 30.89      AAAA
ATOM   2174  CB  VAL A 273      22.436  46.576  69.816  1.00 31.61      AAAA
ATOM   2175  CG1 VAL A 273      22.716  46.403  71.293  1.00 33.17      AAAA
ATOM   2176  CG2 VAL A 273      22.740  47.998  69.372  1.00 31.82      AAAA
ATOM   2177  C   VAL A 273      22.883  44.144  69.266  1.00 30.74      AAAA
ATOM   2178  O   VAL A 273      23.550  43.431  70.022  1.00 31.23      AAAA
```

Fig. 19-33

```
ATOM   2179  N   ALA A 274      21.785  43.706  68.659  1.00 30.25      AAAA
ATOM   2180  CA  ALA A 274      21.327  42.333  68.840  1.00 29.87      AAAA
ATOM   2181  CB  ALA A 274      20.005  42.119  68.112  1.00 29.64      AAAA
ATOM   2182  C   ALA A 274      22.395  41.438  68.247  1.00 29.35      AAAA
ATOM   2183  O   ALA A 274      22.707  40.373  68.778  1.00 29.18      AAAA
ATOM   2184  N   PHE A 275      22.946  41.893  67.127  1.00 29.30      AAAA
ATOM   2185  CA  PHE A 275      23.991  41.170  66.428  1.00 28.91      AAAA
ATOM   2186  CB  PHE A 275      24.375  41.909  65.150  1.00 28.77      AAAA
ATOM   2187  CG  PHE A 275      25.354  41.170  64.308  1.00 28.08      AAAA
ATOM   2188  CD1 PHE A 275      25.015  39.954  63.740  1.00 28.92      AAAA
ATOM   2189  CD2 PHE A 275      26.621  41.684  64.077  1.00 29.48      AAAA
ATOM   2190  CE1 PHE A 275      25.928  39.259  62.945  1.00 29.20      AAAA
ATOM   2191  CE2 PHE A 275      27.546  40.988  63.279  1.00 29.24      AAAA
ATOM   2192  CZ  PHE A 275      27.193  39.779  62.716  1.00 28.30      AAAA
ATOM   2193  C   PHE A 275      25.196  41.058  67.351  1.00 27.64      AAAA
ATOM   2194  O   PHE A 275      25.728  39.975  67.558  1.00 28.65      AAAA
ATOM   2195  N   LEU A 276      25.606  42.189  67.902  1.00 26.81      AAAA
ATOM   2196  CA  LEU A 276      26.732  42.260  68.831  1.00 27.38      AAAA
ATOM   2197  CB  LEU A 276      26.878  43.700  69.353  1.00 27.53      AAAA
ATOM   2198  CG  LEU A 276      28.202  44.213  69.928  1.00 26.37      AAAA
ATOM   2199  CD1 LEU A 276      27.923  45.488  70.721  1.00 25.71      AAAA
ATOM   2200  CD2 LEU A 276      28.842  43.189  70.827  1.00 27.06      AAAA
ATOM   2201  C   LEU A 276      26.486  41.317  70.021  1.00 26.49      AAAA
ATOM   2202  O   LEU A 276      27.387  40.603  70.471  1.00 25.26      AAAA
ATOM   2203  N   LYS A 277      25.257  41.322  70.524  1.00 27.46      AAAA
ATOM   2204  CA  LYS A 277      24.894  40.468  71.642  1.00 28.63      AAAA
ATOM   2205  CB  LYS A 277      23.542  40.862  72.223  1.00 30.63      AAAA
ATOM   2206  CG  LYS A 277      23.590  42.029  73.153  1.00 33.14      AAAA
ATOM   2207  CD  LYS A 277      22.599  41.791  74.268  1.00 34.94      AAAA
ATOM   2208  CE  LYS A 277      22.964  40.519  75.029  1.00 36.17      AAAA
ATOM   2209  NZ  LYS A 277      21.979  40.194  76.104  1.00 38.64      AAAA
ATOM   2210  C   LYS A 277      24.846  38.997  71.297  1.00 28.53      AAAA
ATOM   2211  O   LYS A 277      25.118  38.152  72.146  1.00 28.45      AAAA
ATOM   2212  N   ALA A 278      24.466  38.681  70.064  1.00 28.47      AAAA
ATOM   2213  CA  ALA A 278      24.404  37.280  69.656  1.00 27.66      AAAA
ATOM   2214  CB  ALA A 278      23.941  37.181  68.201  1.00 26.40      AAAA
ATOM   2215  C   ALA A 278      25.833  36.754  69.820  1.00 26.63      AAAA
ATOM   2216  O   ALA A 278      26.081  35.644  70.317  1.00 25.19      AAAA
ATOM   2217  N   PHE A 279      26.764  37.616  69.427  1.00 26.50      AAAA
ATOM   2218  CA  PHE A 279      28.181  37.345  69.481  1.00 25.83      AAAA
ATOM   2219  CB  PHE A 279      28.934  38.521  68.869  1.00 26.35      AAAA
ATOM   2220  CG  PHE A 279      30.413  38.319  68.796  1.00 27.92      AAAA
ATOM   2221  CD1 PHE A 279      30.949  37.256  68.072  1.00 28.58      AAAA
ATOM   2222  CD2 PHE A 279      31.280  39.201  69.434  1.00 28.33      AAAA
ATOM   2223  CE1 PHE A 279      32.330  37.078  67.983  1.00 28.22      AAAA
ATOM   2224  CE2 PHE A 279      32.666  39.030  69.349  1.00 28.11      AAAA
ATOM   2225  CZ  PHE A 279      33.185  37.968  68.622  1.00 28.21      AAAA
ATOM   2226  C   PHE A 279      28.665  37.118  70.901  1.00 25.47      AAAA
ATOM   2227  O   PHE A 279      29.284  36.091  71.202  1.00 24.32      AAAA
ATOM   2228  N   ASN A 280      28.382  38.075  71.778  1.00 25.12      AAAA
ATOM   2229  CA  ASN A 280      28.841  37.944  73.147  1.00 25.05      AAAA
ATOM   2230  CB  ASN A 280      28.708  39.269  73.887  1.00 24.42      AAAA
ATOM   2231  CG  ASN A 280      29.683  40.300  73.364  1.00 24.56      AAAA
ATOM   2232  OD1 ASN A 280      30.841  39.980  73.080  1.00 23.24      AAAA
ATOM   2233  ND2 ASN A 280      29.233  41.543  73.249  1.00 24.59      AAAA
ATOM   2234  C   ASN A 280      28.213  36.814  73.925  1.00 24.79      AAAA
ATOM   2235  O   ASN A 280      28.828  36.272  74.825  1.00 24.96      AAAA
ATOM   2236  N   ILE A 281      26.998  36.444  73.565  1.00 24.87      AAAA
ATOM   2237  CA  ILE A 281      26.332  35.337  74.220  1.00 24.80      AAAA
ATOM   2238  CB  ILE A 281      24.866  35.252  73.780  1.00 24.40      AAAA
ATOM   2239  CG2 ILE A 281      24.297  33.907  74.124  1.00 25.03      AAAA
ATOM   2240  CG1 ILE A 281      24.076  36.386  74.424  1.00 24.70      AAAA
ATOM   2241  CD1 ILE A 281      22.613  36.379  74.069  1.00 26.49      AAAA
ATOM   2242  C   ILE A 281      27.044  34.027  73.884  1.00 25.21      AAAA
ATOM   2243  O   ILE A 281      27.220  33.170  74.750  1.00 24.97      AAAA
ATOM   2244  N   VAL A 282      27.440  33.866  72.620  1.00 25.98      AAAA
```

Fig. 19-34

```
ATOM   2245  CA   VAL A 282      28.150  32.656  72.193  1.00 25.15      AAAA
ATOM   2246  CB   VAL A 282      28.451  32.666  70.677  1.00 23.83      AAAA
ATOM   2247  CG1  VAL A 282      29.315  31.470  70.311  1.00 23.58      AAAA
ATOM   2248  CG2  VAL A 282      27.173  32.633  69.899  1.00 22.73      AAAA
ATOM   2249  C    VAL A 282      29.478  32.553  72.936  1.00 25.73      AAAA
ATOM   2250  O    VAL A 282      29.928  31.457  73.275  1.00 25.31      AAAA
ATOM   2251  N    ARG A 283      30.100  33.702  73.176  1.00 26.90      AAAA
ATOM   2252  CA   ARG A 283      31.372  33.760  73.885  1.00 28.87      AAAA
ATOM   2253  CB   ARG A 283      32.027  35.131  73.684  1.00 28.16      AAAA
ATOM   2254  CG   ARG A 283      32.364  35.440  72.240  1.00 27.22      AAAA
ATOM   2255  CD   ARG A 283      32.821  36.862  72.098  1.00 27.08      AAAA
ATOM   2256  NE   ARG A 283      34.035  37.116  72.854  1.00 26.73      AAAA
ATOM   2257  CZ   ARG A 283      34.514  38.327  73.091  1.00 26.82      AAAA
ATOM   2258  NH1  ARG A 283      33.873  39.384  72.626  1.00 27.36      AAAA
ATOM   2259  NH2  ARG A 283      35.622  38.484  73.798  1.00 26.95      AAAA
ATOM   2260  C    ARG A 283      31.183  33.494  75.376  1.00 30.71      AAAA
ATOM   2261  O    ARG A 283      32.086  32.981  76.027  1.00 30.68      AAAA
ATOM   2262  N    GLU A 284      30.014  33.842  75.911  1.00 32.71      AAAA
ATOM   2263  CA   GLU A 284      29.735  33.623  77.323  1.00 35.53      AAAA
ATOM   2264  CB   GLU A 284      28.482  34.391  77.751  1.00 37.39      AAAA
ATOM   2265  CG   GLU A 284      28.538  35.854  77.392  1.00 41.73      AAAA
ATOM   2266  CD   GLU A 284      27.272  36.631  77.754  1.00 45.27      AAAA
ATOM   2267  OE1  GLU A 284      26.151  36.078  77.610  1.00 46.66      AAAA
ATOM   2268  OE2  GLU A 284      27.405  37.817  78.148  1.00 46.94      AAAA
ATOM   2269  C    GLU A 284      29.524  32.133  77.564  1.00 36.25      AAAA
ATOM   2270  O    GLU A 284      29.920  31.593  78.601  1.00 37.85      AAAA
ATOM   2271  N    VAL A 285      28.916  31.464  76.591  1.00 35.24      AAAA
ATOM   2272  CA   VAL A 285      28.637  30.041  76.708  1.00 33.88      AAAA
ATOM   2273  CB   VAL A 285      27.505  29.619  75.737  1.00 33.71      AAAA
ATOM   2274  CG1  VAL A 285      27.201  28.137  75.888  1.00 32.59      AAAA
ATOM   2275  CG2  VAL A 285      26.254  30.457  76.001  1.00 32.77      AAAA
ATOM   2276  C    VAL A 285      29.847  29.149  76.456  1.00 33.47      AAAA
ATOM   2277  O    VAL A 285      30.140  28.262  77.257  1.00 34.23      AAAA
ATOM   2278  N    PHE A 286      30.568  29.389  75.364  1.00 32.34      AAAA
ATOM   2279  CA   PHE A 286      31.706  28.535  75.036  1.00 29.92      AAAA
ATOM   2280  CB   PHE A 286      31.533  27.960  73.635  1.00 29.77      AAAA
ATOM   2281  CG   PHE A 286      30.267  27.179  73.444  1.00 28.64      AAAA
ATOM   2282  CD1  PHE A 286      29.152  27.772  72.863  1.00 28.75      AAAA
ATOM   2283  CD2  PHE A 286      30.197  25.837  73.827  1.00 28.55      AAAA
ATOM   2284  CE1  PHE A 286      27.983  27.039  72.660  1.00 29.04      AAAA
ATOM   2285  CE2  PHE A 286      29.037  25.095  73.629  1.00 28.19      AAAA
ATOM   2286  CZ   PHE A 286      27.929  25.694  73.045  1.00 28.73      AAAA
ATOM   2287  C    PHE A 286      33.106  29.113  75.132  1.00 29.13      AAAA
ATOM   2288  O    PHE A 286      34.073  28.436  74.760  1.00 28.54      AAAA
ATOM   2289  N    GLY A 287      33.224  30.341  75.637  1.00 28.42      AAAA
ATOM   2290  CA   GLY A 287      34.525  30.987  75.744  1.00 27.07      AAAA
ATOM   2291  C    GLY A 287      34.932  31.611  74.419  1.00 26.64      AAAA
ATOM   2292  O    GLY A 287      34.088  32.042  73.649  1.00 27.13      AAAA
ATOM   2293  N    GLU A 288      36.227  31.665  74.146  1.00 27.20      AAAA
ATOM   2294  CA   GLU A 288      36.719  32.238  72.900  1.00 27.52      AAAA
ATOM   2295  CB   GLU A 288      38.073  32.923  73.108  1.00 28.18      AAAA
ATOM   2296  CG   GLU A 288      38.036  34.177  73.959  1.00 28.88      AAAA
ATOM   2297  CD   GLU A 288      37.329  35.330  73.279  1.00 29.58      AAAA
ATOM   2298  OE1  GLU A 288      37.807  35.813  72.243  1.00 29.94      AAAA
ATOM   2299  OE2  GLU A 288      36.281  35.761  73.782  1.00 31.89      AAAA
ATOM   2300  C    GLU A 288      36.877  31.158  71.843  1.00 27.44      AAAA
ATOM   2301  O    GLU A 288      37.169  30.007  72.162  1.00 27.87      AAAA
ATOM   2302  N    GLY A 289      36.663  31.547  70.589  1.00 26.55      AAAA
ATOM   2303  CA   GLY A 289      36.795  30.638  69.466  1.00 25.25      AAAA
ATOM   2304  C    GLY A 289      37.285  31.414  68.254  1.00 24.53      AAAA
ATOM   2305  O    GLY A 289      37.635  32.586  68.369  1.00 24.40      AAAA
ATOM   2306  N    VAL A 290      37.320  30.765  67.095  1.00 24.04      AAAA
ATOM   2307  CA   VAL A 290      37.756  31.407  65.863  1.00 23.76      AAAA
ATOM   2308  CB   VAL A 290      38.288  30.346  64.867  1.00 24.94      AAAA
ATOM   2309  CG1  VAL A 290      38.835  31.012  63.596  1.00 22.73      AAAA
ATOM   2310  CG2  VAL A 290      39.375  29.506  65.555  1.00 24.74      AAAA
```

Fig. 19-35

```
ATOM   2311  C    VAL A 290      36.536  32.122  65.277  1.00 23.90      AAAA
ATOM   2312  O    VAL A 290      35.497  31.502  65.100  1.00 25.15      AAAA
ATOM   2313  N    TYR A 291      36.662  33.415  64.976  1.00 23.09      AAAA
ATOM   2314  CA   TYR A 291      35.544  34.211  64.446  1.00 21.41      AAAA
ATOM   2315  CB   TYR A 291      35.472  35.540  65.193  1.00 20.57      AAAA
ATOM   2316  CG   TYR A 291      35.511  35.346  66.677  1.00 19.87      AAAA
ATOM   2317  CD1  TYR A 291      36.596  35.782  67.432  1.00 20.86      AAAA
ATOM   2318  CE1  TYR A 291      36.677  35.513  68.793  1.00 21.47      AAAA
ATOM   2319  CD2  TYR A 291      34.509  34.647  67.318  1.00 20.90      AAAA
ATOM   2320  CE2  TYR A 291      34.579  34.372  68.675  1.00 21.90      AAAA
ATOM   2321  CZ   TYR A 291      35.661  34.800  69.403  1.00 21.25      AAAA
ATOM   2322  OH   TYR A 291      35.737  34.469  70.730  1.00 23.75      AAAA
ATOM   2323  C    TYR A 291      35.607  34.483  62.946  1.00 21.25      AAAA
ATOM   2324  O    TYR A 291      36.573  35.077  62.451  1.00 21.10      AAAA
ATOM   2325  N    LEU A 292      34.557  34.084  62.231  1.00 20.92      AAAA
ATOM   2326  CA   LEU A 292      34.518  34.260  60.779  1.00 20.92      AAAA
ATOM   2327  CB   LEU A 292      34.235  32.916  60.080  1.00 19.93      AAAA
ATOM   2328  CG   LEU A 292      35.104  31.688  60.399  1.00 17.31      AAAA
ATOM   2329  CD1  LEU A 292      34.685  30.515  59.528  1.00 16.05      AAAA
ATOM   2330  CD2  LEU A 292      36.552  32.000  60.163  1.00 18.07      AAAA
ATOM   2331  C    LEU A 292      33.515  35.288  60.283  1.00 21.12      AAAA
ATOM   2332  O    LEU A 292      32.652  35.741  61.020  1.00 20.70      AAAA
ATOM   2333  N    GLY A 293      33.660  35.660  59.017  1.00 21.74      AAAA
ATOM   2334  CA   GLY A 293      32.752  36.612  58.410  1.00 21.48      AAAA
ATOM   2335  C    GLY A 293      31.612  35.856  57.770  1.00 21.65      AAAA
ATOM   2336  O    GLY A 293      31.237  34.790  58.235  1.00 22.25      AAAA
ATOM   2337  N    GLY A 294      31.060  36.392  56.691  1.00 22.66      AAAA
ATOM   2338  CA   GLY A 294      29.957  35.714  56.034  1.00 23.61      AAAA
ATOM   2339  C    GLY A 294      29.180  36.653  55.146  1.00 24.56      AAAA
ATOM   2340  O    GLY A 294      29.679  37.727  54.790  1.00 25.54      AAAA
ATOM   2341  N    GLY A 295      27.956  36.265  54.794  1.00 24.06      AAAA
ATOM   2342  CA   GLY A 295      27.139  37.093  53.927  1.00 22.78      AAAA
ATOM   2343  C    GLY A 295      26.902  38.479  54.483  1.00 23.11      AAAA
ATOM   2344  O    GLY A 295      26.870  38.676  55.696  1.00 22.87      AAAA
ATOM   2345  N    GLY A 296      26.733  39.442  53.584  1.00 22.78      AAAA
ATOM   2346  CA   GLY A 296      26.497  40.813  53.993  1.00 23.44      AAAA
ATOM   2347  C    GLY A 296      26.471  41.618  52.718  1.00 23.72      AAAA
ATOM   2348  O    GLY A 296      27.474  41.661  52.004  1.00 23.73      AAAA
ATOM   2349  N    TYR A 297      25.356  42.280  52.425  1.00 23.41      AAAA
ATOM   2350  CA   TYR A 297      25.282  42.991  51.163  1.00 22.71      AAAA
ATOM   2351  CB   TYR A 297      24.252  42.294  50.296  1.00 21.55      AAAA
ATOM   2352  CG   TYR A 297      24.496  40.809  50.317  1.00 21.93      AAAA
ATOM   2353  CD1  TYR A 297      24.036  40.016  51.375  1.00 20.95      AAAA
ATOM   2354  CE1  TYR A 297      24.400  38.678  51.481  1.00 21.59      AAAA
ATOM   2355  CD2  TYR A 297      25.320  40.217  49.358  1.00 21.71      AAAA
ATOM   2356  CE2  TYR A 297      25.688  38.900  49.451  1.00 21.99      AAAA
ATOM   2357  CZ   TYR A 297      25.242  38.127  50.511  1.00 22.18      AAAA
ATOM   2358  OH   TYR A 297      25.721  36.841  50.615  1.00 21.35      AAAA
ATOM   2359  C    TYR A 297      25.042  44.485  51.225  1.00 22.90      AAAA
ATOM   2360  O    TYR A 297      25.106  45.172  50.203  1.00 23.17      AAAA
ATOM   2361  N    HIS A 298      24.772  44.989  52.417  1.00 22.47      AAAA
ATOM   2362  CA   HIS A 298      24.572  46.415  52.566  1.00 24.27      AAAA
ATOM   2363  CB   HIS A 298      23.468  46.726  53.556  1.00 23.17      AAAA
ATOM   2364  CG   HIS A 298      23.097  48.166  53.572  1.00 23.20      AAAA
ATOM   2365  CD2  HIS A 298      23.588  49.201  54.287  1.00 24.25      AAAA
ATOM   2366  ND1  HIS A 298      22.199  48.708  52.680  1.00 23.14      AAAA
ATOM   2367  CE1  HIS A 298      22.151  50.017  52.848  1.00 23.31      AAAA
ATOM   2368  NE2  HIS A 298      22.986  50.342  53.814  1.00 23.62      AAAA
ATOM   2369  C    HIS A 298      25.886  46.976  53.106  1.00 25.17      AAAA
ATOM   2370  O    HIS A 298      26.282  46.687  54.239  1.00 24.47      AAAA
ATOM   2371  N    PRO A 299      26.563  47.818  52.316  1.00 26.37      AAAA
ATOM   2372  CD   PRO A 299      26.178  48.372  51.006  1.00 27.01      AAAA
ATOM   2373  CA   PRO A 299      27.840  48.394  52.752  1.00 27.31      AAAA
ATOM   2374  CB   PRO A 299      28.156  49.383  51.630  1.00 27.04      AAAA
ATOM   2375  CG   PRO A 299      26.743  49.764  51.120  1.00 27.57      AAAA
ATOM   2376  C    PRO A 299      27.824  49.037  54.149  1.00 27.77      AAAA
```

Fig. 19-36

```
ATOM   2377  O    PRO A 299      28.755  48.826  54.939  1.00 28.04       AAAA
ATOM   2378  N    TYR A 300      26.769  49.794  54.452  1.00 27.04       AAAA
ATOM   2379  CA   TYR A 300      26.629  50.477  55.740  1.00 27.59       AAAA
ATOM   2380  CB   TYR A 300      25.425  51.437  55.700  1.00 30.57       AAAA
ATOM   2381  CG   TYR A 300      25.516  52.599  54.718  1.00 32.91       AAAA
ATOM   2382  CD1  TYR A 300      26.181  52.464  53.491  1.00 33.45       AAAA
ATOM   2383  CE1  TYR A 300      26.160  53.487  52.538  1.00 33.91       AAAA
ATOM   2384  CD2  TYR A 300      24.837  53.801  54.969  1.00 34.19       AAAA
ATOM   2385  CE2  TYR A 300      24.809  54.830  54.018  1.00 34.64       AAAA
ATOM   2386  CZ   TYR A 300      25.468  54.657  52.807  1.00 34.56       AAAA
ATOM   2387  OH   TYR A 300      25.389  55.630  51.844  1.00 36.05       AAAA
ATOM   2388  C    TYR A 300      26.454  49.538  56.936  1.00 26.48       AAAA
ATOM   2389  O    TYR A 300      27.073  49.726  57.979  1.00 25.81       AAAA
ATOM   2390  N    ALA A 301      25.581  48.547  56.791  1.00 25.41       AAAA
ATOM   2391  CA   ALA A 301      25.328  47.606  57.865  1.00 24.64       AAAA
ATOM   2392  CB   ALA A 301      24.164  46.731  57.511  1.00 25.32       AAAA
ATOM   2393  C    ALA A 301      26.568  46.775  58.067  1.00 25.53       AAAA
ATOM   2394  O    ALA A 301      27.030  46.567  59.194  1.00 26.39       AAAA
ATOM   2395  N    LEU A 302      27.108  46.304  56.950  1.00 25.83       AAAA
ATOM   2396  CA   LEU A 302      28.323  45.500  56.926  1.00 26.32       AAAA
ATOM   2397  CB   LEU A 302      28.782  45.378  55.479  1.00 27.38       AAAA
ATOM   2398  CG   LEU A 302      30.081  44.723  55.024  1.00 28.18       AAAA
ATOM   2399  CD1  LEU A 302      30.119  44.840  53.502  1.00 29.32       AAAA
ATOM   2400  CD2  LEU A 302      31.296  45.389  55.613  1.00 27.38       AAAA
ATOM   2401  C    LEU A 302      29.398  46.187  57.764  1.00 26.41       AAAA
ATOM   2402  O    LEU A 302      29.874  45.648  58.755  1.00 26.62       AAAA
ATOM   2403  N    ALA A 303      29.756  47.397  57.353  1.00 26.50       AAAA
ATOM   2404  CA   ALA A 303      30.778  48.176  58.022  1.00 25.92       AAAA
ATOM   2405  CB   ALA A 303      31.001  49.475  57.277  1.00 25.24       AAAA
ATOM   2406  C    ALA A 303      30.490  48.464  59.487  1.00 26.03       AAAA
ATOM   2407  O    ALA A 303      31.325  48.175  60.340  1.00 26.95       AAAA
ATOM   2408  N    ARG A 304      29.322  49.028  59.792  1.00 25.29       AAAA
ATOM   2409  CA   ARG A 304      28.999  49.353  61.179  1.00 23.46       AAAA
ATOM   2410  CB   ARG A 304      27.641  50.059  61.291  1.00 23.78       AAAA
ATOM   2411  CG   ARG A 304      27.553  51.451  60.629  1.00 24.59       AAAA
ATOM   2412  CD   ARG A 304      26.302  52.223  61.091  1.00 25.85       AAAA
ATOM   2413  NE   ARG A 304      25.067  51.465  60.869  1.00 27.54       AAAA
ATOM   2414  CZ   ARG A 304      23.978  51.547  61.637  1.00 28.36       AAAA
ATOM   2415  NH1  ARG A 304      23.957  52.362  62.695  1.00 26.48       AAAA
ATOM   2416  NH2  ARG A 304      22.910  50.794  61.358  1.00 28.45       AAAA
ATOM   2417  C    ARG A 304      28.991  48.118  62.053  1.00 23.18       AAAA
ATOM   2418  O    ARG A 304      29.591  48.099  63.135  1.00 22.26       AAAA
ATOM   2419  N    ALA A 305      28.330  47.075  61.560  1.00 23.20       AAAA
ATOM   2420  CA   ALA A 305      28.200  45.817  62.292  1.00 22.33       AAAA
ATOM   2421  CB   ALA A 305      27.319  44.866  61.516  1.00 22.17       AAAA
ATOM   2422  C    ALA A 305      29.516  45.137  62.621  1.00 22.27       AAAA
ATOM   2423  O    ALA A 305      29.763  44.757  63.760  1.00 22.48       AAAA
ATOM   2424  N    TRP A 306      30.366  44.969  61.620  1.00 22.57       AAAA
ATOM   2425  CA   TRP A 306      31.634  44.307  61.861  1.00 21.28       AAAA
ATOM   2426  CB   TRP A 306      32.279  43.885  60.553  1.00 21.07       AAAA
ATOM   2427  CG   TRP A 306      31.703  42.618  60.004  1.00 20.75       AAAA
ATOM   2428  CD2  TRP A 306      31.886  42.103  58.683  1.00 19.54       AAAA
ATOM   2429  CE2  TRP A 306      31.352  40.795  58.668  1.00 19.18       AAAA
ATOM   2430  CE3  TRP A 306      32.456  42.616  57.510  1.00 19.59       AAAA
ATOM   2431  CD1  TRP A 306      31.071  41.632  60.713  1.00 20.51       AAAA
ATOM   2432  NE1  TRP A 306      30.864  40.537  59.922  1.00 19.74       AAAA
ATOM   2433  CZ2  TRP A 306      31.368  39.990  57.524  1.00 19.18       AAAA
ATOM   2434  CZ3  TRP A 306      32.474  41.810  56.367  1.00 18.98       AAAA
ATOM   2435  CH2  TRP A 306      31.933  40.513  56.388  1.00 19.21       AAAA
ATOM   2436  C    TRP A 306      32.571  45.159  62.674  1.00 20.80       AAAA
ATOM   2437  O    TRP A 306      33.459  44.630  63.341  1.00 20.55       AAAA
ATOM   2438  N    THR A 307      32.373  46.475  62.614  1.00 20.17       AAAA
ATOM   2439  CA   THR A 307      33.175  47.399  63.407  1.00 20.54       AAAA
ATOM   2440  CB   THR A 307      32.861  48.881  63.045  1.00 21.09       AAAA
ATOM   2441  OG1  THR A 307      33.329  49.159  61.718  1.00 21.25       AAAA
ATOM   2442  CG2  THR A 307      33.523  49.839  64.030  1.00 20.09       AAAA
```

Fig. 19-37

```
ATOM   2443  C    THR A 307      32.853  47.135  64.893  1.00 20.88      AAAA
ATOM   2444  O    THR A 307      33.738  47.175  65.747  1.00 21.89      AAAA
ATOM   2445  N    LEU A 308      31.588  46.851  65.192  1.00 20.10      AAAA
ATOM   2446  CA   LEU A 308      31.189  46.543  66.559  1.00 21.10      AAAA
ATOM   2447  CB   LEU A 308      29.671  46.340  66.644  1.00 20.99      AAAA
ATOM   2448  CG   LEU A 308      28.897  47.656  66.674  1.00 21.54      AAAA
ATOM   2449  CD1  LEU A 308      27.397  47.473  66.411  1.00 19.91      AAAA
ATOM   2450  CD2  LEU A 308      29.177  48.283  68.045  1.00 21.04      AAAA
ATOM   2451  C    LEU A 308      31.886  45.284  67.052  1.00 21.98      AAAA
ATOM   2452  O    LEU A 308      32.284  45.186  68.215  1.00 22.17      AAAA
ATOM   2453  N    ILE A 309      32.023  44.310  66.165  1.00 22.32      AAAA
ATOM   2454  CA   ILE A 309      32.658  43.069  66.544  1.00 23.12      AAAA
ATOM   2455  CB   ILE A 309      32.590  42.016  65.413  1.00 22.33      AAAA
ATOM   2456  CG2  ILE A 309      33.356  40.787  65.827  1.00 21.76      AAAA
ATOM   2457  CG1  ILE A 309      31.140  41.678  65.061  1.00 22.16      AAAA
ATOM   2458  CD1  ILE A 309      30.366  41.037  66.166  1.00 22.01      AAAA
ATOM   2459  C    ILE A 309      34.115  43.377  66.790  1.00 24.52      AAAA
ATOM   2460  O    ILE A 309      34.734  42.828  67.709  1.00 25.72      AAAA
ATOM   2461  N    TRP A 310      34.673  44.253  65.957  1.00 24.70      AAAA
ATOM   2462  CA   TRP A 310      36.075  44.570  66.099  1.00 24.20      AAAA
ATOM   2463  CB   TRP A 310      36.587  45.417  64.944  1.00 23.29      AAAA
ATOM   2464  CG   TRP A 310      38.040  45.712  65.123  1.00 23.17      AAAA
ATOM   2465  CD2  TRP A 310      39.104  44.752  65.257  1.00 21.36      AAAA
ATOM   2466  CE2  TRP A 310      40.291  45.472  65.490  1.00 20.62      AAAA
ATOM   2467  CE3  TRP A 310      39.165  43.354  65.202  1.00 20.01      AAAA
ATOM   2468  CD1  TRP A 310      38.614  46.938  65.273  1.00 22.82      AAAA
ATOM   2469  NE1  TRP A 310      39.967  46.803  65.497  1.00 22.30      AAAA
ATOM   2470  CZ2  TRP A 310      41.521  44.845  65.668  1.00 19.91      AAAA
ATOM   2471  CZ3  TRP A 310      40.388  42.734  65.381  1.00 19.08      AAAA
ATOM   2472  CH2  TRP A 310      41.547  43.477  65.610  1.00 19.40      AAAA
ATOM   2473  C    TRP A 310      36.318  45.279  67.411  1.00 25.26      AAAA
ATOM   2474  O    TRP A 310      37.262  44.945  68.109  1.00 24.71      AAAA
ATOM   2475  N    CYS A 311      35.467  46.247  67.749  1.00 26.76      AAAA
ATOM   2476  CA   CYS A 311      35.608  46.975  69.007  1.00 27.89      AAAA
ATOM   2477  CB   CYS A 311      34.548  48.081  69.113  1.00 28.98      AAAA
ATOM   2478  SG   CYS A 311      34.798  49.462  67.991  1.00 31.89      AAAA
ATOM   2479  C    CYS A 311      35.495  46.043  70.212  1.00 27.51      AAAA
ATOM   2480  O    CYS A 311      36.289  46.127  71.135  1.00 26.90      AAAA
ATOM   2481  N    GLU A 312      34.495  45.169  70.187  1.00 27.33      AAAA
ATOM   2482  CA   GLU A 312      34.246  44.210  71.250  1.00 28.03      AAAA
ATOM   2483  CB   GLU A 312      33.106  43.287  70.850  1.00 28.55      AAAA
ATOM   2484  CG   GLU A 312      31.903  43.333  71.741  1.00 28.93      AAAA
ATOM   2485  CD   GLU A 312      32.232  42.958  73.154  1.00 29.78      AAAA
ATOM   2486  OE1  GLU A 312      32.954  41.957  73.345  1.00 30.81      AAAA
ATOM   2487  OE2  GLU A 312      31.754  43.653  74.071  1.00 30.79      AAAA
ATOM   2488  C    GLU A 312      35.463  43.357  71.514  1.00 28.91      AAAA
ATOM   2489  O    GLU A 312      35.822  43.110  72.662  1.00 30.57      AAAA
ATOM   2490  N    LEU A 313      36.081  42.889  70.436  1.00 29.04      AAAA
ATOM   2491  CA   LEU A 313      37.266  42.045  70.516  1.00 28.87      AAAA
ATOM   2492  CB   LEU A 313      37.524  41.373  69.157  1.00 29.39      AAAA
ATOM   2493  CG   LEU A 313      36.548  40.311  68.644  1.00 30.32      AAAA
ATOM   2494  CD1  LEU A 313      36.910  39.872  67.215  1.00 30.26      AAAA
ATOM   2495  CD2  LEU A 313      36.582  39.114  69.593  1.00 30.42      AAAA
ATOM   2496  C    LEU A 313      38.474  42.888  70.905  1.00 27.75      AAAA
ATOM   2497  O    LEU A 313      39.215  42.553  71.808  1.00 27.34      AAAA
ATOM   2498  N    SER A 314      38.642  43.986  70.191  1.00 27.95      AAAA
ATOM   2499  CA   SER A 314      39.736  44.927  70.376  1.00 28.62      AAAA
ATOM   2500  CB   SER A 314      39.690  45.937  69.231  1.00 27.49      AAAA
ATOM   2501  OG   SER A 314      40.703  46.904  69.343  1.00 30.12      AAAA
ATOM   2502  C    SER A 314      39.666  45.653  71.727  1.00 29.67      AAAA
ATOM   2503  O    SER A 314      40.488  46.517  72.023  1.00 29.00      AAAA
ATOM   2504  N    GLY A 315      38.676  45.302  72.538  1.00 30.78      AAAA
ATOM   2505  CA   GLY A 315      38.535  45.935  73.827  1.00 32.92      AAAA
ATOM   2506  C    GLY A 315      38.542  47.452  73.784  1.00 34.92      AAAA
ATOM   2507  O    GLY A 315      39.142  48.091  74.647  1.00 35.17      AAAA
ATOM   2508  N    ARG A 316      37.881  48.041  72.794  1.00 36.88      AAAA
```

Fig. 19-38

| | | | | | | | | | |
|---|---|---|---|---|---|---|---|---|---|
| ATOM | 2509 | CA | ARG | A | 316 | 37.841 | 49.493 | 72.702 | 1.00 39.49 | AAAA |
| ATOM | 2510 | CB | ARG | A | 316 | 38.608 | 49.968 | 71.484 | 1.00 39.86 | AAAA |
| ATOM | 2511 | CG | ARG | A | 316 | 37.946 | 49.677 | 70.161 | 1.00 40.77 | AAAA |
| ATOM | 2512 | CD | ARG | A | 316 | 38.843 | 50.226 | 69.077 | 1.00 41.47 | AAAA |
| ATOM | 2513 | NE | ARG | A | 316 | 40.140 | 49.566 | 69.092 | 1.00 42.36 | AAAA |
| ATOM | 2514 | CZ | ARG | A | 316 | 41.224 | 50.057 | 68.515 | 1.00 43.38 | AAAA |
| ATOM | 2515 | NH1 | ARG | A | 316 | 41.159 | 51.217 | 67.882 | 1.00 44.76 | AAAA |
| ATOM | 2516 | NH2 | ARG | A | 316 | 42.361 | 49.385 | 68.556 | 1.00 43.71 | AAAA |
| ATOM | 2517 | C | ARG | A | 316 | 36.418 | 50.015 | 72.631 | 1.00 41.54 | AAAA |
| ATOM | 2518 | O | ARG | A | 316 | 35.564 | 49.429 | 71.959 | 1.00 42.64 | AAAA |
| ATOM | 2519 | N | GLU | A | 317 | 36.163 | 51.119 | 73.329 | 1.00 43.10 | AAAA |
| ATOM | 2520 | CA | GLU | A | 317 | 34.830 | 51.720 | 73.356 | 1.00 44.51 | AAAA |
| ATOM | 2521 | CB | GLU | A | 317 | 34.809 | 52.936 | 74.293 | 1.00 46.17 | AAAA |
| ATOM | 2522 | CG | GLU | A | 317 | 34.472 | 52.614 | 75.759 | 1.00 49.65 | AAAA |
| ATOM | 2523 | CD | GLU | A | 317 | 35.426 | 51.623 | 76.439 | 1.00 52.51 | AAAA |
| ATOM | 2524 | OE1 | GLU | A | 317 | 35.153 | 51.251 | 77.607 | 1.00 53.37 | AAAA |
| ATOM | 2525 | OE2 | GLU | A | 317 | 36.444 | 51.214 | 75.831 | 1.00 54.14 | AAAA |
| ATOM | 2526 | C | GLU | A | 317 | 34.318 | 52.098 | 71.974 | 1.00 43.86 | AAAA |
| ATOM | 2527 | O | GLU | A | 317 | 35.067 | 52.532 | 71.108 | 1.00 42.46 | AAAA |
| ATOM | 2528 | N | VAL | A | 318 | 33.023 | 51.916 | 71.779 | 1.00 44.79 | AAAA |
| ATOM | 2529 | CA | VAL | A | 318 | 32.394 | 52.197 | 70.502 | 1.00 45.57 | AAAA |
| ATOM | 2530 | CB | VAL | A | 318 | 31.098 | 51.369 | 70.324 | 1.00 45.36 | AAAA |
| ATOM | 2531 | CG1 | VAL | A | 318 | 30.537 | 51.558 | 68.924 | 1.00 45.44 | AAAA |
| ATOM | 2532 | CG2 | VAL | A | 318 | 31.366 | 49.911 | 70.612 | 1.00 46.35 | AAAA |
| ATOM | 2533 | C | VAL | A | 318 | 32.007 | 53.652 | 70.377 | 1.00 46.41 | AAAA |
| ATOM | 2534 | O | VAL | A | 318 | 31.199 | 54.145 | 71.165 | 1.00 46.53 | AAAA |
| ATOM | 2535 | N | PRO | A | 319 | 32.584 | 54.370 | 69.396 | 1.00 46.89 | AAAA |
| ATOM | 2536 | CD | PRO | A | 319 | 33.581 | 54.017 | 68.375 | 1.00 46.44 | AAAA |
| ATOM | 2537 | CA | PRO | A | 319 | 32.209 | 55.774 | 69.247 | 1.00 47.62 | AAAA |
| ATOM | 2538 | CB | PRO | A | 319 | 33.022 | 56.206 | 68.024 | 1.00 46.96 | AAAA |
| ATOM | 2539 | CG | PRO | A | 319 | 33.161 | 54.922 | 67.251 | 1.00 46.38 | AAAA |
| ATOM | 2540 | C | PRO | A | 319 | 30.709 | 55.743 | 68.977 | 1.00 48.64 | AAAA |
| ATOM | 2541 | O | PRO | A | 319 | 30.236 | 54.860 | 68.262 | 1.00 48.61 | AAAA |
| ATOM | 2542 | N | GLU | A | 320 | 29.944 | 56.667 | 69.544 | 1.00 49.24 | AAAA |
| ATOM | 2543 | CA | GLU | A | 320 | 28.522 | 56.598 | 69.288 | 1.00 50.01 | AAAA |
| ATOM | 2544 | CB | GLU | A | 320 | 27.720 | 57.330 | 70.363 | 1.00 51.15 | AAAA |
| ATOM | 2545 | CG | GLU | A | 320 | 27.828 | 58.831 | 70.339 | 1.00 53.01 | AAAA |
| ATOM | 2546 | CD | GLU | A | 320 | 26.825 | 59.474 | 71.282 | 1.00 54.34 | AAAA |
| ATOM | 2547 | OE1 | GLU | A | 320 | 25.604 | 59.273 | 71.077 | 1.00 54.04 | AAAA |
| ATOM | 2548 | OE2 | GLU | A | 320 | 27.255 | 60.171 | 72.228 | 1.00 55.06 | AAAA |
| ATOM | 2549 | C | GLU | A | 320 | 28.206 | 57.168 | 67.921 | 1.00 49.78 | AAAA |
| ATOM | 2550 | O | GLU | A | 320 | 27.170 | 56.861 | 67.324 | 1.00 49.79 | AAAA |
| ATOM | 2551 | N | LYS | A | 321 | 29.116 | 57.980 | 67.407 | 1.00 49.26 | AAAA |
| ATOM | 2552 | CA | LYS | A | 321 | 28.906 | 58.589 | 66.109 | 1.00 49.20 | AAAA |
| ATOM | 2553 | CB | LYS | A | 321 | 28.873 | 60.106 | 66.251 | 1.00 50.38 | AAAA |
| ATOM | 2554 | CG | LYS | A | 321 | 30.234 | 60.674 | 66.634 | 1.00 52.88 | AAAA |
| ATOM | 2555 | CD | LYS | A | 321 | 30.717 | 60.180 | 68.002 | 1.00 53.76 | AAAA |
| ATOM | 2556 | CE | LYS | A | 321 | 32.229 | 60.348 | 68.154 | 1.00 55.00 | AAAA |
| ATOM | 2557 | NZ | LYS | A | 321 | 32.715 | 61.725 | 67.829 | 1.00 55.95 | AAAA |
| ATOM | 2558 | C | LYS | A | 321 | 30.037 | 58.207 | 65.171 | 1.00 48.64 | AAAA |
| ATOM | 2559 | O | LYS | A | 321 | 31.052 | 57.650 | 65.590 | 1.00 48.58 | AAAA |
| ATOM | 2560 | N | LEU | A | 322 | 29.854 | 58.511 | 63.894 | 1.00 47.78 | AAAA |
| ATOM | 2561 | CA | LEU | A | 322 | 30.870 | 58.238 | 62.896 | 1.00 46.13 | AAAA |
| ATOM | 2562 | CB | LEU | A | 322 | 30.248 | 57.638 | 61.638 | 1.00 46.84 | AAAA |
| ATOM | 2563 | CG | LEU | A | 322 | 29.240 | 56.504 | 61.848 | 1.00 47.71 | AAAA |
| ATOM | 2564 | CD1 | LEU | A | 322 | 28.788 | 55.998 | 60.491 | 1.00 48.02 | AAAA |
| ATOM | 2565 | CD2 | LEU | A | 322 | 29.853 | 55.374 | 62.667 | 1.00 48.21 | AAAA |
| ATOM | 2566 | C | LEU | A | 322 | 31.427 | 59.608 | 62.580 | 1.00 44.61 | AAAA |
| ATOM | 2567 | O | LEU | A | 322 | 30.674 | 60.571 | 62.491 | 1.00 44.73 | AAAA |
| ATOM | 2568 | N | ASN | A | 323 | 32.741 | 59.706 | 62.447 | 1.00 42.66 | AAAA |
| ATOM | 2569 | CA | ASN | A | 323 | 33.360 | 60.976 | 62.135 | 1.00 41.19 | AAAA |
| ATOM | 2570 | CB | ASN | A | 323 | 34.860 | 60.904 | 62.402 | 1.00 41.07 | AAAA |
| ATOM | 2571 | CG | ASN | A | 323 | 35.576 | 60.001 | 61.436 | 1.00 41.43 | AAAA |
| ATOM | 2572 | OD1 | ASN | A | 323 | 35.117 | 58.901 | 61.147 | 1.00 42.46 | AAAA |
| ATOM | 2573 | ND2 | ASN | A | 323 | 36.720 | 60.449 | 60.943 | 1.00 41.77 | AAAA |
| ATOM | 2574 | C | ASN | A | 323 | 33.068 | 61.223 | 60.658 | 1.00 40.76 | AAAA |

Fig. 19-39

| | | | | | | | | | | |
|---|---|---|---|---|---|---|---|---|---|---|
| ATOM | 2575 | O | ASN | A | 323 | 32.430 | 60.395 | 60.010 | 1.00 40.19 | AAAA |
| ATOM | 2576 | N | ASN | A | 324 | 33.523 | 62.352 | 60.129 | 1.00 40.11 | AAAA |
| ATOM | 2577 | CA | ASN | A | 324 | 33.268 | 62.699 | 58.735 | 1.00 39.99 | AAAA |
| ATOM | 2578 | CB | ASN | A | 324 | 33.711 | 64.128 | 58.472 | 1.00 39.54 | AAAA |
| ATOM | 2579 | CG | ASN | A | 324 | 33.003 | 65.114 | 59.361 | 1.00 40.88 | AAAA |
| ATOM | 2580 | OD1 | ASN | A | 324 | 31.763 | 65.145 | 59.417 | 1.00 40.77 | AAAA |
| ATOM | 2581 | ND2 | ASN | A | 324 | 33.779 | 65.938 | 60.064 | 1.00 40.63 | AAAA |
| ATOM | 2582 | C | ASN | A | 324 | 33.918 | 61.786 | 57.712 | 1.00 40.10 | AAAA |
| ATOM | 2583 | O | ASN | A | 324 | 33.320 | 61.468 | 56.678 | 1.00 39.24 | AAAA |
| ATOM | 2584 | N | LYS | A | 325 | 35.144 | 61.376 | 58.011 | 1.00 40.41 | AAAA |
| ATOM | 2585 | CA | LYS | A | 325 | 35.908 | 60.519 | 57.126 | 1.00 41.41 | AAAA |
| ATOM | 2586 | CB | LYS | A | 325 | 37.262 | 60.201 | 57.761 | 1.00 42.64 | AAAA |
| ATOM | 2587 | CG | LYS | A | 325 | 38.224 | 59.504 | 56.828 | 1.00 44.45 | AAAA |
| ATOM | 2588 | CD | LYS | A | 325 | 39.575 | 59.199 | 57.491 | 1.00 45.61 | AAAA |
| ATOM | 2589 | CE | LYS | A | 325 | 40.358 | 60.464 | 57.850 | 1.00 45.88 | AAAA |
| ATOM | 2590 | NZ | LYS | A | 325 | 41.717 | 60.151 | 58.404 | 1.00 46.27 | AAAA |
| ATOM | 2591 | C | LYS | A | 325 | 35.124 | 59.248 | 56.856 | 1.00 41.56 | AAAA |
| ATOM | 2592 | O | LYS | A | 325 | 35.042 | 58.781 | 55.716 | 1.00 41.35 | AAAA |
| ATOM | 2593 | N | ALA | A | 326 | 34.524 | 58.703 | 57.906 | 1.00 41.32 | AAAA |
| ATOM | 2594 | CA | ALA | A | 326 | 33.732 | 57.492 | 57.774 | 1.00 41.07 | AAAA |
| ATOM | 2595 | CB | ALA | A | 326 | 33.452 | 56.912 | 59.143 | 1.00 40.87 | AAAA |
| ATOM | 2596 | C | ALA | A | 326 | 32.420 | 57.722 | 57.019 | 1.00 41.24 | AAAA |
| ATOM | 2597 | O | ALA | A | 326 | 32.045 | 56.913 | 56.174 | 1.00 40.91 | AAAA |
| ATOM | 2598 | N | LYS | A | 327 | 31.719 | 58.815 | 57.316 | 1.00 41.92 | AAAA |
| ATOM | 2599 | CA | LYS | A | 327 | 30.451 | 59.097 | 56.631 | 1.00 42.20 | AAAA |
| ATOM | 2600 | CB | LYS | A | 327 | 29.796 | 60.374 | 57.170 | 1.00 43.61 | AAAA |
| ATOM | 2601 | CG | LYS | A | 327 | 29.534 | 60.413 | 58.670 | 1.00 45.83 | AAAA |
| ATOM | 2602 | CD | LYS | A | 327 | 28.745 | 61.681 | 59.029 | 1.00 47.34 | AAAA |
| ATOM | 2603 | CE | LYS | A | 327 | 28.682 | 61.952 | 60.538 | 1.00 48.28 | AAAA |
| ATOM | 2604 | NZ | LYS | A | 327 | 28.090 | 60.845 | 61.351 | 1.00 48.98 | AAAA |
| ATOM | 2605 | C | LYS | A | 327 | 30.673 | 59.266 | 55.125 | 1.00 41.33 | AAAA |
| ATOM | 2606 | O | LYS | A | 327 | 29.879 | 58.797 | 54.309 | 1.00 40.78 | AAAA |
| ATOM | 2607 | N | GLU | A | 328 | 31.761 | 59.950 | 54.781 | 1.00 40.39 | AAAA |
| ATOM | 2608 | CA | GLU | A | 328 | 32.129 | 60.217 | 53.399 | 1.00 38.91 | AAAA |
| ATOM | 2609 | CB | GLU | A | 328 | 33.300 | 61.199 | 53.369 | 1.00 40.04 | AAAA |
| ATOM | 2610 | CG | GLU | A | 328 | 32.941 | 62.576 | 53.909 | 1.00 41.94 | AAAA |
| ATOM | 2611 | CD | GLU | A | 328 | 34.131 | 63.515 | 53.994 | 1.00 43.77 | AAAA |
| ATOM | 2612 | OE1 | GLU | A | 328 | 34.904 | 63.595 | 53.010 | 1.00 44.29 | AAAA |
| ATOM | 2613 | OE2 | GLU | A | 328 | 34.285 | 64.189 | 55.040 | 1.00 45.11 | AAAA |
| ATOM | 2614 | C | GLU | A | 328 | 32.497 | 58.938 | 52.675 | 1.00 37.39 | AAAA |
| ATOM | 2615 | O | GLU | A | 328 | 32.114 | 58.722 | 51.525 | 1.00 37.31 | AAAA |
| ATOM | 2616 | N | LEU | A | 329 | 33.255 | 58.091 | 53.355 | 1.00 35.67 | AAAA |
| ATOM | 2617 | CA | LEU | A | 329 | 33.657 | 56.820 | 52.783 | 1.00 33.03 | AAAA |
| ATOM | 2618 | CB | LEU | A | 329 | 34.451 | 56.012 | 53.813 | 1.00 30.62 | AAAA |
| ATOM | 2619 | CG | LEU | A | 329 | 34.760 | 54.549 | 53.481 | 1.00 27.48 | AAAA |
| ATOM | 2620 | CD1 | LEU | A | 329 | 35.549 | 54.453 | 52.193 | 1.00 26.24 | AAAA |
| ATOM | 2621 | CD2 | LEU | A | 329 | 35.514 | 53.936 | 54.622 | 1.00 25.74 | AAAA |
| ATOM | 2622 | C | LEU | A | 329 | 32.405 | 56.057 | 52.368 | 1.00 33.24 | AAAA |
| ATOM | 2623 | O | LEU | A | 329 | 32.239 | 55.708 | 51.205 | 1.00 32.72 | AAAA |
| ATOM | 2624 | N | LEU | A | 330 | 31.519 | 55.810 | 53.327 | 1.00 33.92 | AAAA |
| ATOM | 2625 | CA | LEU | A | 330 | 30.289 | 55.090 | 53.046 | 1.00 34.91 | AAAA |
| ATOM | 2626 | CB | LEU | A | 330 | 29.411 | 55.023 | 54.292 | 1.00 34.02 | AAAA |
| ATOM | 2627 | CG | LEU | A | 330 | 30.067 | 54.236 | 55.418 | 1.00 34.06 | AAAA |
| ATOM | 2628 | CD1 | LEU | A | 330 | 29.096 | 54.060 | 56.571 | 1.00 33.63 | AAAA |
| ATOM | 2629 | CD2 | LEU | A | 330 | 30.512 | 52.892 | 54.884 | 1.00 33.82 | AAAA |
| ATOM | 2630 | C | LEU | A | 330 | 29.499 | 55.695 | 51.907 | 1.00 35.94 | AAAA |
| ATOM | 2631 | O | LEU | A | 330 | 28.984 | 54.968 | 51.060 | 1.00 36.14 | AAAA |
| ATOM | 2632 | N | LYS | A | 331 | 29.415 | 57.022 | 51.883 | 1.00 38.17 | AAAA |
| ATOM | 2633 | CA | LYS | A | 331 | 28.664 | 57.718 | 50.845 | 1.00 41.05 | AAAA |
| ATOM | 2634 | CB | LYS | A | 331 | 28.407 | 59.161 | 51.233 | 1.00 41.83 | AAAA |
| ATOM | 2635 | CG | LYS | A | 331 | 27.584 | 59.358 | 52.497 | 1.00 43.26 | AAAA |
| ATOM | 2636 | CD | LYS | A | 331 | 27.202 | 60.823 | 52.755 | 1.00 44.15 | AAAA |
| ATOM | 2637 | CE | LYS | A | 331 | 26.182 | 61.333 | 51.730 | 1.00 45.71 | AAAA |
| ATOM | 2638 | NZ | LYS | A | 331 | 25.695 | 62.735 | 51.993 | 1.00 45.95 | AAAA |
| ATOM | 2639 | C | LYS | A | 331 | 29.342 | 57.681 | 49.490 | 1.00 42.22 | AAAA |
| ATOM | 2640 | O | LYS | A | 331 | 28.712 | 57.980 | 48.480 | 1.00 41.94 | AAAA |

Fig. 19-40

| | | | | | | | | | | |
|---|---|---|---|---|---|---|---|---|---|---|
| ATOM | 2641 | N | SER | A | 332 | 30.618 | 57.316 | 49.463 | 1.00 44.45 | AAAA |
| ATOM | 2642 | CA | SER | A | 332 | 31.351 | 57.271 | 48.202 | 1.00 46.88 | AAAA |
| ATOM | 2643 | CB | SER | A | 332 | 32.854 | 57.416 | 48.435 | 1.00 46.49 | AAAA |
| ATOM | 2644 | OG | SER | A | 332 | 33.380 | 56.263 | 49.058 | 1.00 45.65 | AAAA |
| ATOM | 2645 | C | SER | A | 332 | 31.093 | 55.959 | 47.494 | 1.00 48.73 | AAAA |
| ATOM | 2646 | O | SER | A | 332 | 31.262 | 55.854 | 46.281 | 1.00 49.51 | AAAA |
| ATOM | 2647 | N | ILE | A | 333 | 30.697 | 54.952 | 48.258 | 1.00 50.62 | AAAA |
| ATOM | 2648 | CA | ILE | A | 333 | 30.420 | 53.648 | 47.686 | 1.00 52.65 | AAAA |
| ATOM | 2649 | CB | ILE | A | 333 | 30.246 | 52.584 | 48.779 | 1.00 52.35 | AAAA |
| ATOM | 2650 | CG2 | ILE | A | 333 | 29.889 | 51.248 | 48.157 | 1.00 51.40 | AAAA |
| ATOM | 2651 | CG1 | ILE | A | 333 | 31.522 | 52.465 | 49.596 | 1.00 52.29 | AAAA |
| ATOM | 2652 | CD1 | ILE | A | 333 | 31.403 | 51.463 | 50.696 | 1.00 53.23 | AAAA |
| ATOM | 2653 | C | ILE | A | 333 | 29.120 | 53.712 | 46.924 | 1.00 54.42 | AAAA |
| ATOM | 2654 | O | ILE | A | 333 | 28.122 | 54.178 | 47.462 | 1.00 55.10 | AAAA |
| ATOM | 2655 | N | ASP | A | 334 | 29.118 | 53.274 | 45.672 | 1.00 56.56 | AAAA |
| ATOM | 2656 | CA | ASP | A | 334 | 27.863 | 53.263 | 44.940 | 1.00 59.13 | AAAA |
| ATOM | 2657 | CB | ASP | A | 334 | 28.050 | 53.460 | 43.433 | 1.00 59.64 | AAAA |
| ATOM | 2658 | CG | ASP | A | 334 | 28.976 | 52.446 | 42.823 | 1.00 59.23 | AAAA |
| ATOM | 2659 | OD1 | ASP | A | 334 | 28.853 | 52.194 | 41.606 | 1.00 58.87 | AAAA |
| ATOM | 2660 | OD2 | ASP | A | 334 | 29.839 | 51.925 | 43.559 | 1.00 59.34 | AAAA |
| ATOM | 2661 | C | ASP | A | 334 | 27.251 | 51.898 | 45.215 | 1.00 60.95 | AAAA |
| ATOM | 2662 | O | ASP | A | 334 | 27.803 | 50.861 | 44.840 | 1.00 61.15 | AAAA |
| ATOM | 2663 | N | PHE | A | 335 | 26.113 | 51.914 | 45.897 | 1.00 62.56 | AAAA |
| ATOM | 2664 | CA | PHE | A | 335 | 25.414 | 50.701 | 46.257 | 1.00 64.12 | AAAA |
| ATOM | 2665 | CB | PHE | A | 335 | 25.311 | 50.621 | 47.779 | 1.00 64.40 | AAAA |
| ATOM | 2666 | CG | PHE | A | 335 | 24.224 | 49.714 | 48.263 | 1.00 64.98 | AAAA |
| ATOM | 2667 | CD1 | PHE | A | 335 | 24.180 | 48.379 | 47.868 | 1.00 65.54 | AAAA |
| ATOM | 2668 | CD2 | PHE | A | 335 | 23.234 | 50.197 | 49.107 | 1.00 65.12 | AAAA |
| ATOM | 2669 | CE1 | PHE | A | 335 | 23.163 | 47.539 | 48.305 | 1.00 65.75 | AAAA |
| ATOM | 2670 | CE2 | PHE | A | 335 | 22.213 | 49.367 | 49.552 | 1.00 65.79 | AAAA |
| ATOM | 2671 | CZ | PHE | A | 335 | 22.177 | 48.034 | 49.150 | 1.00 66.01 | AAAA |
| ATOM | 2672 | C | PHE | A | 335 | 24.025 | 50.626 | 45.640 | 1.00 65.41 | AAAA |
| ATOM | 2673 | O | PHE | A | 335 | 23.591 | 49.564 | 45.184 | 1.00 65.27 | AAAA |
| ATOM | 2674 | N | GLU | A | 336 | 23.338 | 51.763 | 45.618 | 1.00 66.38 | AAAA |
| ATOM | 2675 | CA | GLU | A | 336 | 21.980 | 51.826 | 45.097 | 1.00 67.49 | AAAA |
| ATOM | 2676 | CB | GLU | A | 336 | 21.893 | 51.260 | 43.673 | 1.00 68.25 | AAAA |
| ATOM | 2677 | CG | GLU | A | 336 | 20.459 | 51.230 | 43.116 | 1.00 69.15 | AAAA |
| ATOM | 2678 | CD | GLU | A | 336 | 20.334 | 50.465 | 41.804 | 1.00 69.40 | AAAA |
| ATOM | 2679 | OE1 | GLU | A | 336 | 20.710 | 49.271 | 41.784 | 1.00 69.57 | AAAA |
| ATOM | 2680 | OE2 | GLU | A | 336 | 19.851 | 51.051 | 40.804 | 1.00 69.10 | AAAA |
| ATOM | 2681 | C | GLU | A | 336 | 21.098 | 50.999 | 46.025 | 1.00 67.68 | AAAA |
| ATOM | 2682 | O | GLU | A | 336 | 21.216 | 49.776 | 46.082 | 1.00 67.58 | AAAA |
| ATOM | 2683 | N | GLU | A | 337 | 20.227 | 51.679 | 46.761 | 1.00 67.87 | AAAA |
| ATOM | 2684 | CA | GLU | A | 337 | 19.317 | 51.020 | 47.686 | 1.00 68.66 | AAAA |
| ATOM | 2685 | CB | GLU | A | 337 | 18.583 | 52.085 | 48.502 | 1.00 68.88 | AAAA |
| ATOM | 2686 | CG | GLU | A | 337 | 18.279 | 51.715 | 49.944 | 1.00 68.12 | AAAA |
| ATOM | 2687 | CD | GLU | A | 337 | 19.527 | 51.587 | 50.789 | 1.00 67.70 | AAAA |
| ATOM | 2688 | OE1 | GLU | A | 337 | 20.319 | 52.554 | 50.851 | 1.00 67.05 | AAAA |
| ATOM | 2689 | OE2 | GLU | A | 337 | 19.711 | 50.518 | 51.398 | 1.00 67.79 | AAAA |
| ATOM | 2690 | C | GLU | A | 337 | 18.322 | 50.222 | 46.827 | 1.00 69.28 | AAAA |
| ATOM | 2691 | O | GLU | A | 337 | 17.886 | 50.705 | 45.780 | 1.00 69.50 | AAAA |
| ATOM | 2692 | N | PHE | A | 338 | 17.966 | 49.012 | 47.259 | 1.00 69.55 | AAAA |
| ATOM | 2693 | CA | PHE | A | 338 | 17.035 | 48.176 | 46.497 | 1.00 69.67 | AAAA |
| ATOM | 2694 | CB | PHE | A | 338 | 16.995 | 46.759 | 47.066 | 1.00 70.51 | AAAA |
| ATOM | 2695 | CG | PHE | A | 338 | 16.225 | 45.789 | 46.221 | 1.00 71.57 | AAAA |
| ATOM | 2696 | CD1 | PHE | A | 338 | 16.666 | 45.462 | 44.936 | 1.00 72.04 | AAAA |
| ATOM | 2697 | CD2 | PHE | A | 338 | 15.052 | 45.208 | 46.698 | 1.00 71.69 | AAAA |
| ATOM | 2698 | CE1 | PHE | A | 338 | 15.944 | 44.566 | 44.138 | 1.00 72.23 | AAAA |
| ATOM | 2699 | CE2 | PHE | A | 338 | 14.323 | 44.313 | 45.909 | 1.00 71.93 | AAAA |
| ATOM | 2700 | CZ | PHE | A | 338 | 14.770 | 43.991 | 44.627 | 1.00 72.11 | AAAA |
| ATOM | 2701 | C | PHE | A | 338 | 15.633 | 48.770 | 46.494 | 1.00 69.26 | AAAA |
| ATOM | 2702 | O | PHE | A | 338 | 15.072 | 49.029 | 45.434 | 1.00 68.86 | AAAA |
| ATOM | 2703 | N | ASP | A | 339 | 15.053 | 48.962 | 47.674 | 1.00 69.35 | AAAA |
| ATOM | 2704 | CA | ASP | A | 339 | 13.733 | 49.572 | 47.755 | 1.00 69.61 | AAAA |
| ATOM | 2705 | CB | ASP | A | 339 | 13.134 | 49.457 | 49.157 | 1.00 69.48 | AAAA |
| ATOM | 2706 | CG | ASP | A | 339 | 11.819 | 50.233 | 49.299 | 1.00 69.72 | AAAA |

Fig. 19-41

```
ATOM   2707  OD1 ASP A 339      11.813  51.462  49.058  1.00 69.39       AAAA
ATOM   2708  OD2 ASP A 339      10.790  49.618  49.655  1.00 69.78       AAAA
ATOM   2709  C   ASP A 339      13.972  51.035  47.440  1.00 69.95       AAAA
ATOM   2710  O   ASP A 339      14.305  51.815  48.333  1.00 69.92       AAAA
ATOM   2711  N   ASP A 340      13.810  51.389  46.168  1.00 70.23       AAAA
ATOM   2712  CA  ASP A 340      14.023  52.748  45.699  1.00 70.39       AAAA
ATOM   2713  CB  ASP A 340      12.757  53.283  45.041  1.00 70.64       AAAA
ATOM   2714  CG  ASP A 340      12.397  52.517  43.791  1.00 70.86       AAAA
ATOM   2715  OD1 ASP A 340      12.126  51.302  43.903  1.00 70.93       AAAA
ATOM   2716  OD2 ASP A 340      12.399  53.125  42.699  1.00 70.89       AAAA
ATOM   2717  C   ASP A 340      14.482  53.674  46.807  1.00 70.63       AAAA
ATOM   2718  O   ASP A 340      15.688  53.847  47.008  1.00 71.13       AAAA
ATOM   2719  N   GLU A 341      13.543  54.259  47.544  1.00 69.95       AAAA
ATOM   2720  CA  GLU A 341      13.947  55.150  48.619  1.00 69.17       AAAA
ATOM   2721  CB  GLU A 341      13.636  56.613  48.266  1.00 70.83       AAAA
ATOM   2722  CG  GLU A 341      14.098  57.601  49.347  1.00 73.44       AAAA
ATOM   2723  CD  GLU A 341      13.956  59.071  48.951  1.00 75.27       AAAA
ATOM   2724  OE1 GLU A 341      12.825  59.518  48.646  1.00 76.21       AAAA
ATOM   2725  OE2 GLU A 341      14.984  59.786  48.954  1.00 75.69       AAAA
ATOM   2726  C   GLU A 341      13.367  54.819  49.983  1.00 67.09       AAAA
ATOM   2727  O   GLU A 341      12.233  55.176  50.297  1.00 66.57       AAAA
ATOM   2728  N   VAL A 342      14.158  54.114  50.785  1.00 64.87       AAAA
ATOM   2729  CA  VAL A 342      13.767  53.779  52.148  1.00 62.55       AAAA
ATOM   2730  CB  VAL A 342      14.265  52.377  52.589  1.00 62.81       AAAA
ATOM   2731  CG1 VAL A 342      14.042  52.193  54.081  1.00 62.56       AAAA
ATOM   2732  CG2 VAL A 342      13.513  51.298  51.849  1.00 63.69       AAAA
ATOM   2733  C   VAL A 342      14.483  54.822  52.982  1.00 59.94       AAAA
ATOM   2734  O   VAL A 342      14.022  55.215  54.054  1.00 59.91       AAAA
ATOM   2735  N   ASP A 343      15.609  55.278  52.442  1.00 56.85       AAAA
ATOM   2736  CA  ASP A 343      16.457  56.266  53.085  1.00 54.01       AAAA
ATOM   2737  CB  ASP A 343      15.639  57.446  53.605  1.00 54.18       AAAA
ATOM   2738  CG  ASP A 343      16.505  58.511  54.241  1.00 53.96       AAAA
ATOM   2739  OD1 ASP A 343      15.947  59.485  54.785  1.00 54.59       AAAA
ATOM   2740  OD2 ASP A 343      17.747  58.373  54.191  1.00 53.61       AAAA
ATOM   2741  C   ASP A 343      17.186  55.609  54.242  1.00 51.92       AAAA
ATOM   2742  O   ASP A 343      16.611  55.371  55.307  1.00 51.89       AAAA
ATOM   2743  N   ARG A 344      18.458  55.306  54.029  1.00 48.86       AAAA
ATOM   2744  CA  ARG A 344      19.240  54.676  55.069  1.00 45.59       AAAA
ATOM   2745  CB  ARG A 344      19.847  53.369  54.573  1.00 43.94       AAAA
ATOM   2746  CG  ARG A 344      18.847  52.289  54.220  1.00 41.70       AAAA
ATOM   2747  CD  ARG A 344      17.953  51.955  55.385  1.00 38.94       AAAA
ATOM   2748  NE  ARG A 344      17.139  50.781  55.096  1.00 36.78       AAAA
ATOM   2749  CZ  ARG A 344      16.176  50.316  55.888  1.00 34.81       AAAA
ATOM   2750  NH1 ARG A 344      15.890  50.927  57.033  1.00 34.11       AAAA
ATOM   2751  NH2 ARG A 344      15.506  49.228  55.537  1.00 31.84       AAAA
ATOM   2752  C   ARG A 344      20.340  55.604  55.520  1.00 44.83       AAAA
ATOM   2753  O   ARG A 344      21.308  55.157  56.128  1.00 43.97       A AA
ATOM   2754  N   SER A 345      20.192  56.895  55.226  1.00 44.32       A AA
ATOM   2755  CA  SER A 345      21.199  57.877  55.618  1.00 43.74       AAAA
ATOM   2756  CB  SER A 345      20.860  59.248  55.039  1.00 44.49       AAAA
ATOM   2757  OG  SER A 345      19.645  59.729  55.577  1.00 46.07       AAAA
ATOM   2758  C   SER A 345      21.307  57.977  57.144  1.00 42.82       AAAA
ATOM   2759  O   SER A 345      22.304  58.472  57.674  1.00 42.91       AAAA
ATOM   2760  N   TYR A 346      20.282  57.509  57.849  1.00 41.48       AAAA
ATOM   2761  CA  TYR A 346      20.296  57.549  59.303  1.00 40.35       AAAA
ATOM   2762  CB  TYR A 346      18.947  57.068  59.858  1.00 40.38       AAAA
ATOM   2763  CG  TYR A 346      18.630  55.601  59.609  1.00 39.28       AAAA
ATOM   2764  CD1 TYR A 346      19.293  54.589  60.316  1.00 38.74       AAAA
ATOM   2765  CE1 TYR A 346      19.022  53.243  60.079  1.00 37.71       AAAA
ATOM   2766  CD2 TYR A 346      17.682  55.225  58.653  1.00 38.49       AAAA
ATOM   2767  CE2 TYR A 346      17.405  53.882  58.408  1.00 38.17       AAAA
ATOM   2768  CZ  TYR A 346      18.079  52.899  59.126  1.00 37.59       AAAA
ATOM   2769  OH  TYR A 346      17.794  51.580  58.898  1.00 37.14       AAAA
ATOM   2770  C   TYR A 346      21.436  56.686  59.849  1.00 39.91       AAAA
ATOM   2771  O   TYR A 346      21.967  56.957  60.921  1.00 40.28       AAAA
ATOM   2772  N   MET A 347      21.800  55.640  59.113  1.00 39.14       AAAA
```

Fig. 19-42

| | | | | | | | | | | |
|---|---|---|---|---|---|---|---|---|---|---|
| ATOM | 2773 | CA | MET | A | 347 | 22.879 | 54.756 | 59.530 | 1.00 38.19 | AAAA |
| ATOM | 2774 | CB | MET | A | 347 | 23.042 | 53.582 | 58.566 | 1.00 38.26 | AAAA |
| ATOM | 2775 | CG | MET | A | 347 | 21.973 | 52.523 | 58.694 | 1.00 38.17 | AAAA |
| ATOM | 2776 | SD | MET | A | 347 | 22.317 | 51.115 | 57.641 | 1.00 38.05 | AAAA |
| ATOM | 2777 | CE | MET | A | 347 | 22.237 | 51.892 | 56.101 | 1.00 37.61 | AAAA |
| ATOM | 2778 | C | MET | A | 347 | 24.189 | 55.494 | 59.603 | 1.00 38.00 | AAAA |
| ATOM | 2779 | O | MET | A | 347 | 25.127 | 55.033 | 60.250 | 1.00 37.40 | AAAA |
| ATOM | 2780 | N | LEU | A | 348 | 24.248 | 56.637 | 58.929 | 1.00 38.08 | AAAA |
| ATOM | 2781 | CA | LEU | A | 348 | 25.449 | 57.463 | 58.898 | 1.00 38.07 | AAAA |
| ATOM | 2782 | CB | LEU | A | 348 | 25.445 | 58.330 | 57.638 | 1.00 36.66 | AAAA |
| ATOM | 2783 | CG | LEU | A | 348 | 25.379 | 57.583 | 56.310 | 1.00 35.47 | AAAA |
| ATOM | 2784 | CD1 | LEU | A | 348 | 25.285 | 58.559 | 55.165 | 1.00 34.51 | AAAA |
| ATOM | 2785 | CD2 | LEU | A | 348 | 26.605 | 56.716 | 56.167 | 1.00 36.56 | AAAA |
| ATOM | 2786 | C | LEU | A | 348 | 25.521 | 58.353 | 60.138 | 1.00 39.07 | AAAA |
| ATOM | 2787 | O | LEU | A | 348 | 26.546 | 58.980 | 60.406 | 1.00 38.81 | AAAA |
| ATOM | 2788 | N | GLU | A | 349 | 24.432 | 58.385 | 60.898 | 1.00 39.90 | AAAA |
| ATOM | 2789 | CA | GLU | A | 349 | 24.363 | 59.213 | 62.092 | 1.00 40.95 | AAAA |
| ATOM | 2790 | CB | GLU | A | 349 | 22.961 | 59.821 | 62.203 | 1.00 41.70 | AAAA |
| ATOM | 2791 | CG | GLU | A | 349 | 22.515 | 60.629 | 60.966 | 1.00 42.28 | AAAA |
| ATOM | 2792 | CD | GLU | A | 349 | 23.349 | 61.891 | 60.708 | 1.00 42.51 | AAAA |
| ATOM | 2793 | OE1 | GLU | A | 349 | 23.414 | 62.778 | 61.587 | 1.00 42.38 | AAAA |
| ATOM | 2794 | OE2 | GLU | A | 349 | 23.933 | 61.998 | 59.614 | 1.00 43.34 | AAAA |
| ATOM | 2795 | C | GLU | A | 349 | 24.740 | 58.511 | 63.406 | 1.00 41.12 | AAAA |
| ATOM | 2796 | O | GLU | A | 349 | 24.664 | 59.118 | 64.476 | 1.00 41.38 | AAAA |
| ATOM | 2797 | N | THR | A | 350 | 25.140 | 57.243 | 63.326 | 1.00 40.86 | AAAA |
| ATOM | 2798 | CA | THR | A | 350 | 25.555 | 56.475 | 64.504 | 1.00 40.69 | AAAA |
| ATOM | 2799 | CB | THR | A | 350 | 24.405 | 56.283 | 65.510 | 1.00 41.56 | AAAA |
| ATOM | 2800 | OG1 | THR | A | 350 | 24.062 | 57.549 | 66.078 | 1.00 41.48 | AAAA |
| ATOM | 2801 | CG2 | THR | A | 350 | 24.821 | 55.345 | 66.638 | 1.00 41.19 | AAAA |
| ATOM | 2802 | C | THR | A | 350 | 26.109 | 55.109 | 64.141 | 1.00 40.14 | AAAA |
| ATOM | 2803 | O | THR | A | 350 | 25.857 | 54.595 | 63.055 | 1.00 39.93 | AAAA |
| ATOM | 2804 | N | LEU | A | 351 | 26.865 | 54.527 | 65.067 | 1.00 40.32 | AAAA |
| ATOM | 2805 | CA | LEU | A | 351 | 27.491 | 53.227 | 64.857 | 1.00 40.70 | AAAA |
| ATOM | 2806 | CB | LEU | A | 351 | 28.855 | 53.213 | 65.540 | 1.00 39.89 | AAAA |
| ATOM | 2807 | CG | LEU | A | 351 | 29.911 | 52.290 | 64.951 | 1.00 39.68 | AAAA |
| ATOM | 2808 | CD1 | LEU | A | 351 | 31.170 | 52.403 | 65.772 | 1.00 39.88 | AAAA |
| ATOM | 2809 | CD2 | LEU | A | 351 | 29.414 | 50.861 | 64.945 | 1.00 40.70 | AAAA |
| ATOM | 2810 | C | LEU | A | 351 | 26.612 | 52.091 | 65.384 | 1.00 41.12 | AAAA |
| ATOM | 2811 | O | LEU | A | 351 | 26.467 | 51.060 | 64.736 | 1.00 40.02 | AAAA |
| ATOM | 2812 | N | LYS | A | 352 | 26.040 | 52.292 | 66.567 | 1.00 42.99 | AAAA |
| ATOM | 2813 | CA | LYS | A | 352 | 25.138 | 51.326 | 67.201 | 1.00 43.93 | AAAA |
| ATOM | 2814 | CB | LYS | A | 352 | 25.412 | 51.225 | 68.707 | 1.00 43.38 | AAAA |
| ATOM | 2815 | CG | LYS | A | 352 | 26.743 | 50.597 | 69.055 | 1.00 44.68 | AAAA |
| ATOM | 2816 | CD | LYS | A | 352 | 27.185 | 50.927 | 70.482 | 1.00 45.48 | AAAA |
| ATOM | 2817 | CE | LYS | A | 352 | 26.189 | 50.500 | 71.539 | 1.00 46.21 | AAAA |
| ATOM | 2818 | NZ | LYS | A | 352 | 26.646 | 50.944 | 72.895 | 1.00 47.34 | AAAA |
| ATOM | 2819 | C | LYS | A | 352 | 23.723 | 51.838 | 67.003 | 1.00 44.40 | AAAA |
| ATOM | 2820 | O | LYS | A | 352 | 23.375 | 52.917 | 67.488 | 1.00 45.79 | AAAA |
| ATOM | 2821 | N | ASP | A | 353 | 22.904 | 51.083 | 66.287 | 1.00 44.78 | AAAA |
| ATOM | 2822 | CA | ASP | A | 353 | 21.532 | 51.509 | 66.074 | 1.00 44.79 | AAAA |
| ATOM | 2823 | CB | ASP | A | 353 | 21.050 | 51.030 | 64.702 | 1.00 45.20 | AAAA |
| ATOM | 2824 | CG | ASP | A | 353 | 21.146 | 49.544 | 64.546 | 1.00 45.21 | AAAA |
| ATOM | 2825 | OD1 | ASP | A | 353 | 21.806 | 49.086 | 63.581 | 1.00 45.06 | AAAA |
| ATOM | 2826 | OD2 | ASP | A | 353 | 20.549 | 48.841 | 65.391 | 1.00 45.54 | AAAA |
| ATOM | 2827 | C | ASP | A | 353 | 20.645 | 50.993 | 67.217 | 1.00 44.44 | AAAA |
| ATOM | 2828 | O | ASP | A | 353 | 21.042 | 50.113 | 67.973 | 1.00 44.29 | AAAA |
| ATOM | 2829 | N | PRO | A | 354 | 19.439 | 51.553 | 67.367 | 1.00 44.22 | AAAA |
| ATOM | 2830 | CD | PRO | A | 354 | 18.839 | 52.617 | 66.550 | 1.00 44.38 | AAAA |
| ATOM | 2831 | CA | PRO | A | 354 | 18.500 | 51.163 | 68.419 | 1.00 44.18 | AAAA |
| ATOM | 2832 | CB | PRO | A | 354 | 17.371 | 52.170 | 68.238 | 1.00 44.52 | AAAA |
| ATOM | 2833 | CG | PRO | A | 354 | 17.368 | 52.341 | 66.749 | 1.00 44.66 | AAAA |
| ATOM | 2834 | C | PRO | A | 354 | 17.995 | 49.740 | 68.328 | 1.00 43.87 | AAAA |
| ATOM | 2835 | O | PRO | A | 354 | 17.962 | 49.152 | 67.249 | 1.00 44.48 | AAAA |
| ATOM | 2836 | N | TRP | A | 355 | 17.588 | 49.198 | 69.469 | 1.00 43.23 | AAAA |
| ATOM | 2837 | CA | TRP | A | 355 | 17.051 | 47.851 | 69.500 | 1.00 42.88 | AAAA |
| ATOM | 2838 | CB | TRP | A | 355 | 16.743 | 47.401 | 70.927 | 1.00 46.42 | AAAA |

Fig. 19-43

| | | | | | | | | | |
|---|---|---|---|---|---|---|---|---|---|
| ATOM | 2839 | CG | TRP A 355 | 17.959 | 47.052 | 71.695 | 1.00 | 49.91 | AAAA |
| ATOM | 2840 | CD2 | TRP A 355 | 18.476 | 45.733 | 71.903 | 1.00 | 51.56 | AAAA |
| ATOM | 2841 | CE2 | TRP A 355 | 19.684 | 45.868 | 72.627 | 1.00 | 52.03 | AAAA |
| ATOM | 2842 | CE3 | TRP A 355 | 18.038 | 44.450 | 71.548 | 1.00 | 52.25 | AAAA |
| ATOM | 2843 | CD1 | TRP A 355 | 18.846 | 47.915 | 72.284 | 1.00 | 50.53 | AAAA |
| ATOM | 2844 | NE1 | TRP A 355 | 19.885 | 47.208 | 72.846 | 1.00 | 51.63 | AAAA |
| ATOM | 2845 | CZ2 | TRP A 355 | 20.460 | 44.763 | 73.003 | 1.00 | 52.64 | AAAA |
| ATOM | 2846 | CZ3 | TRP A 355 | 18.810 | 43.352 | 71.921 | 1.00 | 53.12 | AAAA |
| ATOM | 2847 | CH2 | TRP A 355 | 20.008 | 43.518 | 72.642 | 1.00 | 53.02 | AAAA |
| ATOM | 2848 | C | TRP A 355 | 15.788 | 47.767 | 68.675 | 1.00 | 40.28 | AAAA |
| ATOM | 2849 | O | TRP A 355 | 15.017 | 48.720 | 68.591 | 1.00 | 39.82 | AAAA |
| ATOM | 2850 | N | ARG A 356 | 15.591 | 46.610 | 68.065 | 1.00 | 36.83 | AAAA |
| ATOM | 2851 | CA | ARG A 356 | 14.440 | 46.365 | 67.225 | 1.00 | 33.70 | AAAA |
| ATOM | 2852 | CB | ARG A 356 | 14.901 | 46.197 | 65.772 | 1.00 | 29.50 | AAAA |
| ATOM | 2853 | CG | ARG A 356 | 15.635 | 47.423 | 65.256 | 1.00 | 25.22 | AAAA |
| ATOM | 2854 | CD | ARG A 356 | 16.418 | 47.194 | 63.973 | 1.00 | 21.53 | AAAA |
| ATOM | 2855 | NE | ARG A 356 | 17.055 | 48.435 | 63.533 | 1.00 | 18.55 | AAAA |
| ATOM | 2856 | CZ | ARG A 356 | 17.976 | 48.533 | 62.574 | 1.00 | 17.06 | AAAA |
| ATOM | 2857 | NH1 | ARG A 356 | 18.403 | 47.451 | 61.919 | 1.00 | 17.64 | AAAA |
| ATOM | 2858 | NH2 | ARG A 356 | 18.445 | 49.721 | 62.241 | 1.00 | 11.56 | AAAA |
| ATOM | 2859 | C | ARG A 356 | 13.831 | 45.095 | 67.773 | 1.00 | 34.63 | AAAA |
| ATOM | 2860 | O | ARG A 356 | 13.605 | 44.117 | 67.051 | 1.00 | 35.86 | AAAA |
| ATOM | 2861 | N | GLY A 357 | 13.587 | 45.112 | 69.079 | 1.00 | 34.58 | AAAA |
| ATOM | 2862 | CA | GLY A 357 | 13.003 | 43.960 | 69.734 | 1.00 | 34.33 | AAAA |
| ATOM | 2863 | C | GLY A 357 | 11.536 | 43.783 | 69.395 | 1.00 | 34.31 | AAAA |
| ATOM | 2864 | O | GLY A 357 | 11.006 | 44.418 | 68.484 | 1.00 | 33.56 | AAAA |
| ATOM | 2865 | N | GLY A 358 | 10.876 | 42.906 | 70.139 | 1.00 | 34.47 | AAAA |
| ATOM | 2866 | CA | GLY A 358 | 9.468 | 42.656 | 69.916 | 1.00 | 34.61 | AAAA |
| ATOM | 2867 | C | GLY A 358 | 9.114 | 41.389 | 70.655 | 1.00 | 34.47 | AAAA |
| ATOM | 2868 | O | GLY A 358 | 9.962 | 40.821 | 71.345 | 1.00 | 34.27 | AAAA |
| ATOM | 2869 | N | GLU A 359 | 7.869 | 40.948 | 70.523 | 1.00 | 34.16 | AAAA |
| ATOM | 2870 | CA | GLU A 359 | 7.438 | 39.729 | 71.180 | 1.00 | 33.94 | AAAA |
| ATOM | 2871 | CB | GLU A 359 | 5.910 | 39.644 | 71.174 | 1.00 | 34.78 | AAAA |
| ATOM | 2872 | CG | GLU A 359 | 5.278 | 40.648 | 72.123 | 1.00 | 36.70 | AAAA |
| ATOM | 2873 | CD | GLU A 359 | 3.863 | 41.020 | 71.740 | 1.00 | 38.40 | AAAA |
| ATOM | 2874 | OE1 | GLU A 359 | 3.017 | 40.108 | 71.600 | 1.00 | 39.65 | AAAA |
| ATOM | 2875 | OE2 | GLU A 359 | 3.598 | 42.234 | 71.584 | 1.00 | 38.52 | AAAA |
| ATOM | 2876 | C | GLU A 359 | 8.058 | 38.549 | 70.464 | 1.00 | 32.86 | AAAA |
| ATOM | 2877 | O | GLU A 359 | 8.678 | 38.692 | 69.427 | 1.00 | 32.92 | AAAA |
| ATOM | 2878 | N | VAL A 360 | 7.918 | 37.375 | 71.036 | 1.00 | 32.63 | AAAA |
| ATOM | 2879 | CA | VAL A 360 | 8.480 | 36.215 | 70.409 | 1.00 | 32.70 | AAAA |
| ATOM | 2880 | CB | VAL A 360 | 9.422 | 35.472 | 71.376 | 1.00 | 33.24 | AAAA |
| ATOM | 2881 | CG1 | VAL A 360 | 10.017 | 34.252 | 70.701 | 1.00 | 32.99 | AAAA |
| ATOM | 2882 | CG2 | VAL A 360 | 10.521 | 36.406 | 71.827 | 1.00 | 32.09 | AAAA |
| ATOM | 2883 | C | VAL A 360 | 7.339 | 35.319 | 69.976 | 1.00 | 32.81 | AAAA |
| ATOM | 2884 | O | VAL A 360 | 6.702 | 34.660 | 70.791 | 1.00 | 32.02 | AAAA |
| ATOM | 2885 | N | ARG A 361 | 7.084 | 35.321 | 68.674 | 1.00 | 33.12 | AAAA |
| ATOM | 2886 | CA | ARG A 361 | 6.035 | 34.508 | 68.086 | 1.00 | 33.52 | AAAA |
| ATOM | 2887 | CB | ARG A 361 | 6.148 | 34.558 | 66.565 | 1.00 | 33.43 | AAAA |
| ATOM | 2888 | CG | ARG A 361 | 5.731 | 35.885 | 65.967 | 1.00 | 34.35 | AAAA |
| ATOM | 2889 | CD | ARG A 361 | 6.041 | 35.972 | 64.469 | 1.00 | 33.90 | AAAA |
| ATOM | 2890 | NE | ARG A 361 | 7.430 | 36.331 | 64.193 | 1.00 | 31.70 | AAAA |
| ATOM | 2891 | CZ | ARG A 361 | 7.890 | 36.608 | 62.978 | 1.00 | 31.18 | AAAA |
| ATOM | 2892 | NH1 | ARG A 361 | 7.068 | 36.562 | 61.941 | 1.00 | 30.48 | AAAA |
| ATOM | 2893 | NH2 | ARG A 361 | 9.162 | 36.948 | 62.802 | 1.00 | 29.71 | AAAA |
| ATOM | 2894 | C | ARG A 361 | 6.066 | 33.057 | 68.557 | 1.00 | 34.20 | AAAA |
| ATOM | 2895 | O | ARG A 361 | 7.101 | 32.537 | 68.968 | 1.00 | 33.79 | AAAA |
| ATOM | 2896 | N | LYS A 362 | 4.914 | 32.407 | 68.496 | 1.00 | 34.68 | AAAA |
| ATOM | 2897 | CA | LYS A 362 | 4.808 | 31.022 | 68.901 | 1.00 | 35.62 | AAAA |
| ATOM | 2898 | CB | LYS A 362 | 3.350 | 30.555 | 68.782 | 1.00 | 37.80 | AAAA |
| ATOM | 2899 | CG | LYS A 362 | 2.378 | 31.226 | 69.756 | 1.00 | 40.38 | AAAA |
| ATOM | 2900 | CD | LYS A 362 | 2.505 | 32.777 | 69.777 | 1.00 | 42.09 | AAAA |
| ATOM | 2901 | CE | LYS A 362 | 2.208 | 33.446 | 68.420 | 1.00 | 41.94 | AAAA |
| ATOM | 2902 | NZ | LYS A 362 | 2.473 | 34.909 | 68.451 | 1.00 | 39.85 | AAAA |
| ATOM | 2903 | C | LYS A 362 | 5.710 | 30.177 | 68.005 | 1.00 | 35.12 | AAAA |
| ATOM | 2904 | O | LYS A 362 | 6.425 | 29.301 | 68.487 | 1.00 | 34.14 | AAAA |

Fig. 19-44

| ATOM | 2905 | N | GLU A 363 | 5.661 | 30.460 | 66.703 | 1.00 | 35.12 | AAAA |
|---|---|---|---|---|---|---|---|---|---|
| ATOM | 2906 | CA | GLU A 363 | 6.445 | 29.741 | 65.699 | 1.00 | 35.62 | AAAA |
| ATOM | 2907 | CB | GLU A 363 | 6.567 | 30.560 | 64.424 | 1.00 | 36.81 | AAAA |
| ATOM | 2908 | CG | GLU A 363 | 5.280 | 30.808 | 63.711 | 1.00 | 38.66 | AAAA |
| ATOM | 2909 | CD | GLU A 363 | 5.477 | 31.704 | 62.517 | 1.00 | 39.60 | AAAA |
| ATOM | 2910 | OE1 | GLU A 363 | 6.287 | 31.324 | 61.637 | 1.00 | 39.11 | AAAA |
| ATOM | 2911 | OE2 | GLU A 363 | 4.826 | 32.782 | 62.469 | 1.00 | 39.95 | AAAA |
| ATOM | 2912 | C | GLU A 363 | 7.836 | 29.450 | 66.181 | 1.00 | 35.14 | AAAA |
| ATOM | 2913 | O | GLU A 363 | 8.321 | 28.316 | 66.098 | 1.00 | 34.50 | AAAA |
| ATOM | 2914 | N | VAL A 364 | 8.475 | 30.505 | 66.671 | 1.00 | 34.96 | AAAA |
| ATOM | 2915 | CA | VAL A 364 | 9.830 | 30.431 | 67.180 | 1.00 | 34.44 | AAAA |
| ATOM | 2916 | CB | VAL A 364 | 10.338 | 31.821 | 67.570 | 1.00 | 33.68 | AAAA |
| ATOM | 2917 | CG1 | VAL A 364 | 11.739 | 31.722 | 68.162 | 1.00 | 34.13 | AAAA |
| ATOM | 2918 | CG2 | VAL A 364 | 10.337 | 32.715 | 66.347 | 1.00 | 31.83 | AAAA |
| ATOM | 2919 | C | VAL A 364 | 9.908 | 29.499 | 68.370 | 1.00 | 34.44 | AAAA |
| ATOM | 2920 | O | VAL A 364 | 10.789 | 28.640 | 68.430 | 1.00 | 36.01 | AAAA |
| ATOM | 2921 | N | LYS A 365 | 8.980 | 29.649 | 69.305 | 1.00 | 33.27 | AAAA |
| ATOM | 2922 | CA | LYS A 365 | 8.970 | 28.790 | 70.476 | 1.00 | 33.20 | AAAA |
| ATOM | 2923 | CB | LYS A 365 | 7.968 | 29.319 | 71.508 | 1.00 | 34.28 | AAAA |
| ATOM | 2924 | CG | LYS A 365 | 8.307 | 30.705 | 72.033 | 1.00 | 33.67 | AAAA |
| ATOM | 2925 | CD | LYS A 365 | 7.282 | 31.181 | 73.039 | 1.00 | 34.85 | AAAA |
| ATOM | 2926 | CE | LYS A 365 | 7.658 | 32.534 | 73.638 | 1.00 | 36.47 | AAAA |
| ATOM | 2927 | NZ | LYS A 365 | 6.698 | 32.990 | 74.710 | 1.00 | 37.91 | AAAA |
| ATOM | 2928 | C | LYS A 365 | 8.654 | 27.342 | 70.109 | 1.00 | 32.75 | AAAA |
| ATOM | 2929 | O | LYS A 365 | 9.071 | 26.421 | 70.818 | 1.00 | 31.95 | AAAA |
| ATOM | 2930 | N | ASP A 366 | 7.919 | 27.136 | 69.012 | 1.00 | 32.81 | AAAA |
| ATOM | 2931 | CA | ASP A 366 | 7.600 | 25.777 | 68.581 | 1.00 | 33.65 | AAAA |
| ATOM | 2932 | CB | ASP A 366 | 6.459 | 25.726 | 67.557 | 1.00 | 33.98 | AAAA |
| ATOM | 2933 | CG | ASP A 366 | 5.131 | 26.107 | 68.140 | 1.00 | 33.94 | AAAA |
| ATOM | 2934 | OD1 | ASP A 366 | 4.870 | 25.767 | 69.307 | 1.00 | 33.89 | AAAA |
| ATOM | 2935 | OD2 | ASP A 366 | 4.332 | 26.722 | 67.412 | 1.00 | 35.08 | AAAA |
| ATOM | 2936 | C | ASP A 366 | 8.820 | 25.167 | 67.940 | 1.00 | 33.05 | AAAA |
| ATOM | 2937 | O | ASP A 366 | 9.140 | 24.006 | 68.172 | 1.00 | 33.66 | AAAA |
| ATOM | 2938 | N | THR A 367 | 9.473 | 25.959 | 67.102 | 1.00 | 33.07 | AAAA |
| ATOM | 2939 | CA | THR A 367 | 10.684 | 25.540 | 66.412 | 1.00 | 32.27 | AAAA |
| ATOM | 2940 | CB | THR A 367 | 11.304 | 26.719 | 65.641 | 1.00 | 32.28 | AAAA |
| ATOM | 2941 | OG1 | THR A 367 | 10.473 | 27.039 | 64.520 | 1.00 | 30.64 | AAAA |
| ATOM | 2942 | CG2 | THR A 367 | 12.711 | 26.377 | 65.166 | 1.00 | 33.29 | AAAA |
| ATOM | 2943 | C | THR A 367 | 11.680 | 25.044 | 67.442 | 1.00 | 31.71 | AAAA |
| ATOM | 2944 | O | THR A 367 | 12.178 | 23.918 | 67.352 | 1.00 | 30.45 | AAAA |
| ATOM | 2945 | N | LEU A 368 | 11.955 | 25.896 | 68.426 | 1.00 | 32.05 | AAAA |
| ATOM | 2946 | CA | LEU A 368 | 12.888 | 25.560 | 69.482 | 1.00 | 32.49 | AAAA |
| ATOM | 2947 | CB | LEU A 368 | 13.085 | 26.749 | 70.421 | 1.00 | 32.27 | AAAA |
| ATOM | 2948 | CG | LEU A 368 | 14.097 | 27.809 | 69.960 | 1.00 | 32.71 | AAAA |
| ATOM | 2949 | CD1 | LEU A 368 | 15.488 | 27.170 | 69.899 | 1.00 | 33.00 | AAAA |
| ATOM | 2950 | CD2 | LEU A 368 | 13.709 | 28.393 | 68.597 | 1.00 | 31.86 | AAAA |
| ATOM | 2951 | C | LEU A 368 | 12.455 | 24.334 | 70.256 | 1.00 | 33.82 | AAAA |
| ATOM | 2952 | O | LEU A 368 | 13.266 | 23.133 | 70.489 | 1.00 | 34.29 | AAAA |
| ATOM | 2953 | N | GLU A 369 | 11.183 | 24.285 | 70.645 | 1.00 | 34.30 | AAAA |
| ATOM | 2954 | CA | GLU A 369 | 10.687 | 23.135 | 71.375 | 1.00 | 36.07 | AAAA |
| ATOM | 2955 | CB | GLU A 369 | 9.211 | 23.319 | 71.748 | 1.00 | 38.71 | AAAA |
| ATOM | 2956 | CG | GLU A 369 | 8.974 | 24.285 | 72.920 | 1.00 | 40.18 | AAAA |
| ATOM | 2957 | CD | GLU A 369 | 7.509 | 24.359 | 73.341 | 1.00 | 41.56 | AAAA |
| ATOM | 2958 | OE1 | GLU A 369 | 6.917 | 23.276 | 73.572 | 1.00 | 41.83 | AAAA |
| ATOM | 2959 | OE2 | GLU A 369 | 6.957 | 25.489 | 73.451 | 1.00 | 41.74 | AAAA |
| ATOM | 2960 | C | GLU A 369 | 10.893 | 21.822 | 70.611 | 1.00 | 37.16 | AAAA |
| ATOM | 2961 | O | GLU A 369 | 11.338 | 20.831 | 71.196 | 1.00 | 37.00 | AAAA |
| ATOM | 2962 | N | LYS A 370 | 10.586 | 21.788 | 69.315 | 1.00 | 37.71 | AAAA |
| ATOM | 2963 | CA | LYS A 370 | 10.797 | 20.547 | 68.567 | 1.00 | 38.46 | AAAA |
| ATOM | 2964 | CB | LYS A 370 | 10.166 | 20.604 | 67.177 | 1.00 | 39.96 | AAAA |
| ATOM | 2965 | CG | LYS A 370 | 8.646 | 20.532 | 67.186 | 1.00 | 42.68 | AAAA |
| ATOM | 2966 | CD | LYS A 370 | 8.092 | 20.320 | 65.775 | 1.00 | 44.54 | AAAA |
| ATOM | 2967 | CE | LYS A 370 | 6.572 | 20.075 | 65.781 | 1.00 | 45.55 | AAAA |
| ATOM | 2968 | NZ | LYS A 370 | 6.009 | 19.797 | 64.409 | 1.00 | 45.50 | AAAA |
| ATOM | 2969 | C | LYS A 370 | 12.282 | 20.235 | 68.452 | 1.00 | 38.34 | AAAA |
| ATOM | 2970 | O | LYS A 370 | 12.683 | 19.071 | 68.493 | 1.00 | 37.86 | AAAA |

Fig. 19-45

| | | | | | | | | | |
|---|---|---|---|---|---|---|---|---|---|
| ATOM | 2971 | N | ALA | A | 371 | 13.105 | 21.266 | 68.311 | 1.00 37.69 | AAAA |
| ATOM | 2972 | CA | ALA | A | 371 | 14.543 | 21.057 | 68.226 | 1.00 37.20 | AAAA |
| ATOM | 2973 | CB | ALA | A | 371 | 15.258 | 22.375 | 67.936 | 1.00 35.48 | AAAA |
| ATOM | 2974 | C | ALA | A | 371 | 15.023 | 20.477 | 69.558 | 1.00 37.63 | AAAA |
| ATOM | 2975 | O | ALA | A | 371 | 15.920 | 19.626 | 69.585 | 1.00 37.12 | AAAA |
| ATOM | 2976 | N | LYS | A | 372 | 14.426 | 20.930 | 70.665 | 1.00 37.59 | AAAA |
| ATOM | 2977 | CA | LYS | A | 372 | 14.796 | 20.432 | 71.995 | 1.00 37.46 | AAAA |
| ATOM | 2978 | CB | LYS | A | 372 | 14.022 | 21.156 | 73.095 | 1.00 36.52 | AAAA |
| ATOM | 2979 | CG | LYS | A | 372 | 14.287 | 22.634 | 73.111 | 1.00 22.67 | AAAA |
| ATOM | 2980 | CD | LYS | A | 372 | 13.309 | 23.396 | 74.022 | 1.00 22.67 | AAAA |
| ATOM | 2981 | CE | LYS | A | 372 | 13.600 | 24.874 | 73.901 | 1.00 22.67 | AAAA |
| ATOM | 2982 | NZ | LYS | A | 372 | 12.692 | 25.708 | 74.785 | 1.00 22.67 | AAAA |
| ATOM | 2983 | C | LYS | A | 372 | 14.495 | 18.957 | 72.077 | 1.00 37.60 | AAAA |
| ATOM | 2984 | O | LYS | A | 372 | 15.367 | 18.171 | 72.407 | 1.00 37.26 | AAAA |
| ATOM | 2985 | N | ALA | A | 373 | 13.249 | 18.595 | 71.789 | 1.00 38.17 | AAAA |
| ATOM | 2986 | CA | ALA | A | 373 | 12.812 | 17.206 | 71.829 | 1.00 39.55 | AAAA |
| ATOM | 2987 | CB | ALA | A | 373 | 11.365 | 17.109 | 71.395 | 1.00 39.34 | AAAA |
| ATOM | 2988 | C | ALA | A | 373 | 13.675 | 16.277 | 70.972 | 1.00 41.02 | AAAA |
| ATOM | 2989 | O | ALA | A | 373 | 14.366 | 15.410 | 71.561 | 1.00 42.26 | AAAA |
| ATOM | 2990 | OXT | ALA | A | 373 | 13.663 | 16.416 | 69.725 | 1.00 42.06 | AAAA |
| HETATM | 2991 | ZN | ZN | B | 951 | 23.696 | 34.788 | 54.072 | 1.00 27.38 | ZONE |
| HETATM | 2992 | O1 | SHA | C | 1 | 24.578 | 33.295 | 53.458 | 1.00 31.95 | SAHA |
| HETATM | 2993 | O2 | SHA | C | 1 | 24.294 | 35.218 | 51.444 | 1.00 33.51 | SAHA |
| HETATM | 2994 | N1 | SHA | C | 1 | 24.578 | 33.085 | 52.069 | 1.00 34.03 | SAHA |
| HETATM | 2995 | C1 | SHA | C | 1 | 24.063 | 34.053 | 51.246 | 1.00 34.25 | SAHA |
| HETATM | 2996 | C2 | SHA | C | 1 | 23.090 | 33.625 | 50.259 | 1.00 36.87 | SAHA |
| HETATM | 2997 | C3 | SHA | C | 1 | 23.548 | 33.781 | 48.816 | 1.00 39.33 | SAHA |
| HETATM | 2998 | C4 | SHA | C | 1 | 22.498 | 33.274 | 47.852 | 1.00 40.86 | SAHA |
| HETATM | 2999 | C5 | SHA | C | 1 | 21.590 | 34.413 | 47.455 | 1.00 43.37 | SAHA |
| HETATM | 3000 | C6 | SHA | C | 1 | 21.061 | 34.017 | 46.092 | 1.00 46.72 | SAHA |
| HETATM | 3001 | C7 | SHA | C | 1 | 19.754 | 34.714 | 45.787 | 1.00 48.75 | SAHA |
| HETATM | 3002 | C8 | SHA | C | 1 | 19.960 | 35.720 | 44.693 | 1.00 50.75 | SAHA |
| HETATM | 3003 | O3 | SHA | C | 1 | 20.381 | 35.467 | 43.575 | 1.00 51.08 | SAHA |
| HETATM | 3004 | N2 | SHA | C | 1 | 19.591 | 36.956 | 45.085 | 1.00 52.52 | SAHA |
| HETATM | 3005 | C9 | SHA | C | 1 | 19.842 | 38.330 | 44.507 | 1.00 54.25 | SAHA |
| HETATM | 3006 | C10 | SHA | C | 1 | 19.243 | 39.431 | 45.215 | 1.00 55.76 | SAHA |
| HETATM | 3007 | C11 | SHA | C | 1 | 19.423 | 40.804 | 44.727 | 1.00 56.53 | SAHA |
| HETATM | 3008 | C12 | SHA | C | 1 | 20.169 | 41.085 | 43.545 | 1.00 56.58 | SAHA |
| HETATM | 3009 | C13 | SHA | C | 1 | 20.755 | 39.942 | 42.827 | 1.00 55.93 | SAHA |
| HETATM | 3010 | C14 | SHA | C | 1 | 20.612 | 38.546 | 43.304 | 1.00 54.65 | SAHA |
| HETATM | 3011 | OH2 | WAT | D | 2 | 36.485 | 44.023 | 49.378 | 1.00 4.67 | SOLV |
| HETATM | 3012 | OH2 | WAT | D | 3 | 27.702 | 16.865 | 62.162 | 1.00 4.67 | SOLV |
| HETATM | 3013 | OH2 | WAT | D | 4 | 23.251 | 30.387 | 59.575 | 1.00 10.12 | SOLV |
| HETATM | 3014 | OH2 | WAT | D | 5 | 33.825 | 41.862 | 46.926 | 1.00 21.13 | SOLV |
| HETATM | 3015 | OH2 | WAT | D | 6 | 24.866 | 44.453 | 47.867 | 1.00 23.72 | SOLV |
| HETATM | 3016 | OH2 | WAT | D | 7 | 34.145 | 20.442 | 33.590 | 1.00 18.19 | SOLV |
| HETATM | 3017 | OH2 | WAT | D | 8 | 7.921 | 29.753 | 62.099 | 1.00 20.79 | SOLV |
| HETATM | 3018 | OH2 | WAT | D | 9 | 17.863 | 6.978 | 64.018 | 1.00 28.94 | SOLV |
| HETATM | 3019 | OH2 | WAT | D | 10 | 35.580 | 44.610 | 74.823 | 1.00 31.62 | SOLV |
| HETATM | 3020 | OH2 | WAT | D | 11 | 49.208 | 27.797 | 65.303 | 1.00 14.70 | SOLV |
| HETATM | 3021 | OH2 | WAT | D | 12 | 20.490 | 34.049 | 61.067 | 1.00 25.01 | SOLV |
| HETATM | 3022 | OH2 | WAT | D | 13 | 44.757 | 33.106 | 46.084 | 1.00 25.90 | SOLV |
| HETATM | 3023 | OH2 | WAT | D | 14 | 22.457 | 60.823 | 57.444 | 1.00 15.21 | SOLV |
| HETATM | 3024 | OH2 | WAT | D | 15 | 3.399 | 32.742 | 65.163 | 1.00 20.66 | SOLV |
| HETATM | 3025 | OH2 | WAT | D | 16 | 32.273 | 51.414 | 45.610 | 1.00 22.37 | SOLV |
| HETATM | 3026 | OH2 | WAT | D | 17 | 26.328 | 42.873 | 73.427 | 1.00 27.86 | SOLV |
| HETATM | 3027 | OH2 | WAT | D | 18 | 48.249 | 24.121 | 56.778 | 1.00 15.09 | SOLV |
| HETATM | 3028 | OH2 | WAT | D | 19 | 15.249 | 44.552 | 72.082 | 1.00 40.95 | SOLV |
| HETATM | 3029 | OH2 | WAT | D | 20 | 26.444 | 9.269 | 52.633 | 1.00 26.66 | SOLV |
| HETATM | 3030 | OH2 | WAT | D | 21 | 26.554 | 18.383 | 59.650 | 1.00 11.42 | SOLV |
| HETATM | 3031 | OH2 | WAT | D | 22 | 39.456 | 25.964 | 72.316 | 1.00 20.32 | SOLV |
| HETATM | 3032 | OH2 | WAT | D | 23 | 26.743 | 37.600 | 38.359 | 1.00 37.22 | SOLV |
| HETATM | 3033 | OH2 | WAT | D | 24 | 44.666 | 23.818 | 39.068 | 1.00 32.27 | SOLV |
| HETATM | 3034 | OH2 | WAT | D | 25 | 14.714 | 52.213 | 70.663 | 1.00 29.24 | SOLV |
| HETATM | 3035 | OH2 | WAT | D | 26 | 45.129 | 18.856 | 69.864 | 1.00 29.58 | SOLV |
| HETATM | 3036 | OH2 | WAT | D | 27 | 30.024 | 17.886 | 49.758 | 1.00 15.52 | SOLV |

Fig. 19-46

```
HETATM 3037  OH2 WAT D  28    20.659  28.788  43.520  1.00 28.55      SOLV
HETATM 3038  OH2 WAT D  29    32.271  38.000  53.512  1.00 47.72      SOLV
HETATM 3039  OH2 WAT D  30    18.285  29.333  54.536  1.00 21.34      SOLV
HETATM 3040  OH2 WAT D  31    49.978  38.669  73.461  1.00 31.02      SOLV
HETATM 3041  OH2 WAT D  32    21.587  50.386  71.043  1.00 14.52      SOLV
HETATM 3042  OH2 WAT D  33    46.784  32.121  33.375  1.00 31.79      SOLV
HETATM 3043  OH2 WAT D  34    33.359  39.755  49.117  1.00 16.13      SOLV
HETATM 3044  OH2 WAT D  35     7.687  37.657  51.568  1.00 27.22      SOLV
HETATM 3045  OH2 WAT D  36    44.238  35.392  33.961  1.00 19.67      SOLV
HETATM 3046  OH2 WAT D  37    10.908  25.384  58.206  1.00 33.51      SOLV
HETATM 3047  OH2 WAT D  38    36.758  27.243  70.552  1.00 39.61      SOLV
HETATM 3048  OH2 WAT D  39    45.825  46.691  54.654  1.00 32.43      SOLV
HETATM 3049  OH2 WAT D  40    52.489  20.282  52.165  1.00 39.37      SOLV
HETATM 3050  OH2 WAT D  42    12.117  17.831  56.596  1.00 27.74      SOLV
HETATM 3051  OH2 WAT D  43    45.023  26.168  35.172  1.00 14.09      SOLV
HETATM 3052  OH2 WAT D  44    39.392  12.771  62.066  1.00 35.15      SOLV
HETATM 3053  OH2 WAT D  45     3.930  26.970  63.814  1.00 22.23      SOLV
HETATM 3054  OH2 WAT D  46     8.454  19.321  71.677  1.00 32.36      SOLV
HETATM 3055  OH2 WAT D  47    20.280  18.126  73.237  1.00 33.88      SOLV
HETATM 3056  OH2 WAT D  48     9.321  39.409  54.873  1.00 18.57      SOLV
HETATM 3057  OH2 WAT D  49    50.852  41.323  58.048  1.00 21.25      SOLV
HETATM 3058  OH2 WAT D  50    37.134  34.599  60.315  1.00 61.70      SOLV
HETATM 3059  OH2 WAT D  51    14.944  62.815  48.613  1.00 42.50      SOLV
HETATM 3060  OH2 WAT D  52     6.494  33.164  51.420  1.00 40.65      SOLV
HETATM 3061  OH2 WAT D  53    24.913  44.799  72.298  1.00 17.10      SOLV
HETATM 3062  OH2 WAT D  54    51.156  35.095  48.814  1.00 23.05      SOLV
HETATM 3063  OH2 WAT D  55    16.518  41.750  45.596  1.00 49.25      SOLV
HETATM 3064  OH2 WAT D  56    10.326  16.413  61.267  1.00 46.03      SOLV
HETATM 3065  OH2 WAT D  57    25.316  47.708  73.062  1.00 22.73      SOLV
HETATM 3066  OH2 WAT D  58     4.013  33.865  76.173  1.00 44.82      SOLV
HETATM 3067  OH2 WAT D  59    24.846  18.072  36.805  1.00 34.67      SOLV
HETATM 3068  OH2 WAT D  60    15.930  56.853  61.737  1.00 55.56      SOLV
HETATM 3069  OH2 WAT D  61    49.662  44.249  48.982  1.00 28.72      SOLV
HETATM 3070  OH2 WAT D  62    23.232  17.421  53.920  1.00 13.11      SOLV
HETATM 3071  OH2 WAT D  63    39.293  23.035  33.289  1.00 35.79      SOLV
HETATM 3072  OH2 WAT D  64    19.908  20.169  44.339  1.00 24.33      SOLV
HETATM 3073  OH2 WAT D  65    33.259  21.655  69.560  1.00 45.10      SOLV
HETATM 3074  OH2 WAT D  66    27.528  53.947  68.629  1.00 44.79      SOLV
HETATM 3075  OH2 WAT D  67    18.774  48.716  52.865  1.00 54.01      SOLV
HETATM 3076  OH2 WAT D  68    10.877  29.062  63.401  1.00 27.08      SOLV
HETATM 3077  OH2 WAT D  69    43.057  31.367  28.786  1.00 30.16      SOLV
HETATM 3078  OH2 WAT D  70    24.816  44.057  43.447  1.00 20.11      SOLV
HETATM 3079  OH2 WAT D  71    37.368  38.823  46.381  1.00 33.55      SOLV
HETATM 3080  OH2 WAT D  72     9.038  18.327  63.519  1.00 31.34      SOLV
HETATM 3081  OH2 WAT D  73    51.799  20.829  65.265  1.00 28.32      SOLV
HETATM 3082  OH2 WAT D  74    17.556  58.515  57.254  1.00 19.27      SOLV
HETATM 3083  OH2 WAT D  75    28.436  27.904  79.425  1.00 27.13      SOLV
HETATM 3084  OH2 WAT D  76    18.939  35.798  35.800  1.00 94.18      SOLV
HETATM 3085  OH2 WAT D  77    34.359  31.251  46.688  1.00 73.70      SOLV
HETATM 3086  OH2 WAT D  78    44.373  51.649  60.029  1.00 30.23      SOLV
HETATM 3087  OH2 WAT D  79    28.537  63.478  48.324  1.00 21.09      SOLV
HETATM 3088  OH2 WAT D  80     6.869  44.113  72.030  1.00 28.59      SOLV
HETATM 3089  OH2 WAT D  81    42.882  18.761  71.115  1.00 31.80      SOLV
HETATM 3090  OH2 WAT D  82    36.712  59.078  53.901  1.00 40.11      SOLV
HETATM 3091  OH2 WAT D  83    37.506  42.495  40.104  1.00 51.37      SOLV
HETATM 3092  OH2 WAT D  84    40.054  38.439  55.415  1.00 20.07      SOLV
HETATM 3093  OH2 WAT D  85    32.170  56.633  72.920  1.00 45.23      SOLV
HETATM 3094  OH2 WAT D  86    24.470  53.877  47.119  1.00 41.18      SOLV
HETATM 3095  OH2 WAT D  87    48.585  35.663  67.518  1.00 33.40      SOLV
HETATM 3096  OH2 WAT D  88    29.541  57.166  42.788  1.00 44.61      SOLV
HETATM 3097  OH2 WAT D  89    47.814  28.707  41.228  1.00 45.64      SOLV
HETATM 3098  OH2 WAT D  90    49.377  52.112  63.320  1.00 22.26      SOLV
HETATM 3099  OH2 WAT D  91    44.219  43.589  43.912  1.00 39.90      SOLV
HETATM 3100  OH2 WAT D  92    25.913  61.639  75.382  1.00 48.28      SOLV
HETATM 3101  OH2 WAT D  93     8.623  30.749  49.707  1.00 40.37      SOLV
HETATM 3102  OH2 WAT D  94    45.634  41.080  40.990  1.00 21.46      SOLV
```

Fig. 19-47

```
HETATM 3103  OH2 WAT D  95    29.984  34.886  51.725  1.00 35.75      SOLV
HETATM 3104  OH2 WAT D  96    13.051  21.934  49.804  1.00 46.73      SOLV
HETATM 3105  OH2 WAT D  97    32.412  65.913  55.822  1.00 43.39      SOLV
HETATM 3106  OH2 WAT D  98    35.056  43.390  38.348  1.00 34.53      SOLV
HETATM 3107  OH2 WAT D  99    22.360  47.680  60.688  1.00 19.16      SOLV
HETATM 3108  OH2 WAT D 100    50.755  19.722  57.906  1.00 42.45      SOLV
HETATM 3109  OH2 WAT D 101     7.875  37.690  74.094  1.00 37.18      SOLV
HETATM 3110  OH2 WAT D 102    24.080  26.796  43.617  1.00 30.72      SOLV
HETATM 3111  OH2 WAT D 103    45.206  34.126  75.765  1.00 39.89      SOLV
HETATM 3112  OH2 WAT D 104    26.110  54.786  40.685  1.00 29.58      SOLV
HETATM 3113  OH2 WAT D 105    25.918  39.658  77.647  1.00 44.04      SOLV
HETATM 3114  OH2 WAT D 106    41.578  18.191  36.809  1.00 42.22      SOLV
HETATM 3115  OH2 WAT D 107    31.945  51.420  73.896  1.00 41.15      SOLV
HETATM 3116  OH2 WAT D 108    16.722  60.311  51.182  1.00 48.74      SOLV
HETATM 3117  OH2 WAT D 109    43.604  38.573  78.141  1.00 36.22      SOLV
HETATM 3118  OH2 WAT D 110    16.063  15.496  69.430  1.00 55.36      SOLV
HETATM 3119  OH2 WAT D 111    21.630  22.785  49.145  1.00 36.52      SOLV
HETATM 3120  OH2 WAT D 112    27.479  56.647  44.026  1.00 50.82      SOLV
HETATM 3121  OH2 WAT D 113    14.739  51.674  61.674  1.00 35.55      SOLV
HETATM 3122  OH2 WAT D 114    50.063  26.435  54.358  1.00 50.86      SOLV
HETATM 3123  OH2 WAT D 115    43.935  38.427  73.129  1.00 44.21      SOLV
HETATM 3124  OH2 WAT D 116    49.707  31.478  57.709  1.00 36.11      SOLV
HETATM 3125  OH2 WAT D 117    25.032  43.463  55.676  1.00 38.06      SOLV
HETATM 3126  OH2 WAT D 118    10.618  46.623  59.838  1.00 26.33      SOLV
HETATM 3127  OH2 WAT D 119    48.466  33.382  61.437  1.00 19.82      SOLV
HETATM 3128  OH2 WAT D 120    44.157  40.058  37.907  1.00 42.95      SOLV
HETATM 3129  OH2 WAT D 121    51.267  29.446  52.889  1.00 38.93      SOLV
HETATM 3130  OH2 WAT D 122    16.653  15.228  72.975  1.00 45.41      SOLV
HETATM 3131  OH2 WAT D 123    36.898  45.148  41.936  1.00 27.00      SOLV
HETATM 3132  OH2 WAT D 124    49.655  34.591  59.117  1.00 38.97      SOLV
HETATM 3133  OH2 WAT D 125    12.285  57.594  42.107  1.00 23.56      SOLV
HETATM 3134  OH2 WAT D 126    28.294  57.644  73.289  1.00 34.79      SOLV
HETATM 3135  OH2 WAT D 127    19.138  60.403  61.551  1.00 28.58      SOLV
HETATM 3136  OH2 WAT D 128    30.300  33.685  34.047  1.00 27.37      SOLV
HETATM 3137  OH2 WAT D 129    40.898  53.983  47.254  1.00 16.30      SOLV
HETATM 3138  OH2 WAT D 130    43.550  32.160  38.272  1.00 38.86      SOLV
HETATM 3139  OH2 WAT D 131    18.624  13.959  56.194  1.00 37.70      SOLV
HETATM 3140  OH2 WAT D 132    18.580  12.901  62.894  1.00 27.28      SOLV
HETATM 3141  OH2 WAT D 133    35.830  30.296  50.621  1.00 42.47      SOLV
HETATM 3142  OH2 WAT D 134    51.219  35.855  51.878  1.00 20.37      SOLV
HETATM 3143  OH2 WAT D 135    50.428  22.486  49.267  1.00 39.37      SOLV
HETATM 3144  OH2 WAT D 136    51.633  29.369  63.918  1.00 33.99      SOLV
HETATM 3145  OH2 WAT D 137    46.384  43.924  55.825  1.00 22.63      SOLV
HETATM 3146  OH2 WAT D 138    30.356  25.767  28.762  1.00 25.84      SOLV
HETATM 3147  OH2 WAT D 139    25.070  47.842  60.819  1.00 25.00      SOLV
HETATM 3148  OH2 WAT D 140    47.097  49.394  69.367  1.00 30.58      SOLV
HETATM 3149  OH2 WAT D 141    15.246  37.581  73.398  1.00 36.82      SOLV
HETATM 3150  OH2 WAT D 142     8.341  23.099  64.695  1.00 35.89      SOLV
HETATM 3151  OH2 WAT D 143    30.065  18.220  46.048  1.00 14.26      SOLV
HETATM 3152  OH2 WAT D 144    11.930  46.453  57.606  1.00 36.15      SOLV
```

Fig. 19-48

SEQUENCE LISTING

<160> NUMBER OF SEQ ID NOS: 18

<210> SEQ ID NO 1
<211> LENGTH: 375
<212> TYPE: PRT
<213> ORGANISM: Aquifex aeolicus

<400> SEQUENCE: 1

```
Met Lys Lys Val Lys Leu Ile Gly Thr Leu Asp Tyr Gly Lys Tyr Arg
1               5                   10                  15

Tyr Pro Lys Asn His Pro Leu Lys Ile Pro Arg Val Ser Leu Leu Leu
                20                  25                  30

Arg Phe Leu Asp Ala Met Asn Leu Ile Asp Glu Lys Glu Leu Ile Lys
            35                  40                  45

Ser Arg Pro Ala Thr Lys Glu Glu Leu Leu Leu Phe His Thr Glu Asp
        50                  55                  60

Tyr Ile Asn Thr Leu Met Glu Ala Glu Arg Cys Gln Cys Val Pro Lys
65                  70                  75                  80

Gly Ala Arg Glu Lys Tyr Asn Ile Gly Gly Tyr Glu Asn Pro Val Ser
                85                  90                  95

Tyr Ala Met Phe Thr Gly Ser Ser Leu Ala Thr Gly Ser Thr Val Gln
                100                 105                 110

Ala Ile Glu Glu Phe Leu Lys Gly Asn Val Ala Phe Asn Pro Ala Gly
            115                 120                 125

Gly Met His His Ala Phe Lys Ser Arg Ala Asn Gly Phe Cys Tyr Ile
        130                 135                 140

Asn Asp Pro Ala Val Gly Ile Glu Tyr Leu Arg Lys Lys Gly Phe Lys
145                 150                 155                 160

Arg Ile Leu Tyr Ile Asp Leu Asp Ala His His Cys Asp Gly Val Gln
                165                 170                 175

Glu Ala Phe Tyr Asp Thr Asp Gln Val Phe Val Leu Ser Leu His Gln
                180                 185                 190

Ser Pro Glu Tyr Ala Phe Pro Phe Glu Lys Gly Phe Leu Glu Glu Ile
            195                 200                 205

Gly Glu Gly Lys Gly Lys Gly Tyr Asn Leu Asn Ile Pro Leu Pro Lys
        210                 215                 220

Gly Leu Asn Asp Asn Glu Phe Leu Phe Ala Leu Glu Lys Ser Leu Glu
225                 230                 235                 240

Ile Val Lys Glu Val Phe Glu Pro Glu Val Tyr Leu Leu Gln Leu Gly
                245                 250                 255
```

```
Thr Asp Pro Leu Leu Glu Asp Tyr Leu Ser Lys Phe Asn Leu Ser Asn
                260                 265                 270

Val Ala Phe Leu Lys Ala Phe Asn Ile Val Arg Glu Val Phe Gly Glu
            275                 280                 285

Gly Val Tyr Leu Gly Gly Gly Tyr His Pro Tyr Ala Leu Ala Arg
        290                 295                 300

Ala Trp Thr Leu Ile Trp Cys Glu Leu Ser Gly Arg Glu Val Pro Glu
305                 310                 315                 320

Lys Leu Asn Asn Lys Ala Lys Glu Leu Leu Lys Ser Ile Asp Phe Glu
                325                 330                 335

Glu Phe Asp Asp Glu Val Asp Arg Ser Tyr Met Leu Glu Thr Leu Lys
            340                 345                 350

Asp Pro Trp Arg Gly Gly Glu Val Arg Lys Glu Val Lys Asp Thr Leu
        355                 360                 365

Glu Lys Ala Lys Ala Ser Ser
        370             375
```

<210> SEQ ID NO 2
<211> LENGTH: 1127
<212> TYPE: DNA
<213> ORGANISM: Aquifex aeolicus

<400> SEQUENCE: 2

```
atgaagaagg ttaaacttat cggaacttta gactacggaa agtacagata tcccaaaaac    60
catcctctta aaataccaag agtttcccta ctccttaggt ttttagatgc catgaacctt   120
atagatgaga aggaattaat caagagcaga cccgcaacta agaagaact  ccttttattc   180
cacacggaag actacataaa cactttaatg gaagcggaaa ggtgtcagtg cgttccgaag   240
ggagctaggg aaaagtacaa cataggcgga tacgaaaacc ccgtatctta cgcgatgttt   300
acaggctctt ctctcgcaac gggttcaaca gtgcaggcga tagaggaatt tttaaaggga   360
aatgtagctt tcaatcccgc gggaggtatg caccacgctt ttaaaagcag ggcaaacggc   420
ttttgctaca taacgacc cgctgtggga attgagtact tgagaaaaaa aggctttaag   480
agaatactct acatagacct tgatgcccac cactgcgacg tgttcagga agcctttta     540
gatacagacc aggtgttcgt cctgtcccct caccagtcgc ccgagtacgc cttt ccctt    600
gagaagggct tcctggagga gataggagaa ggaaaaggaa agggctacaa cctgaacatt   660
cccctgccaa agggcttgaa cgacaacgag ttcctctttg ccctagaaaa atctctggaa   720
atagtcaaag aagtatttga gcccgaggtt taccttcttc aactcggaac tgacccactc   780
cttgaagatt accttttccaa gttcaacctc tcaaacgttg ccttttttaaa agctttcaac   840
atcgttcgtg aggttttcgg ggagggagta tacctcggag aggcggata  ccatccttac   900
gccctcgcaa gggcatggac cctaatctgg tgcgagcttt cgggaaggga agtgccggaa   960
aagctaaaca ataaagcaaa agagctttta aagagtatag actttgaaga gtttgacgac  1020
gaggtggacc gctcgtacat gctcgaaacc ctaaaggacc cctggagagg aggagaggta  1080
aggaaagaag taaggatac  gcttgaaaag gcgaaagcct catctta              1127
```

<210> SEQ ID NO 3
<211> LENGTH: 375
<212> TYPE: PRT
<213> ORGANISM: Aquifex aeolicus

<400> SEQUENCE: 3

```
Met Lys Lys Val Lys Leu Ile Gly Thr Leu Asp Tyr Gly Lys Tyr Arg
1               5                   10                  15
Tyr Pro Lys Asn His Pro Leu Lys Ile Pro Arg Val Ser Leu Leu Leu
            20                  25                  30
Arg Phe Leu Asp Ala Met Asn Leu Ile Asp Glu Lys Glu Leu Ile Lys
        35                  40                  45
Ser Arg Pro Ala Thr Lys Glu Glu Leu Leu Leu Phe His Thr Glu Asp
    50                  55                  60
Tyr Ile Asn Thr Leu Met Glu Ala Glu Arg Ser Gln Ser Val Pro Lys
65                  70                  75                  80
Gly Ala Arg Glu Lys Tyr Asn Ile Gly Gly Tyr Glu Asn Pro Val Ser
                85                  90                  95
Tyr Ala Met Phe Thr Gly Ser Ser Leu Ala Thr Gly Ser Thr Val Gln
            100                 105                 110
Ala Ile Glu Glu Phe Leu Lys Gly Asn Val Ala Phe Asn Pro Ala Gly
        115                 120                 125
Gly Met His His Ala Phe Lys Ser Arg Ala Asn Gly Phe Cys Tyr Ile
    130                 135                 140
Asn Asp Pro Ala Val Gly Ile Glu Tyr Leu Arg Lys Lys Gly Phe Lys
145                 150                 155                 160
Arg Ile Leu Tyr Ile Asp Leu Asp Ala His His Cys Asp Gly Val Gln
                165                 170                 175
Glu Ala Phe Tyr Asp Thr Asp Gln Val Phe Val Leu Ser Leu His Gln
            180                 185                 190
Ser Pro Glu Tyr Ala Phe Pro Phe Glu Lys Gly Phe Leu Glu Glu Ile
        195                 200                 205
Gly Glu Gly Lys Gly Lys Gly Tyr Asn Leu Asn Ile Pro Leu Pro Lys
    210                 215                 220
Gly Leu Asn Asp Asn Glu Phe Leu Phe Ala Leu Glu Lys Ser Leu Glu
225                 230                 235                 240
Ile Val Lys Glu Val Phe Glu Pro Glu Val Tyr Leu Leu Gln Leu Gly
                245                 250                 255
Thr Asp Pro Leu Leu Glu Asp Tyr Leu Ser Lys Phe Asn Leu Ser Asn
            260                 265                 270
Val Ala Phe Leu Lys Ala Phe Asn Ile Val Arg Glu Val Phe Gly Glu
        275                 280                 285
Gly Val Tyr Leu Gly Gly Gly Tyr His Pro Tyr Ala Leu Ala Arg
    290                 295                 300
Ala Trp Thr Leu Ile Trp Cys Glu Leu Ser Gly Arg Glu Val Pro Glu
305                 310                 315                 320
Lys Leu Asn Asn Lys Ala Lys Glu Leu Leu Lys Ser Ile Asp Phe Glu
                325                 330                 335
Glu Phe Asp Asp Glu Val Asp Arg Ser Tyr Met Leu Glu Thr Leu Lys
            340                 345                 350
Asp Pro Trp Arg Gly Gly Glu Val Arg Lys Glu Val Lys Asp Thr Leu
        355                 360                 365
Glu Lys Ala Lys Ala Ser Ser
    370                 375

<210> SEQ ID NO 4
<211> LENGTH: 1127
<212> TYPE: DNA
<213> ORGANISM: Aquifex aeolicus
```

<400> SEQUENCE: 4

```
atgaagaagg ttaaacttat cggaactta gactacggaa agtacagata tcccaaaaac      60
catcctctta aaataccaag agtttcccta ctccttaggt ttttagatgc catgaacctt     120
atagatgaga aggaattaat caagagcaga cccgcaacta aagaagaact ccttttattc     180
cacacggaag actacataaa cactttaatg gaagcggaaa ggagtcagag cgttccgaag     240
ggagctaggg aaaagtacaa cataggcgga tacgaaaacc ccgtatctta cgcgatgttt     300
acaggctctt ctctcgcaac gggttcaaca gtgcaggcga tagaggaatt tttaaaggga     360
aatgtagctt tcaatcccgc gggaggtatg caccacgctt taaaagcag gcaaacggc      420
ttttgctaca taaacgaccc cgctgtggga attgagtact tgagaaaaaa aggctttaag     480
agaatactct acatagacct tgatgcccac cactgcgacg tgttcagga agccttttac     540
gatacagacc aggtgttcgt cctgtccctt caccagtcgc ccgagtacgc ctttcccttt     600
gagaagggct tcctggagga gataggagaa ggaaaaggaa agggctacaa cctgaacatt     660
cccctgccaa agggcttgaa cgacaacgag ttcctctttg ccctagaaaa atctctggaa     720
atagtcaaag aagtatttga gcccgaggtt taccttcttc aactcggaac tgacccactc     780
cttgaagatt accttttccaa gttcaacctc tcaaacgttg cctttttaaa agctttcaac     840
atcgttcgtg aggttttcgg ggagggagta tacctcggag gaggcggata ccatccttac     900
gccctcgcaa gggcatggac cctaatctgg tgcgagcttt cgggaaggga agtgccggaa     960
aagctaaaca ataaagcaaa agagcttta aagagtatag actttgaaga gtttgacgac    1020
gaggtggacc gctcgtacat gctcgaaacc ctaaaggacc cctggagagg aggagaggta    1080
aggaaagaag taaaggatac gcttgaaaag gcgaaagcct catctta                  1127
```

<210> SEQ ID NO 5
<211> LENGTH: 375
<212> TYPE: PRT
<213> ORGANISM: Aquifex aeolicus

<400> SEQUENCE: 5

```
Met Lys Lys Val Lys Leu Ile Gly Thr Leu Asp Tyr Gly Lys Tyr Arg
1               5                   10                  15

Tyr Pro Lys Asn His Pro Leu Lys Ile Pro Arg Val Ser Leu Leu Leu
            20                  25                  30

Arg Phe Leu Asp Ala Met Asn Leu Ile Asp Glu Lys Glu Leu Ile Lys
        35                  40                  45

Ser Arg Pro Ala Thr Lys Glu Glu Leu Leu Leu Phe His Thr Glu Asp
    50                  55                  60

Tyr Ile Asn Thr Leu Met Glu Ala Glu Arg Cys Gln Cys Val Pro Lys
65                  70                  75                  80

Gly Ala Arg Glu Lys Tyr Asn Ile Gly Gly Tyr Glu Asn Pro Val Ser
                85                  90                  95

Tyr Ala Met Phe Thr Gly Ser Ser Leu Ala Thr Gly Ser Thr Val Gln
            100                 105                 110

Ala Ile Glu Glu Phe Leu Lys Gly Asn Val Ala Phe Asn Pro Ala Gly
        115                 120                 125

Gly Met His His Ala Phe Lys Ser Arg Ala Asn Gly Phe Cys Tyr Ile
    130                 135                 140

Asn Asp Pro Ala Val Gly Ile Glu Tyr Leu Arg Lys Lys Gly Phe Lys
145                 150                 155                 160
```

```
Arg Ile Leu Tyr Ile Asp Leu Asp Ala His His Cys Asp Gly Val Gln
                165                 170                 175

Glu Ala Phe Tyr Asp Thr Asp Gln Val Phe Val Leu Ser Leu His Gln
            180                 185                 190

Ser Pro Glu Tyr Ala Phe Pro Phe Glu Lys Gly Phe Leu Glu Ile
        195                 200                 205

Gly Glu Gly Lys Gly Lys Gly Tyr Asn Leu Asn Ile Pro Leu Pro Lys
    210                 215                 220

Gly Leu Asn Asp Asn Glu Phe Leu Phe Ala Leu Glu Lys Ser Leu Glu
225                 230                 235                 240

Ile Val Lys Glu Val Phe Glu Pro Glu Val Tyr Leu Leu Gln Leu Gly
                245                 250                 255

Thr Asp Pro Leu Leu Glu Asp Tyr Leu Ser Lys Phe Asn Leu Ser Asn
            260                 265                 270

Val Ala Phe Leu Lys Ala Phe Asn Ile Val Arg Glu Val Phe Gly Glu
        275                 280                 285

Gly Val Tyr Leu Gly Gly Gly Phe His Pro Tyr Ala Leu Ala Arg
    290                 295                 300

Ala Trp Thr Leu Ile Trp Cys Glu Leu Ser Gly Arg Glu Val Pro Glu
305                 310                 315                 320

Lys Leu Asn Asn Lys Ala Lys Glu Leu Leu Lys Ser Ile Asp Phe Glu
                325                 330                 335

Glu Phe Asp Asp Glu Val Asp Arg Ser Tyr Met Leu Glu Thr Leu Lys
            340                 345                 350

Asp Pro Trp Arg Gly Gly Glu Val Arg Lys Glu Val Lys Asp Thr Leu
        355                 360                 365

Glu Lys Ala Lys Ala Ser Ser
    370                 375

<210> SEQ ID NO 6
<211> LENGTH: 1127
<212> TYPE: DNA
<213> ORGANISM: Aquifex aeolicus

<400> SEQUENCE: 6
atgaagaagg ttaaacttat cggaacttta gactacggaa agtacagata tcccaaaaac      60
catcctctta aaataccaag agtttcccta ctccttaggt ttttagatgc catgaacctt     120
atagatgaga aggaattaat caagagcaga cccgcaacta agaagaact ccttttattc      180 cacacggaag actacataaa cactttaatg gaagcggaaa ggtgtcagtg cgttccgaag     240
ggagctaggg aaaagtacaa cataggcgga tacgaaaacc ccgtatctta cgcgatgttt     300
acaggctctt ctctcgcaac gggttcaaca gtgcaggcga tagaggaatt tttaaaggga     360
aatgtagctt tcaatcccgc gggaggtatg caccacgctt ttaaaagcag ggcaaacggc     420
ttttgctaca taaacgaccc cgctgtggga attgagtact tgagaaaaaa aggctttaag     480
agaatactct acatagacct tgatgcccac cactgcgacg tgttcagga agccttttac      540 gatacagacc aggtgttcgt cctgtccctt caccagtcgc ccgagtacgc ctttcccttt     600
gagaagggct tcctggagga gataggagaa ggaaaaggaa agggctacaa cctgaacatt     660
cccctgccaa agggcttgaa cgacaacgag ttcctctttg ccctagaaaa atctctggaa     720
atagtcaaag aagtatttga gcccgaggtt taccttcttc aactcggaac tgacccactc     780
cttgaagatt accttttccaa gttcaacctc tcaaacgttg ccttttttaaa agctttcaac     840 atcgttcgtg aggttttcgg ggagggagta tacctcggag gaggcggatt ccatccttac     900
```

```
gccctcgcaa gggcatggac cctaatctgg tgcgagcttt cgggaaggga agtgccggaa      960
aagctaaaca ataaagcaaa agagctttta aagagtatag actttgaaga gtttgacgac     1020
gaggtggacc gctcgtacat gctcgaaacc ctaaaggacc cctggagagg aggagaggta     1080
aggaaagaag taaggatac gcttgaaaag gcgaaagcct catctta                    1127
```

<210> SEQ ID NO 7
<211> LENGTH: 375
<212> TYPE: PRT
<213> ORGANISM: Aquifex aeolicus

<400> SEQUENCE: 7

```
Met Lys Lys Val Lys Leu Ile Gly Thr Leu Asp Tyr Gly Lys Tyr Arg
1               5                   10                  15

Tyr Pro Lys Asn His Pro Leu Lys Ile Pro Arg Val Ser Leu Leu Leu
            20                  25                  30

Arg Phe Leu Asp Ala Met Asn Leu Ile Asp Glu Lys Glu Leu Ile Lys
        35                  40                  45

Ser Arg Pro Ala Thr Lys Glu Glu Leu Leu Leu Phe His Thr Glu Asp
    50                  55                  60

Tyr Ile Asn Thr Leu Met Glu Ala Glu Arg Cys Gln Cys Val Pro Lys
65                  70                  75                  80

Gly Ala Arg Glu Lys Tyr Asn Ile Gly Gly Tyr Glu Asn Pro Val Ser
                85                  90                  95

Tyr Ala Met Phe Thr Gly Ser Ser Leu Ala Thr Gly Ser Thr Val Gln
            100                 105                 110

Ala Ile Glu Glu Phe Leu Lys Gly Asn Val Ala Phe Asn Pro Ala Gly
        115                 120                 125

Gly Met His His Ala Phe Lys Ser Arg Ala Asn Gly Phe Cys Tyr Ile
    130                 135                 140

Asn Asp Pro Ala Val Gly Ile Glu Tyr Leu Arg Lys Lys Gly Phe Lys
145                 150                 155                 160

Arg Ile Leu Tyr Ile Asp Leu Asp Ala His His Cys Asp Gly Val Gln
                165                 170                 175

Glu Ala Phe Tyr Asp Thr Asp Gln Val Phe Val Leu Ser Leu His Gln
            180                 185                 190

Ser Pro Glu Tyr Ala Phe Pro Phe Glu Lys Gly Phe Leu Glu Glu Ile
        195                 200                 205

Gly Glu Gly Lys Gly Lys Gly Tyr Asn Leu Asn Ile Pro Leu Pro Lys
    210                 215                 220

Gly Leu Asn Asp Asn Glu Phe Leu Phe Ala Leu Glu Lys Ser Leu Glu
225                 230                 235                 240

Ile Val Lys Glu Val Phe Glu Pro Glu Val Tyr Leu Leu Gln Leu Gly
                245                 250                 255

Thr Asp Pro Leu Leu Glu Asp Tyr Leu Ser Lys Phe Asn Leu Ser Asn
            260                 265                 270

Val Ala Phe Leu Lys Ala Phe Asn Ile Val Arg Glu Val Phe Gly Glu
        275                 280                 285

Gly Val Tyr Leu Gly Gly Gly Tyr His Pro Tyr Ala Leu Ala Arg
    290                 295                 300

Ala Asn Thr Leu Ile Trp Cys Glu Leu Ser Gly Arg Glu Val Pro Glu
305                 310                 315                 320

Lys Leu Asn Asn Lys Ala Lys Glu Leu Leu Lys Ser Ile Asp Phe Glu
                325                 330                 335
```

```
Glu Phe Asp Asp Glu Val Asp Arg Ser Tyr Met Leu Glu Thr Leu Lys
            340                 345                 350

Asp Pro Trp Arg Gly Gly Val Arg Lys Glu Val Lys Asp Thr Leu
            355                 360                 365

Glu Lys Ala Lys Ala Ser Ser
    370                 375

<210> SEQ ID NO 8
<211> LENGTH: 370
<212> TYPE: PRT
<213> ORGANISM: Homo sapiens

<400> SEQUENCE: 8

Met Arg Lys Val Cys Tyr Tyr Tyr Asp Gly Asp Val Gly Asn Tyr Tyr
1               5                   10                  15

Tyr Gly Gln Gly His Pro Met Lys Pro His Arg Ile Arg Met Thr His
            20                  25                  30

Asn Leu Leu Asn Tyr Gly Leu Tyr Arg Lys Met Glu Ile Tyr Arg
        35                  40                  45

Pro His Lys Ala Asn Ala Glu Glu Met Thr Lys Tyr His Ser Asp Asp
50                  55                  60

Tyr Ile Lys Phe Leu Arg Ser Ile Arg Pro Asp Asn His Ser Glu Ser
65                  70                  75                  80

Lys Gln Met Gln Arg Phe Asn Val Gly Glu Asp Cys Pro Val Phe Asp
                85                  90                  95

Gly Leu Phe Glu Phe Cys Gln Leu Ser Thr Gly Gly Ser Val Ala Ser
            100                 105                 110

Ala Val Lys Leu Asn Lys Gln Asp Ile Ala Val Asn Trp Ala Gly Gly
            115                 120                 125

Leu His His Ala Lys Lys Ser Glu Ala Ser Gly Phe Cys Tyr Val Asn
130                 135                 140

Asp Ile Val Leu Ala Ile Leu Glu Leu Leu Lys Tyr His Gln Arg Val
145                 150                 155                 160

Leu Tyr Ile Asp Ile Asp Ile His His Gly Asp Gly Val Glu Glu Ala
                165                 170                 175

Phe Tyr Thr Thr Asp Arg Val Met Thr Val Ser Phe His Lys Tyr Gly
            180                 185                 190

Glu Tyr Phe Pro Gly Thr Gly Asp Leu Arg Asp Ile Gly Ala Gly Lys
            195                 200                 205

Gly Lys Tyr Tyr Ala Val His Tyr Pro Leu Arg Asp Gly Ile Asp Asp
        210                 215                 220

Glu Ser Tyr Glu Ala Ile Phe Lys Pro Val Met Ser Lys Val Met Glu
225                 230                 235                 240

Met Phe Gln Pro Ser Ala Val Val Leu Gln Cys Gly Ser Asp Ser Leu
                245                 250                 255

Ser Gly Asp Arg Leu Gly Cys Phe Asn Leu Thr Ile Lys Gly His Ala
            260                 265                 270

Lys Cys Val Glu Phe Val Lys Ser Phe Asn Leu Pro Met Leu Met Leu
            275                 280                 285

Gly Gly Gly Gly Tyr Thr Ile Arg His Val Ala Arg Cys Met Thr Tyr
        290                 295                 300

Glu Thr Ala Val Ala Leu Asp Thr Glu Ile Pro Asn Glu Leu Pro Asn
305                 310                 315                 320

Asp Tyr Phe Glu Tyr Phe Gly Pro Asp Phe Ser Asn His Thr Asn Gln
                325                 330                 335
```

```
Asn Thr Asn Glu Tyr Leu Glu Glu Asn Leu Arg Met Leu Pro His Ala
            340                 345                 350

Pro Gly Val Gln Met Gln Ile Pro Glu Asp Ala Ile Pro Glu Glu Ser
            355                 360                 365

Gly Asp
    370

<210> SEQ ID NO 9
<211> LENGTH: 363
<212> TYPE: PRT
<213> ORGANISM: Homo sapiens

<400> SEQUENCE: 9

Leu Ala Gly Thr Gly Leu Val Leu Asp Glu Gln Leu Asn Glu Phe His
1               5                   10                  15

Phe Pro Glu Gly Pro Phe Arg Leu His Ala Ile Lys Glu Gln Leu Ile
                20                  25                  30

Gln Glu Gly Leu Leu Asp Val Ser Phe Gln Ala Arg Glu Ala Glu Lys
            35                  40                  45

Glu Glu Leu Met Leu Val His Ser Leu Glu Tyr Ile Asp Leu Met Glu
    50                  55                  60

Thr Thr Gln Tyr Met Asn Glu Gly Arg Val Leu Ala Asp Thr Tyr
65                  70                  75                  80

Asp Ser Val Tyr Leu His Pro Asn Ser Tyr Ser Cys Ala Cys Leu Ala
                85                  90                  95

Ser Gly Ser Val Leu Arg Leu Val Asp Ala Val Leu Gly Ala Glu Ala
            100                 105                 110

Ile Ile Arg Pro Pro Gly His His Ala Gln His Ser Leu Met Asp Gly
        115                 120                 125

Tyr Cys Met Phe Ser His Val Ala Val Ala Ala Arg Tyr Ala Gln Gln
130                 135                 140

Lys His Ile Arg Arg Val Leu Ile Val Asp Trp Asp Val His His Gly
145                 150                 155                 160

Gln Gly Thr Gln Phe Thr Phe Asp Gln Asp Pro Ser Val Leu Tyr Phe
                165                 170                 175

Ser Ile His Arg Tyr Glu Gln Gly Arg Phe Pro His Leu Lys Ala Ser
            180                 185                 190

Trp Ser Thr Thr Gly Phe Gly Gln Gly Gln Gly Tyr Thr Ile Asn Val
        195                 200                 205

Pro Trp Asn Gln Gly His Arg Asp Ala Asp Tyr Ile Ala Ala Phe Cys
210                 215                 220

His Val Leu Leu Pro Val Ala Leu Glu Phe Gln Pro Gln Leu Val Leu
225                 230                 235                 240

Val Ala Ala Gly Phe Asp Ala Leu Gln Gly Asp Pro Lys Gly Glu Met
                245                 250                 255

Ala Ala Thr Pro Ala Gly Phe Ala Gln Leu Thr His Leu Leu Met Gly
            260                 265                 270

Leu Ala Gly Gly Lys Leu Ile Leu Ser Leu Gly Gly Tyr Asn Leu Arg
        275                 280                 285

Ala Leu Ala Glu Gly Val Ser Ala Ser Leu His Thr Leu Leu Gly Asp
290                 295                 300

Pro Cys Pro Met Leu Glu Ser Gly Ala Pro Cys Arg Ser Ala Gln Ala
305                 310                 315                 320

Ser Val Ser Glu Pro Phe Trp Glu Val Leu Val Arg Ser Thr Glu Thr
                325                 330                 335
```

```
Glu Asp Asn Val Glu Pro Pro Val Leu Pro Ile Leu Thr Trp Pro Leu
                340                 345                 350

Gln Ser Arg Thr Gly Leu Val Tyr Asp Gln Asn
        355                 360

<210> SEQ ID NO 10
<211> LENGTH: 7
<212> TYPE: PRT
<213> ORGANISM: Homo sapiens

<400> SEQUENCE: 10

Ala Gln Thr Gln Gly Thr Arg
1               5

<210> SEQ ID NO 11
<211> LENGTH: 7
<212> TYPE: PRT
<213> ORGANISM: Homo sapiens

<400> SEQUENCE: 11

Asn Leu Glu Ala Glu Ala Leu
1               5

<210> SEQ ID NO 12
<211> LENGTH: 6
<212> TYPE: PRT
<213> ORGANISM: Homo sapiens

<400> SEQUENCE: 12

Cys Leu Trp Asp Asp Ser
1               5

<210> SEQ ID NO 13
<211> LENGTH: 5
<212> TYPE: PRT
<213> ORGANISM: Homo sapiens

<400> SEQUENCE: 13

Ile Arg Asn Gly Met
1               5

<210> SEQ ID NO 14
<211> LENGTH: 6
<212> TYPE: PRT
<213> ORGANISM: Homo sapiens

<400> SEQUENCE: 14

Lys Leu His Ile Ser Pro
1               5

<210> SEQ ID NO 15
<211> LENGTH: 6
<212> TYPE: PRT
<213> ORGANISM: Homo sapiens

<400> SEQUENCE: 15

Cys Ala Leu Glu Ala Leu
1               5

<210> SEQ ID NO 16
<211> LENGTH: 7
<212> TYPE: PRT
<213> ORGANISM: Homo sapiens
```

-continued

```
<400> SEQUENCE: 16

Lys Ile Lys Gln Arg Leu Phe
1               5

<210> SEQ ID NO 17
<211> LENGTH: 7
<212> TYPE: PRT
<213> ORGANISM: Homo sapiens

<400> SEQUENCE: 17

Val Glu Arg Asp Asn Met Glu
1               5

<210> SEQ ID NO 18
<211> LENGTH: 9
<212> TYPE: PRT
<213> ORGANISM: Homo sapiens

<400> SEQUENCE: 18

Glu Ser Glu Glu Glu Gly Pro Trp Glu
1               5
```

CRYSTAL STRUCTURE OF A DEACETYLASE AND INHIBITORS THEREOF

RELATED APPLICATIONS

This application is a continuation of International Application No. PCT/US00/24700, which designated the United States and was filed on Sep. 8, 2000, published in English, which claims the benefit of U.S. Provisional Application No. 60/152,753, filed on Sep. 8, 1999. The entire teachings of the above application(s) are incorporated herein by reference.

GOVERNMENT SUPPORT

The invention was supported, in whole or in part, by a grant ROI CA-65698 from the National Institutes of Health. The Government has certain rights in the invention.

BACKGROUND OF THE INVENTION

The present invention relates to a histone deacetylase homologue from the hyperthermophilic bacterium *Aquifex aeolicus*, HDLP (histone deacetylase-like protein; also known as AcuC1), which shares 35.2% sequence identity with human histone deacetylase (HDAC1), that can be co-crystallized with an inhibitory ligand, and more particularly, to the detailed crystallographic data obtained from said co-crystallization which is disclosed herein. The invention also relates to methods of using the crystal structure and x-ray crystallographic coordinates of the apo-HDLP inhibitor-bound HDLP to design, isolate and screen compounds which bind to and inhibit the active site of HDLP and HDLP-related proteins, such as those proteins belonging to the HDAC family, including HDAC1.

The reversible modification of histones by-acetylation is associated with changes in nucleosome conformation and chromatin structure, and plays an important role in the regulation of gene expression (reviewed in Davie and Chadee, 1998, *J. Cell Biochem. Suppl.* 30–31:203–213). The histone acetylase and deacetylase enzymes that carry out these modifications are involved in many cellular processes such as cell cycle progression and differentiation, and their deregulation is associated with several types of human cancer (reviewed in Kouzarides, 1999, *Curr. Opin. Genet. Dev.* 9:40–48; Hassig et al., 1997, *Chem. Biol.* 4:783–789; Fenrick and Heibert, 1998, *J. Cell. Biochem. Suppl.* 30–31: 194–202).

Recently, several experimental-antitumor compounds, such as trichostatin A (TSA), trapoxin, suberoylanilide hydroxamic acid (SAHA), and phenylbutyrate have been shown to act, at least in part, by inhibiting histone deacetylases. Richon et al., 1998, *Proc. Natl. Acad. Sci., USA* 95:3003–3007; Yoshida et al., 1990, *J. Biol. Chem.* 265: 17174–17179; Kijima et al., 1993, *J. Biol. Chem.* 268: 22429–22435. Additionally, diallyl sulfide and related molecules (Lea et al., 1999, *Int. J. Oncol.* 2:347–352), oxamflatin (Kim et al., 1999, *Oncogene* 15:2461–2470), MS-27-275, a synthetic benzamide derivative (Saito et al., 1999, *Proc. Natl. Acad. Sci.* 96:4592–4597), butarate derivatives (Lea and Tulsyan, 1995, *Anticancer Res.* 15:879–883), FR901228 (Nokajima et al., 1998, *Exp. Cell Res.* 241: 126–133), depudecin (Kwon et al., 1998, *Proc. Natl. Acad. Sci. USA* 95:3356–3361), and m-carboxysinnamic acid bishydroxamide (CBHA; Richon et al., *Proc. Natl. Acad. Sci. USA* 95:3003–3007) have been shown to inhibit histone deacetylases. In vitro, these compounds can inhibit the growth of fibroblast cells by causing cell cycle arrest in the G1 and G2 phases (Richon et al., 1996, *Proc. Natl. Acad. Sci. USA* 93:5705–5708; Kim et al., 1999, *Oncogene* 18:2461–2470; Yoshida et al., 1995, *Bioessays* 17:423–430; Yoshida & Beppu, 1988, *Exp. Cell. Res.* 177:122–131), and can lead to the terminal differentiation and loss of transforming potential of a variety of transformed cell lines. Richon et al., 1996, *Proc. Natl. Acad. Sci. USA* 93:5705–5708; Kim et al., 1999, *Oncogene* 18:2461–2470; Yoshida et al., 1987, *Cancer Res.* 47:3688–3691. In vivo, phenylbutyrate is effective in the treatment of acute promyelocytic leukemia in conjunction with retinoic acid. Warrell et al., 1998, *J. Natl. Cancer Inst.* 90:1621–1625. SAHA is effective in preventing the formation of mammary tumors in rats, and lung tumors in mice. Desai et al., 1999, *Proc. AACR* 40: abstract #2396; Cohen et al., Cancer Res., submitted.

Histone deacetylases catalyze the removal of acetyl groups from the ∈-amino groups of lysine residues clustered near the N-terminus of nucleosomal histones, and this process is associated with transcriptional repression (reviewed in Struhl, 1998, *Genes Dev.* 12:599–606). Deletion of the yeast histone deacetylase gene, rpd3, or its pharmacological inactivation with trichostatin A reduces the transcriptional repression in a subset of promoters, such as those of Ume6-regulated genes. Kadosh & Struhl, 1998, *Mol. Cell. Biol.* 18:5121–5127. This is accompanied by the increased acetylatibn of H4 histones in the repressed promoter and its vicinity, but has no effect on histones at promoter distal regions. Kadosh & Struhl, 1998, *Mol. Cell. Biol.* 18:5121–5127; Rundlett et al., 1998, *Nature* 392:831–835.

Histone deacetylases are recruited to specific promoters by associating with DNA-binding transcriptional repressors, either directly or through co-repressors that bridge the deacetylase to the transcriptional repressors. For example, the Mad and Ume6-repressors bind to the co-repressor Sin3A (Laherty et al., 1997, *Cell* 89.349–356; Hassig et al., 1997, *Cell* 89:341–347; Kadosh & Struhl, 1997, *Cell* 89:365–371), and the nuclear receptors bind N-CoR and the related SMRT co-repressors. Nagy et al., 1997, *Cell* 89:373–380; Alland et al, 1997, *Nature* 387:49–55; Heinzel et al, 1997, *Nature* 20 387:43–48.

The deregulation of histone deacetylase recruitment appears to be one of the mechanisms through which these enzymes contribute to tumorigenesis. In acute promyelocytic leukemia (APL), chromosomal translocations fuse the retinoic acid receptor-α (RARα) to either PLZF or to PML. These fusion oncoproteins have aberrant transcriptional repression activity resulting, in part, through the recruitment of a co-repressor and, in turn, HDACs. Grignani et al, 1998, *Nature* 391:815–818; Lin et al., 1998, *Nature* 391:811–814. Treatment of PLZF-RARα APL cells with TSA enhances their responsiveness to retinoic acid-induced differentiation. Grignani et al, 1998, *Nature* 391:815–818; Lin et al., 1998, *Nature* 391:811–814.

The histone deacetylases comprise a large family of proteins, conserved from yeast to man, and are divided into two related classes. Class I is characterized by human HDACI, 2, 3 (Taunton et al., 1996, *Science* 272:408–411; Yang et al., 1996, *Proc. Natl. Acad. Sci. USA* 93:12845–12850; Emiliani et al., 1998, *Proc. Natl. Acad. Sci. USA* 95:2795–2800), and yeast RPD3 (Videl & Gaber, 1991, *Mol. Cell. Biol.* 11:6317–6327), and class II by the human HDAC4, 5, 6 (Grozinger et al., 1999, *Proc. Natl. Acad. Sci. USA* 96 :4868–4873; Fischle, et al., 1999, *J. Biol. Chem.* 274:11713–11720), and yeast HDA1 (Rundlett et al., 1996, *Proc. Natl. Acad. Sci. USA* 93:14503–14508). The two classes share a ~390 amino acid region of sequence similarity, comprising the deacetylase core, but are divergent outside this region. The histone deacetylase genes belong to an even larger superfamily (Leipe & Landsman, 1997, *Nucleic Acids Res.* 25:3693–3697) that contains the prokaryotic acetoin utilization proteins (AcuC; 28.1%, sequence identity to HDAC1), and the prokaryotic acetylpolyamine amidohydrolases (APAH; 15.0% sequence identity to HDAC1). The enzymatic activity of AcuC is not clear, but its disruption reduces the ability of B. subtilis to breakdown acetoin and utilize it as a carbon source. Grundy et al., 1993, *Mol. Microbiol.* 13:259–271. APAHs catalyze the deacetylation of polyamines by cleaving a non-peptide amide bond (reviewed in Leipe & Landsman, 1997, *Nucleic Acids Res.* 25:3693–3697).

It is useful to address the questions of how HDACs and HDAC-related proteins catalyze the deacetylation of histones and how the above-referenced compounds, particularly those compounds with antitumor activity, inhibit this activity in order to better understand the mechanism of inhibition of HDACs and to facilitate discovery of additional useful compounds which may inhibit this activity. To this end, the present invention has determined the three dimensional structure of a HDAC1-like protein from the thermophilic bacterium *Aquifex aeolicus*, herein after HDLP. The determination, of the nucleic acid coding sequence of HDLP was described by Deckert et al., 1998, *Nature* 392:353–358. The encoded 375 residue protein, whose sequence was determined from the nucleic acid encoding sequence, shares 35.2% amino acid sequence identity with HDAC1, deacetylates histones in vitro, and is inhibited by TSA, SAHA and several other HDAC inhibitors. The determination of the three-dimensional structure of HDLP is useful in the design, identification and screening of new HDAC family inhibitory compounds which are useful for the inhibition of cell growth both in vivo and in vitro.

SUMMARY OF THE INVENTION

In general, it is the object of the present invention to provide detailed three-dimensional structural information for a family of proteins known as histone deacetylases (HDAC), and particularly a homologue from the hyperthermophilic bacterium *Aquifex aeolicus* HDLP (histone deacetylase-like protein) which shares 35.2% sequence identity with human histone deacetylase (HDAC1). It is also an object of the present invention to provide three-dimensional structural information of an HDLP bound to an inhibitory compound.

In one embodiment of the invention, three-dimensional structure information is obtained from a crystal of wild-type HDLP (SEQ ID NO:1) (the nucleic acid encoding wild-type HDLP is SEQ ID,NO:2). In a further embodiment of the invention, three-dimensional information is obtained from a mutant HDLP comprising two mutations (1) cysteine 75 to a serine and (2) cysteine 77 to a serine (Cys75Ser/Cys77Ser double mutant; SEQ ID NO:3) (the nucleic acid encoding-HDLP Cys75Ser/Cys77Ser double mutant is SEQ ID NO:4). The HDLP mutant of the present invention facilitates the determination of three-dimensional structural information of HDLP bound to a zinc atom at its zinc atom-binding site.

In a preferred embodiment of the invention, the three-dimensional structural information is obtained from a co-crystal of a protein-inhibitor compound complex that comprises HDLP or HDLP Cys75Ser/Cys77Ser double mutant and trichostatin A (TSA)! In another preferred embodiment of the invention the three-dimensional structural information is obtained from a co-crystal of a protein-inhibitor compound complex that comprises HDLP or HDLP Cys75Ser/Cys77Ser double mutant and suberoylanilide hydrbxamic acid (SAHA). Any HDLP or HDLP-related protein (e.g. HDAC) inhibitor compound that may be co-crystallized with HDLP may be used to form a co-crystal of the present invention.

The protein crystals and protein-inhibitory complex co-crystals of the present invention diffract to a high resolution limit of at least equal to or greater than 4 angstrom (Å). In a preferred embodiment, the protein crystals and protein-inhibitory complex co-crystals of the present invention diffract to a high resolution limit of greater than 2.5 Å.

A crystal of the present invention may take a variety of forms, all of which are contemplated by the present invention. In a preferred embodiment, the crystal has a space group of C2 with one molecule in the asymmetric unit and with unit dimensions of a=51.4 Å, b=93.8 Å, c=78.7 Å and β=96.9° (see, e.g., Example 2, below). In another preferred embodiment, the crystal has a space group of $P2_12_12_1$ with two molecules in the asymmetric unit and with unit dimensions of a=53.4 Å, b=94.4 Å, c=156.3 Å (see, e.g., Example 2, below). The HDLP structure comprises a parallel β sheet with a helices packing against both faces. At one end of the β sheet, the HDLP has a narrow, tube-like pocket formed by several well-ordered loops. The walls of the pocket are lined with hydrophobic residues and there is a zinc binding site and several polar side chains at the bottom of the pocket. The inhibitory compounds of the present invention bind in the pocket.

The three-dimensional structural information obtained from crystals of HDLP, HDLP Cys75Ser/Cys77Ser double mutant, HDLP Cys75Ser/Cys77Ser double mutant comprising a zinc atom, HDLP comprising an inhibitory compound such as TSA or SAHA, and HDLP Cys7SSer/Cys77Ser double mutant comprising an inhibitor compound such as TSA or SAM may be employed to solve the structure of any HDLP-related protein (e.g. HDAC) crystal, or any mutant HDLP-related protein and particularly any wild type or mutant of HDLP-related protein complexed with a ligand, including a substrate or inhibitor compound. If the crystals are in a different space group than the known structure, molecular replacement may be employed to solve the structure, or if the crystals are in the same space group, refinement and difference fourier methods may be employed. The structure of HDLP-related proteins (e.g. HDAC1) comprise no greater than a 2.0 Å root mean square deviation (rmsd) in the positions of the Cα atoms for at least 50% or more of the amino acids of the full-length HDLP structure.

The present invention also provides a nucleic acid molecule encoding an HDLP Cys75Ser/Cys77Ser double mutant having the amino acid sequence of SEQ ID NO:3 and the nucleic acid sequence of SEQ ID NO:4. It is also contemplated by the invention that mutations be made in HDLP-related proteins at cysteine residues, as with the Cys75Ser/Cys77Ser double mutant, in order to facilitate the determination of the structure of said proteins bound to a zinc atom. Additionally, the present invention provides expression vectors which comprise the nucleic acid molecule encoding an HDLP Cys75Ser/Cys77ser double mutant encoded by the sequence represented by SEQ ID NO:4 operatively linked to expression control sequences.

It is another object of the present invention to provide methods for the design, identification and screening of potential inhibitor compounds of the HDLP/HDAC family. In a preferred embodiment the method for the rational design, identification and screening of potential inhibitor compounds for HDLP and HDLP-related proteins (e.g.

HDACs) comprising deacetylase activity comprises the steps of: (a) using a three-dimensional structure of an HDLP as defined by the atomic coordinates of the present invention; (b) employing said three-dimensional structure to design or select said potential inhibitor compound; (c) synthesizing and/or selecting said potential inhibitor; (d) contacting said potential inhibitor compound with said enzyme in the presence of acetylated substrate; and (e) determining the percent inhibition of deacetylase activity to determine the inhibitory activity of said potential inhibitor compound. In a further preferred embodiment, the binding properties of said rationally designed inhibitory compound may be determined by a method comprising the steps of: (a) forming a complex comprising said inhibitory compound and HDLP or a HDLP-related protein, (b) co-crystallizing said inhibitory compound-HDLP complex; (c) determining said three-dimensional structure of said co-crystal through molecular replacement or refinement and difference fourier with the molecular coordinates of HDLP as defined by the present invention; and (d) analyzing the three-dimensional structure to determine the binding characteristics of said potential. inhibitor compound.

It is a further object of the present invention to identify a defined class of HDLP/HDAC family inhibitor compounds. The HDLP/HDAC family inhibitor compounds of the present invention are represented by formula (I):

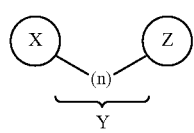

(I)

wherein X comprises a cap group which binds to at least one amino acid selected from the group consisting of proline and leucine; Y comprises an aliphatic chain group which binds to at least one amino acid selected from the group consisting of leucine, phenylalanine and glycine; and Z comprises and active site binding group which binds to at least one amino acid selected from the group consisting of aspartic acid, tyrosine and histidine and may further bind to a zinc atom.

BRIEF DESCRIPTION OF THE DRAWINGS

FIG. 1 is a table listing the statistics from the X-ray crystallographic analysis of a HDLP crystal, a HDLP-TSA co-crystal, and a HDLP-SAHA co-crystal.

FIG. 7 shows (A) a schematic representation of the regions of homology shared between HDLP and HDAC1 in an orientation similar to that of FIG. 4A, and (B) a detailed schematic representation of the homology shared in the pocket and internal cavity between HDLP and HDAC1 in an orientation similar to that of FIG. 4B.

FIG. 10 is the nucleic acid sequence of HDLP from Aquifex aeolicus (SEQ ID NO. 2).

FIG. 11 is the amino acid sequence of full length HDLP from *Aquifex aeolicus* (SEQ ID NO. 1).

FIG. 12 is the nucleic acid sequence of the HDLP active site mutant Tyr297Phe (SEQ ID NO. 6).

FIG. 13 is the amino acid sequence of the HDLP active site mutant Tyr297Phe (SEQ ID NO. 5).

FIG. 14 is the nucleic acid sequence of a double mutant of HDLP from *Aquifex aeolicus* comprising a Cys75Ser and Cys77Ser mutation (SEQ ID NO. 4).

FIG. 15 is the amino acid sequence of a double mutant of HDLP from *Aquifex aeolicus* comprising a Cys75Ser and Cys77Ser mutation (SEQ ID NO. 3).

FIG. 16-1 to 16-49 lists the atomic structure coordinates for HDLP as derived by X-ray diffraction from a crystal of HDLP.

FIGS. 17-1 to 17-49 lists the atomic structure coordinates for HDLP Cys75Ser/Cys77Ser double mutant comprising a zinc atom in the active site as derived by X-ray diffraction from a crystal-of the HDLP Cys7Ser/Cys77Ser double mutant.

FIGS. 18-1 to 18-99 lists the atomic structure coordinates for HDLP Cys75Ser/Cys77Ser double mutant as derived by X-ray diffraction from a co-crystal of HDLP complexed with TSA.

FIGS. 19-1 to 19-48 lists the atomic structure coordinates for HDLP Cys75Ser/Cys77Ser double mutant as derived by X-ray diffraction from-a co-crystal of HDLP complexed with SAHA.

Figure 2:
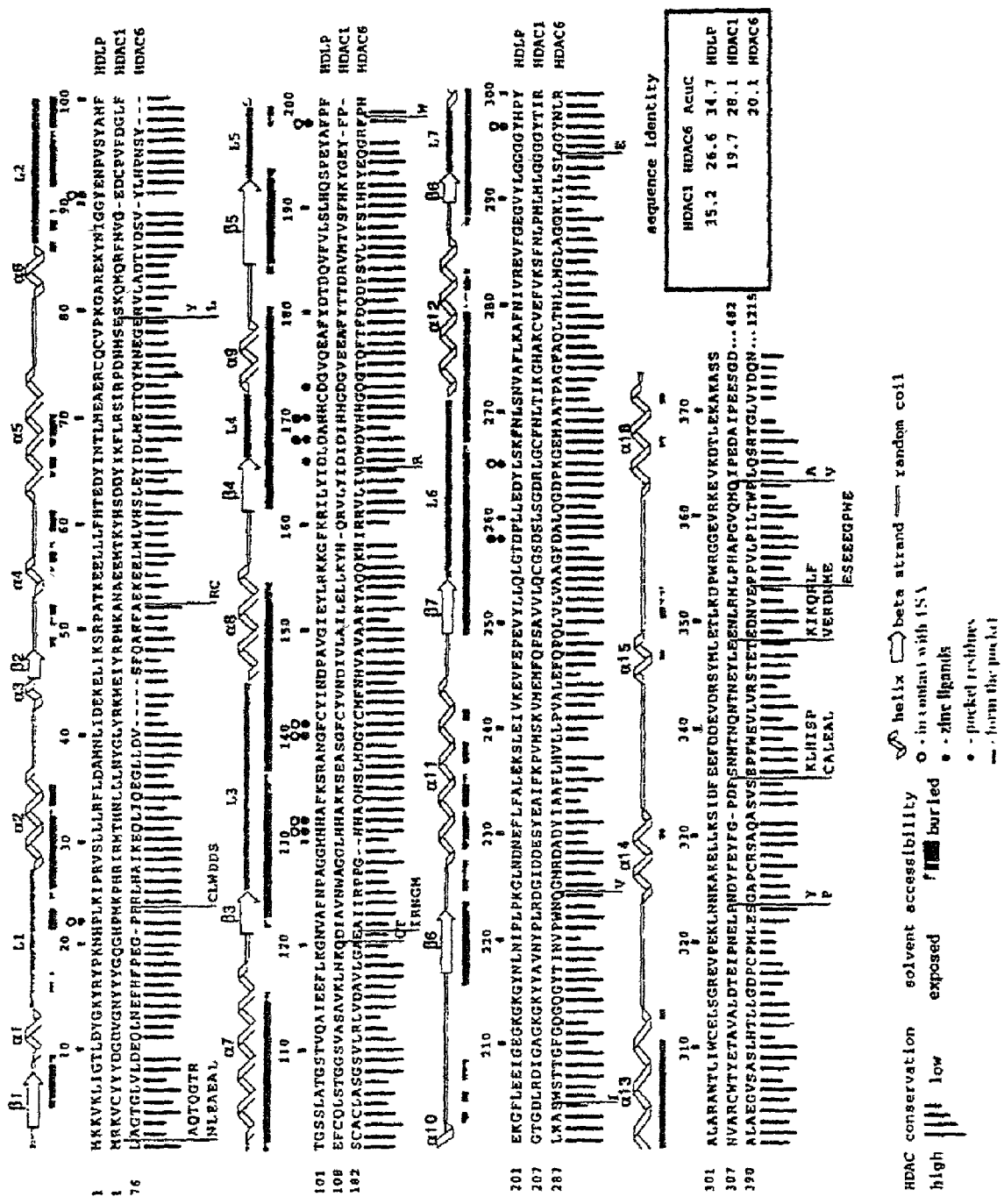
FIG. 2 shows an alignment of various HDAC homologues with percent identity depicted. Included are HDPL (SEQ ID NO:7), HDAC1 (SEQ ID NO:8), and HDACG (SEQ ID NO:9), and variant sequences AQTQGTR (SEQ ID NO:10), NLEAEAL (SEQ ID NO:11), CLWDDS (SEQ ID NO:12), IRNGM (SEQ ID NO:13), KLHISP (SEQ ID NO:14), CALEAL (SEQ ID NO:15), KIKQRLF (SEQ ID NO:16), VERDNME (SEQ ID NO:17), and ESEEEGPWE (SEQ ID NO:18).
Figure 3:
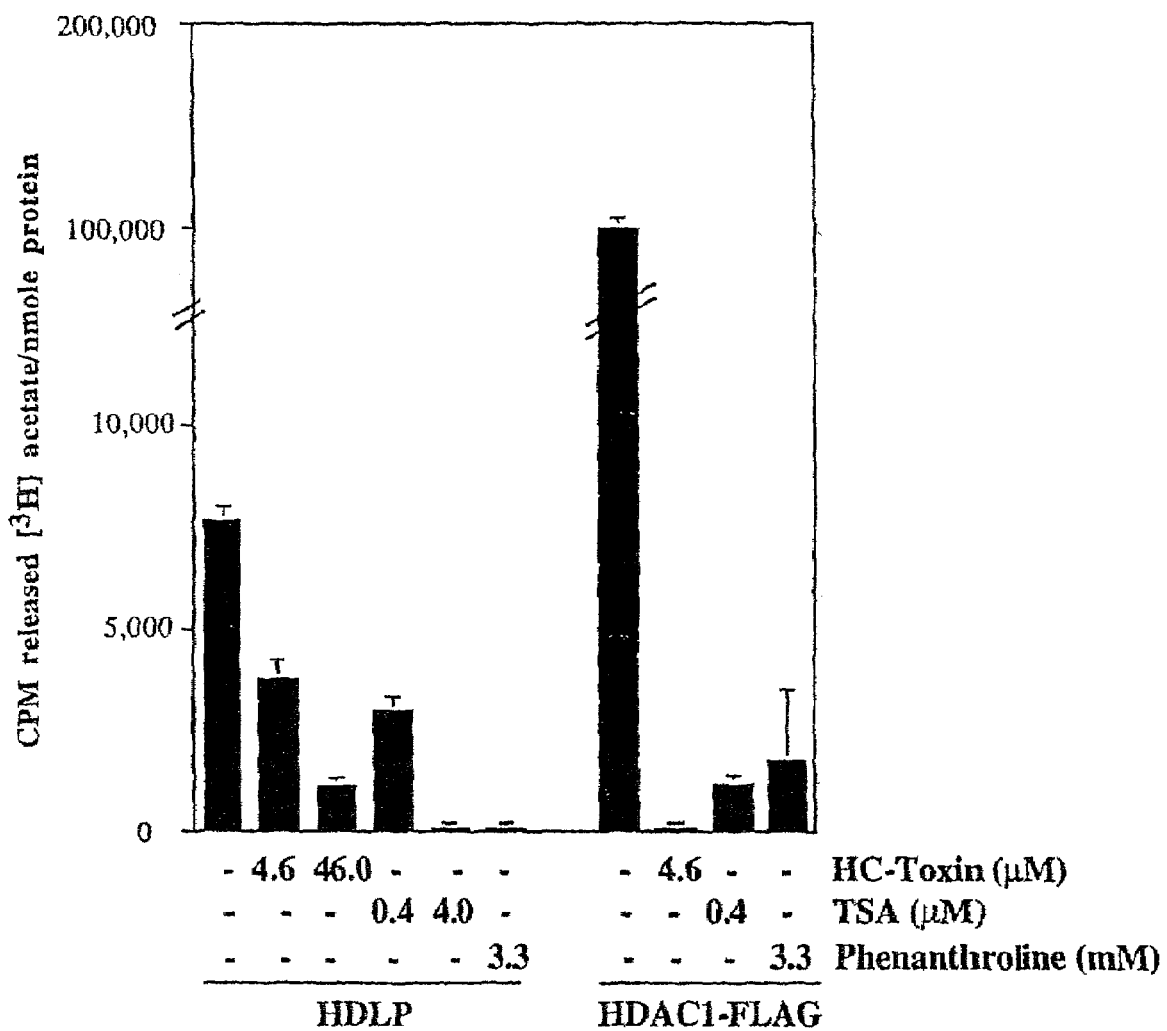
FIG. 3 shows a graph indicating the histone deacetylase activity of HDLP and HDAC1 and the inhibition of HDLP and HDAC1 by the inhibitors TSA and HC-toxin.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention provides crystals of a histone deacetylase (HDAC) homologue grown in the presence and absence of a compound capable of inhibiting the histone deacetylase activity of said HDAC homologue. As referred to herein, a HDAC homologue (as well as a HDLP-related protein) is any protein molecule having (a) greater than 15% sequence identity to over the 375 amino acid residues of HDLP; (b) having no more than twenty insertions or deletions for a total of no more than 100 amino acids; and (c) deacetylase activity. Sequence identity is calculated by the program DNAstar™ using the identity matrix weighing scheme clustal method (DNAstar program, Madison, Wis.).

A HDLP/HDAC inhibitor compound, as used herein, refers to any compound represented by Formula (I):

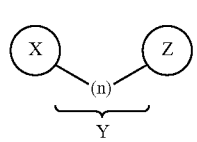

(I)

wherein X comprises a cap group which binds to at least one amino acid selected from the group consisting of tyrosine, proline and leucine; Y comprises an aliphatic chain group from about 5 to about 10 Å, preferably 7 Å, which binds to at least one amino acid selected from the group consisting of phenylalanine and glycine; and Z comprises a active site binding group which binds to at least one amino acid selected from the group consisting of aspartic acid, tyrosine and histidine and which may further bind to a zinc atom. The HDAC inhibitory compounds of the present invention can inhibit greater than 50% of the histone deacetylase activity of a HDAC homologue or a HDLP-related protein.

To grow the crystals of the present invention, the HDAC and HDAC-inhibitory compound complex are purified to greater than 80% total protein and more preferably purified to greater than 90% total protein. For expression and purification purposes, the full-length HDLP (Genbank accession number AE000719) may be subcloned from *Aquifex aeolicus* chromosomal DNA preparation by the polymerase chain reaction (PCR) and inserted into an expression vector.

A large number of vector-host systems known in the art may be used. Possible vectors include, but are not limited to, plasmids or modified viruses, but the vector system must be compatible with the host cell used. Examples of vectors include *E. coli* bacteriophages such as lambda derivatives, or plasmids such as pBR322 derivatives or pUC plasmid derivatives, e.g., pGEX vectors (Amersham-Pharmacia, Piscataway, N.J.), pET vectors (Novagen, Madison, Wis.), pmal-c vectors (Amersham-Pharmacia, Piscataway, N.J.), pFLAG vectors (Chiang and Roeder, 1993, *Pept. Res.* 6:62–64), baculovirus vectors (Invitrogen, Carlsbad, Calif.; Pharmingen, San Diego, Calif.), etc. The insertion into a cloning vector can, for example, be accomplished by ligating the DNA fragment into a cloning vector which has complementary cohesive termini, by blunt end ligation if no complementary cohesive termini are available or by through nucleotide linkers using techniques standard in the art. E.g., Ausubel et al. (eds.), *Current Protocols in Molecular Biology*, (1992). Recombinant vectors comprising the nucleic acid of interest may then be introduced into a host cell compatible with-the vector (e.g. *E. coli*, insect cells, mammalian cells, etc.) via transformation, transfection, infection, electroporation, etc. The nucleic acid may also be placed in a shuttle vector which may be cloned and propagated to large quantities in bacteria and then introduced into a eukaryotic cell host for expression. The vector systems of the present invention may provide expression control sequences and may allow for the expression of proteins in vitro.

In a preferred embodiment, the full length HDLP (SEQ ID NO:2) is subcloned from *Aquifex aeolicus* chromosomal DNA preparation into pGEX4T3 (Amersham-Pharmacia, Piscataway, N.J.). In order, to construct a double mutant comprising a CYS75Ser and Cys77Ser mutation (SEQ ID NO:4), and to construct the HDLP active site mutant Tyr297Phe (SEQ ID NO:5 and SEQ ID NO:6), PCR site directed mutagenesis may be employed with verification by DNA sequencing by methods known to those skilled in the art (see, e.g., Example 1 below). The mutants of the present invention may be subcloned into a suitable expression vector and introduced into a host cell for protein production, as described above. The HDLP nucleic acids of the present invention may be subcloned into an expression vector to create an expression construct such that the resultant HDLP molecule which is produced comprises a fusion protein wherein said fusion protein comprises a tag for ease of purification. As referred to herein, a "tag" is any additional amino acids which are provided in a protein either c-terminally, n-terminally or internally for the ease of purification, for the improvement of production or for any other purpose which may facilitate the goals of the present invention (e.g. to achieve higher levels of production and/or purification). Such tags include tags known to those skilled in the art to be useful in purification such as, but not limited to, his tag, glutathione-s-transferase tag, flag tag, mbp (maltose binding protein) tag, etc. In a preferred embodiment, the wild-type and mutant HDLPs of the present invention are tagged with glutathione-s-transferase (see Example 1 below). In another preferred embodiment, HDAC1 is flag tagged (see Example 1 below). Such tagged proteins may also be engineered to comprise a cleavage site, such as a thrombin, enterokinase or factor X cleavage site, for ease of removal of the tag before, during or after purification. Vector systems which provide a tag and a cleavage site for removal of the tag are particularly useful to make the expression constructs of the present invention.

The tagged HDLPs and HDACs of the present invention may be purified by immuno-affinity or conventional chromatography, including but not limited to, chromatography employing the following: glutathione-sepharose™ (Amersham-Pharmacia, Piscataway, N.J.) or an equivalent resin, nickel or cobalt-purification resins, anion exchange chromatography, cation exchange chromatography, hydrophobic resins, gel filtration, antiflag epitope resin, reverse phase chromatography, etc. After purification, the HDLP and HDLP-inhibitor compound complex may be concentrated to greater than 1 mg/ml for crystallization purposes. In a preferred embodiment HDLP and HDLP-inhibitor complexes are concentrated to greater than 10 mg/ml for crystallization and in a particularly preferred embodiment, HDLP and HDLP-inhibitor complexes are concentrated to greater than 20 mg/ml.

In order to determine whether the purified HDLPs of the present invention demonstrate histone deacetylase activity, the purified HDLPs and also any HDLP-related protein may be assayed by any method known to those skilled in the art for the determination of said activity. In a preferred embodiment, the purified HDLPs of the present invention are incubated in the presence of [$^3$H] acetyl-labeled histone substrate (Carmen et-al., 1996, *J. Biol. Chem.* 271:15837–15844) in a buffer suitable for detection of histone deacetylase activity (see Example 3 below); stopping the reaction; extracting the released acetate and measuring said released acetate, as described by Henzel et al. (*J. Biol. Chem.* 266:21936–21942 (1991); Example 3 below). In a preferred embodiment, the HDLPs of the present invention are inclubated in the presence of $ZnCl_2$ in order to obtain histone deacetylase activity therefrom (Example 3 below).

In another embodiment, the crystals of the present invention comprise purified wild-type HDLP (SEQ ID NO:1) and are grown at room temperature by the hanging-drop vapor-diffusion method from a crystallization solution comprising one or more precipitants selected from the group consisting of isopropanol, polyethylene glycol, and tert butanol (see Example 2 below). The crystallization solution may further comprise one or more salts including salts selected from the group consisting of NaCl and KCl, and one or more buffers including buffers selected from the group consisting of Tris (tris(hydroxymethyl)aminomethane and bis-tris propane-Cl (1, 3-bis[tris(hydroxymethyl)methyl-amino]propane) (see Example 2 below). The pH of the crystallization solution is preferably between pH 5 to 9, although other pH values are also contemplated by the present invention (see Example 2 below).

Any crystallization technique known to those skilled in the art may be employed to obtain the crystals of the present invention, including, but not limited to, batch crystallization, vapor diffusion (either by sitting drop or hanging drop) and micro dialysis. Seeding of the crystals in some instances may be required to obtain X-ray quality crystals. Standard micro and/or macro seeding of crystals may therefore be used.

The crystals of the present invention may form in the space group C2 with one molecule in the asymmetric unit and with unit dimensions of a=51.4 Å, b=93.8 Å, c=78.7 Å and $\beta=96.9°$ (see Example 2 below). The crystals of the present invention may also form in the space group $P2_12_12_1$ with two molecules in the asymmetric unit and with unit dimensions of a=53.4 Å, b=94.4 Å, c=156.3 Å (see Example 2 below). However, the present invention contemplates crystals which form in any space group including, but not limited to, C2, $P2_1$, $P2_12_12_1$, $P3_121$, $P4_32_12_1$, and $C222_1$. The crystals diffract to a resolution greater than 4 Å, preferably greater than 2.5 Å.

To collect diffraction data from the crystals of the present invention, the crystals may be flash-frozen in the crystallization buffer employed for the growth of said crystals, however with preferably higher precipitant concentration (see, e.g., Example 2 below). For example, but not by way of limitation, if the precipitant used was 28% PEG 1500, the crystals may be flash frozen in the same crystallization solution employed for said crystal growth wherein the concentration of the precipitant is increased to 35% (see Example 2 below). If the precipitant is not a sufficient cryoprotectant (i.e. a glass is not formed upon flash-freezing), cryoprotectants (e.g. glycerol, low molecular weight PEGs, alcohols, etc) may be added to the solution in order to achieve glass formation upon flash-freezing, providing the cryoprotectant is compatible with preserving the integrity of the crystals. The flash-frozen crystals are maintained at a temperature of less than –110° C. and preferably less than –150° C. during the collection of the crystallographic data by X-ray diffraction. The X-ray diffraction data may be processed with DENZO and SCALEPACK (Otwinowski & Minor, 1997, *Method Ensemble.* 276:307–326) but any method known to those skilled in the art may be used to process the X-ray diffraction data.

In order to determine the atomic structure of HDLP according to the present invention, multiple isomorphous replacement (MIR) analysis, model building and refinement may be performed. For MIR analysis, the crystals may be soaked in heavy-atoms to produce heavy atom derivatives necessary for MIR analysis. As used herein, heavy atom derivative or derivitization refers to the method of producing a chemically modified form of a protein or protein complex crystal wherein said protein is specifically bound to a heavy atom within the crystal. In practice a crystal is soaked in a solution containing heavy metal atoms or salts, or organometallic compounds, e.g., lead chloride, gold cyanide, thimerosal, lead acetate, uranyl acetate, mercury chloride, gold chloride, etc, which can diffuse through the crystal and bind specifically to the protein. The location(s) of the bound heavy metal atom(s) or salts can be determined by X-ray diffraction analysis of the soaked crystal. This information is used to generate MIR phase information which is used to construct the three-dimensional structure of the crystallized HDLPs and HDLP-related proteins of the, present invention. In a preferred embodiment, the heavy atoms comprise thimerosal, $KAu(CN)_2$ and $Pb(Me)_3OAc$ (see Example 2 below). The MIR phases may be calculated by any program known to those skilled in the art and preferably with the program MLPHARE (The CCP4 suite: Programs for computational crystallography, 1994, *Acta Crystallogr. D.* 50:760–763) and may also use the anomalous diffraction signal from the thimerosal derivative. In a preferred embodiment, the MIR phases were calculated at 2.5 Å and have a mean figure of merit of 0.55 (see FIG. 19 and Example 2 below). The phases may be improved where necessary by solvent flattening by methods known to those skilled in the art including, but not limited to, through the use of the program DM (The CCP4 suite: Programs for computational crystallography, 1994, *Acta Crystallogr. D* 50:760–763).

Thereafter, an initial model of the three-dimensional structure may be built using the program O (Jones et al., 1991, *Acta Crystallogr. A* 47:110–119). The interpretation and building of the structure may be further facilitated by use of the program CNS (Brunger et al., 1998, *Acta Crystallogr. D* 54:905–921).

For the determination of the HDLP-inhibitor compound complex structure, if the space group of the HDLP-inhibitor compound complex crystal is different, molecular replacement may be employed using a known structure of apo-HDLP (as referred to herein, apo-HDLP or apo-HDAC is-the enzyme which is not complexed with an inhibitor compound) or any known HDLP/inhibitor complex structure whose structure may be determined as described above and below in Example 2. If the space group of the HDLP-inhibitor compound crystals is the same, then rigid body refinement and difference fourier may be employed to solve the structure using a known structure of apo-HDLP (as referred to herein, apo-HDLP or apo-HDAC is the enzyme which is not complexed with an inhibitor compound) or any known HDLP/inhibitor complex structure.

The term "molecular replacement" refers to a method that involves generating a preliminary model of the three-dimensional structure of the HDLP crystals of the present invention whose structure coordinates are unknown prior to the employment of molecular replacement. Molecular replacement is achieved by orienting and positioning a molecule whose structure coordinates are known (in this case the previously determined apo-HDLP) within the unit cell as defined by the X-ray diffraction pattern obtained from an HDLP or HDLP-related protein crystal whose structure is unknown so as to best; account for the observed diffraction pattern of the unknown crystal. Phases can then be calculated from this model and combined with the observed amplitudes to give an approximate Fourier synthesis of the structure whose coordinates are unknown. This in turn can be subject to any of several forms of refinement to provide a final, accurate structure.

Any method known to the skilled artisan may be employed to determine the structure by molecular replacement. For example, the program AMORE (The CCP4 suite: Programs for computational crystallography, 1994, *Acta Czystallogr. D.* 50:760–763) may be employed to determine the structure of an unknown histone deacetylase +/−an inhibitor by molecular replacement using the apo-HDLP coordinates (FIG. 16). For the structure determination of the inhibitory compound TSA, the structure of TSA was obtained from the Cambridge Structural Database (Refcode TRCHST, <<hypertext transfer protocol ://world wide web .ccdc.cam.ac.uk >>) may be employed to define the stereochemical restraints used in the refinement with the program CNS (Brunger et al., 1998, *Acta Crystallogr. D* 54:905–921).

The three-dimensional structural information and the atomic coordinates associated with said structural information of HDLP are useful for solving the structure of crystallized proteins which belong to the HDAC family by molecular replacement. Similarly, any structure of a crystallized protein which is thought to be similar in structure based on function or sequence similarity or identity to HDLP may be solved by molecular replacement with the HDLP structural information of the present invention. The structure of HDLP-related proteins as determined by molecular replacement as described above and in Example 2 below, comprise a root mean square deviation (rmsd) of no greater than 2.0 Å in the positions of Cα atoms for at least 50% or more of the amino acids of the structure over the 375 residues of full length HDLP. Such a rmsd may be expected based on the amino acid sequence identity. Chothia & Lesk, 1986, *Embo J.* 5:823–826.

The refined three-dimensional HDLP structures of the present invention, specifically apo-HDLP, Cys75Ser/Cys77Ser double mutant HDLP comprising a zinc atom in the active site, HDLP/TSA complex comprising a zinc atom in the active site, and HDLP/SAHA complex comprising a zinc atom in the active site, are represented by the atomic coordinates set forth in FIGS. 16 to 19 respectively. The refined model for apo-HDLP comprising amino acids 1–375 consists of wild-type HDLP residues 2 to 373 with residues 1, 374 and 375 not modeled and presumed disordered and was determined to a resolution of 1.8 Å. Similarly, the refined model for Cys75Ser/Cys77Ser double mutant HDLP comprising a zinc atom in the active site also consists of residues 2 to 373 with residues 1, 374 and 375 not modeled and presumed disordered and was determined to a resolution of 2.0 Å. The refined model for the HDLP/TSA complex comprising a zinc atom in the active site consists of the Cys75Ser/Cys77Ser double mutant HDLP residues 2 to 373 with residues 1, 374 and 375 not modeled and presumed disordered, has TSA in the binding pocket and was determined to a resolution of 2.1 Å. The HDLP/SAHA complex is similar to the HDLP/TSA complex but has SARA in the binding pocket and was determined to a resolution of 2.5 Å.

For the purposes of further describing the structure of HDLP and HDLP-related proteins, including, but not limited to, HDACs, from the data obtained from the HDLP crystals of the present invention, the definition of the following terms is provided:

The term "β sheet" refers to two or more polypeptide chains (or β strands) that run alongside each other and are linked in a regular manner by hydrogen bonds between the main chain C=O and N-H groups. Therefore all hydrogen bonds in a beta-sheet are between different segments of polypeptide. Most β-sheets in proteins are all-parallel (protein interiors) or all-antiparallel (one side facing solvent, the other facing the hydrophobic core), Hydrogen bonds in antiparallel sheets are perpendicular to the chain direction and spaced evenly as pairs between strands. Hydrogen bonds in parallel sheets are slanted with respect to the chain direction and spaced evenly between strands.

The term "α helix" refers to the most abundant helical conformation found in globular proteins. The average length of an α helix is 10 residues. In an α helix, all amide protons point toward the N-terminus and all carbonyl oxygens point toward the C-terminus. The repeating nature of the phi, psi pairs ensure this orientation. Hydrogen bonds within an α helix also display a repeating pattern in which the backbone C=O of residue X (wherein X refers to any amino acid) hydrogen bonds to the backbone HN of residue X+4. The α helix is a coiled structure characterized by 3.6 residues per turn, and translating along its axis 1.5 Å per amino acid. Thus the pitch is 3.6×1.5 or 5.4 Å. The screw sense of alpha helices is always right-handed.

The term "loop" refers to any other conformation of amino acids (i.e. not a helix, strand or sheet). Additionally, a loop may contain bond interactions between amino acid side chains, but not in a repetitive, regular fashion.

Amino acid residues in peptides shall herein after be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to *Proteins: Structure and Molecular Properties* by Creighton, T. E., W. H. Freeman & Co., New York 1983.

The term "positively charged amino acid" refers to any amino acid having a positively charged side chain under normal physiological conditions. Examples of positively charged amino acids are Arg, Lys and His. The term "negatively charged amino acid" refers to any amino acid having a negatively charged side chain under normal physiological conditions. Examples of negatively charged amino acids are Asp and Glu. The term "hydrophobic amino acid" refers to any amino acid having an uncharged, nonpolar side chain that is relatively insoluble in water. Examples of hydrophobic amino acids are Ala, Leu, Ile, Gly, Val, Pro, Phe, Trp and Met. The term "hydrophilic amino acid" refers to any amino acid having an uncharged, polar side chain that is relatively soluble in water. Examples of hydrophilic amino acids are Ser, Thr, Tyr, Asp, Gln, and Cys. The term "aromatic amino acid" refers to any amino acid comprising a ring structure. Examples of aromatic amino acids are His, S Phe, Trp and Tyr.

The term "charge relay system" refers to a His-Asp arrangement as described by Fersht & Sperling, 1973, *J. Mol. Biol.* 74:137–149; Blow et al., 1969, *Nature* 221: 337–340.

The information obtained from the three-dimensional structures of the present invention reveal that HDLP has a single-domain structure that belongs to the open α/β class of folds (see, e.g., Branden, 1980, *Q. Rev. Biophys.*

Figure 4:
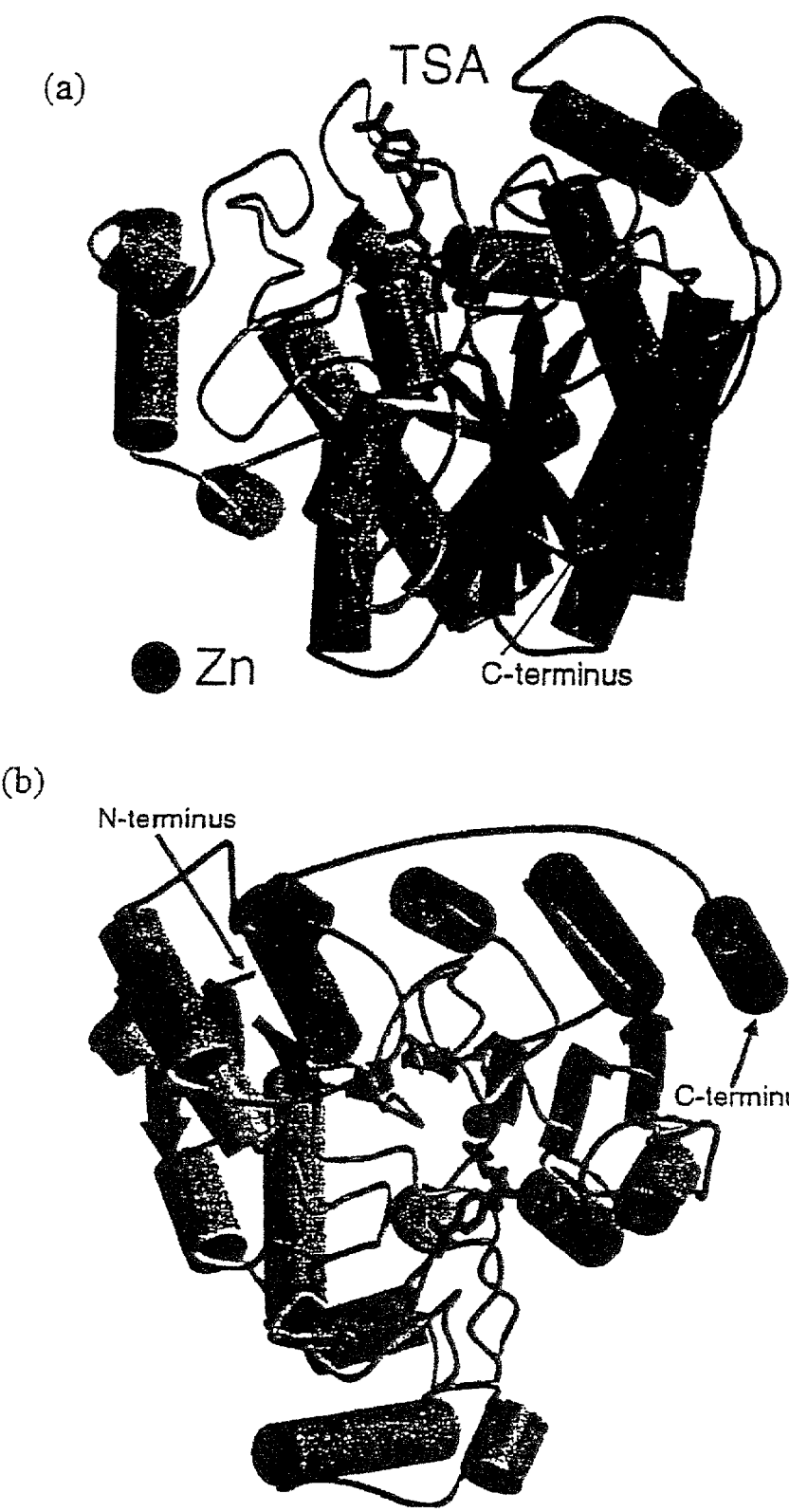
FIG. 4 shows (A & B) a schematic representation of the HDLP-$Zn^{2+}$-TSA complex in two approximately orthogonal views, (C) a topology diagram of HDLP indicating the regions of homology with HDAC1, and (D) a close up schematic representation of the HDLP-$Zn^{2+}$-SAHA complex.
Figure 4C:
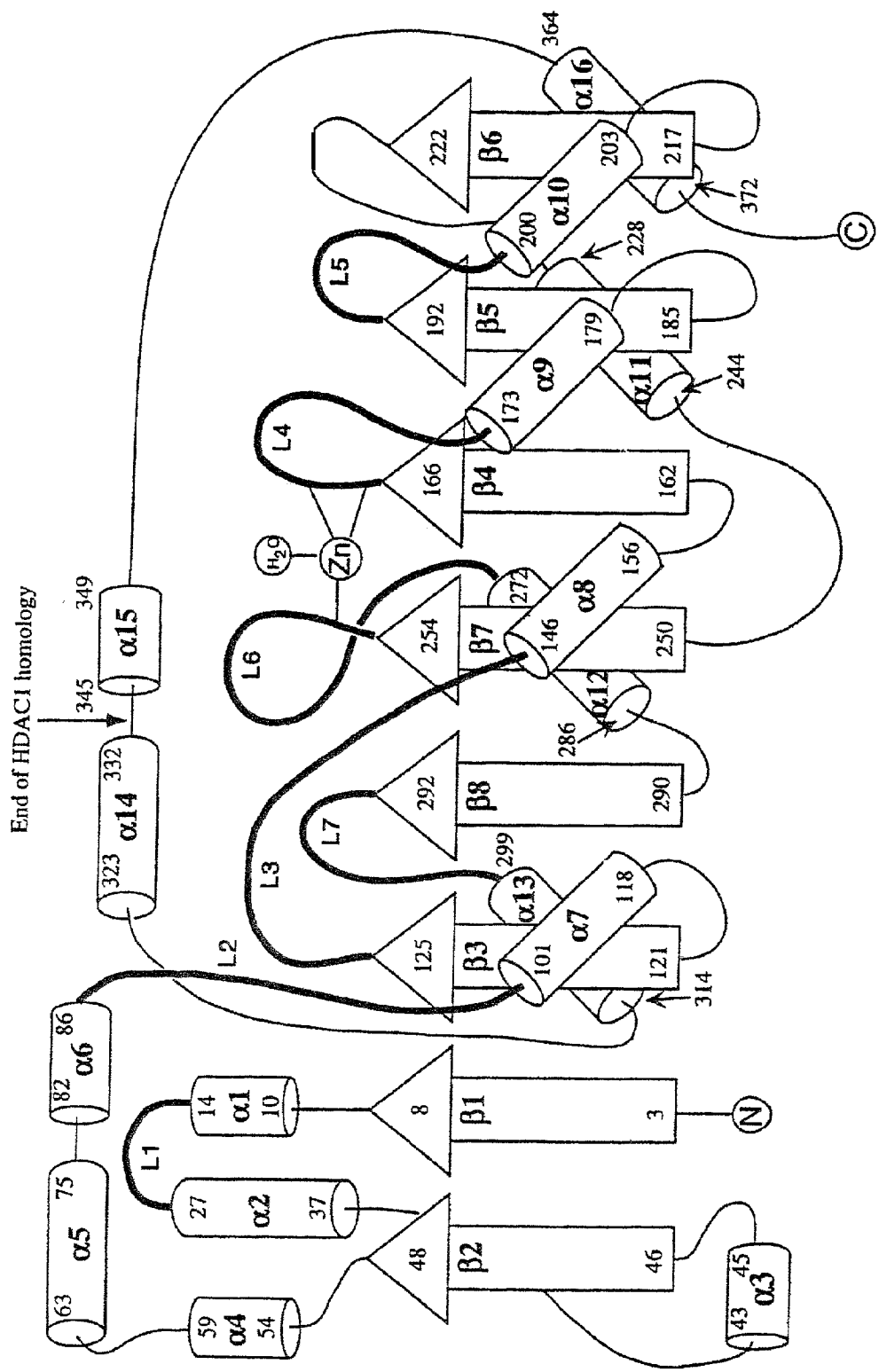

13:317–38). Two orthogonal views of the overall three-dimensional structure of HDLP are depicted in FIG. 4A and 4B. The HDLP structure has a central eight-stranded parallel β sheet (strands arranged as β2-β1-β3-β8-β7-β4-β5-β6), and sixteen α helices (labeled α1 through α16 respectively). See FIG. 4C. Four of the helices pack on either face of the β sheet (α7, α8, α9, α10 and α11, α12, α13, α14) forming the core α/β structure characteristic of this class of folds. Most of the remaining eight, helices are positioned near one side of the β sheet, near stands β2-β1-β3-β8. Large, well defined loops, (Loops L1–L7; FIG. 4C) originate from the C-terminal ends of the β-strands. The extra helices and the large L1–L7 loops are associated with a significant extension of the structure beyond the core α/β motif. This extension of the structure gives rise to two prominent architectural features: a deep, narrow pocket and an internal cavity adjacent to the pocket. These two architectural features comprise the active site (see FIG. 5A). The structure of HDLP-related proteins (e.g. HDA~s) may also comprise the conserved α/β structure characteristic.

The term "active site" comprises any or all of the following sites in HDLP, the substrate binding site, the site where the cleavage of an acetyl group from a substrate occurs or the site where an inhibitor of the HDAC family or, more particularly, HDLP binds. The active site, as referred to herein, comprises Asp166, Asp258, His170, Tyr297, His131, His132, Asp168, Asp173, Phe141, Phe198, Leu265, Pro22 and Gly140, and also a metal bound at the bottom of the pocket by Asp173, Asp168 and His defined by the coordinates listed in FIGS. 16 to 19 with an rmsd of 2.0 Å. The metal which binds at the bottom of the pocket will be a divalent cation selected from the group consisting of zinc, cobalt or manganese.

The deep narrow pocket has a tube-like shape with a depth of ~11 Å. The pocket opening constricts half way down to ~4.5 by 5.5 Å, and becomes wider at the bottom (see FIG. 5A). The pocket and its immediate surroundings are made up of loops L1 through L7.

Figure 5:
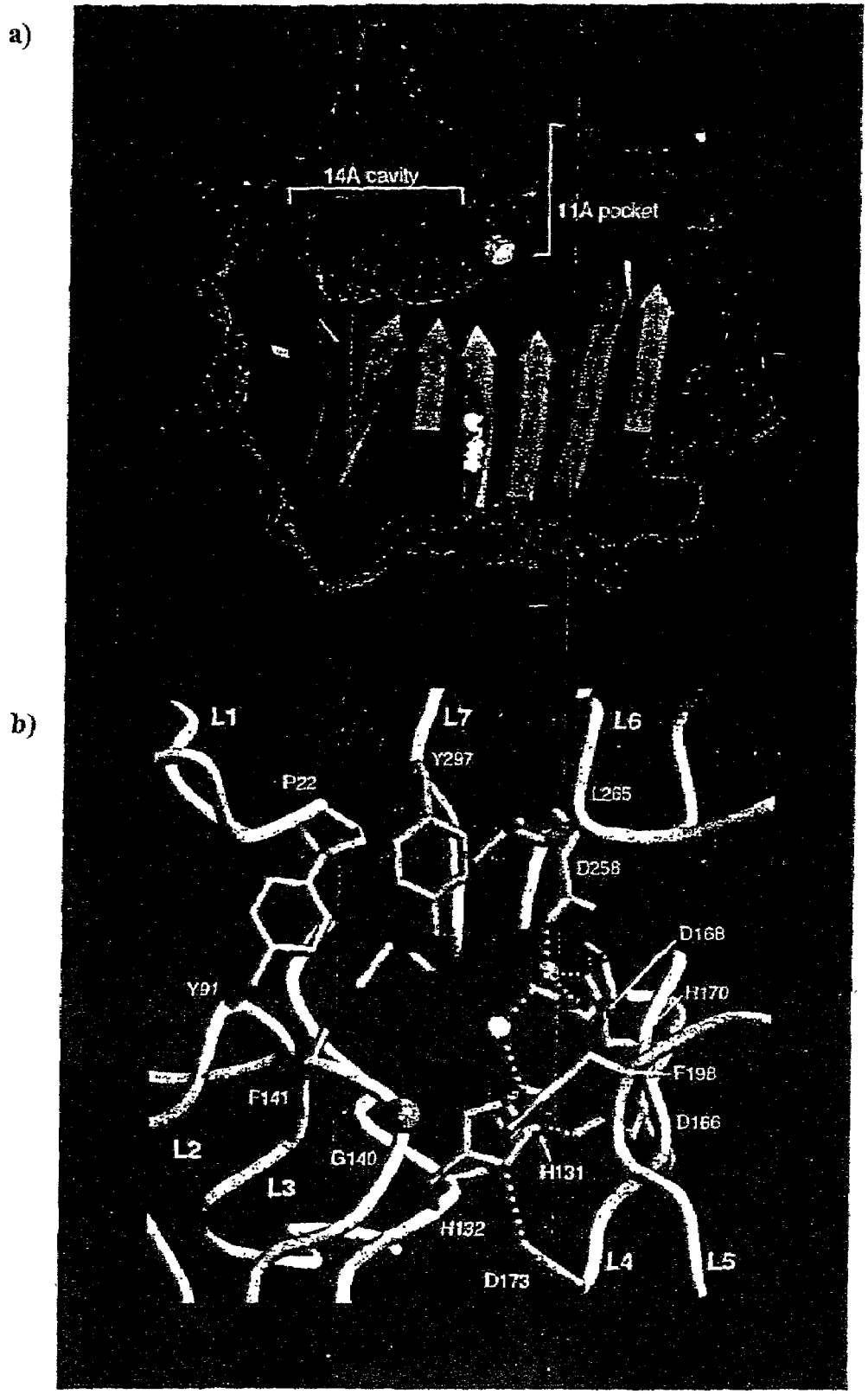
FIG. 5 shows (A) a schematic representation of a slice through a surface representation of HDLP with the pocket internal cavities and position of the β sheet indicated, (B) a schematic representation of a close-up view of the active site looking down into the, pocket in an orientation similar to FIG. 4B.

The walls of the pocket are covered with side chains of hydrophobic and aromatic residues (Pro22, Tyr91near the entrance; and Gly140, Phe141, Phe 198, Leu265 and Tyr297 further down; FIG. 5B). For numbering of amino acids please refer to SEQ ID NO:1. of particular interest are Phe141 and Phe198, whose phenyl groups face each other in parallel at a distance of 7.5 Å, marking the most slender portion of the pocket (see FIG. 5B). Of particular interest is that only one pocket residue differs in HDAC1 when the sequences are aligned (alignment may be accomplished using DNAstar™ MegAlign™ program, Madison, Wis.), this residue is Glu98 of HDAC1 which is Tyr91 in HDLP. The structure reveals that this residue in HDLP is mostly solvent exposed.

Figure 6:
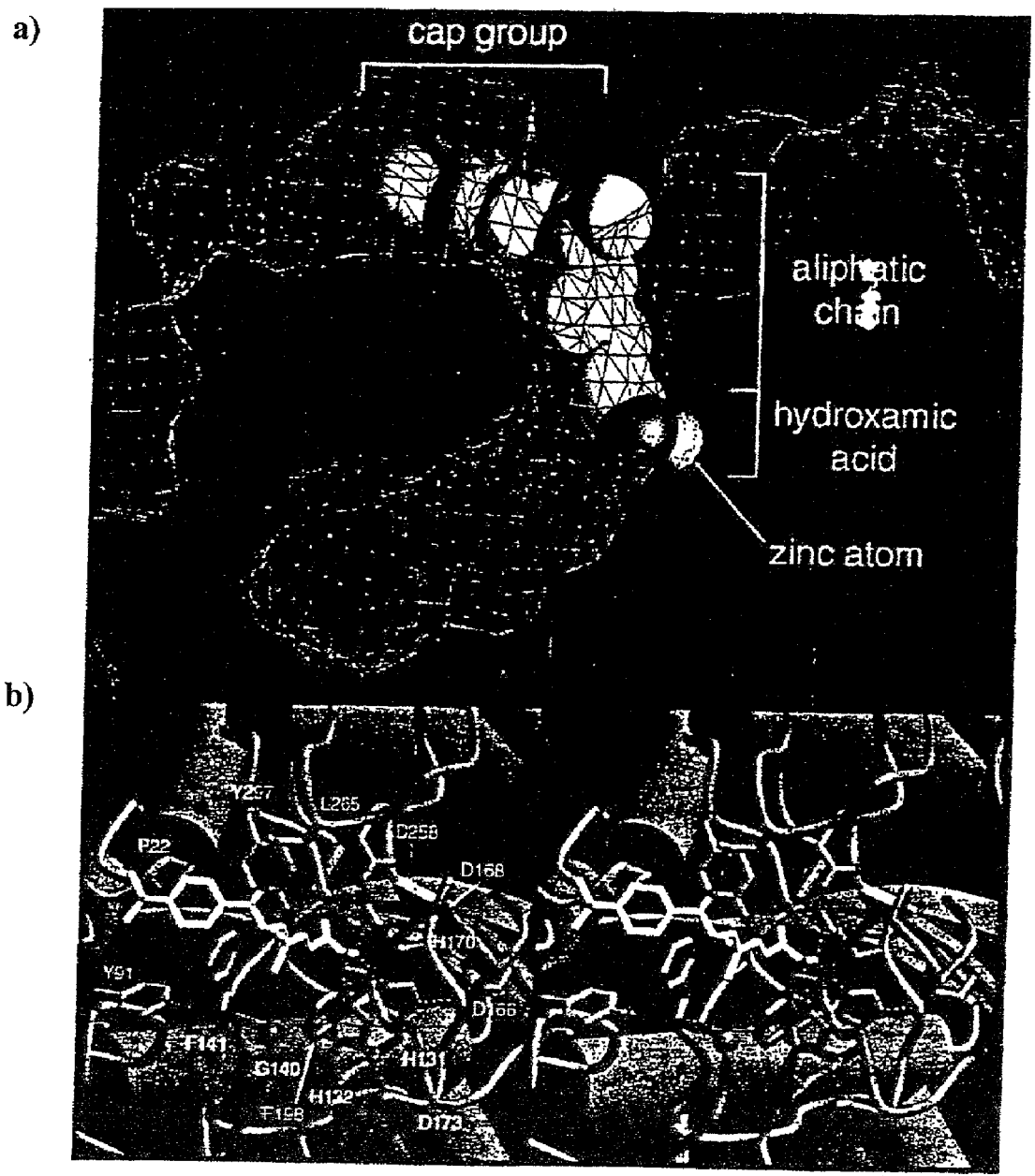
FIG. 6 shows (A) a space-filling representation of TSA in the active site pocket, (B) a closeup stereo view of the structure of the HDLP-$Z^{2+}$-TSA complex in a similar orientation to FIG. 4B, and (C) a schematic representation of the HDLP-TSA interactions.

Near the bottom of the pocket of the active site at its narrowest point, is located a zinc ion (see FIG. 6A). In order to obtain the zinc in the structure, the crystals may be soaked in zinc (e.g. $ZnCl_2$) or co-crystalized in the presence of zinc, The zinc ion is. coordinated by Asp168 (Oδ1, 2.1 Å) His170 (Nδ1, 2.1 Å), Asp258 (Oδ1, 1.9 Å) and a water molecule (2.5 Å). See FIG. 5B and 6B. The amino acid residues that coordinate zinc are arranged in a tetrahedral geometry, but the position of the water molecule, which is also hydrogen bonded to His131, deviates from this geometry by −25°.

In addition to the zinc ligands, the bottom of the pocket contains two histidine (His131 and His132), two aspartic acids (Asp166 and Asp173) and a tyrosine (Tyr297). See FIGS. 5B and 10B. Each of the histidines makes a hydrogen bond through its Nδ1 to an aspartic acid carboxylate oxygen, with the oxygen located in the plane of the imidizole ring (FIG. 5B). This His-Asp arrangement is characteristic of the charge relay system present in the active sites of serine proteases, where it serves to polarize the imidizole Ne and increase its basicity. Fersht & Sperling, 1973, *J. Mol. Biol.* 74:137–149; Blow et al., 1969, *Nature* 2:337–340.

The Asp166-His131 charge pair relay (hereafter referred to as "buried charged relay") is positioned even deeper in the pocket and more buried compared to the Asp173-His132 charge relay (hereafter referred to as "exposed charge relay") which is partially solvent exposed. The buried charge relay makes a hydrogen bond (2.6 Å) to the zinc-bound water molecule referred to above, and this hydrogen bond could contribute to the deviation of the water-zinc coordination from ideal geometry (FIG. 5B). The exposed charge relay is directed to a point ~2.5 Å away from the water molecule and closer to the surface.

Tyr 297 is positioned next to the zinc, opposite from where the two charge relay systems are located. The Tyr hydroxyl group lies 4.4 Å away from the zinc atom and has no interactions with the rest of the protein (FIG. 5B). Next to Tyr297, there is an opening in the pocket wall, which leads to the adjacent internal cavity.

The floor of the internal cavity is made up of portions of the L3 and L7 loops as they emerge from the β strands, and the roof is made up by the α1-L1-α2 segment. The L1 loop appears more flexible than other loops in the structure. This may allow the transient exchange of the cavity contents with the bulk solvent.

The cavity is lined primarily with hydrophobic residues and is particularly rich in glycine residues (Ala127, Gly128, Gly129, Met130, and Phe141 of L3; Gly293, Gly294, Gly295 and Gly296 of L7; and Tyr17, Pro22 and Leu23 of L1). There are only two charged residues in the cavity, (Arg27 and His 21) and these are contributed by the L1 loop.

Figure 8:
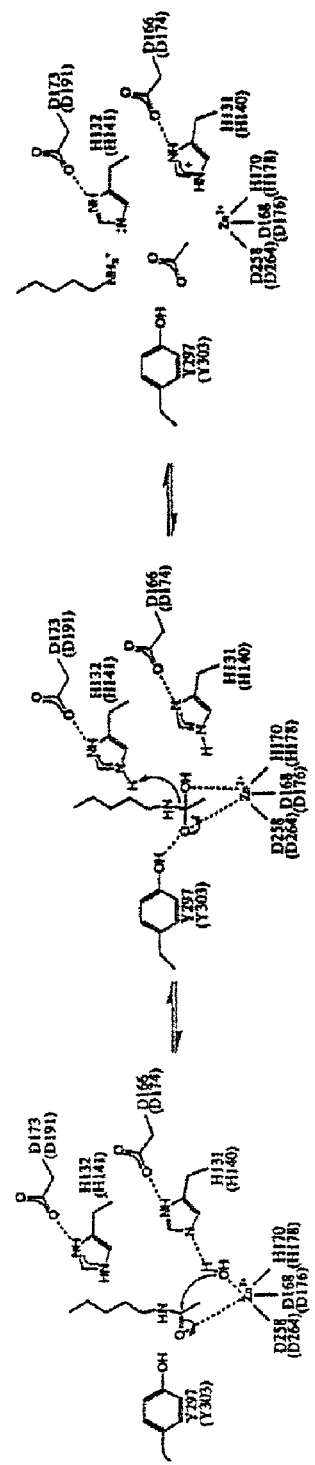
FIG. 8 shows a schematic representation of the proposed catalytic mechanism for the deacetylation of acetylated lysine.

The cavity may provide space for the diffusion of the acetate product away from the catalytic center, which may otherwise be crowded and shielded during deacetylation from the solvent when the substrate is bound. Such a role for the cavity is supported by the observation that the cavity contains three water and two isopropanol molecules (from the crystallization buffer) in the 1.8 Å apo-protein structure. The cavity may also bind another cofactor, in addition to zinc, for the facilitation of the enzymatic activity of the HDLP. A proposed catalytic mechanism for deacetylation is provided in FIG. 8.

The structure of HDLP as defined by the present invention, in conjunction with the HDAC1 sequence homology, shows that the 375-amino acid HDLP protein corresponds to the histone deacetylase catalytic core which is conserved across the HDAC family (see FIG. 2). The 35.2% HDLP-HDAC1-sequence identity predicts structural similarity with a rmsd in Cα positions of ~1.5 Å. Chothia and Lesk describe the relation between the divergence of sequence and the structure of proteins in *Embo J.* 5:823–826 (1986). The 40-residue C-terminus of HDLP is likely to have a divergent structure since this region has lower homology to HDAC1, although the α16 helix in this region is part of the conserved open α/β core fold and HDAC1 is likely to comprise a similar helix. However divergent this C-terminal region may be, this region is outside the active site and is likely to not effect the structure of the active site. Beyond the C-terminus of the histone deacetylase catalytic core, HDAC family members are divergent in length and sequence. In the HDAC family, this region (amino acid residues ~390–482) is highly polar, populated with acidic residues, and is likely to be flexible or loosely folded.

The HDLP-HDAC homology maps primarily to the hydrophobic core and to the L1–L7 loops, with portions of the loops that make up the pocket and adjacent cavity having the highest level of amino acid residue sequence conservation (FIGS. 9A and 9B). specifically, all of the polar residues in the active site (the zinc ligands, the two charge relay systems, and Tyr297) and the hydrophobic residues that make up the walls of the pocket (Gly140, Phe141, Phe198 and Leu265) are identical. Among the residues that make up the internal cavity, the ones closest to the active site are either identical or conservatively substituted (for example, Leu23 → Met and Met130 → Leu). Surface residues around the pocket are conserved to a lesser extent, but are still above 35% average sequence identity.

The information obtained from the inhibitor-bound HDLP complex crystal structures of the present invention reveal detailed information which is useful in the design, isolation, screening and determination of potential inhibitor compounds which may inhibit HDLP/HDAC family members. As described above, the HDLP structure consists of a parallel β sheet with α helices packing against both faces (FIGS. 4A, 4B, and 4C). At one end of the β sheet, 7 loops (L1–L7) form a narrow, tube-like pocket which are lined with hydrophobic residues and which comprise a zinc binding site, several polar side chains, including two Asp-His charge relay systems. Mutation of the zinc ligands and other polar residues at the pocket bottom reduces or eliminates the catalytic activity.

The present inventors found that mutation at the Tyr297Phe site reduced activity. See also, Hassig et al., 1998, *Proc. Natl. Acad. Sci. USA* 95:3519–3524; Kadosh & Struhl, 1998, *Genes Dev.* 12:797–805. The elimination of activity by mutation of these residues indicates that this region is the enzyme active site. Adjacent to the active site, there is an internal cavity that may provide space for the diffusion of the acetate reaction product. Homology at the active site between HDLP and HDAC1, as described above, indicates that they share structural and functional homology.

Figure 6C:
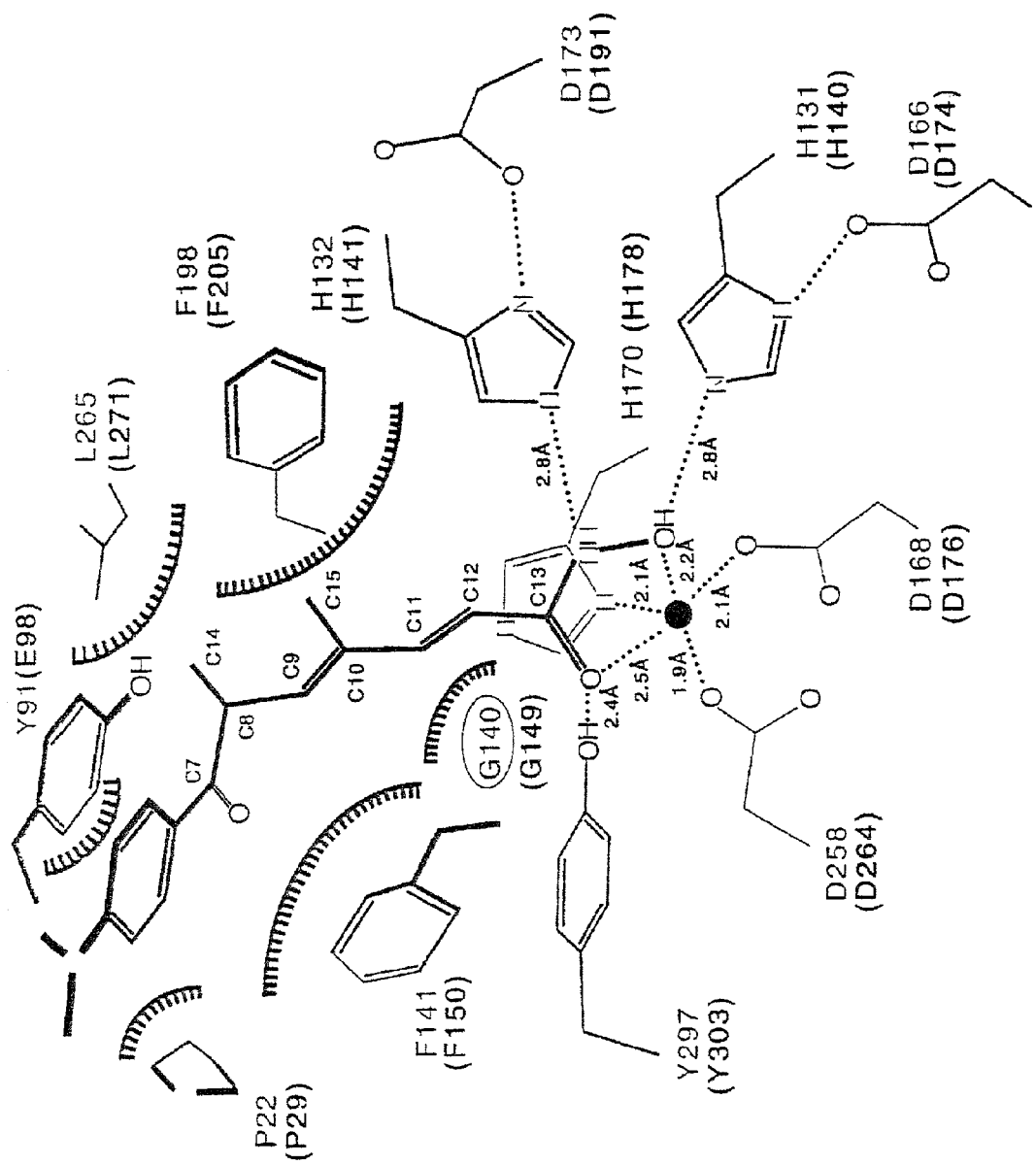

The inhibitor compound, trichostatin A (TSA) (Tsuji et al., 1976, *J. Antibiotics* 29:1–6) binds HDLP by inserting its long aliphatic chain, which has a hydroxamic acid group at one end, into the pocket (FIGS. 6A, 6B and 6C). The aliphatic chain makes multiple contacts in the well-like, hydrophobic portion of the pocket. The hydroxamic acid reaches the polar bottom of the pocket, where it coordinates the zinc in a bidentate fashion and also forms hydrogen bonds with the polar residues in the active site, including the two charge relay system histidines. The aromatic dimethylamino-phenyl group at the other end of the TSA chain makes contacts at the pocket entrance and serves to cap it. The amino acid residues of HDLP which contact TSA are conserved in HDAC, indicating that TSA binds and inhibits HDAC in a similar fashion to HDLP.

In the complex, the hydroxamic acid, most of the aliphatic chain and part of the dimethylamino-phenyl group of TSA are buried (60% of TSA's surface area; FIG. 6A). The hydroxamic acid group binds the zinc in a bidentite fashion forming bonds through its carbonyl (2.4 Å) and hydroxyl groups (2.2 Å) resulting in a penta-coordinated $Zn^{2+}$(FIGS. 6B and 6C). The hydroxamic acid hydroxyl group replaces the water molecule that binds to the zinc in the apo-HDLP structure described above. The hydroxamic acid also hydrogen bonds with both charge relay system histidines (hydroxyl oxygen to His131Nε2, 2.8 Å; and nitrogen to His132 Nε2, 2.8 Å), and the Tyr297 hydroxyl group (2.4 Å; FIGS. 6B and 6C).

The 5-carbon long branched alkene chain of TSA fits snugly in the narrow portion of the pocket making multiple van der Waals contacts with all of the hydrophobic groups lining the pocket (FIGS. 6B and 6C). Near its center, the chain contains a methyl substituted carbon-carbon double bond which is sandwiched between the phenyl groups of the Phe141 and Phe98 at the tightest point of the pocket (FIGS. 6A and 6B). The length of the alkene chain appears optimal for spanning the length of the pocket, and allowing contacts both at the bottom and at the entrance of the pocket, although, the cap group of Formula (I) may provide length to span the pocket allowing for a shorter alkene chain (aliphatic chain).

At the entrance of the pocket, one face of the planar structure formed by the dimethylamino-phenyl and adjacent carbonyl groups of TSA makes contacts at the rim of the pocket (Pro22, Tyr91, Phe141; FIGS. 6B and 6C). This packing is facilitated by the roughly 110° angle in the overall structure of TSA at the junction of the aliphatic chain and the dimethylamino-phenyl group (occurring at the $Sp^3$ hybridized C8 carbon). Upon TSA binding, the side chain of Tyr91, which is mostly solvent exposed, changes conformation to make space for the dimethylamino-phenyl group. This is the only change near the active site observed upon TSA binding.

The hydroxamic acid group is a common motif in zinc metalloprotease inhibitors. See U.S. Pat. Nos. 5,919,940 and 5,917,090; See also, Grams et al., 1995, *Biochemistry* 34:14012–14020; Lovejoy et al., 1999, *Nat. Struct. Biol.* 6:217–221; and Holmes & Matthews, 1981, *Biochemistzy* 20:6912–6920. Like TSA, these inhibitors also coordinate the active site zinc in a bidentate fashion using their hydroxamate hyroxyl and carbonyl oxygens, replace the nucleophilic water molecule with their hydroxamate hydroxyl groups and form hydrogen bonds to the general base (Grams et al., 1995, *Biochemistry* 34:14012–14020; Lovejoy et al., 1999, *Nat. Struct. Biol.* 6:217–221; and Holmes & Matthews, 1918, *Biochemistry* 20:6912–6920).

Figure 4D:
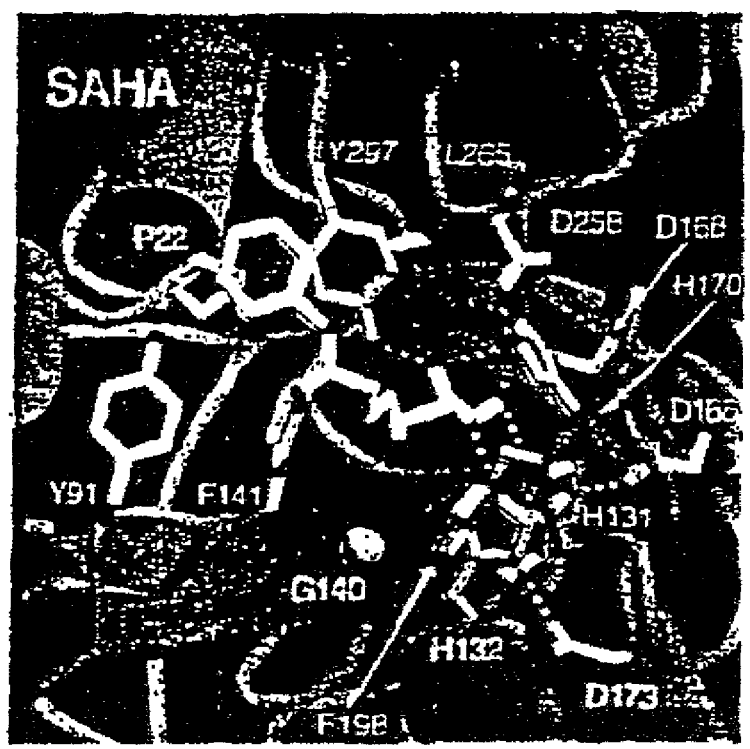

SAHA, which has a ~30-fold weaker inhibitory activity than TSA (Richon et al., 1998, *Proc. Natl. Acad. Sci. USA* 95:3003–3007), binds HDLP similarly to TSA (see, e.g., FIG. 4D). The SARA hydroxamic acid group makes the same contacts to the zinc and active site residues, and the importance of these interactions is underscored by the loss of activity of SAHA derivatives lacking the hydroxamic group (Richon et al., 1998, *Proc. Natl. Acad. Sci. USA* 95:3003–3007)

The six-carbon long aliphatic chain of SAHA packs in the tube-like hydrophobic portion of the pocket. Compared to TSA however, SAHA's aliphatic chain packs less snugly and makes fewer van der waals contacts, in part, because SAHA lacks TSA's C15 methyl group branch. SAHA also lacks TSA's double bonds in this region, and this may lead to increased flexibility of the aliphatic chain. The cap group of SAHA consists of a phenyl-amino ketone group. In the crystal structure, the phenyl group has weak electron density, suggesting that it does not pack as well as the cap group of TSA. This may be due to the larger separation between the hydroxamic and cap groups of SAHA compared to TSA (compare TSA, Formula (II) and SAHA, Formula (III), below).

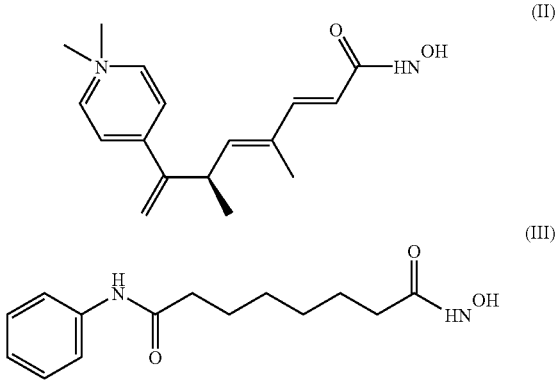

The determination of the structure of HDLP and HDLP bound to an inhibitory compound has enabled, for the first time, the identification of the active site of HDLP and of related HDLP proteins, such as proteins belonging to the HDAC family.

The three-dimensional structural information and the atomic coordinates associated with said structural information of HDLP bound to an inhibitory compound is useful in rational drug design providing for a method of identifying inhibitory compounds which bind to and inhibit the enzymatic activity of HDLP, HDAC family proteins and other histone deacetylase-like proteins related to HDLP. Said method for identifying said potential inhibitor for an enzyme comprising deacetylase activity comprises the steps of (a) using a three-dimensional structure of HDLP as defined by its atomic coordinates listed in FIGS. 16 to 19; (b) employing said three-dimensional structure to design or select said potential inhibitor; (c) synthesizing said potential inhibitor; (d) contacting said potential inhibitor with said enzyme in the presence of an acetylated substrate; and (e) determining the ability of said inhibitor to inhibit said deacetylase activity.

The potential HDLP and HDLP-related (e.g. HDAC) inhibitors identified by the method of the present invention are represented by formula (I)

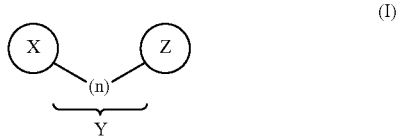

wherein X comprises a cap group which binds to at least one amino acid selected from the group consisting of proline and leucine; Y comprises an aliphatic chain group which binds to at least one amino acid selected from the group consisting of leucine, phenylalanine and glycine; and Z comprises an active site binding group which binds to at least one amino acid selected from the group consisting of aspartic acid, tyrosine and histidine and wherein Z may further bind to a zinc atom and with the provision that the compound of Formula (I) is not TSA, trapoxin, SAHA, SAHA derivatives described in U.S. Pat. Nos. 5,608,108; 5,700,811; 5,773,474; 5,840,960 and 5,668,179.

The present invention permits the use of molecular design techniques to design, identify and synthesize chemical entities and compounds, including inhibitory compounds, capable of binding to the active site of HDLP and HDLP-related proteins. The atomic coordinates of apo-HDLP and inhibitor-bound HDLP may be used in conjunction with computer modeling using a docking program such as GRAM, DOCK, HOOK or AUTODOCK (Dunbrack et al., 1997, *Folding & Design* 2:27–42) to identify potential inhibitors of HDLP and HDLP-related proteins (e.g. HDAC1). This procedure can include computer fitting of potential inhibitors to the active site of HDLP to ascertain how well the shape and the chemical structure of the potential inhibitor will complement the active site or to compare the potential inhibitors with the binding of TSA or SAHA in the active site. See Bugg et al, 1998, *Scientific American* December:92–98; West et-al., 1995, TIPS 16:67–74. The potential inhibitors designed by modeling with a docking program conform to the general formula (I) as described above. Computer programs may also be employed to estimate the attraction, repulsion and stearic hindrance of the HDLP and potential inhibitor compound. Generally, the tighter the fit, the lower the stearic hindrances, the greater the attractive forces, and the greater the specificity which are important features for a specific inhibitory compound which is more likely to interact with HDLP and HDLP-related proteins rather than other classes of proteins. These features are desired particularly where the inhibitory compound is a potential antitumor drug.

The compounds of the present invention may also be designed by visually inspecting the three-dimensional structure to determine more effective deacetylase inhibitors. This type of modeling may be referred to as "manual" drug design. Manual drug design may employ visual inspection and analysis using a graphics visualization program such as "O" (Jones, T. A., Zhou, J. Y., Cowan, S. W., and Kjeldgaard, M., Improved method for building protein models in electron density maps and the location of errors in these models, Acta Crystallog., A47, 110–119.

Initially potential inhibitor compounds can be selected for their structural similarity to the X, Y and Z constituents of formula (I) by manual drug design. The structural analog thus designed can then be modified by computer modeling programs to better define the most likely effective candidates. Reduction of the number of potential candidates is useful as it may not be possible to synthesize and screen a countless number of variations compounds that may have some similarity to known inhibitory molecules. Such analysis has been shown effective in the development of HIV protease inhibitors (Lam et al., 1994, *Science* 263:380–384; Wlodawer et al., 1993, *Ann. Rev. Biochem.* 62:543–585; Appelt, 1993 *Perspectives in Drug Discovery and Design* 1:23–48; Erickson, 1993, *Perspectives in Drug Discovery and Design* 1:109–128. Alternatively, random screening of an small molecule library could lead to potential inhibitors whose inhibitory activity may then be analyzed by computer modeling as described above to better determine their effectiveness as inhibitors.

The compounds designed using the information of the present invention may be competitive or noncompetitive inhibitors. These designed inhibitors may bind to all or a portion of the active site of HDLP and may be more potent, more specific, less toxic and more effective than known inhibitors for HDLP and HDLP-related proteins, and particularly HDACs. The designed inhibitors may also be less potent but have a longer half life in vivo and/or in vitro and therefore be more effective at inhibiting histone deacetylase activity in vivo and/or in vivo for prolonged periods of time. Said designed inhibitors are useful to inhibit the histone deacetylase activity of HDLP and HDLP-related proteins (e.g. HDAC1), to inhibit cell growth in vitro and in viva and may, be particularly useful as antitumor agents.

The present invention also permits the use of molecular design techniques to computationally screen small molecule data bases for chemical entities or compounds that can bind to HDLP in a manner analogous to the TSA and SAHA as defined by the structure of the present invention. Such computational screening may identify various groups which may be defined as "X", "Y" or "Z" of formula (I) above and may be employed to synthesize the potential inhibitors of the present invention comprising formula (I) Such potential inhibitors may be assayed for histone deacetylase inhibitory activity in a histone deacetylase activity assay (see Example 3 below), may be co-crystallized with HDLP to determine the binding characteristics through X-ray crystallography techniques defined above (e.g. said co-crystal structure may be determined by molecular replacement to assess the binding characteristics of said potential inhibitor), or may be assessed based on binding activity by incubating said potential inhibitor with said HDLP, performing gel filtration to separate any free potential inhibitor to HDLP-bound inhibitor, and determining the amount of histone deacetylase activity of the inhibitor-bound HDLP. To measure binding constants (e.g., Kd), methods known to those in the art may be employed such as Biacore™ analysis, isothermal titration calorimetry, Elisa with a known drug on the plate to show competitive binding, or by a deacetylase activity assay.

Figure 9:
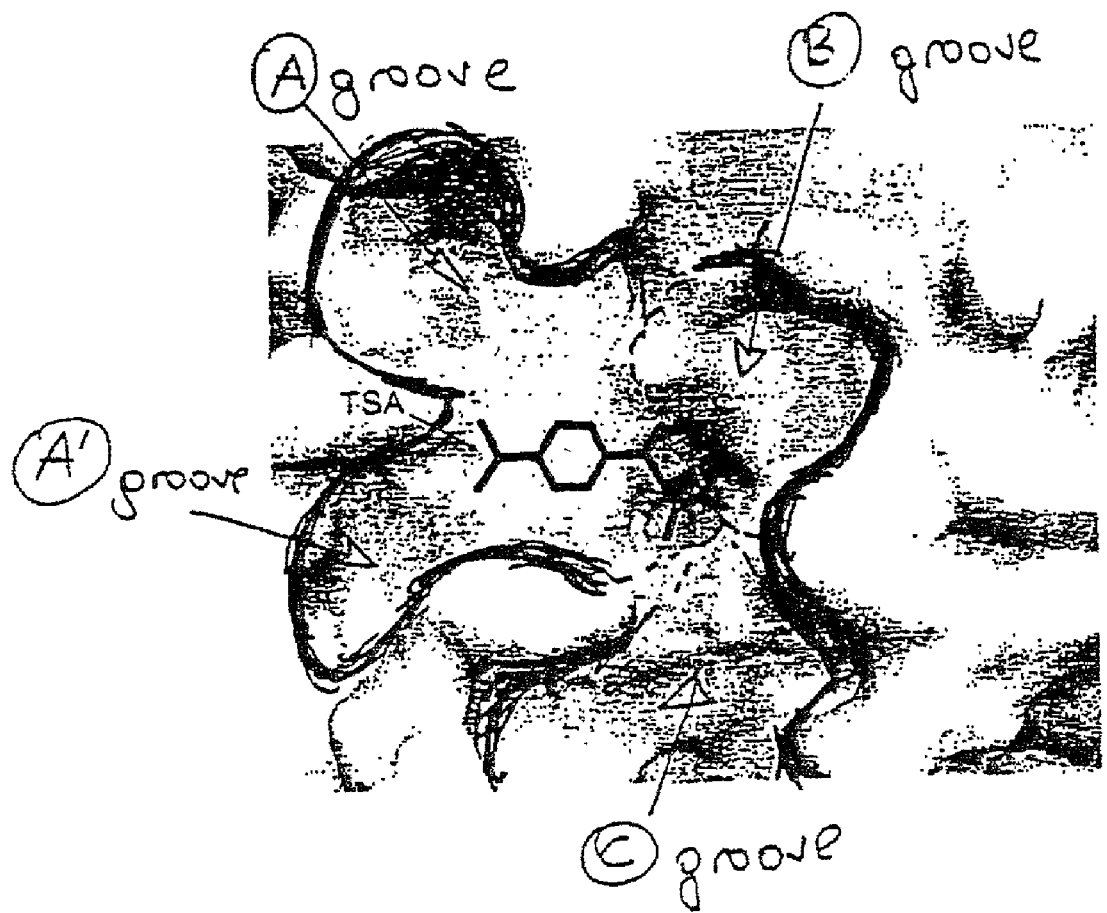
FIG. 9 shows a schematic representation of a space filling diagram showing the conserved amino acids in the active site and nearby grooves.

The design of potential inhibitors of the present invention is further facilitated by reference to FIG. 9, which is a surface representation figure that depicts the surface grooves. Analysis of such grooves gives insight into the constituents of the cap group of formula (I). The surface grooves are labeled groove A, groove A', groove B and groove C, into which additional cap groups may bind. The structure of HDLP bound to either TSA or SAHA shows that the cap groups of TSA and SAHA bind in groove A. By analysis of the amino acid sequence identity of HDLP and HDACs, Groove A is well conserved in HDACs, has a significant hydrophobic component, appears deep enough to allow for significant interactions and is also the largest of the four grooves. In addition to the dimethylamino phenyl group of the TSA, the A groove can fit approximately 200 daltons worth of groups (e.g. groove A could accommodate a naphthalene-like group after an appropriate spacer, etc.). Groove A, as referred to herein, is characterized by the following conserved residues of HDLP: His 21, Pro22, Lys24, Phe141, Leu265 and Phe335. The periphery of groove A comprises unconserved residues. Additionally, Groove A', as referred to herein, comprises primarily unconserved residues.

Groove B is immediately adjacent to the pocket. Of significance is that the bottom of groove B comprises the N-epsilon nitrogen of His170, which coordinates the zinc through its N-delta nitrogen. Significant binding energy may be achieved by contacting the Nε proton of His170 with a carboxylic acid or sulfate group. In addition, groove B may be large enough to fit a phenyl group, the face of which may comprise a partial negative charge which may pack over the N-epsilon proton of His170. The conserved residues of groove B, as referred to herein are: His170, Tyr196 and Leu265.

Groove C is not as well conserved as the other two grooves and the amino acid residues which comprise groove C are mostly polar and solvent exposed. Groove C, as referred to herein comprises the following conserved residues: Asn87, Gly140 and Phe198.

The compounds of the present invention are represented by formula (I):

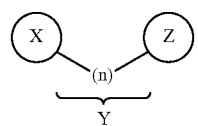

Examples for suitable X constituents wherein X comprises a cap group may be described in three categories, depending upon which surface of groove A, A', B and/or C they are targeted to. The cap group may comprise all three categories on the same compound. Of particular benefit may be replacing the cap group of TSA or SARA with a large, rigid structure. Nonlimiting examples for suitable cap groups (X) of formula (I) which may bind in-groove A are:

(1) attaching a 1–3 methyl linker followed by a phenyl or naphthalene group from the para or meta position of SAHA's phenyl group represented by formula (IV):

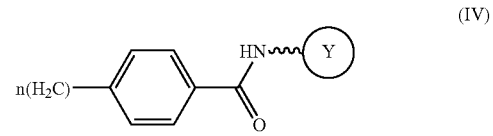

(2) attaching a 2–3 methyl linker followed by a phenyl or naphthalene group from the meta position of TSA's phenyl cap group, or from TSA's dimethyl amino group represented by formula (V):

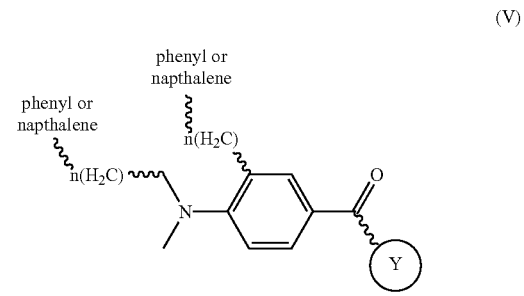

and which may bind in groove B is a 1–3 methyl group spacer followed by a carboxylate, sulfate or phenyl group as represented by formula (VI):

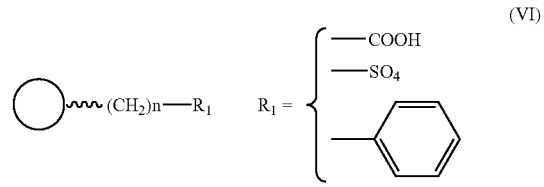

With respect to the aliphatic (Y) group, the diameter of the pocket suggests that one more methyl "side chain" could fit, in addition to the C15 methyl group on the C10 carbon. Nonlimiting suitable examples for Y constituents wherein Y comprises an aliphatic chain group are as follows: (1) add a methyl group to TSA on the C12 carbon (with or without a methyl group on the C10 carbon and with or without double bonds and with or without substituting the X and/or Z constituents of formula (I) as represented by formula (VII):

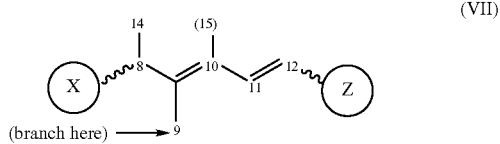

(VII)

(branch here) ⟶ 9

(2) add a methyl group to TSA on the C9 carbon (with or without a methyl group on the C10 carbon; with or without both or either of the double bonds, and with or without substituting the X and/or Z constituents of formula (I) as represented by formula (VIII);

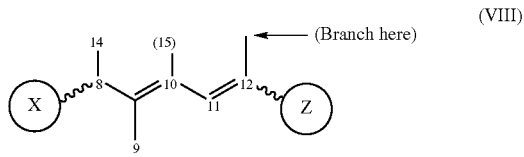

(VIII)

(Branch here)

(3) replace the two alkalene double bonds of TSA with only one between C10 and C11, which may free the C11 and C12 torsion to allow for a better fit, the X and/or Z groups may also be substituted as represented by formula (IX):

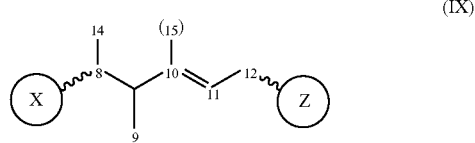

(IX)

(4) cyclize C15 and C12 carbons of TSA through a sulphur atom (or nitrogen atom), the X and/or Z groups may also be substituted as represented by formula (X):

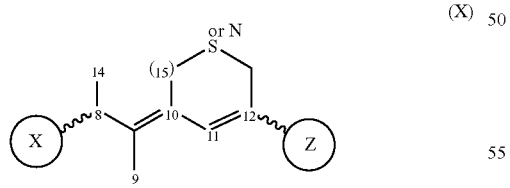

(X)

(5) extend from the C9 carbon of TSA such that the extension approaches and/or enters groove B (see FIG. 9); making C9 sp3 so that it can have some freedom; attach to C9 a 1–3 methyl group spacer which may include a double bond and they attaching thereto a sulfate, carboxylate, sulfate, hyroxyl, or phenyl group which may make an interaction with the N-epsilon proton of His170 which may coordinate the zinc atom as represented by formula (XI):

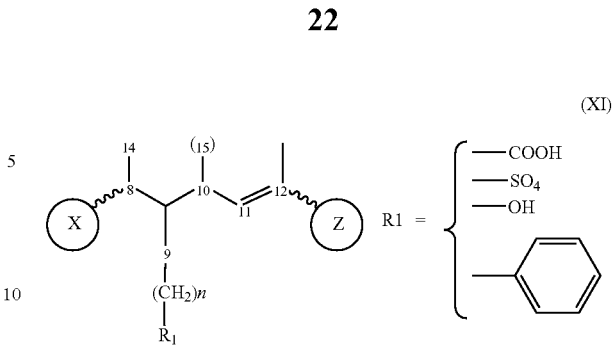

(XI)

(6) extend off the C8 carbon (replacing C14) of TSA such that the extension approaches or enters groove B; attach a 1–3 methyl group spacer (which may include a double bond) and then link thereto a carboxylate, sulfate, hydroxyl or phenyl group such that an interaction is made with the N-epsilon proton of His170 that coordinates the zinc atom; the X and/or Z constituents may also be substituted as represented by formula (XII):

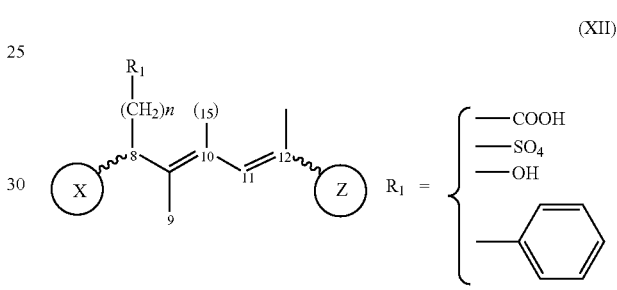

(XII)

(7) substitute the C8 carbon at the end of the aliphatic chain such that the substitution may contact groove A, A', B and or C, in such an example, a cap group (X) may or may not be required and the X and Z constituents may be substituted as well, as represented by formula (XIII):

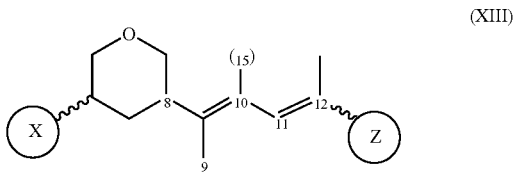

(XIII)

(8) formulas VII through XIII above wherein the aliphatic chain further comprises a methyl group between the active site binding group (Z) and the C8 carbon, and preferably just before the C8 carbon, increasing the distance between X and Z, (9) make the connection between the aliphatic chain and the cap group more rigid (e.g., by closing a 6-membered ring which may or may not comprise oxygen, the X and Z group may also be substituted as represented by formula (XIV):

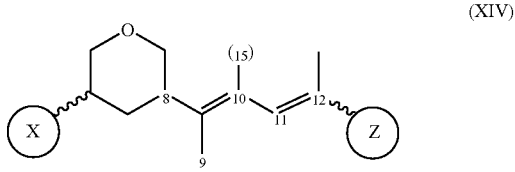

(XIV)

and (10) combining two or more of the changes depicted by formulas (VII–XIV).

Additionally, nonlimiting examples for suitable Z groups wherein Z comprises an active site binding group are as follows: (1) hydroxamic acid, (2) carboxylic acid, (3) sulfonamide, (4) acetamide, (5) epoxyketone, (6) an ester with a methyl linker and a hydroxyl of acetate ester group to lead into the cavity and interact with a conserved arginine (Arg27) as represented by formula (XV):

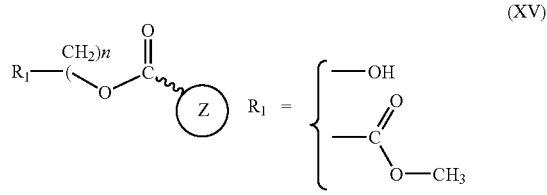

(XV)

and (7) an alphaketone as represented by formula (XVI):

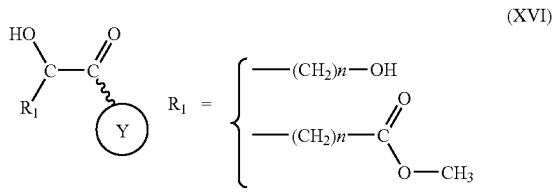

(XVI)

Additionally, other suitable X, Y and Z constituents may be envisioned by the skilled artisan given the three-dimensional structural information of the present invention.

After having determined potential suitable X, Y and Z constituents, the constituents are combined to form a compound of formula (I) using combinatorial chemistry techniques. This may be achieved according to U.S. Pat. Nos. 5,608,108; 5,700,811; 5,773,474; 5,840,960 and 5,668,179, incorporated herein by reference. Any methods known to one of skill in the art may be employed to synthesize compounds of formula (I) comprising X, Y and Z constituents as determined by the methods described above.

As mentioned above, the compounds of formula (I) are useful to inhibit the histone deacetylase activity of HDLP and HDAC-related proteins. Such inhibition may allow for a reduction or cessation of cell growth in vitro and in vivo.

For in vitro use, such reduction or cessation of cell growth is useful to study the role of histone deacetylation and differentiation during the cell cycle and also to study other mechanisms associated with cell cycle arrest and particularly how the repression of transcription is involved in cell cycle progression which may be studies in a yeast model system such as that described by Kadosh & Struhl, 1998, *Mol. Cell. Biol.* 18:5121–5127. In vitro model systems which may be employed to study the effects of potential inhibitors on cell cycle progression and also tumor growth include those described by: Richon et al, 1998, *Proc. Natl. Acad. Sci. USA* 95:3003–3007; Yoshida et al., 1995, *Bioessays* 17:423–430; Kim et al., 1999, *Oncogene* 18:2461–2470; Richon et al., 1996, *Proc. Natl. Acad. Sci. USA* 93:5705–5708; and Yoshida et al., 1987, *Cancer Res.* 47:3688–3691.

For in vivo use, such a reduction or cessation of cell growth is useful to study the effect of said inhibitor compounds in non-human animal model systems of cancer and is also useful for the treatment of cancer in a recipient in need of such treatment. Non-limiting examples of animals which may serve as non-human animal model systems include mice, rats, rabbits, chickens, sheep, goats, cows, pigs, and non-human primates. See, e.g., Desai et al., 1999, *Proc. AACR* 40: abstract #2396; Cohen et al., 1999, *Cancer Res.*, submitted. The compounds of the present invention may be administered to a transgenic non-human animal wherein said animal has developed cancer such as those animal models in which the animal has a propensity for developing cancer (e.g. animal model systems described in U.S. Pat. Nos. 5,777,193, 5,811,634, 5,709,844, 5,698,764, and 5,550,316). Such animal model systems may allow for the determination of toxicity and tumor reduction effectiveness of the compounds of the present invention.

A preferred compound of the present invention may comprise high specific activity for HDLP and HDAC-related proteins, good bioavailability when administered orally, activity in reducing or ceasing cell growth in tumor cell lines, and activity in reducing or ceasing tumor growth in animal models of various cancers.

Accordingly, another aspect of this invention is a method of eradicating or managing cancer in a recipient, which may be an animal and is preferably a human. Said method comprises administering to said recipient a tumor reducing amount of a compound as defined by formula (I) above, or a physiological acceptable salt thereof.

In a further aspect of the invention, there is provided a composition comprising the compound of formula (I) and an excipient or carrier. Administration of the foregoing agents may be local or systemic. Such carriers include any suitable physiological solutions or dispersant or the like, The physiologic solutions include any acceptable solution or dispersion media, such as saline, or buffered saline. The carrier may also include antibacterial and antifungal agents, isotonic and absorption delaying agents, and the like. Except insofar as any conventional media, carrier or agent is incompatible with the active ingredient, its use in the compositions is contemplated.

Routes of administration for the compositions containing the delivery vehicle constructs of the present invention include any conventional and physiologically acceptable routes, such as, for example, oral, pulmonary, parenteral (intramuscular, intraperitoneal, intravenous (IV) or subcutaneous injection), inhalation (via a fine powder formulation or a fine mist), transdermal, nasal, vaginal, rectal, or sublingual routes of administration and can be formulated in dosage forms appropriate for each route of administration.

The following examples are provided to more clearly illustrate the aspects of the invention and are not intended to limit the scope of the invention.

EXAMPLES

Example 1

Protein Production and Purification

Full-length wild-type HDLP (Genbank accession number AE000719) was subcloned from an *Aquifex aeolicus* chromosomal DNA preparation (provided by Robert Huber of Universitaet of Regensburg, Germany) into the pGEX4T3 (Amersham-Pharmacia, Piscataway, N.J.) vector using the polymerase chain reaction (PCR). The cysteine-to-serine and active site mutants were constructed by PCR site directed mutagenesis and were sequenced. The HDLP-glutathione S-transferase (GST) fusion protein was produced in *Escherichia coli*, purified by affinity chromatography using a column of glutathione-sepharose resin (Amersham-Pharmacia, Piscataway, N.J.), and by anion-exchange chromatography (Q-sepharose™; Amersham-Pharmacia, Piscataway, N.J.). HDLP was cleaved from the fusion protein with thrombin at 4° C., was purified by anion-exchange (Q-sepharose™; Amersham-Pharmacia, Piscataway, N.J.) and gel filtration chromatography (Superdex™200; Amersham-Pharmacia, Piscataway, N.J.), and was concentrated to typically 25 mg/ml in a buffer of 25 mM bis-tris propane (BTP), 500 mM NaCl, 5 mM dithiothrietiol (DTT), 2% isopropanol, pH 7.0.

Although, it is not known what metal cofactor HDLP contains in vivo, it is presumed to be zinc because of the arrangement of the ligands and the similarities in the active site to the zinc proteases. The lack of metal in the purified HDLP is presumed due, in part, to the use of DTT during purification. HDLP was reconstituted with $Zn^{2+}$ by mixing the Cys75Ser/Cys77Ser double mutant at 10 mg/ml with a 5-fold molar excess of $ZnCl_2$ in a buffer of 25 mM bis-tris propane, 200 mM NaCl, 1% isopropanol, pH 7.0. Unbound $ZnCl^2$ was removed by fractionating HDLP through a G25 desalting column (Amersham-Pharmacia, Piscataway, N.J.). The HDLP-$Zn^{2+}$-TSA complex was prepared by incubating the $Zn^{2+}$ reconstituted HDLP mutant with 1 mM TSA for 45 minutes, followed by gel filtration chromatography (Superdex™200; Amersham-Pharmacia, Piscataway, N.J.) to remove excess TSA, and concentration to typically 25 mg/ml in a buffer of 25 mM bis-tris propane, 500 mM NaCl, 1% isopropanol, pH 7.0.

FLAG epitope tagged human HDAC1 was overexpressed using a baculovirus expression system in Hi5 (Invitrogen, Carlsbad, Calif.) insect cells grown in suspension in serum-free media (Sf900, Gibco, Grand Island, N.Y.). The fusion protein was purified by anion exchange and affinity chromatography using Anti-FLAG M2 affinity resin (Sigma, St. Louis, Mo.) and FLAG Peptide (Sigma, St. Louis, Mo.).

Example 2

Crystallization and Data Collection

Crystals of apo-HDLP were grown at room temperature by the hanging-drop vapor-diffusion method, from 7.5% isopropanol, 28% PEG 1500, 425 mM NaCl, 100 mM Tris-Cl, pH 7.0. They form in space group C2 with a=51.4 Å, b=93.8 Å, c78.7 Å, β=96.9 Å, and contain one HDLP molecule in the asymmetric unit. Diffraction data were collected with crystals flash-frozen in a buffer of 7.5% isopropanol, 35% PEG 1500, 75 mM NaCl, 100 mM Tris-Cl, pH 8.0, at −170° C.

The structure of the HDLP-$Zn^{2+}$ complex was determined from HDLP Cys75Ser/Cys77Ser double mutant crystals grown from 23% tert-butanol, 27% PEG 1500, 400 mM KCl, 100 mM bis-tris propane-Cl, pH 6.8. Space group and cell dimensions were identical to the apocrystals. The HDLP-$Zn^{2+}$ crystals were harvested and frozen in 27% tert-butanol, 22% PEG 1500, 50 mM KCl, 20 mM NaCl, 0.2 mM $ZnCl_2$, 100 mM bis-tris propane, pH 6.8, at −170° C.

Crystals of the HDLP-$Zn^{2+}$-TSA complex comprised HDLP Cys75Ser/Cys77Ser double mutant and were grown from 23% tert-butanol, 27% PEG 1500, 600 mM KCl, 100 mM bis-tris propane-Cl, pH 6.8, by microseeding. The crystals were grown in the presence of zinc. They form in space group $P2_12_12_1$ with a=53.4 Å, b=94.4 Å, c156.3 Å and contain two HDLP-$Zn^{2+}$-TSA complexes in the asymmetric unit. The HDLP-$Zn^{2+}$-TSA crystals were harvested and frozen in the same cryobuffer as the HDLP-$Zn^{2+}$ crystals except that 0.5mM TSA was added. Data were processed with DENZO and SCALEPACK (Otwinowski & Minor, 1997, *Method. Ensemble.* 276:307–326). MIR analysis, model building and refinement.

The HDLP-$Zn^{2+}$-SAHA complex crystals were grown and evaluated the same as the HDLP-$Zn^{2+}$-TSA crystals. However, the restraints for the SAHA structure were constructed based on stereochemical parameters from TSA. Like the apo-HDLP crystals, the SAHA/HDLP co-crystals grew in space group C2.

Heavy-atom soaks were performed with the apo-HDLP crystals in a buffer of 7.5% isopropanol, 30% PEG 1500, 75 mM NaCl, 100 mM Tris-Cl, pH 8.0, supplemented with 1.0 mM thimerosal for 2h, 5 mM $KAu(CN)_2$ for 1h, and 1 mM $Pb(Me)_3OAc$ for 2h. MIR phases were calculated with the program MLPHARE (The CCP4 suite: Programs for computational crystallography, 1994, *Acta Crystallogr. D* 50:760–763) at 2.5 Å using the anomalous diffraction signal from the thimerosal derivative, and had a mean figure of merit of 0.55. The phases were improved by solvent flattening with the program DM (The CCP4 suite: Programs for computational crystallography, 1994, *Acta Crystallogr. D* 50:760–763), and were used to build the initial model with the program O (Jones et al., 1991, *Acta Crystallogr. A* 47:110–109). Successive rounds of rebuilding and simulated annealing refinement with the program CNS (Brunger et al., 1998, *Acta Crystallogr. D* 54:905–921) allowed interpretation of HDLP from residues 2 to 373. Residues 1, 374, and 375 were not modeled and are presumed to be disordered.

The structure of the HDLP-$Zn^{2+}$-TSA and HDLP-$Zn^{2+}$-SAHA complex were determined by molecular replacement with the program AMORE (The CCP4 suite: Programs for computational crystallography, 1994, *Acta Crystallogr. D* 50:760–763) using the apo-HDLP structure as a search model. The initial electron density maps had strong and continuous difference density for the entire TSA molecule. However the SAHA molecule was not as well ordered in the cap group region. The structure of TSA was obtained from the Cambridge Structural Database (Refcode TRCHST) and was used to define stereochemical restraints used in the refinement with the program CNS. The restraints of SAHA were constructed based on stereochemical parameters from TSA and surrounding amino acid residues. The dimer interface in the HDLP-$Zn^{2+}$-TSA and HDLP-$Zn^{2+}$-SAHA crystals primarily involves Phe200 on the protein surface. The Phe200 side chain contacts Tyr91, whose side chain conformation changes on TSA binding, and part of the dimethyl amino phenyl group of TSA from the second protomer. The HDAC family does not contain a phenylalanine residue at the equivalent position.

EXAMPLE 3

Histone Deacetylase Assays

Purified proteins were assayed by incubating 10 μg of [$^3$H] acetyl-labeled murine erythroleukemia histone substrate and HDAC assay buffer (20 mM Tris-HCl, pH 8.0, 150 mM NaCl, 10% glycerol) for 30–60 minutes at 37° C. in a total volume of 30 μl. The final concentrations of HDLP and HDAC1-FLAG were 3.6 μM and 0.24 μM, respectively. Assays were performed in duplicate. The reactions were stopped and the released acetate was extracted and assayed as described (Hendzel et al., 1991, *J. Biol. Chem.* 266: 21936–21942). [3H] acetyl-labeled murine erythroleukemia histones were prepared essentially as described (Carmen et al., 1996, *J. Biol. Chem.* 271:15837–15844). Inhibitors were added in the absence of substrate and incubated on ice for 20 minutes, substrate was added, and the assay performed as described above. HDLP was incubated with 20 μM $ZnCl_2$ and 20 μM $MnCl_2(H2O)_4$ in HDAC buffer and tested for activity.

Only HDLP dialyzed against $ZnCl_2$ had activity. HDAC1-FLAG was dialyzed against 20 μM $ZnCl_2$ in HDAC buffer which had no effect on activity. Therefore, HDAC1-FLAG contains a metal as purified.

The in vivo substrate of HDLP is not known. HDLP may have a role in acetoin utilization like the *B. subtilis* AcuC gene product, and it has been annotated as such in the genome sequence, but the reaction catalyzed by AcuC is also not known. Furthermore, the *A. aeolicus* genome appears to lack the acua and acuB genes that are part of the acuABC operon of *B. subtilis* (Deckert et al., 1998 *Nature* 2:353–358), and HDLP is as similar to human HDAC1 (35.2% identity) as it is to *B. subtilis* AcuC (34.7% identity).

Throughout the application, various publications are referenced by author, date and citation. The disclosures of these publication in their entireties are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for identifying a potential deacetylase inhibitor compound for an enzyme which comprises deacetylase activity, wherein said enzyme is selected from the group consisting of histone deacetylase-like protein (HDLP) and histone deacetylase 1 (HDAC 1), said method comprising the steps of: a) using a three-dimensional structure of HDLP as defined by atomic coordinates according to FIG. 16; b) employing said three-dimensional structure to design or select said potential inhibitor such that said potential inhibitor is capable of binding to at least one amino acid in the active site of HDLP; c) synthesizing said potential inhibitor; d) in an assay, contacting said potential inhibitor with said enzyme in the presence of an acetylated substrate; and e) determining the deacetylase inhibitory activity of said potential inhibitor.

2. The method of claim 1, wherein the potential deacetylase inhibitor is designed or selected using computer modeling.

3. The method of claim 1, wherein the potential deacetylase inhibitor is designed de novo.

4. The method of claim 1, wherein the potential deacetylase inhibitor is designed based on a known inhibitor.

5. The method of claim 1, wherein said enzyme comprising deacetylase activity is histone deacetylase like protein (HDLP).

6. The method of claim 1, wherein the enzyme is histone deacetylase 1 (HDAC1).

7. A method of using a crystal of an enzyme comprising deacetylase activity for screening for a novel drug
wherein said enzyme is selected from the group consisting of histone deacetylase-like protein (HDLP) and histone deacetylase 1 (HDAC 1);
wherein said crystal effectively diffracts X-rays for the determination of the atomic coordinates of said enzyme to a resolution of greater than 4 Å and wherein the structure of said enzyme comprises a conserved core α/β structure characteristic fold wherein said conserved α/β fold comprises an eight-stranded parallel β sheet and eight α helices and wherein four of the helices pack on either face of said parallel β sheet and wherein said structure of said enzyme comprises a root mean square deviation of less than or equal to 1.5 Å in the positions of Cα. atoms for at least ⅔ or more of the amino acids of histone deacetylase-like protein (HDLP) as defined by the atomic coordinates of HDLP according to FIG. 16; and wherein said method comprises: a) selecting a potential ligand by performing rational drug design with the three-dimensional structure determined for the crystal; b) in an assay, contacting the potential ligand with the ligand binding domain of the enzyme; and c) detecting the binding potential of the potential ligand for the ligand binding domain, wherein the potential ligand is selected as a novel drug based on the potential ligand having a greater affinity for the ligand binding domain than that of a known drug.

8. The method of claim 7, wherein the enzyme is histone deacetylase-like protein (HDLP).

9. The method of claim 7, wherein the enzyme is histone deacetylase 1 (HDAC1).

* * * * *